(12) United States Patent
Beck et al.

(10) Patent No.: US 9,273,298 B2
(45) Date of Patent: Mar. 1, 2016

(54) ISOPRENE SYNTHASE VARIANTS FOR IMPROVED PRODUCTION OF ISOPRENE

(75) Inventors: Zachary Q. Beck, Palo Alto, CA (US); David A. Estell, San Francisco, CA (US); Jeffrey V. Miller, Menlo Park, CA (US); Christopher L. Rife, Redwood City, CA (US); Derek H. Wells, Palo Alto, CA (US)

(73) Assignees: DANISCO US INC., Palo Alto, CA (US); THE GOODYEAR TIRE & RUBBER COMPANY, Akron, OH (US)

( * ) Notice: Subject to any disclaimer, the term of this patent is extended or adjusted under 35 U.S.C. 154(b) by 1143 days.

(21) Appl. No.: 13/283,564

(22) Filed: Oct. 27, 2011

(65) Prior Publication Data

US 2013/0045891 A1    Feb. 21, 2013

Related U.S. Application Data

(60) Provisional application No. 61/407,415, filed on Oct. 27, 2010.

(51) Int. Cl.
| | |
|---|---|
| C12N 9/88 | (2006.01) |
| C12N 1/20 | (2006.01) |
| C12N 15/00 | (2006.01) |
| C12N 1/14 | (2006.01) |
| C07H 21/04 | (2006.01) |
| C12N 15/79 | (2006.01) |
| C12N 15/74 | (2006.01) |
| C12N 15/63 | (2006.01) |
| C12P 5/00 | (2006.01) |

(52) U.S. Cl.
CPC *C12N 9/88* (2013.01); *C12N 15/63* (2013.01); *C12N 15/74* (2013.01); *C12N 15/79* (2013.01); *C12P 5/005* (2013.01); *C12Y 402/03027* (2013.01)

(58) Field of Classification Search
CPC ....................................................... C12N 9/88
See application file for complete search history.

(56) References Cited

U.S. PATENT DOCUMENTS

| | | | |
|---|---|---|---|
| 1,344,713 A | 6/1920 | Peters | |
| 3,686,349 A | 8/1972 | Schliebs et al. | |
| 4,570,029 A | 2/1986 | Kulprathipanja et al. | |
| 4,647,344 A | 3/1987 | Lindner et al. | |
| 4,683,195 A | 7/1987 | Mullis et al. | |
| 4,683,202 A | 7/1987 | Mullis | |
| 4,703,007 A | 10/1987 | Mulholland et al. | |
| 4,846,872 A | 7/1989 | Kamuro et al. | |
| 4,965,188 A | 10/1990 | Mullis et al. | |
| 5,322,770 A | 6/1994 | Gelfand | |
| 5,349,126 A | 9/1994 | Chappell et al. | |
| 5,380,831 A | 1/1995 | Adang et al. | |
| 5,436,391 A | 7/1995 | Fujimoto et al. | |
| 5,545,816 A | 8/1996 | Ausich et al. | |
| 5,849,970 A | 12/1998 | Fall et al. | |
| 5,874,276 A | 2/1999 | Fowler et al. | |
| 6,022,725 A | 2/2000 | Fowler et al. | |
| 6,106,888 A | 8/2000 | Dale et al. | |
| 6,176,176 B1 | 1/2001 | Dale et al. | |
| 6,268,328 B1 | 7/2001 | Mitchinson et al. | |
| 6,270,739 B1 | 8/2001 | Barnicki et al. | |
| 6,294,653 B1 | 9/2001 | Mayfield | |
| 6,582,914 B1 | 6/2003 | Caldwell et al. | |
| 6,806,076 B1 | 10/2004 | Miyake et al. | |
| 6,989,257 B2 | 1/2006 | Berry et al. | |
| 6,998,471 B2 | 2/2006 | Hallahan et al. | |
| 7,129,392 B2 | 10/2006 | Hahn et al. | |
| 7,132,268 B2 | 11/2006 | Miyake et al. | |
| 7,132,527 B2 | 11/2006 | Payne et al. | |
| 7,172,886 B2 | 2/2007 | Keasling et al. | |
| 7,183,089 B2 | 2/2007 | Keasling et al. | |
| 7,208,298 B2 | 4/2007 | Miyake et al. | |
| 7,241,587 B2 | 7/2007 | Dodge et al. | |
| 7,262,041 B2 | 8/2007 | Baldwin et al. | |
| 7,364,885 B2 | 4/2008 | Miyake et al. | |
| 7,371,558 B2 | 5/2008 | Cervin et al. | |
| 7,531,333 B2 | 5/2009 | Miyake et al. | |
| 7,659,097 B2 | 2/2010 | Renninger et al. | |
| 7,785,858 B2 | 8/2010 | Kozlov et al. | |
| 8,173,410 B2 | 5/2012 | Bott et al. | |
| 8,288,148 B2 | 10/2012 | Cervin et al. | |
| 8,420,360 B2 | 4/2013 | Calabria et al. | |
| 8,420,759 B2 | 4/2013 | Feher et al. | |
| 8,518,686 B2 | 8/2013 | Beck et al. | |
| 8,709,785 B2 | 4/2014 | Cervin et al. | |
| 2002/0095818 A1 | 7/2002 | Jain et al. | |
| 2003/0033626 A1 | 2/2003 | Hahn et al. | |
| 2004/0005678 A1 | 1/2004 | Keasling et al. | |
| 2004/0219629 A1 | 11/2004 | Cheng et al. | |
| 2005/0287655 A1 | 12/2005 | Tabata et al. | |
| 2006/0009647 A1 | 1/2006 | Yeates et al. | |

(Continued)

FOREIGN PATENT DOCUMENTS

| | | |
|---|---|---|
| DE | 196 29 568 C1 | 1/1998 |
| EP | 0 215 594 A2 | 3/1987 |

(Continued)

OTHER PUBLICATIONS

Branden et al. Introduction to Protein Structure, Garland Publishing Inc., New York, p. 247, 1991.*

(Continued)

*Primary Examiner* — Yong Pak
(74) *Attorney, Agent, or Firm* — Mintz, Levin, Cohn, Ferris, Glovsky and Popeo, P.C.

(57) ABSTRACT

The present invention provides methods and compositions comprising at least one isoprene synthase enzyme with improved specific productivity. In particular, the present invention provides variant plant isoprene synthases for increased isoprene production in host cells.

20 Claims, 54 Drawing Sheets

(56) References Cited

U.S. PATENT DOCUMENTS

| | | |
|---|---|---|
| 2006/0020095 A1 | 1/2006 | Gandon-Pain |
| 2008/0038805 A1 | 2/2008 | Melis |
| 2008/0178354 A1 | 7/2008 | Chappell |
| 2009/0155874 A1 | 6/2009 | Clark et al. |
| 2009/0282545 A1 | 11/2009 | Eichelberger et al. |
| 2010/0048964 A1 | 2/2010 | Calabria et al. |
| 2010/0086978 A1 | 4/2010 | Beck et al. |
| 2010/0113846 A1 | 5/2010 | McAuliffe et al. |
| 2010/0196977 A1 | 8/2010 | Chotani et al. |
| 2010/0196982 A1 | 8/2010 | Anderson |
| 2010/0285549 A1 | 11/2010 | Muramatsu et al. |
| 2010/0297749 A1 | 11/2010 | Aravanis et al. |
| 2011/0045563 A1 | 2/2011 | Melis |
| 2011/0159557 A1 | 6/2011 | Beck et al. |
| 2011/0178261 A1 | 7/2011 | Feher et al. |
| 2013/0078699 A1 | 3/2013 | Cervin et al. |
| 2013/0252303 A1 | 9/2013 | Beck et al. |
| 2013/0260432 A1 | 10/2013 | Bott et al. |
| 2013/0330796 A1 | 12/2013 | Beck et al. |

FOREIGN PATENT DOCUMENTS

| | | |
|---|---|---|
| EP | 0 215 594 A3 | 3/1987 |
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 238 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 1 118 855 A2 | 7/2001 |
| EP | 1 118 855 A3 | 7/2001 |
| JP | 2006-271379 A | 10/2006 |
| JP | 2008-035831 A | 2/2008 |
| JP | 2008-061506 A | 3/2008 |
| JP | 2008-182950 A | 8/2008 |
| JP | 2009-207402 A | 9/2009 |
| KR | 2001-0084864 A | 9/2001 |
| RU | 2027760 C1 | 9/2000 |
| RU | 2197461 C2 | 1/2003 |
| WO | WO-95/04134 A1 | 2/1995 |
| WO | WO-95/11913 A1 | 5/1995 |
| WO | WO-96/35796 A1 | 11/1996 |
| WO | WO-98/02550 A2 | 1/1998 |
| WO | WO-98/02550 A3 | 1/1998 |
| WO | WO-00/17327 A2 | 3/2000 |
| WO | WO-00/17327 A3 | 3/2000 |
| WO | WO-00/17327 A9 | 3/2000 |
| WO | WO-01/58839 A1 | 8/2001 |
| WO | WO-02/076189 A1 | 10/2002 |
| WO | WO-02/099095 A2 | 12/2002 |
| WO | WO-02/099095 A3 | 12/2002 |
| WO | WO-2004/033646 A2 | 4/2004 |
| WO | WO-2004/033646 A3 | 4/2004 |
| WO | WO-2004/111214 A1 | 12/2004 |
| WO | WO-2005/001036 A2 | 1/2005 |
| WO | WO-2005/001036 C1 | 1/2005 |
| WO | WO-2005/007682 A2 | 1/2005 |
| WO | WO-2005/007682 A3 | 1/2005 |
| WO | WO-2005/078074 A2 | 8/2005 |
| WO | WO-2005/078074 A3 | 8/2005 |
| WO | WO-2006/063752 A1 | 6/2006 |
| WO | WO-2006/085899 A2 | 8/2006 |
| WO | WO-2006/085899 A3 | 8/2006 |
| WO | WO-2007/018062 A1 | 2/2007 |
| WO | WO-2007/136847 A2 | 11/2007 |
| WO | WO-2007/136847 A3 | 11/2007 |
| WO | WO-2007/140339 A2 | 12/2007 |
| WO | WO-2007/140339 A3 | 12/2007 |
| WO | WO-2007/140339 A8 | 12/2007 |
| WO | WO-2008/002472 A2 | 1/2008 |
| WO | WO-2008/002472 A3 | 1/2008 |
| WO | WO-2008/003078 A2 | 1/2008 |
| WO | WO-2008/003078 A3 | 1/2008 |
| WO | WO-2008/003078 A8 | 1/2008 |
| WO | WO-2008/137092 A2 | 11/2008 |
| WO | WO-2008/137092 A3 | 11/2008 |
| WO | WO-2008/153925 A2 | 12/2008 |
| WO | WO-2008/153925 A3 | 12/2008 |
| WO | WO-2008/153925 A9 | 12/2008 |
| WO | WO-2008/153934 A2 | 12/2008 |
| WO | WO-2008/153934 A3 | 12/2008 |
| WO | WO-2008/153935 A2 | 12/2008 |
| WO | WO-2008/153935 A3 | 12/2008 |
| WO | WO-2009/036067 A2 | 3/2009 |
| WO | WO-2009/036067 A3 | 3/2009 |
| WO | WO-2009/064910 A2 | 5/2009 |
| WO | WO-2009/064910 A3 | 5/2009 |
| WO | WO-2009/076676 A2 | 6/2009 |
| WO | WO-2009/076676 A3 | 6/2009 |
| WO | WO-2009/100231 A2 | 8/2009 |
| WO | WO-2009/100231 A3 | 8/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/005525 A1 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2010/148256 A1 | 12/2010 |
| WO | WO-2011/000026 A1 | 1/2011 |
| WO | WO-2011/034863 A1 | 3/2011 |
| WO | WO-2011/159853 A1 | 12/2011 |

OTHER PUBLICATIONS

Albrecht, M. et al. (Aug. 2000). "Novel Hydroxycarotenoids with Improved Antioxidative Properties Produced by Gene Combination in *Escherichia coli*," *Nature Biotechnology* 18:843-846.

Allison, R. et al. (1986). "The Nucleotide Sequence of the Coding Region of Tobacco Etch Virus Genomic RNA: Evidence for the Synthesis of a Single Polyprotein," *Virology* 154:9-20.

Alper, H. et al. (2008). "Uncovering the Gene Knockout Landscape for Improved Lycopene Production in *E. coli*," *Appl. Microbiol. Biotechnol.* 10 pages.

Alterthum, F. et al. (Aug. 1989). "Efficient Ethanol Production from Glucose, Lactose, and Xylose by Recombinant *Escherichia coli*," *Applied Environmental Microbiology* 55(8):1943-1948.

Altschul, S.F. et al. (1990). "Basic Local Alignment Search Tool," *J Mol. Biol.* 215:403-410.

Altschul, S.F. et al. (1996). "Local Alignment Statistics," Chapter 27 in *Multiple Alignment and Phylogenetic Trees*, American Press, Inc. 266:460-480.

Altschul, S.F. et al. (1997). "Gapped BLAST and PSI-BLAST: A New Generation of Protein Database Search Programs," *Nucleic Acids Research* 25(17):3389-3402.

Alves, R. et al. (Nov. 2000). "Effect of Overall Feedback Inhibition in Unbranched Biosynthetic Pathways," *Biophysical Journal* 79(5):2290-2304.

Anderson, M.S. et al. (Nov. 15, 1989). "Isopentenyl Diphosphate: Dimethylallyl Diphosphate Isomerase. An Improved Purification of the Enzyme and Isolation of the Gene from *Saccharomyces Cerevisiae*," *J. Biol. Chem.* 264(32):19169-19175.

Andreassi, J.L. et al. (2004, e-pub. Dec. 4, 2004). "*Streptococcus pneumoniae* Isoprenoid Biosynthesis Is Downregulated by Diphosphomevalonate: An Antimicrobial Target," *Biochemistry* 43(51):16461-16466.

(56) References Cited

OTHER PUBLICATIONS

Andreassi, J.L. et al. (2007, e-pub. Mar. 30, 2007). "Crystal Structure of the *Streptococcus pneumoniae* Mevalonate Kinase in Complex with Diphosphomevalonate," *Protein Science* 16:983-989.
Aon, J.C. et al. (Feb. 2008, e-pub. Dec. 14, 2007). "Suppressing Posttranslational Gluconoylation of Heterologous Proteins by Metabolic Engineering of *Escherichia coli*," *Applied and Environmental Microbiology* 74(4):950-958.
Arai, Y. et al. (2004). "Production of Polyhydroxybutyrate by Polycistronic Expression of Bacterial Genes in Tobacco Plastid," *Plant Cell Physiol.* 45(9):1176-1184.
Ashby, M.N. et al. (Aug. 5, 1990). "Elucidation of the Deficiency in Two Yeast Coenzyme Q Mutants: Characterization of the Structural Gene Encoding Hexaprenyl Pyrophosphate Synthetase," *The Journal of Biological Chemistry* 265(22):13157-13164.
Ausubel, F. M. et al. eds. (1987). "Introduction of DNA into Mammalian Cells," Chapter 9 *in Current Protocols in Molecular Biology.*
Baba, T. et al. (Feb. 21, 2006). "Construction of *Escherichia coli* K-12 In-Frame, Single-Gene Knockout Mutants: The Keio Collection," *Molecular Systems Biology* pp. 1-11.
Ballas, N. et al. (1989). "Efficient Functioning of Plant Promoters and Poly(A) Sites in *Xenopus* Oocytes," *Nucleic Acids Research* 17(19):7891-7903.
Barkovich, R. et al. (2001, e-pub. Dec. 1, 2000). "Metabolic Engineering of Isoprenoids," *Metabolic Engineering* 3:27-39.
Beaucage, S.L. et al. (1981). "Deoxynucleoside Phosphoramidites-A New Class of Key Intermediates for Deoxypolynucleotide Synthesis," *Tetrahedron Letters* 22(20):1859-1862.
Bellion, E. et al. (1993). "Methylamine Utilization in Yeast and Bacteria: Studies Using in vivo NMR," Chapter 32 *in Microbial Growth on $C_1$ Compounds*, Murrell, J.C. et al. eds, Intercept Ltd: Andover, UK, pp. 415-432.
Berman, H. et al. (2007, e-pub. Nov. 16, 2006). "The Worldwide Protein Data Bank (wwPDB): Ensuring a Single, Uniform Archive of PDB Data," *Nucleic Acids Research* 35:D301-D303.
Beytia, E. et al. (Oct. 25, 1970). "Purification and Mechanism of Action of Hog Liver Mevalonic Kinase," *The Journal of Biological Chemistry* 245(20):5450-5458.
Bock, R. et al. (2000). "Extranuclear Inheritance: Plastid Genetics: Manipulation of Plastid Genomes and Biotechnological Applications," *Progress in Botany* 61:76-90.
Bock, R. (2001). "Transgenic Plastids in Basic Research and Plant Biotechnology," *J. Mol. Biol.* 312:425-438.
Bock, R. et al. (Jun. 2004). "Taming Plastids for a Green Future," *Trends in Biotechnology* 22(6):311-318.
Boel, E. et al. (1984). "Two Different Types of Intervening Sequences in the Glucoamylase Gene from *Aspergillus niger*," *The EMBO Journal* 3(7):1581-1585.
Bouvier, F. et al. (2005). "Biogenesis, Molecular Regulation and Function of Plant Isoprenoids," *Progress in Lipid Research* 44:357-429.
Boynton, J.E. et al. (1993). "Chloroplast Transformation in *Chlamydomonas*," *Methods in Enzymology* 217(37):510-536.
Broun, P. et al. (Nov. 13, 1998). "Catalytic Plasticity of Fatty Acid Modification Enzymes Underlying Chemical Diversity of Plant Lipids," *Science* 282:1315-1317.
Brünger, A.T. et al. (1998). "*Crystallography & NMR System*: A New Software Suite for Macromolecular Structure Determination," *Acta Cryst.* D54:905-921.
Bubunenko, M. et al. (Apr. 2007). "Essentiality of Ribosomal and Transcription Antitermination Proteins Analyzed by Systematic Gene Replacement in *Escherichia coli*," *Journal of Bacteriology* 189(7):2844-2853.
Campbell, E.I. et al. (1989). "Improved Transformation Efficiency of *Aspergillus niger* Using the Homologous *niaD* Gene for Nitrate Reductase," *Curr. Genet.* 16:53-56.
Campbell, J.W. et al. (Oct. 2001). "*Escherichia coli* FadR Positively Regulates Transcription of the *fabB* Fatty Acid Biosynthetic Gene," *J. Bacteriol.* 183(20):5982-5990.

Campos, N. et al. (2001). "*Escherichia coli* Engineering to Synthesize Isopentenyl Diphosphate and Dimethylallyl Diphosphate from Mevalonate: A Novel System for the Genetic Analysis of the 2-C-Methyl-D-Erythritol 4-Phospate Pathway for Isoprenoid Biosynthesis," *Biochem. J.* 353:59-67.
Cao, Q.-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.
Chamberlin, M. et al. (Oct. 17, 1970). "New RNA Polymerase from *Escherichia coli* Infected with Bacteriophage T7," *Nature* 228:227-231.
Champenoy, S. et al. (1998). "Expression of the Yeast Mevalonate Kinase Gene in Transgenic Tobacco," *Molecular Breeding* 4:291-300.
Chan, W. et al. (2007, e-pub. Apr. 10, 2007). "A Recombineering Based Approach for High-Throughput Conditional Knockout Targeting Vector Construction," *Nucleic Acids Research* 35(8):e64, 13 pages.
Chappell, J. et al. (1995). "Is the Reaction Catalyzed by 3-Hydroxy-3-Methylglutaryl—Coenzyme A Reductase a Rate-Limiting Step for Isoprenoid Biosynthesis in Plants?" *Plant Physiology* 109:1337-1343.
Chemler, J.A. et al. (May 23, 2006). "Biosynthesis of Isoprenoids, Polyunsaturated Fatty Acids and Flavonoids in *Saccharomyces cerevisiae*," *Microbial Cell Factories* 5:20, 9 pages.
Cherepanov, P.P. et al. (1995). "Gene Disruption in *Escherichia coli*: $Tc^H$ and $Km^H$ Cassettes with the Option of Flp-Catalyzed Excision of the Antibiotic-Resistance Determinant," *Gene* 158(1):9-14.
Chica, R.A. et al. (2005). "Semi-Rational Approaches to Engineering Enzyme Activity: Combining the Benefits of Directed Evolution and Rational Design," *Current Opinion in Biotechnology* 16:378-384.
Cho, H.-J. et al. (1995). "Expression Pattern of Bacterial Polycistronic Genes in Tobacco Cells," *Journal of Fermentation and Bioengineering* 80(2):111-117.
Clarke, S. (1992). "Protein Isoprenylation and Methylation at Carboxyl-Terminal Cysteine Residues," *Annu. Rev. Biochem.* 61:355-386.
Clough, S.J. et al. (1998). "Floral Dip: A Simplified Method for *Agrobacterium*-Mediated Transformation of *Arabidopsis thaliana*," *The Plant Journal* 16(6):735-743.
Collaborative Computational Project, No. 4. (1994). "The *CCP4* Suite: Programs for Protein Crystallography," *Acta Cryst.* D50:760-763.
Cordier, H. et al. (1999). "Heterologous Expression in *Saccharomyces cerevisiae* of an *Arabidopsis thaliana* cDNA Encoding Mevalonate Diphosphate Decarboxylase," *Plant Molecular Biology* 39:953-967.
Cunningham, F.X. et al. (1998). "Genes and Enzymes of Carotenoid Biosynthesis in Plants," *Ann. Rev. Plant Physiol. Plant Mol. Biol.* 49:557-583.
Cunningham, F.X. et al. (Oct. 2000). "Evidence of a Role for LytB in the Nonmevalonate Pathway of Isoprenoid Biosynthesis," *Journal of Bacteriology* 182(20):5841-5848.
Dale, P.J. (1992). "Spread of Engineered Genes to Wild Relatives," *Plant Physiol.* 100:13-15.
Dale, G.E. et al. (2003). "The Protein as a Variable in Protein Crystallization," *Journal of Structural Biology* 142:88-97.
Daniell, H. (1997). "'Transformation and Foreign Gene Expression in Plants Mediated by Microprojectile Bombardment," Chapter 35 *in Methods in Molecular Biology, Recombinant Gene Expression Protocols*, Tuan, R. ed., Humana Press, Inc., Totowa, NJ, 62:463-489.
Daniell, H. et al. (Apr. 1998) "Containment of Herbicide Resistance Through Genetic Engineering of the Chloroplast Genome," *Nature Biotechnology* 16:345-348.
Datsenko, K.A. et al. (Jun. 6, 2000). "One-Step Inactivation of Chromosomal Genes in *Escherichia coli* K-12 Using PCR Products," *PNAS* 97(12):6640-6645.
Datta, S. et al. (2006). "A Set of Recombineering Plasmids for Gram-Negative Bacteria," *Gene* 379:109-115.
Datukishvili, N.T. et al. (2001). "Isolation and Purification of Protein Responsible for the Conversion of Dimethylallylpyrophosphate from Poplar Leaves into Isoprene," *Russian Journal of Plant Physiology* 48(2):222-225.

(56) References Cited

OTHER PUBLICATIONS

Davidson, S. (Oct.-Dec. 2003). "Light Factories," located at <http://www.publish.csiro.au/?act=view_file&file_id=EC117p10.pdf>, last visited on Oct. 2, 2008.

Davis, I.W. et al. (2007). "MolProbity: All-Atom Contacts and Structure Validation for Proteins and Nucleic Acids," *Nucleic Acids Research* 35:W375-W383.

De Cosa, B. et al. (Jan. 2001). "Overexpression of the *Bt cry*2Aa2operon in Chloroplasts Leads to Formation of Insecticidal Crystals," *Nature Biotechnology* 19:71-74.

Del Campo, E. M. et al. (1997). "Plastid *ndhD* Gene of Barley, Sequence and Transcript Editing (Accesion No. Y12258) (PGR 97-090)," *Plant Physiol.* 114:747-749.

Della-Cioppa, G. et al. (1987). "Protein Trafficking in Plant Cells," *Plant Physiol*.84:965-968.

Deppenmeier, U. et al. (2002). "The Genome of *Methanosarcina mazei*: Evidence for Lateral Gene Transfer Between Bacteria and Archaea," *J. Mol. Microbiol. Biotechnol.* 4(4):453-461.

Deroles, S.C. et al. (1988). "Expression and Inheritance of Kanamycin Resistance in a Large Number of Transgenic Petunias Generated by *Agrobacterium*-Mediated Transformation," *Plant Molecular Biology* 11:355-364.

Dettmer, K. et al. (2000). "Stability of Reactive Low Boiling Hydrocarbons on Carbon Based Adsorbents Typically Used for Adsorptive Enrichment and Thermal Desorption," *Fresenius J. Anal. Chem.* 366:70-78.

Devereux, J. et al. (1984). "A Comprehensive Set of Sequence Analysis Programs for the VAX," *Nucleic Acids Research* 12(1):387-395.

Devos, D. et al. (2000). "Practical Limits of Function Prediction," *Proteins: Structure, Function, and Genetics* 41:98-107.

Dewick, P.M. et al. (2002, e-pub. Jan. 22, 2002). "The Biosynthesis of $C_5$—$C_{25}$ Terpenoid Compounds," *Nat. Prod. Rep.* 19:181-222.

Dhe-Paganon, S. et al. (1994). "Mechanism of Mevalonate Pyrophosphate Decarboxylase: Evidence for a Carbocationic Transition State," *Biochemistry* 33(45):13355-13362.

Dorsey, J.K. et al. (Sep. 25, 1968). "The Inhibition of Mevalonic Kinase by Geranyl and Farnesyl Pyrophosphates," *The Journal of Biological Chemistry* 243(18):4667-4670.

Doumith, M. et al. (2000, e-pub. Aug. 25, 2000). "Analysis of Genes Involved in 6-Deoxyhexose Biosynthesis and Transfer in *Saccharopolyspora erythraea*," *Mol. Gen Genet.* 264:477-485.

Dynan, W.S. et al. (Aug. 29, 1985). "Control of Eukaryotic Messenger RNA Synthesis by Sequence-Specific DNA-Binding Proteins," *Nature* 316:774-778.

Eisenreich, W. et al. (Sep. 1998). "The Deoxyxylulose Phosphate Pathway of Terpenoid Biosynthesis in Plants and Microorganisms," *Chemistry and Biology* 5(9):R221-R233.

Eisenreich, W. et al, (Feb. 2001). "Deoxyxylulose Phosphate Pathway to Terpenoids," *Trends in Plant Science* 6(2):78-84.

Elroy-Stein, O. et al. (Aug. 1989). "Cap-Independent Translation of mRNA Conferred by Encephalomyocarditis Virus 5' Sequence Improves the Performance of the Vaccinia Virus/Bacteriophage T7 Hybrid Expression System," *PNAS USA* 86:6126-6130.

EMBL-EBI Accession No. A0PFK2, last updated on Mar. 2, 2010, located at <http://srs.ebi.ac.uk/srsbin/cgi-bin/wgetz?-e+[UNIPROT:A0PFK2_POPNI]+-newld>, last visited on Jun. 2, 2010, 2 pages.

EMBL-EBI Accession No. A9PGR5, last updated on Mar. 2, 2010, located at <http://srs.ebi.ac.uk/srsbin/cgi-bin/wgetz?-e+[UNIPROT:A9PGR5_POPTR]+-newld>, last visited on Jun. 2, 2010, 2 pages.

EMBL-EBI Accession No. AB198180, last updated May 10, 2005, located at <http://www.ebi.ac.uk/cgi-bin/dbfetch?db=embl&id=ab198180&Subm . . . >, last visited on Jul. 8, 2009, 2 pages.

EMBL-EBI Accession No. AY341431, last updated Apr. 16, 2005, located at <http://www.ebi.ac.uk/cgi-bin/dbfetch?db=embl&id=AY341431∈ . . . >, last visited on Nov. 26, 2009, 2 pages.

Emsley, P. et al. (2004). "*Coot*: Model-Building Tools for Molecular Graphics," *Acta Crystallographica* D60:2126-2132.

Emsley, P. et al. (2010). "Features and Development of Coot," *Acta Crystallographica* D66:486-501.

Extended European Search Report mailed on Jun. 14, 2011, for EP Patent Application No. 08860589.4, filed on Dec. 15, 2008, 10 pages.

Fall, R. (Sep. 12, 2003). "Final Technical Report: DE-FG03-97ER20274, 'Microbial Production of Isoprene. Dates Covered: Jun. 15, 2000 to Jun. 14, 2003," located at <http://www.osti.gov/scitech/serylets/purl/814920>, last visited on Nov. 11, 2013, 4 pages.

Farmer, W.R. et al. (May 2000). "Improving Lycopene Production in *Escherichia coli by* Engineering Metabolic Control," *Nature Biotechnology* 18:533-537.

Feng, D.-F. et al. (1987). "Progressive Sequence Alignment as a Prerequisite to Correct Phylogenetic Trees," *Journal of Molecular Evolution* 25:351-360.

Finkelstein, D.B. (1992). "Transformation," Chapter 6 *in Biotechnology of Filamentous Fungi*, Butterworth-Heinemann: Boston, MA, pp. 113-156.

Flores, S. et al. (Aug. 20, 2004, e-pub. Jul. 23, 2004). "Growth-Rate Recovery of *Escherichia coli* Cultures Carrying a Multicopy Plasmid, by Engineering of the Pentose-Phosphate Pathway," *Biotechnology and Bioengineering* 87(4):485-494.

Fu, Z. et al. (2008, e-pub. Feb. 27, 2008). "Biochemical and Structural Basis for Feedback Inhibition of Mevalonate Kinase and Isoprenoid Metabolism," *Biochemistry* 47:3715-3724.

Gallie, D.R. et al. (1989). "Eukaryotic Viral 5'-Leader Sequences Act as Translational Enhancers in Eukaryotes and Prokaryotes," *in Molecular Biology of RNA*, Cech, T.R. ed., Alan R. Liss, Inc: New York, NY, pp. 237-256.

Garret, T.A. et al. (May 15, 1998). "Accumulation of a Lipid A Precursor Lacking the 4'-Phosphate Following Inactivation of the *Escherichia coli IpxK* Gene," *The Journal of Biological Chemistry* 273(20):12457-12465.

GenBank Accession No. AB198180, last updated on May 10, 2005, located at <http://www.ncbi.nlm.nih.gov/nuccore/63108309>, last visited on Jun. 2, 2010, 2 pages.

GenBank Accession No. AJ294819.1, last updated Apr. 15, 2005, located at < http://www.ncbi.nlm.nih.gov/nuccore/AJ294819.1>, last visited on Dec. 7, 2011, 2 pages.

GenBank Accession No. AJ457070, last updated on Apr. 15, 2005, located at <http://www.ncbi.nlm.nih.gov/nuccore/38092202>, last visited on Jun. 2, 2010, 2 pages.

GenBank Accession No. AM410988.1, last updated Aug. 14, 2008, located at < http://www.ncbi.nlm.nih.gov/nuccore/AM410988.1>, last visited on Dec. 7, 2011, 2 pages.

GenBank Accession No. AY182241, last updated on May 4, 2004, located at <http://www.ncbi.nlm.nih.gov/nuccore/32265057>, last visited on Jun. 2, 2010, 2 pages.

GenBank Accession No. AY279379, last updated on Mar. 11, 2005, located at <http://www.ncbi.nlm.nih.gov/nuccore/30984014>, last visited on Jun. 2, 2010, 2 pages.

GenBank Accession No. AY316691, last updated on Feb. 15, 2005, located at <http://www.ncbi.nlm.nih.gov/nuccore/35187003>, last visited on Jun. 2, 2010, 2 pages.

GenBank Accession No. AY341431, last updated on Feb. 15, 2005, located at <http://www.ncbi.nlm.nih.gov/nuccore/33358228>, last visited on Jun. 2, 2010, 3 pages.

GenBank Accession No. EF147555.1, last updated Mar. 24, 2009, located at <http://www.ncbi.nlm.nih.gov/nuccore/EF147555.1>, last visited on Dec. 7, 2011, 2 pages.

GenBank Accession No. EF638224.1, last updated May 3, 2010, located at <http://www.ncbi.nlm.nih.gov/nuccore/EF638224.1>, last visited on Dec. 7, 2011, 2 pages.

GenBank Accession No. EU693027, last updated on May 27, 2008, located at <http://www.ncbi.nlm.nih.gov/nuccore/189017053>, last visited on Jun. 2, 2010, 2 pages.

GenBank Accession No. CAC35696, last updated Apr. 15, 2005, located at <http://www.ncbi.nlm.nih.gov/protein/CAC35696>, last visited on Nov. 1, 2011, 1 page.

Geneseq Database Accession No. AFB74822, "Monoterpene synthetase protein SEQ ID No. 4." Retrieved from EBI accession No. GSP:AFB74822 (Apr. 19, 2007), located at http://ibis/exam/dbfetch.jsp?id=GSP:AFB74822, last visited on Apr. 17, 2012, 2 pages.

(56) References Cited

OTHER PUBLICATIONS

Goedegebuur, F. et al. (2002, e-pub. May 7, 2002). "Cloning and Relational Analysis of 15 Novel Fungal Endoglucanases from Family 12 Glycosyl Hydrolase," *Curr. Genet.* 41:89-98.

Goldschmidt-Clermont, M. (1991). "Transgenic Expression of Aminoglycoside Adenine Transferase in the Chloroplast: A Selectable Marker for Site-Directed Transformation of Chlamydomonas," *Nucleic Acids Res.* 19(15):4083-4089.

Goodwin, T.W. (1971). "Biosynthesis of Carotenoids and Plant Triterpenes: The Fifth CIBA Medal Lecture," *Biochem. J.* 123(3):293-329.

Gräwert, T. et al. (2004, e-pub. Sep. 21, 2004). "IspH Protein of *Escherichia coli*: Studies on Iron-Sulfur Cluster Implementation and Catalysis," *Journal American Chemistry Society* 126:12847-12855.

Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.

Grochowski, L.L. et al. (May 2006). "*Methanocaldococcus jannaschii* Uses a Modified Mevalonate Pathway for Biosynthesis of Isopentenyl Diphosphate," *Journal of Bacteriology* 188(9):3192-3198.

Guda, C. et al. (2000). "Stable Expression for a Biodegradable Protein-Based Polymer in Tobacco Chloroplasts," *Plant Cell Reports* 19:257-262.

Guerineau, F. et al. (1991). "Effect of Deletions in the Cauliflower Mosaic Virus Polyadenylation Sequence on the Choice of the Polyadenylation Sites in Tobacco Protoplasts," *Mol. Gen. Genet.* 226:141-144.

Guo, D.-A. et al. (1995). "Developmental Regulation of Sterol Biosynthesis in *Zea mays*," *Lipids* 30(3):203-219.

Hahn, F.M. et al. (May 12, 1995). "Isolation of *Schizosaccharomyces pombe* Isopentenyl Diphosphate Isomerase in cDNA Clones by Complementation and Synthesis of the Enzyme in *Escherichia coli*," *The Journal of Biological Chemistry* 270(19):11298-11303.

Hahn, F.M. et al. (Feb. 1996). "Open Reading Frame 176 in the Photosynthesis Gene Cluster of *Rhodobacter capsulatus* Encodes *idi*, a Gene for Isopentenyl Diphosphate Isomerase," *Journal of Bacteriology* 178(3):619-624.

Hahn, F.M. et al. (Aug. 1999). "*Escherichia coli* Open Reading Frame 696 Is *idi*, a Nonessential Gene Encoding Isopentenyl Diphosphate Isomerase," *Journal of Bacteriology* 181(15):4499-4504.

Hahn, F.M. et al. (Jan. 2001). "1-Deoxy D-Xylulose 5-Phosphate Synthase, the Gene Product of Open Reading Frame (ORF) 2816 and ORF 2895 in *Rhodobacter capsulatus*," *Journal of Bacteriology* 183(1):1-11.

Hamano, Y. et al. (2001). "Cloning of a Gene Cluster Encoding Enzymes Responsible for the Mevalonate Pathway from a Terpenoid-Antibiotic-Producing *Streptomyces* Strain," *Biosci. Biotechnol. Biochem.* 65(7):1627-1635.

Hamilton, C.M. et al. (Sep. 1989). "New Method for Generating Deletions and Gene Replacements in *Escherichia coli*," *Journal of Bacteriology* 171(9):4617-4622.

Hanai, T. et al. (Dec. 2007). "Engineered Synthetic Pathway for Isopropanol Production in *Escherichia coli*," *Applied and Environmental Microbiology* 73(24):7814-7818.

Harker, M. et al. (1999). "Expression of Prokaryotic 1-Deoxy-D-Xylulose-5-Phosphatases in *Escherichia coli* Increases Carotenoid and Ubiquinone Biosynthesis," *FEBS Letters* 448:115-119.

Harkki, A. et al. (Jun. 1989). "A Novel Fungal Expression System: Secretion of Active Calf Chymosin from the Filamentous Fungus *Trichoderma reesei*," *Bio/Technology* 7:596-603.

Hedl, M. et al. (Apr. 2002). "*Enterococcus faecalis* Acetoacetyl-Coenzyme A Thiolase/3-Hydroxy-3-Methyglutaryl-Coenzyme A Reductase, a Dual-Function Protein of Isopentenyl Diphosphate Biosynthesis," *Journal of Bacteriology* 184(8):2116-2122.

Hedl, M. et al. (Apr. 2004). "Class II 3-Hydroxy-3-Methylglutaryl Coenzyme A Reductases," *Journal of Bacteriology* 186(7):1927-1932.

Hellman, U. et al. (1995). "Improvement of an "In-Gel" Digestion Procedure for the Micropreparation of Internal Protein Fragments for Amino Acid Fragments for Amino Acid Sequencing," *Analytical Biochemistry* 224:451-455.

Henikoff, S. (Nov. 1992). "Amino Acid Substitution Matrices from Protein Blocks," *Proc. Natl. Acad. Sci. USA* 89:10915-10919.

Herbers, K. et al. (Jun. 1996). "Manipulating Metabolic Partitioning in Transgenic Plants", *TIBTECH* 14:198-205.

Herz, S. et al. (Mar. 14, 2000). "Biosynthesis of Terpenoids: YgbB Protein Converts 4-Diphosphocytidyl-2C-Methyl-D-Erythritol 2-Phosphate to 2C-Methyl-D-Erythritol 2,4-Cyclodiphosphate," *PNAS* 97(6):2486-2490.

Higgins, D.G. et al. (1989). "Fast and Sensitive Multiple Sequence Alignments on a Microcomputer," *Cabios Communications* 5(2):151-153.

Hinson, D.D. et al. (1997). "Post-Translation Regulation of Mevalonate Kinase by Intermediates of the Cholesterol and Nonsterol Isoprene Biosynthetic Pathways," *Journal of Lipid Research* 38:2216-2223.

Hoeffler, J.-F. et al. (2002). "Isoprenoid Biosynthesis Via the Methylerythritol Phosphate Pathway. Mechanistic Investigations of the 1-Deoxy-D-Xylulose 5-Phosphate Reductoisomerase," *Eur. J. Biochem.* 269:4446-4457.

Huang, K.-X. et al. (1999). "Overexpression, Purification, and Characterization of the Thermostable Mevalonate Kinase from *Methanococcus jannaschii*," *Protein Expression and Purification* 17:33-40.

Hunter, B.K. (1985). "Formaldehyde Metabolism by *Escherichia coli*. Carbon and Solvent Deuterium Incorporation into Glycerol, 1,2-Propanediol, and 1,3-Propanediol," *Biochemistry* 24(15):4148-4155.

Hyatt, D.C. et al. (Mar. 27, 2007). "Structure of Limonene Synthase, A Simple Model for Terpenoid Cyclase Catalysis," *PNAS* 104(13):5360-5365.

Ilmén, M. et al. (Apr. 1997). "Regulation of Cellulase Gene Expression in the Filamentous Fungus *Trichoderma reesei*," *Appl. Environ. Microbiol.* 63(4):1298-1306.

Innis, M.A. et al. (Apr. 5, 1985). "Expression, Glycosylation, and Secretion of an *Aspergillus* Glucoamylase by *Saccharomyces cerevisiae*," *Science* 228:21-26.

Jenkins, L.S. et al. (Jan. 1987). "Genetic and Molecular Characterization of the Genes Involved in Short-Chain Fatty Acid Degradation in *Escherichia coli*: The *ato* System," *Journal of Bacteriology* 169(1):42-52.

Jeong, S.-W. et al. (2004, e-pub. Jan. 21, 2004). "Dicistronic Expression of the Green Fluorescent Protein and Antibiotic Resistance Genes in the Plastid for Selection and Tracking of Plastid-Transformed Cells in Tobacco," *Plant Cell Rep* 22:747-751.

Jeong, D.-W. et al. (2007). "Cloning and Characterization of a Gene Encoding Phosphoketolase in a *Lactobacillus paraplantarum* Isolated from Kimchi," *Journal of Microbiology and Biotechnology* 17(5):822-829.

Jobling, S.A. et al. (Feb. 12, 1987). "Enhanced Translation of Chimaeric Messenger RNAs Containing a Plant Viral Untranslated Leader Sequence," *Nature* 235:622-625.

Jones, K.L. et al. (2000). "Low-Copy Plasmids Can Perform as Well as or Better Than High-Copy Plasmids for Metabolic Engineering of Bacteria," *Metabolic Engineering* 2:238-338.

Jones, E.Y. et al. (1991). "Methodology Employed for the Structure Determination of Tumour Necrosis Factor, a Case of High Non-Crystallographic Symmetry," *Acta Cryst* A47:753-770.

Joshi, C.P. (1987). "Putative Polyadenylation Signals in Nuclear Genes of Higher Plants: A Compilation and Analysis," *Nucleic Acids Research* 15(23):9627-9640.

Julsing, M.K. et al. (Jul. 2007, e-pub. Apr. 26, 2007). "Functional Analysis of Genes Involved in the Biosynthesis of Isoprene in *Bacillus subtilis*," *Applied Microbiol. Biotechno.* 75(6):1377-1384.

Kacian, D.L. et al. (Oct. 1972). "A Replicating RNA Molecule Suitable for a Detailed Analysis of Extracellular Evolution and Replication," *Proc. Natl. Acad. Sci. USA* 69(10):3038-3042.

Kajiwara, S. et al. (1997). "Expression of an Exogenous Isopentenyl Diphosphate Isomerase Gene Enhances Isoprenoid Biosynthesis in *Escherichia coli*," *Biochem. J.* 324:421-426.

(56) References Cited

OTHER PUBLICATIONS

Kampranis, S.C. et al. (Jun. 2007). "Rational Conversion of Substrate and Product Specificity in a *Salvia* Monoterpene Synthase: Structural Insights into the Evolution of Terpene Synthase Function," *The Plant Cell* 19:1994-2005.

Kaneda, K. et al. (Jan. 30, 2001). "An Unusual Isopentenyl Diphosphate Isomerase Found in the Mevalonate Pathway Gene Cluster from *Streptomyces* sp. Strain CL190," *PNAS* 98(3):932-937.

Karl, T. et al. (2003). "Dynamic Measurements of Partition Coefficients Using Proton-Transfer-Reaction Mass Spectrometry (PTR-MS)," *International Journal of Mass Spectrometry* 223-224:383-395.

Karlin, S. (Jun. 1993). "Applications and Statistics for Multiple High-Scoring Segments in Molecular Sequences," *Proc. Natl. Acad. Sci. USA* 90:5873-5787.

Kavanagh, T.A. et al. (Jul. 1999). "Homeologous Plastid DNA Transformation in Tobacco Is Mediated by Multiple Recombination Events," *Genetics* 152(3):1111-1122.

Keasling, J.D. (Mar. 29, 2004). "Genetic Tools for Metabolic Enzyme Production in *Escherichia Coli*," *presented at* NIGMS 2004 PSI Protein Production & Crystallization Workshop, Bethesda, MD, Mar. 29-31, 2004, located at <http://www-nmr.cabm.rutgers.edu/labdocuments/workshops/psi_ppcw_32904/ppcw_32904.html>, last visited on Jun. 4, 2010, 66 pages.

Keasling, J.D. (May 7, 2005). "Drugs from Bugs: Engineering Microorganisms to Produce New Drugs," *presented at* Engineering a Better World: *Our Environment, Our Health*, Berkeley, CA, May 7, 2005, 62 pages.

Keasling, J.D. (Sep. 23, 2007). "Engineering Microbes for Production of Low-Cost, Effective, Anti-Malarial Drugs," *presented at Enzyme Engineering XIX*, Harrison Hot Springs, British Columbia, Canada, Sep. 23-28, 2007, 152 pages.

Keegan, R.M. et al. (2007). "Automated Search-Model Discovery and Preparation for Structure Solution by Molecular Replacement," *Acta Crystallographica* D63:447-457.

Keeler, K.H. et al. (1996). "Movement of Crop Transgenes into Wild Plants," Chapter 20 *in Herbicide Resistant Crops: Agricultural, Environmental, Economic, Regulatory, and Technical Aspects*, Duke, S.O. ed., Lewis Publishers: Boca Raton, FL., pp. 303-330.

Kelly, J.M. et al. (1985). "Transformation of *Aspergillus niger* by the *amdS* Gene of *Aspergillus nidulans*," *The EMBO Journal* 4(2):475-479.

Khan, M.S. et al. (Sep. 1999). "Fluorescent Antibiotic Resistance Marker for Tracking Plastid Transformation in Higher Plants," *Nature Biotechnology* 17:910-914.

Kieser, T. eds. et al. (Jul. 2000). "Introduction of DNA into *Streptomyces*," Chapter 10 *in Practical Streptomyces Genetics*, pp. 229-252.

Kisselev, L. (Jan. 2002). "Polypeptide Release Factors in Prokaryotes and Eukaryotes: Same Function, Different Structure," *Structure* 10:8-9.

Klein-Marcuschamer, D. et al. (2007, e-pub. Aug. 2, 2007). "Engineering Microbial Cell Factories for Biosynthesis of Isoprenoid Molecules: Beyond Lycopene," *TRENDS in Biotechnology* 25(9):417-424.

Klein-Marcuschamer, D. et al. (Feb. 19, 2008). "Assessing the Potential of Mutational Strategies to Elicit New Phenotypes in Industrial Strains," *PNAS* 105(7):2319-2324.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Köksal, M. et al. (2010, e-pub. Jul. 17, 2010). "Structure of Isoprene Synthase Illuminates the Chemical Mechanism of Teragram Atmospheric Carbon Emission," *J. Mol. Biol.* pp. 1-11.

Kooter, J. M., et al. (Sep. 1999). "Listening to the Silent Genes: Transgene Silencing, Gene Regulation and Pathogen Control," *Trends in Plant Science* 4(9):340-347.

Kota, M. et al. (Mar. 1999). "Overexpression of the *Bacillus thuringiensis* (Bt) Cry2Aa2 Protein in Chloroplasts Confers Resistance to Plants Against Susceptible and Bt-Resistant Insects," *Proc. Natl. Acad. Sci. USA* 96:1840-1845.

Kozak, M. (Oct. 25, 1991). "Structural Features in Eukaryotic mRNAs That Modulate the Initiation of Translation," *The Journal of Biological Chemistry* 266(30):19867-19870.

Kozak, M. (1999). "Initiation of Translation in Prokaryotes and Eukaryotes," *Gene* 234:187-208.

Kunkel, T. A. (Jan. 1985). "Rapid and Efficient Site-Specific Mutagenesis without Phenotypic Selection," *Proc. Natl. Acad. Sci. USA* 82:488-492.

Kuzma, J. et al. (1995). "Bacteria Produce the Volatile Hydrocarbon Isoprene," *Current Microbiology* 30:97-103.

Kuzuyama, T. et al. (1998). "Direct Formation of 2-C Methyl-D-Erythritol 4-Phosphate from 1-Deoxy-D-Xylulose 5-Phosphate by 1-Deoxy-D-Xylulose 5-Phosphate Reductoisomerase, a New Enzyme in the Non-Mevalonate Pathway to Isopentenyl Diphosphate," *Tetrahedron Letters* 39:4509-4512.

Kuzuyama, T. et al. (1998). "Fosmidomycin, a Specific Inhibitor of 1-Deoxy-D-Xylulose 5-Phosphate Reductoisomerase in the Nonmevalonate Pathway for Terpenoid Biosynthesis," *Tetrahedron Letters* 39:7913-7916.

Lange, B.M. et al. (Nov. 23, 1999). "Isopentenyl Diphosphate Biosynthesis Via a Mevalonate-Independent Pathway: Isopentenyl Monophosphate Kinase Catalyzes the Terminal Enzymatic Step," *PNAS* 96(24):13714-13719.

Lange, B.M. et al. (Sep. 2001). "Isoprenoid Biosynthesis. Metabolite Profiling of Peppermint Oil Gland Secretory Cells and Application to Herbicide Target Analysis," *Plant Physiology* 127:305-314.

Law, C.K. (1984). "Heat and Mass Transfer in Combustion: Fundamental Concepts and Analytical Techniques," *Progress in Energy and Combustion Science* 10:295-318.

Lehning, A. et al. (1999). "Isoprene Synthase Activity and Its Relation to Isoprene Emission in *Quercus robur* L. Leaves," *Plant, Cell and Environment* 22:495-504.

Lerner, C.G. et al. (1990). "Low Copy Number Plasmids for Regulated Low-Level Expression of Cloned Genes in *Escherichia coli* with Blue/White Insert Screening Capability," *Nucleic Acids Research* 18(15):4631.

Li, W. et al. (2010, e-pub. Nov. 1, 2009). "Non-Redundant Patent Sequence Databases with Value-Added Annotations at Two Levels," *Nucleic Acids Research* 38:D52-D56.

Lichtenthaler, H.K. et al. (1997). "Biosynthesis of Isoprenoids in Higher Plant Chloroplasts Proceeds Via a Mevalonate-Independent Pathway," *FEBS Letters* 400:271-274.

Lichtenthaler, H.K. (1999). "The 1-Deoxy-D-Xylulose-5-Phosphate Pathway of Isoprenoid Biosynthesis in Plants," *Annu. Rev. Plant Physiol. Plant Mol. Biol.* 50:47-65.

Lin, X.-M. et al. (2008, e-pub. Apr. 26, 2008). "Proteomic Analysis of Nalidixic Acid Resistance in *Escherichia coli*: Identification and Functional Characterization of OM Proteins," *Journal of Proteome Research* pp. A-G.

Lluch, M.A. et al. (2000). "Molecular Cloning and Expression Analysis of the Mevalonate Kinase Gene from *Arabidopsis thaliana*," *Plant Molecular Biology* 42:365-376.

Lois, L.M. et al. (Mar. 1998). "Cloning and Characterization of a Gene from *Escherichia coli* Encoding a Transketolase-Like Enzyme that Catalyzes the Synthesis of D-1-Deoxyxylulose 5-Phosphate, a Common Precursor for Isoprenoid, Thiamin, and Pyridoxol Biosynthesis," *Proc. Natl. Acad. Sci. USA* 95:2105-2110.

Loivamäki, M. et al. (Jun. 2007). "Arabidopsis, A Model to Study Biological Functions of Isoprene Emission?" *Plant Physiology* 144:1066-1078.

Lommel, S.A. et al. (1991). "Identification of the Maize Chlorotic Mottle Virus Capsid Protein Cistron and Characterization of its Subgenomic Messenger RNA," *Virology* 181:382-385.

Lücker, J. et al. (2002). "Monoterpene Biosynthesis in Lemon (*Citrus Limon*). cDNA Isolation and Functional Analysis of Four Monoterpene Synthases," *European Journal of Biochemistry* 269:3160-3171.

Luli, G.W. et al. (Apr. 1990). "Comparison of Growth, Acetate Production, and Acetate Inhibition of *Escherichia coli* in Batch and Fed-Batch Fermentations," *Applied and Environmental Microbiology* 56(4):1004-1011.

(56) References Cited

OTHER PUBLICATIONS

Lüttgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-D-Erythritol," *PNAS* 97(3):1062-1067.
Macejak, D.G. et al. (Sep. 5, 1991). "Internal Initiation of Translation Mediated by the 5' Leader of a Cellular mRNA," *Nature* 353:90-94.
Mahmoud, S.S. et al. (Jul. 17, 2001). "Metabolic Engineering of Essential Oil Yield and Composition in Mint by Altering Expression of Deoxyxylulose Phosphate Reductoisomerase and Menthofuran Synthase," *PNAS* 98(15):8915-8920.
Maldonado-Mendoza, I.E. et al. (Jul. 1997). "Molecular Characterization of Three Differentially Expressed Members of the *Camptotheca acuminata* 3-Hydroxy-3-Methylglutaryl CoA Reductase (HMGR) Gene Family," *Plant Molecular Biology* 34(5):781-790.
Mann, V. et al. (Aug. 2000). "Metabolic Engineering of Astaxanthin Production in Tobacco Flowers," *Nature Biotechnology* 18:888-892.
Martin, V.J.J. et al. (Dec. 5, 2001). "The In Vivo Synthesis of Plant Sesquiterpenes by *Escherichia coli*," *Biotechnology and Bioengineering* 75(5):497-503.
Martin, V.J.J. et al. (Jul. 2003). "Engineering a Mevalonate Pathway in *Escherichia coli* for Production of Terpenoids," *Nature Biotechnology* 21(7):796-802.
Martin, W. et al. (May 14, 1998). "Gene Transfer to the Nucleus and the Evolution of Chloroplasts," *Nature* 393:162-165.
Mashego, M.R. et al. (2007, e-pub. Nov. 8, 2006). "Microbial Metabolomics: Past, Present and Future Methodologies," *Biotechnol. Lett.* 29:1-16.
Matsuoka, S. et al. (Feb. 25, 1991). "Variable Product Specificity of Microsomal Dehydrodolichyl Diphosphate Synthase from Rat Liver," *The Journal of Biological Chemistry* 266(6):3464-3468.
Matteucci, M.D. et al. (1981). "Synthesis of Deoxyoligonucleotides on a Polymer Support," *J. American Chemical Society* 103(11):3185-3191.
Matthews, P.D. et al. (2000). "Metabolic Engineering of Carotenoid Accumulation in *Escherichia coli* by Modulation of the Isoprenoid Precursor Pool with Expression of Deoxyxylulose Phosphate Synthase," *Appl. Microbiol. Biotechnol.* 53:396-400.
Maury, J. et al. (2005, e-pub. Jul. 5, 2005). "Microbial Isoprenoid Production: An Example of Green Chemistry through Metabolic Engineering," *Adv. Biochem. Engin/Biotechnol.* 100:19-51.
McPherson, A. (2004). "Introduction to Protein Crystallization," *Methods* 34:254-265.
Meile, L. et al. (May 2001). "Characterization of the D-Xylulose 5-Phosphate/D-Fructose 6-Phosphate Phosphoketolase Gene (*xfp*) from *Bifidobacterium lactis*," *Journal of Bacteriology* 183(9):2929-2936.
Meinkoth, J. et al. (1984). "Hybridization of Nucleic Acids Immobilized on Solid Supports," *Analytical Biochemistry* 138:267-284.
Meyer, P. et al. (1996). "Homology-Dependent Gene Silencing in Plants," *Ann. Rev. Plant Physiol. Plant Mol. Biol.* 47:23-48.
Millen, R.S. et al. (Mar. 2001). "Many Parallel Losses of *infA* from Chloroplast DNA During Angiosperm Evolution with Multiple Independent Transfers to the Nucleus," *The Plant Cell* 13:645-658.
Miller, B. (2001). "Erstmalige Isolierung Eines Isoprenysthase-Gens and Heterologe Expression Des Aus Der Pappel Stammenden Gens Sowie Charakterisierung der Eingangsgene des Mevalonat-unabhangigen Isoprenoidbiosyntheseweges aus dem Cyanobakterium Synechococcus leopoliensis," located at <http://kups.ub.uni-koeln.de/883/>, last visited on Jun. 23, 2011, English Translation included, 2 pages.
Miller, B. et al. (2001, e-pub. May 10, 2001). "First Isolation of an Isoprene Synthase Gene from Poplar and Successful Expression of the Gene in *Escherichia coli*," *Planta* 213:483-487.
Miller, J., "High-Throughput Screening for Protein Engineering of Industrial Enzymes," published by Genencor on Jun. 5, 2009, Online document-retrieved on Apr. 17, 2012, XP002673697, 32 pages.

Milne, P.J. et al. (1995). "Measurement of Vertical Distribution of Isoprene in Surface Seawater, its Chemical Fate, and its Emission from Several Phytoplankton Monocultures," *Marine Chemistry* 48:237-244.
Mo, H. et al. (2004). "Studies of the Isoprenoid-Mediated Inhibition of Mevalonate Synthesis Applied to Cancer Chemotherapy and Chemoprevention," *Exp. Biol. Med.* 229:567-585.
Mogen, B.D. et al. (Dec. 1990). "Upstream Sequences Other than AAUAAA are Required for Efficient Messenger RNA 3'-End Formation in Plants," *The Plant Cell* 2:1261-1272.
Monson, R.K. et al. (1992). "Relationships Among Isoprene Emission Rate, Photosynthesis, and Isoprene Synthase Activity as Influenced by Temperature," *Plant Physiol.* 98:1175-1180.
Munroe, D. et al. (1990). "Tales of Poly(A): a Review," *Gene* 91:151-158.
Murray, E.E. et al. (1989). "Codon Usage In Plant Genes," *Nucleic Acids Research* 17(2): 477-498.
Nakamura, C.E. et al. (2003). "Metabolic Engineering for the Microbial Production of 1,3-Propanediol," *Current Opinion in Biotechnology* 14:454-459.
Nanchen, A. et al. (Apr. 2008, e-pub. Jan. 25, 2008). "Cyclic AMP-Dependent Catabolite Repression Is the Dominant Control Mechanism of Metabolic Fluxes Under Glucose Limitation in *Escherichia coli*," *Journal of Bacteriology* 190(7):2323-2330.
Nawrath, C. et al. (Dec. 1994). "Targeting of the Polyhydroxybutyrate Biosynthetic Pathway to the Plastids of *Arabidopsis thaliana* Results in High Levels of Polymer Accumulation," *Proc. Natl. Acad. Sci. USA* 91:12760-12764.
Needleman, S. B. et al. (1970). "A General Method Applicable to the Search for Similarities in the Amino Acid Sequence of Two Proteins," *J. Mol. Biol.* 48:443-453.
Neidhardt, F.C. et al. (Sep. 1974). "Culture Medium for Enterobacteria," *Journal of Bacteriology* 119(3):736-747.
Neidhardt, F.C. et al. (1990). "Table 1. Overall Macromolecular Composition of an Average *E. coli* B/r Cell$^a$," Chapter 1 in *Physiology of the Bacterial Cell: A Molecular Approach*, Sinauer Associates, Inc., Sunderland, MA, pp. 4.
Nevalainen, K.M.H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc., New York, NY, pp. 129-148.
Newman, J.D. et al. (Nov. 5, 2006, e-pub. Jul. 28, 2006). "High-Level Production of Amorpha-4,11-Diene in a Two-Phase Partitioning Bioreactor of Metabolically Engineered *Escherichia coli*," *Biotechnology and Bioengineering* 95(4):684-691.
Newman, T. et al. (1994). "Genes Galore: A Summary of Methods for Accessing Results from Large-Scale Partial Sequencing of Anonymous *Arabidopsis* cDNA Clones," *Plant Physiology* 106:1241-1255.
Nielsen, K.M. et al. (1997). "Analysis and Developmental Profile of Carotenoid Pigments in Petals of Three Yellow Petunia Cultivars," *Scientia Horticulturae* 71:257-266.
Niinemets, Ü. et al. (Nov. 2002). "Stomatal Constraints May Affect Emission of Oxygenated Monoterpenoids from the Foliage of *Pinus pinea*," *Plant Physiology* 130:1371-1385.
Noronha, S.B. et al. (May 5, 2000). "Investigation of the TCA Cycle and the Glyoxylate Shunt in *Escherichia coli* BL21 and JM109 Using $^{13}$C-NMR/MS," *Biotechnology and Bioengineering* 68(3):316-327.
Nunberg, J.H. et al. (Nov. 1984). "Molecular Cloning and Characterization of the Glucoamylase Gene of *Aspergillus awamori*," *Mol. Cell. Biol.* 4(11):2306-2315.
Oh, M.-K. et al. (Apr. 12, 2002). "Global Expression Profiling of Acetate-Grown *Escherichia coli*," *The Journal of Biological Chemistry* 277(15):13175-13183.
Okamura, E. et al. (Jun. 22, 2010). "Unprecedented Acetoacetyl-coenzyme a Synthesizing Enzyme of the Thiolase Superfamily Involved in the Mevalonate Pathway," *PNAS* 107(25):11265-11270.
Ondrey, G. et al. (Oct. 2008). "Bio-Based Isoprene," *Chemical Engineering, Access Intelligence Association*, Rockville, MA, 115(1):14.
Oulmouden, A. et al. (1991). "Nucleotide Sequence of the *ERG12* Gene of *Saccharomyces cerevisiae* Encoding Mevalonate Kinase," *Curr. Genet.* 19:9-14.

(56) References Cited

OTHER PUBLICATIONS

Pachuk, C.J. et al. (2000). "Chain Reaction Cloning: A One-Step Method for Directional Ligation of Multiple DNA Fragments," *Gene* 243:19-25.

Pearson, W.R. et al. (Apr. 1988). "Improved Tools for Biological Sequence Comparison," *Proc. Natl. Acad. Sci. USA* 85:2444-2448.

Pegg, S.C.-H. et al. (2006). "Leveraging Enzyme Structure-Function Relationships for Functional Inference and Experimental Design: The Structure-Function Linkage Database," *Biochemistry* 45:2545-2555.

Penttila, M. et al. (1987). "A Versatile Transformation System for the Cellulolytic Filamentous Fungus *Trichoderma reesei*," *Gene* 61:155-164.

Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology: Washington, D.C., pp. 615-624.

Phan, R.M. et al. (2001, e-pub. Sep. 13, 2001). "Synthesis of (*S*)-Isoprenoid Thiodiphosphates as Substrates and Inhibitors," *J. Org. Chem.* 66(20):6705-6710.

Phillips, T.A. et al. (Jul. 1984). "*Ion* Gene Product of *Escherichia coli* Is a Heat-Shock Protein," *Journal of Bacteriology* 159(1):283-287.

Phue, J.-N. et al. (2004). "Transcription Levels of Key Metabolic Genes are the Cause for Different Glucose Utilization Pathways in *E. coli* B (BL21) and *E. coli* K (JM109)," *Journal of Biotechnology* 109:21-30.

Phue, J.-N. et al. (2005, e-pub. Aug. 11, 2005). "Impact of Dissolved Oxygen Concentration on Acetate Accumulation and Physiology of *E. coli* BL21, Evaluating Transcription Levels of Key Genes at Different Dissolved Oxygen Conditions," *Metabolic Engineering* 7:353-363.

Pilloff, D. et al. (Feb. 14, 2003). "The Kinetic Mechanism of Phosphomevalonate Kinase," *The Journal of Biological Chemistry* 278(7):4510-4515.

Pitera, D.J. et al. (2007, e-pub. Nov. 23, 2006). "Balancing a Heterologous Mevalonate Pathway for Improved Isoprenoid Production in *Escherichia coli*," *Metabolic Engineering* 9:193-207.

Pommer, H. et al. (1975). "Industrial Synthesis of Terpene Compounds," *Pure and Applied Chemistry* 43(3-4):527-551.

Potter, D. et al. (Oct. 10, 1997). "Identification of Catalytic Residues in Human Mevalonate Kinase," *The Journal of Biological Chemistry* 272(41):25449-25454.

Pourquié, J. et al. (1988). "Scale Up of Cellulase Production and Utilization," in *Biochemistry and Genetics of Cellulose Degradation*, Aubert, J.-P. et al. eds., Academic Press: San Diego, CA, pp. 71-86.

Proudfoot, N. (Feb. 22, 1991). "Poly(A) Signals," *Cell* 64:671-674.

Ramos-Valdivia, A.C. et al. (1997). "Isopentenyl Diphosphate Isomerase: A Core Enzyme in Isoprenoid Biosynthesis: A Review of its Biochemistry and Function," *Natural Product Reports* 6:591-603.

Raschke, M. et al. (2004, e-pub. Oct. 28, 2004). "A High-Performance Liquid Chromatography Methods for the Analysis of Intermediates of the Deoxyxylulose Phosphate Pathway," *Analytical Biochemistry* 335:235-243.

Re, E.B. et al. (1995). "Co-Expression of Native and Introduced Genes Reveals Cryptic Regulation of HMG CoA Reductase Expression in *Arabidopsis*," *The Plant Journal* 7(5):771-784.

Reiling, K.K. et al. (Jul. 20, 2004, e-pub. Jun. 18, 2004). "Mono and Diterpene Production in *Escherichia coli*," *Biotechnology and Bioengineering* 87(2):200-212.

Rodríguez-Concepción, M. et al. (2000). "Genetic Evidence of Branching in the Isoprenoid Pathway for the Production of Isopentenyl Diphosphate and Dimethylallyl Diphosphate in *Escherichia coli*," *FEBS Letters* 473:328-332.

Rodríguez-Concepción, M. et al. (Nov. 2002). "Elucidation of the Methylerythritol Phosphate Pathway for Isoprenoid Biosynthesis in Bacteria and Plastids. A Metabolic Milestone Achieved Through Genomics," *Plant Physiology* 130:1079-1089.

Rodríguez-Villalón, A. et al. (2008). "Carotenoid Accumulation in Bacteria with Enhanced Supply of Isoprenoid Precursors by Upregulation of Exogenous or Endogenous Pathways," *Journal of Biotechnology* 135:78-84.

Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-*C*-Methylerythritol," *PNAS* 96(21):11758-11763.

Rohdich, F. et al. (Jun. 6, 2000). "Biosynthesis of Terpenoids: 4-Diphosphocytidyl-2C-Methyl-D-Erythritol Synthase of *Arabidopsis thaliana*," *PNAS* 97(12):6451-6456.

Rohmer, M. (1998). "Isoprenoid Biosynthesis Via the Mevalonate-Independent Route, a Novel Target for Antibacterial Drugs?" *Progress in Drug Research* 50:137-154.

Röhrich, R.C. et al. (2005, e-pub. Nov. 2, 2005). "Reconstitution of an Apicoplast-Localised Electron Transfer Pathway Involved in the Isoprenoid Biosynthesis of *Plasmodium falciparum*," *FEBS Letters* 579:6433-6438.

Rondon, M.R. et al. (May 1999). "Toward Functional Genomics in Bacteria: Analysis of Gene Expression in *Escherichia coli* from a Bacterial Artificial Chromosome Library of *Bacillus cereus*," *Proc. Natl. Acad. Sci. USA* 96:6451-6455.

Rosenfeld, J. et al. (1992). "In-Gel Digestion of Proteins for Internal Sequence Analysis After One- or Two-Dimensional Gel Electrophoresis," *Analytical Biochemistry* 203:173-179.

Rost, B. et al. (2004). "The PredictProtein Server," *Nucleic Acids Research* 32:W321-W326.

Sánchez, C. et al. (Apr. 2002). "The Biosynthetic Gene Cluster for the Antitumor Rebeccamycin: Characterization and Generation of Indolocarbazole Derivatives," *Chemistry and Biology* 9(4):519-531.

Sander, R. (Apr. 8, 1999). *Compilation of Henry's Law Constants for Inorganic and Organic Species of Potential Importance in Environmental Chemistry*, 3:1-107.

Sanfaçon, H. et al. (1991). "A Dissection of the Cauliflower Mosaic Virus Polyadenylation Signal," *Genes & Development* 5:141-149.

Sasaki, K. et al. (2005, e-pub. Apr. 7, 2005). "Gene Expression and Characterization of Isoprene Synthase from *Populus alba*," *FEBS Letters* 579:2514-2518.

Schneider, D. et al. (Jul. 9, 2002). "Genomic Comparisons Among *Escherichia coli* Strains B, K-12, and O157:H7 Using Is Elements as Molecular Markers," *BMC Microbiology* 2:18, 8 pages.

Schnitzler, J.-P. et al. (2005, e-pub. Jul. 29, 2005). "Biochemical Properties of Isoprene Synthase in Poplar (*Populus x canescens*)," *Planta* 222(5):777-786.

Schöller, C. et al. (1997). "Volatile Metabolites from Some Gram-Negative Bacteria," *Chemosphere* 35(7):1487-1495.

Scott, E. et al. (2007, e-pub. Mar. 27, 2007). "Biomass in the Manufacture of Industrial Products—The Use of Proteins and Amino Acids," *Appl. Microbiol. Biotechnol.* 75:751-762.

Sen, S. et al. (2007). "Developments in Directed Evolution for Improving Enzyme Functions," *Appl. Biochem. Biotechnol.* 143:212-223.

Serino, G. et al. (1997). "A Negative Selection Scheme Based on the Expression of Cytosine Deaminase in Plastids," *The Plant Journal* 12(3):697-701.

Sharkey, T.D. et al. (Feb. 1, 2005). "Supplemental data for: Evolution of the Isoprene Biosynthetic Pathway in Kudzu," *Plant Physiology* 137(2):700-712.

Sharkey, T.D. et al. (Feb. 2005). "Evolution of the Isoprene Biosynthetic Pathway in Kudzu," *Plant Physiology* 137:700-712.

Sheir-Neiss, G. et al. (Jul. 1984). "Characterization of the Secreted Cellulases of *Trichoderma reesei* Wild Type and Mutants During Controlled Fermentations," *Appl. Microbiol. Biotechnol.* 20(1):46-53.

Shelton, D. et al. (2004, e-pub. Nov. 26, 2004). "Isolation and Partial Characterization of a Putative Monoterpene Synthase from *Melaleuca alternifolia*," *Plant Physiology and Biochemistry* 42:875-882.

Shinozaki, K. et al. (1986). "The Complete Nucleotide Sequence of the Tobacco Chloroplast Genome: its Gene Organization and Expression," *The EMBO Journal* 5(9):2043-2049.

(56) References Cited

OTHER PUBLICATIONS

Shirk, M.C. et al. (2002, e-pub. Jul. 27, 2002). "Isoprene Formation in *Bacillus subtilis*: A Barometer of Central Carbon Assimilation in a Bioreactor?" *Biotechnol. Prog.* 18(5):1109-1115.
Silver, G.M. et al. (1991). "Enzymatic Synthesis of Isoprene from Dimethylallyl Diphosphate in Aspen Leaf Extracts," *Plant Physiol.* 97:1588-1591.
Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.
Sivy, T.L. et al. (2002). "Isoprene Synthase Activity Parallels Fluctuations of Isoprene Release During Growth of *Bacillus subtilis*," *Biochemical and Biophysical Research Communications* 294:71-75.
Siwko, M.E. et al. (2007, e-pub. Oct. 4, 2006). "Does Isoprene Protect Plant Membranes from Thermal Shock? A Molecular Dynamics Study," *Biochimica et Biophysica Acta* 1768:198-206.
Slabinski, L. et al. (2007). "The Challenge of Protein Structure Determination—Lessons from Structural Genomics," *Protein Science* 16:2472-2482.
Slater, S. et al. (Apr. 1992). "Production of Poly-(3-Hydroxybutyrate-Co-3-Hydroxyvalerate) in a Recombinant *Escherichia coli* Strain," *Applied and Environmental Microbiology* 58(4):1089-1094.
Slater, S. et al. (Oct. 1999). "Metabolic Engineering of *Arabidopsis* and *Brassica* for Poly(3-Hydroxybutyrate-*co*-3-Hydroxyvalerate) Copolymer Production," *Nature Biotechnology* 17:1011-1016.
Smit, A. et al. (2000). "Biosynthesis of Isoprenoids Via Mevalonate in Archaea: The Lost Pathway," *Genome Research* 10:1468-1484.
Smith, T.F. et al. (1981). "Comparison of Biosequences," *Advances in Applied Mathematics* 2:482-489.
Sprenger, G.A. et al. (Nov. 1997). "Identification of a Thiamin-Dependent Synthase in *Escherichia coli* Required for the Formation of the 1-Deoxy-D-Xylulose 5-Phosphate Precursor to Isoprenoids, Thiamin, and Pyridoxol,"*Proc. Natl. Acad. Sci. USA* 94:12857-12862.
Starks, C.M. et al. (Sep. 19, 1997). "Structural Basis for Cyclic Terpene Biosynthesis by Tobacco 5-Epi-Aristolochene Synthase," *Science* 277:1815-1820.
Staub, J. M. et al. (1995). "Expression of a Chimeric *uidA* Gene Indicates that Polycistronic mRNAs are Efficiently Translated in Tobacco Plastids," *The Plant Journal* 7(5):845-848.
Staub, J. M. et al. (Mar. 2000). "High-Yield Production of a Human Therapeutic Protein in Tobacco Chloroplast," *Nature Biotechnology* 18:333-338.
Steinbüchel, A. (2003). "Production of Rubber-Like Polymers by Microorganisms," *Current Opinion in Microbiology* 6:261-270.
Steller, I. et al. (1997). "An Algorithm for Automatic Indexing of Oscillation Images using Fourier Analysis," *Journal of Applied Crystallography* 30:1036.1040.
Stermer, B.A. et al. (1994). "Regulation of HMG-CoA Reductase Activity in Plants," *Journal of Lipid Research* 35:1133-1140.
Stevens, D.R. et al. (1997). "Genetic Engineering of Eukaryotic Algae: Progress and Prospects," *J. Phycol.* 33:713-722.
Sulter, G.J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.
Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *Journal of Bacteriology* 184(15):4065-4070.
Takagi, M. et al. (Aug. 2000). "A Gene Cluster for the Mevalonate Pathway from *Streptomyces* sp. Strain CL190," *Journal of Bacteriology* 182(15):4153-4157.
Takahashi, S. et al. (Feb. 1999). "Purification, Characterization, and Cloning of a Eubacterial 3-Hydroxy-3-Methylglutaryl Coenzyme A Reductase, a Key Enzyme Involved in Biosynthesis of Terpenoids," *Journal of Bacteriology* 181(4):1256-1263.

Takara Bio Inc. (Feb. 2008). "Chaperon Plasmid Set," Cat. # 3340, pp. 1-8.
Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.
Thomas, F. et al. (1988). "Expression of the *rp123*, *rp12* and *rps19* Genes in Spinach Chloroplasts," *Nucleic Acids Research* 16(6):2461-2472.
Thomason, L.C. et al. (2007, e-pub. Apr. 16, 2007). "Multicopy Plasmid Modification with Phage λ Red Recombineering," *Plasmid* 58:148-158.
Thouvenot, B. et al. (2004). "The Strong Efficiency of the *Escherichia coli gapA* P1 Promoter Depends on a Complex Combination of Functional Determinants," *Biochem. J.* 383:371-382.
Timberlake, W.E. (1991). "Cloning and Analysis of Fungal Genes," Chapter 3 *in More Gene Manipulations in Fungi*, Bennett, J.W. et al. eds., Academic Press, San Diego, CA, pp. 70-76.
Tokuriki, N. et al. (2009, e-pub. Sep. 16, 2009). "Stability Effects of Mutations and Protein Evolvability," *Current Opinion in Structural Biology* 19(5):596-604.
Toriyama, K. et al. (1985). "Cell Suspension and Protoplast Culture in Rice," *Plant Science* 41:179-183.
Tsay, Y.H. et al. (Feb. 1991). "Cloning and Characterization of *ERG8*, an Essential Gene of *Saccharomyces cerevisiae* That Encodes Phosphomevalonate Kinase," *Molecular and Cellular Biology* 11(2):620-631.
Tsudsuki, T. (Apr. 27, 1998) "Direct submission, bases 1-155939", *Data Processing Center*, Submitted Feb. 27, 1998, Aichi-Gakuin University, Aichi, Japan, 12 pages.
UniProt Database Accession No. A2XGY9, last updated Jul. 27, 2011, located at <http://www.uniprot.org/jobs/201109112CDIG8GYZL.txt>, last visited on Sep. 11, 2011, 2 pages.
UniProt Database Accession No. A5AR04, last updated Jul. 27, 2011, located at <http://www.uniprot.org./jobs/20110911315BAWWKZ7.txt>, last visited on Sep. 11, 2011, 1 page.
UniProt Database Accession No. A5AV19, last updated on Oct. 16, 2013, located at http://www.uniprot.org/uniprot/A5AV19, last visited on Oct. 29, 2013, 3 pages.
UniProt Database Accession No. A5B7V4, last updated Jul. 27, 2011, located at <http://www.uniprot.org/jobs/2011091150O6CWCI3L.txt>, last visited on Sep. 11, 2011, 1 page.
UniProt Database Accession No. A5BKK1, last updated Jul. 27, 2011, located at <http://www.uniprot.org/jobs/20110911315BB1QWK6.txt>, last visited on Sep. 11, 2011, 1 page.
UniProt Database Accession No. A5BLS5, last updated Jul. 27, 2011, located at <http://www.uniprot.org/jobs/201109112CDIFUU28L.txt>, last visited on Sep. 11, 2011, 1 page.
UniProt Database Accession No. A7IZZ1, last updated on Oct. 16, 2013, located at http://www.uniprot.org/uniprot/A7IZZ1, last visited on Oct. 29, 2013, 5 pages.
UniProt Database Accession No. A9PGR5, last updated Jul. 27, 2011, located at <http://www.uniprot.org/jobs/201109112CDIFT06PL.txt>, last visited on Sep. 11, 2011, 1 pages.
UniProt Database Accession No. A9Q7C9, last updated on Oct. 16, 2013, located at http://www.uniprot.org/uniprot/A9Q7C9, last visited on Oct. 29, 2013, 3 pages.
UniProt Database Accession No. B1P189, last updated Jul. 27, 2011, located at <http://www.uniprot.org/jobs/201109112CDIFX17BK.txt>, last visited on Sep. 11, 2011, 1 page.
UniProt Database Accession No. B3GEM8, last updated Jul. 27, 2011, located at <http://www.uniprot.org/jobs/20110911315BAG9N17.txt>, last visited on Sep. 11, 2011, 1 page.
UniProt Database Accession No. B3TPQ7, "SubName: Full=Alpha-terpineol synthase." Retrieved from EBI accession No. UNIPROT:B3TPQ7 (Sep. 2, 2008), last updated on May 16, 2012, located at http://www.uniprot.org/uniprot/B3TPQ7, last visited on Jul. 23, 2012, 5 pages, (XP-002674045, XP-002674053).
UniProt Database Accession No. B6F137, last updated on Oct. 16, 2013, located at http://www.uniprot.org/uniprot/B6F137, last visited on Oct. 29, 2013, 3 pages.

(56) References Cited

OTHER PUBLICATIONS

UniProt Database Accession No. B7FLI6, last updated Jul. 27, 2011, located at <http://www.uniprot.org/jobs/20110911315BAXCRQU.txt>, last visited on Sep. 11, 2011, 1 page.
UniProt Database Accession No. B9HE95, last updated Jul. 27, 2011, located at <http://www.uniprot.org/jobs/201109112CDIFY9X6U.txt>, last visited on Sep. 11, 2011, 2 pages.
UniProt Database Accession No. B9MXU1, last updated Jul. 27, 2011, located at < http://www.uniprot.org/jobs/201109112CDIFV8DIC.txt>, last visited on Sep. 11, 2011, 2 pages.
UniProt Database Accession No. B9PAP5, last updated Jul. 27, 2011, located at <http://www.uniprot.org/jobs/201109112CDIG1HNFH.txt>, last visited on Sep. 11, 2011, 2 pages.
UniProt Database Accession No. B9RPM0, "SubName: Full=(R)-limonene synthase." Retrieved from EBI accession No. UNIPROT:B9RPM0 (Mar. 24, 2009), last updated on May 16, 2012, located at http://www.uniprot.org/uniprot/B9RPM0, last visited on Jul. 23, 2012, 3 pages.
UniProt Database Accession No. B9T537, last updated Nov. 30, 2010, located at <http://www.uniprotorg/jobs/20110911315BB065GR.txt>, last visited on Sep. 11, 2011, 1 pages.
UniProt Database Accession No. B9T825, last updated Jul. 27, 2011, located at <http://www.uniprot.org/jobs/20110911315BALANC9.txt>, last visited on Sep. 11, 2011, 1 page.
UniProt Database Accession No. D7LHH0, last updated on Oct. 16, 2013, located at http://www.uniprot.org/uniprot/D7LHH0, last visited on Oct. 29, 2013, 4 pages.
UniProt Database Accession No. G1JUH1, last updated on Oct. 16, 2013, located at http://www.uniprot.org/uniprot/G1JUH1, last visited on Oct. 29, 2013, 5 pages.
UniProt Database Accession No. Q0PCI3, last updated Jul. 27, 2011, located at <http://www.uniprot.org/jobs/20110911315BAPL92C.txt>, last visited on Sep. 11, 2011, 1 page.
UniProt Database Accession No. Q0PCI4, last updated Jul. 27, 2011, located at <http://www.uniprot.org/jobs/20110911315BAQURQ8.txt>, last visited on Sep. 11, 2011, 1 page.
UniProt Database Accession No. Q50L36, last updated May 31, 2011, located at <http://www.uniprot.org/jobs/201109112CDIGBF1M4.txt>, last visited on Sep. 11, 2011, 2 pages.
UniProt Database Accession No. Q5SBP1, last updated Apr. 5, 2011, located at < http://www.uniprot.org/jobs/201109112CDIGFFR1Q.txt>, last visited on Sep. 11, 2011, 2 pages.
UniProt Database Accession No. Q5SBP2, last updated Apr. 5, 2011, located at <http://www.uniprot.org/jobs/201109112CDIG4W1U8.txt>, last visited on Sep. 11, 2011, 2 pages.
UniProt Database Accession No. Q5SBP4, last updated Jul. 27, 2011, located at <http://www.uniprot.org/jobs/20110914OO0OYGHJF.txt>, last visited on Sep. 11, 2011, 2 pages.
UniProt Database Accession No. Q5UB07, last updated Jul. 27, 2011, located at <http://www.uniprot.org/jobs/201109112CDIFZCWUC.txt>, last visited on Sep. 11, 2011, 1 page.
UniProt Database Accession No. Q672F7, last updated Jul. 27, 2011, located at <http://www.uniprot.org/jobs/201109112CDIFWBP6O.txt >, last visited on Sep. 11, 2011, 1 page.
UniProt Database Accession No. Q6EJ97, last updated Apr. 5, 2011, located at <http://www.uniprot.org/jobs/20110911315BARZM8D.txt>, last visited on Sep. 11, 2011, 2 pages.
UniProt Database Accession No. Q6PWU1, "SubName: Full=(-)-a-terpineol synthase." Retrieved from EBI accession No. UNIPROT:Q6PWU1 (Jul. 5, 2004), last updated on Jul. 11, 2012, located at http://www.uniprot.org/uniprot/Q6PWU1, last visited on Jul. 23, 2012, 4 pages.
UniProt Database Accession No. Q7Y1V1, last updated Jul. 27, 2011, located at <http://www.uniprot.org/jobs/201109112CDIG0LK2O.txt>, last visited on Sep. 11, 2011, 1 page.
UniProt Database Accession No. Q8L5K1, last updated on Oct. 16, 2013, located at http://www.uniprot.org/uniprot/Q8L5K1, last visited on Oct. 29, 2013, 3 pages.

UniProt Database Accession No. Q93X23, last updated on Oct. 16, 2013, located at http://www.uniprot.org/uniprot/Q93X23, last visited on Oct. 29, 2013, 5 pages.
UniProt Database Accession No. Q941H1, last updated Jul. 27, 2011, located at <http://www.uniprot.org/jobs/201109112CDIG6PW6Y.txt>, last visited on Sep. 11, 2011, 1 page.
UniProt Database Accession No. Q9AR86, last updated May 31, 2011, located at <http://www.uniprot.org/jobs/201109114OO0P1KMN7.txt>, last visited on Sep. 11, 2011, 2 pages.
UniProt Database Accession No. Q9LIA1; Q84UU7, last updated Jul. 27, 2011, located at <http://www.uniprot.org/jobs/20110911315BB4RI8G.txt>, last visited on Sep. 11, 2011, 3 pages.
UniProt Database Accession No. Q9LRZ6, "RecName: Full=Beta-myrcene/(E)-beta-ocimene synthase 2, chloroplastic; EC=4.2.3.15; AltName: Full=Terpenoid synthase 24; Short=AtTpS24; Flags: Precursor." Retrieved from EBI accession No. UNIPROT:Q9LRZ6 (Oct. 1, 2000); last updated on Jul. 11, 2012, located at http://www.uniprot.org/uniprot/Q9LRZ6, last visited on Jul. 23, 2012, 8 pages.
UniProt Database Accession No. Q7XAS7, last updated Apr. 5, 2011, located at <http://www.uniprot.org/jobs/201109112CDIGCK99G.txt>, last visited on Sep. 11, 2011, 2 pages.
UniProt Database Accession No. Q9FQ26, last updated Jul. 27, 2011, located at <http://www.uniprot.org/jobs/20110911315BB3SH2Y.txt>, last visited on Sep. 11, 2011, 1 page.
Vadali, R.V. et al. (2005, e-pub. Sep. 2, 2005). "Enhanced Lycopene Productivity by Manipulation of Carbon Flow to Isopentenyl Diphosphate in *Escherichia coli*," *Biotechnol. Prog.* 21(5):1558-1561.
Vagin, A. et al. (1997). "*MOLREP*: An Automated Program for Molecular Replacement," *Journal of Applied Crystallography* 30:1022-1025.
Vandamme, E.J. et al. (2002, e-pub. 2002). "Bioflavours and Fragrances Via Fermentation and Biocatalysis," *Journal of Chemical Technology and Biotechnology* 77:1323-1332.
Van Den Hondel, C.A.M.J.J. et al. (1991). "Heterologous Gene Expression in Filamentous Fingi," Chapter 18 *in More Gene Manipulations in Fungi*, Bennett, J.W. et al. eds., Academic Press, Inc.: San Diego, CA, pp. 396-428.
Van De Walle, M. et al. (Jan. 5, 1998). "Proposed Mechanism of Acetate Accumulation in Two Recombinant *Escherichia coli* Strains During High Density Fermentation," *Biotechnology and Bioengineering* 57(1):71-78.
Van Hylckama, J.E.T. et al. (Apr. 2000). "Characterization of the Gene Cluster Involved in Isoprene Metabolism in *Rhodococcus* sp. Strain AD45," *Journal of Bacteriology* 182(7):1956-1963.
Vane, L.M. (2005, e-pub. Apr. 21, 2005). "A Review of Pervaporation for Product Recovery from Biomass Fermentation Processes," *Journal of Chemical Technology and Biotechnology* 80:603-629.
Velikova, V. et al. (2005). "Consequences of Inhibition of Isoprene Synthesis in *Phragmites australis* Leaves Exposed to Elevated Temperatures," *Agriculture, Ecosystems & Environment* 106:209-217.
Vidal, M. et al. (2006, e-pub. Nov. 23, 2005). "Evaluation of Lower Flammability Limits of Fuel-Air-Diluent Mixtures Using Calculated Adiabatic Flame Temperatures," *Journal of Hazardous Materials* 130:21-27.
Voss, S. et al. (1997). "Mutagenesis of a Flexible Loop in Streptavidin Leads to Higher Affinity for the *Strep*-tag II Peptide and Improved Performance in Recombinant Protein Purification," *Protein Engineering* 10(8):975-982.
Voynova, N.E. et al. (Jan. 2004). "*Staphylococcus aureus* Mevalonate Kinase: Isolation and Characterization of an Enzyme of the Isoprenoid Biosynthetic Pathway," *Journal of Bacteriology* 186(1):61-67.
Wagner, W.P. et al. (Aug. 1999). "Three Distinct Phases of Isoprene Formation During Growth and Sporulation of *Bacillus subtilis*," *Journal of Bacteriology* 181(15):4700-4703.
Wagner, W.P. et al. (Jan. 2000, e-pub. Nov. 18, 1999). "Isoprene Biosynthesis in *Bacillus subtilis* Via the Methylerythritol Phosphate Pathway," *J. Nat. Prod.* 63(1):37-40.
Wang, C.-W. et al. (Jan. 20, 1999). "Engineered Isoprenoid Pathway Enhances Astaxanthin Production in *Escherichia coli*," *Biotechnology and Bioengineering* 62(2):235-241.

(56) References Cited

OTHER PUBLICATIONS

Ward, M. et al. (Aug. 1993). "Use of *Aspergillus* Overproducing Mutants, Cured for Integrated Plasmid, to Overproduce Heterologous Proteins," *Appl. Microbiol. Biotechnol.* 39(6):738-743.

Weissermel, K. et al. (2003). *Industrial Organic Chemistry, 4th, Completely Revised Edition*, translated by Lindley, C.R. et al., Wiley-VCH GmbH & Co. KGaA, Weinheim, Germany, pp. 117-222.

Whisstock, J.C. et al. (2003). "Prediction of Protein Function from Protein Sequence and Structure," *Quarterly Reviews of Biophysics* 36(3):307-340.

Whittington, D.A. et al. (Nov. 26, 2002). "Bornyl Diphosphate Synthase: Structure and Strategy for Carbocation Manipulation by a Terpenoid Cyclase," *PNAS* 99(24):15375-15380.

Wilde, R.J. et al. (1986). "Transcript Analysis of the Citrate Synthase and Succinate Dehydrogenase Genes of *Escherichia coli* K12," *Journal of General Microbiology* 132:3239-3251.

Wildermuth, M.C. et al. (1998). "Biochemical Characterization of Stromal and Thylakoid-Bound Isoforms of Isoprene Synthase in Willow Leaves," *Plant Physiology* 116:1111-1123.

Wilding, E.I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.

Wilkins, K. (1996). "Volatile Metabolites from Actinomycetes," *Chemosphere* 32(7):1427-1434.

Williams, D.C. et al. (1998). "Truncation of Limonene Synthase Preprotein Provides a Fully Active 'Pseudomature' Form of This Monoterpene Cyclase and Reveals the Function of the Amino-Terminal Arginine Pair," *Biochemistry* 37(35):12213-12220.

Wishart, M.J. et al. (Nov. 10, 1995). "A Single Mutation Converts a Novel Phosphotyrosine Binding Domain into a Dual-Specificity Phosphatase," *The Journal of Biological Chemistry* 270(45):26782-26785.

Withers, S.T. et al. (Oct. 2007, e-pub. Aug. 10, 2007). "Identification of Isopentenol Biosynthetic Genes from *Bacillus subtilis* by a Screening Method Based on Isoprenoid Precursor Toxicity," *Applied and Environmental Microbiology* 73(19):6277-6283.

Witkowski, A. et al. (1999, e-pub. Aug. 18, 1999). "Conversion of β-Ketoacyl Synthase to a Malonyl Decarboxylase by Replacement of the Active-Site Cysteine with Glutamine," *Biochemistry* 38(36):11643-11650.

Wolfertz, M. et al. (2003). "Biochemical Regulation of Isoprene Emission," *Plant, Cell and Environment* 26:1357-1364.

Wolfertz, M. et al. (Aug. 2004). "Rapid Regulation of the Methylerythritol 4-Phosphate Pathway During Isoprene Synthesis," *Plant Physiology* 135:1939-1945.

Wu, D.Y. et al. (1989). "The Ligation Amplification Reaction (LAR)-Amplification of Specific DNA Sequences Using Sequential Rounds of Template-Dependent Ligation," *Genomics* 4:560-569.

Xia, X.-X. et al. (2008). "Comparison of the Extracellular Proteomes of *Escherichia coli* B and K-12 Strains During High Cell Density Cultivation," *Proteomics* 8:1-15.

Yamada, K. et al. (1989). "Production of Glycerol from Methanol by a Mutant Strain of *Candida boidinii* No. 2201," *Agric. Biol. Chem.* 53(2):541-543.

Yang, D. et al. (Mar. 15, 2002, published ahead of print Dec. 19, 2001). "Structure of the *Methanococcus jannaschii* Mevalonate Kinase, a Member of the GHMP Kinase Superfamily," *The Journal of Biological Chemistry* 277(11):9462-9467.

Ye, X. et al. (Jan. 14, 2000). "Engineering the Provitamin A (β-Carotene) Biosynthetic Pathway into (Carotenoid-Free) Rice Endosperm," *Science* 287:303-305.

Yelton, M.M. et al. (Mar. 1984). "Transformation of *Aspergillus nidulans* by Using a *trpC* Plasmid," *Proc. Natl. Acad. Sci. USA* 81:1470-1474.

Yoon, S.-H. et al. (2007, e-pub. May 15, 2007). "Increased β-Carotene Production in Recombinant *Escherichia coli* Harboring an Engineered Isoprenoid Precursor Pathway with Mevalonate Addition," *Biotechnol. Prog.* 23(3):599-605.

Yoon, S.-H. et al. (2009). "Combinatorial Expression of Bacterial Whole Mevalonate Pathway for the Production of β-Carotene in *E. coli*," *Journal of Biotechnology* 140:218-226.

Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.

International Search Report mailed on Jul. 24, 2012, for PCT Patent Application No. PCT/US2011/058188, filed on Oct. 27, 2011, ten pages.

Baldwin, S.A. et. al. (1978). "Novel Kinetic and Structural Properties of the Class-I D-Fructose 1,6-Bisphosphate Aldolase from *Escherichia coli* (Crookes' Strain)," *Biochem. J.* 169(3):643-652.

Berka, R.M. et al. (1989). "The Development of Gene Expression Systems for Filamentous Fungi," *Biotechnology Advances* 7(2):127-154.

Bhayana, V. et al. (1984). "Amino Acid Sequence of *Escherichia coli* Citrate Synthase," *Biochemistry* 23:2900-2905 (Figure 5).

Bologna, F.P. et al. (Aug. 2007). "*Escherichia coli* Malic Enzymes: Two Isoforms with Substantial Differences in Kinetic Properties, Metabolic Regulation, and Structure," *Journal of Bacteriology* 189(16):5937-5946.

Bologna, F.P. et al. (2010). "Characterization of *Escherichia coli* EutD: a Phosphotransacetylase of the Ethanolamine Operon," *The Journal of Microbiology* 48(5):629-636.

Branlant, G. et al. (1985). "Nucleotide Sequence of the *Escherichia coli* Gap Gene. Different evolutionary behavior of the $NAD^+$-binding domain and of the catalytic domain of D-glyceraldehyde-3-phosphate dehydrogenase," *Eur. J. Biochem.* 150:61-66.

Bunch, P.K. et al. (1997). "The *IdhA* Gene Encoding The Fermentative Lactate Dehydrogenase of *Escherichia coli*," *Microbiology* 143:187-195.

Dawes, E.A. et al. (1966). "The Route to Ethanol Formation in *Zymomonas mobilis*," *Biochem. J.* 98:795-803.

Duckworth, H.W. et al. (1987). "Structural Basis for Regulation in Gram-Negative Bacterial Citrate Synthases," *Biochem. Soc. Symp.* 54:83-92.

Egan, S.E. et al. (Jul. 1992). "Molecular Characterization of the Entner-Doudoroff Pathway in *Escherichia coli*: Sequence Analysis and Localization of Promoters for the *edd-eda* Operon," *Journal of Bacteriology* 174(14):4638-4646.

Fowler, Z.L. et. al. (Sep. 2009). "Increased Malonyl Coenzyme A Biosynthesis by Tuning the *Escherichia coli* Metabolic Network and Its Application to Flavanone Production," *Applied and Environmental Microbiology* 75(18):5831-5839.

GenBank Accession No. AB266390, last updated on Aug. 11, 2006, located at <http://www.ebi.ac.uk/ena/data/view/AB266390&display=text>, last visited on May 13, 2014, 2 pages.

GenBank Accession No. AB540131.1, last updated on Oct. 9, 2013, located at <http://www.ncbi.nlm.nih.gov/nuccore/299758081>, last visited on May 13, 2014, 2 pages.

GenBank Accession No. JN173037, created Jan. 19, 2012, last updated on Apr. 17, 2013, located at http://www.ebi.ac.uk/ena/data/view/JN173037&display=text, last visited on May 13, 2014, 2 pages.

GenBank Accession No. JN173038, created Jan. 19, 2012, last updated on Apr. 17, 2013, located at http://www.ebi.ac.uk/ena/data/view/JN173038&display=text, last visited on May 13, 2014, 2 pages.

GenBank Accession No. JN173039, created Jan. 19, 2012, last updated on Apr. 17, 2013, located at http://www.ebi.ac.uk/ena/data/view/JN173039&display=text, last visited on May 13, 2014, 2 pages.

GenBank Accession No. JN173040, created Jan. 19, 2012, last updated on Apr. 17, 2013, located at http://www.ebi.ac.uk/ena/data/view/JN173040&display=text, last visited on May 13, 2014, 2 pages.

GenBank Accession No. JN173041, created Jan. 19, 2012, last updated on Apr. 17, 2013, located at http://www.ebi.ac.uk/ena/data/view/JN173041&display=text, last visited on May 13, 2014, 2 pages.

GenBank Accession No. JN173042, created Jan. 19, 2012, last updated on Apr. 17, 2013, located at http://www.ebi.ac.uk/ena/data/view/JN173042&display=text, last visited on May 13, 2014, 2 pages.

GenBank Accession No. JN173043, created Jan. 19, 2012, last updated on Apr. 17, 2013, located at http://www.ebi.ac.uk/ena/data/view/JN173043&display=text, last visited on May 13, 2014, 2 pages.

(56) References Cited

OTHER PUBLICATIONS

GenBank Accession No. NC_001416, last updated on Mar. 11, 2011, located at http://www.ncbi.nlm.nih.gov/nuccore/9626243?report=genbank, last visited on May 13, 2014, 42 pages.
Iwakura, M. et al. (1979). "Studies on Regulatory Functions of Malic Enzymes," *J. Biochem.* 85:1355-1365.
Kakuda, H. et al. (1994). "Identification and Characterization of the *ackA* (Acetate Kinase A)-*pta* (Phosphotransacetylase) Operon and Complementation Analysis of Acetate Utilization by an *ackA-pta* Deletion Mutant of *Escherichia coli*," *J. Biochem.* 116:916-922.
Kotlarz, D. et al. (1975). "Regulation of the Amount and of the Activity of Phosphofructokinases and Pyruvate Kinases in *Escherichia coli*," *Biochimica et Biophysica Acta* 381:257-268.
Lindberg, P. et al. (2010). "Engineering a Platform for Photosynthetic Isoprene Production in Cyanobacteria, Using *Synechocystis* as the Model Organism," *Metabolic Engineering* 12(1):70-79.
Maurus, R. et al. (2003). "Insights into the Evolution of Allosteric Properties. The NADH Binding Site of Hexameric Type II Citrate Synthases," *Biochemistry* 42:5555-5565.
Miao, L. et al. (2006, e-pub. Mar. 15, 2006). "Effect of Culture Conditions on Mycelial Growth, Antibacterial Activity, and Metabolite Profiles of the Marine-derived Fungus *Arthrinium c.f. saccharicola*," *Appl. Microbiol. Biotechnol.* 72:1063-1073.
Murrell, J.C. et al. (1993). "Detection of Methylotrophic Bacteria in Natural Samples by Molecular Probing Techniques," *Chemosphere* 26(1-4):1-11.
Ner, S.S. et al. (Nov. 8, 1983). "Complete Sequence of the *glt* A Gene Encoding Citrate Synthase in *Escherichia coli*," *Biochemistry* 22(23):5243-5249.
Ogasawara, H. et al. (2007). "PdhR (Pyruvate Dehydrogenase Complex Regulator) Controls the Respiratory Electron Transport System in *Escherichia coli*," *Journal of Bacteriology* 189(15):5534-5541.
Peekhaus, N. et al. (Jul. 1998). "What's for Dinner?: Entner-Doudoroff Metabolism in *Escherichia coli*," *Journal of Bacteriology* 180(14):3495-3502.
Quant, P.A. et al. (1989). "Treatment of Rats With Glucagon or Mannoheptulose Increases Mitochondrial 3-Hydroxy-3-Methylglutaryl-CoA Synthase Activity and Decreases Succinyl-CoA Content in Liver," *Biochem. J.* 262:159-164.
Romanos, M.A. et al. (1992). "Foreign Gene Expression in Yeast: a Review," *Yeast* 8(6):423-488.
Sánchez, A.M. et al. (2005). "Novel Pathway Engineering Design of the Anaerobic Central Metabolic Pathway in *Escherichia coli* to Increase Succinate Yield and Productivity," *Metabolic Engineering* 7:229-239.
Shimizu, M. et al. (1969). "Phosphotransacetylase of *Escherichia coli* B, Purification and Properties," *Biochimica et Biophysica Acta* 191:550-558.
Sprenger, G.A. (1995). "Genetics of Pentose-Phosphate Pathway Enzymes of *Escherichia coli* K-12," *Arch. Microbiol.* 164:324-330.
Stokell, D.J. et al. (Sep. 12, 2003). "Probing the Roles of Key Residues in the Unique Regulatory NADH Binding Site of Type II Citrate Synthase of *Escherichia coli*," *The Journal of Biological Chemistry* 278(37):35435-35443.
Stülke, J. et al. (2000). "Regulation of Carbon Catabolism in *Bacillus* Species," *Annu. Rev. Microbiol.* 54:849-880.
Tabata, K. et al. (2004). "Production of Mevalonate by a Metabolically-engineered *Escherichia coli*," *Biotechnology Letters* 26:1487-1491.
Underwood, S.A. et al. (2002). "Flux through Citrate Synthase Limits the Growth of Ethanologenic *Escherichia coli* KO11 During Xylose Fermentation," *Applied and Environmental Microbiology* 68(3):1071-1081.
UniProt Database Accession No. H2CSU6, Mar. 21, 2012, located at http://www.uniprot.org/uniprot/H2CSU6.txt, last visited on May 13, 2014, 1 page.
Wiegand, G. et al. (1986). "Citrate Synthase: Structure, Control, and Mechanism," *Ann. Rev. Biophys. Biophys. Chem.* 15:97-117.
Wolfe, A.J. (2005). "The Acetate Switch," *Microbiol. Mol. Biol. Rev.* 69(1):12-50.
International Search Report mailed on Jun. 18, 2009, for PCT Patent Application No. PCT/US08/86869, filed on Dec. 15, 2008, one page.
International Search Report mailed on Dec. 8, 2009, for PCT Application No. PCT/US2009/041581, filed on Apr. 23, 2009, nine pages.
International Search Report mailed on Dec. 30, 2010, for PCT Application No. PCT/US2010/032134, filed on Apr. 22, 2010, 15 pages.
International Search Report mailed on Jan. 31, 2014 for PCT Patent Application No. PCT/US2013/039151 filed on May 1, 2013, 6 pages.

\* cited by examiner

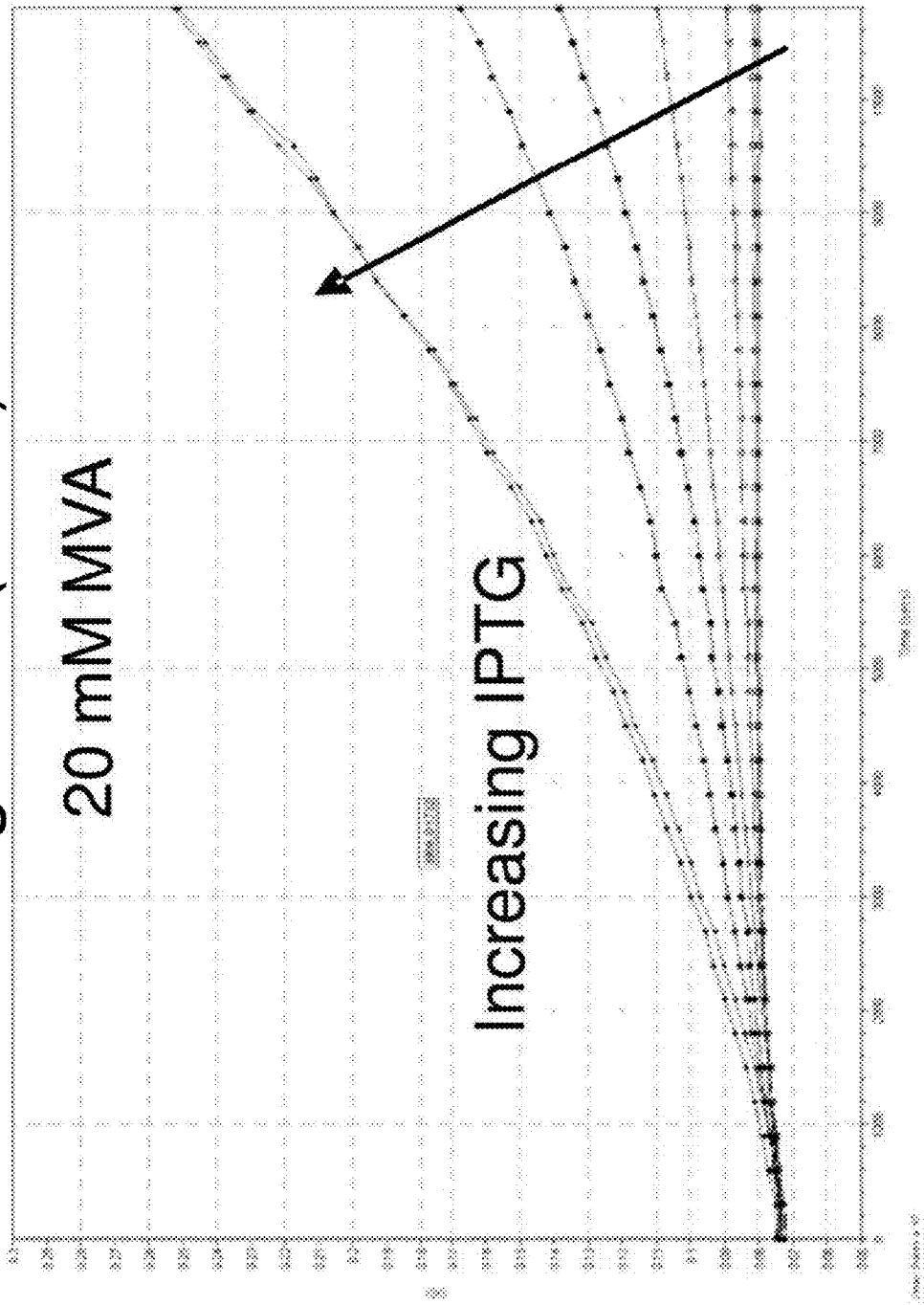

Figure 20A

Met Glu Ala Arg Arg Ser Ala Asn Tyr Glu Pro Asn Ser Trp Asp Tyr
1               5                   10                  15
Asp Tyr Leu Ser Leu Ser Asp Thr Asp Glu Ser Ile Glu Val Tyr Lys
            20                  25                  30
Asp Lys Ala Lys Leu Glu Ala Glu Val Arg Arg Glu Ile Asn Asn
        35                  40                  45
Glu Lys Ala Glu Phe Leu Thr Leu Glu Leu Ile Asp Asn Val Gln
50                  55                  60
Arg Leu Gly Leu Gly Tyr Arg Phe Glu Ser Asp Ile Arg Gly Ala Leu
65              70                  75              80
Asp Arg Phe Val Ser Ser Gly Gly Phe Asp Ala Val Thr Lys Thr Ser
            85                  90                  95
Leu His Gly Thr Ala Leu Ser Phe Arg Leu Arg Gln His Gly Phe
    100                 105                 110
Glu Val Ser Gln Glu Ala Phe Ser Gly Phe Lys Asp Gln Asn Gly Asn
            115                 120                 125
Phe Leu Glu Asn Leu Lys Glu Ala Ile Lys Ala Ile Leu Ser Leu Tyr
130                 135                 140
Glu Ala Ser Phe Leu Ala Leu Glu Gly Glu Asn Ile Leu Asp Glu Ala
145                 150                 155                 160
Lys Val Phe Ala Ile Ser His Leu Lys Glu Leu Ser Glu Glu Lys Ile
            165                 170                 175
Gly Lys Glu Ala Glu Gln Val Asn His Ala Leu Glu Leu Pro Leu
    180                 185                 190
His Arg Arg Thr Gln Arg Leu Glu Ala Val Trp Ser Ile Glu Ala Tyr
            195                 200                 205
Arg Lys Lys Glu Asp Ala Asn Gln Val Leu Leu Glu Leu Ala Ile Leu
210                 215                 220
Asp Tyr Asn Met Ile Gln Ser Val Tyr Gln Arg Asp Leu Arg Glu Thr
            225                 230                 235                 240
Ser Arg Trp Trp Arg Arg Val Gly Leu Ala Thr Lys Leu His Phe Ala
            245                 250                 255
Arg Asp Arg Leu Ile Glu Ser Phe Tyr Trp Ala Val Gly Val Ala Phe
        260                 265                 270

Figure 20B

Glu Pro Gln Tyr Ser Asp Cys Arg Asn Ser Val Ala Lys Met Phe Ser
275                 280                 285
Phe Val Thr Ile Ile Asp Asp Ile Tyr Asp Val Tyr Gly Thr Leu Asp
290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
325                 330                 335
Asn Thr Ile Asn Glu Ile Ala Tyr Asp Asn Leu Lys Asp Lys Gly Glu
340                 345                 350
Asn Ile Leu Pro Tyr Leu Thr Lys Ala Trp Ala Asp Leu Cys Asn Ala
355                 360                 365
Phe Leu Gln Glu Ala Lys Trp Leu Tyr Asn Lys Ser Thr Pro Thr Phe
370                 375                 380
Asp Asp Tyr Phe Gly Asn Ala Trp Lys Ser Ser Ser Gly Pro Leu Gln
385                 390                 395                 400
Leu Val Phe Ala Tyr Phe Ala Val Gln Asn Ile Lys Lys Glu Glu
405                 410                 415
Ile Glu Asn Leu Gln Lys Tyr His Asp Thr Ile Ser Arg Pro Ser His
420                 425                 430
Ile Phe Arg Leu Cys Asn Asp Leu Ala Ser Ala Ser Ala Glu Ile Ala
435                 440                 445
Arg Gly Glu Thr Ala Asn Ser Val Ser Cys Tyr Met Arg Thr Lys Gly
450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Gly Gly Ser Leu Phe Ala
485                 490                 495
Lys Pro Phe Val Glu Thr Ala Ile Asn Leu Ala Arg Gln Ser His Cys
500                 505                 510
Thr Tyr His Asn Gly Asp Ala His Thr Ser Pro Asp Glu Leu Thr Arg
515                 520                 525
Lys Arg Val Leu Ser Val Ile Thr Glu Pro Ile Leu Pro Phe Glu Arg
530                 535                 540

Figure 42
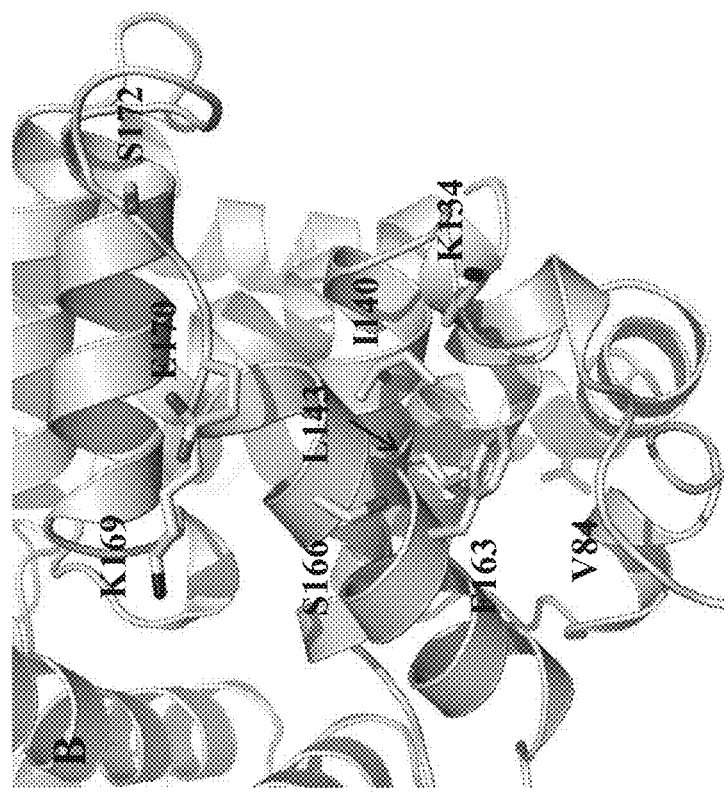
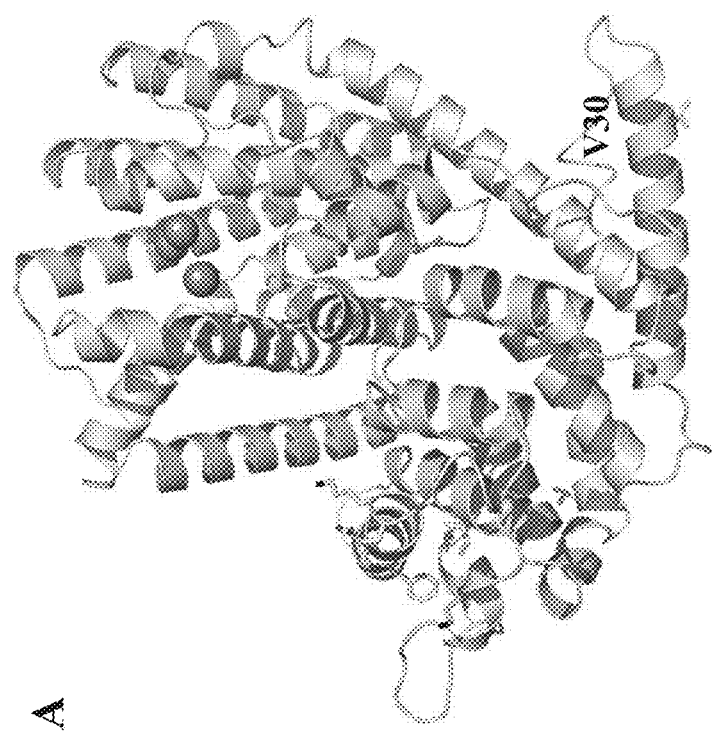

US 9,273,298 B2

ISOPRENE SYNTHASE VARIANTS FOR IMPROVED PRODUCTION OF ISOPRENE

CROSS-REFERENCE TO RELATED APPLICATIONS

This application claims priority benefit of U.S. provisional patent application No. 61/407,415, filed on Oct. 27, 2010, the content of which is hereby incorporated by reference herein in its entirety.

FIELD OF THE INVENTION

The present invention provides methods and compositions comprising isoprene synthase variants. In particular, the present invention provides variant plant isoprene synthases for increased isoprene production in host cells.

BACKGROUND OF THE INVENTION

Isoprenoids are isoprene polymers that find use in pharmaceuticals, neutraceuticals, flavors, fragrances, and rubber products. Natural isoprenoid supplies, however, are limited due to ecological concerns. For this reason, and to provide isoprenoid compositions having fewer impurities and greater uniformity, isoprenoids such as rubber are often produced synthetically.

Isoprene(2-methyl-1,3-butadiene) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes (Weissermel and Arpe, Industrial Organic Chemistry, 4$^{th}$ ed., Wiley-VCH, pp. 117-122, 2003). The C5 skeleton can also be synthesized from smaller subunits. It would be desirable, however, to have a commercially viable method of producing isoprene that was independent of nonrenewable resources.

Biosynthetic production of isoprene occurs by two distinct metabolic pathways (Julsing et al., Appl Microbiol Biotechnol, 75:1377-1384, 2007). In eukaryotes and archae, isoprene is formed via the mevalonate (MVA) pathway, while some eubacteria and higher plants produce isoprene via the methylerythritol phosphate (MEP) pathway. Isoprene emissions from plants are light and temperature-dependent with increases linked to leaf development. An isoprene-producing enzyme, isoprene synthase, has been identified in Aspen trees (Silver and Fall, Plant Physiol, 97:1588-1591, 1991; and Silver and Fall, J Biol Chem, 270:13010-13016, 1995) and is believed to be responsible for the in vivo production of isoprene from whole leaves. Bacterial production of isoprene has also been described (Kuzma et al., Curr Microbiol, 30:97-103, 1995; and Wilkins, Chemosphere, 32:1427-1434, 1996), and varies in amount with the phase of bacterial growth and the nutrient content of the culture medium (U.S. Pat. No. 5,849,970 to Fall et al.; and Wagner et al., J Bacteriol, 181: 4700-4703, 1999). The levels of isoprene obtainable through bacterial systems of the prior art, however, are insufficient for commercial uses.

Thus what the art needs is an efficient, large scale isoprene biological production process to provide feedstock for the manufacture of isoprenoids.

All patents, patent applications, articles and publications mentioned herein are hereby expressly incorporated herein by reference.

SUMMARY OF THE INVENTION

The present invention provides compositions comprising at least one isoprene synthase polypeptide variant and method of making and using such variants. The variant comprises one or more amino acid residue substitution(s) from a parent isoprene synthase polypeptide, wherein the parent isoprene synthase may be a wild type or non-wild type sequence. The invention provides amino acid residue substitutions at particular positions within the polypeptide, wherein the substitution may result in at least one improved property as compared to its parent sequence. In some particularly preferred embodiments, the at least one improved property is selected from but not limited to the group consisting of: specific productivity, yield, cellular performance index, specific activity, growth of the host cell in which the polypeptide variant is expressed, expression, stability and solubility. In particular, the present invention provides variant plant isoprene synthases for increased isoprene production in host cells.

In one aspect, the invention provides for isolated polypeptides having improved isoprene synthase activity, wherein the polypeptide comprises one or more substitutions(s) at one or more residue(s) in N-terminus region, surface loop, surface, active site, dimer interface, substrate capture loop, or in a buried region and wherein the polypeptide has at least 30% increase in specific activity of isoprene synthase compared to wild-type isoprene synthase of SEQ ID NO:1. In some embodiments, the substitution in the N-terminus region is at a residue selected from the group consisting of X2, X22, X36, X43, and X58. In some embodiments, the substitution is at a residue selected from the group consisting of E2, S22, K36, R43, and E58. In some embodiments, wherein the substitution is selected from the group consisting of E2V, S22K, S22R, K36D, K36E, K36H, K36W, R43E, and E58F. In some embodiments, the substitution in the buried region is at a residue selected from the group consisting of X71, X89, X118, X161, X228, X268, X282, X288, X331, X391, X392, X437, X460, X461, X481, X488, and X502. In some embodiments, the substitution is at a residue selected from the group consisting of R71, F89, A118, K161, M228, V268, S282, S288, C331, A391, W392, C437, M460, R461, T481, E488, and T502. In some embodiments, the substitution is selected from the group consisting of R71I, F89D, F89E, A118E, A118P, K161C, M228Y, V268I, S282H, S282W, S288A, S288T, S288Y, C331P, A391G, W392C, W392F, W392M, W392S, W392V, W392Y, C437L, C437M, M460A, R461A, R461Y, T481Y, E488L, T502F and T502M. In some embodiments, the substitution in the surface loop is at a residue selected from the group consisting of X120, X151, X153, X254, X380, and X409. In some embodiments, the substitution is at a residue selected from the group consisting of S120, L151, H254, S380, and V409. In some embodiments, the substitution is selected from the group consisting of S120M, S120Q, L151F, L151Y, G153P, H254C, S380E, and V409T. In some embodiments, the substitution in the dimer interface is at X247. In some embodiments, wherein the substitution is at V247. In some embodiments, the substitution is V247M. In some embodiments, the substitution on the surface is at a residue selected from the group consisting of X348, X376, and X389. In some embodiments, the substitution is at a residue selected from the group consisting of K348, L376, and G389. In some embodiments, the substitution is selected from the group consisting of K348Y, and G389D. In some embodiments, the substitution in the substrate capture loop is at a residue selected from the group consisting of X443, X444, X447 and X448. In some embodiments, the substitution is at a residue selected from the group consisting of S444, I447 and A448. In some embodiments, the substitution is selected from the group consisting of S444S, I447T and A448V.

In another aspect, the invention provides for isolated polypeptides having improved isoprene synthase activity, wherein the polypeptide comprises the following immutable residues with residue numbering corresponding to SEQ ID NO:1: X4, X9, X243, X258, X259, X262, X266, X280, X294, X295, X298, X305, X387, X396, X397, X435, X439, X446, X449, X450, X514, and X518, and wherein the polypeptide further comprises one or more substitutions(s) at residues selected from the group consisting of: X2, X22, X36, X43, X58, X71, X89, X118, X120, X151, X153, X161, X228, X234, X247, X254, X268, X282, X288, X331, X348, X376, X380, X389, X391, X392, X409, X437, X443, X444, X447, X448, X460, X461, X481, X488, and X502, and wherein the polypeptide has at least 30% increase in specific activity of isoprene synthase compared to wild-type isoprene synthase of SEQ ID NO:1. In some embodiments, the substitutions are at residues selected from the group consisting of: E2, S22, K36, R43, E58, R71, F89, A118, S120, L151, K161, M228, Q234, V247, H254, V268, S282, S288, C331, K348, L376, S380, G389, A391, W392, V409, C437, S444, I447, A448, M460, R461, T481, E488, and T502. In some embodiments, the substitution(s) are selected from the group consisting of: E2V, S22K, S22R, K36D, K36E, K36H, K36W, R43E, E58F, R71I, F89D, F89E, A118E, A118P, S120M, S120Q, L151F, L151Y, G153P, K161C, M228Y, Q234R, V247I, V247L, V247M, H254C, V268I, S282H, S282W, S288A, S288T, S288Y, C331P, K348Y, S380E, G389D, A391G, W392C, W392F, W392M, W392S, W392V, W392Y, V409T, C437L, C437M, S444D, S444E, I447T, I447V, A448V, M460A, R461A, T481Y, E488L, T502F and T502M.

In another aspect, the invention provides for isolated polypeptides having improved isoprene synthase activity, wherein the polypeptide comprises the following immutable residues with residue numbering corresponding to SEQ ID NO:1: X4, X9, X243, X258, X259, X262, X266, X280, X294, X295, X298, X305, X387, X396, X397, X435, X439, X446, X449, X450, X514, and X518, and wherein the polypeptide further comprises one or more substitutions(s) at residues selected from the group consisting of: X134, X138, X143, X156, X159, X163, X166, X167, X170, X414, X421, and X491 and wherein a host cell expressing the polypeptide has at least 50% more growth compared to the growth of a host cell expressing wild-type isoprene synthase of SEQ ID NO:1 under similar growth conditions. In some embodiments, the substitution is at a residue selected from the group consisting of K134, K138, L143, I156, E159, F163, S166, H167, E170, K414, and Q421. In some embodiments, the substitution is selected from the group consisting of K134P, K138C, L143F, L143V, I156G, E159G, E159Q, F163C, F163E, F163Q, F163V, F163Y, S166C, S166D, S166G, S166P, S166V, H167M, E170G, E170H, E170K, E170N, E170R, E170S, E170W, K414F, K414G, K414N, K414P, and Q421R.

In another aspect, the invention provides for isolated polypeptides having improved isoprene synthase activity, wherein the polypeptide comprises the following immutable residues with residue numbering corresponding to SEQ ID NO:1: X4, X9, X243, X258, X259, X262, X266, X280, X294, X295, X298, X305, X387, X396, X397, X435, X439, X446, X449, X450, X514, and X518, and wherein the polypeptide further comprises one or more substitutions(s) at residues selected from the group consisting of: X29, X47, X86, X94, X131, X134, X156, X162, X169, X178, X179, X231, X242, X369, X414, and X421 and wherein a host cell expressing the polypeptide has at least 50% more growth compared to the growth of a host cell expressing wild-type isoprene synthase of SEQ ID NO:1 under similar growth conditions. In some embodiments, the substitution is at a residue selected from the group consisting of E29, N47, S86, K94, E131, K134, I156, V162, K169, K178, E179, S231, R242, F369, K414, and Q421. In some embodiments, the substitution is selected from the group consisting of E29N, N47V, S86C, K94A, E131F, K134E, K134P, I156G, V162P, K169C, K178E, E179T, S231D, S231K, S231R, S231T, S231V, R242N, R242I, F369C, K414C, K414F, K414G, K414N, and Q421D.

In another aspect, the invention provides for isolated polypeptides having improved isoprene synthase activity, wherein the polypeptide comprises the following immutable residues with residue numbering corresponding to SEQ ID NO:1: X4, X9, X243, X258, X259, X262, X266, X280, X294, X295, X298, X305, X387, X396, X397, X435, X439, X446, X449, X450, X514, and X518, and wherein the polypeptide further comprises one or more substitutions(s) at residues selected from the group consisting of: X30, X84, X134, X140, X143, X163, X166, X169, X170 and X172 and wherein the polypeptide has at least 20% increase in specific activity of isoprene synthase compared to wild-type isoprene synthase of SEQ ID NO:1 and at least 20% more growth in a host cell expressing the polypeptide compared to the growth of a host cell expressing wild-type isoprene synthase of SEQ ID NO:1 under similar growth conditions. In some embodiments, the substitution is at a residue selected from the group consisting of V84, K134, I140, L143, F163, S166, K169, E170 and S172. In some embodiments, the substitution is selected from the group consisting of V30K, V84T, K134C, K134D, K134E, I140S, I140T, L143F, L143I, L143M, L143V, F163I, F163M, S166P, S166V, K169Q, E170H, E170K, and S172V.

In another aspect, the invention provides for isolated polypeptides having improved isoprene synthase activity, wherein the polypeptide comprises one or more substitution(s) in: (i) the N-terminus, (ii) the N-terminal helix region from residues 134 to 179 wherein the residue numbering corresponds to SEQ ID NO:1 (wild type MEA isoprene synthase) or (iii) at other residues outside of the N-terminal helix region that interact with the N-terminal helix region, and wherein the polypeptide has at least 20% increase in specific activity of isoprene synthase compared to wild-type isoprene synthase of SEQ ID NO:1. In some embodiments, the substitutions are at residues selected from the group consisting of: X30, X84, X134, X140, X143, X163, X166, X169, X170 and X172. In some embodiments, the substitutions are at residues selected from the group consisting of: V84, K134, I140, L143, F163, S166, K169, E170 and S172. In some embodiments, the substitutions are selected from the group consisting of: V30K, V84T, K134C, K134D, K134E, I140S, I140T, L143F, L143I, L143M, L143V, F163I, F163M, S166P, S166V, K169Q, E170H, E170K, and S172V.

In another aspect, the invention provides for isolated polypeptides having improved isoprene synthase activity, wherein the polypeptide comprises one or more substitutions(s) at residues corresponding to SEQ ID NO:1 selected from the group consisting of: X2, X22, X36, X43, X58, X71, X89, X118, X120, X151, X153, X161, X228, X234, X247, X254, X268, X282, X288, X331, X348, X376, X380, X389, X391, X392, X409, X437, X443, X444, X447, X448, X460, X461, X481, X488, and X502, and wherein the polypeptide has at least 30% increase in specific activity of isoprene synthase compared to wild-type isoprene synthase of SEQ ID NO:1. In some embodiments, the substitution is at a residue selected from the group consisting of E2, S22, K36, R43, E58, R71, F89, A118, S120, L151, K161, M228, Q234, V247, H254, V268, S282, S288, C331, K348, L376, S380, G389, A391, W392, V409, C437, S444, I447, A448, M460, R461, T481, E488, and T502. In some embodiments, the substitution is selected from the group consisting of E2V, S22K, S22R, K36D, K36E, K36H, K36W, R43E, E58F, R71I, F89D, F89E, A118E, A118P, S120M, S120Q, L151F, L151Y, G153P, K161C, M228Y, Q234R, V247I, V247L, V247M, H254C, V268I, S282H, S282W, S288A, S288T, S288Y, C331P, K348Y, S380E, G389D, A391G, W392C, W392F, W392M, W392S, W392V, W392Y, V409T, C437L, C437M, S444D, S444E, I447T, I447V, A448V, M460A, R461A, T481Y, E488L, T502F and T502M.

In another aspect, the invention provides for isolated polypeptides having improved isoprene synthase activity, wherein the polypeptide comprises one or more substitutions(s) at one or more residue(s) in N-terminus region, N-terminal helix region, surface loop, surface, active site, dimer interface, substrate capture loop, or in a buried region and wherein the polypeptide has at least 40% increase in specific activity of isoprene synthase compared to wild-type isoprene synthase of SEQ ID NO:1. In some embodiments, the substitution in the N-terminus region is at a residue selected from the group consisting of: X18, X36, and X82. In some embodiments, the substitution is at a residue selected from the group consisting of Y18, K36, and R82. In some embodiments, the substitution is selected from the group consisting of: Y18E, Y18D, Y18S, K36P, and R82Q. In some embodiments, the substitution in the N-terminus helix region is at a residue selected from the group consisting of: X137, X143, X163, and X170. In some embodiments, the substitution is at a residue selected from the group consisting of: I137, L143, F163, and E170. In some embodiments, the substitution is selected from the group consisting of: I137C, L143N, F163I, F163Q, and E170G. In some embodiments, the substitution in the surface loop is at a residue selected from the group consisting of: X87, X409, and X542. In some embodiments, the substitution is at a residue selected from the group consisting of: G87, V409, and F542. In some embodiments, the substitution is selected from the group consisting of: G87S, G87N, G87R, V409S, and F542N. In some embodiments, the substitution in the surface is at residue X251. In some embodiments, the substitution is at residue T251. In some embodiments, the substitution is T251E. In some embodiments, the substitution in the dimer interface is at residue X242. In some embodiments, the substitution is at residue R242. In some embodiments, the substitution is R242T. In some embodiments, the substitution in the buried region is at a residue selected from the group consisting of: X437, X460, and X461. In some embodiments, the substitution is at a residue selected from the group consisting of: C437, M460, and R461. In some embodiments, the substitution is selected from the group consisting of: C437M, C437K, M460Q, M460G, M460A, R461D, R461S, R461T, and R461. In some embodiments, the substitution in the substrate capture loop is at a residue selected from the group consisting of: X443, X444, and X447. In some embodiments, the substitution is at a residue selected from the group consisting of: S444, and I447. In some embodiments, the substitution is selected from the group consisting of: S444P, I447Q, I447T, I447M, I447E, I447S, and I447R.

In another aspect, the invention provides for isolated polypeptides having isoprene synthase activity and providing improved growth activity when the polypeptide is expressed in a host cell, wherein the polypeptide comprises one or more substitutions(s) at residues corresponding to SEQ ID NO:1 selected from the group consisting of: X134, X138, X143, X156, X159, X163, X166, X167, X170, X414, X421, and X491 and wherein a host cell expressing the polypeptide has at least 50% more growth compared to the growth of a host cell expressing wild-type isoprene synthase of SEQ ID NO:1 under similar growth conditions. In some embodiments, the substitution is at a residue selected from the group consisting of K134, K138, L143, I156, E159, F163, S166, H167, E170, K414, and Q421. In some embodiments, the substitution is selected from the group consisting of K134P, K138C, L143F, L143V, I156G, E159G, E159Q, F163C, F163E, F163Q, F163V, F163Y, S166C, S166D, S166G, S166P, S166V, H167M, E170G, E170H, E170K, E170N, E170R, E170S, E170W, K414F, K414G, K414N, K414P, and Q421R.

In another aspect, the invention provides for isolated polypeptides having isoprene synthase activity and providing improved growth activity when the polypeptide is expressed in a host cell, wherein the polypeptide comprises one or more substitutions(s) at residues corresponding to SEQ ID NO:1 selected from the group consisting of: X29, X47, X86, X94, X131, X134, X156, X162, X169, X178, X179, X231, X242, X369, X414, and X421 and wherein a host cell expressing the polypeptide has at least 50% more growth compared to the growth of a host cell expressing wild-type isoprene synthase of SEQ ID NO:1 under similar growth conditions. In some embodiments, the substitution is at a residue selected from the group consisting of E29, N47, S86, K94, E131, K134, I156, V162, K169, K178, E179, S231, R242, F369, K414, and Q421. In some embodiments, the substitution is selected from the group consisting of E29N, N47V, S86C, K94A, E131F, K134E, K134P, I156G, V162P, K169C, K178E, E179T, S231D, S231K, S231R, S231T, S231V, R242N, R242I, F369C, K414C, K414F, K414G, K414N, and Q421D.

In another aspect, the invention provides for isolated polypeptides having isoprene synthase activity and providing improved growth activity when the polypeptide is expressed in a host cell, wherein the polypeptide comprises one or more substitutions(s) at residues corresponding to SEQ ID NO:1 selected from the group consisting of: X50, X81, X134, X137, X143, X156, X159, X166, X167, X169, X170, and X414 and wherein a host cell expressing the polypeptide has at least 30% more growth compared to the growth of a host cell expressing wild-type isoprene synthase of SEQ ID NO:1 under similar growth conditions. In some embodiments, the substitution is at a residue selected from the group consisting of K50, D81, K134, I137, L143, I156, E159, S166, H167, K169, E170, and K414. In some embodiments, the substitution is selected from the group consisting of K50S, D81F, K134E, K134P, I137N, L143V, I156G, E159D, E159G, E159Q, S166C, S166W, H167M, H167N, K169C, E170H, E170K, E170W, K414C, K414F, K414G, K414N, and K414P.

In another aspect, the invention provides for isolated polypeptides having improved isoprene synthase activity and providing improved growth activity when the polypeptide is expressed in a host cell, wherein the polypeptide comprises one or more substitutions(s) at residues corresponding to SEQ ID NO:1 selected from the group consisting of: X30, X84, X134, X140, X143, X163, X166, X169, X170 and X172 and wherein the polypeptide has at least 20% increase in specific activity of isoprene synthase compared to wild-type isoprene synthase of SEQ ID NO:1 and at least 20% more growth in a host cell expressing the polypeptide compared to the growth of a host cell expressing wild-type isoprene synthase of SEQ ID NO:1 under similar growth conditions. In some embodiments, the substitution is at a residue selected from the group consisting of V84, K134, I140, L143, F163, S166, K169, E170 and S172. In some embodiments, the substitutions are selected from the group consisting of: V30K, V84T, K134C, K134D, K134E, I140S, I140T, L143F, L143I, L143M, L143V, F163I, F163M, S166P, S166V, K169Q, E170H, E170K, and S172V.

In another aspect, the invention provides for isolated polypeptides with improved isoprene synthase properties wherein the polypeptide comprises two or more substitution(s) residues corresponding to SEQ ID NO:1 selected from the group consisting of: X22, X71, X87, X162, X242, X288, X409, X414, X443, X444, X460, and X502 wherein the residue numbering corresponds to SEQ ID NO:1, and wherein the polypeptide has at least 160% increase in specific activity of isoprene synthase compared to wild-type isoprene synthase of SEQ ID NO:1. In some embodiments, the substitution is at a residue selected from the group consisting of S22, R71, G87, V162, R242, S288, V409, K414, S444, M460, and T502. In some embodiments, the substitutions are selected from the group consisting of S22R, R71I or R, G87R, V162P, R242N, S288C, V409T, KX414F, S444D, M460A, and T502M. In some embodiments, the substitution is selected from the group consisting of: a) S22R, R71I, S288C, S444D, M460A, and T502M; b) G87R, V162P, R242N, S288C, V409T, K414R, and S444D; or c) G87R, V162P, R242N, S288C, V409T, and K414F.

In another aspect, the invention provides for isolated polypeptides with improved isoprene synthase properties wherein the polypeptide comprises two or more substitution(s) residues corresponding to SEQ ID NO:1 selected from the group consisting of: X47, X87, X156, X162, X170, X231, X242, X288, X409, X414, and X447 wherein the residue numbering corresponds to SEQ ID NO:1, and wherein the polypeptide has at least 30% increase in specific activity of isoprene synthase as compared to wild-type isoprene synthase of SEQ ID NO:1 and at least 30% more growth when the polypeptide is expressed in a host cell, as compared to wild-type isoprene synthase of SEQ ID NO:1 under similar growth conditions. In some embodiments, the substitutions are at residues selected from the group consisting of N47, G87, I156, V162, E170, S231, R242, S288, V409, K414, and I447. In some embodiments, the substitutions are selected from the group consisting of N47V, G87R, I156G, V162P, E170H, S231T, R242N, S288C, S288T, V409T, and K414F. In some embodiments, the substitutions are selected from the group consisting of N47V, I156G, E170H, S231T, S288T, and K414F.

In another aspect, the invention provides for isolated polypeptides with improved isoprene synthase properties wherein the polypeptide comprises one or more substitution(s) at residues corresponding to SEQ ID NO:1 selected from the group consisting of: X2, X18, X19, X21, X24, X26, X27, X29, X37, X42, X47, X48, X49, X56, X81, X82, X84, X93, X94, X95, X120, X123, X126, X131, X132, X134, X137, X139, X143, X151, X155, X166, X167, X169, X170, X171, X175, X179, X180, X197, X229, X231, X240, X242, X245, X246, X247, X251, X271, X282, X306, X317, X319, X369, X371, X376, X379, X380, X389, X392, X393, X408, X409, X421, X422, X423, X429, X437, X443, X444, X447, X455, X458, X461, X464, X466, X470, X473, X500, X502, X506, X513, X525 and, X531 and wherein the polypeptide has (a) minimum performance indices (PI) relative to SEQ ID NO:1 for specific activity and expression are greater than or equal to a PI of 0.9 and where at least one PI relative to SEQ ID NO:1 for specific activity or growth is greater than or equal to a PI of 1.0; and (b) minimum performance indices (PI) relative to SEQ ID NO:1 for specific activity and expression are greater than or equal to a PI of 0.8 and where at least one PI relative to SEQ ID NO:1 for specific activity or growth is greater than or equal to a PI of 1.2; and (c) minimum performance indices (PI) relative to SEQ ID NO:1 for specific activity and expression are greater than or equal to a PI of 0.5 and where at least one PI relative to SEQ ID NO:1 for specific activity or growth is greater than or equal to a PI of 1.5.

In some embodiments, the substitution is at a residue selected from the group consisting of E2, Y18, L19, S21, T24, E26, S27, E29, K37, V42, N47, N48, E49, L56, D81, R82, V84, T93, K94, T95, S120, K123, N126, E131, N132, K134, I137, A139, L143, L151, N155, S166, H167, K169, E170, L171, K175, E179, L180, Q197, I229, S231, T240, R242, R245, R246, V247, T251, A271, S282, L306, D317, N319, F369, Q371, L376, K379, S380, G389, W392, K393, V408, V409, Q421, K422, Y423, R429, C437, S444, I447, S455, C458, R461, G464, S466, A470, S473, V500, T502, L506, T513, E525 and, V531. In some embodiments, the substitution is selected from the group consisting of E2A or K or P, Y18D or E or K or S, L19Y, S21W, T24L or V, E26C, S27D or N, E29N, K37C or D or P or Q or S, V42M, N47D or S, N48D or G or T, E49L or V, L56E or F or G or I or K or T or V or Y, D81Q, R82N or T or V or Y, V84M, T93C or F or R or S, K94G or P, T95D or F or G or I or N or W, S120C or G or M or Q, K123V, N126E, E131H or K or L or M or T or W or Y, N132I or P, K134A, I137T, A139C or Q, L143C or D or E or H or K or M or Q or T or V or Y, L151A or F, N155A or C or G or H or Q or R or S or W, S166N, H167F or I or N or Q or V, K169A or C or H or N or Q or V, E170L or S or W or Y, L171A or N or Q or T or V or Y, K175C or F or I or Q or R, E179D, L180A or I, Q197C or D or N, I229C, S231A, T240C, R242G, R245C or K or M or Q or T or V, R246N, V247L or M, T251D or E or N or P or Q or S, A271T, S282Y, L306C, D317N, N319M, F369C or D or E or G or S, Q371F, L376I or M, K379G or Q, S380E, G389A or D or E or K or N or Q or S or V, W392Y, K393C or I or T or V, V408T, V409T, Q421H, K422D, Y423N or S, R429E or F or Q, C437M, S444D or E, I447T, S455A, C458T, R461A, G464C or M or N or Q or S, S466D, A470I or L, S473I, V500A or C, T502M, L506M, T513C or G or K or N, E525F or R, V531E or H or K or Q or R or S.

In another aspect, the invention provides for isolated polypeptides with improved isoprene synthase properties wherein the polypeptide comprises one or more substitution(s) at residues corresponding to SEQ ID NO:1 selected from the group consisting of: X2, X6, X18, X20, X22, X23, X24, X25, X26, X27, X28, X29, X30, X31, X32, X36, X37, X42, X44, X47, X48, X49, X50, X53, X54, X55, X56, X58, X59, X68, X71, X74, X77, X78, X79, X81, X82, X83, X84, X86, X87, X91, X93, X94, X95, X97, X98, X99, X109, X115, X116, X117, X118, X120, X123, X125, X126, X127, X128, X130, X131, X132, X133, X134, X136, X137, X138, X139, X140, X143, X151, X153, X155, X156, X159, X160, X161, X162, X163, X164, X166, X167, X169, X170, X171, X172, X175, X176, X177, X178, X179, X180, X181, X182, X190, X194, X197, X204, X211, X215, X217, X219, X221, X228, X229, X231, X232, X235, X241, X242, X245, X246, X247, X251, X254, X271, X272, X278, X279, X282, X296, X302, X317, X319, X320, X327, X331, X348, X351, X357, X361, X364, X365, X368, X369, X370, X371, X373, X377, X380, X383, X386, X389, X392, X393, X407, X408, X409, X410, X411, X414, X422, X423, X424, X428, X429, X432, X436, X437, X440, X443, X444, X447, X448, X457, X460, X461, X462, X463, X464, X465, X466, X468, X470, X471, X472, X473, X475, X480, X490, X491, X492, X494, X496, X500, X501, X502, X503, X510, X513, X515, X519, X525, X531, X536, X537, X540, X541, X542, and X544 and wherein the polypeptide has (a) minimum performance indices (PI) relative to SEQ ID NO:1 for specific activity and expression are greater than or equal to a PI of 0.9 and where at least one PI relative to SEQ ID NO:1 for specific activity or growth is greater than or equal to a PI of 1.0; and (b) minimum performance indices (PI) relative to SEQ ID NO:1 for specific activity and expression are greater than or equal to a PI of 0.8 and where at least one PI relative to SEQ ID NO:1 for specific activity or growth is greater than or equal to a PI of 1.2. In some embodiments, wherein the substitution is at a residue selected from the group consisting of E2, S6, Y18, L20, S22, D23, T24, D25, E26, S27, I28, E29, Y31, K32, K36, K37, V42, R44, N47, N48, E49, K50, F53, L54, T55, L56, E58, L59, L68, R71, S74, R77, G78, A79, D81, R82, F83, V84, S86, G87, A91, T93, K94, T95, L97, H98, G99, Q109, S115, Q116, E117, A118, S120, K123, Q125, N126, G127, N128, L130, E131, N132, L133, K134, D136, I137, K138, A139, I140, L143, L151, N155, I156, E159, A160, K161, V162, F163, A164, S166, H167, K169, E170, L171, S172, K175, I176, G177, K178, E179, L180, A181, E182, L190, R194, Q197, S204, K211, N215, V217, L219, L221, M228, I229, S231, V232, R235, S241, R242, R245, R246, V247, T251, H254, A271, F272, D278, C279, S282, I296, T302, D317, N319, A320, Y327, C331, K348, G351, Y357, A361, D364, L365, A368, F369, L370, Q371, A373, Y377, S380, T383, D386, G389, W392, K393, A407, V408, V409, Q410, N411, K414, K422, Y423, H424, S428, R429, H432, L436, C437, L440, S444, I447, A448, S457, M460, R461, T462, K463, G464, I465, S466, E468, A470, T471, E472, S473, M475, E480, L490, G492, L494, A496, V500, E501, T502, A503, S510, T513, H515, A519, E525, V531, T536, E537, L540, P541, F542, and R544. In some embodiments, the substitution is at a residue selected from the group consisting of E2C or D or N or T or V, S6N or T, Y18A or Q or R, L20T, S22Q, D23N, T24C, D25T, E26D or H or K or M or R or S or V, S27A or C or G or H or I or L or M or P or Q, I28D or N, E29Q, V30A or D or E or M or R or T, Y31N, K32E, K36A or C or D or E or M or N or P or Q, K37A or E or G or H or M or N or R or T, V42F or I, R44N or Q, N47A or G or H or M or Q or T or W, N48H or I or K, E49A or C, K50A or D or E or F or H or S or Y, F53E or H or N or P or Q or V, L54M, T55C or D or E, L56C or N, E58N, L59H or T, L68I, R71K or M, S74D or E or N or Y, R77L, G78A or D or F or L or M, A79Q or T, D81A or F or G or M or R or S or T or V, R82A or E or H or I or K or M or Q or S, F83W, V84A, S86A or D or M, G87D or P, A91K or W, T93A or D or E or G or L or N or P or Y, K94A or D or E or H or I or L or M or N or R or S or T, T95A or E or P or Q or S or V or Y, L97F, H98A or D or F or G or I or L or M or N or Q, G99E or F or M, Q109E, S115A, Q116A or C or D or E or I or P, E117C or F or L or M or V, A118M, S120H or T or V, K123L or T, Q125E or I or Y, N126A or C or D or M or T or V, G127C, N128C or D or P or Q, L130E, E131A or C or P or Q or S or V, N132C or D or F or H or L or R or W or Y, L133D, K134E or M or Q or S or T or V, D136E, I137E or H or N, K138I or N, A139N, I140M or W, L143S, L151C or H or I, G153C, N155I or T or V or Y, I156D or N or T, E159M, A160I, K161A or C or N or Q, V162S, F163E or Q, A164T, S166A or D or G, H167A or E or G or K or M or R or S or T or W, K169D or I or M or S or T, E170H or K or M or Q or T or V, L171H or K or R or S, S172A or C, K175S, I176M, G177A or C, K178A or F or R or S or T, E179A or C or L or M or N, L180C or Q or T, A181H or Q or S or V, E182S, L190I or M, R194L, Q197S, S204C, K211A or N or Q, N215C or H, V217I, L219C, L221M, M228F or Y, I229V, S231K or Q or T, V232I, R235K, S241A or M or T, R242A or D or E or H or I or M or N or Q or S or T, R245I or L, R246D or K, V247T, T251A or G or K or R, H254D, A271C or V, F272D or G or P or W, D278A or E or N or Q or S or T or V or W, C279A, S282A or Q, I296V, T302H, D317E or Q, N319F, A320C, Y327M, C331P, K348R or Y, G351D or N, Y357M, A361T, D364E or V, L365C or M, A368N, F369M or N or R or T or V, L370G or Q, Q371C or S, A373G, Y377W, S380A or C or D or Q or T or V, T383S, D386E or N, G389H or I, W392I or S or T or V, K393Q, A407G, V408I, V409H or I, Q410C or D or K or L or M or T, N411G, K414E or G or L or N or P, K422A or N or T, Y423Q, H424E or P or Q or V, S428E or Q, R429I or L or T or W or Y, H432E, L436M or Y, C437K or T, L440I, S444P, I447A or E or M or Q or S, A448E or M or N or P or Q or V, S457N or T, M460Q or R or S, R461D or E or G or Q or S or T, T462Q, K463A or D or E, G464L or R, I465A or C or G or S or T, S466P, E468D, A470M, T471E or H or Q, E472D or S, S473L or V, M475T, E480N, L490A or D or E or F or H or M, G492C, L494D, A496P or T, V500L or M, E501D, T502A or C or R or V, A503I, S510C or V, T513V, H515N, A519S or T, E525A or C or P or Q or S, V531A or M or T, T536A or F or G, E537K or T, L540A or P, P541M, F542P, and R544C.

In another aspect, the invention provides for isolated polypeptides with improved isoprene synthase properties wherein the polypeptide comprises one or more substitution (s) at residues corresponding to SEQ ID NO:1 selected from the group consisting of: X2, X3, X13, X17, X18, X19, X20, X23, X25, X26, X27, X28, X29, X30, X31, X32, X33, X34, X36, X37, X40, X41, X42, X43, X44, X45, X46, X47, X48, X49, X50, X51, X53, X54, X55, X56, X57, X59, X60, X62, X71, X73, X74, X75, X77, X78, X79, X81, X82, X83, X84, X85, X86, X87, X88, X89, X91, X92, X93, X94, X95, X97, X98, X99, X100, X101, X102, X103, X107, X109, X111, X113, X114, X115, X116, X117, X118, X119, X120, X121, X123, X124, X125, X127, X128, X129, X130, X131, X133, X134, X135, X136, X137, X138, X139, X140, X143, X146, X151, X152, X153, X155, X156, X158, X160, X161, X162, X163, X166, X167, X169, X170, X171, X172, X175, X176, X177, X178, X179, X180, X181, X182, X183, X185, X187, X193, X194, X196, X197, X204, X210, X211, X212, X215, X216, X217, X218, X219, X220, X222, X223, X224, X226, X228, X229, X231, X232, X235, X240, X241, X242, X246, X251, X253, X260, X268, X270, X271, X272, X275, X276, X278, X282, X307, X314, X315, X317, X320, X321, X323, X328, X329, X331, X332, X333, X343, X345, X346, X350, X351, X352, X356, X357, X360, X361, X363, X364, X366, X367, X368, X369, X370, X371, X378, X379, X380, X383, X386, X389, X390, X392, X393, X402, X405, X408, X409, X410, X413, X414, X418, X422, X423, X424, X425, X426, X428, X429, X431, X432, X437, X444, X447, X448, X457, X460, X461, X462, X463, X464, X466, X467, X468, X469, X471, X472, X475, X484, X489, X490, X491, X492, X493, X494, X497, X500, X501, X502, X503, X504, X506, X509, X510, X511, X513, X515, X517, X519, X522, X528, X529, X531, X534, X535, X536, X537, X539, X540, X542, and X544 and wherein the polypeptide has (a) minimum performance indices (PI) relative to SEQ ID NO:1 for specific activity and expression are greater than or equal to a PI of 0.9 and where at least one PI relative to SEQ ID NO:1 for specific activity or growth is greater than or equal to a PI of 1.0; or (b) minimum performance indices (PI) relative to SEQ ID NO:1 for specific activity and expression are greater than or equal to a PI of 0.8 and where at least one PI relative to SEQ ID NO:1 for specific activity or growth is greater than or equal to a PI of 1.2 and (c) minimum performance indices (PI) relative to SEQ ID NO:1 for specific activity and expression are greater than or equal to a PI of 0.5 and where at least one PI relative to SEQ ID NO:1 for specific activity or growth is greater than or equal to a PI of 1.5. In some embodiments, the substitution is at a residue selected from the group consisting of E2, A3, S13, D17, Y18, L19, L20, D23, D25, E26, S27, I28, E29, Y31, K32, D33, K34, K36, K37, A40, E41, V42, R43, R44, E45, I46, N47, N48, E49, K50, A51, F53, L54, T55, L56, L57, L59, I60, N62, R71, E73, S74, D75, R77, G78, A79, D81, R82, F83, V84, S85, S86, G87, G88, F89, A91, V92, T93, K94, T95, L97, H98, G99, T100, A101, L102, S103, L107, Q109, G111, E113, V114, S115, Q116, E117, A118, F119, S120, G121, K123, D124, Q125, G127, N128, F129, L130, E131, L133, K134, E135, D136, I137, K138, A139, I140, L143, A146, L151, E152, N155, I156, D158, A160, K161, V162, F163, S166, H167, K169, E170, L171, S172, K175, I176, G177, K178, E179, L180, A181, E182, Q183, N185, A187, H193, R194, T196, Q197, S204, K210, K211, E212, N215, Q216, V217, L218, L219, E220, A222, I223, L224, Y226, M228, I229, S231, V232, R235, T240, S241, R242, R246, T251, L253, L260, V268, V270, A271, F272, Q275, Y276, D278, S282, E307, E314, R315, D317, A320, I321, D323, M328, K329, C331, F332, L333, A343, D345, N346, K350, G351, E352, P356, Y357, K360, A361, A363, D364, C366, N367, A368, F369, L370, Q371, N378, K379, S380, T383, D386, G389, N390, W392, K393, V402, Y405, V408, V409, Q410, K413, K414, E418, K422, Y423, H424, D425, T426, S428, R429, S431, H432, C437, S444, I447, A448, S457, M460, R461, T462, K463, G464, S466, E467, E468, L469, T471, E472, M475, K484, K489, L490, G492, S493, L494, K497, V500, E501, T502, A503, I504, L506, Q509, S510, H511, T513, H515, Q517, A519, S522, R528, K529, V531, V534, I535, T536, E537, I539, L540, F542, and R544. In some embodiments, the substitution is selected from the group consisting of E2H or I or S, A3E or G or K or N or Q or R or T, S13Q or T, D17E, Y18F or M or N, L19F, L20I or V, D23T, D25A or E or S, E26G or N or Q or T, S27E or F or K or V, I28E or F or M or P, E29D or P or R or T, V30N or Q, Y31Q or W, K32D or G or N or R, D33N, K34D or E or Q or S, K36F or R, K37F or I, A40C or D or E or F or M or N or P or Q or V, E41C or D or F or N or Q or S or V, V42A or S or T, R43I or Q, R44A or D or K or M or Y, E45C or M or N or Q, I46F or V, N47E or I or K or R or V, N48A or C or E or F or L or Q or R or S, E49G or H or I or R or S or W, K50C or G or M or N or P or R, A51E or G or L or Q or T, F53D, L54A or C or E or H or I or Q, T55A or H or N or Q or S or Y, L56H or Q or R or S, L57I, L59F or M or S or V or Y, I60C or V, N62V, R71I, E73D, S74G or M or P, D75E, R77A or N or T or V, G78E or I or K or N or P or Q or V or W, A79M or R or Y, D81C or E or H or L or N, R82C or F or G or L or W, F83G or H or I or L or V, V84F or H or L or N or Q or R or S or T or W or Y, S85C or L or N or R, S86C or N, G87C or E or F or K or L or N or T, G88C or D or I or V or W or Y, F89C or I, A91C or D or E or G or H or L or R or S or T or V or Y, V92A or C or E or F or G or I or L or Q or W, T93H or I or Q or V or W, K94C or V or Y, T95C or H or K or M, L97A or M or P, H98C or S or T or V or W, G99A or C or H or P or Q or T, T100A or I or L or M or V, A101S, L102M, S103A or C or G or L, L107C or F, Q109C or N or S, G111A, E113C or H or V, V114C, S115D or Y, Q116G or H or L or S or T or V, E117A or D or I, A118I or V, F119L or M, S120A or D or E or F or K or N or R or W or Y, G121D or L or V or W, K123I or S or W or Y, D124C or E, Q125A or D or G or H or K or L or N or S or T or V or W, G127D or F or W, N128A, F129L or Y, L130A or C or D or Q or V or Y, E131D or F or G or R, L133E or G or I or P or Q or T or V or Y, K134D or G or H or I or L or N or R or W or Y, E135H or S, D136N, I137A or C or D or G or P or Q or S or V, K138C or D or E or P or R or S or V, A139P or S or T or V, I140N or Q or S or T or V, L143A or F or G or N or R or W, A146M, L151E or G or M or N or Q or R or S or T or V or W, E152A or D or I or M or P, G153D, N155E or K or M, I156E or K or L or R or Y, D158E, A160F or H or S, K161L or R or S or Y, V162D or F or N or P or T, F163C or H or I or M or V or W or Y, S166C or E or H or K or P or Q or V or W, H167C or L or P, K169E or G or R, E170G or I or N or R, L171C or E or G or I or M or W, S172G or N or Q or R, K175A or G or H or N or P or T or V, I176A or C or N or Q or V, G177D or E or H or N or P or T, K178D or E or G or I or L or M or N or P or Q or V or Y, E179G or I or P or Q or S or T or V or W or Y, L180F or H or V or W, A181F or M or N or W, E182H or N, Q183A or L, N185D, A187C or S, H193W, R194I, T196V, Q197G, S204A or F or M or W or Y, K210M, K211D or E or F or G or H or I or M or R or S or T or V, E212A or D or M or P or Q or T, N215D or Y, Q216A or E or N, V217C or E or K or N or P or Q or T, L218V, L219I or M or V, E220D or N, A222S, I223C, L224A or C or T or V, Y226F, M228H or R, I229A, S231D or G or H or R or V, V232Q, R235A or D or N, T240V, S241C, R242K or L, R246H or Q, T251H, L253M, L260M, V268I, V270I, A271S, F272Q, Q275E, Y276F or H or Q, D278L or M or R or Y, S282C, E307Q or R, E314H, R315G or K, D317S, A320N or T, I321L or M, D323I or T, M328L, K329G or Q or R, C331T, F332Y, L333F, A343I or V, D345Y, N346A, K350H or W or Y, G351E or M, E352F or I or M or V, P356M or S, Y357E, K360Q, A361Q or S or V, A363S, D364N or T, C366A, N367D or E or M, A368D or Q, F369H or Q, L370A or D or E or F or H or N or R or S or T or V, Q371G or H or I or N or P or R or T or W or Y, N378D, K379E or R or S, S380K or N, T383Q, D386K or S, G389C or M or P or R or T, N390S, W392F or M, K393H or R, V402F or I or L, Y405F, V408Q or S, V409C or Q or S, Q410E or G or H or I or R, K413P, K414C or H or I or Q, E418N, K422G or H or Q or R, Y423G, H424D or G or I or S or T, D425P, T426A or M or Q, S428V, R429A or C or D or G or H or K or N, S431G, H432A or M, C437N, S444N or Q or T, I447K or R, A448H or S or T, S457D, M460A or E or G, R461N, T462K, K463G or N, G464A or D or E or F or H or V or Y, S466E or G or K or N or T, E467N, E468A or N or P or Q, L469A or N, T471N, E472A or G or N, M475I, K484A, K489R, L490I or Y, G492T or V, S493C or G or K or V, L494G or I or Q or V, K497M or T, V500I or Y, E501N, T502H, A503L or M, I504L, L506 I or V, Q509A, S510T, H511I or M, T513S, H515Q, G517P, A519C, S522A or K, R528K, K529A, V531G or N, V534A or S, I535C or S or T, T536M, E537H or N or Q, I539V, L540E or Q or R or V, F542M, and R544G or N or P or Q or S.

In another aspect, the invention provides for isolated polypeptides having improved isoprene synthase activity, wherein the polypeptide comprises one or more substitutions(s) at residues corresponding to SEQ ID NO:1 selected from the group consisting of: X22, X36, X43, X58, X87, X89, X118, X151, X234, X247, X254, X282, X288, X391, X392, X437, X443, X447, X481, X488, X502, and X542 and wherein the polypeptide has at least 30% increase in specific activity of isoprene synthase compared to wild-type isoprene synthase of SEQ ID NO:1. In some embodiments, the substitution is at a residue selected from the group consisting of S22, K36, R43, E58, G87, F89, A118, L151, Q234, V247, H254, S282, S288, A391, W392, C437, I447, T481, E488, T502 and F542. In some embodiments, the substitution is selected from the group consisting of S22K or R, K36H or W, R43E, E58F, G87S or R, F89D, A118E, L151Y, G153P, Q234R, V247I, H254C, S282H or W, S288A or T or Y, A391G, W392C, C437L, I447V, T481Y, E488L, T502F and F542N.

In another aspect, the invention provides for isolated polypeptides having isoprene synthase activity and providing improved growth activity when the polypeptide is expressed in a host cell, wherein the polypeptide comprises one or more substitutions(s) at residues corresponding to SEQ ID NO:1 selected from the group consisting of: X30, X134, X143, X156, X159, X172, X414, and X421, and wherein a host cell expressing the polypeptide has at least 20% more growth compared to the growth of a host cell expressing wild-type isoprene synthase of SEQ ID NO:1 under similar growth conditions. In some embodiments, the substitution is at a residue selected from the group consisting of K134, L143, I156, E159, S172, K414, and Q421. In some embodiments, the substitution is at a residue selected from the group consisting of V30K, K134C or P, L143I, I156G, E159D, S172V, K414F, and Q421R or D.

In another aspect, the invention provides for recombinant host cells comprising any of the polypeptides described above and in the rest of the specification. In some embodiments, the host cell is selected from the group consisting of a bacterial, algal, fungal, yeast, cyanobacterial, or Clostridial cell. In some embodiments, the host cell is a bacterial cell. In some embodiments, the bacterial cell is a gram-positive bacterial cell or gram-negative bacterial cell. In some embodiments, the bacterial cell is selected from the group consisting of *E. coli, L. acidophilus, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes, Clostridium* sp., *Corynebacterium* sp., and *C. glutamicum* cells. In some embodiments, the host cell is an algal cell. In some embodiments, the algal cell is selected from the group consisting of green algae, red algae, glaucophytes, chlorarachniophytes, euglenids, chromista, or dinoflagellates. In some embodiments, the host cell is a fungal cell. In some embodiments, the fungal cell is a filamentous fungi. In some embodiments, the host cell is a yeast cell. In some embodiments, the yeast cell is selected from the group consisting of *Saccharomyces* sp., *Schizosaccharomyces* sp., *Pichia* sp., or *Candida* sp. In some embodiments, the yeast cell is a *Saccharomyces cerevisiae* cell.

In another aspect, the invention provides for methods for identifying a polypeptide having improved isoprene synthase activity and/or improved growth characteristics when the polypeptide is expressed in a host cell, the method comprising screening a site evaluation library or combinatorial library for one or more substitution(s) in the polypeptide that improves specific activity and/or growth of the host cell when the polypeptide is expressed as compared to the specific activity and growth of a host cell expressing wild-type isoprene synthase of SEQ ID NO:1.

In another aspect, the invention provides for non-naturally occurring isoprene synthase variants comprising an amino acid residue substitution selected from the group consisting of: X003C, X003D, X003E, X003F, X003G, X003H, X003I, X003K, X003L, X003M, X003N, X003P, X003Q, X003R, X003S, X003T, X003V, X003W, X003Y, X007C, X007D, X007E, X007F, X007G, X007H, X007I, X007K, X007L, X007M, X007N, X007P, X007Q, X007R, X007S, X007T, X007V, X007W, X007Y, X009A, X009C, X009D, X009E, X009F, X009G, X009H, X009I, X009K, X009L, X009M, X009N, X009P, X009Q, X009R, X009S, X009T, X009V, X009W, X012A, X012C, X012D, X012E, X012F, X012G, X012H, X012I, X012K, X012L, X012M, X012P, X012Q, X012R, X012S, X012T, X012V, X012W, X012Y, X013A, X013C, X013D, X013E, X013F, X013G, X013H, X013I, X013K, X013L, X013M, X013N, X01P3, X013Q, X013R, X013T, X013V, X013W, X013Y, X016A, X016C, X016D, X016E, X016F, X016G, X016H, X016, X016K, X016L, X016M, X016N, X016P, X016Q, X016R, X016S, X016T, X016V, X016W, X018A, X018C, X018D, X0E18, X018F, X018G, X018H, X018I, X018K, X018L, X018M, X018N, X018P, X018Q, X018R, X018S, X018T, X018V, X018W, X020A, X020C, X020D, X020E, X020F, X020G, X020H, X020I, X020K, X020M, X020N, X020P, X020Q, X020R, X020S, X020T, X020V, X020W, X020Y, X023A, X023C, X023E, X023F, X023G, X023H, X023I, X023K, X023L, X023M, X023N, X023P, X023Q, X023R, X023S, X023T, X023V, X023W, X023Y, X025A, X025C, X025E, X025F, X025G, X025H, X025I, X025K, X025L, X025M, X025N, X025P, X025Q, X025R, X025S, X025T, X025V, X025W, X025Y, X026A, X026C, X026D, X026F, X026G, X026H, X026I, X026K, X026L, X026M, X026N, X026P, X026Q, X026R, X026S, X026T, X026V, X026W, X026Y, X027A, X027C, X027D, X027E, X027F, X027G, X027H, X027I, X027K, X027L, X027M, X027N, X027P, X027Q, X0R27, X027V, X027W, X027Y, X033A, X033C, X033E, X033F, X033G, X033H, X033I, X033K, X033L, X033M, X033N, X033P, X033Q, X033R, X033S, X033T, X033V, X033W, X033Y, X036A, X036C, X036D, X036E, X036F, X036G, X036G, X036I, X036L, X036M, X036N, X036P, X036Q, X036R, X036S, X036T, X036V, X036W, X036Y, X044A, X044C, X044D, X044E, X044F, X044G, X044H, X044I, X044K, X044L, X044M, X044N, X044P, X044Q, X044S, X044T, X044V, X044W, X044Y, X050A, X050C, X050D, X050E, X050F, X050G, X050H, X050I, X050L, X050M, X050N, X050P, X050Q, X050R, X050S, X050T, X050V, X050W, X050Y, X053A, X053C, X053D, X053E, X053G, X053H, X053I, X053K, X053L, X053M, X053N, X053P, X053Q, X053R, X053S, X053T, X053V, X053W, X053Y, X059A, X059C, X059D, X059E, X059F, X059G, X059H, X059I, X059K, X059M, X059N, X059P, X059Q, X059R, X059S, X059T, X059V, X059W, X059Y, X069A, X069C, X069D, X069E, X069F, X069H, X069I, X069K, X069L, X069M, X069N, X069P, X069Q, X069R, X069S, X069T, X069V, X069W, X069Y, X074A, X074C, X074D, X074E, X074F, X074G, X074H, X074I, X074K, X074L, X074M, X074N, X074P, X074Q, X074R, X074T, X074V, X074W, X074Y, X078A, X078C, X078D, X078E, X078F, X078H, X078I, X078K, X078L, X078M, X078N, X078P, X078Q, X078R, X078S, X078T, X078V, X078W, X078Y, X081A, X081C, X081E, X081F, X081G, X081H, X081I, X081K, X081L, X081M, X081N, X081P, X081Q, X081R, X081S, X081T, X081V, X081W, X081Y, X087A, X087C, X087D, X087E, X087F, X087H, X087I, X087K, X087L, X087M, X087N, X087P, X087Q, X087R, X087S, X087T, X087V, X087W, X087Y, X099A, X099C, X099D, X099E, X099F, X099H, X099I, X099K, X099L, X099M, X099N, X099P, X099Q, X099R, X099S, X099T, X099V, X099W, X099Y, X116A, X116C, X116D, X116E, X116F, X116G, X116H, X116I, X116K, X116L, X116M, X116N, X116P, X116R, X116S, X116T, X116V, X116W, X116Y, X117A, X117C, X117D, X117F, X117G, X117H, X117I, X117K, X117L, X117M, X117N, X117P, X117Q, X117R, X117S, X117T, X117V, X117W, X117Y, X120A, X120C, X120D, X120E, X120F, X120G, X120H, X120I, X120K, X120L, X120M, X120N, X120P, X120Q, X120R, X120T, X120V, X120W, X120Y, X121A, X121C, X121D, X121E, X121F, X121H, X121I, X121K, X121L, X121M, X121N, X121P, X121Q, X121R, X121S, X121T, X121V, X121W, X121Y, X125A, X125C, X125D, X125E, X125F, X125G, X125H, X125I, X125K, X125L, X125M, X125N, X125P, X125R, X125S, X125T, X125V, X125W, X125Y, X127A, X127C, X127D, X127E, X127F, X127H, X127I, X127K, X127L, X127M, X127N, X127P, X127Q, X127R, X127S, X127T, X127V, X127W, X127Y, X139C, X139D, X139E, X139F, X139G, X139H, X139I, X139K, X139L, X139M, X139N, X139P, X139Q, X139R, X139S, X139T, X139V, X139W, X139Y, X165A, X165C, X165D, X165E, X165F, X165G, X165H, X165K, X165L, X165M, X165N, X165P, X165Q, X165R, X165S, X165T, X165V, X165W, X165Y, X173A, X173C, X173D, X173F, X173G, X173H, X173I, X173K, X173L, X173M, X173N, X173P, X173Q, X173R, X173S, X173T, X173V, X173W, X173Y, X174A, X174C, X174D, X174F, X174G, X174H, X174I, X174K, X174L, X174M, X174N, X174P, X174Q, X174R, X174S, X174T, X174V, X174W, X174Y, X177A, X177C, X177D, X177E, X177F, X177H, X177I, X177K, X177L, X177M, X177N, X177P, X177Q, X177R, X177S, X177T, X177V, X177W, X177Y, X179A, X179C, X179D, X179F, X179G, X179H, X179I, X179K, X179L, X179M, X179N, X179P, X179Q, X179R, X179S, X179T, X179V, X179W, X179Y, X194A, X194C, X194D, X194E, X194F, X194G, X194H, X194I, X194K, X194L, X194M, X194N, X194P, X194Q, X194S, X194T, X194V, X194W, X194Y, X197A, X197C, X197D, X197E, X197F, X197G, X197H, X197I, X197K, X197L, X197M, X197N, X197P, X197R, X197S, X197T, X197V, X197W, X197Y, X202A, X202C, X202D, X202E, X202F, X202G, X202H, X202I, X202K, X202L, X202M, X202N, X202P, X202Q, X202R, X202S, X202T, X202W, X202Y, X216A, X216C, X216D, X216E, X216F, X216G, X216H, X216I, X216K, X216L, X216M, X216N, X216P, X216R, X216S, X216T, X216V, X216W, X216Y, X240A, X240C, X240D, X240E, X240F, X240G, X240H, X240I, X240K, X240L, X240M, X240N, X240P, X240Q, X240R, X240S, X240V, X240W, X240Y, X246A, X246C, X246D, X246E, X246F, X246G, X246H, X246I, X246K, X246L, X246M, X246N, X246P, X246Q, X246S, X246T, X246V, X246W, X246Y, X251A, X251C, X251D, X251E, X251F, X251G, X251H, X251I, X251K, X251L, X251M, X251N, X251P, X251Q, X251R, X251S, X251V, X251W, X251Y, X254A, X254C, X254D, X254E, X254F, X254G, X254I, X254K, X254L, X254M, X254N, X254P, X254Q, X254R, X254S, X254T, X254V, X254W, X254Y, X287A, X287C, X287D, X287E, X287G, X287H, X287I, X287K, X287L, X287M, X287N, X287P, X287Q, X287R, X287S, X287T, X287V, X287W, X287Y, X290A, X290C, X290D, X290E, X290F, X290G, X290H, X290I, X290K, X290L, X290M, X290N, X290P, X290Q, X290R, X290S, X290T, X290W, X290Y, X308A, X308C, X308D, X308E, X308F, X308G, X308H, X308I, X308K, X308M, X308N, X308P, X308Q, X308R, X308S, X308T, X308V, X308W, X308Y, X376A, X376C, X376D, X376E, X376F, X376G, X376H, X376I, X376K, X376L, X376M, X376N, X376P, X376Q, X376R, X376S, X376T, X376V, X376W, X376Y, X377A, X377C, X377D, X377E, X377F, X377G, X377H, X377I, X377K, X377L, X377M, X377N, X377P, X377Q, X377R, X377S, X377T, X377V, X377W, X379A, X379C, X379D, X379E, X379F, X379G, X379H, X379I, X379L, X379M, X379N, X379P, X379Q, X379R, X379S, X379T, X379V, X379W, X379Y, X389A, X389C, X389D, X389E, X389F, X389H, X389I, X389K, X389L, X389M, X389N, X389P, X389Q, X389R, X389S, X389T, X389V, X389W, X389Y, X397A, X397C, X397D, X397E, X397F, X397H, X397I, X397K, X397L, X397M, X397N, X397P, X397Q, X397R, X397S, X397T, X397V, X397W, X397Y, X400A, X400C, X400D, X400E, X400F, X400G, X400H, X400I, X400K, X400L, X400M, X400N, X400P, X400R, X400S, X400T, X400V, X400W, X400Y, X403A, X403C, X403D, X403E, X403G, X403H, X403I, X403K, X403L, X403M, X403N, X403P, X403Q, X403R, X403S, X403T, X403V, X403W, X403Y, X421A, X421C, X421D, X421E, X421F, X421G, X421H, X421I, X421K, X421L, X421M, X421N, X421P, X421R, X421S, X421T, X421V, X421W, X421Y, X426A, X426C, X426D, X426E, X426F, X426G, X426H, X426I, X426K, X426L, X426M, X426N, X426P, X426Q, X426R, X426S, X426V, X426W, X426Y, X430A, X430C, X430D, X430E, X430F, X430G, X430H, X430I, X430K, X430L, X430M, X430N, X430Q, X430R, X430S, X430T, X430V, X430W, X430Y, X434A, X434C, X434D, X434E, X434G, X434H, X434I, X434K, X434L, X434M, X434N, X434P, X434Q, X434R, X434S, X434T, X434V, X434W, X434Y, X445C, X445D, X445E, X445F, X445G, X445H, X445I, X445K, X445L, X445M, X445N, X445P, X445Q, X445R, X445S, X445T, X445V, X445W, X445Y, X448C, X448D, X448E, X448F, X448G, X448H, X448I, X448K, X448L, X448M, X448N, X448P, X448Q, X448R, X448S, X448T, X448V, X448W, X448Y, X457A, X457C, X457D, X457E, X457F, X457G, X457H, X457I, X457K, X457L, X457M, X457N, X457P, X457Q, X457R, X457T, X457V, X457W, X457Y, X462A, X462C, X462D, X462E, X462F, X462G, X462H, X462I, X462K, X462L, X462M, X462N, X462P, X462Q, X462R, X462S, X462V, X462W, X462Y, X476A, X476C, X476D, X476E, X476F, X476G, X476H, X476I, X476K, X476L, X476M, X476P, X476Q, X476R, X476S, X476T, X476V, X476W, X476Y, X487A, X487C, X487D, X487E, X487F, X487G, X487H, X487I, X487L, X487M, X487N, X487P, X487Q, X487R, X487S, X487T, X487V, X487W, X487Y, X488A, X488C, X488D, X488F, X488G, X488H, X488I, X488K, X488L, X488M, X488N, X488P, X488Q, X488R, X488S, X488T, X488V, X488W, X488Y, X489A, X489C, X489D, X489E, X489F, X489G, X489H, X489I, X489L, X489M, X489N, X489P, X489Q, X489R, X489S, X489T, X489V, X489W, X489Y, X490A, X490C, X490D, X490E, X490F, X490G, X490H, X490I, X490K, X490M, X490N, X490P, X490Q, X490R, X490S, X490T, X490V, X490W, X490Y, X491A, X491C, X491D, X491E, X491F, X491H, X491I, X491K, X491L, X491M, X491N, X491P, X491Q, X491R, X491S, X491T, X491V, X491W, X491Y, X492A, X492C, X492D, X492E, X492F, X492H, X492I, X492K, X492L, X492M, X492N, X492P, X492Q, X492R, X492S, X492T, X492V, X492W, X492Y, X493A, X493C, X493D, X493E, X493F, X493G, X493H, X493I, X493K, X493L, X493M, X493N, X493P, X493Q, X493R, X493T, X493V, X493W, X493Y, X495A, X495C, X495D, X495E, X495G, X495H, X495I, X495K, X495L, X495M, X495N, X495P, X495Q, X495R, X495S, X495T, X495V, X495W, X495Y, X496C, X496D, X496E, X496F, X496G, X496H, X496I, X496K, X496L, X496M, X496N, X496P, X496Q, X496R, X496S, X496T, X496V, X496W, X496Y, X497A, X497C, X497D, X497E, X497F, X497G, X497H, X497I, X497L, X497M, X497N, X497P, X497Q, X497R, X497S, X497T, X497V, X497W, X497Y, X498A, X498C, X498D, X498E, X498F, X498G, X498H, X498I, X498K, X498L, X498M, X498N, X498Q, X498R, X498S, X498T, X498V, X498W, X498Y, X509A, X509C, X509D, X509E, X509F, X509G, X509H, X509I, X509K, X509L, X509M, X509N, X509P, X509R, X509S, X509T, X509V, X509W, X509Y, X514A, X514C, X514D, X514E, X514F, X514G, X514H, X514I, X514K, X514L, X514M, X514N, X514P, X514Q, X514R, X514S, X514T, X514V, X514W, X521A, X521C, X521D, X521E, X521F, X521G, X521H, X521I, X521K, X521L, X521M, X521N, X521P, X521Q, X521R, X521S, X521V, X521W, X521Y, X539A, X539C, X539D, X539E, X539F, X539G, X539H, X539K, X539L, X539M, X539N, X539P, X539Q, X539R, X539S, X539T, X539V, X539W, X539Y, X540A, X540C, X540D, X540E, X540F, X540G, X540H, X540I, X540K, X540L, X540M, X540N, X540P, X540Q, X540R, X540S, X540T, X540V, X540W, X540Y, X544A, X544C, X544D, X544E, X544F, X544G, X544H, X544I, X544K, X544L, X544M, X544N, X544P, X544Q, X544S, X544T, X544V, X544W, and X544Y;

wherein X represents any amino acid; and wherein each amino acid residue position is numbered by correspondence with an amino acid residue position in the *P. alba* isoprene synthase sequence as shown in FIG. 20.

In another embodiment, the variant comprises the amino acid residues: N438, E451, and Y514. In another embodiment, the variant comprises the amino acid residues: F287, G397, N438, E451, and Y514. In any of the embodiments, the variant comprises a substitution selected from the group consisting of: X003H, X003T, X033H, X033I, X033K, X033S, X033T, X033V, X033W, X033Y, X036L, X044F, X044H, X044T, X050I, X050L, X050W, X053I, X053L, X053T, X053V, X053W, X053Y, X059A, X059C, X059F, X059G, X059H, X059I, X059K, X059M, X059R, X069S, X074I, X074K, X074W, X078I, X078L, X078W, X078Y, X087K, X087L, X087T, X099I, X099K, X099L, X099T, X099V, X099Y, X116F, X116I, X116T, X116V, X116W, X116Y, X117F, X117I, X117L, X117W, X120I, X120L, X139T, X165H, X165Y, X173H, X173T, X173V, X173W, X174H, X174I, X177L, X177T, X177V, X179H, X179I, X179K, X179L, X179T, X179V, X179W, X202H, X254K, X376I, X377W, X389K, X421E, X421H, X421R, X448H, X448T, X448V, X462H, X462K, X462V, X476V, X487T, X489I, X489R, X489T, X489W, X490H, X490I, X490T, X490V, X490W, X491H, X491I, X491K, X491L, X491T, X491V, X491W, X491Y, X492A, X492D, X492E, X492H, X492I, X492K, X492T, X492V, X493E, X493G, X493I, X493K, X493L, X493R, X493T, X493V, X493W, X495H, X495K, X495L, X495M, X495R, X495S, X495T, X495V, X495W, X495Y, X496H, X498H, X509I, X509T, X509V, X539L, X539T, X539V, X540H, X540I, X540K, X540T, X540V, X540Y, X544S, X544T, X544V, and X544W.

In any of the embodiments herein, the variant comprises a substitution selected from the group consisting of: X003T, X016I, X033F, X033H, X033I, X033V, X036I, X044F, X044M, X050H, X050I, X050T, X050W, X053I, X059C, X059E, X059F, X059H, X059I, X059K, X059Q, X059R, X059T, X069S, X069T, X074H, X074I, X074K, X074T, X074V, X074W, X078F, X078H, X078I, X078R, X078T, X078V, X078W, X078Y, X099I, X099K, X099T, X099V, X116F, X116I, X116N, X116P, X116T, X116V, X116W, X117C, X117F, X117I, X117L, X117M, X117W, X125F, X125V, X125W, X127H, X127T, X139T, X165F, X165H, X165K, X165Y, X173F, X173H, X173K, X173R, X173T, X173V, X174H, X174I, X174T, X179G, X179I, X179S, X216A, X421R, X448R, X448T, X448V, X462H, X462I, X462K, X462V, X462W, X476R, X476V, X487F, X487H, X487T, X487W, X489R, X490F, X490H, X490I, X490V, X490W, X491C, X491H, X491I, X491L, X491T, X491V, X491W, X492A, X492E, X493G, X493I, X493L, X493T, X493V, X493W, X495L, X498C, X540I, X540S, X540T, X540V, and X544K.

In any of the embodiments herein, the variant comprises a substitution selected from the group consisting of: X003T, X033H, X033I, X033V, X044F, X050I, X050W, X053I, X059C, X059F, X059H, X059I, X059K, X059R, X069S, X074I, X074K, X074W, X078I, X099I, X099K, X099T, X099V, X116F, X116I, X116T, X116V, X116W, X117F, X117I, X117L, X117W, X139T, X165H, X165Y, X173H, X173T, X173V, X173W, X174H, X174I, X078W, X078Y, X179I, X421R, X448T, X448V, X462H, X462K, X462V, X487T, X489R, X490H, X490I, X490V, X490W, X491I, X491H, X491L, X491T, X491V, X491W, X492A, X492E, X493G, X493I, X493L, X493T, X493V, X493W, X495L, X540I, X540T, X540V.

In any of the embodiments herein, the variant comprises a substitution selected from the group consisting of: X003F, X003H, X003I, X003K, X003R, X003T, X003Y, X013L, X016I, X016L, X016M, X018C, X018G, X020M, X020S, X020T, X020V, X020Y, X023H, X025H, X025I, X025K, X025L, X025T, X025V, X033F, X033H, X033I, X033K, X033L, X033Q, X033R, X033S, X033T, X033V, X033W, X033Y, X036I, X036L, X036R, X036T, X036V, X036W, X036Y, X044C, X044F, X044H, X044I, X044K, X044T, X044V, X044Y, X050H, X050I, X050L, X050T, X050V, X050W, X050Y, X053G, X053H, X053I, X053K, X053L, X053R, X053S, X053T, X053V, X053W, X053Y, X059A, X059C, X059D, X059E, X059F, X059G, X059H, X059I, X059K, X059M, X059N, X059Q, X059R, X059T, X059V, X059W, X069A, X069H, X069I, X069K, X069L, X069M, X069N, X069Q, X069R, X069S, X069T, X069V, X074H, X074I, X074K, X074L, X074T, X074V, X074W, X074Y, X078F, X078H, X078I, X078K, X078L, X078T, X078V, X078W, X078Y, X087H, X087I, X087K, X087L, X087M, X087R, X087T, X087V, X087W, X087Y, X099F, X099I, X099K, X099L, X099R, X099S, X099T, X099V, X099W, X099Y, X116A, X116F, X116I, X116K, X116L, X116S, X116T, X116V, X116W, X116Y, X117F, X117H, X117I, X117L, X117M, X117W, X120F, X120H, X120I, X120K, X120L, X120T, X120V, X120W, X120Y, X121F, X121H, X121I, X121K, X121L, X121T, X121V, X121W, X121Y, X125H, X125I, X125M, X125T, X125W, X125Y, X127F, X127H, X127I, X127L, X127T, X127V, X127Y, X139C, X139H, X139I, X139P, X139S, X139T, X139V, X165A, X165D, X165F, X165H, X165K, X165L, X165R, X165T, X165Y, X173F, X173G, X173H, X173I, X173K, X173L, X173M, X173R, X173S, X173T, X173V, X173W, X173Y, X174F, X174H, X174I, X174K, X174L, X174R, X174T, X174V, X174W, X174Y, X177A, X177H, X177I, X177K, X177L, X177M, X177P, X177T, X177V, X177Y, X179F, X179G, X179H, X179I, X179K, X179L, X179M, X179S, X179T, X179V, X179W, X179Y, X194H, X197H, X197I, X197M, X197T, X197V, X202F, X202H, X202I, X202K, X202R, X202T, X202Y, X246H, X246K, X246T, X251H, X251K, X251N, X251Y, X254F, X254I, X254K, X254R, X254T, X254V, X254W, X308H, X308I, X308W, X376I, X376Y, X377H, X377I, X377L, X377V, X377W, X379H, X379R, X379T, X379V, X389H, X389I, X389K, X389L, X389M, X389R, X389S, X389T, X389V, X389Y, X403T, X403V, X421E, X421G, X421H, X421I, X421K, X421L, X421P, X421R, X421V, X421W, X426I, X426V, X430S, X430T, X430V, X445H, X448H, X448I, X448R, X448S, X448T, X448V, X457H, X457Q, X457R, X457T, X462F, X462G, X462H, X462I, X462K, X462L, X462S, X462V, X462W, X462Y, X476R, X476T, X476V, X476W, X476Y, X487A, X487C, X487F, X487G, X487H, X487L, X487M, X487R, X487S, X487T, X487V, X487W, X489H, X489I, X489L, X489R, X489T, X489V, X489W, X490F, X490H, X490I, X490M, X490T, X490V, X490W, X491A, X491C, X491F, X491H, X491I, X491K, X491L, X491M, X491N, X491R, X491S, X491T, X491V, X491W, X491Y, X492A, X492C, X492D, X492E, X492H, X492I, X492K, X492L, X492R, X492T, X492V, X492W, X492Y, X493A, X493C, X493E, X493G, X493I, X493K, X493L, X493M, X493R, X493T, X493V, X493W, X493Y, X495A, X495G, X495H, X495I, X495K, X495L, X495M, X495Q, X495R, X495S, X495T, X495V, X495W, X495Y, X496H, X496I, X496K, X496L, X496R, X496T, X496V, X496Y, X497H, X497I, X497L, X497T, X497V, X498F, X498G, X498H, X498I, X498K, X498L, X498R, X498S, X498T, X498V, X498Y, X509I, X509M, X509S, X509T, X509V, X539K, X539L, X539T, X539V, X540E, X540F, X540G, X540H, X540I, X540K, X540M, X540Q, X540R, X540S, X540T, X540V, X540W, X540Y, X544C, X544H, X544I, X544K, X544L, X544S, X544T, X544V, and X544W.

In any of the embodiments herein, the variant comprises a substitution selected from the group consisting of: X003T, X013L, X117I, X165Y, X421R, X495L, X509T, and X540V. In any of the embodiments herein, the variant comprises X003T. In any of the embodiments herein, the variant comprises X495L. In any of the embodiments herein, the variant comprises X509T.

In any of the embodiments herein, a surface hydrophobic amino acid residue is substituted. In any of the embodiments herein, a symmetry contact amino acid residue is substituted. In any of the embodiments herein, a conservation amino acid residue is substituted. In any of the embodiments herein, an N-terminal loop amino acid residue is substituted. In any of the embodiments herein, a surface hydrophilic amino acid residue is substituted. In any of the embodiments herein, a surface loop amino acid residue is substituted. In any of the embodiments herein, an active site amino acid residue is substituted. In any of the embodiments herein, a flexible loop amino acid residue is substituted. In any of the embodiments herein, a hydrophobic pocket amino acid residue is substituted. In any of the embodiments herein, a C-terminal amino acid residue is substituted.

In any of the embodiments herein, amino acid residue 509 has a beta-branched carbon. In any of the embodiments herein, the variant has a N-terminal truncation.

In any of the embodiments herein, the N-terminal truncation comprises amino acid residues corresponding to those shown in FIG. 21A-21B.

In any of the embodiments herein, the variant is a variant of a plant isoprene synthase. In any of the embodiments herein, the variant is a poplar variant. In any of the embodiments herein, the variant is a *P. alba* variant. In any of the embodiments herein, the variant is a *P. tremuloides* variant. In any of the embodiments herein, the variant is a *P. trichocharpa* variant. In any of the embodiments herein, the variant is a *P. nigra* variant. In any of the embodiments herein, the variant is a *P. alba* v. *tremuloides* variant. In any of the embodiments herein, the variant is a kudzu variant. In any of the embodiments herein, the variant is an aspen variant. In any of the embodiments herein, the variant is an English oak variant. In any of the embodiments herein, the variant is a willow variant.

In any of the embodiments herein, the variant comprises an amino acid sequence having at least 40% sequence identity to a wild-type isoprene synthase. In any of the embodiments herein, the variant comprises an amino acid sequence having at least 60% sequence identity to a wild-type isoprene synthase. In any of the embodiments herein, the variant comprises an amino acid sequence having at least 80% sequence identity to a wild-type isoprene synthase. In any of the embodiments herein, the variant comprises an amino acid sequence having at least 90% sequence identity to a wild-type isoprene synthase.

In any of the embodiments herein, a host cell comprising a heterologous polynucleotide sequence encoding the variant in operable combination with a promoter has a growth index of at least about 0.8, 0.9, 1.0, 1.1, 1.2, 1.3, or 1.4 as compared with MEA *P. alba* isoprene synthase.

In another aspect, the invention provides isoprene synthase variants of any of the embodiments herein, wherein a host cell comprising a heterologous polynucleotide sequence encoding the variant in operable combination with a promoter has a performance index of at least about 0.8, 0.9, 1.0, or 1.1, as compared with MEA *P. alba* isoprene synthase.

In another aspect, the invention provides isoprene synthase variants of any of the embodiments herein, wherein a host cell comprising a heterologous polynucleotide sequence encoding the variant in operable combination with a promoter has one or more of the following as compared with MEA *P. alba* isoprene synthase:
 at least about 105% specific productivity,
 at least about 105% yield, and
 at least about 105% cellular performance index.

In another aspect, the invention provides isoprene synthase variants of any of the embodiments herein, wherein a host cell comprising a heterologous polynucleotide sequence encoding the variant in operable combination with a promoter has one or more of the following as compared with MEA *P. alba* isoprene synthase:
 at least about 110% specific productivity,
 at least about 110% yield, and
 at least about 110% cellular performance index.

In another aspect, the invention provides isoprene synthase variants of any of the embodiments herein, wherein a host cell comprising a heterologous polynucleotide sequence encoding the variant in operable combination with a promoter has one or more of the following as compared with MEA *P. alba* isoprene synthase:
 at least about 120% specific productivity,
 at least about 120% yield, and
 at least about 120% cellular performance index.

In another aspect, the invention provides isoprene synthase variants of any of the embodiments herein, wherein a host cell comprising a heterologous polynucleotide sequence encoding the variant in operable combination with a promoter has one or more of the following as compared with MEA *P. alba* isoprene synthase:
 at least about 150% specific productivity,
 at least about 150% yield, and
 at least about 150% cellular performance index.

In another aspect, the invention provides isoprene synthase variants of any of the embodiments herein, wherein a host cell comprising a heterologous polynucleotide sequence encoding the variant in operable combination with a promoter has one or more of the following as compared with MEA *P. alba* isoprene synthase:
 at least about 200% specific productivity,
 at least about 200% yield, and
 at least about 200% cellular performance index.

In another aspect, the invention provides isoprene synthase variants of any of the embodiments herein, wherein the substitution comprises X491S.

In another aspect, the invention provides isoprene synthase variants of any of the embodiments herein wherein the variant does not comprise a substitution selected from the group consisting of those listed in Table D.

In another aspect, the invention provides isoprene synthase variants of any of the embodiments herein, wherein the variant is not listed in Table E or Table F.

In another aspect, the invention provides compositions comprising any isoprene synthase variant described herein and a carrier.

In another aspect, the invention provides kits comprising any isoprene synthase variant described herein in a container.

In another aspect, the invention provides nucleic acids encoding any isoprene synthase variant described herein.

In another aspect, the invention provides compositions comprising nucleic acids encoding any isoprene synthase variant described herein and a carrier.

In another aspect, the invention provides kits comprising nucleic acids encoding any isoprene synthase variant described herein in a container.

In another aspect, the invention provides host cells comprising a heterologous polynucleotide sequence encoding any isoprene synthase variant described herein in operable combination with a promoter. In one embodiment, the polynucleotide sequence is contained within a plasmid. In another embodiment, the polynucleotide sequence is integrated into a chromosome of the host cell. In another embodiment, the host cell is selected from the group consisting of gram-positive bacterial cells, gram-negative bacterial cells, filamentous fungal cells, or yeast cells. In another embodiment, the host cell is a gram-negative bacterial cell. In another embodiment, the host cell is selected from the group consisting of *Escherichia* sp. (*E. coli*), *Panteoa* sp. (*P. citrea*), *Bacillus* sp. (*B. subtilis*), *Yarrowia* sp. (*Y. lipolytica*), and *Trichoderma* (*T. reesei*). In another embodiment, the host cell is *E. coli*.

In any of the embodiments herein, the host cell is cultured in a medium comprising a carbon source selected from the group consisting of glucose, glycerol, glycerine, dihydroxyacetone, yeast extract, biomass, molasses, sucrose, and oil. In any of the embodiments herein, the host cell is cultured in a medium comprising glucose.

In any of the embodiments herein, the host cell further comprises a heterologous or native nucleic acid encoding an IDI polypeptide and/or a heterologous or native nucleic acid encoding a DXS polypeptide, optionally in combination with the native DXP pathway.

In any of the embodiments herein, the host cell comprises one vector encoding the isoprene synthase variant, the IDI polypeptide, and the DXS polypeptide.

In any of the embodiments herein, the host cell further comprises a heterologous nucleic acid encoding an MVA pathway polypeptide selected from the group consisting of an MVA pathway polypeptide from *Saccharomyces cerevisiae* and *Enterococcus faecalis*.

In any of the embodiments herein, the host cell further comprises one or more nucleic acids encoding an MVA pathway polypeptide and a DXS polypeptide and wherein one vector encodes the isoprene synthase variant, the MVA pathway polypeptide, and the DXS polypeptide.

In any of the embodiments herein, the host cell further comprises one or more nucleic acids encoding a DXS polypeptide, an IDI polypeptide, one or more of the rest of the DXP pathway polypeptides, and/or a MVA pathway polypeptide.

In another aspect, the invention provides methods of producing a host cell capable of producing isoprene, the method comprising introducing a heterologous polynucleotide sequence encoding any isoprene synthase variant described herein into the host cell.

In another aspect, the invention provides methods of producing isoprene, comprising: (a) culturing the host cells comprising heterologous polynucleotide sequences encoding any isoprene synthase variant described herein under suitable culture conditions for production of isoprene; and (b) producing the isoprene. In one embodiment, the method further comprises (c) recovering the isoprene.

In another aspect, the invention provides methods of producing isoprene, comprising: (a) providing: (i) a host cell; and (ii) a nucleic acid encoding any isoprene synthase variant described herein in operable combination with a promoter; (b) introducing the nucleic acid into the host cell to produce a transformed host cell; and (c) culturing the transformed host cells under suitable culture conditions for production of isoprene. In one embodiment, the method further comprises (d) recovering the isoprene.

In another aspect, the invention provides methods of producing an isoprene synthase variant, comprising: (a) providing: (i) a host cell; and (ii) a nucleic acid encoding any isoprene synthase variant described herein in operable combination with a promoter; (b) introducing the nucleic acid into the host cell to produce a transformed host cell; and (c) culturing the transformed host cells under suitable culture conditions for production of the isoprene synthase variant. In one embodiment, the method further comprises isolating the isoprene synthase variant.

In another aspect, the invention provides methods of screening an isoprene synthase variant, comprising: (a) contacting a host cell with a medium comprising about 10 μM to about 70 μM IPTG, and about 5 mM to about 20 mM mevalonic acid (MVA), wherein the host cell comprises a nucleic acid encoding an isoprene synthase variant in operable combination with a promoter; and (b) measuring the growth rate of the host cell; wherein an increased growth rate indicates an isoprene synthase variant with an increased ability to convert DMAPP to isoprene within the host cell. In one embodiment, the IPTG is present in the medium at a concentration from about 10 μM to about 60 μM. In another embodiment, the IPTG is present in the medium at a concentration from about 20 μM to about 60 μM. In another embodiment, the is present in the medium at a concentration from about 40 μM to about 60 μM. In another embodiment, the IPTG is present in the medium at a concentration of about 50 μM. In another embodiment, the MVA is present in the medium at a concentration of about 5 mM to about 20 mM. In another embodiment, the MVA is present in the medium at a concentration of about 7 mM to about 15 mM. In another embodiment, the MVA is present in the medium at a concentration of about 8 mM to about 12 mM. In another embodiment, the MVA is present in the medium at a concentration of about 10 mM. In one embodiment, the host cell is MD09-170.

Also provided is an expression vector comprising a polynucleotide sequence encoding the isoprene synthase variant in operable combination with a promoter.

Also provided is a lysate of the host cell, wherein the lysate further comprises lysozyme. In some embodiments, the lysate has a neutral pH (6.5 to 7.5), while in other embodiments the lysate has a basic pH (above 7.5 and below 9.5). The present invention further provides methods of detecting isoprene synthase activity, comprising: (a) culturing host cells comprising the expression vector under conditions suitable for producing the isoprene synthase variant; (b) lysing the host cells with a lysis buffer comprising lysozyme to produce a cell lysate; and (c) detecting isoprene synthase activity in the cell lysate by measuring isoprene production from dimethylallyl diphosphate (DMAPP).

BRIEF DESCRIPTION OF THE DRAWINGS

FIG. 20A-B depicts the sequence MEA *P. alba* (SEQ ID NO: 1).

FIG. 42 shows monomer view of wild type IspS showing the location of sites from Table 23 (A). $Mg^{2+}$ (spheres) are placed based on a structural alignment with PDB 1N24. B) Close-up view of sites in A.

GENERAL DESCRIPTION OF THE INVENTION

Figure 1:
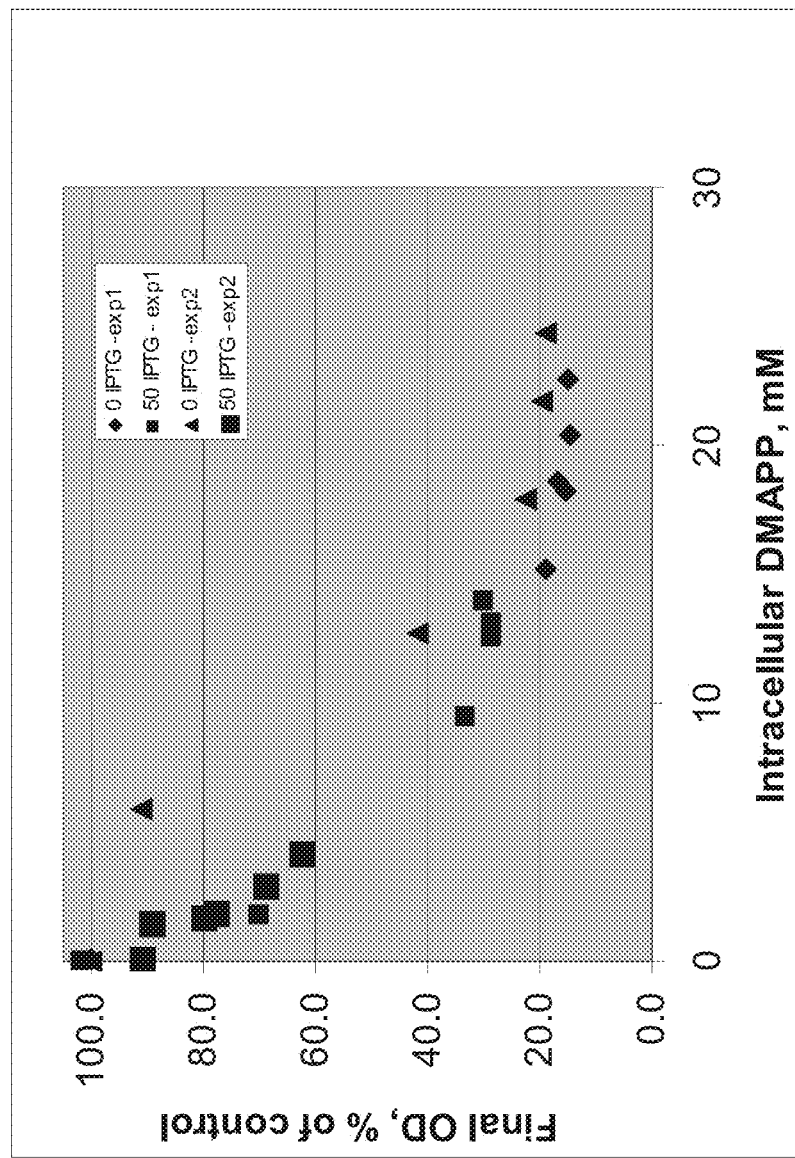
FIG. 1 shows the relationship between growth and DMAPP concentration in assay strain. DW425 was grown in the presence of various concentrations of mevalonate (0, 10, 20, 30, 40, 50 mM mevalonate in exp1, and 0, 2.5, 5, 10, 20 mM mevalonate in expt2) and IPTG (0 μM IPTG and 50 μM IPTG). Cells were harvested and collected for metabolite analysis upon completion of the growth experiment.

The present invention provides methods and compositions comprising at least one isoprene synthase variant enzyme. The variant comprises one or more amino acid residue substitution(s) from a parent isoprene synthase polypeptide, wherein the parent isoprene synthase may be a wild type or non-wild type sequence. The invention provides amino acid residue substitutions at particular positions within the polypeptide, wherein the substitution may result in at least one improved property as compared to its parent sequence or a reference sequence. In some particularly preferred embodiments, at least one improved property is selected from but not limited to the group consisting of: specific productivity, yield, and cellular performance index. In particular, the present invention provides variant plant isoprene synthases for increased isoprene production in host cells. Biosynthetically produced isoprene of the present invention finds use in the manufacture of rubber, polymers, and elastomers.

The practice of the present invention will employ, unless otherwise indicated, conventional techniques of protein chemistry, molecular biology (including recombinant techniques), microbiology, cell biology, biochemistry, nucleic acid chemistry, and enzymology, which are within the skill of the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly and individually referred to herein as "Sambrook"). *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987, including supplements through 2001); *PCR: The Polymerase Chain Reaction*, (Mullis et al., eds., 1994); *Current Protocols in Nucleic Acid Chemistry* John Wiley & Sons, Inc., New York, 2000); and Agrawal, ed., *Protocols for Oligonucleotides and Analogs, Synthesis and Properties* Humana Press Inc., New Jersey, 1993). Accordingly, the terms defined immediately below are more fully described by reference to the Specification as a whole.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, a number of terms are defined below.

DEFINITIONS

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Accordingly, the terms defined immediately below are more fully described by reference to the Specification as a whole.

"X" refers to any amino acid residue. However, when in the context of an amino acid substitution (e.g. "X003C"), it is to be understood that "X" refers to an amino acid residue other than the amino acid residue resulting from the substitution (e.g., X is an amino acid residue other than C). In some embodiments, the additional zeros in front of the residue position are not included, thus for example "X003" can also be referred to as "X3" to refer to residue position 3.

"Isoprene" refers to 2-methyl-1,3-butadiene (CAS#78-79-5). It can refer to the direct and final volatile C5 hydrocarbon product from the elimination of pyrophosphate from 3,3-dimethylallyl pyrophosphate (DMAPP). It may not involve the linking or polymerization of one or more isopentenyl diphosphate (IPP) molecules to one or more DMAPP molecules. Isoprene is not limited by the method of its manufacture.

As used herein, the terms "isoprene synthase," "isoprene synthase variant", and "IspS," refer to enzymes that catalyze the elimination of pyrophosphate from diemethylallyl diphosphate (DMAPP) to form isoprene. An "isoprene synthase" may be a wild type sequence or an isoprene synthase variant.

An "isoprene synthase variant" indicates a non-wild type polypeptide having isoprene synthase activity. One skilled in the art can measure isoprene synthase activity using known methods. See, for example, by GC-MS (see, e.g., WO 2009/132220, Example 3) or Silver et al., J. Biol. Chem. 270: 13010-13016, 1995. Variants may have substitutions, additions, deletions, and/or truncations from a wild type isoprene synthase sequence. Variants may have substitutions, additions, deletions, and/or truncations from a non-wild type isoprene synthase sequence. The variants described herein contain at least one amino acid residue substitution from a parent isoprene synthase polypeptide. In some embodiments, the parent isoprene synthase polypeptide is a wild type sequence. In some embodiments, the parent isoprene synthase polypeptide is a non-wild type sequence. In various embodiments, the variant will have at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild type isoprene synthase. In various embodiments, the variant will have at least about 40%, at least about 50%, at least about 60%, at least about 70%, at least about 80%, at least about 90%, at least about 91%, at least about 92%, at least about 93%, at least about 94%, at least about 95%, at least about 96%, at least about 97%, at least about 98%, at least about 99% sequence identity to a wild type isoprene synthase. In various embodiments, the number of differing amino acid residues between the variant and the wild type may be one or more, e.g. 1, 2, 3, 4, 5, 10, 15, 20, 30, 40, 50, or more amino acid residues. Wild type isoprene synthases can include any isoprene synthases from plants, for example, kudzu isoprene synthases, poplar isoprene synthases, English oak isoprene synthases, and willow isoprene synthases.

As used herein, the term "naturally-occurring" refers to anything (e.g., proteins, amino acids, or nucleic acid sequences) that is found in nature (e.g., has not been manipulated by means of recombinant or chemical methods). As used herein, the term "non-naturally occurring" refers to anything that is not found in nature (e.g., recombinantly produced or chemically synthesized proteins, amino acids, or nucleic acid sequences produced in the laboratory).

As used herein, an amino acid residue of an amino acid sequence of interest that "corresponds to" or is "corresponding to" or in "correspondence with" an amino acid residue of a reference amino acid sequence indicates that the amino acid residue of the sequence of interest is at a location homologous or equivalent to an enumerated residue in the reference amino acid sequence. One skilled in the art can determine whether a particular amino acid residue position in a polypeptide corresponds to that of a homologous reference sequence. For example, the sequence of an isoprene synthase polypeptide may be aligned with that of a reference sequence (e.g. SEQ ID NO: 1 (FIG. 20) using known techniques (e.g., basic local alignment search tool (BLAST), ClustalW2, Structure based sequences alignment program (STRAP), or the like). In addition, crystal structure coordinates of a reference sequence may be used as an aid in determining a homologous polypeptide residue's three dimensional structure (see, for example, PCT/US2010/032134 (WO 2010/124146)). In another aspect, equivalent residues may be identified by determining homology at the level of tertiary structure. Using such methods, the amino acid residues of an isoprene synthase polypeptide or isoprene synthase variant may be numbered according to the corresponding amino acid residue position numbering of the reference sequence. For example, the amino acid sequence of SEQ ID NO: 1 (FIG. 20) may be used for determining amino acid residue position numbering of each amino acid residue of an isoprene synthase variant of interest.

The term "identical" in the context of two nucleic acids or polypeptide sequences refers to the residues in the two sequences that are the same when aligned for maximum correspondence, as measured using one of the following sequence comparison or analysis algorithms.

As used herein, "homology" refers to sequence similarity or identity, with identity being preferred. Homology may be determined using standard techniques known in the art (see, e.g., Smith and Waterman, Adv. Appl. Math. 2:482 [1981]; Needleman and Wunsch, J. Mol. Biol. 48:443 [1970\; Pearson and Lipman, Proc. Natl. Acad. Sci. USA 85:2444 [1988]; software programs such as GAP, BESTFIT, FASTA, and TFASTA in the Wisconsin Genetics Software Package (Genetics Computer Group, Madison, Wis.); and Devereux et al., Nucl. Acid Res. 12:387-395 [1984]). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (see Feng and Doolittle, J. Mol. Evol. 35:351-360 [1987]). The method is similar to that described by Higgins and Sharp (see Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (see Altschul et al., J. Mol. Biol. 215:403-410 [1990]; and Karlin and Altschul, Proc. Natl. Acad. Sci. USA 90:5873-5787 [1993]). A particularly useful BLAST program is the WU-BLAST-2 program (see Altschul et al., Meth. Enzymol. 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (see Altschul, et al., J. Mol. Biol., 215:403-410 [1990]). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915 [1992]) alignments (B) of 50, expectation (E) of 10, M'S, N'-4, and a comparison of both strands.

The BLAST algorithm then performs a statistical analysis of the similarity between two sequences (see, e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a isoprene synthase nucleic acid of this invention if the smallest sum probability in a comparison of the test nucleic acid to a isoprene synthase nucleic acid is less than about 0.1, more preferably less than about 0.01, and most preferably less than about 0.001. Where the test nucleic acid encodes an isoprene synthase polypeptide, it is considered similar to a specified isoprene synthase nucleic acid if the comparison results in a smallest sum probability of less than about 0.5, and more preferably less than about 0.2.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference amino acid sequence means that the subject amino acid sequence is identical (i.e., on an amino acid-by-amino acid basis) by a specified percentage to the reference amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Percent sequence identity" or "% identity" or "% sequence identity" of a subject nucleic acid sequence to a reference nucleic acid sequence means that the subject nucleic acid sequence is identical (i.e., on a nucleotide-by-nucleotide basis for a polynucleotide sequence) by a specified percentage to the reference sequence over a comparison length when the sequences are optimally aligned. Thus, 80% nucleotide sequence identity or 80% identity with respect to two nucleic acid sequences means that 80% of the nucleotide residues in two optimally aligned nucleic acid sequences are identical.

The "percent sequence identity" or "% sequence identity" or "% identity" of a subject sequence to a reference sequence can be calculated by optimally aligning the two sequences and comparing the two optimally aligned sequences over the comparison length. The number of positions in the optimal alignment at which identical residues occur in both sequences is determined, thereby providing the number of matched positions, and the number of matched positions is then divided by the total number of positions of the comparison length (which, unless otherwise specified, is the length of the reference sequence). The resulting number is multiplied by 100 to yield the percent sequence identity of the subject sequence to the reference sequence.

"Optimal alignment" or "optimally aligned" refers to the alignment of two (or more) sequences giving the highest percent identity score. For example, optimal alignment of two polypeptide sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

Two sequences (e.g., polypeptide sequences) may be deemed "optimally aligned" when they are aligned using defined parameters, such as a defined amino acid substitution matrix, gap existence penalty (also termed gap open penalty), and gap extension penalty, so as to achieve the highest similarity score possible for that pair of sequences. The BLOSUM62 scoring matrix (see Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to e.g., the BLASTP program for amino acid sequences and the BLASTN program for nucleic acid sequences (see, e.g., Altschul et al., Nucleic Acids Res. 25(17):3389-3402 (1997); see also the National Center for Biotechnology Information (NCBI) website) or CLUSTALW program.

A polypeptide of interest may be said to be "substantially identical" to a reference polypeptide if the polypeptide of interest comprises an amino acid sequence having at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, e.g., where the two peptides differ only by a conservative amino acid substitution or one or more conservative amino acid substitutions.

A nucleic acid of interest may be said to be "substantially identical" to a reference nucleic acid if the nucleic acid of interest comprises a nucleotide sequence having at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

A "nucleic acid" refers to two or more deoxyribonucleotides and/or ribonucleotides in either single or double-stranded form. It is to be understood that mutations, including single nucleotide mutations, can occur within a nucleic acid as defined herein.

A "recombinant nucleic acid" refers to a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of an anaerobic microorganism, or which exists as a separate molecule (e.g., a cDNA, a genomic DNA fragment, or a cDNA fragment produced by PCR or restriction endonuclease digestion) independent of other sequences. A recombinant nucleic acid may be obtained using molecular biology techniques that are known in the art, or part or all of a recombinant nucleic acid may be chemically synthesized.

A "heterologous nucleic acid" can be a nucleic acid whose nucleic acid sequence is from another species than the host cell or another strain of the same species of the host cell. In some embodiments, the sequence is not identical to that of another nucleic acid naturally found in the same host cell. In some embodiments, a heterologous nucleic acid is not identical to a wild-type nucleic acid that is found in the same host cell in nature.

An "endogenous nucleic acid" is a nucleic acid whose nucleic acid sequence is naturally found in the host cell. In some embodiments, an endogenous nucleic acid is identical to a wild-type nucleic acid that is found in the host cell in nature. In some embodiments, one or more copies of endogenous nucleic acids are introduced into a host cell.

A nucleic acid or protein of the invention may be in isolated or purified form. As used herein, "isolated," with respect to nucleic acid or protein, means separated from other components, such as, but not limited to a cell or cell culture. It is preferably in a homogeneous state although it can be in either a dry or aqueous solution. Purity and homogeneity are typically determined using analytical chemistry techniques, such as polyacrylamide gel electrophoresis or high performance liquid chromatography. A protein or nucleic acid that is the predominant species present in a preparation is substantially purified. The term "purified" denotes that a nucleic acid or protein gives rise to essentially one band in an electrophoretic gel. Particularly, "purified" means that when isolated, the isolate contains at least 90%, at least 95%, at least 98%, or more preferably at least 99% of nucleic acid or protein by weight of the isolate.

Purified polypeptides may be obtained by a number of methods including, for example, laboratory synthesis, chromatography, preparative electrophoresis, gel electrophoresis, centrifugation, precipitation, affinity purification, etc. (see, generally, R Scopes, Protein Purification, Springer-Verlag, N.Y. (1982), Deutscher, Methods in Enzymology Vol. 182: Guide to Protein Purification, Academic Press, Inc. N.Y. (1990)).

"Polypeptides" includes polypeptides, proteins, peptides, fragments of polypeptides, and fusion polypeptides. It is also understood that a polypeptide may be coded for by more than one nucleotide sequence due to the degeneracy of the genetic code.

A "heterologous polypeptide" is a polypeptide encoded by a heterologous nucleic acid. In some embodiments, the sequence is not identical to that of another polypeptide encoded by a nucleic acid naturally found in the same host cell. Examples of heterologous proteins include enzymes such as isoprene synthases. In some embodiments, the genes encoding the proteins are naturally occurring genes, while in other embodiments mutated and/or synthetic genes are used.

An "endogenous polypeptide" is a polypeptide whose amino acid sequence is naturally found in the host cell. In some embodiments, an endogenous polypeptide is identical to a wild-type polypeptide that is found in the host cell in nature.

As used herein, the term "terpenoid" or "isoprenoids" refers to a large and diverse class of naturally-occurring organic chemicals similar to terpenes. Terpenoids are derived from five-carbon isoprene units assembled and modified in a variety of ways, and are classified in groups based on the number of isoprene units used in group members. Hemiterpenoids have one isoprene unit. Monoterpenoids have two isoprene units. Sesquiterpenoids have three isoprene units. Diterpenoids have four isoprene units. Sesterterpenoids have five isoprene units. Triterpenoids have six isoprene units. Tetraterpenoids have eight isoprene units. Polyterpenoids have more than eight isoprene units.

As used herein, the term "headspace" refers to the vapor/air mixture trapped above a solid or liquid sample in a sealed vessel.

As used herein, the singular terms "a," "an," and "the" include the plural reference unless the context clearly indicates otherwise.

Unless otherwise indicated, nucleic acids are written left to right in 5' to 3' orientation; amino acid sequences are written left to right in amino to carboxy orientation, respectively.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Reference to "about" a value or parameter herein also includes (and describes) embodiments that are directed to that value or parameter per se.

It is understood that all aspects and embodiments of the invention described herein include "comprising," "consisting," and "consisting essentially of" aspects and embodiments. It is to be understood that methods or compositions "consisting essentially of" the recited elements include only the specified steps or materials and those that do not materially affect the basic and novel characteristics of those methods and compositions.

It is to be understood that this invention is not limited to the particular methodology, protocols, and reagents described, as these may vary, depending upon the context they are used by those of skill in the art.

DETAILED DESCRIPTION OF THE INVENTION

Isoprene monomer is employed in the manufacture of polyisoprene and various copolymers (with isobutylene, butadiene, styrene, or other monomers). Building a strain (prokaryotic or eukaryotic) capable of producing commercially viable levels of isoprene requires optimization of part of or the entire DXP or MVA pathway or both MVA and DXP pathways. A key enzyme in the pathway is isoprene synthase (IspS), which converts the precursor DMAPP to isoprene.

Isoprene synthases (IspS) that have been identified include those from plants such as poplar, English oak and kudzu vine. Some of the plant IspS enzymes identified have been partially characterized in part by expression in *E. coli* and some of the kinetic parameters of these enzymes have been determined in vitro with purified protein. However, the kinetic parameters ($K_m$, rate, etc.) of the native IspS enzymes are insufficient for commercial production of isoprene in a biological host. Thus, one problem to be solved is the provision of isoprene synthase variants (e.g. with substitutions at specific residues) which have improved properties such that a greater amount of isoprene can be biologically produced.

To solve this problem as described herein, an isoprene synthase may be expressed in a host (e.g. a bacterial host). In addition, isoprene synthase variants are engineered for a change in a property of interest. Characterization of IspS variants is accomplished via any means or test suitable and is preferably based on the assessment of properties of interest. These variants are useful for the commercial production of isoprene in a biological host.

Properties of interest include, but are not limited to: increased intracellular activity, specific productivity of cells expressing IspS (g/L/OD/hr) (described in greater detail below), yield (g/g glucose) (e.g., Equation 2 below), and cellular performance index (grams of isoprene/gram of dry cell weight). Without being bound by theory, these properties can be achieved by one or a combination of any of the following properties of IspS: increased cellular viability (e.g., better growth of host cells due to relief of substrate (e.g., DMAPP) toxicity or reduced isoprene synthase enzyme toxicity to the host cell), increased $k_{cat}$, decreased $K_m$, increased specific activity, increased solubility, decreased insolubility, improved ribosome binding, increased translation initiation rate, increased translation elongation rate, increased transcription initiation rate, increased transcription elongation rate, decreased secondary structure of DNA, decreased secondary structure of RNA, increased secondary structure of DNA, increased secondary structure of RNA, increased folding rates, increased affinity for intracellular chaperones, increased stability, decreased protein turnover, decreased exposure to intracellular protease, decreased affinity for intracellular protease, decreased localization to the periplasm, improved localization to the cytoplasm, decreased inclusion body formation, decreased membrane localization, increased expression due to a more favorable codon, increased DNA stability, increased RNA stability, and decreased RNA degradation. In brief, any mutation that has a positive effect on the properties of nucleic acid sequences (DNA and RNA) encoding or expressing the IspS variant, or the biochemical properties of the IspS enzyme itself, could allow for greater activity within the cell. Other properties of interest include pH optima, temperature stability (e.g., $T_m$ value), as well as sensitivity to potential inhibitors including substrate or product inhibition. Oxidative and proteolytic stability are also of interest. Furthermore, activation or inhibition due to metal ion effects and ionic strength is of interest.

These properties and parameters can be assessed by the conversion of DMAPP to isoprene in vitro with purified or partially purified isoprene synthase or in vivo in the context of a host organism such as *E. coli* expressing the DXP pathway, the MVA pathway, or both. It is contemplated that enzymes having various degrees of stability, solubility, activity, and/or expression level in one or more of test conditions will find use in the present invention for the production of isoprene in a diversity of hosts.

The invention features compositions and methods for the production of increased amounts of isoprene. In particular, these compositions and methods may increase the rate of isoprene production and the total amount of isoprene that is produced. The biosynthetic processes for isoprene production described herein are a desirable alternative to using natural rubber. As discussed further below, the amount of isoprene produced by cells can be greatly increased by introducing a heterologous nucleic acid encoding an isoprene synthase (IspS) variant into the cells.

Additionally, isoprene production by cells containing a heterologous isoprene synthase nucleic acid can be enhanced by increasing the amount of one or more DXP pathway polypeptides (e.g., a 1-deoxy-D-xylulose-5-phosphate synthase (DXS) polypeptide) and/or an isopentenyl diphosphate isomerase (IDI) polypeptide, expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

Figure 22:
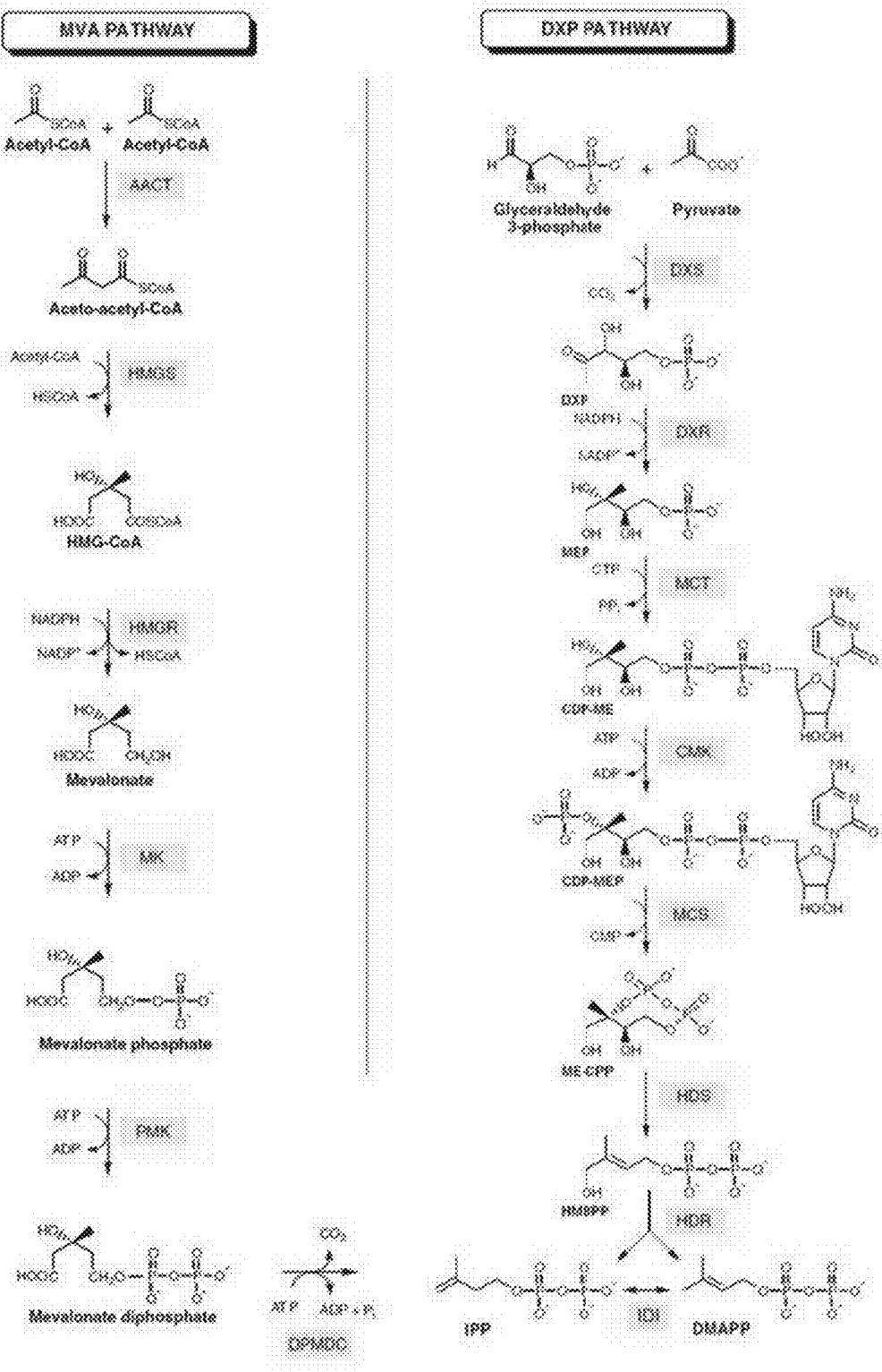
FIG. 22 shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34. Assay: J. Bacteriol., 184: 2116-2122, 2002; MVK; Mevalonate kinase, ERG12, EC 2.7.1.36. Assay: Curr Genet. 19:9-14, 1991. PMK; Phosphomevalonate kinase, ERG8, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.
Figure 23:
FIG. 23 shows a monomer view of wild type IspS showing the location of sites where substitutions are not tolerated.
Figure 24:
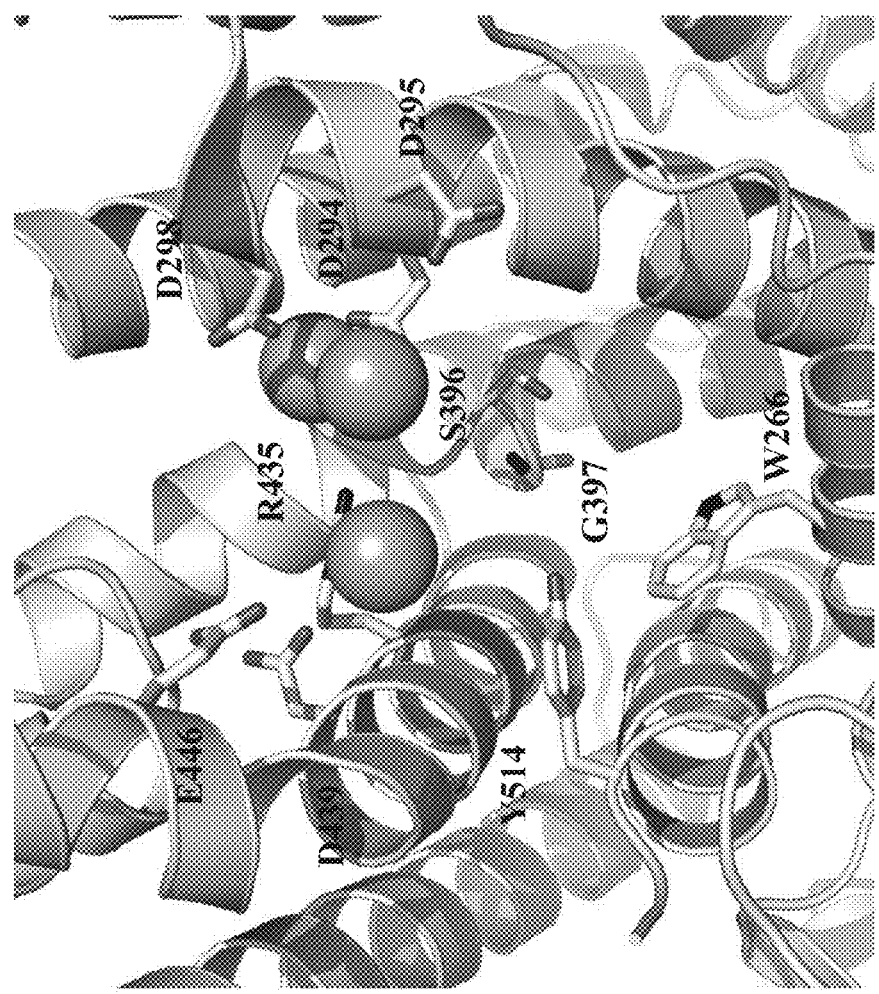
FIG. 24 shows the location of residues in the active site of IspS that do not tolerate substitution. $Mg^{2+}$ (spheres) are placed based on a structural alignment with PDB 1N24.

The encoded DXS and IDI polypeptides are part of the DXP pathway for the biosynthesis of isoprene (FIG. 22). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount of IPP that is converted into DMAPP, which in turn is converted into isoprene.

As is further detailed below, in some embodiments, the production of isoprene by cells containing a heterologous isoprene synthase nucleic acid can be augmented by increasing expression of one or more MVA polypeptide(s) in the cells (FIG. 22). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain the entire MVA pathway, which includes AA-CoA thiolase, HMG-CoA synthase, HMG-CoA reductase, MVK, PMK, MVD, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

In some embodiments, at least a portion of the cells maintain the heterologous isoprene synthase, DXS, IDI, other DXP pathway and/or MVA pathway nucleic acids for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, other DXP pathway and/or MVA pathway nucleic acids also comprises a selective marker, such as a kanamycin, ampicillin, carbenicillin, gentamicin, hygromycin, phleomycin, bleomycin, neomycin, or chloramphenicol antibiotic resistance nucleic acid Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., J. Biol. Chem. 270:13010-13016, 1995 and references therein.

In one embodiment, DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 µl of 1M $MgCl_2$, 1 mM (250 µg/ml) DMAPP, 65 µl of Plant Extract Buffer (PEB) (50 mM Tris-HCl, pH 8.0, 20 mM $MgCl_2$, 5% glycerol, and 2 mM DTT) is added to 25 µl of cell extract in a 20 ml Headspace vial with a metal screw cap and teflon coated silicon septum (Agilent Technologies) and cultured at 37° C. for 15 minutes with shaking. The reaction is quenched by adding 200 µl of 250 mM EDTA or by heat inactivation, and isoprene is quantified by GC/MS.

Isoprene Synthase Parent Sequences

Isoprene synthase variants may be generated from a parent isoprene synthase, wherein the parent isoprene synthase may be an isoprene synthase as described herein, including wild type and non-wild type isoprene synthases. Exemplary parent isoprene synthase nucleic acids include nucleic acids that encode a polypeptide, fragment of a polypeptide, peptide, or fusion polypeptide that has at least one activity of an isoprene synthase polypeptide. Exemplary parent isoprene synthase polypeptides and nucleic acids include naturally-occurring polypeptides and nucleic acids from any of the source organisms described herein as well as variant polypeptides and nucleic acids derived from any of the source organisms described herein.

In some embodiments, the parent isoprene synthase is from the family Fabaceae, the family Salicaceae, or the family Fagaceae. In some embodiments, the parent isoprene synthase polypeptide or nucleic acid is a naturally-occurring polypeptide or nucleic acid from *Pueraria montana* (kudzu) (Sharkey et al., Plant Physiology 137: 700-712, 2005), poplar (such as *Populus alba* x *tremula* CAC35696, Miller et al., Planta 213: 483-487, 2001) or *Populus alba*, aspen (such as *Populus tremuloides*) Silver et al., JBC 270(22): 13010-1316, l995), or English Oak (*Quercus robur*) (Zimmer et al., WO 98/02550). Suitable parent isoprene synthases include, but are not limited to, those identified by GenBank Accession Nos. AY341431, AY316691, AB198180, AJ294819.1, EU693027.1, EF638224.1, AM410988.1, EF147555.1, AY279379, AJ457070, and AY182241. Additional parent sequences are described in PCT/US2009/041581 (WO 2009/132220) and PCT/US2010/032134 (WO 2010/124146).

Figure 21A:
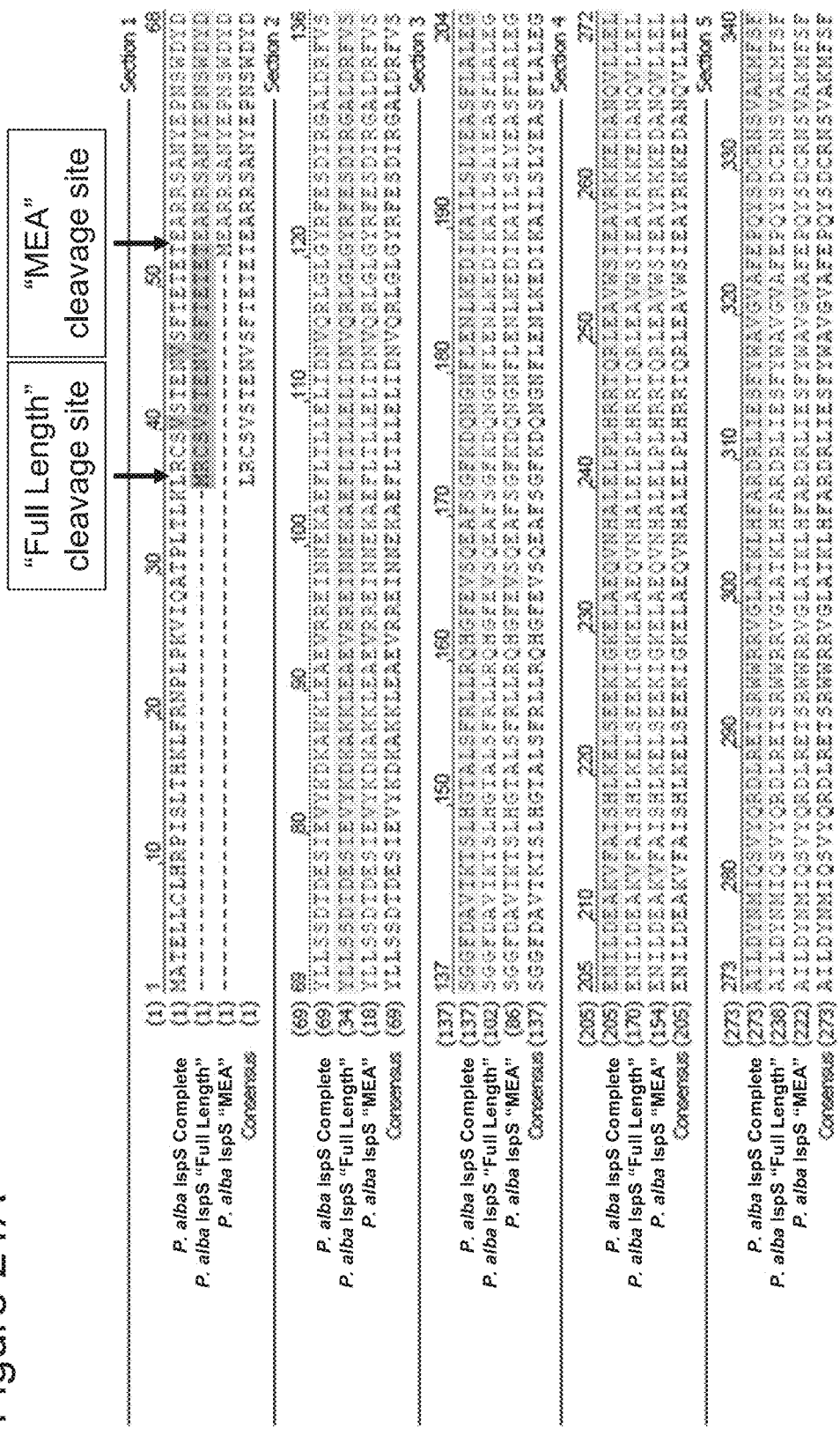
FIGS. 21A-B show the alignment of N-terminally cleaved *P. alba* IspS sequences (SEQ ID NO:38, SEQ ID NO:39, SEQ ID NO:1, SEQ ID NO:40).
Figure 21B:
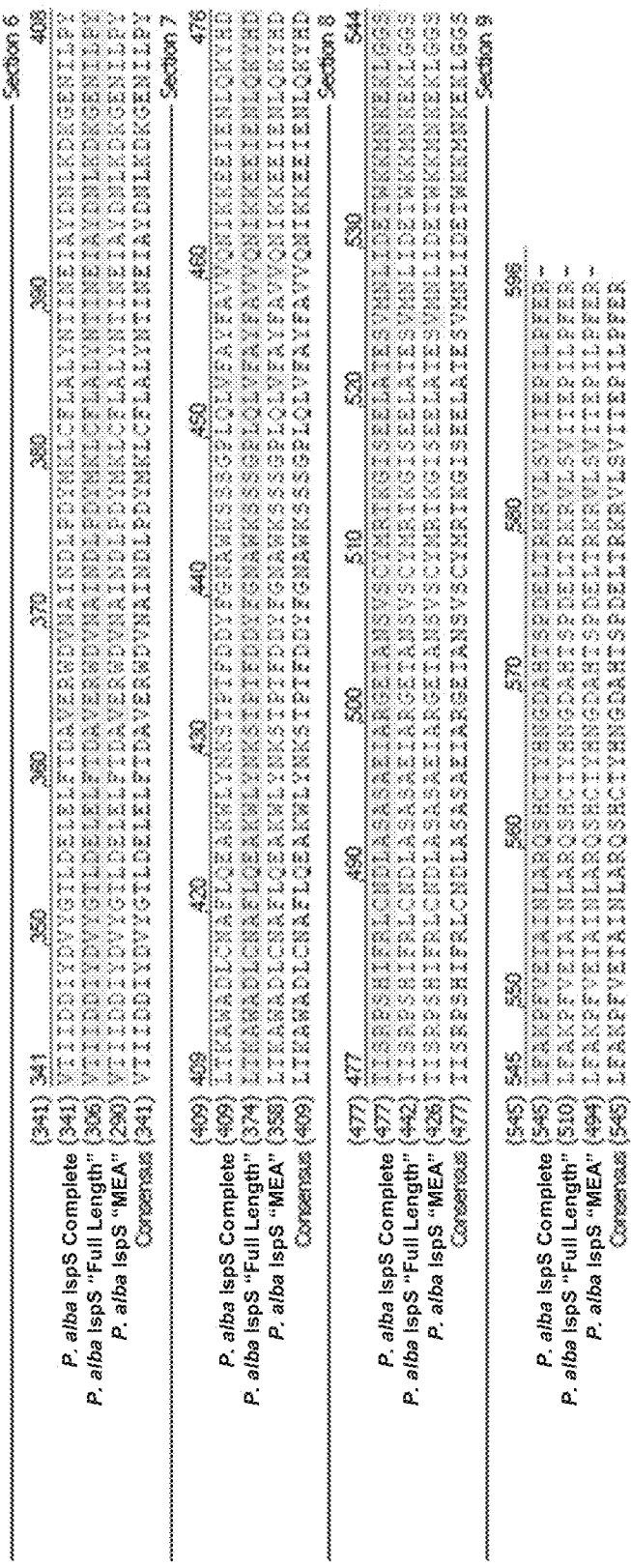

In various embodiments, the parent isoprene synthase has at least about 50%, at least about 60%, at least about 70%, at least about 80%, at least about 90%, at least about 92%, at least about 94%, at least about 96%, at least about 98%, at least about 99% sequence identity with MEA *P. alba*. In other embodiments, the parent isoprene synthase has at least about 50%, at least about 60%, at least about 70%, at least about 80%, at least about 90%, at least about 92%, at least about 94%, at least about 96%, at least about 98%, at least about 99% sequence identity with full-length *P. alba* or complete *P. alba* (see, e.g., FIGS. 21A and 21B).

Several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

Isoprene Synthase Variants

Polypeptides, e.g. isoprene synthase, have a three-dimensional structure determined by the primary amino acid sequence and the environment surrounding the polypeptide. This three-dimensional structure establishes the polypeptide's activity, stability, binding affinity, binding specificity, and other biochemical attributes. Thus, knowledge of a protein's three-dimensional structure can provide much guidance in designing improvements to its biological activity; for example, greater catalytic activity and/or solubility. Crystal structure coordinates for various isoprene synthases are described in WO2009/132220 and PCT/US2010/032134 (WO 2010/124146).

The inventors have identified residue locations, the mutation (e.g., substitution) of which in a parent isoprene synthase may result in one or more improved properties in the variant. In one aspect of the invention, the mutation is a substitution at a location corresponding to the position in MEA *P. alba* isoprene synthase (SEQ ID NO:1) as denoted below.

| Location | Definition |
|---|---|
| N-term | Residues 1-215 |
| Hinge Region | Residues 216-245 |
| C-term | Residues 246-544 |
| N-term helices | Residues 134-179 |
| Dimer Interface | Residues 240-255 and 316-353 |
| Substrate Capture Loops | Residues 441-454 and 515-527 |
| Active Site | Residues within 8 Å of active site based on PDB 3N0G |
| Buried | Surface Accessibility below 35% and located internally |
| Surface | Residues located on the surface of the structure |
| Surface Loop | Residues in loops located on the surface of the structure |

As such, in one aspect, isoprene variants with one or more substitution(s) in these locations (e.g., as described in Examples 7-9) can be made and screened for improved isoprene synthase properties, which are described in greater detail below. Exemplary properties that one of skill can use for identification purposes include, but are not limited to, increased specific activity as compared to specific activity of MEA P. alba isoprene synthase and growth of a recombinant host cell in which the isoprene synthase variant is being expressed as compared to the growth a recombinant host cell expressing MEA P. alba isoprene synthase under similar growth conditions. In one aspect, substitutions can be made in the N-terminal helices or at residues that would have some interaction with residues in the N-terminal helices such that it improves isoprene synthase properties.

The sequence of MEA P. alba isoprene synthase is as follows (and is also shown in FIG. 20):

```
                                             (SEQ ID NO: 1)
MEARRSANYEPNSWDYDYLLSSDTDESIEVYKDKAKKLEAEVRREINNEK

AEFLTLLELIDNVQRLGLGYRFESDIRGALDRFVSSGGFDAVTKTSLHGT

ALSFRLLRQHGFEVSQEAFSGFKDQNGNFLENLKEDIKAILSLYEASFLA

LEGENILDEAKVFAISHLKELSEEKIGKELAEQVNHALELPLHRRTQRLE

AVWSIEAYRKKEDANQVLLELAILDYNMIQSVYQRDLRETSRWWRRVGLA

TKLHFARDRLIESFYWAVGVAFEPQYSDCRNSVAKMFSFVTIIDDIYDVY

GTLDELELFTDAVERWDVNAINDLPDYMKLCFLALYNTINEIAYDNLKDK

GENILPYLTKAWADLCNAFLQEAKWLYNKSTPTFDDYFGNAWKSSSGPLQ

LVFAYFAVVQNIKKEEIENLQKYHDTISRPSHIFRLCNDLASASAEIARG

ETANSVSCYMRTKGISEELATESVMNLIDETWKKMNKEKLGGSLFAKPFV

ETAINLARQSHCTYHNGDAHTSPDELTRKRVLSVITEPILPFER.
```

Combinations of the substitutions described herein can be made and screened for improved isoprene synthase properties. Non-limiting examples of isoprene synthase variants with combinations of substitutions that have one or more improved isoprene synthase properties are described in Table 25 (Variants 1-27) and Table 26 (Variants 1-12).

In one aspect, residues identified for mutation of MEA P. alba include those listed in Table A. Residues and residue numbering in Table A corresponds to the residue numbering of the MEA P. alba shown in SEQ ID NO:1 (FIG. 20).

TABLE A

| Mutagenesis Sites | | |
|---|---|---|
| Position | Residue | Selection Criteria |
| 3 | A | surface hydrophobic |
| 7 | A | symmetry contact |
| 9 | Y | symmetry contact |
| 12 | N | Conservation |
| 13 | S | Conservation |
| 16 | Y | N-terminal loop |
| 18 | Y | N-terminal loop |
| 20 | L | Conservation |
| 23 | D | Conservation |
| 25 | D | surface hydrophilic |
| 26 | E | symmetry contact |
| 27 | S | surface hydrophilic |
| 33 | D | symmetry contact |
| 36 | K | symmetry contact |
| 44 | R | symmetry contact |
| 50 | K | surface hydrophilic |
| 53 | F | Conservation |
| 59 | L | surface hydrophobic |
| 69 | G | Conservation |
| 74 | S | surface hydrophilic |
| 78 | G | Conservation |

TABLE A-continued

| Mutagenesis Sites | | |
|---|---|---|
| Position | Residue | Selection Criteria |
| 81 | D | surface hydrophilic |
| 87 | G | surface hydrophobic |
| 99 | G | Conservation |
| 116 | Q | Conservation |
| 117 | E | symmetry contact |
| 120 | S | surface hydrophilic |
| 121 | G | surface loop |
| 125 | Q | surface hydrophilic |
| 127 | G | Conservation |
| 139 | A | Conservation |
| 165 | I | surface hydrophobic |
| 173 | E | surface hydrophilic |
| 174 | E | symmetry contact |
| 177 | G | Conservation |
| 179 | E | surface hydrophilic |
| 194 | R | Conservation |
| 197 | Q | Conservation |
| 202 | V | Conservation |
| 216 | Q | Conservation |
| 240 | T | Conservation |
| 246 | R | symmetry contact |
| 251 | T | surface hydrophilic |
| 254 | H | Conservation |
| 287 | F | active site |
| 290 | V | active site |
| 308 | L | surface hydrophobic |
| 376 | L | flexible loops |
| 377 | Y | symmetry contact |
| 379 | K | Conservation |
| 389 | G | Conservation |
| 397 | G | active site |
| 400 | Q | hydrophobic pocket |
| 403 | F | active site |
| 421 | Q | Conservation |
| 426 | T | Conservation |
| 430 | P | Misc |
| 434 | F | active site |
| 445 | A | surface hydrophobic |
| 448 | A | Conservation |
| 457 | S | flexible loops |
| 462 | T | Conservation |
| 476 | N | surface hydrophilic |
| 487 | K | surface loop |
| 488 | E | surface loop |
| 489 | K | surface loop |
| 490 | L | surface loop |
| 491 | G | surface loop |
| 492 | G | surface loop |
| 493 | S | surface loop |
| 495 | F | surface loop |
| 496 | A | surface loop |
| 497 | K | surface loop |
| 498 | P | Conservation |
| 509 | Q | Conservation |
| 514 | Y | active site |
| 521 | T | Conservation |
| 539 | I | C-terminal |
| 540 | L | surface hydrophobic |
| 544 | R | Conservation |

As used in Table A, "surface hydrophobic" indicates a hydrophobic amino acid residue present on the surface of the protein, "surface hydrophilic" indicates a hydrophilic amino acid residue present on the surface of the protein, "symmetry contact" indicates a residue on the surface of the isoprene synthase molecule which contacts another isoprene synthase molecule in the crystal structure, "conservation" indicates a residue common to most terpene synthases, "N-terminal loop" indicates a residue present in the N-terminal loop of the protein, "surface loop" indicates a residue present in a surface loop of the protein, "active site" indicates a residue present in the active site of the protein, "flexible loop" indicates a residue present in a flexible loop region of the protein, "hydrophobic pocket" indicates a residue present in the hydrophobic pocket of the protein, and "C-terminal" indicates a residue present in the C-terminal region of the protein.

As further described in the Examples below, various isoprene synthase variants were made with substitutions at the residue locations shown in Table A. Any of the variants described herein (including in Tables A, B, the claims, or the Examples) may be used in the compositions and methods of the invention. Specific substitutions generated for MEA *P. alba* variants are shown in Table B.

TABLE B

Exemplary Amino Acid Substitutions for MEA *P. alba*

| | | | | | | | | | |
|---|---|---|---|---|---|---|---|---|---|
| A003C | A003D | A003E | A003F | A003G | A003H | A003I | A003K | A003L | A003M |
| A003N | A003P | A003Q | A003R | A003S | A003T | A003V | A003W | A003Y | A007C |
| A007D | A007E | A007F | A007G | A007H | A007I | A007K | A007L | A007M | A007N |
| A007P | A007Q | A007R | A007S | A007T | A007V | A007W | A007Y | Y009A | Y009C |
| Y009D | Y009E | Y009F | Y009G | Y009H | Y009I | Y009K | Y009L | Y009M | Y009N |
| Y009P | Y009Q | Y009R | Y009S | Y009T | Y009V | Y009W | N012A | N012C | N012D |
| N012E | N012F | N012G | N012H | N012I | N012K | N012L | N012M | N012P | N012Q |
| N012R | N012S | N012T | N012V | N012W | N012Y | S013A | S013C | S013D | S013E |
| S013F | S013G | S013H | S013I | S013K | S013L | S013M | S013N | S01P3 | S013Q |
| S013R | S013T | S013V | S013W | S013Y | Y016A | Y016C | Y016D | Y016E | Y016F |
| Y016G | Y016H | Y016I | Y016K | Y016L | Y016M | Y016N | Y016P | Y016Q | Y016R |
| Y016S | Y016T | Y016V | Y016W | Y018A | Y018C | Y018D | Y0E18 | Y018F | Y018G |
| Y018H | Y018I | Y018K | Y018L | Y018M | Y018N | Y018P | Y018Q | Y018R | Y018S |
| Y018T | Y018V | Y018W | L020A | L020C | L020D | L020E | L020F | L020G | L020H |
| L020I | L020K | L020M | L020N | L020P | L020Q | L020R | L020S | L020T | L020V |
| L020W | L020Y | D023A | D023C | D023E | D023F | D023G | D023H | D023I | D023K |
| D023L | D023M | D023N | D023P | D023Q | D023R | D023S | D023T | D023V | D023W |
| D023Y | D025A | D025C | D025E | D025F | D025G | D025H | D025I | D025K | D025L |
| D025M | D025N | D025P | D025Q | D025R | D025S | D025T | D025V | D025W | D025Y |
| E026A | E026C | E026D | E026F | E026G | E026H | E026I | E026K | E026L | E026M |
| E026N | E026P | E026Q | E026R | E026S | E026T | E026V | E026W | E026Y | S027A |
| S027C | S027D | S027E | S027F | S027G | S027H | S027I | S027K | S027L | S027M |
| S027N | S027P | S027Q | S0R27 | S027V | S027W | S027Y | D033A | D033C | D033E |
| D033F | D033G | D033H | D033I | D033K | D033L | D033M | D033N | D033P | D033Q |
| D033R | D033S | D033T | D033V | D033W | D033Y | K036A | K036C | K036D | K036E |
| K036F | K036G | K036G | K036I | K036L | K036M | K036N | K036P | K036Q | K036R |
| K036S | K036T | K036V | K036W | K036Y | R044A | R044C | R044D | R044E | R044F |
| R044G | R044H | R044I | R044K | R044L | R044M | R044N | R044P | R044Q | R044S |
| R044T | R044V | R044W | R044Y | K050A | K050C | K050D | K050E | K050F | K050G |
| K050H | K050I | K050L | K050M | K050N | K050P | K050Q | K050R | K050S | K050T |
| K050V | K050W | K050Y | F053A | F053C | F053D | F053E | F053G | F053H | F053I |
| F053K | F053L | F053M | F053N | F053P | F053Q | F053R | F053S | F053T | F053V |
| F053W | F053Y | L059A | L059C | L059D | L059E | L059F | L059G | L059H | L059I |
| L059K | L059M | L059N | L059P | L059Q | L059R | L059S | L059T | L059V | L059W |
| L059Y | G069A | G069C | G069D | G069E | G069F | G069H | G069I | G069K | G069L |
| G069M | G069N | G069P | G069Q | G069R | G069S | G069T | G069V | G069W | G069Y |
| S074A | S074C | S074D | S074E | S074F | S074G | S074H | S074I | S074K | S074L |
| S074M | S074N | S074P | S074Q | S074R | S074T | S074V | S074W | S074Y | G078A |
| G078C | G078D | G078E | G078F | G078H | G078I | G078K | G078L | G078M | G078N |
| G078P | G078Q | G078R | G078S | G078T | G078V | G078W | G078Y | D081A | D081C |
| D081E | D081G | D081H | D081I | D081K | D081L | D081M | D081N | D081P |
| D081Q | D081R | D081S | D081T | D081V | D081W | D081Y | G087A | G087C | G087D |
| G087E | G087F | G087H | G087I | G087K | G087L | G087M | G087N | G087P | G087Q |
| G087R | G087S | G087T | G087V | G087W | G087Y | G099A | G099C | G099D | G099E |
| G099F | G099H | G099I | G099K | G099L | G099M | G099N | G099P | G099Q | G099R |
| G099S | G099T | G099V | G099W | G099Y | Q116A | Q116C | Q116D | Q116E | Q116F |
| Q116G | Q116H | Q116I | Q116K | Q116L | Q116M | Q116N | Q116P | Q116R | Q116S |
| Q116T | Q116V | Q116W | Q116Y | E117A | E117C | E117D | E117F | E117G | E117H |
| E117I | E117K | E117L | E117M | E117N | E117P | E117Q | E117R | E117S | E117T |
| E117V | E117W | E117Y | S120A | S120C | S120D | S120E | S120F | S120G | S120H |
| S120I | S120K | S120L | S120M | S120N | S120P | S120Q | S120R | S120T | S120V |
| S120W | S120Y | G121A | G121C | G121D | G121E | G121F | G121H | G121I | G121K |
| G121L | G121M | G121N | G121P | G121Q | G121R | G121S | G121T | G121V | G121W |
| G121Y | Q125A | Q125C | Q125D | Q125E | Q125F | Q125G | Q125H | Q125I | Q125K |
| Q125L | Q125M | Q125N | Q125P | Q125R | Q125S | Q125T | Q125V | Q125W | Q125Y |
| G127A | G127C | G127D | G127E | G127F | G127H | G127I | G127K | G127L | G127M |
| G127N | G127P | G127Q | G127R | G127S | G127T | G127V | G127W | G127Y | A139C |
| A139D | A139E | A139F | A139G | A139H | A139I | A139K | A139L | A139M | A139N |
| A139P | A139Q | A139R | A139S | A139T | A139V | A139W | A139Y | I165A | I165C |
| I165D | I165E | I165F | I165G | I165H | I165K | I165L | I165M | I165N | I165P |
| I165Q | I165R | I165S | I165T | I165V | I165W | I165Y | E173A | E173C | E173D |
| E173F | E173H | E173I | E173K | E173L | E173M | E173N | E173P | E173Q |
| E173R | E173S | E173T | E173V | E173W | E173Y | E174A | E174C | E174D | E174F |
| E174G | E174H | E174I | E174K | E174L | E174M | E174N | E174P | E174Q | E174R |
| E174S | E174T | E174V | E174W | E174Y | G177A | G177C | G177D | G177E | G177F |
| G177H | G177I | G177L | G177M | G177N | G177P | G177Q | G177R | G177S |
| G177T | G177V | G177W | G177Y | E179A | E179C | E179D | E179F | E179G | E179H |
| E179I | E179K | E179L | E179M | E179N | E179P | E179Q | E179R | E179S | E179T |
| E179V | E179W | E179Y | R194A | R194C | R194D | R194E | R194F | R194G | R194H |
| R194I | R194K | R194L | R194M | R194N | R194P | R194Q | R194S | R194T | R194V |
| R194W | R194Y | Q197A | Q197C | Q197D | Q197E | Q197F | Q197G | Q197H | Q197I |

TABLE B-continued

| Exemplary Amino Acid Substitutions for MEA *P. alba* | | | | | | | | | |
|---|---|---|---|---|---|---|---|---|---|
| Q197K | Q197L | Q197M | Q197N | Q197P | Q197R | Q197S | Q197T | Q197V | Q197W |
| Q197Y | V202A | V202C | V202D | V202E | V202F | V202G | V202H | V202I | V202K |
| V202L | V202M | V202N | V202P | V202Q | V202R | V202S | V202T | V202W | V202Y |
| Q216A | Q216C | Q216D | Q216E | Q216F | Q216G | Q216H | Q216I | Q216K | Q216L |
| Q216M | Q216N | Q216P | Q216R | Q216S | Q216T | Q216V | Q216W | Q216Y | T240A |
| T240C | T240D | T240E | T240F | T240G | T240H | T240I | T240K | T240L | T240M |
| T240N | T240P | T240Q | T240R | T240S | T240V | T240W | T240Y | R246A | R246C |
| R246D | R246E | R246F | R246G | R246H | R246I | R246K | R246L | R246M | R246N |
| R246P | R246Q | R246S | R246T | R246V | R246W | R246Y | T251A | T251C | T251D |
| T251E | T251F | T251G | T251H | T251I | T251K | T251L | T251M | T251N | T251P |
| T251Q | T251R | T251S | T251V | T251W | T251Y | H254A | H254C | H254D | H254E |
| H254F | H254G | H254I | H254K | H254L | H254M | H254N | H254P | H254Q | H254R |
| H254S | H254T | H254V | H254W | H254Y | F287A | F287C | F287D | F287E | F287G |
| F287H | F287I | F287K | F287L | F287M | F287N | F287P | F287Q | F287R | F287S |
| F287T | F287V | F287W | F287Y | V290A | V290C | V290D | V290E | V290F | V290G |
| V290H | V290I | V290K | V290L | V290M | V290N | V290P | V290Q | V290R | V290S |
| V290T | V290W | V290Y | L308A | L308C | L308D | L308E | L308F | L308G | L308H |
| L308I | L308K | L308M | L308N | L308P | L308Q | L308R | L308S | L308T | L308V |
| L308W | L308Y | L376A | L376C | L376D | L376E | L376F | L376G | L376H | L376I |
| L376K | L376M | L376N | L376P | L376Q | L376R | L376S | L376T | L376V | L376W |
| L376Y | Y377A | Y377C | Y377D | Y377E | Y377F | Y377G | Y377H | Y377I | Y377K |
| Y377L | Y377M | Y377N | Y377P | Y377Q | Y377R | Y377S | Y377T | Y377V | Y377W |
| K379A | K379C | K379D | K379E | K379F | K379G | K379H | K379I | K379L | K379M |
| K379N | K379P | K379Q | K379R | K379S | K379T | K379V | K379W | K379Y | G389A |
| G389C | G389D | G389E | G389F | G389H | G389I | G389K | G389L | G389M | G389N |
| G389P | G389Q | G389R | G389S | G389T | G389V | G389W | G389Y | G397A | G397C |
| G397D | G397E | G397F | G397H | G397I | G397K | G397L | G397M | G397N | G397P |
| G397Q | G397R | G397S | G397T | G397V | G397W | G397Y | Q400A | Q400C | Q400D |
| Q400E | Q400F | Q400G | Q400H | Q400I | Q400K | Q400L | Q400M | Q400N | Q400P |
| Q400R | Q400S | Q400T | Q400V | Q400W | Q400Y | F403A | F403C | F403D | F403E |
| F403G | F403H | F403I | F403K | F403L | F403M | F403N | F403P | F403Q | F403R |
| F403S | F403T | F403V | F403W | F403Y | Q421A | Q421C | Q421D | Q421E | Q421F |
| Q421G | Q421H | Q421I | Q421K | Q421L | Q421M | Q421N | Q421P | Q421R | Q421S |
| Q421T | Q421V | Q421W | Q421Y | T426A | T426C | T426D | T426E | T426F | T426G |
| T426H | T426I | T426K | T426L | T426M | T426N | T426P | T426Q | T426R | T426S |
| T426V | T426W | T426Y | P430A | P430C | P430D | P430E | P430F | P430G | P430H |
| P430I | P430K | P430L | P430M | P430N | P430Q | P430R | P430S | P430T | P430V |
| P430W | P430Y | F434A | F434C | F434D | F434E | F434G | F434H | F434I | F434K |
| F434L | F434M | F434N | F434P | F434Q | F434R | F434S | F434T | F434V | F434W |
| F434Y | A445C | A445D | A445E | A445F | A445G | A445H | A445I | A445K | A445L |
| A445M | A445N | A445P | A445Q | A445R | A445S | A445T | A445V | A445W | A445Y |
| A448C | A448D | A448E | A448F | A448G | A448H | A448I | A448K | A448L | A448M |
| A448N | A448P | A448Q | A448R | A448S | A448T | A448V | A448W | A448Y | S457A |
| S457C | S457D | S457E | S457F | S457G | S457H | S457I | S457K | S457L | S457M |
| S457N | S457P | S457Q | S457R | S457T | S457V | S457W | S457Y | T462A | T462C |
| T462D | T462E | T462F | T462G | T462H | T462I | T462K | T462L | T462M | T462N |
| T462P | T462Q | T462R | T462S | T462V | T462W | T462Y | N476A | N476C | N476D |
| N476E | N476F | N476G | N476H | N476I | N476K | N476L | N476M | N476P | N476Q |
| N476R | N476S | N476T | N476V | N476W | N476Y | K487A | K487C | K487D | K487E |
| K487F | K487G | K487H | K487I | K487L | K487M | K487N | K487P | K487Q | K487R |
| K487S | K487T | K487V | K487W | K487Y | E488A | E488C | E488D | E488F | E488G |
| E488H | E488I | E488K | E488L | E488M | E488N | E488P | E488Q | E488R | E488S |
| E488T | E488V | E488W | E488Y | K489A | K489C | K489D | K489E | K489F | K489G |
| K489H | K489I | K489L | K489M | K489N | K489P | K489Q | K489R | K489S | K489T |
| K489V | K489W | K489Y | L490A | L490C | L490D | L490E | L490F | L490G | L490H |
| L490I | L490K | L490M | L490N | L490P | L490Q | L490R | L490S | L490T | L490V |
| L490W | L490Y | G491A | G491C | G491D | G491E | G491F | G491H | G491I | G491K |
| G491L | G491M | G491N | G491P | G491Q | G491R | G491S | G491T | G491V | G491W |
| G491Y | G492A | G492C | G492D | G492E | G492F | G492H | G492I | G492K | G492L |
| G492M | G492N | G492P | G492Q | G492R | G492S | G492T | G492V | G492W | G492Y |
| S493A | S493C | S493D | S493E | S493F | S493G | S493H | S493I | S493K | S493L |
| S493M | S493N | S493P | S493Q | S493R | S493T | S493V | S493W | S493Y | F495A |
| F495C | F495D | F495E | F495G | F495H | F495I | F495K | F495L | F495M | F495N |
| F495P | F495Q | F495R | F495S | F495T | F495V | F495W | F495Y | A496C | A496D |
| A496E | A496F | A496G | A496H | A496I | A496K | A496L | A496M | A496N | A496P |
| A496Q | A496R | A496S | A496T | A496V | A496W | A496Y | K497A | K497C | K497D |
| K497E | K497F | K497G | K497H | K497I | K497L | K497M | K497N | K497P | K497Q |
| K497R | K497S | K497T | K497V | K497W | K497Y | P498A | P498C | P498D | P498E |
| P498F | P498G | P498H | P498I | P498K | P498L | P498M | P498N | P498Q | P498R |
| P498S | P498T | P498V | P498W | P498Y | Q509A | Q509C | Q509D | Q509E | Q509F |
| Q509G | Q509H | Q509I | Q509K | Q509L | Q509M | Q509N | Q509P | Q509R | Q509S |
| Q509T | Q509V | Q509W | Q509Y | Y514A | Y514C | Y514D | Y514E | Y514F | Y514G |
| Y514H | Y514I | Y514K | Y514L | Y514M | Y514N | Y514P | Y514Q | Y514R | Y514S |
| Y514T | Y514V | Y514W | T521A | T521C | T521D | T521E | T521F | T521G | T521H |
| T521I | T521K | T521L | T521M | T521N | T521P | T521Q | T521R | T521S | T521V |
| T521W | T521Y | I539A | I539C | I539D | I539E | I539F | I539G | I539H | I539K |
| I539L | I539M | I539N | I539P | I539Q | I539R | I539S | I539T | I539V | I539W |
| I539Y | L540A | L540C | L540D | L540E | L540F | L540G | L540H | L540I | L540K |

TABLE B-continued

Exemplary Amino Acid Substitutions for MEA *P. alba*

| | | | | | | | | | |
|---|---|---|---|---|---|---|---|---|---|
| L540M | L540N | L540P | L540Q | L540R | L540S | L540T | L540V | L540W | L540Y |
| R544A | R544C | R544D | R544E | R544F | R544G | R544H | R544I | R544K | R544L |
| R544M | R544N | R544P | R544Q | R544S | R544T | R544V | R544W | R544Y | |

Table B describes specific substitutions in MEA *P. alba*. Corresponding residues in other parent isoprene synthases may be similarly mutated to generate isoprene synthase variants of the invention. Table C shows exemplary substitutions of the invention, wherein "X" refers to any amino acid residue. However, it is to be understood that "X" refers to an amino acid residue other than the amino acid residue resulting from the substitution (e.g., for "X3C", X is an amino acid residue other than C). Residue numbering in Table C corresponds to that of the MEA *P. alba* sequence. Accordingly, it is to be understood that residue "003" for a different parent sequence (e.g. wild type *P. tremuloides*) indicates the residue in the *P. tremuloides* sequence which corresponds to residue 003 of MEA *P. alba*, and that residue "003" of the *P. tremuloides* sequence is not necessarily the third sequential residue in the amino acid sequence of *P. tremuloides*.

TABLE C

Exemplary amino acid residue substitutions

| | | | | | | | | | |
|---|---|---|---|---|---|---|---|---|---|
| X003C | X003D | X003E | X003F | X003G | X003H | X003I | X003K | X003L | X003M |
| X003N | X003P | X003Q | X003R | X003S | X003T | X003V | X003W | X003Y | X007C |
| X007D | X007E | X007F | X007G | X007H | X007I | X007K | X007L | X007M | X007N |
| X007P | X007Q | X007R | X007S | X007T | X007V | X007W | X007Y | X009A | X009C |
| X009D | X009E | X009F | X009G | X009H | X009I | X009K | X009L | X009M | X009N |
| X009P | X009Q | X009R | X009S | X009T | X009V | X009W | X012A | X012C | X012D |
| X012E | X012F | X012G | X012H | X012I | X012K | X012L | X012M | X012P | X012Q |
| X012R | X012S | X012T | X012V | X012W | X012Y | X013A | X013C | X013D | X013E |
| X013F | X013G | X013H | X013I | X013K | X013L | X013M | X013N | X01P3 | X013Q |
| X013R | X013T | X013V | X013W | X013Y | X016A | X016C | X016D | X016E | X016F |
| X016G | X016H | X016I | X016K | X016L | X016M | X016N | X016P | X016Q | X016R |
| X016S | X016T | X016V | X016W | X018A | X018C | X018D | X0E18 | X018F | X018G |
| X018H | X018I | X018K | X018L | X018M | X018N | X018P | X018Q | X018R | X018S |
| X018T | X018V | X018W | X020A | X020C | X020D | X020E | X020F | X020G | X020H |
| X020I | X020K | X020M | X020N | X020P | X020Q | X020R | X020S | X020T | X020V |
| X020W | X020Y | X023A | X023C | X023E | X023F | X023G | X023H | X023I | X023K |
| X023L | X023M | X023N | X023P | X023Q | X023R | X023S | X023T | X023V | X023W |
| X023Y | X025A | X025C | X025E | X025F | X025G | X025H | X025I | X025K | X025L |
| X025M | X025N | X025P | X025Q | X025R | X025S | X025T | X025V | X025W | X025Y |
| X026A | X026C | X026D | X026F | X026G | X026H | X026I | X026K | X026L | X026M |
| X026N | X026P | X026Q | X026R | X026S | X026T | X026V | X026W | X026Y | X027A |
| X027C | X027D | X027E | X027F | X027G | X027H | X027I | X027K | X027L | X027M |
| X027N | X027P | X027Q | X0R27 | X027V | X027W | X027Y | X033A | X033C | X033E |
| X033F | X033G | X033H | X033I | X033K | X033L | X033M | X033N | X033P | X033Q |
| X033R | X033S | X033T | X033V | X033W | X033Y | X036A | X036C | X036D | X036E |
| X036F | X036G | X036G | X036I | X036L | X036M | X036N | X036P | X036Q | X036R |
| X036S | X036T | X036V | X036W | X036Y | X044A | X044C | X044D | X044E | X044F |
| X044G | X044H | X044I | X044K | X044L | X044M | X044N | X044P | X044Q | X044S |
| X044T | X044V | X044W | X044Y | X050A | X050C | X050D | X050E | X050F | X050G |
| X050H | X050I | X050L | X050M | X050N | X050P | X050Q | X050R | X050S | X050T |
| X050V | X050W | X050Y | X053A | X053C | X053D | X053E | X053G | X053H | X053I |
| X053K | X053L | X053M | X053N | X053P | X053Q | X053R | X053S | X053T | X053V |
| X053W | X053Y | X059A | X059C | X059D | X059E | X059F | X059G | X059H | X059I |
| X059K | X059M | X059N | X059P | X059Q | X059R | X059S | X059T | X059V | X059W |
| X059Y | X069A | X069C | X069D | X069E | X069F | X069H | X069I | X069K | X069L |
| X069M | X069N | X069P | X069Q | X069R | X069S | X069T | X069V | X069W | X069Y |
| X074A | X074C | X074D | X074E | X074F | X074G | X074H | X074I | X074K | X074L |
| X074M | X074N | X074P | X074Q | X074R | X074T | X074V | X074W | X074Y | X078A |
| X078C | X078D | X078E | X078F | X078H | X078I | X078K | X078L | X078M | X078N |
| X078P | X078Q | X078R | X078S | X078T | X078V | X078W | X078Y | X081A | X081C |
| X081E | X081F | X081G | X081H | X081I | X081K | X081L | X081M | X081N | X081P |
| X081Q | X081R | X081S | X081T | X081V | X081W | X081Y | X087A | X087C | X087D |
| X087E | X087F | X087H | X087I | X087K | X087L | X087M | X087N | X087P | X087Q |
| X087R | X087S | X087T | X087V | X087W | X087Y | X099A | X099C | X099D | X099E |
| X099F | X099H | X099I | X099K | X099L | X099M | X099N | X099P | X099Q | X099R |
| X099S | X099T | X099V | X099W | X099Y | X116A | X116C | X116D | X116E | X116F |
| X116G | X116H | X116I | X116K | X116L | X116M | X116N | X116P | X116R | X116S |
| X116T | X116V | X116W | X116Y | X117A | X117C | X117D | X117F | X117G | X117H |
| X117I | X117K | X117L | X117M | X117N | X117P | X117Q | X117R | X117S | X117T |
| X117V | X117W | X117Y | X120A | X120C | X120D | X120E | X120F | X120G | X120H |
| X120I | X120K | X120L | X120M | X120N | X120P | X120Q | X120R | X120T | X120V |
| X120W | X120Y | X121A | X121C | X121D | X121E | X121F | X121H | X121I | X121K |
| X121L | X121M | X121N | X121P | X121Q | X121R | X121S | X121T | X121V | X121W |
| X121Y | X125A | X125C | X125D | X125E | X125F | X125G | X125H | X125I | X125K |
| X125L | X125M | X125N | X125P | X125R | X125S | X125T | X125V | X125W | X125Y |
| X127A | X127C | X127D | X127E | X127F | X127H | X127I | X127K | X127L | X127M |
| X127N | X127P | X127Q | X127R | X127S | X127T | X127V | X127W | X127Y | X139C |

TABLE C-continued

Exemplary amino acid residue substitutions

| | | | | | | | | |
|---|---|---|---|---|---|---|---|---|
| X139D | X139E | X139F | X139G | X139H | X139I | X139K | X139L | X139M | X139N |
| X139P | X139Q | X139R | X139S | X139T | X139V | X139W | X139Y | X165A | X165C |
| X165D | X165E | X165F | X165G | X165H | X165K | X165L | X165M | X165N | X165P |
| X165Q | X165R | X165S | X165T | X165V | X165W | X165Y | X173A | X173C | X173D |
| X173F | X173G | X173H | X173I | X173K | X173L | X173M | X173N | X173P | X173Q |
| X173R | X173S | X173T | X173V | X173W | X173Y | X174A | X174C | X174D | X174F |
| X174G | X174H | X174I | X174K | X174L | X174M | X174N | X174P | X174Q | X174R |
| X174S | X174T | X174V | X174W | X174Y | X177A | X177C | X177D | X177E | X177F |
| X177H | X177I | X177K | X177L | X177M | X177N | X177P | X177Q | X177R | X177S |
| X177T | X177V | X177W | X177Y | X179A | X179C | X179D | X179F | X179G | X179H |
| X179I | X179K | X179L | X179M | X179N | X179P | X179Q | X179R | X179S | X179T |
| X179V | X179W | X179Y | X194A | X194C | X194D | X194E | X194F | X194G | X194H |
| X194I | X194K | X194L | X194M | X194N | X194P | X194Q | X194S | X194T | X194V |
| X194W | X194Y | X197A | X197C | X197D | X197E | X197F | X197G | X197H | X197I |
| X197K | X197L | X197M | X197N | X197P | X197R | X197S | X197T | X197V | X197W |
| X197Y | X202A | X202C | X202D | X202E | X202F | X202G | X202H | X202I | X202K |
| X202L | X202M | X202N | X202P | X202Q | X202R | X202S | X202T | X202W | X202Y |
| X216A | X216C | X216D | X216E | X216F | X216G | X216H | X216I | X216K | X216L |
| X216M | X216N | X216P | X216R | X216S | X216T | X216V | X216W | X216Y | X240A |
| X240C | X240D | X240E | X240F | X240G | X240H | X240I | X240K | X240L | X240M |
| X240N | X240P | X240Q | X240R | X240S | X240V | X240W | X240Y | X246A | X246C |
| X246D | X246E | X246F | X246G | X246H | X246I | X246K | X246L | X246M | X246N |
| X246P | X246Q | X246S | X246T | X246V | X246W | X246Y | X251A | X251C | X251D |
| X251E | X251F | X251G | X251H | X251I | X251K | X251L | X251M | X251N | X251P |
| X251Q | X251R | X251S | X251V | X251W | X251Y | X254A | X254C | X254D | X254E |
| X254F | X254G | X254I | X254K | X254L | X254M | X254N | X254P | X254Q | X254R |
| X254S | X254T | X254V | X254W | X254Y | X287A | X287C | X287D | X287E | X287G |
| X287H | X287I | X287K | X287L | X287M | X287N | X287P | X287Q | X287R | X287S |
| X287T | X287V | X287W | X287Y | X290A | X290C | X290D | X290E | X290F | X290G |
| X290H | X290I | X290K | X290L | X290M | X290N | X290P | X290Q | X290R | X290S |
| X290T | X290W | X290Y | X308A | X308C | X308D | X308E | X308F | X308G | X308H |
| X308I | X308K | X308M | X308N | X308P | X308Q | X308R | X308S | X308T | X308V |
| X308W | X308Y | X376A | X376C | X376D | X376E | X376F | X376G | X376H | X376I |
| X376K | X376M | X376N | X376P | X376Q | X376R | X376S | X376T | X376V | X376W |
| X376Y | X377A | X377C | X377D | X377E | X377F | X377G | X377H | X377I | X377K |
| X377L | X377M | X377N | X377P | X377Q | X377R | X377S | X377T | X377V | X377W |
| X379A | X379C | X379D | X379E | X379F | X379G | X379H | X379I | X379L | X379M |
| X379N | X379P | X379Q | X379R | X379S | X379T | X379V | X379W | X379Y | X389A |
| X389C | X389D | X389E | X389F | X389H | X389I | X389K | X389L | X389M | X389N |
| X389P | X389Q | X389R | X389S | X389T | X389V | X389Y | X397A | X397C | X397C |
| X397D | X397E | X397F | X397H | X397I | X397K | X397L | X397M | X397N | X397P |
| X397Q | X397R | X397S | X397T | X397V | X397W | X397Y | X400A | X400C | X400D |
| X400E | X400F | X400G | X400H | X400I | X400K | X400L | X400M | X400N | X400P |
| X400R | X400S | X400T | X400V | X400W | X400Y | X403A | X403C | X403D | X403E |
| X403G | X403H | X403I | X403K | X403L | X403M | X403N | X403P | X403Q | X403R |
| X403S | X403T | X403V | X403W | X403Y | X421A | X421C | X421D | X421E | X421F |
| X421G | X421H | X421I | X421K | X421L | X421M | X421N | X421P | X421R | X421S |
| X421T | X421V | X421W | X421Y | X426A | X426C | X426D | X426E | X426F | X426G |
| X426H | X426I | X426K | X426L | X426M | X426N | X426P | X426Q | X426R | X426S |
| X426V | X426W | X426Y | X430A | X430C | X430D | X430E | X430F | X430G | X430H |
| X430I | X430K | X430L | X430M | X430N | X430Q | X430R | X430S | X430T | X430V |
| X430W | X430Y | X434A | X434C | X434D | X434E | X434F | X434H | X434I | X434K |
| X434L | X434M | X434N | X434P | X434Q | X434R | X434S | X434T | X434V | X434W |
| X434Y | X445C | X445D | X445E | X445F | X445G | X445H | X445I | X445K | X445L |
| X445M | X445N | X445P | X445Q | X445R | X445S | X445T | X445V | X445W | X445Y |
| X448C | X448D | X448E | X448F | X448G | X448H | X448I | X448K | X448L | X448M |
| X448N | X448P | X448Q | X448R | X448S | X448T | X448V | X448W | X448Y | X457A |
| X457C | X457D | X457E | X457F | X457G | X457H | X457I | X457K | X457L | X457M |
| X457N | X457P | X457Q | X457R | X457T | X457V | X457W | X457Y | X462A | X462C |
| X462D | X462E | X462F | X462G | X462H | X462I | X462K | X462L | X462M | X462N |
| X462P | X462Q | X462R | X462S | X462V | X462W | X462Y | X476A | X476C | X476D |
| X476E | X476F | X476G | X476H | X476I | X476K | X476L | X476M | X476P | X476Q |
| X476R | X476S | X476T | X476V | X476W | X476Y | X487A | X487C | X487D | X487E |
| X487F | X487G | X487H | X487I | X487L | X487M | X487N | X487P | X487Q | X487R |
| X487S | X487T | X487V | X487W | X487Y | X488A | X488C | X488D | X488F | X488G |
| X488H | X488I | X488K | X488L | X488M | X488N | X488P | X488Q | X488R | X488S |
| X488T | X488V | X488W | X488Y | X489A | X489C | X489D | X489E | X489F | X489G |
| X489H | X489I | X489L | X489M | X489N | X489P | X489Q | X489R | X489S | X489T |
| X489V | X489W | X489Y | X490A | X490C | X490D | X490E | X490F | X490G | X490H |
| X490I | X490K | X490M | X490N | X490P | X490Q | X490R | X490S | X490T | X490V |
| X490W | X490Y | X491A | X491C | X491D | X491E | X491F | X491H | X491I | X491K |
| X491L | X491M | X491N | X491P | X491Q | X491R | X491S | X491T | X491V | X491W |
| X491Y | X492A | X492C | X492D | X492E | X492F | X492H | X492I | X492K | X492L |
| X492M | X492N | X492P | X492Q | X492R | X492S | X492T | X492V | X492W | X492Y |
| X493A | X493C | X493D | X493E | X493F | X493G | X493H | X493I | X493K | X493L |
| X493M | X493N | X493P | X493Q | X493R | X493T | X493V | X493W | X493Y | X495A |
| X495C | X495D | X495E | X495G | X495H | X495I | X495K | X495L | X495M | X495N |
| X495P | X495Q | X495R | X495S | X495T | X495V | X495W | X495Y | X496C | X496D |

TABLE C-continued

Exemplary amino acid residue substitutions

| | | | | | | | | |
|---|---|---|---|---|---|---|---|---|
| X496E | X496F | X496G | X496H | X496I | X496K | X496L | X496M | X496N | X496P |
| X496Q | X496R | X496S | X496T | X496V | X496W | X497A | X497C | X497D |
| X497E | X497F | X497G | X497H | X497I | X497L | X497M | X497N | X497P | X497Q |
| X497R | X497S | X497T | X497V | X497W | X497Y | X498A | X498C | X498D | X498E |
| X498F | X498G | X498H | X498I | X498K | X498L | X498M | X498N | X498Q | X498R |
| X498S | X498T | X498V | X498W | X498Y | X509A | X509C | X509D | X509E | X509F |
| X509G | X509H | X509I | X509K | X509L | X509M | X509N | X509P | X509R | X509S |
| X509T | X509V | X509W | X509Y | X514A | X514C | X514D | X514E | X514F | X514G |
| X514H | X514I | X514K | X514L | X514M | X514N | X514P | X514Q | X514R | X514S |
| X514T | X514V | X514W | X521A | X521C | X521D | X521E | X521F | X521G | X521H |
| X521I | X521K | X521L | X521M | X521N | X521P | X521Q | X521R | X521S | X521V |
| X521W | X521Y | X539A | X539C | X539D | X539E | X539F | X539G | X539H | X539K |
| X539L | X539M | X539N | X539P | X539Q | X539R | X539S | X539T | X539V | X539W |
| X539Y | X540A | X540C | X540D | X540E | X540F | X540G | X540H | X540I | X540K |
| X540M | X540N | X540P | X540Q | X540R | X540S | X540T | X540V | X540W | X540Y |
| X544A | X544C | X544D | X544E | X544F | X544G | X544H | X544I | X544K | X544L |
| X544M | X544N | X544P | X544Q | X544S | X544T | X544V | X544W | X544Y | |

In some embodiments, the variant comprises a substitution selected from the group consisting of: X003T, X013L, X165Y, X421R, X495L, X509T, and X540V. In some embodiments, the variant comprises X003T. In some embodiments, the variant comprises X013L. In some embodiments, the variant comprises X165Y. In some embodiments, the variant comprises X421R. In some embodiments, the variant comprises X495L. In some embodiments, the variant comprises X509T. In some embodiments, the variant comprises X540V. In some embodiments, the variant comprises the substitution X491S. In some embodiments, the variant further comprises the substitution X491S, in addition to another substitution selected from the group consisting of: X003C, X003D, X003E, X003F, X003G, X003H, X003I, X003K, X003L, X003M, X003N, X003P, X003Q, X003R, X003S, X003T, X003V, X003W, X003Y, X007C, X007D, X007E, X007F, X007G, X007H, X007I, X007K, X007L, X007M, X007N, X007P, X007Q, X007R, X007S, X007T, X007V, X007W, X007Y, X009A, X009C, X009D, X009E, X009F, X009G, X009H, X009I, X009K, X009L, X009M, X009N, X009P, X009Q, X009R, X009S, X009T, X009V, X009W, X012A, X012C, X012D, X012E, X012F, X012G, X012H, X012I, X012K, X012L, X012M, X012P, X012Q, X012R, X012S, X012T, X012V, X012W, X012Y, X013A, X013C, X013D, X013E, X013F, X013G, X013H, X013I, X013K, X013L, X013M, X013N, X01P3, X013Q, X013R, X013T, X013V, X013W, X013Y, X016A, X016C, X016D, X016E, X016F, X016G, X016H, X016I, X016K, X016L, X016M, X016N, X016P, X016Q, X016R, X016S, X016T, X016V, X016W, X018A, X018C, X018D, X0E18, X018F, X018G, X018H, X018I, X018K, X018L, X018M, X018N, X018P, X018Q, X018R, X018S, X018T, X018V, X018W, X020A, X020C, X020D, X020E, X020F, X020G, X020H, X020I, X020K, X020M, X020N, X020P, X020Q, X020R, X020S, X020T, X020V, X020W, X020Y, X023A, X023C, X023E, X023F, X023G, X023H, X023I, X023K, X023L, X023M, X023N, X023P, X023Q, X023R, X023S, X023T, X023V, X023W, X023Y, X025A, X025C, X025E, X025F, X025G, X025H, X025I, X025K, X025L, X025M, X025N, X025P, X025Q, X025R, X025S, X025T, X025V, X025W, X025Y, X026A, X026C, X026D, X026F, X026G, X026H, X026I, X026K, X026L, X026M, X026N, X026P, X026Q, X026R, X026S, X026T, X026V, X026W, X026Y, X027A, X027C, X027D, X027E, X027F, X027G, X027H, X027I, X027K, X027L, X027M, X027N, X027P, X027Q, X0R27, X027V, X027W, X027Y, X033A, X033C, X033E, X033F, X033G, X033H, X033I, X033K, X033L, X033M, X033N, X033P, X033Q, X033R, X033S, X033T, X033V, X033W, X033Y, X036A, X036C, X036D, X036E, X036F, X036G, X036G, X036I, X036L, X036M, X036N, X036P, X036Q, X036R, X036S, X036T, X036V, X036W, X036Y, X044A, X044C, X044D, X044E, X044F, X044G, X044H, X044I, X044K, X044L, X044M, X044N, X044P, X044Q, X044S, X044T, X044V, X044W, X044Y, X050A, X050C, X050D, X050E, X050F, X050G, X050H, X050I, X050L, X050M, X050N, X050P, X050Q, X050R, X050S, X050T, X050V, X050W, X050Y, X053A, X053C, X053D, X053E, X053G, X053H, X053I, X053K, X053L, X053M, X053N, X053P, X053Q, X053R, X053S, X053T, X053V, X053W, X053Y, X059A, X059C, X059D, X059E, X059F, X059G, X059H, X059I, X059K, X059M, X059N, X059P, X059Q, X059R, X059S, X059T, X059V, X059W, X059Y, X069A, X069C, X069D, X069E, X069F, X069H, X069I, X069K, X069L, X069M, X069N, X069P, X069Q, X069R, X069S, X069T, X069V, X069W, X069Y, X074A, X074C, X074D, X074E, X074F, X074G, X074H, X074I, X074K, X074L, X074M, X074N, X074P, X074Q, X074R, X074T, X074V, X074W, X074Y, X078A, X078C, X078D, X078E, X078F, X078H, X078I, X078K, X078L, X078M, X078N, X078P, X078Q, X078R, X078S, X078T, X078V, X078W, X078Y, X081A, X081C, X081E, X081F, X081G, X081H, X081I, X081K, X081L, X081M, X081N, X081P, X081Q, X081R, X081S, X081T, X081V, X081W, X081Y, X087A, X087C, X087D, X087E, X087F, X087H, X087I, X087K, X087L, X087M, X087N, X087P, X087Q, X087R, X087S, X087T, X087V, X087W, X087Y, X099A, X099C, X099D, X099E, X099F, X099H, X099I, X099K, X099L, X099M, X099N, X099P, X099Q, X099R, X099S, X099T, X099V, X099W, X099Y, X116A, X116C, X116D, X116E, X116F, X116G, X116H, X116I, X116K, X116L, X116M, X116N, X116P, X116R, X116S, X116T, X116V, X116W, X116Y, X117A, X117C, X117D, X117F, X117G, X117H, X117I, X117K, X117L, X117M, X117N, X117P, X117Q, X117R, X117S, X117T, X117V, X117W, X117Y, X120A, X120C, X120D, X120E, X120F, X120G, X120H, X120I, X120K, X120L, X120M, X120N, X120P, X120Q, X120R, X120T, X120V, X120W, X120Y, X121A, X121C, X121D, X121E, X121F, X121H, X121I, X121K, X121L, X121M, X121N, X121P, X121Q, X121R, X121S, X121T, X121V, X121W, X121Y, X125A, X125C, X125D, X125E, X125F, X125G, X125H, X125I, X125K, X125L, X125M, X125N, X125P, X125R, X125S, X125T, X125V, X125W, X125Y, X127A, X127C, X127D, X127E, X127F, X127H, X127I, X127K, X127L, X127M, X127N, X127P, X127Q, X127R, X127S, X127T, X127V, X127W, X127Y, X139C, X139D, X139E, X139F, X139G, X139H, X139I, X139K, X139L, X139M, X139N, X139P, X139Q, X139R, X139S, X139T, X139V, X139W, X139Y, X165A, X165C, X165D, X165E, X165F, X165G, X165H, X165K, X165L, X165M, X165N, X165P, X165Q, X165R, X165S, X165T, X165V, X165W, X165Y, X173A, X173C, X173D, X173F, X173G, X173H, X173I, X173K, X173L, X173M, X173N, X173P, X173Q, X173R, X173S, X173T, X173V, X173W, X173Y, X174A, X174C, X174D, X174F, X174G, X174H, X174I, X174K, X174L, X174M, X174N, X174P, X174Q, X174R, X174S, X174T, X174V, X174W, X174Y, X177A, X177C, X177D, X177E, X177F, X177H, X177I, X177K, X177L, X177M, X177N, X177P, X177Q, X177R, X177S, X177T, X177V, X177W, X177Y, X179A, X179C, X179D, X179F, X179G, X179H, X179I, X179K, X179L, X179M, X179N, X179P, X179Q, X179R, X179S, X179T, X179V, X179W, X179Y, X194A, X194C, X194D, X194E, X194F, X194G, X194H, X194I, X194K, X194L, X194M, X194N, X194P, X194Q, X194S, X194T, X194V, X194W, X194Y, X197A, X197C, X197D, X197E, X197F, X197G, X197H, X197I, X197K, X197L, X197M, X197N, X197P, X197R, X197S, X197T, X197V, X197W, X197Y, X202A, X202C, X202D, X202E, X202F, X202G, X202H, X202I, X202K, X202L, X202M, X202N, X202P, X202Q, X202R, X202S, X202T, X202W, X202Y, X216A, X216C, X216D, X216E, X216F, X216G, X216H, X216I, X216K, X216L, X216M, X216N, X216P, X216R, X216S, X216T, X216V, X216W, X216Y, X240A, X240C, X240D, X240E, X240F, X240G, X240H, X240I, X240K, X240L, X240M, X240N, X240P, X240Q, X240R, X240S, X240V, X240W, X240Y, X246A, X246C, X246D, X246E, X246F, X246G, X246H, X246I, X246K, X246L, X246M, X246N, X246P, X246Q, X246S, X246T, X246V, X246W, X246Y, X251A, X251C, X251D, X251E, X251F, X251G, X251H, X251I, X251K, X251L, X251M, X251N, X251P, X251Q, X251R, X251S, X251V, X251W, X251Y, X254A, X254C, X254D, X254E, X254F, X254G, X254I, X254K, X254L, X254M, X254N, X254P, X254Q, X254R, X254S, X254T, X254V, X254W, X254Y, X287A, X287C, X287D, X287E, X287G, X287H, X287I, X287K, X287L, X287M, X287N, X287P, X287Q, X287R, X287S, X287T, X287V, X287W, X287Y, X290A, X290C, X290D, X290E, X290F, X290G, X290H, X290I, X290K, X290L, X290M, X290N, X290P, X290Q, X290R, X290S, X290T, X290W, X290Y, X308A, X308C, X308D, X308E, X308F, X308G, X308H, X308I, X308K, X308M, X308N, X308P, X308Q, X308R, X308S, X308T, X308V, X308W, X308Y, X376A, X376C, X376D, X376E, X376F, X376G, X376H, X376I, X376K, X376M, X376N, X376P, X376Q, X376R, X376S, X376T, X376V, X376W, X376Y, X377A, X377C, X377D, X377E, X377F, X377G, X377H, X377I, X377K, X377L, X377M, X377N, X377P, X377Q, X377R, X377S, X377T, X377V, X377W, X379A, X379C, X379D, X379E, X379F, X379G, X379H, X379I, X379L, X379M, X379N, X379P, X379Q, X379R, X379S, X379T, X379V, X379W, X379Y, X389A, X389C, X389D, X389E, X389F, X389H, X389I, X389K, X389L, X389M, X389N, X389P, X389Q, X389R, X389S, X389T, X389V, X389W, X389Y, X397A, X397C, X397D, X397E, X397F, X397H, X397I, X397K, X397L, X397M, X397N, X397P, X397Q, X397R, X397S, X397T, X397V, X397W, X397Y, X400A, X400C, X400D, X400E, X400F, X400G, X400H, X400I, X400K, X400L, X400M, X400N, X400P, X400R, X400S, X400T, X400V, X400W, X400Y, X403A, X403C, X403D, X403E, X403G, X403H, X403I, X403K, X403L, X403M, X403N, X403P, X403Q, X403R, X403S, X403T, X403V, X403W, X403Y, X421A, X421C, X421D, X421E, X421F, X421G, X421H, X421I, X421K, X421L, X421M, X421N, X421P, X421R, X421S, X421T, X421V, X421W, X421Y, X426A, X426C, X426D, X426E, X426F, X426G, X426H, X426I, X426K, X426L, X426M, X426N, X426P, X426Q, X426R, X426S, X426V, X426W, X426Y, X430A, X430C, X430D, X430E, X430F, X430G, X430H, X430I, X430K, X430L, X430M, X430N, X430Q, X430R, X430S, X430T, X430V, X430W, X430Y, X434A, X434C, X434D, X434E, X434G, X434H, X434I, X434K, X434L, X434M, X434N, X434P, X434Q, X434R, X434S, X434T, X434V, X434W, X434Y, X445C, X445D, X445E, X445F, X445G, X445H, X445I, X445K, X445L, X445M, X445N, X445P, X445Q, X445R, X445S, X445T, X445V, X445W, X445Y, X448C, X448D, X448E, X448F, X448G, X448H, X448I, X448K, X448L, X448M, X448N, X448P, X448Q, X448R, X448S, X448T, X448V, X448W, X448Y, X457A, X457C, X457D, X457E, X457F, X457G, X457H, X457I, X457K, X457L, X457M, X457N, X457P, X457Q, X457R, X457T, X457V, X457W, X457Y, X462A, X462C, X462D, X462E, X462F, X462G, X462H, X462I, X462K, X462L, X462M, X462N, X462P, X462Q, X462R, X462S, X462V, X462W, X462Y, X476A, X476C, X476D, X476E, X476F, X476G, X476H, X476I, X476K, X476L, X476M, X476P, X476Q, X476R, X476S, X476T, X476V, X476W, X476Y, X487A, X487C, X487D, X487E, X487G, X487H, X487I, X487L, X487M, X487N, X487P, X487Q, X487R, X487S, X487T, X487V, X487W, X487Y, X488A, X488C, X488D, X488F, X488G, X488H, X488I, X488K, X488L, X488M, X488N, X488P, X488Q, X488R, X488S, X488T, X488V, X488W, X488Y, X489A, X489C, X489D, X489E, X489F, X489G, X489H, X489I, X489L, X489M, X489N, X489P, X489Q, X489R, X489S, X489T, X489V, X489W, X489Y, X490A, X490C, X490D, X490E, X490F, X490G, X490H, X490I, X490K, X490M, X490N, X490P, X490Q, X490R, X490S, X490T, X490V, X490W, X490Y, X491A, X491C, X491D, X491E, X491F, X491H, X491I, X491K, X491L, X491M, X491N, X491P, X491Q, X491R, X491S, X491T, X491V, X491W, X491Y, X492A, X492C, X492D, X492E, X492F, X492H, X492I, X492K, X492L, X492M, X492N, X492P, X492Q, X492R, X492S, X492T, X492V, X492W, X492Y, X493A, X493C, X493D, X493E, X493F, X493G, X493H, X493I, X493K, X493L, X493M, X493N, X493P, X493Q, X493R, X493T, X493V, X493W, X493Y, X495A, X495C, X495D, X495E, X495G, X495H, X495I, X495K, X495L, X495M, X495N, X495P, X495Q, X495R, X495S, X495T, X495V, X495W, X495Y, X496C, X496D, X496E, X496F, X496G, X496H, X496I, X496K, X496L, X496M, X496N, X496P, X496Q, X496R, X496S, X496T, X496V, X496W, X496Y, X497A, X497C, X497D, X497E, X497F, X497G, X497H, X497I, X497L, X497M, X497N, X497P, X497Q, X497R, X497S, X497T, X497V, X497W, X497Y, X498A, X498C, X498D, X498E, X498F, X498G, X498H, X498I, X498K, X498L, X498M, X498N, X498Q, X498R, X498S, X498T, X498V, X498W, X498Y, X509A, X509C, X509D, X509E, X509F, X509G, X509H, X509I, X509K, X509L, X509M, X509N, X509P, X509R, X509S, X509T, X509V, X509W, X509Y, X514A, X514C, X514D, X514E, X514F, X514G, X514H, X514I, X514K, X514L, X514M, X514N, X514P, X514Q, X514R, X514S, X514T, X514V, X514W, X521A, X521C, X521D, X521E, X521F, X521G, X521H, X521I, X521K, X521L, X521M, X521N, X521P, X521Q, X521R, X521S, X521V, X521W, X521Y, X539A, X539C, X539D, X539E, X539F, X539G, X539H, X539K, X539L, X539M, X539N, X539P, X539Q, X539R, X539S, X539T, X539V, X539W, X539Y, X540A, X540C, X540D, X540E, X540F, X540G, X540H, X540I, X540K, X540M, X540N, X540P, X540Q, X540R, X540S, X540T, X540V, X540W, X540Y, X544A, X544C, X544D, X544E, X544F, X544G, X544H, X544I, X544K, X544L, X544M, X544N, X544P, X544Q, X544S, X544T, X544V, X544W, and X544Y; wherein X represents any amino acid; and wherein each amino acid residue position is numbered by correspondence with an amino acid residue position in the *P. alba* isoprene synthase sequence as shown in FIG. 20. The substitution X491S may be combined with any other substitution described in Tables B or C.

In some embodiments, the variant comprises the amino acid residues: N438, E451, and Y514. In some embodiments, the variant comprises the amino acid residues: F287, G397, N438, E451, and Y514. In some embodiments, the variant comprises S491. In some embodiments, the variant comprises S491 in addition to a substitution selected from the group consisting of: X003C, X003D, X003E, X003F, X003G, X003H, X003I, X003K, X003L, X003M, X003N, X003P, X003Q, X003R, X003S, X003T, X003V, X003W, X003Y, X007C, X007D, X007E, X007F, X007G, X007H, X007I, X007K, X007L, X007M, X007N, X007P, X007Q, X007R, X007S, X007T, X007V, X007W, X007Y, X009A, X009C, X009D, X009E, X009F, X009G, X009H, X009I, X009K, X009L, X009M, X009N, X009P, X009Q, X009R, X009S, X009T, X009V, X009W, X012A, X012C, X012D, X012E, X012F, X012G, X012H, X012I, X012K, X012L, X012M, X012P, X012Q, X012R, X012S, X012T, X012V, X012W, X012Y, X013A, X013C, X013D, X013E, X013F, X013G, X013H, X013I, X013K, X013L, X013M, X013N, X01P3, X013Q, X013R, X013T, X013V, X013W, X013Y, X016A, X016C, X016D, X016E, X016F, X016G, X016H, X016I, X016K, X016L, X016M, X016N, X016P, X016Q, X016R, X016S, X016T, X016V, X016W, X018A, X018C, X018D, X0E18, X018F, X018G, X018H, X018I, X018K, X018L, X018M, X018N, X018P, X018Q, X018R, X018S, X018T, X018V, X018W, X020A, X020C, X020D, X020E, X020F, X020G, X020H, X020I, X020K, X020M, X020N, X020P, X020Q, X020R, X020S, X020T, X020V, X020W, X020Y, X023A, X023C, X023E, X023F, X023G, X023H, X023I, X023K, X023L, X023M, X023N, X023P, X023Q, X023R, X023S, X023T, X023V, X023W, X023Y, X025A, X025C, X025E, X025F, X025G, X025H, X025I, X025K, X025L, X025M, X025N, X025P, X025Q, X025R, X025S, X025T, X025V, X025W, X025Y, X026A, X026C, X026D, X026F, X026G, X026H, X026I, X026K, X026L, X026M, X026N, X026P, X026Q, X026R, X026S, X026T, X026V, X026W, X026Y, X027A, X027C, X027D, X027E, X027F, X027G, X027H, X027I, X027K, X027L, X027M, X027N, X027P, X027Q, X0R27, X027V, X027W, X027Y, X033A, X033C, X033E, X033F, X033G, X033H, X033I, X033K, X033L, X033M, X033N, X033P, X033Q, X033R, X033S, X033T, X033V, X033W, X033Y, X036A, X036C, X036D, X036E, X036F, X036G, X036G, X036I, X036L, X036M, X036N, X036P, X036Q, X036R, X036S, X036T, X036V, X036W, X036Y, X044A, X044C, X044D, X044E, X044F, X044G, X044H, X044I, X044K, X044L, X044M, X044N, X044P, X044Q, X044S, X044T, X044V, X044W, X044Y, X050A, X050C, X050D, X050E, X050F, X050G, X050H, X050I, X050L, X050M, X050N, X050P, X050Q, X050R, X050S, X050T, X050V, X050W, X050Y, X053A, X053C, X053D, X053E, X053G, X053H, X053I, X053K, X053L, X053M, X053N, X053P, X053Q, X053R, X053S, X053T, X053V, X053W, X053Y, X059A, X059C, X059D, X059E, X059F, X059G, X059H, X059I, X059K, X059M, X059N, X059P, X059Q, X059R, X059S, X059T, X059V, X059W, X059Y, X069A, X069C, X069D, X069E, X069F, X069H, X069I, X069K, X069L, X069M, X069N, X069P, X069Q, X069R, X069S, X069T, X069V, X069W, X069Y, X074A, X074C, X074D, X074E, X074F, X074G, X074H, X074I, X074K, X074L, X074M, X074N, X074P, X074Q, X074R, X074T, X074V, X074W, X074Y, X078A, X078C, X078D, X078E, X078F, X078H, X078I, X078K, X078L, X078M, X078N, X078P, X078Q, X078R, X078S, X078T, X078V, X078W, X078Y, X081A, X081C, X081E, X081F, X081G, X081H, X081I, X081K, X081L, X081M, X081N, X081P, X081Q, X081R, X081S, X081T, X081V, X081W, X081Y, X087A, X087C, X087D, X087E, X087F, X087H, X087I, X087K, X087L, X087M, X087N, X087P, X087Q, X087R, X087S, X087T, X087V, X087W, X087Y, X099A, X099C, X099D, X099E, X099F, X099H, X099I, X099K, X099L, X099M, X099N, X099P, X099Q, X099R, X099S, X099T, X099V, X099W, X099Y, X116A, X116C, X116D, X116E, X116F, X116G, X116H, X116I, X116K, X116L, X116M, X116N, X116P, X116R, X116S, X116T, X116V, X116W, X116Y, X117A, X117C, X117D, X117F, X117G, X117H, X117I, X117K, X117L, X117M, X117N, X117P, X117Q, X117R, X117S, X117T, X117V, X117W, X117Y, X120A, X120C, X120D, X120E, X120F, X120G, X120H, X120I, X120K, X120L, X120M, X120N, X120P, X120Q, X120R, X120T, X120V, X120W, X120Y, X121A, X121C, X121D, X121E, X121F, X121H, X121I, X121K, X121L, X121M, X121N, X121P, X121Q, X121R, X121S, X121T, X121V, X121W, X121Y, X125A, X125C, X125D, X125E, X125F, X125G, X125H, X125I, X125K, X125L, X125M, X125N, X125P, X125R, X125S, X125T, X125V, X125W, X125Y, X127A, X127C, X127D, X127E, X127F, X127H, X127I, X127K, X127L, X127M, X127N, X127P, X127Q, X127R, X127S, X127T, X127V, X127W, X127Y, X139C, X139D, X139E, X139F, X139G, X139H, X139I, X139K, X139L, X139M, X139N, X139P, X139Q, X139R, X139S, X139T, X139V, X139W, X139Y, X165A, X165C, X165D, X165E, X165F, X165G, X165H, X165K, X165L, X165M, X165N, X165P, X165Q, X165R, X165S, X165T, X165V, X165W, X165Y, X173A, X173C, X173D, X173F, X173G, X173H, X173I, X173K, X173L, X173M, X173N, X173P, X173Q, X173R, X173S, X173T, X173V, X173W, X173Y, X174A, X174C, X174D, X174F, X174G, X174H, X174I, X174K, X174L, X174M, X174N, X174P, X174Q, X174R, X174S, X174T, X174V, X174W, X174Y, X177A, X177C, X177D, X177E, X177F, X177H, X177I, X177K, X177L, X177M, X177N, X177P, X177Q, X177R, X177S, X177T, X177V, X177W, X177Y, X179A, X179C, X179D, X179F, X179G, X179H, X179I, X179L, X179M, X179N, X179P, X179Q, X179R, X179S, X179T, X179V, X179W, X179Y, X194A, X194C, X194D, X194E, X194F, X194G, X194H, X194I, X194K, X194L, X194M, X194N, X194P, X194Q, X194S, X194T, X194V, X194W, X194Y, X197A, X197C, X197D, X197E, X197F, X197G, X197H, X197I, X197K, X197L, X197M, X197N, X197P, X197R, X197S, X197T, X197V, X197W, X197Y, X202A, X202C, X202D, X202E, X202F, X202G, X202H, X202I, X202K, X202L, X202M, X202N, X202P, X202Q, X202R, X202S, X202T, X202W, X202Y, X216A, X216C, X216D, X216E, X216F, X216G, X216H, X216I, X216K, X216L, X216M, X216N, X216P, X216R, X216S, X216T, X216V, X216W, X216Y, X240A, X240C, X240D, X240E, X240F, X240G, X240H, X240I, X240K, X240L, X240M, X240N, X240P, X240Q, X240R, X240S, X240V, X240W, X240Y, X246A, X246C, X246D, X246E, X246F, X246G, X246H, X246I, X246K, X246L, X246M, X246N, X246P, X246Q, X246S, X246T, X246V, X246W, X246Y, X251A, X251C, X251D, X251E, X251F, X251G, X251H, X251I, X251K, X251L, X251M, X251N, X251P, X251Q, X251R, X251S, X251V, X251W, X251Y, X254A, X254C, X254D, X254E, X254F, X254G, X254I, X254K, X254L, X254M, X254N, X254P, X254Q, X254R, X254S, X254T, X254V, X254W, X254Y, X287A, X287C, X287D, X287E, X287G, X287H, X287I, X287K, X287L, X287M, X287N, X287P, X287Q, X287R, X287S, X287T, X287V, X287W, X287Y, X290A, X290C, X290D, X290E, X290F, X290G, X290H, X290I, X290K, X290L, X290M, X290N, X290P, X290Q, X290R, X290S, X290T, X290W, X290Y, X308A, X308C, X308D, X308E, X308F, X308G, X308H, X308I, X308K, X308M, X308N, X308P, X308Q, X308R, X308S, X308T, X308V, X308W, X308Y, X376A, X376C, X376D, X376E, X376F, X376G, X376H, X376I, X376K, X376M, X376N, X376P, X376Q, X376R, X376S, X376T, X376V, X376W, X376Y, X377A, X377C, X377D, X377E, X377F, X377G, X377H, X377I, X377K, X377L, X377M, X377N, X377P, X377Q, X377R, X377S, X377T, X377V, X377W, X379A, X379C, X379D, X379E, X379F, X379G, X379H, X379I, X379L, X379M, X379N, X379P, X379Q, X379R, X379S, X379T, X379V, X379W, X379Y, X389A, X389C, X389D, X389E, X389F, X389H, X389I, X389K, X389L, X389M, X389N, X389P, X389Q, X389R, X389S, X389T, X389V, X389W, X389Y, X397A, X397C, X397D, X397E, X397F, X397H, X397I, X397K, X397L, X397M, X397N, X397P, X397Q, X397R, X397S, X397T, X397V, X397W, X397Y, X400A, X400C, X400D, X400E, X400F, X400G, X400H, X400I, X400K, X400L, X400M, X400N, X400P, X400R, X400S, X400T, X400V, X400W, X400Y, X403A, X403C, X403D, X403E, X403G, X403H, X403I, X403K, X403L, X403M, X403N, X403P, X403Q, X403R, X403S, X403T, X403V, X403W, X403Y, X421A, X421C, X421D, X421E, X421F, X421G, X421H, X421I, X421K, X421L, X421M, X421N, X421P, X421R, X421S, X421T, X421V, X421W, X421Y, X426A, X426C, X426D, X426E, X426F, X426G, X426H, X426I, X426K, X426L, X426M, X426N, X426P, X426Q, X426R, X426S, X426V, X426W, X426Y, X430A, X430C, X430D, X430E, X430F, X430G, X430H, X430I, X430K, X430L, X430M, X430N, X430Q, X430R, X430S, X430T, X430V, X430W, X430Y, X434A, X434C, X434D, X434E, X434G, X434H, X434I, X434K, X434L, X434M, X434N, X434P, X434Q, X434R, X434S, X434T, X434V, X434W, X434Y, X445C, X445D, X445E, X445F, X445G, X445H, X445I, X445K, X445L, X445M, X445N, X445P, X445Q, X445R, X445S, X445T, X445V, X445W, X445Y, X448C, X448D, X448E, X448F, X448G, X448H, X448I, X448K, X448L, X448M, X448N, X448P, X448Q, X448R, X448S, X448T, X448V, X448W, X448Y, X457A, X457C, X457D, X457E, X457F, X457G, X457H, X457I, X457K, X457L, X457M, X457N, X457P, X457Q, X457R, X457T, X457V, X457W, X457Y, X462A, X462C, X462D, X462E, X462F, X462G, X462H, X462I, X462K, X462L, X462M, X462N, X462P, X462Q, X462R, X462S, X462V, X462W, X462Y, X476A, X476C, X476D, X476E, X476F, X476G, X476H, X476I, X476K, X476L, X476M, X476P, X476Q, X476R, X476S, X476T, X476V, X476W, X476Y, X487A, X487C, X487D, X487E, X487F, X487G, X487H, X487I, X487L, X487M, X487N, X487P, X487Q, X487R, X487S, X487T, X487V, X487W, X487Y, X488A, X488C, X488D, X488F, X488G, X488H, X488I, X488K, X488L, X488M, X488N, X488P, X488Q, X488R, X488S, X488T, X488V, X488W, X488Y, X489A, X489C, X489D, X489E, X489F, X489G, X489H, X489I, X489L, X489M, X489N, X489P, X489Q, X489R, X489S, X489T, X489V, X489W, X489Y, X490A, X490C, X490D, X490E, X490F, X490G, X490H, X490I, X490K, X490M, X490N, X490P, X490Q, X490R, X490S, X490T, X490V, X490W, X490Y, X491A, X491C, X491D, X491E, X491F, X491H, X491I, X491K, X491L, X491M, X491N, X491P, X491Q, X491R, X491S, X491T, X491V, X491W, X491Y, X492A, X492C, X492D, X492E, X492F, X492H, X492I, X492K, X492L, X492M, X492N, X492P, X492Q, X492R, X492S, X492T, X492V, X492W, X492Y, X493A, X493C, X493D, X493E, X493F, X493G, X493H, X493I, X493K, X493L, X493M, X493N, X493P, X493Q, X493R, X493T, X493V, X493W, X493Y, X495A, X495C, X495D, X495E, X495G, X495H, X495I, X495K, X495L, X495M, X495N, X495P, X495Q, X495R, X495S, X495T, X495V, X495W, X495Y, X496C, X496D, X496E, X496F, X496G, X496H, X496I, X496K, X496L, X496M, X496N, X496P, X496Q, X496R, X496S, X496T, X496V, X496W, X496Y, X497A, X497C, X497D, X497E, X497F, X497G, X497H, X497I, X497L, X497M, X497N, X497P, X497Q, X497R, X497S, X497T, X497V, X497W, X497Y, X498A, X498C, X498D, X498E, X498F, X498G, X498H, X498I, X498K, X498L, X498M, X498N, X498Q, X498R, X498S, X498T, X498V, X498W, X498Y, X509A, X509C, X509D, X509E, X509F, X509G, X509H, X509I, X509K, X509L, X509M, X509N, X509P, X509R, X509S, X509T, X509V, X509W, X509Y, X514A, X514C, X514D, X514E, X514F, X514G, X514H, X514I, X514K, X514L, X514M, X514N, X514P, X514Q, X514R, X514S, X514T, X514V, X514W, X521A, X521C, X521D, X521E, X521F, X521G, X521H, X521I, X521K, X521L, X521M, X521N, X521P, X521Q, X521R, X521S, X521V, X521W, X521Y, X539A, X539C, X539D, X539E, X539F, X539G, X539H, X539K, X539L, X539M, X539N, X539P, X539Q, X539R, X539S, X539T, X539V, X539W, X539Y, X540A, X540C, X540D, X540E, X540F, X540G, X540H, X540I, X540K, X540M, X540N, X540P, X540Q, X540R, X540S, X540T, X540V, X540W, X540Y, X544A, X544C, X544D, X544E, X544F, X544G, X544H, X544I, X544K, X544L, X544M, X544N, X544P, X544Q, X544S, X544T, X544V, X544W, and X544Y; wherein X represents any amino acid; and wherein each amino acid residue position is numbered by correspondence with an amino acid residue position in the *P. alba* isoprene synthase sequence as shown in FIG. 20.

In some embodiments, the isoprene synthase variant is not a wild-type isoprene synthase sequence. In some embodiments, the isoprene synthase variant is not a sequence described in PCT/US2009/041581 (WO 2009/132220) or PCT/US2010/032134 (WO 2010/124146).

In some embodiments, the isoprene synthase variant does not comprise an amino acid residue substitution disclosed in PCT/US2009/041581 (WO 2009/132220).

In some embodiments, the isoprene synthase variant does not comprise an amino acid residue substitution in Table D.

TABLE D

| Amino Acid Substitutions |
|---|
| For the following sequences, the SEQ ID NOS and residue numbering are as used in PCT/US2010/032134 (WO 2010/124146): |
| Met 1, Arg 2, Arg 3, Ser 4, Ala 5, Asn 6, Tyr 7, Glu 8, Pro 9, Asn 10, Ser 11, Trp 12, Asp 13, Tyr 14, Asp 15, Tyr 16, Leu 17, Leu 18, Ser 19, Ser 20, Asp 21, Thr 22, Asp 23, Glu 24, Ser 25, Ile 26, Glu 27, Val 28, Leu 438, Ala 439, Ser 440, Ala 441, Ser 442, Ala 443, Glu 444, Ile 445, Ala 446, Arg 447, Gly 448, Glu 449, Thr 450, Ala 451, Asn 452, Ser 453, Tyr 512, His 513, Asn 514, Gly 515, Asp 516, Ala 517, His 518, Thr 519, Ser 520, |

TABLE D-continued

Amino Acid Substitutions

Pro 521, Asp 522, Glu 523, Leu 524, Thr 525, Arg 526, D293, Y385, S392, D437, S261,
W264, F285, T289, S393, S394, F432, Y512, 40, A441, S442, A443, E444, I445, A446,
R447, G448, E449, T450, A451, N452, S453, Y512, H513, N514, G515, D516, A517,
H518, T519, S520, P521, D522, E523, L524, L17, L18, S19, S20, S239, R243, F253,
A254, R255, D256, R257, I259, E260, D293, Y295, D296, V297, Y298, G299, T300,
E303, Y325, L374, Y375, V529, L530, T534, D293, Y295, V297, E370, A371, W373,
L374, S378, T379, P380, F382, Y385, F386, R433, L434 C435, N436, D437, V454,
S455, C456, Y457, M458, T469, V472, I476, Y512, E187, L188, R255, R257, F270,
E271, Q273, Y274, F285, V288, A439, S440, S442, S508, H509, C510, T511, Y512,
R528, V529, L530, S531, or V532 of SEQ ID NO: 11 as listed in PCT/US2010/032134
(WO 2010/124146) wherein amino acid residue numbering is described at page 84,
paragraph [0295] of PCT/US2010/032134 (WO 2010/124146).
A20, N21, Y22, Q23, P24, N25, L26, E30, F31, Q33, L35, E36, N37, L39, K40, V41,
K43, L44, C57, R61, V62, D63, Q65, K87, E94, N95, L99, D100, N105, K137, E138,
G143, E144, N182, L184, K185, G187, N189, T190, P225, H226, K247, T257, E258,
M259, D266, R271, W278, C291, F299, V302, Y309, D310, N334, D353, S357, I358,
E361, L377, F381, E384, N389, I392, I393, K398, Y399, E401, N402, A403, S406,
S407, S408, G409, A411, L413, C421, Q423, Q424, E425, D426, H430, L432, R433,
S434, D437, R443, C446, F449, A456, T457, S458, A459, A460, E461, L462, E463,
R464, G465, E466, T467, T468, N469, H476, N478, D479, Q485, D508, P513, A515,
M523, S527, Y531, Q532, Y533, L537, G538, R539, Y542, A543, or P557 of SEQ ID
NO: 42 as listed in PCT/US2010/032134 (WO 2010/124146).
L70R of SEQ ID NO: 42 as listed in PCT/US2010/032134 (WO 2010/124146).
A22, N23, Y24, E25, P26, N27, K272, R274, W281, F302, V305, Y312, D313, L380,
F384, E387, Y402, N404, A406, S409, S410, S411, G412, L414, Q415, L416, F449,
N453, L454, A455, S456, A457, S4548, A459, E460, I461, A462, R463, G464, E465,
T466, N469, C497, L521, S525, S537, or E540 of SEQ ID NO: 43 as listed in
PCT/US2010/032134 (WO 2010/124146).
I28, V30, L130, G153, V299, L303, L469, L494, R198, I229, L260, D311, D323, A443,
A453, N454, H515, A519, E525, F388, N438, E451, D345, R528, T536, D304, E314,
D311, D323, A443, A453, or N545 of SEQ ID NO: 45 as listed in PCT/US2010/032134
(WO 2010/124146).
T536F, T536Y, T536V, T536I, T536M, T536H, T536C, T536L, T536K, T536A, T536S,
T536G, A443S, A443G, A443R, A443Q, A453L, A453N, A453I, A453V, H515M,
H515Q, A519H, A519S, A519G, A519W, A519T, D311M, D311F, D311L, D311G,
D311A, D311T, D311R, D311V, D311E, D323M, D323W, D323Y, D323T,
D323I, D323S, D323V, D323A, D323G, D323Q, I229V, I229L, I229C, I229T, I229P,
I229N, L260N, L260M, L260I, I28W, I28T, I28R, I28Y, V30K, L130W, L130K, L130S,
L130Y, L130R, L130V, L130I, L130E, L130D, G153K, G153H, G153L, G153W,
L303I, L469A, L469Q, L494P, L494C, L494I, L494V, L494S, L494G, L494D, I28W,
I28T, I28R, I28Y, V30K, L130W, L130K, L130S, L130Y, L130R, L130V, L130I,
L130E, L130D, G153K, G153H, G153L, G153W, L303I, L469A, L469Q, L494P,
L494C, L494I, L494V, L494S, L494G, G491S, L494D, A453N, G491S, L494P, T536C,
A452N/G491S, A452N/L494P, A452N/T536C, A452N/G491S/L494P, A452N/G491S/
T536C, A453N/L494P/T536C, A453N/G491S/L494P/T536C, G491S/L494P,
G491S/T536C, G491S/L494P/T536C, or L494P/T536C of SEQ ID NO: 45 as listed in
PCT/US2010/032134 (WO 2010/124146).

For the following sequences, the SEQ ID NOS and residue numbering are as used in
PCT/US2009/041581 (WO 2009/132220):
An amino acid substitution corresponding to a substitution at one of the following
residues: L26, E30, F31, Q33, L35, E36, N37, L39, K40, V41, K43, L44, R61, V62, D63,
Q65, K87, E94, N95, L99, D100, N105, K137, E138, G143, E144, N182, L184, K185,
G187, N189, T190, P225, H226, K247, T257, E258, M259, D266, N334, D353, S357,
I358I, E361, N389, I392, I393, K398, E401, C421, Q423, Q424, E425, D426, H430,
L432, R433, S434, D437, R443, L462, E463, H476, N478, D479, Q485, D508, P513,
A515, Q532, Y533, L537, G538, R539, Y542, A543, P557, P24, N25, Y309, D310,
L377, F381, E384, Y399, N402, A403, S406, S407, G409, A411, L413, F449, A456,
T457, S458, A459, A460, E461, L462, E463, R464, G465, E466, T467, T468, N469,
M523, S527, Y531, A20, N21, Y22, Q23, R271, W278, F299, V302, S408, Arg 269, Asp
306, Asp 310, Glu 384, Arg 450, Asn 453, Phe 381, Tyr 399, Ala 403, Asn 469,
Tyr 309, Asp 310, Leu 377, Glu 384, Asn 402, Ser 407, Residues 20-25, Ala 456, Thr
457, Ser 458, Ala 459, Ala 460, Glu 461, Leu 462, Glu 463, Arg 464, Gly 465, Glu 466,
Thr 467, Thr 468, Arg 271, Trp 278, Phe 299, Val 302, Ser 408, Phe 449, Ser 458, Tyr
531, Gly 409, Ala 411, Leu 413, Met 523, or Ser 527 of SEQ ID NO: 2 as listed in
PCT/US2009/041581 (WO 2009/132220)

An amino acid substitution corresponding to one of the following substitutions: V10M,
F12S, T15A, E18G, V58I, V58F, L70Q, L70V, L70T, T71P, V79L, E89D, G94A,
S119F, F120L, G127R, E175V, T212I, S257A, R262G, A266G, F280L, N297K, F305L,
L319M, E323K, A328T, D342E, A359T, K366N, E368D, L374M, S396T, V418S,
K438N, H440R, T442I, T442A, I449V, A469S, K500R, K505Q, G507S, S509N, F511Y,
N532K, L70R, L70W, G94E, F305L, V418M, V418T, T442V of SEQ ID NO: 120 as
listed in PCT/US2009/041581 (WO 2009/132220)

A combination of amino acid substitutions corresponding to one of the following
combinations of substitutions: G127R/F511Y, L70Q/G94A/R262G/F305L, F12S/
T15A/E18G/N297K, S396T/T442I, V10M/E323K, F120L/A266G, K438N/K500R, TABLE D-continued Amino Acid Substitutions V79L/S509N, E175V/S257A/E368D/A469S, T71P/L374M, F280L/H440R,
E89D/H440R, V58F/A328T/N532K, S119F/D342E/I449V, K366N/G507S of SEQ ID
NO: 120 as listed in PCT/US2009/041581 (WO 2009/132220)

An amino acid substitution corresponding to a substitution at one of the following
residues: F303, V306, F385, S412, Q416, F450, V418, or T442 of SEQ ID NO: 120 as
listed in PCT/US2009/041581 (WO 2009/132220)

An amino acid substitution corresponding to a substitution at one of the following
residues: Lys 272, Asp 309, Asp 313, Glu 387, Arg 450, Asn 453, Phe 384, Tyr 402, Ala
406, Ser 409, Ala 460, Asn 469, Phe 384, Tyr 402, Ala 406, Ser 409, Asn 469, Tyr 312,
Asp 313, Leu 380, Glu 387, Asn 404, Ser 410, Arg 274, Trp 281, Phe 302, Val 305, Ser
411, Gln 415, Phe 449, Gly 412, Leu 414, Leu 416, Leu 521, Ser 525, Ala 22, Asn 23,
Tyr 24, Glu 25, Pro 26, Asn 27, or Cys 497 of SEQ ID NO: 7 as listed in
PCT/US2009/041581 (WO 2009/132220)

An amino acid substitution, or a combination of amino acid substitutions corresponding
to one of the following: K272R, K272R/N453D, K272R/N453D/C497W, or 272R/497W
of SEQ ID NO: 7 as listed in PCT/US2009/041581 (WO 2009/132220)

An amino acid substitution corresponding to a substitution at one of the following
residues: L454, A455, S456, A457, S458, A459, E460, I461, A462, R463, G464, E465,
or T466 of SEQ ID NO: 9 as listed in PCT/US2009/041581 (WO 2009/132220)

An amino acid substitution corresponding to a substitution at one of the following
residues: Leu 454, Ala 455, Ser 456, Ala 457, Ser 458, Ala 459, Glu 460, Ile 461, Ala
462, Arg 463, Gly 464, Glu 465, or Thr 466 of SEQ ID NO: 124 as listed in
PCT/US2009/041581 (WO 2009/132220)

An amino acid substitution corresponding to a substitution at one of the following
residues: Met 1, Arg 2, Arg 3, Ser 4, Ala 5, Asn 6, Tyr 7, Glu 8, Pro 9, Asn 10, Ser 11,,
Trp 12, Asp 13, Tyr 14, Asp 15, Tyr 16 Leu 17, Leu 18, Ser 19, Ser 20, Asp 21, Thr 22,
Asp 23, Glu 24, Ser 25, Ile 26, Glu 27, Val 28, Leu 438, Ala 439, Ser 440, Ala 441, Ser
442, Ala 443, Glu 444, Ile 445, Ala 446, Arg 447, Gly 448, Glu 449, Thr 450, Ala 451,
Asn 452, Ser 453, Tyr 512, His 513, Asn 514, Gly 515, Asp 516, Ala 517, His 518, Thr
519, Ser 520, Pro 521, Asp 522, Glu 523, Leu 524, Thr 525, Arg 526, L17, L18, S19,
S20, S239, R243, F253, A254, R255, D256, R257, I259, E260, D293, Y295, D296,
V297, Y298, G299, T300, E303, Y325, L374, Y375, V529, L530, T534, D293, Y295,
V297, E370, A371, W373, L374, S378, T379, P380, F382, Y385, F386, R433, L434
C435, N436, D437, V454, S455, C456, Y457, M458, T469, V472, I476, Y512, E187,
L188, R255, R257, F270, E271, Q273, Y274, F285, V288, A439, S440, S442, S508,
H509, C510, T511, Y512, R528, V529, L530, S531, V532, Asp 293, Tyr 385, Ser 392,
Asp 437, Ser 440, Ala 441, Ser 442, Ala 443, Glu 444, Ile 445, Ala 446 Arg 447, Gly
448, Glu 449, Thr 450, Ala 451, Asn 452, Ser 453, Tyr 512, His 513, Asn 514, Gly 515,
Asp 516, Ala 517, His 518, Thr 519, Ser 520, Pro 521, Asp 522, Glu 523, Leu 524, Ser
261, Trp 264, Phe 285, Thr 289, Ser 393, Ser 394, Phe 432, or Tyr 512 of SEQ ID NO:
164 as listed in PCT/US2009/041581 (WO 2009/132220) wherein the amino acid residue
numbering is described at page 127, paragraph [0467], of PCT/US2009/041581 (WO
2009/132220)

In some embodiments, the isoprene synthase variant does not comprise a sequence in Table E. In some embodiments, the sequences shown in Tables E and F can have one or more substitution selected from those shown in those Tables.

TABLE E

Isoprene Synthase Sequences

For the following sequences, the SEQ ID NOS and residue numbering are as used in
PCT/US2010/032134 (WO 2010/124146):
SEQ ID NO: 5 (P. tremuloides IspS in P. tremuloides pET24a)
SEQ ID NO: 9 (P. alba isoprene synthase variant in pDu30)
SEQ ID NO: 11 (P. tremuloides isoprene synthase variant P. trem. TRC-pET200 in pDu3)
SEQ ID NO: 13 (P. trichocharpa isoprene synthase)
SEQ ID NO: 16 (P. alba isoprene synthase)
SEQ ID NO: 20 (P. alba FL (+) TEV in MD09-161)
SEQ ID NO: 42 (kudzu isoprene synthase) - L70R variant
SEQ ID NO: 43 (Populus alba x tremuloides)
SEQ ID NO: 45 (P. alba isoprene synthase) - having any one of the following mutations
or combinations of substitutions: T536F, T536Y, T536V, T536I, T536M, T536H,
T536C, T536L, T536K, T536A, T536S, T536G, A443G, A443S, A443R, A443Q,
A453L, A453N, A453I, A453V, H515M, H515Q, A519H, A519S, A519G, A519W,
A519T, D311M, D311F, D311L, D311G, D311I, D311A, D311T, D311R, D311V,
D311E, D323M, D323W, D323Y, D323F, D323I, D323S, D323V, D323A, D323G,
D323Q, I229V, I229L, I229C, I229T, I229P, I229N, L260N, L260M, L260I, I28W,
I28T, I28R, I28Y, V30K, L130W, L130K, L130S, L130Y, L130R, L130V, L130I,

TABLE E-continued

Isoprene Synthase Sequences

L130E, L130D, G153K, G153H, G153L, G153W, L303I, L469A, L469Q, L494P,
L494C, L494I, L494V, L494S, L494G, L494D, I28W, I28T, I28R, I28Y, V30K, L130W,
L130K, L130S, L130Y, L130R, L130V, L130I, L130E, L130D, G153K, G153H, G153L,
G153W, L303I, L469A, L469Q, L494P, L494C, L494I, L494V, L494S, L494G, G491S,
L494D, A453N, G491S, L494P, T536C, A452N/G491S, A452N/L494P, A452N/T536C,
A452N/G491S/L494P, A452N/G491S/T536C, A453N/L494P/T536C,
A453N/G491S/L494P/T536C, G491S/L494P, G491S/T536C, G491S/L494P/T536C,
L494P/T536C

For the following sequences, the SEQ ID NOS and residue numbering are as used in
PCT/US2009/041581 (WO 2009/132220):
SEQ ID NO: 2
SEQ ID NO: 2 A20G variant
SEQ ID NO: 2 S408D variant
SEQ ID NO: 2 C57S/C291S/C421S/C446S variant
SEQ ID NO: 150 of Kudzu TRC (MEA) in pDu50.
SEQ ID NO: 152 of KudzuTRC (-4) in pDu50-4.
SEQ ID NO: 120
SEQ ID NO: 120 - having any one of the following mutations: V10M, F12S, T15A,
E18G, V58I, V58F, L70Q, L70V, L70T, T71P, V79L, E89D, G94A, S119F, F120L,
G127R, E175V, T212I, S257A, R262G, A266G, F280L, N297K, F305L, L319M,
E323K, A328T, D342E, A359T, K366N, E368D, L374M, S396T, V418S, K438N,
H440R, T442I, T442A, I449V, A469S, K500R, K505Q, G507S, S509N, F511Y, N532K,
L70R, L70W, G94E, F305L, V418M, V418T, T442V
SEQ ID NO: 120 - having any one of the following combinations of mutations:
G127R/F511Y, L70Q/G94A/R262G/F305L, F12S/T15A/E18G/N297K, S396T/T442I,
V10M/E323K, F120L/A266G, K438N/K500R, V79L/S509N,
E175V/S257A/E368D/A469S, T71P/L374M, F280L/H440R, E89D/H440R,
V58F/A328T/N532K, S119F/D342E/I449V, K366N/G507S
SEQ ID NO: 122 (MEA variant)
SEQ ID NO: 124 (MSV variant)
SEQ ID NO: 126 (MVS variant)
SEQ ID NO: 128 (MTE variant)
SEQ ID NO: 130 (MNV variant)
TRC (-3) variant (SEQ ID NO: 136)
TRC (-4) variant (SEQ ID NO: 138)
TRC (-5) variant (SEQ ID NO: 140)
TRC (-6) variant (SEQ ID NO: 142)
TRC (-7) variant (SEQ ID NO: 144)
SEQ ID NO: 7
SEQ ID NO: 7 - having any one or more of the following substitutions: K272R, N453D,
C497W
SEQ ID NO: 7 - having any one of the following combinations of substitutions:
K272R/N453D; K272R/N453D/C497W, 272R/497W
(SEQ ID NO: 132) of P. alba MEA(+)TEV in MD09-163.
(SEQ ID NO: 134) of P. alba FL(+)TEV in MD09-161.
(SEQ ID NO: 162) of IspS variant P. alba TRC-pET200 in pDu30.
Sequences for MD08-99, MD08-100, MD09-167, MD08-104, MD08-102
MET variant of P. tremuloides isoprene synthase (SEQ ID NO: 146).
(SEQ ID NO: 158) of P. tremuloides IspS in P. trichocharpa pET24a.
(SEQ ID NO: 164) of IspS variant P. trem TRC-pET200 in pDu31.
MET variant of P. trichocharpa isoprene synthase (SEQ ID NO: 148).
(SEQ ID NO: 160) of P. trichocharpa IspS in P. trichocharpa pET24a.
(SEQ ID NO: 166) of IspS variant P. trich TRC-pET200 in pDu32.

In some embodiments, the isoprene synthase variant does not comprise a sequence in Table F.

TABLE F

For the following sequences, the SEQ ID NOS and residue numbering are as used in
PCT/US2010/032134 (WO 2010/124146)
SEQ ID NO: 11 (P. tremuloides isoprene synthase variant P. trem. TRC-pET200 in pDu3)
having a substitution at one of the following residues: Met 1, Arg 2, Arg 3, Ser 4, Ala 5,
Asn 6, Tyr 7, Glu 8, Pro 9, Asn 10, Ser 11, Trp 12, Asp 13, Tyr 14, Asp 15, Tyr 16, Leu
17, Leu 18, Ser 19, Ser 20, Asp 21, Thr 22, Asp 23, Glu 24, Ser 25, Ile 26, Glu 27, Val
28, Leu 438, Ala 439, Ser 440, Ala 441, Ser 442, Ala 443, Glu 444, Ile 445, Ala 446, Arg
447, Gly 448, Glu 449, Thr 450, Ala 451, Asn 452, Ser 453, Tyr 512, His 513, Asn 514,
Gly 515, Asp 516, Ala 517, His 518, Thr 519, Ser 520, Pro 521, Asp 522, Glu 523, Leu
524, Thr 525, Arg 526, D293, Y385, S392, D437, S261, W264, F285, T289, S393, S394,
F432, Y512, 40, A441, S442, A443, E444, I445, A446, R447, G448, E449, T450, A451,
N452, S453, Y512, H513, N514, G515, D516, A517, H518, T519, S520, P521, D522,
E523, L524, L17, L18, S19, S20, S239, R243, F253, A254, R255, D256, R257, I259,
E260, D293, Y295, D296, V297, Y298, G299, T300, E303, Y325, L374, Y375, V529,
L530, T534, D293, Y295, V297, E370, A371, W373, L374, S378, T379, P380, F382, TABLE F-continued Y385, F386, R433, L434 C435, N436, D437, V454, S455, C456, Y457, M458, T469,
V472, I476, Y512, E187, L188, R255, R257, F270, E271, Q273, Y274, F285, V288,
A439, S440, S442, S508, H509, C510, T511, Y512, R528, V529, L530, S531, or V532,
wherein amino acid residue numbering is described at page 84, paragraph [0295] of
PCT/US2010/032134 (WO 2010/124146).

SEQ ID NO: 42 (kudzu isoprene synthase) having a substitution at one of the following
residues: A20, N21, Y22, Q23, P24, N25, L26, E30, F31, Q33, L35, E36, N37, L39, K40,
V41, K43, L44, C57, R61, V62, D63, Q65, K87, E94, N95, L99, D100, N105, K137,
E138, G143, E144, N182, L184, K185, G187, N189, T190, P225, H226, K247, T257,
E258, M259, D266, R271, W278, C291, F299, V302, Y309, D310, N334, D353, S357,
I3581, E361, L377, F381, E384, N389, I392, I393, K398, Y399, E401, N402, A403,
S406, S407, S408, G409, A411, L413, C421, Q423, Q424, E425, D426, H430, L432,
R433, S434, D437, R443, C446, F449, A456, T457, S458, A459, A460, E461, L462,
E463, R464, G465, E466, T467, T468, N469, H476, N478, D479, Q485, D508, P513,
A515, M523, S527, Y531, Q532, Y533, L537, G538, R539, Y542, A543, and P557

SEQ ID NO: 43 (Populus alba x tremuloides) having a substitution at one of the
following residues: A22, N23, Y24, E25, P26, N27, K272, R274, W281, F302, V305,
Y312, D313, L380, F384, E387, Y402, N404, A406, S409, S410, S411, G412, L414,
Q415, L416, F449, N453, L454, A455, S456, A457, S4548, A459, E460, I461, A462,
R463, G464, E465, T466, N469, C497, L521, S525, S537, or E540

SEQ ID NO: 45 (P. alba isoprene synthase) having a substitution at one of the following
residues: I28, V30, L130, G153, V299, L303, L469, L494, R198, I229, L260, D311,
D323, A443, A453, N454, H515, A519, E525, F388, N438, E451, D345, R528, T536,
D304, E314, D311, D323, A443, A453, N545

For the following sequences, the SEQ ID NOS and residue numbering are as used in
PCT/US2009/041581 (WO 2009/132220):
SEQ ID NO: 2 having a substitution at one of the following residues: L26, E30, F31,
Q33, L35, E36, N37, L39, K40, V41, K43, L44, R61, V62, D63, Q65, K87, E94, N95,
L99, D100, N105, K137, E138, G143, E144, N182, L184, K185, G187, N189, T190,
P225, H226, K247, T257, E258, M259, D266, N334, D353, S357, I3581, E361, N389,
I392, I393, K398, E401, C421, Q423, Q424, E425, D426, H430, L432, R433, S434,
D437, R443, L462, E463, H476, N478, D479, Q485, D508, P513, A515, Q532, Y533,
L537, G538, R539, Y542, A543, P557, P24, N25, Y309, D310, L377, F381, E384, Y399,
N402, A403, S406, S407, G409, A411, L413, F449, A456, T457, S458, A459, A460,
E461, L462, E463, R464, G465, E466, T467, T468, N469, M523, S527, Y531, A20,
N21, Y22, Q23, R271, W278, F299, V302, S408, Arg 269, Asp 306, Asp 310, Glu 384,
Arg 450, Asn 453, Phe 381, Tyr 399, Ala 403, Ser 406, Asn 469, Tyr 309, Asp 310, Leu
377, Glu 384, Asn 402, Ser 407, Residues 20-25, Ala 456, Thr 457, Ser 458, Ala 459, Ala
460, Glu 461, Leu 462, Glu 463, Arg 464, Gly 465, Glu 466, Thr 467, Thr 468, Arg 271,
Trp 278, Phe 299, Val 302, Ser 408, Phe 449, Ser 458, Tyr 531, Gly 409, Ala 411, Leu
413, Met 523, or Ser 527

SEQ ID NO: 120 having a substitution at one of the following residues: F303, V306,
F385, S412, Q416, F450, V418, T442

SEQ ID NO: 7 - having a substitution at one of the following residues: Lys 272, Asp 309,
Asp 313, Glu 387, Arg 450, Asn 453, Phe 384, Tyr 402, Ala 406, Ser 409, Ala 460, Asn
469, Phe 384, Tyr 402, Ala 406, Ser 409, Asn 469, Tyr 312, Asp 313, Leu 380, Glu 387,
Asn 404, Ser 410, Arg 274, Trp 281, Phe 302, Val 305, Ser 411, Gln 415, Phe 449, Gly
412, Leu 414, Leu 416, Leu 521, Ser 525, Ala 22, Asn 23, Tyr 24, Glu 25, Pro 26, Asn
27, Cys 497

SEQ ID NO: 9 - having a substitution at one of the following residues 454-466:
LASASAEIARGET SEQ ID NO: 124 (MSV variant) - having a substitution at one of the following residues:
Leu 454, Ala 455, Ser 456, Ala 457, Ser 458, Ala 459, Glu 460, Ile 461, Ala 462, Arg
463, Gly 464, Glu 465, Thr 466, SEQ ID NO: 164 having a substitution at one of the following residues: Met 1, Arg 2,
Arg 3, Ser 4, Ala 5, Asn 6, Tyr 7, Glu 8, Pro 9, Asn 10, Ser 11, Trp 12, Asp 13, Tyr 14,
Asp 15, Tyr 16 Leu 17, Leu 18, Ser 19, Ser 20, Asp 21, Thr 22, Asp 23, Glu 24, Ser 25,
Ile 26, Glu 27, Val 28, Leu 438, Ala 439, Ser 440, Ala 441, Ser 442, Ala 443, Glu 444,
Ile 445, Ala 446, Arg 447, Gly 448, Glu 449, Thr 450, Ala 451, Asn 452, Ser 453, Tyr
512, His 513, Asn 514, Gly 515, Asp 516, Ala 517, His 518, Thr 519, Ser 520, Pro 521,
Asp 522, Glu 523, Leu 524, Thr 525, Arg 526, L17, L18, S19, S20, S239, R243, F253,
A254, R255, D256, R257, I259, E260, D293, Y295, D296, V297, Y298, G299, T300,
E303, Y325, L374, Y375, V529, L530, T534, D293, Y295, V297, E370, A371, W373,
L374, S378, T379, P380, F382, Y385, F386, R433, L434 C435, N436, D437, V454,
S455, C456, Y457, M458, T469, V472, I476, Y512, E187, L188, R255, R257, F270,
E271, Q273, Y274, F285, V288, A439, S440, S442, S508, H509, C510, T511, Y512,
R528, V529, L530, S531, V532, Asp 293, Tyr 385, Ser 392, Asp 437, Ser 440, Ala 441,
Ser 442, Ala 443, Glu 444, Ile 445, Ala 446 Arg 447, Gly 448, Glu 449, Thr 450, Ala
451, Asn 452, Ser 453, Tyr 512, His 513, Asn 514, Gly 515, Asp 516, Ala 517, His TABLE F-continued 518, Thr 519, Ser 520, Pro 521, Asp 522, Glu 523, Leu 524, Ser 261, Trp 264, Phe 285, Thr 289, Ser 393, Ser 394, Phe 432, Tyr 512 wherein the amino acid residue numbering is described at page 127, paragraph [0467], of PCT/US2009/041581 (WO 2009/132220)

Residue numbering for the sequences and substitutions in Tables 4-6 are as defined in PCT/US2009/041581 (WO 2009/132220) or PCT/US2010/032134 (WO 2010/124146), as noted. One of skill in the art can determine how residues of Tables 4-6 correspond with those of a reference sequence, such as MEA P. alba (FIG. 20) (SEQ ID NO:1).

N-Terminal Truncation

In some embodiments, the variant comprises an N-terminal region truncation comprising truncation of one or more amino acid residues of the N-terminal region. See, for example, Example 10. Examples of N-terminal truncations are described in PCT/US2009/041581 (WO 2009/132220). In some embodiments, the isoprene synthase variant comprising an N-terminal truncation has an increased specific activity compared to a full length isoprene synthase. Examples of N-terminal truncations include, for example, the residues corresponding to the N-terminal truncated residues of P. alba isoprene synthases: MEA variant, MSV variant, MVS variant, MTE variant, MNV variant, a TRC (−3) variant, a TRC (−4) variant, a TRC (−5) variant, a TRC (−6) variant and a TRC (−7) variant; P. tremuloides isoprene synthase: MET variant; and P. trichocharpa isoprene synthase: MET variant, wherein the sequences are described in PCT/US2009/041581 (WO 2009/132220). In some embodiments, the truncated residues of the variant correspond to the residues truncated in the P. alba isoprene synthase MEA variant (See FIG. 21A-21B).

Isoprene Synthase Variant Properties

In some embodiments, the variant has at least one improved property over a reference sequence. In some embodiments, the reference sequence is the parent sequence. In some embodiments, the reference sequence is a wild-type isoprene synthase. In some embodiments, the reference sequence is MEA P. alba (SEQ ID NO:1), also shown in FIG. 20.

Properties of interest include, but are not limited to: increased intracellular activity, specific productivity, yield, and cellular performance index. In some embodiments, specific productivity increase at least about 2, 3, 4, 5, 6 7, 8, 9, 10 times or more. In one embodiment, specific productivity is about 20 mg/L/OD/hr. In other embodiments, yield increase at least about 2, 3, 4, 5 times or more. In other embodiments, cell performance index increase at least about 2, 3, 4, 5 times or more. In other embodiments, intracellular activity increase at least about 2, 3, 4, 5, 6, 7, 8, 9, 10 times or more.

Without being bound by theory, these properties can be achieved by one or a combination of any of the following properties of IspS: increased cellular viability, increased $k_{cat}$, decreased $K_m$, increased specific activity, increased solubility, decreased insolubility, improved ribosome binding, increased translation initiation rate, increased translation elongation rate, increased transcription initiation rate, increased transcription elongation rate, decreased secondary structure of DNA, decreased secondary structure of RNA, increased secondary structure of DNA, increased secondary structure of RNA, increased folding rates, increased affinity for intracellular chaperones, increased stability, decreased protein turnover, decreased exposure to intracellular protease, decreased affinity for intracellular protease, decreased localization to the periplasm, improved localization to the cytoplasm, decreased inclusion body formation, decreased membrane localization, increased expression due to a more favorable codon, increased DNA stability, increased RNA stability, and decreased RNA degradation. In brief, any mutation that has a positive effect on the properties of nucleic acid sequences (DNA and RNA) encoding or expressing the IspS variant, or the biochemical properties of the IspS enzyme itself, could allow for greater activity within the cell. Other properties of interest include pH optima, temperature stability (e.g., $T_m$ value), as well as sensitivity to potential inhibitors including substrate or product inhibition. Oxidative and proteolytic stability are also of interest. Furthermore, activation or inhibition due to metal ion effects and ionic strength is of interest.

In one embodiment, specific activity values can be calculated for every variant in the entire set of SELs by dividing the molar amount of isoprene produced in a given amount of time by the specific amount of protein in each sample. Performance index (PI) can be calculated by dividing the specific activity of any given variant by the average of several WT specific activity measurements from the same microtiter plate. For example, a variant that displayed a PI value of 1.5 for specific activity would be 50% improved over WT. PIs for protein concentration and isoprene produced can also be calculated in the same fashion. These measurements were used for detailed data analysis as shown in the Examples.

Growth index or performance index of a host cell comprising a nucleic acid encoding an isoprene synthase variant may also be used to indicate whether a particular variant has a property of interest. Growth index and performance index may be determined according to methods known to one of skill in the art and/or as taught herein. Growth and performance index may be determined for a particular variant by comparison with a reference sequence. In some embodiments, the reference sequence is the parent sequence of the variant. In some embodiments, the reference sequence is a wild type sequence. In some embodiments, the reference sequence is MEA P. alba. In some embodiments, growth index is determined according to the method in Example 2. In some embodiments, growth index is determined according to the method in Example 4. In various embodiments, the growth index of the variant is at least about 0.8, at least about 0.9, at least about 1.0, at least about 1.1, at least about 1.2, at least about 1.3, as compared with the reference sequence. In various embodiments, the performance index of the variant is at least about 0.7, at least about 0.8, at least about 0.9, at least about 1.0, at least about 1.1, at least about 1.2, as compared with the reference sequence.

Methods for determining the properties of interest are known tone of skill in the art. Certain methods are further described herein in the Examples. Variants can be assessed based on the desired outcome or property to be improved. For example, a variant isoprene synthase engineered for increased specific activity can be tested for the conversion of DMAPP to isoprene in vitro with purified or partially purified variant isoprene synthase or in vivo in the context of a host organism such as E. coli. In some cases, the E. coli may also express the DXP pathway, the MVA pathway, or both. Improved activity is assessed in comparison with other isoprene synthases; for example, a wild type isoprene synthase, a parent isoprene synthase, or other reference polypeptide. It is contemplated that enzymes having various degrees of e.g. stability, solubility, activity, and/or expression level in one or more of test conditions will find use in the present invention for the production of isoprene in a diversity of hosts. High throughput methods may provide an investigation of these properties in an economical manner.

There is a strong correlation between increased intracellular DMAPP levels and growth inhibition of *E. coli*, which can be alleviated by the expression of *P. alba* Isoprene Synthase (IspS). Without being bound by theory, increased levels of IspS activity should therefore allow for better growth due to more rapid conversion of DMAPP to isoprene. By monitoring the growth rates of *E. coli* expressing variants of IspS under these conditions, the inventors have identified mutant IspS enzymes that display increased ability to convert DMAPP to isoprene within the cell.

The invention also contemplates methods for screening for isoprene synthase variants, comprising: (a) contacting a host cell with a medium comprising about 10 µM to about 70 µM IPTG, and about 5 mM to about 20 mM mevalonic acid (MVA), wherein the host cell comprises a nucleic acid encoding an isoprene synthase variant in operable combination with a promoter; and (b) measuring the growth rate of the host cell. The variant growth rate may be compared to that of a reference isoprene synthase (e.g. a parent isoprene synthase, a wild-type isoprene synthase, or MEA *P. alba* isoprene synthase. The methods may be used to screen for variants having a particular property of interest, for example, one or more of the properties described herein. In some embodiments, an increased growth rate indicates an isoprene synthase variant with an increased ability to convert DMAPP to isoprene within the host cell synthase. Growth rates may be analyzed, for example, according to methods known in the art, or as exemplified in the Examples below. In some embodiments, the method further comprises determining a growth index for the variant. In some embodiments, the method further comprises determining a performance index for the variant. Growth rate of the cells in exponential phase and/or final density of the cells may be taken into consideration as factors when selecting variants. As exemplified below, for the variants shown in the examples, the growth rate of the cells in exponential phase was a consideration. In addition, growth rate and final density was also taken into consideration when selecting for variants described herein.

In some embodiments, the IPTG is present in the medium at a concentration from about 10 µM to about 60 µM. In some embodiments, the IPTG is present in the medium at a concentration from about 10 µM to about 200 µM. In some embodiments, the IPTG is present in the medium at a concentration from about 20 µM to about 60 µM. In some embodiments, IPTG is present in the medium at a concentration from about 20 µM to about 120 µM. In some embodiments, the IPTG is present in the medium at a concentration from about 40 µM to about 60 µM. In some embodiments, the IPTG is present in the medium at a concentration from about 40 µM to about 100 µM. In some embodiments, the IPTG is present in the medium at a concentration of about 40 µM. In some embodiments, the IPTG is present in the medium at a concentration of about 50 µM, 60 µM, 70 µM, 80 µM, 90 µM, 100 µM, 110 µM, 120 µM, 130 µM, 140 µM, 150 µM, 160 µM, 170 µM, 180 µM, 190 µM, or 200 µM.

In some embodiments, the MVA is present in the medium at a concentration of about 5 mM to about 20 mM. In some embodiments, the MVA is present in the medium at a concentration of about 7 mM to about 15 mM. In some embodiments, the MVA is present in the medium at a concentration of about 8 mM to about 12 mM. In some embodiments, the MVA is present in the medium at a concentration of about 10 mM. In some embodiments, the host cell is MD09-170.

In another aspect, one or more improved properties can be seen by analyzing productive positions as further described below and exemplified in the Examples. Productive positions can be described as those positions within a molecule (e.g., enzyme such as isoprene synthase) that are most useful for making combinatorial variants exhibiting an improved characteristic, where the position itself allows for at least one combinable mutation. Combinable mutations can be described as those substitutions in a molecule that can be used to make selected combinatorial variants. Combinable mutations do not significantly decrease expression, specific activity or growth, while at the same time improving at least one desired characteristic of the molecule such as growth or specific activity. Positions in IspS containing all combinable mutations can be determined using performance index (PI) values resulting from the DMAPP assay for specific activity, growth curves of MEA *P. alba* expressing the indicated IspS variant and protein determination, as exemplified in Example 1 and Example 2. Productive positions can be the positions which have shown a certain degree of tolerance for multiple substitutions, while at the same time meeting a set of criteria for combinability as set forth below.

When evaluating the data set, the most productive positions were determined when the following criteria were applied. For positions containing substitutions where the minimum performance indices (PI) relative to wild type IspS for specific activity and expression are greater than or equal to a PI of 0.9 and where at least one PI relative to wild type IspS for specific activity or growth is greater than or equal to a PI of 1.0, these positions are classified as Group A. For positions containing substitutions where the minimum performance indices (PI) relative to wild type IspS for specific activity and expression are greater than or equal to a PI of 0.8 and where at least one PI relative to wild type IspS for specific activity or growth is greater than or equal to a PI of 1.2, these positions are classified as Group B. For positions containing substitutions where the minimum performance indices (PI) relative to wild type IspS for specific activity and expression are greater than or equal to a PI of 0.5 and where at least one PI relative to wild type IspS for specific activity or growth is greater than or equal to a PI of 1.5, these positions are classified as Group C.

Groups A, B, and C can further contain positions that have differing degrees of tolerance for multiple substitutions. To measure this degree of substitutions tolerated, a Rank can be assigned to each position. The Rank can be assigned according to the percentage of the substitutions within each position that fall within groups A, B, or C. Exemplary combinable positions and substitutions are shown in Table 31.

The criteria to determine the Rank for productive positions are as follows: Positions where less than 15% but greater than 0% of the substitutions at a given position fall within groups A, B, or C are given a Rank of "1." Positions where less than 30%, but greater than, or equal to 15% of the substitutions at a given position fall within groups A, B, or C are given a Rank of "2." Positions where less than 50%, but greater than, or equal to 30% of the substitutions at a given position fall within groups A, B, or C are given a Rank of "3." Positions where greater than, or equal to 50% of the substitutions at a given position fall within groups A, B, or C are given a Rank of "4."

Substitutions can be further assigned a Suitability Score based on the group(s) the substitution is a member of, and where a higher score represents a substitution more suitable for use in making combinatorial variants. Exemplary suitability scores are represented and described in Table 30. Suitability scores and rank for individual substitutions of IspS that fit the above criteria are exemplified in Table 31.

TABLE 30

| Suitability Score for the defined groups. | |
|---|---|
| Substitutions Occur in Group(s): | Suitability Score |
| A, B and C | +++++ |
| A and B | ++++ |
| A or (B and C) | +++ |
| B | ++ |
| C | + |

Accordingly, in one aspect of the invention, an isoprene synthase variant can be a polypeptide (e.g., an isolated polypeptide) with improved isoprene synthase properties that are scored +++++ as exemplified in the Examples. These polypeptides can have one or more substitution(s) at residue positions with numbering that corresponds to SEQ ID NO: 1 (MEA *P. alba* isoprene synthase) that is indicated in the column labeled +++++ as exemplified in the Examples. Some non-limiting examples are isolated polypeptides with improved isoprene synthase properties wherein the polypeptide comprises one or more substitution(s) at residues corresponding to SEQ ID NO:1 selected from the group consisting of: X2, X18, X19, X21, X24, X26, X27, X29, X37, X42, X47, X48, X49, X56, X81, X82, X84, X93, X94, X95, X120, X123, X126, X131, X132, X134, X137, X139, X143, X151, X155, X166, X167, X169, X170, X171, X175, X179, X180, X197, X229, X231, X240, X242, X245, X246, X247, X251, X271, X282, X306, X317, X319, X369, X371, X376, X379, X380, X389, X392, X393, X408, X409, X421, X422, X423, X429, X437, X443, X444, X447, X455, X458, X461, X464, X466, X470, X473, X500, X502, X506, X513, X525 and, X531. In some embodiments, these substitutions can be at a residue selected from the group consisting of E2, Y18, L19, S21, T24, E26, S27, E29, K37, V42, N47, N48, E49, L56, D81, R82, V84, T93, K94, T95, S120, K123, N126, E131, N132, K134, I137, A139, L143, L151, N155, S166, H167, K169, E170, L171, K175, E179, L180, Q197, I229, S231, T240, R242, R245, R246, V247, T251, A271, S282, L306, D317, N319, F369, Q371, L376, K379, S380, G389, W392, K393, V408, V409, Q421, K422, Y423, R429, C437, A443, S444, I447, S455, C458, R461, G464, S466, A470, S473, V500, T502, L506, T513, E525 and, V531. In some embodiments, the substitution is selected from the group consisting of E2A or K or P, Y18D or E or K or S, L19Y, S21W, T24L or V, E26C, S27D or N, E29N, K37C or D or P or Q or S, V42M, N47D or S, N48D or G or T, E49L or V, L56E or F or G or I or K or T or V or Y, D81Q, R82N or T or V or Y, V84M, T93C or F or R or S, K94G or P, T95D or F or G or I or N or W, S120C or G or M or Q, K123V, N126E, E131H or K or L or M or T or W or Y, N132I or P, K134A, I137T, A139C or Q, L143C or D or E or H or K or M or Q or T or V or Y, L151A or F, N155A or C or G or H or Q or R or S or W, S166N, H167F or I or N or Q or V, K169A or C or H or N or Q or V, E170L or S or W or Y, L171A or N or Q or T or V or Y, K175C or F or I or Q or R, E179D, L180A or I, Q197C or D or N, I229C, S231A, T240C, R242G, R245C or K or M or Q or T or V, R246N, V247L or M, T251D or E or N or P or Q or S, A271T, S282Y, L306C, D317N, N319M, F369C or D or E or G or S, Q371F, L376I or M, K379G or Q, S380E, G389A or D or E or K or N or Q or S or V, W392Y, K393C or I or T or V, V408T, V409T, Q421H, K422D, Y423N or S, R429E or F or Q, C437M, A443Q, S444D or E, I447T, S455A, C458T, R461A, G464C or M or N or Q or S, S466D, A470I or L, S473I, V500A or C, T502M, L506M, T513C or G or K or N, E525F or R, V531E or H or K or Q or R or S.

In another aspect of the invention, an isoprene synthase variant can be a polypeptide (e.g., an isolated polypeptide) with improved isoprene synthase properties that are scored ++++ as exemplified in the Examples. These polypeptides can have one or more substitution(s) at residue positions with numbering that corresponds to SEQ ID NO: 1 (MEA *P. alba* isoprene synthase) that is indicated in the column labeled ++++ as exemplified in the Examples. Some non-limiting examples are isolated polypeptides with improved isoprene synthase properties wherein the polypeptide comprises one or more substitution(s) at residues corresponding to SEQ ID NO:1 selected from the group consisting of: X2, X6, X18, X20, X22, X23, X24, X25, X26, X27, X28, X29, X30, X31, X32, X36, X37, X42, X44, X47, X48, X49, X50, X53, X54, X55, X56, X58, X59, X68, X71, X74, X77, X78, X79, X81, X82, X83, X84, X86, X87, X91, X93, X94, X95, X97, X98, X99, X109, X115, X116, X117, X118, X120, X123, X125, X126, X127, X128, X130, X131, X132, X133, X134, X136, X137, X138, X139, X140, X143, X151, X153, X155, X156, X159, X160, X161, X162, X163, X164, X166, X167, X169, X170, X171, X172, X175, X176, X177, X178, X179, X180, X181, X182, X190, X194, X197, X204, X211, X215, X217, X219, X221, X228, X229, X231, X232, X235, X241, X242, X245, X246, X247, X251, X254, X271, X272, X278, X279, X282, X296, X302, X317, X319, X320, X327, X331, X348, X351, X357, X361, X364, X365, X368, X369, X370, X371, X373, X377, X380, X383, X386, X389, X392, X393, X407, X408, X409, X410, X411, X414, X422, X423, X424, X428, X429, X432, X436, X437, X440, X443, X444, X447, X448, X457, X460, X461, X462, X463, X464, X465, X466, X468, X470, X471, X472, X473, X475, X480, X490, X491, X492, X494, X496, X500, X501, X502, X503, X510, X513, X515, X519, X525, X531, X536, X537, X540, X541, X542, and X544.

In some embodiments, these substitutions can be at a residue selected from the group consisting of: E2, S6, Y18, L20, S22, D23, T24, D25, E26, S27, I28, E29, V30, Y31, K32, K36, K37, V42, R44, N47, N48, E49, K50, F53, L54, T55, L56, E58, L59, L68, R71, S74, R77, G78, A79, D81, R82, F83, V84, S86, G87, A91, T93, K94, T95, L97, H98, G99, Q109, S115, Q116, E117, A118, S120, K123, Q125, N126, G127, N128, L130, E131, N132, L133, K134, D136, I137, K138, A139, I140, L143, L151, G153, N155, I156, E159, A160, K161, V162, F163, A164, S166, H167, K169, E170, L171, S172, K175, I176, G177, K178, E179, L180, A181, E182, L190, R194, Q197, S204, K211, N215, V217, L219, L221, M228, I229, S231, V232, R235, S241, R242, R245, R246, V247, T251, H254, A271, F272, D278, C279, S282, I296, T302, D317, N319, A320, Y327, C331, K348, G351, Y357, A361, D364, L365, A368, F369, L370, Q371, A373, Y377, S380, T383, D386, G389, W392, K393, A407, V408, V409, Q410, N411, K414, K422, Y423, H424, S428, R429, H432, L436, C437, L440, A443, S444, I447, A448, S457, M460, R461, T462, K463, G464, I465, S466, E468, A470, T471, E472, S473, M475, E480, L490, G491, G492, L494, A496, V500, E501, T502, A503, S510, T513, H515, A519, E525, V531, T536, E537, L540, P541, F542, and R544.

In other embodiments, the substitution is at a residue selected from the group consisting of: E2C or D or N or T or V, S6N or T, Y18A or Q or R, L20T, S22Q, D23N, T24C, D25T, E26D or H or K or M or R or S or V, S27A or C or G or H or I or L or M or P or Q, 128D or N, E29Q, V30A or D or E or M or R or T, Y31N, K32E, K36A or C or D or E or M or N or P or Q, K37A or E or G or H or M or N or R or T, V42F or I, R44N or Q, N47A or G or H or M or Q or T or W, N48H or I or K, E49A or C, K50A or D or E or F or H or S or Y, F53E or H or N or P or Q or V, L54M, T55C or D or E, L56C or N, E58N, L59H or T, L68I, R71K or M, S74D or E or N or Y, R77L, G78A or D or F or L or M, A79Q or T, D81A or F or G or M or R or S or T or V, R82A or E or H or I or K or M or Q or S, F83W, V84A, S86A or D or M, G87D or P, A91K or W, T93A or D or E or G or L or N or P or Y, K94A or D or E or H or I or L or M or N or R or S or T, T95A or E or P or Q or S or V or Y, L97F, H98A or D or F or G or I or L or M or N or Q, G99E or F or M, Q109E, S115A, Q116A or C or D or E or I or P, E117C or F or L or M or V, A118M, S120H or T or V, K123L or T, Q125E or I or Y, N126A or C or D or M or T or V, G127C, N128C or D or P or Q, L130E, E131A or C or P or Q or S or V, N132C or D or F or H or L or R or W or Y, L133D, K134E or M or Q or S or T or V, D136E, I137E or H or N, K138I or N, A139N, I140M or W, L143S, L151C or H or I, G153C, N155I or T or V or Y, I156D or N or T, E159M, A160I, K161A or C or N or Q, V162S, F163E or Q, A164T, S166A or D or G, H167A or E or G or K or M or R or S or T or W, K169D or I or M or S or T, E170H or K or M or Q or T or V, L171H or K or R or S, S172A or C, K175S, I176M, G177A or C, K178A or F or R or S or T, E179A or C or L or M or N, L180C or Q or T, A181H or Q or S or V, E182S, L190I or M, R194L, Q197S, S204C, K211A or N or Q, N215C or H, V217I, L219C, L221M, M228F or Y, I229V, S231K or Q or T, V232I, R235K, S241A or M or T, R242A or D or E or H or I or M or N or Q or S or T, R245I or L, R246D or K, V247T, T251A or G or K or R, H254D, A271C or V, F272D or G or P or W, D278A or E or N or Q or S or T or V or W, C279A, S282A or Q, I296V, T302H, D317E or Q, N319F, A320C, Y327M, C331P, K348R or Y, G351D or N, Y357M, A361T, D364E or V, L365C or M, A368N, F369M or N or R or T or V, L370G or Q, Q371C or S, A373G, Y377W, S380A or C or D or Q or T or V, T383S, D386E or N, G389H or I, W392I or S or T or V, K393Q, A407G, V408I, V409H or I, Q410C or D or K or L or M or T, N411G, K414E or G or L or N or P, K422A or N or T, Y423Q, H424E or P or Q or V, S428E or Q, R429I or L or T or W or Y, H432E, L436M or Y, C437K or T, L440I, A443R, S444P, I447A or E or M or Q or S, A448E or M or N or P or Q or V, S457N or T, M460Q or R or S, R461D or E or G or Q or S or T, T462Q, K463A or D or E, G464L or R, I465A or C or G or S or T, S466P, E468D, A470M, T471E or H or Q, E472D or S, S473L or V, M475T, E480N, L490A or D or E or F or H or M, G491E or K or S or T or V or Y, G492C, L494D, A496P or T, V500L or M, E501D, T502A or C or R or V, A503I, S510C or V, T513V, H515N, A519S or T, E525A or C or P or Q or S, V531A or M or T, T536A or F or G, E537K or T, L540A or P, P541M, F542P, and R544C.

In another aspect of the invention, an isoprene synthase variant can be a polypeptide (e.g., an isolated polypeptide) with improved isoprene synthase properties that are scored +++ as exemplified in the Examples. These polypeptides can have one or more substitution(s) at residue positions with numbering that corresponds to SEQ ID NO: 1 (MEA P. alba isoprene synthase) that is indicated in the column labeled +++ as exemplified in the Examples. Some non-limiting examples are isolated polypeptides with improved isoprene synthase properties wherein the polypeptide comprises one or more substitution(s) at residues corresponding to SEQ ID NO:1 selected from the group consisting of: X2, X3, X13, X17, X18, X19, X20, X23, X25, X26, X27, X28, X29, X30, X31, X32, X33, X34, X36, X37, X40, X41, X42, X43, X44, X45, X46, X47, X48, X49, X50, X51, X53, X54, X55, X56, X57, X59, X60, X62, X71, X73, X74, X75, X77, X78, X79, X81, X82, X83, X84, X85, X86, X87, X88, X89, X91, X92, X93, X94, X95, X97, X98, X99, X100, X101, X102, X103, X107, X109, X111, X113, X114, X115, X116, X117, X118, X119, X120, X121, X123, X124, X125, X127, X128, X129, X130, X131, X133, X134, X135, X136, X137, X138, X139, X140, X143, X146, X151, X152, X153, X155, X156, X158, X160, X161, X162, X163, X166, X167, X169, X170, X171, X172, X175, X176, X177, X178, X179, X180, X181, X182, X183, X185, X187, X193, X194, X196, X197, X204, X210, X211, X212, X215, X216, X217, X218, X219, X220, X222, X223, X224, X226, X228, X229, X231, X232, X235, X240, X241, X242, X246, X251, X253, X260, X268, X270, X271, X272, X275, X276, X278, X282, X307, X314, X315, X317, X320, X321, X323, X328, X329, X331, X332, X333, X343, X345, X346, X350, X351, X352, X356, X357, X360, X361, X363, X364, X366, X367, X368, X369, X370, X371, X378, X379, X380, X383, X386, X389, X390, X392, X393, X402, X405, X408, X409, X410, X413, X414, X418, X422, X423, X424, X425, X426, X428, X429, X431, X432, X437, X444, X447, X448, X457, X460, X461, X462, X463, X464, X466, X467, X468, X469, X471, X472, X475, X484, X489, X490, X491, X492, X493, X494, X497, X500, X501, X502, X503, X504, X506, X509, X510, X511, X513, X515, X517, X519, X522, X528, X529, X531, X534, X535, X536, X537, X539, X540, X542, and X544.

In some embodiments, these substitutions can be at a residue selected from the group consisting of: E2, A3, S13, D17, Y18, L19, L20, D23, D25, E26, S27, I28, E29, V30, Y31, K32, D33, K34, K36, K37, A40, E41, V42, R43, R44, E45, I46, N47, N48, E49, K50, A51, F53, L54, T55, L56, L57, L59, I60, N62, R71, E73, S74, D75, R77, G78, A79, D81, R82, F83, V84, S85, S86, G87, G88, F89, A91, V92, T93, K94, T95, L97, H98, G99, T100, A101, L102, S103, L107, Q109, G111, E113, V114, S115, Q116, E117, A118, F119, S120, G121, K123, D124, Q125, G127, N128, F129, L130, E131, L133, K134, E135, D136, I137, K138, A139, I140, L143, A146, L151, E152, G153, N155, I156, D158, A160, K161, V162, F163, S166, H167, K169, E170, L171, S172, K175, I176, G177, K178, E179, L180, A181, E182, Q183, N185, A187, H193, R194, T196, Q197, S204, K210, K211, E212, N215, Q216, V217, L218, L219, E220, A222, I223, L224, Y226, M228, I229, S231, V232, R235, T240, S241, R242, R246, T251, L253, L260, V268, V270, A271, F272, Q275, D278, S282, E307, E314, R315, D317, A320, I321, D323, M328, K329, C331, F332, L333, A343, D345, N346, K350, G351, E352, P356, Y357, K360, A361, A363, D364, C366, N367, A368, F369, L370, Q371, N378, K379, S380, T383, D386, G389, N390, W392, K393, V402, Y405, V408, V409, Q410, K413, K414, E418, K422, Y423, H424, D425, T426, S428, R429, S431, H432, C437, S444, I447, A448, S457, M460, R461, T462, K463, G464, S466, E467, E468, L469, T471, E472, M475, K484, K489, L490, G491, G492, S493, L494, K497, V500, E501, T502, A503, I504, L506, Q509, S510, H511, T513, H515, G517, A519, S522, R528, K529, V531, V534, I535, T536, E537, I539, L540, F542, and R544.

In other embodiments, the substitution is at a residue selected from the group consisting of: E2H or I or S, A3E or G or K or N or Q or R or T, S13Q or T, D17E, Y18F or M or N, L19F, L20I or V, D23T, D25A or E or S, E26G or N or Q or T, S27E or F or K or V, I28E or F or M or P, E29D or P or R or T, V30N or Q, Y31Q or W, K32D or G or N or R, D33N, K34D or E or Q or S, K36F or R, K37F or I, A40C or D or E or F or M or N or P or Q or V, E41C or D or F or N or Q or S or V, V42A or S or T, R43I or Q, R44A or D or K or M or Y, E45C or M or N or Q, I46F or V, N47E or I or K or R or V, N48A or C or E or F or L or Q or R or S, E49G or H or I or R or S or W, K50C or G or M or N or P or R, A51E or G or L or Q or T, F53D, L54A or C or E or H or I or Q, T55A or H or N or Q or S or Y, L56H or Q or R or S, L57I, L59F or M or S or V or Y, I60C or V, N62V, R71I, E73D, S74G or M or P, D75E, R77A or N or T or V, G78E or I or K or N or P or Q or V or W, A79M or R or Y, D81C or E or H or L or N, R82C or F or G or L or W, F83G or H or I or L or V, V84F or H or L or N or Q or R or S or T or W or Y, S85C or L or N or R, S86C or N, G87C or E or F or K or L or N or T, G88C or D or I or V or W or Y, F89C or I, A91C or D or E or G or H or L or R or S or T or V or Y, V92A or C or E or F or G or I or L or Q or W, T93H or I or Q or V or W, K94C or V or Y, T95C or H or K or M, L97A or M or P, H98C or S or T or V or W, G99A or C or H or P or Q or T, T100A or I or L or M or V, A101S, L102M, S103A or C or G or L, L107C or F, Q109C or N or S, G111A, E113C or H or V, V114C, S115D or Y, Q116G or H or L or S or T or V, E117A or D or I, A118I or V, F119L or M, S120A or D or E or F or K or N or R or W or Y, G121D or L or V or W, K123I or S or W or Y, D124C or E, Q125A or D or G or H or K or L or N or S or T or V or W, G127D or F or W, N128A, F129L or Y, L130A or C or D or Q or V or Y, E131D or F or G or R, L133E or G or I or P or Q or T or V or Y, K134D or G or H or I or L or N or R or W or Y, E135H or S, D136N, I137A or C or D or G or P or Q or S or V, K138C or D or E or P or R or S or V, A139P or S or T or V, I140N or Q or S or T or V, L143A or F or G or N or R or W, A146M, L151E or G or M or N or Q or R or S or T or V or W, E152A or D or I or M or P, G153D, N155E or K or M, I156E or K or L or R or Y, D158E, A160F or H or S, K161L or R or S or Y, V162D or F or N or P or T, F163C or H or I or M or V or W or Y, S166C or E or H or K or P or Q or V or W, H167C or L or P, K169E or G or R, E170G or I or N or R, L171C or E or G or I or M or W, S172G or N or Q or R, K175A or G or H or N or P or T or V, I176A or C or N or Q or V, G177D or E or H or N or P or T, K178D or E or G or I or L or M or N or P or Q or V or Y, E179G or I or P or Q or S or T or V or W or Y, L180F or H or V or W, A181F or M or N or W, E182H or N, Q183A or L, N185D, A187C or S, H193W, R194I, T196V, Q197G, S204A or F or M or W or Y, K210M, K211D or E or F or G or H or I or M or R or S or T or V, E212A or D or M or P or Q or T, N215D or Y, Q216A or E or N, V217C or E or K or N or P or Q or T, L218V, L219I or M or V, E220D or N, A222S, I223C, L224A or C or T or V, Y226F, M228H or R, I229A, S231D or G or H or R or V, V232Q, R235A or D or N, T240V, S241C, R242K or L, R246H or Q, T251H, L253M, L260M, V268I, V270I, A271S, F272Q, Q275E, Y276F or H or Q, D278L or M or R or Y, S282C, E307Q or R, E314H, R315G or K, D317S, A320N or T, I321L or M, D323I or T, M328L, K329G or Q or R, C331T, F332Y, L333F, A343I or V, D345Y, N346A, K350H or W or Y, G351E or M, E352F or I or M or V, P356M or S, Y357E, K360Q, A361Q or S or V, A363S, D364N or T, C366A, N367D or E or M, A368D or Q, F369H or Q, L370A or D or E or F or H or N or R or S or T or V, Q371G or H or I or N or P or R or T or W or Y, N378D, K379E or R or S, S380K or N, T383Q, D386K or S, G389C or M or P or R or T, N390S, W392F or M, K393H or R, V402F or I or L, Y405F, V408Q or S, V409C or Q or S, Q410E or G or H or I or R, K413P, K414C or H or I or Q, E418N, K422G or H or Q or R, Y423G, H424D or G or I or S or T, D425P, T426A or M or Q, S428V, R429A or C or D or G or H or K or N, S431G, H432A or M, C437N, S444N or Q or T, I447K or R, A448H or S or T, S457D, M460A or E or G, R461N, T462S, K463G or N, G464A or D or E or F or H or V or Y, S466E or G or K or N or T, E467N, E468A or N or P or Q, L469A or N, T471N, E472A or G or N, M475I, K484A, K489R, L490I or Y, G491A or C or M or N or Q, G492T or V, S493C or G or K or V, L494G or I or Q or V, K497M or T, V500I or Y, E501N, T502H, A503L or M, I504L, L506 I or V, Q509A, S510T, H511I or M, T513S, H515Q, G517P, A519C, S522A or K, R528K, K529A, V531G or N, V534A or S, I535C or S or T, T536M, E537H or N or Q, I539V, L540E or Q or R or V, F542M, and R544G or N or P or Q or S.

In another aspect of the invention, an isoprene synthase variant can be a polypeptide (e.g., an isolated polypeptide) with improved isoprene synthase properties that are scored ++ as exemplified in the Examples. These polypeptides can have one or more substitution(s) at residue positions with numbering that corresponds to SEQ ID NO: 1 (MEA *P. alba* isoprene synthase) that is indicated in the column labeled ++ as exemplified in the Examples. In another aspect of the invention, an isoprene synthase variant can be a polypeptide (e.g., an isolated polypeptide) with improved isoprene synthase properties that are scored + as exemplified in the Examples. These polypeptides can have one or more substitution(s) at residue positions with numbering that corresponds to SEQ ID NO: 1 (MEA *P. alba* isoprene synthase) that is indicated in the column labeled + as exemplified in the Examples.

In another aspect of the invention, an isoprene synthase variant can be a polypeptide (e.g., an isolated polypeptide) with improved isoprene synthase properties that has one or more substitution(s) at residue positions with numbering that corresponds to SEQ ID NO: 1 (MEA *P. alba* isoprene synthase) that has a rank of 4 as shown in Table 31 of Example 11. In another aspect, an isoprene synthase variant can be a polypeptide (e.g., an isolated polypeptide) with improved isoprene synthase properties that has one or more substitution(s) at residue positions with numbering that corresponds to SEQ ID NO: 1 (MEA *P. alba* isoprene synthase) that has a rank of 3 as shown in Table 31 of Example 11. In another aspect, an isoprene synthase variant can be a polypeptide (e.g., an isolated polypeptide) with improved isoprene synthase properties that has one or more substitution(s) at residue positions with numbering that corresponds to SEQ ID NO: 1 (MEA *P. alba* isoprene synthase) that has a rank of 2 as shown in Table 31 of Example 11. In another aspect, an isoprene synthase variant can be a polypeptide (e.g., an isolated polypeptide) with improved isoprene synthase properties that has one or more substitution(s) at residue positions with numbering that corresponds to SEQ ID NO: 1 (MEA *P. alba* isoprene synthase) that has a rank of 1 as shown in Table 31 of Example 11.

Exemplary Nucleic Acids

Nucleic acids encoding the isoprene synthase variants of the invention are provided and contemplated within the scope of the invention. In various embodiments, the nucleic acid is a recombinant nucleic acid. For instance, in some embodiments, an isoprene synthase variant nucleic acid is operably linked to another nucleic acid encoding all or a portion of another polypeptide such that the recombinant nucleic acid encodes a fusion polypeptide that includes an isoprene synthase variant and all or part of another polypeptide (e.g., a peptide that facilitates purification or detection of the fusion polypeptide, such as a His-tag). In some embodiments, part or all of a recombinant nucleic acid is chemically synthesized. In some aspects, the nucleic acid is a heterologous nucleic acid. By "heterologous nucleic acid" is meant a nucleic acid whose nucleic acid sequence is not identical to that of another nucleic acid naturally found in the same host cell.

In some embodiments, the nucleic acid includes at least or about 50, 100, 150, 200, 300, 400, 500, 600, 700, 800, or more contiguous nucleotides from a naturally-occurring isoprene synthase nucleic acid. In some aspects, the nucleic acid has one or more mutations compared to the sequence of a wild-type (i.e., a sequence occurring in nature) isoprene synthase nucleic acid. In some embodiments, the nucleic acid has one or more mutations (e.g., a silent mutation) that increase the transcription or translation of isoprene synthase nucleic acid. In some embodiments, the nucleic acid is a degenerate variant of any nucleic acid encoding an isoprene synthase polypeptide.

An isoprene synthase nucleic acid can be incorporated into a vector, such as an expression vector, using standard techniques known to one of skill in the art. Methods used to ligate the DNA construct comprising a nucleic acid of interest such as isoprene synthase, a promoter, a terminator, and other sequences and to insert them into a suitable vector are well known in the art. Additionally, vectors can be constructed using known recombination techniques (e.g., Invitrogen Life Technologies, Gateway Technology).

In some embodiments, it may be desirable to over-express isoprene synthase nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, 2nd ed., Cold Spring Harbor, 2001.

Exemplary Pathway Polypeptides

As noted above, one or more polypeptides from the DXP pathway and/or MVA pathway can be used to increase the production of isoprene in conjunction with using the isoprene synthase variants described herein. Accordingly, in certain aspects, the one or more nucleic acids encoding one or more MVA pathway polypeptides is a heterologous nucleic acid. In other aspects, the one or more nucleic acids encoding one or more MVA pathway polypeptides is a copy of an endogenous nucleic acid. In any of the aspects herein, one or more MVA pathway polypeptides can be selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; (f) an enzyme that converts mevalonate 5-pyrophosphate to isopentenyl pyrophosphate; and (g) an enzyme that converts isopentenyl pyrophosphate to dimethylallyl diphosphate. In any of the aspects herein, one or more MVA pathway polypeptides is selected from (a) an enzyme that condenses acetoacetyl-CoA with acetyl-CoA to form HMG-CoA (e.g., HMG synthase); (b) an enzyme that converts HMG-CoA to mevalonate; (c) an enzyme that phosphorylates mevalonate to mevalonate 5-phosphate; (d) an enzyme that converts mevalonate 5-phosphate to mevalonate 5-pyrophosphate; and (e) an enzyme that converts mevalonate 5-pyrophosphate to isopentenyl pyrophosphate.

In any of the aspects herein, the enzyme that phosphorylates mevalonate to mevalonate 5-phosphate can be selected from the group consisting of M. mazei mevalonate kinase, Lactobacillus mevalonate kinase polypeptide, Lactobacillus sakei mevalonate kinase polypeptide, yeast mevalonate kinase polypeptide, Saccharomyces cerevisiae mevalonate kinase polypeptide, Streptococcus mevalonate kinase polypeptide, Streptococcus pneumoniae mevalonate kinase polypeptide, and Streptomyces mevalonate kinase polypeptide, or Streptomyces CL190 mevalonate kinase polypeptide.

In any of the aspects herein, the enzyme that phosphorylates mevalonate to mevalonate 5-phosphate is M. mazei mevalonate kinase.

Upper MVA Pathway Polypeptides

The upper portion of the MVA pathway uses acetyl Co-A produced during cellular metabolism as the initial substrate for conversion to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production.

Non-limiting examples of upper MVA pathway polypeptides include acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention.

In certain embodiments, various options of mvaE and mvaS genes from L. grayi, E. faecium, E. gallinarum, E. casseliflavus and/or E. faecalis alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides. Thus, in certain aspects, any of the combinations of genes contemplated in can be expressed in recombinant cells in any of the ways described herein.

Additional non-limiting examples of upper MVA pathway polypeptides which can be used herein are described in International Patent Application Publication No. WO2009/076676; WO2010/003007 and WO2010/148150.

Genes Encoding mvaE and mvaS Polypeptides

In certain embodiments, various options of mvaE and mvaS genes from L. grayi, E. faecium, E. gallinarum, E. casseliflavus and/or E. faecalis alone or in combination with one or more other mvaE and mvaS genes encoding proteins from the upper MVA pathway are contemplated within the scope of the invention. In L. grayi, E. faecium, E. gallinarum, E. casseliflavus, and E. faecalis, the mvaE gene encodes a polypeptide that possesses both thiolase and HMG-CoA reductase activities. In fact, the mvaE gene product represented the first bifunctional enzyme of IPP biosynthesis found in eubacteria and the first example of HMG-CoA reductase fused to another protein in nature (Hedl, et al., J.

Bacteriol. 2002 April; 184(8): 2116-2122). The mvaS gene, on the other hand, encodes a polypeptide having an HMG-CoA synthase activity.

Accordingly, recombinant cells (e.g., *E. coli*) can be engineered to express one or more mvaE and mvaS genes from *L. grayi, E. faecium, E. gallinarum, E. casseliflavus* and/or *E. faecalis*, to produce mevalonate. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

In any of the aspects herein, the recombinant host cells can further comprise one or more nucleic acids encoding one or more 1-deoxy-D-xylulose 5-phosphate (DXP) pathway polypeptides. In one aspect, one or more nucleic acids that encode for one or more DXP pathway polypeptides is a heterologous nucleic acid. In another aspect, the one or more nucleic acids encoding one or more DXP pathway polypeptides is a copy of an endogenous nucleic acid. In another aspect, the one or more DXP pathway polypeptides is selected from (a) 1-deoxy-D-xylulose-5-phosphate synthase (DXS), (b) 1-deoxy-D-xylulose-5-phosphate reductoisomerase (DXR), (c) 4-diphosphocytidyl-2C-methyl-D-erythritol synthase (MCT), (d) 4-diphosphocytidyl-2-C-methyl-D-erythritol kinase (CMK), (e) 2C-methyl-D-erythritol 2,4-cyclodiphosphate synthase (MCS), (f) 1-hydroxy-2-methyl-2-(E)-butenyl 4-diphosphate synthase (HDS), and (g) 1-hydroxy-2-methyl-2-(E)-butenyl 4-diphosphate reductase (HDR). In another aspect, the DXP pathway polypeptide is DXS.

In another aspect, one of skill in the art can use an alternate metabolic process which can potentially produce three molecules of acetyl-CoA from one molecule of glucose using a pathway which does not rely on the Wood-Ljungdahl pathway enzymes. Instead, it makes use of a phosphoketolase enzyme found in certain organisms, particularly among Bifidobacteria [see, for example, Biology of the Prokaryotes (ed. Lengeler, Drews and Schlegel); Blackwell Science, New York, 1999, p. 299-301; Meile et al., *J. of Bacteriology*, 2001, 183:9, 2929-36; Jeong et al., *J. Microbiol. Biotechnol.*, 2007, 17:5, 822-829]. Phosphoketolase enzymes allow for formation of acetyl-CoA (via acetyl-phosphate) from xylulose 5-phosphate or fructose 6-phosphate rather than through oxidation of pyruvate as in typical metabolism. Increased biosynthesis of acetyl CoA by the use of a phosphoketolase polypeptide can result in increased productivity of the upper mevalonate-dependent biosynthetic pathway which can substantially increase biosynthesis of mevalonate and, consequently, of downstream isoprenoid precursor molecules such as DMAPP and IPP. Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183:2929-2936, 2001). Any polypeptide identified as having phosphoketolase peptide activity is suitable for use in the present invention. Exemplary phosphoketolase nucleic acids include, but are not limited to, a phosphoketolase isolated from *Lactobacillus reuteri, Bifidobacterium longum, Ferrimonas balearica, Pedobacter saltans, Streptomyces griseus*, and/or *Nocardiopsis dassonvillei*.

Acetoacetyl-CoA Synthase Gene

In another aspect, acetoacetyl-CoA synthase gene (aka nphT7) can be used. The acetoacetyl-CoA synthase gene is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., *PNAS* Vol 107, No. 25, pp. 11265-11270 (2010), the contents of which are expressly incorporated herein for teaching about nphT7. An acetoacetyl-CoA synthase gene from an actinomycete of the genus *Streptomyces* CL190 strain was described in JP Patent Publication (Kokai) No. 2008-61506 A and US2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In any of the aspects or embodiments described herein, an enzyme that has the ability to synthesize acetoacetyl-CoA from malonyl-CoA and acetyl-CoA can be used. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used.

Exemplary Host Cells

A variety of host cells can be used to make a recombinant host cell that can express isoprene synthase variants and to produce isoprene in the methods of the claimed invention. The host cell may be a cell that naturally produces isoprene or a cell that does not naturally produce isoprene. In some embodiments, the host cell naturally produces isoprene using the DXP pathway, and an isoprene synthase variant, DXP pathway polypeptide (e.g., DXS), and/or IDI nucleic acid is added to enhance production of isoprene using this pathway. In some embodiments, the host cell naturally produces isoprene using the MVA pathway, and an isoprene synthase variant and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase variants, DXS, IDI, or MVA pathway nucleic acids are added to enhance production of isoprene by one or both of these pathways.

In some embodiments, the host cell is a yeast, such as *Saccharomyces* sp., *Schizosaccharomyces* sp., *Pichia* sp., *Candida* sp. or *Y. lipolytica*.

In some embodiments, the host cell is a bacterium, such as strains of *Bacillus* such as *B. licheniformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, strains of Archaea such as *Methanosarcina mazei* or strains of *Corynebacterium* such as *C. glutamicum*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium,*

*B. coagulans, B. circulans, B. lautus,* and *B. thuringiensis.* It is recognized that the genus *Bacillus* continues to undergo taxonomical reorganization. Thus, it is intended that the genus include species that have been reclassified, including but not limited to such organisms as *B. stearothermophilus,* which is now named "*Geobacillus stearothermophilus.*" The production of resistant endospores in the presence of oxygen is considered the defining feature of the genus *Bacillus,* although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus.*

In some embodiments, the host cell is a gram-positive bacterium. Non-limiting examples include strains of *Streptomyces* (e.g., *S. lividans, S. coelicolor,* or *S. griseus*) and *Bacillus.* In some embodiments, the source organism is a gram-negative bacterium, such as *E. coli* or *Pseudomonas* sp.

In some embodiments, the host cell is a plant, such as a plant from the family Fabaceae, such as the Faboideae subfamily. In some embodiments, the source organism is kudzu, poplar (such as *Populus alba* x *tremula* CAC35696), aspen (such as *Populus tremuloides*), or *Quercus robur.*

In some embodiments, the host cell is an algae, such as a green algae, red algae, glaucophytes, chlorarachniophytes, euglenids, chromista, or dinoflagellates.

In some embodiments, the host cell is a cyanobacteria, such as cyanobacteria classified into any of the following groups based on morphology: Chroococcales, Pleurocapsales, Oscillatoriales, Nostocales, or Stigonematales.

In some embodiments, the host cell is an anaerobic organisms. An "anaerobe" is an organism that does not require oxygen for growth. An anaerobe can be an obligate anaerobe, a facultative anaerobe, or an aerotolerant organism. Such organisms can be any of the organisms listed above, bacteria, yeast, etc. An "obligate anaerobe" is an anaerobe for which atmospheric levels of oxygen can be lethal. Examples of obligate anaerobes include, but are not limited to, *Clostridium, Eurobacterium, Bacteroides, Peptostreptococcus, Butyribacterium, Veillonella,* and *Actinomyces.* In one embodiment, the obligate anaerobes can be any one or combination selected from the group consisting of *Clostridium ljungdahlii, Clostridium autoethanogenum, Eurobacterium limosum, Clostridium carboxydivorans, Peptostreptococcus productus,* and *Butyribacterium methylotrophicum.* A "facultative anaerobe" is an anaerobe that is capable of performing aerobic respiration in the presence of oxygen and is capable of performing anaerobic fermentation under oxygen-limited or oxygen-free conditions. Examples of facultative anaerobes include, but are not limited to, *Escherichia, Pantoea,* yeast, and *Yarrowia.*

In some embodiments, the host cell is a photosynthetic cell. In other embodiments, the host cell is a non-photosynthetic cell.

Other exemplary host cells that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Transformation Methods

Isoprene synthase, DXS, IDI, and/or MVA pathway nucleic acids or vectors containing them can be inserted into a host cell (e.g., a bacterial cell) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, 3rd ed., Cold Spring Harbor, 2001; and Campbell et al., Curr Genet, 16:53-56, 1989, which are each hereby incorporated by reference in their entireties, particularly with respect to transformation methods). The introduced nucleic acids may be integrated into chromosomal DNA or maintained as extrachromosomal replicating sequences.

Other exemplary transformation methods that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Cell Culture Media

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharides), invert sugar (e.g., enzymatically treated sucrose syrup), glycerol, glycerine (e.g., a glycerine byproduct of a biodiesel or soap-making process), dihydroxyacetone, one-carbon source, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source; beet sugar or cane sugar molasses), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

Exemplary lipids are any substance containing one or more fatty acids that are C4 and above fatty acids that are saturated, unsaturated, or branched.

Exemplary fatty acids include compounds of the formula R—COOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more C12-C22 fatty acids, such as a C12 saturated fatty acid, a C14 saturated fatty acid, a C16 saturated fatty acid, a C18 saturated fatty acid, a C20 saturated fatty acid, or a C22 saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, fatty acid, monoglyceride, diglyceride, or triglyceride that is added before and/or during the culturing of the host cells. In some embodiments, the carbon source includes both (i) a lipid, fatty acid, monoglyceride, diglyceride, or triglyceride and (ii) a carbohydrate, such as glucose. In some embodiments, the ratio of the lipid, fatty acid, monoglyceride, diglyceride, or triglyceride to the carbohydrate is about 1:1 on a carbon basis (i.e., one carbon in the lipid, fatty acid, monoglyceride, diglyceride, or triglyceride per carbohydrate carbon). In particular embodiments, the amount of the lipid, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., Bioresource Technology 96 (18): 2014-2018, 2005; U.S. Pat. No. 6,176,176; U.S. Pat. No. 6,106,888). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., Bioresource Technology 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry-to-dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., Agric. Biol. Chem., 53(2) 541-543, 1989) and in bacteria (Hunter et. al., Biochemistry, 24, 4148-4155, 1985). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, Bacterial Metabolism, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth Cl Compd., Int. Symp., 7th ed., 415-32. Editors: Murrell et al., Publisher: Intercept, Andover, UK, 1993). Similarly, various species of Candida metabolize alanine or oleic acid (Sulter et al., Arch. Microbiol. 153(5), 485-9, 1990).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988; and Ilmen et al., Appl. Environ. Microbiol. 63:1298-1306, 1997). Exemplary growth media are common commercially prepared media such as Luria Bertani (LB) broth, Sabouraud Dextrose (SD) broth, or Yeast medium (YM) broth. One skilled in the art of microbiology or fermentation science would know other defined or synthetic growth media that may also be used, and the appropriate medium for growth of particular host cells.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Other exemplary cell culture media that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

Exemplary Production of Isoprene

In some embodiments, the cells are cultured in a culture medium under conditions permitting the production of isoprene by the cells. In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/gwcm/hr). In some embodiments, the amount of isoprene is between about 2 to about 5,000 nmole/gwcm/hr, such as between about 2 to about 100 nmole/gwcm/hr, about 100 to about 500 nmole/gwcm/hr, about 150 to about 500 nmole/gwcm/hr, about 500 to about 1,000 nmole/gwcm/hr, about 1,000 to about 2,000 nmole/gwcm/hr, or about 2,000 to about 5,000 nmole/gwcm/hr. The amount of isoprene in units of nmole/gwcm/hr can be measured as disclosed in U.S. Pat. No. 5,849,970. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, e.g., Greenberg et al, Atmos. Environ. 27A: 2689-2692, 1993; Silver et al., Plant Physiol. 97:1588-1591, 1991). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/gwcm/h). In some embodiments, the amount of isoprene is between about 2 to about 5,000 ng/gwcm/h, such as between about 2 to about 100 ng/gwcm/h, about 100 to about 500 ng/gwcm/h, about 500 to about 1,000 ng/gwcm/h, about 1,000 to about 2,000 ng/gwcm/h, or about 2,000 to about 5,000 ng/gwcm/h. The amount of isoprene in ng/gwcm/h can be calculated by multiplying the value for isoprene production in the units of nmole/gwcm/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/L broth, wherein the volume of broth includes the volume of the cells and the cell medium). In some embodiments, the amount of isoprene is between about 2 to about 5,000 mg/L broth, such as between about 2 to about 100 mg/L broth, about 100 to about 500 mg/L broth, about 500 to about 1,000 mg/L broth, about 1,000 to about 2,000 mg/L broth, or about 2,000 to about 5,000 mg/L broth. The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace. If the $OD_{600}$ value is not 1.0, then the measurement can be normalized to an $OD_{600}$ value of 1.0 by dividing by the $OD_{600}$ value. The value of mg isoprene/L headspace can be converted to mg/Lbroth/hr/$OD_{600}$ of culture broth by multiplying by a factor of 38. The value in units of mg/Lbroth/hr/$OD_{600}$ can be multiplied by the number of hours and the $OD_{600}$ value to obtain the cumulative titer in units of mg of isoprene/L of broth.

The instantaneous isoprene production rate in mg/L broth/hr in a fermentor can be measured by taking a sample of the fermentor off-gas, analyzing it for the amount of isoprene (in units such as mg of isoprene per L of gas), and multiplying this value by the rate at which off-gas is passed though each liter of broth (e.g., at 1 vvm (volume of air/volume of broth/minute) this is 60 Lgas per hour). Thus, an off-gas level of 1 mg/Lgas corresponds to an instantaneous production rate of 60 mg/Lbroth/hr at air flow of 1 vvm. If desired, the value in the units mg/Lbroth/hr can be divided by the $OD_{600}$ value to obtain the specific rate in units of mg/Lbroth/hr/OD. The average value of mg isoprene/Lgas can be converted to the total product productivity (grams of isoprene per liter of fermentation broth, mg/Lbroth) by multiplying this average off-gas isoprene concentration by the total amount of off-gas sparged per liter of fermentation broth during the fermentation. Thus, an average off-gas isoprene concentration of 0.5 mg/Lbroth/hr over 10 hours at 1 vvm corresponds to a total product concentration of 300 mg isoprene/Lbroth.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, or 1.6% of the carbon in the cell culture medium into isoprene. In some embodiments, the percent conversion of carbon into isoprene is between about 0.002 to about 1.6%, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

$$\% \text{ Carbon Yield}=(\text{moles carbon in isoprene produced})/(\text{moles carbon in carbon source})*100 \quad \text{Equation 1}$$

For this calculation, yeast extract can be assumed to contain 50% w/w carbon.

$$\% \text{ Carbon Yield}=(39.1 \text{ g isoprene}*1/68.1 \text{ mol/g}*5 \text{ C/mol})/[(181221 \text{ g glucose}*1/180 \text{ mol/g}*6 \text{ C/mol})+(17780 \text{ g yeast extract}*0.5*1/12 \text{ mol/g})]*100=0.042\% \quad \text{Equation 2}$$

One skilled in the art can readily convert the rates of isoprene production or amount of isoprene produced into any other units. Exemplary equations are listed below for interconverting between units.

Units for Rate of Isoprene Production (Total and Specific)

$$1 \text{ g isoprene}/L_{broth}/\text{hr}=14.7 \text{ mmol isoprene}/L_{broth}/\text{hr} \text{ (total volumetric rate)} \quad \text{Equation 3}$$

$$1 \text{ nmol isoprene}/g_{wcm}/\text{hr}=1 \text{ nmol isoprene}/L_{broth}\text{hr}/OD_{600}(\text{This conversion assumes that one liter of broth with an } OD_{600} \text{ value of 1 has a wet cell weight of 1 gram.}) \quad \text{Equation 4}$$

$$1 \text{ nmol isoprene}/g_{wcm}/\text{hr}=68.1 \text{ ng isoprene}/g_{wcm}/\text{hr} \text{ (given the molecular weight of isoprene)} \quad \text{Equation 5}$$

$$1 \text{ nmol isoprene}/L_{gas}O_2/\text{hr}=90 \text{ nmol isoprene}/L_{broth}/\text{hr} \text{ (at an } O_2 \text{ flow rate of 90 L/hr per L of culture broth)} \quad \text{Equation 6}$$

$$1 \text{ μg isoprene}/L_{gas} \text{ isoprene in off-gas}=60 \text{ μg isoprene}/L_{broth}/\text{hr at a flow rate of 60 } L_{gas} \text{ per } L_{broth}(1 \text{ vvm}) \quad \text{Equation 7}$$

Units for Titer (Total and Specific)

$$1 \text{ nmol isoprene/mg cell protein}=150 \text{ nmol isoprene}/L_{broth}/OD_{600}(\text{This conversion assumes that one liter of broth with an } OD_{600} \text{ value of 1 has a total cell protein of approximately 150 mg})(\text{specific productivity}) \quad \text{Equation 8}$$

$$1 \text{ g isoprene}/L_{broth}=14.7 \text{ mmol isoprene}/L_{broth}(\text{total titer}) \quad \text{Equation 9}$$

If desired, Equation 10 can be used to convert any of the units that include the wet weight of the cells into the corresponding units that include the dry weight of the cells.

$$\text{Dry weight of cells}=(\text{wet weight of cells})/3.3 \quad \text{Equation 10}$$

In some embodiments encompassed by the invention, a cell comprising a heterologous nucleic acid encoding an isoprene synthase variant polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase variant polypeptide.

In some embodiments encompassed by the invention, a cell comprising a heterologous nucleic acid encoding an isoprene synthase variant polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

Exemplary Isoprene Purification Methods

In some embodiments, any of the methods described herein further include recovering the isoprene. For example, the isoprene produced using the compositions and methods of the invention can be recovered using standard techniques, such as gas stripping, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029). In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation. In some embodiments, membrane enrichment of a dilute isoprene vapor stream above the dew point of the vapor resulting in the condensation of liquid isoprene. In some embodiments, the recovery is performed as described in U.S. Provisional Patent Appl. No. 61/288,142, filed on Dec. 18, 2009.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. See, e.g. U.S. Patent Application Publication No. 2009/0203102, PCT publication WO 2009/076676 and U.S. patent application Ser. No. 12/496,573. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. It is also to be understood that one, some, or all of the properties of the various embodiments described herein may be combined to form other embodiments of the present invention. These and other aspects of the invention will become apparent to one of skill in the art.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); $diH_2O$ (deionized water); aa and AA (amino acid); by (base pair); kb (kilobase pair); kD (kilodaltons); gm (grams); μg and ug (micrograms); mg (milligrams); ng (nanograms); μl and ul (microliters); ml (milliliters); mm (millimeters); qs (quantity sufficient); nm (nanometers); μm and um (micrometer); M (molar); mM (millimolar); μM and uM (micromolar); pM (picomolar); U (units); MW (molecular weight); sec (seconds); min (minute/minutes); hr (hour/hours); $OD_{600}$ (optical density at 600 nm); BSA (bovine serum albumin); DMAPP (dimethylallyl diphosphate); DTT (dithiothreitol); EtOH (ethanol); IPTG (isopropyl-beta-D-thiogalactopyranoside); isoprene(2-methyl-1,3-butadiene); IspS (isoprene synthase); PAGE (polyacrylamide gel electrophoresis); PBS (phosphate buffered saline [150 mM NaCl, 10 mM sodium phosphate buffer, pH 7.2]); and SDS (sodium dodecyl sulfate).

The following abbreviations apply to companies whose products or services may have been referred to in the experimental examples: Agilent (Agilent Technologies, Santa Clara, Calif.); Becton Coulter (Becton Coulter, Inc., Fullerton, Calif.); Bio-Rad (Bio-Rad Laboratories, Hercules, Calif.); Cayman Chemical (Cayman Chemical Co., Ann Arbor, Mich.); CTC Analytics (CTC Analytics A.G., Zwingen, Switzerland); EMS (Electron Microscopy Supply, Hatfield, Pa.); Epicentre (Epicentre Biotechnologies, Madison, Wis.); Integrated DNA Technologies (Integrated DNA Technologies, Coralville, Iowa); Invitrogen (Invitrogen Corp., Carlsbad, Calif.); Molecular Dynamics (Molecular Dynamics, Sunnyvale, Calif.); Novagen (Novagen, Inc., Madison, Wis.); Perkin Elmer (Perkin Elmer, Waltham, Mass.); Roche (Roche Applied Science, Indianapolis, Ind.); Sigma (Sigma-Aldrich, St. Louis, Mo.); Stratagene (Stratagene Cloning Systems, La Jolla, Calif.); Qiagen (Qiagen, Inc., Valencia, Calif.); Takara (Takara Bio USA, Madison, Wis.); Thomson Instrument (Thomson Instrument Co., Oceanside, Calif.); V&P Scientific (V&P Scientific, Inc., San Diego, Calif.); and Zinsser (Zinsser North America, Northridge, Calif.).

EXAMPLES

The following examples are provides for illustrative purposes and are not meant to limit the invention in any manner.

Example 1

Isoprene Synthase Growth Screen: Validation, Optimization and Limitations

This Example describes the development of an in vivo screen to select improved variants of isoprene synthase. The inventors have found that the in vivo screen can be used to select cells that contain less isoprene synthase activity than a control (in our case, the best validated isoprene synthase MEA-Poplar Alba). In addition, the in vivo screen can be used to select cells that contain more isoprene synthase activity than a control (in our case, the best validated isoprene synthase MEA-Poplar Alba).

Methods

Strains: The screening strain contained a constitutively expressed lower pathway and variants of isoprene synthase expressed from a pET plasmid. The screening strains were DW425-positive control.

Assay conditions: Strains were grown overnight in LB medium containing 50 uM kanamycin at 34° C. The overnight cultures were diluted to approximately 0.2 $OD_{600}$ in TM3 media containing 1% glucose, 0.1% yeast extract, 8 mM $MgSO_4$ and one of the following concentrations of IPTG: 0, 10, 20, 30, 40, 50, 60, or 70 uM. Cells were grown for approximately 2 hours post-induction and transferred to a 96-well clear bottom microtiter plate containing various concentrations of mevalonate (0, 5, 7.5, 10, 15, 20 mM) and the same media used in the day culture to a final $OD_{600}$ of 0.2-0.3. The plates were monitored in kinetic mode on a Spectramax UV-Vis spectrophotometer. The experiment was monitored at 34 C for 3 hours with shaking for 1 minute prior to each measurement (taken every 5 minutes).

Data analysis: All data were transferred to Excel. The absorbance measurements were converted to their natural log. A line was then fit to the series using the function "LINEST" to yield the exponential growth constant (growth rate).

Metabolite analysis was performed by using the following protocol for methanol/water extraction of metabolites at small-scale (MVA, DXP):

1. Samples from small-scale experiment was quenched; commonly 1 ml sample was spun down, the supernatant was discarded, 100 µl pure methanol was loaded onto the pellet, and the samples was stored at −80C until there was time for metabolite extraction and analysis.

2. Samples were taken from storage in −80C; pellets were resuspended (recommended to break pellet with glass capillary tubes).

3. The sample was spun down in a refrigerated microcentrifuge at 14000 g (rfc) for 4 min.

4. The supernatant was placed into clean 1.5 mL Eppendorf tubes.

5. The pellet was resuspended in 100 µl 6:1 MeOH/5 mM $NH_4OAc$ pH 8.0. Centrifuge at 14000 g (rfc) for 4 min. The samples may be extracted in 6:1 MeOH/5 mM $NH_4OAc$ pH 7.0 if the metabolites of interest are not stable at pH 8.0 (for example, DXP metabolites, or CoA-containing metabolites).

6. The supernatant was combined with the supernatant from step 4.

7. Steps 5-6 were repeated, extracting with 100 µl 1:1 MeOH/5 mM $NH_4OAc$ pH 8.0 (or pH 7.0, see above). Sample pellets can be discarded after taking the supernatant. 1.5 ml Eppendorf tubes containing accumulated supernatant fractions were closed and extract was mixed by vortexing.

8. In order to remove suspended debris, 1.5 ml Eppendorf tubes were centrifuged at 14000 g (rfc) for 4 min.

9. ~200 µl extract were placed into LC/MS vials containing conical inserts. The remaining extracts were stored at −20° C.

Without being bound by theory, it is recommended to use repeat pipettors for dispensing 2% formic acid (for fast pipetting and consistent volumes). Repeat pipettors significantly improve time efficiency over standard pipettors, and because they are technically positive displacement pipettes, they are quite precise (and accurate, assuming good calibration and proper maintenance). Further recommendations include, but are not limited to: keep Eppendorf tubes on ice (at 0° C.) whenever possible, the microcentrifuge should be set at −9° C.; allow ~20 min. for the centrifuge to cool, for resuspending pellets, the use of the glass capillary tubes is recommended. Mechanical breaking of the cell pellet is usually very fast with just a little physical assistance. It is not recommended to vortex the resuspended pellets, as the cell mass ends up on the sides of the tubes very easily, potentially causing significant experimental error due to the low volumes of the samples.

Without being bound by theory, the following recommendations are given for conducting LC/MS analysis:

1. The LC/MS vials should be kept on the tray at 4° C. during the analysis. The column should be at room temperature. The tray/column temperatures will be set automatically after starting the sequence in Xcalibur, but it is better to set the tray temperature in advance.

2. Use standards prepared as in the attached spreadsheet for calibration. Record standard preparation date as labeled on each tube.

3. LC/MS method for isoprenoids and MVA pathway metabolites (currently on new TSQ Quantum Access)—Method file: IPS_BioBasic100_090316 (or similar, see latest date extension); HPLC column: Macherey-Nagel Nucleodex beta-OH EC 2 mm×100 mm (particle size 5 µm, pore size 100 Å), C/N 720351.20; Guard column: 721460.40 (2 mm guard column not currently available). LC/MS method for DXP pathway metabolites: Method development C18-ion pair\Metabolites_C18_TBAip_11, with tributylammonium acetate as an ion-pair reagent; HPLC column: C18 Phenomenex Synergi 4µ. Hydro-RP 80A 150×2.0 mm, C/N 00F-4375-B0; Guard column: Security Guard Cartridges AQ C18 4×2.0 mm, C/N AJ0-7510. For LC/MS method for detection of CoA-containing metabolites, see "Protocol for acidic extraction of metabolites at small-scale (CoAs, etc.)."

4. After analysis, samples should be stored at −20° C.; standards should be stored at −80° C.

5. Metabolite quantitation can be easily determined using LCQuan software package. After back-calculation of all dilutions (including initial methanol quench), concentrations should be normalized to OD and converted to intracellular concentrations, utilizing the assumption that the intracellular volume of 1 L of fermentation broth at 200 OD is ~50 mL.

Results

A system has previously been developed to select DMAPP utilizing enzymes from pools of plasmids that express unknown proteins (Appl Environ Microbiol. 2007 October; 73(19): 6277-6283). The inventors have refined and optimized the screening protocol to enable selection cells that contain isoprene synthase activity. The screen is based on experimental results concluding that the concentration of DMAPP in *E. coli* correlates with cell growth rate (FIG. 1). Therefore, without being bound by theory, the growth rate of these cells can be thought of as a biosensor for intracellular DMAPP concentrations. Without being bound by theory, the underlying rationale of this screen was that the concentration of DMAPP in a cell can be decreased by increasing the enzyme activity of DMAPP consuming enzymes (isoprene synthase) and, thus, would result in increased growth rate.

Figure 2:
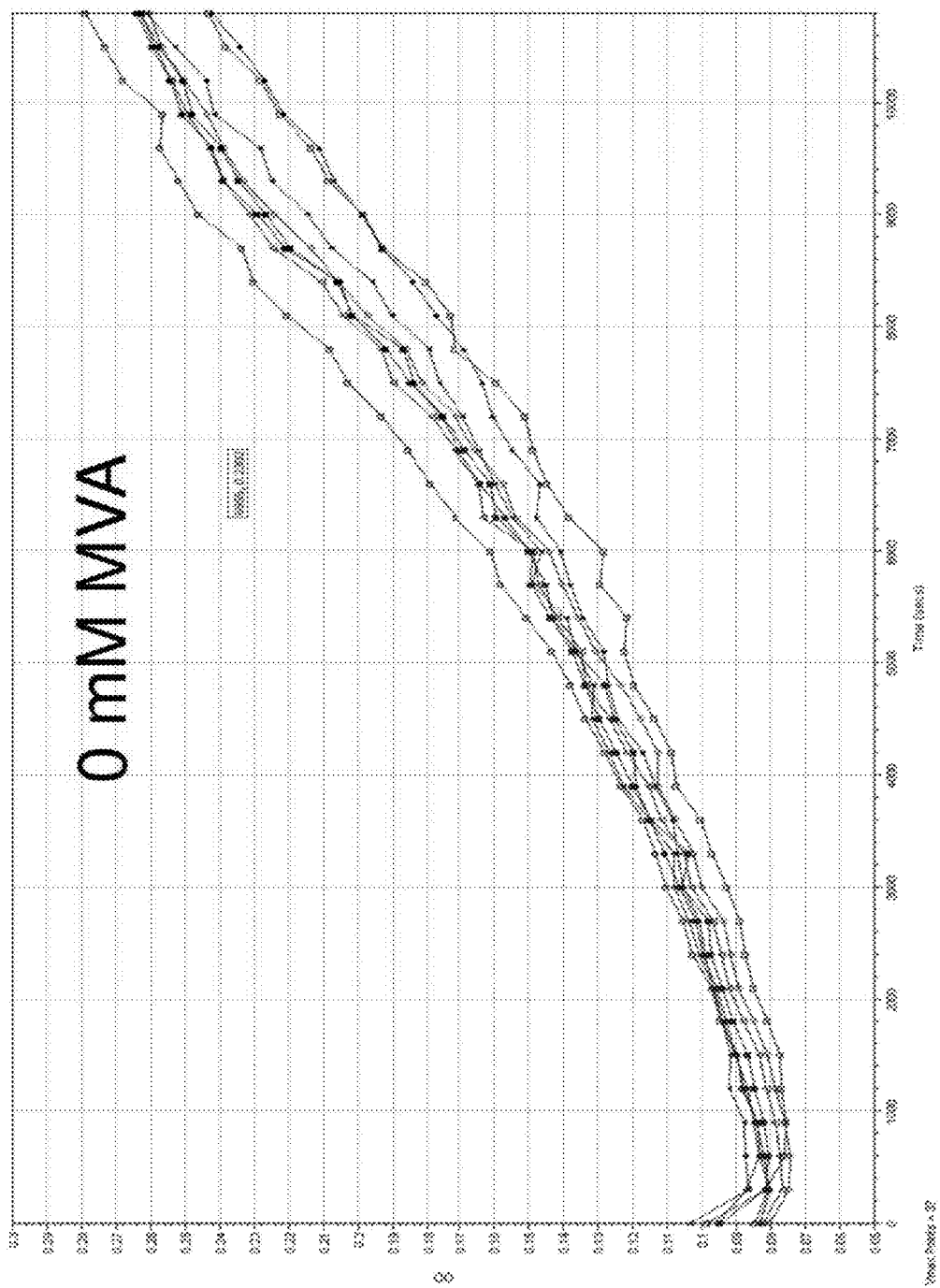
FIG. 2 shows DW425 growth in the presence of varying concentrations of IPTG (0, 10, 20, 30, 40, 50, 60, and 70 μM) and mevalonate (0, 5, 7.5, 10, 15, 20 mM).
Figure 2:
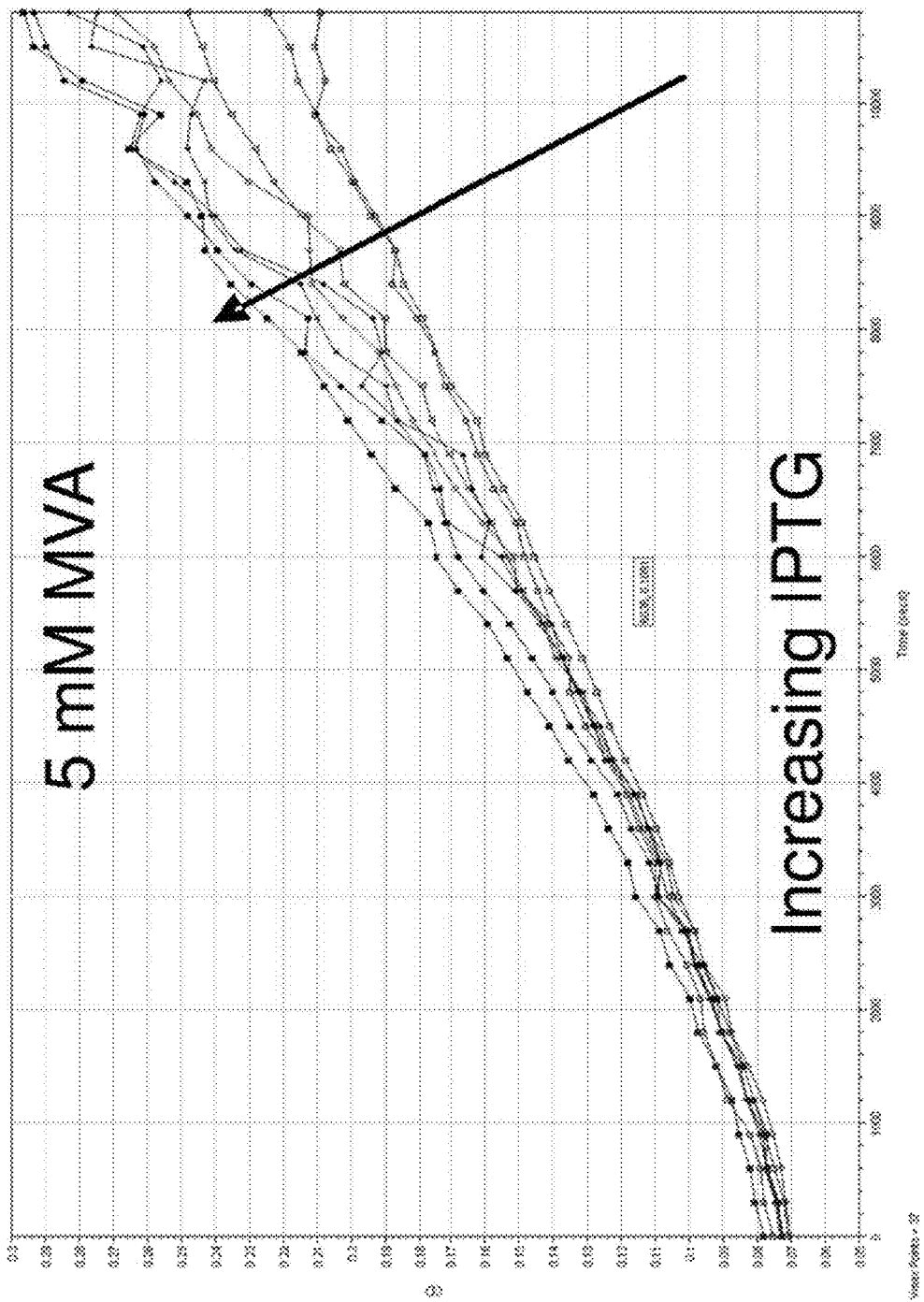
Figure 2:
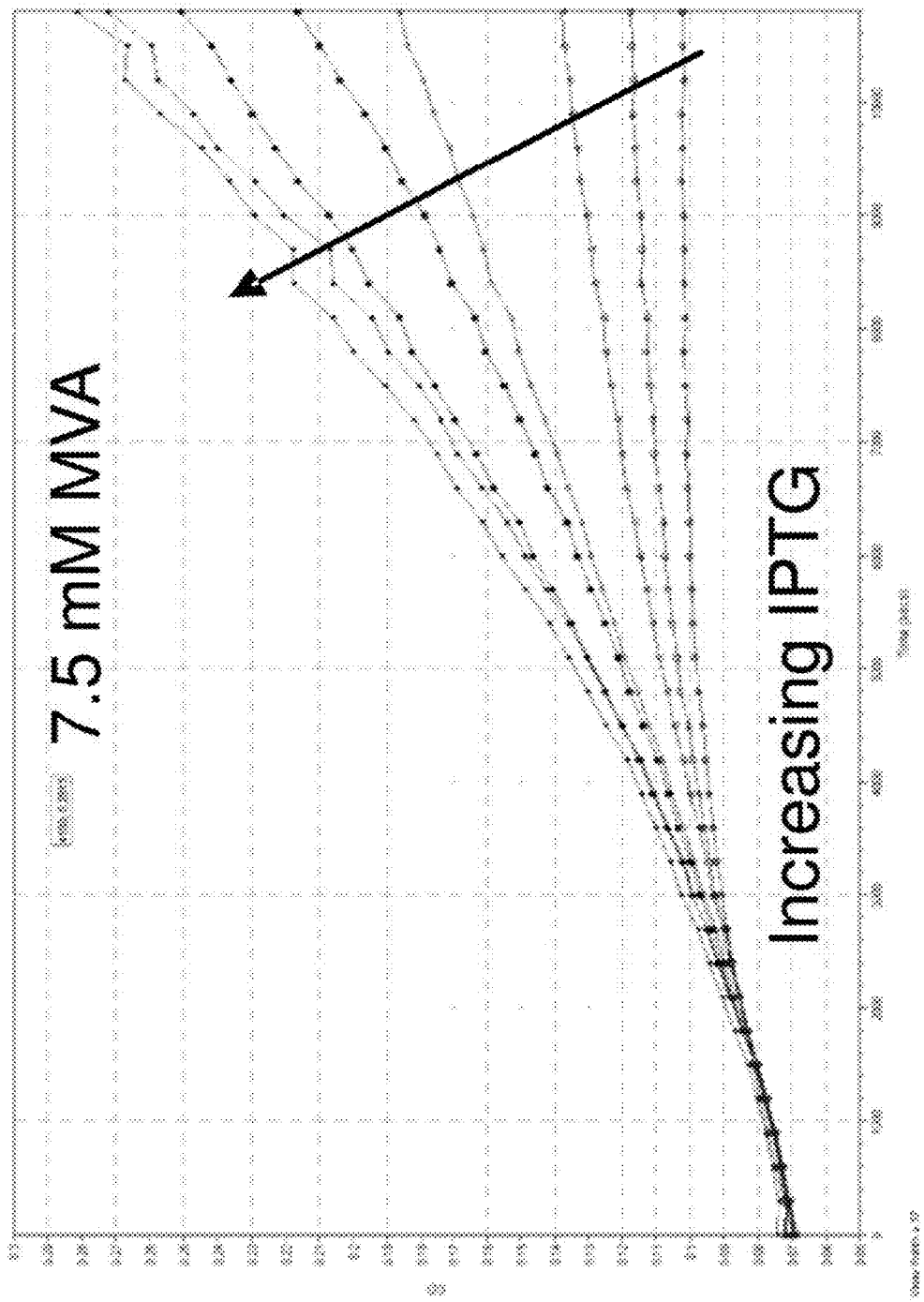
Figure 2:
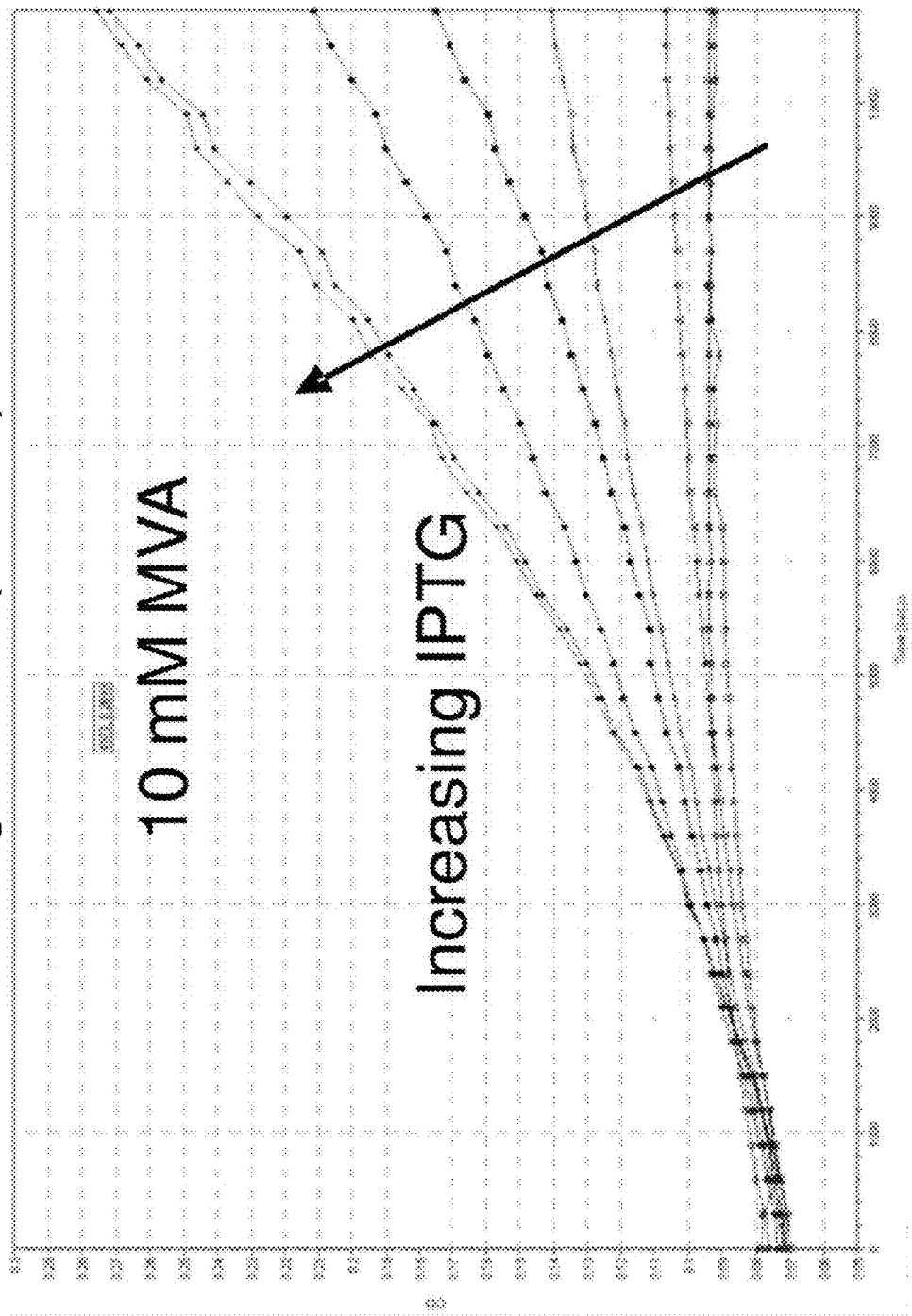
Figure 2:
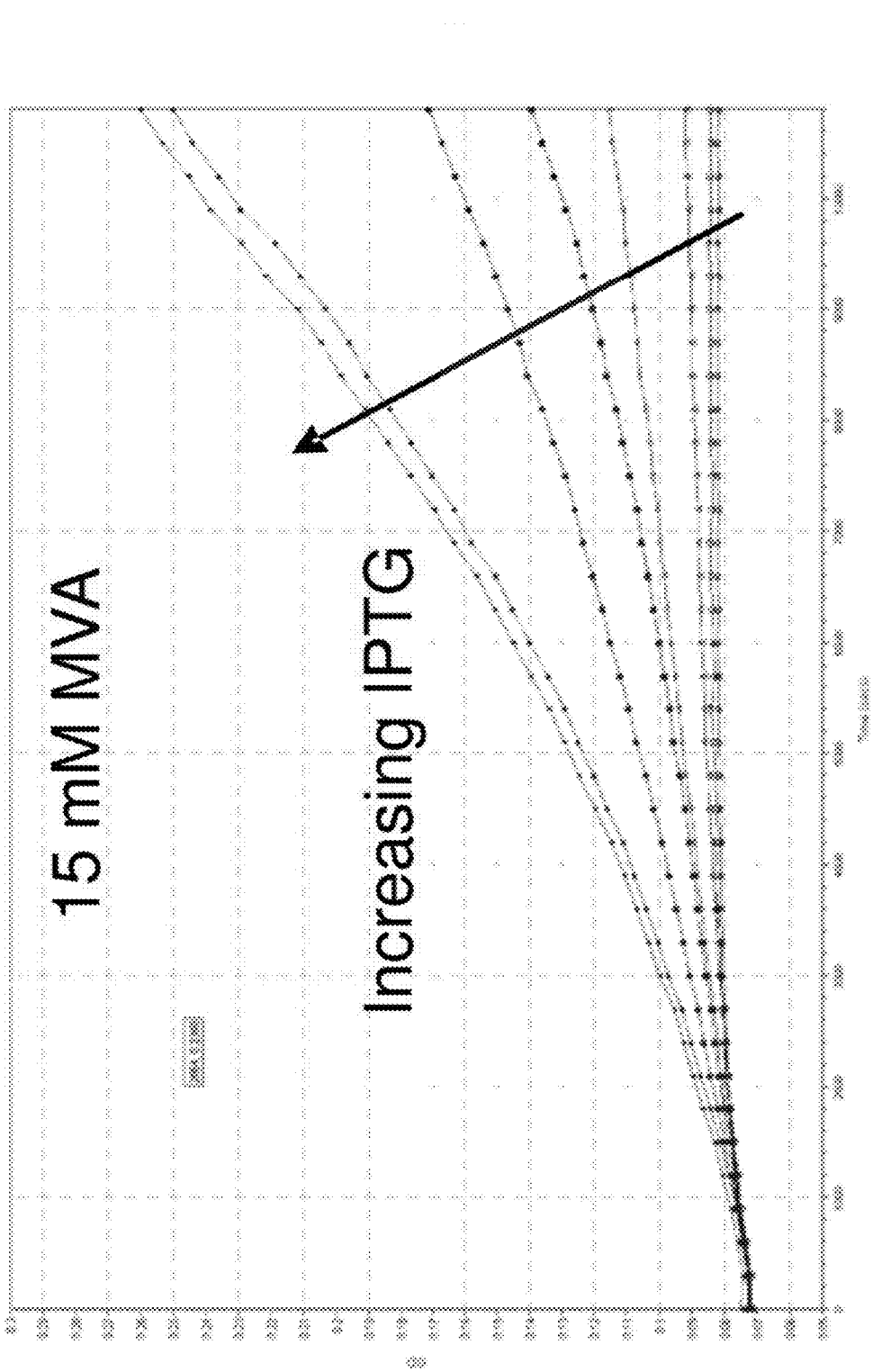
Figure 3:
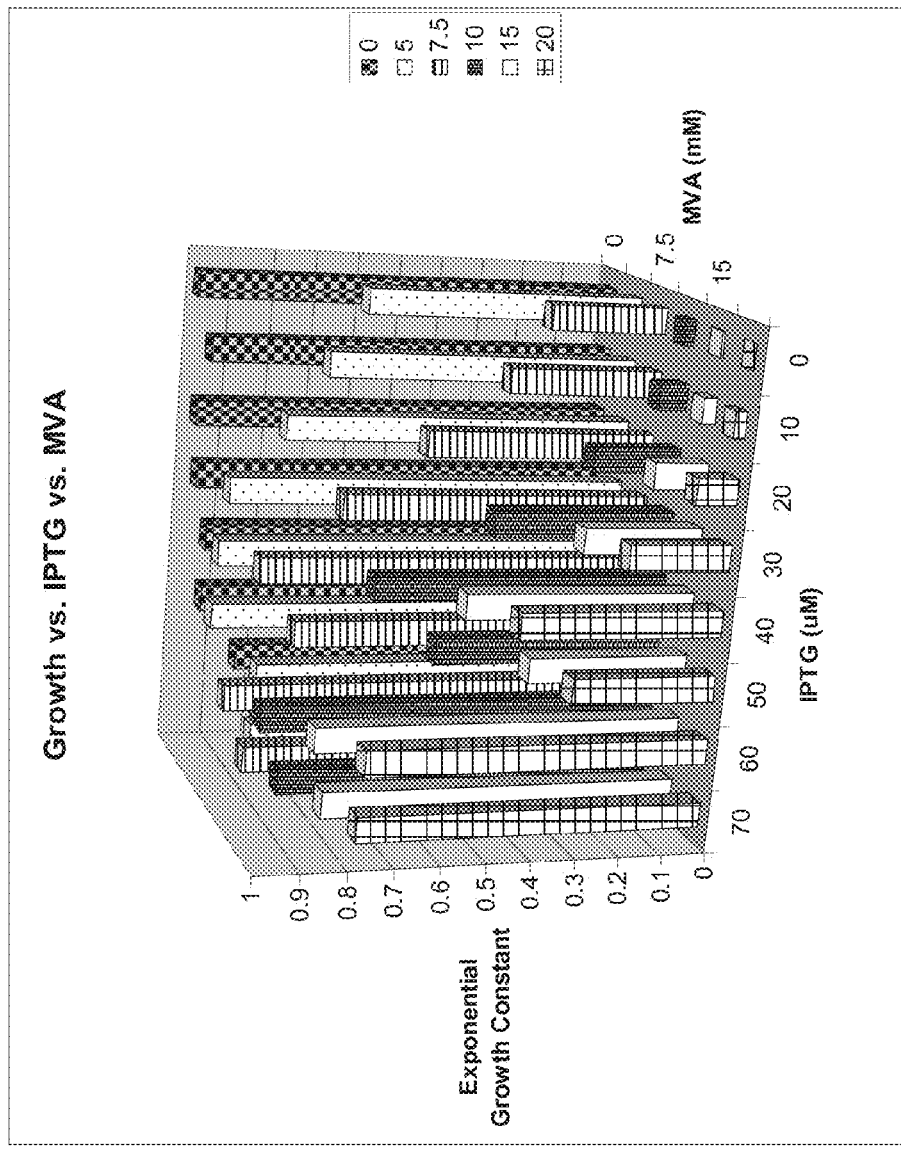
FIG. 3 shows growth as a function of [IPTG] and [mevalonate].

To test this hypothesis, DW425 cells were grown in media containing a matrix of IPTG and mevalonate concentrations (FIG. 2 and FIG. 3). Cells grown in the presence of 60 uM IPTG, and greater, resulted in impaired growth without addition of mevalonate (compared to non-induced cells). At IPTG concentrations of 0-50 µM IPTG, growth was unimpaired, compared to non-induced cells. Cell growth was inhibited with all concentrations of mevalonate in uninduced cells. Increasing the concentration of IPTG resulted in increased growth rate for any given mevalonate concentration screened (FIG. 2 and FIG. 3). Earlier studies were performed to determine that the concentration of enzyme expressed in the cells correlates with the concentration of IPTG present. Therefore, increased isoprene synthase expression/activity in these strains results in improved growth.

Example 2

Analysis of *P. alba* Isoprene Synthase SELs by DMAPP Toxicity Relief

There is a strong correlation between increased intracellular DMAPP levels and growth inhibition of *E. coli*, which can be alleviated by the expression of *P. alba* Isoprene Synthase (IspS). Without being bound by theory, increased levels of IspS activity should therefore allow for better growth due to more rapid conversion of DMAPP to isoprene. By monitoring the growth rates of *E. coli* expressing variants of IspS under these conditions, the inventors can identify mutant IspS enzymes that display increased ability to convert DMAPP to isoprene within the cell.

Figure 4:
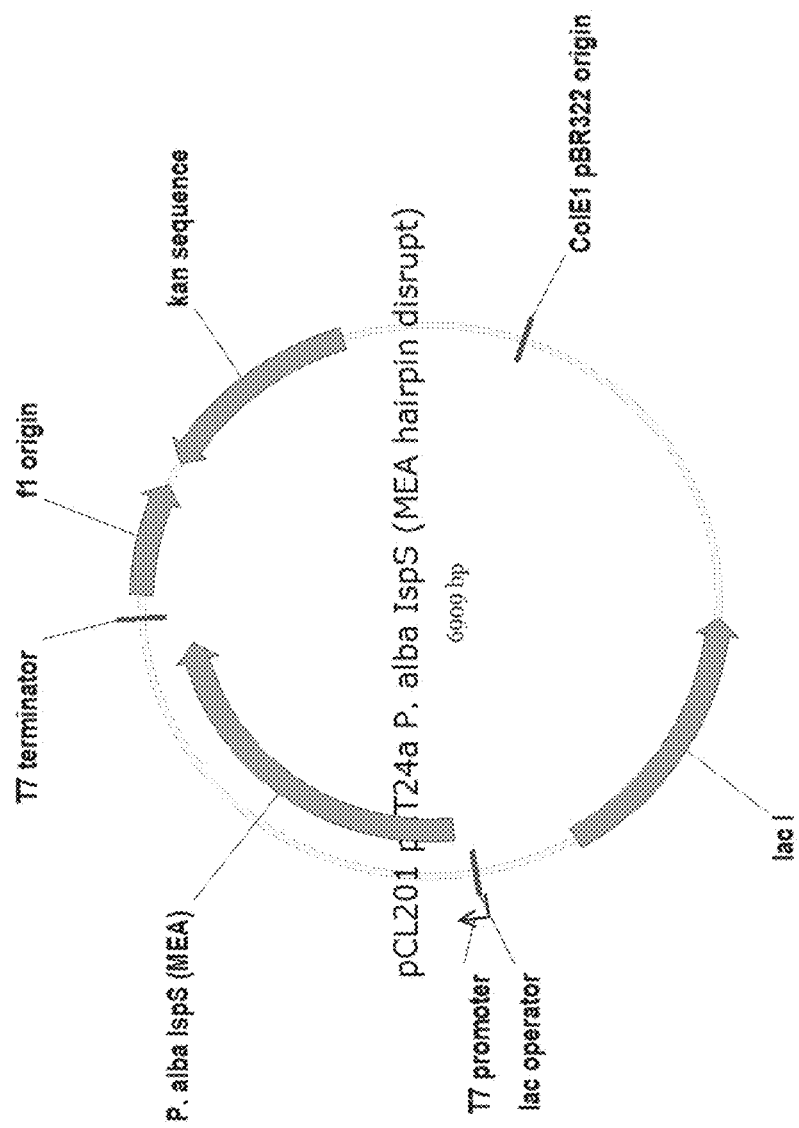
FIG. 4 shows a map of pCL201.

Methods:
1) Plasmid and Strain Construction:

SEL Plasmid Backbone—The plasmid backbone used to generate SELs was constructed by QuikChange (Stratagene) PCR on the template pDu39 (see Table 1 for primer sequences). The PCR product was treated with 1 µl DpnI (Roche) for 3 hours, and then 1 µl of the entire reaction was transformed into chemically competent *E. coli* Top10 cells (Invitrogen) according to the manufacturer's recommended protocol. Cells were recovered and plated on LB medium containing 50 µg/ml kanamycin. The next day, positive colonies were chosen for growth, plasmid purification (Qiagen) and sequencing (Quintara Biosciences). Plasmids which harbored the correct base changes were selected for sequencing of the entire open reading frame to confirm the integrity of the coding sequence. One of these plasmids, pCL201 (see FIG. 4), was selected as the backbone for construction of SELs (by Verdezyne and DNA2.0).

TABLE 1

QuikChange and Sequencing Primers

```
MEA Hairpin Disrupt (pET) F   ggagatatacatatggaagcacgtcgctctgcgaactacgaacctaa (SEQ ID NO: 2)
MEA Hairpin Disrupt (pET) R   ttaggttcgtagttcgcagagcgacgtgcttccatatgtatatctcc (SEQ ID NO: 3)

T7 Forward                    taatacgactcactataggg (SEQ ID NO: 4)
T7 Reverse                    gctagttattgctcagcgg (SEQ ID NO: 5)

EL-1000                       gcactgtctttccgtctgctgc (SEQ ID NO: 6)

QB1493                        cttcggcaacgcatggaaat (SEQ ID NO: 7)

A-rev                         ctcgtacaggctcaggatag (SEQ ID NO: 8)

A-rev2                        ttacgtcccaacgctcaact (SEQ ID NO: 9)

PCR and cycling parameters:
QuikChange PCR:

1 ul pDu39
 5 ul 10X PfuUltra HF buffer
 1 ul dNTPs
 1 ul (50uM) MEA Hairpin Disrupt (pET) F
 1 ul (50uM) MEA Hairpin Disrupt (pET) R
 2 ul DMSO
39 ul diH2O
 1 ul PfuUltra HF Polymerase (Stratagene)
PCR Cycling Parameters for QuikChange:

1. 95° C. 1 min.
2. 95° C. 50 sec.
3. 60° C. 50 sec.
4. 68° C. 7 min.
5. Go to step 2-18 cycles
6. 68° C. 7 min
```

Sequence of pCL201: (SEQ ID NO: 10)

tggcgaatgggacgcgccctgtagcggcgcattaagcgcggcgggtgtggtggttacgcgcagcgtgaccgctacacttgcc agcgccctagcgcccgctcctttcgctttcttcccttcctttctcgccacgttcgccggctttccccgtcaagctctaaatcgggggc tcccttaagggttccgatttagtgctttacggcacctcgaccccaaaaaacttgattagggtgatggttcacgtagtgggccatcgc cctgatagacggtttttcgccctttgacgttggagtccacgttctttaatagtggactcttgttccaaactggaacaacactcaaccct atctcggtctattcttttgatttataagggattttgccgatttcggcctattggttaaaaaatgagctgatttaacaaaaatttaacgcga attttaacaaaatattaacgtttacaatttcaggtggcacttttcggggaaatgtgcgcggaacccctatttgtttatttttctaaatacat tcaaatatgtatccgctcatgaattaattcttagaaaaactcatcgagcatcaaatgaaactgcaatttattcatatcaggattatcaat accatattttttgaaaaagccgtttctgtaatgaaggagaaaactcaccgaggcagttccataggatggcaagatcctggtatcggt ctgcgattccgactcgtccaacatcaatacaacctattaatttccctcgtcaaaaataaggttatcaagtgagaaatcaccatgagt gacgactgaatccggtgagaatggcaaaagtttatgcatttctttccagacttgttcaacaggccagccattacgctcgtcatcaaa TABLE 1-continued QuikChange and Sequencing Primers atcactcgcatcaaccaaaccgttattcattcgtgattgcgcctgagcgagacgaaatacgcgatcgctgttaaaaggacaattac
aaacaggaatcgaatgcaaccggcgcaggaacactgccagcgcatcaacaatattttcacctgaatcaggatattcttctaatac
ctggaatgctgttttcccggggatcgcagtggtgagtaaccatgcatcatcaggagtacggataaaatgcttgatggtcggaaga
ggcataaattccgtcagccagtttagtctgaccatctcatctgtaacatcattggcaacgctacctttgccatgtttcagaaacaactc
tggcgcatcgggcttcccatacaatcgatagattgtcgcacctgattgcccgacattatcgcgagcccatttatacccatataaatc
agcatccatgttggaatttaatcgcggcctagagcaagacgtttcccgttgaatatggctcataacacccttgtattactgtttatgt
aagcagacagttttattgttcatgaccaaaatcccttaacgtgagttttcgttccactgagcgtcagaccccgtagaaaagatcaaa
ggatcttcttgagatcctttttttctgcgcgtaatctgctgcttgcaaacaaaaaaaccaccgctaccagcggtggtttgtttgccgga
tcaagagctaccaactcttttccgaaggtaactggcttcagcagagcgcagataccaaatactgtccttctagtgtagccgtagtt
aggccaccacttcaagaactctgtagcaccgcctacatacctcgctctgctaatcctgttaccagtggctgctgccagtggcgata
agtcgtgtcttaccgggttggactcaagacgatagttaccggataaggcgcagcggtcgggctgaacggggggttcgtgcaca
cagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccaggggggaaacg
cctggtatctttatagtcctgtcgggtttcgccacctctgacttgagcgtcgattttgtgatgctcgtcagggggcggagcctatg
gaaaaacgccagcaacgcggccttttttacggttcctggccttttgctggccttttgctcacatgttctttcctgcgttatcccctgattc
tgtggataaccgtattaccgcctttgagtgagctgataccgctcgccgcagccgaacgaccgagcgcagcgagtcagtgagcg
aggaagcggaagagcgcctgatgcggtattttctccttacgcatctgtgcggtatttcacaccgcatatatggtgcactctcagtac
aatctgctctgatgccgcatagttaagccagtatacactccgctatcgctacgtgactgggtcatggctgcgccccgacacccgc
caacacccgctgacgcgccctgacgggcttgtctgctcccggcatccgcttacagacaagctgtgaccgtctccgggagctgc
atgtgtcagaggttttcaccgtcatcaccgaaacgcgcgaggcagctgcggtaaagctcatcagcgtggtcgtgaagcgattca
cagatgtctgcctgttcatccgcgtccagctcgttgagtttctccagaagcgttaatgtctggcttctgataaagcgggccatgttaa
gggcggttttttcctgtttggtcactgatgcctccgtgtaagggggatttctgttcatgggggtaatgataccgatgaaacgagaga
ggatgctcacgatacgggttactgatgatgaacatgcccggttactggaacgttgtgagggtaaacaactggcggtatggatgc
ggcgggaccagagaaaaatcactcagggtcaatgccagcgcttcgttaatacagatgtaggtgttccacagggtagccagcag
catcctgcgatgcagatccggaacataatggtgcagggcgctgacttccgcgtttccagactttacgaaacacggaaaccgaag
accattcatgttgttgctcaggtcgcagacgttttgcagcagcagtcgcttcacgttcgctcgcgtatcggtgattcattctgctaac
cagtaaggcaaccccgccagcctagccgggtcctcaacgacaggagcacgatcatgcgcacccgtggggccgccatgccg
gcgataatggcctgcttctcgccgaaacgtttggtggcgggaccagtgacgaaggcttgagcgagggcgtgcaagattccgaa
taccgcaagcgacaggccgatcatcgtcgcgctccagcgaaagcggtcctcgccgaaaatgacccagagcgctgccggcac
ctgtcctacgagttgcatgataaagaagacagtcataagtgcggcgacgatagtcatgccccgcgcccaccggaaggagctga
ctgggttgaaggctctcaagggcatcggtcgagatcccggtgcctaatgagtgagctaacttacattaattgcgttgcgctcactg
cccgctttccagtcgggaaacctgtcgtgccagctgcattaatgaatcggccaacgcgcggggagaggcggtttgcgtattggg
cgccagggtggtttttcttttcaccagtgagacgggcaacagctgattgcccttcaccgcctggccctgagagagttgcagcaag
cggtccacgctggtttgccccagcaggcgaaaatcctgtttgatggtggttaacggcgggatataacatgagctgtcttcggtatc
gtcgtatcccactaccgagatatccgcaccaacgcgcagcccggactcggtaatggcgcgcattgcgcccagcgccatctgat
cgttggcaaccagcatcgcagtgggaacgatgccctcattcagcatttgcatggtttgttgaaaaccggacatggcactccagtc
gccttcccgttccgctatcggctgaatttgattgcgagtgagatatttatgccagccagccagacgcagacgcgccgagacaga
acttaatgggcccgctaacagcgcgatttgctggtgacccaatgcgaccagatgctccacgcccagtcgcgtaccgtcttcatgg
gagaaaataatactgttgatgggtgtctggtcagagacatcaagaaataacgccggaacattagtgcaggcagcttccacagca

TABLE 1-continued

QuikChange and Sequencing Primers

```
atggcatcctggtcatccagcggatagttaatgatcagcccactgacgcgttgcgcgagaagattgtgcaccgccgctttacagg
cttcgacgccgcttcgttctaccatcgacaccaccacgctggcacccagttgatcggcgcgagatttaatcgccgcgacaatttg
cgacggcgcgtgcagggccagactggaggtggcaacgccaatcagcaacgactgtttgcccgccagttgttgtgccacgcgg
ttgggaatgtaattcagctccgccatcgccgcttccactttttcccgcgttttcgcagaaacgtggctggcctggttcaccacgcgg
gaaacggtctgataagagacaccggcatactctgcgacatcgtataacgttactggtttcacattcaccaccctgaattgactctctt
ccgggcgctatcatgccataccgcgaaaggttttgcgccattcgatggtgtccgggatctcgacgctctcccttatgcgactcctg
cattaggaagcagcccagtagtaggttgaggccgttgagcaccgccgccgcaaggaatggtgcatgcaaggagatggcgcc
caacagtccccggccacggggcctgccaccatacccacgccgaaacaagcgctcatgagcccgaagtggcgagcccgatc
ttccccatcggtgatgtcggcgatataggcgccagcaaccgcacctgtggcgccggtgatgccggccacgatgcgtccggcgt
agaggatcgagatctcgatcccgcgaaattaatacgactcactatagggaattgtgagcggataacaattcccctctagaaata
attttgtttaactttaagaaggagatatacatatggaagcacgtcgctctgcgaactacgaacctaacagctgggactatgattacct
gctgtcctccgacacggacgagtccatcgaagtatacaaagacaaagcgaaaaagctggaagccgaagttcgtcgcgagatta
ataacgaaaaagcagaatttctgaccctgctggaactgattgacaacgtccagcgcctgggcctgggttaccgtttcgagtctgat
atccgtggtgcgctggatcgcttcgtttcctccggcggcttcgatgcggtaaccaagacttccctgcacggtacggcactgtctttc
cgtctgctgcgtcaacacggttttgaggtttctcaggaagcgttcagcggcttcaaagaccaaaacggcaacttcctggagaacc
tgaaggaagatatcaaagctatcctgagcctgtacgaggccagcttcctggctctggaaggcgaaaacatcctggacgaggcg
aaggttttcgcaatctctcatctgaaagaactgtctgaagaaaagatcggtaaagagctggcagaacaggtgaaccatgcactgg
aactgccactgcatcgccgtactcagcgtctggaagcagtatggtctatcgaggcctaccgtaaaaaggaggacgcgaatcag
gttctgctggagctggcaattctggattacaacatgatccagtctgtataccagcgtgatctgcgtgaaacgtcccgttggtggcgt
cgtgtgggtctggcgaccaaactgcactttgctcgtgaccgcctgattgagagcttctactgggccgtgggtgtagcattcgaac
cgcaatactccgactgccgtaactccgtcgcaaaaatgttttctttcgtaaccattatcgacgatatctacgatgtatacggcaccct
ggacgaactggagctgtttactgatgcagttgagcgttgggacgtaaacgccatcaacgacctgccggattacatgaaactgtgc
tttctggctctgtataacactattaacgaaatcgcctacgacaacctgaaagataaaggtgagaacatcctgccgtatctgaccaaa
gcctgggctgacctgtgcaacgctttcctgcaagaagccaagtggctgtacaacaaatctactccgacctttgacgactacttcgg
caacgcatggaaatcctcttctggcccgctgcaactggtgttcgcttacttcgctgtcgtgcagaacattaaaaaggaagagatcg
aaaacctgcaaaaataccatgacaccatctctcgtccttcccatatcttccgtctgtgcaatgacctggctagcgcgtctgcggaaa
ttgcgcgtggtgaaaccgcaaatagcgtttcttgttacatgcgcactaaaggtatctccgaagaactggctaccgaaagcgtgatg
aatctgatcgatgaaacctggaaaaagatgaacaaggaaaaactgggtggtagcctgttcgcgaaaccgttcgtggaaaccgc
gatcaacctggcacgtcaatctcactgcacttatcataacggcgacgcgcatacctctccggatgagctgacccgcaaacgcgtt
ctgtctgtaatcactgaaccgattctgccgtttgaacgctaaggatccgaattcgagctccgtcgacaagcttgcggccgcactcg
agcaccaccaccaccaccactgagatccggctgctaacaaagcccgaaaggaagctgagttggctgctgccaccgctgagca
ataactagcataaccccttggggcctctaaacgggtcttgaggggttttttgctgaaaggaggaactatatccggat
```

Amino Acid Sequence of P. alba IspS: (SEQ ID NO: 1)

```
MEARRSANYEPNSWDYDYLLSSDTDESIEVYKDKAKKLEAEVRREINNEKAEFL
TLLELIDNVQRLGLGYRFESDIRGALDRFVSSGGFDAVTKTSLHGTALSFRLLRQ
HGFEVSQEAFSGFKDQNGNFLENLKEDIKAILSLYEASFLALEGENILDEAKVFAI
SHLKELSEEKIGKELAEQVNHALELPLHRRTQRLEAVWSIEAYRKKEDANQVLL
ELAILDYNMIQSVYQRDLRETSRWWRRVGLATKLHFARDRLIESFYWAVGVAFE
PQYSDCRNSVAKMFSFVTIIDDIYDVYGTLDELELFTDAVERWDVNAINDLPDY
```

TABLE 1-continued

QuikChange and Sequencing Primers

MKLCFLALYNTINEIAYDNLKDKGENILPYLTKAWADLCNAFLQEAKWLYNKST

PTFDDYFGNAWKSSSGPLQLVFAYFAVVQNIKKEEIENLQKYHDTISRPSHIFRLC

NDLASASAEIARGETANSVSCYMRTKGISEELATESVMNLIDETWKKMNKEKLG

GSLFAKPFVETAINLARQSHCTYHNGDAHTSPDELTRKRVLSVITEPILPFER

SEL Expression Host—A P1 lysate of MCM521 (described herein) was made and transduced into BL21(DE3) according to standard molecular biology techniques (Miller, A Short Course in Bacterial Genetics). Transductants were selected on LB medium plates containing 20 µg/ml of kanamycin. Positive colonies were further verified by PCR to confirm the presence of PL.2-mKKDyI in the BL21 DE3 strain. 1 µl of pCP20 plasmid was then transformed into this strain and positive colonies were selected for on LB containing 50 µg/ml carbenicillin and incubated overnight at 30° C. Positive transformants were streaked on an LB plate and incubated at 37° C. to induce loss of the pCP20 plasmid. To confirm the loss of the neomycin (kanamycin) resistance marker, colonies that grew at 37° C. were patched onto LB medium containing either 20 µg/ml of kanamycin, 50 µg/ml of carbenicillin, or no antibiotics. The strains with integrated PL.2 mKKDyI without the kanamycin resistance marker that have lost pCP20 should be sensitive to kanamycin and carbenicillin. Four colonies sensitive to kanamycin and carbenicillin were checked by PCR for the presence of mKKDyI in BL21(DE3) with the parental BL21(DE3) strain as a control. The resulting strain, MD09-170, was used for expression of IspS variants in the growth assay on SELs described below. Control strains for the growth assay harbored either the empty pET24a+ vector or pCL201 as negative and positive controls for IspS expression, respectively (see Table 2).

TABLE 2

Strains

| Strain | Plasmid | Description |
|---|---|---|
| MD09-170 | | BL21 (DE3) PL.2-mKKDyI |
| DW424 | pET24a+ | BL21 (DE3) PL.2-mKKDyI + vector (negative control) |
| DW425 | pCL201 | BL21 (DE3) PL.2-mKKDyI + P. alba IspS (wild type control) |

2) Construction of SELs:

25 Site Evaluation Libraries (SELs) of IspS were analyzed previously for specific activity. Table 3 lists the residues included in these libraries. For the growth assay, plasmids harboring variant IspS enzymes in these libraries were purified and transformed into the expression host MD09-170: Original libraries were replicated directly from glycerol stocks and grown at 30° C. overnight in LB containing 50 µg/ml kanamycin in 96 deep-well plates (VWR). Cells from the overnight growth were harvested by centrifugation (Eppendorf 5804 R), and supernatants were discarded. Plasmid purification was performed on cell pellets using a Hamilton Microlab STAR robot using the Nucleospin Multi-96 Plus Plasmid purification kit (Macherey Nagel) according to the manufacturers' recommended protocols. 3 µl of the resulting plasmid DNA for each variant was transformed into chemically competent MD09-170 cells in a flat-bottom 96-well polystyrene plate (Falcon) using an Eppendorf Thermomixer R set to 42° C. Cells were recovered for 2 hours in LB medium, and then diluted and incubated overnight in LB medium containing 50 µg/ml kanamycin. Glycerol stocks of plates containing MD09-170 cells with variants from all 25 original libraries were made and stored at −80° C. prior to analysis by growth assay.

A second set of 80 SELs was ordered and manufactured by DNA2.0. These libraries were transformed directly into the screening host MD09-170. Table 4 lists all 80 residues that were chosen for this set. Sites were picked primarily based upon their location in the recently solved crystal structure of P. alba IspS. Strains DW425 and DW424 (see Table 2) were seeded back into 96-well plates for the wild type and negative controls, respectively.

TABLE 3

Sites selected for 25 SELs

| Description | Sites |
|---|---|
| Surface hydrophobic residues | I28, V30, L130, G153, V299, L303, L469, L494 |
| Hinge region | R198, I229, L260 |
| Negatively charged area | D311, D323 |
| Flexible loops | A443, A453, N454, H515, A519, E525 |
| Active site | F388, N438, E451 |
| Miscellaneous | D345, R528, T536 |

TABLE 4

Sites selected for 80 SELs

| Position | Residue | Selection Criteria |
|---|---|---|
| 3 | A | surface hydrophobic |
| 7 | A | symmetry contact |
| 9 | Y | symmetry contact |
| 12 | N | conservation |
| 13 | S | conservation |
| 16 | Y | N-terminal loop |
| 18 | Y | N-terminal loop |
| 20 | L | conservation |
| 23 | D | conservation |
| 25 | D | surface hydrophilic |
| 26 | E | symmetry contact |
| 27 | S | surface hydrophilic |
| 33 | D | symmetry contact |
| 36 | K | symmetry contact |
| 44 | R | symmetry contact |
| 50 | K | surface hydrophilic |
| 53 | F | conservation |
| 59 | L | surface hydrophobic |
| 69 | G | conservation |
| 74 | S | surface hydrophilic |
| 78 | G | conservation |
| 81 | D | surface hydrophilic |
| 87 | G | surface hydrophobic |
| 99 | G | conservation |
| 116 | Q | conservation |
| 117 | E | symmetry contact |
| 120 | S | surface hydrophilic |

TABLE 4-continued

Sites selected for 80 SELs

| Position | Residue | Selection Criteria |
|---|---|---|
| 121 | G | surface loop |
| 125 | Q | surface hydrophilic |
| 127 | G | conservation |
| 139 | A | conservation |
| 165 | I | surface hydrophobic |
| 173 | E | surface hydrophilic |
| 174 | E | symmetry contact |
| 177 | G | conservation |
| 179 | E | surface hydrophilic |
| 194 | R | conservation |
| 197 | Q | conservation |
| 202 | V | conservation |
| 216 | Q | conservation |
| 240 | T | conservation |
| 246 | R | symmetry contact |
| 251 | T | surface hydrophilic |
| 254 | H | conservation |
| 287 | F | active site |
| 290 | V | active site |
| 308 | L | surface hydrophobic |
| 376 | L | flexible loops |
| 377 | Y | symmetry contact |
| 379 | K | conservation |
| 389 | G | conservation |
| 397 | G | active site |
| 400 | Q | hydrophobic pocket |
| 403 | F | active site |
| 421 | Q | conservation |
| 426 | T | conservation |
| 430 | P | misc |
| 434 | F | active site |
| 445 | A | surface hydrophobic |
| 448 | A | conservation |
| 457 | S | flexible loops |
| 462 | T | conservation |
| 476 | N | surface hydrophilic |
| 487 | K | surface loop |
| 488 | E | surface loop |
| 489 | K | surface loop |
| 490 | L | surface loop |
| 491 | G | surface loop |
| 492 | G | surface loop |
| 493 | S | surface loop |
| 495 | F | surface loop |
| 496 | A | surface loop |
| 497 | K | surface loop |
| 498 | P | conservation |
| 509 | Q | conservation |
| 514 | Y | active site |
| 521 | T | conservation |
| 539 | I | C-terminal |
| 540 | L | surface hydrophobic |
| 544 | R | conservation |

3) Growth Assay for Increased IspS Activity

For the growth assay, glycerol stocks of SELs were inoculated into 200 µl LB medium containing 50 µg/ml kanamycin in flat bottom microtiter plates (Cellstar) and grown overnight at 30° C. using the System Duetz (Enzyscreen BV). For pre-induction, 7 µl of the overnight culture from each well was inoculated into 100 µl of TM3 medium containing 50 µM IPTG and 50 µg/ml kanamycin, and plates were grown for 2 hours at 30° C. Pre-induced cultures were then diluted 1:10 into TM3 medium containing 11 mM mevalonic acid, 50 µM IPTG and 50 µg/ml kanamycin in glass-bottom 96 square-well microtiter plates (Matrical). Cultures were grown at 34° C. and shaken at 225 rpm for approximately 10 hours in a Growth Profiler 1152 (Enzyscreen). Growth curves were generated for each IspS variant according to the manufacturer's recommended protocol. Negative controls were strains harboring the empty pET24a+ vector (DW424), and positive controls were strains expressing wild type *P. alba* IspS (DW425) grown either with or without MVA.

For data analysis, the relative growth rate of each variant over a given period of time was measured against wild type controls. Specifically, a line was fit to the series using the "LINEST" function in Microsoft Excel to yield the exponential growth constant (growth rate). These values were then divided by the average of 4 (in most cases) growth constants from the positive controls to yield a "Growth Index" number for each variant. The Growth Index values for variants in all 105 SEL libraries are listed in Table 5. In some cases, a particular variant was either absent from the glycerol stock, did not grow in the overnight LB culture, or was not transferred to the final plate for growth assay. Values for these particular wells are listed as ND (Not Determined). In the instances where a particular variant was not generated in initial mutagenesis of *P. alba* IspS, the wild type residue was substituted.

TABLE 5

| Variant | GI |
|---|---|
| Growth Index Ranking for Plate 001. | |
| V30L | 1.61 |
| V30K | 1.52 |
| I28T | 1.46 |
| V30Y | 1.45 |
| V30W | 1.39 |
| I28S | 1.38 |
| G153W | 1.34 |
| I28R | 1.31 |
| L130Y | 1.29 |
| V30S | 1.26 |
| V30V | 1.25 |
| V30F | 1.22 |
| L130L | 1.20 |
| L130K | 1.17 |
| I28I | 1.15 |
| L130G | 1.15 |
| L130I | 1.14 |
| V30R | 1.13 |
| G153Y | 1.12 |
| L130L | 1.12 |
| V30I | 1.11 |
| I28Y | 1.10 |
| L130V | 1.09 |
| L130L | 1.09 |
| V30P | 1.08 |
| V30E | 1.07 |
| G153G | 1.07 |
| L130R | 1.05 |
| V30T | 1.05 |
| L130L | 1.04 |
| V30Q | 1.04 |
| I28P | 1.03 |
| G153S | 1.02 |
| G153R | 1.01 |
| G153C | 1.00 |
| L130D | 0.97 |
| G153G | 0.97 |
| L130E | 0.96 |
| G153A | 0.96 |
| V30V | 0.95 |
| V30M | 0.94 |
| I28I | 0.92 |
| G153G | 0.92 |
| L130L | 0.91 |
| G153T | 0.90 |
| V30G | 0.89 |
| L130W | 0.88 |
| L130Q | 0.88 |
| G153Q | 0.86 |
| G153G | 0.86 |
| G153M | 0.83 |
| G153N | 0.83 |
| G153D | 0.81 |
| L130P | 0.76 |
| V30N | 0.60 |

TABLE 5-continued

| Variant | GI |
| --- | --- |
| I28I | 0.57 |
| I28I | 0.55 |
| I28L | 0.52 |
| I28W | 0.42 |
| I28D | 0.38 |
| G153K | 0.32 |
| G153L | 0.32 |
| G153P | 0.32 |
| V30C | 0.31 |
| G153V | 0.31 |
| I28E | 0.29 |
| L130A | 0.28 |
| I28G | 0.28 |
| I28F | 0.27 |
| V30A | 0.26 |
| I28A | ND |
| L130M | 0.22 |
| I28M | 0.15 |
| L130C | 0.15 |
| I28N | 0.14 |
| I28C | 0.10 |
| I28V | ND |
| V30D | ND |
| L130S | ND |
| G153H | ND |

Growth Index Ranking for Plate 002.

| Variant | GI |
| --- | --- |
| R198R | 1.11 |
| R198R | 1.08 |
| I229L | 1.00 |
| R198R | 0.98 |
| I229C | 0.94 |
| L260L | 0.89 |
| L260L | 0.88 |
| R198R | 0.87 |
| I229I | 0.86 |
| R198K | 0.84 |
| V299V | 0.82 |
| I229T | 0.80 |
| I229V | 0.78 |
| I229M | 0.78 |
| L260M | 0.77 |
| L260L | 0.75 |
| L260W | 0.74 |
| R198C | 0.74 |
| V299L | 0.72 |
| V299V | 0.69 |
| R198M | 0.68 |
| L260Y | 0.66 |
| R198V | 0.64 |
| R198A | 0.62 |
| I229A | 0.62 |
| V299V | 0.62 |
| L260Q | 0.61 |
| V299V | 0.60 |
| I229H | 0.57 |
| L260I | 0.54 |
| R198I | 0.52 |
| I229N | 0.49 |
| I229F | 0.45 |
| I229S | 0.45 |
| L260H | 0.45 |
| R198T | 0.42 |
| L260P | 0.40 |
| L260V | 0.38 |
| I229G | 0.36 |
| I229Q | 0.35 |
| R198S | 0.35 |
| L260G | 0.34 |
| V299T | 0.29 |
| L260C | 0.25 |
| V299A | 0.25 |
| R198G | 0.24 |
| R198N | 0.23 |
| L260A | 0.22 |
| V299M | 0.22 |
| L260S | ND |
| V299S | 0.15 |
| L260D | 0.15 |
| V299N | 0.14 |
| L260E | 0.11 |
| I229Y | 0.11 |
| V299R | 0.10 |
| R198L | 0.10 |
| I229K | 0.09 |
| R198F | 0.08 |
| I229W | 0.08 |
| R198H | 0.07 |
| V299E | 0.05 |
| V299K | 0.03 |
| R198Y | 0.03 |
| V299W | 0.02 |
| R198D | 0.02 |
| I229D | 0.02 |
| I229R | 0.01 |
| V299Y | 0.01 |
| V299G | 0.01 |
| I229E | 0.01 |
| L260R | 0.01 |
| R198P | ND |
| L260K | 0.00 |
| L260T | 0.00 |
| V299I | ND |
| I229P | −0.02 |
| V299H | −0.03 |
| V299P | −0.04 |
| V299D | −0.05 |

Growth Index Ranking for Plate 003.

| Variant | GI |
| --- | --- |
| L303L | 1.10 |
| L303L | 1.10 |
| D311D | 1.08 |
| L303L | 1.06 |
| L303L | 0.99 |
| D311W | 0.99 |
| D311L | 0.98 |
| D311K | 0.98 |
| L303W | 0.96 |
| D311F | 0.93 |
| D311S | 0.92 |
| D311G | 0.90 |
| D323K | 0.89 |
| L303T | 0.88 |
| D311R | 0.87 |
| L303R | 0.85 |
| D311T | 0.84 |
| D311V | 0.82 |
| L303L | 0.81 |
| L303V | 0.81 |
| L303I | 0.80 |
| D311D | 0.80 |
| D311A | 0.80 |
| L303S | 0.79 |
| D311I | 0.78 |
| L303M | 0.77 |
| D323L | 0.77 |
| D323R | 0.75 |
| D311D | 0.75 |
| L303E | 0.74 |
| D323Y | 0.74 |
| L303C | 0.74 |
| D323S | 0.74 |
| D345L | 0.73 |
| D311Q | 0.73 |
| L303G | 0.72 |
| D323G | 0.71 |
| D311D | 0.71 |
| D345G | 0.70 |
| D323T | 0.69 |
| D311E | 0.69 |
| D323M | 0.69 |
| D323N | 0.68 |
| D345W | 0.68 |
| D311D | 0.67 |
| L303Q | 0.67 |
| D345D | 0.66 |

TABLE 5-continued

| Variant | GI |
|---|---|
| L303A | 0.66 |
| D323E | 0.66 |
| L303P | 0.66 |
| D323A | 0.66 |
| D345M | 0.66 |
| D345A | 0.65 |
| D323D | 0.64 |
| D323V | 0.63 |
| D323C | 0.62 |
| L303H | 0.62 |
| L303D | 0.62 |
| D323F | 0.61 |
| D345S | 0.61 |
| D323I | 0.61 |
| D345V | 0.59 |
| D323Q | 0.58 |
| D345T | 0.58 |
| D323W | 0.57 |
| D345Y | 0.57 |
| D345R | 0.56 |
| D345N | 0.55 |
| D345K | 0.53 |
| D345Q | 0.53 |
| D345I | 0.53 |
| D345D | 0.53 |
| D345E | 0.52 |
| D345C | 0.51 |
| D345D | 0.41 |
| D345P | 0.37 |
| D311M | ND |
| D323P | ND |
| D323H | ND |
| D311P | −0.02 |
| Growth Index Ranking for Plate 004. | |
| E451E | 1.48 |
| A443A | 1.36 |
| A443A | 1.34 |
| A443A | 1.29 |
| F388F | 1.28 |
| N438N | 1.27 |
| A443A | 1.20 |
| F388V | 1.20 |
| A443A | 1.17 |
| A443A | 1.15 |
| A443A | 1.13 |
| E451E | 1.13 |
| A443A | 1.12 |
| F388Q | 0.96 |
| F388T | 0.89 |
| F388F | 0.89 |
| A443S | 0.86 |
| A443H | 0.85 |
| A443L | 0.84 |
| A443N | 0.82 |
| F388R | 0.74 |
| F388S | 0.68 |
| A443Q | 0.66 |
| A443I | 0.63 |
| A443G | 0.50 |
| A443R | 0.44 |
| F388D | 0.42 |
| A443V | 0.40 |
| A443F | 0.28 |
| A443P | 0.06 |
| E451Q | 0.06 |
| A443T | 0.03 |
| F388H | ND |
| F388L | 0.00 |
| F388F | −0.01 |
| F388F | −0.01 |
| E451W | −0.01 |
| E451K | −0.01 |
| F388A | −0.02 |
| N438A | −0.02 |
| E451G | −0.02 |
| E451H | −0.02 |
| F388P | −0.02 |

TABLE 5-continued

| Variant | GI |
|---|---|
| E451D | −0.02 |
| E451R | −0.03 |
| F388Y | ND |
| F388K | −0.03 |
| E451Y | −0.03 |
| E451F | −0.03 |
| F388C | −0.03 |
| E451I | −0.03 |
| N438F | −0.04 |
| E451V | −0.04 |
| N438H | −0.04 |
| E451A | −0.04 |
| E451C | −0.04 |
| E451T | −0.04 |
| N438T | −0.04 |
| N438D | −0.04 |
| N438E | −0.04 |
| E451L | −0.05 |
| N438I | −0.05 |
| N438W | ND |
| E451P | −0.05 |
| N438V | −0.05 |
| F388F | −0.05 |
| N438M | −0.05 |
| N438L | −0.05 |
| N438C | −0.05 |
| N438K | −0.06 |
| E451S | −0.06 |
| F388F | −0.06 |
| E451N | −0.06 |
| N438R | −0.06 |
| N438Y | −0.06 |
| N438Q | −0.06 |
| N438P | −0.06 |
| N438G | −0.07 |
| F388G | −0.08 |
| N438S | −0.09 |
| Growth Index Ranking for Plate 005. | |
| N454N | 1.10 |
| L494L | 1.06 |
| L469W | 1.06 |
| L494K | 1.03 |
| L469L | 1.00 |
| L469R | 0.98 |
| L469L | 0.98 |
| L494L | 0.98 |
| L494W | 0.97 |
| L494Y | 0.95 |
| L469V | 0.95 |
| L494G | 0.94 |
| L469F | 0.93 |
| L494I | 0.93 |
| L469I | 0.92 |
| A453T | 0.91 |
| A453A | 0.90 |
| L494V | 0.90 |
| L494R | 0.89 |
| A453W | 0.88 |
| L469N | 0.88 |
| A453C | 0.88 |
| L469T | 0.88 |
| L469S | 0.87 |
| L469H | 0.87 |
| N454N | 0.86 |
| L494C | 0.86 |
| L494D | 0.86 |
| L494E | 0.86 |
| L469C | 0.85 |
| A453S | 0.85 |
| A453A | 0.85 |
| N454S | 0.84 |
| A453A | 0.84 |
| L469P | 0.83 |
| L494S | 0.83 |
| N454G | 0.83 |
| A453N | 0.83 |
| L494H | 0.83 |

TABLE 5-continued

| Variant | GI |
| --- | --- |
| L469A | 0.83 |
| L469L | 0.82 |
| L494N | 0.81 |
| L469Q | 0.79 |
| L494L | 0.78 |
| A453E | 0.77 |
| L469L | 0.77 |
| N454H | 0.76 |
| A453L | 0.76 |
| A453H | 0.75 |
| L469G | 0.75 |
| L494Q | 0.74 |
| N454A | 0.73 |
| L494P | 0.73 |
| N454T | 0.73 |
| L469L | 0.73 |
| N454E | 0.72 |
| A453I | 0.70 |
| L494A | 0.69 |
| N454Y | 0.67 |
| N454W | 0.66 |
| A453V | 0.64 |
| N454V | 0.63 |
| A453F | 0.62 |
| N454Q | 0.62 |
| N454L | 0.61 |
| A453R | 0.59 |
| N454D | 0.56 |
| A453D | 0.54 |
| N454C | 0.53 |
| N454F | 0.49 |
| A453K | 0.45 |
| L494T | 0.42 |
| N454I | 0.31 |
| A453G | 0.26 |
| N454M | 0.22 |
| L469Y | 0.19 |
| A453P | 0.02 |
| N454P | 0.00 |
| A453Y | ND |
| N454R | −0.03 |
| Growth Index Ranking for Plate 006. | |
| A519W | 1.27 |
| E525K | 1.13 |
| H515Y | 1.07 |
| R528K | 1.05 |
| E525E | 1.01 |
| A519K | 0.99 |
| H515K | 0.98 |
| H515W | 0.97 |
| H515R | 0.96 |
| E525W | 0.94 |
| R528R | 0.92 |
| R528R | 0.92 |
| A519A | 0.91 |
| E525L | 0.89 |
| A519R | 0.89 |
| A519A | 0.87 |
| R528V | 0.85 |
| A519A | 0.85 |
| E525V | 0.85 |
| A519G | 0.85 |
| H515G | 0.85 |
| A519A | 0.85 |
| R528R | 0.85 |
| E525R | 0.83 |
| E525E | 0.83 |
| E525D | 0.83 |
| E525T | 0.82 |
| E525C | 0.81 |
| E525G | 0.80 |
| E525M | 0.79 |
| H515F | 0.78 |
| H515M | 0.78 |
| H515V | 0.78 |
| E525F | 0.77 |
| A519H | 0.76 |
| A519F | 0.76 |
| H515Q | 0.73 |
| A519Y | 0.73 |
| H515T | 0.73 |
| E525H | 0.73 |
| E525N | 0.73 |
| E525Q | 0.72 |
| R528M | 0.70 |
| H515N | 0.70 |
| E525A | 0.69 |
| R528F | 0.69 |
| E525E | 0.67 |
| R528H | 0.67 |
| A519S | 0.66 |
| A519L | 0.66 |
| H515E | 0.66 |
| E525S | 0.64 |
| H515S | 0.63 |
| A519T | 0.61 |
| R528Y | 0.61 |
| R528T | 0.60 |
| R528L | 0.59 |
| H515A | 0.58 |
| A519C | 0.50 |
| R528A | 0.49 |
| A519V | 0.45 |
| A519Q | 0.44 |
| R528S | 0.43 |
| A519E | 0.39 |
| E525P | 0.37 |
| R528N | 0.35 |
| R528E | 0.34 |
| A519D | 0.33 |
| R528G | 0.33 |
| R528C | 0.31 |
| R528W | 0.30 |
| H515L | 0.15 |
| R528D | 0.08 |
| A519P | 0.00 |
| H515H | −0.01 |
| H515H | ND |
| H515P | −0.02 |
| R528P | −0.02 |
| H515H | ND |
| H515H | ND |
| Growth Index Ranking for Plate 007. | |
| T536L | 0.62 |
| T536T | 0.59 |
| T536Y | 0.58 |
| T536I | 0.49 |
| T536H | 0.46 |
| T536F | 0.45 |
| T536G | 0.42 |
| T536T | 0.40 |
| T536V | 0.38 |
| T536S | 0.36 |
| T536K | 0.31 |
| T536T | 0.30 |
| T536M | 0.29 |
| T536N | 0.29 |
| T536C | 0.27 |
| T536A | 0.26 |
| T536D | 0.18 |
| T536R | 0.15 |
| T536E | 0.14 |
| T536P | 0.01 |
| Growth Index Ranking for Plate 008. | |
| G78L | 1.33 |
| G78Y | 1.31 |
| G78W | 1.27 |
| G78I | 1.26 |
| S74K | 1.24 |
| K36L | 1.23 |
| S74W | 1.22 |
| S74I | 1.20 |
| K36K | 1.20 |

TABLE 5-continued

| Variant | GI |
|---|---|
| K36I | 1.19 |
| G78V | 1.19 |
| K36V | 1.19 |
| G78H | 1.18 |
| G78T | 1.18 |
| S74V | 1.17 |
| K36Y | 1.17 |
| S74L | 1.14 |
| S74T | 1.14 |
| S74Y | 1.13 |
| G78K | 1.13 |
| K36R | 1.11 |
| S74H | 1.10 |
| K36T | 1.07 |
| G78F | 1.01 |
| K36W | 1.01 |
| S74G | 0.98 |
| K36S | 0.98 |
| G78R | 0.97 |
| S74R | 0.97 |
| K36H | 0.97 |
| K36F | 0.95 |
| S74S | 0.94 |
| G78G | 0.91 |
| G78S | 0.91 |
| S74F | 0.86 |
| G78C | 0.84 |
| K36G | 0.83 |
| S74C | 0.78 |
| K36M | 0.77 |
| A7G | 0.77 |
| S74Q | 0.77 |
| G78P | 0.76 |
| S74P | 0.76 |
| G78E | 0.74 |
| S74N | 0.72 |
| G78D | 0.72 |
| K36N | 0.72 |
| S74E | 0.72 |
| S74D | 0.70 |
| S74A | 0.70 |
| G78M | 0.70 |
| A7A | 0.69 |
| K36C | 0.69 |
| G78N | 0.68 |
| G78Q | 0.68 |
| G78A | 0.66 |
| S74M | 0.65 |
| K36Q | 0.65 |
| K36P | 0.61 |
| K36D | 0.58 |
| K36A | 0.56 |
| K36E | 0.54 |
| A7W | 0.50 |
| A7V | 0.39 |
| A7C | 0.34 |
| A7H | 0.31 |
| A7P | 0.31 |
| A7Y | 0.30 |
| A7S | 0.30 |
| A7T | 0.29 |
| A7I | 0.29 |
| A7F | 0.20 |
| A7Q | 0.19 |
| A7E | 0.17 |
| A7N | 0.16 |
| A7L | 0.09 |
| A7D | 0.07 |
| A7R | 0.07 |
| A7M | 0.06 |
| A7K | −0.02 |

Growth Index Ranking for Plate 009.

| Variant | GI |
|---|---|
| R44H | 1.30 |
| R44T | 1.27 |
| R44F | 1.21 |
| G121I | 1.17 |
| R44V | 1.17 |
| G121L | 1.15 |
| G121H | 1.14 |
| R44Y | 1.13 |
| R44I | 1.10 |
| G121F | 1.09 |
| G121T | 1.07 |
| G121Y | 1.07 |
| R44K | 1.04 |
| G121V | 1.03 |
| G121K | 1.02 |
| G121W | 1.00 |
| R44C | 1.00 |
| R44A | 1.00 |
| Q216H | 0.99 |
| R44M | 0.99 |
| R44L | 0.99 |
| R44D | 0.96 |
| R44N | 0.96 |
| R44S | 0.95 |
| Q216I | 0.94 |
| G121A | 0.94 |
| Q216T | 0.92 |
| G121G | 0.91 |
| Q216V | 0.90 |
| G121M | 0.90 |
| Q216K | 0.89 |
| G121C | 0.88 |
| E488I | 0.88 |
| Q216F | 0.87 |
| Q216L | 0.87 |
| G121R | 0.87 |
| Q216W | 0.86 |
| Q216Y | 0.84 |
| Q216A | 0.83 |
| G121P | 0.83 |
| R44E | 0.82 |
| Q216C | 0.81 |
| R44Q | 0.80 |
| R44W | 0.79 |
| R44P | 0.78 |
| Q216G | 0.78 |
| R44R | 0.78 |
| E488A | 0.77 |
| E488L | 0.76 |
| G121D | 0.75 |
| Q216E | 0.75 |
| G121S | 0.74 |
| Q216S | 0.74 |
| G121N | 0.74 |
| G121Q | 0.72 |
| E488V | 0.72 |
| Q216M | 0.72 |
| Q216N | 0.71 |
| G121E | 0.71 |
| E488W | 0.70 |
| Q216D | 0.70 |
| Q216Q | 0.68 |
| E488F | 0.67 |
| E488C | 0.66 |
| E488E | 0.66 |
| E488G | 0.66 |
| E488D | 0.65 |
| E488T | 0.65 |
| E488H | 0.64 |
| E488Q | 0.61 |
| Q216P | 0.60 |
| Q216R | 0.60 |
| E488R | 0.54 |
| R44G | 0.53 |
| E488M | 0.52 |
| E488Y | 0.44 |
| E488S | 0.43 |
| E488K | 0.32 |
| E488N | 0.25 |
| E488P | 0.17 |

TABLE 5-continued

| Variant | GI |
|---|---|
| Growth Index Ranking for Plate 010. | |
| E179L | 1.46 |
| E179I | 1.40 |
| T251T | 1.36 |
| E179K | 1.35 |
| E179H | 1.33 |
| E179W | 1.26 |
| G177V | 1.26 |
| G177T | 1.25 |
| E179T | 1.23 |
| G177L | 1.22 |
| E179V | 1.22 |
| G177I | 1.18 |
| R246R | 1.17 |
| E179Y | 1.14 |
| G177H | 1.14 |
| G177K | 1.13 |
| R246K | 1.13 |
| E179F | 1.11 |
| G177P | 1.11 |
| T251N | 1.10 |
| T251Y | 1.09 |
| E179S | 1.07 |
| E179G | 1.05 |
| T251H | 1.04 |
| R246T | 1.04 |
| G177Y | 1.03 |
| R246H | 1.03 |
| G177A | 1.03 |
| T251K | 1.01 |
| G177M | 1.01 |
| E179M | 1.01 |
| G177W | 1.00 |
| T251S | 1.00 |
| E179A | 0.96 |
| T251R | 0.94 |
| E179R | 0.94 |
| E179C | 0.94 |
| R246G | 0.94 |
| G177G | 0.93 |
| G177N | 0.93 |
| T251G | 0.92 |
| G177S | 0.92 |
| T251Q | 0.91 |
| G177R | 0.90 |
| R246S | 0.90 |
| G177C | 0.88 |
| R246N | 0.87 |
| R246Q | 0.85 |
| E179D | 0.84 |
| E179P | 0.82 |
| G177F | 0.81 |
| R246E | 0.80 |
| E179N | 0.79 |
| T251E | 0.79 |
| R246D | 0.79 |
| G177D | 0.79 |
| T251D | 0.78 |
| T251C | 0.77 |
| T251M | 0.76 |
| R246A | 0.75 |
| E179Q | 0.74 |
| G177E | 0.74 |
| T251A | 0.74 |
| T251W | 0.73 |
| T251V | 0.71 |
| T251F | 0.71 |
| T251L | 0.69 |
| R246M | 0.65 |
| R246Y | 0.61 |
| R246C | 0.61 |
| R246L | 0.54 |
| R246V | 0.53 |
| R246W | 0.53 |
| T251I | 0.52 |
| G177Q | 0.44 |
| R246I | 0.40 |
| T251P | 0.37 |
| R246F | 0.30 |
| R246P | 0.01 |
| E179E | 0.00 |
| Growth Index Ranking for Plate 011. | |
| H254H | 1.32 |
| H254K | 1.20 |
| L308H | 1.19 |
| L308I | 1.18 |
| H254F | 1.17 |
| H254V | 1.16 |
| H254W | 1.15 |
| H254I | 1.12 |
| H254T | 1.11 |
| H254R | 1.07 |
| L308W | 1.07 |
| L308L | 1.05 |
| H254Y | 0.97 |
| L308R | 0.94 |
| V290I | 0.92 |
| L308Y | 0.92 |
| V290V | 0.89 |
| H254G | 0.89 |
| H254L | 0.88 |
| H254S | 0.87 |
| L308C | 0.85 |
| H254D | 0.85 |
| L308G | 0.84 |
| H254E | 0.81 |
| H254A | 0.80 |
| H254C | 0.78 |
| L308D | 0.76 |
| F287F | 0.74 |
| L308N | 0.71 |
| L308E | 0.71 |
| L308S | 0.69 |
| H254M | 0.68 |
| H254Q | 0.68 |
| L308Q | 0.65 |
| L308V | 0.59 |
| H254N | 0.59 |
| V290T | 0.59 |
| V290L | 0.48 |
| F287W | 0.42 |
| F287L | 0.39 |
| F287M | 0.26 |
| F287V | 0.21 |
| L308P | 0.20 |
| L308A | 0.19 |
| F287Y | 0.19 |
| V290C | 0.18 |
| L308T | 0.17 |
| V290A | 0.17 |
| V290S | 0.16 |
| V290G | 0.15 |
| L308K | 0.15 |
| F287A | 0.10 |
| F287H | 0.09 |
| F287K | 0.08 |
| L308F | 0.06 |
| V290H | 0.04 |
| F287T | 0.04 |
| V290K | 0.04 |
| F287Q | 0.03 |
| V290W | 0.03 |
| F287S | 0.02 |
| V290Y | 0.02 |
| L308M | 0.02 |
| F287G | 0.02 |
| F287I | 0.01 |
| F287N | 0.01 |
| F287R | 0.01 |
| V290R | 0.00 |
| H254P | ND |
| V290F | 0.00 |
| F287C | 0.00 |
| F287P | −0.01 |

TABLE 5-continued

| Variant | GI |
|---|---|
| V290M | −0.01 |
| V290Q | −0.02 |
| F287D | −0.02 |
| V290E | −0.02 |
| F287E | −0.02 |
| V290N | −0.03 |
| V290D | −0.03 |
| V290P | −0.03 |

Growth Index Ranking for Plate 012.

| Variant | GI |
|---|---|
| Q421R | 1.39 |
| Q421H | 1.26 |
| Q421E | 1.24 |
| T426I | 1.19 |
| Q421G | 1.16 |
| Q421V | 1.13 |
| Q421K | 1.12 |
| P430S | 1.10 |
| P430T | 1.10 |
| Q421I | 1.09 |
| Q421T | 1.08 |
| Q421Q | 1.08 |
| P430V | 1.06 |
| T426Y | 1.05 |
| Q421W | 1.05 |
| Q421L | 1.05 |
| Q421M | 0.92 |
| Q421A | 0.91 |
| Q421Y | 0.91 |
| T426S | 0.86 |
| T426G | 0.86 |
| Q421D | 0.86 |
| T426H | 0.86 |
| Q421S | 0.83 |
| T426F | 0.82 |
| T426L | 0.82 |
| P430A | 0.78 |
| Q421N | 0.77 |
| T426C | 0.76 |
| Q421P | 0.74 |
| T426W | 0.73 |
| P430C | 0.72 |
| T426A | 0.68 |
| T426M | 0.66 |
| T426D | 0.66 |
| T426N | 0.60 |
| T426A | 0.59 |
| T426E | 0.59 |
| F434I | 0.55 |
| F434L | 0.48 |
| T426Y | 0.48 |
| T426P | 0.46 |
| F434V | 0.46 |
| F434M | 0.45 |
| F434T | 0.44 |
| T426K | 0.40 |
| T426R | 0.38 |
| P430G | 0.30 |
| F434F | 0.24 |
| F434C | 0.23 |
| F434A | 0.17 |
| F434Y | 0.14 |
| F434S | 0.10 |
| F434H | 0.09 |
| F434K | 0.05 |
| F434N | 0.05 |
| T426T | 0.04 |
| F434Q | 0.04 |
| F434G | 0.03 |
| P430H | 0.02 |
| P430I | 0.02 |
| P430W | 0.02 |
| F434P | 0.01 |
| P430K | 0.01 |
| P430Q | 0.01 |
| Q421F | 0.01 |
| F434E | 0.01 |
| F434D | 0.01 |
| F434W | 0.01 |
| Q421C | 0.00 |
| P430R | 0.00 |
| F434R | 0.00 |
| P430M | 0.00 |
| P430D | 0.00 |
| P430E | 0.00 |
| P430F | 0.00 |
| P430P | 0.00 |
| P430L | 0.00 |
| P430Y | 0.00 |
| P430N | −0.01 |

Growth Index Ranking for Plate 013.

| Variant | GI |
|---|---|
| A445H | 1.18 |
| F403V | 1.06 |
| G397G | 1.05 |
| F403T | 1.03 |
| F403I | 0.93 |
| A445S | 0.92 |
| F403Y | 0.91 |
| F403L | 0.91 |
| A445K | 0.86 |
| F403S | 0.81 |
| F403H | 0.78 |
| F403F | 0.76 |
| A445Q | 0.74 |
| Q400Q | 0.74 |
| F403A | 0.72 |
| F403G | 0.71 |
| F403M | 0.70 |
| A445T | 0.70 |
| A445R | 0.68 |
| A445A | 0.68 |
| F403C | 0.67 |
| A445E | 0.67 |
| A445C | 0.65 |
| A445N | 0.64 |
| A445G | 0.62 |
| A445D | 0.62 |
| A445F | 0.61 |
| Q400L | 0.61 |
| A445M | 0.60 |
| F403N | 0.58 |
| A445L | 0.53 |
| A445Y | 0.53 |
| A445P | 0.52 |
| Q400H | 0.52 |
| A445Y | 0.51 |
| Q400T | 0.51 |
| Q400C | 0.46 |
| A445W | 0.44 |
| Q400N | 0.43 |
| Q400M | 0.43 |
| A445I | 0.42 |
| G397A | 0.40 |
| F403Q | 0.38 |
| Q400S | 0.27 |
| Q400V | 0.20 |
| F403E | 0.18 |
| G397V | 0.16 |
| G397I | 0.09 |
| Q400G | 0.09 |
| G397M | 0.08 |
| F403W | 0.05 |
| G397C | 0.05 |
| Q400E | 0.02 |
| Q400A | 0.01 |
| F403D | 0.01 |
| Q400P | 0.01 |
| Q400I | 0.00 |
| G397Q | 0.00 |
| G397R | 0.00 |
| G397P | 0.00 |
| G397S | 0.00 |
| G397Y | 0.00 |
| G397N | 0.00 |
| F403P | −0.01 |

TABLE 5-continued

| Variant | GI |
|---|---|
| F403K | −0.01 |
| G397L | −0.01 |
| Q400R | −0.01 |
| Q400F | −0.01 |
| Q400K | −0.02 |
| G397E | −0.02 |
| Q400D | −0.02 |
| G397F | −0.02 |
| G397H | −0.02 |
| F403R | −0.02 |
| Q400Y | −0.02 |
| G397D | −0.02 |
| Q400W | −0.03 |
| G397K | −0.03 |
| G397W | −0.03 |
| G397T | −0.03 |
| Growth Index Ranking for Plate 014. | |
| D33T | 1.49 |
| D33V | 1.46 |
| F53L | 1.44 |
| G99T | 1.43 |
| D33Y | 1.39 |
| K50K | 1.35 |
| F53T | 1.34 |
| K50I | 1.33 |
| K50L | 1.33 |
| G99V | 1.32 |
| D33W | 1.30 |
| F53W | 1.27 |
| G99I | 1.27 |
| F53V | 1.26 |
| F53I | 1.26 |
| D33H | 1.26 |
| G99K | 1.24 |
| F53Y | 1.24 |
| D33I | 1.23 |
| G99Y | 1.23 |
| G99L | 1.23 |
| D33S | 1.22 |
| K50W | 1.22 |
| D33K | 1.21 |
| D33R | 1.18 |
| K50H | 1.18 |
| K50Y | 1.17 |
| F53R | 1.17 |
| K50T | 1.14 |
| D33L | 1.13 |
| F53S | 1.12 |
| K50V | 1.11 |
| G99S | 1.11 |
| G99R | 1.09 |
| F53K | 1.08 |
| D33Q | 1.07 |
| D33F | 1.07 |
| F53F | 1.06 |
| F53H | 1.05 |
| F53G | 1.05 |
| G99W | 1.03 |
| G99F | 1.02 |
| D33G | 0.97 |
| F53Q | 0.96 |
| G99Q | 0.94 |
| K50S | 0.91 |
| F53E | 0.90 |
| F53P | 0.87 |
| D33E | 0.83 |
| K50E | 0.83 |
| D33P | 0.82 |
| D33D | 0.81 |
| G99P | 0.80 |
| G99E | 0.78 |
| K50G | 0.77 |
| K50Q | 0.74 |
| F53D | 0.71 |
| K50P | 0.70 |
| G99D | 0.70 |
| K50D | 0.68 |
| D33N | 0.64 |
| G99N | 0.57 |
| D33C | 0.50 |
| G99C | 0.46 |
| F53C | 0.44 |
| F53N | 0.43 |
| K50C | 0.43 |
| G99M | 0.43 |
| K50N | 0.35 |
| G99H | ND |
| K50A | 0.27 |
| G99A | 0.22 |
| F53A | 0.16 |
| K50M | 0.11 |
| D33A | 0.04 |
| K50R | ND |
| G99G | ND |
| K50F | ND |
| D33M | −0.03 |
| F53M | −0.07 |
| Growth Index Ranking for Plate 015. | |
| D23H | 1.04 |
| D23V | 0.96 |
| D23T | 0.94 |
| E26G | 0.93 |
| D81T | 0.93 |
| D23F | 0.92 |
| D23S | 0.91 |
| D23I | 0.89 |
| D23K | 0.88 |
| D23W | 0.88 |
| D23E | 0.86 |
| D81V | 0.85 |
| D81H | 0.85 |
| D81L | 0.84 |
| D81F | 0.83 |
| D23G | 0.82 |
| D23L | 0.82 |
| D23D | 0.82 |
| D23R | 0.81 |
| D81A | 0.81 |
| D23C | 0.81 |
| D81S | 0.80 |
| S27H | 0.80 |
| D81Y | 0.80 |
| D81G | 0.80 |
| S27L | 0.78 |
| D23P | 0.78 |
| D23M | 0.77 |
| D23N | 0.76 |
| D23Y | 0.75 |
| S27Q | 0.73 |
| D81C | 0.71 |
| D81M | 0.70 |
| D81N | 0.69 |
| D81I | 0.69 |
| E26H | 0.68 |
| S27K | 0.67 |
| S27I | 0.67 |
| D23Q | 0.66 |
| E26I | 0.65 |
| E26V | 0.65 |
| E26K | 0.64 |
| S27T | 0.64 |
| D81Q | 0.63 |
| S27M | 0.63 |
| D81W | 0.62 |
| D81R | 0.62 |
| D81K | 0.61 |
| S27G | 0.59 |
| S27C | 0.59 |
| S27V | 0.58 |
| E26L | 0.58 |
| E26T | 0.55 |
| E26Q | 0.55 |
| E26E | 0.54 |
| S27N | 0.54 |

TABLE 5-continued

| Variant | GI |
|---|---|
| S27S | 0.54 |
| S27R | 0.54 |
| D23A | 0.53 |
| E26S | 0.52 |
| S27E | 0.51 |
| D81E | 0.51 |
| S27A | 0.49 |
| E26N | 0.49 |
| E26P | 0.49 |
| E26D | 0.47 |
| E26M | 0.46 |
| S27F | 0.46 |
| E26R | 0.46 |
| E26C | 0.45 |
| S27D | 0.44 |
| D81P | 0.42 |
| S27P | 0.41 |
| S27Y | 0.38 |
| E26W | 0.34 |
| E26F | 0.33 |
| S27W | 0.30 |
| E26Y | 0.29 |
| E26A | 0.24 |
| D81D | 0.01 |
| Growth Index Ranking for Plate 016. | |
| G69S | 1.21 |
| G69M | 1.16 |
| L20M | 1.14 |
| G69G | 1.13 |
| G69K | 1.12 |
| G69T | 1.11 |
| G69I | 1.10 |
| G69L | 1.10 |
| Y16M | 1.09 |
| Y16I | 1.09 |
| L20V | 1.08 |
| G69V | 1.08 |
| L20S | 1.08 |
| G69H | 1.08 |
| G69R | 1.06 |
| G69Q | 1.05 |
| Y16L | 1.05 |
| G69N | 1.04 |
| Y18G | 1.03 |
| L20Y | 1.03 |
| G69A | 1.03 |
| L20L | 1.03 |
| Y16Y | 1.01 |
| L20T | 1.01 |
| Y18C | 1.00 |
| L20W | 1.00 |
| G69E | 1.00 |
| G69C | 0.99 |
| Y18H | 0.97 |
| L20F | 0.97 |
| L20I | 0.96 |
| G69F | 0.96 |
| Y18N | 0.96 |
| Y18Y | 0.95 |
| L20A | 0.95 |
| G69Y | 0.94 |
| G69W | 0.92 |
| Y18I | 0.91 |
| Y18W | 0.91 |
| Y16V | 0.91 |
| Y16H | 0.86 |
| Y16F | 0.85 |
| G69D | 0.84 |
| Y18R | 0.83 |
| Y18F | 0.82 |
| Y18T | 0.80 |
| Y18V | 0.78 |
| Y16T | 0.77 |
| L20H | 0.77 |
| Y18M | 0.76 |
| L20N | 0.76 |
| Y18L | 0.75 |
| L20G | 0.75 |
| L20Q | 0.75 |
| Y18Q | 0.74 |
| L20C | 0.74 |
| Y16W | 0.73 |
| Y18S | 0.72 |
| G69P | 0.72 |
| Y18D | 0.67 |
| L20E | 0.66 |
| Y18K | 0.65 |
| Y18E | 0.61 |
| Y16E | 0.53 |
| L20R | 0.53 |
| Y16C | 0.50 |
| Y18P | 0.49 |
| Y16Q | 0.48 |
| Y16P | 0.48 |
| Y18A | 0.45 |
| L20D | 0.45 |
| Y16S | 0.44 |
| Y16N | 0.41 |
| Y16D | 0.40 |
| Y16K | 0.39 |
| L20K | 0.36 |
| L20P | 0.36 |
| Y16G | 0.36 |
| Y16A | 0.34 |
| Y16R | 0.21 |
| Growth Index Ranking for Plate 017. | |
| A3T | 1.39 |
| A3H | 1.21 |
| A3K | 1.13 |
| A3F | 1.10 |
| A3Y | 1.09 |
| A3I | 1.05 |
| S13L | 1.04 |
| A3R | 1.04 |
| A3Q | 0.97 |
| A3E | 0.94 |
| S13T | 0.90 |
| A3N | 0.89 |
| S13H | 0.87 |
| S13K | 0.85 |
| Y9F | 0.84 |
| N12S | 0.83 |
| A3L | 0.83 |
| S13I | 0.82 |
| S13V | 0.81 |
| A3D | 0.79 |
| N12T | 0.79 |
| A3G | 0.78 |
| S13R | 0.76 |
| S13G | 0.76 |
| A3P | 0.76 |
| N12C | 0.73 |
| A3A | 0.73 |
| S13Y | 0.72 |
| N12A | 0.72 |
| A3W | 0.70 |
| S13M | 0.69 |
| S13S | 0.68 |
| A3C | 0.68 |
| N12N | 0.68 |
| S13N | 0.67 |
| S13F | 0.67 |
| S13W | 0.64 |
| S13Q | 0.62 |
| N12M | 0.61 |
| N12V | 0.59 |
| S13A | 0.57 |
| Y9W | 0.56 |
| S13C | 0.56 |
| A3S | 0.51 |
| S13E | 0.50 |
| N12H | 0.48 |
| N12I | 0.44 |
| N12P | 0.43 |

TABLE 5-continued

| Variant | GI |
|---|---|
| N12R | 0.41 |
| N12Q | 0.38 |
| S13D | 0.35 |
| N12G | 0.33 |
| Y9H | 0.31 |
| N12K | 0.29 |
| N12D | 0.27 |
| N12L | 0.25 |
| N12F | 0.25 |
| Y9I | 0.22 |
| Y9V | 0.20 |
| S13P | 0.18 |
| A3M | 0.16 |
| Y9T | 0.15 |
| N12E | 0.15 |
| A3V | 0.14 |
| N12W | 0.14 |
| Y9R | 0.11 |
| Y9P | 0.10 |
| Y9L | 0.09 |
| Y9A | 0.09 |
| Y9S | 0.08 |
| Y9C | 0.05 |
| Y9N | 0.04 |
| Y9Y | 0.04 |
| Y9K | 0.03 |
| Y9Q | 0.03 |
| Y9M | 0.02 |
| Y9G | 0.01 |
| Y9D | −0.01 |
| Y9E | −0.01 |
| N12Y | −0.01 |
| Growth Index Ranking for Plate 018. | |
| A139T | 1.29 |
| Q197T | 1.19 |
| G127T | 1.19 |
| R194H | 1.16 |
| Q197V | 1.15 |
| G127H | 1.13 |
| G127F | 1.08 |
| A139P | 1.07 |
| A139H | 1.07 |
| A139S | 1.07 |
| A139V | 1.07 |
| G127V | 1.05 |
| Q197H | 1.04 |
| A139I | 1.04 |
| Q197I | 1.04 |
| A139C | 1.03 |
| G127I | 1.03 |
| G127L | 1.03 |
| Q197M | 1.01 |
| G127Y | 1.01 |
| Q197F | 0.99 |
| A139Q | 0.98 |
| A139G | 0.97 |
| Q197Y | 0.97 |
| Q197S | 0.97 |
| G127S | 0.96 |
| Q197E | 0.95 |
| A139E | 0.95 |
| R194R | 0.93 |
| R194Y | 0.92 |
| Q197L | 0.91 |
| Q197N | 0.90 |
| Q197K | 0.90 |
| Q197D | 0.89 |
| A139L | 0.88 |
| G127E | 0.88 |
| A139D | 0.87 |
| G127P | 0.87 |
| G127C | 0.87 |
| R194L | 0.87 |
| Q197C | 0.87 |
| G127W | 0.86 |
| Q197R | 0.86 |
| G127D | 0.85 |
| A139M | 0.84 |
| R194W | 0.84 |
| Q197G | 0.83 |
| Q197A | 0.83 |
| A139A | 0.83 |
| A139N | 0.83 |
| Q197W | 0.83 |
| R194F | 0.82 |
| Q197P | 0.82 |
| A139F | 0.82 |
| R194K | 0.81 |
| G127M | 0.80 |
| A139W | 0.80 |
| Q197Q | 0.75 |
| G127N | 0.74 |
| R194C | 0.72 |
| G127Q | 0.71 |
| G127A | 0.70 |
| R194M | 0.68 |
| R194I | 0.65 |
| R194Q | 0.61 |
| G127R | 0.59 |
| G127K | 0.58 |
| A139Y | 0.56 |
| R194V | 0.43 |
| A139R | 0.30 |
| A139K | 0.30 |
| R194A | 0.27 |
| R194N | 0.18 |
| R194T | 0.15 |
| R194S | 0.08 |
| R194E | 0.03 |
| R194D | 0.02 |
| G127G | 0.00 |
| R194P | −0.01 |
| R194G | −0.03 |
| Growth Index Ranking for Plate 019. | |
| L59H | 1.96 |
| L59K | 1.49 |
| Q116V | 1.47 |
| L59I | 1.46 |
| E117I | 1.42 |
| L59R | 1.41 |
| Q116W | 1.36 |
| Q116T | 1.36 |
| Q116Y | 1.32 |
| E117L | 1.29 |
| L59G | 1.28 |
| E117W | 1.27 |
| L59F | 1.26 |
| L59A | 1.25 |
| Q116I | 1.22 |
| L59M | 1.22 |
| E117F | 1.21 |
| L59C | 1.21 |
| Q116F | 1.20 |
| L59E | 1.19 |
| L59T | 1.18 |
| L59D | 1.12 |
| Q116L | 1.12 |
| Q116K | 1.09 |
| L59L | 1.09 |
| E117H | 1.08 |
| Q125M | 1.06 |
| L59W | 1.06 |
| Q125I | 1.05 |
| L59N | 1.05 |
| Q125W | 1.05 |
| L59V | 1.05 |
| L59Q | 1.04 |
| Q125H | 1.02 |
| Q116S | 1.02 |
| Q125Y | 1.01 |
| Q125T | 1.01 |
| Q116A | 1.01 |
| E117M | 1.00 |
| Q116C | 0.99 |

TABLE 5-continued

| Variant | GI |
|---|---|
| Q125P | 0.99 |
| E117V | 0.99 |
| L59Y | 0.97 |
| Q125N | 0.97 |
| Q116D | 0.97 |
| Q125V | 0.96 |
| E117A | 0.95 |
| E117Y | 0.94 |
| Q125A | 0.93 |
| Q125L | 0.93 |
| Q116E | 0.92 |
| Q116H | 0.92 |
| Q125F | 0.92 |
| Q116P | 0.91 |
| Q116R | 0.91 |
| E117C | 0.90 |
| Q125C | 0.90 |
| Q125R | 0.89 |
| Q125K | 0.89 |
| Q116G | 0.86 |
| E117T | 0.86 |
| Q125S | 0.85 |
| Q125D | 0.83 |
| E117N | 0.82 |
| Q125G | 0.82 |
| Q116Q | 0.81 |
| Q116N | 0.80 |
| E117R | 0.80 |
| E117S | 0.80 |
| Q116M | 0.76 |
| L59S | 0.74 |
| Q125E | 0.73 |
| E117G | 0.70 |
| E117D | 0.70 |
| Q125Q | 0.69 |
| E117Q | 0.66 |
| E117K | 0.55 |
| E117P | 0.44 |
| E117E | 0.26 |
| L59P | 0.03 |
| Growth Index Ranking for Plate 020. | |
| Y377W | 1.26 |
| G389K | 1.24 |
| L376L | 1.24 |
| Y377Y | 1.23 |
| L376I | 1.20 |
| G389T | 1.18 |
| Y377V | 1.17 |
| G389L | 1.16 |
| G389H | 1.13 |
| G389V | 1.12 |
| K379R | 1.12 |
| Y377H | 1.12 |
| Y377L | 1.10 |
| K379V | 1.10 |
| L376Y | 1.09 |
| K379T | 1.09 |
| G389R | 1.06 |
| K379H | 1.04 |
| G389I | 1.03 |
| Y377I | 1.03 |
| G389Y | 1.01 |
| G389M | 1.01 |
| G389S | 1.01 |
| Y377T | 0.98 |
| G389N | 0.96 |
| Y377F | 0.95 |
| K379L | 0.95 |
| G389G | 0.94 |
| K379G | 0.93 |
| L376F | 0.92 |
| K379W | 0.92 |
| G389F | 0.88 |
| K379S | 0.88 |
| G389W | 0.87 |
| K379I | 0.86 |
| K379A | 0.86 |
| K379P | 0.83 |
| G389C | 0.83 |
| G389P | 0.82 |
| K379Q | 0.81 |
| G389Q | 0.80 |
| K379N | 0.79 |
| K379C | 0.78 |
| K379M | 0.77 |
| K379E | 0.77 |
| Y377S | 0.77 |
| G389E | 0.77 |
| G389A | 0.75 |
| G389D | 0.73 |
| K379D | 0.70 |
| Y377G | 0.69 |
| K379F | 0.69 |
| L376M | 0.65 |
| Y377P | 0.61 |
| Y377K | 0.60 |
| L376V | 0.60 |
| Y377M | 0.59 |
| Y377D | 0.58 |
| L376W | 0.57 |
| Y377N | 0.57 |
| Y377E | 0.56 |
| Y377C | 0.55 |
| Y377A | 0.54 |
| Y377Q | 0.49 |
| L376H | 0.49 |
| L376T | 0.48 |
| L376Q | 0.48 |
| L376C | 0.43 |
| L376A | 0.23 |
| Y377R | 0.23 |
| L376K | 0.22 |
| L376S | 0.17 |
| L376N | 0.16 |
| L376G | 0.14 |
| L376R | 0.12 |
| L376P | 0.11 |
| L376D | 0.08 |
| L376E | 0.08 |
| K379Y | 0.00 |
| K379K | −0.01 |
| Growth Index Ranking for Plate 021. | |
| I165Y | 1.46 |
| E173H | 1.25 |
| V202H | 1.24 |
| I165H | 1.24 |
| E173W | 1.23 |
| E174I | 1.23 |
| E173T | 1.23 |
| E173V | 1.20 |
| E174H | 1.20 |
| E173L | 1.19 |
| E173I | 1.19 |
| V202T | 1.18 |
| E173Y | 1.18 |
| V202R | 1.16 |
| E174L | 1.16 |
| I165K | 1.16 |
| E174V | 1.15 |
| V202I | 1.15 |
| E174T | 1.14 |
| I165T | 1.14 |
| E173F | 1.14 |
| E174K | 1.13 |
| E173K | 1.12 |
| I165F | 1.11 |
| E174F | 1.11 |
| V202K | 1.09 |
| E173R | 1.08 |
| E173G | 1.08 |
| E174R | 1.07 |
| E174W | 1.05 |
| I165R | 1.05 |
| I165I | 1.04 |

TABLE 5-continued

| Variant | GI |
|---|---|
| I165D | 1.03 |
| I165A | 1.02 |
| V202F | 1.02 |
| V202Y | 1.02 |
| E173M | 1.01 |
| E173S | 1.01 |
| I165L | 1.00 |
| E174Y | 1.00 |
| I165G | 0.99 |
| V202W | 0.98 |
| I165W | 0.98 |
| I165S | 0.95 |
| I165N | 0.95 |
| E174M | 0.94 |
| E174A | 0.94 |
| E173A | 0.94 |
| V202C | 0.93 |
| V202L | 0.93 |
| V202M | 0.93 |
| V202A | 0.92 |
| I165M | 0.91 |
| E173Q | 0.90 |
| I165Q | 0.90 |
| V202Q | 0.90 |
| E174G | 0.90 |
| E173N | 0.88 |
| V202N | 0.88 |
| E174S | 0.87 |
| E174N | 0.86 |
| E173P | 0.86 |
| V202S | 0.85 |
| V202E | 0.85 |
| V202D | 0.84 |
| E173C | 0.83 |
| E174C | 0.83 |
| I165E | 0.83 |
| E173E | 0.81 |
| V202G | 0.81 |
| I165C | 0.79 |
| E174Q | 0.72 |
| E174D | 0.70 |
| E174E | 0.69 |
| E174P | 0.68 |
| I165P | 0.67 |
| E173D | 0.65 |
| I165V | 0.61 |
| V202P | 0.35 |
| V202V | 0.32 |

Growth Index Ranking for Plate 022.

| Variant | GI |
|---|---|
| K489K | 1.65 |
| G491I | 1.57 |
| L490I | 1.52 |
| L490H | 1.46 |
| G491H | 1.41 |
| L490V | 1.41 |
| I539V | 1.40 |
| G491V | 1.36 |
| G491L | 1.36 |
| K489W | 1.35 |
| L490W | 1.34 |
| G491W | 1.33 |
| G491T | 1.33 |
| G491Y | 1.31 |
| G491K | 1.29 |
| I539T | 1.26 |
| L490L | 1.25 |
| K489R | 1.24 |
| L490T | 1.21 |
| K489I | 1.21 |
| I539L | 1.21 |
| K489T | 1.20 |
| I539I | 1.17 |
| G491R | 1.16 |
| G491M | 1.14 |
| K489Y | 1.14 |
| L490F | 1.14 |
| G491F | 1.13 |
| K489H | 1.08 |
| G491A | 1.08 |
| G491C | 1.05 |
| K489L | 1.05 |
| L490M | 1.04 |
| G491S | 1.03 |
| I539K | 1.00 |
| G491N | 1.00 |
| L490S | 0.98 |
| G491D | 0.96 |
| I539M | 0.96 |
| L490N | 0.95 |
| K489A | 0.94 |
| L490K | 0.94 |
| G491E | 0.94 |
| G491Q | 0.93 |
| K489F | 0.93 |
| G491G | 0.91 |
| L490R | 0.90 |
| L490A | 0.90 |
| I539S | 0.90 |
| I539H | 0.89 |
| I539C | 0.88 |
| L490C | 0.88 |
| K489S | 0.88 |
| L490G | 0.86 |
| K489G | 0.84 |
| K489Y | 0.83 |
| L490D | 0.78 |
| I539A | 0.77 |
| L490E | 0.75 |
| K489C | 0.68 |
| I539Y | 0.67 |
| K489Q | 0.66 |
| I539F | 0.65 |
| I539R | 0.64 |
| I539W | 0.64 |
| I539Q | 0.64 |
| L490Q | 0.62 |
| K489D | 0.62 |
| K489N | 0.61 |
| K489E | 0.58 |
| I539P | 0.53 |
| K489P | 0.50 |
| I539E | 0.36 |
| I539N | 0.32 |
| I539G | 0.28 |
| K489M | 0.23 |
| G491P | 0.21 |
| L490P | 0.17 |
| I539D | −0.01 |
| L490Y | −0.01 |

Growth Index Ranking for Plate 023.

| Variant | GI |
|---|---|
| Q509T | 1.49 |
| K487T | 1.39 |
| Q509V | 1.34 |
| Q509I | 1.30 |
| K487H | 1.19 |
| K487K | 1.18 |
| K487V | 1.12 |
| K487L | 1.11 |
| Y514Y | 1.08 |
| K487C | 1.06 |
| K487W | 1.05 |
| Q509S | 1.03 |
| K487R | 1.03 |
| K487F | 1.03 |
| K487A | 0.99 |
| K487G | 0.97 |
| K487S | 0.93 |
| Q509G | 0.91 |
| Q509Q | 0.90 |
| K487E | 0.90 |
| Q509C | 0.90 |
| K487I | 0.90 |
| K487M | 0.87 |
| Q509A | 0.86 |

TABLE 5-continued

| Variant | GI |
|---|---|
| K487A | 0.81 |
| Q509M | 0.80 |
| T521G | 0.77 |
| T521E | 0.77 |
| Q509N | 0.74 |
| T521S | 0.73 |
| K487D | 0.69 |
| K487Y | 0.61 |
| T521L | 0.60 |
| Q509H | 0.53 |
| T521Q | 0.51 |
| K487N | 0.44 |
| Q509E | 0.40 |
| T521V | 0.36 |
| Q509D | 0.28 |
| Q509K | 0.26 |
| Q509L | 0.16 |
| K487P | 0.15 |
| T521M | 0.13 |
| T521H | 0.02 |
| Y514H | 0.01 |
| Y514T | 0.01 |
| Q509F | 0.01 |
| Y514V | 0.00 |
| T521T | 0.00 |
| Q509Y | 0.00 |
| T521A | −0.01 |
| Y514I | −0.01 |
| Y514W | −0.01 |
| T521N | −0.01 |
| Q509R | −0.01 |
| Y514D | −0.02 |
| Y514S | −0.02 |
| T521F | −0.02 |
| T521C | −0.02 |
| Q509P | −0.02 |
| T521Y | −0.02 |
| Y514P | −0.02 |
| T521K | −0.02 |
| Y514R | −0.02 |
| Y514A | −0.02 |
| Y514L | −0.02 |
| Y514N | −0.03 |
| T521I | −0.03 |
| T521R | −0.03 |
| Q509W | −0.03 |
| Y514Q | −0.03 |
| T521P | −0.03 |
| Y514E | −0.03 |
| Y514K | −0.03 |
| Y514C | −0.03 |
| T521W | −0.03 |
| T521D | −0.03 |
| Y514F | −0.04 |
| Y514G | −0.04 |
| Y514M | −0.04 |

Growth Index Ranking for Plate 024.

| Variant | GI |
|---|---|
| L540V | 1.73 |
| L540T | 1.58 |
| T462T | 1.43 |
| A448T | 1.35 |
| L540H | 1.34 |
| R544T | 1.33 |
| T462V | 1.31 |
| L540I | 1.31 |
| R544W | 1.28 |
| L540K | 1.28 |
| A448H | 1.26 |
| T462K | 1.26 |
| T462H | 1.26 |
| R544V | 1.26 |
| R544S | 1.23 |
| A448Y | 1.23 |
| L540Y | 1.20 |
| R544K | 1.19 |
| T462I | 1.18 |
| L540W | 1.18 |
| A448R | 1.15 |
| T462W | 1.14 |
| T462Y | 1.14 |
| L540R | 1.14 |
| L540S | 1.12 |
| L540L | 1.12 |
| R544H | 1.11 |
| A448S | 1.11 |
| L540Q | 1.09 |
| L540M | 1.09 |
| T462F | 1.08 |
| T462S | 1.06 |
| L540G | 1.05 |
| R544I | 1.05 |
| R544C | 1.04 |
| T462L | 1.04 |
| L540F | 1.03 |
| R544L | 1.02 |
| T462G | 1.02 |
| A448I | 1.01 |
| L540E | 1.01 |
| L540A | 1.00 |
| R544M | 0.98 |
| L540N | 0.98 |
| L540P | 0.96 |
| R544F | 0.95 |
| R544P | 0.95 |
| T462R | 0.94 |
| L540D | 0.93 |
| T462A | 0.93 |
| R544G | 0.91 |
| L540C | 0.90 |
| T462M | 0.89 |
| A448K | 0.89 |
| R544N | 0.89 |
| A448Y | 0.88 |
| A448G | 0.87 |
| R544R | 0.86 |
| R544Q | 0.86 |
| A448L | 0.85 |
| T462C | 0.84 |
| R544E | 0.84 |
| T462D | 0.84 |
| R544A | 0.83 |
| R544D | 0.83 |
| T462Q | 0.83 |
| A448C | 0.83 |
| A448Q | 0.82 |
| T462N | 0.81 |
| A448N | 0.79 |
| A448M | 0.78 |
| A448F | 0.78 |
| A448A | 0.77 |
| A448D | 0.74 |
| A448W | 0.72 |
| A448E | 0.72 |
| A448P | 0.70 |
| T462P | 0.60 |
| R544Y | 0.50 |
| T462E | −0.08 |

Growth Index Ranking for Plate 025.

| Variant | GI |
|---|---|
| P498H | 1.26 |
| S457S | 1.23 |
| A496H | 1.20 |
| A496T | 1.17 |
| S457H | 1.16 |
| P498T | 1.16 |
| A496I | 1.14 |
| K497T | 1.13 |
| K497V | 1.12 |
| P498R | 1.12 |
| K497K | 1.12 |
| P498I | 1.11 |
| P498K | 1.11 |
| P498V | 1.10 |
| S457R | 1.10 |
| P498Y | 1.10 |

TABLE 5-continued

| Variant | GI |
|---|---|
| P498L | 1.09 |
| S457T | 1.09 |
| A496L | 1.06 |
| A496R | 1.06 |
| S457Q | 1.06 |
| A496V | 1.04 |
| K497H | 1.04 |
| P498S | 1.03 |
| A496K | 1.03 |
| K497L | 1.03 |
| K497I | 1.02 |
| P498F | 1.02 |
| A496Y | 1.01 |
| P498G | 1.01 |
| K497Y | 0.99 |
| S457Y | 0.99 |
| A496W | 0.98 |
| A496F | 0.97 |
| K497G | 0.96 |
| K497F | 0.94 |
| A496S | 0.93 |
| K497S | 0.92 |
| P498W | 0.90 |
| P498P | 0.88 |
| P498M | 0.86 |
| P498D | 0.86 |
| P498E | 0.86 |
| K497R | 0.85 |
| K497A | 0.84 |
| A496M | 0.84 |
| S457K | 0.84 |
| K497W | 0.82 |
| A496G | 0.82 |
| A496P | 0.82 |
| S457N | 0.82 |
| K497D | 0.81 |
| P498Q | 0.81 |
| S457F | 0.80 |
| P498N | 0.80 |
| A496E | 0.80 |
| A496A | 0.76 |
| A496Q | 0.76 |
| S457M | 0.76 |
| S457D | 0.75 |
| K497Q | 0.75 |
| P498C | 0.75 |
| A496D | 0.74 |
| S457W | 0.74 |
| S457E | 0.74 |
| K497M | 0.74 |
| K497N | 0.73 |
| K497E | 0.72 |
| A496C | 0.70 |
| K497P | 0.69 |
| A496N | 0.66 |
| S457G | 0.65 |
| P498A | 0.64 |
| K497C | 0.64 |
| S457L | 0.62 |
| S457V | 0.59 |
| S457C | 0.47 |
| S457I | 0.43 |
| S457A | 0.33 |
| S457P | 0.14 |
| Growth Index Ranking for Plate 026. | |
| G87K | 1.34 |
| S120L | 1.34 |
| G87T | 1.24 |
| G87L | 1.24 |
| S120I | 1.20 |
| S120K | 1.18 |
| G87V | 1.17 |
| G87Y | 1.17 |
| S120T | 1.16 |
| T240T | 1.15 |
| S120W | 1.14 |
| G87H | 1.12 |
| G87W | 1.11 |
| D25H | 1.11 |
| G87I | 1.10 |
| D25L | 1.10 |
| D25I | 1.09 |
| S120H | 1.08 |
| S120Y | 1.07 |
| D25T | 1.06 |
| S120V | 1.05 |
| G87M | 1.04 |
| G87R | 1.03 |
| D25V | 1.02 |
| S120F | 1.01 |
| D25K | 1.00 |
| D25Y | 1.00 |
| T240L | 0.99 |
| G87F | 0.99 |
| G87P | 0.98 |
| D25P | 0.97 |
| S120M | 0.96 |
| G87S | 0.96 |
| T240I | 0.96 |
| T240V | 0.95 |
| G87D | 0.94 |
| D25N | 0.93 |
| D25D | 0.93 |
| D25M | 0.90 |
| D25A | 0.89 |
| G87C | 0.89 |
| S120C | 0.88 |
| S120E | 0.88 |
| G87A | 0.88 |
| D25G | 0.88 |
| S120D | 0.88 |
| D25F | 0.88 |
| S120G | 0.87 |
| D25W | 0.86 |
| S120R | 0.84 |
| S120A | 0.82 |
| D25E | 0.82 |
| G87E | 0.81 |
| T240M | 0.81 |
| G87N | 0.80 |
| D25S | 0.80 |
| S120N | 0.80 |
| D25R | 0.77 |
| T240A | 0.76 |
| G87Q | 0.75 |
| S120Q | 0.74 |
| D25Q | 0.73 |
| S120S | 0.69 |
| T240N | 0.69 |
| T240C | 0.67 |
| T240Q | 0.67 |
| D25C | 0.66 |
| S120P | 0.60 |
| T240S | 0.56 |
| T240G | 0.35 |
| T240H | 0.15 |
| T240Y | 0.09 |
| T240E | 0.08 |
| T240W | 0.08 |
| T240F | 0.05 |
| T240D | 0.03 |
| T240K | 0.02 |
| T240P | 0.01 |
| T240R | 0.01 |
| G87G | −0.01 |
| Growth Index Ranking for Plate 027. | |
| F495L | 1.84 |
| F495T | 1.56 |
| S493T | 1.53 |
| G492A | 1.48 |
| F495Y | 1.45 |
| F495K | 1.45 |
| F495W | 1.44 |
| S493V | 1.40 |

TABLE 5-continued

| Variant | GI |
| --- | --- |
| F495S | 1.40 |
| G492T | 1.38 |
| F495V | 1.38 |
| G492H | 1.38 |
| G492V | 1.37 |
| S493R | 1.35 |
| F495H | 1.31 |
| G492K | 1.30 |
| S493W | 1.29 |
| F495R | 1.28 |
| S493E | 1.27 |
| G492I | 1.26 |
| S493L | 1.26 |
| F495M | 1.25 |
| G492E | 1.25 |
| G492D | 1.24 |
| N476Y | 1.24 |
| S493K | 1.23 |
| S493G | 1.21 |
| S493I | 1.20 |
| S493S | 1.20 |
| G492L | 1.18 |
| G492W | 1.18 |
| F495Q | 1.16 |
| F495I | 1.15 |
| N476W | 1.15 |
| N476V | 1.14 |
| N476R | 1.13 |
| G492G | 1.11 |
| G492C | 1.11 |
| N476T | 1.09 |
| S493M | 1.09 |
| S493Y | 1.08 |
| F495F | 1.07 |
| G492Y | 1.07 |
| G492R | 1.06 |
| S493C | 1.04 |
| S493A | 1.03 |
| F495G | 1.02 |
| F495A | 1.02 |
| G492N | 0.99 |
| F495N | 0.98 |
| F495D | 0.96 |
| S493H | 0.95 |
| F495C | 0.95 |
| F495P | 0.95 |
| G492F | 0.94 |
| F495E | 0.94 |
| G492Q | 0.93 |
| S493P | 0.93 |
| G492M | 0.89 |
| G492P | 0.89 |
| G492S | 0.86 |
| N476Q | 0.83 |
| S493Q | 0.83 |
| N476S | 0.82 |
| S493F | 0.81 |
| S493N | 0.79 |
| N476D | 0.73 |
| N476M | 0.71 |
| N476P | 0.64 |
| N476E | 0.62 |
| N476A | 0.02 |
| N476N | 0.01 |
| S493D | 0.00 |
| N476I | −0.01 |
| N476H | −0.01 |
| N476G | −0.02 |
| N476F | −0.04 |
| N476C | −0.04 |
| N476K | −0.05 |
| N476L | −0.08 |

Results/Discussion

Table 6 lists all variants identified that displayed growth indices of 1.2 or higher. Without being bound by theory, mutations at these positions may result in increased intracellular activity of IspS by several different means. Without being bound by theory, increased intracellular activity could be a result of one or a combination of any of the following properties of IspS: increased cellular viability, increased kcat, decreased Km, increased specific activity, increased solubility, decreased insolubility, improved ribosome binding, increased translation initiation rate, increased translation elongation rate, increased transcription initiation rate, increased transcription elongation rate, decreased secondary structure of DNA, decreased secondary structure of RNA, increased secondary structure of DNA, increased secondary structure of RNA, increased folding rates, increased affinity for intracellular chaperones, increased stability, decreased protein turnover, decreased exposure to intracellular protease, decreased affinity for intracellular protease, decreased localization to the periplasm, improved localization to the cytoplasm, decreased inclusion body formation, decreased membrane localization, increased expression due to a more favorable codon, increased DNA stability, increased RNA stability, and decreased RNA degradation.

Without being bound by theory, any mutation that has a positive effect on the properties of nucleic acid sequences (DNA and RNA) encoding or expressing IspS, or the biochemical properties of the IspS enzyme itself, could allow for greater activity within the cell. All variants with a growth index of 1.2 or higher are subjected to secondary growth assays in a matrix of mevalonic acid and IPTG. These variants are also pooled together and subjected to several rounds of enrichment under IPTG induction and mevalonic acid pathway flux to determine which enzymes allow for the best growth in competition experiments. The most promising variants are examined further for benefits to specific productivity in isoprene producing strains.

Some variants of interest include, but are not limited to, A3T, S13L, I165Y, Q421R, F495L, Q509T, and L540V. All of these variants displayed growth advantages over wild type in secondary assays utilizing IPTG/mevalonic acid matrices. The A3T variant is of particular interest because threonine in this position is found in homologous isoprene synthase enzymes from the related species *P. nigra*, *P. tremuloides* and *P. trichocharpa*. Alteration to a consensus sequence for IspS from Poplar species could allow for a more active enzyme.

Figure 5:
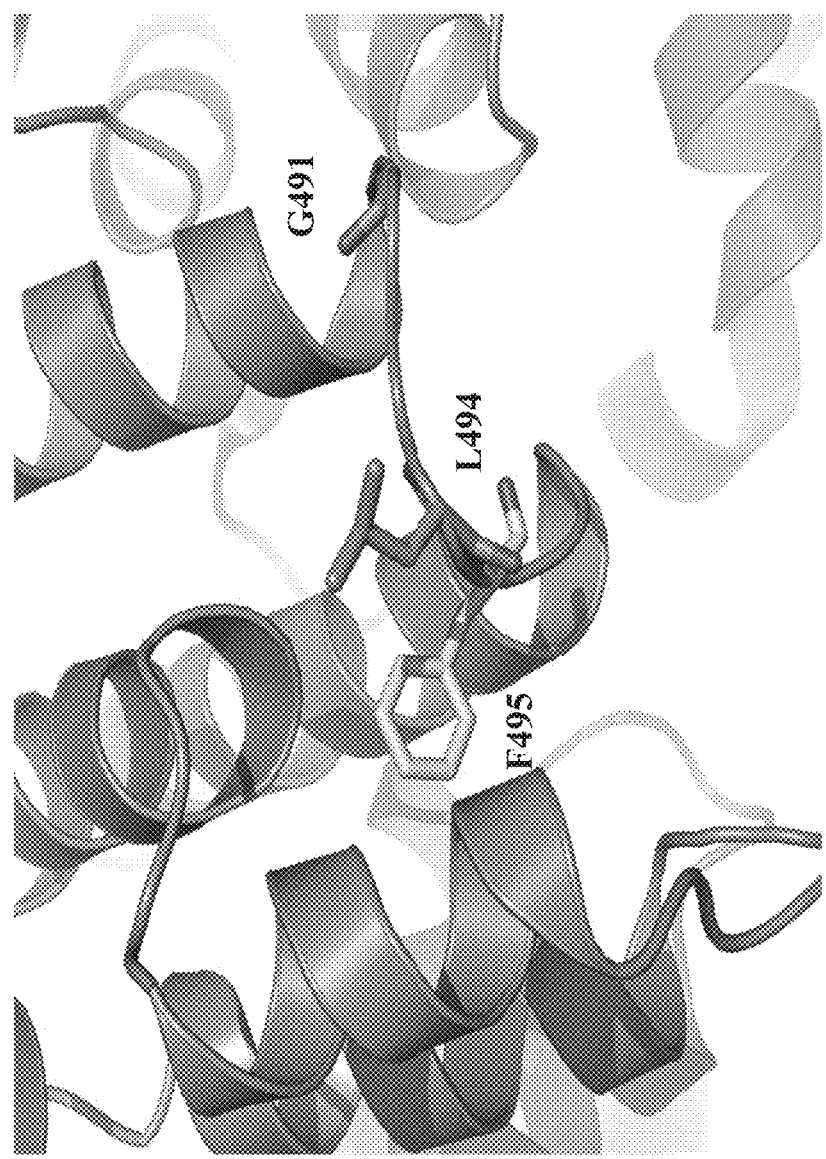
FIG. 5 shows a view of Wild Type IspS showing the location of Phe495 with respect to Gly491 and Leu494, all in stick representation.
Figure 6:
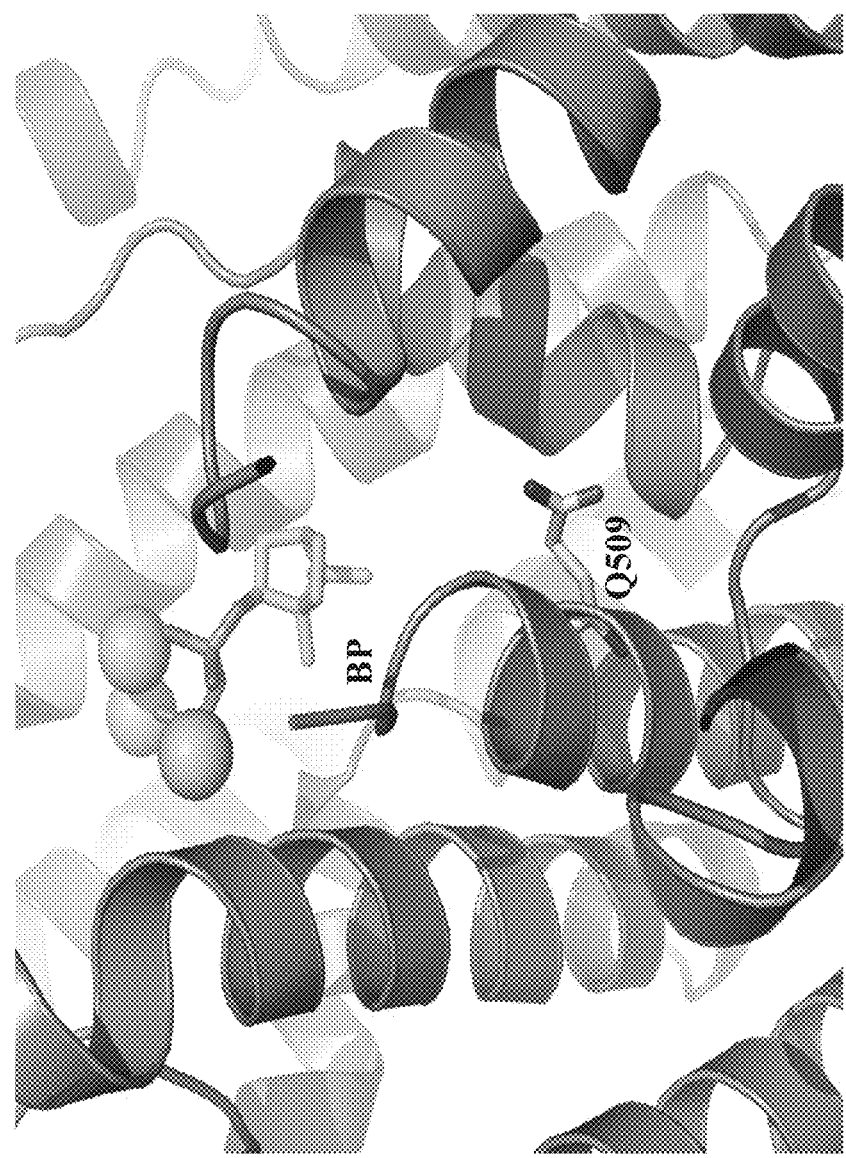
FIG. 6 shows a view of Wild Type IspS showing the location of Gln509, in stick representation, with respect to the active site. The magnesium ions and (+)-bornyl diphosphate in the active site are modeled based on a structural alignment with PDB 1N24.

The F495L variant is of particular interest because of its location in an exposed surface loop that spans residues K487 to K497. FIG. 5 shows that this variant is proximal to both G491S and L494P, which display positive effects on cell viability in vivo, and specific activity of IspS in vitro, respectively. Additionally, there are several other variants which displayed high growth indices in this surface loop. Together, the benefit of the variants in this loop may indicate that it plays a critical role in enzyme activity within the cell. The Q509T variant is of particular interest because both Q509I and Q509V variants also displayed growth benefits, and these are the only amino acid residues that are branched at the beta carbon. FIG. 6 shows that Q509 is located near but not within the active site of IspS. The presence of a branched structure at the beta carbon of this particular amino acid may confer a benefit to enzyme activity.

Figure 7:
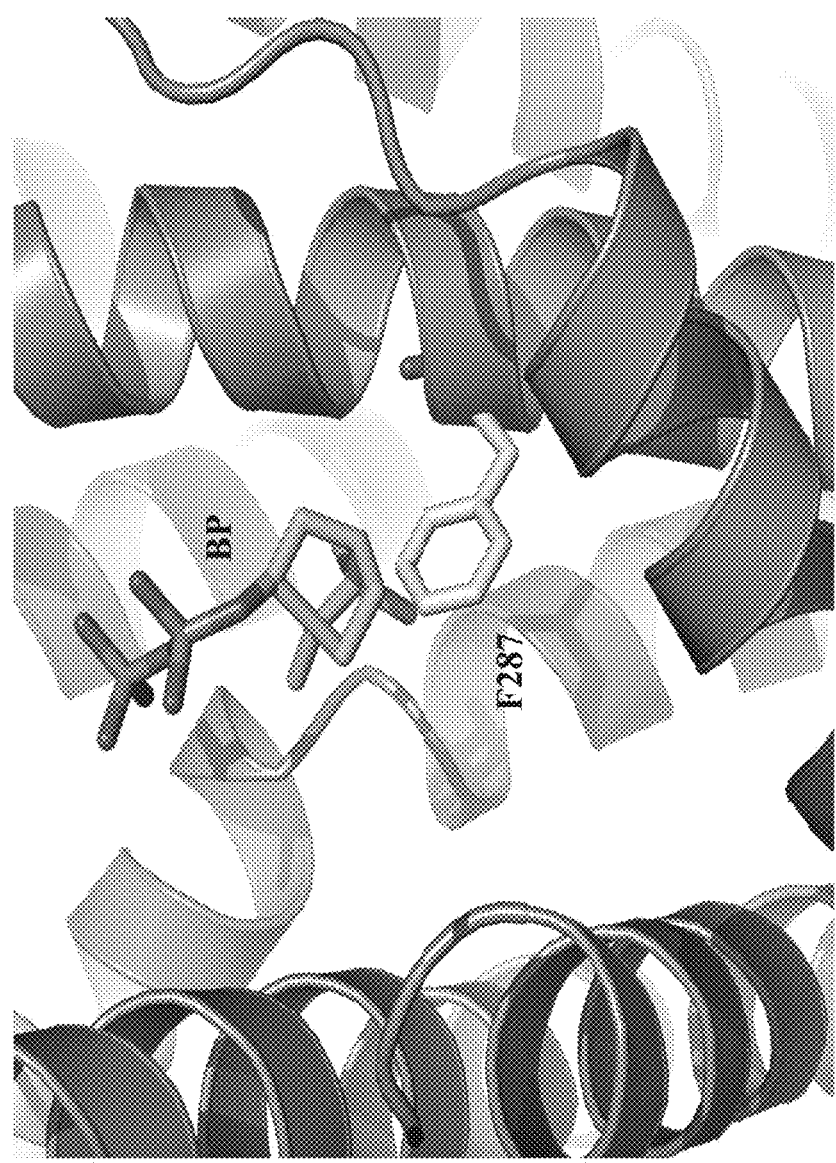
FIG. 7 shows a view of Wild Type IspS showing residue Phe287 in stick representation. (+)-bornyl diphospate (BP) is placed based on a structural alignment with PDB 1N24.

Residues listed in Table 7 are necessary for growth under high DMAPP pressure and thus, can be considered in one embodiment as immutable residues. Substitution of the wild type amino acid with any other residue results in minimal to no growth under the growth rate assay conditions. Growth index values for each position are shown in Table 7. Phenylalanine 287 (F287) is located in the active site, and defines the bottom of the active site cavity (FIG. 7). Based on structural alignments with other terpene synthases, F287 determines the length of the substrate that can be accommodated into the active site, thereby preventing access to the active site by isoprenoids with more than five carbons.

Figure 8:
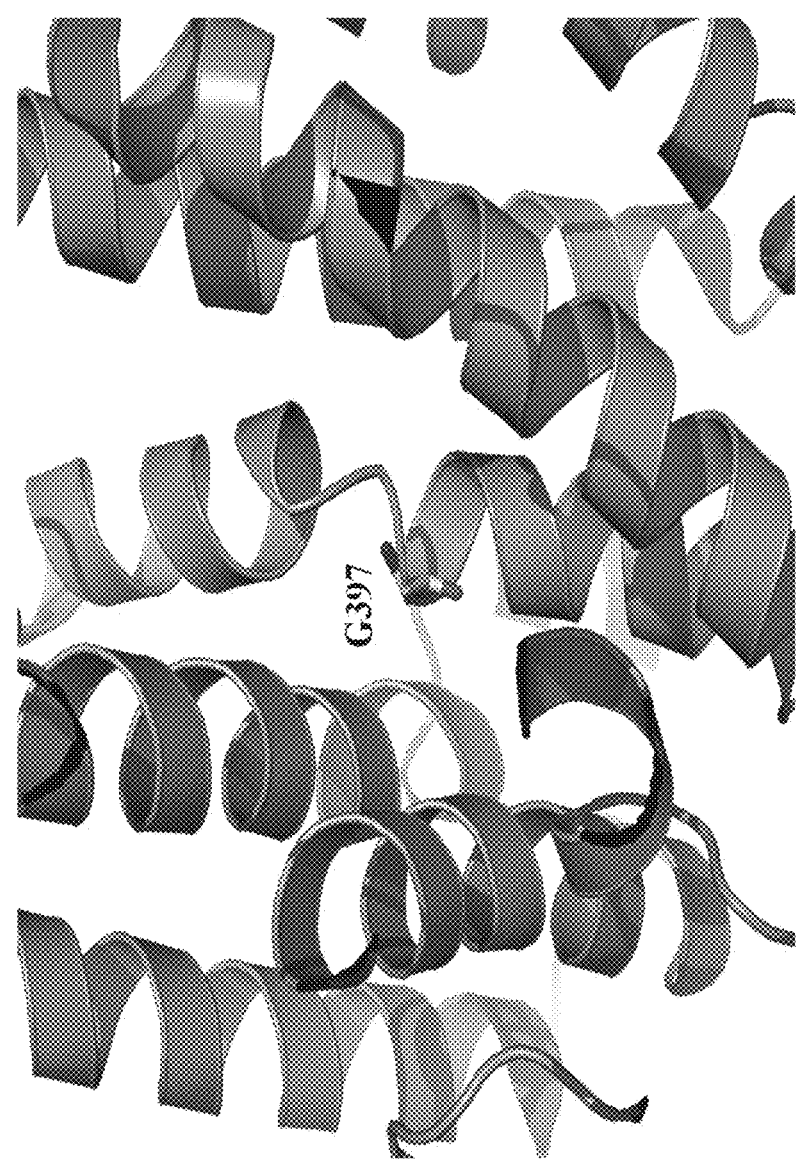
FIG. 8 shows a view of Wild Type IspS showing residue Gly397 in stick representation.

Glycine 397 (G397) is located on the side of the active site cavity (FIG. 8). This residue occurs at a kink in an alpha-helix, suggesting that the conformational flexibility of glycine (and other small amino acids) may be required at this position to allow the helix to bend. The bend in the helix is adjacent to the putative substrate binding position in the active site.

Figure 9:
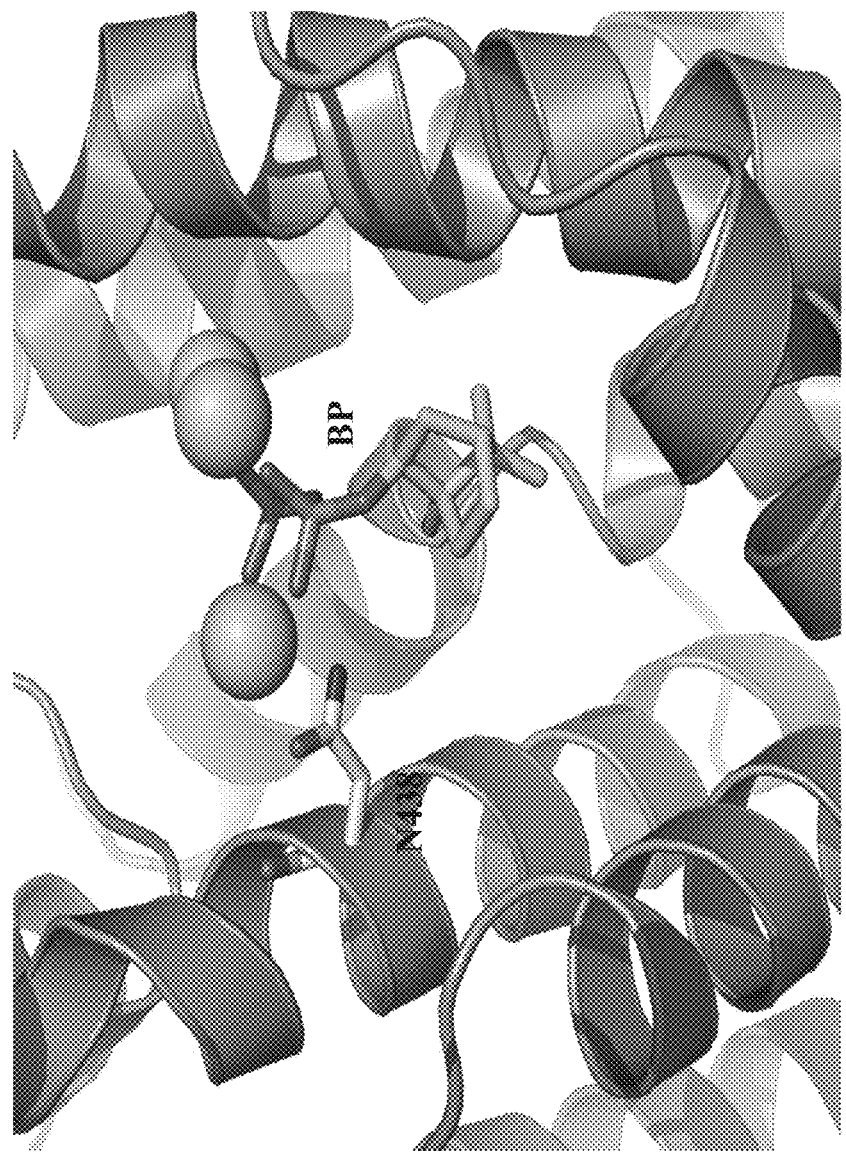
FIG. 9 shows an active site view of Wild Type IspS showing residue Asn438 in stick representation. (+)-bornyl diphospate (BP) and Mg2+ (spheres) are placed based on a structural alignment with PDB 1N24.

Asparagine 438 (N438) is positioned at the top of the active site (FIG. 9). Structural alignments with other terpene synthases indicate that N428 may be involved directly in coordination of the magnesium ions, as well as having possible interactions with the substrate.

Figure 10:
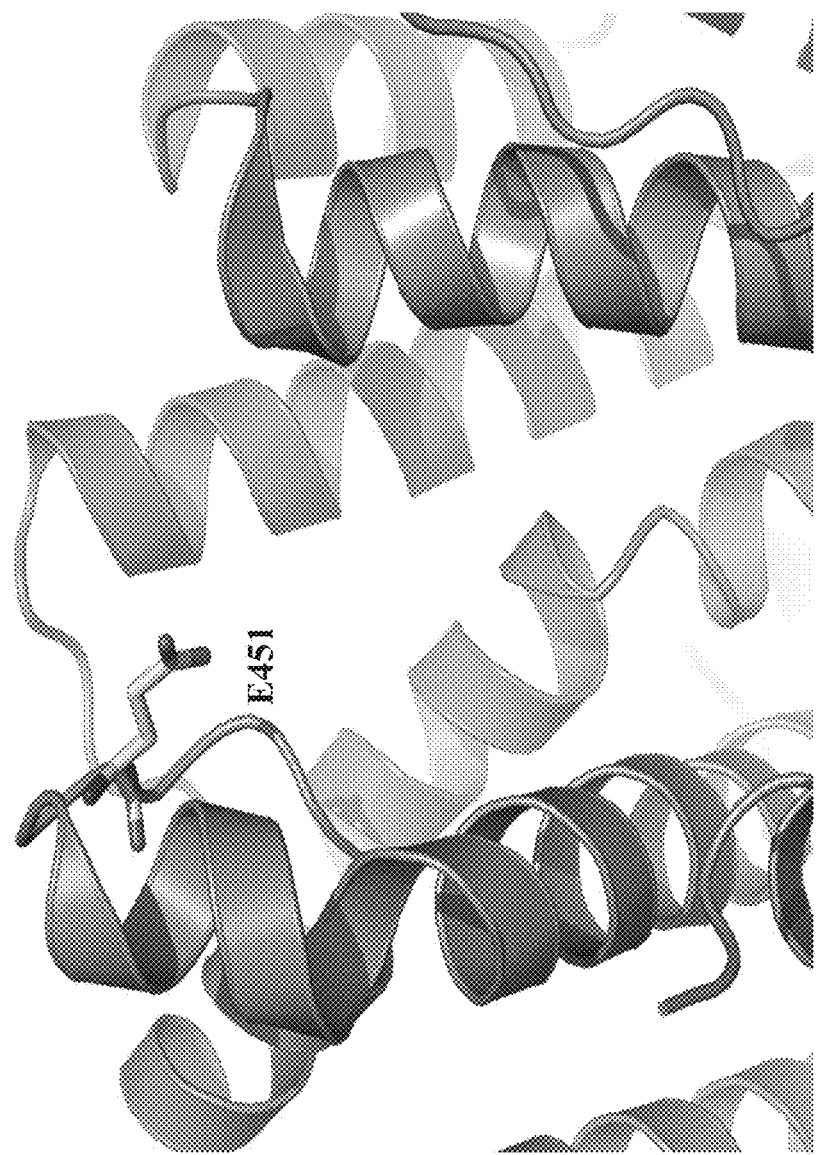
FIG. 10 shows a view of Wild Type IspS showing residue Glu451 in stick representation.

Glutamate 451 (E451) is on a substrate access loop located above the active site (FIG. 10). Based on homology modeling and structure-based alignments with other terpene synthases, these loops may have an open position for substrate capture, and then close over the active site once substrate is bound. Residue E451 is proposed to have a role in coordinating one or more magnesium ions during this process.

Figure 11:
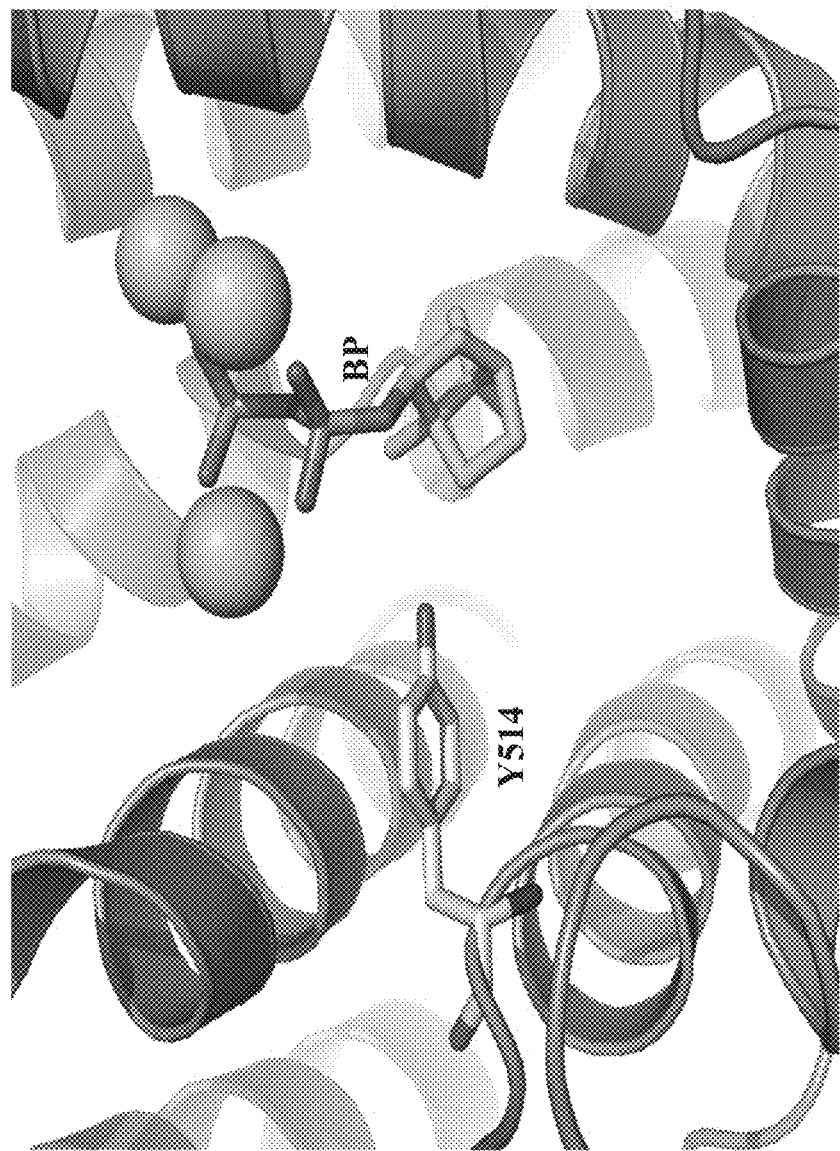
FIG. 11 shows an active site view of Wild Type IspS showing residue Tyr514 in stick representation. (+)-bornyl diphospate (BP) and Mg2+ (spheres) are placed based on a structural alignment with PDB 1N24.

Tyrosine 514 (Y514) is in the active site, below N438 (FIG. 11). Y514 may be involved in substrate binding, or it may play a direct role in catalysis.

TABLE 6

Variants with Growth Index value equal to or greater than 1.2.

| Variant | GI |
|---|---|
| L59H | 1.96 |
| F495L | 1.84 |
| L540V | 1.73 |
| V30L | 1.61 |
| L540T | 1.58 |
| G491I | 1.57 |
| F495T | 1.56 |
| S493T | 1.53 |
| V30K | 1.52 |
| L490I | 1.52 |
| D33T | 1.49 |
| Q509T | 1.49 |
| L59K | 1.49 |
| G492A | 1.48 |
| Q116V | 1.47 |
| L59I | 1.46 |
| E179L | 1.46 |
| L490H | 1.46 |
| I28T | 1.46 |
| D33V | 1.46 |
| I165Y | 1.46 |
| F495Y | 1.45 |
| F495K | 1.45 |
| V30Y | 1.45 |
| F53L | 1.44 |
| F495W | 1.44 |
| G99T | 1.43 |
| T462T | 1.43 |
| E117I | 1.42 |
| G491H | 1.41 |
| L59R | 1.41 |
| L490V | 1.41 |
| S493V | 1.40 |
| E179I | 1.40 |
| I539V | 1.40 |
| F495S | 1.40 |
| D33Y | 1.39 |
| Q421R | 1.39 |
| V30W | 1.39 |
| A3T | 1.39 |
| K487T | 1.39 |
| G492T | 1.38 |
| F495V | 1.38 |

TABLE 6-continued

Variants with Growth Index value equal to or greater than 1.2.

| Variant | GI |
|---|---|
| G492H | 1.38 |
| I28S | 1.38 |
| G492V | 1.37 |
| A443A | 1.36 |
| Q116W | 1.36 |
| G491V | 1.36 |
| Q116T | 1.36 |
| G491L | 1.36 |
| A448T | 1.35 |
| S493R | 1.35 |
| K489W | 1.35 |
| E179K | 1.35 |
| G153W | 1.34 |
| L490W | 1.34 |
| L540H | 1.34 |
| G87K | 1.34 |
| S120L | 1.34 |
| F53T | 1.34 |
| Q509V | 1.34 |
| G78L | 1.33 |
| K50I | 1.33 |
| K50L | 1.33 |
| R544T | 1.33 |
| E179H | 1.33 |
| G491W | 1.33 |
| G491T | 1.33 |
| Q116Y | 1.32 |
| G99V | 1.32 |
| F495H | 1.31 |
| G491Y | 1.31 |
| G78Y | 1.31 |
| T462V | 1.31 |
| L540I | 1.31 |
| I28R | 1.31 |
| G492K | 1.30 |
| Q509I | 1.30 |
| D33W | 1.30 |
| R44H | 1.30 |
| G491K | 1.29 |
| A139T | 1.29 |
| L130Y | 1.29 |
| E117L | 1.29 |
| S493W | 1.29 |
| F495R | 1.28 |
| R544W | 1.28 |
| L540K | 1.28 |
| L59G | 1.28 |
| A519W | 1.27 |
| S493E | 1.27 |
| F53W | 1.27 |
| E117W | 1.27 |
| G99I | 1.27 |
| G78W | 1.27 |
| R44T | 1.27 |
| E179W | 1.26 |
| A448H | 1.26 |
| F53V | 1.26 |
| Y377W | 1.26 |
| F53I | 1.26 |
| G492I | 1.26 |
| T462K | 1.26 |
| T462H | 1.26 |
| S493L | 1.26 |
| G177V | 1.26 |
| G78I | 1.26 |
| P498H | 1.26 |
| L59F | 1.26 |
| D33H | 1.26 |
| V30S | 1.26 |
| Q421H | 1.26 |
| I539T | 1.26 |
| R544V | 1.26 |
| F495M | 1.25 |
| E173H | 1.25 |
| G492E | 1.25 |
| L59A | 1.25 |

TABLE 6-continued

Variants with Growth Index value equal to or greater than 1.2.

| Variant | GI |
|---|---|
| G177T | 1.25 |
| G87T | 1.24 |
| G99K | 1.24 |
| V202H | 1.24 |
| S74K | 1.24 |
| G389K | 1.24 |
| G87L | 1.24 |
| G492D | 1.24 |
| Q421E | 1.24 |
| N476Y | 1.24 |
| I165H | 1.24 |
| F53Y | 1.24 |
| K489R | 1.24 |
| K36L | 1.23 |
| D33I | 1.23 |
| R544S | 1.23 |
| E179T | 1.23 |
| A448V | 1.23 |
| G99Y | 1.23 |
| E173W | 1.23 |
| S493K | 1.23 |
| G99L | 1.23 |
| E174I | 1.23 |
| E173T | 1.23 |
| D33S | 1.22 |
| G177L | 1.22 |
| V30F | 1.22 |
| K50W | 1.22 |
| Q116I | 1.22 |
| E179V | 1.22 |
| S74W | 1.22 |
| L59M | 1.22 |
| D33K | 1.21 |
| L490T | 1.21 |
| A3H | 1.21 |
| K489I | 1.21 |
| I539L | 1.21 |
| R44F | 1.21 |
| E117F | 1.21 |
| L59C | 1.21 |
| S493G | 1.21 |
| G69S | 1.21 |
| E173V | 1.20 |
| L540Y | 1.20 |
| S493I | 1.20 |
| S120I | 1.20 |
| Q116F | 1.20 |
| A496H | 1.20 |
| H254K | 1.20 |
| S74I | 1.20 |
| K489T | 1.20 |
| L376I | 1.20 |
| E174H | 1.20 |

TABLE 7

Growth index values for the immutable sites.

| Variant | GI |
|---|---|
| F287 | |
| F287A | 0.10 |
| F287C | 0.00 |
| F287D | −0.02 |
| F287E | −0.02 |
| F287F | 0.74 |
| F287G | 0.02 |
| F287H | 0.09 |
| F287I | 0.01 |
| F287K | 0.08 |
| F287L | 0.39 |
| F287M | 0.26 |
| F287N | 0.01 |
| F287P | −0.01 |
| F287Q | 0.03 |
| F287R | 0.01 |
| F287S | 0.02 |
| F287T | 0.04 |
| F287V | 0.21 |
| F287W | 0.42 |
| F287Y | 0.19 |
| G397 | |
| G397A | 0.40 |
| G397C | 0.05 |
| G397D | −0.02 |
| G397E | −0.02 |
| G397F | −0.02 |
| G397G | 1.05 |
| G397H | −0.02 |
| G397I | 0.09 |
| G397K | −0.03 |
| G397L | −0.01 |
| G397M | 0.08 |
| G397N | 0.00 |
| G397P | 0.00 |
| G397Q | 0.00 |
| G397R | 0.00 |
| G397S | 0.00 |
| G397T | −0.03 |
| G397V | 0.16 |
| G397W | −0.03 |
| G397Y | 0.00 |
| N438 | |
| N438A | −0.02 |
| N438C | −0.05 |
| N438D | −0.04 |
| N438E | −0.04 |
| N438F | −0.04 |
| N438G | −0.07 |
| N438H | −0.04 |
| N438I | −0.05 |
| N438K | −0.06 |
| N438L | −0.05 |
| N438M | −0.05 |
| N438N | 1.27 |
| N438P | −0.06 |
| N438Q | −0.06 |
| N438R | −0.06 |
| N438S | −0.09 |
| N438T | −0.04 |
| N438V | −0.05 |
| N438W | −0.05 |
| N438Y | −0.06 |
| E451 | |
| E451A | −0.04 |
| E451C | −0.04 |
| E451D | −0.02 |
| E451E | 1.48 |
| E451E | 1.13 |
| E451F | −0.03 |
| E451G | −0.02 |
| E451H | −0.02 |
| E451I | −0.03 |
| E451K | −0.01 |
| E451L | −0.05 |
| E451N | −0.06 |
| E451P | −0.05 |
| E451Q | 0.06 |
| E451R | −0.03 |
| E451S | −0.06 |
| E451T | −0.04 |
| E451V | −0.04 |
| E451W | −0.01 |
| E451Y | −0.03 |

TABLE 7-continued

Growth index values for the immutable sites.

| Variant | GI |
|---|---|
| Y514 | |
| Y514A | −0.02 |
| Y514C | −0.03 |
| Y514D | −0.02 |
| Y514E | −0.03 |
| Y514F | −0.04 |
| Y514G | −0.04 |
| Y514H | 0.01 |
| Y514I | −0.01 |
| Y514K | −0.03 |
| Y514L | −0.02 |
| Y514M | −0.04 |
| Y514N | −0.03 |
| Y514P | −0.02 |
| Y514Q | −0.03 |
| Y514R | −0.02 |
| Y514S | −0.02 |
| Y514T | 0.01 |
| Y514V | 0.00 |
| Y514W | −0.01 |
| Y514Y | 1.08 |

Example 3

Positional Analysis of Growth Index

This Example shows the results of analysis of SEL data displayed is by position. The growth index that corresponds to the particular mutation is shown as below in Table 8:

TABLE 8

| Mutation | Growth Index | Mutation | Growth Index | Mutation | Growth Index | Mutation | Growth Index | Mutation | Growth Index |
|---|---|---|---|---|---|---|---|---|---|
| A3A | 0.729 | A7A | 0.695 | Y9A | 0.088 | N12A | 0.719 | S13A | 0.572 |
| A3C | 0.677 | A7C | 0.337 | Y9C | 0.048 | N12C | 0.731 | S13C | 0.560 |
| A3D | 0.792 | A7D | 0.070 | Y9D | −0.009 | N12D | 0.267 | S13D | 0.351 |
| A3E | 0.936 | A7E | 0.167 | Y9E | −0.011 | N12E | 0.146 | S13E | 0.496 |
| A3F | 1.103 | A7F | 0.203 | Y9F | 0.839 | N12F | 0.251 | S13F | 0.667 |
| A3G | 0.780 | A7G | 0.766 | Y9G | 0.013 | N12G | 0.329 | S13G | 0.763 |
| A3H | 1.211 | A7H | 0.309 | Y9H | 0.314 | N12H | 0.478 | S13H | 0.869 |
| A3I | 1.051 | A7I | 0.291 | Y9I | 0.216 | N12I | 0.442 | S13I | 0.823 |
| A3K | 1.135 | A7K | −0.020 | Y9K | 0.035 | N12K | 0.293 | S13K | 0.853 |
| A3L | 0.830 | A7L | 0.092 | Y9L | 0.094 | N12L | 0.252 | S13L | 1.039 |
| A3M | 0.157 | A7M | 0.063 | Y9M | 0.016 | N12M | 0.606 | S13M | 0.686 |
| A3N | 0.889 | A7N | 0.156 | Y9N | 0.043 | N12N | 0.676 | S13N | 0.672 |
| A3P | 0.763 | A7P | 0.309 | Y9P | 0.100 | N12P | 0.428 | S13P | 0.177 |
| A3Q | 0.966 | A7Q | 0.188 | Y9Q | 0.028 | N12Q | 0.378 | S13Q | 0.616 |
| A3R | 1.037 | A7R | 0.069 | Y9R | 0.115 | N12R | 0.406 | S13R | 0.764 |
| A3S | 0.511 | A7S | 0.301 | Y9S | 0.079 | N12S | 0.833 | S13S | 0.682 |
| A3T | 1.391 | A7T | 0.294 | Y9T | 0.154 | N12T | 0.790 | S13T | 0.903 |
| A3V | 0.144 | A7V | 0.392 | Y9V | 0.201 | N12V | 0.588 | S13V | 0.809 |
| A3W | 0.702 | A7W | 0.501 | Y9W | 0.561 | N12W | 0.137 | S13W | 0.643 |
| A3Y | 1.092 | A7Y | 0.305 | Y9Y | 0.036 | N12Y | −0.012 | S13Y | 0.724 |
| Y16A | 0.337 | Y18A | 0.453 | L20A | 0.946 | D23A | 0.530 | D25A | 0.889 |
| Y16C | 0.497 | Y18C | 1.005 | L20C | 0.739 | D23C | 0.807 | D25C | 0.659 |
| Y16D | 0.402 | Y18D | 0.669 | L20D | 0.450 | D23D | 0.819 | D25D | 0.926 |
| Y16E | 0.533 | Y18E | 0.610 | L20E | 0.655 | D23E | 0.855 | D25E | 0.822 |
| Y16F | 0.846 | Y18F | 0.825 | L20F | 0.966 | D23F | 0.921 | D25F | 0.878 |
| Y16G | 0.356 | Y18G | 1.031 | L20G | 0.749 | D23G | 0.825 | D25G | 0.878 |
| Y16H | 0.863 | Y18H | 0.973 | L20H | 0.772 | D23H | 1.039 | D25H | 1.111 |
| Y16I | 1.088 | Y18I | 0.913 | L20I | 0.962 | D23I | 0.893 | D25I | 1.087 |
| Y16K | 0.394 | Y18K | 0.652 | L20K | 0.364 | D23K | 0.883 | D25K | 1.003 |
| Y16L | 1.049 | Y18L | 0.750 | L20L | 1.025 | D23L | 0.822 | D25L | 1.096 |
| Y16M | 1.092 | Y18M | 0.762 | L20M | 1.139 | D23M | 0.766 | D25M | 0.900 |
| Y16N | 0.409 | Y18N | 0.955 | L20N | 0.755 | D23N | 0.763 | D25N | 0.929 |
| Y16P | 0.479 | Y18P | 0.486 | L20P | 0.357 | D23P | 0.783 | D25P | 0.965 |
| Y16Q | 0.481 | Y18Q | 0.739 | L20Q | 0.746 | D23Q | 0.665 | D25Q | 0.726 |
| Y16R | 0.214 | Y18R | 0.825 | L20R | 0.526 | D23R | 0.813 | D25R | 0.774 |
| Y16S | 0.438 | Y18S | 0.720 | L20S | 1.080 | D23S | 0.910 | D25S | 0.802 |
| Y16T | 0.772 | Y18T | 0.799 | L20T | 1.007 | D23T | 0.939 | D25T | 1.057 |
| Y16V | 0.911 | Y18V | 0.783 | L20V | 1.083 | D23V | 0.957 | D25V | 1.023 |
| Y16W | 0.730 | Y18W | 0.912 | L20W | 0.998 | D23W | 0.879 | D25W | 0.859 |
| Y16Y | 1.014 | Y18Y | 0.949 | L20Y | 1.031 | D23Y | 0.747 | D25Y | 0.998 |
| E26A | 0.244 | S27A | 0.493 | I28A | 0.256 | V30A | 0.256 | D33A | 0.039 |
| E26C | 0.455 | S27C | 0.593 | I28C | 0.101 | V30C | 0.308 | D33C | 0.496 |
| E26D | 0.475 | S27D | 0.442 | I28D | 0.383 | V30D | −0.014 | D33D | 0.813 |
| E26E | 0.541 | S27E | 0.510 | I28E | 0.286 | V30E | 1.072 | D33E | 0.831 |
| E26F | 0.331 | S27F | 0.457 | I28F | 0.269 | V30F | 1.219 | D33F | 1.069 |
| E26G | 0.935 | S27G | 0.594 | I28G | 0.283 | V30G | 0.887 | D33G | 0.971 |
| E26H | 0.685 | S27H | 0.801 | I28I | 0.566 | V30V | 0.950 | D33H | 1.259 |
| E26I | 0.655 | S27I | 0.669 | I28I | 0.551 | V30I | 1.107 | D33I | 1.234 |
| E26K | 0.637 | S27K | 0.674 | I28I | 0.920 | V30K | 1.523 | D33K | 1.215 |
| E26L | 0.576 | S27L | 0.783 | I28L | 0.518 | V30L | 1.614 | D33L | 1.128 |
| E26M | 0.462 | S27M | 0.631 | I28M | 0.151 | V30M | 0.939 | D33M | −0.034 |
| E26N | 0.492 | S27N | 0.540 | I28N | 0.143 | V30N | 0.603 | D33N | 0.639 |

TABLE 8-continued

| Mutation | Growth Index | Mutation | Growth Index | Mutation | Growth Index | Mutation | Growth Index | Mutation | Growth Index |
|---|---|---|---|---|---|---|---|---|---|
| E26P | 0.485 | S27P | 0.408 | I28P | 1.030 | V30P | 1.079 | D33P | 0.819 |
| E26Q | 0.549 | S27Q | 0.728 | I28I | 1.153 | V30Q | 1.036 | D33Q | 1.073 |
| E26R | 0.455 | S27R | 0.537 | I28R | 1.307 | V30R | 1.130 | D33R | 1.181 |
| E26S | 0.515 | S27S | 0.539 | I28S | 1.378 | V30S | 1.259 | D33S | 1.223 |
| E26T | 0.553 | S27V | 0.585 | I28T | 1.455 | V30T | 1.052 | D33T | 1.495 |
| E26V | 0.646 | S27W | 0.302 | I28V | −0.006 | V30V | 1.253 | D33V | 1.455 |
| E26W | 0.337 | S27Y | 0.383 | I28W | 0.418 | V30W | 1.392 | D33W | 1.298 |
| E26Y | 0.287 | | | I28Y | 1.104 | V30Y | 1.448 | D33Y | 1.395 |
| K36A | 0.562 | R44A | 0.997 | K50A | 0.268 | F53A | 0.160 | L59A | 1.247 |
| K36C | 0.695 | R44C | 1.000 | K50C | 0.430 | F53C | 0.441 | L59C | 1.207 |
| K36D | 0.583 | R44D | 0.957 | K50D | 0.681 | F53D | 0.715 | L59D | 1.122 |
| K36E | 0.537 | R44E | 0.818 | K50E | 0.825 | F53E | 0.905 | L59E | 1.193 |
| K36F | 0.946 | R44F | 1.209 | K50F | −0.011 | F53F | 1.055 | L59F | 1.259 |
| K36G | 0.829 | R44G | 0.531 | K50G | 0.768 | F53G | 1.048 | L59G | 1.276 |
| K36H | 0.973 | R44H | 1.296 | K50H | 1.178 | F53H | 1.054 | L59H | 1.962 |
| K36I | 1.194 | R44I | 1.095 | K50I | 1.335 | F53I | 1.262 | L59I | 1.464 |
| K36K | 1.195 | R44K | 1.039 | K50K | 1.354 | F53K | 1.081 | L59K | 1.485 |
| K36L | 1.235 | R44L | 0.989 | K50L | 1.334 | F53L | 1.445 | L59L | 1.087 |
| K36M | 0.775 | R44M | 0.995 | K50M | 0.106 | F53M | −0.071 | L59M | 1.216 |
| K36N | 0.719 | R44N | 0.956 | K50N | 0.348 | F53N | 0.431 | L59N | 1.052 |
| K36P | 0.605 | R44P | 0.785 | K50P | 0.700 | F53P | 0.874 | L59P | 0.031 |
| K36Q | 0.645 | R44Q | 0.803 | K50Q | 0.739 | F53Q | 0.960 | L59Q | 1.036 |
| K36R | 1.112 | R44R | 0.776 | K50R | −0.003 | F53R | 1.167 | L59R | 1.410 |
| K36S | 0.975 | R44S | 0.951 | K50S | 0.905 | F53S | 1.117 | L59S | 0.736 |
| K36T | 1.073 | R44T | 1.268 | K50T | 1.140 | F53T | 1.338 | L59T | 1.184 |
| K36V | 1.190 | R44V | 1.172 | K50V | 1.113 | F53V | 1.264 | L59V | 1.045 |
| K36W | 1.008 | R44W | 0.788 | K50W | 1.219 | F53W | 1.273 | L59W | 1.060 |
| K36Y | 1.169 | R44Y | 1.127 | K50Y | 1.169 | F53Y | 1.238 | L59Y | 0.974 |
| G69A | 1.029 | S74A | 0.699 | G78A | 0.663 | D81A | 0.810 | G87A | 0.879 |
| G69C | 0.989 | S74C | 0.778 | G78C | 0.837 | D81C | 0.714 | G87C | 0.887 |
| G69D | 0.844 | S74D | 0.701 | G78D | 0.720 | D81D | 0.011 | G87D | 0.938 |
| G69E | 0.997 | S74E | 0.717 | G78E | 0.740 | D81E | 0.506 | G87E | 0.812 |
| G69F | 0.957 | S74F | 0.860 | G78F | 1.011 | D81F | 0.826 | G87F | 0.991 |
| G69G | 1.132 | S74G | 0.977 | G78G | 0.914 | D81G | 0.796 | G87G | −0.006 |
| G69H | 1.078 | S74H | 1.104 | G78H | 1.180 | D81H | 0.850 | G87H | 1.125 |
| G69I | 1.102 | S74I | 1.200 | G78I | 1.260 | D81I | 0.685 | G87I | 1.103 |
| G69K | 1.125 | S74K | 1.243 | G78K | 1.128 | D81K | 0.609 | G87K | 1.342 |
| G69L | 1.098 | S74L | 1.141 | G78L | 1.335 | D81L | 0.840 | G87L | 1.242 |
| G69M | 1.162 | S74M | 0.650 | G78M | 0.699 | D81M | 0.701 | G87M | 1.039 |
| G69N | 1.039 | S74N | 0.724 | G78N | 0.678 | D81N | 0.691 | G87N | 0.804 |
| G69P | 0.717 | S74P | 0.761 | G78P | 0.764 | D81P | 0.423 | G87P | 0.979 |
| G69Q | 1.050 | S74Q | 0.765 | G78Q | 0.675 | D81Q | 0.632 | G87Q | 0.747 |
| G69R | 1.056 | S74R | 0.974 | G78R | 0.975 | D81R | 0.616 | G87R | 1.028 |
| G69S | 1.205 | S74S | 0.945 | G78S | 0.910 | D81S | 0.802 | G87S | 0.961 |
| G69T | 1.109 | S74T | 1.140 | G78T | 1.179 | D81T | 0.928 | G87T | 1.245 |
| G69V | 1.080 | S74V | 1.174 | G78V | 1.190 | D81V | 0.854 | G87V | 1.171 |
| G69W | 0.922 | S74W | 1.217 | G78W | 1.270 | D81W | 0.618 | G87W | 1.114 |
| G69Y | 0.936 | S74Y | 1.130 | G78Y | 1.313 | D81Y | 0.799 | G87Y | 1.170 |
| G99A | 0.217 | Q116A | 1.006 | E117A | 0.953 | S120A | 0.823 | G121A | 0.944 |
| G99C | 0.460 | Q116C | 0.993 | E117C | 0.905 | S120C | 0.883 | G121C | 0.880 |
| G99D | 0.695 | Q116D | 0.966 | E117D | 0.702 | S120D | 0.878 | G121D | 0.752 |
| G99E | 0.780 | Q116E | 0.925 | E117E | 0.255 | S120E | 0.880 | G121E | 0.710 |
| G99F | 1.024 | Q116F | 1.202 | E117F | 1.208 | S120F | 1.012 | G121F | 1.090 |
| G99G | −0.004 | Q116G | 0.865 | E117G | 0.703 | S120G | 0.874 | G121G | 0.912 |
| G99H | 0.289 | Q116H | 0.922 | E117H | 1.077 | S120H | 1.083 | G121H | 1.145 |
| G99I | 1.271 | Q116I | 1.219 | E117I | 1.417 | S120I | 1.202 | G121I | 1.174 |
| G99K | 1.244 | Q116K | 1.092 | E117K | 0.553 | S120K | 1.180 | G121K | 1.023 |
| G99L | 1.228 | Q116L | 1.117 | E117L | 1.288 | S120L | 1.339 | G121L | 1.147 |
| G99M | 0.427 | Q116M | 0.764 | E117M | 1.004 | S120M | 0.963 | G121M | 0.898 |
| G99N | 0.572 | Q116N | 0.804 | E117N | 0.817 | S120N | 0.798 | G121N | 0.740 |
| G99P | 0.797 | Q116P | 0.911 | E117P | 0.438 | S120P | 0.595 | G121P | 0.829 |
| G99Q | 0.937 | Q116Q | 0.815 | E117Q | 0.664 | S120Q | 0.745 | G121Q | 0.724 |
| G99R | 1.092 | Q116R | 0.908 | E117R | 0.803 | S120R | 0.844 | G121R | 0.866 |
| G99S | 1.110 | Q116S | 1.017 | E117S | 0.803 | S120S | 0.694 | G121S | 0.742 |
| G99T | 1.430 | Q116T | 1.360 | E117T | 0.864 | S120T | 1.165 | G121T | 1.070 |
| G99V | 1.319 | Q116V | 1.472 | E117V | 0.988 | S120V | 1.050 | G121V | 1.026 |
| G99W | 1.025 | Q116W | 1.361 | E117W | 1.272 | S120W | 1.144 | G121W | 1.001 |
| G99Y | 1.231 | Q116Y | 1.325 | E117Y | 0.936 | S120Y | 1.072 | G121Y | 1.069 |
| Q125A | 0.928 | G127A | 0.704 | I28A | 0.256 | L130A | 0.283 | A139A | 0.831 |
| Q125C | 0.897 | G127C | 0.870 | I28C | 0.101 | L130C | 0.150 | A139C | 1.031 |
| Q125D | 0.827 | G127D | 0.853 | I28D | 0.383 | L130D | 0.966 | A139D | 0.874 |
| Q125E | 0.732 | G127E | 0.879 | I28E | 0.286 | L130E | 0.961 | A139E | 0.950 |
| Q125F | 0.918 | G127F | 1.084 | I28F | 0.269 | L130L | 1.116 | A139F | 0.816 |
| Q125G | 0.815 | G127G | 0.000 | I28G | 0.283 | L130G | 1.151 | A139G | 0.973 |
| Q125H | 1.020 | G127H | 1.125 | I28I | 0.566 | L130L | 1.092 | A139H | 1.073 |
| Q125I | 1.053 | G127I | 1.030 | I28I | 0.551 | L130I | 1.141 | A139I | 1.042 |
| Q125K | 0.888 | G127K | 0.582 | I28I | 0.920 | L130K | 1.170 | A139K | 0.301 |

TABLE 8-continued

| Mutation | Growth Index | Mutation | Growth Index | Mutation | Growth Index | Mutation | Growth Index | Mutation | Growth Index |
|---|---|---|---|---|---|---|---|---|---|
| Q125L | 0.926 | G127L | 1.028 | I28L | 0.518 | L130L | 1.200 | A139L | 0.881 |
| Q125M | 1.060 | G127M | 0.802 | I28M | 0.151 | L130M | 0.218 | A139M | 0.844 |
| Q125N | 0.970 | G127N | 0.744 | I28N | 0.143 | L130L | 0.908 | A139N | 0.830 |
| Q125P | 0.990 | G127P | 0.871 | I28P | 1.030 | L130P | 0.761 | A139P | 1.074 |
| Q125Q | 0.690 | G127Q | 0.709 | I28I | 1.153 | L130Q | 0.879 | A139Q | 0.976 |
| Q125R | 0.889 | G127R | 0.593 | I28R | 1.307 | L130R | 1.054 | A139R | 0.305 |
| Q125S | 0.853 | G127S | 0.959 | I28S | 1.378 | L130S | −0.031 | A139S | 1.072 |
| Q125T | 1.007 | G127T | 1.185 | I28T | 1.455 | L130L | 1.041 | A139T | 1.291 |
| Q125V | 0.957 | G127V | 1.047 | I28V | −0.006 | L130V | 1.093 | A139V | 1.067 |
| Q125W | 1.051 | G127W | 0.859 | I28W | 0.418 | L130W | 0.885 | A139W | 0.798 |
| Q125Y | 1.010 | G127Y | 1.008 | I28Y | 1.104 | L130Y | 1.289 | A139Y | 0.562 |
| G153A | 0.961 | I165A | 1.022 | E173A | 0.936 | E174A | 0.939 | G177A | 1.025 |
| G153C | 1.001 | I165C | 0.793 | E173C | 0.831 | E174C | 0.828 | G177C | 0.884 |
| G153D | 0.814 | I165D | 1.030 | E173D | 0.651 | E174D | 0.698 | G177D | 0.786 |
| G153G | 0.862 | I165E | 0.826 | E173E | 0.813 | E174E | 0.686 | G177E | 0.741 |
| G153G | 0.918 | I165F | 1.114 | E173F | 1.135 | E174F | 1.110 | G177F | 0.810 |
| G153G | 1.070 | I165G | 0.991 | E173G | 1.077 | E174G | 0.899 | G177G | 0.933 |
| G153H | −0.042 | I165H | 1.239 | E173H | 1.250 | E174H | 1.196 | G177H | 1.139 |
| G153G | 0.966 | I165I | 1.036 | E173I | 1.188 | E174I | 1.227 | G177I | 1.175 |
| G153K | 0.324 | I165K | 1.157 | E173K | 1.119 | E174K | 1.131 | G177K | 1.130 |
| G153L | 0.323 | I165L | 1.003 | E173L | 1.190 | E174L | 1.162 | G177L | 1.222 |
| G153M | 0.833 | I165M | 0.911 | E173M | 1.013 | E174M | 0.943 | G177M | 1.008 |
| G153N | 0.826 | I165N | 0.949 | E173N | 0.885 | E174N | 0.858 | G177N | 0.928 |
| G153P | 0.317 | I165P | 0.667 | E173P | 0.856 | E174P | 0.685 | G177P | 1.106 |
| G153Q | 0.863 | I165Q | 0.904 | E173Q | 0.905 | E174Q | 0.721 | G177Q | 0.436 |
| G153R | 1.011 | I165R | 1.050 | E173R | 1.078 | E174R | 1.073 | G177R | 0.898 |
| G153S | 1.021 | I165S | 0.950 | E173S | 1.006 | E174S | 0.873 | G177S | 0.915 |
| G153T | 0.899 | I165T | 1.142 | E173T | 1.226 | E174T | 1.145 | G177T | 1.245 |
| G153V | 0.307 | I165V | 0.611 | E173V | 1.205 | E174V | 1.154 | G177V | 1.260 |
| G153W | 1.345 | I165W | 0.983 | E173W | 1.228 | E174W | 1.054 | G177W | 0.998 |
| G153Y | 1.120 | I165Y | 1.455 | E173Y | 1.183 | E174Y | 1.003 | G177Y | 1.031 |
| E179A | 0.956 | R194A | 0.268 | Q197A | 0.834 | R198A | 0.622 | V202A | 0.921 |
| E179C | 0.938 | R194C | 0.725 | Q197C | 0.867 | R198C | 0.735 | V202C | 0.935 |
| E179D | 0.844 | R194D | 0.016 | Q197D | 0.892 | R198D | 0.016 | V202D | 0.840 |
| E179E | 0.000 | R194E | 0.028 | Q197E | 0.951 | R198E | 0.983 | V202E | 0.846 |
| E179F | 1.111 | R194F | 0.823 | Q197F | 0.995 | R198F | 0.083 | V202F | 1.016 |
| E179G | 1.055 | R194G | −0.027 | Q197G | 0.835 | R198G | 0.242 | V202G | 0.812 |
| E179H | 1.328 | R194H | 1.157 | Q197H | 1.042 | R198H | 0.068 | V202H | 1.244 |
| E179I | 1.403 | R194I | 0.651 | Q197I | 1.040 | R198I | 0.519 | V202I | 1.147 |
| E179K | 1.348 | R194K | 0.813 | Q197K | 0.896 | R198K | 0.837 | V202K | 1.091 |
| E179L | 1.460 | R194L | 0.869 | Q197L | 0.909 | R198L | 0.099 | V202L | 0.930 |
| E179M | 1.007 | R194M | 0.675 | Q197M | 1.012 | R198M | 0.681 | V202M | 0.928 |
| E179N | 0.791 | R194N | 0.183 | Q197N | 0.904 | R198N | 0.233 | V202N | 0.883 |
| E179P | 0.820 | R194P | −0.006 | Q197P | 0.822 | R198P | 0.006 | V202P | 0.345 |
| E179Q | 0.744 | R194Q | 0.606 | Q197Q | 0.748 | R198R | 0.875 | V202Q | 0.900 |
| E179R | 0.939 | R194R | 0.928 | Q197R | 0.857 | R198R | 1.112 | V202R | 1.163 |
| E179S | 1.067 | R194S | 0.077 | Q197S | 0.968 | R198S | 0.346 | V202S | 0.849 |
| E179T | 1.232 | R194T | 0.151 | Q197T | 1.186 | R198T | 0.418 | V202T | 1.184 |
| E179V | 1.218 | R194V | 0.425 | Q197V | 1.153 | R198V | 0.642 | V202V | 0.323 |
| E179W | 1.264 | R194W | 0.838 | Q197W | 0.826 | R198R | 1.079 | V202W | 0.984 |
| E179Y | 1.140 | R194Y | 0.915 | Q197Y | 0.972 | R198Y | 0.028 | V202Y | 1.016 |
| Q216A | 0.831 | I229A | 0.621 | T240A | 0.755 | R246A | 0.749 | T251A | 0.738 |
| Q216C | 0.810 | I229C | 0.939 | T240C | 0.675 | R246C | 0.610 | T251C | 0.773 |
| Q216D | 0.700 | I229D | 0.016 | T240D | 0.034 | R246D | 0.788 | T251D | 0.782 |
| Q216E | 0.748 | I229E | 0.010 | T240E | 0.084 | R246E | 0.803 | T251E | 0.788 |
| Q216F | 0.873 | I229F | 0.454 | T240F | 0.055 | R246F | 0.296 | T251F | 0.711 |
| Q216G | 0.779 | I229G | 0.358 | T240G | 0.346 | R246G | 0.936 | T251G | 0.917 |
| Q216H | 0.995 | I229H | 0.574 | T240H | 0.155 | R246H | 1.028 | T251H | 1.039 |
| Q216I | 0.944 | I229I | 0.855 | T240I | 0.957 | R246I | 0.398 | T251I | 0.520 |
| Q216K | 0.885 | I229K | 0.093 | T240K | 0.016 | R246K | 1.126 | T251K | 1.012 |
| Q216L | 0.873 | I229L | 1.000 | T240L | 0.993 | R246L | 0.535 | T251L | 0.695 |
| Q216M | 0.715 | I229M | 0.779 | T240M | 0.812 | R246M | 0.645 | T251M | 0.764 |
| Q216N | 0.714 | I229N | 0.495 | T240N | 0.693 | R246N | 0.872 | T251N | 1.097 |
| Q216P | 0.599 | I229P | −0.017 | T240P | 0.013 | R246P | 0.009 | T251P | 0.374 |
| Q216Q | 0.680 | I229Q | 0.349 | T240Q | 0.669 | R246Q | 0.853 | T251Q | 0.906 |
| Q216R | 0.595 | I229R | 0.013 | T240R | 0.006 | R246R | 1.167 | T251R | 0.942 |
| Q216S | 0.740 | I229S | 0.453 | T240S | 0.557 | R246S | 0.896 | T251S | 0.996 |
| Q216T | 0.917 | I229T | 0.803 | T240T | 1.150 | R246T | 1.038 | T251T | 1.361 |
| Q216V | 0.899 | I229V | 0.782 | T240V | 0.950 | R246V | 0.534 | T251V | 0.713 |
| Q216W | 0.864 | I229W | 0.082 | T240W | 0.077 | R246W | 0.526 | T251W | 0.730 |
| Q216Y | 0.843 | I229Y | 0.106 | T240Y | 0.087 | R246Y | 0.614 | T251Y | 1.093 |
| H254A | 0.796 | L260A | 0.224 | F287A | 0.097 | V290A | 0.167 | V299A | 0.247 |
| H254C | 0.784 | L260C | 0.248 | F287C | −0.002 | V290C | 0.180 | V299V | 0.618 |
| H254D | 0.848 | L260D | 0.145 | F287D | −0.018 | V290D | −0.027 | V299D | −0.050 |
| H254E | 0.813 | L260E | 0.108 | F287E | −0.019 | V290E | −0.018 | V299E | 0.048 |
| H254F | 1.172 | L260L | 0.892 | F287F | 0.745 | V290F | 0.000 | V299V | 0.816 |
| H254G | 0.889 | L260G | 0.339 | F287G | 0.017 | V290G | 0.150 | V299G | 0.012 |

TABLE 8-continued

| Mutation | Growth Index | Mutation | Growth Index | Mutation | Growth Index | Mutation | Growth Index | Mutation | Growth Index |
|---|---|---|---|---|---|---|---|---|---|
| H254H | 1.325 | L260H | 0.449 | F287H | 0.086 | V290H | 0.040 | V299H | −0.034 |
| H254I | 1.116 | L260I | 0.543 | F287I | 0.011 | V290I | 0.922 | V299I | −0.005 |
| H254K | 1.201 | L260K | 0.003 | F287K | 0.077 | V290K | 0.035 | V299K | 0.034 |
| H254L | 0.877 | L260L | 0.884 | F287L | 0.389 | V290L | 0.484 | V299L | 0.719 |
| H254M | 0.679 | L260M | 0.772 | F287M | 0.261 | V290M | −0.015 | V299M | 0.222 |
| H254N | 0.593 | L260L | 0.746 | F287N | 0.009 | V290N | −0.026 | V299N | 0.137 |
| H254P | 0.001 | L260P | 0.400 | F287P | −0.014 | V290P | −0.033 | V299P | −0.039 |
| H254Q | 0.678 | L260Q | 0.611 | F287Q | 0.033 | V290Q | −0.016 | V299V | 0.603 |
| H254R | 1.066 | L260R | 0.008 | F287R | 0.005 | V290R | 0.003 | V299R | 0.102 |
| H254S | 0.874 | L260S | 0.176 | F287S | 0.021 | V290S | 0.164 | V299S | 0.150 |
| H254T | 1.108 | L260T | −0.002 | F287T | 0.036 | V290T | 0.592 | V299T | 0.292 |
| H254V | 1.160 | L260V | 0.379 | F287V | 0.213 | V290V | 0.893 | V299V | 0.691 |
| H254W | 1.150 | L260W | 0.741 | F287W | 0.419 | V290W | 0.033 | V299W | 0.021 |
| H254Y | 0.966 | L260Y | 0.659 | F287Y | 0.185 | V290Y | 0.018 | V299Y | 0.013 |
| L303A | 0.663 | L308A | 0.191 | D311A | 0.800 | D323A | 0.658 | D345A | 0.654 |
| L303C | 0.737 | L308C | 0.852 | D311D | 0.747 | D323C | 0.624 | D345C | 0.513 |
| L303D | 0.616 | L308D | 0.760 | D311D | 0.672 | D323D | 0.644 | D345D | 0.527 |
| L303E | 0.741 | L308E | 0.706 | D311E | 0.688 | D323E | 0.661 | D345E | 0.517 |
| L303L | 0.990 | L308F | 0.056 | D311F | 0.933 | D323F | 0.613 | D345D | 0.664 |
| L303G | 0.717 | L308G | 0.842 | D311G | 0.897 | D323G | 0.707 | D345G | 0.700 |
| L303H | 0.621 | L308H | 1.186 | D311D | 0.800 | D323H | −0.013 | D345D | 0.406 |
| L303I | 0.804 | L308I | 1.180 | D311I | 0.783 | D323I | 0.608 | D345I | 0.528 |
| L303L | 1.097 | L308K | 0.149 | D311K | 0.977 | D323K | 0.890 | D345K | 0.532 |
| L303L | 1.104 | L308L | 1.049 | D311L | 0.978 | D323L | 0.768 | D345L | 0.730 |
| L303M | 0.770 | L308M | 0.017 | D311M | −0.008 | D323M | 0.687 | D345M | 0.657 |
| L303L | 0.812 | L308N | 0.714 | D311D | 0.706 | D323N | 0.681 | D345N | 0.547 |
| L303P | 0.661 | L308P | 0.203 | D311P | −0.016 | D323P | −0.012 | D345P | 0.368 |
| L303Q | 0.670 | L308Q | 0.647 | D311Q | 0.727 | D323Q | 0.582 | D345Q | 0.532 |
| L303R | 0.853 | L308R | 0.938 | D311R | 0.873 | D323R | 0.755 | D345R | 0.558 |
| L303S | 0.793 | L308S | 0.685 | D311S | 0.916 | D323S | 0.735 | D345S | 0.610 |
| L303T | 0.876 | L308T | 0.171 | D311T | 0.843 | D323T | 0.694 | D345T | 0.579 |
| L303V | 0.810 | L308V | 0.594 | D311V | 0.818 | D323V | 0.625 | D345V | 0.587 |
| L303W | 0.955 | L308W | 1.066 | D311W | 0.987 | D323W | 0.568 | D345W | 0.679 |
| L303L | 1.064 | L308Y | 0.918 | D311D | 1.083 | D323Y | 0.739 | D345Y | 0.567 |
| L376A | 0.233 | Y377A | 0.536 | K379A | 0.856 | F388A | −0.016 | G389A | 0.746 |
| L376C | 0.432 | Y377C | 0.551 | K379C | 0.775 | F388C | −0.034 | G389C | 0.826 |
| L376D | 0.081 | Y377D | 0.575 | K379D | 0.695 | F388D | 0.424 | G389D | 0.730 |
| L376E | 0.076 | Y377E | 0.565 | K379E | 0.770 | F388F | −0.012 | G389E | 0.766 |
| L376F | 0.918 | Y377F | 0.950 | K379F | 0.690 | F388F | −0.009 | G389F | 0.875 |
| L376G | 0.136 | Y377G | 0.690 | K379G | 0.930 | F388G | −0.077 | G389G | 0.943 |
| L376H | 0.488 | Y377H | 1.119 | K379H | 1.036 | F388H | 0.000 | G389H | 1.125 |
| L376I | 1.199 | Y377I | 1.033 | K379I | 0.862 | F388F | −0.048 | G389I | 1.034 |
| L376K | 0.223 | Y377K | 0.602 | K379K | −0.011 | F388K | −0.029 | G389K | 1.242 |
| L376L | 1.236 | Y377L | 1.105 | K379L | 0.947 | F388L | −0.001 | G389L | 1.158 |
| L376M | 0.649 | Y377M | 0.586 | K379M | 0.775 | F388F | −0.059 | G389M | 1.008 |
| L376N | 0.157 | Y377N | 0.567 | K379N | 0.791 | F388F | 0.885 | G389N | 0.963 |
| L376P | 0.114 | Y377P | 0.607 | K379P | 0.834 | F388P | −0.023 | G389P | 0.822 |
| L376Q | 0.479 | Y377Q | 0.490 | K379Q | 0.814 | F388Q | 0.956 | G389Q | 0.804 |
| L376R | 0.119 | Y377R | 0.231 | K379R | 1.122 | F388R | 0.738 | G389R | 1.059 |
| L376S | 0.174 | Y377S | 0.767 | K379S | 0.875 | F388S | 0.682 | G389S | 1.005 |
| L376T | 0.483 | Y377T | 0.975 | K379T | 1.088 | F388T | 0.893 | G389T | 1.178 |
| L376V | 0.601 | Y377V | 1.171 | K379V | 1.096 | F388V | 1.200 | G389V | 1.122 |
| L376W | 0.570 | Y377W | 1.263 | K379W | 0.916 | F388F | 1.285 | G389W | 0.870 |
| L376Y | 1.091 | Y377Y | 1.226 | K379Y | −0.003 | F388Y | −0.026 | G389Y | 1.012 |
| G397A | 0.396 | Q400A | 0.011 | F403A | 0.720 | Q421A | 0.911 | T426A | 0.680 |
| G397C | 0.053 | Q400C | 0.459 | F403C | 0.673 | Q421C | 0.005 | T426C | 0.760 |
| G397D | −0.022 | Q400D | −0.017 | F403D | 0.008 | Q421D | 0.862 | T426D | 0.657 |
| G397E | −0.016 | Q400E | 0.021 | F403E | 0.178 | Q421E | 1.241 | T426E | 0.585 |
| G397F | −0.017 | Q400F | −0.014 | F403F | 0.757 | Q421F | 0.011 | T426F | 0.818 |
| G397G | 1.047 | Q400G | 0.088 | F403G | 0.712 | Q421G | 1.157 | T426G | 0.863 |
| G397H | −0.018 | Q400H | 0.520 | F403H | 0.781 | Q421H | 1.257 | T426H | 0.858 |
| G397I | 0.093 | Q400I | 0.003 | F403I | 0.932 | Q421I | 1.086 | T426I | 1.195 |
| G397K | −0.028 | Q400K | −0.016 | F403K | −0.006 | Q421K | 1.115 | T426K | 0.400 |
| G397L | −0.006 | Q400L | 0.610 | F403L | 0.909 | Q421L | 1.047 | T426L | 0.817 |
| G397M | 0.075 | Q400M | 0.425 | F403M | 0.701 | Q421M | 0.917 | T426M | 0.658 |
| G397N | −0.004 | Q400N | 0.430 | F403N | 0.579 | Q421N | 0.765 | T426N | 0.599 |
| G397P | −0.002 | Q400P | 0.007 | F403P | −0.006 | Q421P | 0.742 | T426P | 0.462 |
| G397Q | 0.003 | Q400Q | 0.737 | F403Q | 0.381 | Q421Q | 1.081 | T426Q | 0.587 |
| G397R | 0.000 | Q400R | −0.011 | F403R | −0.018 | Q421R | 1.393 | T426R | 0.375 |
| G397S | −0.002 | Q400S | 0.273 | F403S | 0.806 | Q421S | 0.835 | T426S | 0.863 |
| G397T | −0.034 | Q400T | 0.505 | F403T | 1.032 | Q421T | 1.084 | T426T | 0.044 |
| G397V | 0.160 | Q400V | 0.204 | F403V | 1.055 | Q421V | 1.130 | T426V | 1.054 |
| G397W | −0.029 | Q400W | −0.026 | F403W | 0.053 | Q421W | 1.048 | T426W | 0.730 |
| G397Y | −0.004 | Q400Y | −0.018 | F403Y | 0.912 | Q421Y | 0.905 | T426Y | 0.479 |
| P430A | 0.777 | F434A | 0.170 | N438A | −0.019 | A443A | 1.166 | A445A | 0.681 |
| P430C | 0.718 | F434C | 0.232 | N438C | −0.054 | A443A | 1.116 | A445C | 0.653 |
| P430D | 0.002 | F434D | 0.009 | N438D | −0.044 | A443A | 1.128 | A445D | 0.619 |

TABLE 8-continued

| Mutation | Growth Index | Mutation | Growth Index | Mutation | Growth Index | Mutation | Growth Index | Mutation | Growth Index |
|---|---|---|---|---|---|---|---|---|---|
| P430E | 0.002 | F434E | 0.011 | N438E | −0.044 | A443A | 1.154 | A445E | 0.669 |
| P430F | −0.001 | F434F | 0.240 | N438F | −0.036 | A443F | 0.283 | A445F | 0.613 |
| P430G | 0.300 | F434G | 0.032 | N438G | −0.070 | A443G | 0.504 | A445G | 0.624 |
| P430H | 0.023 | F434H | 0.085 | N438H | −0.036 | A443H | 0.847 | A445H | 1.183 |
| P430I | 0.021 | F434I | 0.554 | N438I | −0.046 | A443I | 0.625 | A445I | 0.416 |
| P430K | 0.014 | F434K | 0.053 | N438K | −0.057 | A443A | 1.342 | A445K | 0.858 |
| P430L | −0.003 | F434L | 0.480 | N438L | −0.053 | A443L | 0.840 | A445L | 0.532 |
| P430M | 0.002 | F434M | 0.454 | N438M | −0.053 | A443A | 1.365 | A445M | 0.596 |
| P430N | −0.009 | F434N | 0.053 | N438N | 1.271 | A443N | 0.818 | A445N | 0.639 |
| P430P | −0.003 | F434P | 0.014 | N438P | −0.063 | A443P | 0.059 | A445P | 0.525 |
| P430Q | 0.013 | F434Q | 0.040 | N438Q | −0.063 | A443Q | 0.665 | A445Q | 0.737 |
| P430R | 0.004 | F434R | 0.003 | N438R | −0.060 | A443R | 0.435 | A445R | 0.685 |
| P430S | 1.103 | F434S | 0.102 | N438S | −0.089 | A443S | 0.860 | A445S | 0.918 |
| P430T | 1.096 | F434T | 0.438 | N438T | −0.042 | A443T | 0.028 | A445T | 0.698 |
| P430V | 1.061 | F434V | 0.460 | N438V | −0.047 | A443V | 0.397 | A445V | 0.513 |
| P430W | 0.019 | F434W | 0.006 | N438W | −0.046 | A443A | 1.290 | A445W | 0.440 |
| P430Y | −0.005 | F434Y | 0.136 | N438Y | −0.062 | A443A | 1.205 | A445Y | 0.528 |
| A448A | 0.765 | E451A | −0.037 | A453A | 0.901 | N454A | 0.735 | S457A | 0.330 |
| A448C | 0.826 | E451C | −0.041 | A453C | 0.877 | N454C | 0.530 | S457C | 0.466 |
| A448D | 0.737 | E451D | −0.023 | A453D | 0.541 | N454D | 0.555 | S457D | 0.753 |
| A448E | 0.721 | E451E | 1.127 | A453E | 0.770 | N454E | 0.720 | S457E | 0.738 |
| A448F | 0.780 | E451F | −0.033 | A453F | 0.621 | N454F | 0.490 | S457F | 0.802 |
| A448G | 0.871 | E451G | −0.022 | A453G | 0.258 | N454G | 0.830 | S457G | 0.648 |
| A448H | 1.264 | E451H | −0.022 | A453H | 0.755 | N454H | 0.763 | S457H | 1.160 |
| A448I | 1.013 | E451I | −0.035 | A453I | 0.704 | N454I | 0.313 | S457I | 0.435 |
| A448K | 0.887 | E451K | −0.015 | A453K | 0.448 | N454N | 1.099 | S457K | 0.836 |
| A448L | 0.855 | E451L | −0.045 | A453L | 0.762 | N454L | 0.610 | S457L | 0.615 |
| A448M | 0.780 | E451E | 1.477 | A453A | 0.836 | N454M | 0.224 | S457M | 0.758 |
| A448N | 0.794 | E451N | −0.060 | A453N | 0.826 | N454N | 0.865 | S457N | 0.816 |
| A448P | 0.698 | E451P | −0.046 | A453P | 0.021 | N454P | −0.003 | S457P | 0.138 |
| A448Q | 0.822 | E451Q | 0.056 | A453A | 0.848 | N454Q | 0.619 | S457Q | 1.057 |
| A448R | 1.147 | E451R | −0.026 | A453R | 0.586 | N454R | −0.027 | S457R | 1.104 |
| A448S | 1.107 | E451S | −0.058 | A453S | 0.848 | N454S | 0.840 | S457S | 1.230 |
| A448T | 1.354 | E451T | −0.041 | A453T | 0.909 | N454T | 0.733 | S457T | 1.086 |
| A448V | 1.232 | E451V | −0.036 | A453V | 0.642 | N454V | 0.630 | S457V | 0.594 |
| A448W | 0.725 | E451W | −0.013 | A453W | 0.885 | N454W | 0.657 | S457W | 0.743 |
| A448Y | 0.884 | E451Y | −0.033 | A453Y | −0.013 | N454Y | 0.671 | S457Y | 0.989 |
| T462A | 0.930 | L469A | 0.825 | N476A | 0.018 | K487A | 1.149 | E488A | 0.766 |
| T462C | 0.845 | L469C | 0.850 | N476C | −0.039 | K487C | 1.026 | E488C | 0.664 |
| T462D | 0.839 | L469L | 0.728 | N476D | 0.728 | K487D | 0.819 | E488D | 0.650 |
| T462E | −0.077 | L469L | 0.768 | N476E | 0.624 | K487E | 0.935 | E488E | 0.661 |
| T462F | 1.080 | L469F | 0.928 | N476F | −0.035 | K487F | 1.119 | E488F | 0.667 |
| T462G | 1.022 | L469G | 0.748 | N476G | −0.017 | K487G | 1.215 | E488G | 0.655 |
| T462H | 1.261 | L469H | 0.868 | N476H | −0.013 | K487H | 1.212 | E488H | 0.641 |
| T462I | 1.182 | L469I | 0.917 | N476I | −0.011 | K487I | 0.992 | E488I | 0.878 |
| T462K | 1.261 | L469L | 1.002 | N476K | −0.046 | K487K | 1.248 | E488K | 0.322 |
| T462L | 1.037 | L469L | 0.980 | N476L | −0.078 | K487L | 1.144 | E488L | 0.756 |
| T462M | 0.890 | L469L | 0.821 | N476M | 0.705 | K487M | 1.251 | E488M | 0.516 |
| T462N | 0.809 | L469N | 0.879 | N476N | 0.008 | K487N | 0.492 | E488N | 0.247 |
| T462P | 0.599 | L469P | 0.835 | N476P | 0.642 | K487P | 0.264 | E488P | 0.166 |
| T462Q | 0.827 | L469Q | 0.787 | N476Q | 0.835 | K487Q | 0.925 | E488Q | 0.613 |
| T462R | 0.941 | L469R | 0.983 | N476R | 1.126 | K487R | 1.314 | E488R | 0.539 |
| T462S | 1.058 | L469S | 0.871 | N476S | 0.819 | K487S | 1.122 | E488S | 0.429 |
| T462T | 1.427 | L469T | 0.875 | N476T | 1.087 | K487T | 1.382 | E488T | 0.648 |
| T462V | 1.312 | L469V | 0.946 | N476V | 1.146 | K487V | 1.365 | E488V | 0.723 |
| T462W | 1.141 | L469W | 1.056 | N476W | 1.146 | K487W | 1.380 | E488W | 0.705 |
| T462Y | 1.139 | L469Y | 0.192 | N476Y | 1.241 | K487Y | 0.970 | E488Y | 0.436 |
| K489A | 0.943 | L490A | 0.897 | G491A | 1.076 | G492A | 1.485 | S493A | 1.031 |
| K489C | 0.678 | L490C | 0.880 | G491C | 1.053 | G492C | 1.109 | S493C | 1.043 |
| K489D | 0.618 | L490D | 0.782 | G491D | 0.963 | G492D | 1.242 | S493D | −0.003 |
| K489E | 0.579 | L490E | 0.751 | G491E | 0.939 | G492E | 1.249 | S493E | 1.273 |
| K489F | 0.926 | L490F | 1.137 | G491F | 1.127 | G492F | 0.945 | S493F | 0.812 |
| K489G | 0.842 | L490G | 0.861 | G491G | 0.914 | G492G | 1.114 | S493G | 1.205 |
| K489H | 1.081 | L490H | 1.458 | G491H | 1.413 | G492H | 1.379 | S493H | 0.954 |
| K489I | 1.210 | L490I | 1.522 | G491I | 1.569 | G492I | 1.262 | S493I | 1.202 |
| K489K | 1.647 | L490K | 0.940 | G491K | 1.292 | G492K | 1.304 | S493K | 1.228 |
| K489L | 1.045 | L490L | 1.246 | G491L | 1.358 | G492L | 1.179 | S493L | 1.261 |
| K489M | 0.231 | L490M | 1.044 | G491M | 1.142 | G492M | 0.889 | S493M | 1.086 |
| K489N | 0.612 | L490N | 0.954 | G491N | 1.000 | G492N | 0.987 | S493N | 0.794 |
| K489P | 0.504 | L490P | 0.174 | G491P | 0.206 | G492P | 0.888 | S493P | 0.933 |
| K489Q | 0.664 | L490Q | 0.622 | G491Q | 0.932 | G492Q | 0.934 | S493Q | 0.832 |
| K489R | 1.236 | L490R | 0.900 | G491R | 1.157 | G492R | 1.064 | S493R | 1.352 |
| K489S | 0.875 | L490S | 0.985 | G491S | 1.034 | G492S | 0.858 | S493S | 1.195 |
| K489T | 1.200 | L490T | 1.214 | G491T | 1.326 | G492T | 1.384 | S493T | 1.530 |
| K489V | 1.138 | L490V | 1.406 | G491V | 1.360 | G492V | 1.367 | S493V | 1.404 |
| K489W | 1.350 | L490W | 1.343 | G491W | 1.328 | G492W | 1.178 | S493W | 1.287 |
| K489Y | 0.830 | L490Y | −0.007 | G491Y | 1.313 | G492Y | 1.073 | S493Y | 1.078 |

TABLE 8-continued

| Mutation | Growth Index | Mutation | Growth Index | Mutation | Growth Index | Mutation | Growth Index | Mutation | Growth Index |
|---|---|---|---|---|---|---|---|---|---|
| L494A | 0.687 | F495A | 1.025 | A496A | 0.763 | K497A | 0.841 | P498A | 0.636 |
| L494C | 0.864 | F495C | 0.948 | A496C | 0.701 | K497C | 0.636 | P498C | 0.746 |
| L494D | 0.863 | F495D | 0.955 | A496D | 0.744 | K497D | 0.811 | P498D | 0.862 |
| L494E | 0.856 | F495E | 0.944 | A496E | 0.795 | K497E | 0.718 | P498E | 0.857 |
| L494L | 0.976 | F495F | 1.074 | A496F | 0.971 | K497F | 0.936 | P498F | 1.017 |
| L494G | 0.935 | F495G | 1.025 | A496G | 0.819 | K497G | 0.962 | P498G | 1.011 |
| L494H | 0.825 | F495H | 1.314 | A496H | 1.201 | K497H | 1.035 | P498H | 1.259 |
| L494I | 0.927 | F495I | 1.147 | A496I | 1.144 | K497I | 1.023 | P498I | 1.107 |
| L494K | 1.029 | F495K | 1.448 | A496K | 1.030 | K497K | 1.118 | P498K | 1.107 |
| L494L | 1.056 | F495L | 1.836 | A496L | 1.061 | K497L | 1.029 | P498L | 1.089 |
| L494L | 0.784 | F495M | 1.254 | A496M | 0.839 | K497M | 0.735 | P498M | 0.864 |
| L494N | 0.815 | F495N | 0.982 | A496N | 0.664 | K497N | 0.730 | P498N | 0.798 |
| L494P | 0.734 | F495P | 0.946 | A496P | 0.816 | K497P | 0.691 | P498P | 0.882 |
| L494Q | 0.736 | F495Q | 1.161 | A496Q | 0.762 | K497Q | 0.746 | P498Q | 0.805 |
| L494R | 0.889 | F495R | 1.285 | A496R | 1.058 | K497R | 0.854 | P498R | 1.121 |
| L494S | 0.832 | F495S | 1.399 | A496S | 0.933 | K497S | 0.923 | P498S | 1.032 |
| L494T | 0.425 | F495T | 1.565 | A496T | 1.172 | K497T | 1.133 | P498T | 1.155 |
| L494V | 0.895 | F495V | 1.379 | A496V | 1.036 | K497V | 1.124 | P498V | 1.105 |
| L494W | 0.974 | F495W | 1.442 | A496W | 0.982 | K497W | 0.822 | P498W | 0.904 |
| L494Y | 0.949 | F495Y | 1.452 | A496Y | 1.014 | K497Y | 0.991 | P498Y | 1.103 |
| Q509A | 0.977 | Y514A | −0.015 | H515H | −0.006 | A519A | 0.853 | T521A | −0.015 |
| Q509C | 0.844 | Y514C | −0.008 | H515E | 0.657 | A519C | 0.502 | T521C | 0.003 |
| Q509D | 0.334 | Y514D | 0.018 | H515F | 0.782 | A519D | 0.334 | T521D | 0.008 |
| Q509E | 0.425 | Y514E | 0.002 | H515G | 0.850 | A519E | 0.394 | T521E | 0.823 |
| Q509F | 0.021 | Y514F | 0.004 | H515H | −0.023 | A519F | 0.757 | T521F | 0.000 |
| Q509G | 0.767 | Y514G | 0.013 | H515H | −0.015 | A519G | 0.851 | T521G | 0.981 |
| Q509H | 0.406 | Y514H | 0.026 | H515K | 0.984 | A519H | 0.759 | T521H | 0.018 |
| Q509I | 1.111 | Y514I | 0.022 | H515L | 0.146 | A519A | 0.866 | T521I | 0.012 |
| Q509K | 0.290 | Y514K | 0.017 | H515M | 0.777 | A519K | 0.991 | T521K | 0.007 |
| Q509L | 0.154 | Y514L | −0.004 | H515N | 0.696 | A519L | 0.658 | T521L | 0.712 |
| Q509M | 1.046 | Y514M | −0.016 | H515P | −0.015 | A519A | 0.909 | T521M | 0.218 |
| Q509N | 0.558 | Y514N | −0.011 | H515Q | 0.735 | A519A | 0.849 | T521N | −0.027 |
| Q509P | 0.012 | Y514P | 0.006 | H515R | 0.961 | A519P | 0.000 | T521P | 0.012 |
| Q509Q | 0.887 | Y514Q | 0.018 | H515S | 0.626 | A519Q | 0.437 | T521Q | 0.497 |
| Q509R | −0.002 | Y514R | 0.001 | H515T | 0.727 | A519R | 0.887 | T521R | −0.006 |
| Q509S | 1.004 | Y514S | 0.011 | H515V | 0.777 | A519S | 0.658 | T521S | 0.841 |
| Q509T | 1.440 | Y514T | 0.021 | H515W | 0.966 | A519T | 0.609 | T521T | 0.005 |
| Q509V | 1.307 | Y514V | 0.020 | H515Y | 1.072 | A519V | 0.451 | T521V | 0.450 |
| Q509W | −0.003 | Y514W | 0.009 | | | A519W | 1.274 | T521W | 0.012 |
| Q509Y | −0.006 | Y514Y | 1.093 | | | A519Y | 0.727 | T521Y | −0.004 |
| E525A | 0.693 | R528A | 0.491 | T536A | 0.263 | I539A | 0.765 | L540A | 0.998 |
| E525C | 0.810 | R528C | 0.305 | T536C | 0.272 | I539C | 0.884 | L540C | 0.901 |
| E525D | 0.827 | R528D | 0.084 | T536D | 0.175 | I539D | −0.007 | L540D | 0.931 |
| E525E | 0.671 | R528E | 0.343 | T536E | 0.143 | I539E | 0.355 | L540E | 1.007 |
| E525F | 0.770 | R528F | 0.692 | T536F | 0.454 | I539F | 0.651 | L540F | 1.031 |
| E525G | 0.800 | R528G | 0.333 | T536G | 0.415 | I539G | 0.279 | L540G | 1.052 |
| E525H | 0.727 | R528H | 0.669 | T536H | 0.457 | I539H | 0.885 | L540H | 1.343 |
| E525E | 0.829 | R528R | 0.921 | T536I | 0.486 | I539I | 1.169 | L540I | 1.309 |
| E525K | 1.131 | R528K | 1.047 | T536K | 0.308 | I539K | 1.004 | L540K | 1.278 |
| E525L | 0.889 | R528L | 0.588 | T536L | 0.625 | I539L | 1.209 | L540L | 1.119 |
| E525M | 0.788 | R528M | 0.704 | T536M | 0.294 | I539M | 0.960 | L540M | 1.089 |
| E525N | 0.726 | R528N | 0.349 | T536N | 0.289 | I539N | 0.319 | L540N | 0.975 |
| E525P | 0.366 | R528P | −0.018 | T536P | 0.011 | I539P | 0.530 | L540P | 0.963 |
| E525Q | 0.722 | R528R | 0.845 | T536T | 0.303 | I539Q | 0.637 | L540Q | 1.095 |
| E525R | 0.833 | R528R | 0.924 | T536R | 0.149 | I539R | 0.645 | L540R | 1.135 |
| E525S | 0.638 | R528S | 0.425 | T536S | 0.355 | I539S | 0.895 | L540S | 1.122 |
| E525T | 0.822 | R528T | 0.595 | T536T | 0.402 | I539T | 1.257 | L540T | 1.580 |
| E525V | 0.851 | R528V | 0.854 | T536V | 0.382 | I539V | 1.403 | L540V | 1.726 |
| E525W | 0.942 | R528W | 0.296 | T536T | 0.591 | I539W | 0.644 | L540W | 1.177 |
| E525E | 1.014 | R528Y | 0.606 | T536Y | 0.579 | I539Y | 0.672 | L540Y | 1.203 |
| R544A | 0.832 | | | | | | | | |
| R544C | 1.041 | | | | | | | | |
| R544D | 0.831 | | | | | | | | |
| R544E | 0.843 | | | | | | | | |
| R544F | 0.953 | | | | | | | | |
| R544G | 0.910 | | | | | | | | |
| R544H | 1.113 | | | | | | | | |
| R544I | 1.050 | | | | | | | | |
| R544K | 1.189 | | | | | | | | |
| R544L | 1.022 | | | | | | | | |
| R544M | 0.982 | | | | | | | | |
| R544N | 0.885 | | | | | | | | |
| R544P | 0.951 | | | | | | | | |
| R544Q | 0.865 | | | | | | | | |
| R544R | 0.865 | | | | | | | | |
| R544S | 1.232 | | | | | | | | |
| R544T | 1.331 | | | | | | | | |

TABLE 8-continued

| Mutation | Growth Index | Mutation | Growth Index | Mutation | Growth Index | Mutation | Growth Index | Mutation | Growth Index |
|---|---|---|---|---|---|---|---|---|---|
| R544V | 1.257 | | | | | | | | |
| R544W | 1.280 | | | | | | | | |
| R544Y | 0.504 | | | | | | | | |

Example 4

Analysis of Growth Data for *E. Coli* Clones Expressing Single-Site Mutants of Isoprene Synthase This example demonstrates the analysis of growth data by performance index instead of growth index. G-values were determined at regular time intervals using the Enzyscreen Growth Profiler 1152. The growth rate for each sample was calculated by linear regression using Excel. This is given by the rise of the G-value with respect to time ($\Delta G/\Delta t$). This value is termed "Slope." The final cell density of each sample was estimated from the final G-value minus the initial G-value. This number is termed "Delta."

For each 96-well plate, each "Slope" and "Delta" value was normalized by dividing it by the average values of the wells containing the wild-type controls. Several obvious wild-type outliers were rejected when performing this calculation. The normalized values are termed the "Performance Index" or "P.I."

The "Slope PI" and the "Delta PI" are highly correlated, so an additional PI, called the "Average PI" was calculated from them. This is simply the mean of the two PI values. Table 9 shows the various PI values for all variants at all positions analyzed, and Table 10 shows the top 150 variants with the highest values for normalized average PI.

TABLE 9

| Variant | Slope PI | Delta PI | Avg PI | Norm Slope PI | Norm Delta PI | Norm Avg PI |
|---|---|---|---|---|---|---|
| A3A | 0.841076 | 0.875095 | 0.858086 | 0.7934 | 0.8064 | 0.8000 |
| A3C | 0.789685 | 0.806075 | 0.79788 | 0.7449 | 0.7428 | 0.7438 |
| A3D | 0.915678 | 0.963838 | 0.939758 | 0.8638 | 0.8881 | 0.8761 |
| A3E | 0.955539 | 1.010676 | 0.983107 | 0.9014 | 0.9313 | 0.9165 |
| A3F | 1.02453 | 1.05258 | 1.038555 | 0.9665 | 0.9699 | 0.9682 |
| A3G | 0.897839 | 0.931793 | 0.914816 | 0.8469 | 0.8586 | 0.8528 |
| A3H | 0.965518 | 1.01314 | 0.989329 | 0.9108 | 0.9336 | 0.9223 |
| A3I | 0.934467 | 1.003281 | 0.968874 | 0.8815 | 0.9245 | 0.9032 |
| A3K | 1.041742 | 1.055045 | 1.048394 | 0.9827 | 0.9722 | 0.9774 |
| A3L | 0.897744 | 0.951514 | 0.924629 | 0.8469 | 0.8768 | 0.8620 |
| A3M | 0.423923 | 0.463432 | 0.443677 | 0.3999 | 0.4270 | 0.4136 |
| A3N | 0.941676 | 0.961373 | 0.951525 | 0.8883 | 0.8859 | 0.8871 |
| A3P | 0.897654 | 0.917002 | 0.907328 | 0.8468 | 0.8450 | 0.8459 |
| A3Q | 1.008068 | 1.040255 | 1.024162 | 0.9509 | 0.9585 | 0.9548 |
| A3R | 1.042771 | 1.106812 | 1.074791 | 0.9837 | 1.0199 | 1.0020 |
| A3S | 0.752869 | 0.811004 | 0.781936 | 0.7102 | 0.7473 | 0.7290 |
| A3T | 1.100956 | 1.190624 | 1.14579 | 1.0386 | 1.0971 | 1.0682 |
| A3V | 0.409904 | 0.465896 | 0.4379 | 0.3867 | 0.4293 | 0.4082 |
| A3W | 0.875926 | 0.941654 | 0.90879 | 0.8263 | 0.8677 | 0.8472 |
| A3Y | 0.97426 | 1.04765 | 1.010955 | 0.9190 | 0.9654 | 0.9425 |
| A7A | 0.671295 | 0.589149 | 0.630222 | 0.7943 | 0.6838 | 0.7385 |
| A7C | 0.432727 | 0.345109 | 0.388918 | 0.5120 | 0.4006 | 0.4558 |
| A7D | 0.128681 | 0.009861 | 0.069271 | 0.1523 | 0.0114 | 0.0812 |
| A7E | 0.210737 | 0.160228 | 0.185483 | 0.2493 | 0.1860 | 0.2174 |
| A7F | 0.354182 | 0.258831 | 0.306507 | 0.4191 | 0.3004 | 0.3592 |
| A7G | 0.666027 | 0.660635 | 0.663331 | 0.7880 | 0.7668 | 0.7773 |
| A7H | 0.384921 | 0.340178 | 0.36255 | 0.4554 | 0.3948 | 0.4249 |
| A7I | 0.295123 | 0.288412 | 0.291768 | 0.3492 | 0.3348 | 0.3419 |
| A7K | 0.016319 | 0.081347 | 0.048833 | 0.0193 | 0.0944 | 0.0572 |
| A7L | 0.167392 | 0.202135 | 0.184764 | 0.1981 | 0.2346 | 0.2165 |
| A7M | 0.215773 | 0.189809 | 0.202791 | 0.2553 | 0.2203 | 0.2376 |

TABLE 9-continued

| Variant | Slope PI | Delta PI | Avg PI | Norm Slope PI | Norm Delta PI | Norm Avg PI |
|---|---|---|---|---|---|---|
| A7N | 0.319846 | 0.261297 | 0.290572 | 0.3784 | 0.3033 | 0.3405 |
| A7P | 0.327703 | 0.261297 | 0.2945 | 0.3877 | 0.3033 | 0.3451 |
| A7Q | 0.276703 | 0.244041 | 0.260372 | 0.3274 | 0.2833 | 0.3051 |
| A7R | 0.240467 | 0.251436 | 0.245952 | 0.2845 | 0.2918 | 0.2882 |
| A7S | 0.426395 | 0.458501 | 0.442448 | 0.5045 | 0.5322 | 0.5185 |
| A7T | 0.411256 | 0.446176 | 0.428716 | 0.4866 | 0.5179 | 0.5024 |
| A7V | 0.544081 | 0.557103 | 0.550592 | 0.6437 | 0.6466 | 0.6452 |
| A7W | 0.544657 | 0.57929 | 0.561973 | 0.6444 | 0.6724 | 0.6585 |
| A7Y | 0.320163 | 0.350038 | 0.3351 | 0.3788 | 0.4063 | 0.3927 |
| Y9A | 0.257267 | 0.246507 | 0.251887 | 0.2427 | 0.2271 | 0.2348 |
| Y9C | 0.183255 | 0.182414 | 0.182834 | 0.1729 | 0.1681 | 0.1704 |
| Y9D | 0.034026 | 0.091208 | 0.062617 | 0.0321 | 0.0840 | 0.0584 |
| Y9E | −0.01448 | −0.01232 | −0.0134 | −0.0137 | −0.0114 | −0.0125 |
| Y9F | 1.00751 | 1.04272 | 1.025115 | 0.9504 | 0.9608 | 0.9557 |
| Y9G | 0.093756 | 0.108462 | 0.101109 | 0.0884 | 0.0999 | 0.0943 |
| Y9H | 0.618885 | 0.744448 | 0.681666 | 0.5838 | 0.6860 | 0.6355 |
| Y9I | 0.517363 | 0.579288 | 0.548325 | 0.4880 | 0.5338 | 0.5112 |
| Y9K | 0.182975 | 0.187345 | 0.18516 | 0.1726 | 0.1726 | 0.1726 |
| Y9L | 0.371301 | 0.409199 | 0.39025 | 0.3503 | 0.3771 | 0.3638 |
| Y9M | 0.194273 | 0.229251 | 0.211762 | 0.1833 | 0.2112 | 0.1974 |
| Y9N | 0.210955 | 0.229251 | 0.220103 | 0.1990 | 0.2112 | 0.2052 |
| Y9P | 0.342432 | 0.431386 | 0.386909 | 0.3230 | 0.3975 | 0.3607 |
| Y9Q | 0.176212 | 0.246507 | 0.211359 | 0.1662 | 0.2271 | 0.1970 |
| Y9R | 0.375158 | 0.433852 | 0.404505 | 0.3539 | 0.3998 | 0.3771 |
| Y9S | 0.330182 | 0.352505 | 0.341343 | 0.3115 | 0.3248 | 0.3182 |
| Y9T | 0.434153 | 0.490547 | 0.46235 | 0.4095 | 0.4520 | 0.4310 |
| Y9V | 0.470581 | 0.532453 | 0.501517 | 0.4439 | 0.4906 | 0.4675 |
| Y9W | 0.812232 | 0.84798 | 0.830106 | 0.7662 | 0.7814 | 0.7739 |
| Y9Y | 0.195035 | 0.310598 | 0.252816 | 0.1840 | 0.2862 | 0.2357 |
| N12A | 0.871587 | 0.867702 | 0.869644 | 0.8222 | 0.7995 | 0.8107 |
| N12C | 0.916719 | 0.976164 | 0.946441 | 0.8648 | 0.8995 | 0.8823 |
| N12D | 0.561783 | 0.626126 | 0.593955 | 0.5299 | 0.5769 | 0.5537 |
| N12E | 0.477841 | 0.547243 | 0.512542 | 0.4508 | 0.5043 | 0.4778 |
| N12F | 0.567358 | 0.626125 | 0.596741 | 0.5352 | 0.5769 | 0.5563 |
| N12G | 0.684853 | 0.717333 | 0.701093 | 0.6460 | 0.6610 | 0.6536 |
| N12H | 0.810808 | 0.919468 | 0.865138 | 0.7649 | 0.8472 | 0.8065 |
| N12I | 0.756778 | 0.838119 | 0.797449 | 0.7139 | 0.7723 | 0.7434 |
| N12K | 0.649287 | 0.722262 | 0.685774 | 0.6125 | 0.6655 | 0.6393 |
| N12L | 0.538939 | 0.589149 | 0.564044 | 0.5084 | 0.5429 | 0.5258 |
| N12M | 0.814588 | 0.860305 | 0.837447 | 0.7684 | 0.7927 | 0.7807 |
| N12N | 0.920787 | 0.909607 | 0.915197 | 0.8686 | 0.8382 | 0.8532 |
| N12P | 0.771118 | 0.811006 | 0.791062 | 0.7274 | 0.7473 | 0.7375 |
| N12Q | 0.683834 | 0.724728 | 0.704281 | 0.6451 | 0.6678 | 0.6566 |
| N12R | 0.695487 | 0.719798 | 0.707643 | 0.6561 | 0.6633 | 0.6597 |
| N12S | 1.002791 | 1.050116 | 1.026453 | 0.9460 | 0.9676 | 0.9569 |
| N12T | 0.951928 | 1.057511 | 1.00472 | 0.8980 | 0.9744 | 0.9367 |
| N12V | 0.856073 | 0.909607 | 0.88284 | 0.8076 | 0.8382 | 0.8230 |
| N12W | 0.459353 | 0.44864 | 0.453997 | 0.4333 | 0.4134 | 0.4232 |
| N12Y | −0.00549 | 0.064091 | 0.029301 | −0.0052 | 0.0591 | 0.0273 |
| S13A | 0.839388 | 0.852911 | 0.84615 | 0.7918 | 0.7859 | 0.7888 |
| S13C | 0.879913 | 0.880027 | 0.87997 | 0.8300 | 0.8109 | 0.8204 |
| S13D | 0.725086 | 0.766635 | 0.74586 | 0.6840 | 0.7064 | 0.6953 |
| S13E | 0.846514 | 0.877561 | 0.862037 | 0.7985 | 0.8086 | 0.8036 |
| S13F | 0.97893 | 0.988489 | 0.983709 | 0.9234 | 0.9108 | 0.9171 |
| S13G | 0.986121 | 0.9737 | 0.979911 | 0.9302 | 0.8972 | 0.9135 |
| S13H | 1.001156 | 1.052581 | 1.026869 | 0.9444 | 0.9699 | 0.9573 |
| S13I | 0.998662 | 1.020535 | 1.009598 | 0.9421 | 0.9404 | 0.9412 |
| S13K | 1.051537 | 1.069836 | 1.060686 | 0.9919 | 0.9858 | 0.9888 |
| S13L | 0.918125 | 0.986023 | 0.952074 | 0.8661 | 0.9086 | 0.8876 |
| S13M | 0.872911 | 0.880027 | 0.876469 | 0.8234 | 0.8109 | 0.8171 |
| S13N | 0.88043 | 0.917002 | 0.898716 | 0.8305 | 0.8450 | 0.8378 |
| S13P | 0.446478 | 0.468362 | 0.45742 | 0.4212 | 0.4316 | 0.4264 |
| S13Q | 0.910396 | 0.949047 | 0.929722 | 0.8588 | 0.8745 | 0.8667 |
| S13R | 0.996836 | 1.023 | 1.009918 | 0.9403 | 0.9426 | 0.9415 |

TABLE 9-continued

| Variant | Slope PI | Delta PI | Avg PI | Norm Slope PI | Norm Delta PI | Norm Avg PI |
|---|---|---|---|---|---|---|
| S13S | 0.951103 | 0.978628 | 0.964865 | 0.8972 | 0.9018 | 0.8995 |
| S13T | 1.003299 | 1.055045 | 1.029172 | 0.9464 | 0.9722 | 0.9595 |
| S13V | 0.976195 | 1.005745 | 0.99097 | 0.9209 | 0.9267 | 0.9238 |
| S13W | 0.88426 | 0.897281 | 0.89077 | 0.8341 | 0.8268 | 0.8304 |
| S13Y | 0.858918 | 0.882492 | 0.870705 | 0.8102 | 0.8132 | 0.8117 |
| Y16A | 0.581078 | 0.59901 | 0.590044 | 0.5829 | 0.5870 | 0.5850 |
| Y16C | 0.749132 | 0.719797 | 0.734464 | 0.7515 | 0.7053 | 0.7281 |
| Y16D | 0.650874 | 0.616266 | 0.63357 | 0.6529 | 0.6039 | 0.6281 |
| Y16E | 0.754326 | 0.754308 | 0.754317 | 0.7567 | 0.7391 | 0.7478 |
| Y16F | 0.922821 | 0.978629 | 0.950725 | 0.9258 | 0.9589 | 0.9425 |
| Y16G | 0.648257 | 0.658171 | 0.653214 | 0.6503 | 0.6449 | 0.6476 |
| Y16H | 0.984379 | 1.04272 | 1.01355 | 0.9875 | 1.0217 | 1.0048 |
| Y16I | 1.110586 | 1.183220 | 1.146907 | 1.1141 | 1.1594 | 1.1370 |
| Y16K | 0.633379 | 0.680357 | 0.656868 | 0.6354 | 0.6667 | 0.6512 |
| Y16L | 0.993195 | 1.05258 | 1.022887 | 0.9964 | 1.0314 | 1.0141 |
| Y16M | 0.982897 | 0.939188 | 0.961042 | 0.9860 | 0.9203 | 0.9528 |
| Y16N | 0.657766 | 0.643281 | 0.650573 | 0.6599 | 0.6304 | 0.6450 |
| Y16P | 0.651509 | 0.608869 | 0.630189 | 0.6536 | 0.5966 | 0.6248 |
| Y16Q | 0.672027 | 0.655707 | 0.663867 | 0.6742 | 0.6425 | 0.6582 |
| Y16R | 0.471778 | 0.502872 | 0.487325 | 0.4733 | 0.4928 | 0.4831 |
| Y16S | 0.647752 | 0.62859 | 0.638171 | 0.6498 | 0.6159 | 0.6327 |
| Y16T | 0.882118 | 0.912073 | 0.897096 | 0.8849 | 0.8937 | 0.8894 |
| Y16V | 0.970716 | 0.934257 | 0.952486 | 0.9738 | 0.9155 | 0.9443 |
| Y16W | 0.858273 | 0.8677 | 0.862987 | 0.8610 | 0.8502 | 0.8556 |
| Y16Y | 0.94774 | 0.946583 | 0.947162 | 0.9508 | 0.9275 | 0.9390 |
| Y18A | 0.708163 | 0.727193 | 0.717678 | 0.7104 | 0.7126 | 0.7115 |
| Y18C | 0.996454 | 1.069837 | 1.033146 | 0.9996 | 1.0483 | 1.0243 |
| Y18D | 0.786961 | 0.815934 | 0.801448 | 0.7895 | 0.7995 | 0.7946 |
| Y18E | 0.791922 | 0.872631 | 0.832277 | 0.7944 | 0.8551 | 0.8251 |
| Y18F | 0.885444 | 0.939188 | 0.912316 | 0.8883 | 0.9203 | 0.9045 |
| Y18G | 0.95546 | 0.978628 | 0.967044 | 0.9585 | 0.9589 | 0.9587 |
| Y18H | 0.934606 | 1.01314 | 0.973873 | 0.9376 | 0.9928 | 0.9655 |
| Y18I | 0.954393 | 0.981093 | 0.967743 | 0.9574 | 0.9614 | 0.9594 |
| Y18K | 0.852615 | 0.929327 | 0.890971 | 0.8553 | 0.9106 | 0.8833 |
| Y18L | 0.8412 | 0.872631 | 0.856916 | 0.8439 | 0.8551 | 0.8495 |
| Y18M | 0.872384 | 0.882492 | 0.877438 | 0.8752 | 0.8647 | 0.8699 |
| Y18N | 0.957651 | 0.936722 | 0.947187 | 0.9607 | 0.9179 | 0.9390 |
| Y18P | 0.690836 | 0.692681 | 0.691759 | 0.6930 | 0.6787 | 0.6858 |
| Y18Q | 0.855777 | 0.887422 | 0.871599 | 0.8585 | 0.8696 | 0.8641 |
| Y18R | 0.876823 | 0.909607 | 0.893215 | 0.8796 | 0.8913 | 0.8855 |
| Y18S | 0.844527 | 0.8677 | 0.856114 | 0.8472 | 0.8502 | 0.8487 |
| Y18T | 0.883639 | 0.909607 | 0.896623 | 0.8865 | 0.8913 | 0.8889 |
| Y18V | 0.888847 | 0.929329 | 0.909088 | 0.8917 | 0.9106 | 0.9013 |
| Y18W | 0.902053 | 0.921932 | 0.911992 | 0.9049 | 0.9034 | 0.9041 |
| Y18Y | 0.946152 | 0.971233 | 0.958692 | 0.9492 | 0.9517 | 0.9504 |
| L20A | 0.93322 | 0.956442 | 0.944831 | 0.9362 | 0.9372 | 0.9367 |
| L20C | 0.879087 | 0.912071 | 0.895579 | 0.8819 | 0.8937 | 0.8879 |
| L20D | 0.721215 | 0.744449 | 0.732832 | 0.7235 | 0.7295 | 0.7265 |
| L20E | 0.814706 | 0.857841 | 0.836274 | 0.8173 | 0.8406 | 0.8291 |
| L20F | 0.962116 | 1.004883 | 0.9835 | 0.9652 | 1.0266 | 0.9962 |
| L20G | 0.89571 | 0.902212 | 0.898961 | 0.8986 | 0.8841 | 0.8912 |
| L20H | 0.884568 | 0.919468 | 0.902018 | 0.8874 | 0.9010 | 0.8943 |
| L20I | 0.973702 | 1.037791 | 1.005746 | 0.9768 | 1.0169 | 0.9971 |
| L20K | 0.601549 | 0.680357 | 0.640929 | 0.6034 | 0.6667 | 0.6354 |
| L20L | 0.962287 | 1.00821 | 0.985249 | 0.9654 | 0.9879 | 0.9768 |
| L20M | 0.894027 | 0.783889 | 0.838958 | 0.8969 | 0.7681 | 0.8317 |
| L20N | 0.757659 | 0.66803 | 0.712845 | 0.7601 | 0.6546 | 0.7067 |
| L20P | 0.510336 | 0.384549 | 0.447443 | 0.5120 | 0.3768 | 0.4436 |
| L20Q | 0.735085 | 0.640915 | 0.688 | 0.7374 | 0.6280 | 0.6821 |
| L20R | 0.568511 | 0.441247 | 0.504879 | 0.5703 | 0.4324 | 0.5005 |
| L20S | 0.911517 | 0.781425 | 0.846471 | 0.9144 | 0.7657 | 0.8392 |
| L20T | 0.830691 | 0.722262 | 0.776476 | 0.8333 | 0.7077 | 0.7698 |
| L20V | 0.890579 | 0.8184 | 0.854489 | 0.8934 | 0.8019 | 0.8471 |
| L20W | 0.793477 | 0.695147 | 0.744312 | 0.7960 | 0.6812 | 0.7379 |
| L20Y | 0.86859 | 0.79868 | 0.833635 | 0.8714 | 0.7826 | 0.8265 |
| D23A | 0.668265 | 0.722264 | 0.695264 | 0.6587 | 0.6741 | 0.6666 |
| D23C | 0.921045 | 0.995884 | 0.958466 | 0.9079 | 0.9294 | 0.9189 |
| D23D | 0.979625 | 1.094487 | 1.037056 | 0.9656 | 1.0215 | 0.9943 |
| D23E | 0.958963 | 1.035325 | 0.997144 | 0.9452 | 0.9663 | 0.9560 |
| D23F | 1.007696 | 1.089557 | 1.048627 | 0.9933 | 1.0169 | 1.0054 |
| D23G | 0.935015 | 0.99342 | 0.964217 | 0.9216 | 0.9271 | 0.9245 |
| D23H | 1.014915 | 1.096952 | 1.055934 | 1.0004 | 1.0238 | 1.0124 |
| D23I | 1.011778 | 1.087092 | 1.049435 | 0.9973 | 1.0146 | 1.0062 |
| D23K | 0.89626 | 0.988489 | 0.942374 | 0.8834 | 0.9225 | 0.9035 |
| D23L | 0.89881 | 0.978629 | 0.93872 | 0.8859 | 0.9133 | 0.9000 |
| D23M | 0.929831 | 1.000815 | 0.965323 | 0.9165 | 0.9341 | 0.9255 |
| D23N | 0.900818 | 0.939188 | 0.920003 | 0.8879 | 0.8765 | 0.8821 |
| D23P | 0.955377 | 1.00821 | 0.981793 | 0.9417 | 0.9410 | 0.9413 |
| D23Q | 0.86317 | 0.914538 | 0.888854 | 0.8508 | 0.8535 | 0.8522 |
| D23R | 0.891678 | 0.882492 | 0.887085 | 0.8789 | 0.8236 | 0.8505 |
| D23S | 0.983757 | 0.976164 | 0.97996 | 0.9697 | 0.9110 | 0.9396 |
| D23T | 0.987211 | 1.04765 | 1.017431 | 0.9731 | 0.9778 | 0.9755 |
| D23V | 0.981413 | 0.990954 | 0.986184 | 0.9674 | 0.9248 | 0.9455 |
| D23W | 0.962897 | 1.01314 | 0.988018 | 0.9491 | 0.9456 | 0.9473 |
| D23Y | 0.915963 | 0.998349 | 0.957156 | 0.9028 | 0.9317 | 0.9177 |
| D25A | 0.932111 | 0.941654 | 0.936882 | 0.9044 | 0.9233 | 0.9138 |
| D25C | 0.824987 | 0.845516 | 0.835251 | 0.8004 | 0.8290 | 0.8146 |
| D25D | 0.974822 | 0.99342 | 0.984121 | 0.9458 | 0.9740 | 0.9598 |
| D25E | 0.935075 | 0.931793 | 0.933434 | 0.9072 | 0.9136 | 0.9104 |
| D25F | 0.891328 | 0.904678 | 0.898003 | 0.8648 | 0.8870 | 0.8758 |
| D25G | 0.924167 | 0.934257 | 0.929212 | 0.8967 | 0.9160 | 0.9063 |
| D25H | 0.821734 | 0.749379 | 0.785557 | 0.7973 | 0.7347 | 0.7662 |
| D25I | 0.788924 | 0.685286 | 0.737105 | 0.7654 | 0.6719 | 0.7189 |
| D25K | 0.85584 | 0.823329 | 0.839585 | 0.8304 | 0.8072 | 0.8189 |
| D25L | 0.80602 | 0.751843 | 0.778931 | 0.7820 | 0.7372 | 0.7597 |
| D25M | 0.923419 | 0.912071 | 0.917745 | 0.8959 | 0.8943 | 0.8951 |
| D25N | 0.964519 | 0.986025 | 0.975272 | 0.9358 | 0.9668 | 0.9512 |
| D25P | 1.019405 | 0.976164 | 0.997784 | 0.9891 | 0.9571 | 0.9732 |
| D25Q | 0.915245 | 0.907143 | 0.911194 | 0.8880 | 0.8894 | 0.8887 |
| D25R | 0.878894 | 0.811004 | 0.844949 | 0.8527 | 0.7952 | 0.8241 |
| D25S | 0.905114 | 0.919466 | 0.91229 | 0.8782 | 0.9015 | 0.8898 |
| D25T | 0.889802 | 0.803609 | 0.846706 | 0.8633 | 0.7879 | 0.8258 |
| D25V | 0.912281 | 0.815935 | 0.864108 | 0.8851 | 0.8000 | 0.8428 |
| D25W | 0.88183 | 0.875097 | 0.878463 | 0.8556 | 0.8580 | 0.8568 |
| D25Y | 0.816353 | 0.764169 | 0.790261 | 0.7921 | 0.7492 | 0.7708 |
| E26A | 0.460938 | 0.470827 | 0.465883 | 0.4543 | 0.4394 | 0.4467 |
| E26C | 0.897705 | 0.921934 | 0.909819 | 0.8848 | 0.8604 | 0.8723 |
| E26D | 0.917818 | 1.005745 | 0.961781 | 0.9047 | 0.9387 | 0.9221 |
| E26E | 0.937988 | 0.953978 | 0.945983 | 0.9246 | 0.8903 | 0.9070 |
| E26F | 0.728423 | 0.786353 | 0.757388 | 0.7180 | 0.7339 | 0.7262 |
| E26G | 0.982523 | 1.025466 | 1.003995 | 0.9684 | 0.9571 | 0.9626 |
| E26H | 0.990437 | 1.023 | 1.006719 | 0.9762 | 0.9548 | 0.9652 |
| E26I | 0.970598 | 1.023 | 0.996799 | 0.9567 | 0.9548 | 0.9557 |
| E26K | 1.02199 | 1.069836 | 1.045913 | 1.0073 | 0.9985 | 1.0028 |
| E26L | 0.982897 | 1.00821 | 0.995553 | 0.9688 | 0.9410 | 0.9545 |
| E26M | 0.881881 | 0.897282 | 0.889582 | 0.8692 | 0.8374 | 0.8529 |
| E26N | 0.954222 | 0.934258 | 0.94424 | 0.9406 | 0.8719 | 0.9053 |
| E26P | 0.919239 | 1.000813 | 0.960026 | 0.9061 | 0.9340 | 0.9204 |
| E26Q | 0.912036 | 0.919468 | 0.915752 | 0.8990 | 0.8581 | 0.8780 |
| E26R | 0.911776 | 0.946583 | 0.92918 | 0.8987 | 0.8834 | 0.8909 |
| E26S | 0.911389 | 0.926862 | 0.919125 | 0.8983 | 0.8650 | 0.8812 |
| E26T | 0.885083 | 0.894817 | 0.88995 | 0.8724 | 0.8351 | 0.8533 |
| E26V | 0.930337 | 0.926863 | 0.9286 | 0.9170 | 0.8650 | 0.8903 |
| E26W | 0.744128 | 0.825795 | 0.784961 | 0.7335 | 0.7707 | 0.7526 |
| E26Y | 0.720488 | 0.751843 | 0.736165 | 0.7102 | 0.7017 | 0.7058 |
| S27A | 0.900108 | 0.929329 | 0.914718 | 0.8872 | 0.8673 | 0.8770 |
| S27C | 0.8943 | 0.929329 | 0.911814 | 0.8815 | 0.8673 | 0.8742 |
| S27D | 0.864964 | 0.921934 | 0.893449 | 0.8526 | 0.8604 | 0.8566 |
| S27E | 0.899559 | 0.899748 | 0.899654 | 0.8867 | 0.8397 | 0.8626 |
| S27F | 0.909897 | 0.990954 | 0.950426 | 0.8969 | 0.9248 | 0.9112 |
| S27G | 0.971394 | 1.005745 | 0.988569 | 0.9575 | 0.9387 | 0.9478 |
| S27H | 0.94353 | 0.971234 | 0.957382 | 0.9300 | 0.9064 | 0.9179 |
| S27I | 0.955692 | 0.973698 | 0.964695 | 0.9420 | 0.9087 | 0.9249 |
| S27K | 0.996892 | 1.00821 | 1.002551 | 0.9826 | 0.9410 | 0.9612 |
| S27L | 0.998001 | 1.050116 | 1.024058 | 0.9837 | 0.9801 | 0.9818 |
| S27M | 0.874455 | 0.897282 | 0.885869 | 0.8619 | 0.8374 | 0.8493 |
| S27N | 0.908225 | 0.924398 | 0.916312 | 0.8952 | 0.8627 | 0.8785 |
| S27P | 0.884944 | 0.909607 | 0.897276 | 0.8723 | 0.8489 | 0.8603 |
| S27Q | 0.876555 | 0.894817 | 0.885686 | 0.8640 | 0.8351 | 0.8492 |
| S27R | 0.960083 | 0.966303 | 0.963193 | 0.9463 | 0.9018 | 0.9235 |
| S27S | 0.924077 | 0.907143 | 0.91561 | 0.9108 | 0.8466 | 0.8779 |
| S27T | 0.934904 | 0.958909 | 0.946907 | 0.9215 | 0.8949 | 0.9079 |
| S27V | 0.954229 | 1.005745 | 0.979987 | 0.9406 | 0.9387 | 0.9396 |
| S27W | 0.819984 | 0.899746 | 0.859865 | 0.8082 | 0.8397 | 0.8244 |
| S27Y | 0.865823 | 0.899746 | 0.882785 | 0.8534 | 0.8397 | 0.8464 |
| I28A | 0.55899 | 0.401805 | 0.480398 | 0.6422 | 0.4885 | 0.5654 |
| I28C | 0.292015 | 0.244041 | 0.268028 | 0.3355 | 0.2967 | 0.3161 |
| I28D | 0.580518 | 0.488082 | 0.5343 | 0.6670 | 0.5934 | 0.6302 |
| I28E | 0.497945 | 0.478221 | 0.488083 | 0.5721 | 0.5814 | 0.5768 |
| I28F | 0.51176 | 0.451106 | 0.481433 | 0.5880 | 0.5485 | 0.5682 |
| I28G | 0.555709 | 0.537384 | 0.546547 | 0.6385 | 0.6533 | 0.6459 |
| I28I | 0.927103 | 0.855375 | 0.891239 | 1.0652 | 1.0400 | 1.0526 |

TABLE 9-continued

| Variant | Slope PI | Delta PI | Avg PI | Norm Slope PI | Norm Delta PI | Norm Avg PI |
|---|---|---|---|---|---|---|
| I28I | 0.830023 | 0.741982 | 0.786003 | 0.9536 | 0.9021 | 0.9279 |
| I28I | 0.66361 | 0.58915 | 0.62638 | 0.7624 | 0.7163 | 0.7394 |
| I28I | 0.628008 | 0.569429 | 0.598718 | 0.7215 | 0.6923 | 0.7069 |
| I28L | 0.655925 | 0.626125 | 0.641025 | 0.7536 | 0.7612 | 0.7574 |
| I28M | 0.333144 | 0.369759 | 0.351451 | 0.3828 | 0.4496 | 0.4162 |
| I28N | 0.34526 | 0.362364 | 0.353812 | 0.3967 | 0.4406 | 0.4186 |
| I28P | 0.877167 | 0.838121 | 0.857644 | 1.0078 | 1.0190 | 1.0134 |
| I28R | 1.026571 | 0.949049 | 0.98781 | 1.1794 | 1.1538 | 1.1666 |
| I28S | 1.00392 | 0.9737 | 0.98881 | 1.1534 | 1.1838 | 1.1686 |
| I28T | 0.970822 | 0.875097 | 0.922959 | 1.1154 | 1.0639 | 1.0897 |
| I28V | −0.13366 | −0.1479 | −0.14078 | −0.1536 | −0.1798 | −0.1667 |
| I28W | 0.595226 | 0.586685 | 0.590956 | 0.6839 | 0.7133 | 0.6986 |
| I28Y | 0.905689 | 0.84798 | 0.876835 | 1.0406 | 1.0310 | 1.0358 |
| V30A | 0.49262 | 0.458501 | 0.475561 | 0.5660 | 0.5574 | 0.5617 |
| V30C | 0.489915 | 0.441245 | 0.46558 | 0.5629 | 0.5365 | 0.5497 |
| V30D | −0.16469 | −0.212 | −0.18834 | −0.1892 | −0.2577 | −0.2235 |
| V30E | 0.958734 | 0.941654 | 0.950194 | 1.1015 | 1.1449 | 1.1232 |
| V30F | 1.016354 | 0.944118 | 0.980236 | 1.1677 | 1.1479 | 1.1578 |
| V30G | 0.926009 | 0.877561 | 0.901785 | 1.0639 | 1.0669 | 1.0654 |
| V30I | 0.921087 | 0.919466 | 0.920277 | 1.0583 | 1.1179 | 1.0881 |
| V30K | 0.981241 | 0.892351 | 0.936796 | 1.1274 | 1.0849 | 1.1061 |
| V30L | 1.025017 | 0.963838 | 0.994427 | 1.1777 | 1.1718 | 1.1747 |
| V30M | 0.828642 | 0.769099 | 0.79887 | 0.9520 | 0.9351 | 0.9436 |
| V30N | 0.725951 | 0.712403 | 0.719177 | 0.8341 | 0.8661 | 0.8501 |
| V30P | 0.904539 | 0.865236 | 0.884887 | 1.0392 | 1.0519 | 1.0456 |
| V30Q | 0.821821 | 0.796215 | 0.809018 | 0.9442 | 0.9680 | 0.9561 |
| V30R | 0.89481 | 0.8184 | 0.856605 | 1.0281 | 0.9950 | 1.0115 |
| V30S | 0.894666 | 0.899746 | 0.897206 | 1.0279 | 1.0939 | 1.0609 |
| V30T | 0.886838 | 0.855375 | 0.871106 | 1.0189 | 1.0400 | 1.0294 |
| V30V | 0.942098 | 0.929329 | 0.935713 | 1.0824 | 1.1299 | 1.1061 |
| V30V | 0.895184 | 0.830726 | 0.862955 | 1.0285 | 1.0100 | 1.0192 |
| V30W | 0.909575 | 0.845515 | 0.877545 | 1.0450 | 1.0280 | 1.0365 |
| V30Y | 0.950876 | 0.875097 | 0.912986 | 1.0925 | 1.0639 | 1.0782 |
| D33A | 0.185281 | 0.18488 | 0.18508 | 0.1820 | 0.1861 | 0.1840 |
| D33C | 0.733284 | 0.774028 | 0.753656 | 0.7203 | 0.7792 | 0.7494 |
| D33D | 0.903864 | 0.931793 | 0.917828 | 0.8879 | 0.9380 | 0.9126 |
| D33E | 0.914698 | 0.917002 | 0.91585 | 0.8985 | 0.9231 | 0.9106 |
| D33F | 1.097951 | 1.133928 | 1.11594 | 1.0785 | 1.1414 | 1.1096 |
| D33G | 1.006107 | 1.035325 | 1.020716 | 0.9883 | 1.0422 | 1.0149 |
| D33H | 1.110918 | 1.111741 | 1.111329 | 1.0912 | 1.1191 | 1.1050 |
| D33I | 1.08364 | 1.151183 | 1.117411 | 1.0645 | 1.1588 | 1.1111 |
| D33K | 1.005204 | 1.003279 | 1.004241 | 0.9874 | 1.0099 | 0.9985 |
| D33L | 0.934104 | 0.946583 | 0.940343 | 0.9176 | 0.9529 | 0.9350 |
| D33M | −0.09815 | −0.14051 | −0.11933 | −0.0964 | −0.1414 | −0.1186 |
| D33N | 0.679909 | 0.660637 | 0.670273 | 0.6679 | 0.6650 | 0.6665 |
| D33P | 0.775789 | 0.732123 | 0.753956 | 0.7621 | 0.7370 | 0.7497 |
| D33Q | 0.893861 | 0.840585 | 0.867223 | 0.8780 | 0.8462 | 0.8623 |
| D33R | 0.996353 | 0.936722 | 0.966538 | 0.9787 | 0.9429 | 0.9610 |
| D33S | 0.981573 | 0.961373 | 0.971473 | 0.9642 | 0.9677 | 0.9659 |
| D33T | 1.049742 | 0.976164 | 1.012868 | 1.0310 | 0.9826 | 1.0071 |
| D33V | 1.069913 | 1.079696 | 1.074805 | 1.0510 | 1.0868 | 1.0687 |
| D33W | 0.951181 | 0.912071 | 0.931626 | 0.9343 | 0.9181 | 0.9263 |
| D33Y | 0.918413 | 0.872631 | 0.895522 | 0.9021 | 0.8784 | 0.8904 |
| K36A | 0.425617 | 0.396874 | 0.411246 | 0.5036 | 0.4607 | 0.4819 |
| K36C | 0.48603 | 0.500408 | 0.493219 | 0.5751 | 0.5808 | 0.5780 |
| K36D | 0.414739 | 0.416596 | 0.415667 | 0.4907 | 0.4835 | 0.4871 |
| K36E | 0.390965 | 0.384549 | 0.387757 | 0.4626 | 0.4464 | 0.4544 |
| K36F | 0.844385 | 0.835655 | 0.84002 | 0.9991 | 0.9700 | 0.9844 |
| K36G | 0.619661 | 0.606405 | 0.613033 | 0.7332 | 0.7039 | 0.7184 |
| K36H | 0.851724 | 0.845515 | 0.848619 | 1.0077 | 0.9814 | 0.9944 |
| K36I | 0.921059 | 0.956444 | 0.938751 | 1.0898 | 1.1102 | 1.1001 |
| K36K | 0.849365 | 0.865236 | 0.8573 | 1.0050 | 1.0043 | 1.0046 |
| K36L | 0.862057 | 0.884958 | 0.873507 | 1.0200 | 1.0272 | 1.0236 |
| K36M | 0.462831 | 0.458501 | 0.460666 | 0.5476 | 0.5322 | 0.5398 |
| K36N | 0.43808 | 0.456036 | 0.447058 | 0.5183 | 0.5293 | 0.5239 |
| K36P | 0.402391 | 0.389479 | 0.395935 | 0.4761 | 0.4521 | 0.4640 |
| K36Q | 0.405902 | 0.426455 | 0.416179 | 0.4803 | 0.4950 | 0.4877 |
| K36R | 0.847753 | 0.917002 | 0.882378 | 1.0030 | 1.0644 | 1.0340 |
| K36S | 0.652241 | 0.655706 | 0.653973 | 0.7717 | 0.7611 | 0.7664 |
| K36T | 0.835722 | 0.875097 | 0.85541 | 0.9888 | 1.0157 | 1.0024 |
| K36V | 0.888651 | 0.917002 | 0.902827 | 1.0514 | 1.0644 | 1.0580 |
| K36W | 0.77557 | 0.865236 | 0.820403 | 0.9176 | 1.0043 | 0.9614 |
| K36Y | 0.806307 | 0.820865 | 0.813586 | 0.9540 | 0.9528 | 0.9534 |
| R44A | 1.077139 | 1.087092 | 1.082116 | 1.0430 | 1.0607 | 1.0518 |
| R44C | 1.08871 | 1.00821 | 1.04846 | 1.0542 | 0.9838 | 1.0191 |
| R44D | 1.025074 | 1.03286 | 1.028967 | 0.9926 | 1.0078 | 1.0002 |
| R44E | 0.985039 | 1.015605 | 1.000322 | 0.9538 | 0.9910 | 0.9723 |
| R44F | 1.119938 | 1.092023 | 1.10598 | 1.0845 | 1.0655 | 1.0750 |
| R44G | 0.770043 | 0.764169 | 0.767106 | 0.7457 | 0.7456 | 0.7457 |
| R44H | 1.059496 | 1.025465 | 1.04248 | 1.0259 | 1.0006 | 1.0133 |
| R44I | 1.017044 | 0.986025 | 1.001534 | 0.9848 | 0.9621 | 0.9735 |
| R44K | 1.009618 | 0.993418 | 1.001518 | 0.9776 | 0.9693 | 0.9735 |
| R44L | 0.946674 | 0.921934 | 0.934304 | 0.9167 | 0.8996 | 0.9082 |
| R44M | 1.115994 | 1.136392 | 1.126193 | 1.0807 | 1.1088 | 1.0947 |
| R44N | 1.087271 | 1.089557 | 1.088414 | 1.0528 | 1.0631 | 1.0580 |
| R44P | 0.944573 | 0.894817 | 0.919695 | 0.9147 | 0.8731 | 0.8940 |
| R44Q | 0.935708 | 0.884958 | 0.910333 | 0.9061 | 0.8635 | 0.8849 |
| R44R | 0.922987 | 0.914537 | 0.918762 | 0.8938 | 0.8924 | 0.8931 |
| R44S | 1.035378 | 0.998349 | 1.016863 | 1.0026 | 0.9741 | 0.9884 |
| R44T | 1.094293 | 1.035325 | 1.064809 | 1.0596 | 1.0102 | 1.0350 |
| R44V | 1.094696 | 1.067372 | 1.081034 | 1.0600 | 1.0415 | 1.0508 |
| R44W | 0.949379 | 0.958908 | 0.954144 | 0.9193 | 0.9357 | 0.9275 |
| R44Y | 1.051294 | 1.01314 | 1.032217 | 1.0180 | 0.9886 | 1.0033 |
| K50A | 0.535496 | 0.537383 | 0.536439 | 0.5260 | 0.5409 | 0.5334 |
| K50C | 0.694326 | 0.759238 | 0.726782 | 0.6820 | 0.7643 | 0.7226 |
| K50D | 0.804135 | 0.79868 | 0.801407 | 0.7899 | 0.8040 | 0.7968 |
| K50E | 0.905242 | 0.914538 | 0.90989 | 0.8892 | 0.9206 | 0.9047 |
| K50F | −0.08302 | −0.2046 | −0.14381 | −0.0815 | −0.2060 | −0.1430 |
| K50G | 0.954182 | 0.929327 | 0.941754 | 0.9373 | 0.9355 | 0.9364 |
| K50H | 1.081359 | 1.094487 | 1.087923 | 1.0622 | 1.1017 | 1.0817 |
| K50I | 1.093654 | 1.064906 | 1.07928 | 1.0743 | 1.0720 | 1.0731 |
| K50K | 1.122473 | 1.111741 | 1.117107 | 1.1026 | 1.1191 | 1.1108 |
| K50L | 1.033651 | 1.089556 | 1.061603 | 1.0153 | 1.0968 | 1.0556 |
| K50M | 0.325919 | 0.295807 | 0.310863 | 0.3201 | 0.2978 | 0.3091 |
| K50N | 0.615730 | 0.63352 | 0.624627 | 0.6048 | 0.6377 | 0.6211 |
| K50P | 0.839438 | 0.904678 | 0.872058 | 0.8246 | 0.9107 | 0.8671 |
| K50Q | 0.855571 | 0.860307 | 0.857939 | 0.8404 | 0.8660 | 0.8531 |
| K50R | −0.00771 | 0.03451 | 0.013399 | −0.0076 | 0.0347 | 0.0133 |
| K50S | 0.994568 | 0.971233 | 0.9829 | 0.9770 | 0.9777 | 0.9773 |
| K50T | 1.109699 | 1.136392 | 1.123046 | 1.0900 | 1.1439 | 1.1167 |
| K50V | 1.036983 | 1.020535 | 1.028759 | 1.0186 | 1.0273 | 1.0229 |
| K50W | 1.09828 | 1.119138 | 1.108709 | 1.0788 | 1.1266 | 1.1024 |
| K50Y | 1.036993 | 1.030396 | 1.033694 | 1.0186 | 1.0372 | 1.0278 |
| F53A | 0.410994 | 0.443711 | 0.427353 | 0.4037 | 0.4467 | 0.4249 |
| F53C | 0.666376 | 0.692681 | 0.679528 | 0.6546 | 0.6973 | 0.6757 |
| F53D | 0.848226 | 0.887422 | 0.867824 | 0.8332 | 0.8933 | 0.8629 |
| F53E | 0.860013 | 0.815934 | 0.837973 | 0.8448 | 0.8213 | 0.8332 |
| F53F | 0.941764 | 0.909607 | 0.925686 | 0.9251 | 0.9156 | 0.9204 |
| F53G | 1.002614 | 1.023 | 1.012807 | 0.9849 | 1.0298 | 1.0070 |
| F53H | 1.014 | 1.02793 | 1.020965 | 0.9960 | 1.0347 | 1.0152 |
| F53I | 1.110952 | 1.106812 | 1.108882 | 1.0913 | 1.1141 | 1.1026 |
| F53K | 1.05283 | 1.067372 | 1.060101 | 1.0342 | 1.0744 | 1.0541 |
| F53L | 0.977713 | 1.03286 | 1.005287 | 0.9604 | 1.0397 | 0.9996 |
| F53M | −0.08443 | −0.09614 | −0.09028 | −0.0829 | −0.0968 | −0.0898 |
| F53N | 0.640621 | 0.643381 | 0.642001 | 0.6293 | 0.6476 | 0.6383 |
| F53P | 0.879404 | 0.8184 | 0.848902 | 0.8638 | 0.8238 | 0.8441 |
| F53Q | 0.926589 | 0.830724 | 0.878657 | 0.9102 | 0.8362 | 0.8737 |
| F53R | 1.02633 | 0.99342 | 1.009875 | 1.0082 | 1.0000 | 1.0041 |
| F53S | 0.965143 | 0.880027 | 0.922585 | 0.9481 | 0.8859 | 0.9173 |
| F53T | 1.059278 | 0.951513 | 1.005395 | 1.0405 | 0.9578 | 0.9997 |
| F53V | 1.015588 | 0.921932 | 0.96876 | 0.9976 | 0.9280 | 0.9632 |
| F53W | 0.989198 | 0.921932 | 0.955565 | 0.9717 | 0.9280 | 0.9501 |
| F53Y | 0.968885 | 0.855375 | 0.91213 | 0.9517 | 0.8610 | 0.9069 |
| L59A | 1.087587 | 1.092021 | 1.089804 | 1.0484 | 1.0411 | 1.0448 |
| L59C | 1.115246 | 1.17337 | 1.144308 | 1.0751 | 1.1187 | 1.0970 |
| L59D | 1.08114 | 1.04765 | 1.064395 | 1.0422 | 0.9988 | 1.0204 |
| L59E | 1.112454 | 1.180763 | 1.146609 | 1.0724 | 1.1257 | 1.0992 |
| L59F | 1.068131 | 1.156114 | 1.112123 | 1.0297 | 1.1022 | 1.0662 |
| L59G | 1.100021 | 1.101882 | 1.100952 | 1.0604 | 1.0505 | 1.0554 |
| L59H | 1.223234 | 1.230066 | 1.22665 | 1.1792 | 1.1727 | 1.1759 |
| L59I | 1.162188 | 1.121602 | 1.141895 | 1.1203 | 1.0693 | 1.0947 |
| L59K | 1.117002 | 1.106812 | 1.111907 | 1.0768 | 1.0552 | 1.0659 |
| L59L | 0.940169 | 0.966305 | 0.953237 | 0.9063 | 0.9213 | 0.9138 |
| L59M | 1.072535 | 1.087092 | 1.079813 | 1.0339 | 1.0364 | 1.0352 |
| L59N | 1.07878 | 1.119136 | 1.098958 | 1.0399 | 1.0670 | 1.0535 |
| L59P | 0.19649 | 0.298273 | 0.247381 | 0.1894 | 0.2844 | 0.2372 |
| L59Q | 1.123362 | 1.180763 | 1.152063 | 1.0829 | 1.1257 | 1.1044 |
| L59R | 1.163944 | 1.183229 | 1.173587 | 1.1220 | 1.1281 | 1.1251 |
| L59S | 1.035119 | 1.045186 | 1.040153 | 0.9979 | 0.9965 | 0.9972 |
| L59T | 1.198452 | 1.230064 | 1.214258 | 1.1553 | 1.1727 | 1.1641 |
| L59V | 1.058489 | 1.079696 | 1.069093 | 1.0204 | 1.0294 | 1.0249 |
| L59W | 0.987342 | 0.956444 | 0.971893 | 0.9518 | 0.9119 | 0.9317 |

TABLE 9-continued

| Variant | Slope PI | Delta PI | Avg PI | Norm Slope PI | Norm Delta PI | Norm Avg PI |
|---|---|---|---|---|---|---|
| L59Y | 1.014252 | 1.04272 | 1.028486 | 0.9777 | 0.9941 | 0.9860 |
| G69A | 0.97252 | 1.01314 | 0.99283 | 0.9756 | 0.9928 | 0.9843 |
| G69C | 0.984973 | 0.951513 | 0.968243 | 0.9881 | 0.9324 | 0.9599 |
| G69D | 0.923646 | 0.929327 | 0.926487 | 0.9266 | 0.9106 | 0.9185 |
| G69E | 0.904835 | 0.872631 | 0.888733 | 0.9077 | 0.8551 | 0.8811 |
| G69F | 0.913936 | 0.956444 | 0.93519 | 0.9168 | 0.9372 | 0.9271 |
| G69G | 0.953943 | 0.946583 | 0.950263 | 0.9570 | 0.9275 | 0.9421 |
| G69H | 0.975453 | 0.961373 | 0.968413 | 0.9786 | 0.9420 | 0.9601 |
| G69I | 0.971462 | 0.9737 | 0.972581 | 0.9746 | 0.9541 | 0.9642 |
| G69K | 0.985227 | 1.094487 | 1.039857 | 0.9884 | 1.0725 | 1.0309 |
| G69L | 0.934008 | 0.953978 | 0.943993 | 0.9370 | 0.9348 | 0.9359 |
| G69M | 0.96156 | 0.986023 | 0.973791 | 0.9646 | 0.9662 | 0.9654 |
| G69N | 1.006376 | 0.995884 | 1.00113 | 1.0096 | 0.9758 | 0.9925 |
| G69P | 0.853303 | 0.897281 | 0.875292 | 0.8560 | 0.8792 | 0.8678 |
| G69Q | 1.004772 | 1.035325 | 1.020049 | 1.0080 | 1.0145 | 1.0113 |
| G69R | 0.960165 | 0.988489 | 0.974327 | 0.9632 | 0.9686 | 0.9659 |
| G69S | 1.081175 | 1.190624 | 1.1359 | 1.0846 | 1.1667 | 1.1261 |
| G69T | 1.123227 | 1.244856 | 1.184041 | 1.1268 | 1.2198 | 1.1739 |
| G69V | 1.014851 | 1.062442 | 1.038646 | 1.0181 | 1.0411 | 1.0297 |
| G69W | 0.946529 | 1.005745 | 0.976137 | 0.9495 | 0.9855 | 0.9677 |
| G69Y | 0.880459 | 0.931793 | 0.906126 | 0.8833 | 0.9130 | 0.8983 |
| S74A | 0.68747 | 0.655706 | 0.671588 | 0.8134 | 0.7611 | 0.7870 |
| S74C | 0.684102 | 0.65324 | 0.668671 | 0.8094 | 0.7582 | 0.7836 |
| S74D | 0.644298 | 0.59901 | 0.621654 | 0.7623 | 0.6953 | 0.7285 |
| S74E | 0.61828 | 0.62859 | 0.623435 | 0.7315 | 0.7296 | 0.7306 |
| S74F | 0.879067 | 0.870167 | 0.874617 | 1.0401 | 1.0100 | 1.0249 |
| S74G | 0.862921 | 0.855377 | 0.859149 | 1.0210 | 0.9928 | 1.0068 |
| S74H | 0.922584 | 0.953978 | 0.938281 | 1.0916 | 1.1073 | 1.0995 |
| S74I | 0.920512 | 0.934258 | 0.927385 | 1.0891 | 1.0844 | 1.0867 |
| S74K | 0.935737 | 0.981093 | 0.958415 | 1.1071 | 1.1388 | 1.1231 |
| S74L | 0.817417 | 0.897282 | 0.85735 | 0.9672 | 1.0415 | 1.0047 |
| S74M | 0.625935 | 0.571894 | 0.598915 | 0.7406 | 0.6638 | 0.7018 |
| S74N | 0.597701 | 0.57929 | 0.588495 | 0.7072 | 0.6724 | 0.6896 |
| S74P | 0.649421 | 0.643381 | 0.646401 | 0.7684 | 0.7468 | 0.7575 |
| S74Q | 0.588923 | 0.569429 | 0.579176 | 0.6968 | 0.6609 | 0.6787 |
| S74R | 0.879901 | 0.924398 | 0.902149 | 1.0411 | 1.0730 | 1.0572 |
| S74S | 0.812438 | 0.855377 | 0.833908 | 0.9613 | 0.9928 | 0.9772 |
| S74T | 0.959568 | 1.025465 | 0.992516 | 1.1353 | 1.1903 | 1.1631 |
| S74V | 0.978132 | 1.035325 | 1.006729 | 1.1573 | 1.2017 | 1.1797 |
| S74W | 0.951107 | 1.003279 | 0.977193 | 1.1253 | 1.1645 | 1.1451 |
| S74Y | 0.811517 | 0.845516 | 0.828517 | 0.9602 | 0.9814 | 0.9709 |
| G78A | 0.560775 | 0.500408 | 0.530592 | 0.6635 | 0.5808 | 0.6218 |
| G78C | 0.628641 | 0.574359 | 0.6015 | 0.7438 | 0.6667 | 0.7049 |
| G78D | 0.545693 | 0.500407 | 0.52305 | 0.6457 | 0.5808 | 0.6129 |
| G78E | 0.534382 | 0.488082 | 0.511232 | 0.6323 | 0.5665 | 0.5991 |
| G78F | 0.881369 | 0.936722 | 0.909046 | 1.0428 | 1.0873 | 1.0653 |
| G78G | 0.709545 | 0.744448 | 0.726996 | 0.8395 | 0.8641 | 0.8519 |
| G78H | 0.964058 | 0.968769 | 0.966413 | 1.1407 | 1.1245 | 1.1325 |
| G78I | 0.987889 | 1.037791 | 1.01284 | 1.1689 | 1.2046 | 1.1869 |
| G78K | 0.870893 | 0.926863 | 0.898878 | 1.0304 | 1.0758 | 1.0533 |
| G78L | 0.874721 | 0.880027 | 0.877374 | 1.0350 | 1.0215 | 1.0281 |
| G78M | 0.541348 | 0.475757 | 0.508552 | 0.6405 | 0.5522 | 0.5959 |
| G78N | 0.519761 | 0.520128 | 0.519945 | 0.6150 | 0.6037 | 0.6093 |
| G78P | 0.583685 | 0.59408 | 0.588882 | 0.6906 | 0.6896 | 0.6901 |
| G78Q | 0.493628 | 0.478221 | 0.485925 | 0.5841 | 0.5551 | 0.5694 |
| G78R | 0.888881 | 0.934258 | 0.91157 | 1.0517 | 1.0844 | 1.0682 |
| G78S | 0.747824 | 0.77896 | 0.763392 | 0.8848 | 0.9041 | 0.8946 |
| G78T | 0.954445 | 1.010674 | 0.982559 | 1.1293 | 1.1731 | 1.1514 |
| G78V | 0.936888 | 1.03286 | 0.984874 | 1.1085 | 1.1989 | 1.1541 |
| G78W | 0.927391 | 0.995885 | 0.961638 | 1.0973 | 1.1559 | 1.1269 |
| G78Y | 0.911705 | 0.921932 | 0.916818 | 1.0787 | 1.0701 | 1.0744 |
| D81A | 0.916483 | 0.867702 | 0.892092 | 0.9034 | 0.8098 | 0.8553 |
| D81C | 0.925517 | 0.968769 | 0.947143 | 0.9123 | 0.9041 | 0.9081 |
| D81D | −0.03069 | −0.07642 | −0.05355 | −0.0303 | −0.0713 | −0.0513 |
| D81E | 0.937051 | 0.944118 | 0.940584 | 0.9236 | 0.8811 | 0.9018 |
| D81F | 1.001651 | 0.99342 | 0.997535 | 0.9873 | 0.9271 | 0.9564 |
| D81G | 1.040707 | 1.064906 | 1.052807 | 1.0258 | 0.9939 | 1.0094 |
| D81H | 1.004087 | 1.025465 | 1.014776 | 0.9897 | 0.9571 | 0.9729 |
| D81I | 0.846262 | 0.835655 | 0.840959 | 0.8341 | 0.7799 | 0.8063 |
| D81K | 0.976405 | 1.015605 | 0.996005 | 0.9624 | 0.9479 | 0.9549 |
| D81L | 0.928099 | 0.941654 | 0.934876 | 0.9148 | 0.8788 | 0.8963 |
| D81M | 0.855268 | 0.872631 | 0.86395 | 0.8430 | 0.8144 | 0.8283 |
| D81N | 0.865179 | 0.892351 | 0.878765 | 0.8528 | 0.8328 | 0.8425 |
| D81P | 0.811314 | 0.81347 | 0.812392 | 0.7997 | 0.7592 | 0.7789 |
| D81Q | 0.917372 | 0.931793 | 0.924582 | 0.9042 | 0.8696 | 0.8865 |
| D81R | 1.029281 | 1.040255 | 1.034768 | 1.0145 | 0.9709 | 0.9921 |
| D81S | 0.942145 | 0.956444 | 0.949294 | 0.9286 | 0.8926 | 0.9102 |
| D81T | 0.962869 | 0.988489 | 0.975679 | 0.9491 | 0.9225 | 0.9354 |
| D81V | 0.900584 | 0.934257 | 0.917421 | 0.8877 | 0.8719 | 0.8796 |
| D81W | 0.95404 | 0.998349 | 0.976195 | 0.9404 | 0.9317 | 0.9359 |
| D81Y | 0.853337 | 0.882491 | 0.867914 | 0.8411 | 0.8236 | 0.8321 |
| G87A | 0.971944 | 0.951513 | 0.961728 | 0.9430 | 0.9329 | 0.9380 |
| G87C | 0.947135 | 0.936724 | 0.941929 | 0.9189 | 0.9184 | 0.9187 |
| G87D | 0.974592 | 0.976164 | 0.975378 | 0.9456 | 0.9571 | 0.9513 |
| G87E | 0.979226 | 1.01314 | 0.996183 | 0.9501 | 0.9934 | 0.9716 |
| G87F | 1.040817 | 1.050116 | 1.045467 | 1.0098 | 1.0296 | 1.0197 |
| G87G | −0.06577 | −0.08628 | −0.07602 | −0.0638 | −0.0846 | −0.0741 |
| G87H | 0.964432 | 0.904678 | 0.934555 | 0.9357 | 0.8870 | 0.9115 |
| G87I | 0.996005 | 0.909607 | 0.952806 | 0.9664 | 0.8918 | 0.9293 |
| G87K | 1.05184 | 1.003279 | 1.02756 | 1.0205 | 0.9837 | 1.0022 |
| G87L | 1.049855 | 0.995884 | 1.022869 | 1.0186 | 0.9764 | 0.9976 |
| G87M | 1.007978 | 1.052581 | 1.03028 | 0.9780 | 1.0320 | 1.0049 |
| G87N | 0.92906 | 0.934258 | 0.931659 | 0.9014 | 0.9160 | 0.9087 |
| G87P | 0.984723 | 1.03286 | 1.008791 | 0.9554 | 1.0127 | 0.9839 |
| G87Q | 0.948487 | 0.976164 | 0.962326 | 0.9203 | 0.9571 | 0.9386 |
| G87R | 1.078435 | 1.087092 | 1.082763 | 1.0463 | 1.0659 | 1.0560 |
| G87S | 0.960115 | 0.921934 | 0.941024 | 0.9315 | 0.9039 | 0.9178 |
| G87T | 0.991831 | 0.899746 | 0.945789 | 0.9623 | 0.8822 | 0.9225 |
| G87V | 0.981154 | 0.914538 | 0.947846 | 0.9519 | 0.8967 | 0.9245 |
| G87W | 0.985615 | 0.926862 | 0.956238 | 0.9563 | 0.9088 | 0.9326 |
| G87Y | 0.919015 | 0.81347 | 0.866242 | 0.8917 | 0.7976 | 0.8449 |
| G99A | 0.477121 | 0.547243 | 0.512182 | 0.4687 | 0.5509 | 0.5093 |
| G99C | 0.71413 | 0.764169 | 0.73915 | 0.7015 | 0.7692 | 0.7349 |
| G99D | 0.855208 | 0.872631 | 0.863919 | 0.8401 | 0.8784 | 0.8590 |
| G99E | 0.957423 | 1.03286 | 0.995141 | 0.9405 | 1.0397 | 0.9895 |
| G99F | 1.073895 | 1.057511 | 1.065703 | 1.0549 | 1.0645 | 1.0596 |
| G99G | −0.07016 | −0.03451 | −0.05234 | −0.0689 | −0.0347 | −0.0520 |
| G99H | 1.041054 | 1.023 | 1.032027 | 1.0226 | 1.0298 | 1.0262 |
| G99I | 1.161186 | 1.239926 | 1.200556 | 1.1406 | 1.2481 | 1.1937 |
| G99K | 1.136314 | 1.21281 | 1.174562 | 1.1162 | 1.2208 | 1.1679 |
| G99L | 1.042984 | 1.064906 | 1.053945 | 1.0245 | 1.0720 | 1.0479 |
| G99M | 0.646589 | 0.640917 | 0.643753 | 0.6351 | 0.6452 | 0.6401 |
| G99N | 0.776838 | 0.823331 | 0.800084 | 0.7631 | 0.8288 | 0.7955 |
| G99P | 0.912539 | 0.931793 | 0.922166 | 0.8964 | 0.9380 | 0.9169 |
| G99Q | 0.975166 | 0.961373 | 0.96827 | 0.9579 | 0.9677 | 0.9628 |
| G99R | 1.040288 | 1.074765 | 1.057526 | 1.0219 | 1.0819 | 1.0515 |
| G99S | 1.036505 | 0.983559 | 1.010032 | 1.0182 | 0.9901 | 1.0043 |
| G99T | 1.124624 | 1.131463 | 1.128043 | 1.1047 | 1.1390 | 1.1216 |
| G99V | 1.147162 | 1.188159 | 1.16766 | 1.1268 | 1.1960 | 1.1610 |
| G99W | 1.026598 | 1.059976 | 1.043287 | 1.0084 | 1.0670 | 1.0374 |
| G99Y | 1.035496 | 1.040255 | 1.037875 | 1.0172 | 1.0471 | 1.0320 |
| Q116A | 1.010309 | 1.04272 | 1.026515 | 0.9739 | 0.9941 | 0.9841 |
| Q116C | 1.068505 | 1.087092 | 1.077799 | 1.0300 | 1.0364 | 1.0332 |
| Q116D | 1.047207 | 1.02793 | 1.037568 | 1.0095 | 0.9800 | 0.9947 |
| Q116E | 1.058288 | 1.087092 | 1.07269 | 1.0202 | 1.0364 | 1.0284 |
| Q116F | 1.097661 | 1.151184 | 1.124422 | 1.0581 | 1.0975 | 1.0779 |
| Q116G | 1.007661 | 1.040255 | 1.023958 | 0.9714 | 0.9918 | 0.9816 |
| Q116H | 1.082406 | 1.025465 | 1.053935 | 1.0434 | 0.9777 | 1.0104 |
| Q116I | 1.151107 | 1.180763 | 1.165935 | 1.1097 | 1.1257 | 1.1177 |
| Q116K | 1.054115 | 1.03286 | 1.043487 | 1.0162 | 0.9847 | 1.0004 |
| Q116L | 1.043638 | 1.052581 | 1.04811 | 1.0061 | 1.0035 | 1.0048 |
| Q116M | 0.949351 | 0.956442 | 0.952896 | 0.9152 | 0.9119 | 0.9135 |
| Q116N | 1.110872 | 1.141322 | 1.126097 | 1.0709 | 1.0881 | 1.0796 |
| Q116P | 1.109346 | 1.124067 | 1.116707 | 1.0694 | 1.0717 | 1.0705 |
| Q116Q | 1.002596 | 1.064906 | 1.033751 | 0.9665 | 1.0153 | 0.9910 |
| Q116R | 0.981528 | 1.03286 | 1.007194 | 0.9462 | 0.9847 | 0.9656 |
| Q116S | 0.990767 | 0.990954 | 0.990861 | 0.9551 | 0.9448 | 0.9499 |
| Q116T | 1.106554 | 1.116672 | 1.111613 | 1.0667 | 1.0646 | 1.0657 |
| Q116V | 1.189502 | 1.247321 | 1.218412 | 1.1467 | 1.1892 | 1.1680 |
| Q116W | 1.145149 | 1.148717 | 1.146933 | 1.1039 | 1.0952 | 1.0995 |
| Q116Y | 1.085831 | 1.089557 | 1.087694 | 1.0467 | 1.0388 | 1.0427 |
| E117A | 1.028615 | 1.035325 | 1.03197 | 0.9916 | 0.9871 | 0.9893 |
| E117C | 1.090465 | 1.141323 | 1.115894 | 1.0512 | 1.0881 | 1.0698 |
| E117D | 1.025679 | 1.106812 | 1.066245 | 0.9887 | 1.0552 | 1.0222 |
| E117E | 0.646197 | 0.81347 | 0.729834 | 0.6229 | 0.7756 | 0.6997 |
| E117F | 1.095329 | 1.153648 | 1.124489 | 1.0559 | 1.0999 | 1.0780 |
| E117G | 0.911676 | 0.912073 | 0.911874 | 0.8789 | 0.8696 | 0.8742 |
| E117H | 1.059381 | 1.055045 | 1.057213 | 1.0212 | 1.0059 | 1.0135 |
| E117I | 1.187747 | 1.257181 | 1.222464 | 1.1450 | 1.1986 | 1.1719 |
| E117K | 0.936082 | 0.961373 | 0.948728 | 0.9024 | 0.9166 | 0.9095 |
| E117L | 1.132889 | 1.170903 | 1.151896 | 1.0921 | 1.1163 | 1.1043 |
| E117M | 1.094063 | 1.131463 | 1.112763 | 1.0547 | 1.0787 | 1.0668 |

TABLE 9-continued

| Variant | Slope PI | Delta PI | Avg PI | Norm Slope PI | Norm Delta PI | Norm Avg PI |
|---|---|---|---|---|---|---|
| E117N | 0.989846 | 1.064906 | 1.027376 | 0.9542 | 1.0153 | 0.9849 |
| E117P | 0.815834 | 0.840587 | 0.82821 | 0.7865 | 0.8014 | 0.7940 |
| E117Q | 0.947049 | 1.04272 | 0.994885 | 0.9130 | 0.9941 | 0.9538 |
| E117R | 0.971599 | 1.079696 | 1.025647 | 0.9366 | 1.0294 | 0.9833 |
| E117S | 0.952545 | 1.015605 | 0.984075 | 0.9182 | 0.9683 | 0.9434 |
| E117T | 1.01834 | 1.074767 | 1.046553 | 0.9817 | 1.0247 | 1.0033 |
| E117V | 1.086638 | 1.119136 | 1.102887 | 1.0475 | 1.0670 | 1.0573 |
| E117W | 1.121175 | 1.136394 | 1.128784 | 1.0808 | 1.0834 | 1.0821 |
| E117Y | 1.013274 | 1.000813 | 1.007044 | 0.9768 | 0.9542 | 0.9654 |
| S120A | 0.941378 | 0.966303 | 0.953841 | 0.9134 | 0.9474 | 0.9303 |
| S120C | 0.947163 | 0.958908 | 0.953036 | 0.9190 | 0.9402 | 0.9295 |
| S120D | 0.8875 | 0.897282 | 0.892391 | 0.8611 | 0.8798 | 0.8704 |
| S120E | 0.998192 | 1.089556 | 1.043874 | 0.9685 | 1.0683 | 1.0181 |
| S120F | 1.044358 | 1.023 | 1.033679 | 1.0133 | 1.0030 | 1.0082 |
| S120G | 0.988292 | 0.961373 | 0.974833 | 0.9589 | 0.9426 | 0.9508 |
| S120H | 0.979255 | 0.934258 | 0.956756 | 0.9501 | 0.9160 | 0.9331 |
| S120I | 0.987659 | 0.880027 | 0.933843 | 0.9583 | 0.8628 | 0.9108 |
| S120K | 1.068822 | 0.986025 | 1.027423 | 1.0370 | 0.9668 | 1.0021 |
| S120L | 1.082493 | 1.025465 | 1.053979 | 1.0503 | 1.0054 | 1.0280 |
| S120M | 1.01408 | 1.018071 | 1.016075 | 0.9839 | 0.9982 | 0.9910 |
| S120N | 0.922268 | 0.971234 | 0.946751 | 0.8948 | 0.9523 | 0.9234 |
| S120P | 0.813561 | 0.825795 | 0.819678 | 0.7893 | 0.8097 | 0.7995 |
| S120Q | 0.962907 | 1.055047 | 1.008977 | 0.9342 | 1.0344 | 0.9841 |
| S120R | 0.996811 | 1.005745 | 1.001278 | 0.9671 | 0.9861 | 0.9766 |
| S120S | 0.833276 | 0.825795 | 0.829535 | 0.8085 | 0.8097 | 0.8091 |
| S120T | 0.983428 | 0.897282 | 0.940355 | 0.9542 | 0.8798 | 0.9172 |
| S120V | 0.982276 | 0.907142 | 0.944709 | 0.9530 | 0.8894 | 0.9214 |
| S120W | 1.100222 | 1.025465 | 1.062843 | 1.0675 | 1.0054 | 1.0366 |
| S120Y | 1.030571 | 0.976164 | 1.003368 | 0.9999 | 0.9571 | 0.9786 |
| G121A | 1.088364 | 1.02793 | 1.058147 | 1.0539 | 1.0030 | 1.0286 |
| G121C | 1.051755 | 1.047652 | 1.049703 | 1.0185 | 1.0222 | 1.0203 |
| G121D | 0.996898 | 0.981093 | 0.988996 | 0.9653 | 0.9573 | 0.9613 |
| G121E | 0.918066 | 0.894817 | 0.906441 | 0.8890 | 0.8731 | 0.8811 |
| G121F | 1.083616 | 1.077231 | 1.080423 | 1.0493 | 1.0511 | 1.0502 |
| G121G | 1.009475 | 0.953978 | 0.981726 | 0.9775 | 0.9308 | 0.9543 |
| G121H | 1.080306 | 1.055045 | 1.067675 | 1.0461 | 1.0295 | 1.0378 |
| G121I | 1.087386 | 1.03286 | 1.060123 | 1.0530 | 1.0078 | 1.0305 |
| G121K | 1.029305 | 1.072301 | 1.050803 | 0.9967 | 1.0463 | 1.0214 |
| G121L | 1.059698 | 1.02793 | 1.043814 | 1.0261 | 1.0030 | 1.0146 |
| G121M | 1.049279 | 1.018069 | 1.033674 | 1.0161 | 0.9934 | 1.0048 |
| G121N | 0.991055 | 0.953978 | 0.972516 | 0.9597 | 0.9308 | 0.9453 |
| G121P | 1.000006 | 0.961373 | 0.98069 | 0.9683 | 0.9381 | 0.9533 |
| G121Q | 0.86551 | 0.872631 | 0.869071 | 0.8381 | 0.8515 | 0.8448 |
| G121R | 0.985845 | 0.981093 | 0.983469 | 0.9546 | 0.9573 | 0.9560 |
| G121S | 0.871756 | 0.921932 | 0.896844 | 0.8442 | 0.8996 | 0.8718 |
| G121T | 1.013044 | 1.045186 | 1.029115 | 0.9810 | 1.0198 | 1.0003 |
| G121V | 1.050805 | 1.045186 | 1.047995 | 1.0175 | 1.0198 | 1.0187 |
| G121W | 1.016152 | 1.000815 | 1.008484 | 0.9840 | 0.9765 | 0.9803 |
| G121Y | 0.956172 | 0.956442 | 0.956307 | 0.9259 | 0.9333 | 0.9296 |
| Q125A | 1.020901 | 1.064906 | 1.042903 | 0.9841 | 1.0153 | 0.9998 |
| Q125C | 0.988177 | 1.03286 | 1.010518 | 0.9526 | 0.9847 | 0.9687 |
| Q125D | 1.001445 | 1.077231 | 1.039338 | 0.9654 | 1.0270 | 0.9964 |
| Q125E | 1.022426 | 1.106812 | 1.064619 | 0.9856 | 1.0552 | 1.0206 |
| Q125F | 1.080593 | 1.207879 | 1.144236 | 1.0417 | 1.1516 | 1.0969 |
| Q125G | 1.0228 | 1.01314 | 1.01797 | 0.9860 | 0.9659 | 0.9759 |
| Q125H | 0.946905 | 0.951513 | 0.949209 | 0.9128 | 0.9072 | 0.9100 |
| Q125I | 1.008295 | 1.032861 | 1.020578 | 0.9720 | 0.9847 | 0.9784 |
| Q125K | 0.955913 | 0.971234 | 0.963574 | 0.9215 | 0.9260 | 0.9237 |
| Q125L | 1.002654 | 1.055047 | 1.02885 | 0.9666 | 1.0059 | 0.9863 |
| Q125M | 0.97416 | 1.087092 | 1.030626 | 0.9391 | 1.0364 | 0.9880 |
| Q125N | 0.990134 | 1.087092 | 1.038613 | 0.9545 | 1.0364 | 0.9957 |
| Q125P | 0.983917 | 1.101882 | 1.042899 | 0.9485 | 1.0505 | 0.9998 |
| Q125Q | 0.952545 | 1.087092 | 1.019818 | 0.9182 | 1.0364 | 0.9777 |
| Q125R | 1.016123 | 1.133928 | 1.075026 | 0.9795 | 1.0811 | 1.0306 |
| Q125S | 1.000754 | 1.045186 | 1.02297 | 0.9647 | 0.9965 | 0.9807 |
| Q125T | 1.038803 | 1.067372 | 1.053087 | 1.0014 | 1.0176 | 1.0096 |
| Q125V | 1.08209 | 1.178299 | 1.130195 | 1.0431 | 1.1234 | 1.0835 |
| Q125W | 1.054892 | 1.163507 | 1.109199 | 1.0169 | 1.1093 | 1.0634 |
| Q125Y | 0.96236 | 1.010674 | 0.986517 | 0.9277 | 0.9636 | 0.9457 |
| G127A | 0.848239 | 0.914537 | 0.881388 | 0.8203 | 0.8432 | 0.8320 |
| G127C | 0.962846 | 0.998598 | 0.980598 | 0.9311 | 0.9205 | 0.9256 |
| G127D | 1.014163 | 1.064906 | 1.039534 | 0.9807 | 0.9818 | 0.9813 |
| G127E | 1.030802 | 1.151183 | 1.090992 | 0.9968 | 1.0614 | 1.0299 |
| G127F | 1.04349 | 1.116672 | 1.080081 | 1.0091 | 1.0295 | 1.0196 |
| G127G | −0.06339 | −0.05916 | −0.06128 | −0.0613 | −0.0545 | −0.0578 |
| G127H | 1.147312 | 1.321273 | 1.234293 | 1.1095 | 1.2182 | 1.1651 |
| G127I | 1.069241 | 1.136392 | 1.102817 | 1.0340 | 1.0477 | 1.0410 |
| G127K | 0.908555 | 0.973698 | 0.941127 | 0.8786 | 0.8977 | 0.8884 |
| G127L | 1.031639 | 1.055047 | 1.043343 | 0.9976 | 0.9727 | 0.9849 |
| G127M | 0.903629 | 0.946583 | 0.925106 | 0.8738 | 0.8727 | 0.8733 |
| G127N | 0.909154 | 0.926863 | 0.918009 | 0.8792 | 0.8545 | 0.8666 |
| G127P | 0.960143 | 1.025465 | 0.992804 | 0.9285 | 0.9455 | 0.9372 |
| G127Q | 0.915942 | 0.99342 | 0.954681 | 0.8857 | 0.9159 | 0.9012 |
| G127R | 0.847937 | 0.951514 | 0.899726 | 0.8200 | 0.8773 | 0.8493 |
| G125S | 1.052151 | 1.136394 | 1.094272 | 1.0174 | 1.0477 | 1.0329 |
| G127T | 1.129834 | 1.22267 | 1.176252 | 1.0926 | 1.1273 | 1.1103 |
| G127V | 1.069044 | 1.163507 | 1.116276 | 1.0338 | 1.0727 | 1.0537 |
| G127W | 0.991198 | 1.040255 | 1.015726 | 0.9585 | 0.9591 | 0.9588 |
| G127Y | 0.980079 | 1.055045 | 1.017562 | 0.9477 | 0.9727 | 0.9605 |
| L130A | 0.40288 | 0.411665 | 0.407272 | 0.4629 | 0.5005 | 0.4817 |
| L130C | 0.388634 | 0.377154 | 0.382894 | 0.4465 | 0.4585 | 0.4525 |
| L130D | 0.794593 | 0.796214 | 0.795404 | 0.9129 | 0.9680 | 0.9405 |
| L130E | 0.795198 | 0.771564 | 0.783381 | 0.9136 | 0.9381 | 0.9258 |
| L130G | 0.845076 | 0.77896 | 0.812018 | 0.9709 | 0.9471 | 0.9590 |
| L130I | 0.839982 | 0.79868 | 0.819331 | 0.9651 | 0.9710 | 0.9680 |
| L130K | 0.880046 | 0.806075 | 0.84306 | 1.0111 | 0.9800 | 0.9956 |
| L130L | 0.851696 | 0.808539 | 0.830117 | 0.9785 | 0.9830 | 0.9808 |
| L130L | 0.854142 | 0.803609 | 0.828875 | 0.9813 | 0.9770 | 0.9792 |
| L130L | 0.833823 | 0.776494 | 0.805158 | 0.9580 | 0.9441 | 0.9510 |
| L130L | 0.803516 | 0.764169 | 0.783843 | 0.9232 | 0.9291 | 0.9261 |
| L130L | 0.779686 | 0.766635 | 0.77316 | 0.8958 | 0.9321 | 0.9139 |
| L130M | 0.387108 | 0.362364 | 0.374736 | 0.4448 | 0.4406 | 0.4427 |
| L130P | 0.725231 | 0.729657 | 0.727444 | 0.8332 | 0.8871 | 0.8602 |
| L130Q | 0.77911 | 0.732123 | 0.755616 | 0.8951 | 0.8901 | 0.8926 |
| L130R | 0.842457 | 0.801145 | 0.821801 | 0.9679 | 0.9740 | 0.9710 |
| L130S | −0.17381 | −0.12572 | −0.14976 | −0.1997 | −0.1528 | −0.1763 |
| L130V | 0.818367 | 0.830724 | 0.824546 | 0.9402 | 1.0100 | 0.9751 |
| L130W | 0.749724 | 0.705008 | 0.727366 | 0.8614 | 0.8571 | 0.8593 |
| L130Y | 0.877601 | 0.835655 | 0.856728 | 1.0085 | 1.0160 | 1.0123 |
| A139A | 0.889837 | 0.914537 | 0.902187 | 0.8605 | 0.8432 | 0.8516 |
| A139C | 0.988592 | 1.082162 | 1.035377 | 0.9560 | 0.9977 | 0.9774 |
| A139D | 0.937983 | 0.99342 | 0.965701 | 0.9070 | 0.9159 | 0.9116 |
| A139E | 0.966098 | 1.077231 | 1.021665 | 0.9342 | 0.9932 | 0.9644 |
| A139F | 0.905755 | 0.934257 | 0.920006 | 0.8759 | 0.8614 | 0.8684 |
| A139G | 1.007398 | 1.045186 | 1.026292 | 0.9742 | 0.9636 | 0.9688 |
| A139H | 1.057229 | 1.114208 | 1.085718 | 1.0224 | 1.0273 | 1.0249 |
| A139I | 1.063597 | 1.106812 | 1.085204 | 1.0285 | 1.0205 | 1.0244 |
| A139K | 0.611651 | 0.62879 | 0.620121 | 0.5915 | 0.5795 | 0.5854 |
| A139L | 0.950874 | 0.983559 | 0.967217 | 0.9195 | 0.9068 | 0.9130 |
| A139M | 0.879421 | 0.865236 | 0.872328 | 0.8504 | 0.7977 | 0.8234 |
| A139N | 0.883792 | 0.909607 | 0.8967 | 0.8546 | 0.8386 | 0.8464 |
| A139P | 0.985901 | 1.018071 | 1.001986 | 0.9534 | 0.9386 | 0.9458 |
| A139Q | 0.954284 | 1.010674 | 0.982479 | 0.9228 | 0.9318 | 0.9274 |
| A139R | 0.581226 | 0.640915 | 0.611071 | 0.5621 | 0.5909 | 0.5768 |
| A139S | 1.039675 | 1.072301 | 1.055988 | 1.0054 | 0.9886 | 0.9968 |
| A139T | 1.147503 | 1.220255 | 1.183854 | 1.1096 | 1.1250 | 1.1175 |
| A139V | 1.060937 | 1.06244 | 1.061689 | 1.0259 | 0.9795 | 1.0022 |
| A139W | 0.938067 | 0.941654 | 0.93986 | 0.9071 | 0.8682 | 0.8872 |
| A139Y | 0.744418 | 0.838121 | 0.791269 | 0.7199 | 0.7727 | 0.7469 |
| G153A | 0.790334 | 0.690216 | 0.740275 | 0.9080 | 0.8392 | 0.8736 |
| G153C | 0.848185 | 0.756774 | 0.802479 | 0.9745 | 0.9201 | 0.9473 |
| G153D | 0.773468 | 0.759238 | 0.766353 | 0.8887 | 0.9231 | 0.9059 |
| G153G | 0.841939 | 0.833191 | 0.837565 | 0.9673 | 1.0130 | 0.9902 |
| G153G | 0.811143 | 0.761704 | 0.786423 | 0.9319 | 0.9261 | 0.9290 |
| G153G | 0.793126 | 0.776494 | 0.78481 | 0.9112 | 0.9441 | 0.9276 |
| G153G | 0.737233 | 0.737053 | 0.737143 | 0.8470 | 0.8961 | 0.8716 |
| G153H | −0.11023 | −0.106 | −0.10812 | −0.1266 | −0.1289 | −0.1278 |
| G153K | 0.504996 | 0.529987 | 0.517492 | 0.5802 | 0.6444 | 0.6123 |
| G153L | 0.515501 | 0.534919 | 0.52521 | 0.5923 | 0.6504 | 0.6213 |
| G153M | 0.739794 | 0.665566 | 0.70268 | 0.8500 | 0.8092 | 0.8296 |
| G153N | 0.754041 | 0.658171 | 0.706106 | 0.8663 | 0.8002 | 0.8333 |
| G153P | 0.446945 | 0.423991 | 0.435468 | 0.5135 | 0.5155 | 0.5145 |
| G153Q | 0.721777 | 0.677823 | 0.699835 | 0.8293 | 0.8242 | 0.8267 |
| G153R | 0.871728 | 0.80854 | 0.840134 | 1.0015 | 0.9830 | 0.9923 |
| G153S | 0.840874 | 0.786355 | 0.813614 | 0.9661 | 0.9560 | 0.9611 |
| G153T | 0.78783 | 0.732123 | 0.759977 | 0.9052 | 0.8901 | 0.8976 |
| G153V | 0.511587 | 0.500407 | 0.505997 | 0.5878 | 0.6084 | 0.5981 |
| G153W | 0.93024 | 0.867702 | 0.898971 | 1.0688 | 1.0549 | 1.0619 |
| G153Y | 0.848674 | 0.857841 | 0.853257 | 0.9751 | 1.0430 | 1.0090 |
| I165A | 0.915907 | 0.899746 | 0.907827 | 0.9454 | 0.9240 | 0.9347 |
| I165C | 0.860683 | 0.862772 | 0.861728 | 0.8884 | 0.8861 | 0.8873 |
| I165D | 0.958548 | 0.986025 | 0.972287 | 0.9895 | 1.0127 | 1.0011 |

TABLE 9-continued

| Variant | Slope PI | Delta PI | Avg PI | Norm Slope PI | Norm Delta PI | Norm Avg PI |
|---|---|---|---|---|---|---|
| I165E | 0.845598 | 0.860305 | 0.852952 | 0.8729 | 0.8835 | 0.8782 |
| I165F | 1.014278 | 1.052581 | 1.03343 | 1.0470 | 1.0810 | 1.0640 |
| I165G | 0.953951 | 0.988489 | 0.97122 | 0.9847 | 1.0152 | 1.0000 |
| I165H | 1.020528 | 1.050116 | 1.035322 | 1.0534 | 1.0785 | 1.0660 |
| I165I | 0.964169 | 0.995885 | 0.980027 | 0.9953 | 1.0228 | 1.0091 |
| I165K | 1.033234 | 1.06244 | 1.047837 | 1.0665 | 1.0911 | 1.0789 |
| I165L | 0.986277 | 1.020535 | 1.003406 | 1.0181 | 1.0481 | 1.0331 |
| I165M | 0.906048 | 0.857841 | 0.881945 | 0.9353 | 0.8810 | 0.9081 |
| I165N | 0.91803 | 0.880027 | 0.899028 | 0.9476 | 0.9038 | 0.9257 |
| I165P | 0.743388 | 0.746913 | 0.745151 | 0.7674 | 0.7671 | 0.7672 |
| I165Q | 0.848672 | 0.860307 | 0.854489 | 0.8760 | 0.8835 | 0.8798 |
| I165R | 0.971592 | 1.015605 | 0.993599 | 1.0029 | 1.0430 | 1.0230 |
| I165S | 0.875097 | 0.882724 | 0.9191 | 0.8987 | 0.9089 | |
| I165T | 0.942097 | 0.949049 | 0.945573 | 0.9725 | 0.9747 | 0.9736 |
| I165V | 0.729273 | 0.714867 | 0.72207 | 0.7528 | 0.7342 | 0.7435 |
| I165W | 0.937282 | 0.956444 | 0.946863 | 0.9675 | 0.9823 | 0.9749 |
| I165Y | 1.047089 | 1.020535 | 1.033812 | 1.0809 | 1.0481 | 1.0644 |
| E173A | 0.980306 | 0.978629 | 0.979468 | 1.0119 | 1.0051 | 1.0085 |
| E173C | 0.936034 | 0.971233 | 0.953633 | 0.9662 | 0.9975 | 0.9819 |
| E173D | 0.832873 | 0.892353 | 0.862613 | 0.8597 | 0.9165 | 0.8882 |
| E173E | 0.853486 | 0.884958 | 0.869222 | 0.8810 | 0.9089 | 0.8950 |
| E173F | 1.082143 | 1.138858 | 1.1105 | 1.1170 | 1.1696 | 1.1434 |
| E173G | 1.003778 | 1.000815 | 1.002296 | 1.0361 | 1.0278 | 1.0320 |
| E173H | 1.053843 | 1.079696 | 1.06677 | 1.0878 | 1.1089 | 1.0984 |
| E173I | 1.027437 | 1.022999 | 1.025218 | 1.0606 | 1.0506 | 1.0556 |
| E173K | 1.024202 | 1.045185 | 1.034693 | 1.0572 | 1.0734 | 1.0653 |
| E173L | 1.007377 | 1.020535 | 1.013956 | 1.0399 | 1.0481 | 1.0440 |
| E173M | 0.976904 | 0.931793 | 0.954349 | 1.0084 | 0.9570 | 0.9826 |
| E173N | 0.949381 | 1.003279 | 0.97633 | 0.9800 | 1.0304 | 1.0053 |
| E173P | 0.837159 | 0.872631 | 0.854895 | 0.8642 | 0.8962 | 0.8802 |
| E173Q | 0.844411 | 0.870167 | 0.857289 | 0.8716 | 0.8937 | 0.8827 |
| E173R | 1.074678 | 1.087092 | 1.080885 | 1.1093 | 1.1165 | 1.1129 |
| E173S | 0.971814 | 0.993418 | 0.982616 | 1.0031 | 1.0203 | 1.0117 |
| E173T | 1.078933 | 1.077231 | 1.078082 | 1.1137 | 1.1063 | 1.1100 |
| E173V | 1.087401 | 1.099418 | 1.093409 | 1.1225 | 1.1291 | 1.1258 |
| E173W | 1.061328 | 1.067372 | 1.06435 | 1.0955 | 1.0962 | 1.0959 |
| E173Y | 0.998503 | 0.995885 | 0.997194 | 1.0307 | 1.0228 | 1.0267 |
| E174A | 0.878286 | 0.867702 | 0.872994 | 0.9066 | 0.8911 | 0.8989 |
| E174C | 0.826376 | 0.887422 | 0.856899 | 0.8530 | 0.9114 | 0.8823 |
| E174D | 0.686488 | 0.717333 | 0.70191 | 0.7086 | 0.7367 | 0.7227 |
| E174E | 0.610155 | 0.63845 | 0.624302 | 0.6298 | 0.6557 | 0.6428 |
| E174F | 0.993605 | 0.98849 | 0.991033 | 1.0256 | 1.0152 | 1.0204 |
| E174G | 0.875195 | 0.921934 | 0.898564 | 0.9034 | 0.9468 | 0.9252 |
| E174H | 1.05931 | 1.08216 | 1.070735 | 1.0935 | 1.1114 | 1.1025 |
| E174I | 1.06009 | 1.055045 | 1.057568 | 1.0943 | 1.0835 | 1.0889 |
| E174K | 0.963129 | 0.990954 | 0.977042 | 0.9942 | 1.0177 | 1.0060 |
| E174L | 0.978313 | 1.02793 | 1.003121 | 1.0099 | 1.0557 | 1.0328 |
| E174M | 0.816944 | 0.820865 | 0.818905 | 0.8433 | 0.8430 | 0.8432 |
| E174N | 0.734617 | 0.81347 | 0.774044 | 0.7583 | 0.8354 | 0.7970 |
| E174P | 0.588806 | 0.653124 | 0.621024 | 0.6078 | 0.6709 | 0.6394 |
| E174Q | 0.565478 | 0.60887 | 0.587174 | 0.5837 | 0.6253 | 0.6046 |
| E174R | 0.911732 | 0.956444 | 0.934088 | 0.9411 | 0.9823 | 0.9618 |
| E174S | 0.841302 | 0.894817 | 0.868059 | 0.8684 | 0.9190 | 0.8938 |
| E174T | 1.009482 | 1.055047 | 1.032264 | 1.0420 | 1.0835 | 1.0628 |
| E174V | 1.018064 | 1.04272 | 1.030392 | 1.0509 | 1.0709 | 1.0609 |
| E174W | 0.975489 | 1.022999 | 0.999244 | 1.0069 | 1.0506 | 1.0288 |
| E174Y | 0.871071 | 0.917002 | 0.894037 | 0.8992 | 0.9418 | 0.9205 |
| G177A | 0.951797 | 1.008209 | 0.980003 | 1.0150 | 0.9915 | 1.0028 |
| G177C | 0.865799 | 0.889887 | 0.877843 | 0.9233 | 0.8752 | 0.8982 |
| G177D | 0.772806 | 0.81347 | 0.793138 | 0.8241 | 0.8000 | 0.8116 |
| G177E | 0.855956 | 0.902212 | 0.879084 | 0.9128 | 0.8873 | 0.8995 |
| G177F | 0.77485 | 0.806075 | 0.790462 | 0.8263 | 0.7927 | 0.8088 |
| G177G | 0.921606 | 1.01314 | 0.967373 | 0.9828 | 0.9964 | 0.9898 |
| G177H | 0.798796 | 0.902212 | 0.850504 | 0.8518 | 0.8873 | 0.8703 |
| G177I | 0.841478 | 0.887422 | 0.86445 | 0.8973 | 0.8727 | 0.8845 |
| G177K | 0.797069 | 0.81347 | 0.805269 | 0.8500 | 0.8000 | 0.8240 |
| G177L | 0.834254 | 0.877562 | 0.855908 | 0.8896 | 0.8630 | 0.8758 |
| G177M | 0.955682 | 0.968769 | 0.962225 | 1.0191 | 0.9527 | 0.9846 |
| G177N | 0.892537 | 0.926863 | 0.9097 | 0.9518 | 0.9115 | 0.9308 |
| G177P | 0.94843 | 1.003281 | 0.975855 | 1.0114 | 0.9867 | 0.9985 |
| G177Q | 0.765496 | 0.78882 | 0.777158 | 0.8163 | 0.7758 | 0.7952 |
| G177R | 0.814596 | 0.840585 | 0.827591 | 0.8687 | 0.8267 | 0.8468 |
| G177S | 0.970879 | 1.059975 | 1.015427 | 1.0353 | 1.0424 | 1.0390 |
| G177T | 0.926153 | 1.005745 | 0.965949 | 0.9876 | 0.9891 | 0.9884 |
| G177V | 0.90756 | 0.98849 | 0.948025 | 0.9678 | 0.9721 | 0.9700 |
| G177W | 0.790737 | 0.865236 | 0.827987 | 0.8432 | 0.8509 | 0.8472 |
| G177Y | 0.793327 | 0.840585 | 0.816956 | 0.8460 | 0.8267 | 0.8359 |
| E179A | 0.969872 | 1.005745 | 0.987808 | 1.0342 | 0.9891 | 1.0108 |
| E179C | 0.935939 | 0.978629 | 0.957284 | 0.9981 | 0.9624 | 0.9795 |
| E179D | 0.908193 | 0.929327 | 0.91876 | 0.9685 | 0.9139 | 0.9401 |
| E179E | 0.003655 | 0.071486 | 0.037571 | 0.0039 | 0.0703 | 0.0384 |
| E179F | 0.996725 | 1.03286 | 1.014792 | 1.0629 | 1.0158 | 1.0384 |
| E179G | 1.070203 | 1.087092 | 1.078647 | 1.1412 | 1.0691 | 1.1037 |
| E179H | 0.971253 | 1.077231 | 1.024242 | 1.0357 | 1.0594 | 1.0480 |
| E179I | 1.027233 | 1.055045 | 1.041139 | 1.0954 | 1.0376 | 1.0653 |
| E179K | 1.002654 | 1.018071 | 1.010362 | 1.0692 | 1.0012 | 1.0338 |
| E179L | 0.951509 | 0.983559 | 0.967534 | 1.0147 | 0.9673 | 0.9900 |
| E179M | 0.961641 | 1.005745 | 0.983693 | 1.0255 | 0.9891 | 1.0065 |
| E179N | 0.892709 | 0.870167 | 0.881438 | 0.9520 | 0.8558 | 0.9019 |
| E179P | 0.907244 | 0.944118 | 0.925681 | 0.9675 | 0.9285 | 0.9472 |
| E179Q | 0.882319 | 0.951513 | 0.916916 | 0.9409 | 0.9358 | 0.9382 |
| E179R | 0.926671 | 1.020535 | 0.973603 | 0.9882 | 1.0036 | 0.9962 |
| E179S | 1.049078 | 1.059975 | 1.054526 | 1.1187 | 1.0424 | 1.0790 |
| E179T | 0.887557 | 0.951513 | 0.919535 | 0.9465 | 0.9358 | 0.9409 |
| E179V | 0.950041 | 1.000813 | 0.975427 | 1.0131 | 0.9842 | 0.9981 |
| E179W | 0.978507 | 1.003279 | 0.990893 | 1.0434 | 0.9867 | 1.0139 |
| E179Y | 0.878261 | 0.897282 | 0.887772 | 0.9365 | 0.8824 | 0.9084 |
| R194A | 0.469726 | 0.401805 | 0.435766 | 0.4542 | 0.3705 | 0.4113 |
| R194C | 0.784501 | 0.744449 | 0.764475 | 0.7586 | 0.6864 | 0.7216 |
| R194D | 0.039586 | 0 | 0.019793 | 0.0383 | 0.0000 | 0.0187 |
| R194E | 0.121664 | 0.073952 | 0.097808 | 0.1177 | 0.0682 | 0.0923 |
| R194F | 0.879892 | 0.880027 | 0.879959 | 0.8509 | 0.8114 | 0.8306 |
| R194G | −0.02142 | −0.07395 | −0.04769 | −0.0207 | −0.0682 | −0.0450 |
| R194H | 1.017062 | 1.008209 | 1.012636 | 0.9835 | 0.9295 | 0.9559 |
| R194I | 0.856465 | 0.892351 | 0.874408 | 0.8282 | 0.8227 | 0.8254 |
| R194K | 0.922356 | 0.899746 | 0.911051 | 0.8919 | 0.8295 | 0.8600 |
| R194L | 0.876215 | 0.850446 | 0.86333 | 0.8473 | 0.7841 | 0.8149 |
| R194M | 0.806405 | 0.81347 | 0.809937 | 0.7798 | 0.7500 | 0.7645 |
| R194N | 0.404952 | 0.389479 | 0.397215 | 0.3916 | 0.3591 | 0.3750 |
| R194P | 0.015807 | 0.049301 | 0.032554 | 0.0153 | 0.0455 | 0.0307 |
| R194Q | 0.79203 | 0.855375 | 0.823703 | 0.7659 | 0.7886 | 0.7775 |
| R194R | 0.927518 | 0.961373 | 0.944446 | 0.8969 | 0.8864 | 0.8915 |
| R194S | 0.282735 | 0.278551 | 0.280643 | 0.2734 | 0.2568 | 0.2649 |
| R194T | 0.451988 | 0.505338 | 0.478663 | 0.4371 | 0.4659 | 0.4518 |
| R194V | 0.728372 | 0.783889 | 0.756131 | 0.7043 | 0.7227 | 0.7138 |
| R194W | 0.93906 | 0.956444 | 0.947752 | 0.9081 | 0.8818 | 0.8946 |
| R194Y | 0.905526 | 0.981093 | 0.94331 | 0.8757 | 0.9045 | 0.8904 |
| Q197A | 0.891065 | 0.882492 | 0.886778 | 0.8617 | 0.8136 | 0.8371 |
| Q197C | 0.865353 | 0.872631 | 0.868992 | 0.8368 | 0.8045 | 0.8203 |
| Q197D | 0.91067 | 0.926863 | 0.918767 | 0.8806 | 0.8545 | 0.8673 |
| Q197E | 0.909473 | 0.944118 | 0.926795 | 0.8795 | 0.8705 | 0.8749 |
| Q197F | 1.020749 | 1.022999 | 1.021874 | 0.9871 | 0.9432 | 0.9646 |
| Q197G | 0.931358 | 0.924398 | 0.927878 | 0.9006 | 0.8523 | 0.8759 |
| Q197H | 1.023785 | 1.06737 | 1.045578 | 0.9900 | 0.9841 | 0.9870 |
| Q197I | 1.02063 | 1.022999 | 1.021815 | 0.9870 | 0.9432 | 0.9645 |
| Q197K | 0.915172 | 0.877562 | 0.896367 | 0.8850 | 0.8091 | 0.8461 |
| Q197L | 0.980751 | 1.030394 | 1.005573 | 0.9484 | 0.9500 | 0.9492 |
| Q197M | 0.930394 | 0.838121 | 0.884258 | 0.8997 | 0.7727 | 0.8347 |
| Q197N | 0.895307 | 0.845516 | 0.870411 | 0.8658 | 0.7795 | 0.8216 |
| Q197P | 0.835951 | 0.801145 | 0.818548 | 0.8084 | 0.7386 | 0.7727 |
| Q197Q | 0.772515 | 0.751844 | 0.762179 | 0.7470 | 0.6932 | 0.7195 |
| Q197R | 0.873059 | 0.806075 | 0.839567 | 0.8443 | 0.7432 | 0.7925 |
| Q197S | 0.913069 | 0.894817 | 0.903943 | 0.8829 | 0.8250 | 0.8533 |
| Q197T | 1.018188 | 1.018071 | 1.01813 | 0.9846 | 0.9386 | 0.9611 |
| Q197V | 1.002852 | 0.941654 | 0.972273 | 0.9698 | 0.8682 | 0.9178 |
| Q197W | 0.876104 | 0.830724 | 0.853414 | 0.8472 | 0.7659 | 0.8056 |
| Q197Y | 0.900649 | 0.899746 | 0.900198 | 0.8709 | 0.8295 | 0.8497 |
| R198A | 0.857078 | 0.843051 | 0.850064 | 0.7779 | 0.7439 | 0.7606 |
| R198C | 0.924484 | 0.907142 | 0.915813 | 0.8391 | 0.8004 | 0.8195 |
| R198D | 0.056958 | 0.118323 | 0.087641 | 0.0517 | 0.1044 | 0.0784 |
| R198F | 0.306377 | 0.458501 | 0.382439 | 0.2781 | 0.4046 | 0.3422 |
| R198G | 0.551219 | 0.63352 | 0.59237 | 0.5003 | 0.5590 | 0.5301 |
| R198H | 0.312882 | 0.406735 | 0.359808 | 0.2840 | 0.3589 | 0.3220 |
| R198I | 0.84004 | 0.917002 | 0.878521 | 0.7624 | 0.8091 | 0.7861 |
| R198K | 0.910698 | 0.973698 | 0.942198 | 0.8266 | 0.8592 | 0.8431 |
| R198L | 0.294922 | 0.431386 | 0.363154 | 0.2677 | 0.3806 | 0.3250 |
| R198M | 0.87239 | 0.872631 | 0.87251 | 0.7918 | 0.7700 | 0.7807 |
| R198N | 0.604867 | 0.64831 | 0.626589 | 0.5490 | 0.5720 | 0.5607 |
| R198P | 0.041128 | 0.069022 | 0.055075 | 0.0373 | 0.0609 | 0.0493 |
| R198R | 1.114008 | 1.180763 | 1.147386 | 1.0111 | 1.0419 | 1.0267 |
| R198R | 1.139451 | 1.141323 | 1.140387 | 1.0342 | 1.0071 | 1.0204 |
| R198R | 1.074923 | 1.138858 | 1.106891 | 0.9756 | 1.0049 | 0.9905 |

TABLE 9-continued

| Variant | Slope PI | Delta PI | Avg PI | Norm Slope PI | Norm Delta PI | Norm Avg PI |
|---|---|---|---|---|---|---|
| R198R | 0.830887 | 0.830724 | 0.830806 | 0.7541 | 0.7330 | 0.7434 |
| R198S | 0.721547 | 0.786353 | 0.75395 | 0.6549 | 0.6939 | 0.6746 |
| R198T | 0.810884 | 0.815935 | 0.81341 | 0.7360 | 0.7200 | 0.7278 |
| R198V | 0.917979 | 0.971233 | 0.944606 | 0.8332 | 0.8570 | 0.8452 |
| R198Y | 0.076415 | 0.108464 | 0.092439 | 0.0694 | 0.0957 | 0.0827 |
| V202A | 0.949033 | 0.953978 | 0.951506 | 0.9796 | 0.9797 | 0.9797 |
| V202C | 0.927689 | 0.926863 | 0.927276 | 0.9576 | 0.9519 | 0.9547 |
| V202D | 0.851528 | 0.84798 | 0.849754 | 0.8790 | 0.8709 | 0.8749 |
| V202E | 0.826789 | 0.830726 | 0.828758 | 0.8534 | 0.8532 | 0.8533 |
| V202F | 0.921287 | 0.921932 | 0.92161 | 0.9510 | 0.9468 | 0.9489 |
| V202G | 0.899929 | 0.894817 | 0.897373 | 0.9289 | 0.9190 | 0.9240 |
| V202H | 0.999256 | 0.973698 | 0.986477 | 1.0315 | 1.0000 | 1.0157 |
| V202I | 0.977418 | 0.998349 | 0.987884 | 1.0089 | 1.0253 | 1.0171 |
| V202K | 0.985028 | 0.963838 | 0.974433 | 1.0168 | 0.9899 | 1.0033 |
| V202L | 0.922361 | 0.917002 | 0.919682 | 0.9521 | 0.9418 | 0.9469 |
| V202M | 0.877846 | 0.892351 | 0.885098 | 0.9062 | 0.9165 | 0.9113 |
| V202N | 0.92427 | 0.934257 | 0.929264 | 0.9541 | 0.9595 | 0.9568 |
| V202P | 0.548722 | 0.554639 | 0.55168 | 0.5664 | 0.5696 | 0.5680 |
| V202Q | 0.867669 | 0.907143 | 0.887406 | 0.8956 | 0.9316 | 0.9137 |
| V202R | 0.978015 | 1.018069 | 0.998042 | 1.0096 | 1.0456 | 1.0276 |
| V202S | 0.930685 | 0.931239 | 0.931239 | 0.9607 | 0.9570 | 0.9588 |
| V202T | 1.001542 | 1.01314 | 1.007341 | 1.0338 | 1.0405 | 1.0372 |
| V202V | 0.534708 | 0.571894 | 0.553301 | 0.5519 | 0.5873 | 0.5697 |
| V202W | 0.954133 | 0.98849 | 0.971312 | 0.9849 | 1.0152 | 1.0001 |
| V202Y | 0.947739 | 0.973698 | 0.960719 | 0.9783 | 1.0000 | 0.9892 |
| Q216A | 1.121348 | 1.114208 | 1.117778 | 1.0858 | 1.0872 | 1.0865 |
| Q216C | 1.081946 | 1.023 | 1.052473 | 1.0477 | 0.9982 | 1.0230 |
| Q216D | 1.05918 | 1.079696 | 1.069438 | 1.0256 | 1.0535 | 1.0395 |
| Q216E | 0.937349 | 0.958908 | 0.948128 | 0.9077 | 0.9357 | 0.9216 |
| Q216F | 1.012152 | 1.057511 | 1.034831 | 0.9801 | 1.0319 | 1.0059 |
| Q216G | 0.91654 | 0.956442 | 0.936491 | 0.8875 | 0.9333 | 0.9103 |
| Q216H | 1.030082 | 1.064906 | 1.047494 | 0.9975 | 1.0391 | 1.0182 |
| Q216I | 1.060648 | 1.040255 | 1.050451 | 1.0271 | 1.0150 | 1.0211 |
| Q216K | 1.024758 | 1.000813 | 1.012786 | 0.9923 | 0.9765 | 0.9845 |
| Q216L | 0.915907 | 0.929329 | 0.922618 | 0.8869 | 0.9068 | 0.8968 |
| Q216M | 1.076564 | 1.084626 | 1.080595 | 1.0425 | 1.0583 | 1.0504 |
| Q216N | 1.035867 | 1.02793 | 1.031899 | 1.0031 | 1.0030 | 1.0030 |
| Q216P | 0.965612 | 0.941654 | 0.953633 | 0.9350 | 0.9188 | 0.9270 |
| Q216Q | 0.889486 | 0.894817 | 0.892151 | 0.8613 | 0.8731 | 0.8672 |
| Q216R | 0.903128 | 0.865236 | 0.884182 | 0.8745 | 0.8443 | 0.8595 |
| Q216S | 0.874836 | 0.907142 | 0.890989 | 0.8471 | 0.8851 | 0.8661 |
| Q216T | 1.003949 | 1.082162 | 1.043056 | 0.9722 | 1.0559 | 1.0139 |
| Q216V | 1.015145 | 1.032861 | 1.024003 | 0.9830 | 1.0078 | 0.9954 |
| Q216W | 1.079902 | 1.06737 | 1.073636 | 1.0457 | 1.0415 | 1.0436 |
| Q216Y | 0.942098 | 0.981095 | 0.961597 | 0.9123 | 0.9573 | 0.9347 |
| I229A | 0.944141 | 0.904678 | 0.924409 | 0.8569 | 0.7983 | 0.8272 |
| I229C | 1.067383 | 1.084627 | 1.076005 | 0.9688 | 0.9570 | 0.9628 |
| I229D | 0.144252 | 0.226785 | 0.185518 | 0.1309 | 0.2001 | 0.1660 |
| I229E | 0.044669 | 0.064093 | 0.054381 | 0.0405 | 0.0566 | 0.0487 |
| I229F | 0.838744 | 0.840585 | 0.839664 | 0.7613 | 0.7417 | 0.7513 |
| I229G | 0.784549 | 0.751843 | 0.768196 | 0.7121 | 0.6634 | 0.6874 |
| I229H | 0.946732 | 0.926863 | 0.936797 | 0.8593 | 0.8178 | 0.8383 |
| I229I | 1.10546 | 1.198019 | 1.15174 | 1.0033 | 1.0571 | 1.0306 |
| I229K | 0.354902 | 0.42892 | 0.391911 | 0.3221 | 0.3785 | 0.3507 |
| I229L | 1.0913 | 1.077232 | 1.084266 | 0.9905 | 0.9505 | 0.9702 |
| I229M | 0.950991 | 0.939188 | 0.94509 | 0.8631 | 0.8287 | 0.8457 |
| I229N | 0.842687 | 0.843051 | 0.842869 | 0.7648 | 0.7439 | 0.7542 |
| I229P | 0.01134 | 0.056696 | 0.034018 | 0.0103 | 0.0500 | 0.0304 |
| I229Q | 0.617157 | 0.611334 | 0.614246 | 0.5601 | 0.5394 | 0.5496 |
| I229R | 0.104908 | 0.165158 | 0.135033 | 0.0952 | 0.1457 | 0.1208 |
| I229S | 0.82018 | 0.835655 | 0.827918 | 0.7444 | 0.7374 | 0.7408 |
| I229T | 1.022887 | 0.995884 | 1.009385 | 0.9284 | 0.8787 | 0.9032 |
| I229V | 1.020844 | 1.099418 | 1.060131 | 0.9265 | 0.9701 | 0.9486 |
| I229W | 0.336799 | 0.39441 | 0.365604 | 0.3057 | 0.3480 | 0.3271 |
| I229Y | 0.370156 | 0.357434 | 0.363795 | 0.3360 | 0.3154 | 0.3255 |
| T240A | 0.959539 | 0.981095 | 0.970317 | 0.9310 | 0.9619 | 0.9464 |
| T240C | 0.905849 | 0.929327 | 0.917609 | 0.8789 | 0.9112 | 0.8950 |
| T240D | 0.192518 | 0.226785 | 0.209652 | 0.1868 | 0.2224 | 0.2045 |
| T240E | 0.36486 | 0.45357 | 0.409215 | 0.3540 | 0.4447 | 0.3991 |
| T240F | 0.261622 | 0.330319 | 0.295971 | 0.2538 | 0.3239 | 0.2887 |
| T240G | 0.702666 | 0.724728 | 0.713697 | 0.6818 | 0.7106 | 0.6961 |
| T240H | 0.385324 | 0.389481 | 0.387402 | 0.3739 | 0.3819 | 0.3778 |
| T240I | 0.954186 | 0.921934 | 0.93806 | 0.9258 | 0.9039 | 0.9149 |
| T240K | 0.01557 | 0 | 0.007785 | 0.0151 | 0.0000 | 0.0076 |
| T240L | 0.919044 | 0.857841 | 0.888442 | 0.8917 | 0.8411 | 0.8665 |
| T240M | 0.85443 | 0.894817 | 0.874624 | 0.8290 | 0.8773 | 0.8530 |
| T240N | 0.83224 | 0.912073 | 0.872156 | 0.8075 | 0.8943 | 0.8506 |
| T240P | 0.032293 | 0.165158 | 0.098725 | 0.0313 | 0.1619 | 0.0963 |
| T240Q | 0.897602 | 1.018069 | 0.957836 | 0.8709 | 0.9982 | 0.9342 |
| T240R | 0.010592 | 0.101067 | 0.055829 | 0.0103 | 0.0991 | 0.0545 |
| T240S | 0.77059 | 0.840585 | 0.805588 | 0.7477 | 0.8242 | 0.7857 |
| T240T | 0.976981 | 0.936722 | 0.956851 | 0.9479 | 0.9184 | 0.9332 |
| T240V | 0.907906 | 0.892351 | 0.900128 | 0.8809 | 0.8749 | 0.8779 |
| T240W | 0.206620 | 0.231715 | 0.219168 | 0.2005 | 0.2272 | 0.2138 |
| T240Y | 0.156801 | 0.187345 | 0.172073 | 0.1521 | 0.1837 | 0.1678 |
| R246A | 0.88111 | 0.944118 | 0.912614 | 0.9396 | 0.9285 | 0.9338 |
| R246C | 0.750702 | 0.788819 | 0.769761 | 0.8005 | 0.7758 | 0.7876 |
| R246D | 0.8561 | 0.877562 | 0.866831 | 0.9129 | 0.8630 | 0.8870 |
| R246E | 0.890982 | 0.926862 | 0.908922 | 0.9501 | 0.9115 | 0.9300 |
| R246F | 0.528108 | 0.591614 | 0.559861 | 0.5632 | 0.5818 | 0.5729 |
| R246G | 0.957236 | 0.976164 | 0.9667 | 1.0208 | 0.9600 | 0.9892 |
| R246H | 0.854315 | 0.909607 | 0.881961 | 0.9110 | 0.8945 | 0.9024 |
| R246I | 0.543132 | 0.557103 | 0.550117 | 0.5792 | 0.5479 | 0.5629 |
| R246K | 0.979082 | 1.000815 | 0.989948 | 1.0441 | 0.9842 | 1.0129 |
| R246L | 0.597989 | 0.623661 | 0.610825 | 0.6377 | 0.6133 | 0.6250 |
| R246M | 0.807862 | 0.852911 | 0.830387 | 0.8615 | 0.8388 | 0.8497 |
| R246N | 0.936629 | 0.951513 | 0.944071 | 0.9988 | 0.9358 | 0.9660 |
| R246P | 0.05172 | 0.152835 | 0.102277 | 0.0552 | 0.1503 | 0.1047 |
| R246Q | 0.934471 | 0.951513 | 0.942992 | 0.9965 | 0.9358 | 0.9649 |
| R246R | 1.049452 | 1.074767 | 1.062109 | 1.1191 | 1.0570 | 1.0868 |
| R246S | 0.963051 | 1.037791 | 1.000421 | 1.0270 | 1.0206 | 1.0237 |
| R246T | 0.876074 | 0.887422 | 0.881748 | 0.9342 | 0.8727 | 0.9022 |
| R246V | 0.689197 | 0.712403 | 0.7008 | 0.7349 | 0.7006 | 0.7171 |
| R246W | 0.690348 | 0.724728 | 0.707538 | 0.7362 | 0.7127 | 0.7240 |
| R246Y | 0.677109 | 0.690217 | 0.683663 | 0.7220 | 0.6788 | 0.6995 |
| T251A | 0.842515 | 0.897282 | 0.869898 | 0.8984 | 0.8824 | 0.8901 |
| T251C | 0.869425 | 0.894817 | 0.882121 | 0.9271 | 0.8800 | 0.9026 |
| T251D | 0.890925 | 0.990954 | 0.940939 | 0.9500 | 0.9745 | 0.9628 |
| T251E | 0.879038 | 0.939188 | 0.909113 | 0.9374 | 0.9236 | 0.9302 |
| T251F | 0.880247 | 0.897282 | 0.888765 | 0.9387 | 0.8824 | 0.9094 |
| T251G | 0.968835 | 1.052581 | 1.010708 | 1.0331 | 1.0352 | 1.0342 |
| T251H | 0.929348 | 0.990954 | 0.960151 | 0.9910 | 0.9745 | 0.9825 |
| T251I | 0.672705 | 0.717333 | 0.695019 | 0.7173 | 0.7055 | 0.7112 |
| T251K | 0.989328 | 1.000815 | 0.995071 | 1.0550 | 0.9842 | 1.0182 |
| T251L | 0.755077 | 0.776494 | 0.765786 | 0.8052 | 0.7636 | 0.7836 |
| T251M | 0.760027 | 0.82826 | 0.794144 | 0.8105 | 0.8145 | 0.8126 |
| T251N | 0.941666 | 0.944118 | 0.942892 | 1.0042 | 0.9285 | 0.9648 |
| T251P | 0.587225 | 0.638451 | 0.612838 | 0.6262 | 0.6279 | 0.6271 |
| T251Q | 0.877283 | 0.914537 | 0.89591 | 0.9355 | 0.8994 | 0.9167 |
| T251R | 0.926527 | 0.949049 | 0.937788 | 0.9880 | 0.9333 | 0.9596 |
| T251S | 0.946962 | 0.976164 | 0.961563 | 1.0098 | 0.9600 | 0.9839 |
| T251T | 1.014684 | 1.057511 | 1.036098 | 1.0820 | 1.0400 | 1.0602 |
| T251V | 0.774562 | 0.811004 | 0.792783 | 0.8260 | 0.7976 | 0.8112 |
| T251W | 0.760373 | 0.791284 | 0.775829 | 0.8108 | 0.7782 | 0.7938 |
| T251Y | 0.920915 | 0.966303 | 0.943609 | 0.9820 | 0.9503 | 0.9655 |
| H254A | 0.997934 | 1.003281 | 1.000607 | 0.9329 | 0.9743 | 0.9532 |
| H254C | 0.967972 | 0.909607 | 0.938789 | 0.9049 | 0.8833 | 0.8943 |
| H254D | 1.026859 | 1.005745 | 1.016302 | 0.9600 | 0.9767 | 0.9682 |
| H254E | 0.992609 | 0.956444 | 0.974527 | 0.9280 | 0.9288 | 0.9284 |
| H254F | 1.050201 | 1.003281 | 1.026741 | 0.9818 | 0.9743 | 0.9781 |
| H254G | 1.014886 | 0.973698 | 0.994292 | 0.9488 | 0.9455 | 0.9472 |
| H254H | 1.0835 | 1.059975 | 1.071738 | 1.0129 | 1.0293 | 1.0210 |
| H254I | 1.005906 | 0.914538 | 0.960222 | 0.9404 | 0.8881 | 0.9147 |
| H254K | 1.023866 | 0.934258 | 0.979062 | 0.9572 | 0.9072 | 0.9327 |
| H254L | 0.892191 | 0.875095 | 0.883643 | 0.8341 | 0.8498 | 0.8418 |
| H254M | 0.914295 | 0.912071 | 0.913183 | 0.8547 | 0.8857 | 0.8699 |
| H254N | 0.847292 | 0.870166 | 0.858729 | 0.7921 | 0.8450 | 0.8181 |
| H254P | 0.013757 | 0.056696 | 0.035227 | 0.0129 | 0.0551 | 0.0336 |
| H254Q | 1.022685 | 1.00821 | 1.015448 | 0.9561 | 0.9791 | 0.9673 |
| H254R | 1.118901 | 1.089557 | 1.104229 | 1.0460 | 1.0580 | 1.0519 |
| H254S | 1.06652 | 1.077232 | 1.071876 | 0.9971 | 1.0461 | 1.0211 |
| H254T | 1.062173 | 1.025466 | 1.04382 | 0.9930 | 0.9958 | 0.9944 |
| H254V | 1.046919 | 0.998234 | 1.022634 | 0.9787 | 0.9695 | 0.9742 |
| H254W | 1.018023 | 0.968769 | 0.993396 | 0.9517 | 0.9408 | 0.9463 |
| H254Y | 0.983572 | 0.936722 | 0.960147 | 0.9195 | 0.9096 | 0.9147 |
| L260A | 0.630799 | 0.606405 | 0.618602 | 0.5725 | 0.5351 | 0.5535 |
| L260C | 0.597132 | 0.606405 | 0.601866 | 0.5421 | 0.5351 | 0.5386 |
| L260D | 0.459091 | 0.497943 | 0.478517 | 0.4167 | 0.4394 | 0.4282 |
| L260E | 0.318206 | 0.369759 | 0.343982 | 0.2888 | 0.3263 | 0.3078 |
| L260G | 0.768547 | 0.82826 | 0.798404 | 0.6975 | 0.7308 | 0.7144 |
| L260H | 0.880362 | 0.904678 | 0.89252 | 0.7990 | 0.7983 | 0.7986 |
| L260I | 0.934586 | 0.998349 | 0.966468 | 0.8482 | 0.8809 | 0.8648 |

TABLE 9-continued

| Variant | Slope PI | Delta PI | Avg PI | Norm Slope PI | Norm Delta PI | Norm Avg PI |
|---|---|---|---|---|---|---|
| L260K | 0.084703 | 0.152833 | 0.118768 | 0.0769 | 0.1349 | 0.1063 |
| L260L | 1.148661 | 1.161043 | 1.154852 | 1.0425 | 1.0245 | 1.0334 |
| L260L | 1.109432 | 1.138858 | 1.124145 | 1.0069 | 1.0049 | 1.0059 |
| L260L | 0.930614 | 0.944119 | 0.937367 | 0.8446 | 0.8331 | 0.8388 |
| L260M | 1.007316 | 1.018069 | 1.012693 | 0.9142 | 0.8983 | 0.9062 |
| L260P | 0.654861 | 0.672961 | 0.663911 | 0.5944 | 0.5938 | 0.5941 |
| L260Q | 0.699817 | 0.682822 | 0.69132 | 0.6352 | 0.6025 | 0.6186 |
| L260R | 0.079609 | 0.182415 | 0.131012 | 0.0723 | 0.1610 | 0.1172 |
| L260S | 0.479986 | 0.557104 | 0.518545 | 0.4356 | 0.4916 | 0.4640 |
| L260T | 0.069593 | 0.192275 | 0.130934 | 0.0632 | 0.1697 | 0.1172 |
| L260V | 0.703875 | 0.825795 | 0.764835 | 0.6388 | 0.7287 | 0.6844 |
| L260W | 0.969095 | 1.03286 | 1.000977 | 0.8796 | 0.9114 | 0.8957 |
| L260Y | 0.913489 | 0.981095 | 0.947292 | 0.8291 | 0.8657 | 0.8476 |
| F287A | 0.388432 | 0.475757 | 0.432095 | 0.3631 | 0.4620 | 0.4116 |
| F287C | 0.008663 | 0.039441 | 0.024052 | 0.0081 | 0.0383 | 0.0229 |
| F287D | −0.06015 | 0.004931 | −0.02761 | −0.0562 | 0.0048 | −0.0263 |
| F287E | −0.08738 | −0.06656 | −0.07697 | −0.0817 | −0.0646 | −0.0733 |
| F287F | 1.023433 | 0.988489 | 1.005961 | 0.9568 | 0.9599 | 0.9583 |
| F287G | 0.130235 | 0.207065 | 0.16865 | 0.1218 | 0.2011 | 0.1607 |
| F287H | 0.29118 | 0.325388 | 0.308284 | 0.2722 | 0.3160 | 0.2937 |
| F287I | 0.110089 | 0.167624 | 0.138856 | 0.1029 | 0.1628 | 0.1323 |
| F287K | 0.15136 | 0.115857 | 0.133609 | 0.1415 | 0.1125 | 0.1273 |
| F287L | 0.724655 | 0.707472 | 0.716064 | 0.6775 | 0.6870 | 0.6821 |
| F287M | 0.530526 | 0.510267 | 0.520396 | 0.4960 | 0.4955 | 0.4957 |
| F287N | 0.059577 | 0.105998 | 0.082788 | 0.0557 | 0.1029 | 0.0789 |
| F287P | −0.09492 | −0.04684 | −0.07088 | −0.0887 | −0.0455 | −0.0675 |
| F287Q | 0.184805 | 0.266227 | 0.225516 | 0.1728 | 0.2585 | 0.2148 |
| F287R | 0.048784 | 0.086277 | 0.06753 | 0.0456 | 0.0838 | 0.0643 |
| F287S | 0.127446 | 0.197204 | 0.162525 | 0.1195 | 0.1915 | 0.1548 |
| F287T | 0.261132 | 0.43878 | 0.349956 | 0.2441 | 0.4261 | 0.3334 |
| F287V | 0.447865 | 0.451106 | 0.449486 | 0.4187 | 0.4381 | 0.4282 |
| F287W | 0.677598 | 0.63352 | 0.655559 | 0.6335 | 0.6152 | 0.6245 |
| F287Y | 0.501542 | 0.525058 | 0.5133 | 0.4689 | 0.5099 | 0.4890 |
| V290A | 0.431604 | 0.478221 | 0.454913 | 0.4035 | 0.4644 | 0.4334 |
| V290C | 0.452211 | 0.463431 | 0.457821 | 0.4228 | 0.4500 | 0.4361 |
| V290D | −0.12051 | −0.07888 | −0.09969 | −0.1127 | −0.0766 | −0.0950 |
| V290E | −0.08041 | −0.07642 | −0.07842 | −0.0752 | −0.0742 | −0.0747 |
| V290F | 0.072414 | 0.162692 | 0.117554 | 0.0677 | 0.1580 | 0.1120 |
| V290G | 0.449995 | 0.456036 | 0.453016 | 0.4207 | 0.4428 | 0.4316 |
| V290H | 0.17689 | 0.182414 | 0.179652 | 0.1654 | 0.1771 | 0.1711 |
| V290I | 0.990134 | 0.961373 | 0.975754 | 0.9256 | 0.9336 | 0.9295 |
| V290K | 0.08148 | 0.078881 | 0.080181 | 0.0762 | 0.0766 | 0.0764 |
| V290L | 0.763597 | 0.732123 | 0.74786 | 0.7139 | 0.7110 | 0.7124 |
| V290M | −0.09576 | −0.05177 | −0.07376 | −0.0895 | −0.0503 | −0.0703 |
| V290N | −0.0944 | −0.02712 | −0.06076 | −0.0883 | −0.0263 | −0.0579 |
| V290P | −0.10773 | −0.08628 | −0.097 | −0.1007 | −0.0838 | −0.0924 |
| V290Q | −0.07316 | −0.00247 | −0.03781 | −0.0684 | −0.0024 | −0.0360 |
| V290R | 0.053303 | 0.096137 | 0.07472 | 0.0498 | 0.0934 | 0.0712 |
| V290S | 0.503327 | 0.591614 | 0.547471 | 0.4705 | 0.5745 | 0.5215 |
| V290T | 0.802768 | 0.791284 | 0.797026 | 0.7505 | 0.7684 | 0.7593 |
| V290V | 0.934787 | 0.892351 | 0.913569 | 0.8739 | 0.8665 | 0.8703 |
| V290W | 0.062916 | 0.032046 | 0.047481 | 0.0588 | 0.0311 | 0.0452 |
| V290Y | 0.032896 | 0.051766 | 0.042331 | 0.0308 | 0.0503 | 0.0403 |
| V299A | 0.567682 | 0.549702 | 0.558696 | 0.5152 | 0.4850 | 0.4999 |
| V299D | 0.086689 | 0.123253 | 0.104971 | 0.0787 | 0.1088 | 0.0939 |
| V299E | 0.094287 | 0.078881 | 0.086584 | 0.0856 | 0.0696 | 0.0775 |
| V299G | 0.043171 | 0.128182 | 0.085677 | 0.0392 | 0.1131 | 0.0767 |
| V299H | −0.01949 | 0.091208 | 0.035861 | −0.0177 | 0.0805 | 0.0321 |
| V299I | 0.038826 | 0.16516 | 0.101993 | 0.0352 | 0.1457 | 0.0913 |
| V299K | 0.198792 | 0.273622 | 0.236207 | 0.1804 | 0.2414 | 0.2114 |
| V299L | 0.892997 | 0.909607 | 0.901302 | 0.8105 | 0.8026 | 0.8065 |
| V299M | 0.447664 | 0.465896 | 0.45678 | 0.4063 | 0.4111 | 0.4087 |
| V299N | 0.324826 | 0.340178 | 0.332502 | 0.2948 | 0.3002 | 0.2975 |
| V299P | 0.062081 | 0.16023 | 0.111156 | 0.0563 | 0.1414 | 0.0995 |
| V299R | 0.268817 | 0.354969 | 0.311893 | 0.2440 | 0.3132 | 0.2791 |
| V299S | 0.364458 | 0.423991 | 0.394224 | 0.3308 | 0.3741 | 0.3528 |
| V299T | 0.496305 | 0.554639 | 0.525472 | 0.4504 | 0.4894 | 0.4702 |
| V299V | 0.936226 | 0.939188 | 0.937707 | 0.8497 | 0.8287 | 0.8391 |
| V299V | 0.81497 | 0.934258 | 0.874614 | 0.7397 | 0.8244 | 0.7826 |
| V299V | 0.855006 | 0.818401 | 0.836703 | 0.7760 | 0.7221 | 0.7487 |
| V299V | 0.553435 | 0.603941 | 0.578688 | 0.5023 | 0.5329 | 0.5178 |
| V299W | 0.143935 | 0.305668 | 0.224802 | 0.1306 | 0.2697 | 0.2012 |
| V299Y | 0.111441 | 0.23418 | 0.17281 | 0.1011 | 0.2066 | 0.1546 |
| L303A | 0.868882 | 0.8184 | 0.843641 | 0.8362 | 0.8321 | 0.8341 |
| L303C | 0.88512 | 0.823331 | 0.854225 | 0.8518 | 0.8371 | 0.8444 |
| L303D | 0.842991 | 0.8184 | 0.830695 | 0.8112 | 0.8321 | 0.8217 |
| L303E | 0.87804 | 0.865236 | 0.871638 | 0.8450 | 0.8797 | 0.8623 |
| L303G | 0.872081 | 0.79868 | 0.83538 | 0.8392 | 0.8120 | 0.8256 |
| L303H | 0.850293 | 0.801145 | 0.825719 | 0.8183 | 0.8145 | 0.8164 |
| L303I | 0.92506 | 0.857841 | 0.89145 | 0.8902 | 0.8722 | 0.8812 |
| L303L | 1.098714 | 1.037791 | 1.068253 | 1.0573 | 1.0551 | 1.0562 |
| L303L | 1.038183 | 0.953978 | 0.996081 | 0.9991 | 0.9699 | 0.9845 |
| L303L | 1.006023 | 0.961373 | 0.983698 | 0.9681 | 0.9774 | 0.9728 |
| L303L | 1.014327 | 0.951513 | 0.98292 | 0.9761 | 0.9674 | 0.9718 |
| L303L | 0.967658 | 0.99342 | 0.980539 | 0.9312 | 1.0100 | 0.9706 |
| L303M | 0.923782 | 0.857841 | 0.890812 | 0.8890 | 0.8722 | 0.8806 |
| L303P | 0.900754 | 0.931793 | 0.916274 | 0.8668 | 0.9474 | 0.9071 |
| L303Q | 0.869998 | 0.907143 | 0.88857 | 0.8372 | 0.9223 | 0.8798 |
| L303R | 0.941052 | 0.872631 | 0.906841 | 0.9056 | 0.8872 | 0.8964 |
| L303S | 0.942037 | 0.899746 | 0.920892 | 0.9066 | 0.9148 | 0.9107 |
| L303T | 0.990962 | 1.040255 | 1.015608 | 0.9536 | 1.0576 | 1.0056 |
| L303V | 0.975954 | 0.929329 | 0.952641 | 0.9392 | 0.9449 | 0.9420 |
| L303W | 1.04484 | 1.045185 | 1.045012 | 1.0055 | 1.0627 | 1.0341 |
| L308A | 0.478143 | 0.483151 | 0.480647 | 0.4470 | 0.4692 | 0.4579 |
| L308C | 0.963626 | 0.904678 | 0.934152 | 0.9009 | 0.8785 | 0.8899 |
| L308D | 0.910727 | 0.855377 | 0.883052 | 0.8514 | 0.8306 | 0.8412 |
| L308E | 0.935593 | 0.907143 | 0.921368 | 0.8747 | 0.8809 | 0.8777 |
| L308F | 0.232639 | 0.278551 | 0.255595 | 0.2175 | 0.2705 | 0.2435 |
| L308G | 0.996782 | 0.958908 | 0.977845 | 0.9319 | 0.9312 | 0.9315 |
| L308H | 1.067584 | 0.995885 | 1.031735 | 0.9981 | 0.9671 | 0.9829 |
| L308I | 1.040731 | 0.953978 | 0.997355 | 0.9730 | 0.9264 | 0.9501 |
| L308K | 0.296361 | 0.281017 | 0.288689 | 0.2771 | 0.2729 | 0.2750 |
| L308L | 1.042458 | 0.981093 | 1.011776 | 0.9746 | 0.9527 | 0.9639 |
| L308M | 0.022795 | 0.01479 | 0.018792 | 0.0213 | 0.0144 | 0.0179 |
| L308N | 0.877123 | 0.850446 | 0.863792 | 0.8200 | 0.8259 | 0.8229 |
| L308P | 0.534756 | 0.584219 | 0.559488 | 0.4999 | 0.5673 | 0.5330 |
| L308Q | 0.908049 | 0.860305 | 0.884177 | 0.8489 | 0.8354 | 0.8423 |
| L308R | 1.029938 | 1.000815 | 1.015377 | 0.9629 | 0.9719 | 0.9673 |
| L308S | 0.932513 | 0.897281 | 0.914897 | 0.8718 | 0.8713 | 0.8716 |
| L308T | 0.364256 | 0.42892 | 0.396588 | 0.3405 | 0.4165 | 0.3778 |
| L308V | 0.777786 | 0.741984 | 0.759885 | 0.7271 | 0.7205 | 0.7239 |
| L308W | 1.054575 | 0.986023 | 1.020299 | 0.9859 | 0.9575 | 0.9720 |
| L308Y | 1.013418 | 0.968769 | 0.991093 | 0.9474 | 0.9408 | 0.9441 |
| D311A | 0.983403 | 0.976164 | 0.979783 | 0.9464 | 0.9925 | 0.9694 |
| D311D | 1.097318 | 1.057511 | 1.077414 | 1.0560 | 1.0752 | 1.0656 |
| D311D | 1.052809 | 1.047652 | 1.05023 | 1.0132 | 1.0652 | 1.0392 |
| D311D | 0.955966 | 0.988489 | 0.972227 | 0.9200 | 1.0050 | 0.9625 |
| D311D | 0.952961 | 0.966305 | 0.959633 | 0.9171 | 0.9825 | 0.9498 |
| D311D | 0.921972 | 0.912073 | 0.917023 | 0.8873 | 0.9273 | 0.9073 |
| D311E | 0.923668 | 0.934258 | 0.928963 | 0.8889 | 0.9499 | 0.9194 |
| D311F | 0.993141 | 0.971234 | 0.982187 | 0.9557 | 0.9875 | 0.9716 |
| D311G | 1.079426 | 1.06737 | 1.073398 | 1.0388 | 1.0852 | 1.0620 |
| D311I | 1.027412 | 0.958909 | 0.993161 | 0.9887 | 0.9749 | 0.9818 |
| D311K | 1.09767 | 1.074767 | 1.086218 | 1.0563 | 1.0927 | 1.0745 |
| D311L | 1.166364 | 1.114207 | 1.140285 | 1.1224 | 1.1328 | 1.1276 |
| D311M | −0.05328 | 0.032045 | −0.01062 | −0.0513 | 0.0326 | −0.0093 |
| D311P | 0.004075 | 0.105998 | 0.055037 | 0.0039 | 0.1078 | 0.0558 |
| D311Q | 0.961645 | 0.981093 | 0.971369 | 0.9254 | 0.9975 | 0.9615 |
| D311R | 1.051623 | 1.04765 | 1.049636 | 1.0120 | 1.0652 | 1.0386 |
| D311S | 1.074702 | 1.096952 | 1.085827 | 1.0342 | 1.1153 | 1.0748 |
| D311T | 1.050506 | 1.023 | 1.036753 | 1.0109 | 1.0401 | 1.0255 |
| D311V | 0.963848 | 0.961373 | 0.962611 | 0.9275 | 0.9774 | 0.9525 |
| D311W | 1.004721 | 0.956444 | 0.980583 | 0.9669 | 0.9724 | 0.9697 |
| D323A | 0.931655 | 0.931793 | 0.931724 | 0.8966 | 0.9474 | 0.9220 |
| D323C | 0.952229 | 0.988489 | 0.970359 | 0.9164 | 1.0050 | 0.9607 |
| D323D | 0.88439 | 0.870167 | 0.877279 | 0.8511 | 0.8847 | 0.8679 |
| D323E | 0.887855 | 0.897281 | 0.892568 | 0.8544 | 0.9123 | 0.8833 |
| D323F | 0.881747 | 0.892351 | 0.887049 | 0.8485 | 0.9073 | 0.8779 |
| D323G | 0.917764 | 0.889886 | 0.903825 | 0.8832 | 0.9048 | 0.8940 |
| D323H | −0.01931 | 0.073952 | 0.02732 | −0.0186 | 0.0752 | 0.0283 |
| D323I | 0.86388 | 0.875095 | 0.869488 | 0.8313 | 0.8897 | 0.8605 |
| D323K | 0.963618 | 0.929327 | 0.946473 | 0.9273 | 0.9449 | 0.9361 |
| D323L | 0.98729 | 0.978629 | 0.982959 | 0.9501 | 0.9950 | 0.9725 |
| D323M | 0.898337 | 0.931793 | 0.915065 | 0.8645 | 0.9474 | 0.9059 |
| D323N | 0.858017 | 0.865236 | 0.861627 | 0.8257 | 0.8797 | 0.8527 |
| D323P | −0.0136 | 0.056696 | 0.021547 | −0.0131 | 0.0576 | 0.0223 |
| D323Q | 0.782422 | 0.825795 | 0.804011 | 0.7528 | 0.8396 | 0.7962 |
| D323R | 0.923648 | 0.958908 | 0.941278 | 0.8889 | 0.9749 | 0.9319 |
| D323S | 0.938127 | 0.934257 | 0.936192 | 0.9028 | 0.9499 | 0.9263 |
| D323T | 0.961283 | 0.968769 | 0.965026 | 0.9251 | 0.9850 | 0.9550 |
| D323V | 0.872531 | 0.843051 | 0.857791 | 0.8397 | 0.8571 | 0.8484 |
| D323W | 0.814603 | 0.830724 | 0.822664 | 0.7839 | 0.8446 | 0.8143 |

TABLE 9-continued

| Variant | Slope PI | Delta PI | Avg PI | Norm Slope PI | Norm Delta PI | Norm Avg PI |
|---|---|---|---|---|---|---|
| D323Y | 0.843049 | 0.845516 | 0.844282 | 0.8113 | 0.8597 | 0.8355 |
| D345A | 0.866212 | 0.929329 | 0.89777 | 0.8336 | 0.9449 | 0.8892 |
| D345C | 0.724641 | 0.756774 | 0.740708 | 0.6974 | 0.7694 | 0.7334 |
| D345D | 0.879461 | 0.919468 | 0.899464 | 0.8463 | 0.9348 | 0.8906 |
| D345D | 0.893846 | 0.904676 | 0.899261 | 0.8602 | 0.9198 | 0.8900 |
| D345D | 0.741739 | 0.77896 | 0.760349 | 0.7138 | 0.7920 | 0.7529 |
| D345E | 0.819211 | 0.860305 | 0.839758 | 0.7884 | 0.8747 | 0.8315 |
| D345G | 0.94356 | 0.934258 | 0.938909 | 0.9080 | 0.9499 | 0.9290 |
| D345I | 0.842373 | 0.850446 | 0.84641 | 0.8106 | 0.8647 | 0.8377 |
| D345K | 0.790149 | 0.766633 | 0.778391 | 0.7604 | 0.7794 | 0.7699 |
| D345L | 0.825363 | 0.825795 | 0.825579 | 0.7943 | 0.8396 | 0.8169 |
| D345M | 0.849185 | 0.803609 | 0.826397 | 0.8172 | 0.8170 | 0.8171 |
| D345N | 0.761185 | 0.732123 | 0.746654 | 0.7325 | 0.7444 | 0.7384 |
| D345P | 0.679192 | 0.670496 | 0.674844 | 0.6536 | 0.6817 | 0.6677 |
| D345Q | 0.78652 | 0.741982 | 0.764251 | 0.7569 | 0.7544 | 0.7556 |
| D345R | 0.791666 | 0.781424 | 0.786545 | 0.7619 | 0.7945 | 0.7782 |
| D345S | 0.797667 | 0.764168 | 0.780917 | 0.7676 | 0.7769 | 0.7723 |
| D345T | 0.829168 | 0.835655 | 0.832411 | 0.7979 | 0.8496 | 0.8238 |
| D345V | 0.880199 | 0.852911 | 0.866555 | 0.8471 | 0.8672 | 0.8571 |
| D345W | 0.890583 | 0.872631 | 0.881607 | 0.8570 | 0.8872 | 0.8721 |
| D345Y | 0.76092 | 0.709937 | 0.735429 | 0.7323 | 0.7218 | 0.7270 |
| L376A | 0.546954 | 0.539848 | 0.543401 | 0.5261 | 0.5271 | 0.5266 |
| L376C | 0.668242 | 0.668032 | 0.668137 | 0.6428 | 0.6522 | 0.6475 |
| L376D | 0.381512 | 0.354969 | 0.36824 | 0.3670 | 0.3466 | 0.3568 |
| L376E | 0.34704 | 0.325388 | 0.336214 | 0.3338 | 0.3177 | 0.3258 |
| L376F | 0.991984 | 0.951513 | 0.971748 | 0.9541 | 0.9290 | 0.9417 |
| L376G | 0.369197 | 0.350038 | 0.359617 | 0.3551 | 0.3418 | 0.3485 |
| L376H | 0.59479 | 0.571894 | 0.583342 | 0.5721 | 0.5584 | 0.5653 |
| L376I | 0.950184 | 0.917002 | 0.933593 | 0.9139 | 0.8953 | 0.9047 |
| L376K | 0.339914 | 0.295807 | 0.317861 | 0.3269 | 0.2888 | 0.3080 |
| L376L | 0.977857 | 0.958909 | 0.968383 | 0.9406 | 0.9362 | 0.9384 |
| L376M | 0.832215 | 0.857841 | 0.845028 | 0.8005 | 0.8375 | 0.8189 |
| L376N | 0.421847 | 0.453572 | 0.43771 | 0.4058 | 0.4428 | 0.4242 |
| L376P | 0.400258 | 0.391945 | 0.396101 | 0.3850 | 0.3827 | 0.3838 |
| L376Q | 0.71292 | 0.776494 | 0.744707 | 0.6857 | 0.7581 | 0.7217 |
| L376R | 0.396991 | 0.357433 | 0.377212 | 0.3818 | 0.3490 | 0.3655 |
| L376S | 0.44018 | 0.451106 | 0.445643 | 0.4234 | 0.4404 | 0.4318 |
| L376T | 0.677354 | 0.670496 | 0.673925 | 0.6515 | 0.6546 | 0.6531 |
| L376V | 0.703304 | 0.672961 | 0.688133 | 0.6765 | 0.6570 | 0.6668 |
| L376W | 0.646239 | 0.631056 | 0.638647 | 0.6216 | 0.6161 | 0.6189 |
| L376Y | 0.873191 | 0.882492 | 0.877842 | 0.8399 | 0.8616 | 0.8507 |
| Y377A | 0.765627 | 0.80854 | 0.787084 | 0.7364 | 0.7894 | 0.7627 |
| Y377C | 0.776452 | 0.811004 | 0.793728 | 0.7468 | 0.7918 | 0.7692 |
| Y377D | 0.787087 | 0.855375 | 0.821231 | 0.7571 | 0.8351 | 0.7958 |
| Y377E | 0.771556 | 0.825796 | 0.798676 | 0.7421 | 0.8063 | 0.7740 |
| Y377F | 1.054267 | 1.072301 | 1.063284 | 1.0141 | 1.0469 | 1.0304 |
| Y377G | 0.886538 | 0.924398 | 0.905468 | 0.8527 | 0.9025 | 0.8774 |
| Y377H | 1.057704 | 1.074765 | 1.066235 | 1.0174 | 1.0493 | 1.0332 |
| Y377I | 1.003129 | 1.02793 | 1.015529 | 0.9649 | 1.0036 | 0.9841 |
| Y377K | 0.745557 | 0.734588 | 0.740073 | 0.7171 | 0.7172 | 0.7172 |
| Y377L | 0.906005 | 0.904676 | 0.905341 | 0.8714 | 0.8833 | 0.8773 |
| Y377M | 0.738039 | 0.776494 | 0.757267 | 0.7099 | 0.7581 | 0.7338 |
| Y377N | 0.772271 | 0.825795 | 0.799033 | 0.7428 | 0.8063 | 0.7743 |
| Y377P | 0.787111 | 0.8184 | 0.802755 | 0.7571 | 0.7990 | 0.7779 |
| Y377Q | 0.756295 | 0.838119 | 0.797207 | 0.7274 | 0.8183 | 0.7725 |
| Y377R | 0.681127 | 0.734588 | 0.707858 | 0.6551 | 0.7172 | 0.6859 |
| Y377S | 0.910937 | 0.971234 | 0.941086 | 0.8762 | 0.9483 | 0.9120 |
| Y377T | 1.008667 | 1.03286 | 1.020763 | 0.9702 | 1.0084 | 0.9892 |
| Y377V | 1.024703 | 1.059976 | 1.04234 | 0.9856 | 1.0349 | 1.0101 |
| Y377W | 0.999081 | 0.981095 | 0.990088 | 0.9610 | 0.9579 | 0.9594 |
| Y377Y | 0.956892 | 0.963839 | 0.960365 | 0.9204 | 0.9410 | 0.9306 |
| K379A | 0.931713 | 0.956444 | 0.944078 | 0.8962 | 0.9338 | 0.9149 |
| K379C | 0.92492 | 0.993418 | 0.959169 | 0.8896 | 0.9699 | 0.9295 |
| K379D | 0.893185 | 0.939188 | 0.916187 | 0.8591 | 0.9170 | 0.8878 |
| K379E | 0.904979 | 0.973698 | 0.939339 | 0.8705 | 0.9507 | 0.9103 |
| K379F | 0.923782 | 0.981095 | 0.952438 | 0.8885 | 0.9579 | 0.9230 |
| K379G | 1.010179 | 1.069836 | 1.040007 | 0.9716 | 1.0445 | 1.0078 |
| K379H | 1.06764 | 1.055045 | 1.061343 | 1.0269 | 1.0301 | 1.0285 |
| K379I | 0.967564 | 0.968769 | 0.968166 | 0.9307 | 0.9458 | 0.9382 |
| K379K | -0.11219 | -0.2046 | -0.1584 | -0.1079 | -0.1998 | -0.1535 |
| K379L | 0.90248 | 0.899114 | 0.901114 | 0.8681 | 0.8785 | 0.8732 |
| K379M | 0.842405 | 0.887422 | 0.864913 | 0.8103 | 0.8664 | 0.8381 |
| K379N | 0.846613 | 0.907142 | 0.876877 | 0.8143 | 0.8857 | 0.8497 |
| K379P | 0.898274 | 0.981093 | 0.939684 | 0.8640 | 0.9579 | 0.9106 |
| K379Q | 0.877998 | 0.936724 | 0.907361 | 0.8445 | 0.9146 | 0.8793 |
| K379R | 1.063799 | 1.114207 | 1.089003 | 1.0232 | 1.0878 | 1.0553 |
| K379S | 0.961328 | 1.00821 | 0.984769 | 0.9247 | 0.9844 | 0.9543 |
| K379T | 1.042687 | 1.045185 | 1.043936 | 1.0029 | 1.0205 | 1.0116 |
| K379V | 1.045386 | 1.057511 | 1.051449 | 1.0055 | 1.0325 | 1.0189 |
| K379W | 0.911923 | 0.926863 | 0.919393 | 0.8771 | 0.9049 | 0.8909 |
| K379Y | 0.002898 | -0.0074 | -0.00225 | 0.0028 | -0.0072 | -0.0022 |
| F388A | -0.02633 | 0.032046 | 0.002858 | -0.0293 | 0.0373 | 0.0033 |
| F388C | -0.08415 | -0.0567 | -0.07042 | -0.0985 | -0.0683 | -0.0836 |
| F388D | 0.561886 | 0.566965 | 0.564425 | 0.6576 | 0.6832 | 0.6702 |
| F388F | 0.901743 | 0.860307 | 0.881025 | 1.0554 | 1.0366 | 1.0461 |
| F388F | 0.803685 | 0.783889 | 0.793787 | 0.9406 | 0.9446 | 0.9426 |
| F388F | 0.002607 | 0.064091 | 0.033349 | 0.0031 | 0.0772 | 0.0396 |
| F388F | -0.03908 | 0.022186 | -0.00845 | -0.0457 | 0.0267 | -0.0100 |
| F388F | 0 | -0.02296 | -0.04592 | 0 | -0.0537 | -0.0273 |
| F388F | -0.10699 | -0.07149 | -0.08924 | -0.1252 | -0.0861 | -0.1060 |
| F388G | -0.05346 | 0.012325 | -0.02057 | -0.0626 | 0.0149 | -0.0244 |
| F388H | -0.03276 | -0.0493 | -0.04103 | -0.0383 | -0.0594 | -0.0487 |
| F388K | -0.09733 | -0.08628 | -0.0918 | -0.1139 | -0.1040 | -0.1090 |
| F388L | -0.0857 | -0.10353 | -0.09462 | -0.1003 | -0.1248 | -0.1124 |
| F388P | -0.07827 | -0.07395 | -0.07611 | -0.0916 | -0.0891 | -0.0904 |
| F388Q | 0.834965 | 0.830724 | 0.832845 | 0.9772 | 1.0010 | 0.9889 |
| F388R | 0.71435 | 0.695147 | 0.704748 | 0.8361 | 0.8376 | 0.8368 |
| F388S | 0.680726 | 0.655706 | 0.668216 | 0.7967 | 0.7901 | 0.7935 |
| F388T | 0.8318 | 0.776494 | 0.804147 | 0.9735 | 0.9356 | 0.9549 |
| F388V | 0.875021 | 0.835655 | 0.855338 | 1.0241 | 1.0069 | 1.0156 |
| F388Y | -0.01409 | -0.03205 | -0.02307 | -0.0165 | -0.0386 | -0.0274 |
| G389A | 0.7806 | 0.774028 | 0.777314 | 0.7508 | 0.7557 | 0.7533 |
| G389C | 0.843335 | 0.917002 | 0.880169 | 0.8112 | 0.8953 | 0.8529 |
| G389D | 0.849775 | 0.921932 | 0.885853 | 0.8174 | 0.9001 | 0.8584 |
| G389E | 0.8556 | 0.924398 | 0.889999 | 0.8230 | 0.9025 | 0.8624 |
| G389F | 0.993634 | 1.089556 | 1.041595 | 0.9557 | 1.0638 | 1.0094 |
| G389G | 0.915677 | 0.926863 | 0.92127 | 0.8807 | 0.9049 | 0.8928 |
| G389H | 1.016473 | 1.003279 | 1.009876 | 0.9777 | 0.9795 | 0.9786 |
| G389I | 0.988919 | 0.998349 | 0.993634 | 0.9512 | 0.9747 | 0.9629 |
| G389K | 0.97236 | 0.99342 | 0.98289 | 0.9353 | 0.9699 | 0.9525 |
| G389L | 0.944618 | 0.929327 | 0.936972 | 0.9086 | 0.9073 | 0.9080 |
| G389M | 0.857645 | 0.936724 | 0.897184 | 0.8249 | 0.9146 | 0.8694 |
| G389N | 0.863595 | 0.934258 | 0.898927 | 0.8307 | 0.9122 | 0.8711 |
| G389P | 0.843466 | 0.936722 | 0.890094 | 0.8113 | 0.9146 | 0.8625 |
| G389Q | 0.794968 | 0.870166 | 0.832567 | 0.7646 | 0.8496 | 0.8068 |
| G389R | 0.979429 | 1.05258 | 1.016005 | 0.9421 | 1.0277 | 0.9846 |
| G389S | 0.878321 | 0.949049 | 0.913685 | 0.8448 | 0.9266 | 0.8854 |
| G389T | 0.979282 | 0.978629 | 0.978956 | 0.9419 | 0.9555 | 0.9487 |
| G389V | 0.918558 | 0.926863 | 0.92271 | 0.8835 | 0.9049 | 0.8941 |
| G389W | 0.900267 | 0.946583 | 0.923425 | 0.8659 | 0.9242 | 0.8948 |
| G389Y | 0.918286 | 0.978628 | 0.948457 | 0.8833 | 0.9555 | 0.9191 |
| G397A | 0.597351 | 0.591614 | 0.594483 | 0.5981 | 0.5801 | 0.5890 |
| G397C | 0.229114 | 0.192275 | 0.210694 | 0.2294 | 0.1885 | 0.2087 |
| G397D | -0.08329 | -0.05916 | -0.07123 | -0.0834 | -0.0580 | -0.0706 |
| G397E | 0.154365 | 0.276087 | 0.215226 | 0.1545 | 0.2707 | 0.2132 |
| G397F | -0.07308 | -0.0074 | -0.04024 | -0.0732 | -0.0073 | -0.0399 |
| G397G | 1.078447 | 1.089557 | 1.084002 | 1.0797 | 1.0683 | 1.0739 |
| G397H | -0.07095 | -0.11586 | -0.0934 | -0.0710 | -0.1136 | -0.0925 |
| G397I | 0.291335 | 0.384549 | 0.337942 | 0.2917 | 0.3770 | 0.3348 |
| G397K | -0.08229 | 0.004931 | -0.03868 | -0.0824 | 0.0048 | -0.0383 |
| G397L | 0.107435 | 0.189809 | 0.148622 | 0.1076 | 0.1861 | 0.1472 |
| G397M | 0.265317 | 0.2539 | 0.259608 | 0.2656 | 0.2489 | 0.2572 |
| G397N | -0.13766 | -0.24404 | -0.19085 | -0.1378 | -0.2393 | -0.1891 |
| G397P | -0.07362 | -0.12572 | -0.09967 | -0.0737 | -0.1233 | -0.0987 |
| G397Q | 0.140775 | 0.23911 | 0.189942 | 0.1409 | 0.2344 | 0.1882 |
| G397R | 0.080162 | 0.133113 | 0.106637 | 0.0803 | 0.1305 | 0.1056 |
| G397S | 0.05052 | 0.083813 | 0.067166 | 0.0506 | 0.0822 | 0.0665 |
| G397T | -0.10325 | -0.09367 | -0.09846 | -0.1034 | -0.0918 | -0.0975 |
| G397V | 0.389573 | 0.387013 | 0.388293 | 0.3900 | 0.3795 | 0.3847 |
| G397W | 0.183366 | 0.305668 | 0.244517 | 0.1836 | 0.2997 | 0.2422 |
| G397Y | 0.080021 | 0.182414 | 0.131218 | 0.0801 | 0.1789 | 0.1300 |
| Q400A | 0.064461 | 0.012326 | 0.038394 | 0.0645 | 0.0121 | 0.0380 |
| Q400C | 0.704523 | 0.643381 | 0.673952 | 0.7054 | 0.6308 | 0.6677 |
| Q400D | -0.06538 | -0.14051 | -0.10294 | -0.0655 | -0.1378 | -0.1020 |
| Q400E | -0.0223 | -0.106 | -0.06415 | -0.0223 | -0.1039 | -0.0636 |
| Q400F | -0.13884 | -0.19967 | -0.16925 | -0.1390 | -0.1958 | -0.1677 |
| Q400G | 0.267108 | 0.2046 | 0.235854 | 0.2674 | 0.2006 | 0.2337 |
| Q400H | 0.732842 | 0.734587 | 0.733714 | 0.7337 | 0.7202 | 0.7269 |
| Q400I | 0.180413 | 0.315529 | 0.247971 | 0.1806 | 0.3094 | 0.2457 |
| Q400K | -0.08584 | -0.13311 | -0.10947 | -0.0859 | -0.1305 | -0.1085 |
| Q400L | 0.804621 | 0.815935 | 0.810278 | 0.8056 | 0.8000 | 0.8028 |
| Q400M | 0.655434 | 0.621195 | 0.638314 | 0.6562 | 0.6091 | 0.6324 |

TABLE 9-continued

| Variant | Slope PI | Delta PI | Avg PI | Norm Slope PI | Norm Delta PI | Norm Avg PI |
|---|---|---|---|---|---|---|
| Q400N | 0.689038 | 0.675427 | 0.682232 | 0.6899 | 0.6622 | 0.6759 |
| Q400P | 0.004829 | −0.03451 | −0.01484 | 0.0048 | −0.0338 | −0.0147 |
| Q400Q | 0.891347 | 0.902212 | 0.89678 | 0.8924 | 0.8846 | 0.8885 |
| Q400R | −0.09195 | −0.17009 | −0.13102 | −0.0921 | −0.1668 | −0.1298 |
| Q400S | 0.566328 | 0.557104 | 0.561716 | 0.5670 | 0.5462 | 0.5565 |
| Q400T | 0.875023 | 0.84798 | 0.861502 | 0.8761 | 0.8314 | 0.8535 |
| Q400V | 0.503872 | 0.470827 | 0.48735 | 0.5045 | 0.4616 | 0.4828 |
| Q400W | −0.07606 | −0.16762 | −0.12184 | −0.0761 | −0.1643 | −0.1207 |
| Q400Y | −0.07408 | −0.08135 | −0.07771 | −0.0742 | −0.0798 | −0.0770 |
| F403A | 0.826519 | 0.806075 | 0.816297 | 0.8275 | 0.7903 | 0.8087 |
| F403C | 0.813364 | 0.850446 | 0.831905 | 0.8143 | 0.8338 | 0.8242 |
| F403D | 0.037737 | −0.06163 | −0.01195 | 0.0378 | −0.0604 | −0.0118 |
| F403E | 0.484274 | 0.350039 | 0.417156 | 0.4849 | 0.3432 | 0.4133 |
| F403F | 0.940886 | 0.953978 | 0.947432 | 0.9420 | 0.9353 | 0.9386 |
| F403G | 0.894442 | 0.939188 | 0.916815 | 0.8955 | 0.9208 | 0.9083 |
| F403H | 1.0214 | 1.005745 | 1.013572 | 1.0226 | 0.9861 | 1.0042 |
| F403I | 1.025548 | 1.057511 | 1.04153 | 1.0268 | 1.0369 | 1.0319 |
| F403K | −0.00809 | −0.05423 | −0.03116 | −0.0081 | −0.0532 | −0.0309 |
| F403L | 0.909381 | 0.944119 | 0.92675 | 0.9105 | 0.9257 | 0.9182 |
| F403M | 0.815011 | 0.867702 | 0.841356 | 0.8160 | 0.8508 | 0.8336 |
| F403N | 0.673777 | 0.705008 | 0.689392 | 0.6746 | 0.6912 | 0.6830 |
| F403P | 0.11051 | 0.16023 | 0.13537 | 0.1106 | 0.1571 | 0.1341 |
| F403Q | 0.529052 | 0.537383 | 0.533217 | 0.5297 | 0.5269 | 0.5283 |
| F403R | −0.0964 | −0.14297 | −0.11968 | −0.0965 | −0.1402 | −0.1186 |
| F403S | 0.875838 | 0.956442 | 0.91614 | 0.8769 | 0.9378 | 0.9076 |
| F403T | 0.986142 | 1.020535 | 1.003339 | 0.9873 | 1.0006 | 0.9940 |
| F403V | 0.968791 | 0.998349 | 0.98357 | 0.9700 | 0.9789 | 0.9744 |
| F403W | 0.119339 | 0.128184 | 0.123761 | 0.1195 | 0.1257 | 0.1226 |
| F403Y | 0.873877 | 0.877562 | 0.87572 | 0.8749 | 0.8604 | 0.8676 |
| Q421A | 0.935651 | 0.936722 | 0.936187 | 0.8594 | 0.8356 | 0.8473 |
| Q421C | 0.036667 | 0.147904 | 0.092286 | 0.0337 | 0.1319 | 0.0835 |
| Q421D | 0.884535 | 0.936722 | 0.910629 | 0.8125 | 0.8356 | 0.8242 |
| Q421E | 1.092221 | 1.109277 | 1.100749 | 1.0032 | 0.9896 | 0.9963 |
| Q421F | −0.00515 | 0.051766 | 0.023307 | −0.0047 | 0.0462 | 0.0211 |
| Q421G | 1.033133 | 1.119136 | 1.076135 | 0.9490 | 0.9984 | 0.9740 |
| Q421H | 0.899128 | 0.976164 | 0.937646 | 0.8259 | 0.8708 | 0.8487 |
| Q421I | 0.902379 | 0.926862 | 0.914621 | 0.8289 | 0.8268 | 0.8278 |
| Q421K | 0.909431 | 0.958908 | 0.934169 | 0.8353 | 0.8554 | 0.8455 |
| Q421L | 0.905603 | 0.924398 | 0.915 | 0.8318 | 0.8246 | 0.8282 |
| Q421M | 0.968979 | 0.988489 | 0.978734 | 0.8900 | 0.8818 | 0.8859 |
| Q421N | 0.929952 | 0.956444 | 0.943198 | 0.8542 | 0.8532 | 0.8537 |
| Q421P | 0.967224 | 1.01314 | 0.990182 | 0.8884 | 0.9038 | 0.8962 |
| Q421Q | 1.115246 | 1.188159 | 1.151702 | 1.0244 | 1.0599 | 1.0424 |
| Q421R | 1.164807 | 1.220205 | 1.192506 | 1.0699 | 1.0885 | 1.0793 |
| Q421S | 0.981528 | 1.040256 | 1.010892 | 0.9016 | 0.9280 | 0.9150 |
| Q421T | 0.933953 | 1.000815 | 0.967384 | 0.8579 | 0.8928 | 0.8756 |
| Q421V | 0.98101 | 1.030394 | 1.005702 | 0.9011 | 0.9192 | 0.9103 |
| Q421W | 0.968663 | 0.976164 | 0.972413 | 0.8897 | 0.8708 | 0.8801 |
| Q421Y | 0.9189 | 0.912071 | 0.915486 | 0.8440 | 0.8136 | 0.8286 |
| T426A | 0.814395 | 0.852911 | 0.833653 | 0.7480 | 0.7609 | 0.7545 |
| T426C | 0.931477 | 0.988489 | 0.959983 | 0.8556 | 0.8818 | 0.8689 |
| T426D | 0.877052 | 0.902212 | 0.889632 | 0.8056 | 0.8048 | 0.8052 |
| T426E | 0.853423 | 0.887422 | 0.870422 | 0.7839 | 0.7916 | 0.7878 |
| T426F | 1.035263 | 1.059976 | 1.04762 | 0.9509 | 0.9456 | 0.9482 |
| T426G | 0.952085 | 1.02793 | 0.990008 | 0.8745 | 0.9170 | 0.8961 |
| T426H | 0.95148 | 1.030396 | 0.990938 | 0.8740 | 0.9192 | 0.8969 |
| T426I | 1.12578 | 1.195554 | 1.160667 | 1.0341 | 1.0665 | 1.0505 |
| T426K | 0.67613 | 0.707472 | 0.691801 | 0.6210 | 0.6311 | 0.6262 |
| T426L | 0.921174 | 0.958908 | 0.940041 | 0.8461 | 0.8554 | 0.8508 |
| T426M | 0.79091 | 0.830724 | 0.810817 | 0.7265 | 0.7411 | 0.7339 |
| T426N | 0.791744 | 0.78882 | 0.790282 | 0.7272 | 0.7037 | 0.7153 |
| T426P | 0.747047 | 0.791284 | 0.769166 | 0.6862 | 0.7059 | 0.6962 |
| T426Q | 0.812553 | 0.875697 | 0.843825 | 0.7464 | 0.7806 | 0.7638 |
| T426R | 0.683757 | 0.724728 | 0.704242 | 0.6280 | 0.6465 | 0.6374 |
| T426S | 0.882952 | 0.936722 | 0.909837 | 0.8110 | 0.8356 | 0.8235 |
| T426T | 0.059721 | 0.118323 | 0.089022 | 0.0549 | 0.1056 | 0.0806 |
| T426V | 0.98527 | 0.98849 | 0.98688 | 0.9050 | 0.8818 | 0.8932 |
| T426W | 0.863035 | 0.894817 | 0.878926 | 0.7927 | 0.7982 | 0.7955 |
| T426Y | 0.654688 | 0.640917 | 0.647802 | 0.6013 | 0.5717 | 0.5863 |
| P430A | 0.950876 | 1.010674 | 0.980775 | 0.8734 | 0.9016 | 0.8877 |
| P430C | 1.00769 | 1.055068 | 1.031368 | 0.9256 | 0.9412 | 0.9335 |
| P430D | 0.007771 | 0.073952 | 0.040861 | 0.0071 | 0.0660 | 0.0370 |
| P430E | 0.013584 | 0.103533 | 0.058559 | 0.0125 | 0.0924 | 0.0530 |
| P430F | −0.02789 | 0.086277 | 0.029194 | −0.0256 | 0.0770 | 0.0264 |
| P430G | 0.554961 | 0.64831 | 0.601636 | 0.5097 | 0.5783 | 0.5445 |
| P430H | 0.046078 | 0.142973 | 0.094525 | 0.0423 | 0.1275 | 0.0856 |
| P430I | 0.078314 | 0.202134 | 0.140224 | 0.0719 | 0.1803 | 0.1269 |
| P430K | 0.00095 | 0.073952 | 0.037451 | 0.0009 | 0.0660 | 0.0339 |
| P430L | −0.02078 | 0 | −0.01039 | −0.0191 | 0.0000 | −0.0094 |
| P430M | −0.00196 | 0.093672 | 0.045857 | −0.0018 | 0.0836 | 0.0415 |
| P430N | −0.00527 | 0.073952 | 0.034342 | −0.0048 | 0.0660 | 0.0311 |
| P430P | −0.00665 | 0.061627 | 0.027489 | −0.0061 | 0.0550 | 0.0249 |
| P430Q | 0.014592 | 0.157764 | 0.086178 | 0.0134 | 0.1407 | 0.0780 |
| P430R | −0.01664 | 0.078881 | 0.031123 | −0.0153 | 0.0704 | 0.0282 |
| P430S | 1.045912 | 1.074767 | 1.060339 | 0.9607 | 0.9588 | 0.9597 |
| P430T | 0.923995 | 0.949049 | 0.936522 | 0.8487 | 0.8466 | 0.8477 |
| P430V | 1.051553 | 1.050116 | 1.050834 | 0.9659 | 0.9368 | 0.9511 |
| P430W | 0.023313 | 0.056697 | 0.040005 | 0.0214 | 0.0506 | 0.0362 |
| P430Y | −0.0394 | 0.01972 | −0.00984 | −0.0362 | 0.0176 | −0.0089 |
| F434A | 0.398678 | 0.441245 | 0.419962 | 0.3662 | 0.3936 | 0.3801 |
| F434C | 0.567653 | 0.621195 | 0.594424 | 0.5214 | 0.5542 | 0.5380 |
| F434D | 0.020953 | 0.032046 | 0.0265 | 0.0192 | 0.0286 | 0.0240 |
| F434E | 0.054886 | 0.046837 | 0.050861 | 0.0504 | 0.0418 | 0.0460 |
| F434F | 0.706897 | 0.771564 | 0.739231 | 0.6493 | 0.6883 | 0.6691 |
| F434G | 0.158815 | 0.310598 | 0.234706 | 0.1459 | 0.2771 | 0.2124 |
| F434H | 0.26781 | 0.285948 | 0.276879 | 0.2460 | 0.2551 | 0.2506 |
| F434I | 0.784116 | 0.801145 | 0.792631 | 0.7202 | 0.7147 | 0.7174 |
| F434K | 0.257823 | 0.295807 | 0.276815 | 0.2368 | 0.2639 | 0.2505 |
| F434L | 0.731016 | 0.707472 | 0.719244 | 0.6715 | 0.6311 | 0.6510 |
| F434M | 0.654113 | 0.744449 | 0.699281 | 0.6008 | 0.6641 | 0.6329 |
| F434N | 0.165665 | 0.226785 | 0.196225 | 0.1522 | 0.2023 | 0.1776 |
| F434P | 0.013988 | 0.073952 | 0.04397 | 0.0128 | 0.0660 | 0.0398 |
| F434Q | 0.147562 | 0.21446 | 0.181011 | 0.1355 | 0.1913 | 0.1638 |
| F434R | −0.01946 | 0.076417 | 0.028481 | −0.0179 | 0.0682 | 0.0258 |
| F434S | 0.170069 | 0.256366 | 0.213217 | 0.1562 | 0.2287 | 0.1930 |
| F434T | 0.544254 | 0.559568 | 0.551911 | 0.4999 | 0.4992 | 0.4995 |
| F434V | 0.614538 | 0.643381 | 0.628959 | 0.5645 | 0.5739 | 0.5693 |
| F434W | −0.00895 | 0.027117 | 0.009083 | −0.0082 | 0.0242 | 0.0082 |
| F434Y | 0.29567 | 0.285946 | 0.290808 | 0.2716 | 0.2551 | 0.2632 |
| N438A | −0.05403 | 0.002466 | −0.02578 | −0.0632 | 0.0030 | −0.0306 |
| N438C | −0.11799 | −0.05177 | −0.08488 | −0.1381 | −0.0624 | −0.1008 |
| N438D | −0.08269 | −0.13065 | −0.10667 | −0.0968 | −0.1574 | −0.1267 |
| N438E | −0.06916 | 0.073952 | 0.002395 | −0.0809 | 0.0891 | 0.0028 |
| N438F | −0.07683 | 0.007395 | −0.03472 | −0.0899 | 0.0089 | −0.0412 |
| N438G | −0.09931 | −0.06163 | −0.08047 | −0.1162 | −0.0743 | −0.0956 |
| N438H | −0.06164 | −0.01726 | −0.03945 | −0.0721 | −0.0208 | −0.0468 |
| N438I | −0.06455 | 0.022186 | −0.02118 | −0.0755 | 0.0267 | −0.0252 |
| N438K | −0.0894 | −0.01479 | −0.05209 | −0.1046 | −0.0178 | −0.0619 |
| N438L | −0.09131 | −0.00493 | −0.04812 | −0.1069 | −0.0059 | −0.0571 |
| N438M | −0.09952 | 0 | −0.04976 | −0.1165 | 0.0000 | −0.0591 |
| N438N | 0.842163 | 0.83319 | 0.837676 | 0.9857 | 1.0040 | 0.9947 |
| N438P | −0.08636 | −0.02219 | −0.05427 | −0.1011 | −0.0267 | −0.0644 |
| N438Q | −0.08818 | 0.041906 | −0.02314 | −0.1032 | 0.0505 | −0.0275 |
| N438R | −0.07316 | 0.029581 | −0.02179 | −0.0856 | 0.0356 | −0.0259 |
| N438S | −0.10587 | −0.01233 | −0.0591 | −0.1239 | −0.0149 | −0.0702 |
| N438T | −0.07834 | −0.02219 | −0.05026 | −0.0917 | −0.0267 | −0.0597 |
| N438V | −0.05169 | 0.004931 | −0.02338 | −0.0605 | 0.0059 | −0.0278 |
| N438W | −0.02769 | 0 | −0.01385 | −0.0324 | 0.0000 | −0.0164 |
| N438Y | −0.04875 | 0.041906 | −0.00342 | −0.0571 | 0.0505 | −0.0041 |
| A443A | 0.914207 | 0.877565 | 0.895884 | 1.0700 | 1.0574 | 1.0638 |
| A443A | 0.848618 | 0.862771 | 0.855694 | 0.9932 | 1.0396 | 1.0161 |
| A443A | 0.850985 | 0.835655 | 0.84332 | 0.9960 | 1.0069 | 1.0014 |
| A443A | 0.866073 | 0.8184 | 0.842236 | 1.0136 | 0.9861 | 1.0001 |
| A443A | 0.840422 | 0.840585 | 0.840503 | 0.9836 | 1.0129 | 0.9980 |
| A443A | 0.847625 | 0.82826 | 0.837943 | 0.9921 | 0.9980 | 0.9950 |
| A443A | 0.839211 | 0.811004 | 0.825108 | 0.9822 | 0.9772 | 0.9798 |
| A443A | 0.809008 | 0.766635 | 0.787822 | 0.9469 | 0.9238 | 0.9355 |
| A443F | 0.398831 | 0.391945 | 0.395388 | 0.4668 | 0.4723 | 0.4695 |
| A443G | 0.549538 | 0.571894 | 0.560716 | 0.6432 | 0.6891 | 0.6658 |
| A443H | 0.78205 | 0.756774 | 0.769412 | 0.9153 | 0.9119 | 0.9136 |
| A443I | 0.610687 | 0.606405 | 0.608546 | 0.7147 | 0.7307 | 0.7226 |
| A443L | 0.714923 | 0.709937 | 0.71243 | 0.8367 | 0.8554 | 0.8460 |
| A443N | 0.684977 | 0.650776 | 0.667876 | 0.8017 | 0.7842 | 0.7931 |
| A443P | 0.155216 | 0.236646 | 0.195931 | 0.1817 | 0.2851 | 0.2327 |
| A443Q | 0.684383 | 0.707472 | 0.695927 | 0.8010 | 0.8525 | 0.8264 |
| A443R | 0.53939 | 0.562034 | 0.550712 | 0.6313 | 0.6772 | 0.6539 |
| A443S | 0.794402 | 0.776494 | 0.785448 | 0.9298 | 0.9356 | 0.9327 |
| A443T | 0.141646 | 0.197206 | 0.169426 | 0.1658 | 0.2376 | 0.2012 |
| A443V | 0.483844 | 0.485616 | 0.48473 | 0.5663 | 0.5851 | 0.5756 |
| A445A | 0.787462 | 0.8184 | 0.802931 | 0.7884 | 0.8024 | 0.7955 |
| A445C | 0.724794 | 0.766633 | 0.745714 | 0.7257 | 0.7517 | 0.7388 |
| A445D | 0.792211 | 0.830726 | 0.811469 | 0.7932 | 0.8145 | 0.8039 |

TABLE 9-continued

| Variant | Slope PI | Delta PI | Avg PI | Norm Slope PI | Norm Delta PI | Norm Avg PI |
|---|---|---|---|---|---|---|
| A445E | 0.778018 | 0.79868 | 0.788349 | 0.7789 | 0.7831 | 0.7810 |
| A445F | 0.804425 | 0.870167 | 0.837296 | 0.8054 | 0.8532 | 0.8295 |
| A445G | 0.78537 | 0.825796 | 0.805583 | 0.7863 | 0.8097 | 0.7981 |
| A445H | 0.99763 | 1.04765 | 1.02264 | 0.9988 | 1.0272 | 1.0132 |
| A445I | 0.597113 | 0.579288 | 0.5882 | 0.5978 | 0.5680 | 0.5827 |
| A445K | 0.836833 | 0.892353 | 0.864593 | 0.8378 | 0.8749 | 0.8566 |
| A445L | 0.664485 | 0.712403 | 0.688444 | 0.6653 | 0.6985 | 0.6821 |
| A445M | 0.725768 | 0.700078 | 0.712923 | 0.7266 | 0.6864 | 0.7063 |
| A445N | 0.753583 | 0.769099 | 0.761341 | 0.7545 | 0.7541 | 0.7543 |
| A445P | 0.714935 | 0.685286 | 0.700111 | 0.7158 | 0.6719 | 0.6936 |
| A445Q | 0.87368 | 0.892351 | 0.883016 | 0.8747 | 0.8749 | 0.8748 |
| A445R | 0.867135 | 0.860307 | 0.863721 | 0.8682 | 0.8435 | 0.8557 |
| A445S | 0.941787 | 0.986023 | 0.963905 | 0.9429 | 0.9668 | 0.9550 |
| A445T | 0.836067 | 0.882492 | 0.85928 | 0.8371 | 0.8653 | 0.8513 |
| A445V | 0.733278 | 0.722264 | 0.727771 | 0.7342 | 0.7082 | 0.7210 |
| A445W | 0.652522 | 0.690216 | 0.671369 | 0.6533 | 0.6767 | 0.6651 |
| A445Y | 0.662599 | 0.714867 | 0.688733 | 0.6634 | 0.7009 | 0.6823 |
| A448A | 0.663117 | 0.668032 | 0.665574 | 0.7609 | 0.7661 | 0.7635 |
| A448C | 0.750692 | 0.739518 | 0.745105 | 0.8614 | 0.8481 | 0.8547 |
| A448D | 0.737357 | 0.766635 | 0.751996 | 0.8461 | 0.8792 | 0.8626 |
| A448E | 0.724955 | 0.712401 | 0.718678 | 0.8319 | 0.8170 | 0.8244 |
| A448F | 0.77141 | 0.803611 | 0.78751 | 0.8852 | 0.9216 | 0.9034 |
| A448G | 0.804701 | 0.811004 | 0.807852 | 0.9234 | 0.9300 | 0.9267 |
| A448H | 0.872851 | 0.899748 | 0.886299 | 1.0016 | 1.0318 | 1.0167 |
| A448I | 0.849406 | 0.872631 | 0.861018 | 0.9747 | 1.0007 | 0.9877 |
| A448K | 0.832392 | 0.838121 | 0.835256 | 0.9552 | 0.9611 | 0.9582 |
| A448L | 0.817039 | 0.835655 | 0.826347 | 0.9376 | 0.9583 | 0.9479 |
| A448M | 0.734114 | 0.729657 | 0.731886 | 0.8424 | 0.8367 | 0.8396 |
| A448N | 0.759698 | 0.766633 | 0.763166 | 0.8718 | 0.8792 | 0.8755 |
| A448P | 0.708464 | 0.732123 | 0.720293 | 0.8130 | 0.8396 | 0.8263 |
| A448Q | 0.788421 | 0.78882 | 0.788621 | 0.9047 | 0.9046 | 0.9047 |
| A448R | 0.953238 | 0.986023 | 0.96963 | 1.0939 | 1.1307 | 1.1123 |
| A448S | 0.910818 | 0.939188 | 0.925003 | 1.0452 | 1.0770 | 1.0611 |
| A448T | 1.006534 | 1.023 | 1.014767 | 1.1550 | 1.1731 | 1.1641 |
| A448V | 0.979666 | 1.02793 | 1.003798 | 1.1242 | 1.1788 | 1.1515 |
| A448W | 0.753898 | 0.791284 | 0.772591 | 0.8651 | 0.9074 | 0.8863 |
| A448Y | 0.814076 | 0.81347 | 0.813773 | 0.9342 | 0.9329 | 0.9335 |
| E451A | −0.01918 | −0.03204 | −0.02561 | −0.0225 | −0.0386 | −0.0304 |
| E451C | −0.06244 | −0.03205 | −0.04724 | −0.0731 | −0.0386 | −0.0561 |
| E451D | −0.03066 | −0.00986 | −0.02026 | −0.0359 | −0.0119 | −0.0241 |
| E451E | 0.909118 | 0.872631 | 0.890875 | 1.0640 | 1.0515 | 1.0578 |
| E451E | 0.871733 | 0.840585 | 0.856159 | 1.0203 | 1.0129 | 1.0166 |
| E451F | −0.07063 | −0.02465 | −0.04764 | −0.0827 | −0.0297 | −0.0566 |
| E451G | −0.04052 | 0.019721 | −0.0104 | −0.0474 | −0.0238 | −0.0124 |
| E451H | −0.04452 | 0.00493 | −0.01979 | −0.0521 | 0.0059 | −0.0235 |
| E451I | −0.05684 | −0.00986 | −0.03335 | −0.0665 | −0.0119 | −0.0396 |
| E451K | −0.00685 | 0.061627 | 0.02739 | −0.0080 | 0.0743 | 0.0325 |
| E451L | −0.02988 | 0.017256 | −0.00631 | −0.0350 | 0.0208 | −0.0075 |
| E451N | −0.06335 | 0.012326 | −0.02551 | −0.0741 | 0.0149 | −0.0303 |
| E451P | −0.06653 | 0.01479 | −0.02587 | −0.0779 | 0.0178 | −0.0307 |
| E451Q | 0.142617 | 0.19967 | 0.171143 | 0.1669 | 0.2406 | 0.2032 |
| E451R | −0.03615 | −0.02958 | −0.03287 | −0.0423 | −0.0356 | −0.0390 |
| E451S | −0.06224 | 0.004931 | −0.02866 | −0.0728 | 0.0059 | −0.0340 |
| E451T | −0.04946 | 0.059161 | 0.004848 | −0.0579 | 0.0713 | 0.0058 |
| E451V | −0.05277 | −0.02958 | −0.04117 | −0.0618 | −0.0356 | −0.0489 |
| E451W | −0.03711 | 0.007395 | −0.01486 | −0.0434 | 0.0089 | −0.0176 |
| E451Y | −0.03552 | −0.00986 | −0.02269 | −0.0416 | −0.0119 | −0.0269 |
| A453A | 0.991488 | 0.926863 | 0.959176 | 0.8702 | 0.8816 | 0.8757 |
| A453A | 0.957803 | 0.921932 | 0.939868 | 0.8406 | 0.8769 | 0.8580 |
| A453A | 0.973895 | 0.897282 | 0.935589 | 0.8547 | 0.8535 | 0.8541 |
| A453C | 0.969478 | 0.909607 | 0.939542 | 0.8509 | 0.8652 | 0.8577 |
| A453D | 0.672073 | 0.66803 | 0.670051 | 0.5899 | 0.6354 | 0.6117 |
| A453E | 0.876832 | 0.820865 | 0.848849 | 0.7696 | 0.7808 | 0.7749 |
| A453F | 0.698501 | 0.687752 | 0.693126 | 0.6130 | 0.6542 | 0.6328 |
| A453G | 0.310928 | 0.293342 | 0.302135 | 0.2729 | 0.2790 | 0.2758 |
| A453H | 0.896636 | 0.806075 | 0.851355 | 0.7869 | 0.7667 | 0.7772 |
| A453I | 0.826973 | 0.739518 | 0.783246 | 0.7258 | 0.7034 | 0.7151 |
| A453K | 0.404086 | 0.332783 | 0.368434 | 0.3547 | 0.3165 | 0.3364 |
| A453L | 0.873466 | 0.786355 | 0.82991 | 0.7666 | 0.7479 | 0.7577 |
| A453N | 0.951409 | 0.924398 | 0.937903 | 0.8350 | 0.8793 | 0.8562 |
| A453P | 0.119923 | 0.19967 | 0.159796 | 0.1053 | 0.1899 | 0.1459 |
| A453R | 0.656169 | 0.645846 | 0.651008 | 0.5759 | 0.6143 | 0.5943 |
| A453S | 0.994789 | 0.971234 | 0.983011 | 0.8731 | 0.9238 | 0.8974 |
| A453T | 1.005282 | 0.951513 | 0.978397 | 0.8823 | 0.9050 | 0.8932 |
| A453V | 0.785532 | 0.761704 | 0.773618 | 0.6894 | 0.7245 | 0.7063 |
| A453W | 0.970097 | 0.884956 | 0.927526 | 0.8514 | 0.8417 | 0.8468 |
| A453Y | −0.02672 | 0.017256 | −0.00473 | −0.0235 | 0.0164 | −0.0043 |
| N454A | 0.814964 | 0.781425 | 0.798194 | 0.7153 | 0.7433 | 0.7287 |
| N454C | 0.672715 | 0.707472 | 0.690093 | 0.5904 | 0.6729 | 0.6300 |
| N454D | 0.632572 | 0.64831 | 0.640441 | 0.5552 | 0.6166 | 0.5847 |
| N454E | 0.908891 | 0.899748 | 0.90432 | 0.7977 | 0.8558 | 0.8256 |
| N454F | 0.48827 | 0.512733 | 0.500501 | 0.4285 | 0.4877 | 0.4569 |
| N454G | 0.950226 | 0.941654 | 0.94594 | 0.8340 | 0.8957 | 0.8636 |
| N454H | 0.947561 | 0.978629 | 0.963095 | 0.8316 | 0.9308 | 0.8792 |
| N454I | 0.304004 | 0.298273 | 0.301138 | 0.2668 | 0.2837 | 0.2749 |
| N454L | 0.655935 | 0.626125 | 0.64103 | 0.5757 | 0.5955 | 0.5852 |
| N454M | 0.261435 | 0.320457 | 0.290946 | 0.2295 | 0.3048 | 0.2656 |
| N454N | 1.198247 | 1.153648 | 1.175948 | 1.0517 | 1.0973 | 1.0736 |
| N454N | 1.009139 | 1.000815 | 1.004977 | 0.8857 | 0.9519 | 0.9175 |
| N454P | 0.041641 | 0.194739 | 0.11819 | 0.0365 | 0.1852 | 0.1079 |
| N454Q | 0.742853 | 0.744449 | 0.743651 | 0.6520 | 0.7081 | 0.6789 |
| N454R | 0.050986 | 0.182415 | 0.116701 | 0.0447 | 0.1735 | 0.1065 |
| N454S | 0.984395 | 0.99342 | 0.988907 | 0.8640 | 0.9449 | 0.9028 |
| N454T | 0.869855 | 0.830726 | 0.85029 | 0.7634 | 0.7902 | 0.7763 |
| N454V | 0.723018 | 0.77403 | 0.748524 | 0.6346 | 0.7362 | 0.6834 |
| N454W | 0.605156 | 0.571894 | 0.588525 | 0.5311 | 0.5440 | 0.5373 |
| N454Y | 0.83781 | 0.825795 | 0.831802 | 0.7353 | 0.7855 | 0.7594 |
| S457A | 0.586332 | 0.63352 | 0.609926 | 0.5705 | 0.6624 | 0.6148 |
| S457C | 0.763769 | 0.79375 | 0.778759 | 0.7431 | 0.8299 | 0.7849 |
| S457D | 0.94607 | 0.946583 | 0.946326 | 0.9204 | 0.9897 | 0.9538 |
| S457E | 0.926124 | 0.902212 | 0.914168 | 0.9010 | 0.9433 | 0.9214 |
| S457F | 0.90143 | 0.830724 | 0.866077 | 0.8770 | 0.8686 | 0.8729 |
| S457G | 0.839378 | 0.783889 | 0.811633 | 0.8166 | 0.8196 | 0.8181 |
| S457H | 1.010799 | 0.85291 | 0.931854 | 0.9834 | 0.8918 | 0.9392 |
| S457I | 0.656645 | 0.58915 | 0.622898 | 0.6389 | 0.6160 | 0.6278 |
| S457K | 0.892393 | 0.845515 | 0.868954 | 0.8682 | 0.8840 | 0.8758 |
| S457L | 0.767338 | 0.712403 | 0.73987 | 0.7466 | 0.7448 | 0.7457 |
| S457M | 0.784981 | 0.803609 | 0.794295 | 0.7637 | 0.8402 | 0.8006 |
| S457N | 0.828901 | 0.838119 | 0.83351 | 0.8065 | 0.8763 | 0.8401 |
| S457P | 0.293972 | 0.350039 | 0.322005 | 0.2860 | 0.3660 | 0.3246 |
| S457Q | 0.941004 | 0.904676 | 0.92284 | 0.9155 | 0.9459 | 0.9302 |
| S457R | 0.921001 | 0.835655 | 0.878328 | 0.8961 | 0.8737 | 0.8853 |
| S457S | 1.015375 | 0.956442 | 0.985909 | 0.9879 | 1.0000 | 0.9937 |
| S457T | 0.851264 | 0.746913 | 0.799089 | 0.8282 | 0.7809 | 0.8054 |
| S457V | 0.654861 | 0.626125 | 0.640493 | 0.6371 | 0.6546 | 0.6456 |
| S457W | 0.787082 | 0.746913 | 0.766998 | 0.7658 | 0.7809 | 0.7731 |
| S457Y | 0.842802 | 0.759238 | 0.80102 | 0.8200 | 0.7938 | 0.8074 |
| T462A | 0.782547 | 0.803609 | 0.793078 | 0.8980 | 0.9216 | 0.9098 |
| T462C | 0.760346 | 0.737053 | 0.748699 | 0.8725 | 0.8452 | 0.8589 |
| T462D | 0.781031 | 0.783889 | 0.78246 | 0.8963 | 0.8989 | 0.8976 |
| T462E | 0.060105 | 0.125718 | 0.092911 | 0.0690 | 0.1442 | 0.1066 |
| T462F | 0.88095 | 0.855375 | 0.868163 | 1.0109 | 0.9809 | 0.9959 |
| T462G | 0.867927 | 0.862771 | 0.865349 | 0.9960 | 0.9894 | 0.9927 |
| T462H | 0.929841 | 0.956444 | 0.943142 | 1.0670 | 1.0968 | 1.0819 |
| T462I | 0.937846 | 0.971234 | 0.95454 | 1.0762 | 1.1138 | 1.0950 |
| T462K | 0.924406 | 0.949047 | 0.936727 | 1.0608 | 1.0883 | 1.0746 |
| T462L | 0.85688 | 0.880027 | 0.868453 | 0.9833 | 1.0092 | 0.9962 |
| T462M | 0.76087 | 0.79375 | 0.77731 | 0.8731 | 0.9102 | 0.8917 |
| T462N | 0.75397 | 0.771563 | 0.762766 | 0.8652 | 0.8848 | 0.8750 |
| T462P | 0.677567 | 0.682821 | 0.680191 | 0.7775 | 0.7830 | 0.7803 |
| T462Q | 0.722024 | 0.670496 | 0.69626 | 0.8285 | 0.7689 | 0.7987 |
| T462R | 0.820794 | 0.79868 | 0.809737 | 0.9419 | 0.9159 | 0.9289 |
| T462S | 0.804003 | 0.815935 | 0.809969 | 0.9226 | 0.9357 | 0.9292 |
| T462T | 0.931453 | 0.917002 | 0.924228 | 1.0689 | 1.0516 | 1.0602 |
| T462V | 0.948208 | 0.941652 | 0.94493 | 1.0881 | 1.0799 | 1.0840 |
| T462W | 0.950774 | 0.995884 | 0.973329 | 1.0910 | 1.1420 | 1.1166 |
| T462Y | 0.89853 | 0.917002 | 0.907766 | 1.0311 | 1.0516 | 1.0413 |
| L469A | 0.967927 | 0.907143 | 0.937535 | 0.8495 | 0.8628 | 0.8559 |
| L469C | 0.966252 | 0.907142 | 0.936697 | 0.8480 | 0.8628 | 0.8551 |
| L469F | 1.062129 | 1.025466 | 1.043797 | 0.9322 | 0.9754 | 0.9529 |
| L469G | 0.854161 | 0.808539 | 0.83135 | 0.7497 | 0.7690 | 0.7590 |
| L469H | 0.99608 | 0.961373 | 0.978727 | 0.8742 | 0.9144 | 0.8935 |
| L469I | 1.084091 | 1.037791 | 1.060941 | 0.9515 | 0.9871 | 0.9686 |
| L469L | 1.168593 | 1.131463 | 1.150028 | 1.0256 | 1.0762 | 1.0499 |
| L469L | 1.148405 | 1.079696 | 1.114051 | 1.0079 | 1.0270 | 1.0171 |
| L469L | 0.968969 | 0.971233 | 0.970101 | 0.8504 | 0.9238 | 0.8856 |
| L469L | 0.945209 | 0.951514 | 0.948362 | 0.8296 | 0.9050 | 0.8658 |
| L469L | 0.900731 | 0.880027 | 0.890379 | 0.7905 | 0.8370 | 0.8129 |
| L469N | 1.010525 | 0.973698 | 0.992112 | 0.8869 | 0.9261 | 0.9057 |
| L469P | 0.99925 | 1.023 | 1.011125 | 0.8770 | 0.9730 | 0.9231 |
| L469Q | 0.972109 | 0.98849 | 0.980299 | 0.8532 | 0.9402 | 0.8949 |
| L469R | 1.119898 | 1.082162 | 1.10103 | 0.9829 | 1.0293 | 1.0052 |

TABLE 9-continued

| Variant | Slope PI | Delta PI | Avg PI | Norm Slope PI | Norm Delta PI | Norm Avg PI |
|---|---|---|---|---|---|---|
| L469S | 1.009601 | 0.995884 | 1.002743 | 0.8861 | 0.9472 | 0.9154 |
| L469T | 1.069382 | 1.050116 | 1.059749 | 0.9386 | 0.9988 | 0.9675 |
| L469V | 1.130172 | 1.092023 | 1.111097 | 0.9919 | 1.0387 | 1.0144 |
| L469W | 1.210486 | 1.198019 | 1.204252 | 1.0624 | 1.1395 | 1.0994 |
| L469Y | 0.355964 | 0.396874 | 0.376419 | 0.3124 | 0.3775 | 0.3436 |
| N476A | −0.02596 | 0.027117 | 0.000578 | −0.0278 | 0.0274 | 0.0006 |
| N476C | −0.05661 | 0.049302 | −0.00366 | −0.0606 | 0.0499 | −0.0038 |
| N476D | 0.835319 | 0.902212 | 0.868766 | 0.8939 | 0.9127 | 0.9036 |
| N476E | 0.785038 | 0.872653 | 0.828835 | 0.8401 | 0.8828 | 0.8620 |
| N476F | −0.08401 | −0.0493 | −0.06666 | −0.0899 | −0.0499 | −0.0693 |
| N476G | −0.11069 | −0.03698 | −0.07383 | −0.1184 | −0.0374 | −0.0768 |
| N476H | −0.08695 | −0.10353 | −0.09524 | −0.0930 | −0.1047 | −0.0991 |
| N476I | −0.13306 | −0.12572 | −0.12939 | −0.1424 | −0.1272 | −0.1346 |
| N476K | −0.00089 | 0.105998 | 0.052553 | −0.0010 | 0.1072 | 0.0547 |
| N476L | −0.08332 | −0.01479 | −0.04906 | −0.0892 | −0.0150 | −0.0510 |
| N476M | 0.788233 | 0.81347 | 0.800851 | 0.8435 | 0.8229 | 0.8329 |
| N476N | 0.014362 | 0.093672 | 0.054017 | 0.0154 | 0.0948 | 0.0562 |
| N476P | 0.726584 | 0.734587 | 0.730585 | 0.7775 | 0.7431 | 0.7598 |
| N476Q | 0.873196 | 0.904678 | 0.888937 | 0.9344 | 0.9152 | 0.9245 |
| N476R | 1.023405 | 1.050116 | 1.03676 | 1.0951 | 1.0623 | 1.0783 |
| N476S | 0.92362 | 0.953978 | 0.938799 | 0.9883 | 0.9651 | 0.9764 |
| N476T | 0.963482 | 0.867702 | 0.915592 | 1.0310 | 0.8778 | 0.9523 |
| N476V | 1.085918 | 1.109277 | 1.097597 | 1.1620 | 1.1222 | 1.1415 |
| N476W | 0.989415 | 0.963839 | 0.976627 | 1.0588 | 0.9751 | 1.0157 |
| N476Y | 0.982392 | 0.981095 | 0.981743 | 1.0512 | 0.9925 | 1.0211 |
| K487A | 0.996236 | 1.062442 | 1.029339 | 0.9531 | 0.9664 | 0.9599 |
| K487C | 0.89743 | 0.949049 | 0.923239 | 0.8586 | 0.8632 | 0.8610 |
| K487D | 0.840989 | 0.884956 | 0.862972 | 0.8046 | 0.8049 | 0.8048 |
| K487E | 0.879355 | 0.862771 | 0.871063 | 0.8413 | 0.7848 | 0.8123 |
| K487F | 1.138386 | 1.180763 | 1.159575 | 1.0891 | 1.0740 | 1.0814 |
| K487G | 1.072535 | 1.111741 | 1.092138 | 1.0261 | 1.0112 | 1.0185 |
| K487H | 1.134673 | 1.198019 | 1.166346 | 1.0856 | 1.0897 | 1.0877 |
| K487I | 1.044674 | 1.104346 | 1.07451 | 0.9995 | 1.0045 | 1.0020 |
| K487K | 1.127248 | 1.161043 | 1.144146 | 1.0785 | 1.0561 | 1.0670 |
| K487L | 1.095099 | 1.087092 | 1.091095 | 1.0477 | 0.9888 | 1.0175 |
| K487M | 0.988464 | 1.040255 | 1.014359 | 0.9457 | 0.9462 | 0.9459 |
| K487N | 0.608523 | 0.645845 | 0.627184 | 0.5822 | 0.5874 | 0.5849 |
| K487P | 0.367853 | 0.389497 | 0.378666 | 0.3519 | 0.3543 | 0.3531 |
| K487Q | 0.803689 | 0.803611 | 0.80365 | 0.7689 | 0.7309 | 0.7494 |
| K487R | 1.115015 | 1.114207 | 1.114611 | 1.0668 | 1.0135 | 1.0394 |
| K487S | 0.897919 | 0.907142 | 0.90253 | 0.8591 | 0.8251 | 0.8417 |
| K487T | 1.165469 | 1.156112 | 1.160791 | 1.1150 | 1.0516 | 1.0825 |
| K487V | 1.112426 | 1.084626 | 1.098526 | 1.0643 | 0.9865 | 1.0244 |
| K487W | 1.157698 | 1.220205 | 1.188952 | 1.1076 | 1.1099 | 1.1088 |
| K487Y | 0.810424 | 0.820865 | 0.815644 | 0.7753 | 0.7466 | 0.7606 |
| E488A | 0.952142 | 0.899748 | 0.925945 | 0.9220 | 0.8779 | 0.9000 |
| E488C | 0.937752 | 0.897281 | 0.917517 | 0.9081 | 0.8755 | 0.8919 |
| E488D | 0.960748 | 0.904678 | 0.932713 | 0.9303 | 0.8827 | 0.9066 |
| E488E | 0.848904 | 0.880027 | 0.864465 | 0.8220 | 0.8587 | 0.8403 |
| E488F | 0.877974 | 0.867702 | 0.872838 | 0.8502 | 0.8467 | 0.8484 |
| E488G | 0.962274 | 0.951513 | 0.956893 | 0.9318 | 0.9284 | 0.9301 |
| E488H | 0.904308 | 0.882492 | 0.8934 | 0.8757 | 0.8611 | 0.8684 |
| E488I | 1.045682 | 1.050116 | 1.047899 | 1.0126 | 1.0247 | 1.0186 |
| E488K | 0.616006 | 0.653241 | 0.634624 | 0.5965 | 0.6374 | 0.6169 |
| E488L | 0.885226 | 0.875097 | 0.880162 | 0.8572 | 0.8539 | 0.8555 |
| E488M | 0.822828 | 0.811004 | 0.816916 | 0.7968 | 0.7913 | 0.7941 |
| E488N | 0.483123 | 0.485618 | 0.48437 | 0.4678 | 0.4738 | 0.4708 |
| E488P | 0.336108 | 0.354969 | 0.345538 | 0.3255 | 0.3464 | 0.3359 |
| E488Q | 0.729088 | 0.751843 | 0.740465 | 0.7060 | 0.7336 | 0.7198 |
| E488R | 0.773871 | 0.801145 | 0.787508 | 0.7494 | 0.7817 | 0.7655 |
| E488S | 0.73634 | 0.788819 | 0.762579 | 0.7130 | 0.7697 | 0.7412 |
| E488T | 0.884362 | 0.899748 | 0.892055 | 0.8564 | 0.8779 | 0.8671 |
| E488V | 0.910841 | 0.949049 | 0.929945 | 0.8820 | 0.9260 | 0.9039 |
| E488W | 0.847753 | 0.897282 | 0.872518 | 0.8209 | 0.8755 | 0.8481 |
| E488Y | 0.64637 | 0.690217 | 0.668294 | 0.6259 | 0.6735 | 0.6496 |
| K489A | 0.870846 | 0.835655 | 0.853251 | 0.9056 | 0.9052 | 0.9054 |
| K489C | 0.778031 | 0.77896 | 0.778495 | 0.8091 | 0.8438 | 0.8261 |
| K489D | 0.730676 | 0.754308 | 0.742492 | 0.7598 | 0.8171 | 0.7879 |
| K489E | 0.796913 | 0.80854 | 0.802726 | 0.8287 | 0.8758 | 0.8518 |
| K489F | 0.880779 | 0.870166 | 0.875473 | 0.9159 | 0.9426 | 0.9290 |
| K489G | 0.9409 | 0.929315 | 0.935108 | 0.9785 | 1.0067 | 0.9923 |
| K489H | 0.892127 | 0.865236 | 0.878681 | 0.9277 | 0.9372 | 0.9324 |
| K489I | 0.940892 | 0.862772 | 0.901832 | 0.9784 | 0.9346 | 0.9570 |
| K489K | 0.992922 | 0.968769 | 0.980845 | 1.0326 | 1.0494 | 1.0408 |
| K489L | 0.88776 | 0.882491 | 0.885125 | 0.9232 | 0.9559 | 0.9392 |
| K489M | 0.499463 | 0.470826 | 0.485145 | 0.5194 | 0.5100 | 0.5148 |
| K489N | 0.754418 | 0.744449 | 0.749434 | 0.7845 | 0.8064 | 0.7952 |
| K489P | 0.691978 | 0.717333 | 0.704655 | 0.7196 | 0.7770 | 0.7477 |
| K489Q | 0.828015 | 0.835655 | 0.831835 | 0.8611 | 0.9052 | 0.8827 |
| K489R | 1.017588 | 1.023 | 1.020294 | 1.0582 | 1.1081 | 1.0827 |
| K489S | 0.911797 | 0.875097 | 0.893447 | 0.9482 | 0.9479 | 0.9481 |
| K489T | 0.964601 | 0.909607 | 0.937104 | 1.0031 | 0.9853 | 0.9944 |
| K489V | 0.954155 | 0.946583 | 0.950369 | 0.9922 | 1.0254 | 1.0085 |
| K489W | 0.988038 | 0.941652 | 0.964845 | 1.0275 | 1.0200 | 1.0238 |
| K489Y | 0.823558 | 0.838119 | 0.830839 | 0.8564 | 0.9079 | 0.8816 |
| L490A | 0.92952 | 0.887422 | 0.908471 | 0.9666 | 0.9613 | 0.9640 |
| L490C | 0.928948 | 0.924398 | 0.926673 | 0.9660 | 1.0013 | 0.9833 |
| L490D | 0.909462 | 0.919468 | 0.914465 | 0.9458 | 0.9960 | 0.9704 |
| L490E | 0.876323 | 0.840585 | 0.858454 | 0.9113 | 0.9105 | 0.9109 |
| L490F | 1.017422 | 0.986025 | 1.001723 | 1.0580 | 1.0681 | 1.0630 |
| L490G | 0.960217 | 0.953978 | 0.957097 | 0.9985 | 1.0334 | 1.0156 |
| L490H | 1.055247 | 1.02793 | 1.041588 | 1.0974 | 1.1135 | 1.1053 |
| L490I | 1.086573 | 1.050116 | 1.068344 | 1.1299 | 1.1375 | 1.1337 |
| L490K | 0.931524 | 0.897281 | 0.914402 | 0.9687 | 0.9720 | 0.9703 |
| L490L | 0.991259 | 0.986025 | 0.988642 | 1.0308 | 1.0681 | 1.0491 |
| L490M | 0.943057 | 0.909607 | 0.926332 | 0.9807 | 0.9853 | 0.9830 |
| L490N | 0.932653 | 0.961373 | 0.947013 | 0.9699 | 1.0414 | 1.0049 |
| L490P | 0.398986 | 0.41413 | 0.406558 | 0.4149 | 0.4486 | 0.4314 |
| L490Q | 0.796459 | 0.80854 | 0.802499 | 0.8282 | 0.8758 | 0.8516 |
| L490R | 0.904869 | 0.912073 | 0.908471 | 0.9410 | 0.9880 | 0.9640 |
| L490S | 0.95059 | 0.971234 | 0.960912 | 0.9885 | 1.0521 | 1.0197 |
| L490T | 0.95216 | 0.924398 | 0.938279 | 0.9902 | 1.0013 | 0.9956 |
| L490V | 1.02697 | 1.01314 | 1.020055 | 1.0680 | 1.0975 | 1.0824 |
| L490W | 1.02336 | 1.032861 | 1.028111 | 1.0642 | 1.1188 | 1.0910 |
| L490Y | −0.00193 | 0.064091 | 0.031081 | −0.0020 | 0.0694 | 0.0330 |
| G491A | 0.971946 | 0.931793 | 0.951869 | 1.0107 | 1.0093 | 1.0101 |
| G491C | 1.000956 | 1.00821 | 1.004583 | 1.0409 | 1.0921 | 1.0660 |
| G491D | 0.972656 | 0.988489 | 0.980572 | 1.0115 | 1.0708 | 1.0405 |
| G491E | 0.992443 | 0.988489 | 0.990466 | 1.0321 | 1.0708 | 1.0510 |
| G491F | 0.999983 | 1.000813 | 1.000398 | 1.0399 | 1.0841 | 1.0616 |
| G491G | 0.949171 | 0.949047 | 0.949109 | 0.9871 | 1.0280 | 1.0071 |
| G491H | 1.032527 | 0.971233 | 1.00188 | 1.0737 | 1.0521 | 1.0631 |
| G491I | 1.061556 | 1.037791 | 1.049673 | 1.1039 | 1.1242 | 1.1138 |
| G491K | 0.997581 | 0.951514 | 0.974547 | 1.0374 | 1.0307 | 1.0341 |
| G491L | 1.023542 | 1.01314 | 1.018341 | 1.0644 | 1.0975 | 1.0806 |
| G491M | 0.999026 | 0.990954 | 0.99499 | 1.0389 | 1.0734 | 1.0558 |
| G491N | 0.971288 | 0.978629 | 0.974958 | 1.0101 | 1.0601 | 1.0346 |
| G491P | 0.469685 | 0.564499 | 0.517092 | 0.4884 | 0.6115 | 0.5487 |
| G491Q | 0.940275 | 0.968769 | 0.954522 | 0.9778 | 1.0494 | 1.0129 |
| G491R | 0.993143 | 0.978629 | 0.985886 | 1.0328 | 1.0601 | 1.0462 |
| G491S | 0.972597 | 0.978628 | 0.975612 | 1.0114 | 1.0601 | 1.0353 |
| G491T | 1.01659 | 0.988489 | 1.002539 | 1.0572 | 1.0708 | 1.0638 |
| G491V | 1.012542 | 1.005745 | 1.009143 | 1.0530 | 1.0895 | 1.0708 |
| G491W | 1.031219 | 0.998349 | 1.014784 | 1.0724 | 1.0814 | 1.0768 |
| G491Y | 0.99794 | 0.958908 | 0.978424 | 1.0378 | 1.0387 | 1.0382 |
| G492A | 1.016037 | 1.02793 | 1.021984 | 1.0872 | 1.1399 | 1.0629 |
| G492C | 0.862259 | 0.926863 | 0.894561 | 0.9227 | 0.9377 | 0.9304 |
| G492D | 0.894206 | 0.968769 | 0.931487 | 0.9569 | 0.9800 | 0.9688 |
| G492E | 1.028326 | 1.126532 | 1.077429 | 1.1004 | 1.1396 | 1.1206 |
| G492F | 0.796234 | 0.82826 | 0.812247 | 0.8520 | 0.8379 | 0.8448 |
| G492G | 0.954128 | 0.986025 | 0.970076 | 1.0210 | 0.9975 | 1.0089 |
| G492H | 1.003891 | 0.976164 | 0.990028 | 1.0742 | 0.9875 | 1.0297 |
| G492I | 0.932974 | 0.875097 | 0.904036 | 0.9984 | 0.8853 | 0.9402 |
| G492K | 0.996322 | 1.025465 | 1.010893 | 1.0661 | 1.0374 | 1.0514 |
| G492L | 0.898293 | 0.914537 | 0.906415 | 0.9612 | 0.9252 | 0.9427 |
| G492M | 0.888824 | 0.919468 | 0.904146 | 0.9511 | 0.9302 | 0.9403 |
| G492N | 0.778505 | 0.806075 | 0.79229 | 0.8331 | 0.8155 | 0.8240 |
| G492P | 0.816641 | 0.875097 | 0.845869 | 0.8739 | 0.8853 | 0.8797 |
| G492Q | 0.884529 | 0.986025 | 0.935309 | 0.9466 | 0.9975 | 0.9728 |
| G492R | 0.892853 | 0.939188 | 0.916021 | 0.9554 | 0.9501 | 0.9527 |
| G492S | 0.836585 | 0.899748 | 0.868167 | 0.8952 | 0.9102 | 0.9029 |
| G492T | 1.025794 | 1.01314 | 1.019467 | 1.0977 | 1.0249 | 1.0603 |
| G492V | 1.039091 | 0.99342 | 1.016255 | 1.1119 | 1.0050 | 1.0569 |
| G492W | 0.962273 | 0.941652 | 0.951963 | 1.0297 | 0.9526 | 0.9901 |
| G492Y | 0.892623 | 0.877561 | 0.885092 | 0.9552 | 0.8878 | 0.9205 |
| S493A | 0.931506 | 0.978629 | 0.955068 | 0.9968 | 0.9900 | 0.9933 |
| S493C | 0.863611 | 0.924398 | 0.894004 | 0.9241 | 0.9352 | 0.9298 |
| S493D | 0.00095 | 0.061627 | 0.031289 | 0.0010 | 0.0623 | 0.0325 |
| S493E | 0.970159 | 1.037789 | 1.003974 | 1.0381 | 1.0499 | 1.0442 |
| S493F | 0.814798 | 0.882491 | 0.848644 | 0.8719 | 0.8928 | 0.8826 |
| S493G | 1.036472 | 1.03286 | 1.034666 | 1.1091 | 1.0449 | 1.0761 |
| S493H | 0.931448 | 0.929327 | 0.930388 | 0.9967 | 0.9401 | 0.9676 |

TABLE 9-continued

| Variant | Slope PI | Delta PI | Avg PI | Norm Slope PI | Norm Delta PI | Norm Avg PI |
|---|---|---|---|---|---|---|
| S493I | 1.045164 | 1.059976 | 1.05257 | 1.1184 | 1.0723 | 1.0947 |
| S493K | 1.017649 | 1.00821 | 1.012929 | 1.0890 | 1.0200 | 1.0535 |
| S493L | 1.046085 | 1.089557 | 1.067821 | 1.1194 | 1.1022 | 1.1106 |
| S493M | 0.892738 | 0.912073 | 0.902406 | 0.9553 | 0.9227 | 0.9385 |
| S493N | 0.787312 | 0.793748 | 0.79053 | 0.8425 | 0.8030 | 0.8222 |
| S493P | 0.826944 | 0.838121 | 0.832532 | 0.8849 | 0.8479 | 0.8659 |
| S493Q | 0.790133 | 0.889887 | 0.84001 | 0.8455 | 0.9002 | 0.8736 |
| S493R | 1.005848 | 0.998349 | 1.002099 | 1.0763 | 1.0100 | 1.0422 |
| S493S | 0.995113 | 0.981093 | 0.988103 | 1.0649 | 0.9925 | 1.0277 |
| S493T | 1.08658 | 1.08216 | 1.08437 | 1.1627 | 1.0948 | 1.1278 |
| S493V | 1.068649 | 0.990954 | 1.029802 | 1.1435 | 1.0025 | 1.0710 |
| S493W | 1.008353 | 1.040255 | 1.024304 | 1.0790 | 1.0524 | 1.0653 |
| S493Y | 0.899214 | 0.929327 | 0.91427 | 0.9622 | 0.9401 | 0.9509 |
| L494A | 0.84922 | 0.850446 | 0.849833 | 0.7453 | 0.8089 | 0.7758 |
| L494C | 1.038704 | 1.02793 | 1.033317 | 0.9116 | 0.9777 | 0.9433 |
| L494D | 1.106021 | 1.089556 | 1.097788 | 0.9707 | 1.0363 | 1.0022 |
| L494E | 1.112208 | 1.161043 | 1.136626 | 0.9761 | 1.1043 | 1.0377 |
| L494G | 1.129441 | 1.064906 | 1.097173 | 0.9913 | 1.0129 | 1.0016 |
| L494H | 1.05315 | 1.025465 | 1.039307 | 0.9243 | 0.9754 | 0.9488 |
| L494I | 1.132167 | 1.089556 | 1.110861 | 0.9937 | 1.0363 | 1.0141 |
| L494K | 1.18235 | 1.111743 | 1.147046 | 1.0377 | 1.0572 | 1.0472 |
| L494L | 1.282111 | 1.267041 | 1.274576 | 1.1253 | 1.2052 | 1.1636 |
| L494L | 1.193277 | 1.131463 | 1.16237 | 1.0473 | 1.0762 | 1.0612 |
| L494L | 0.997205 | 0.941652 | 0.969428 | 0.8752 | 0.8957 | 0.8850 |
| L494N | 1.011554 | 0.949049 | 0.980302 | 0.8878 | 0.9027 | 0.8949 |
| L494P | 0.877713 | 0.786353 | 0.832033 | 0.7703 | 0.7479 | 0.7596 |
| L494Q | 0.933545 | 0.845515 | 0.88953 | 0.8193 | 0.8042 | 0.8121 |
| L494R | 1.064744 | 0.968769 | 1.016756 | 0.9345 | 0.9215 | 0.9282 |
| L494S | 1.045267 | 0.966303 | 1.005785 | 0.9174 | 0.9191 | 0.9182 |
| L494T | 0.553156 | 0.458501 | 0.505829 | 0.4855 | 0.4361 | 0.4618 |
| L494V | 1.0636 | 0.944118 | 1.003859 | 0.9335 | 0.8980 | 0.9165 |
| L494W | 1.114723 | 0.9737 | 1.044211 | 0.9783 | 0.9261 | 0.9533 |
| L494Y | 1.096308 | 1.015605 | 1.055956 | 0.9622 | 0.9660 | 0.9640 |
| F495A | 0.852329 | 0.82826 | 0.840295 | 0.9121 | 0.8379 | 0.8739 |
| F495C | 0.826023 | 0.845516 | 0.835769 | 0.8839 | 0.8554 | 0.8692 |
| F495D | 0.844183 | 0.912071 | 0.878127 | 0.9033 | 0.9227 | 0.9133 |
| F495E | 0.855034 | 0.936722 | 0.895878 | 0.9150 | 0.9476 | 0.9318 |
| F495F | 0.950761 | 0.958908 | 0.954834 | 1.0174 | 0.9701 | 0.9931 |
| F495G | 0.897775 | 0.850446 | 0.87411 | 0.9607 | 0.8603 | 0.9091 |
| F495H | 1.014857 | 0.978629 | 0.996743 | 1.0860 | 0.9900 | 1.0367 |
| F495I | 0.95905 | 0.857841 | 0.908445 | 1.0263 | 0.8678 | 0.9448 |
| F495K | 1.006683 | 0.973698 | 0.990191 | 1.0772 | 0.9850 | 1.0298 |
| F495L | 1.042055 | 1.104346 | 1.073201 | 1.1151 | 1.1172 | 1.1162 |
| F495M | 0.898062 | 0.897282 | 0.897672 | 0.9610 | 0.9077 | 0.9336 |
| F495N | 0.763855 | 0.771564 | 0.76771 | 0.8174 | 0.7805 | 0.7985 |
| F495P | 0.775634 | 0.791284 | 0.78347 | 0.8300 | 0.8005 | 0.8148 |
| F495Q | 0.794623 | 0.8677 | 0.831161 | 0.8503 | 0.8778 | 0.8644 |
| F495R | 0.933953 | 0.904678 | 0.919315 | 0.9994 | 0.9152 | 0.9561 |
| F495S | 0.917403 | 0.904678 | 0.91104 | 0.9817 | 0.9152 | 0.9475 |
| F495T | 0.971196 | 0.894817 | 0.933006 | 1.0393 | 0.9052 | 0.9704 |
| F495V | 0.938673 | 0.857841 | 0.898257 | 1.0045 | 0.8678 | 0.9342 |
| F495W | 0.841334 | 0.761704 | 0.801519 | 0.9003 | 0.7706 | 0.8336 |
| F495Y | 0.962964 | 0.902212 | 0.932588 | 1.0304 | 0.9127 | 0.9699 |
| A496A | 0.937723 | 1.02793 | 0.982827 | 0.9123 | 1.0747 | 0.9906 |
| A496C | 0.915475 | 0.953978 | 0.934727 | 0.8907 | 0.9974 | 0.9421 |
| A496D | 0.960402 | 0.944118 | 0.95226 | 0.9344 | 0.9871 | 0.9598 |
| A496E | 0.976463 | 1.003279 | 0.989871 | 0.9500 | 1.0490 | 0.9977 |
| A496F | 0.965094 | 0.939188 | 0.952141 | 0.9390 | 0.9820 | 0.9597 |
| A496G | 0.958935 | 0.944118 | 0.951526 | 0.9330 | 0.9871 | 0.9591 |
| A496H | 0.923505 | 0.793748 | 0.858627 | 0.8985 | 0.8299 | 0.8654 |
| A496I | 0.992609 | 0.934257 | 0.963433 | 0.9657 | 0.9768 | 0.9711 |
| A496K | 0.885139 | 0.838121 | 0.86163 | 0.8612 | 0.8763 | 0.8685 |
| A496L | 0.877772 | 0.875097 | 0.876434 | 0.8540 | 0.9149 | 0.8834 |
| A496M | 0.976462 | 0.978628 | 0.977545 | 0.9500 | 1.0232 | 0.9853 |
| A496N | 0.933867 | 0.939188 | 0.936527 | 0.9086 | 0.9820 | 0.9439 |
| A496P | 1.042573 | 1.022999 | 1.032786 | 1.0143 | 1.0696 | 1.0410 |
| A496Q | 1.012727 | 1.00821 | 1.010469 | 0.9853 | 1.0541 | 1.0185 |
| A496R | 1.033565 | 0.944118 | 0.988841 | 1.0056 | 0.9871 | 0.9967 |
| A496S | 1.022714 | 0.983559 | 1.003137 | 0.9950 | 1.0284 | 1.0111 |
| A496T | 0.975081 | 0.877562 | 0.926322 | 0.9487 | 0.9175 | 0.9337 |
| A496V | 0.959539 | 0.921932 | 0.940735 | 0.9336 | 0.9639 | 0.9482 |
| A496W | 0.940601 | 0.912073 | 0.926337 | 0.9151 | 0.9536 | 0.9337 |
| A496Y | 0.874807 | 0.840585 | 0.857696 | 0.8511 | 0.8789 | 0.8645 |
| K497A | 1.047754 | 1.035325 | 1.04154 | 1.0194 | 1.0825 | 1.0498 |
| K497C | 0.948516 | 1.000815 | 0.974665 | 0.9228 | 1.0464 | 0.9824 |
| K497D | 0.99353 | 0.983559 | 0.988545 | 0.9666 | 1.0284 | 0.9964 |
| K497E | 0.945063 | 0.944119 | 0.944591 | 0.9195 | 0.9871 | 0.9521 |
| K497F | 0.970304 | 0.949049 | 0.959676 | 0.9440 | 0.9923 | 0.9673 |
| K497G | 1.020181 | 0.929327 | 0.974754 | 0.9926 | 0.9716 | 0.9825 |
| K497H | 0.922354 | 0.8184 | 0.870377 | 0.8974 | 0.8557 | 0.8773 |
| K497I | 0.968749 | 0.919466 | 0.944108 | 0.9425 | 0.9613 | 0.9516 |
| K497K | 0.999258 | 0.949049 | 0.974153 | 0.9722 | 0.9923 | 0.9819 |
| K497L | 0.927621 | 0.904678 | 0.916149 | 0.9025 | 0.9459 | 0.9234 |
| K497M | 0.921576 | 0.897281 | 0.909429 | 0.8966 | 0.9381 | 0.9166 |
| K497N | 1.005647 | 0.966303 | 0.985975 | 0.9784 | 1.0103 | 0.9938 |
| K497P | 0.90897 | 0.840585 | 0.874778 | 0.8844 | 0.8789 | 0.8817 |
| K497Q | 0.929664 | 0.958909 | 0.944287 | 0.9045 | 1.0026 | 0.9518 |
| K497R | 0.946731 | 0.880027 | 0.913379 | 0.9211 | 0.9201 | 0.9206 |
| K497S | 0.994681 | 0.914538 | 0.95461 | 0.9677 | 0.9562 | 0.9622 |
| K497T | 0.964346 | 0.843051 | 0.903698 | 0.9382 | 0.8814 | 0.9109 |
| K497V | 0.959856 | 0.875097 | 0.917476 | 0.9339 | 0.9149 | 0.9247 |
| K497W | 0.882002 | 0.825795 | 0.853899 | 0.8581 | 0.8634 | 0.8607 |
| K497Y | 0.940256 | 0.909607 | 0.924931 | 0.9148 | 0.9510 | 0.9323 |
| P498A | 0.900739 | 0.912073 | 0.906406 | 0.8763 | 0.9536 | 0.9136 |
| P498C | 1.044272 | 1.069837 | 1.057054 | 1.0160 | 1.1186 | 1.0654 |
| P498D | 1.013274 | 0.953978 | 0.983626 | 0.9858 | 0.9974 | 0.9914 |
| P498E | 1.03404 | 1.020535 | 1.027338 | 1.0061 | 1.0670 | 1.0355 |
| P498F | 1.034515 | 0.961373 | 0.997944 | 1.0065 | 1.0052 | 1.0058 |
| P498G | 1.057223 | 1.025466 | 1.041344 | 1.0286 | 1.0722 | 1.0496 |
| P498H | 1.026916 | 0.884958 | 0.955937 | 0.9991 | 0.9253 | 0.9635 |
| P498I | 1.010137 | 0.909607 | 0.959872 | 0.9828 | 0.9510 | 0.9675 |
| P498K | 1.062749 | 1.035325 | 1.049037 | 1.0340 | 1.0825 | 1.0573 |
| P498L | 0.975455 | 0.939188 | 0.957322 | 0.9490 | 0.9820 | 0.9649 |
| P498M | 0.981528 | 1.003279 | 0.992404 | 0.9549 | 1.0490 | 1.0003 |
| P498N | 0.980492 | 0.981093 | 0.980793 | 0.9539 | 1.0258 | 0.9886 |
| P498P | 0.991084 | 0.968769 | 0.979926 | 0.9642 | 1.0129 | 0.9877 |
| P498Q | 0.972749 | 0.973698 | 0.973224 | 0.9464 | 1.0180 | 0.9809 |
| P498R | 1.07596 | 0.986025 | 1.030992 | 1.0468 | 1.0309 | 1.0392 |
| P498S | 1.067383 | 1.02793 | 1.047657 | 1.0385 | 1.0747 | 1.0560 |
| P498T | 1.002251 | 0.84798 | 0.925116 | 0.9751 | 0.8866 | 0.9324 |
| P498V | 1.012526 | 0.944118 | 0.978322 | 0.9851 | 0.9871 | 0.9861 |
| P498W | 0.905315 | 0.843051 | 0.874183 | 0.8808 | 0.8814 | 0.8811 |
| P498Y | 0.973412 | 0.919468 | 0.94644 | 0.9470 | 0.9613 | 0.9539 |
| Q509A | 0.843234 | 0.897282 | 0.870258 | 0.8067 | 0.8161 | 0.8116 |
| Q509C | 0.814194 | 0.867702 | 0.840948 | 0.7790 | 0.7892 | 0.7842 |
| Q509D | 0.614107 | 0.682822 | 0.648464 | 0.5875 | 0.6211 | 0.6047 |
| Q509E | 0.70258 | 0.769099 | 0.73584 | 0.6722 | 0.6996 | 0.6862 |
| Q509F | 0.070715 | 0.18488 | 0.127797 | 0.0677 | 0.1682 | 0.1192 |
| Q509G | 0.923419 | 0.993418 | 0.958418 | 0.8834 | 0.9036 | 0.8938 |
| Q509H | 0.539304 | 0.601475 | 0.570389 | 0.5160 | 0.5471 | 0.5319 |
| Q509I | 0.934154 | 0.961373 | 0.947764 | 0.8937 | 0.8744 | 0.8838 |
| Q509K | 0.501456 | 0.539848 | 0.520652 | 0.4798 | 0.4910 | 0.4855 |
| Q509L | 0.364026 | 0.436316 | 0.400171 | 0.3483 | 0.3969 | 0.3732 |
| Q509M | 0.87498 | 0.914537 | 0.894758 | 0.8371 | 0.8318 | 0.8344 |
| Q509N | 0.723504 | 0.796214 | 0.759859 | 0.6922 | 0.7242 | 0.7086 |
| Q509P | 0.008171 | 0.071486 | 0.03983 | 0.0078 | 0.0650 | 0.0371 |
| Q509Q | 0.917605 | 0.956444 | 0.937024 | 0.8779 | 0.8700 | 0.8738 |
| Q509R | 0.009556 | 0.103533 | 0.056544 | 0.0091 | 0.0942 | 0.0527 |
| Q509S | 1.020527 | 1.119136 | 1.069832 | 0.9764 | 1.0179 | 0.9977 |
| Q509T | 1.035602 | 1.067272 | 1.051216 | 0.9903 | 0.9709 | 0.9803 |
| Q509V | 1.058489 | 1.077231 | 1.06786 | 1.0127 | 0.9798 | 0.9958 |
| Q509W | 0.002993 | 0.093672 | 0.048332 | 0.0029 | 0.0852 | 0.0451 |
| Q509Y | −0.00524 | 0.012326 | 0.003544 | −0.0050 | 0.0112 | 0.0033 |
| Y514A | 0.006159 | 0.101067 | 0.053613 | 0.0059 | 0.0919 | 0.0500 |
| Y514C | 0.033559 | 0.110928 | 0.072243 | 0.0321 | 0.1009 | 0.0674 |
| Y514D | 0.04795 | 0.103533 | 0.075741 | 0.0459 | 0.0942 | 0.0706 |
| Y514E | 0.004403 | 0.046835 | 0.025619 | 0.0042 | 0.0426 | 0.0239 |
| Y514F | 0.027975 | 0.135577 | 0.081776 | 0.0268 | 0.1233 | 0.0763 |
| Y514G | −0.00262 | 0.051766 | 0.024574 | −0.0025 | 0.0471 | 0.0229 |
| Y514H | 0.022737 | 0.140508 | 0.081623 | 0.0218 | 0.1278 | 0.0761 |
| Y514I | 0.013729 | 0.056697 | 0.035213 | 0.0131 | 0.0516 | 0.0328 |
| Y514K | 0.036207 | 0.118323 | 0.077265 | 0.0346 | 0.1076 | 0.0721 |
| Y514L | −0.02317 | 0.036976 | 0.006904 | −0.0222 | 0.0336 | 0.0064 |
| Y514M | −0.00656 | 0.101068 | 0.047253 | −0.0063 | 0.0919 | 0.0441 |
| Y514N | 0.00354 | 0.083813 | 0.043677 | 0.0034 | 0.0762 | 0.0407 |
| Y514P | 0.002476 | 0.024651 | 0.013563 | 0.0024 | 0.0224 | 0.0126 |
| Y514Q | 0.034768 | 0.078881 | 0.056825 | 0.0333 | 0.0717 | 0.0530 |
| Y514R | −0.01056 | 0.078883 | 0.03416 | −0.0101 | 0.0717 | 0.0319 |
| Y514S | −0.01134 | 0.093672 | 0.041166 | −0.0108 | 0.0852 | 0.0384 |
| Y514T | 0.012491 | 0.056696 | 0.034593 | 0.0120 | 0.0516 | 0.0323 |
| Y514V | 0.074285 | 0.133113 | 0.103699 | 0.0711 | 0.1211 | 0.0967 |
| Y514W | 0.000202 | 0.105998 | 0.0531 | 0.0002 | 0.0964 | 0.0495 |

TABLE 9-continued

| Variant | Slope PI | Delta PI | Avg PI | Norm Slope PI | Norm Delta PI | Norm Avg PI |
|---|---|---|---|---|---|---|
| Y514Y | 1.06721 | 1.057511 | 1.06236 | 1.0210 | 0.9619 | 0.9907 |
| H515A | 0.745895 | 0.744448 | 0.745171 | 0.7777 | 0.8157 | 0.7962 |
| H515E | 0.833459 | 0.771563 | 0.802511 | 0.8689 | 0.8454 | 0.8575 |
| H515F | 0.823238 | 0.774028 | 0.798633 | 0.8583 | 0.8481 | 0.8533 |
| H515G | 0.93037 | 0.862771 | 0.89657 | 0.9700 | 0.9453 | 0.9580 |
| H515H | −0.0244 | 0.004931 | −0.00973 | −0.0254 | 0.0054 | −0.0104 |
| H515H | −0.0068 | −0.02219 | −0.01449 | −0.0071 | −0.0243 | −0.0155 |
| H515H | −0.04435 | −0.06656 | −0.05545 | −0.0462 | −0.0729 | −0.0593 |
| H515H | −0.02747 | −0.08628 | −0.05687 | −0.0286 | −0.0945 | −0.0608 |
| H515K | 0.910517 | 0.867702 | 0.88911 | 0.9493 | 0.9507 | 0.9500 |
| H515L | 0.36678 | 0.345108 | 0.355944 | 0.3824 | 0.3781 | 0.3803 |
| H515M | 0.853516 | 0.783889 | 0.818703 | 0.8899 | 0.8589 | 0.8748 |
| H515N | 0.829668 | 0.764168 | 0.796918 | 0.8650 | 0.8373 | 0.8515 |
| H515P | −0.03132 | −0.00986 | −0.02059 | −0.0327 | −0.0108 | −0.0220 |
| H515Q | 0.860328 | 0.840585 | 0.850456 | 0.8970 | 0.9210 | 0.9087 |
| H515R | 0.960882 | 0.892353 | 0.926618 | 1.0018 | 0.9777 | 0.9901 |
| H515S | 0.788993 | 0.727192 | 0.758092 | 0.8226 | 0.7968 | 0.8100 |
| H515T | 0.825248 | 0.77896 | 0.802104 | 0.8604 | 0.8535 | 0.8570 |
| H515V | 0.914933 | 0.936722 | 0.925828 | 0.9539 | 1.0263 | 0.9892 |
| H515W | 0.934157 | 0.931793 | 0.932975 | 0.9739 | 1.0209 | 0.9968 |
| H515Y | 1.079383 | 1.05258 | 1.065981 | 1.1253 | 1.1533 | 1.1390 |
| A519A | 0.896149 | 0.850446 | 0.873297 | 0.9343 | 0.9318 | 0.9331 |
| A519A | 0.843245 | 0.845515 | 0.84438 | 0.8791 | 0.9264 | 0.9022 |
| A519A | 0.80734 | 0.815935 | 0.811638 | 0.8417 | 0.8940 | 0.8672 |
| A519A | 0.796001 | 0.702542 | 0.749272 | 0.8299 | 0.7698 | 0.8006 |
| A519C | 0.632644 | 0.596546 | 0.614595 | 0.6596 | 0.6536 | 0.6567 |
| A519D | 0.482005 | 0.520128 | 0.501067 | 0.5025 | 0.5699 | 0.5354 |
| A519E | 0.597896 | 0.616266 | 0.607081 | 0.6234 | 0.6752 | 0.6486 |
| A519F | 0.782016 | 0.791284 | 0.78665 | 0.8153 | 0.8670 | 0.8405 |
| A519G | 0.895705 | 0.84798 | 0.871843 | 0.9338 | 0.9291 | 0.9315 |
| A519H | 0.795534 | 0.764169 | 0.779852 | 0.8294 | 0.8373 | 0.8332 |
| A519K | 0.903621 | 0.872631 | 0.888126 | 0.9421 | 0.9561 | 0.9489 |
| A519L | 0.801397 | 0.803609 | 0.802503 | 0.8355 | 0.8805 | 0.8574 |
| A519P | −0.00583 | 0.098601 | 0.046384 | −0.0061 | 0.1080 | 0.0496 |
| A519Q | 0.595566 | 0.675426 | 0.635496 | 0.6209 | 0.7400 | 0.6790 |
| A519R | 0.845564 | 0.850446 | 0.848005 | 0.8816 | 0.9318 | 0.9061 |
| A519S | 0.75083 | 0.769099 | 0.759964 | 0.7828 | 0.8427 | 0.8120 |
| A519T | 0.718533 | 0.719797 | 0.719165 | 0.7491 | 0.7887 | 0.7684 |
| A519V | 0.64074 | 0.682821 | 0.66178 | 0.6680 | 0.7481 | 0.7071 |
| A519W | 1.028502 | 1.045185 | 1.036843 | 1.0723 | 1.1452 | 1.1078 |
| A519Y | 0.796949 | 0.818401 | 0.807675 | 0.8309 | 0.8967 | 0.8630 |
| T521A | 0.014851 | 0.115857 | 0.065354 | 0.0142 | 0.1054 | 0.0609 |
| T521C | 0.02645 | 0.108462 | 0.067456 | 0.0253 | 0.0987 | 0.0629 |
| T521D | 0.008289 | 0.054232 | 0.03126 | 0.0079 | 0.0493 | 0.0292 |
| T521E | 0.90379 | 0.887422 | 0.895606 | 0.8647 | 0.8072 | 0.8352 |
| T521F | −0.01215 | 0.091201 | 0.03953 | −0.0116 | 0.0830 | 0.0369 |
| T521G | 0.957179 | 0.990954 | 0.974067 | 0.9157 | 0.9013 | 0.9084 |
| T521H | 0.012347 | 0.032046 | 0.022197 | 0.0118 | 0.0291 | 0.0207 |
| T521I | −0.01836 | 0.019721 | 0.00068 | −0.0176 | 0.0179 | 0.0006 |
| T521K | −0.00688 | 0.022186 | 0.007654 | −0.0066 | 0.0202 | 0.0071 |
| T521L | 0.830772 | 0.79868 | 0.814726 | 0.7948 | 0.7265 | 0.7598 |
| T521M | 0.510321 | 0.59408 | 0.5522 | 0.4882 | 0.5404 | 0.5150 |
| T521N | 0.009555 | 0.118323 | 0.063939 | 0.0091 | 0.1076 | 0.0596 |
| T521P | 0.022309 | 0.036976 | 0.029641 | 0.0213 | 0.0336 | 0.0276 |
| T521Q | 0.720943 | 0.759238 | 0.74009 | 0.6897 | 0.6906 | 0.6902 |
| T521R | −0.00256 | 0.064091 | 0.030765 | −0.0025 | 0.0583 | 0.0287 |
| T521S | 0.985874 | 1.020535 | 1.003204 | 0.9432 | 0.9283 | 0.9355 |
| T521T | 0.060844 | 0.115859 | 0.088351 | 0.0582 | 0.1054 | 0.0824 |
| T521V | 0.756404 | 0.769099 | 0.762592 | 0.7234 | 0.6996 | 0.7112 |
| T521W | 0.039085 | 0.133113 | 0.086099 | 0.0374 | 0.1211 | 0.0803 |
| T521Y | 0.034883 | −0.02219 | 0.006349 | 0.0334 | −0.0202 | 0.0059 |
| E525A | 0.804193 | 0.79868 | 0.801436 | 0.8384 | 0.8751 | 0.8563 |
| E525C | 0.844929 | 0.820865 | 0.832897 | 0.8809 | 0.8994 | 0.8899 |
| E525D | 0.824525 | 0.815935 | 0.82023 | 0.8596 | 0.8940 | 0.8764 |
| E525E | 0.980194 | 0.934257 | 0.957225 | 1.0219 | 1.0236 | 1.0228 |
| E525E | 0.877849 | 0.860307 | 0.869078 | 0.9152 | 0.9426 | 0.9286 |
| E525E | 0.769558 | 0.801145 | 0.785352 | 0.8023 | 0.8778 | 0.8391 |
| E525F | 0.791795 | 0.761704 | 0.776749 | 0.8255 | 0.8346 | 0.8299 |
| E525G | 0.86885 | 0.796215 | 0.832533 | 0.9058 | 0.8724 | 0.8895 |
| E525H | 0.839596 | 0.815935 | 0.827766 | 0.8753 | 0.8940 | 0.8844 |
| E525K | 1.00776 | 1.040255 | 1.024008 | 1.0507 | 1.1398 | 1.0941 |
| E525L | 0.949874 | 0.988489 | 0.969181 | 0.9903 | 1.0831 | 1.0355 |
| E525M | 0.78098 | 0.724728 | 0.752854 | 0.8142 | 0.7941 | 0.8044 |
| E525N | 0.795743 | 0.732123 | 0.763933 | 0.8296 | 0.8022 | 0.8162 |
| E525P | 0.581641 | 0.581754 | 0.581697 | 0.6064 | 0.6374 | 0.6215 |
| E525Q | 0.725042 | 0.705006 | 0.715024 | 0.7559 | 0.7725 | 0.7640 |
| E525R | 0.805382 | 0.771563 | 0.788472 | 0.8397 | 0.8454 | 0.8425 |
| E525S | 0.756158 | 0.734588 | 0.745373 | 0.7884 | 0.8049 | 0.7964 |
| E525T | 0.865915 | 0.825796 | 0.845856 | 0.9028 | 0.9048 | 0.9038 |
| E525V | 0.872496 | 0.845516 | 0.859006 | 0.9096 | 0.9264 | 0.9178 |
| E525W | 0.901802 | 0.894817 | 0.898309 | 0.9402 | 0.9804 | 0.9598 |
| R528A | 0.596877 | 0.63352 | 0.615199 | 0.6223 | 0.6941 | 0.6573 |
| R528C | 0.471068 | 0.532453 | 0.50176 | 0.4911 | 0.5834 | 0.5361 |
| R528D | 0.253986 | 0.340178 | 0.297082 | 0.2648 | 0.3727 | 0.3174 |
| R528E | 0.567494 | 0.668032 | 0.617763 | 0.5917 | 0.7319 | 0.6601 |
| R528F | 0.790137 | 0.865236 | 0.827686 | 0.8238 | 0.9480 | 0.8844 |
| R528G | 0.531474 | 0.542314 | 0.536894 | 0.5541 | 0.5942 | 0.5736 |
| R528H | 0.761739 | 0.815935 | 0.788837 | 0.7942 | 0.8940 | 0.8428 |
| R528K | 0.949743 | 0.907143 | 0.928443 | 0.9902 | 0.9939 | 0.9920 |
| R528L | 0.76786 | 0.820865 | 0.794363 | 0.8006 | 0.8994 | 0.8487 |
| R528M | 0.738201 | 0.732123 | 0.735162 | 0.7696 | 0.8022 | 0.7855 |
| R528N | 0.564926 | 0.60887 | 0.586898 | 0.5890 | 0.6671 | 0.6271 |
| R528P | −0.02058 | 0.064091 | 0.021753 | −0.0215 | 0.0702 | 0.0232 |
| R528R | 0.922893 | 0.865236 | 0.894065 | 0.9622 | 0.9480 | 0.9553 |
| R528R | 0.866645 | 0.857841 | 0.862243 | 0.9035 | 0.9399 | 0.9213 |
| R528R | 0.80489 | 0.79375 | 0.79932 | 0.8392 | 0.8697 | 0.8540 |
| R528S | 0.631812 | 0.611234 | 0.621573 | 0.6587 | 0.6698 | 0.6641 |
| R528T | 0.720739 | 0.677893 | 0.699316 | 0.7514 | 0.7427 | 0.7472 |
| R528V | 0.857453 | 0.850446 | 0.85395 | 0.8940 | 0.9318 | 0.9124 |
| R528W | 0.495593 | 0.522592 | 0.509093 | 0.5167 | 0.5726 | 0.5439 |
| R528Y | 0.726729 | 0.668032 | 0.69738 | 0.7577 | 0.7319 | 0.7451 |
| T536A | 0.836816 | 0.8184 | 0.827608 | 0.5979 | 0.5998 | 0.5988 |
| T536C | 0.915101 | 0.912073 | 0.913587 | 0.6538 | 0.6685 | 0.6611 |
| T536D | 0.773756 | 0.788819 | 0.781287 | 0.5528 | 0.5781 | 0.5653 |
| T536E | 0.729461 | 0.764169 | 0.746815 | 0.5212 | 0.5601 | 0.5404 |
| T536F | 1.161728 | 1.21281 | 1.187269 | 0.8300 | 0.8889 | 0.8591 |
| T536G | 1.133349 | 1.128999 | 1.131174 | 0.8098 | 0.8275 | 0.8185 |
| T536H | 1.145956 | 1.163509 | 1.154732 | 0.8188 | 0.8528 | 0.8356 |
| T536I | 0.879527 | 0.884956 | 0.882242 | 0.6284 | 0.6486 | 0.6384 |
| T536K | 0.911618 | 0.880027 | 0.895822 | 0.6513 | 0.6450 | 0.6482 |
| T536L | 1.174536 | 1.151183 | 1.162859 | 0.8392 | 0.8437 | 0.8414 |
| T536M | 0.976348 | 0.971234 | 0.973791 | 0.6976 | 0.7118 | 0.7046 |
| T536N | 0.987918 | 0.998349 | 0.993134 | 0.7059 | 0.7317 | 0.7186 |
| T536P | 0.279294 | 0.303202 | 0.291248 | 0.1996 | 0.2222 | 0.2107 |
| T536R | 0.70848 | 0.653241 | 0.680861 | 0.5062 | 0.4788 | 0.4927 |
| T536S | 1.11752 | 1.163509 | 1.140514 | 0.7985 | 0.8528 | 0.8253 |
| T536T | 1.249568 | 1.225134 | 1.237351 | 0.8928 | 0.8979 | 0.8953 |
| T536T | 1.131996 | 1.121622 | 1.126799 | 0.8088 | 0.8220 | 0.8153 |
| T536T | 1.034716 | 1.018069 | 1.026393 | 0.7393 | 0.7462 | 0.7427 |
| T536V | 1.137379 | 1.153648 | 1.145513 | 0.8127 | 0.8455 | 0.8289 |
| T536Y | 1.212182 | 1.232531 | 1.222356 | 0.8661 | 0.9033 | 0.8845 |
| I539A | 0.799576 | 0.823331 | 0.811454 | 0.8315 | 0.8919 | 0.8611 |
| I539C | 0.845684 | 0.875097 | 0.860391 | 0.8794 | 0.9479 | 0.9130 |
| I539D | 0.033062 | 0.066557 | 0.049809 | 0.0344 | 0.0721 | 0.0529 |
| I539E | 0.541628 | 0.586683 | 0.564156 | 0.5632 | 0.6355 | 0.5986 |
| I539F | 0.792832 | 0.845516 | 0.819174 | 0.8245 | 0.9159 | 0.8693 |
| I539G | 0.518784 | 0.566963 | 0.542873 | 0.5395 | 0.6142 | 0.5761 |
| I539H | 0.790285 | 0.81347 | 0.801878 | 0.8218 | 0.8812 | 0.8509 |
| I539I | 0.916701 | 0.944118 | 0.930409 | 0.9533 | 1.0227 | 0.9873 |
| I539K | 0.937916 | 0.956442 | 0.947179 | 0.9754 | 1.0360 | 1.0051 |
| I539L | 0.95073 | 0.990954 | 0.970842 | 0.9887 | 1.0734 | 1.0302 |
| I539M | 0.865998 | 0.845516 | 0.855757 | 0.9006 | 0.9159 | 0.9081 |
| I539N | 0.495955 | 0.534917 | 0.515436 | 0.5158 | 0.5794 | 0.5469 |
| I539P | 0.64276 | 0.709917 | 0.676349 | 0.6684 | 0.7690 | 0.7177 |
| I539Q | 0.749304 | 0.781424 | 0.765364 | 0.7792 | 0.8465 | 0.8122 |
| I539R | 0.747375 | 0.79375 | 0.770562 | 0.7772 | 0.8598 | 0.8177 |
| I539S | 0.835958 | 0.875097 | 0.855527 | 0.8693 | 0.9479 | 0.9078 |
| I539T | 0.920394 | 0.934257 | 0.927326 | 0.9571 | 1.0120 | 0.9840 |
| I539V | 0.980864 | 1.015604 | 0.998236 | 1.0200 | 1.1001 | 1.0593 |
| I539W | 0.712773 | 0.751843 | 0.732308 | 0.7412 | 0.8144 | 0.7771 |
| I539Y | 0.695299 | 0.769099 | 0.732199 | 0.7231 | 0.8331 | 0.7770 |
| L540A | 0.743534 | 0.754308 | 0.748921 | 0.8532 | 0.8650 | 0.8591 |
| L540C | 0.725959 | 0.749379 | 0.737669 | 0.8331 | 0.8594 | 0.8462 |
| L540D | 0.812091 | 0.81347 | 0.812781 | 0.9319 | 0.9329 | 0.9324 |
| L540E | 0.797371 | 0.803611 | 0.800491 | 0.9150 | 0.9216 | 0.9183 |
| L540F | 0.876809 | 0.882492 | 0.879651 | 1.0062 | 1.0120 | 1.0091 |
| L540G | 0.777617 | 0.803611 | 0.790614 | 0.8923 | 0.9216 | 0.9069 |
| L540H | 0.915792 | 0.929327 | 0.92256 | 1.0509 | 1.0657 | 1.0583 |
| L540I | 0.9617 | 0.966303 | 0.964002 | 1.1036 | 1.1081 | 1.1059 |
| L540K | 0.88224 | 0.919468 | 0.900854 | 1.0124 | 1.0544 | 1.0334 |
| L540L | 0.857056 | 0.875097 | 0.866077 | 0.9835 | 1.0035 | 0.9935 |
| L540M | 0.897116 | 0.926863 | 0.911989 | 1.0295 | 1.0629 | 1.0462 |

TABLE 9-continued

| Variant | Slope PI | Delta PI | Avg PI | Norm Slope PI | Norm Delta PI | Norm Avg PI |
|---|---|---|---|---|---|---|
| L540N | 0.834345 | 0.8677 | 0.851022 | 0.9574 | 0.9951 | 0.9762 |
| L540P | 0.863591 | 0.899746 | 0.881669 | 0.9910 | 1.0318 | 1.0114 |
| L540Q | 0.843641 | 0.82826 | 0.835951 | 0.9681 | 0.9498 | 0.9590 |
| L540R | 0.91412 | 0.934258 | 0.924189 | 1.0490 | 1.0714 | 1.0602 |
| L540S | 0.927158 | 0.978628 | 0.952893 | 1.0639 | 1.1223 | 1.0931 |
| L540T | 1.02144 | 1.00821 | 1.014825 | 1.1721 | 1.1562 | 1.1642 |
| L540V | 0.971854 | 0.956444 | 0.964149 | 1.1152 | 1.0968 | 1.1060 |
| L540W | 0.917478 | 0.931793 | 0.924635 | 1.0528 | 1.0686 | 1.0607 |
| L540Y | 0.909351 | 0.919468 | 0.91441 | 1.0435 | 1.0544 | 1.0490 |
| R544A | 0.781221 | 0.77403 | 0.777626 | 0.8965 | 0.8876 | 0.8921 |
| R544C | 0.838912 | 0.880027 | 0.859469 | 0.9627 | 1.0092 | 0.9859 |
| R544D | 0.816611 | 0.855375 | 0.835993 | 0.9371 | 0.9809 | 0.9590 |
| R544E | 0.732804 | 0.732123 | 0.732463 | 0.8409 | 0.8396 | 0.8402 |
| R544F | 0.872383 | 0.936722 | 0.904553 | 1.0011 | 1.0742 | 1.0377 |
| R544G | 0.853798 | 0.912073 | 0.882935 | 0.9798 | 1.0459 | 1.0129 |
| R544H | 0.902236 | 0.912073 | 0.907154 | 1.0353 | 1.0459 | 1.0406 |
| R544I | 0.884967 | 0.892351 | 0.888659 | 1.0155 | 1.0233 | 1.0194 |
| R544K | 0.915488 | 0.986025 | 0.950756 | 1.0505 | 1.1307 | 1.0907 |
| R544L | 0.870343 | 0.875095 | 0.872719 | 0.9987 | 1.0035 | 1.0011 |
| R544M | 0.802716 | 0.803609 | 0.803163 | 0.9211 | 0.9216 | 0.9213 |
| R544N | 0.753139 | 0.79375 | 0.773445 | 0.8642 | 0.9102 | 0.8873 |
| R544P | 0.788391 | 0.783889 | 0.78614 | 0.9047 | 0.8989 | 0.9018 |
| R544Q | 0.740588 | 0.737054 | 0.738821 | 0.8498 | 0.8452 | 0.8475 |
| R544R | 0.730537 | 0.741984 | 0.73626 | 0.8383 | 0.8509 | 0.8446 |
| R544S | 0.894148 | 0.917002 | 0.905575 | 1.0261 | 1.0516 | 1.0388 |
| R544T | 0.874489 | 0.840587 | 0.857538 | 1.0035 | 0.9640 | 0.9837 |
| R544V | 0.876547 | 0.880027 | 0.878287 | 1.0059 | 1.0092 | 1.0075 |
| R544W | 0.874069 | 0.907142 | 0.890605 | 1.0030 | 1.0403 | 1.0217 |
| R544Y | 0.604547 | 0.645846 | 0.625197 | 0.6937 | 0.7406 | 0.7172 |

TABLE 10

Top 150 Variants for Norm Avg PI

| Variant | Slope PI | Delta PI | Avg PI | Norm Slope PI | Norm Delta PI | Norm Avg PI |
|---|---|---|---|---|---|---|
| G99I | 1.161186 | 1.239926 | 1.200556 | 1.1406 | 1.2481 | 1.1937 |
| G78I | 0.987889 | 1.037791 | 1.01284 | 1.1689 | 1.2046 | 1.1869 |
| S74V | 0.978132 | 1.035325 | 1.006729 | 1.1573 | 1.2017 | 1.1797 |
| L59H | 1.223234 | 1.230066 | 1.22665 | 1.1792 | 1.1727 | 1.1759 |
| V30L | 1.025017 | 0.963838 | 0.994427 | 1.1777 | 1.1718 | 1.1747 |
| G69T | 1.123227 | 1.244856 | 1.184041 | 1.1268 | 1.2198 | 1.1739 |
| E117I | 1.187747 | 1.257181 | 1.222464 | 1.1450 | 1.1986 | 1.1719 |
| I28S | 1.00392 | 0.9737 | 0.98881 | 1.1534 | 1.1838 | 1.1686 |
| Q116V | 1.189502 | 1.247321 | 1.218412 | 1.1467 | 1.1892 | 1.1680 |
| G99K | 1.136314 | 1.21281 | 1.174562 | 1.1162 | 1.2208 | 1.1679 |
| I28R | 1.026571 | 0.949049 | 0.98781 | 1.1794 | 1.1538 | 1.1666 |
| G127H | 1.147312 | 1.321273 | 1.234293 | 1.1095 | 1.2182 | 1.1651 |
| L540T | 1.02144 | 1.00821 | 1.014825 | 1.1721 | 1.1562 | 1.1642 |
| A448T | 1.006534 | 1.023 | 1.014767 | 1.1550 | 1.1731 | 1.1641 |
| L59T | 1.198452 | 1.230064 | 1.214258 | 1.1553 | 1.1727 | 1.1641 |
| L494L | 1.282111 | 1.267041 | 1.274576 | 1.1253 | 1.2052 | 1.1636 |
| S74T | 0.959568 | 1.025465 | 0.992516 | 1.1353 | 1.1903 | 1.1631 |
| G99V | 1.147162 | 1.188159 | 1.16766 | 1.1268 | 1.1960 | 1.1610 |
| V30F | 1.016354 | 0.944118 | 0.980236 | 1.1677 | 1.1479 | 1.1578 |
| G78V | 0.936888 | 1.03286 | 0.984874 | 1.1085 | 1.1989 | 1.1541 |
| A448V | 0.979666 | 1.02793 | 1.003798 | 1.1242 | 1.1788 | 1.1515 |
| G78T | 0.954445 | 1.010674 | 0.982559 | 1.1293 | 1.1731 | 1.1514 |
| S74W | 0.951107 | 1.003279 | 0.977193 | 1.1253 | 1.1645 | 1.1451 |
| E173F | 1.082143 | 1.138858 | 1.1105 | 1.1170 | 1.1696 | 1.1434 |
| N476V | 1.085918 | 1.109277 | 1.097597 | 1.1620 | 1.1222 | 1.1415 |
| H515Y | 1.079383 | 1.05258 | 1.065981 | 1.1253 | 1.1533 | 1.1390 |
| Y16I | 1.110586 | 1.183229 | 1.146907 | 1.1141 | 1.1594 | 1.1370 |
| L490I | 1.086573 | 1.050116 | 1.068344 | 1.1299 | 1.1375 | 1.1337 |
| G78H | 0.964058 | 0.968769 | 0.966413 | 1.1407 | 1.1245 | 1.1325 |
| S493T | 1.08658 | 1.08216 | 1.08437 | 1.1627 | 1.0948 | 1.1278 |
| D311L | 1.166364 | 1.114207 | 1.140285 | 1.1224 | 1.1328 | 1.1276 |
| G78W | 0.927391 | 0.995885 | 0.961638 | 1.0973 | 1.1559 | 1.1269 |
| G69S | 1.081175 | 1.190624 | 1.1359 | 1.0846 | 1.1667 | 1.1261 |
| E173V | 1.087401 | 1.099418 | 1.093409 | 1.1225 | 1.1291 | 1.1258 |
| L59R | 1.163944 | 1.183229 | 1.173587 | 1.1220 | 1.1281 | 1.1251 |

TABLE 10-continued

Top 150 Variants for Norm Avg PI

| Variant | Slope PI | Delta PI | Avg PI | Norm Slope PI | Norm Delta PI | Norm Avg PI |
|---|---|---|---|---|---|---|
| V30E | 0.958734 | 0.941654 | 0.950194 | 1.1015 | 1.1449 | 1.1232 |
| S74K | 0.935737 | 0.981093 | 0.958415 | 1.1071 | 1.1388 | 1.1231 |
| G99T | 1.124624 | 1.131463 | 1.128043 | 1.1047 | 1.1390 | 1.1216 |
| G492E | 1.028326 | 1.126532 | 1.077429 | 1.1004 | 1.1396 | 1.1206 |
| Q116I | 1.151107 | 1.180763 | 1.165935 | 1.1097 | 1.1257 | 1.1177 |
| A139T | 1.147503 | 1.220205 | 1.183854 | 1.1096 | 1.1250 | 1.1175 |
| K50T | 1.109699 | 1.136392 | 1.123046 | 1.1090 | 1.1439 | 1.1167 |
| T462W | 0.950774 | 0.995884 | 0.973329 | 1.0910 | 1.1420 | 1.1166 |
| F495L | 1.042055 | 1.104346 | 1.073201 | 1.1151 | 1.1172 | 1.1162 |
| G491I | 1.061556 | 1.037791 | 1.049673 | 1.1039 | 1.1242 | 1.1138 |
| E173R | 1.074678 | 1.087092 | 1.080885 | 1.1093 | 1.1165 | 1.1129 |
| A448R | 0.953238 | 0.986023 | 0.96963 | 1.0939 | 1.1307 | 1.1123 |
| D33I | 1.08364 | 1.151183 | 1.117411 | 1.0645 | 1.1588 | 1.1111 |
| K50K | 1.122473 | 1.111741 | 1.117107 | 1.1026 | 1.1191 | 1.1108 |
| S493L | 1.046085 | 1.089557 | 1.067821 | 1.1194 | 1.1022 | 1.1106 |
| G127T | 1.129834 | 1.22267 | 1.176252 | 1.0926 | 1.1273 | 1.1103 |
| E173T | 1.078933 | 1.077231 | 1.078082 | 1.1137 | 1.1063 | 1.1100 |
| D33F | 1.097951 | 1.133928 | 1.11594 | 1.0785 | 1.1414 | 1.1096 |
| K487W | 1.157698 | 1.220205 | 1.188952 | 1.1076 | 1.1099 | 1.1088 |
| A519W | 1.028502 | 1.045185 | 1.036843 | 1.0723 | 1.1452 | 1.1078 |
| V30K | 0.981241 | 0.892351 | 0.936796 | 1.1274 | 1.0849 | 1.1061 |
| V30V | 0.942098 | 0.929329 | 0.935713 | 1.0824 | 1.1299 | 1.1061 |
| L540V | 0.971854 | 0.956444 | 0.964149 | 1.1152 | 1.0968 | 1.1060 |
| L540I | 0.9617 | 0.966303 | 0.964002 | 1.1036 | 1.1081 | 1.1059 |
| L490H | 1.055247 | 1.02793 | 1.041588 | 1.0974 | 1.1135 | 1.1053 |
| D33H | 1.110918 | 1.111741 | 1.111329 | 1.0912 | 1.1191 | 1.1050 |
| L59Q | 1.123362 | 1.180763 | 1.152063 | 1.0829 | 1.1257 | 1.1044 |
| E117L | 1.132889 | 1.170903 | 1.151896 | 1.0921 | 1.1163 | 1.1043 |
| E179G | 1.070203 | 1.087092 | 1.078647 | 1.1412 | 1.0691 | 1.1037 |
| F53I | 1.110952 | 1.106812 | 1.108882 | 1.0913 | 1.1141 | 1.1026 |
| E174H | 1.05931 | 1.08216 | 1.070735 | 1.0935 | 1.1114 | 1.1025 |
| K50W | 1.09828 | 1.119138 | 1.108709 | 1.0788 | 1.1266 | 1.1024 |
| K36I | 0.921059 | 0.956444 | 0.938751 | 1.0898 | 1.1102 | 1.1001 |
| Q116W | 1.145149 | 1.148717 | 1.146933 | 1.1039 | 1.0952 | 1.0995 |
| S74H | 0.922584 | 0.953978 | 0.938281 | 1.0916 | 1.1073 | 1.0995 |
| L469W | 1.210486 | 1.198019 | 1.204252 | 1.0624 | 1.1395 | 1.0994 |
| L59E | 1.112454 | 1.180763 | 1.146609 | 1.0724 | 1.1257 | 1.0992 |
| E173H | 1.053843 | 1.079696 | 1.06677 | 1.0878 | 1.1089 | 1.0984 |
| L59C | 1.115246 | 1.17337 | 1.144308 | 1.0751 | 1.1187 | 1.0970 |
| Q125F | 1.080593 | 1.207879 | 1.144236 | 1.0417 | 1.1516 | 1.0969 |
| E173W | 1.061328 | 1.067372 | 1.06435 | 1.0955 | 1.0962 | 1.0959 |
| T462I | 0.937846 | 0.971234 | 0.95454 | 1.0762 | 1.1138 | 1.0950 |
| S493I | 1.045164 | 1.059976 | 1.05257 | 1.1184 | 1.0723 | 1.0947 |
| L59I | 1.162183 | 1.121602 | 1.141895 | 1.1203 | 1.0693 | 1.0947 |
| R44M | 1.115994 | 1.136392 | 1.126193 | 1.0807 | 1.1088 | 1.0947 |
| E525K | 1.00776 | 1.040255 | 1.024008 | 1.0507 | 1.1398 | 1.0941 |
| L540S | 0.927158 | 0.978628 | 0.952893 | 1.0639 | 1.1223 | 1.0931 |
| L490W | 1.02336 | 1.032861 | 1.028111 | 1.0642 | 1.1188 | 1.0910 |
| R544K | 0.915488 | 0.986025 | 0.950756 | 1.0505 | 1.1307 | 1.0907 |
| I28T | 0.970822 | 0.875097 | 0.922959 | 1.1154 | 1.0639 | 1.0897 |
| E174I | 1.06009 | 1.055045 | 1.057568 | 1.0943 | 1.0835 | 1.0889 |
| V30I | 0.921207 | 0.919466 | 0.920277 | 1.0583 | 1.1179 | 1.0881 |
| K487H | 1.134673 | 1.198019 | 1.166346 | 1.0856 | 1.0897 | 1.0877 |
| R246R | 1.049452 | 1.074767 | 1.062109 | 1.1191 | 1.0570 | 1.0868 |
| S74I | 0.920512 | 0.934258 | 0.927385 | 1.0891 | 1.0844 | 1.0867 |
| Q216A | 1.121348 | 1.114208 | 1.117778 | 1.0858 | 1.0872 | 1.0865 |
| T462V | 0.948208 | 0.941652 | 0.94493 | 1.0881 | 1.0799 | 1.0840 |
| Q125V | 1.08209 | 1.178299 | 1.130195 | 1.0431 | 1.1234 | 1.0835 |
| K489R | 1.017588 | 1.023 | 1.020294 | 1.0582 | 1.1081 | 1.0827 |
| K487T | 1.165469 | 1.156112 | 1.160791 | 1.1150 | 1.0516 | 1.0825 |
| L490V | 1.02697 | 1.01314 | 1.020055 | 1.0680 | 1.0975 | 1.0824 |
| E117W | 1.121175 | 1.136394 | 1.128784 | 1.0808 | 1.0834 | 1.0821 |
| T462H | 0.929841 | 0.956444 | 0.943142 | 1.0670 | 1.0968 | 1.0819 |
| K50H | 1.081359 | 1.094487 | 1.087923 | 1.0622 | 1.1017 | 1.0817 |
| K487F | 1.138386 | 1.180763 | 1.159575 | 1.0891 | 1.0740 | 1.0814 |
| G491L | 1.023542 | 1.01314 | 1.018341 | 1.0644 | 1.0975 | 1.0806 |
| Q116N | 1.110872 | 1.141322 | 1.126097 | 1.0709 | 1.0881 | 1.0796 |
| Q421R | 1.164807 | 1.220205 | 1.192506 | 1.0699 | 1.0885 | 1.0793 |
| E179S | 1.049078 | 1.059975 | 1.054526 | 1.1187 | 1.0424 | 1.0790 |
| I165K | 1.033234 | 1.06244 | 1.047837 | 1.0665 | 1.0911 | 1.0789 |
| N476R | 1.023405 | 1.050116 | 1.03676 | 1.0951 | 1.0623 | 1.0783 |
| V30Y | 0.950876 | 0.875097 | 0.912986 | 1.0925 | 1.0639 | 1.0782 |
| E117F | 1.095329 | 1.153648 | 1.124489 | 1.0559 | 1.0999 | 1.0780 |
| Q116F | 1.097661 | 1.151184 | 1.124422 | 1.0581 | 1.0975 | 1.0779 |

TABLE 10-continued

Top 150 Variants for Norm Avg PI

| Variant | Slope PI | Delta PI | Avg PI | Norm Slope PI | Norm Delta PI | Norm Avg PI |
|---|---|---|---|---|---|---|
| G491W | 1.031219 | 0.998349 | 1.014784 | 1.0724 | 1.0814 | 1.0768 |
| S493G | 1.036472 | 1.03286 | 1.034666 | 1.1091 | 1.0449 | 1.0761 |
| R44F | 1.119938 | 1.092023 | 1.10598 | 1.0845 | 1.0655 | 1.0750 |
| D311S | 1.074702 | 1.096952 | 1.085827 | 1.0342 | 1.1153 | 1.0748 |
| T462K | 0.924406 | 0.949047 | 0.936727 | 1.0608 | 1.0883 | 1.0746 |
| D311K | 1.09767 | 1.074767 | 1.086218 | 1.0563 | 1.0927 | 1.0745 |
| G78Y | 0.911705 | 0.921932 | 0.916818 | 1.0787 | 1.0701 | 1.0744 |
| G397G | 1.078447 | 1.089557 | 1.084002 | 1.0797 | 1.0683 | 1.0739 |
| N454N | 1.198247 | 1.153648 | 1.175948 | 1.0517 | 1.0973 | 1.0736 |
| K50I | 1.093654 | 1.064906 | 1.07928 | 1.0743 | 1.0720 | 1.0731 |
| S493V | 1.068649 | 0.990954 | 1.029802 | 1.1435 | 1.0025 | 1.0710 |
| G491V | 1.012542 | 1.005745 | 1.009143 | 1.0530 | 1.0895 | 1.0708 |
| Q116P | 1.109346 | 1.124067 | 1.116707 | 1.0694 | 1.0717 | 1.0705 |
| E117C | 1.090465 | 1.141323 | 1.115894 | 1.0512 | 1.0881 | 1.0698 |
| D33V | 1.069913 | 1.079696 | 1.074805 | 1.0510 | 1.0868 | 1.0687 |
| G78R | 0.888881 | 0.934258 | 0.91157 | 1.0517 | 1.0844 | 1.0682 |
| A3T | 1.100956 | 1.190624 | 1.14579 | 1.0386 | 1.0971 | 1.0682 |
| K487K | 1.127248 | 1.161043 | 1.144146 | 1.0785 | 1.0561 | 1.0670 |
| E117M | 1.094063 | 1.131463 | 1.112763 | 1.0547 | 1.0787 | 1.0668 |
| L59F | 1.068131 | 1.156114 | 1.112123 | 1.0297 | 1.1022 | 1.0662 |
| G491C | 1.000956 | 1.00821 | 1.004583 | 1.0409 | 1.0921 | 1.0660 |
| I165H | 1.020528 | 1.050116 | 1.035322 | 1.0534 | 1.0785 | 1.0660 |
| L59K | 1.117002 | 1.106812 | 1.111907 | 1.0768 | 1.0552 | 1.0659 |
| Q116T | 1.106554 | 1.116672 | 1.111613 | 1.0667 | 1.0646 | 1.0657 |
| D311D | 1.097318 | 1.057511 | 1.077414 | 1.0560 | 1.0752 | 1.0656 |
| P498C | 1.044272 | 1.069837 | 1.057054 | 1.0160 | 1.1186 | 1.0654 |
| V30G | 0.926009 | 0.877561 | 0.901785 | 1.0639 | 1.0669 | 1.0654 |
| E173K | 1.024202 | 1.045185 | 1.034693 | 1.0572 | 1.0734 | 1.0653 |
| E179I | 1.027233 | 1.055045 | 1.041139 | 1.0954 | 1.0376 | 1.0653 |
| S493W | 1.008353 | 1.040255 | 1.024304 | 1.0790 | 1.0524 | 1.0653 |
| G78F | 0.881369 | 0.936722 | 0.909046 | 1.0428 | 1.0873 | 1.0653 |
| I165Y | 1.047089 | 1.020535 | 1.033812 | 1.0809 | 1.0481 | 1.0644 |
| I165F | 1.014278 | 1.052581 | 1.03343 | 1.0470 | 1.0810 | 1.0640 |
| G491T | 1.01659 | 0.988489 | 1.002539 | 1.0572 | 1.0708 | 1.0638 |
| A443A | 0.914207 | 0.877561 | 0.895884 | 1.0700 | 1.0574 | 1.0638 |
| Q125W | 1.054892 | 1.163507 | 1.109199 | 1.0169 | 1.1093 | 1.0634 |
| G491H | 1.032527 | 0.971233 | 1.00188 | 1.0737 | 1.0521 | 1.0631 |
| L490F | 1.017422 | 0.986025 | 1.001723 | 1.0580 | 1.0681 | 1.0630 |
| G492A | 1.016037 | 1.02793 | 1.021984 | 1.0872 | 1.0399 | 1.0629 |
| E174T | 1.009482 | 1.055047 | 1.032264 | 1.0420 | 1.0835 | 1.0628 |
| D311G | 1.079426 | 1.06737 | 1.073398 | 1.0388 | 1.0852 | 1.0620 |

Example 5

Increased Viability of G491S Isoprene Synthase Mutant

The following example shows that isoprene producing *Escherichia coli* expressing the G491S variant of isoprene synthase have increased viability during fermentation when compared to the cells expressing the wild type isoprene synthase. The experiments were performed at 14 L-fed batch scale.

Strain Construction

The promoter in front of the citrate synthase gene (gltA) in BL21 (Novagen) has been replaced by a constitutive low expression promoter, namely GI1.2 (U.S. Pat. No. 7,371,558). Two wild-type promoters have been described for gltA (Wilde, R, and J. Guest. 1986. J. Gen. Microbiol. 132:3239-3251) and the synthetic promoter was inserted just after the −35 region of the distal promoter. A PCR product was obtained using primers UpgltACm-F and DngltA1.xgiCm-R (see Table 11), and plasmid FRT-gb2-Cm-FRT from Gene Bridges (Heidelberg, Germany) as a template. The PCR product was purified and used in a lambda red-mediated recombination as described by the manufacturer (Gene Bridges, Heidelberg, Germany). Several colonies were selected for further characterization. The promoter region was amplified using primers gltAPromSeqF and gltApromSeqR (see Table 11) and DNA extracted by resuspending a colony in 30 uL H2O, heating at 95 C for 4 min, spinning down, and using 2 uL of that material as a template in a 50 uL reaction. After observing the sequencing results of the PCR product obtained, a colony harboring each of the three different promoters GI1.2, GI1.5 and GI1.6 (U.S. Pat. No. 7,371,558) was saved for further use (Table 11).

Strain MD09-313 was built by transducing CMP258 with a P1 lysate from strain MCM521 and selecting for colonies on Luria-Bertani plates containing 20 ug/ml kanamycin. CMP258 and MCM521 can be made as described below. P1 lysates are prepared according to the method described in Ausubel, et al., *Current Protocols in Molecular Biology*. John Wiley and Sons, Inc. The kanamycin marker was removed using the protocol recommended by the manufacturer (Gene Bridges, Heidelberg, Germany) to form strain MD09-314.

A P1 lysate was made from strains CMP141, CMP142 and CMP143 and was used to transduce strain MD09-314, to form CMP440, CMP441 and CMP442 respectively (Table 11). The chloramphenicol marker was removed using the protocol recommended by the manufacturer (Gene Bridges, Heidelberg, Germany) to form strains CMP451, CMP452 and CMP453 respectively (Table 11).

For construction of isoprene production strains, the upper MVA pathway plasmid and either pDW34 (containing wild type Isoprene Synthase) or pCHL243 (containing the G491S variant of Isoprene Synthase, see below) were transformed into strain CMP451 by electroporation. Strains were recovered in liquid LB medium for one hour at 37° C., and plated onto selective solid agar medium plates containing 50 μg/ml of carbenicillin and 50 μg/ml of spectinomycin, and incubated overnight at 37° C. Isolates resistant to these antibiotics and harboring either the plasmid containing wild type IspS (strain CMP457, see Table 12 for genotype), or G491S IspS (strain DW415, see Table 12 for genotype), were chosen for further study.

Construction of Strains MCM518-521 and 528-531: Lambda Promoters Driving Integrated mKKDyI P1 transduction enables movement of up to 100 kb of DNA between bacterial strains (Thomason et al. 2007). A 17,257 bp deletion in *E. coli* BL21(DE3) was replaced by moving a piece of the bacterial chromosome from *E. coli* K12 MG1655 to *E. coli* BL21(DE3) using P1 transduction.

Two strategies were used employing different selectable markers to identify colonies containing the recombined bacterial chromosome. First, we inserted an antibiotic marker in a gene close to the 17,257 bp sequence to be transferred, whose deletion was not likely to be detrimental to the strain. A strain containing that antibiotic marker will likely have the 17,257 bp piece of bacterial chromosome transduced at the same time as the marker. In this case, we inserted a gene encoding kanamycin resistance ("kan$^R$") into the ybgS gene, encoding a 126 amino acid protein of unknown function. Second, since it is known that a number of genes involved in utilization of galactose are close to pgl in the 17,257 bp piece to be transduced into *E. coli* BL21(DE3), colonies transduced with a P1 lysate obtained from *E. coli* K12 MG1655 (which contains the 17,257 bp sequence deleted in *E. coli* BL21 (DE3)) and isolated in M9 medium (6 g/L Na$_2$HPO$_4$, 3 g/L KH$_2$PO$_4$, 0.5 g/L NaCl, 0.5 g/L NH$_4$Cl, 0.1 mM CaCl$_2$, 2 mM MgSO$_4$) containing 0.4% (w/v) galactose will likely contain the 17,257 bp piece of bacterial chromosome.

Primers MCM120 and MCM224 were used to amplify the chloramphenicol resistance ("Cm$^R$") cassette from the Gene-Bridges FRT-gb2-Cm-FRT template using the Stratagene Herculase™ II Fusion kit (Agilent Technologies, Stratagene Products Division, La Jolla, Calif.) according to the manufacturer's protocol. Four 50 µL PCR reactions were cycled as follows: 95° C./2 minutes; 30 cycles of 95° C./20 seconds, 55° C./20 seconds, 72° C./1 minute; and 72° C./3 minutes. Reactions were then cooled to 4° C. The four reactions were pooled, loaded onto a Qiagen PCR column according to the manufacturer's protocol and eluted with 60 µL elution buffer ("EB") at 55° C.

Plasmid pRedET-carbenicillin$^R$ (GeneBridges, Heidelberg, Germany) was electroporated into *E. coli* BL21(DE3) strain MCM446 (Cm$^R$, gi1.6mKKDyI A1-3) using standard procedures. Transformants were recovered by shaking for one hour in SOC medium at 30° C. and then selected on LB+50 µg/mL carbenicillin ("LB/carb50") plates at 30° C. overnight. A carbenicillin-resistant colony was frozen as strain MCM508.

Strain MCM508 was grown from a fresh streak in 5 mL LB/carb50 at 30° C. to an OD$_{600}$ of ~0.5. At that point, 40 mM L-arabinose was added, and the culture was incubated at 37° C. for 1.5 hours. Cells were then harvested by centrifugation, electroporated with 3 µL of purified amplicons as described above, and then recovered in 500 µL SOC medium at 37° C. for 1.5-3 hours. Transformants were selected on LB+10 µg/mL kanamycin (LB/kan10) plates at 37° C.

Recombination of the amplicon at the target locus was confirmed by PCR with primers GB-DW and MCM208. The resulting amplicons were sequenced to identify four clones having the sequences listed below. Four carbenicillin-sensitive clones were frozen as strains MCM518-MCM521.

Strains MCM518-MCM521 were re-streaked onto LB/kan10 and grown overnight at 37° C. Colonies of strains MCM518-MCM521 were picked, cultured in LB/kan10 at 37° C. and electrotransformed with plasmid pCP20, which encodes the yeast Flp recombinase, chloramphenicol and ampicillin resistance genes and confers temperature sensitive replication on host cells (Cherepanov, P. P. et al., *Gene* 158 (1):9-14 (1995)). Cells were recovered in 500 µL SOC medium by shaking at 30° C. for 1 hour. Transformants were selected on LB/carb50 plates at 30° C. overnight. The following morning a colony from each plate was grown at 30° C. in LB/carb50 medium until visibly turbid. The culture was then shifted to 37° C. for at least 3 hours. Cells were streaked from that culture onto LB plates and grown overnight at 37° C.

The following day colonies were patched to LB, LB/carb50 and LB/kan10. Clones that were sensitive to both carbenicillin and kanamycin (i.e., which could not grow on carb50 and kan10) were cultured in liquid LB and frozen as strains MCM528-MCM531. *E. coli* strains

| Strain | Description | Parent |
|---|---|---|
| MCM508 | BL21 gi1.6-mKKDyI + predet.-carb | MCM446 |
| MCM518 | BL21 neo-PL.6-mKKDyI, clone 10 | MCM508 |
| MCM519 | BL21 neo-PL.0-mKKDyI, clone 11 | MCM508 |
| MCM520 | BL21 neo-PL.0-mKKDyI (bad RBS in front of mMVK), clone 13 | MCM508 |
| MCM521 | BL21 neo-PL.2-mKKDyI, clone 15 | MCM508 |
| MCM528 | BL21 PL.6-mKKDyI, neo$^R$ looped out | MCM518 |
| MCM529 | BL21 PL.0-mKKDyI, neo$^R$ looped out | MCM519 |
| MCM530 | BL21 PL.0-mKKDyI (bad RBS in front of mMVK), neo$^R$ looped out | MCM520 |
| MCM531 | BL21 PL.2-mKKDyI, neo$^R$ looped out | MCM521 |

Primer Sequences

| Primer name | Sequence (5' → 3') |
|---|---|
| MCM120 | AAAGTAGCCGAAGATGACGGTTTGTCACA TGGAGTTGGCAGGATGTTTGATTAAAAGC AATTAACCCTCACTAAAGGGCGG (SEQ ID NO: 11) |
| MCM224 | TAAATCTTACCCGGCGCAGAACAGGATAC CATGTTTTTTTACCTCCTTTGCACCTTCA TGGTGGTCAGTGCGTCCTGCTGATGTGCT CAGTATCACCGCCAGTGGTATTTANGTCA ACACCGCCAGAGATAATTTATCACCGCAG ATGGTTATCTGTATGTTTTTTATATGAAT TTAATACGACTCACTATAGGGCTCG (SEQ ID NO: 12) |
| GB-DW | AAAGACCGACCAAGCGACGTCTGA (SEQ ID NO: 13) |
| MCM208 | GCTCTGAATAGTGATAGAGTCA (SEQ ID NO: 14) |

The assemblies integrated into the chromosomes of strains MCM518-MCM521 include new P$_L$ promoters derived from bacteriophage lambda (λ) and the very beginning of the mMVK ORF, with sequences from the Gene Bridges FRT-gb2-Cm-FRT cassette integrated upstream of the promoter/mMVK assembly, as well as the remainder of the mMVK ORF followed by the rest of the lower MVA pathway integron from strain MCM508.

```
Promoter/mMVK sequence integrated into MCM518 (SEQ ID NO: 15)
aaagaccgaccaagcgacgtctgagagctccctggcgaattcggtaccaataaaagagctttattttcatgatctgtgtgttggttttttgtgtgc ggcgcggaagttcctattctctagaaagtataggaacttcctcgagccctatagtgagtcgtattaaattcatataaaaaacatacagataacca tctgcggtgataaattatctctggcggtgttgacataaataccactggcggtgatactgagcacatcagcaggacgcactgaccaccatgaa ggtgcaaaggaggtaaaaaaacatggtatcctgttctgcgccgggtaagatttacctgttcggtgaacacgccgtagtttatggcgaaactgc aattgcgtgtgcggtggaactgcgtacccgtgttcgcgcggaactcaatgactctatcactattcagagc Promoter/mMVK sequence integrated into MCM519 (SEQ ID NO: 16)
aaagaccgaccaagcgacgtctgagagctccctggcgaattcggtaccaataaaagagctttattttcatgatctgtgtgttggttttttgtgtgc ggcgcggaagttcctattctctagaaagtataggaacttcctcgagccctatagtgagtcgtattaaattcatataaaaaacatacagataacca tctgcggtgataaattatctctggcggtgttgacctaaataccactggcggtgatactgagcacatcagcaggacgcactgaccaccatgaa ggtgcaaaggaggtaaaaaaacatggtatcctgttctgcgccgggtaagatttacctgttcggtgaacacgccgtagtttatggcgaaactgc aattgcgtgtgcggtggaactgcgtacccgtgttcgcgcggaactcaatgactctatcactattcagagc
```

-continued

Figure 12:
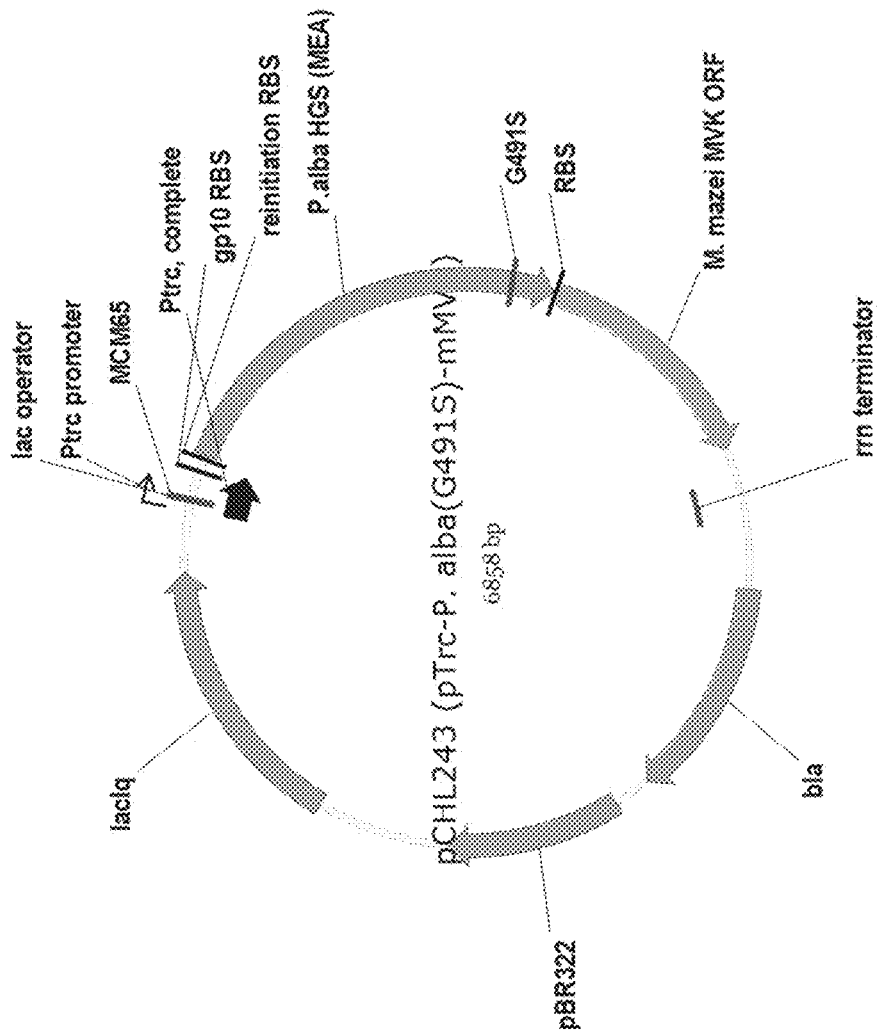
FIG. 12 shows a map of pCHL243, containing *P. alba* Isoprene Synthase with the G491S mutation.

Promoter/mMVK sequence integrated into MCM520 (SEQ ID NO: 17)
aaagaccgaccaagcgacgtctgagagctccctggcgaattcggtaccaataaaagagctttattttcatgatctgtgtgttggttttttgtgtgc ggcgcggaagttcctattctctagaaagtataggaacttcctcgagccctatagtgagtcgtattaaattcatataaaaaacatacagataacca tctgcggtgataaattatctctggcggtgttgacctaaataccactggcggtgatactgagcacatcagcaggacgcactgaccaccatgaa ggtgcaaaggtaaaaaaacatggtatcctgttctgcgccgggtaagatttacctgttcggtgaacacgccgtagtttatggcgaaactgcaatt gcgtgtgcggtggaactgcgtacccgtgttcgcgcggaactcaatgactctatcactattcagagc Promoter/mMVK sequence integrated into MCM521 (SEQ ID NO: 18)
aaagaccgaccaagcgacgtctgagagctccctggcgaattcggtaccaataaaagagctttattttcatgatctgtgtgttggttttttgtgtgc ggcgcggaagttcctattctctagaaagtataggaacttcctcgagccctatagtgagtcgtattaaattcatataaaaaacatacagataacca tctgcggtgataaattatctctggcggtgttgacgtaaataccactggcggtgatactgagcacatcagcaggacgcactgaccaccatgaa ggtgcaaaggaggtaaaaaaacatggtatcctgttctgcgccgggtaagatttacctgttcggtgaacacgccgtagtttatggcgaaactgc aattgcgtgtgcggtggaactgcgtacccgtgttcgcgcggaactcaatgactctatcactattcagagc Construction of pTrc-MEA-Alba (G491S)-mMVK:

The G491S mutation was introduced into pDW34 (pTrc-MEA-Alba-mMVK) by QuikChange (Stratagene) mutagenesis (see below for PCR cycling parameters). The PCR product was then treated with 1 μl of DpnI (Roche) and incubated at 37° C. to digest the parental DNA template. 1 μl of this solution was then transformed into MCM531 by electroporation using standard molecular biology techniques. Transformed cells were recovered in liquid LB medium for one hour, and then plated onto LB solid agar plates containing 50 μg/ml of carbenicillin and 5 mM mevalonic acid. Plasmids were purified from isolated colonies, and sequenced completely (Quintara Biosciences) to verify the presence of the G491S mutation (in pCHL243, see FIG. 12).

PCR Mixture for QuikChange Reaction

| | |
|---|---|
| Template DNA (pTrc-MEA-Alba-mMVK) | ~100 ng |
| G507S QC 2 For | 50 uM |
| G507S QC 2 Rev | 50 uM |
| dNTPs (Roche) | 1 ul |
| 10X pfu II fusion buffer | 5 ul |
| Pfu Ultra II | 1 ul |
| Water | add enough to reach 50 ul total |

PCR Cycling Parameters for QuikChange Reaction:
95° C.—1 minute
(95° C. 50 seconds, 60° C. 50 seconds, 68° C. 3 minutes) 18 rounds
68° C.-10 minutes

TABLE 11

Primers

| | |
|---|---|
| UpgltACm-F | TATTTAATTTTTAATCATCTAATTTGACAATC ATTCAACAAAGTTGTTACAATTAACCCTCACT AAAGGGCGG (SEQ ID NO: 19) |
| DngltA1.xgiCm-R | TCAACAGCTGTATCCCCGTTGAGGGTGAGTTT TGCTTTTGTATCAGCCATATATTCCACCAGCT ATTTGTTAGTGAATAAAAGTGGTTGAATTATT TGCTCAGGATGTGGCATHGTCAAGGGCTAATA CGACTCACTATAGGGCTCG (SEQ ID NO: 20) |
| gltAPromSeqF | GGCAGTATAGGCTGTTCACAAAATC (SEQ ID NO: 21) |
| gltApromSeqR | CTTGACCCAGCGTGCCTTTCAGC (SEQ ID NO: 22) |
| G507S QC 2 For | GAAAAACTGAGTGGTAGCCTGTTCGCGAAAC (SEQ ID NO: 23) |
| G507S QC 2 Rev | AGGCTACCACTCAGTTTTTCCTTGTTCATCT (SEQ ID NO: 24) |

TABLE 12

E. coli strains

| Strain | Description | Parent |
|---|---|---|
| CMP141 | BL21 Cm-GI1.2 gltA | BL21 |
| CMP142 | BL21 Cm-GI1.5 gltA | BL21 |
| CMP143 | BL21 Cm-GI1.6 gltA | BL21 |
| CMP258 | BL21 pgl+ | BL21 |
| MD09-313 | BL21 pgl+ neo-PL.2-mKKDyI | CMP258 |
| MCM521 | BL21 neo-PL.2-mKKDyI | As described herein |
| MD09-314 | BL21 pgl + PL.2-mKKDyI | MD09-313 |
| CMP440 | BL21 pgl + PL.2 mKKDyI Cm-GI1.2 gltA | MD09-314 |

TABLE 12-continued

E. coli strains

| | | |
|---|---|---|
| CMP441 | BL21 pgl + PL.2 mKKDyI Cm-GI1.5 gltA | MD09-314 |
| CMP442 | BL21 pgl + PL.2 mKKDyI Cm-GI1.6 gltA | MD09-314 |
| CMP451 | BL21 pgl + PL.2 mKKDyI GI1.2 gltA | CMP440 |
| CMP452 | BL21 pgl + PL.2 mKKDyI GI1.5 gltA | CMP441 |
| CMP453 | BL21 pgl + PL.2 mKKDyI GI1.6 gltA | CMP442 |
| CMP457 | BL21 pgl + PL.2 mKKDyI GI1.2 gltA, pDW34 (pTrc-P. alba-mMVK), MCM82 (pCL-Upper MVA pathway) | CMP451 |
| DW415 | BL21 pgl + PL.2 mKKDyI GI1.2 gltA, pCHL243 (pTrc-P. alba(G491S)-mMVK), MCM82 (pCL-Upper MVA pathway) | CMP451 |

Sequence of pCHL243 (SEQ ID NO: 25)

gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctcttttaacaatttatcagacaatctgtgtgggcactcgaccggaattatcgattaactttattattaaaaattaaagaggtatat
attaatgtatcgattaaataaggaggaataaaccatggaagctcgtcgttctgcgaactacgaacctaacagctgggactatgattacctgctg
tcctccgacacggacgagtccatcgaagtatacaaagacaaagcgaaaaagctggaagccgaagttcgtcgcgagattaataacgaaaaa
gcagaatttctgaccctgctggaactgattgacaacgtccagcgcctgggcctgggttaccgtttcgagtctgatatccgtggtgcgctggat
cgcttcgtttcctccggcggcttcgatgcggtaaccaagacttccctgcacggtacggcactgtctttccgtctgctgcgtcaacacggttttg
aggtttctcaggaagcgttcagcggcttcaaagaccaaaacggcaacttcctggagaacctgaaggaagatatcaaagctatcctgagcct
gtacgaggccagcttcctggctctggaaggcgaaaacatcctggacgaggcgaaggttttcgcaatctctcatctgaaagaactgtctgaag
aaaagatcggtaaagagctggcagaacaggtgaaccatgcactggaactgccactgcatcgccgtactcagcgtctggaagcagtatggt
ctatcgaggcctaccgtaaaaaggaggacgcgaatcaggttctgctggagctggcaattctggattacaacatgatcccagtctgtataccag
cgtgatctgcgtgaaacgtcccgttggtggcgtcgtgtgggtctggcgaccaaactgcactttgctcgtgaccgcctgattgagagcttctac
tgggcgtgggtgtagcattcgaaccgcaatactccgactgccgtaactccgtcgcaaaaatgttttctttcgtaaccattatcgacgatatcta
cgatgtatacggcaccctggacgaactggagctgtttactgatgcagttgagcgttgggacgtaaacgccatcaacgacctgccggattaca
tgaaactgtgctttctggctctgtataacactattaacgaaatcgcctacgacaacctgaaagataaaggtgagaacatcctgccgtatctgac
caaagcctgggctgacctgtgcaacgcttttctgcaagaagccaagtggctgtacaacaaatctactccgaccttttgacgactacttcggca
acgcatggaaatcctcttctggcccgctgcaactggtgttcgcttacttcgctgcgtgcagaacattaaaaaggaagagatcgaaaacctgc
aaaaataccatgacaccatctctcgtccttcccatatcttccgtctgtgcaatgacctggctagcgcgtctgcggaaattgcgcgtggtgaaac
cgcaaatagcgtttcttgttacatgcgcactaaaggtatctccgaagaactggctaccgaaagcgtgatgaatctgatcgatgaaacctggaa
aaagatgaacaaggaaaaactgagtggtagcctgttcgcgaaaccgttcgtggaaaccgcgatcaacctggcacgtcaatctcactgcact
tatcataacggcgacgcgcatacctctccggatgagctgacccgcaaacgcgttctgtctgtaatcactgaaccgattctgccgtttgaacgc
taactgcataaaggaggtaaaaaaacatggtatcctgttctgcgccgggtaagatttacctgttcggtgaacacgccgtagtttatggcgaaa
ctgcaattcgtgtgcggtggaactgcgtacccgtgttcgcgcggaactcaatgactctatcactattcagagccagatcggccgcaccggt
ctggatttcgaaaagcacccttatgtgtctgcggtaattgagaaaatgcgcaaatctattcctattaacggtgttttcttgaccgtcgattccgac
atcccggtgggctccggtctgggtagcagcgcagccgttactatcgcgtctattggtgcgctgaacgagctgttcggctttggcctcagcct
gcaagaaatcgctaaactgggccacgaaatcgaaattaaagtacagggtgccgcgtccccaaccgatacgtatgtttctaccttcggcggc TABLE 12-continued E. coli strains gtggttaccatcccggaacgtcgcaaactgaaaactccggactgcggcattgtgattggcgataccggcgttttctcctccaccaaagagtta gtagctaacgtacgtcagctgcgcgaaagctacccggatttgatcgaaccgctgatgacctctattggcaaaatctctcgtatcggcgaaca actggttctgtctggcgactacgcatccatcggccgcctgatgaacgtcaaccagggtctcctggacgccctgggcgttaacatcttagaact gagccagctgatctattccgctcgtgcggcaggtgcgtttggcgctaaaatcacgggcgctggcggcggtggctgtatggttgcgctgacc gctccggaaaaatgcaaccaagtggcagaagcggtagcaggcgctggcggtaaagtgactatcactaaaccgaccgagcaaggtctga aagtagattaaagtctagttaaagtttaaacggtctccagcttggctgttttggcggatgagagaagattttcagcctgatacagattaaatcag aacgcagaagcggtctgataaaacagaatttgcctggcggcagtagcgcggtggtcccacctgaccccatgccgaactcagaagtgaaa cgccgtagcgccgatggtagtgtggggtctccccatgcgagagtagggaactgccaggcatcaaataaaacgaaaggctcagtcgaaag actgggcctttcgttttatctgttgtttgtcggtgaacgctctcctgagtaggacaaatccgccgggagcggatttgaacgttgcgaagcaacg gcccggagggtggcgggcaggacgcccgccataaactgccaggcatcaaattaagcagaaggccatcctgacggatggccttttttgcgtt tctacaaactcttttgtttattttttctaaatacattcaaatatgtatccgctcatgagacaataaccctgataaatgcttcaataatattgaaaaagga agagtatgagtattcaacatttccgtgtcgcccttattccctttttttgcggcattttgccttcctgtttttgctcacccagaaacgctggtgaaagta aaagatgctgaagatcagttgggtgcacgagtgggttacatcgaactggatctcaacagcggtaagatccttgagagttttcgccccgaaga acgttttccaatgatgagcacttttaaagttctgctatgtggcgcggtattatcccgtgttgacgccgggcaagagcaactcggtcgccgcata cactattctcagaatgacttggttgagtactcaccagtcacagaaaagcatcttacggatggcatgacagtaagagaattatgcagtgctgcc ataaccatgagtgataacactgcggccaacttacttctgacaacgatcggaggaccgaaggagctaaccgcttttttgcacaacatggggga tcatgtaactcgccttgatcgttgggaaccggagctgaatgaagccataccaaacgacgagcgtgacaccacgatgcctgtagcaatggca acaacgttgcgcaaactattaactggcgaactacttactctagcttcccggcaacaattaatagactggatggaggcggataaagttgcagg accacttctgcgctcggcccttccggctggctggtttattgctgataaatctggagccggtgagcgtgggtctcgcggtatcattgcagcact ggggccagatggtaagccctcccgtatcgtagttatctacacgacggggagtcaggcaactatggatgaacgaaatagacagatcgctga gataggtgcctcactgattaagcattggtaactgtcagaccaagtttactcatatatactttagattgatttaaaacttcattttaatttaaaaggat ctaggtgaagatcctttttgataatctcatgaccaaaatcccttaacgtgagttttcgttccactgagcgtcagaccccgtagaaaagatcaaag gatcttcttgagatcctttttttctgcgcgtaatctgctgcttgcaaacaaaaaaaccaccgctaccagcggtggtttgtttgccggatcaagagc taccaactctttttccgaaggtaactggcttcagcagagcgcagataccaaatactgtccttctagtgtagccgtagttaggccaccacttcaa gaactctgtagcaccgcctacatacctcgctctgctaatcctgttaccagtggctgctgccagtggcgataagtcgtgtcttaccgggttggac tcaagacgatagttaccggataaggcgcagcggtcgggctgaacggggggttcgtgcacacagcccagcttggagcgaacgacctaca ccgaactgagatacctacagcgtgagctatgagaaagcgccacgcttcccgaagggagaaaggcggacaggtatccggtaagcggcag ggtcggaacaggagagcgcacgagggagcttccaggggaaacgcctggtatctttatagtcctgtcgggtttcgccacctctgacttgag cgtcgatttttgtgatgctcgtcaggggggcggagcctatggaaaaacgccagcaacgcggcctttttacggttcctggccttttgctggcctt ttgctcacatgttctttcctgcgttatcccctgattctgtggataaccgtattaccgcctttgagtgagctgataccgctcgccgcagccgaacga ccgagcgcagcgagtcagtgagcgaggaagcggaagagcgcctgatgcggtattttctccttacgcatctgtgcggtatttcacaccgcat atggtgcactctcagtacaatctgctctgatgccgcatagttaagccagtatacactccgctatcgctacgtgactgggtcatggctgcgcccc gacacccgccaacacccgctgacgcgccctgacgggcttgtctgctcccggcatccgcttacagacaagctgtgaccgtctccgggagct gcatgtgtcagaggttttcaccgtcatcaccgaaacgcgcgaggcagcagatcaattcgcgcgcgaaggcgaagcggcatgcatttacgtt gacaccatcgaatggtgcaaaacctttcgcggtatggcatgatagcgcccggaagagagtcaattcagggtggtgaatgtgaaaccagtaa cgttatacgatgtcgcagagtatgccggtgtctcttatcagaccgtttcccgcgtggtgaaccaggccagccacgtttctgcgaaaacgcgg gaaaaagtggaagcggcgatggcggagctgaattacattcccaaccgcgtggcacaacaactggcgggcaaacagtcgttgctgattgg cgttgccacctccagtctggccctgcacgcgccgtcgcaaattgtcgcggcgattaaatctcgcgccgatcaactgggtgccagcgtggtg gtgtcgatggtagaacgaagcggcgtcgaagcctgtaaagcggcggtgcacaatcttctcgcgcaacgcgtcagtgggctgatcattaact TABLE 12-continued E. coli strains

```
atccgctggatgaccaggatgccattgctgtggaagctgcctgcactaatgttccggcgttatttcttgatgtctctgaccagacacccatcaa cagtattattttctcccatgaagacggtacgcgactgggcgtggagcatctggtcgcattgggtcaccagcaaatcgcgctgttagcgggcc cattaagttctgtctcggcgcgtctgcgtctggctggctggcataaatatctcactcgcaatcaaattcagccgatagcggaacgggaaggc gactggagtgccatgtccggttttcaacaaaccatgcaaatgctgaatgagggcatcgttcccactgcgatgctggttgccaacgatcagat ggcgctgggcgcaatgcgcgccattaccgagtccgggctgcgcgttggtgcggatatctcggtagtgggatacgacgataccgaagaca gctcatgttatatcccgccgtcaaccaccatcaaacaggattttcgcctgctggggcaaaccagcgtggaccgcttgctgcaactctctcagg gccaggcggtgaagggcaatcagctgttgcccgtctcactggtgaaaagaaaaaccaccctggcgcccaatacgcaaaccgcctctccc cgcgcgttggccgattcattaatgcagctggcacgacaggtttcccgactggaaagcgggcagtgagcgcaacgcaattaatgtgagttag cgcgaattgatctg
```

Fermentation Conditions for Fermentation Number 20100307 and 20100436
Fermentations:
Fermentation 20100307: CMP437
Fermentation 20100437: DW415
Medium Recipe (Per Liter Fermentation Medium):
K2HPO4 7.5 g, MgSO4*7H2O 2 g, citric acid monohydrate 2 g, ferric ammonium citrate 0.3 g, yeast extract 0.5 g, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.
1000× Modified Trace Metal Solution (Per Liter):
Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.
Vitamin Solution (Per Liter):
Thiamine hydrochloride 1.0 g, D-(+)-biotin 1.0 g, nicotinic acid 1.0 g, D-pantothenic acid 4.8 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.
Feed Solution (Per Kilogram):
Glucose 0.57 kg, Di H2O 0.38 kg, K2HPO4 7.5 g, and 100% Foamblast 10 g. All components were mixed together and autoclaved. Macro Salt Solution 3.4 mL, 1000× Modified Trace Metal Solution 0.8 ml, and Vitamin Solution 6.7 mL were added after the solution had cooled to 25° C.
Macro Salt Solution (Per Liter):
MgS04*7H2O 296 g, citric acid monohydrate 296 g, ferric ammonium citrate 49.6 g. All components were dissolved in water, q.s. to volume and filter sterilized with 0.22 micron filter.
Fermentation of the two strains was performed in a 15-L bioreactor at pH 7.0 and at a temperature of 34° C. Frozen vials of the E. coli strains were thawed and inoculated into tryptone-yeast extract medium (LB) for the bioreactors. After the inoculum grew to an optical density of 1.0, measured at 550 nm ($OD_{550}$), 500 mL was used to inoculate 15-L bioreactors and bring the initial tank volume to 5 L. The feed solution was fed at an exponential rate (up to 4.5 g/min) for 10 h and then pulse feeding began. Pulses lasted 30 min and were triggered by a pH rise above 7.04. The pulse feedrate was adaptable and equaled the TCER/300. The max rate for a given pulse did not exceed 13.5 g/min. The total amount of glucose delivered to the bioreactor during the fermentations was between 7.4 and 7.5 kg. Induction was achieved by adding a IPTG to the tank to bring the concentration to 200 uM when the cells were at an $OD_{550}$ of 6.

The isoprene level in the off-gas from the bioreactor was determined using an iSCAN (Hamilton Sundstrand) mass spectrometer.
Experimental Procedure for Membrane Potential and Viability Determination Membrane potential was used to assess viability of the bacteria during fermentation. Broth from the fermentor was collected and immediately diluted 150-fold into PBS buffer. The cells were then further diluted 150-fold into PBS buffer containing 1 µM bis-(1,3-dibutylbarbituric acid)trimethine oxonol (DiBAC4(3), (Invitrogen, Cat. No. B-438). Samples were allowed to stain for 10 minutes before quantification of green fluorescence at the single cell level using flow cytometry (FACSCalibur, Becton Dickinson). An excitation wave length of 488 nm and an emission wave length of 530 nm were used.

Figure 13:
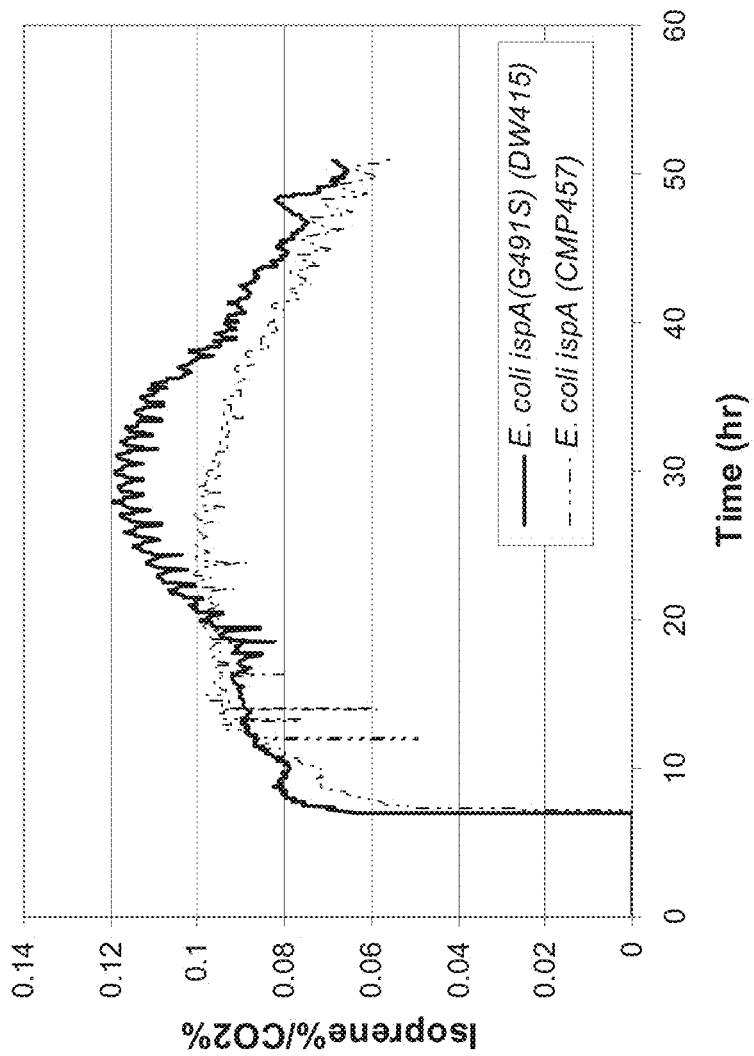
FIG. 13 shows the ratio between isoprene concentration (%) and CO2(%) in the offgas, showing that strain DW415 expressing the G491S mutant of isoprene synthase has increased levels of isoprene production when compared to respiration rate throughout significant parts of the fermentation.
Figure 14:
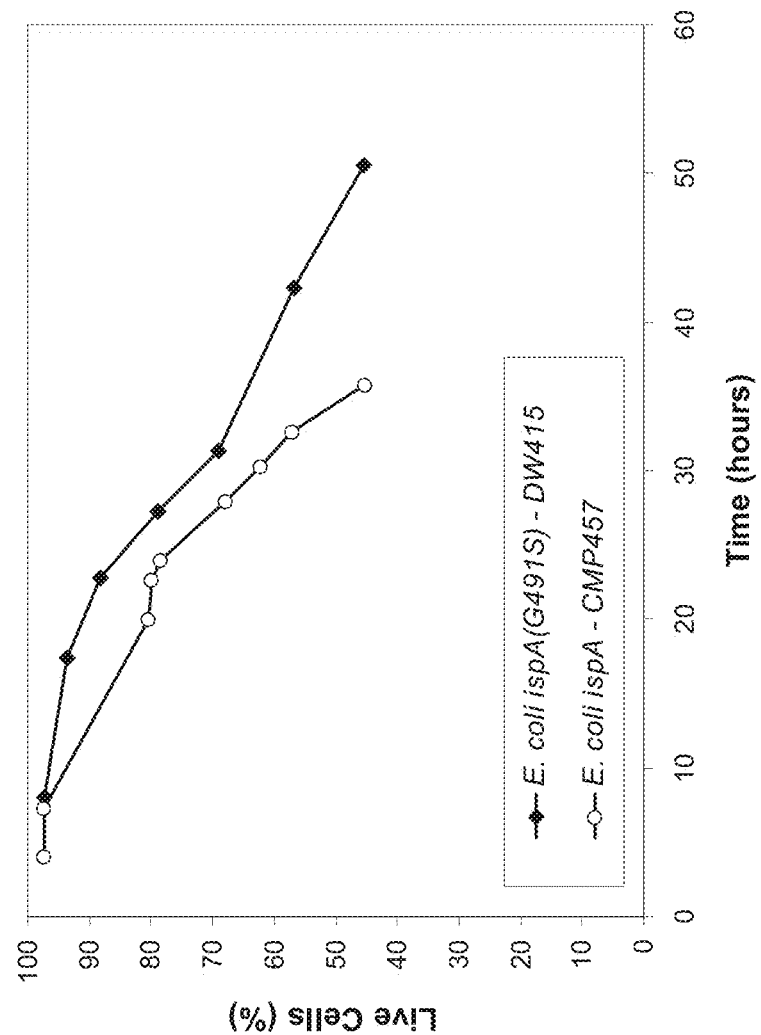
FIG. 14 shows expression of the isoprene synthase variant G491S results in increased viability during fermentation. Staining with DiBAC4(3) was used to determine the fraction of live and dead cells in the fermentation broth based on the presence or absence of a membrane potential.
Figure 15:
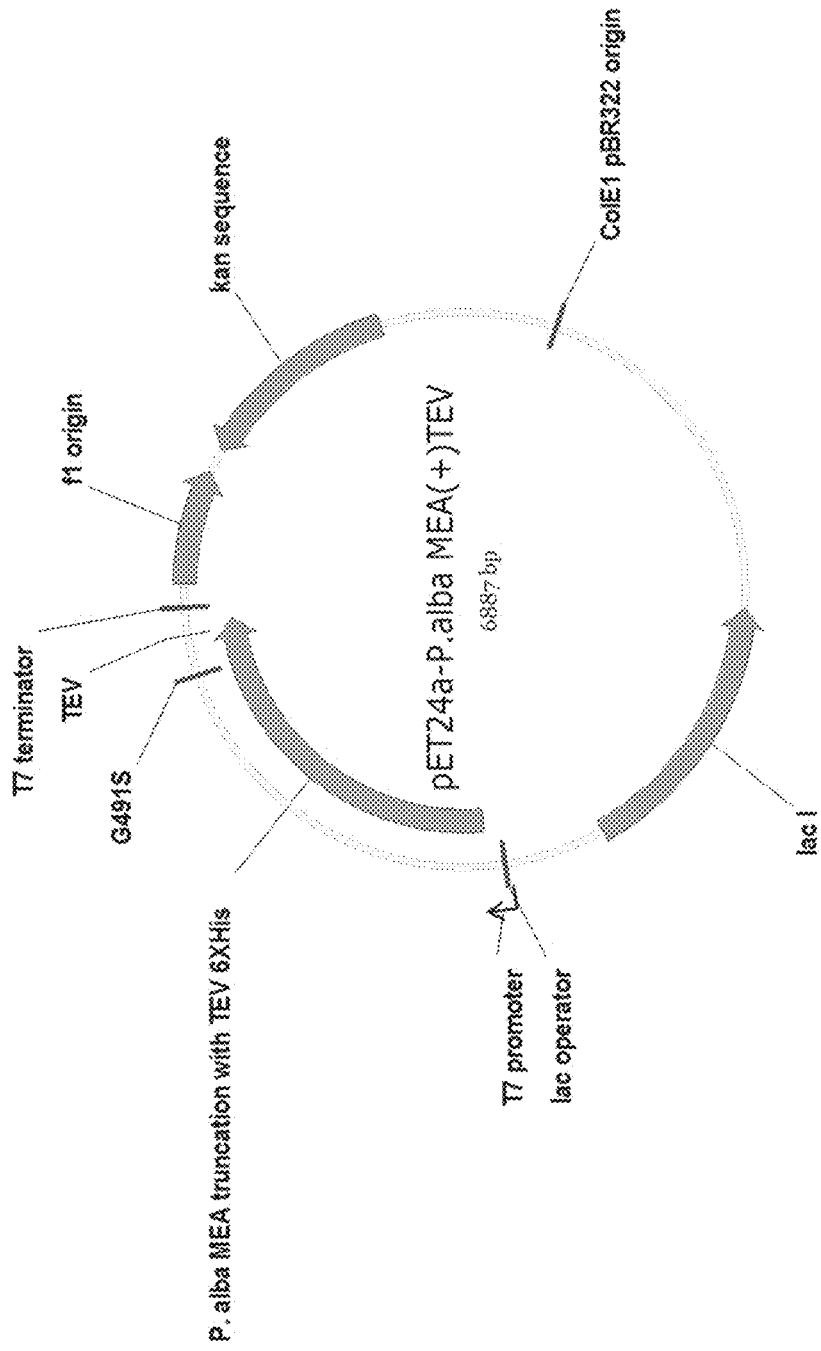
FIG. 15 is a map of plasmid MD09-163 with G491S.

Initially, an exponentially growing culture and a heat killed culture of E. coli BL21 was stained with DiBAC4(3) to determine green fluorescence levels from healthy and dead cells respectively. This information was used to create gates for analyzing the flow cytometry data to determine the fraction of cells with intact membrane potential and the fraction of cells without membrane potential. The data was also gated on appropriate cell size (forward scatter versus side scatter measured at 488 nm) to identify only intact bacteria. The level of green fluorescence from the cells passing these criteria was then used to determine the fraction of cells with a healthy membrane potential and the fraction of cells with no membrane potential in the fermentation samples. Cells with intact membrane potential were assumed to be alive and metabolically active, while cells with no membrane potential were assumed to be dead and metabolically inactive.
Results:

Two strains (CMP437 and DW415) producing isoprene via the mevalonic acid pathway were analyzed for their viability during fed batch conditions. The two strains were isogenic except for the presence of a G491S mutation in the isoprene synthase encoded by the DW415 strain. The two strains showed similar growth during the fermentation and produced significant amounts of isoprene. The ratio between the concentration of isoprene (%) and $CO_2$(%) in the offgas shows that strain DM415 expressing the G491S mutant of isoprene synthase has increased levels of isoprene production rate when compared to respiration rate throughout significant parts of the as shown on FIG. 13. The membrane potential of individual bacteria during the fermentation was furthermore determined by staining the bacteria with the DiBAC4(3) dye and analyzing the resulting levels of green fluorescence using flow cytometry. The DiBAC4(3) dye penetrates into bacteria that have lost their membrane potential. Bacteria without a membrane potential are generally assumed to be dead. Strain DW415, expressing the G491S allele of the isoprene synthase, had significantly increased viability throughout most of the fermentation as shown in FIG. 14.

Example 6

Construction of a 6×His-Tagged G491S Variant of *P. alba* Isoprene Synthase for Crystallization This Example described the construction of G491S variant *P. alba* isoprene synthase for crystallization.

The *P. alba* isoprene synthase (IspS) enzyme harboring the G491S mutation (previously referred to as G507S in non-truncated IspS sequences) was identified by enrichment for variants that better tolerate exposure to high MVA pathway flux within *E. coli* host cells. To more precisely determine the beneficial property of G491S, the variant enzyme was purified and its crystal structure was solved to a resolution of 2.6 Å and then compared to the structure of the parental, unmodified wild type enzyme.

Methods

The G491S variant was constructed in the vector backbone MD09-163 (encoding the WT enzyme, see FIG. 1), which harbors a TEV protease site and 6×His tag at the C-terminal end of IspS. The G491S variant was generated using the QuikChange Mutagenesis Kit (Stratagene) according to the manufacturer's recommended protocol (see below for PCR reaction and cycling parameters). The QuikChange reaction was transformed into chemically competent *E. coli* TOP10 cells (Invitrogen) according to the manufacturer's recommended protocol and plated onto LB Kan50 selective media plates. Colonies resistant to kanamycin were directly screened by PCR and verified by sequencing using the primers QB1493 and T7 Reverse (Quintara Biosciences). TOP10 cells were grown in selective medium, and plasmids were purified (Qiagen) and then transformed into chemically competent BL21 DE3 pLysS (Invitrogen) according to the manufacturer's recommended protocol, prior to expression of the IspS variants.

QuikChange Mutagenesis
35 µl $H_2O$
5 µl 10×Pfu Ultra II rxn Buffer
6 µl 2.5 mM dNTPs (Roche)
1 µl 20 µM G507S QC 2 For
1 µl 20 µM G507S QC 2 Rev
1 µl Pfu Ultra II HS Polymerase (Stratagene)
1 µl DNA template (MD09-163)
QuikChange Mutagenesis—Cycling Parameters
1) 95° C.—4 min
2) 95° C.—20 sec
3) 52° C.—20 sec
4) 68° C.—7 min
5) goto Step 2—5×
6) 95° C.—20 sec
7) 55° C.—20 sec
8) 68° C.—7 min
9) goto Step 2—20×
10) 68° C.—10 min
11) 4° C.—forever

TABLE 13

QuikChange and Sequencing Primers

| | |
|---|---|
| G507S QC 2 For | gaaaaactgagtggtagcctgttcgcgaaac (SEQ ID NO: 23) |
| G507S QC 2 Rev | aggctaccactcagtttttccttgttcatct (SEQ ID NO: 24) |
| T7 Forward | taatacgactcactataggg (SEQ ID NO: 4) |
| T7 Reverse | gctagttattgctcagcgg (SEQ ID NO: 5) |
| EL-1000 | gcactgtctttccgtctgctgc (SEQ ID NO: 6) |
| A-rev | ctcgtacaggctcaggatag (SEQ ID NO: 8) |
| A-rev-2 | ttacgtcccaacgctcaact (SEQ ID NO: 9) |
| QB1493 | cttcggcaacgcatggaaat (SEQ ID NO: 7) |

TABLE 14

Plasmids:

| | |
|---|---|
| MD09-163 | pET24a-P.alba TRC (MEA WT) C-Term (+) TEV, His tag |
| pDW100 | pET24a-P.alba TRC (MEA G491S) C-Term (+) TEV, His tag |

TABLE 15

Strains:

| | |
|---|---|
| MD09-167 | BL21(DE3) pLysS, MD09-163 (WT) |
| DW398 | BL21(DE3) pLysS, pDW100 (G491S) |

1) Amino Acid Sequence of *P. alba* MEA(+)TEV - MD09-163 (WT) (SEQ ID NO: 26)

MEARRSANYEPNSWDYDYLLSSDTDESIEVYKDKAKKLEAEVRREINNEKAEFLTLLEL

IDNVQRLGLGYRFESDIRGALDRFVSSGGFDAVTKTSLHGTALSFRLLRQHGFEVSQEAF

SGFKDQNGNFLENLKEDIKAILSLYEASFLALEGENILDEAKVFAISHLKELSEEKIGKEL

TABLE 15-continued

Strains:

AEQVNHALELPLHRRTQRLEAVWSIEAYRKKEDANQVLLELAILDYNMIQSVYQRDLR

ETSRWWRRVGLATKLHFARDRLIESFYWAVGVAFEPQYSDCRNSVAKMFSFVTIIDDIY

DVYGTLDELELFTDAVERWDVNAINDLPDYMKLCFLALYNTINEIAYDNLKDKGENILP

YLTKAWADLCNAFLQEAKWLYNKSTPTFDDYFGNAWKSSSGPLQLVFAYFAVVQNIK

KEEIENLQKYHDTISRPSHIFRLCNDLASASAEIARGETANSVSCYMRTKGISEELATESV

MNLIDETWKKMNKEKLGGSLFAKPFVETAINLARQSHCTYHNGDAHTSPDELTRKRVL

SVITEPILPFERENLYFQGLEHHHHHH

DNA sequence of MD09-163 (SEQ ID NO: 27)

tggcgaatgggacgcgccctgtagcggcgcattaagcgcggcgggtgtggtggttacgcgcagcgtgaccgctacacttgccagcgccc tagcgcccgctcctttcgctttcttcccttcctttctcgccacgttcgccggctttcccgtcaagctctaaatcggggctcccttttagggttcc gatttagtgctttacggcacctcgaccccaaaaaacttgattagggtgatggttcacgtagtgggccatcgccctgatagacgtttttcgccc tttgacgttggagtccacgttctttaatagtggactcttgttccaaactggaacaacactcaaccctatctcggtctattcttttgatttataagggat tttgccgatttcggcctattggttaaaaaatgagctgatttaacaaaaatttaacgcgaattttaacaaaatattaacgtttacaatttcaggtggca cttttcggggaaatgtgcgcggaaccccctatttgtttattttttctaaatacattcaaatatgtatccgctcatgaattaattcttagaaaaactcatcg agcatcaaatgaaactgcaatttattcatatcaggattatcaataccatattttgaaaaagccgtttctgtaatgaaggagaaaactcaccgag gcagttccataggatggcaagatcctggtatcggtctgcgattccgactcgtccaacatcaatacaacctattaatttcccctcgtcaaaataa ggttatcaagtgagaaatcaccatgagtgacgactgaatccggtgagaatggcaaaagtttatgcatttcttttccagacttgttcaacaggcca gccattacgctcgtcatcaaaatcactcgcatcaaccaaaccgttattcattcgtgattgcgcctgagcgagacgaaatacgcgatcgctgtta aaaggacaattacaaacaggaatcgaatgcaaccggcgcaggaacactgccagcgcatcaacaatattttcacctgaatcaggatattcttc taatacctggaatgctgttttcccggggatcgcagtggtgagtaaccatgcatcatcaggagtacggataaaatgcttgatggtcggaagag gcataaattccgtcagccagtttagtctgaccatctcatctgtaacatcattggcaacgctaccttttgccatgtttcagaaacaactctggcgcat cgggcttcccatacaatcgatagattgtcgcacctgattgcccgacattatcgcgagcccatttatacccatataaatcagcatccatgttggaa tttaatcgcggcctagagcaagacgtttcccgttgaatatggctcataacaccccttgtattactgtttatgtaagcagacagttttattgttcatga ccaaaatcccttaacgtgagttttcgttccactgagcgtcagaccccgtagaaaagatcaaaggatcttcttgagatccttttttttctgcgcgtaa tctgctgcttgcaaacaaaaaaaccaccgctaccagcggtggtttgtttgccggatcaagagctaccaactctttttccgaaggtaactggctt cagcagagcgcagataccaaatactgtccttctagtgtagccgtagttaggccaccacttcaagaactctgtagcaccgcctacatacctcgc tctgctaatcctgttaccagtggctgctgccagtggcgataagtcgtgtcttaccgggttggactcaagacgatagttaccggataaggcgca gcggtcgggctgaacggggggttcgtgcacacagcccagcttggagcgaacgacctacaccgaactgagatacctacagcgtgagctat gagaaagcgccacgcttcccgaagggagaaaggcggacaggtatccggtaagcggcagggtcggaacaggagagcgcacgaggga gcttccaggggaaacgcctggtatctttatagtcctgtcgggtttcgccacctctgacttgagcgtcgatttttgtgatgctcgtcaggggggg cggagcctatggaaaaacgccagcaacgcggccttttttacggttcctggccttttgctggccttttgctcacatgttcttcctgcgttatcccct gattctgtggataaccgtattaccgcctttgagtgagctgataccgctcgccgcagccgaacgaccgagcgcagcgagtcagtgagcgag gaagcggaagagcgcctgatgcggtattttctccttacgcatctgtgcggtatttcacaccgcatatatggtgcactctcagtacaatctgctct gatgccgcatagttaagccagtatacactccgctatcgctacgtgactgggtcatggctgcgccccgacacccgccaacacccgctgacgc gccctgacgggcttgtctgctcccggcatccgcttacagacaagctgtgaccgtctccgggagctgcatgtgtcagaggttttcaccgtcatc accgaaacgcgcgaggcagctgcggtaaagctcatcagcgtggtcgtgaagcgattcacagatgtctgcctgttcatccgcgtccagctcg ttgagtttctccagaagcgttaatgtctggcttctgataaagcgggccatgttaagggcggttttttcctgtttggtcactgatgcctccgtgtaag ggggatttctgttcatgggggtaatgataccgatgaaacgagagaggatgctcacgatacgggttactgatgatgaacatgcccggttactg gaacgttgtgagggtaaacaactggcggtatggatgcggcgggaccagagaaaaatcactcagggtcaatgccagcgcttcgttaataca

TABLE 15-continued

Strains:

gatgtaggtgttccacagggtagccagcagcatcctgcgatgcagatccggaacataatggtgcagggcgctgacttccgcgtttccagac tttacgaaacacggaaaccgaagaccattcatgttgttgctcaggtcgcagacgttttgcagcagcagtcgcttcacgttcgctcgcgtatcg gtgattcattctgctaaccagtaaggcaaccccgccagcctagccgggtcctcaacgacaggagcacgatcatgcgcacccgtgggcc gccatgccggcgataatggcctgcttctcgccgaaacgtttggtggcgggaccagtgacgaaggcttgagcgagggcgtgcaagattccg aataccgcaagcgacaggccgatcatcgtcgcgctccagcgaaagcggtcctcgccgaaaatgacccagagcgctgccggcacctgtc ctacgagttgcatgataaagaagacagtcataagtgcggcgacgatagtcatgccccgcgcccaccggaaggagctgactgggttgaag gctctcaagggcatcggtcgagatcccggtgcctaatgagtgagctaacttacattaattgcgttgcgctcactgcccgctttccagtcggga aacctgtcgtgccagctgcattaatgaatcggccaacgcgcggggagaggcggtttgcgtattgggcgccagggtggttttttcttttcacca gtgagacgggcaacagctgattgcccttcaccgcctggccctgagagagttgcagcaagcggtccacgctggtttgcccagcaggcga aaatcctgtttgatggtggttaacggcgggatataacatgagctgtcttcggtatcgtcgtatcccactaccgagatatccgcaccaacgcgc agcccggactcggtaatggcgcgcattgcgcccagcgccatctgatcgttggcaaccagcatcgcagtgggaacgatgccctcattcagc atttgcatggtttgttgaaaaccggacatggcactccagtcgccttcccgttccgctatcggctgaatttgattgcgagtgagatatttatgccag ccagccagacgcagacgcgccgagacagaacttaatgggcccgctaacagcgcgatttgctggtgacccaatgcgaccagatgctccac gcccagtcgcgtaccgtcttcatgggagaaaataatactgttgatgggtgtctggtcagagacatcaagaaataacgccggaacattagtgc aggcagcttccacagcaatggcatcctggtcatccagcggatagttaatgatcagcccactgacgcgttgcgcgagaagattgtgcaccgc cgctttacaggcttcgacgccgcttcgttctaccatcgacaccaccacgctggcacccagttgatcggcgcgagatttaatcgccgcgacaa tttgcgacggcgcgtgcagggccagactggaggtggcaacgccaatcagcaacgactgtttgcccgccagttgttgtgccacgcggttgg gaatgtaattcagctccgccatcgccgcttccacttttttcccgcgttttcgcagaaacgtggctggcctggttcaccacgcgggaaacggtct gataagagacaccggcatactctgcgacatcgtataacgttactggtttcacattcaccaccctgaattgactctcttccgggcgctatcatgc cataccgcgaaaggttttgcgccattcgatggtgtccgggatctcgacgctctcccttatgcgactcctgcattaggaagcagcccagtagta ggttgaggccgttgagcaccgccgccaaggaatggtgcatgcaaggagatggcgcccaacagtcccccggccacggggcctgcca ccataccccacgccgaaacaagcgctcatgagcccgaagtggcgagcccgatcttccccatcggtgatgtcggcgatataggcgccagca accgcacctgtggcgccggtgatgccggccacgatgcgtccggcgtagaggatcgagatctcgatcccgcgaaattaatacgactcacta taggggaattgtgagcggataacaattcccctctagaaataattttgtttaactttaagaaggagatatacatatggaagctcgtcgttctgcga actacgaacctaacagctgggactatgattacctgctgtcctccgacacggacgagtccatcgaagtatacaaagacaaagcgaaaaagct ggaagccgaagttcgtcgcgagattaataacgaaaaagcagaatttctgaccctgctggaactgattgacaacgtccagcgcctgggcctg ggttaccgtttcgagtctgatatccgtggtgcgctggatcgcttcgtttcctccggcggcttcgatgcggtaaccaagacttccctgcacggta cggcactgtctttccgtctgctgcgtcaacacggttttgaggtttctcaggaagcgttcagcggcttcaaagaccaaaacggcaacttcctgg agaacctgaaggaagatatcaaagctatcctgagcctgtacgaggccagcttcctggctctggaaggcgaaaacatcctggacgaggcga aggttttcgcaatctctcatctgaaagaactgtctgaagaaaagatcggtaaagagctggcagaacaggtgaaccatgcactggaactgcca ctgcatcgccgtactcagcgtctggaagcagtatggtctatcgaggcctaccgtaaaaaggaggacgcgaatcaggttctgctggagctgg caattctggattacaacatgatccagtctgtataccagcgtgatctgcgtgaaacgtcccgttggtggcgtcgtgtgggtctggcgaccaaac tgcactttgctcgtgaccgcctgattgagagcttctactgggccgtgggtgtagcattcgaaccgcaatactccgactgccgtaactccgtcg caaaaatgttttctttcgtaaccattatcgacgatatctacgatgtatacgcgcaccctgacgaactggagctgtttactgatgcagttgagcgtt gggacgtaaacgccatcaacgacctgccggattacatgaaactgtgctttctggctctgtataacactattaacgaaatcgcctacgacaacc tgaaagataaaggtgagaacatcctgccgtatctgaccaaagcctgggctgacctgtgcaacgctttcctgcaagaagccaagtggctgta caacaaatctactccgaccttttgacgactactcggcaacgcatggaaatcctcttctggcccgctgcaactggtgttcgcttacttcgctgtcg tgcagaacattaaaaaggaagagatcgaaaacctgcaaaaataccatgacaccatctctcgtccttcccatatcttccgtctgtgcaatgacct ggctagcgcgtctgcggaaattgcgcgtggtgaaaccgcaaatagcgtttcttgttacatgcgcactaaaggtatctccgaagaactggcta TABLE 15-continued Strains:

ccgaaagcgtgatgaatctgatcgatgaaacctggaaaaagatgaacaaggaaaaactgggtggtagcctgttcgcgaaaccgttcgtgg aaaccgcgatcaacctggcacgtcaatctcactgcacttatcataacggcgacgcgcatacctctccggatgagctgacccgcaaacgcgt tctgtctgtaatcactgaaccgattctgccgtttgaacgcgaaaacctgtattttcagggcctcgagcaccaccaccaccaccactgagatc cggctgctaacaaagcccgaaaggaagctgagttggctgctgccaccgctgagcaataactagcataaccccttggggcctctaaacggg tcttgagggttttttgctgaaaggaggaactatatccggat 3) Amino Acid Sequence of *P. alba* MEA G491S (+)TEV - pDW100(G491S) (SEQ ID NO: 28)

MEARRSANYEPNSWDYDYLLSSDTDESIEVYKDKAKKLEAEVRREINNEKAEFLTLLEL

IDNVQRLGLGYRFESDIRGALDRFVSSGGFDAVTKTSLHGTALSFRLLRQHGFEVSQEAF

SGFKDQNGNFLENLKEDIKAILSLYEASFLALEGENILDEAKVFAISHLKELSEEKIGKEL

AEQVNHALELPLHRRTQRLEAVWSIEAYRKKEDANQVLLELAILDYNMIQSVYQRDLR

ETSRWWRRVGLATKLHFARDRLIESFYWAVGVAFEPQYSDCRNSVAKMFSFVTIIDDIY

DVYGTLDELELFTDAVERWDVNAINDLPDYMKLCFLALYNTINEIAYDNLKDKGENILP

YLTKAWADLCNAFLQEAKWLYNKSTPTFDDYFGNAWKSSSGPLQLVFAYFAVVQNIK

KEEIENLQKYHDTISRPSHIFRLCNDLASASAEIARGETANSVSCYMRTKGISEELATESV

MNLIDETWKKMNKEKLSGSLFAKPFVETAINLARQSHCTYHNGDAHTSPDELTRKRVL

SVITEPILPFERENLYFQGLEHHHHHH

DNA sequence of pDW100 (SEQ ID NO: 29)

tggcgaatgggacgcgccctgtagcggcgcattaagcgcggcgggtgtggtggttacgcgcagcgtgaccgctacacttgccagcgccc tagcgcccgctcctttcgctttcttcccttcctttctcgccacgttcgccggctttccccgtcaagctctaaatcgggggctccctttaggttcc gatttagtgctttacggcacctcgaccccaaaaaacttgattagggtgatggttcacgtagtgggccatcgcccgatagacggttttttcgccc tttgacgttggagtccacgttctttaatagtggactcttgttccaaactggaacaacactcaaccctatctcggtctattcttttgatttataagggat tttgccgatttcggcctattggttaaaaaatgagctgatttaacaaaaatttaacgcgaattttaacaaaatattaacgtttacaatttcaggtggca cttttcggggaaatgtgcgcggaacccctatttgtttatttttctaaatacattcaaatatgtatccgctcatgaattaattcttagaaaaactcatcg agcatcaaatgaaactgcaatttattcatatcaggattatcaataccatattttgaaaagccgtttctgtaatgaaggagaaaactcaccgag gcagttccataggatggcaagatcctggtatcggtctgcgattccgactcgtccaacatcaatacaacctattaatttcccctcgtcaaaaataa ggttatcaagtgagaaatcaccatgagtgacgactgaatccggtgagaatggcaaaagtttatgcatttctttccagacttgttcaacaggcca gccattacgctcgtcatcaaaatcactcgcatcaaccaaaccgttattcattcgtgattgcgcctgagcgagacgaaatacgcgatcgctgtta aaaggacaattacaaacaggaatcgaatgcaaccggcgcaggaacactgccagcgcatcaacaatattttcacctgaatcaggatattcttc taatacctggaatgctgtttttccggggatcgcagtggtgagtaaccatgcatcatcaggagtacggataaaatgcttgatggtcggaagag gcataaattccgtcagccagtttagtctgaccatctcatctgtaacatcattggcaacgctaccttgccatgtttcagaaacaactctggcgcat cgggcttcccatacaatcgatagattgtcgcacctgattgcccgacattatcgcgagcccatttatacccatataaatcagcatccatgttggaa tttaatcgcggcctagagcaagacgtttcccgttgaatatggctcataacaccccttgtattactgtttatgtaagcagacagttttattgttcatga ccaaaatcccttaacgtgagttttcgttccactgagcgtcagaccccgtagaaaagatcaaaggatcttcttgagatcctttttttctgcgcgtaa tctgctgcttgcaaacaaaaaaaccaccgctaccagcggtggtttgtttgccggatcaagagctaccaactctttttccgaaggtaactggctt cagcagagcgcagataccaaatactgtccttctagtgtagccgtagttaggccaccacttcaagaactctgtagcaccgcctacatacctcgc tctgctaatcctgttaccagtggctgctgccagtggcgataagtcgtgtcttaccgggttggactcaagacgatagttaccggataaggcgca gcggtcgggctgaacggggggttcgtgcacacagcccagcttggagcgaacgacctacaccgaactgagatacctacagcgtgagctat gagaaagcgccacgcttcccgaagggagaaaggcggacaggtatccggtaagcggcagggtcggaacaggagagcgcacgaggga gcttccagggggaaacgcctggtatctttatagtcctgtcgggtttcgccacctctgacttgagcgtcgatttttgtgatgctcgtcagggggg TABLE 15-continued Strains:

cggagcctatggaaaaacgccagcaacgcggccttttacggttcctggccttttgctggccttttgctcacatgttctttcctgcgttatcccct gattctgtggataaccgtattaccgcctttgagtgagctgataccgctcgccgcagccgaacgaccgagcgcagcgagtcagtgagcgag gaagcggaagagcgcctgatgcggtattttctccttacgcatctgtgcggtatttcacaccgcatatatggtgcactctcagtacaatctgctct gatgccgcatagttaagccagtatacactccgctatcgctacgtgactgggtcatggctgcgccccgacacccgccaacacccgctgacgc gccctgacgggcttgtctgctcccggcatccgcttacagacaagctgtgaccgtctccgggagctgcatgtgtcagaggttttcaccgtcatc accgaaacgcgcgaggcagctgcggtaaagctcatcagcgtggtcgtgaagcgattcacagatgtctgcctgttcatccgcgtccagctcg ttgagtttctccagaagcgttaatgtctggcttctgataaagcgggccatgttaagggcggttttttcctgtttggtcactgatgcctccgtgtaag ggggatttctgttcatgggggtaatgataccgatgaaacgagagaggatgctcacgatacgggttactgatgatgaacatgcccggttactg gaacgttgtgagggtaaacaactggcggtatggatgcggcgggaccagagaaaaatcactcagggtcaatgccagcgcttcgttaataca gatgtaggtgttccacagggtagccagcagcatcctgcgatgcagatccggaacataatggtgcagggcgctgacttccgcgtttccagac tttacgaaacacggaaaccgaagaccattcatgttgttgctcaggtcgcagacgttttgcagcagcagtcgcttcacgttcgctcgcgtatcg gtgattcattctgctaaccagtaaggcaaccccgccagcctagccgggtcctcaacgacaggagcacgatcatgcgcacccgtgggcc gccatgccggcgataatggcctgcttctcgccgaaacgtttggtggcgggaccagtgacgaaggcttgagcgagggcgtgcaagattccg aataccgcaagcgacaggccgatcatcgtcgcgctccagcgaaagcggtcctcgccgaaaatgacccagagcgctgccggcacctgtc ctacgagttgcatgataaagaagacagtcataagtcgggcgacgatagtcatgccccgcgcccaccggaaggagctgactgggttgaag gctctcaagggcatcggtcgagatcccggtgcctaatgagtgagctaacttacattaattgcgttgcgctcactgcccgctttccagtcggga aacctgtcgtgccagctgcattaatgaatcggccaacgcgcggggagaggcggtttgcgtattgggcgcagggtggttttcttttcacca gtgagacgggcaacagctgattgcccttcaccgcctggccctgagagagttgcagcaagcggtccacgctggtttgcccagcaggcga aaatcctgtttgatggtggttaacggcgggatataacatgagctgtcttcggtatcgtcgtatcccactaccgagatatccgcaccaacgcgc agcccggactcggtaatggcgcgcattgcgcccagcgccatctgatcgttggcaaccagcatcgcagtgggaacgatgccctcattcagc atttgcatggtttgttgaaaaccggacatggcactccagtcgccttcccgttccgctatcggctgaatttgattgcgagtgagatatttatgccag ccagccagacgcagacgcgccgagacagaacttaatgggcccgctaacagcgcgatttgctggtgacccaatgcgaccagatgctccac gcccagtcgcgtaccgtcttcatgggagaaaataatactgttgatgggtgtctggtcagagacatcaagaaataacgccggaacattagtgc aggcagcttccacagcaatggcatcctggtcatccagcggatagttaatgatcagcccactgacgcgttgcgcgagaagattgtgcaccgc cgctttacaggcttcgacgccgcttcgttctaccatcgacaccaccacgctggcacccagttgatcggcgcgagatttaatcgccgcgacaa tttgcgacggcgcgtgcagggccagactggaggtggcaacgccaatcagcaacgactgtttgcccgccagttgttgtgccacgcggttgg gaatgtaattcagctccgccatcgccgcttccactttttcccgcgttttcgcagaaacgtggctggcctggttcaccacgcgggaaacggtct gataagagacaccggcatactctgcgacatcgtataacgttactggtttcacattcaccaccctgaattgactctcttccgggcgctatcatgc cataccgcgaaaggttttgcgccattcgatggtgtccgggatctcgacgctctcccttatgcgactcctgcattaggaagcagcccagtagta ggttgaggccgttgagcaccgccgccaaggaatggtgcatgcaaggagatggcgcccaacagtccccggccacgggcctgcca ccatacccacgccgaaacaagcgctcatgagcccgaagtggcgagcccgatcttccccatcggtgatgtcggcgatataggcgccagca accgcacctgtggcgccggtgatgccggccacgatgcgtccggcgtagaggatcgagatctcgatcccgcgaaattaatacgactcacta taggggaattgtgagcggataacaattcccctctagaaataattttgtttaacttaagaaggagatatacat<u>atggaagctcgtcgttctgcga</u>

<u>actacgaacctaacagctgggactatgattacctgctgtcctccgacacggacgagtccatcgaagtatacaaagacaaagcgaaaaagct</u>

<u>ggaagccgaagttcgtcgcgagattaataacgaaaaagcagaatttctgaccctgctggaactgattgacaacgtccagcgcctgggcctg</u>

<u>ggttaccgtttcgagtctgatatccgtggtgcgctggatcgcttcgtttcctccggcggcttcgatgcggtaaccaagacttccctgcacggta</u>

<u>cggcactgtctttccgtctgctgcgtcaacacggttttgaggtttctcaggaagcgttcagcggcttcaaagaccaaaacggcaacttcctgg</u>

<u>agaacctgaaggaagatatcaaagctatcctgagcctgtacgaggccagcttcctggctctggaaggcgaaaacatcctggacgaggca</u>

<u>aggttttcgcaatctctcatctgaaagaactgtctgaagaaaagatcggtaaagagctggcagaacaggtgaaccatgcactggaactgcca</u>

TABLE 15-continued

Strains:

```
ctgcatcgccgtactcagcgtctggaagcagtatggtctatcgaggcctaccgtaaaaaggaggacgcgaatcaggttctgctggagctgg caattctggattacaacatgatccagtctgtataccagcgtgatctgcgtgaaacgtcccgttggtggcgtcgtgtgggtctggcgaccaaac tgcactttgctcgtgaccgcctgattgagagcttctactgggccgtgggtgtagcattcgaaccgcaatactccgactgccgtaactccgtcg caaaaatgttttctttcgtaaccattatcgacgatatctacgatgtatacggcaccctggacgaactggagctgtttactgatgcagttgagcgtt gggacgtaaacgccatcaacgacctgccggattacatgaaactgtgattctggctctgtataacactattaacgaaatcgcctacgacaacc tgaaagataaaggtgagaacatcctgccgtatctgaccaaagcctgggctgacctgtgcaacgctttcctgcaagaagccaagtggctgta caacaaatctactccgacctttgacgactacttcggcaacgcatggaaatcctcttctggcccgctgcaactggtgttcgcttacttcgctgtcg tgcagaacattaaaaaggaagagatcgaaaacctgcaaaaataccatgacaccatctctcgtccttcccatatcttccgtctgtgcaatgacct ggctagcgcgtctgcggaaattgcgcgtggtgaaaccgcaaatagcgtttcttgttacatgcgcactaaaggtatctccgaagaactggcta ccgaaagcgtgatgaatctgatcgatgaaacctggaaaaagatgaacaaggaaaaactgAGTggtagcctgttcgcgaaaccgttcgtg gaaaccgcgatcaacctggcacgtcaatctcactgcacttatcataacggcgacgcgcatacctctccggatgagctgacccgcaaacgc gttctgtctgtaatcactgaaccgattctgccgtttgaacgcgaaaacctgtatttcagggcctcgagcaccaccaccaccaccactgaga tccggctgctaacaaagcccgaaaggaagctgagttggctgctgccaccgctgagcaataactagcataacccttggggcctctaaacg ggtcttgaggggttttttgctgaaaggaggaactatatccggat
```

Expression and Purification of IspS-G491S
Expression of 6×His-tagged IspS-G491S

N-terminally 6×His-tagged IspS was expressed and purified from strain DW398. The growth procedure is suitable for histidine tagged enzymes expressed in BL21(λDE3)pLysS cells. A 10 ml of overnight culture was prepared for each 1 L of planned growth. The appropriate antibiotics (50 mg/ml kanamycin, 25 mg/ml chloramphenicol) was added to 10 ml of LB medium in a 25 ml flask and was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1 L day culture was inoculated with 10 ml of overnight culture and grown at 30-37° C. with shaking at ~220 rpm until the $OD_{600}$ reached ~0.4-0.6. Day cultures were then induced with 400 μM IPTG and allowed to continue growing at 30° C. with shaking at 220 rpm for ~5-6 hours. Cells were then harvested by centrifugation at 10,000×g for 10 min, 4° C. Following Harvest, cells were used directly or stored at −80° C. until ready to process Purification of 6×His-Tagged IspS For purification of histidine tagged enzymes from BL21 (λDE3)pLysS cells, cells were gently resuspended in fresh Lysis buffer (Lysis buffer: Ni wash buffer+0.5 mM PMST, 0.01% Tween-20, 1 mg/ml lysozyme, 0.2 mg/ml DNaseI; Ni wash buffer: 50 mM $NaH_2PO_4$, 300 mM NaCl, 20 mM Imidazole, pH 8.0). Approximately 40-50 ml of lysis buffer was used per 1 L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 μl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 μl).

The clarified lysate was run over HisTrap HP columns (GE healthcare) using a gradient from 0-100% Ni buffer B. Following loading of the lysate on the column, the column was washed with Ni wash buffer (50 mM $NaH_2PO_4$, 300 mm NaCl, 20 mM imidazole, ph 8.0). The his-tagged IspS was then eluted from the column using a gradient from 0-100% Ni elution buffer (50 mM $NaH_2PO_4$, 300 mM NaCl, 500 mM imidazole, ph 8.0) and fractions containing the his-tagged IspS were collected. The column was then washed with Ni stripping buffer (20 mM NaH2PO4, 0.5 m NaCl, 50 mM EDTA, ph 7.4). Samples were then analyzed by SDS-PAGE gel (4-12% gel NUPAGE, Invitrogen) according to manufacturer's directions. Desired fractions were concentrated on spin filters (Vivaspin-20, Sartoris,) and then desalted over a Hi Prep 26/10 Desalting column (GE heathcare) packed with Sephadex G25 resin. The G-25 buffer consisted of 50 mM HEPES, 50 mM NaCl, and 1 mM DTT, pH 7.4. Fractions were then analyzed and concentrated. The samples were then stored at −80° C.

TEV Cleavage (IspS-G491S from Strain DW398)

Figure 16:
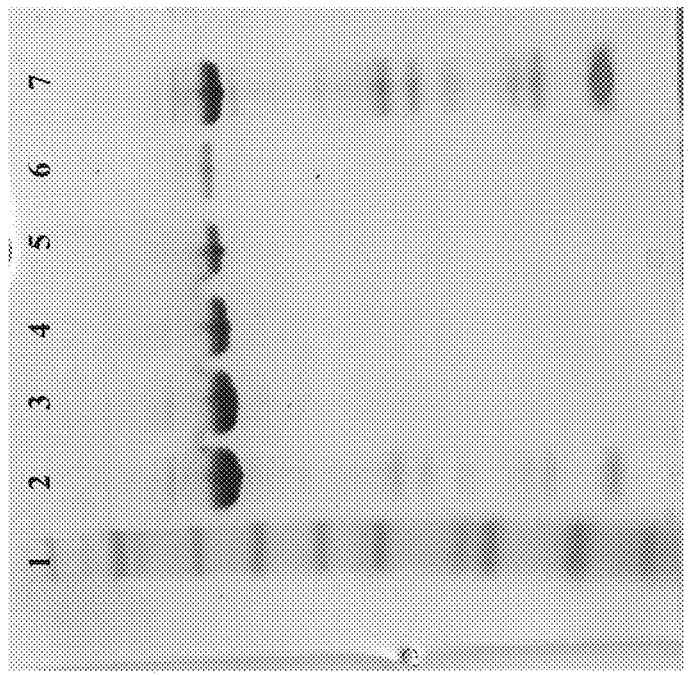
FIG. 16 shows a SDS-PAGE gel showing IspS-G491S at different stages of the purification. Lane 1—molecular weight standard; Lane 2-IspS-G491S digested with TurboTEV; Lanes 3-5-IspS-G491S in flow-though after second Ni column; Lanes 6-7-IspS-G491S fractions from second Ni column.

Strain DW398 is described above. Digestion was performed with TurboTEV Protease from Eton Bioscience Inc. One unit of TurboTEV per 10 μg of purified protein was used. The digest was performed at 4° C. overnight. Samples were passed through another Ni column equilibrated in the Ni buffer to remove uncleaved enzyme, tag, TurboTEV protease (which is also tagged), and impurities. The Ni column pass though and washes were analyzed using SDS-PAGE gel (NUPAGE, Invitrogen; FIG. 16) and DMAPP activity assays. Samples containing pure enzyme were pooled and desalted into 50 mM NaCl pH 7.4 buffer containing 1 mM DTT and stored at −80° C.

Crystal Structure Determination

Construct DW398 was purified as described and a concentrated protein solution was then prepared for surveying possible crystallization conditions. The construct was purified independently and surveyed as described below. All in-house crystallization screens were set up using the hanging drop vapor diffusion method. At a minimum, the construct was surveyed using the following commercial screens: the Crystal Screen from Hampton Research (Aliso Viejo, Calif.) and the JCSG+ Suite from Qiagen (Valencia, Calif.).

Initial crystallization screens were setup using the Crystal Screen from Hampton Research and the JCSG+ Suite from Qiagen. Crystals from this construct were observed in numerous conditions; optimization included 100 variations of pH, precipitating agents, concentrations, and inhibitors. From the optimization experiments, ten different DW398 crystals were screened in-house for diffraction. A crystal composed of IspS-G491S protein was obtained that diffracted to 3.5 Å in house. The large, rod-shaped crystals belong to the tetragonal space group $P4_32_12$, and have unit cell dimensions a=154.75, b=154.75, c=142.20. The crystals were grown by mixing 2.5 µL of protein (10 mg/ml protein) with 2.5 µL of precipitant solution [0.1 M Sodium Malonate pH 7.0, 18% (wt/vol) Polyethylene glycol 3350, 0.2 M Sodium Thiocyanate] and equilibrated against 500 µL of precipitant. Prior to flash-freezing the crystal in liquid nitrogen, the crystals were cryoprotected by swishing through 0.1 M Sodium Malonate pH 7.0, 18% (wt/vol) Polyethylene glycol 3350, 0.2 M Sodium Thiocyanate, and 25% (wt/vol) ethylene glycol.

The crystal was sent to Stanford Synchrotron Radiation Laboratory, and data were collected at Beamline 7-1 to 2.6 Å resolution. Data were integrated using Mosflm (Leslie, A. (1998) *J. of Appl. Crystallography* 30, 1036-1040) and scaled using SCALA (Collaborative Computational Project, N. (1994) *Acta Crystallographica Section D* 50, 760-763). The data were phased with MOLREP (Vagin, A., and Teplyakov, A. (1997) *J. of Appl. Crystallography* 30, 1022-1025), using the previously determined structure of IspS from *P. alba* as the starting model as described in WO 2009/132220. The crystal contains one dimer in the asymmetric unit with a solvent content of 63%.

Refinement with Refmac5 (Collaborative Computational Project, N. (1994) *Acta Crystallographica Section D* 50, 760-763) was used with iterative manual rebuilding steps using the visualization program Coot (Emsley, P., et al. (2010) *Acta Crystallographica Section D* 66, 486-501). During refinement, the geometry of the protein was checked using Molprobity (Davis, I. W., et al. (2007) *Nucl. Acids Res.,* 35:W375-W383). The current model has an $R_{Work}$ value of 23.5% and an $R_{Free}$ value of 28.6%.

Figure 17:
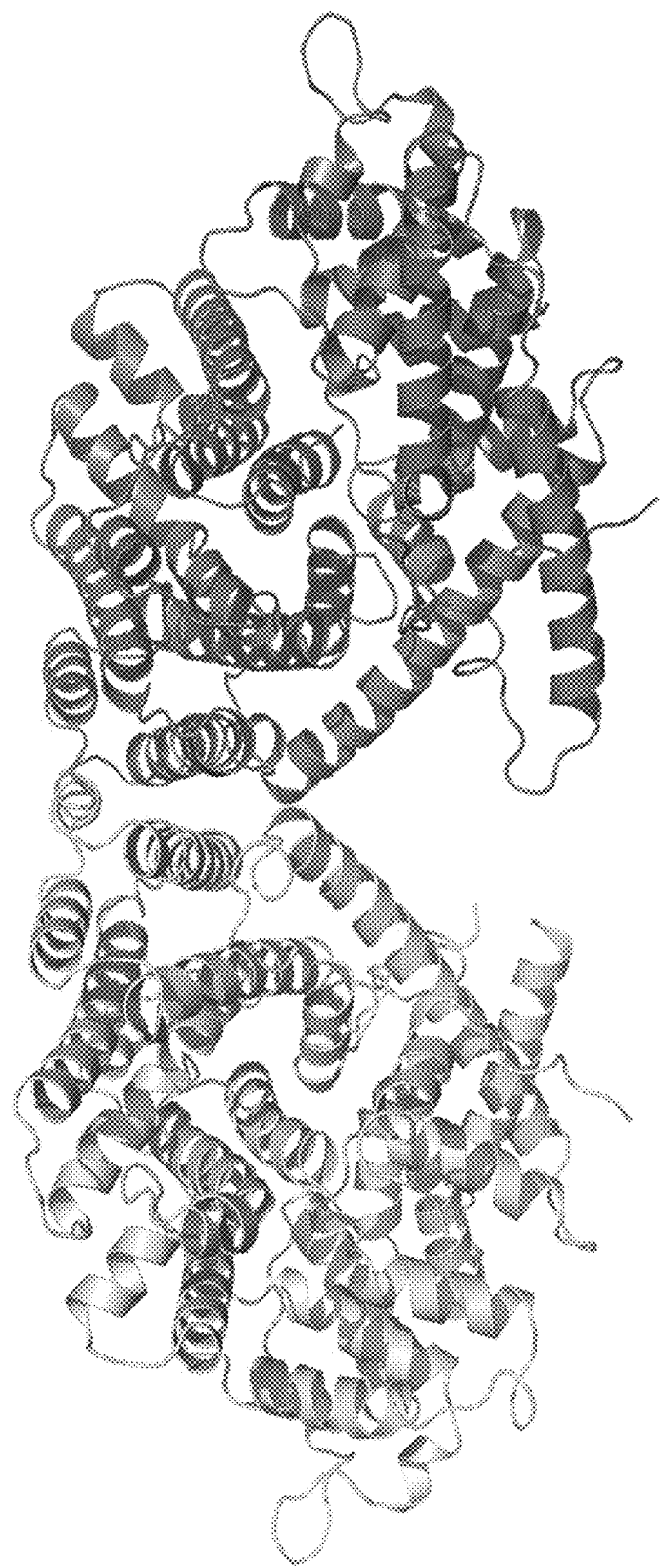
FIG. 17 shows IspS-G491S forming a dimer. Monomer A is light grey, monomer B is dark grey.
Figure 18:
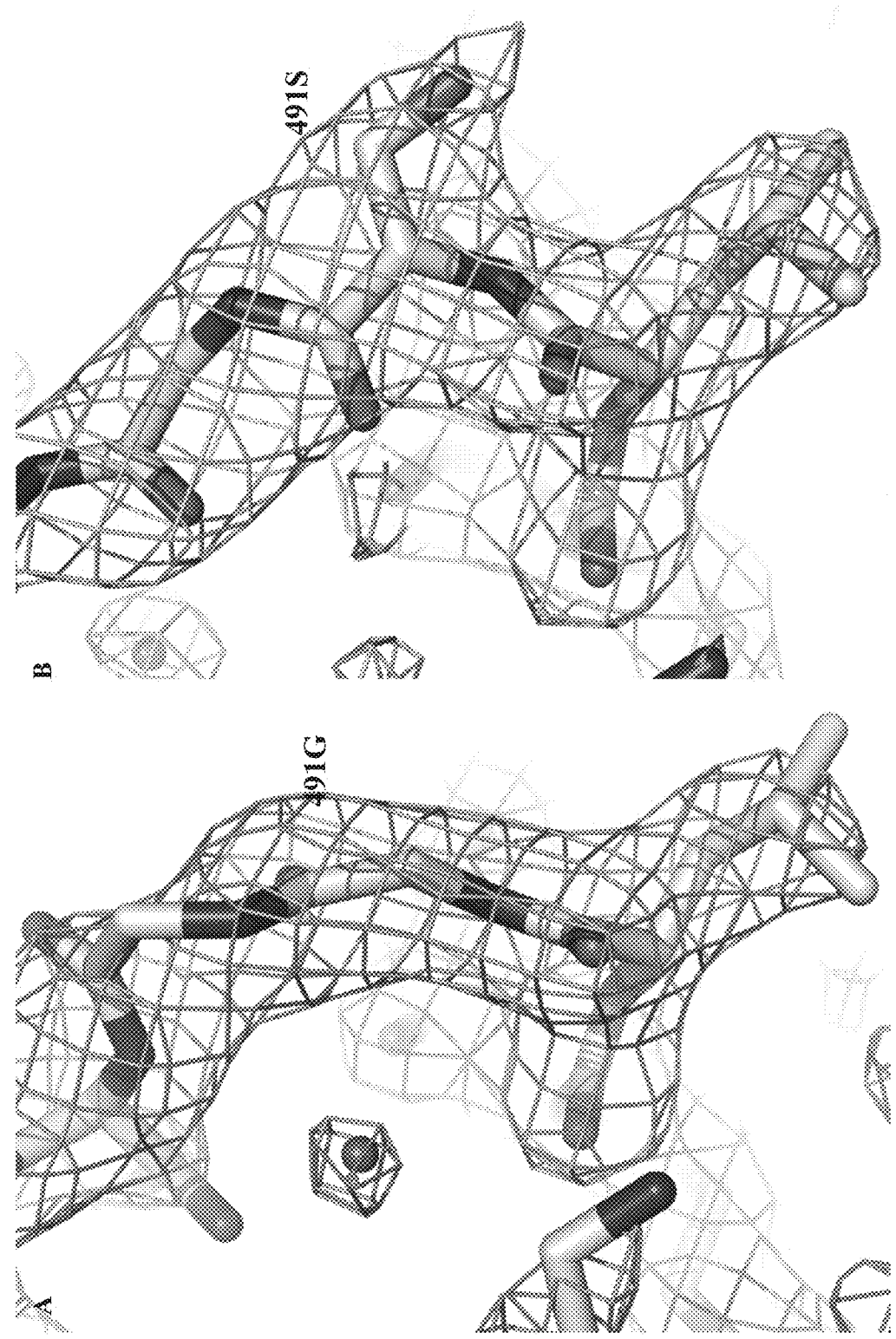
FIG. 18 is an $2F_O-2F_C$ electron density map at residue 491 contoured at 1-sigma. A shows 491G, B shows 491S.
Figure 19:
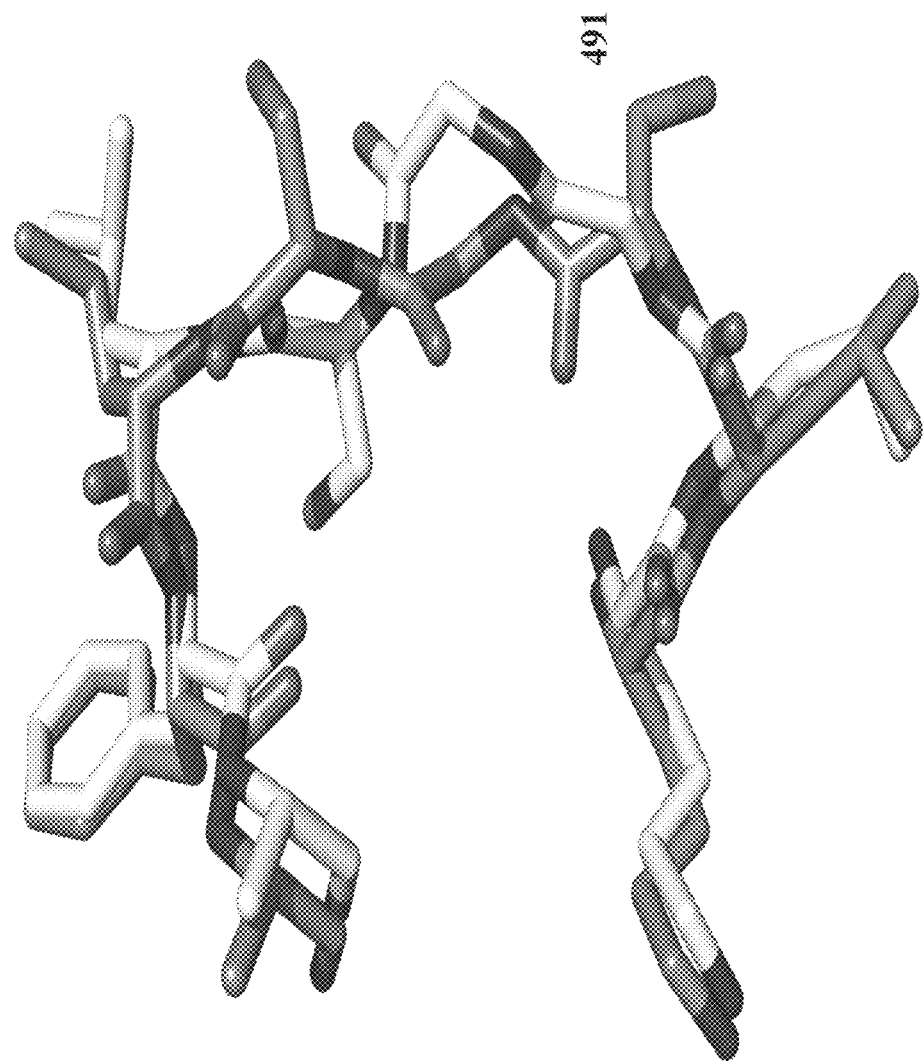
FIG. 19 is an alignment of the loop containing residue 491. Wild type IspS is light grey and IspS-G491S is dark grey. The G491S mutation results in an alternate loop structure.

The structure consists of a dimer (FIG. 17). Each monomer is comprised of two helical domains, a C-terminal domain containing the active site and N-terminal domain with unknown function. The electron density clearly supports the presence of a serine at position 491 in strain DW398 (FIG. 18). Structural alignment of the wild type IspS and IspS-G491S show that the overall fold is unchanged, however the conformation of the loop containing residues 490-497 does vary between the wild type and variant proteins (FIG. 19). Coordinates are provided in Appendix 1.

Example 7

Primary Specific Activity Assay for *P. alba* IspS Complete Site Evaluation Libraries (SELs)

Site Evaluation Libraries (SELs) of the entire *P. alba* isoprene synthase (MEA *P. alba*) backbone (544 amino acids) were built in the parent vector pCL201 (FIG. 4), and screened for specific activity to identify isoprene synthase (IspS) molecules with improved characteristics. In most cases, the SEL at a given position contained all 20 possible amino acid substitutions including the wild type. Numbering of each library corresponds to the ORF of MEA *P. alba* (FIG. 20), where the starting methionine is position 1. Individual strains, built in the MD09-170 background, that contained variants for expression were arrayed into microtiter plates such that each well corresponded to a specific amino acid substitution at the given position in MEA *P. alba*. Microtiter plates contained four SELs, or four positions in MEA *P. alba* with all possible substitutions. Remaining wells were used for control strains. Plates were grown, induced, and lysed, in order to measure the amount of isoprene produced per the specific amount of IspS protein in each sample. Specific activity values were calculated for all variants in the entire set of SELs.

Methods

Cell Growth and Lysis

Glycerol stocks of MEA *P. alba* IspS libraries were thawed briefly and inoculated into microtiter plates (Cellstar) containing liquid LB medium with kanamycin at a concentration of 20 ug/ml. Cultures were grown overnight at 250 rpm, 30° C. to saturation in a shaking incubator using the Enzyscreen clamp system (Enzyscreen). The next day, cultures were removed and inoculated using a Liquidator96 pipettor (Rainin Instruments) at a ratio of 1:10 into TM3-glucose medium containing 50 ug/ml kanamycin and 50 uM IPTG. Wild type controls were grown separately and inoculated into each microtiter plate containing TM3-glucose with a titration of IPTG concentrations, from 30 uM to 65 uM, in separate wells. Plates were returned to the shaking incubator at 250 rpm, 30° C. and induced for five hours. Plates were then removed from the incubator and cultures were harvested into polypropylene microtiter plates (Nunc) by centrifugation at 3700 rpm for 20 minutes at 4° C. in a tabletop centrifuge. The supernatant was removed and pellets were stored at −80° C. prior to lysis, DMAPP assay, and protein determination.

Prior to cell lysis, plates were removed from the −80° C. freezer and thawed on the bench for 10 minutes. Pellets were thoroughly resuspended in 200 ul of lysis buffer (100 mM Tris, 100 mM NaCl pH 7.6 buffer, 1 mg/ml BSA, 50 U/ul Epicentre readylyse lysozyme, 0.1 mg/ml DNase, 0.5 mM PMSF/AEBSF, 5 mM MgCl2) using a Biomek automated workstation (Beckman Coulter), removed, and shaken at room temperature at 450 rpm for 30 minutes. Lysates were then spun at 3200 rpm at 4° C. for 10 minutes, and 150 ul of the supernatant was transferred using a Biomek to a new microtiter plate for DMAPP and dot blot assay.

DMAPP Assay

For the DMAPP assay, 25 ul of lysate was added to 75 ul of DMAPP assay buffer (100 mM Tris/100 mM NaCl pH 7.6, 1 mg/ml BSA, 50 mM $MgCl_2$, 1 mM DMAPP) in a 96-well glass block (Zinser) using a Liquidator96 pipettor (Rainin Instruments). Glass blocks were sealed with aluminum foil seals (Beckman Coulter) and incubated at 450 rpm for one minute at room temperature. Blocks were then incubated at 34° C. in a water bath for 30 minutes, and the reaction was stopped by incubation at 70° C. for two minutes. Blocks were cooled briefly before loading onto the GC-MS.

Sealed glass blocks were loaded onto an Agilent 7890a Gas Chromatography (GC) System equipped with a flame ionization detector (FID) and a CTC CombiPAL autosampler. The GC FID method parameters are described below:

Column: ZB-5 ms
Dimensions: 15 m×0.25 mm×0.25 µm
Oven:

| Ramp (° C./min) | Temperature (° C.) | Hold Time (min) |
| --- | --- | --- |

-continued

| 0 | 37 | 28 |
|---|---|---|
| Total Run Time: | | 28 minutes |
| Front Inlet Temperature: | | 110° C. |
| Split Ratio: | | 50:1 |
| Flow Rate: | | 3.4 mL/min |
| Injection Volume: | | 100 μL |
| Headspace Syringe Volume: | | 1 mL |
| Detector Temperature | | 160° C. |
| Hydrogen Flow: | | 40 mL/min |
| Air Flow: | | 400 mL/min |
| Makeup Flow: | | 0.1 mL/min |
| Makeup Gas Type: | | Helium |

Chemstation software (version E.02.00.493) was used to control the GC and Cycle Composer software (version 1.5.2) was used to control the CTC autosampler. The Cycle Composer software was programmed to continuously inject one sample after another in sequence for a total of 48 injections. 0.2% v/v isoprene balanced with nitrogen gas from Air Liquide was used as the standard for determining calibration response factors. Three separate 2 mL vials were filled with the calibration gas and analyzed using the method described above to determine an average response factor. Calculated response factors allowed for the conversion of individual sample peak area counts to isoprene concentrations using Microsoft Excel.

Protein Determination

Prior to the protein determination assay, several wild type samples from each plate were analyzed by GC-MS for isoprene, and protein concentration was back-calculated from the known specific activity of MEA P. alba to determine the average amount of IspS for all samples in the microtiter plate. For the dot blot assay, nitrocellulose membranes (Invitrogen) were soaked in 1×PBS buffer (10 mM Sodium Phosphate, 150 mM NaCl, PH7.8+/−0.2) and equilibrated for at least 5 minutes. Lysates were then diluted in 1×PBS using a Hamilton MicroLab STAR liquid handling workstation to achieve loading concentration between 0.025-0.5 ug of P. alba IspS. Purified standards were added at concentrations between 0.025-1 ug. The blotting unit (Minifold-1, Whatman) was assembled according to the manufacturer's recommended protocol. Vacuum was applied briefly to remove excess 1×PBS buffer. Samples (approximately 200 ul of each) were transferred to the Minifold-1, and vacuum was applied at 20 kPa. After samples were filtered completely, wells were washed once with 200 ul of 1×PBS buffer. After the wash buffer passed completely through the membrane, the vacuum was removed, and membranes were removed carefully with forceps, labeled, and dried on clean filter paper.

Immunodetection of P. alba IspS molecules at each position on nitrocellulose membranes was carried out using the WesternBreeze kit from Invitrogen. Primary monoclonal or polyclonal antibody (anti-mouse against purified P. alba IspS, Prosci Incorporated) was diluted 1:5000 in blocking solution, and secondary antibody (Alexa Fluor 488 goat anti-mouse IgG (H+L), Invitrogen) was diluted to a concentration of 2 ug/ml in blocking solution. Fluorescent spots were quantified using a Storm 860 Molecular Imager (GMI, Inc.) and ImageQuant software (GE Healthcare), according to the manufacturers' recommended protocols, and specific protein concentrations for each sample were determined by comparison to known standards using Microsoft Excel.

Results

Specific activity values were calculated for every variant in the entire set of SELs by dividing the molar amount of isoprene produced in a given amount of time by the specific amount of protein in each sample. Performance index (PI) was calculated by dividing the specific activity of any given variant by the average of several WT specific activity measurements from the same microtiter plate. A variant that displayed a PI value of 1.5 for specific activity, for example, was 50% improved over WT. PIs for protein concentration and isoprene produced were also calculated in the same fashion, and these measurements were used for detailed data analysis.

Table 16 provides precise definitions for locations of the residues listed in Tables 17 and 18. For example, a residue listed as "N-term" in Table 17 or 18, is between residue 1 and 215 of reference sequence MEA P. alba IspS (SEQ ID NO:1).

TABLE 16

Definitions of locations of MEA P. alba IspS amino acid positions

| Location | Definition |
|---|---|
| N-term | Residues 1-215 |
| Hinge Region | Residues 216-245 |
| C-term | Residues 246-544 |
| N-term helices | Residues 134-179 |
| Dimer Interface | Residues 240-255 and 316-353 |
| Substrate Capture Loops | Residues 441-454 and 515-527 |
| Active Site | Residues within 8 Å of active site based on PDB 3N0G |
| Buried | Surface Accessibility below 35% and located internally |
| Surface | Residues located on the surface of the structure |
| Surface Loop | Residues in loops located on the surface of the structure |

Surface accessibilities and putative functions of amino acids of interest in the structure of MEA P. alba are also listed in Tables 17 and 18. Surface accessibility was calculated using the program MOE, which is written and supported by the Chemical Computing Group, Inc. An estimate for the water-accessible surface area of each residue was determined using a probe having a specified radius. The estimate was then compared against a library of peptides and the ratio between them was reported as the percent surface accessibility. Tables 17 and 18 also list the putative functions of each residue. For example, functions include but aren't limited to metal binding (in the active site), substrate capture, altered loop shape, alternative interactions in a pocket, and dimer formation.

Figure 25:
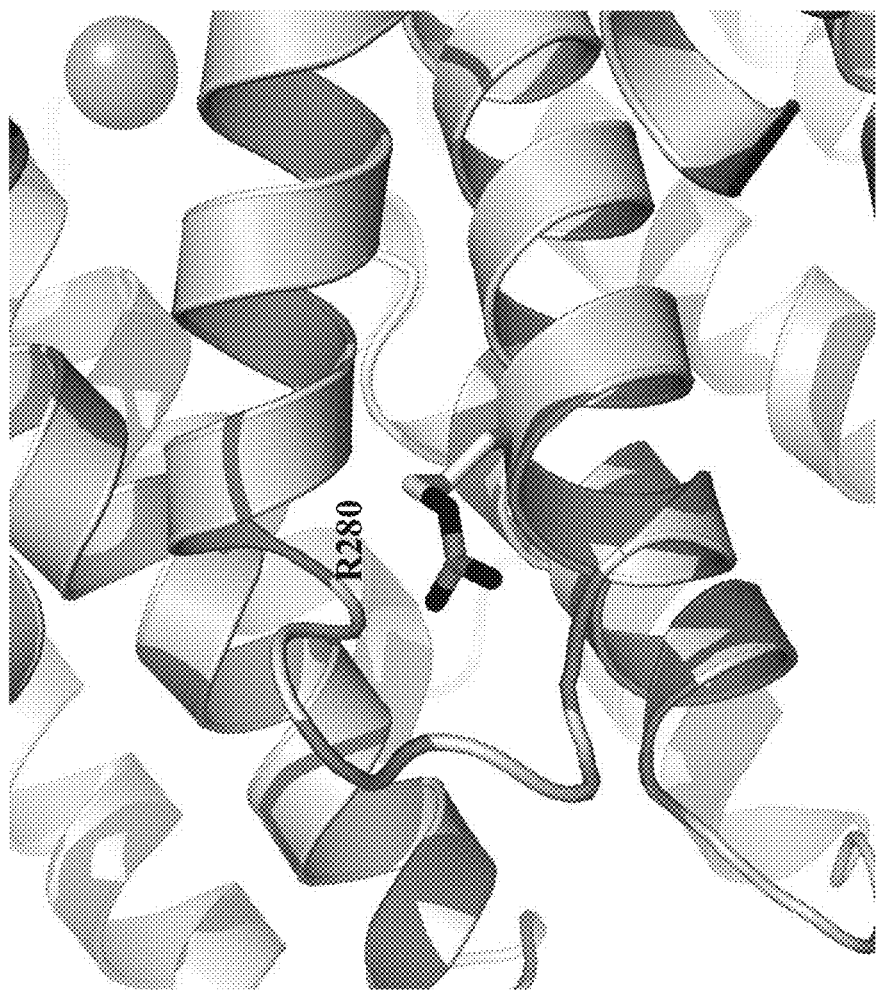
FIG. 25 shows the location of buried sites in IspS that do not tolerate substitution. $Mg^{2+}$ (spheres) are placed based on a structural alignment with PDB 1N24.
Figure 26:
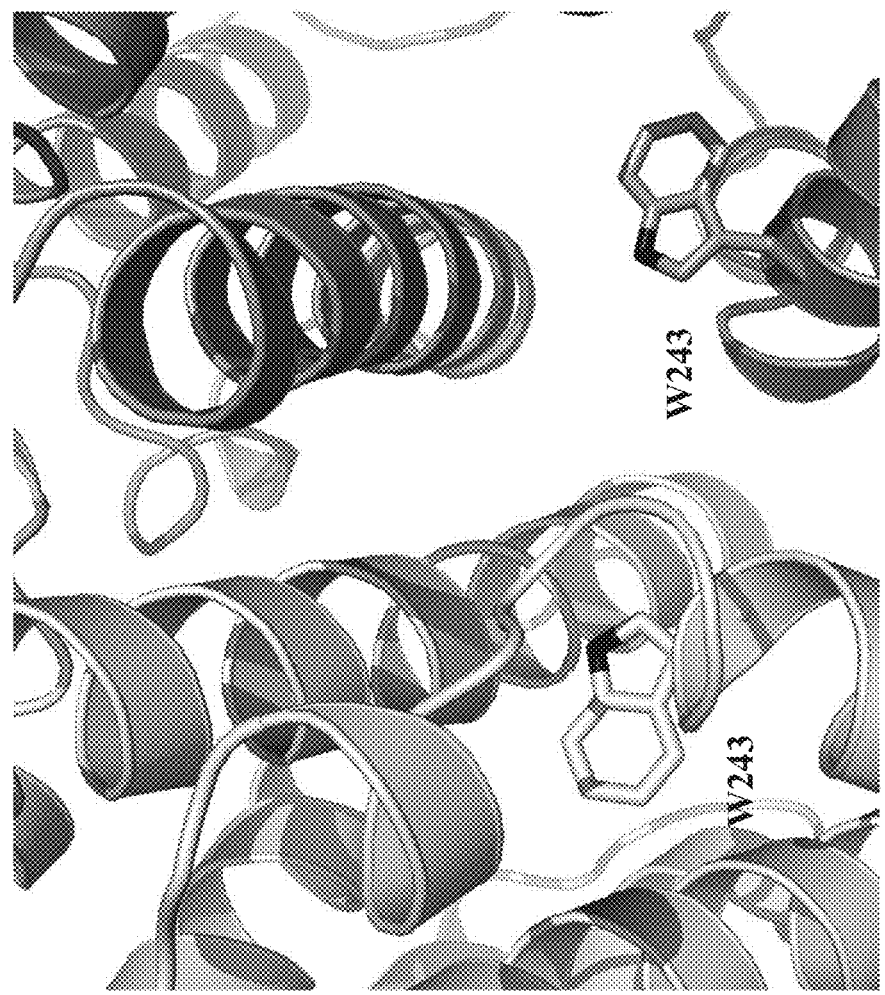
FIG. 26 shows residues located at the dimer interface of IspS that do not tolerate substitution. Chain A is light gray and chain B is dark gray.
Figure 27:
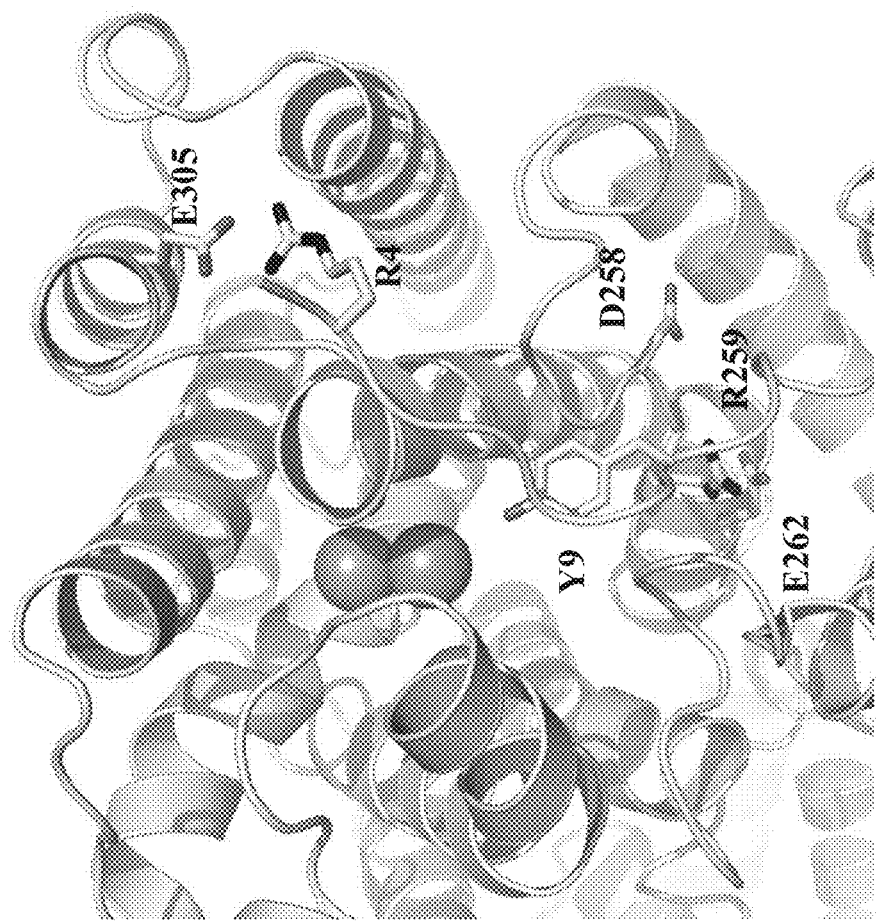
FIG. 27 shows the location of N-terminally located or interacting sites of IspS that do not tolerate substitution. $Mg^{2+}$ (spheres) and residues 1-50 are modeled based on a structural alignment with PDB 1N24.
Figure 28:
FIG. 28 shows the location of N-terminally located or interacting sites of IspS that do not tolerate substitution. $Mg^{2+}$ (spheres) are placed based on a structural alignment with PDB 1N24.
Figure 29:
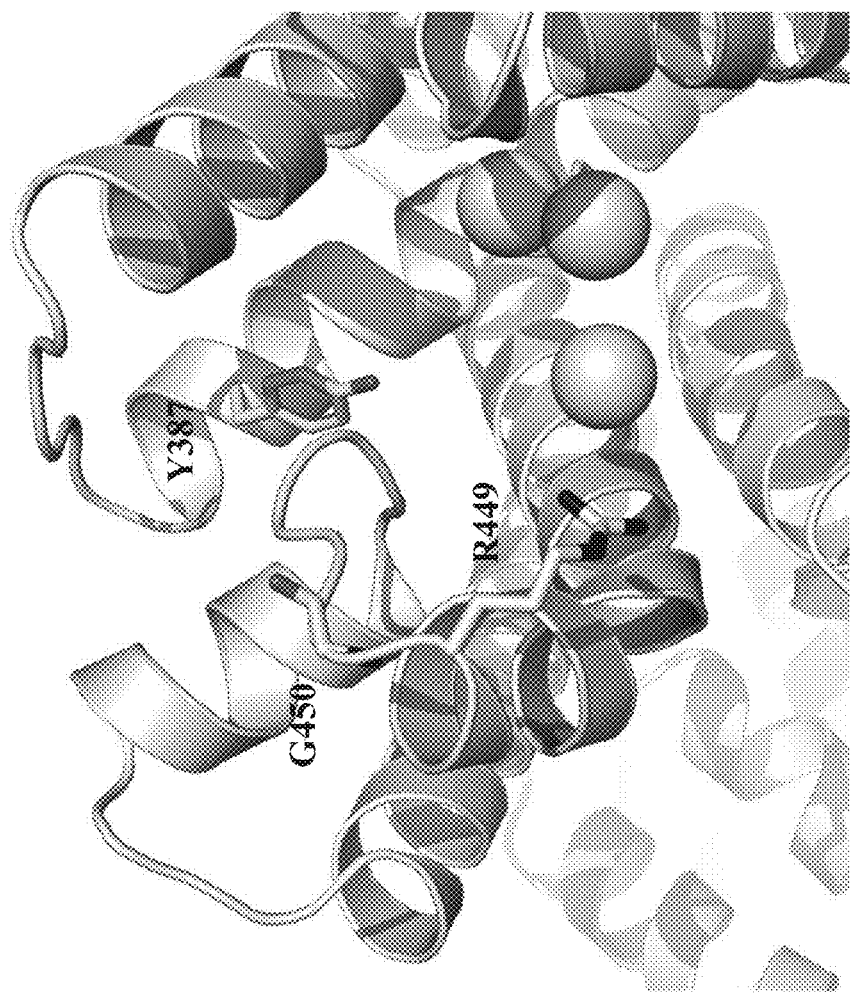
FIG. 29 shows the proposed substrate capture loop positions of IspS that do not tolerate substitution. $Mg^{2+}$ (spheres) are placed based on a structural alignment with PDB 1N24.

From the primary data, positions in MEA P. alba which tolerated no changes from the wild type residue were identified (see Table 17, FIGS. 23-29). MEA P. alba variants with amino acid substitutions other than wild type at these positions displayed specific activity no higher than 30% (PI≤0.3) of the value of WT, and were therefore functionally inactive. Wild type residues at these positions represent a minimum set that is required for the efficient conversion of DMAPP to isoprene by MEA P. alba. Many of these positions map to or near the active site of MEA P. alba (see FIG. 24), and are putatively involved in but are not limited to metal binding (for substrate orientation), substrate capture, substrate binding, and catalysis. FIG. 25, for example, shows a position that has an unknown role in enzyme function. FIG. 26 shows positions that may be involved in IspS dimer formation, and FIGS. 27 and 28 show positions that are in or interact with the N-terminus and may be involved in loop closure or function of the active site. FIG. 29 shows positions located in the substrate capture loops that tolerate no substitutions.

Figure 30:
FIG. 30 shows the monomer view of wild type IspS showing the location of sites where variants demonstrate improved specific activity.
Figure 31:
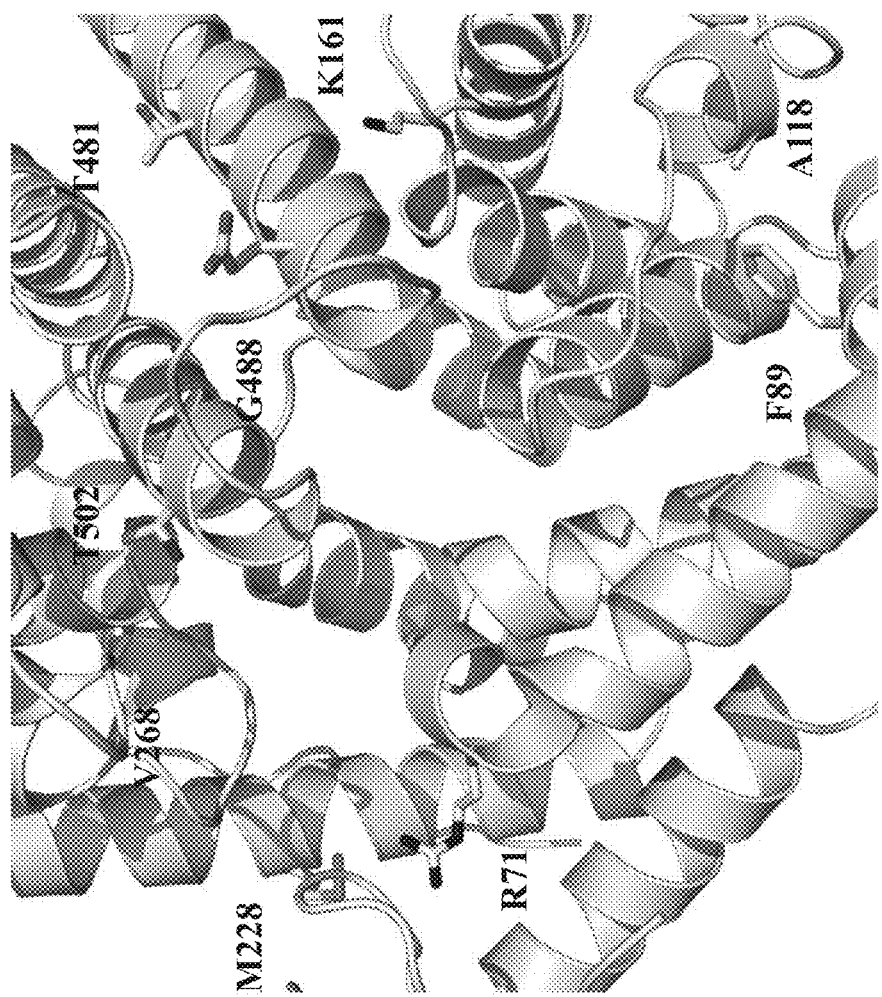
FIG. 31 shows the location of buried sites that are in or interact with the N-terminus of IspS, where variants demonstrated increased specific activity.
Figure 32:
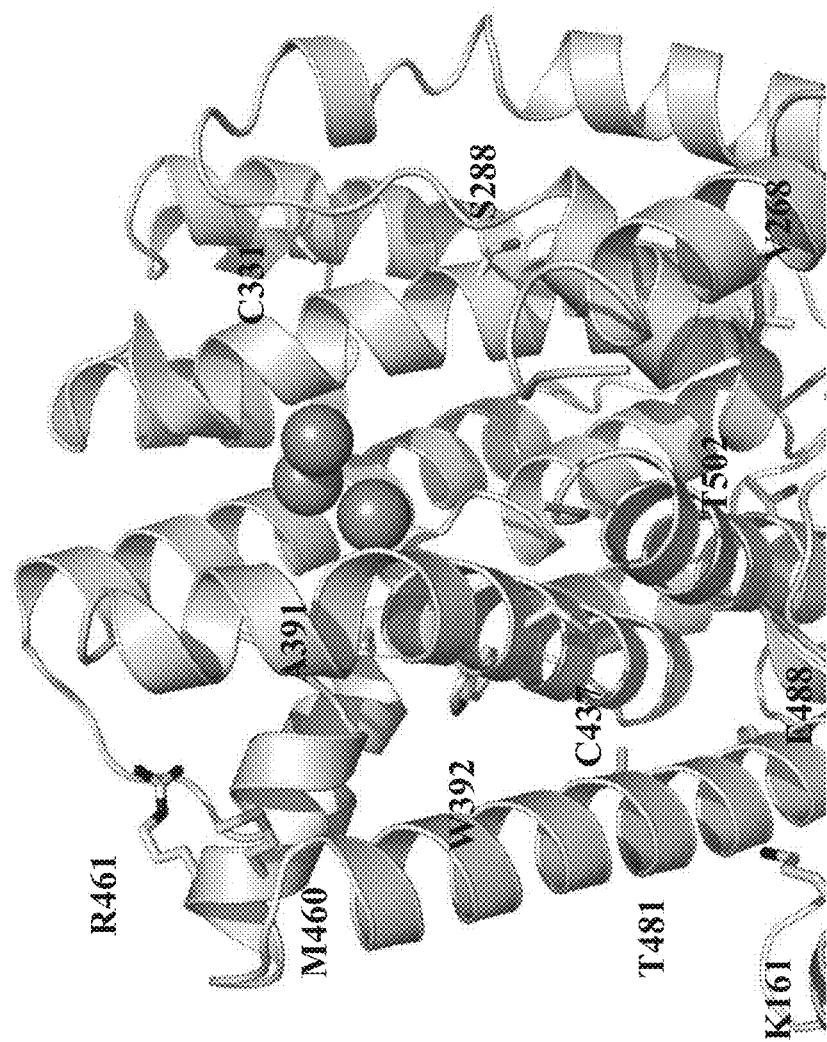
FIG. 32 shows the location of buried sites that are in or interact with the C-terminus of IspS, where variants demonstrated increased specific activity. $Mg^{2+}$ (spheres) are placed based on a structural alignment with PDB 1N24
Figure 33:
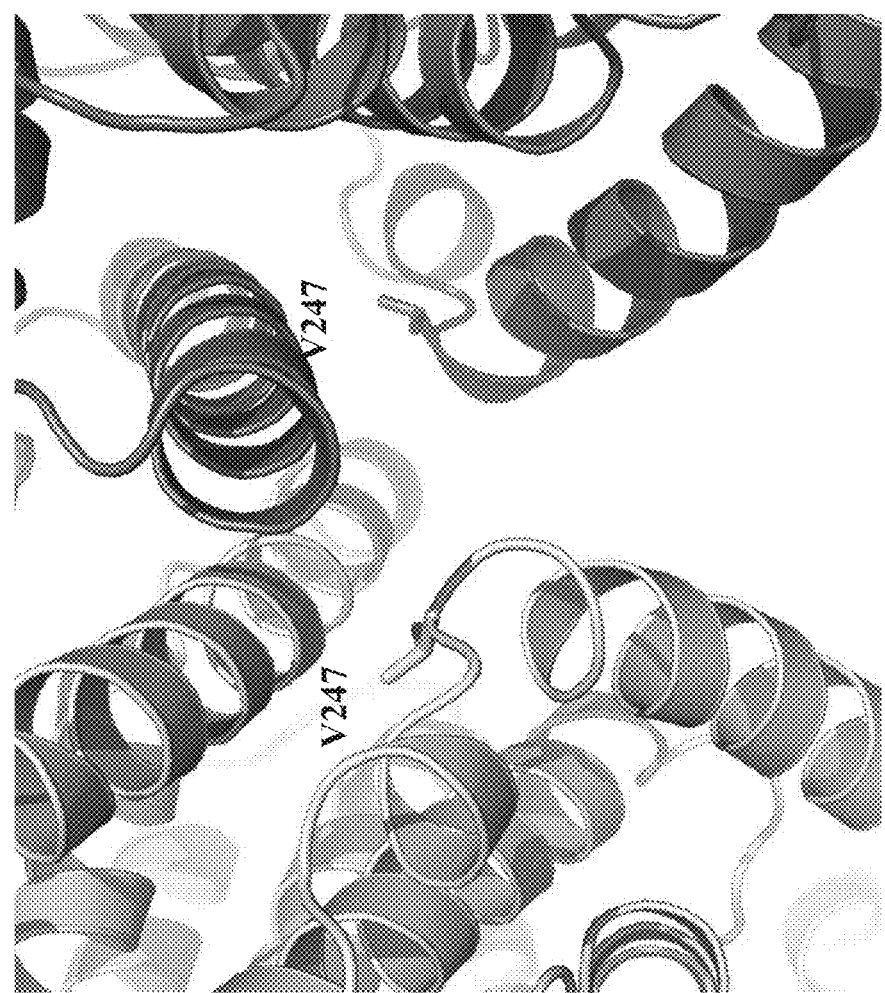
FIG. 33 shows the dimer interface of IspS, with chain A in light gray and chain B in dark gray. Variants at position 247 demonstrated improved specific activity.
Figure 34:
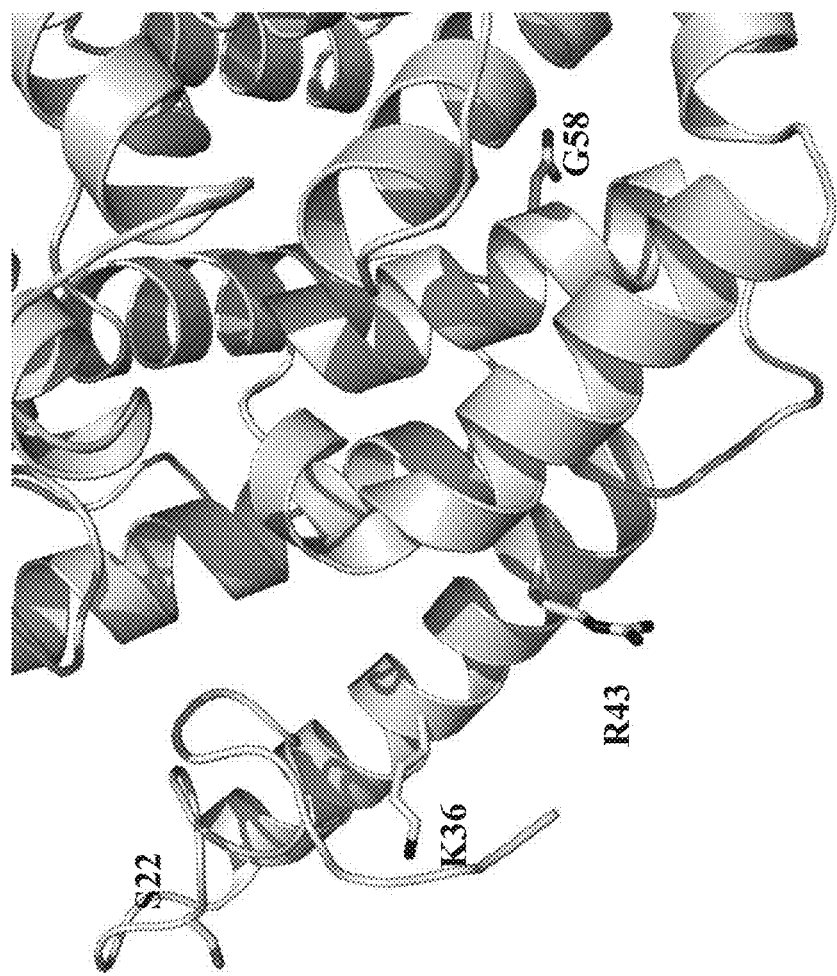
FIG. 34 shows the location of N-terminal sites of IspS where variants demonstrated improved specific activity.
Figure 35:
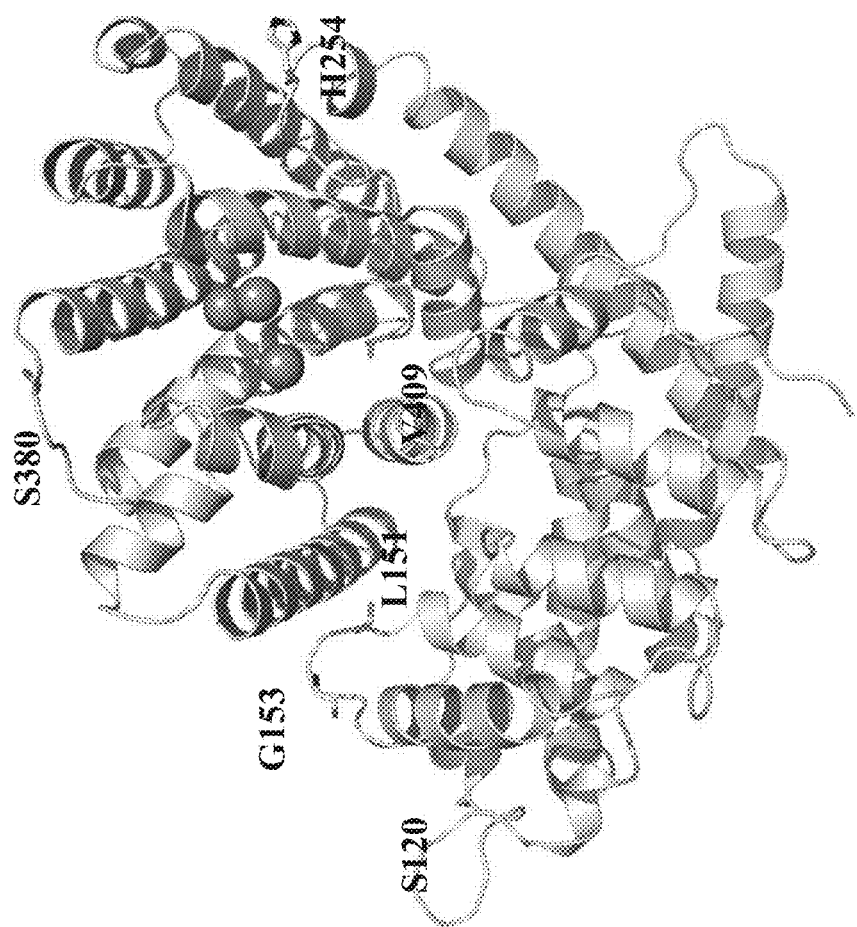
FIG. 35 shows the surface loop positions of IspS where variants demonstrated improved specific activity. $Mg^{2+}$ (spheres) are placed based on a structural alignment with PDB 1N24.
Figure 36:
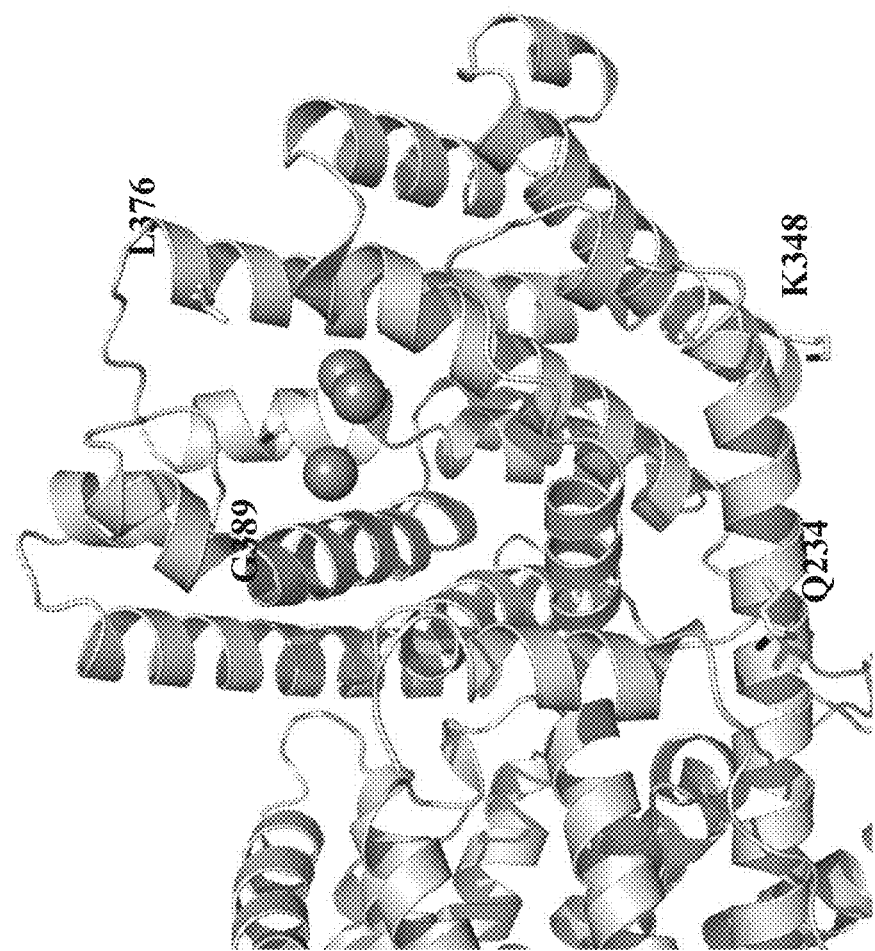
FIG. 36 shows the surface positions of IspS where variants demonstrated improved specific activity. $Mg^{2+}$ (spheres) are placed based on a structural alignment with PDB 1N24.
Figure 37:
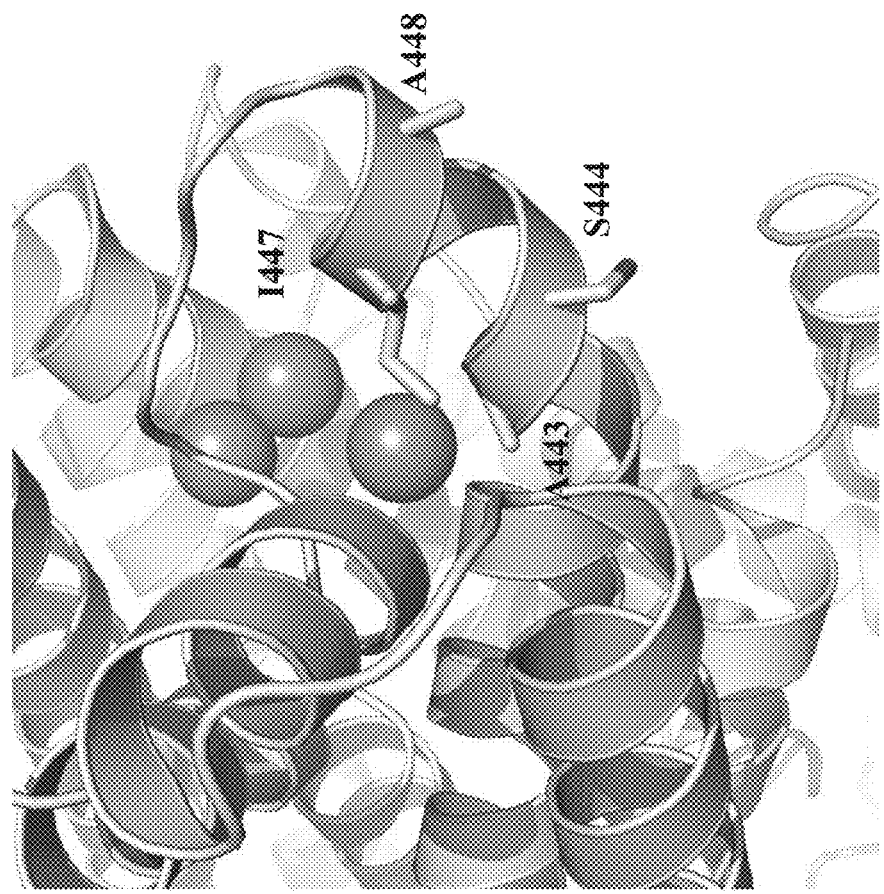
FIG. 37 shows the proposed substrate capture loop positions of IspS where variants demonstrated improved specific activity. $Mg^{2+}$ (spheres) are placed based on a structural alignment with PDB 1N24.

Variants that displayed specific activity higher than WT in the primary in vitro assay were selected for retesting. Variants were tested following the methods described above, except that polyclonal antibody in addition to monoclonal antibody was used for immunodetection, according to standard biochemical practices. Table 18 lists a set of retested variants that showed higher specific activity (a PI>1.3) than WT. FIG. 30 shows all positions in the crystal structure of IspS where variants displayed increased specific activity upon retest. In comparison to the wild type enzyme, these variants confer specific activity benefits to IspS by alteration/enhancement of the putative functions listed in Table 18. FIG. 31 shows buried positions in or that interact with the N-terminus of IspS and where variants displayed increased specific activity. FIG. 32 shows buried positions that are in or interact with the C-terminus of IspS, and where variants displayed increased specific activity. FIG. 33 shows position 247, where improved variants may positively affect dimerization of IspS, and FIG. 34 shows additional sites at the N-terminus where variants display clear specific activity benefits. FIG. 35 shows the locations of positions on surface loops where variants displayed high specific activity, and FIG. 36 shows positions on the surface of the enzyme that are not in loops, and where variants displayed increased specific activity. FIG. 37 shows positions in proposed substrate capture loops where variants displayed increased specific activity relative to wild type. Particular positions in this region have variants which displayed increased activity, whereas adjacent positions are immutable (see Table 17 and FIG. 29). This indicates that the proposed "substrate capture loops" in IspS are critical in the enzymatic conversion of DMAPP to isoprene, and are highly sensitive to perturbation, which can result in either negative or positive effects on activity. All variants listed in Table 18 and shown in FIGS. 30 through 37 or any combination thereof represent mutations in IspS that allow the enzyme to more efficiently convert DMAPP to isoprene.

TABLE 17

Positions in MEA *P. alba* displaying PI specific activity values ≤ 0.3 for all non-WT amino acid substitutions.

| Residue | Position | Location | % Surface Accessibility | Function |
|---|---|---|---|---|
| R | 4 | N-term | Not calc. | Conserved twin R presumably needed for N-term loop closure |
| Y | 9 | N-term | 65 | Based on model, this points into active site and interacts with D295 (part of DDxxD) |
| W | 243 | Dimer Interface | 9 | Base of dimer interface, in a hydrophobic pocket |
| D | 258 | N-term | 44 | Near active site; possible interaction with closed N-term tail (W244) |
| R | 259 | N-term | 29 | Near active site; possible interaction with closed N-term tail |
| E | 262 | N-term | 24 | Near active site; possible interaction with closed N-term tail |
| W | 266 | Active Site | 3 | Bottom of active site |
| R | 280 | Buried | 1 | Interacts with backbone of P274, possible loop stabilization |
| D | 294 | Active Site | 32 | Part of DDxxD motif |
| D | 295 | Active Site | 12 | Part of DDxxD motif |
| D | 298 | Active Site | 55 | Part of DDxxD motif |
| E | 305 | N-term | 19 | Possible interaction with R004 when N-term loop is closed |
| Y | 387 | Substrate Capture Loops | 7 | Substrate capture loop; role unknown |
| S | 396 | Active Site | 0 | points into active site |
| G | 397 | Active Site | 0 | in active site; allows for kink in helix |
| R | 435 | Active Site | 13 | points into active site |
| D | 439 | Active Site | 5 | likely metal binding |
| E | 446 | Active Site | 17 | likely metal binding |
| R | 449 | Substrate Capture Loops | 64 | Substrate capture loop; role unknown |
| G | 450 | Substrate Capture Loops | 78 | Substrate capture loop; role unknown, though likely structural |
| Y | 514 | Active Site | 28 | probably catalytic residue |
| D | 518 | Substrate Capture Loops | Not calc. | Substrate capture loop; role unknown |

TABLE 18

Retested variants of MEA *P. alba* displaying PI specific activity values > 1.3.

| Position | Mutation | Location | Charge Change | % Surface Accessibility | Function |
|---|---|---|---|---|---|
| 2 | V | N-term | 1 | Not calc. | alternate surface interactions |
| 22 | K | N-term | 1 | 54 | alternate surface interactions |
| 22 | R | N-term | 1 | 54 | alternate surface interactions |
| 36 | D | N-term | −2 | 33 | alternate interactions with nearby residues |
| 36 | E | N-term | −2 | 33 | alternate interactions with nearby residues |
| 36 | H | N-term | −1 | 33 | alternate interactions with nearby residues |
| 36 | W | N-term | −1 | 33 | alternate interactions with nearby residues |
| 43 | E | N-term | −2 | 52 | alternate interactions with nearby residues |
| 58 | F | N-term | 1 | 20 | alternate interactions with nearby residues |
| 71 | I | Buried | −1 | 3 | alternate interactions in hydrophobic pocket |
| 89 | D | Buried | −1 | 5 | alternate interactions in pocket |
| 89 | E | Buried | −1 | 5 | alternate interactions in pocket |
| 118 | E | Buried | −1 | 10 | alternate interactions in pocket |
| 118 | P | Buried | 0 | 10 | alternate interactions in pocket |
| 120 | M | surface loop | 0 | 52 | alternate surface interactions |
| 120 | Q | surface loop | 0 | 52 | alternate surface interactions |
| 151 | F | surface loop | 0 | 14 | alternate interactions in pocket |
| 151 | Y | surface loop | 0 | 14 | alternate interactions in pocket |
| 153 | P | surface loop | 0 | 40 | affect shape of loop |
| 161 | C | Buried | −1 | 10 | alternate interactions in pocket |
| 228 | Y | Buried | 0 | 5 | alternate interactions in pocket |
| 234 | R | Hinge region | 1 | 24 | alternate surface interactions |
| 247 | I | dimer interface | 0 | 5 | alternate interactions in pocket |
| 247 | L | dimer interface | 0 | 5 | alternate interactions in pocket |
| 247 | M | dimer interface | 0 | 5 | alternate interactions in pocket |
| 254 | C | surface loop | 0 | 89 | alternate surface interactions |
| 268 | I | Buried | 0 | 2 | alternate interactions in pocket |
| 282 | H | Buried | 0 | 8 | alternate interactions in pocket |
| 282 | W | Buried | 0 | 8 | alternate interactions in pocket |
| 288 | A | Buried | 0 | 0 | alternate interactions in pocket |
| 288 | T | Buried | 0 | 0 | alternate interactions in pocket |
| 288 | Y | Buried | 0 | 0 | alternate interactions in pocket |
| 331 | P | Buried | 0 | 0 | alternate interactions in pocket |
| 348 | Y | Dimer interface | −1 | 16 | alternate surface interactions |
| 376 | L | surface | 0 | 63 | alternate surface interactions |
| 380 | E | surface loop | −1 | 33 | alternate surface interactions |
| 389 | D | surface | −1 | 18 | alternate surface interactions |

TABLE 18-continued

Retested variants of MEA *P. alba* displaying PI specific activity values > 1.3.

| Position | Mutation | Location | Charge Change | % Surface Accessibility | Function |
|---|---|---|---|---|---|
| 391 | G | Buried | 0 | 0 | alternate interactions in pocket |
| 392 | C | Buried | 0 | 7 | alternate interactions in pocket |
| 392 | F | Buried | 0 | 7 | alternate interactions in pocket |
| 392 | M | Buried | 0 | 7 | alternate interactions in pocket |
| 392 | S | Buried | 0 | 7 | alternate interactions in pocket |
| 392 | V | Buried | 0 | 7 | alternate interactions in pocket |
| 392 | Y | Buried | 0 | 7 | alternate interactions in pocket |
| 409 | T | surface loop | 0 | 14 | alternate interactions in pocket |
| 437 | L | Buried | 0 | 7 | alternate interactions in pocket |
| 437 | M | Buried | 0 | 7 | alternate interactions in pocket |
| 443 | G | Substrate Capture Loops | 0 | 4 | affect shape of loop |
| 443 | Q | Substrate Capture Loops | 0 | 4 | affect shape of loop |
| 443 | R | Substrate Capture Loops | 1 | 4 | affect shape of loop |
| 443 | S | Substrate Capture Loops | 0 | 4 | affect shape of loop |
| 444 | D | Substrate Capture Loops | −1 | 56 | affect shape of loop |
| 444 | E | Substrate Capture Loops | −1 | 56 | affect shape of loop |
| 447 | T | Substrate Capture Loops | 0 | 23 | alternate interactions in pocket |
| 447 | V | Substrate Capture Loops | 0 | 23 | alternate interactions in pocket |
| 448 | V | Substrate Capture Loops | 0 | 77 | alternate surface interactions |
| 460 | A | Buried | 0 | 21 | alternate interactions in pocket |
| 461 | A | Buried | −1 | 32 | alternate interactions in pocket |
| 481 | Y | Buried | 0 | 0 | alternate interactions in pocket |
| 488 | L | Buried | 1 | 13 | alternate interactions in pocket |
| 502 | F | Buried | 0 | 1 | alternate interactions in pocket |
| 502 | M | Buried | 0 | 1 | alternate interactions in pocket |

Example 8

Growth Assay on 1024 Variants Selected from the Primary Screen

The primary in vitro specific activity screen identified variants of MEA *P. alba* that enhance the ability of the enzyme to catalyze the conversion DMAPP to isoprene. Since IspS must function inside a living cell, it was additionally necessary to measure the capability of the enzyme to convert DMAPP to isoprene in vivo. Examples 1 and 2 describe the methodology in determining the in vivo effectiveness of IspS. Essentially, by conversion of DMAPP to isoprene, IspS relieves the toxic effect of DMAPP on the growth of *E. coli*. Increased performance in comparison to wild type during the course of a growth curve indicates improved isoprene synthase function within a given strain. IspS variants that display both improved specific activity and the best growth performance are indicative of the enzymes best suited to improved isoprene production during fermentation.

Methods

Growth Assay and Specific Activity Measurements 1024 variants from the primary specific activity screen were selected for growth study and to confirm increased specific activity increases relative to the wild type MEA *P. alba* enzyme. Variants at positions that displayed high mutability (tolerance to mutation), and increased performance for both specific activity and expression not significantly less than wild type, were chosen for this study. Individual variants were isolated from their original glycerol stock plates and re-arrayed for the growth assay. Variants were induced at both low and high levels of IPTG, and their growth curves were determined in the presence of mevalonic acid (MVA). In these strains, MVA is taken up and drives flux through the mevalonic acid pathway to DMAPP, which is toxic to cell growth. Expression of functional *P. alba* IspS molecules allows for the conversion of DMAPP to isoprene, and the relief of growth inhibition. In these assays, better performing IspS molecules more effectively convert DMAPP to isoprene and result in improved growth.

Glycerol stocks of MEA *P. alba* IspS libraries were thawed briefly and inoculated into microtiter plates containing liquid LB with kanamycin at a concentration of 20 µg/ml. Cultures were grown overnight at 250 rpm, 30° C. to saturation in a shaking incubator. The next day, cultures were removed and inoculated at a ratio of 1:10 into TM3-glucose medium containing 50 ug/ml kanamycin and 40 or 100 uM IPTG (Sigma). Wild type controls were grown separately and inoculated into each microtiter plate containing TM3-glucose with a titration of IPTG concentrations, from 30 uM to 65 µM (for cultures induced at 40 µM), or 40 to 200 µM (for cultures induced at 100 µM), in separate wells. Plates were returned to the shaking incubator at 250 rpm, 30° C. and pre-induced for two hours. Cultures were then diluted into TM3-glucose medium containing 50 µg/ml kanamycin, 40 or 100 µM IPTG, and 20 mM MVA at a ratio of 1:10 in microtiter plates (Matrical). WT controls with or without MVA were included, as well as appropriate controls with titrations of IPTG. Plates were transferred to a Growth Profiler 1152 (Enzyscreen) and growth curves and optical densities (ODs) were determined according to the manufacturer's recommendation over a ten-hour time course. Performance indices (PIs) for growth of each strain were determined by comparison to four replicate WT strains induced at either 40 or 100 µM IPTG. PI values for OD at 300 minutes, Max OD, and area under the curve were calculated. Specific activity for all variants in this study, induced at the 40 µM IPTG level, was also determined according to the methods described in the previous example. Samples were isolated from the same pre-induction plate as the samples used in the growth assays.

Results

Figure 38:
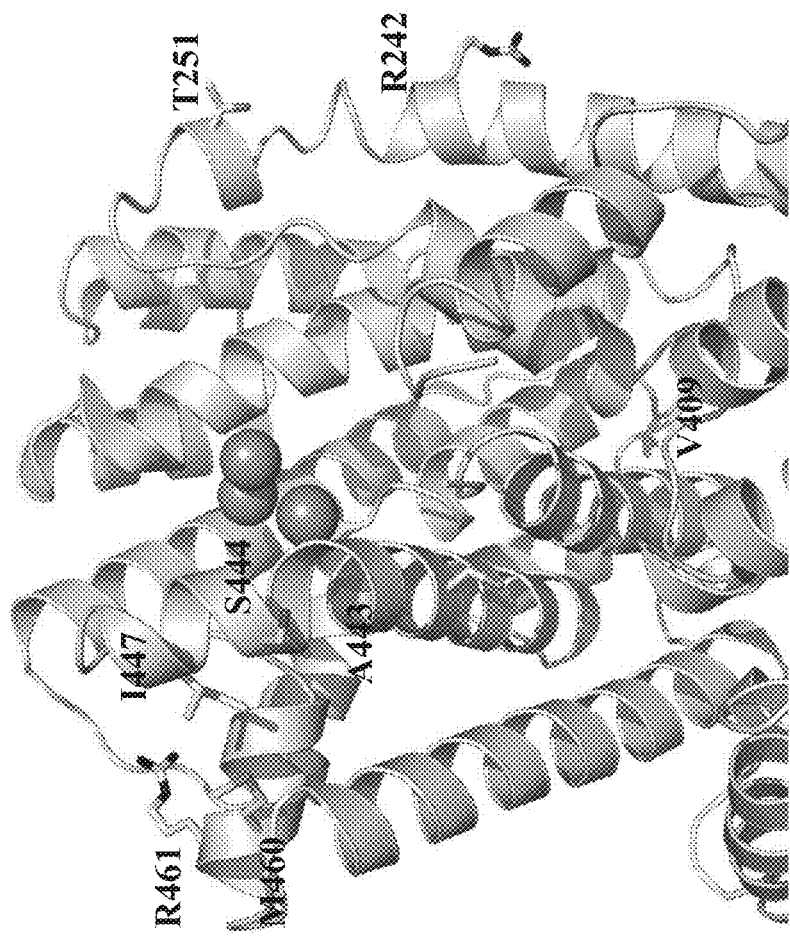
FIG. 38 shows positions of IspS demonstrating improved activity. $Mg^{2+}$ (spheres) are placed based on a structural alignment with PDB 1N24.
Figure 39:
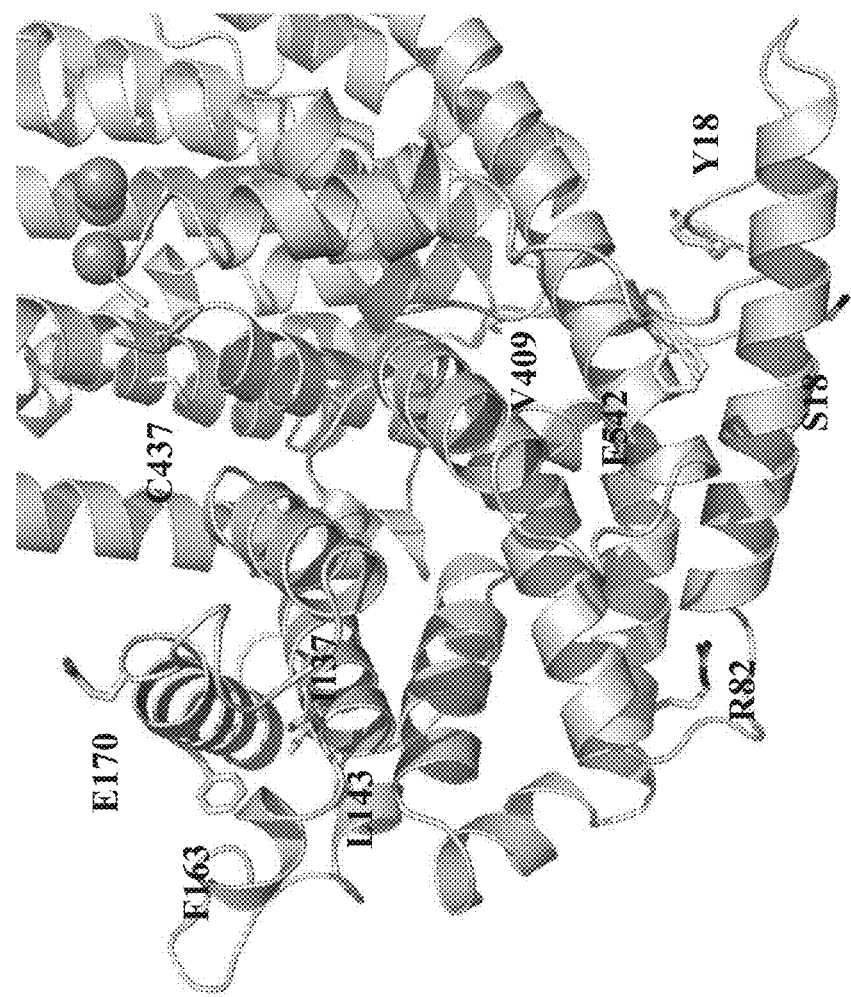
FIG. 39 shows positions of IspS demonstrating improved activity. $Mg^{2+}$ (spheres) are placed based on a structural alignment with PDB 1N24.

Table 16 provides definitions for locations of the residues listed in Tables 19 through 23. Table 19 lists all variants that displayed a PI value for specific activity greater than 1.4. Locations, surface accessibilities, and putative functions are also listed. Table 19 lists several variants that enhance the enzymatic efficiency of IspS, either alone or in combination. Locations of positions where variants displayed improved specific activity are shown in FIGS. 38 and 39. Variants with improved specific activity may allow for more efficient conversion of DMAPP to isoprene, and allow for improved cellular production of isoprene during fermentation.

Figure 40:
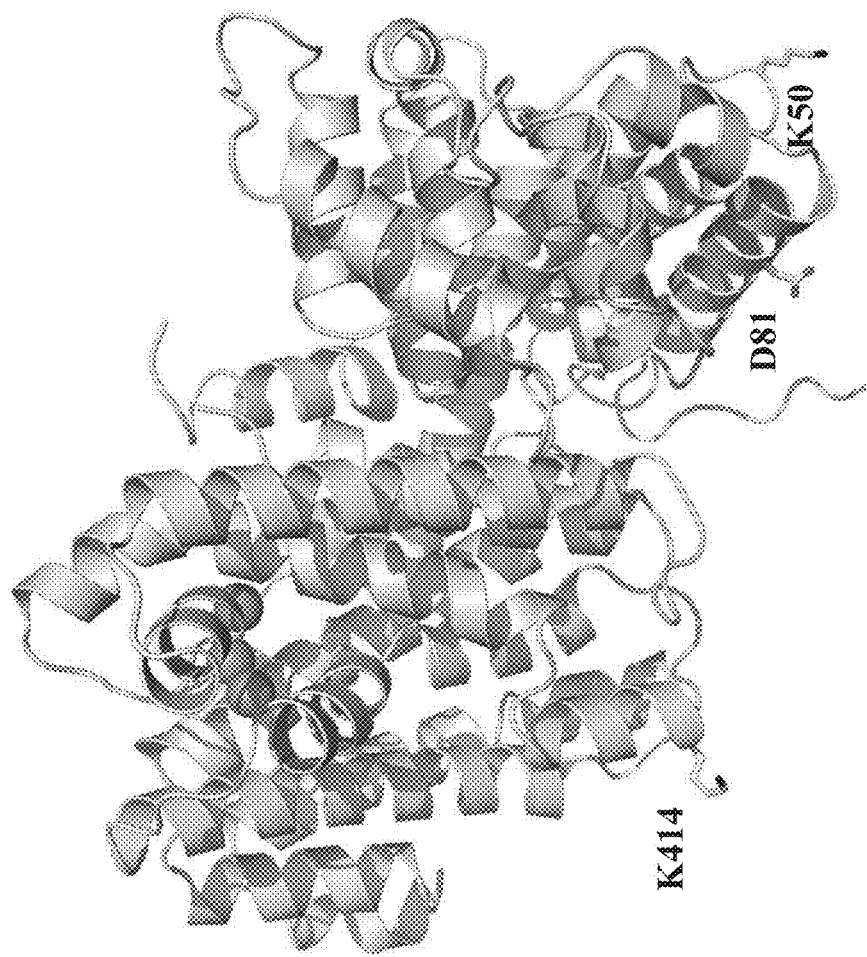
FIG. 40 shows monomer view of IspS showing N-terminal and Surface Loop positions demonstrating improved growth. $Mg^{2+}$ (spheres) are placed based on a structural alignment with PDB 1N24.
Figure 41:
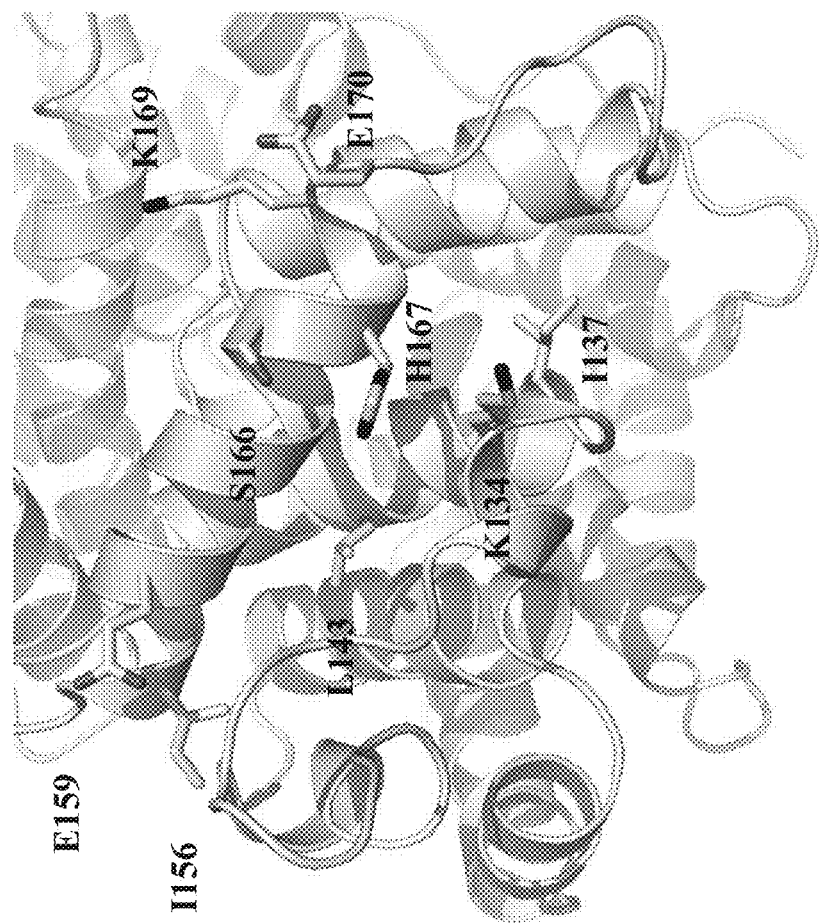
FIG. 41 shows monomer view of IspS showing N-terminal Helix positions demonstrating improved growth.
Figure 43:
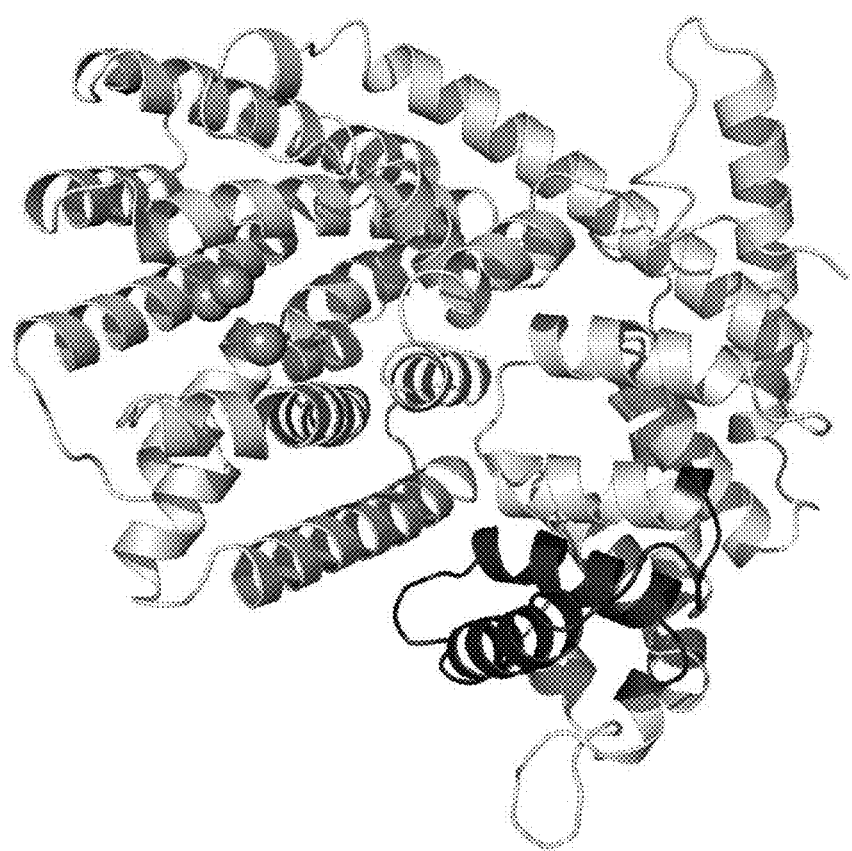
FIG. 43 shows monomer view of IspS with location of sites where variants demonstrate improved growth colored dark gray. $Mg^{2+}$ (spheres) are placed based on a structural alignment with PDB 1N24.
Figure 44:
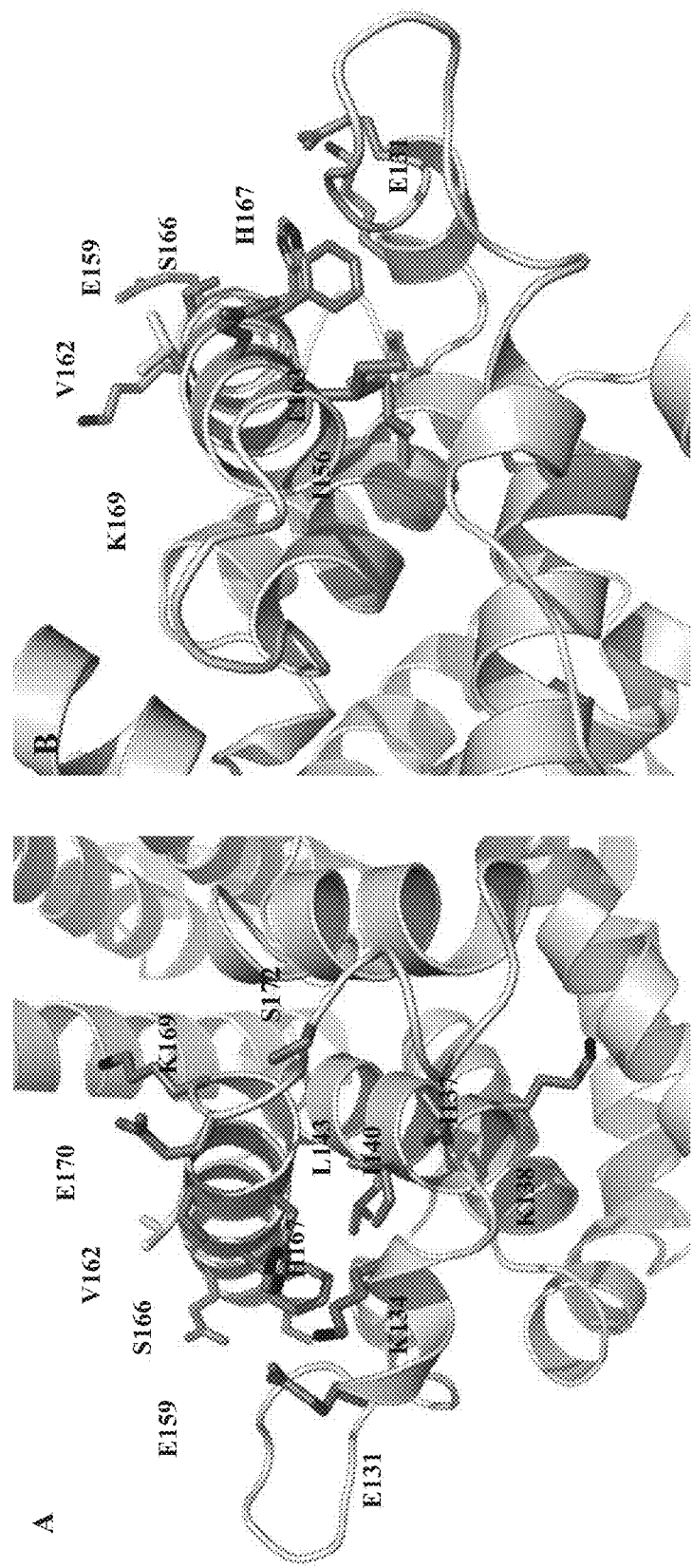
FIG. 44 shows view of IspS with location of sites where variants demonstrate improved growth shown as sticks. A and B are separated by 180°.

Tables 20 and 21 list variants with improved growth at the 40 uM and 100 uM induction level, respectively. While several different growth parameters were measured, all correlated well with each other, so only PI values for maximum OD (OD Max) were examined for variants listed in Tables 20 and 21. Listed variants displayed OD Max values that were 50% better than WT (PI of 1.5 or greater) at the given induction level. Variants that displayed improved growth (a PI value greater than 1.3 for OD Max) in both 40 uM and 100 uM IPTG induction conditions are listed in Table 22, and shown in FIGS. 40 and 41. These variants represent mutations that may allow for the highest overall growth performance and conversion of DMAPP to isoprene in cells expressing IspS. Several of these variants map near or within a particular N-terminal helix region of MEA *P. alba*, spanning residues 134 to 179. Several changes at or near this location ("N-term helices" in Tables 16, 20 through 23) displayed a growth benefit at either or both growth conditions. Not only do multiple variants map to this location in MEA *P. alba*, but the variants that displayed the largest benefit to growth are facing outwards from the helix and are located on the surface of the enzyme (see FIGS. 41, 43, and 44).

Table 23 lists variants that displayed improved performance (PI greater than 1.2) for all three parameters of specific activity, OD Max at 40 uM, and 100 uM IPTG. Several of these variants are listed in Table 22, and the majority of them are also located in or near the N-terminal helix described above, with the exceptions of V30K and V84T (see FIG. 42). This indicates that alterations at the helix spanning residues 150 to 172 are critical not only for improved growth of the host cell, but also for improved enzymatic activity. Since there is no obvious catalytic role for the N-terminal helix (see FIG. 43), these variants may influence IspS activity either intra-molecularly through conformational change of the enzyme structure, or inter-molecularly via the above-mentioned interactions with an unidentified enzyme, cellular process or structure. MEA *P. alba* enzymes harboring variants at this particular location, either alone or in combination with other variants conferring beneficial properties such as improved catalytic rates, likely will allow for improved growth rate of host strains, and improved isoprene production during fermentation.

TABLE 19

Retested variants of MEA *P. alba* that displayed PI values for specific activity > 1.4.

| Position | Mutation | Location | Charge Change | % Surface Accessibility | Function |
|---|---|---|---|---|---|
| 18 | E | N-term | −1 | 64 | alternate interactions with nearby residues |
| 18 | D | N-term | −1 | 64 | alternate interactions with nearby residues |
| 18 | S | N-term | 0 | 64 | alternate interactions with nearby residues |
| 36 | P | N-term | −1 | 33 | alternate interactions with nearby residues |
| 82 | Q | N-term | −1 | 27 | alternate interactions with nearby residues |

TABLE 19-continued

Retested variants of MEA *P. alba* that displayed PI values for specific activity > 1.4.

| Position | Mutation | Location | Charge Change | % Surface Accessibility | Function |
|---|---|---|---|---|---|
| 87 | S | surface loop | 0 | 35 | alternate surface interactions |
| 87 | N | surface loop | 0 | 35 | alternate surface interactions |
| 87 | R | surface loop | 1 | 35 | alternate surface interactions |
| 137 | C | N-term helices | 0 | 15 | alternate interactions in pocket |
| 143 | N | N-term helices | 0 | 1 | alternate interactions in hydrophobic pocket |
| 163 | I | N-term helices | 0 | 10 | alternate interactions in pocket |
| 163 | Q | N-term helices | 0 | 10 | alternate interactions in pocket |
| 170 | G | N-term helices | 1 | 79 | alternate surface interactions |
| 242 | T | Dimer interface | −1 | 35 | improve dimer interface interactions |
| 251 | E | surface | −1 | 74 | alternate interactions with nearby residues |
| 409 | S | surface loop | 0 | 14 | alternate interactions in pocket |
| 437 | M | Buried | 0 | 7 | alternate interactions in pocket |
| 437 | K | Buried | 1 | 7 | alternate interactions in pocket |
| 443 | G | Substrate Capture Loops | 0 | 4 | affect shape of loop |
| 443 | S | Substrate Capture Loops | 0 | 4 | affect shape of loop |
| 443 | Q | Substrate Capture Loops | 0 | 4 | affect shape of loop |
| 444 | p | Substrate Capture Loops | 0 | 56 | affect shape of loop |
| 447 | Q | Substrate Capture Loops | 0 | 23 | alternate interactions in pocket |
| 447 | T | Substrate Capture Loops | 0 | 23 | alternate interactions in pocket |
| 447 | M | Substrate Capture Loops | 0 | 23 | alternate interactions in pocket |
| 447 | E | Substrate Capture Loops | −1 | 23 | alternate interactions in pocket |
| 447 | S | Substrate Capture Loops | 0 | 23 | alternate interactions in pocket |
| 447 | R | Substrate Capture Loops | 1 | 23 | alternate interactions in pocket |
| 460 | Q | Buried | 0 | 21 | alternate interactions in pocket |
| 460 | S | Buried | 0 | 21 | alternate interactions in pocket |
| 460 | G | Buried | 0 | 21 | alternate interactions in pocket |
| 460 | A | Buried | 0 | 21 | alternate interactions in pocket |
| 461 | D | Buried | −2 | 32 | alternate interactions in pocket |
| 461 | S | Buried | −1 | 32 | alternate interactions in pocket |
| 461 | T | Buried | −1 | 32 | alternate interactions in pocket |

TABLE 19-continued

Retested variants of MEA *P. alba* that displayed
PI values for specific activity > 1.4.

| Position | Mutation | Location | Charge Change | % Surface Accessibility | Function |
|---|---|---|---|---|---|
| 461 | E | Buried | −2 | 32 | alternate interactions in pocket |
| 542 | N | surface loop | 0 | 17 | alternate interactions with nearby residues |

TABLE 20

Variants of MEA *P. alba* that displayed
PI values > 1.5 for OD Max at 40 mM IPTG

| Position | Mutation | Location | Charge Change | % Surface Accessibility | Function |
|---|---|---|---|---|---|
| 134 | P | N-term helices | −1 | 37 | loop stabilization |
| 138 | C | N-term helices | −1 | 53 | alternate interctions with nearby residues |
| 143 | F | N-term helices | 0 | 1 | alternate interactions in hydrophobic pocket |
| 143 | V | N-term helices | 0 | 1 | alternate interactions in hydrophobic pocket |
| 156 | G | N-term helices | 0 | 13 | allow more flexibility in loop |
| 159 | G | N-term helices | 1 | 32 | alternate interctions with nearby residues |
| 159 | Q | N-term helices | 1 | 32 | alternate interctions with nearby residues |
| 163 | C | N-term helices | 0 | 10 | alternate interctions with nearby residues |
| 163 | E | N-term helices | −1 | 10 | alternate interctions with nearby residues |
| 163 | Q | N-term helices | 0 | 10 | alternate interctions with nearby residues |
| 163 | V | N-term helices | 0 | 10 | alternate interctions with nearby residues |
| 163 | Y | N-term helices | 0 | 10 | alternate interctions with nearby residues |
| 166 | C | N-term helices | 0 | 46 | alternate surface interactions |
| 166 | D | N-term helices | −1 | 46 | alternate surface interactions |
| 166 | G | N-term helices | 0 | 46 | alternate surface interactions |
| 166 | P | N-term helices | 0 | 46 | alternate surface interactions |
| 166 | V | N-term helices | 0 | 46 | alternate surface interactions |
| 167 | M | N-term helices | 0 | 21 | alternate interctions with nearby residues |
| 170 | G | N-term helices | 1 | 79 | alternate surface interactions |
| 170 | H | N-term helices | 1 | 79 | alternate surface interactions |
| 170 | K | N-term helices | 2 | 79 | alternate surface interactions |
| 170 | N | N-term helices | 1 | 79 | alternate surface interactions |
| 170 | R | N-term helices | 2 | 79 | alternate surface interactions |
| 170 | S | N-term helices | 1 | 79 | alternate surface interactions |
| 170 | W | N-term helices | 1 | 79 | alternate surface interactions |
| 414 | F | surface loop | −1 | 70 | alternate surface interactions |
| 414 | G | surface loop | −1 | 70 | alternate surface interactions |
| 414 | N | surface loop | −1 | 70 | alternate surface interactions |
| 414 | P | surface loop | −1 | 70 | alternate surface interactions |

TABLE 20-continued

Variants of MEA *P. alba* that displayed
PI values > 1.5 for OD Max at 40 mM IPTG

| Position | Mutation | Location | Charge Change | % Surface Accessibility | Function |
|---|---|---|---|---|---|
| 421 | R | surface loop | 1 | 23 | alternate surface interactions |
| 491 | Q | surface loop | 0 | 58 | alternate surface interactions |
| 491 | V | surface loop | 0 | 58 | alternate surface interactions |
| 491 | Y | surface loop | 0 | 58 | alternate surface interactions |

TABLE 21

Variants of MEA *P. alba* that displayed
PI values > 1.5 for OD Max at 100 mM IPTG

| Position | Mutation | Location | Charge Change | % Surface Accessibility | Function |
|---|---|---|---|---|---|
| 29 | N | N-term | 1 | 34 | alternate surface interactions |
| 47 | V | surface loop | 0 | 16 | affect shape of loop |
| 86 | C | surface loop | 0 | 59 | alternate interactions |
| 94 | A | surface loop | −1 | 73 | affect shape of loop |
| 131 | F | N-term helices | 1 | 58 | improved interaction with neighboring his |
| 134 | E | N-term helices | −2 | 37 | loop stabilization |
| 134 | P | N-term helices | −1 | 37 | loop stabilization |
| 156 | G | N-term helices | 0 | 13 | allow more flexibility in loop |
| 162 | P | N-term helices | 0 | 60 | loop stabilization |
| 169 | C | N-term helices | −1 | 60 | alternate surface interactions |
| 178 | E | N-term helices | −2 | 73 | alternate surface interactions |
| 179 | T | N-term helices | 1 | 46 | alternate surface interactions |
| 231 | D | hinge region | −1 | 33 | alternate surface interactions |
| 231 | K | hinge region | 1 | 33 | alternate surface interactions |
| 231 | R | hinge region | 1 | 33 | alternate surface interactions |
| 231 | T | hinge region | 0 | 33 | alternate surface interactions |
| 231 | V | hinge region | 0 | 33 | alternate surface interactions |
| 242 | N | dimer interface | −1 | 35 | improve dimer interface interactions |
| 242 | I | dimer interface | −1 | 35 | improve dimer interface interactions |
| 369 | C | active site | 0 | 2 | alter active site cavity |
| 414 | C | surface loop | −1 | 70 | alternate surface interactions |
| 414 | F | surface loop | −1 | 70 | alternate surface interactions |
| 414 | G | surface loop | −1 | 70 | alternate surface interactions |
| 414 | N | surface loop | −1 | 70 | alternate surface interactions |
| 421 | D | surface loop | −1 | 23 | alternate surface interactions |

TABLE 22

Variants of MEA *P. alba* that displayed PI values > 1.3 for OD Max at 40 and 100 mM IPTG

| Position | Mutation | Location | Charge Change | % Surface Accessibility | Function |
|---|---|---|---|---|---|
| 50 | S | N-term | −1 | 86 | alternate surface interactions |
| 81 | F | N-term | 1 | 48 | alternate surface interactions |
| 134 | E | N-term helices | −2 | 37 | improved interaction with neighboring his |
| 134 | P | N-term helices | −1 | 37 | loop stabilization |
| 137 | N | N-term helices | 0 | 15 | alternate interactions in pocket |
| 143 | V | N-term helices | 0 | 1 | alternate interactions in hydrophobic pocket |
| 156 | G | N-term helices | 0 | 13 | allow more flexibility in loop |
| 159 | D | N-term helices | 0 | 32 | alternate interactions with nearby residues |
| 159 | G | N-term helices | 1 | 32 | allow more flexibility in loop |
| 159 | Q | N-term helices | 1 | 32 | alternate interactions with nearby residues |
| 166 | C | N-term helices | 0 | 46 | alternate surface interactions |
| 166 | W | N-term helices | 0 | 46 | alternate surface interactions |
| 167 | M | N-term helices | 0 | 21 | alternate interactions with nearby residues |
| 167 | N | N-term helices | 0 | 21 | alternate interactions with nearby residues |
| 169 | C | N-term helices | −1 | 60 | alternate surface interactions |
| 170 | H | N-term helices | 1 | 79 | alternate surface interactions |
| 170 | K | N-term helices | 2 | 79 | alternate surface interactions |
| 170 | W | N-term helices | 1 | 79 | alternate surface interactions |
| 414 | C | surface loop | −1 | 70 | alternate surface interactions |
| 414 | F | surface loop | −1 | 70 | alternate surface interactions |
| 414 | G | surface loop | −1 | 70 | alternate surface interactions |
| 414 | N | surface loop | −1 | 70 | alternate surface interactions |
| 414 | P | surface loop | −1 | 70 | alternate surface interactions |

TABLE 23

Variants of MEA *P. alba* that displayed PI values > 1.2 for Specific Activity, OD Max at 40 μM IPTG, and 100 μM IPTG

| Position | Mutation | Location | Charge Change | % Surface Accessibility | Function |
|---|---|---|---|---|---|
| 30 | K | N-term | 1 | 60 | replace surface hydrophobic w/charged |
| 84 | T | N-term | 0 | 30 | polar residue for better solvent interactions |
| 134 | C | N-term helices | −1 | 37 | size reduction, improved interaction with neighboring His |
| 134 | D | N-term helices | −2 | 37 | improved interaction with neighboring his |
| 134 | E | N-term helices | −2 | 37 | improved interaction with neighboring his |
| 140 | S | N-term helices | 0 | 1 | may improve interactions with other polar residues in pocket |
| 140 | T | N-term helices | 0 | 1 | may improve interactions with other |

TABLE 23-continued Variants of MEA *P. alba* that displayed PI values > 1.2 for Specific Activity, OD Max at 40 µM IPTG, and 100 µM IPTG

| Position | Mutation | Location | Charge Change | % Surface Accessibility | Function |
|---|---|---|---|---|---|
| 143 | F | N-term helices | 0 | 1 | polar residues in pocket alternate interactions in hydrophobic pocket |
| 143 | I | N-term helices | 0 | 1 | alternate interactions in hydrophobic pocket |
| 143 | M | N-term helices | 0 | 1 | alternate interactions in hydrophobic pocket |
| 143 | V | N-term helices | 0 | 1 | alternate interactions in hydrophobic pocket |
| 163 | I | N-term helices | 0 | 10 | alternate interactions in pocket |
| 163 | M | N-term helices | 0 | 10 | alternate interactions in pocket |
| 166 | P | N-term helices | 0 | 45 | stabilize helix |
| 166 | V | N-term helices | 0 | 45 | alternate surface interactions |
| 169 | Q | N-term helices | −1 | 60 | alternate surface interactions |
| 170 | H | N-term helices | 1 | 80 | alternate surface interactions |
| 170 | K | N-term helices | 2 | 80 | alternate surface interactions |
| 172 | V | N-term helices | 0 | 47 | affect shape of loop |

Example 9

Specific Activity and Growth Assays on Combinatorial Libraries

Single variants of MEA *P. alba* IspS improved for specific activity, growth, or both traits were selected for combination into three seven-member libraries.

Methods

Libraries were constructed in the pCL201 vector and transformed into the MD09-170 screening strain (DNA2.0). 160 individual variants, representing approximately 80 to 90% of the 128 possible combinations in each library, were screened for both specific activity and growth following the methods described in the previous examples. Table 24 lists the variants chosen for combinatorial libraries, their locations in the crystal structure, surface accessibilities, and selection criteria (either specific activity, growth or both). Putative functions for the amino acids at these positions were listed in Examples 7 and 8.

TABLE 24

Variants chosen for combinatorial libraries

| Residue | Position | Mutation | Library | Location | % Surface Accessibility | Selection Criteria |
|---|---|---|---|---|---|---|
| S | 288 | C | 1/2 | C-term | 0 | Growth (Solubility) |
| S | 22 | R | 1 | N-term | 54 | Specific Activity |
| R | 71 | I | 1 | N-term | 3 | Specific Activity |
| S | 444 | D | 1/2 | SubLoop | 56 | Specific Activity |
| M | 460 | A | 1 | SubLoop | 21 | Specific Activity |
| A | 443 | G | 1 | SubLoop | 4 | Specific Activity |
| T | 502 | M | 1 | Buried | 1 | Specific Activity |
| V | 409 | T | 2 | surface loop | 14 | Growth/Specific Activity |
| R | 242 | N | 2 | DimInt | 35 | Growth/Specific Activity |
| K | 414 | F | 2 | surface loop | 70 | Growth |
| V | 162 | P | 2 | N-term helix | 60 | Growth |
| G | 87 | R | 2 | surface loop | 35 | Growth/Specific Activity |
| S | 288 | T | 3 | C-term | 0 | Growth/Specific Activity |
| N | 47 | V | 3 | surface loop | 16 | Growth |
| I | 447 | T | 3 | SubLoop | 23 | Specific Activity |
| E | 170 | H | 3 | N-term helix | 79 | Growth |
| S | 231 | T | 3 | hinge region | 33 | Growth |

TABLE 24-continued

Variants chosen for combinatorial libraries

| Residue | Position | Mutation | Library | Location | % Surface Accessibility | Selection Criteria |
|---|---|---|---|---|---|---|
| K | 414 | N | 3 | surface loop | 70 | Growth |
| I | 156 | G | 3 | N-term helix | 13 | Growth |

Results

Figure 45:
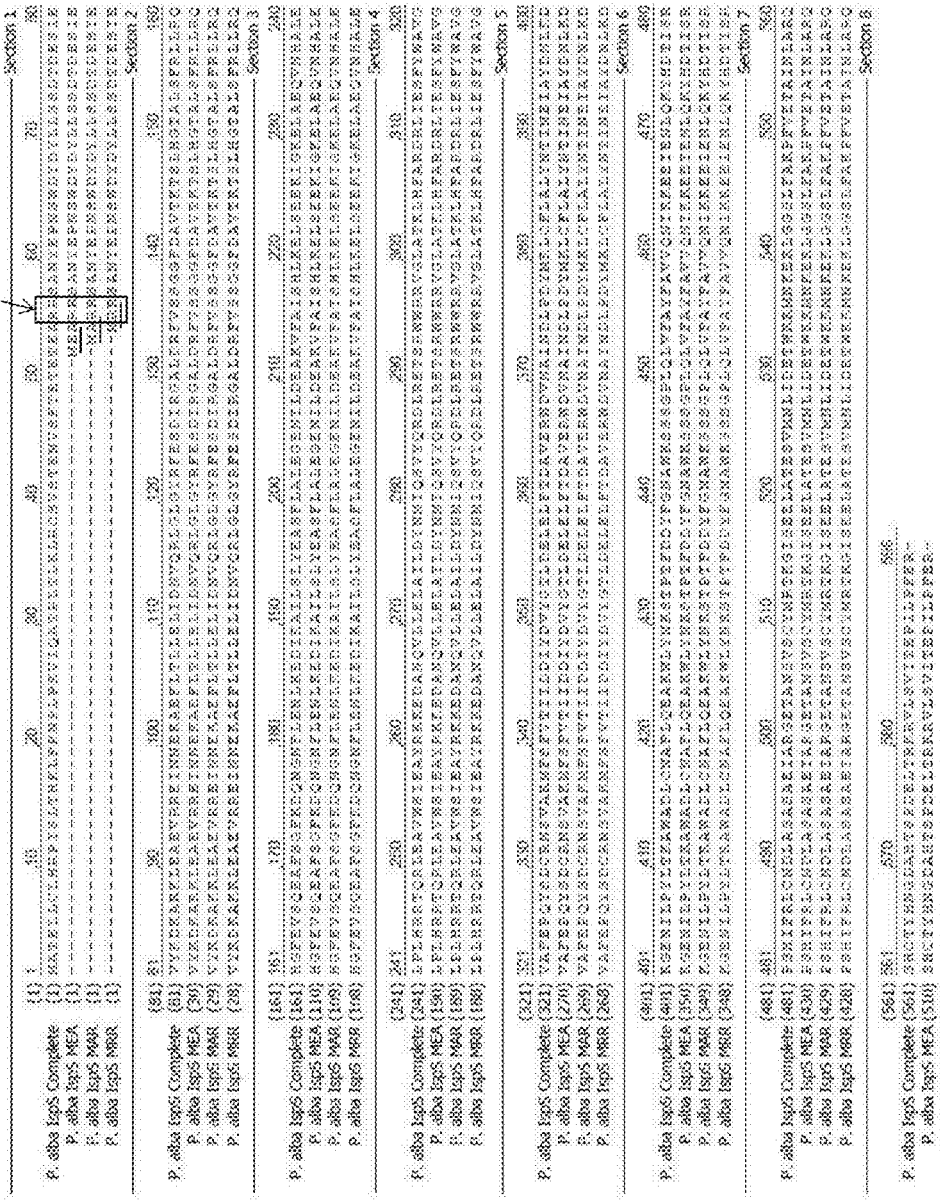
FIG. 45 shows an alignment of N-terminally truncated *P. alba* IspS molecules (SEQ ID NO:41, SEQ ID NO:1, SEQ ID NO:34, SEQ ID NO:36).

Combinatorial variants displaying significantly improved specific activity and/or growth performance were identified. Table 25 contains a list of combinatorial variants that displayed performance index (PI) values for specific activity greater than 2.6. The left hand column lists the variant number, and the subsequent columns list the genotype for the 7 different positions in that library. Variants with improved specific activity allow for more efficient enzymatic conversion of DMAPP to isoprene, likely by improved kinetic parameters. Table 26 contains a list of combinatorial variants that displayed PI values greater than 1.3 for specific activity, OD Max at 40 uM, and OD Max at 100 uM. IspS variants improved for both specific activity and growth parameters also convert DMAPP to isoprene more efficiently than the WT enzyme, and likely are beneficial to growth of the host strain by mediation of a deleterious effect of IspS within the host.

Since each library member contained any combination of seven possible mutations, effects of variants were observed multiple times in different configurations. This provided a robust internal control to help identify the most effective combinations present in each library. For example, the S444D mutation was present in the highest specific activity combinatorial variants, suggesting that this variant, in combination with other improved variants, is particularly beneficial for in vitro activity. M460A, A443G, and I447T also displayed this type of effect. Similarly, the V162P mutation was present in all combinatorial variants with improved properties for both specific activity and growth, suggesting that V162P works well in combination with other variants and may be an ideal mutation for more efficient conversion of DMAPP to isoprene within the host cell, for the reasons described in the previous paragraph. I156G and E170H also showed this effect. The variants G087R, R242N, and S288T also displayed improved specific activity in combination with other variants, but were not always among the highest performers for the in vitro assay. The combinatorial variants listed in Tables 25 and 26 may represent significantly improved IspS enzymes that allow for optimal conversion of DMAPP into isoprene during fermentation of host cells. The presence or absence of individual mutations in these particular combinatorial variants additionally may signify the best overall mutations that can be combined in future variants of IspS, critical to the optimization of isoprene production by fermentation of microorganisms.

TABLE 25

| Combinatorial variants of MEA *P. alba* displaying PI specific activity values >2.6. | | | | | | | |
|---|---|---|---|---|---|---|---|
| Variant | Pos 1 | Pos 2 | Pos 3 | Pos 4 | Pos 5 | Pos 6 | Pos 7 |
| 1 | 022R | 071I | 288C | 443A | 444D | 460A | 502M |
| 2 | 022R | 071I | 288C | 443G | 444D | 460A | 502M |
| 3 | 022S | 071I | 288C | 443A | 444S | 460A | 502T |
| 4 | 022S | 071R | 288C | 443A | 444D | 460A | 502T |
| 5 | 087G | 162P | 242N | 288S | 409T | 414F | 444D |
| 6 | 087G | 162P | 242N | 288S | 409T | 414K | 444D |
| 7 | 087G | 162P | 242R | 288C | 409T | 414F | 444D |
| 8 | 087G | 162V | 242N | 288C | 409V | 414F | 444D |
| 9 | 087G | 162V | 242R | 288C | 409T | 414F | 444D |
| 10 | 087G | 162V | 242R | 288C | 409V | 414K | 444D |
| 11 | 087R | 162P | 242N | 288C | 409T | 414F | 444D |
| 12 | 087R | 162P | 242N | 288C | 409T | 414K | 444D |
| 13 | 087R | 162P | 242N | 288S | 409T | 414K | 444D |
| 14 | 087R | 162P | 242N | 288S | 409V | 414F | 444D |
| 15 | 087R | 162P | 242N | 288S | 409V | 414K | 444D |
| 16 | 087R | 162P | 242R | 288C | 409T | 414F | 444D |
| 17 | 087R | 162P | 242R | 288C | 409V | 414F | 444D |
| 18 | 087R | 162P | 242R | 288C | 409V | 414K | 444D |
| 19 | 087R | 162P | 242R | 288S | 409T | 414F | 444D |
| 20 | 087R | 162P | 242R | 288S | 409V | 414K | 444D |
| 21 | 087R | 162V | 242N | 288C | 409V | 414F | 444D |
| 22 | 087R | 162V | 242N | 288S | 409T | 414F | 444D |
| 23 | 087R | 162V | 242N | 288S | 409T | 414K | 444D |
| 24 | 087R | 162V | 242N | 288S | 409V | 414F | 444D |
| 25 | 087R | 162V | 242R | 288C | 409T | 414K | 444D |
| 26 | 087R | 162V | 242R | 288C | 409V | 414K | 444D |
| 27 | 087R | 162V | 242R | 288S | 409V | 414F | 444D |

TABLE 26

| Combinatorial variants of MEA *P. alba* displaying PI >1.3 for specific activity, OD Max at 40 μM IPTG, and OD Max at 100 μM IPTG. | | | | | | | |
|---|---|---|---|---|---|---|---|
| Variant | Pos 1 | Pos 2 | Pos 3 | Pos 4 | Pos 5 | Pos 6 | Pos 7 |
| 1 | 047N | 156G | 170H | 231S | 288T | 414K | 447I |
| 2 | 047V | 156G | 170H | 231S | 288T | 414K | 447I |
| 3 | 047V | 156I | 170H | 231S | 288T | 414F | 447I |
| 4 | 047V | 156I | 170H | 231T | 288T | 414K | 447I |
| 5 | 087G | 162P | 242N | 288C | 409T | 414F | 444S |
| 6 | 087G | 162P | 242N | 288C | 409V | 414K | 444S |
| 7 | 087G | 162P | 242N | 288S | 409T | 414F | 444S |
| 8 | 087G | 162P | 242R | 288C | 409T | 414K | 444S |
| 9 | 087G | 162P | 242R | 288S | 409T | 414K | 444S |
| 10 | 087R | 162P | 242N | 288C | 409T | 414F | 444S |
| 11 | 087R | 162P | 242N | 288C | 409V | 414K | 444S |
| 12 | 087R | 162P | 242R | 288C | 409V | 414K | 444S |

Example 10

Specific Activity Determination of N-Terminal Truncations of MEA *P. alba* IspS

Isoprene synthase contains tandem arginine residues at the N-terminus that are necessary for proper enzymatic conversion of DMAPP to isoprene. As a truncated variant, MEA *P. alba* demonstrates high specific activity in comparison to enzymes with longer N-terminal regions, up to the naturally occurring chloroplast targeting peptide. The MEA *P. alba* enzyme has only two residues upstream of the tandem arginine residues (see FIG. 45), yet the function of these residues with regard to enzyme activity was not reported. N-terminal truncations of the MEA *P. alba* enzyme therefore were generated and assayed to determine if further truncations confer a specific activity benefit to IspS.

Methods

Figure 46:
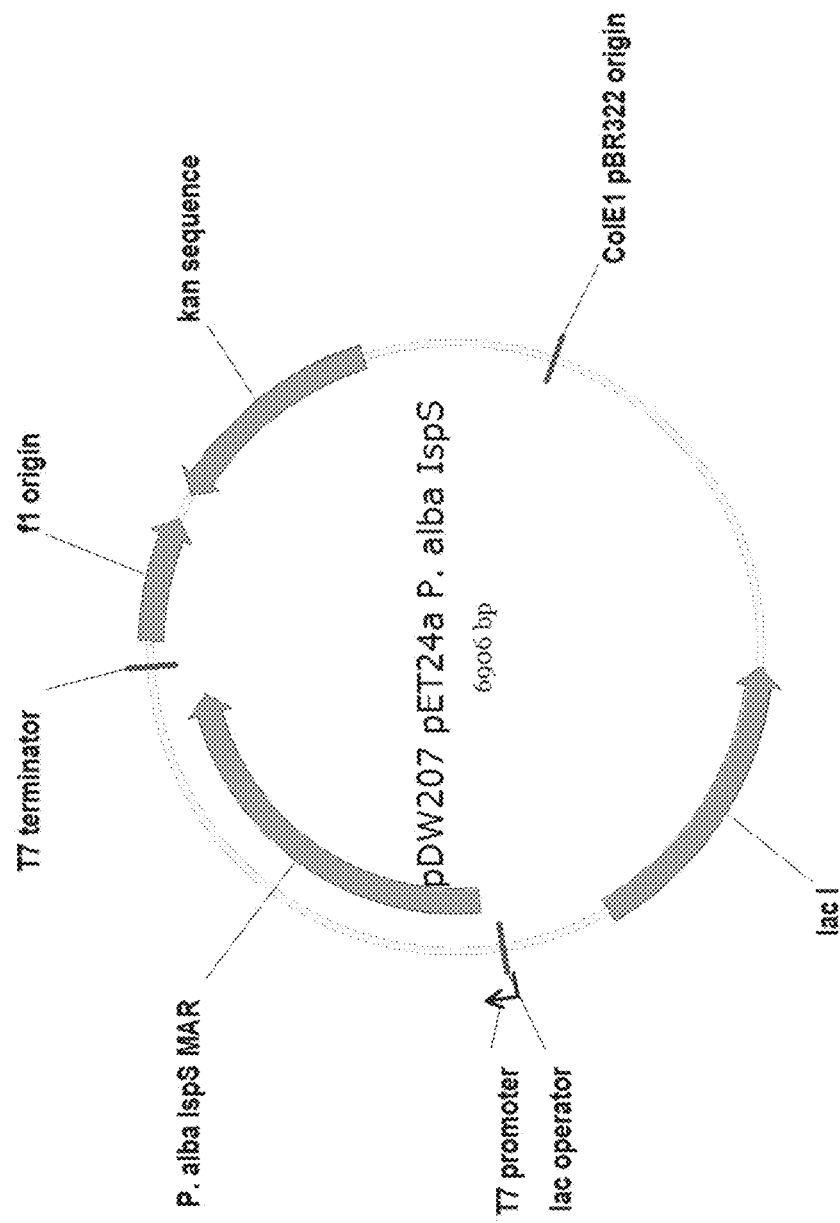
FIG. 46 shows a plasmid map of pDW207 harboring the *P. alba* IspS MAR variant.
Figure 47:
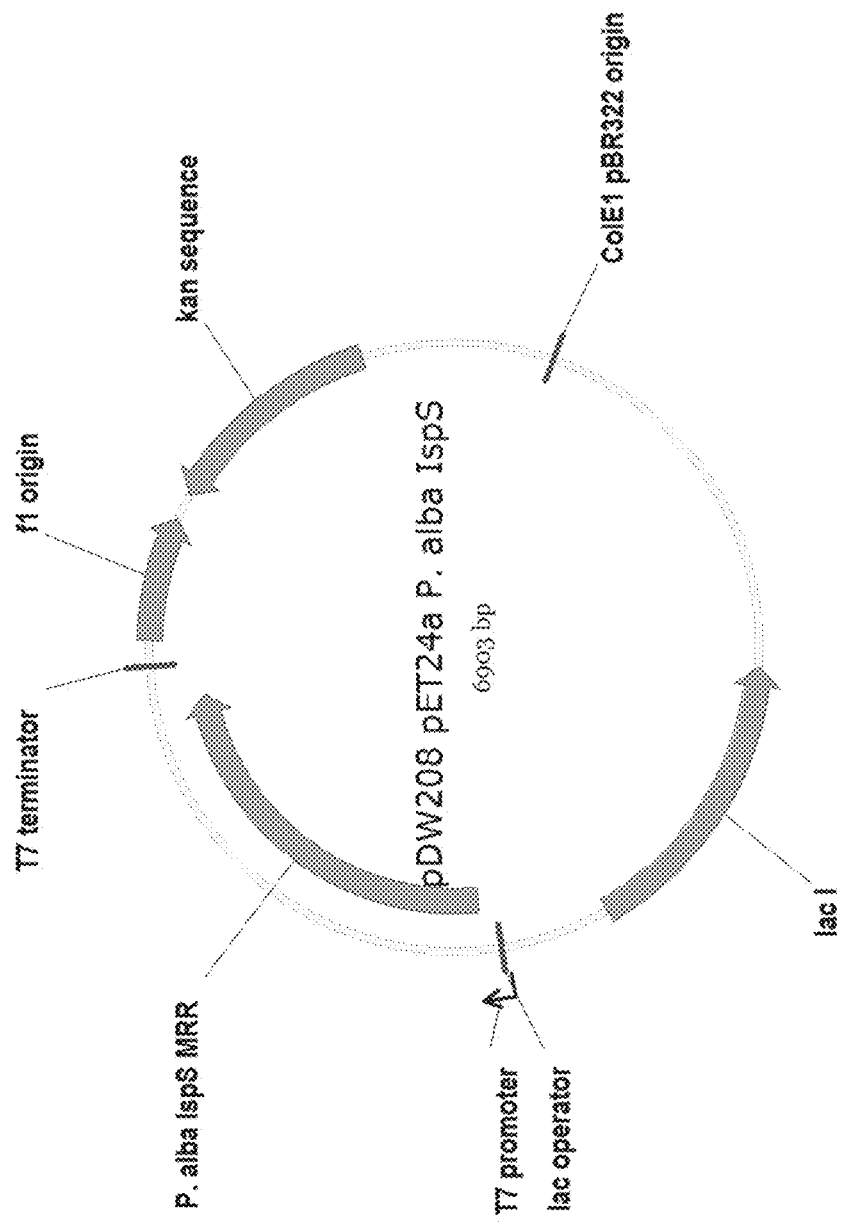
FIG. 47 shows a plasmid map of pDW208 harboring the *P. alba* IspS MRR variant.

The two truncations of MEA *P. alba* were constructed by QuikChange (Stratagene) PCR on the template pCL201 (see Table 27 for primer sequences) as previously described following the manufacturer's recommended protocol. The PCR product was treated with 1 μl DpnI (Roche) for 3 hours, and then 1 μl of the entire reaction was transformed into chemically competent *E. coli* Top10 cells (Invitrogen) according to the manufacturer's recommended protocol. Cells were recovered and plated on LB medium containing 50 μg/ml kanamycin. The next day, positive colonies were chosen for growth, plasmid purification (Qiagen) and sequencing (Quintara Biosciences). Plasmids which harbored the correct truncations were selected for sequencing of the entire open reading frame to confirm the integrity of the coding sequence. These plasmids, pDW207 (see FIG. 46) and pDW208 (see FIG. 47), were transformed by electroporation into the expression strain MD09-170 for determination of specific activity (see Table 28). Specific activity was determined as previously described. At least 30 replicates of each truncation were analyzed in comparison to MEA *P. alba*.

TABLE 27

| Primers used for QuikChange Mutagenesis | |
|---|---|
| HgS MRR Forward | TATACATATGCGTCGCTCTGCGAACTACGA (SEQ ID NO: 30) |
| HgS MRR Reverse | CAGAGCGACGCATATGTATATCTCCTTCTT (SEQ ID NO: 31) |
| HgS MAR Forward | TATACATATGGCACGTCGCTCTGCGAACTA (SEQ ID NO: 32) |
| HgS MAR Reverse | AGCGACGTGCCATATGTATATCTCCTTCTT (SEQ ID NO: 33) |

TABLE 28

Strains with N-terminal truncations

| Strain | Plasmid | Description |
|---|---|---|
| DW618 | pDW207 | BL21 (DE3) PL.2-mKKDyI + *P. alba* IspS MAR (−1 from MEA *P. alba*) |
| DW619 | pDW208 | BL21 (DE3) PL.2-mKKDyI + *P. alba* IspS MRR (−2 from MEA *P. alba*) |

Results

Specific activities of the truncated molecules of *P. alba* IspS expressed in strains DW618 (MAR) or DW619 (MRR) were either not improved or slightly lower, respectively, than the parental MEA *P. alba* enzyme. Table 29 shows performance index values for both the MAR and MRR truncations of *P. alba* IspS. The MAR truncation displayed specific activity that was approximately equivalent to the control MEA *P. alba* molecule, and the MRR truncation displayed specific activity that was approximately 81% of the control. Although these truncations did not have increased specific activity in comparison to MEA *P. alba*, they retained sufficient activity to be of potential future use in fermentation strains that convert DMAPP to isoprene via an IspS enzyme, where complete removal of the N-terminus up to but not including the tandem arginine residues is required.

TABLE 29

Performance index values for truncated variants of *P. alba* IspS

| Strain | Variant | PI Specific Activity | Standard Deviation |
|---|---|---|---|
| DW618 | MAR | 0.983189 | 0.091889 |
| DW619 | MRR | 0.813857 | 0.072938 |

Amino Acid Sequence of *P. alba* IspS MAR (SEQ ID NO: 34)

MARRSANYEPNSWDYDYLLSSDTDESIEVYKDKAKKLEAEVRREINNEKAEFLTLLELI

DNVQRLGLGYRFESDIRGALDRFVSSGGFDAVTKTSLHGTALSFRLLRQHGFEVSQEAF

SGFKDQNGNFLENLKEDIKAILSLYEASFLALEGENILDEAKVFAISHLKELSEEKIGKEL

AEQVNHALELPLHRRTQRLEAVWSIEAYRKKEDANQVLLELAILDYNMIQSVYQRDLR

ETSRWWRRVGLATKLHFARDRLIESFYWAVGVAFEPQYSDCRNSVAKMFSFVTIIDDIY

DVYGTLDELELFTDAVERWDVNAINDLPDYMKLCFLALYNTINEIAYDNLKDKGENILP

YLTKAWADLCNAFLQEAKWLYNKSTPTFDDYFGNAWKSSSGPLQLVFAYFAVVQNIK

KEEIENLQKYHDTISRPSHIFRLCNDLASASAEIARGETANSVSCYMRTKGISEELATESV

MNLIDETWKKMNKEKLGGSLFAKPFVETAINLARQSHCTYHNGDAHTSPDELTRKRVL

SVITEPILPFER

TABLE 29-continued

Performance index values for truncated variants of *P. alba* IspS

DNA Sequence of plasmid pDW207 (SEQ ID NO: 35)

tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttcccgtcaagtctaaatcggggctccctttaggttcc
gatttagtgctttacggcacctcgaccccaaaaaacttgattagggtgatggttcacgtagtgggccatcgccctgatagacggttttcgccc
tttgacgttggagtccacgttctttaatagtggactcttgttccaaactggaacaacactcaaccctatctcggtctattcttttgatttataagggat
tttgccgatttcggcctattggttaaaaaatgagctgatttaacaaaaatttaacgcgaatttttaacaaaatattaacgtttacaatttcaggtggca
cttttcggggaaatgtgcgcggaacccctatttgtttattttctaaatacattcaaatatgtatccgctcatgaattaattcttagaaaaactcatcg
agcatcaaatgaaactgcaatttattcatatcaggattatcaataccatattttgaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacaccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccaggggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaacccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcgga TABLE 29-continued Performance index values for truncated variants of *P. alba* IspS aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgcccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag
ccagccagacgcagacgcgccgagacagaacttaatgggcccgctaacagcgcgatttgctggtgacccaatgcgaccagatgctccac
gcccagtcgcgtaccgtcttcatgggagaaaataatactgttgatggg TABLE 29-continued Performance index values for truncated variants of P. alba IspS Amino Acid Sequence of P. alba IspS MRR (SEQ ID NO: 36)

MRRSANYEPNSWDYDYLLSSDTDESIEVYKDKAKKLEAEVRREINNEKAEFLTLLELID
NVQRLGLGYRFESDIRGALDRFVSSGGFDAVTKTSLHGTALSFRLLRQHGFEVSQEAFS
GFKDQNGNFLENLKEDIKAILSLYEASFLALEGENILDEAKVFAISHLKELSEEKIGKELA
EQVNHALELPLHRRTQRLEAVWSIEAYRKKEDANQVLLELAILDYNMIQSVYQRDLRET
SRWWRRVGLATKLHFARDRLIESFYWAVGVAFEPQYSDCRNSVAKMFSFVTIIDDIYDV
YGTLDELELFTDAVERWDVNAINDLPDYMKLCFLALYNTINEIAYDNLKDKGENILPYL
TKAWADLCNAFLQEAKWLYNKSTPTFDDYFGNAWKSSSGPLQLVFAYFAVVQNIKKE
EIENLQKYHDTISRPSHIFRLCNDLASASAEIARGETANSVSCYMRTKGISEELATESVMN
LIDETWKKMNKEKLGGSLFAKPFVETAINLARQSHCTYHNGDAHTSPDELTRKRVLSVI
TEPILPFER

Sequence of plasmid pDW208 (SEQ ID NO: 37)

tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgggggctcccctttagggttcc
gatttagtgctttacggcacctcgaccccaaaaaacttgattagggtgatggttcacgtagtgggccatcgccctgatagacggttttcgccc
tttgacgttggagtccacgttctttaatagtggactcttgttccaaactggaacaacactcaaccctatctcggtctattcttttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaacccctatttgtttatttttctaaatacattcaaatatgtatccgctcatgaattaattcttagaaaaactcatcg
agcatcaaatgaaactgcaatttattcatatcaggattatcaataccatattttttgaaaaagccgtttctgtaatgaaggagaaaactcaccgag
gcagttccataggatggcaagatcctggtatcggtctgcgattccgactcgtccaacatcaatacaacctattaatttcccctcgtcaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctaccttttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacacccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccaggggggaaacgcctggtatctttatagtcctgtcgggtttcgccacctctgacttgagcgtcgatttttgtgatgctcgtcaggggg
cggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc TABLE 29-continued Performance index values for truncated variants of *P. alba* IspS accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtgggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggttttctttttcacca
gtgagacgggcaacagctgattgcccttcaccgcctggccctgagagagttgcagcaagcggtccacgctggtttgcccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaatttgattgcgagtgagatatttatgccag
ccagccagacgcagacgcgccgagacagaacttaatgggccgctaacagcgcgatttgctggtgacccaatgcgaccagatgctccac
gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccacttttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtccccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
tagggggaattgtgagcggataacaattcccctctagaaataattttgtttaacttaagaaggagatatacatatgcgtcgctctgcgaactacg
aacctaacagctgggactatgattacctgctgtcctccgacacggacgagtccatcgaagtatacaaagacaaagcgaaaaagctggaag
ccgaagttcgtcgcgagattaataacgaaaaagcagaatttctgaccctgctggaactgattgacaacgtccagcgcctgggcctgggttac
cgtttcgagtctgatatccgtggtgcgctggatcgcttcgtttcctccggcggcttcgatgcggtaaccaagacttccctgcacggtacggca
ctgtctttccgtctgctgcgtcaacacggttttgaggtttctcaggaagcgttcagcggcttcaaagaccaaaacggcaacttcctggagaac
ctgaaggaagatatcaaagctatcctgagcctgtacgaggccagcttcctggctctggaaggcgaaaacatcctggacgaggcgaaggtt
tcgcaatctctcatctgaaagaactgtctgaagaaaagatcggtaaagagctggcagaacaggtgaaccatgcactggaactgccactgca
tcgccgtactcagcgtctggaagcagtatggtctatcgaggcctaccgtaaaaaggaggacgcgaatcaggttctgctggagctggcaatt
ctggattacaacatgatccagtctgtataccagcgtgatctgcgtgaaacgtcccgttggtggcgtcgtgtgggtctggcgaccaaactgcac
tttgctcgtgaccgcctgattgagagcttctactgggccgtgggtgtagcattcgaaccgcaatactccgactgccgtaactccgtcgcaaaa
atgttttcttcgtaaccattatcgacgatatctacgatgtatacggcacccctggacgaactggagctgtttactgatgcagttgagcgttgggac
gtaaacgccatcaacgacctgccggattacatgaaactgtgctttctggctctgtataacactattaacgaaatcgcctacgacaacctgaaa TABLE 29-continued Performance index values for truncated variants of P. alba IspS

```
gataaaggtgagaacatcctgccgtatctgaccaaagcctgggctgacctgtgcaacgctttcctgcaagaagccaagtggctgtacaaca
aatctactccgacctttgacgactacttcggcaacgcatggaaatcctcttctggcccgctgcaactggtgttcgcttacttcgctgtcgtgcag
aacattaaaaaggaagagatcgaaaacctgcaaaaataccatgacaccatctctcgtccttcccatatcttccgtctgtgcaatgacctggcta
gcgcgtctgcggaaattgcgcgtggtgaaaccgcaaatagcgtttcttgttacatgcgcactaaaggtatctccgaagaactggctaccgaa
agcgtgatgaatctgatcgatgaaacctggaaaaagatgaacaaggaaaaactgggtggtagcctgttcgcgaaaccgttcgtggaaacc
gcgatcaacctggcacgtcaatctcactgcacttatcataacggcgacgcgcatacctctccggatgagctgacccgcaaacgcgttctgtc
tgtaatcactgaaccgattctgccgtttgaacgctaaggatccgaattcgagctccgtcgacaagcttgcggccgcactcgagcaccaccac
caccaccactgagatccggctgctaacaaagcccgaaaggaagctgagttggctgctgccaccgctgagcaataactagcataacccctt
ggggcctctaaacgggtcttgaggggttttttgctgaaaggaggaactatatccggat
```

Example 11

Productive Mutations, Combinable Mutations and Suitability Score

Productive positions are described as those positions within a molecule that are most useful for making combinatorial variants exhibiting an improved characteristic, where the position itself allows for at least one combinable mutation. Combinable mutations can be described as those substitutions in a molecule that can be used to make selected combinatorial variants. Combinable mutations do not significantly decrease expression, specific activity or growth, while at the same time improving at least one desired characteristic of the molecule such as growth or specific activity. Positions in IspS containing all combinable mutations were determined using performance index (PI) values resulting from the DMAPP assay for specific activity and protein determination, as described in Example 7. Productive positions are the positions which have shown a certain degree of tolerance for multiple substitutions, while at the same time meeting a set of criteria for combinability as set forth below.

When evaluating the data set, the most productive positions were determined when the following criteria were applied:

Positions containing substitutions where the minimum performance indices (PI) relative to wild type IspS for specific activity and expression are greater than or equal to a PI of 0.9 and where at least one PI relative to wild type IspS for specific activity or growth is greater than or equal to a PI of 1.0 (Group A).

Positions containing substitutions where the minimum performance indices (PI) relative to wild type IspS for specific activity and expression are greater than or equal to a PI of 0.8 and where at least one PI relative to wild type IspS for specific activity or growth is greater than or equal to a PI of 1.2 (Group B).

Positions containing substitutions where the minimum performance indices (PI) relative to wild type IspS for specific activity and expression are greater than or equal to a PI of 0.5 and where at least one PI relative to wild type IspS for specific activity or growth is greater than or equal to a PI of 1.5 (Group C).

Groups A, B, and C further contain positions that have differing degrees of tolerance for multiple substitutions. To measure this degree of substitutions tolerated, a Rank was assigned to each position. The Rank was assigned according to the percentage of the substitutions within each position that fall within groups A, B, or C. Combinable positions and substitutions are shown in Table 31.

The criteria to determine the Rank for productive positions are as follows:

Positions where less than 15% but greater than 0% of the substitutions at a given position fall within groups A, B, or C are given a Rank of "1".

Positions where less than 30%, but greater than, or equal to 15% of the substitutions at a given position fall within groups A, B, or C are given a Rank of "2".

Positions where less than 50%, but greater than, or equal to 30% of the substitutions at a given position fall within groups A, B, or C are given a Rank of "3".

Positions where greater than, or equal to 50% of the substitutions at a given position fall within groups A, B, or C are given a Rank of "4".

Substitutions are further assigned a Suitability Score based on the group(s) the substitution is a member of, and where a higher score represents a substitution more suitable for use in making combinatorial variants. Suitability scores are represented and defined in Table 30. Suitability scores and Rank for individual substitutions of IspS that fit the above criteria are represented in Table 31.

TABLE 30

Suitability Score for the defined groups.

| Substitutions Occur in Group(s): | Suitability Score |
|---|---|
| A, B and C | +++++ |
| A and B | ++++ |
| A or (B and C) | +++ |
| B | ++ |
| C | + |

TABLE 31

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 2 | 4 | Q | FGLR | EHIS | CDNTV | AKP |
| 3 | 2 | | | AEGKNQRT | | |
| 6 | 1 | | | S | NT | |
| 13 | 2 | N | M | SQT | | |
| 17 | 1 | T | | DE | | |
| 18 | 3 | H | | YFMN | AQR | DEKS |
| 19 | 1 | | | LF | | Y |
| 20 | 2 | | | LIV | T | |
| 21 | 1 | M | | S | | W |
| 22 | 3 | AHKNRTY | | S | Q | |
| 23 | 2 | K | EG | DT | N | |
| 24 | 2 | AMS | | T | C | LV |
| 25 | 2 | | NQ | DAES | T | |
| 26 | 4 | Y | L | EGNQT | DHKMRSV | C |
| 27 | 4 | | RY | SEFKV | ACGHILMPQ | DN |
| 28 | 3 | | CW | IEFMP | DN | |
| 29 | 2 | | G | EDPRT | Q | N |
| 30 | 3 | | | VNQ | ADEMRT | |
| 31 | 2 | L | D | YQW | N | |
| 32 | 2 | | C | KDGNR | E | |
| 33 | 2 | K | E | DN | | |
| 34 | 2 | | | KDEQS | | |
| 36 | 4 | HTWY | GS | KFR | ACDEMNPQ | |
| 37 | 4 | | WY | KFI | AEGHMNRT | CDPQS |
| 40 | 3 | | | ACDEFMNPQV | | |
| 41 | 3 | M | | ECDFNQSV | | |
| 42 | 3 | C | L | VAST | FI | M |
| 43 | 2 | | G | RIQ | | |
| 44 | 2 | | | RADKMY | NQ | |
| 45 | 2 | | | ECMNQ | | |
| 46 | 1 | | | IFV | | |
| 47 | 4 | C | F | NEIKRV | AGHMQTW | DS |
| 48 | 4 | | | NACEFLQRS | HIK | DGT |
| 49 | 3 | | | EGHIRSW | AC | LV |
| 50 | 4 | | IQV | KCGMNPR | ADEFHSY | |
| 51 | 2 | | | AEGLQT | | |

TABLE 31-continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 52 | 1 | | D | E | | |
| 53 | 3 | | CGMS | FD | EHNPQV | |
| 54 | 2 | | | LACEHIQ | M | |
| 55 | 3 | | PW | TAHNQSY | CDE | |
| 56 | 4 | | | LHQRS | CN | EFGIKTVY |
| 57 | 1 | | | LI | | |
| 58 | 3 | ADFGHRSY | C | E | N | |
| 59 | 3 | | C | LFMSVY | HT | |
| 60 | 1 | | | ICV | | |
| 62 | 1 | | | NV | | |
| 63 | 1 | C | | V | | |
| 68 | 1 | | | L | I | |
| 69 | 1 | | AQ | G | | |
| 71 | 2 | HLV | | RI | KM | |
| 73 | 1 | | | ED | | |
| 74 | 3 | Q | AC | SGMP | DENY | |
| 75 | 1 | | | DE | | |
| 77 | 2 | | | RANTV | L | |
| 78 | 4 | | | GEIKNPQVW | ADFLM | |
| 79 | 3 | C | LN | AMRY | QT | |
| 81 | 4 | | W | DCEHLN | AFGMRSTV | Q |
| 82 | 4 | | D | RCFGLW | AEHIKMQS | NTVY |
| 83 | 2 | | | FGHILV | W | |
| 84 | 4 | | | VFHLNQRSTWY | A | M |
| 85 | 2 | | GM | SCLNR | | |
| 86 | 2 | | GQ | SCN | ADM | |
| 87 | 4 | | HMQSV | GCEFKLNT | DP | |
| 88 | 2 | | | GCDIVWY | | |
| 89 | 2 | | HM | FCI | | |
| 91 | 4 | | F | ACDEGHLRST VY | KW | |
| 92 | 3 | | D | VACEFGILQW | | |
| 93 | 4 | | M | THIQVW | ADEGLNPY | CFRS |
| 94 | 4 | | FQ | KCVY | ADEHILMNR ST | GP |
| 95 | 4 | | R | TCHKM | AEPQSVY | DFGINW |
| 96 | 2 | CG | DNQ | S | | |

TABLE 31-continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 97 | 2 | | | LAMP | F | |
| 98 | 4 | | P | HCSTVW | ADFGILMNQ | |
| 99 | 4 | | DNS | GACHPQT | EFM | |
| 100 | 2 | | C | TAILMV | | |
| 101 | 1 | | | AS | | |
| 102 | 1 | | | LM | | |
| 103 | 2 | | M | SACGL | | |
| 107 | 2 | | A | LCF | | |
| 109 | 2 | | | QCNS | E | |
| 110 | 1 | | A | H | | |
| 111 | 1 | | | GA | | |
| 113 | 2 | | MPQ | ECHV | | |
| 114 | 2 | | AM | VC | | |
| 115 | 2 | | | SDY | A | |
| 116 | 4 | | | QGHLSTV | ACDEIP | |
| 117 | 3 | | QW | EADI | CFLMV | |
| 118 | 2 | | | AIV | M | |
| 119 | 1 | | | FLM | | |
| 120 | 4 | IL | | SADEFKNRWY | HTV | CGMQ |
| 121 | 2 | | FM | GDLVW | | |
| 123 | 2 | | | KISWY | LT | V |
| 124 | 1 | | | DCE | | |
| 125 | 4 | | CP | QADGHKLNST VW | EIY | |
| 126 | 4 | FR | GSY | N | ACDMTV | E |
| 127 | 3 | L | EMNS | GDFW | C | |
| 128 | 3 | | ELMST | NA | CDPQ | |
| 129 | 2 | | W | FLY | | |
| 130 | 3 | | | LACDQVY | E | |
| 131 | 4 | | N | EDFGR | ACPQSV | HKLMTWY |
| 132 | 4 | | QS | N | CDFHLRWY | IP |
| 133 | 3 | | | LEGIPQTVY | D | |
| 134 | 4 | | CFP | KDGHILNRWY | EMQSTV | A |
| 135 | 2 | G | | EHS | | |
| 136 | 1 | | | DN | E | |
| 137 | 4 | | | IACDGPQSV | EHN | T |
| 138 | 4 | L | FMQT | KCDEPRSV | IN | |

TABLE 31-continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 139 | 3 | DG | | APSTV | N | CQ |
| 140 | 3 | C | A | INQSTV | MW | |
| 143 | 4 | | I | LAFGNRW | S | CDEHKMQT VY |
| 146 | 1 | | | AM | | |
| 149 | 1 | | W | L | | |
| 150 | 1 | | GS | A | | |
| 151 | 4 | | | LEGMNQRSTVW | CHI | AF |
| 152 | 2 | | | EADIMP | | |
| 153 | 1 | | | GD | C | |
| 155 | 4 | | | NEKM | ITVY | ACGHQRSW |
| 156 | 4 | V | ACGMQS | IEKLRY | DNT | |
| 158 | 1 | | | DE | | |
| 159 | 2 | D | C | E | M | |
| 160 | 2 | | GY | AFHS | I | |
| 161 | 3 | M | | KLRSY | ACNQ | |
| 162 | 3 | | GH | VDFNPT | S | |
| 163 | 3 | | | FCHIMVWY | EQ | |
| 164 | 2 | C | S | A | T | |
| 165 | 1 | | D | I | | |
| 166 | 4 | | Y | SCEHKPQVW | ADG | N |
| 167 | 4 | | Y | HCLP | AEGKMRSTW | FINQV |
| 169 | 4 | | P | KEGR | DIMST | ACHNQV |
| 170 | 4 | | | EGINR | HKMQTV | LSWY |
| 171 | 4 | | | LCEGIMW | HKRS | ANQTVY |
| 172 | 3 | V | HKT | SGNQR | AC | |
| 173 | 1 | | Q | E | | |
| 175 | 4 | | | KAGHNPTV | S | CFIQR |
| 176 | 2 | | | IACNQV | M | |
| 177 | 3 | S | | GDEHNPT | AC | |
| 178 | 4 | | C | KDEGILMNPQ VY | AFRST | |
| 179 | 4 | | | EGIPQSTVWY | ACLMN | D |
| 180 | 4 | KMR | E | LFHVW | CQT | AI |
| 181 | 4 | GIK | CTY | AFMNW | HQSV | |
| 182 | 2 | | | EHN | S | |
| 183 | 2 | | M | QAL | | |

TABLE 31-continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 185 | 1 | | A | ND | | |
| 187 | 1 | | | ACS | | |
| 188 | 1 | | M | L | | |
| 190 | 2 | C | | L | IM | |
| 193 | 1 | | Q | HW | | |
| 194 | 2 | HWY | | RI | L | |
| 196 | 1 | | | TV | | |
| 197 | 3 | AEHIPT | | QG | S | CDN |
| 203 | 1 | | F | W | | |
| 204 | 2 | | | SAFMWY | C | |
| 208 | 1 | | A | Y | | |
| 210 | 1 | | | KM | | |
| 211 | 4 | L | C | KDEFGHIMRSTV | ANQ | |
| 212 | 2 | | | EADMPQT | | |
| 215 | 2 | | W | NDY | CH | |
| 216 | 2 | | | QAEN | | |
| 217 | 3 | AM | D | VCEKNPQT | I | |
| 218 | 1 | M | | LV | | |
| 219 | 2 | A | | LIMV | C | |
| 220 | 1 | | | EDN | | |
| 221 | 1 | | | L | M | |
| 222 | 1 | | | AS | | |
| 223 | 1 | | | IC | | |
| 224 | 2 | | | LACTV | | |
| 226 | 1 | | | YF | | |
| 228 | 2 | L | | MHR | FY | |
| 229 | 2 | | | IA | V | C |
| 231 | 4 | M | CI | SDGHRV | KQT | A |
| 232 | 1 | | | VQ | I | |
| 234 | 1 | | R | Q | | |
| 235 | 2 | | E | RADN | K | |
| 238 | 1 | K | | R | | |
| 240 | 2 | ILM | | TV | | C |
| 241 | 2 | L | | SC | AMT | |
| 242 | 4 | | | RKL | ADEHIMNQST | G |
| 245 | 4 | AEGN | | R | IL | CKMQTV |

TABLE 31-continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 246 | 2 | | E | RHQ | DK | N |
| 247 | 2 | I | | V | T | LM |
| 249 | 1 | I | | L | | |
| 251 | 3 | | | TH | AGKR | DENPQS |
| 253 | 1 | | | LM | | |
| 254 | 2 | R | CET | H | D | |
| 260 | 1 | | | LM | | |
| 268 | 1 | | | VI | | |
| 270 | 1 | | | VI | | |
| 271 | 2 | | | AS | CV | T |
| 272 | 2 | HS | | FQ | DGPW | |
| 275 | 1 | | | QE | | |
| 276 | 2 | | M | YFHQ | | |
| 278 | 4 | | FHIK | DLMRY | AENQSTVW | |
| 279 | 1 | | | C | A | |
| 282 | 3 | HIW | R | SC | AQ | Y |
| 296 | 1 | M | | I | V | |
| 297 | 1 | | F | Y | | |
| 302 | 1 | | | T | H | |
| 306 | 1 | | | L | | C |
| 307 | 1 | | | EQR | | |
| 308 | 1 | | S | L | | |
| 314 | 1 | | F | EH | | |
| 315 | 2 | M | | RGK | | |
| 317 | 2 | C | | DS | EQ | N |
| 319 | 1 | | | N | F | M |
| 320 | 2 | | | ANT | C | |
| 321 | 1 | | | ILM | | |
| 322 | 1 | | D | N | | |
| 323 | 1 | | | DIT | | |
| 327 | 2 | NQ | | Y | M | |
| 328 | 1 | | | ML | | |
| 329 | 2 | A | | KGQR | | |
| 331 | 1 | | | CT | P | |
| 332 | 1 | | | FY | | |
| 333 | 1 | | | LF | | |

TABLE 31-continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 336 | 1 | | M | Y | | |
| 343 | 1 | | | AIV | | |
| 345 | 1 | | | DY | | |
| 346 | 1 | | | NA | | |
| 348 | 2 | F | | K | RY | |
| 350 | 2 | | | KHWY | | |
| 351 | 2 | | | GEM | DN | |
| 352 | 2 | | | EFIMV | | |
| 356 | 1 | | | PMS | | |
| 357 | 2 | | N | YE | M | |
| 358 | 1 | M | A | L | | |
| 359 | 1 | A | | T | | |
| 360 | 1 | | | KQ | | |
| 361 | 2 | M | | AQSV | T | |
| 363 | 1 | | C | AS | | |
| 364 | 2 | | | DNT | EV | |
| 365 | 2 | | IV | L | CM | |
| 366 | 1 | | | CA | | |
| 367 | 2 | | | NDEM | | |
| 368 | 2 | LY | | ADQ | N | |
| 369 | 4 | | KW | FHQ | MNRTV | CDEGS |
| 370 | 4 | | | LADEFHNRSTV | GQ | |
| 371 | 4 | | | QGHINPRTWY | CS | F |
| 373 | 1 | | S | A | G | |
| 376 | 1 | | | L | | IM |
| 377 | 2 | FHV | | Y | W | |
| 378 | 1 | | | ND | | |
| 379 | 4 | CDNP | AHT | KERS | | GQ |
| 380 | 3 | | GR | SKN | ACDQTV | E |
| 383 | 1 | | | TQ | S | |
| 386 | 2 | | | DKS | EN | |
| 389 | 4 | F | L | GCMPRT | HI | ADEKNQSV |
| 390 | 1 | | T | NS | | |
| 392 | 3 | C | A | WFM | ISTV | Y |
| 393 | 3 | LM | | KHR | Q | CITV |
| 402 | 2 | | | VFIL | | |

TABLE 31-continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 403 | 2 | ACT | | F | | |
| 405 | 1 | | | YF | | |
| 407 | 1 | | | A | G | |
| 408 | 2 | | GN | VQS | I | T |
| 409 | 2 | | R | VCQS | HI | T |
| 410 | 4 | | PY | QEGHIR | CDKLMT | |
| 411 | 2 | CDE | | N | G | |
| 413 | 1 | | | KP | | |
| 414 | 3 | | A | KCHIQ | EGLNP | |
| 415 | 2 | MNP | S | E | | |
| 418 | 1 | | | EN | | |
| 421 | 2 | PW | | Q | | H |
| 422 | 4 | Y | CESV | KGHQR | ANT | D |
| 423 | 4 | ACDEFHMTV | | YG | Q | NS |
| 424 | 3 | | CN | HDGIST | EPQV | |
| 425 | 4 | ACEFKLMNQRSTV | | DP | | |
| 426 | 2 | GY | | TAMQ | | |
| 428 | 2 | AMN | R | SV | EQ | |
| 429 | 4 | M | SV | RACDGHKN | ILTWY | EFQ |
| 431 | 1 | | | SG | | |
| 432 | 2 | | QT | HAM | E | |
| 436 | 2 | I | | L | MY | |
| 437 | 3 | EFLW | H | CN | KT | M |
| 440 | 1 | M | | L | I | |
| 443 | 2 | G | | A | R | Q |
| 444 | 2 | | K | SNQT | P | DE |
| 445 | 1 | QS | | A | | |
| 447 | 3 | VY | | IKR | AEMQS | T |
| 448 | 3 | L | | AHST | EMNPQV | |
| 453 | 1 | V | | A | | |
| 455 | 1 | G | | S | | A |
| 457 | 2 | | Q | SD | NT | |
| 458 | 1 | | | C | | T |
| 460 | 2 | | C | MAEG | QRS | |
| 461 | 3 | F | | RN | DEGQST | A |

TABLE 31-continued

Suitability Score and Rank of positions in IspS with substitutions within the positions that are combinable.

| POSITION | RANK | VARIANTS SUITABILIT

TABLE 31-continued

Suitability Score and Rank of positions in IspS with substitutions within the positions that are combinable.

| POSITION | RANK | VARIANTS SUITABILITY SCORE (+) | VARIANTS SUITABILITY SCORE (++) | VARIANTS SUITABILITY SCORE (+++) WT AA 1ST | VARIANTS SUITABILITY SCORE (++++) | VARIANTS SUITABILITY SCORE (+++++) |
|---|---|---|---|---|---|---|
| 509 | 2 | STV | | QA | | |
| 510 | 2 | | | ST | CV | |
| 511 | 2 | | Y | HIM | | |
| 512 | 1 | Q | | C | | |
| 513 | 4 | AEILMQRY | | TS | V | CGKN |
| 515 | 2 | AGV | | HQ | N | |
| 516 | 1 | | DR | N | | |
| 517 | 1 | | | GP | | |
| 519 | 2 | W | | AC | ST | |
| 522 | 1 | | | SAK | | |
| 525 | 3 | | G | E | ACPQS | FR |
| 528 | 1 | | | RK | | |
| 529 | 1 | | | KA | | |
| 531 | 4 | CD | | VGN | AMT | EHKQRS |
| 534 | 2 | GM | | VAS | | |
| 535 | 2 | AGM | | ICST | | |
| 536 | 2 | K | | TM | AFG | |
| 537 | 2 | IV | | EHNQ | KT | |
| 538 | 1 | K | | P | | |
| 539 | 1 | | | IV | | |
| 540 | 2 | | D | LEQRV | AP | |
| 541 | 1 | L | | P | M | |
| 542 | 2 | IL | QY | FM | P | |
| 543 | 1 | | D | E | | |
| 544 | 2 | | | RGNPQS | C | |

Example 12

Less Combinable Improved Variants with Enhanced Specific Activity or Growth Activity Table 32 lists variants that were either in suitability groups B or C, or not listed in Table 31. These "less combinable" variants did not fit the criteria for combinability as described above, yet displayed improved performance for either specific activity or growth upon retest.

TABLE 32

Positions in MEA P. alba with less combinable improved mutations that displayed PI specific activity values >1.3

| Residue | Position | Mutation | Location | Charge Change | % Surface Accessibility | Function |
|---|---|---|---|---|---|---|
| S | 22 | K | N-term | 1 | 54 | alternate surface interactions |
| S | 22 | R | N-term | 1 | 54 | alternate surface interactions |
| K | 36 | H | N-term | −1 | 33 | alternate interactions with nearby residues |
| K | 36 | W | N-term | −1 | 33 | alternate interactions with nearby residues |
| R | 43 | E | N-term | −2 | 52 | alternate interactions with nearby residues |
| E | 58 | F | N-term | 1 | 20 | alternate interactions with nearby residues |
| G | 87 | S | surface loop | 0

TABLE 33-continued

Positions in MEA *P. alba* with less combinable improved mutations that displayed PI values >1.3 for OD Max at 40 uM and 100 uM IPTG

| Residue | Position | Mutation | Location | Charge Change | % Surface Accessibility | Function |
|---|---|---|---|---|---|---|
| L | 143 | I | N-term helix | 0 | 1 | alternate interactions in hydrophobic pocket |
| I | 156 | G | N-term helix | 0 | 13 | allow more flexibility in loop |
| E | 159 | D | N-term helix | 0 | 32 | alternate interactions with nearby residues |
| E | 159 | G | N-term helix | 1 | 32 | alternate interactions with nearby residues |
| E | 159 | Q | N-term helix | 1 | 32 | alternate interactions with nearby residues |
| S | 172 | V | N-term helix | 0 | 47 | affect shape of loop |
| K | 414 | F | surface loop | −1 | 70 | alternate surface interactions |
| Q | 421 | R | surface loop | 1 | 23 | alternate surface interactions |
| Q | 421 | D | surface loop | −1 | 23 | alternate surface interactions |

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields, are intended to be within the scope of the following claims.

APPENDIX 1

| | | | | | | | | | | |
|---|---|---|---|---|---|---|---|---|---|---|
| ATOM | 1 | N | SER | A | 6 | 57.852 | −35.562 | −29.199 | 1.00 | 48.03 N |
| ATOM | 2 | CA | SER | A | 6 | 58.221 | −34.126 | −29.362 | 1.00 | 48.39 C |
| ATOM | 4 | CB | SER | A | 6 | 56.988 | −33.233 | −29.166 | 1.00 | 48.63 C |
| ATOM | 7 | OG | SER | A | 6 | 57.237 | −31.904 | −29.599 | 1.00 | 47.21 O |
| ATOM | 9 | C | SER | A | 6 | 59.320 | −33.739 | −28.363 | 1.00 | 48.42 C |
| ATOM | 10 | O | SER | A | 6 | 59.140 | −33.874 | −27.147 | 1.00 | 48.63 O |
| ATOM | 14 | N | ALA | A | 7 | 60.451 | −33.258 | −28.882 | 1.00 | 47.57 N |
| ATOM | 15 | CA | ALA | A | 7 | 61.585 | −32.851 | −28.052 | 1.00 | 46.90 C |
| ATOM | 17 | CB | ALA | A | 7 | 62.883 | −33.002 | −28.822 | 1.00 | 46.86 C |
| ATOM | 21 | C | ALA | A | 7 | 61.428 | −31.414 | −27.567 | 1.00 | 46.82 C |
| ATOM | 22 | O | ALA | A | 7 | 60.887 | −30.566 | −28.275 | 1.00 | 46.12 O |
| ATOM | 24 | N | ASN | A | 8 | 61.910 | −31.151 | −26.354 | 1.00 | 47.66 N |
| ATOM | 25 | CA | ASN | A | 8 | 61.854 | −29.817 | −25.756 | 1.00 | 48.08 C |
| ATOM | 27 | CB | ASN | A | 8 | 61.091 | −29.857 | −24.426 | 1.00 | 48.06 C |
| ATOM | 30 | CG | ASN | A | 8 | 60.878 | −28.470 | −23.828 | 1.00 | 49.99 C |
| ATOM | 31 | OD1 | ASN | A | 8 | 60.837 | −27.463 | −24.546 | 1.00 | 51.29 O |
| ATOM | 32 | ND2 | ASN | A | 8 | 60.734 | −28.413 | −22.508 | 1.00 | 49.83 N |
| ATOM | 35 | C | ASN | A | 8 | 63.253 | −29.233 | −25.544 | 1.00 | 48.15 C |
| ATOM | 36 | O | ASN | A | 8 | 63.937 | −29.570 | −24.574 | 1.00 | 47.83 O |
| ATOM | 38 | N | TYR | A | 9 | 63.659 | −28.351 | −26.456 | 1.00 | 48.38 N |
| ATOM | 39 | CA | TYR | A | 9 | 64.948 | −27.667 | −26.370 | 1.00 | 48.44 C |
| ATOM | 41 | CB | TYR | A | 9 | 65.635 | −27.673 | −27.736 | 1.00 | 47.95 C |
| ATOM | 44 | CG | TYR | A | 9 | 65.797 | −29.046 | −28.349 | 1.00 | 44.89 C |
| ATOM | 45 | CD1 | TYR | A | 9 | 66.464 | −30.064 | −27.668 | 1.00 | 41.90 C |
| ATOM | 47 | CE1 | TYR | A | 9 | 66.619 | −31.321 | −28.237 | 1.00 | 40.74 C |
| ATOM | 49 | CZ | TYR | A | 9 | 66.110 | −31.565 | −29.506 | 1.00 | 38.55 C |
| ATOM | 50 | OH | TYR | A | 9 | 66.253 | −32.801 | −30.091 | 1.00 | 37.89 O |
| ATOM | 52 | CE2 | TYR | A | 9 | 65.452 | −30.574 | −30.198 | 1.00 | 37.42 C |
| ATOM | 54 | CD2 | TYR | A | 9 | 65.300 | −29.323 | −29.623 | 1.00 | 40.75 C |
| ATOM | 56 | C | TYR | A | 9 | 64.809 | −26.220 | −25.884 | 1.00 | 49.82 C |
| ATOM | 57 | O | TYR | A | 9 | 65.778 | −25.458 | −25.923 | 1.00 | 49.95 O |
| ATOM | 59 | N | GLU | A | 10 | 63.615 | −25.836 | −25.434 | 1.00 | 51.30 N |
| ATOM | 60 | CA | GLU | A | 10 | 63.393 | −24.476 | −24.935 | 1.00 | 52.39 C |
| ATOM | 62 | CB | GLU | A | 10 | 61.901 | −24.104 | −24.946 | 1.00 | 53.08 C |
| ATOM | 65 | CG | GLU | A | 10 | 61.341 | −23.787 | −26.340 | 1.00 | 55.31 C |
| ATOM | 68 | CD | GLU | A | 10 | 61.948 | −22.531 | −26.962 | 1.00 | 58.35 C |
| ATOM | 69 | OE1 | GLU | A | 10 | 61.645 | −21.419 | −26.475 | 1.00 | 58.63 O |
| ATOM | 70 | OE2 | GLU | A | 10 | 62.719 | −22.656 | −27.943 | 1.00 | 58.45 O |
| ATOM | 71 | C | GLU | A | 10 | 63.970 | −24.336 | −23.527 | 1.00 | 52.09 C |
| ATOM | 72 | O | GLU | A | 10 | 63.803 | −25.235 | −22.701 | 1.00 | 51.48 O |
| ATOM | 74 | N | PRO | A | 11 | 64.654 | −23.206 | −23.252 | 1.00 | 52.23 N |
| ATOM | 75 | CA | PRO | A | 11 | 65.326 | −23.016 | −21.968 | 1.00 | 51.84 C |
| ATOM | 77 | CB | PRO | A | 11 | 66.232 | −21.808 | −22.226 | 1.00 | 51.99 C |
| ATOM | 80 | CG | PRO | A | 11 | 65.483 | −21.004 | −23.234 | 1.00 | 52.61 C |

APPENDIX 1-continued

| ATOM | 83 | CD | PRO | A | 11 | 64.767 | −22.007 | −24.109 | 1.00 | 52.51 | C |
|---|---|---|---|---|---|---|---|---|---|---|---|
| ATOM | 86 | C | PRO | A | 11 | 64.352 | −22.710 | −20.838 | 1.00 | 50.93 | C |
| ATOM | 87 | O | PRO | A | 11 | 63.336 | −22.054 | −21.060 | 1.00 | 51.02 | O |
| ATOM | 88 | N | ASN | A | 12 | 64.671 | −23.192 | −19.641 | 1.00 | 50.14 | N |
| ATOM | 89 | CA | ASN | A | 12 | 63.903 | −22.874 | −18.442 | 1.00 | 49.76 | C |
| ATOM | 91 | CB | ASN | A | 12 | 64.149 | −23.932 | −17.361 | 1.00 | 50.42 | C |
| ATOM | 94 | CG | ASN | A | 12 | 63.646 | −25.311 | −17.765 | 1.00 | 51.17 | C |
| ATOM | 95 | OD1 | ASN | A | 12 | 64.408 | −26.280 | −17.814 | 1.00 | 51.99 | O |
| ATOM | 96 | ND2 | ASN | A | 12 | 62.357 | −25.400 | −18.065 | 1.00 | 53.64 | N |
| ATOM | 99 | C | ASN | A | 12 | 64.266 | −21.489 | −17.904 | 1.00 | 48.64 | C |
| ATOM | 100 | O | ASN | A | 12 | 65.371 | −20.991 | −18.139 | 1.00 | 47.42 | O |
| ATOM | 102 | N | SER | A | 13 | 63.331 | −20.881 | −17.175 | 1.00 | 48.28 | N |
| ATOM | 103 | CA | SER | A | 13 | 63.564 | −19.584 | −16.514 | 1.00 | 47.88 | C |
| ATOM | 105 | CB | SER | A | 13 | 62.232 | −18.959 | −16.071 | 1.00 | 47.65 | C |
| ATOM | 108 | OG | SER | A | 13 | 61.426 | −19.896 | −15.372 | 1.00 | 45.33 | O |
| ATOM | 110 | C | SER | A | 13 | 64.522 | −19.677 | −15.310 | 1.00 | 47.96 | C |
| ATOM | 111 | O | SER | A | 13 | 64.897 | −18.650 | −14.738 | 1.00 | 48.86 | O |
| ATOM | 113 | N | TRP | A | 14 | 64.901 | −20.901 | −14.930 | 1.00 | 47.44 | N |
| ATOM | 114 | CA | TRP | A | 14 | 65.867 | −21.142 | −13.848 | 1.00 | 46.79 | C |
| ATOM | 116 | CB | TRP | A | 14 | 65.278 | −22.098 | −12.793 | 1.00 | 47.11 | C |
| ATOM | 119 | CG | TRP | A | 14 | 64.534 | −23.290 | −13.337 | 1.00 | 49.29 | C |
| ATOM | 120 | CD1 | TRP | A | 14 | 63.180 | −23.428 | −13.440 | 1.00 | 52.50 | C |
| ATOM | 122 | NE1 | TRP | A | 14 | 62.866 | −24.650 | −13.981 | 1.00 | 54.55 | N |
| ATOM | 124 | CE2 | TRP | A | 14 | 64.026 | −25.333 | −14.235 | 1.00 | 55.28 | C |
| ATOM | 125 | CD2 | TRP | A | 14 | 65.100 | −24.504 | −13.842 | 1.00 | 51.73 | C |
| ATOM | 126 | CE3 | TRP | A | 14 | 66.410 | −24.972 | −14.004 | 1.00 | 55.03 | C |
| ATOM | 128 | CZ3 | TRP | A | 14 | 66.607 | −26.239 | −14.548 | 1.00 | 58.13 | C |
| ATOM | 130 | CH2 | TRP | A | 14 | 65.516 | −27.041 | −14.928 | 1.00 | 60.71 | C |
| ATOM | 132 | CZ2 | TRP | A | 14 | 64.222 | −26.607 | −14.778 | 1.00 | 58.33 | C |
| ATOM | 134 | C | TRP | A | 14 | 67.228 | −21.664 | −14.343 | 1.00 | 46.01 | C |
| ATOM | 135 | O | TRP | A | 14 | 68.079 | −22.022 | −13.538 | 1.00 | 45.81 | O |
| ATOM | 137 | N | ASP | A | 15 | 67.445 | −21.692 | −15.656 | 1.00 | 45.26 | N |
| ATOM | 138 | CA | ASP | A | 15 | 68.724 | −22.154 | −16.200 | 1.00 | 44.40 | C |
| ATOM | 140 | CB | ASP | A | 15 | 68.628 | −22.388 | −17.715 | 1.00 | 44.60 | C |
| ATOM | 143 | CG | ASP | A | 15 | 67.990 | −23.730 | −18.068 | 1.00 | 46.58 | C |
| ATOM | 144 | OD1 | ASP | A | 15 | 68.236 | −24.739 | −17.357 | 1.00 | 48.71 | O |
| ATOM | 145 | OD2 | ASP | A | 15 | 67.253 | −23.779 | −19.079 | 1.00 | 48.05 | O |
| ATOM | 146 | C | ASP | A | 15 | 69.843 | −21.163 | −15.886 | 1.00 | 43.10 | C |
| ATOM | 147 | O | ASP | A | 15 | 69.627 | −19.956 | −15.900 | 1.00 | 42.96 | O |
| ATOM | 149 | N | TYR | A | 16 | 71.037 | −21.682 | −15.608 | 1.00 | 42.15 | N |
| ATOM | 150 | CA | TYR | A | 16 | 72.183 | −20.841 | −15.252 | 1.00 | 41.48 | C |
| ATOM | 152 | CB | TYR | A | 16 | 73.367 | −21.689 | −14.758 | 1.00 | 40.41 | C |
| ATOM | 155 | CG | TYR | A | 16 | 73.116 | −22.434 | −13.462 | 1.00 | 34.99 | C |
| ATOM | 156 | CD1 | TYR | A | 16 | 72.755 | −21.754 | −12.302 | 1.00 | 31.52 | C |
| ATOM | 158 | CE1 | TYR | A | 16 | 72.523 | −22.434 | −11.109 | 1.00 | 26.87 | C |
| ATOM | 160 | CZ | TYR | A | 16 | 72.661 | −23.806 | −11.068 | 1.00 | 26.53 | C |
| ATOM | 161 | OH | TYR | A | 16 | 72.428 | −24.472 | −9.884 | 1.00 | 23.41 | O |
| ATOM | 163 | CE2 | TYR | A | 16 | 73.028 | −24.506 | −12.207 | 1.00 | 24.79 | C |
| ATOM | 165 | CD2 | TYR | A | 16 | 73.255 | −23.820 | −13.391 | 1.00 | 28.38 | C |
| ATOM | 167 | C | TYR | A | 16 | 72.645 | −19.941 | −16.405 | 1.00 | 43.23 | C |
| ATOM | 168 | O | TYR | A | 16 | 73.366 | −18.975 | −16.170 | 1.00 | 42.92 | O |
| ATOM | 170 | N | ASP | A | 17 | 72.260 | −20.272 | −17.639 | 1.00 | 45.46 | N |
| ATOM | 171 | CA | ASP | A | 17 | 72.480 | −19.381 | −18.789 | 1.00 | 47.17 | C |
| ATOM | 173 | CB | ASP | A | 17 | 72.177 | −20.100 | −20.123 | 1.00 | 47.23 | C |
| ATOM | 176 | CG | ASP | A | 17 | 73.341 | −20.971 | −20.625 | 1.00 | 48.12 | C |
| ATOM | 177 | OD1 | ASP | A | 17 | 74.518 | −20.677 | −20.315 | 1.00 | 47.64 | O |
| ATOM | 178 | OD2 | ASP | A | 17 | 73.074 | −21.946 | −21.364 | 1.00 | 47.90 | O |
| ATOM | 179 | C | ASP | A | 17 | 71.607 | −18.119 | −18.661 | 1.00 | 48.86 | C |
| ATOM | 180 | O | ASP | A | 17 | 72.085 | −16.998 | −18.874 | 1.00 | 48.22 | O |
| ATOM | 182 | N | TYR | A | 18 | 70.337 | −18.315 | −18.301 | 1.00 | 50.67 | N |
| ATOM | 183 | CA | TYR | A | 18 | 69.374 | −17.218 | −18.165 | 1.00 | 52.74 | C |
| ATOM | 185 | CB | TYR | A | 18 | 67.939 | −17.763 | −18.164 | 1.00 | 53.75 | C |
| ATOM | 188 | CG | TYR | A | 18 | 66.859 | −16.697 | −18.156 | 1.00 | 60.91 | C |
| ATOM | 189 | CD1 | TYR | A | 18 | 66.458 | −16.071 | −19.339 | 1.00 | 65.86 | C |
| ATOM | 191 | CE1 | TYR | A | 18 | 65.463 | −15.095 | −19.335 | 1.00 | 68.28 | C |
| ATOM | 193 | CZ | TYR | A | 18 | 64.855 | −14.737 | −18.137 | 1.00 | 70.56 | C |
| ATOM | 194 | OH | TYR | A | 18 | 63.869 | −13.774 | −18.121 | 1.00 | 72.76 | O |
| ATOM | 196 | CE2 | TYR | A | 18 | 65.233 | −15.346 | −16.950 | 1.00 | 68.19 | C |
| ATOM | 198 | CD2 | TYR | A | 18 | 66.227 | −16.322 | −16.965 | 1.00 | 65.97 | C |
| ATOM | 200 | C | TYR | A | 18 | 69.656 | −16.396 | −16.906 | 1.00 | 52.94 | C |
| ATOM | 201 | O | TYR | A | 18 | 70.007 | −15.222 | −17.004 | 1.00 | 53.20 | O |
| ATOM | 203 | N | LEU | A | 19 | 69.507 | −17.011 | −15.730 | 1.00 | 53.94 | N |
| ATOM | 204 | CA | LEU | A | 19 | 69.968 | −16.411 | −14.472 | 1.00 | 54.31 | C |
| ATOM | 206 | CB | LEU | A | 19 | 69.536 | −17.246 | −13.261 | 1.00 | 53.90 | C |
| ATOM | 209 | CG | LEU | A | 19 | 68.046 | −17.390 | −12.950 | 1.00 | 53.47 | C |
| ATOM | 211 | CD1 | LEU | A | 19 | 67.848 | −18.469 | −11.894 | 1.00 | 52.00 | C |
| ATOM | 215 | CD2 | LEU | A | 19 | 67.445 | −16.067 | −12.493 | 1.00 | 52.71 | C |
| ATOM | 219 | C | LEU | A | 19 | 71.483 | −16.381 | −14.523 | 1.00 | 55.57 | C |
| ATOM | 220 | O | LEU | A | 19 | 72.078 | −16.875 | −15.480 | 1.00 | 56.83 | O |
| ATOM | 222 | N | LEU | A | 20 | 72.121 | −15.805 | −13.510 | 1.00 | 56.21 | N |

APPENDIX 1-continued

| | | | | | | | | | | |
|---|---|---|---|---|---|---|---|---|---|---|
| ATOM | 223 | CA | LEU | A | 20 | 73.577 | −15.890 | −13.397 | 1.00 | 56.88 | C |
| ATOM | 225 | CB | LEU | A | 20 | 73.968 | −17.352 | −13.124 | 1.00 | 56.40 | C |
| ATOM | 228 | CG | LEU | A | 20 | 74.997 | −17.636 | −12.034 | 1.00 | 55.69 | C |
| ATOM | 230 | CD1 | LEU | A | 20 | 74.571 | −17.015 | −10.709 | 1.00 | 53.68 | C |
| ATOM | 234 | CD2 | LEU | A | 20 | 75.192 | −19.138 | −11.885 | 1.00 | 52.71 | C |
| ATOM | 238 | C | LEU | A | 20 | 74.295 | −15.361 | −14.659 | 1.00 | 58.48 | C |
| ATOM | 239 | O | LEU | A | 20 | 75.410 | −15.788 | −14.977 | 1.00 | 58.46 | O |
| ATOM | 241 | N | SER | A | 21 | 73.650 | −14.432 | −15.368 | 1.00 | 60.28 | N |
| ATOM | 242 | CA | SER | A | 21 | 74.213 | −13.838 | −16.577 | 1.00 | 61.62 | C |
| ATOM | 244 | CB | SER | A | 21 | 73.171 | −13.789 | −17.701 | 1.00 | 61.64 | C |
| ATOM | 247 | OG | SER | A | 21 | 73.794 | −13.866 | −18.974 | 1.00 | 59.12 | O |
| ATOM | 249 | C | SER | A | 21 | 74.719 | −12.437 | −16.246 | 1.00 | 63.66 | C |
| ATOM | 250 | O | SER | A | 21 | 74.176 | −11.759 | −15.365 | 1.00 | 63.30 | O |
| ATOM | 252 | N | SER | A | 22 | 75.756 | −12.014 | −16.966 | 1.00 | 66.64 | N |
| ATOM | 253 | CA | SER | A | 22 | 76.506 | −10.806 | −16.625 | 1.00 | 68.86 | C |
| ATOM | 255 | CB | SER | A | 22 | 77.810 | −10.746 | −17.433 | 1.00 | 69.20 | C |
| ATOM | 258 | OG | SER | A | 22 | 77.555 | −10.584 | −18.820 | 1.00 | 69.64 | O |
| ATOM | 260 | C | SER | A | 22 | 75.720 | −9.518 | −16.850 | 1.00 | 70.68 | C |
| ATOM | 261 | O | SER | A | 22 | 74.900 | −9.426 | −17.769 | 1.00 | 71.20 | O |
| ATOM | 263 | N | ASP | A | 23 | 75.978 | −8.534 | −15.990 | 1.00 | 72.36 | N |
| ATOM | 264 | CA | ASP | A | 23 | 75.526 | −7.162 | −16.208 | 1.00 | 73.53 | C |
| ATOM | 266 | CB | ASP | A | 23 | 75.173 | −6.482 | −14.876 | 1.00 | 73.91 | C |
| ATOM | 269 | CG | ASP | A | 23 | 74.200 | −7.312 | −14.024 | 1.00 | 76.32 | C |
| ATOM | 270 | OD1 | ASP | A | 23 | 73.930 | −8.489 | −14.364 | 1.00 | 78.08 | O |
| ATOM | 271 | OD2 | ASP | A | 23 | 73.708 | −6.787 | −13.000 | 1.00 | 78.94 | O |
| ATOM | 272 | C | ASP | A | 23 | 76.683 | −6.472 | −16.932 | 1.00 | 73.70 | C |
| ATOM | 273 | O | ASP | A | 23 | 76.527 | −5.994 | −18.056 | 1.00 | 73.41 | O |
| ATOM | 275 | N | THR | A | 24 | 77.839 | −6.429 | −16.269 | 1.00 | 74.34 | N |
| ATOM | 276 | CA | THR | A | 24 | 79.148 | −6.312 | −16.935 | 1.00 | 74.64 | C |
| ATOM | 278 | CB | THR | A | 24 | 79.549 | −4.836 | −17.203 | 1.00 | 74.73 | C |
| ATOM | 280 | OG1 | THR | A | 24 | 78.431 | −4.113 | −17.732 | 1.00 | 75.12 | O |
| ATOM | 282 | CG2 | THR | A | 24 | 80.707 | −4.755 | −18.199 | 1.00 | 74.19 | C |
| ATOM | 286 | C | THR | A | 24 | 80.233 | −7.012 | −16.086 | 1.00 | 74.73 | C |
| ATOM | 287 | O | THR | A | 24 | 81.413 | −6.648 | −16.143 | 1.00 | 74.53 | O |
| ATOM | 289 | N | ASP | A | 25 | 79.821 | −8.029 | −15.321 | 1.00 | 74.69 | N |
| ATOM | 290 | CA | ASP | A | 25 | 80.692 | −8.720 | −14.362 | 1.00 | 74.42 | C |
| ATOM | 292 | CB | ASP | A | 25 | 79.931 | −9.032 | −13.064 | 1.00 | 74.45 | C |
| ATOM | 295 | CG | ASP | A | 25 | 79.439 | −7.782 | −12.345 | 1.00 | 75.87 | C |
| ATOM | 296 | OD1 | ASP | A | 25 | 80.097 | −6.723 | −12.442 | 1.00 | 78.52 | O |
| ATOM | 297 | OD2 | ASP | A | 25 | 78.390 | −7.868 | −11.668 | 1.00 | 75.22 | O |
| ATOM | 298 | C | ASP | A | 25 | 81.208 | −10.032 | −14.949 | 1.00 | 73.89 | C |
| ATOM | 299 | O | ASP | A | 25 | 80.416 | −10.901 | −15.329 | 1.00 | 74.17 | O |
| ATOM | 301 | N | GLU | A | 26 | 82.533 | −10.174 | −15.005 | 1.00 | 72.59 | N |
| ATOM | 302 | CA | GLU | A | 26 | 83.176 | −11.412 | −15.464 | 1.00 | 71.44 | C |
| ATOM | 304 | CB | GLU | A | 26 | 84.542 | −11.099 | −16.083 | 1.00 | 71.52 | C |
| ATOM | 307 | CG | GLU | A | 26 | 84.462 | −10.218 | −17.329 | 1.00 | 72.73 | C |
| ATOM | 310 | CD | GLU | A | 26 | 85.791 | −9.577 | −17.706 | 1.00 | 73.49 | C |
| ATOM | 311 | OE1 | GLU | A | 26 | 86.857 | −10.178 | −17.448 | 1.00 | 75.86 | O |
| ATOM | 312 | OE2 | GLU | A | 26 | 85.764 | −8.465 | −18.273 | 1.00 | 72.72 | O |
| ATOM | 313 | C | GLU | A | 26 | 83.328 | −12.449 | −14.338 | 1.00 | 70.01 | C |
| ATOM | 314 | O | GLU | A | 26 | 83.745 | −13.583 | −14.589 | 1.00 | 70.09 | O |
| ATOM | 316 | N | SER | A | 27 | 82.996 | −12.054 | −13.106 | 1.00 | 68.20 | N |
| ATOM | 317 | CA | SER | A | 27 | 82.992 | −12.965 | −11.953 | 1.00 | 66.37 | C |
| ATOM | 319 | CB | SER | A | 27 | 83.203 | −12.185 | −10.647 | 1.00 | 66.19 | C |
| ATOM | 322 | OG | SER | A | 27 | 82.281 | −11.114 | −10.526 | 1.00 | 64.64 | O |
| ATOM | 324 | C | SER | A | 27 | 81.696 | −13.783 | −11.874 | 1.00 | 64.84 | C |
| ATOM | 325 | O | SER | A | 27 | 81.675 | −14.864 | −11.278 | 1.00 | 64.63 | O |
| ATOM | 327 | N | ILE | A | 28 | 80.623 | −13.266 | −12.471 | 1.00 | 62.61 | N |
| ATOM | 328 | CA | ILE | A | 28 | 79.354 | −13.989 | −12.539 | 1.00 | 61.02 | C |
| ATOM | 330 | CB | ILE | A | 28 | 78.169 | −13.038 | −12.860 | 1.00 | 61.01 | C |
| ATOM | 332 | CG1 | ILE | A | 28 | 78.014 | −11.979 | −11.759 | 1.00 | 61.43 | C |
| ATOM | 335 | CD1 | ILE | A | 28 | 76.755 | −11.111 | −11.888 | 1.00 | 61.10 | C |
| ATOM | 339 | CG2 | ILE | A | 28 | 76.870 | −13.822 | −13.007 | 1.00 | 59.79 | C |
| ATOM | 343 | C | ILE | A | 28 | 79.409 | −15.124 | −13.569 | 1.00 | 60.14 | C |
| ATOM | 344 | O | ILE | A | 28 | 78.617 | −16.063 | −13.490 | 1.00 | 60.44 | O |
| ATOM | 346 | N | GLU | A | 29 | 80.349 | −15.051 | −14.514 | 1.00 | 58.86 | N |
| ATOM | 347 | CA | GLU | A | 29 | 80.458 | −16.054 | −15.583 | 1.00 | 58.37 | C |
| ATOM | 349 | CB | GLU | A | 29 | 80.872 | −15.396 | −16.903 | 1.00 | 59.02 | C |
| ATOM | 352 | CG | GLU | A | 29 | 79.753 | −14.583 | −17.554 | 1.00 | 61.53 | C |
| ATOM | 355 | CD | GLU | A | 29 | 80.073 | −14.176 | −18.984 | 1.00 | 65.33 | C |
| ATOM | 356 | OE1 | GLU | A | 29 | 80.488 | −15.052 | −19.775 | 1.00 | 67.45 | O |
| ATOM | 357 | OE2 | GLU | A | 29 | 79.904 | −12.982 | −19.320 | 1.00 | 67.36 | O |
| ATOM | 358 | C | GLU | A | 29 | 81.396 | −17.229 | −15.256 | 1.00 | 57.04 | C |
| ATOM | 359 | O | GLU | A | 29 | 81.179 | −18.343 | −15.739 | 1.00 | 57.21 | O |
| ATOM | 361 | N | VAL | A | 30 | 82.438 | −16.983 | −14.463 | 1.00 | 55.15 | N |
| ATOM | 362 | CA | VAL | A | 30 | 83.268 | −18.068 | −13.914 | 1.00 | 53.30 | C |
| ATOM | 364 | CB | VAL | A | 30 | 84.483 | −17.510 | −13.117 | 1.00 | 53.38 | C |
| ATOM | 366 | CG1 | VAL | A | 30 | 85.039 | −18.555 | −12.151 | 1.00 | 52.60 | C |
| ATOM | 370 | CG2 | VAL | A | 30 | 85.573 | −17.023 | −14.073 | 1.00 | 53.38 | C |
| ATOM | 374 | C | VAL | A | 30 | 82.404 | −18.950 | −13.004 | 1.00 | 51.50 | C |

APPENDIX 1-continued

| | | | | | | | | | | | |
|---|---|---|---|---|---|---|---|---|---|---|---|
| ATOM | 375 | O | VAL | A | 30 | 82.421 | −20.180 | −13.099 | 1.00 | 51.26 | O |
| ATOM | 377 | N | TYR | A | 31 | 81.660 | −18.280 | −12.129 | 1.00 | 49.11 | N |
| ATOM | 378 | CA | TYR | A | 31 | 80.650 | −18.870 | −11.254 | 1.00 | 47.25 | C |
| ATOM | 380 | CB | TYR | A | 31 | 79.947 | −17.705 | −10.543 | 1.00 | 47.92 | C |
| ATOM | 383 | CG | TYR | A | 31 | 79.090 | −18.009 | −9.336 | 1.00 | 51.28 | C |
| ATOM | 384 | CD1 | TYR | A | 31 | 79.633 | −18.024 | −8.051 | 1.00 | 55.50 | C |
| ATOM | 386 | CE1 | TYR | A | 31 | 78.826 | −18.268 | −6.923 | 1.00 | 59.62 | C |
| ATOM | 388 | CZ | TYR | A | 31 | 77.454 | −18.472 | −7.083 | 1.00 | 62.10 | C |
| ATOM | 389 | OH | TYR | A | 31 | 76.634 | −18.714 | −5.992 | 1.00 | 59.44 | O |
| ATOM | 391 | CE2 | TYR | A | 31 | 76.898 | −18.436 | −8.354 | 1.00 | 61.47 | C |
| ATOM | 393 | CD2 | TYR | A | 31 | 77.717 | −18.193 | −9.468 | 1.00 | 57.47 | C |
| ATOM | 395 | C | TYR | A | 31 | 79.647 | −19.714 | −12.064 | 1.00 | 45.23 | C |
| ATOM | 396 | O | TYR | A | 31 | 79.352 | −20.858 | −11.713 | 1.00 | 44.76 | O |
| ATOM | 398 | N | LYS | A | 32 | 79.154 | −19.138 | −13.163 | 1.00 | 42.92 | N |
| ATOM | 399 | CA | LYS | A | 32 | 78.141 | −19.767 | −14.032 | 1.00 | 40.55 | C |
| ATOM | 401 | CB | LYS | A | 32 | 77.680 | −18.764 | −15.106 | 1.00 | 40.76 | C |
| ATOM | 404 | CG | LYS | A | 32 | 77.038 | −19.362 | −16.366 | 1.00 | 40.67 | C |
| ATOM | 407 | CD | LYS | A | 32 | 76.894 | −18.308 | −17.472 | 1.00 | 42.03 | C |
| ATOM | 410 | CE | LYS | A | 32 | 77.173 | −18.889 | −18.857 | 1.00 | 42.97 | C |
| ATOM | 413 | NZ | LYS | A | 32 | 77.209 | −17.838 | −19.913 | 1.00 | 42.04 | N |
| ATOM | 417 | C | LYS | A | 32 | 78.596 | −21.068 | −14.700 | 1.00 | 38.15 | C |
| ATOM | 418 | O | LYS | A | 32 | 77.855 | −22.048 | −14.695 | 1.00 | 38.36 | O |
| ATOM | 420 | N | ASP | A | 33 | 79.790 | −21.070 | −15.292 | 1.00 | 35.64 | N |
| ATOM | 421 | CA | ASP | A | 33 | 80.311 | −22.259 | −15.982 | 1.00 | 33.78 | C |
| ATOM | 423 | CB | ASP | A | 33 | 81.601 | −21.929 | −16.738 | 1.00 | 34.72 | C |
| ATOM | 426 | CG | ASP | A | 33 | 81.354 | −21.081 | −17.969 | 1.00 | 36.54 | C |
| ATOM | 427 | OD1 | ASP | A | 33 | 80.594 | −21.527 | −18.859 | 1.00 | 40.72 | O |
| ATOM | 428 | OD2 | ASP | A | 33 | 81.928 | −19.975 | −18.048 | 1.00 | 37.20 | O |
| ATOM | 429 | C | ASP | A | 33 | 80.573 | −23.393 | −15.009 | 1.00 | 31.24 | C |
| ATOM | 430 | O | ASP | A | 33 | 80.470 | −24.561 | −15.367 | 1.00 | 30.51 | O |
| ATOM | 432 | N | LYS | A | 34 | 80.914 | −23.027 | −13.777 | 1.00 | 29.73 | N |
| ATOM | 433 | CA | LYS | A | 34 | 81.107 | −23.977 | −12.684 | 1.00 | 28.39 | C |
| ATOM | 435 | CB | LYS | A | 34 | 81.706 | −23.259 | −11.469 | 1.00 | 29.61 | C |
| ATOM | 438 | CG | LYS | A | 34 | 82.593 | −24.116 | −10.557 | 1.00 | 33.47 | C |
| ATOM | 441 | CD | LYS | A | 34 | 83.235 | −23.222 | −9.474 | 1.00 | 38.41 | C |
| ATOM | 444 | CE | LYS | A | 34 | 84.737 | −23.462 | −9.306 | 1.00 | 40.10 | C |
| ATOM | 447 | NZ | LYS | A | 34 | 85.408 | −22.281 | −8.672 | 1.00 | 38.56 | N |
| ATOM | 451 | C | LYS | A | 34 | 79.782 | −24.605 | −12.286 | 1.00 | 25.39 | C |
| ATOM | 452 | O | LYS | A | 34 | 79.742 | −25.751 | −11.879 | 1.00 | 25.45 | O |
| ATOM | 454 | N | ALA | A | 35 | 78.701 | −23.844 | −12.387 | 1.00 | 23.04 | N |
| ATOM | 455 | CA | ALA | A | 35 | 77.375 | −24.362 | −12.075 | 1.00 | 21.87 | C |
| ATOM | 457 | CB | ALA | A | 35 | 76.354 | −23.237 | −12.076 | 1.00 | 21.62 | C |
| ATOM | 461 | C | ALA | A | 35 | 76.985 | −25.436 | −13.082 | 1.00 | 20.42 | C |
| ATOM | 462 | O | ALA | A | 35 | 76.625 | −26.554 | −12.713 | 1.00 | 19.70 | O |
| ATOM | 464 | N | LYS | A | 36 | 77.081 | −25.082 | −14.357 | 1.00 | 18.77 | N |
| ATOM | 465 | CA | LYS | A | 36 | 76.691 | −25.966 | −15.444 | 1.00 | 18.24 | C |
| ATOM | 467 | CB | LYS | A | 36 | 76.929 | −25.269 | −16.789 | 1.00 | 18.00 | C |
| ATOM | 470 | CG | LYS | A | 36 | 75.987 | −24.105 | −17.043 | 1.00 | 18.92 | C |
| ATOM | 473 | CD | LYS | A | 36 | 76.557 | −23.085 | −18.024 | 1.00 | 21.70 | C |
| ATOM | 476 | CE | LYS | A | 36 | 76.472 | −23.540 | −19.465 | 1.00 | 19.59 | C |
| ATOM | 479 | NZ | LYS | A | 36 | 77.258 | −22.646 | −20.331 | 1.00 | 19.67 | N |
| ATOM | 483 | C | LYS | A | 36 | 77.446 | −27.294 | −15.387 | 1.00 | 17.53 | C |
| ATOM | 484 | O | LYS | A | 36 | 76.857 | −28.356 | −15.554 | 1.00 | 17.14 | O |
| ATOM | 486 | N | LYS | A | 37 | 78.746 | −27.223 | −15.131 | 1.00 | 17.40 | N |
| ATOM | 487 | CA | LYS | A | 37 | 79.589 | −28.417 | −15.044 | 1.00 | 17.76 | C |
| ATOM | 489 | CB | LYS | A | 37 | 81.051 | −27.991 | −14.895 | 1.00 | 18.24 | C |
| ATOM | 492 | CG | LYS | A | 37 | 82.076 | −29.104 | −15.034 | 1.00 | 22.01 | C |
| ATOM | 495 | CD | LYS | A | 37 | 83.467 | −28.513 | −15.299 | 1.00 | 28.55 | C |
| ATOM | 498 | CE | LYS | A | 37 | 84.524 | −29.586 | −15.533 | 1.00 | 29.97 | C |
| ATOM | 501 | NZ | LYS | A | 37 | 84.955 | −30.203 | −14.254 | 1.00 | 33.41 | N |
| ATOM | 505 | C | LYS | A | 37 | 79.165 | −29.324 | −13.875 | 1.00 | 16.90 | C |
| ATOM | 506 | O | LYS | A | 37 | 79.098 | −30.549 | −14.016 | 1.00 | 17.17 | O |
| ATOM | 508 | N | LEU | A | 38 | 78.872 | −28.713 | −12.729 | 1.00 | 15.23 | N |
| ATOM | 509 | CA | LEU | A | 38 | 78.439 | −29.450 | −11.545 | 1.00 | 13.91 | C |
| ATOM | 511 | CB | LEU | A | 38 | 78.450 | −28.535 | −10.316 | 1.00 | 13.03 | C |
| ATOM | 514 | CG | LEU | A | 38 | 79.814 | −27.984 | −9.882 | 1.00 | 10.93 | C |
| ATOM | 516 | CD1 | LEU | A | 38 | 79.634 | −26.844 | −8.889 | 1.00 | 9.71 | C |
| ATOM | 520 | CD2 | LEU | A | 38 | 80.688 | −29.059 | −9.291 | 1.00 | 6.81 | C |
| ATOM | 524 | C | LEU | A | 38 | 77.044 | −30.030 | −11.753 | 1.00 | 14.10 | C |
| ATOM | 525 | O | LEU | A | 38 | 76.768 | −31.184 | −11.386 | 1.00 | 14.32 | O |
| ATOM | 527 | N | GLU | A | 39 | 76.175 | −29.215 | −12.349 | 1.00 | 14.06 | N |
| ATOM | 528 | CA | GLU | A | 39 | 74.796 | −29.597 | −12.644 | 1.00 | 13.26 | C |
| ATOM | 530 | CB | GLU | A | 39 | 74.045 | −28.406 | −13.243 | 1.00 | 13.22 | C |
| ATOM | 533 | CG | GLU | A | 39 | 72.555 | −28.631 | −13.379 | 1.00 | 16.71 | C |
| ATOM | 536 | CD | GLU | A | 39 | 71.829 | −27.489 | −14.055 | 1.00 | 16.18 | C |
| ATOM | 537 | OE1 | GLU | A | 39 | 72.470 | −26.668 | −14.731 | 1.00 | 16.33 | O |
| ATOM | 538 | OE2 | GLU | A | 39 | 70.596 | −27.425 | −13.921 | 1.00 | 20.26 | O |
| ATOM | 539 | C | GLU | A | 39 | 74.764 | −30.772 | −13.610 | 1.00 | 12.52 | C |
| ATOM | 540 | O | GLU | A | 39 | 74.024 | −31.729 | −13.413 | 1.00 | 12.91 | O |
| ATOM | 542 | N | ALA | A | 40 | 75.581 | −30.698 | −14.652 | 1.00 | 11.95 | N |

APPENDIX 1-continued

| ATOM | 543 | CA | ALA | A | 40 | 75.680 | −31.779 | −15.616 | 1.00 | 11.90 | C |
|---|---|---|---|---|---|---|---|---|---|---|---|
| ATOM | 545 | CB | ALA | A | 40 | 76.712 | −31.435 | −16.686 | 1.00 | 11.71 | C |
| ATOM | 549 | C | ALA | A | 40 | 76.026 | −33.114 | −14.944 | 1.00 | 12.35 | C |
| ATOM | 550 | O | ALA | A | 40 | 75.418 | −34.142 | −15.241 | 1.00 | 12.86 | O |
| ATOM | 552 | N | GLU | A | 41 | 77.001 | −33.098 | −14.040 | 1.00 | 12.31 | N |
| ATOM | 553 | CA | GLU | A | 41 | 77.411 | −34.316 | −13.341 | 1.00 | 11.84 | C |
| ATOM | 555 | CB | GLU | A | 41 | 78.657 | −34.063 | −12.503 | 1.00 | 12.96 | C |
| ATOM | 558 | CG | GLU | A | 41 | 79.319 | −35.339 | −11.995 | 1.00 | 16.43 | C |
| ATOM | 561 | CD | GLU | A | 41 | 80.689 | −35.094 | −11.380 | 1.00 | 20.65 | C |
| ATOM | 562 | OE1 | GLU | A | 41 | 81.384 | −34.141 | −11.813 | 1.00 | 21.41 | O |
| ATOM | 563 | OE2 | GLU | A | 41 | 81.063 | −35.863 | −10.464 | 1.00 | 22.80 | O |
| ATOM | 564 | C | GLU | A | 41 | 76.318 | −34.881 | −12.445 | 1.00 | 11.21 | C |
| ATOM | 565 | O | GLU | A | 41 | 76.197 | −36.096 | −12.317 | 1.00 | 10.59 | O |
| ATOM | 567 | N | VAL | A | 42 | 75.533 | −34.014 | −11.812 | 1.00 | 10.59 | N |
| ATOM | 568 | CA | VAL | A | 42 | 74.455 | −34.504 | −10.953 | 1.00 | 10.83 | C |
| ATOM | 570 | CB | VAL | A | 42 | 73.874 | −33.410 | −10.059 | 1.00 | 9.83 | C |
| ATOM | 572 | CG1 | VAL | A | 42 | 72.666 | −33.930 | −9.327 | 1.00 | 8.79 | C |
| ATOM | 576 | CG2 | VAL | A | 42 | 74.927 | −32.942 | −9.073 | 1.00 | 6.37 | C |
| ATOM | 580 | C | VAL | A | 42 | 73.364 | −35.139 | −11.801 | 1.00 | 12.18 | C |
| ATOM | 581 | O | VAL | A | 42 | 72.809 | −36.175 | −11.434 | 1.00 | 13.46 | O |
| ATOM | 583 | N | ARG | A | 43 | 73.082 | −34.524 | −12.944 | 1.00 | 13.15 | N |
| ATOM | 584 | CA | ARG | A | 43 | 72.164 | −35.088 | −13.933 | 1.00 | 13.17 | C |
| ATOM | 586 | CB | ARG | A | 43 | 72.038 | −34.128 | −15.121 | 1.00 | 13.87 | C |
| ATOM | 589 | CG | ARG | A | 43 | 71.145 | −34.608 | −16.242 | 1.00 | 15.13 | C |
| ATOM | 592 | CD | ARG | A | 43 | 71.899 | −35.461 | −17.242 | 1.00 | 15.36 | C |
| ATOM | 595 | NE | ARG | A | 43 | 70.996 | −36.139 | −18.157 | 1.00 | 13.99 | N |
| ATOM | 597 | CZ | ARG | A | 43 | 71.379 | −37.012 | −19.079 | 1.00 | 12.96 | C |
| ATOM | 598 | NH1 | ARG | A | 43 | 70.469 | −37.573 | −19.859 | 1.00 | 14.01 | N |
| ATOM | 601 | NH2 | ARG | A | 43 | 72.665 | −37.326 | −19.234 | 1.00 | 16.32 | N |
| ATOM | 604 | C | ARG | A | 43 | 72.629 | −36.471 | −14.402 | 1.00 | 12.96 | C |
| ATOM | 605 | O | ARG | A | 43 | 71.830 | −37.399 | −14.510 | 1.00 | 12.10 | O |
| ATOM | 607 | N | ARG | A | 44 | 73.919 | −36.604 | −14.689 | 1.00 | 13.18 | N |
| ATOM | 608 | CA | ARG | A | 44 | 74.473 | −37.899 | −15.083 | 1.00 | 13.52 | C |
| ATOM | 610 | CB | ARG | A | 44 | 75.973 | −37.796 | −15.348 | 1.00 | 13.04 | C |
| ATOM | 613 | CG | ARG | A | 44 | 76.587 | −39.071 | −15.934 | 1.00 | 13.55 | C |
| ATOM | 616 | CD | ARG | A | 44 | 78.096 | −38.945 | −16.116 | 1.00 | 10.92 | C |
| ATOM | 619 | NE | ARG | A | 44 | 78.768 | −38.750 | −14.837 | 1.00 | 10.95 | N |
| ATOM | 621 | CZ | ARG | A | 44 | 80.014 | −38.310 | −14.688 | 1.00 | 13.62 | C |
| ATOM | 622 | NH1 | ARG | A | 44 | 80.511 | −38.162 | −13.470 | 1.00 | 18.93 | N |
| ATOM | 625 | NH2 | ARG | A | 44 | 80.772 | −38.013 | −15.735 | 1.00 | 13.99 | N |
| ATOM | 628 | C | ARG | A | 44 | 74.206 | −38.967 | −14.017 | 1.00 | 13.83 | C |
| ATOM | 629 | O | ARG | A | 44 | 73.723 | −40.046 | −14.329 | 1.00 | 14.61 | O |
| ATOM | 631 | N | GLU | A | 45 | 74.497 | −38.652 | −12.761 | 1.00 | 13.69 | N |
| ATOM | 632 | CA | GLU | A | 45 | 74.333 | −39.615 | −11.673 | 1.00 | 13.28 | C |
| ATOM | 634 | CB | GLU | A | 45 | 75.006 | −39.097 | −10.400 | 1.00 | 13.92 | C |
| ATOM | 637 | CG | GLU | A | 45 | 76.501 | −38.906 | −10.534 | 1.00 | 13.86 | C |
| ATOM | 640 | CD | GLU | A | 45 | 77.179 | −40.128 | −11.080 | 1.00 | 15.34 | C |
| ATOM | 641 | OE1 | GLU | A | 45 | 76.958 | −41.210 | −10.505 | 1.00 | 21.32 | O |
| ATOM | 642 | OE2 | GLU | A | 45 | 77.917 | −40.010 | −12.085 | 1.00 | 15.78 | O |
| ATOM | 643 | C | GLU | A | 45 | 72.876 | −39.953 | −11.378 | 1.00 | 13.56 | C |
| ATOM | 644 | O | GLU | A | 45 | 72.577 | −41.089 | −11.022 | 1.00 | 12.52 | O |
| ATOM | 646 | N | ILE | A | 46 | 71.976 | −38.974 | −11.510 | 1.00 | 13.94 | N |
| ATOM | 647 | CA | ILE | A | 46 | 70.543 | −39.242 | −11.371 | 1.00 | 13.70 | C |
| ATOM | 649 | CB | ILE | A | 46 | 69.698 | −37.947 | −11.340 | 1.00 | 13.76 | C |
| ATOM | 651 | CG1 | ILE | A | 46 | 69.950 | −37.174 | −10.052 | 1.00 | 13.82 | C |
| ATOM | 654 | CD1 | ILE | A | 46 | 69.283 | −35.834 | −10.025 | 1.00 | 12.62 | C |
| ATOM | 658 | CG2 | ILE | A | 46 | 68.219 | −38.269 | −11.388 | 1.00 | 9.73 | C |
| ATOM | 662 | C | ILE | A | 46 | 70.015 | −40.170 | −12.475 | 1.00 | 14.01 | C |
| ATOM | 663 | O | ILE | A | 46 | 69.145 | −40.996 | −12.213 | 1.00 | 16.46 | O |
| ATOM | 665 | N | ASN | A | 47 | 70.541 | −40.040 | −13.692 | 1.00 | 13.63 | N |
| ATOM | 666 | CA | ASN | A | 47 | 70.114 | −40.866 | −14.826 | 1.00 | 12.95 | C |
| ATOM | 668 | CB | ASN | A | 47 | 70.261 | −40.077 | −16.126 | 1.00 | 13.09 | C |
| ATOM | 671 | CG | ASN | A | 47 | 69.156 | −39.073 | −16.327 | 1.00 | 12.33 | C |
| ATOM | 672 | OD1 | ASN | A | 47 | 68.181 | −39.363 | −17.007 | 1.00 | 17.25 | O |
| ATOM | 673 | ND2 | ASN | A | 47 | 69.301 | −37.886 | −15.747 | 1.00 | 6.46 | N |
| ATOM | 676 | C | ASN | A | 47 | 70.848 | −42.209 | −14.981 | 1.00 | 13.75 | C |
| ATOM | 677 | O | ASN | A | 47 | 70.493 | −43.004 | −15.859 | 1.00 | 14.81 | O |
| ATOM | 679 | N | ASN | A | 48 | 71.857 | −42.467 | −14.149 | 1.00 | 13.90 | N |
| ATOM | 680 | CA | ASN | A | 48 | 72.651 | −43.713 | −14.233 | 1.00 | 14.21 | C |
| ATOM | 682 | CB | ASN | A | 48 | 73.577 | −43.823 | −13.012 | 1.00 | 13.88 | C |
| ATOM | 685 | CG | ASN | A | 48 | 74.474 | −45.057 | −13.049 | 1.00 | 13.81 | C |
| ATOM | 686 | OD1 | ASN | A | 48 | 74.410 | −45.866 | −13.971 | 1.00 | 14.91 | O |
| ATOM | 687 | ND2 | ASN | A | 48 | 75.314 | −45.201 | −12.033 | 1.00 | 7.59 | N |
| ATOM | 690 | C | ASN | A | 48 | 71.775 | −44.968 | −14.343 | 1.00 | 15.13 | C |
| ATOM | 691 | O | ASN | A | 48 | 71.114 | −45.346 | −13.383 | 1.00 | 16.48 | O |
| ATOM | 693 | N | GLU | A | 49 | 71.790 | −45.620 | −15.505 | 1.00 | 15.77 | N |
| ATOM | 694 | CA | GLU | A | 49 | 70.895 | −46.763 | −15.762 | 1.00 | 16.49 | C |
| ATOM | 696 | CB | GLU | A | 49 | 70.848 | −47.114 | −17.256 | 1.00 | 16.02 | C |
| ATOM | 699 | CG | GLU | A | 49 | 70.388 | −45.984 | −18.170 | 1.00 | 17.82 | C |
| ATOM | 702 | CD | GLU | A | 49 | 71.524 | −45.093 | −18.666 | 1.00 | 20.53 | C |

APPENDIX 1-continued

| | | | | | | | | | | | |
|---|---|---|---|---|---|---|---|---|---|---|---|
| ATOM | 703 | OE1 | GLU | A | 49 | 72.654 | −45.198 | −18.125 | 1.00 | 17.54 | O |
| ATOM | 704 | OE2 | GLU | A | 49 | 71.276 | −44.290 | −19.599 | 1.00 | 18.89 | O |
| ATOM | 705 | C | GLU | A | 49 | 71.251 | −48.032 | −14.975 | 1.00 | 17.20 | C |
| ATOM | 706 | O | GLU | A | 49 | 70.432 | −48.950 | −14.899 | 1.00 | 17.66 | O |
| ATOM | 708 | N | LYS | A | 50 | 72.461 | −48.092 | −14.417 | 1.00 | 17.04 | N |
| ATOM | 709 | CA | LYS | A | 50 | 72.896 | −49.226 | −13.608 | 1.00 | 17.60 | C |
| ATOM | 711 | CB | LYS | A | 50 | 74.172 | −49.859 | −14.192 | 1.00 | 18.24 | C |
| ATOM | 714 | CG | LYS | A | 50 | 74.171 | −50.048 | −15.713 | 1.00 | 21.29 | C |
| ATOM | 717 | CD | LYS | A | 50 | 73.928 | −51.487 | −16.166 | 1.00 | 24.29 | C |
| ATOM | 720 | CE | LYS | A | 50 | 73.721 | −51.580 | −17.703 | 1.00 | 26.19 | C |
| ATOM | 723 | NZ | LYS | A | 50 | 72.596 | −50.702 | −18.227 | 1.00 | 22.19 | N |
| ATOM | 727 | C | LYS | A | 50 | 73.153 | −48.790 | −12.163 | 1.00 | 17.58 | C |
| ATOM | 728 | O | LYS | A | 50 | 73.908 | −49.437 | −11.442 | 1.00 | 18.10 | O |
| ATOM | 730 | N | ALA | A | 51 | 72.523 | −47.704 | −11.731 | 1.00 | 18.24 | N |
| ATOM | 731 | CA | ALA | A | 51 | 72.652 | −47.252 | −10.342 | 1.00 | 18.83 | C |
| ATOM | 733 | CB | ALA | A | 51 | 71.860 | −45.964 | −10.129 | 1.00 | 18.12 | C |
| ATOM | 737 | C | ALA | A | 51 | 72.177 | −48.329 | −9.358 | 1.00 | 19.47 | C |
| ATOM | 738 | O | ALA | A | 51 | 71.185 | −49.015 | −9.605 | 1.00 | 18.83 | O |
| ATOM | 740 | N | GLU | A | 52 | 72.896 | −48.470 | −8.249 | 1.00 | 20.59 | N |
| ATOM | 741 | CA | GLU | A | 52 | 72.472 | −49.342 | −7.152 | 1.00 | 21.65 | C |
| ATOM | 743 | CB | GLU | A | 52 | 73.602 | −49.469 | −6.120 | 1.00 | 23.29 | C |
| ATOM | 746 | CG | GLU | A | 52 | 73.756 | −50.850 | −5.504 | 1.00 | 30.52 | C |
| ATOM | 749 | CD | GLU | A | 52 | 74.671 | −51.767 | −6.316 | 1.00 | 39.49 | C |
| ATOM | 750 | OE1 | GLU | A | 52 | 74.697 | −51.642 | −7.560 | 1.00 | 42.22 | O |
| ATOM | 751 | OE2 | GLU | A | 52 | 75.362 | −52.622 | −5.709 | 1.00 | 45.07 | O |
| ATOM | 752 | C | GLU | A | 52 | 71.220 | −48.724 | −6.513 | 1.00 | 20.22 | C |
| ATOM | 753 | O | GLU | A | 52 | 71.126 | −47.506 | −6.397 | 1.00 | 20.92 | O |
| ATOM | 755 | N | PHE | A | 53 | 70.275 | −49.557 | −6.088 | 1.00 | 20.22 | N |
| ATOM | 756 | CA | PHE | A | 53 | 68.934 | −49.085 | −5.680 | 1.00 | 20.14 | C |
| ATOM | 758 | CB | PHE | A | 53 | 67.996 | −50.258 | −5.359 | 1.00 | 19.60 | C |
| ATOM | 761 | CG | PHE | A | 53 | 67.673 | −51.137 | −6.554 | 1.00 | 21.97 | C |
| ATOM | 762 | CD1 | PHE | A | 53 | 67.408 | −50.586 | −7.807 | 1.00 | 20.30 | C |
| ATOM | 764 | CE1 | PHE | A | 53 | 67.111 | −51.395 | −8.894 | 1.00 | 20.87 | C |
| ATOM | 766 | CZ | PHE | A | 53 | 67.060 | −52.770 | −8.741 | 1.00 | 22.56 | C |
| ATOM | 768 | CE2 | PHE | A | 53 | 67.313 | −53.336 | −7.498 | 1.00 | 21.00 | C |
| ATOM | 770 | CD2 | PHE | A | 53 | 67.616 | −52.522 | −6.414 | 1.00 | 20.77 | C |
| ATOM | 772 | C | PHE | A | 53 | 68.928 | −48.104 | −4.513 | 1.00 | 20.34 | C |
| ATOM | 773 | O | PHE | A | 53 | 68.429 | −46.997 | −4.651 | 1.00 | 20.72 | O |
| ATOM | 775 | N | LEU | A | 54 | 69.476 | −48.502 | −3.369 | 1.00 | 20.88 | N |
| ATOM | 776 | CA | LEU | A | 54 | 69.530 | −47.612 | −2.206 | 1.00 | 20.79 | C |
| ATOM | 778 | CB | LEU | A | 54 | 70.065 | −48.344 | −0.973 | 1.00 | 21.67 | C |
| ATOM | 781 | CG | LEU | A | 54 | 69.308 | −49.602 | −0.514 | 1.00 | 25.55 | C |
| ATOM | 783 | CD1 | LEU | A | 54 | 69.953 | −50.193 | 0.747 | 1.00 | 26.34 | C |
| ATOM | 787 | CD2 | LEU | A | 54 | 67.820 | −49.318 | −0.285 | 1.00 | 21.98 | C |
| ATOM | 791 | C | LEU | A | 54 | 70.387 | −46.381 | −2.488 | 1.00 | 19.98 | C |
| ATOM | 792 | O | LEU | A | 54 | 70.029 | −45.273 | −2.103 | 1.00 | 21.36 | O |
| ATOM | 794 | N | THR | A | 55 | 71.508 | −46.569 | −3.171 | 1.00 | 18.78 | N |
| ATOM | 795 | CA | THR | A | 55 | 72.389 | −45.449 | −3.516 | 1.00 | 18.31 | C |
| ATOM | 797 | CB | THR | A | 55 | 73.642 | −45.948 | −4.244 | 1.00 | 17.70 | C |
| ATOM | 799 | OG1 | THR | A | 55 | 74.213 | −47.011 | −3.483 | 1.00 | 19.06 | O |
| ATOM | 801 | CG2 | THR | A | 55 | 74.666 | −44.843 | −4.394 | 1.00 | 15.55 | C |
| ATOM | 805 | C | THR | A | 55 | 71.675 | −44.386 | −4.364 | 1.00 | 17.24 | C |
| ATOM | 806 | O | THR | A | 55 | 71.851 | −43.181 | −4.141 | 1.00 | 15.19 | O |
| ATOM | 808 | N | LEU | A | 56 | 70.866 | −44.849 | −5.316 | 1.00 | 16.83 | N |
| ATOM | 809 | CA | LEU | A | 56 | 70.043 | −43.973 | −6.140 | 1.00 | 16.53 | C |
| ATOM | 811 | CB | LEU | A | 56 | 69.344 | −44.783 | −7.243 | 1.00 | 16.93 | C |
| ATOM | 814 | CG | LEU | A | 56 | 68.366 | −44.034 | −8.166 | 1.00 | 16.70 | C |
| ATOM | 816 | CD1 | LEU | A | 56 | 69.015 | −42.788 | −8.765 | 1.00 | 14.20 | C |
| ATOM | 820 | CD2 | LEU | A | 56 | 67.870 | −44.958 | −9.264 | 1.00 | 16.46 | C |
| ATOM | 824 | C | LEU | A | 56 | 69.005 | −43.216 | −5.316 | 1.00 | 16.09 | C |
| ATOM | 825 | O | LEU | A | 56 | 68.849 | −42.011 | −5.471 | 1.00 | 16.47 | O |
| ATOM | 827 | N | LEU | A | 57 | 68.289 | −43.923 | −4.449 | 1.00 | 15.87 | N |
| ATOM | 828 | CA | LEU | A | 57 | 67.250 | −43.294 | −3.634 | 1.00 | 15.86 | C |
| ATOM | 830 | CB | LEU | A | 57 | 66.493 | −44.330 | −2.792 | 1.00 | 15.00 | C |
| ATOM | 833 | CG | LEU | A | 57 | 65.729 | −45.421 | −3.558 | 1.00 | 15.34 | C |
| ATOM | 835 | CD1 | LEU | A | 57 | 65.235 | −46.483 | −2.586 | 1.00 | 12.24 | C |
| ATOM | 839 | CD2 | LEU | A | 57 | 64.570 | −44.873 | −4.400 | 1.00 | 5.90 | C |
| ATOM | 843 | C | LEU | A | 57 | 67.853 | −42.215 | −2.737 | 1.00 | 16.86 | C |
| ATOM | 844 | O | LEU | A | 57 | 67.292 | −41.123 | −2.608 | 1.00 | 17.20 | O |
| ATOM | 846 | N | GLU | A | 58 | 69.008 | −42.509 | −2.140 | 1.00 | 17.19 | N |
| ATOM | 847 | CA | GLU | A | 58 | 69.682 | −41.542 | −1.272 | 1.00 | 18.11 | C |
| ATOM | 849 | CB | GLU | A | 58 | 70.804 | −42.209 | −0.463 | 1.00 | 18.65 | C |
| ATOM | 852 | CG | GLU | A | 58 | 70.276 | −43.185 | 0.603 | 1.00 | 24.37 | C |
| ATOM | 855 | CD | GLU | A | 58 | 71.362 | −43.844 | 1.450 | 1.00 | 30.28 | C |
| ATOM | 856 | OE1 | GLU | A | 58 | 72.569 | −43.605 | 1.214 | 1.00 | 37.36 | O |
| ATOM | 857 | OE2 | GLU | A | 58 | 70.997 | −44.607 | 2.368 | 1.00 | 33.82 | O |
| ATOM | 858 | C | GLU | A | 58 | 70.200 | −40.324 | −2.042 | 1.00 | 18.11 | C |
| ATOM | 859 | O | GLU | A | 58 | 70.117 | −39.200 | −1.533 | 1.00 | 19.13 | O |
| ATOM | 861 | N | LEU | A | 59 | 70.716 | −40.532 | −3.258 | 1.00 | 17.41 | N |
| ATOM | 862 | CA | LEU | A | 59 | 71.157 | −39.418 | −4.114 | 1.00 | 15.69 | C |

APPENDIX 1-continued

| | | | | | | | | | | |
|---|---|---|---|---|---|---|---|---|---|---|
| ATOM | 864 | CB | LEU | A | 59 | 71.742 | −39.923 | −5.444 | 1.00 | 15.51 C |
| ATOM | 867 | CG | LEU | A | 59 | 72.022 | −38.864 | −6.532 | 1.00 | 16.03 C |
| ATOM | 869 | CD1 | LEU | A | 59 | 73.046 | −37.855 | −6.046 | 1.00 | 8.96 C |
| ATOM | 873 | CD2 | LEU | A | 59 | 72.455 | −39.485 | −7.871 | 1.00 | 10.61 C |
| ATOM | 877 | C | LEU | A | 59 | 69.985 | −38.487 | −4.374 | 1.00 | 15.15 C |
| ATOM | 878 | O | LEU | A | 59 | 70.112 | −37.274 | −4.248 | 1.00 | 16.65 O |
| ATOM | 880 | N | ILE | A | 60 | 68.833 | −39.061 | −4.711 | 1.00 | 14.37 N |
| ATOM | 881 | CA | ILE | A | 60 | 67.636 | −38.270 | −4.976 | 1.00 | 13.67 C |
| ATOM | 883 | CB | ILE | A | 60 | 66.475 | −39.137 | −5.492 | 1.00 | 13.84 C |
| ATOM | 885 | CG1 | ILE | A | 60 | 66.815 | −39.738 | −6.857 | 1.00 | 11.78 C |
| ATOM | 888 | CD1 | ILE | A | 60 | 65.883 | −40.833 | −7.294 | 1.00 | 13.41 C |
| ATOM | 892 | CG2 | ILE | A | 60 | 65.210 | −38.305 | −5.607 | 1.00 | 12.65 C |
| ATOM | 896 | C | ILE | A | 60 | 67.208 | −37.544 | −3.710 | 1.00 | 13.90 C |
| ATOM | 897 | O | ILE | A | 60 | 66.960 | −36.345 | −3.730 | 1.00 | 14.71 O |
| ATOM | 899 | N | ASP | A | 61 | 67.152 | −38.269 | −2.601 | 1.00 | 14.05 N |
| ATOM | 900 | CA | ASP | A | 61 | 66.865 | −37.652 | −1.310 | 1.00 | 14.37 C |
| ATOM | 902 | CB | ASP | A | 61 | 66.992 | −38.685 | −0.196 | 1.00 | 15.27 C |
| ATOM | 905 | CG | ASP | A | 61 | 66.334 | −38.249 | 1.077 | 1.00 | 15.09 C |
| ATOM | 906 | OD1 | ASP | A | 61 | 65.373 | −37.449 | 1.015 | 1.00 | 18.28 O |
| ATOM | 907 | OD2 | ASP | A | 61 | 66.764 | −38.731 | 2.144 | 1.00 | 19.88 O |
| ATOM | 908 | C | ASP | A | 61 | 67.786 | −36.465 | −1.010 | 1.00 | 13.95 C |
| ATOM | 909 | O | ASP | A | 61 | 67.312 | −35.376 | −0.700 | 1.00 | 14.30 O |
| ATOM | 911 | N | ASN | A | 62 | 69.095 | −36.673 | −1.111 | 1.00 | 13.73 N |
| ATOM | 912 | CA | ASN | A | 62 | 70.056 | −35.601 | −0.859 | 1.00 | 14.39 C |
| ATOM | 914 | CB | ASN | A | 62 | 71.498 | −36.078 | −1.056 | 1.00 | 15.08 C |
| ATOM | 917 | CG | ASN | A | 62 | 71.973 | −37.004 | 0.039 | 1.00 | 14.59 C |
| ATOM | 918 | OD1 | ASN | A | 62 | 71.511 | −36.934 | 1.165 | 1.00 | 15.77 O |
| ATOM | 919 | ND2 | ASN | A | 62 | 72.919 | −37.871 | −0.292 | 1.00 | 16.01 N |
| ATOM | 922 | C | ASN | A | 62 | 69.811 | −34.415 | −1.776 | 1.00 | 14.95 C |
| ATOM | 923 | O | ASN | A | 62 | 69.708 | −33.282 | −1.313 | 1.00 | 16.30 O |
| ATOM | 925 | N | VAL | A | 63 | 69.707 | −34.681 | −3.077 | 1.00 | 14.64 N |
| ATOM | 926 | CA | VAL | A | 63 | 69.485 | −33.621 | −4.054 | 1.00 | 14.05 C |
| ATOM | 928 | CB | VAL | A | 63 | 69.239 | −34.185 | −5.464 | 1.00 | 13.98 C |
| ATOM | 930 | CG1 | VAL | A | 63 | 68.736 | −33.090 | −6.399 | 1.00 | 11.96 C |
| ATOM | 934 | CG2 | VAL | A | 63 | 70.511 | −34.805 | −6.016 | 1.00 | 11.21 C |
| ATOM | 938 | C | VAL | A | 63 | 68.297 | −32.758 | −3.633 | 1.00 | 14.72 C |
| ATOM | 939 | O | VAL | A | 63 | 68.385 | −31.525 | −3.603 | 1.00 | 14.02 O |
| ATOM | 941 | N | GLN | A | 64 | 67.197 | −33.415 | −3.288 | 1.00 | 14.83 N |
| ATOM | 942 | CA | GLN | A | 64 | 65.991 | −32.703 | −2.892 | 1.00 | 16.08 C |
| ATOM | 944 | CB | GLN | A | 64 | 64.807 | −33.675 | −2.766 | 1.00 | 15.92 C |
| ATOM | 947 | CG | GLN | A | 64 | 64.437 | −34.322 | −4.099 | 1.00 | 13.35 C |
| ATOM | 950 | CD | GLN | A | 64 | 63.079 | −34.965 | −4.090 | 1.00 | 12.31 C |
| ATOM | 951 | OE1 | GLN | A | 64 | 62.366 | −34.925 | −5.091 | 1.00 | 16.14 O |
| ATOM | 952 | NE2 | GLN | A | 64 | 62.704 | −35.559 | −2.958 | 1.00 | 9.25 N |
| ATOM | 955 | C | GLN | A | 64 | 66.205 | −31.929 | −1.595 | 1.00 | 16.42 C |
| ATOM | 956 | O | GLN | A | 64 | 65.885 | −30.743 | −1.517 | 1.00 | 15.20 O |
| ATOM | 958 | N | ARG | A | 65 | 66.768 | −32.599 | −0.593 | 1.00 | 17.50 N |
| ATOM | 959 | CA | ARG | A | 65 | 66.913 | −32.006 | 0.739 | 1.00 | 17.71 C |
| ATOM | 961 | CB | ARG | A | 65 | 67.418 | −33.041 | 1.757 | 1.00 | 17.94 C |
| ATOM | 964 | CG | ARG | A | 65 | 66.368 | −34.108 | 2.094 | 1.00 | 18.27 C |
| ATOM | 967 | CD | ARG | A | 65 | 66.709 | −34.903 | 3.331 | 1.00 | 19.29 C |
| ATOM | 970 | NE | ARG | A | 65 | 66.763 | −34.043 | 4.501 | 1.00 | 25.35 N |
| ATOM | 972 | CZ | ARG | A | 65 | 67.051 | −34.456 | 5.732 | 1.00 | 29.90 C |
| ATOM | 973 | NH1 | ARG | A | 65 | 67.298 | −35.737 | 5.976 | 1.00 | 28.26 N |
| ATOM | 976 | NH2 | ARG | A | 65 | 67.086 | −33.576 | 6.730 | 1.00 | 33.55 N |
| ATOM | 979 | C | ARG | A | 65 | 67.827 | −30.798 | 0.702 | 1.00 | 16.77 C |
| ATOM | 980 | O | ARG | A | 65 | 67.580 | −29.813 | 1.389 | 1.00 | 17.22 O |
| ATOM | 982 | N | LEU | A | 66 | 68.858 | −30.867 | −0.136 | 1.00 | 16.24 N |
| ATOM | 983 | CA | LEU | A | 66 | 69.815 | −29.773 | −0.285 | 1.00 | 14.99 C |
| ATOM | 985 | CB | LEU | A | 66 | 71.091 | −30.282 | −0.950 | 1.00 | 14.29 C |
| ATOM | 988 | CG | LEU | A | 66 | 71.926 | −31.262 | −0.120 | 1.00 | 14.21 C |
| ATOM | 990 | CD1 | LEU | A | 66 | 72.898 | −32.029 | −1.013 | 1.00 | 12.16 C |
| ATOM | 994 | CD2 | LEU | A | 66 | 72.694 | −30.519 | 0.985 | 1.00 | 12.46 C |
| ATOM | 998 | C | LEU | A | 66 | 69.244 | −28.603 | −1.085 | 1.00 | 15.42 C |
| ATOM | 999 | O | LEU | A | 66 | 69.945 | −27.617 | −1.307 | 1.00 | 15.95 O |
| ATOM | 1001 | N | GLY | A | 67 | 67.990 | −28.725 | −1.530 | 1.00 | 15.16 N |
| ATOM | 1002 | CA | GLY | A | 67 | 67.254 | −27.625 | −2.151 | 1.00 | 14.99 C |
| ATOM | 1005 | C | GLY | A | 67 | 67.272 | −27.602 | −3.668 | 1.00 | 15.18 C |
| ATOM | 1006 | O | GLY | A | 67 | 66.767 | −26.657 | −4.268 | 1.00 | 16.15 O |
| ATOM | 1008 | N | LEU | A | 68 | 67.829 | −28.644 | −4.288 | 1.00 | 14.91 N |
| ATOM | 1009 | CA | LEU | A | 68 | 68.013 | −28.703 | −5.745 | 1.00 | 14.20 C |
| ATOM | 1011 | CB | LEU | A | 68 | 69.394 | −29.293 | −6.074 | 1.00 | 13.73 C |
| ATOM | 1014 | CG | LEU | A | 68 | 70.598 | −28.464 | −5.621 | 1.00 | 12.88 C |
| ATOM | 1016 | CD1 | LEU | A | 68 | 71.849 | −29.339 | −5.475 | 1.00 | 8.92 C |
| ATOM | 1020 | CD2 | LEU | A | 68 | 70.858 | −27.277 | −6.568 | 1.00 | 8.96 C |
| ATOM | 1024 | C | LEU | A | 68 | 66.933 | −29.502 | −6.488 | 1.00 | 14.67 C |
| ATOM | 1025 | O | LEU | A | 68 | 66.989 | −29.619 | −7.711 | 1.00 | 14.49 O |
| ATOM | 1027 | N | GLY | A | 69 | 65.956 | −30.047 | −5.763 | 1.00 | 15.47 N |
| ATOM | 1028 | CA | GLY | A | 69 | 64.867 | −30.817 | −6.374 | 1.00 | 14.82 C |
| ATOM | 1031 | C | GLY | A | 69 | 64.230 | −30.163 | −7.592 | 1.00 | 15.77 C |

APPENDIX 1-continued

| | | | | | | | | | | |
|---|---|---|---|---|---|---|---|---|---|---|
| ATOM | 1032 | O | GLY | A | 69 | 64.091 | −30.794 | −8.650 | 1.00 | 15.84 | O |
| ATOM | 1034 | N | TYR | A | 70 | 63.861 | −28.889 | −7.451 | 1.00 | 16.45 | N |
| ATOM | 1035 | CA | TYR | A | 70 | 63.181 | −28.131 | −8.521 | 1.00 | 16.04 | C |
| ATOM | 1037 | CB | TYR | A | 70 | 62.941 | −26.686 | −8.080 | 1.00 | 15.12 | C |
| ATOM | 1040 | CG | TYR | A | 70 | 64.159 | −25.789 | −8.181 | 1.00 | 14.52 | C |
| ATOM | 1041 | CD1 | TYR | A | 70 | 65.151 | −25.816 | −7.210 | 1.00 | 12.49 | C |
| ATOM | 1043 | CE1 | TYR | A | 70 | 66.277 | −24.998 | −7.303 | 1.00 | 13.94 | C |
| ATOM | 1045 | CZ | TYR | A | 70 | 66.405 | −24.132 | −8.371 | 1.00 | 16.38 | C |
| ATOM | 1046 | OH | TYR | A | 70 | 67.512 | −23.315 | −8.466 | 1.00 | 14.89 | O |
| ATOM | 1048 | CE2 | TYR | A | 70 | 65.425 | −24.088 | −9.353 | 1.00 | 14.01 | C |
| ATOM | 1050 | CD2 | TYR | A | 70 | 64.314 | −24.910 | −9.254 | 1.00 | 11.99 | C |
| ATOM | 1052 | C | TYR | A | 70 | 63.955 | −28.131 | −9.835 | 1.00 | 18.04 | C |
| ATOM | 1053 | O | TYR | A | 70 | 63.385 | −27.959 | −10.913 | 1.00 | 20.46 | O |
| ATOM | 1055 | N | ARG | A | 71 | 65.258 | −28.327 | −9.732 | 1.00 | 18.33 | N |
| ATOM | 1056 | CA | ARG | A | 71 | 66.156 | −28.251 | −10.873 | 1.00 | 18.97 | C |
| ATOM | 1058 | CB | ARG | A | 71 | 67.521 | −27.791 | −10.352 | 1.00 | 19.28 | C |
| ATOM | 1061 | CG | ARG | A | 71 | 68.522 | −27.420 | −11.395 | 1.00 | 20.34 | C |
| ATOM | 1064 | CD | ARG | A | 71 | 69.657 | −26.634 | −10.770 | 1.00 | 19.82 | C |
| ATOM | 1067 | NE | ARG | A | 71 | 69.326 | −25.224 | −10.689 | 1.00 | 21.37 | N |
| ATOM | 1069 | CZ | ARG | A | 71 | 69.326 | −24.404 | −11.732 | 1.00 | 23.52 | C |
| ATOM | 1070 | NH1 | ARG | A | 71 | 69.009 | −23.138 | −11.563 | 1.00 | 27.16 | N |
| ATOM | 1073 | NH2 | ARG | A | 71 | 69.643 | −24.842 | −12.944 | 1.00 | 24.15 | N |
| ATOM | 1076 | C | ARG | A | 71 | 66.289 | −29.586 | −11.615 | 1.00 | 18.48 | C |
| ATOM | 1077 | O | ARG | A | 71 | 66.647 | −29.601 | −12.790 | 1.00 | 18.00 | O |
| ATOM | 1079 | N | PHE | A | 72 | 66.002 | −30.691 | −10.925 | 1.00 | 18.29 | N |
| ATOM | 1080 | CA | PHE | A | 72 | 66.179 | −32.039 | −11.465 | 1.00 | 18.27 | C |
| ATOM | 1082 | CB | PHE | A | 72 | 67.269 | −32.777 | −10.667 | 1.00 | 18.42 | C |
| ATOM | 1085 | CG | PHE | A | 72 | 68.626 | −32.144 | −10.767 | 1.00 | 16.33 | C |
| ATOM | 1086 | CD1 | PHE | A | 72 | 69.394 | −32.302 | −11.907 | 1.00 | 11.77 | C |
| ATOM | 1088 | CE1 | PHE | A | 72 | 70.641 | −31.707 | −12.007 | 1.00 | 16.47 | C |
| ATOM | 1090 | CZ | PHE | A | 72 | 71.136 | −30.940 | −10.954 | 1.00 | 15.78 | C |
| ATOM | 1092 | CE2 | PHE | A | 72 | 70.383 | −30.777 | −9.821 | 1.00 | 15.51 | C |
| ATOM | 1094 | CD2 | PHE | A | 72 | 69.129 | −31.376 | −9.729 | 1.00 | 16.02 | C |
| ATOM | 1096 | C | PHE | A | 72 | 64.881 | −32.862 | −11.451 | 1.00 | 18.90 | C |
| ATOM | 1097 | O | PHE | A | 72 | 64.910 | −34.093 | −11.493 | 1.00 | 17.74 | O |
| ATOM | 1099 | N | GLU | A | 73 | 63.740 | −32.188 | −11.426 | 1.00 | 20.36 | N |
| ATOM | 1100 | CA | GLU | A | 73 | 62.466 | −32.882 | −11.261 | 1.00 | 21.99 | C |
| ATOM | 1102 | CB | GLU | A | 73 | 61.307 | −31.884 | −11.219 | 1.00 | 22.99 | C |
| ATOM | 1105 | CG | GLU | A | 73 | 59.995 | −32.529 | −10.830 | 1.00 | 29.40 | C |
| ATOM | 1108 | CD | GLU | A | 73 | 58.845 | −31.560 | −10.766 | 1.00 | 35.93 | C |
| ATOM | 1109 | OE1 | GLU | A | 73 | 59.091 | −30.335 | −10.727 | 1.00 | 42.73 | O |
| ATOM | 1110 | OE2 | GLU | A | 73 | 57.690 | −32.036 | −10.751 | 1.00 | 39.11 | O |
| ATOM | 1111 | C | GLU | A | 73 | 62.201 | −33.955 | −12.323 | 1.00 | 21.43 | C |
| ATOM | 1112 | O | GLU | A | 73 | 61.886 | −35.093 | −11.987 | 1.00 | 21.47 | O |
| ATOM | 1114 | N | SER | A | 74 | 62.318 | −33.606 | −13.598 | 1.00 | 21.46 | N |
| ATOM | 1115 | CA | SER | A | 74 | 62.074 | −34.594 | −14.649 | 1.00 | 21.83 | C |
| ATOM | 1117 | CB | SER | A | 74 | 62.037 | −33.936 | −16.024 | 1.00 | 22.03 | C |
| ATOM | 1120 | OG | SER | A | 74 | 63.243 | −33.257 | −16.273 | 1.00 | 27.93 | O |
| ATOM | 1122 | C | SER | A | 74 | 63.121 | −35.707 | −14.615 | 1.00 | 20.53 | C |
| ATOM | 1123 | O | SER | A | 74 | 62.792 | −36.883 | −14.794 | 1.00 | 20.23 | O |
| ATOM | 1125 | N | ASP | A | 75 | 64.378 | −35.333 | −14.383 | 1.00 | 19.65 | N |
| ATOM | 1126 | CA | ASP | A | 75 | 65.449 | −36.315 | −14.220 | 1.00 | 18.66 | C |
| ATOM | 1128 | CB | ASP | A | 75 | 66.790 | −35.625 | −13.949 | 1.00 | 18.80 | C |
| ATOM | 1131 | CG | ASP | A | 75 | 67.381 | −34.969 | −15.191 | 1.00 | 19.71 | C |
| ATOM | 1132 | OD1 | ASP | A | 75 | 67.482 | −35.634 | −16.240 | 1.00 | 18.92 | O |
| ATOM | 1133 | OD2 | ASP | A | 75 | 67.766 | −33.786 | −15.111 | 1.00 | 23.76 | O |
| ATOM | 1134 | C | ASP | A | 75 | 65.114 | −37.274 | −13.083 | 1.00 | 17.66 | C |
| ATOM | 1135 | O | ASP | A | 75 | 65.232 | −38.486 | −13.230 | 1.00 | 17.70 | O |
| ATOM | 1137 | N | ILE | A | 76 | 64.678 | −36.722 | −11.954 | 1.00 | 17.25 | N |
| ATOM | 1138 | CA | ILE | A | 76 | 64.221 | −37.523 | −10.820 | 1.00 | 16.28 | C |
| ATOM | 1140 | CB | ILE | A | 76 | 63.938 | −36.633 | −9.594 | 1.00 | 16.35 | C |
| ATOM | 1142 | CG1 | ILE | A | 76 | 65.258 | −36.073 | −9.040 | 1.00 | 15.94 | C |
| ATOM | 1145 | CD1 | ILE | A | 76 | 65.092 | −34.884 | −8.092 | 1.00 | 11.79 | C |
| ATOM | 1149 | CG2 | ILE | A | 76 | 63.211 | −37.426 | −8.510 | 1.00 | 13.58 | C |
| ATOM | 1153 | C | ILE | A | 76 | 62.986 | −38.386 | −11.143 | 1.00 | 17.08 | C |
| ATOM | 1154 | O | ILE | A | 76 | 62.922 | −39.539 | −10.713 | 1.00 | 17.23 | O |
| ATOM | 1156 | N | ARG | A | 77 | 62.018 | −37.856 | −11.898 | 1.00 | 17.36 | N |
| ATOM | 1157 | CA | ARG | A | 77 | 60.833 | −38.650 | −12.271 | 1.00 | 18.20 | C |
| ATOM | 1159 | CB | ARG | A | 77 | 59.809 | −37.829 | −13.054 | 1.00 | 19.55 | C |
| ATOM | 1162 | CG | ARG | A | 77 | 59.093 | −36.786 | −12.211 | 1.00 | 30.35 | C |
| ATOM | 1165 | CD | ARG | A | 77 | 58.514 | −35.644 | −13.053 | 1.00 | 39.84 | C |
| ATOM | 1168 | NE | ARG | A | 77 | 57.449 | −36.103 | −13.934 | 1.00 | 48.68 | N |
| ATOM | 1170 | CZ | ARG | A | 77 | 56.226 | −36.450 | −13.531 | 1.00 | 59.20 | C |
| ATOM | 1171 | NH1 | ARG | A | 77 | 55.887 | −36.403 | −12.241 | 1.00 | 61.69 | N |
| ATOM | 1174 | NH2 | ARG | A | 77 | 55.326 | −36.852 | −14.426 | 1.00 | 62.52 | N |
| ATOM | 1177 | C | ARG | A | 77 | 61.240 | −39.866 | −13.081 | 1.00 | 17.19 | C |
| ATOM | 1178 | O | ARG | A | 77 | 60.773 | −40.975 | −12.819 | 1.00 | 17.85 | O |
| ATOM | 1180 | N | GLY | A | 78 | 62.119 | −39.659 | −14.056 | 1.00 | 15.51 | N |
| ATOM | 1181 | CA | GLY | A | 78 | 62.591 | −40.742 | −14.899 | 1.00 | 14.70 | C |
| ATOM | 1184 | C | GLY | A | 78 | 63.378 | −41.766 | −14.113 | 1.00 | 15.16 | C |

APPENDIX 1-continued

| ATOM | 1185 | O | GLY | A | 78 | 63.211 | −42.967 | −14.316 | 1.00 | 17.14 | O |
|---|---|---|---|---|---|---|---|---|---|---|---|
| ATOM | 1187 | N | ALA | A | 79 | 64.239 | −41.301 | −13.212 | 1.00 | 14.47 | N |
| ATOM | 1188 | CA | ALA | A | 79 | 65.013 | −42.204 | −12.368 | 1.00 | 14.61 | C |
| ATOM | 1190 | CB | ALA | A | 79 | 65.937 | −41.425 | −11.455 | 1.00 | 13.92 | C |
| ATOM | 1194 | C | ALA | A | 79 | 64.089 | −43.105 | −11.551 | 1.00 | 15.53 | C |
| ATOM | 1195 | O | ALA | A | 79 | 64.291 | −44.312 | −11.484 | 1.00 | 16.20 | O |
| ATOM | 1197 | N | LEU | A | 80 | 63.067 | −42.509 | −10.947 | 1.00 | 17.11 | N |
| ATOM | 1198 | CA | LEU | A | 80 | 62.078 | −43.259 | −10.188 | 1.00 | 18.35 | C |
| ATOM | 1200 | CB | LEU | A | 80 | 61.165 | −42.304 | −9.408 | 1.00 | 19.36 | C |
| ATOM | 1203 | CG | LEU | A | 80 | 61.820 | −41.589 | −8.218 | 1.00 | 18.62 | C |
| ATOM | 1205 | CD1 | LEU | A | 80 | 60.915 | −40.475 | −7.707 | 1.00 | 15.51 | C |
| ATOM | 1209 | CD2 | LEU | A | 80 | 62.176 | −42.587 | −7.097 | 1.00 | 12.92 | C |
| ATOM | 1213 | C | LEU | A | 80 | 61.244 | −44.178 | −11.082 | 1.00 | 19.46 | C |
| ATOM | 1214 | O | LEU | A | 80 | 60.869 | −45.262 | −10.661 | 1.00 | 20.30 | O |
| ATOM | 1216 | N | ASP | A | 81 | 60.960 | −43.754 | −12.308 | 1.00 | 20.42 | N |
| ATOM | 1217 | CA | ASP | A | 81 | 60.266 | −44.616 | −13.263 | 1.00 | 22.07 | C |
| ATOM | 1219 | CB | ASP | A | 81 | 59.981 | −43.877 | −14.576 | 1.00 | 23.40 | C |
| ATOM | 1222 | CG | ASP | A | 81 | 58.910 | −44.558 | −15.419 | 1.00 | 27.38 | C |
| ATOM | 1223 | OD1 | ASP | A | 81 | 57.775 | −44.718 | −14.925 | 1.00 | 35.42 | O |
| ATOM | 1224 | OD2 | ASP | A | 81 | 59.193 | −44.912 | −16.583 | 1.00 | 33.33 | O |
| ATOM | 1225 | C | ASP | A | 81 | 61.093 | −45.862 | −13.544 | 1.00 | 22.17 | C |
| ATOM | 1226 | O | ASP | A | 81 | 60.561 | −46.971 | −13.568 | 1.00 | 23.66 | O |
| ATOM | 1228 | N | ARG | A | 82 | 62.393 | −45.681 | −13.750 | 1.00 | 22.55 | N |
| ATOM | 1229 | CA | ARG | A | 82 | 63.291 | −46.817 | −13.984 | 1.00 | 23.77 | C |
| ATOM | 1231 | CB | ARG | A | 82 | 64.667 | −46.337 | −14.463 | 1.00 | 25.05 | C |
| ATOM | 1234 | CG | ARG | A | 82 | 65.692 | −47.463 | −14.709 | 1.00 | 27.16 | C |
| ATOM | 1237 | CD | ARG | A | 82 | 67.027 | −46.899 | −15.176 | 1.00 | 28.82 | C |
| ATOM | 1240 | NE | ARG | A | 82 | 66.881 | −46.132 | −16.416 | 1.00 | 30.19 | N |
| ATOM | 1242 | CZ | ARG | A | 82 | 67.011 | −46.623 | −17.654 | 1.00 | 31.69 | C |
| ATOM | 1243 | NH1 | ARG | A | 82 | 67.310 | −47.905 | −17.872 | 1.00 | 27.72 | N |
| ATOM | 1246 | NH2 | ARG | A | 82 | 66.845 | −45.812 | −18.694 | 1.00 | 32.14 | N |
| ATOM | 1249 | C | ARG | A | 82 | 63.443 | −47.680 | −12.728 | 1.00 | 23.10 | C |
| ATOM | 1250 | O | ARG | A | 82 | 63.508 | −48.903 | −12.815 | 1.00 | 23.80 | O |
| ATOM | 1252 | N | PHE | A | 83 | 63.504 | −47.033 | −11.567 | 1.00 | 21.87 | N |
| ATOM | 1253 | CA | PHE | A | 83 | 63.604 | −47.734 | −10.302 | 1.00 | 20.68 | C |
| ATOM | 1255 | CB | PHE | A | 83 | 63.547 | −46.722 | −9.145 | 1.00 | 20.79 | C |
| ATOM | 1258 | CG | PHE | A | 83 | 63.463 | −47.349 | −7.779 | 1.00 | 18.77 | C |
| ATOM | 1259 | CD1 | PHE | A | 83 | 64.586 | −47.868 | −7.175 | 1.00 | 18.63 | C |
| ATOM | 1261 | CE1 | PHE | A | 83 | 64.513 | −48.454 | −5.918 | 1.00 | 21.29 | C |
| ATOM | 1263 | CZ | PHE | A | 83 | 63.302 | −48.514 | −5.247 | 1.00 | 21.04 | C |
| ATOM | 1265 | CE2 | PHE | A | 83 | 62.166 | −47.989 | −5.841 | 1.00 | 22.98 | C |
| ATOM | 1267 | CD2 | PHE | A | 83 | 62.253 | −47.409 | −7.101 | 1.00 | 20.98 | C |
| ATOM | 1269 | C | PHE | A | 83 | 62.499 | −48.787 | −10.198 | 1.00 | 21.01 | C |
| ATOM | 1270 | O | PHE | A | 83 | 62.756 | −49.926 | −9.820 | 1.00 | 21.25 | O |
| ATOM | 1272 | N | VAL | A | 84 | 61.276 | −48.413 | −10.565 | 1.00 | 22.16 | N |
| ATOM | 1273 | CA | VAL | A | 84 | 60.132 | −49.323 | −10.463 | 1.00 | 22.20 | C |
| ATOM | 1275 | CB | VAL | A | 84 | 58.785 | −48.578 | −10.590 | 1.00 | 22.42 | C |
| ATOM | 1277 | CG1 | VAL | A | 84 | 57.626 | −49.567 | −10.704 | 1.00 | 17.38 | C |
| ATOM | 1281 | CG2 | VAL | A | 84 | 58.587 | −47.644 | −9.400 | 1.00 | 19.99 | C |
| ATOM | 1285 | C | VAL | A | 84 | 60.207 | −50.394 | −11.528 | 1.00 | 23.13 | C |
| ATOM | 1286 | O | VAL | A | 84 | 60.197 | −51.581 | −11.212 | 1.00 | 23.07 | O |
| ATOM | 1288 | N | SER | A | 85 | 60.320 | −49.966 | −12.784 | 1.00 | 24.55 | N |
| ATOM | 1289 | CA | SER | A | 85 | 60.202 | −50.883 | −13.920 | 1.00 | 25.78 | C |
| ATOM | 1291 | CB | SER | A | 85 | 60.133 | −50.116 | −15.244 | 1.00 | 26.02 | C |
| ATOM | 1294 | OG | SER | A | 85 | 61.407 | −49.643 | −15.636 | 1.00 | 29.26 | O |
| ATOM | 1296 | C | SER | A | 85 | 61.324 | −51.917 | −13.969 | 1.00 | 25.92 | C |
| ATOM | 1297 | O | SER | A | 85 | 61.161 | −52.969 | −14.583 | 1.00 | 26.29 | O |
| ATOM | 1299 | N | SER | A | 86 | 62.451 | −51.621 | −13.320 | 1.00 | 26.24 | N |
| ATOM | 1300 | CA | SER | A | 86 | 63.561 | −52.573 | −13.221 | 1.00 | 26.71 | C |
| ATOM | 1302 | CB | SER | A | 86 | 64.903 | −51.845 | −13.353 | 1.00 | 26.89 | C |
| ATOM | 1305 | OG | SER | A | 86 | 65.247 | −51.174 | −12.156 | 1.00 | 27.56 | O |
| ATOM | 1307 | C | SER | A | 86 | 63.535 | −53.394 | −11.923 | 1.00 | 26.91 | C |
| ATOM | 1308 | O | SER | A | 86 | 64.525 | −54.046 | −11.579 | 1.00 | 26.48 | O |
| ATOM | 1310 | N | GLY | A | 87 | 62.409 | −53.359 | −11.210 | 1.00 | 27.49 | N |
| ATOM | 1311 | CA | GLY | A | 87 | 62.201 | −54.201 | −10.031 | 1.00 | 27.23 | C |
| ATOM | 1314 | C | GLY | A | 87 | 62.861 | −53.717 | −8.754 | 1.00 | 26.76 | C |
| ATOM | 1315 | O | GLY | A | 87 | 62.991 | −54.476 | −7.798 | 1.00 | 27.05 | O |
| ATOM | 1317 | N | GLY | A | 88 | 63.272 | −52.455 | −8.727 | 1.00 | 26.57 | N |
| ATOM | 1318 | CA | GLY | A | 88 | 63.930 | −51.891 | −7.555 | 1.00 | 26.30 | C |
| ATOM | 1321 | C | GLY | A | 88 | 62.978 | −51.772 | −6.384 | 1.00 | 26.50 | C |
| ATOM | 1322 | O | GLY | A | 88 | 63.340 | −52.072 | −5.244 | 1.00 | 26.40 | O |
| ATOM | 1324 | N | PHE | A | 89 | 61.752 | −51.342 | −6.666 | 1.00 | 26.08 | N |
| ATOM | 1325 | CA | PHE | A | 89 | 60.745 | −51.205 | −5.628 | 1.00 | 26.31 | C |
| ATOM | 1327 | CB | PHE | A | 89 | 59.531 | −50.444 | −6.153 | 1.00 | 25.89 | C |
| ATOM | 1330 | CG | PHE | A | 89 | 58.544 | −50.075 | −5.085 | 1.00 | 23.78 | C |
| ATOM | 1331 | CD1 | PHE | A | 89 | 58.946 | −49.360 | −3.967 | 1.00 | 23.52 | C |
| ATOM | 1333 | CE1 | PHE | A | 89 | 58.044 | −49.015 | −2.985 | 1.00 | 22.50 | C |
| ATOM | 1335 | CZ | PHE | A | 89 | 56.724 | −49.375 | −3.110 | 1.00 | 23.15 | C |
| ATOM | 1337 | CE2 | PHE | A | 89 | 56.308 | −50.081 | −4.214 | 1.00 | 24.72 | C |
| ATOM | 1339 | CD2 | PHE | A | 89 | 57.216 | −50.429 | −5.199 | 1.00 | 23.79 | C |

APPENDIX 1-continued

| | | | | | | | | | | |
|---|---|---|---|---|---|---|---|---|---|---|
| ATOM | 1341 | C | PHE | A | 89 | 60.315 | −52.564 | −5.097 | 1.00 | 27.43 | C |
| ATOM | 1342 | O | PHE | A | 89 | 60.014 | −52.712 | −3.916 | 1.00 | 27.98 | O |
| ATOM | 1344 | N | ASP | A | 90 | 60.282 | −53.549 | −5.984 | 1.00 | 28.22 | N |
| ATOM | 1345 | CA | ASP | A | 90 | 60.010 | −54.916 | −5.598 | 1.00 | 28.96 | C |
| ATOM | 1347 | CB | ASP | A | 90 | 59.849 | −55.805 | −6.835 | 1.00 | 30.61 | C |
| ATOM | 1350 | CG | ASP | A | 90 | 58.799 | −56.871 | −6.645 | 1.00 | 35.50 | C |
| ATOM | 1351 | OD1 | ASP | A | 90 | 57.601 | −56.517 | −6.719 | 1.00 | 42.54 | O |
| ATOM | 1352 | OD2 | ASP | A | 90 | 59.167 | −58.048 | −6.425 | 1.00 | 37.40 | O |
| ATOM | 1353 | C | ASP | A | 90 | 61.162 | −55.420 | −4.744 | 1.00 | 28.08 | C |
| ATOM | 1354 | O | ASP | A | 90 | 60.949 | −56.017 | −3.698 | 1.00 | 27.56 | O |
| ATOM | 1356 | N | ALA | A | 91 | 62.388 | −55.165 | −5.189 | 1.00 | 27.90 | N |
| ATOM | 1357 | CA | ALA | A | 91 | 63.570 | −55.562 | −4.425 | 1.00 | 28.29 | C |
| ATOM | 1359 | CB | ALA | A | 91 | 64.843 | −55.090 | −5.125 | 1.00 | 28.02 | C |
| ATOM | 1363 | C | ALA | A | 91 | 63.530 | −55.041 | −2.981 | 1.00 | 27.99 | C |
| ATOM | 1364 | O | ALA | A | 91 | 63.595 | −55.823 | −2.037 | 1.00 | 28.71 | O |
| ATOM | 1366 | N | VAL | A | 92 | 63.409 | −53.727 | −2.819 | 1.00 | 27.52 | N |
| ATOM | 1367 | CA | VAL | A | 92 | 63.439 | −53.115 | −1.491 | 1.00 | 27.31 | C |
| ATOM | 1369 | CB | VAL | A | 92 | 63.424 | −51.558 | −1.541 | 1.00 | 27.02 | C |
| ATOM | 1371 | CG1 | VAL | A | 92 | 64.645 | −51.030 | −2.280 | 1.00 | 22.62 | C |
| ATOM | 1375 | CG2 | VAL | A | 92 | 62.146 | −51.048 | −2.164 | 1.00 | 26.79 | C |
| ATOM | 1379 | C | VAL | A | 92 | 62.294 | −53.589 | −0.602 | 1.00 | 27.90 | C |
| ATOM | 1380 | O | VAL | A | 92 | 62.497 | −53.821 | 0.590 | 1.00 | 28.35 | O |
| ATOM | 1382 | N | THR | A | 93 | 61.104 | −53.760 | −1.170 | 1.00 | 28.23 | N |
| ATOM | 1383 | CA | THR | A | 93 | 59.960 | −54.211 | −0.370 | 1.00 | 29.05 | C |
| ATOM | 1385 | CB | THR | A | 93 | 58.649 | −54.319 | −1.187 | 1.00 | 29.02 | C |
| ATOM | 1387 | OG1 | THR | A | 93 | 58.818 | −55.245 | −2.266 | 1.00 | 28.86 | O |
| ATOM | 1389 | CG2 | THR | A | 93 | 58.222 | −52.950 | −1.721 | 1.00 | 29.04 | C |
| ATOM | 1393 | C | THR | A | 93 | 60.216 | −55.550 | 0.317 | 1.00 | 29.41 | C |
| ATOM | 1394 | O | THR | A | 93 | 59.603 | −55.830 | 1.350 | 1.00 | 30.18 | O |
| ATOM | 1396 | N | LYS | A | 94 | 61.117 | −56.359 | −0.248 | 1.00 | 29.78 | N |
| ATOM | 1397 | CA | LYS | A | 94 | 61.424 | −57.697 | 0.274 | 1.00 | 30.05 | C |
| ATOM | 1399 | CB | LYS | A | 94 | 61.405 | −58.728 | −0.869 | 1.00 | 30.16 | C |
| ATOM | 1402 | CG | LYS | A | 94 | 60.132 | −58.717 | −1.748 | 1.00 | 34.75 | C |
| ATOM | 1405 | CD | LYS | A | 94 | 58.824 | −58.774 | −0.928 | 1.00 | 41.79 | C |
| ATOM | 1408 | CE | LYS | A | 94 | 57.580 | −58.482 | −1.788 | 1.00 | 47.02 | C |
| ATOM | 1411 | NZ | LYS | A | 94 | 56.435 | −57.895 | −1.002 | 1.00 | 45.97 | N |
| ATOM | 1415 | C | LYS | A | 94 | 62.762 | −57.786 | 1.015 | 1.00 | 29.38 | C |
| ATOM | 1416 | O | LYS | A | 94 | 63.217 | −58.882 | 1.317 | 1.00 | 30.59 | O |
| ATOM | 1418 | N | THR | A | 95 | 63.382 | −56.651 | 1.331 | 1.00 | 28.34 | N |
| ATOM | 1419 | CA | THR | A | 95 | 64.706 | −56.656 | 1.973 | 1.00 | 27.18 | C |
| ATOM | 1421 | CB | THR | A | 95 | 65.834 | −56.656 | 0.918 | 1.00 | 27.59 | C |
| ATOM | 1423 | OG1 | THR | A | 95 | 65.532 | −55.696 | −0.105 | 1.00 | 27.34 | O |
| ATOM | 1425 | CG2 | THR | A | 95 | 66.004 | −58.039 | 0.291 | 1.00 | 26.29 | C |
| ATOM | 1429 | C | THR | A | 95 | 64.987 | −55.478 | 2.911 | 1.00 | 26.86 | C |
| ATOM | 1430 | O | THR | A | 95 | 65.660 | −55.656 | 3.924 | 1.00 | 26.77 | O |
| ATOM | 1432 | N | SER | A | 96 | 64.493 | −54.284 | 2.572 | 1.00 | 26.14 | N |
| ATOM | 1433 | CA | SER | A | 96 | 64.907 | −53.049 | 3.248 | 1.00 | 24.86 | C |
| ATOM | 1435 | CB | SER | A | 96 | 65.881 | −52.280 | 2.352 | 1.00 | 24.50 | C |
| ATOM | 1438 | OG | SER | A | 96 | 66.217 | −51.027 | 2.923 | 1.00 | 24.84 | O |
| ATOM | 1440 | C | SER | A | 96 | 63.741 | −52.135 | 3.612 | 1.00 | 24.07 | C |
| ATOM | 1441 | O | SER | A | 96 | 63.058 | −51.607 | 2.726 | 1.00 | 23.24 | O |
| ATOM | 1443 | N | LEU | A | 97 | 63.531 | −51.933 | 4.916 | 1.00 | 23.40 | N |
| ATOM | 1444 | CA | LEU | A | 97 | 62.540 | −50.963 | 5.394 | 1.00 | 22.78 | C |
| ATOM | 1446 | CB | LEU | A | 97 | 62.418 | −50.978 | 6.924 | 1.00 | 23.20 | C |
| ATOM | 1449 | CG | LEU | A | 97 | 61.506 | −49.892 | 7.521 | 1.00 | 22.25 | C |
| ATOM | 1451 | CD1 | LEU | A | 97 | 60.078 | −50.016 | 6.988 | 1.00 | 19.42 | C |
| ATOM | 1455 | CD2 | LEU | A | 97 | 61.505 | −49.949 | 9.035 | 1.00 | 22.20 | C |
| ATOM | 1459 | C | LEU | A | 97 | 62.958 | −49.580 | 4.955 | 1.00 | 21.37 | C |
| ATOM | 1460 | O | LEU | A | 97 | 62.136 | −48.800 | 4.462 | 1.00 | 21.91 | O |
| ATOM | 1462 | N | HIS | A | 98 | 64.241 | −49.281 | 5.145 | 1.00 | 19.60 | N |
| ATOM | 1463 | CA | HIS | A | 98 | 64.787 | −47.994 | 4.741 | 1.00 | 19.79 | C |
| ATOM | 1465 | CB | HIS | A | 98 | 66.300 | −47.943 | 4.974 | 1.00 | 19.76 | C |
| ATOM | 1468 | CG | HIS | A | 98 | 66.939 | −46.689 | 4.467 | 1.00 | 22.66 | C |
| ATOM | 1469 | ND1 | HIS | A | 98 | 66.379 | −45.443 | 4.656 | 1.00 | 23.03 | N |
| ATOM | 1471 | CE1 | HIS | A | 98 | 67.149 | −44.529 | 4.096 | 1.00 | 23.75 | C |
| ATOM | 1473 | NE2 | HIS | A | 98 | 68.190 | −45.135 | 3.554 | 1.00 | 25.40 | N |
| ATOM | 1475 | CD2 | HIS | A | 98 | 68.083 | −46.486 | 3.774 | 1.00 | 25.37 | C |
| ATOM | 1477 | C | HIS | A | 98 | 64.452 | −47.701 | 3.276 | 1.00 | 18.86 | C |
| ATOM | 1478 | O | HIS | A | 98 | 63.821 | −46.687 | 2.968 | 1.00 | 16.70 | O |
| ATOM | 1480 | N | GLY | A | 99 | 64.858 | −48.607 | 2.388 | 1.00 | 18.34 | N |
| ATOM | 1481 | CA | GLY | A | 99 | 64.601 | −48.453 | 0.956 | 1.00 | 17.49 | C |
| ATOM | 1484 | C | GLY | A | 99 | 63.128 | −48.291 | 0.648 | 1.00 | 17.45 | C |
| ATOM | 1485 | O | GLY | A | 99 | 62.745 | −47.404 | −0.117 | 1.00 | 16.89 | O |
| ATOM | 1487 | N | THR | A | 100 | 62.307 | −49.145 | 1.265 | 1.00 | 17.77 | N |
| ATOM | 1488 | CA | THR | A | 100 | 60.853 | −49.139 | 1.070 | 1.00 | 16.46 | C |
| ATOM | 1490 | CB | THR | A | 100 | 60.189 | −50.304 | 1.838 | 1.00 | 16.82 | C |
| ATOM | 1492 | OG1 | THR | A | 100 | 60.722 | −51.549 | 1.362 | 1.00 | 16.05 | O |
| ATOM | 1494 | CG2 | THR | A | 100 | 58.672 | −50.301 | 1.664 | 1.00 | 12.76 | C |
| ATOM | 1498 | C | THR | A | 100 | 60.247 | −47.808 | 1.502 | 1.00 | 16.62 | C |
| ATOM | 1499 | O | THR | A | 100 | 59.548 | −47.158 | 0.725 | 1.00 | 18.20 | O |

APPENDIX 1-continued

| | | | | | | | | | | | |
|---|---|---|---|---|---|---|---|---|---|---|---|
| ATOM | 1501 | N | ALA | A | 101 | 60.531 | −47.390 | 2.729 | 1.00 | 16.33 | N |
| ATOM | 1502 | CA | ALA | A | 101 | 60.011 | −46.111 | 3.232 | 1.00 | 16.05 | C |
| ATOM | 1504 | CB | ALA | A | 101 | 60.475 | −45.881 | 4.666 | 1.00 | 15.37 | C |
| ATOM | 1508 | C | ALA | A | 101 | 60.431 | −44.936 | 2.337 | 1.00 | 15.29 | C |
| ATOM | 1509 | O | ALA | A | 101 | 59.605 | −44.122 | 1.922 | 1.00 | 15.29 | O |
| ATOM | 1511 | N | LEU | A | 102 | 61.721 | −44.867 | 2.034 | 1.00 | 15.18 | N |
| ATOM | 1512 | CA | LEU | A | 102 | 62.270 | −43.768 | 1.254 | 1.00 | 15.07 | C |
| ATOM | 1514 | CB | LEU | A | 102 | 63.801 | −43.856 | 1.224 | 1.00 | 14.12 | C |
| ATOM | 1517 | CG | LEU | A | 102 | 64.545 | −42.770 | 0.448 | 1.00 | 12.87 | C |
| ATOM | 1519 | CD1 | LEU | A | 102 | 64.090 | −41.367 | 0.868 | 1.00 | 8.26 | C |
| ATOM | 1523 | CD2 | LEU | A | 102 | 66.045 | −42.944 | 0.631 | 1.00 | 5.88 | C |
| ATOM | 1527 | C | LEU | A | 102 | 61.692 | −43.765 | −0.160 | 1.00 | 15.44 | C |
| ATOM | 1528 | O | LEU | A | 102 | 61.268 | −42.726 | −0.666 | 1.00 | 15.75 | O |
| ATOM | 1530 | N | SER | A | 103 | 61.649 | −44.935 | −0.787 | 1.00 | 15.40 | N |
| ATOM | 1531 | CA | SER | A | 103 | 61.088 | −45.041 | −2.129 | 1.00 | 15.43 | C |
| ATOM | 1533 | CB | SER | A | 103 | 61.362 | −46.424 | −2.714 | 1.00 | 15.47 | C |
| ATOM | 1536 | OG | SER | A | 103 | 60.768 | −47.430 | −1.924 | 1.00 | 17.65 | O |
| ATOM | 1538 | C | SER | A | 103 | 59.589 | −44.717 | −2.141 | 1.00 | 15.00 | C |
| ATOM | 1539 | O | SER | A | 103 | 59.122 | −43.981 | −2.998 | 1.00 | 15.23 | O |
| ATOM | 1541 | N | PHE | A | 104 | 58.839 | −45.253 | −1.183 | 1.00 | 15.40 | N |
| ATOM | 1542 | CA | PHE | A | 104 | 57.417 | −44.909 | −1.037 | 1.00 | 15.09 | C |
| ATOM | 1544 | CB | PHE | A | 104 | 56.851 | −45.462 | 0.279 | 1.00 | 15.48 | C |
| ATOM | 1547 | CG | PHE | A | 104 | 55.379 | −45.221 | 0.447 | 1.00 | 13.12 | C |
| ATOM | 1548 | CD1 | PHE | A | 104 | 54.908 | −44.003 | 0.884 | 1.00 | 15.81 | C |
| ATOM | 1550 | CE1 | PHE | A | 104 | 53.546 | −43.777 | 1.022 | 1.00 | 19.45 | C |
| ATOM | 1552 | CZ | PHE | A | 104 | 52.642 | −44.778 | 0.712 | 1.00 | 15.26 | C |
| ATOM | 1554 | CE2 | PHE | A | 104 | 53.102 | −45.988 | 0.270 | 1.00 | 12.72 | C |
| ATOM | 1556 | CD2 | PHE | A | 104 | 54.464 | −46.206 | 0.134 | 1.00 | 13.12 | C |
| ATOM | 1558 | C | PHE | A | 104 | 57.201 | −43.399 | −1.053 | 1.00 | 14.62 | C |
| ATOM | 1559 | O | PHE | A | 104 | 56.311 | −42.888 | −1.725 | 1.00 | 15.32 | O |
| ATOM | 1561 | N | ARG | A | 105 | 58.011 | −42.698 | −0.274 | 1.00 | 14.38 | N |
| ATOM | 1562 | CA | ARG | A | 105 | 57.886 | −41.258 | −0.132 | 1.00 | 14.61 | C |
| ATOM | 1564 | CB | ARG | A | 105 | 58.856 | −40.764 | 0.946 | 1.00 | 14.63 | C |
| ATOM | 1567 | CG | ARG | A | 105 | 58.932 | −39.258 | 1.101 | 1.00 | 14.01 | C |
| ATOM | 1570 | CD | ARG | A | 105 | 59.503 | −38.878 | 2.476 | 1.00 | 13.58 | C |
| ATOM | 1573 | NE | ARG | A | 105 | 60.954 | −39.024 | 2.549 | 1.00 | 13.53 | N |
| ATOM | 1575 | CZ | ARG | A | 105 | 61.829 | −38.179 | 2.004 | 1.00 | 13.34 | C |
| ATOM | 1576 | NH1 | ARG | A | 105 | 61.414 | −37.118 | 1.317 | 1.00 | 16.92 | N |
| ATOM | 1579 | NH2 | ARG | A | 105 | 63.130 | −38.400 | 2.133 | 1.00 | 14.85 | N |
| ATOM | 1582 | C | ARG | A | 105 | 58.173 | −40.585 | −1.470 | 1.00 | 14.87 | C |
| ATOM | 1583 | O | ARG | A | 105 | 57.314 | −39.910 | −2.026 | 1.00 | 14.73 | O |
| ATOM | 1585 | N | LEU | A | 106 | 59.379 | −40.809 | −1.983 | 1.00 | 14.52 | N |
| ATOM | 1586 | CA | LEU | A | 106 | 59.816 | −40.217 | −3.231 | 1.00 | 13.90 | C |
| ATOM | 1588 | CB | LEU | A | 106 | 61.226 | −40.709 | −3.575 | 1.00 | 14.07 | C |
| ATOM | 1591 | CG | LEU | A | 106 | 62.348 | −40.279 | −2.620 | 1.00 | 13.34 | C |
| ATOM | 1593 | CD1 | LEU | A | 106 | 63.702 | −40.880 | −3.034 | 1.00 | 8.71 | C |
| ATOM | 1597 | CD2 | LEU | A | 106 | 62.435 | −38.759 | −2.549 | 1.00 | 9.95 | C |
| ATOM | 1601 | C | LEU | A | 106 | 58.850 | −40.525 | −4.379 | 1.00 | 13.52 | C |
| ATOM | 1602 | O | LEU | A | 106 | 58.539 | −39.651 | −5.179 | 1.00 | 12.39 | O |
| ATOM | 1604 | N | LEU | A | 107 | 58.363 | −41.761 | −4.446 | 1.00 | 13.69 | N |
| ATOM | 1605 | CA | LEU | A | 107 | 57.404 | −42.146 | −5.483 | 1.00 | 13.52 | C |
| ATOM | 1607 | CB | LEU | A | 107 | 57.124 | −43.648 | −5.421 | 1.00 | 13.66 | C |
| ATOM | 1610 | CG | LEU | A | 107 | 58.226 | −44.573 | −5.948 | 1.00 | 13.30 | C |
| ATOM | 1612 | CD1 | LEU | A | 107 | 57.914 | −46.015 | −5.554 | 1.00 | 8.00 | C |
| ATOM | 1616 | CD2 | LEU | A | 107 | 58.401 | −44.452 | −7.463 | 1.00 | 7.05 | C |
| ATOM | 1620 | C | LEU | A | 107 | 56.092 | −41.356 | −5.382 | 1.00 | 13.91 | C |
| ATOM | 1621 | O | LEU | A | 107 | 55.621 | −40.801 | −6.367 | 1.00 | 13.47 | O |
| ATOM | 1623 | N | ARG | A | 108 | 55.506 | −41.288 | −4.191 | 1.00 | 15.25 | N |
| ATOM | 1624 | CA | ARG | A | 108 | 54.240 | −40.571 | −4.036 | 1.00 | 15.54 | C |
| ATOM | 1626 | CB | ARG | A | 108 | 53.622 | −40.792 | −2.653 | 1.00 | 14.65 | C |
| ATOM | 1629 | CG | ARG | A | 108 | 52.283 | −40.069 | −2.498 | 1.00 | 14.11 | C |
| ATOM | 1632 | CD | ARG | A | 108 | 51.478 | −40.584 | −1.329 | 1.00 | 13.98 | C |
| ATOM | 1635 | NE | ARG | A | 108 | 50.905 | −41.900 | −1.590 | 1.00 | 13.21 | N |
| ATOM | 1637 | CZ | ARG | A | 108 | 50.220 | −42.608 | −0.699 | 1.00 | 11.52 | C |
| ATOM | 1638 | NH1 | ARG | A | 108 | 50.016 | −42.135 | 0.526 | 1.00 | 15.17 | N |
| ATOM | 1641 | NH2 | ARG | A | 108 | 49.742 | −43.797 | −1.033 | 1.00 | 11.32 | N |
| ATOM | 1644 | C | ARG | A | 108 | 54.439 | −39.083 | −4.297 | 1.00 | 15.28 | C |
| ATOM | 1645 | O | ARG | A | 108 | 53.662 | −38.455 | −5.022 | 1.00 | 16.16 | O |
| ATOM | 1647 | N | GLN | A | 109 | 55.494 | −38.527 | −3.721 | 1.00 | 15.32 | N |
| ATOM | 1648 | CA | GLN | A | 109 | 55.827 | −37.130 | −3.931 | 1.00 | 16.35 | C |
| ATOM | 1650 | CB | GLN | A | 109 | 57.220 | −36.830 | −3.391 | 1.00 | 16.28 | C |
| ATOM | 1653 | CG | GLN | A | 109 | 57.749 | −35.448 | −3.742 | 1.00 | 16.44 | C |
| ATOM | 1656 | CD | GLN | A | 109 | 59.160 | −35.218 | −3.238 | 1.00 | 16.11 | C |
| ATOM | 1657 | OE1 | GLN | A | 109 | 59.712 | −36.020 | −2.486 | 1.00 | 17.10 | O |
| ATOM | 1658 | NE2 | GLN | A | 109 | 59.750 | −34.121 | −3.657 | 1.00 | 14.50 | N |
| ATOM | 1661 | C | GLN | A | 109 | 55.761 | −36.775 | −5.411 | 1.00 | 17.47 | C |
| ATOM | 1662 | O | GLN | A | 109 | 55.292 | −35.703 | −5.767 | 1.00 | 18.79 | O |
| ATOM | 1664 | N | HIS | A | 110 | 56.215 | −37.694 | −6.258 | 1.00 | 18.11 | N |
| ATOM | 1665 | CA | HIS | A | 110 | 56.276 | −37.479 | −7.692 | 1.00 | 17.45 | C |
| ATOM | 1667 | CB | HIS | A | 110 | 57.636 | −37.946 | −8.205 | 1.00 | 16.72 | C |

APPENDIX 1-continued

| ATOM | 1670 | CG | HIS | A | 110 | 58.751 | −37.033 | −7.802 | 1.00 | 18.12 | C |
|------|------|-----|-----|---|-----|--------|---------|--------|------|-------|---|
| ATOM | 1671 | ND1 | HIS | A | 110 | 59.086 | −35.909 | −8.526 | 1.00 | 20.00 | N |
| ATOM | 1673 | CE1 | HIS | A | 110 | 60.076 | −35.278 | −7.918 | 1.00 | 19.23 | C |
| ATOM | 1675 | NE2 | HIS | A | 110 | 60.387 | −35.946 | −6.822 | 1.00 | 14.94 | N |
| ATOM | 1677 | CD2 | HIS | A | 110 | 59.567 | −37.042 | −6.720 | 1.00 | 16.29 | C |
| ATOM | 1679 | C | HIS | A | 110 | 55.113 | −38.113 | −8.465 | 1.00 | 18.62 | C |
| ATOM | 1680 | O | HIS | A | 110 | 55.185 | −38.271 | −9.688 | 1.00 | 19.67 | O |
| ATOM | 1682 | N | GLY | A | 111 | 54.035 | −38.453 | −7.760 | 1.00 | 18.20 | N |
| ATOM | 1683 | CA | GLY | A | 111 | 52.774 | −38.816 | −8.411 | 1.00 | 18.59 | C |
| ATOM | 1686 | C | GLY | A | 111 | 52.623 | −40.265 | −8.853 | 1.00 | 19.26 | C |
| ATOM | 1687 | O | GLY | A | 111 | 51.684 | −40.595 | −9.563 | 1.00 | 19.34 | O |
| ATOM | 1689 | N | PHE | A | 112 | 53.545 | −41.130 | −8.447 | 1.00 | 19.84 | N |
| ATOM | 1690 | CA | PHE | A | 112 | 53.432 | −42.552 | −8.726 | 1.00 | 20.51 | C |
| ATOM | 1692 | CB | PHE | A | 112 | 54.798 | −43.231 | −8.594 | 1.00 | 20.41 | C |
| ATOM | 1695 | CG | PHE | A | 112 | 55.781 | −42.814 | −9.652 | 1.00 | 22.40 | C |
| ATOM | 1696 | CD1 | PHE | A | 112 | 55.858 | −43.504 | −10.853 | 1.00 | 24.53 | C |
| ATOM | 1698 | CE1 | PHE | A | 112 | 56.754 | −43.118 | −11.842 | 1.00 | 25.91 | C |
| ATOM | 1700 | CZ | PHE | A | 112 | 57.589 | −42.028 | −11.639 | 1.00 | 25.44 | C |
| ATOM | 1702 | CE2 | PHE | A | 112 | 57.526 | −41.328 | −10.448 | 1.00 | 24.79 | C |
| ATOM | 1704 | CD2 | PHE | A | 112 | 56.620 | −41.723 | −9.458 | 1.00 | 26.40 | C |
| ATOM | 1706 | C | PHE | A | 112 | 52.432 | −43.172 | −7.762 | 1.00 | 21.15 | C |
| ATOM | 1707 | O | PHE | A | 112 | 52.259 | −42.676 | −6.646 | 1.00 | 22.39 | O |
| ATOM | 1709 | N | GLU | A | 113 | 51.760 | −44.233 | −8.204 | 1.00 | 21.63 | N |
| ATOM | 1710 | CA | GLU | A | 113 | 50.861 | −45.009 | −7.338 | 1.00 | 22.15 | C |
| ATOM | 1712 | CB | GLU | A | 113 | 49.839 | −45.809 | −8.152 | 1.00 | 23.20 | C |
| ATOM | 1715 | CG | GLU | A | 113 | 48.570 | −45.030 | −8.479 | 1.00 | 31.69 | C |
| ATOM | 1718 | CD | GLU | A | 113 | 47.538 | −45.842 | −9.263 | 1.00 | 38.97 | C |
| ATOM | 1719 | OE1 | GLU | A | 113 | 47.666 | −47.087 | −9.346 | 1.00 | 36.67 | O |
| ATOM | 1720 | OE2 | GLU | A | 113 | 46.586 | −45.219 | −9.788 | 1.00 | 44.13 | O |
| ATOM | 1721 | C | GLU | A | 113 | 51.647 | −45.975 | −6.474 | 1.00 | 19.83 | C |
| ATOM | 1722 | O | GLU | A | 113 | 52.300 | −46.880 | −6.996 | 1.00 | 19.13 | O |
| ATOM | 1724 | N | VAL | A | 114 | 51.582 | −45.771 | −5.159 | 1.00 | 17.92 | N |
| ATOM | 1725 | CA | VAL | A | 114 | 52.137 | −46.708 | −4.186 | 1.00 | 17.14 | C |
| ATOM | 1727 | CB | VAL | A | 114 | 53.416 | −46.179 | −3.524 | 1.00 | 16.87 | C |
| ATOM | 1729 | CG1 | VAL | A | 114 | 54.578 | −46.310 | −4.477 | 1.00 | 18.62 | C |
| ATOM | 1733 | CG2 | VAL | A | 114 | 53.242 | −44.740 | −3.074 | 1.00 | 13.97 | C |
| ATOM | 1737 | C | VAL | A | 114 | 51.101 | −47.017 | −3.115 | 1.00 | 17.20 | C |
| ATOM | 1738 | O | VAL | A | 114 | 50.317 | −46.155 | −2.729 | 1.00 | 16.91 | O |
| ATOM | 1740 | N | SER | A | 115 | 51.098 | −48.261 | −2.653 | 1.00 | 17.44 | N |
| ATOM | 1741 | CA | SER | A | 115 | 50.093 | −48.744 | −1.715 | 1.00 | 17.58 | C |
| ATOM | 1743 | CB | SER | A | 115 | 49.510 | −50.067 | −2.222 | 1.00 | 18.10 | C |
| ATOM | 1746 | OG | SER | A | 115 | 48.625 | −50.653 | −1.285 | 1.00 | 19.87 | O |
| ATOM | 1748 | C | SER | A | 115 | 50.749 | −48.945 | −0.367 | 1.00 | 17.16 | C |
| ATOM | 1749 | O | SER | A | 115 | 51.937 | −49.249 | −0.290 | 1.00 | 16.28 | O |
| ATOM | 1751 | N | GLN | A | 116 | 49.981 | −48.782 | 0.702 | 1.00 | 17.89 | N |
| ATOM | 1752 | CA | GLN | A | 116 | 50.503 | −49.064 | 2.037 | 1.00 | 18.00 | C |
| ATOM | 1754 | CB | GLN | A | 116 | 49.526 | −48.604 | 3.124 | 1.00 | 17.32 | C |
| ATOM | 1757 | CG | GLN | A | 116 | 48.277 | −49.444 | 3.250 | 1.00 | 18.24 | C |
| ATOM | 1760 | CD | GLN | A | 116 | 47.336 | −48.939 | 4.323 | 1.00 | 18.00 | C |
| ATOM | 1761 | OE1 | GLN | A | 116 | 47.647 | −47.988 | 5.038 | 1.00 | 15.54 | O |
| ATOM | 1762 | NE2 | GLN | A | 116 | 46.178 | −49.585 | 4.448 | 1.00 | 15.61 | N |
| ATOM | 1765 | C | GLN | A | 116 | 50.858 | −50.553 | 2.189 | 1.00 | 17.90 | C |
| ATOM | 1766 | O | GLN | A | 116 | 51.615 | −50.913 | 3.085 | 1.00 | 16.82 | O |
| ATOM | 1768 | N | GLU | A | 117 | 50.332 | −51.400 | 1.298 | 1.00 | 18.90 | N |
| ATOM | 1769 | CA | GLU | A | 117 | 50.718 | −52.827 | 1.223 | 1.00 | 20.56 | C |
| ATOM | 1771 | CB | GLU | A | 117 | 49.960 | −53.551 | 0.104 | 1.00 | 21.42 | C |
| ATOM | 1774 | CG | GLU | A | 117 | 48.453 | −53.591 | 0.271 | 1.00 | 26.18 | C |
| ATOM | 1777 | CD | GLU | A | 117 | 47.764 | −54.316 | −0.870 | 1.00 | 32.39 | C |
| ATOM | 1778 | OE1 | GLU | A | 117 | 47.922 | −55.549 | −0.962 | 1.00 | 37.41 | O |
| ATOM | 1779 | OE2 | GLU | A | 117 | 47.058 | −53.657 | −1.667 | 1.00 | 37.11 | O |
| ATOM | 1780 | C | GLU | A | 117 | 52.218 | −53.055 | 1.009 | 1.00 | 19.86 | C |
| ATOM | 1781 | O | GLU | A | 117 | 52.731 | −54.133 | 1.304 | 1.00 | 20.64 | O |
| ATOM | 1783 | N | ALA | A | 118 | 52.914 | −52.054 | 0.482 | 1.00 | 19.35 | N |
| ATOM | 1784 | CA | ALA | A | 118 | 54.369 | −52.091 | 0.387 | 1.00 | 19.23 | C |
| ATOM | 1786 | CB | ALA | A | 118 | 54.896 | −50.768 | −0.178 | 1.00 | 18.70 | C |
| ATOM | 1790 | C | ALA | A | 118 | 55.043 | −52.400 | 1.729 | 1.00 | 19.77 | C |
| ATOM | 1791 | O | ALA | A | 118 | 56.108 | −53.011 | 1.758 | 1.00 | 21.53 | O |
| ATOM | 1793 | N | PHE | A | 119 | 54.427 | −51.993 | 2.835 | 1.00 | 19.93 | N |
| ATOM | 1794 | CA | PHE | A | 119 | 55.022 | −52.188 | 4.158 | 1.00 | 20.71 | C |
| ATOM | 1796 | CB | PHE | A | 119 | 54.604 | −51.044 | 5.090 | 1.00 | 20.67 | C |
| ATOM | 1799 | CG | PHE | A | 119 | 55.135 | −49.704 | 4.665 | 1.00 | 18.33 | C |
| ATOM | 1800 | CD1 | PHE | A | 119 | 56.475 | −49.395 | 4.834 | 1.00 | 16.96 | C |
| ATOM | 1802 | CE1 | PHE | A | 119 | 56.983 | −48.173 | 4.434 | 1.00 | 16.52 | C |
| ATOM | 1804 | CZ | PHE | A | 119 | 56.149 | −47.239 | 3.859 | 1.00 | 20.21 | C |
| ATOM | 1806 | CE2 | PHE | A | 119 | 54.797 | −47.533 | 3.685 | 1.00 | 19.31 | C |
| ATOM | 1808 | CD2 | PHE | A | 119 | 54.304 | −48.765 | 4.082 | 1.00 | 19.09 | C |
| ATOM | 1810 | C | PHE | A | 119 | 54.704 | −53.531 | 4.807 | 1.00 | 21.86 | C |
| ATOM | 1811 | O | PHE | A | 119 | 55.182 | −53.810 | 5.906 | 1.00 | 22.54 | O |
| ATOM | 1813 | N | SER | A | 120 | 53.931 | −54.375 | 4.127 | 1.00 | 23.53 | N |
| ATOM | 1814 | CA | SER | A | 120 | 53.434 | −55.622 | 4.729 | 1.00 | 24.35 | C |

APPENDIX 1-continued

| ATOM | 1816 | CB | SER | A | 120 | 52.443 | −56.329 | 3.798 | 1.00 | 24.27 | C |
|---|---|---|---|---|---|---|---|---|---|---|---|
| ATOM | 1819 | OG | SER | A | 120 | 53.064 | −56.712 | 2.585 | 1.00 | 24.63 | O |
| ATOM | 1821 | C | SER | A | 120 | 54.532 | −56.593 | 5.128 | 1.00 | 24.71 | C |
| ATOM | 1822 | O | SER | A | 120 | 54.361 | −57.352 | 6.067 | 1.00 | 25.50 | O |
| ATOM | 1824 | N | GLY | A | 121 | 55.658 | −56.568 | 4.425 | 1.00 | 25.99 | N |
| ATOM | 1825 | CA | GLY | A | 121 | 56.753 | −57.494 | 4.710 | 1.00 | 26.71 | C |
| ATOM | 1828 | C | GLY | A | 121 | 57.490 | −57.240 | 6.014 | 1.00 | 27.42 | C |
| ATOM | 1829 | O | GLY | A | 121 | 58.220 | −58.105 | 6.487 | 1.00 | 28.57 | O |
| ATOM | 1831 | N | PHE | A | 122 | 57.304 | −56.063 | 6.600 | 1.00 | 28.38 | N |
| ATOM | 1832 | CA | PHE | A | 122 | 58.040 | −55.671 | 7.797 | 1.00 | 29.58 | C |
| ATOM | 1834 | CB | PHE | A | 122 | 58.606 | −54.264 | 7.601 | 1.00 | 29.62 | C |
| ATOM | 1837 | CG | PHE | A | 122 | 59.415 | −54.123 | 6.351 | 1.00 | 27.63 | C |
| ATOM | 1838 | CD1 | PHE | A | 122 | 60.746 | −54.496 | 6.330 | 1.00 | 26.30 | C |
| ATOM | 1840 | CE1 | PHE | A | 122 | 61.494 | −54.386 | 5.173 | 1.00 | 27.39 | C |
| ATOM | 1842 | CZ | PHE | A | 122 | 60.910 | −53.905 | 4.016 | 1.00 | 27.09 | C |
| ATOM | 1844 | CE2 | PHE | A | 122 | 59.579 | −53.540 | 4.020 | 1.00 | 28.00 | C |
| ATOM | 1846 | CD2 | PHE | A | 122 | 58.835 | −53.652 | 5.184 | 1.00 | 28.29 | C |
| ATOM | 1848 | C | PHE | A | 122 | 57.197 | −55.741 | 9.072 | 1.00 | 31.01 | C |
| ATOM | 1849 | O | PHE | A | 122 | 57.557 | −55.149 | 10.095 | 1.00 | 30.74 | O |
| ATOM | 1851 | N | LYS | A | 123 | 56.087 | −56.475 | 9.011 | 1.00 | 32.62 | N |
| ATOM | 1852 | CA | LYS | A | 123 | 55.214 | −56.656 | 10.167 | 1.00 | 34.07 | C |
| ATOM | 1854 | CB | LYS | A | 123 | 53.767 | −56.311 | 9.805 | 1.00 | 34.24 | C |
| ATOM | 1857 | CG | LYS | A | 123 | 53.525 | −54.803 | 9.728 | 1.00 | 37.62 | C |
| ATOM | 1860 | CD | LYS | A | 123 | 52.080 | −54.455 | 9.384 | 1.00 | 42.42 | C |
| ATOM | 1863 | CE | LYS | A | 123 | 51.801 | −54.630 | 7.901 | 1.00 | 43.47 | C |
| ATOM | 1866 | NZ | LYS | A | 123 | 50.397 | −54.325 | 7.535 | 1.00 | 44.54 | N |
| ATOM | 1870 | C | LYS | A | 123 | 55.339 | −58.077 | 10.720 | 1.00 | 34.52 | C |
| ATOM | 1871 | O | LYS | A | 123 | 55.757 | −58.998 | 10.014 | 1.00 | 34.29 | O |
| ATOM | 1873 | N | ASP | A | 124 | 54.990 | −58.238 | 11.992 | 1.00 | 35.13 | N |
| ATOM | 1874 | CA | ASP | A | 124 | 55.210 | −59.495 | 12.709 | 1.00 | 35.78 | C |
| ATOM | 1876 | CB | ASP | A | 124 | 55.701 | −59.205 | 14.144 | 1.00 | 35.47 | C |
| ATOM | 1879 | CG | ASP | A | 124 | 54.628 | −58.584 | 15.036 | 1.00 | 34.26 | C |
| ATOM | 1880 | OD1 | ASP | A | 124 | 53.429 | −58.695 | 14.720 | 1.00 | 33.09 | O |
| ATOM | 1881 | OD2 | ASP | A | 124 | 54.988 | −57.982 | 16.068 | 1.00 | 34.68 | O |
| ATOM | 1882 | C | ASP | A | 124 | 53.957 | −60.386 | 12.710 | 1.00 | 36.80 | C |
| ATOM | 1883 | O | ASP | A | 124 | 53.014 | −60.151 | 11.952 | 1.00 | 36.25 | O |
| ATOM | 1885 | N | GLN | A | 125 | 53.978 | −61.414 | 13.559 | 1.00 | 37.90 | N |
| ATOM | 1886 | CA | GLN | A | 125 | 52.849 | −62.326 | 13.772 | 1.00 | 38.52 | C |
| ATOM | 1888 | CB | GLN | A | 125 | 53.025 | −63.037 | 15.120 | 1.00 | 38.94 | C |
| ATOM | 1891 | CG | GLN | A | 125 | 54.246 | −63.958 | 15.208 | 1.00 | 41.34 | C |
| ATOM | 1894 | CD | GLN | A | 125 | 53.891 | −65.410 | 15.483 | 1.00 | 43.70 | C |
| ATOM | 1895 | OE1 | GLN | A | 125 | 52.855 | −65.910 | 15.040 | 1.00 | 46.32 | O |
| ATOM | 1896 | NE2 | GLN | A | 125 | 54.756 | −66.096 | 16.223 | 1.00 | 43.96 | N |
| ATOM | 1899 | C | GLN | A | 125 | 51.491 | −61.624 | 13.774 | 1.00 | 38.20 | C |
| ATOM | 1900 | O | GLN | A | 125 | 50.581 | −62.010 | 13.036 | 1.00 | 38.02 | O |
| ATOM | 1902 | N | ASN | A | 126 | 51.375 | −60.587 | 14.601 | 1.00 | 37.77 | N |
| ATOM | 1903 | CA | ASN | A | 126 | 50.088 | −59.951 | 14.891 | 1.00 | 37.44 | C |
| ATOM | 1905 | CB | ASN | A | 126 | 49.985 | −59.662 | 16.396 | 1.00 | 38.30 | C |
| ATOM | 1908 | CG | ASN | A | 126 | 50.409 | −60.850 | 17.255 | 1.00 | 38.88 | C |
| ATOM | 1909 | OD1 | ASN | A | 126 | 51.597 | −61.043 | 17.524 | 1.00 | 38.90 | O |
| ATOM | 1910 | ND2 | ASN | A | 126 | 49.438 | −61.642 | 17.695 | 1.00 | 37.03 | N |
| ATOM | 1913 | C | ASN | A | 126 | 49.814 | −58.664 | 14.100 | 1.00 | 36.17 | C |
| ATOM | 1914 | O | ASN | A | 126 | 48.929 | −57.894 | 14.464 | 1.00 | 35.23 | O |
| ATOM | 1916 | N | GLY | A | 127 | 50.561 | −58.439 | 13.022 | 1.00 | 35.58 | N |
| ATOM | 1917 | CA | GLY | A | 127 | 50.360 | −57.266 | 12.171 | 1.00 | 35.27 | C |
| ATOM | 1920 | C | GLY | A | 127 | 50.951 | −55.967 | 12.696 | 1.00 | 34.56 | C |
| ATOM | 1921 | O | GLY | A | 127 | 50.592 | −54.891 | 12.220 | 1.00 | 34.71 | O |
| ATOM | 1923 | N | ASN | A | 128 | 51.848 | −56.064 | 13.678 | 1.00 | 33.89 | N |
| ATOM | 1924 | CA | ASN | A | 128 | 52.581 | −54.903 | 14.194 | 1.00 | 33.13 | C |
| ATOM | 1926 | CB | ASN | A | 128 | 52.707 | −54.977 | 15.718 | 1.00 | 33.17 | C |
| ATOM | 1929 | CG | ASN | A | 128 | 51.360 | −54.972 | 16.417 | 1.00 | 33.60 | C |
| ATOM | 1930 | OD1 | ASN | A | 128 | 50.516 | −54.113 | 16.161 | 1.00 | 33.68 | O |
| ATOM | 1931 | ND2 | ASN | A | 128 | 51.153 | −55.937 | 17.308 | 1.00 | 33.04 | N |
| ATOM | 1934 | C | ASN | A | 128 | 53.967 | −54.854 | 13.569 | 1.00 | 31.75 | C |
| ATOM | 1935 | O | ASN | A | 128 | 54.506 | −55.888 | 13.185 | 1.00 | 31.35 | O |
| ATOM | 1937 | N | PHE | A | 129 | 54.538 | −53.657 | 13.462 | 1.00 | 30.95 | N |
| ATOM | 1938 | CA | PHE | A | 129 | 55.879 | −53.497 | 12.889 | 1.00 | 30.05 | C |
| ATOM | 1940 | CB | PHE | A | 129 | 56.254 | −52.014 | 12.763 | 1.00 | 29.58 | C |
| ATOM | 1943 | CG | PHE | A | 129 | 55.710 | −51.358 | 11.528 | 1.00 | 26.87 | C |
| ATOM | 1944 | CD1 | PHE | A | 129 | 56.350 | −51.513 | 10.306 | 1.00 | 27.70 | C |
| ATOM | 1946 | CE1 | PHE | A | 129 | 55.848 | −50.912 | 9.155 | 1.00 | 26.40 | C |
| ATOM | 1948 | CZ | PHE | A | 129 | 54.697 | −50.149 | 9.224 | 1.00 | 25.73 | C |
| ATOM | 1950 | CE2 | PHE | A | 129 | 54.052 | −49.986 | 10.439 | 1.00 | 25.95 | C |
| ATOM | 1952 | CD2 | PHE | A | 129 | 54.559 | −50.591 | 11.581 | 1.00 | 26.69 | C |
| ATOM | 1954 | C | PHE | A | 129 | 56.904 | −54.236 | 13.744 | 1.00 | 29.69 | C |
| ATOM | 1955 | O | PHE | A | 129 | 56.896 | −54.097 | 14.967 | 1.00 | 29.85 | O |
| ATOM | 1957 | N | LEU | A | 130 | 57.765 | −55.022 | 13.094 | 1.00 | 29.51 | N |
| ATOM | 1958 | CA | LEU | A | 130 | 58.768 | −55.851 | 13.781 | 1.00 | 30.01 | C |
| ATOM | 1960 | CB | LEU | A | 130 | 59.696 | −56.532 | 12.771 | 1.00 | 29.98 | C |
| ATOM | 1963 | CG | LEU | A | 130 | 59.116 | −57.641 | 11.888 | 1.00 | 31.00 | C |

APPENDIX 1-continued

| | | | | | | | | | | |
|---|---|---|---|---|---|---|---|---|---|---|
| ATOM | 1965 | CD1 | LEU | A | 130 | 59.911 | −57.754 | 10.584 | 1.00 | 29.05 | C |
| ATOM | 1969 | CD2 | LEU | A | 130 | 59.070 | −58.985 | 12.628 | 1.00 | 29.48 | C |
| ATOM | 1973 | C | LEU | A | 130 | 59.615 | −55.029 | 14.744 | 1.00 | 30.46 | C |
| ATOM | 1974 | O | LEU | A | 130 | 60.207 | −54.031 | 14.354 | 1.00 | 29.85 | O |
| ATOM | 1976 | N | GLU | A | 131 | 59.678 | −55.468 | 15.996 | 1.00 | 31.94 | N |
| ATOM | 1977 | CA | GLU | A | 131 | 60.332 | −54.705 | 17.059 | 1.00 | 32.91 | C |
| ATOM | 1979 | CB | GLU | A | 131 | 60.176 | −55.432 | 18.406 | 1.00 | 33.63 | C |
| ATOM | 1982 | CG | GLU | A | 131 | 60.572 | −54.624 | 19.645 | 1.00 | 36.72 | C |
| ATOM | 1985 | CD | GLU | A | 131 | 59.574 | −53.525 | 20.003 | 1.00 | 41.20 | C |
| ATOM | 1986 | OE1 | GLU | A | 131 | 58.831 | −53.043 | 19.116 | 1.00 | 42.35 | O |
| ATOM | 1987 | OE2 | GLU | A | 131 | 59.542 | −53.131 | 21.187 | 1.00 | 43.80 | O |
| ATOM | 1988 | C | GLU | A | 131 | 61.806 | −54.439 | 16.755 | 1.00 | 32.75 | C |
| ATOM | 1989 | O | GLU | A | 131 | 62.278 | −53.322 | 16.955 | 1.00 | 32.97 | O |
| ATOM | 1991 | N | ASN | A | 132 | 62.519 | −55.447 | 16.247 | 1.00 | 32.39 | N |
| ATOM | 1992 | CA | ASN | A | 132 | 63.955 | −55.305 | 15.963 | 1.00 | 32.47 | C |
| ATOM | 1994 | CB | ASN | A | 132 | 64.608 | −56.663 | 15.690 | 1.00 | 32.78 | C |
| ATOM | 1997 | CG | ASN | A | 132 | 64.119 | −57.311 | 14.409 | 1.00 | 34.78 | C |
| ATOM | 1998 | OD1 | ASN | A | 132 | 64.090 | −56.688 | 13.346 | 1.00 | 37.50 | O |
| ATOM | 1999 | ND2 | ASN | A | 132 | 63.742 | −58.581 | 14.502 | 1.00 | 37.80 | N |
| ATOM | 2002 | C | ASN | A | 132 | 64.293 | −54.328 | 14.831 | 1.00 | 32.35 | C |
| ATOM | 2003 | O | ASN | A | 132 | 65.459 | −53.979 | 14.649 | 1.00 | 32.24 | O |
| ATOM | 2005 | N | LEU | A | 133 | 63.288 | −53.897 | 14.070 | 1.00 | 32.07 | N |
| ATOM | 2006 | CA | LEU | A | 133 | 63.482 | −52.837 | 13.078 | 1.00 | 31.79 | C |
| ATOM | 2008 | CB | LEU | A | 133 | 62.191 | −52.553 | 12.300 | 1.00 | 31.54 | C |
| ATOM | 2011 | CG | LEU | A | 133 | 61.723 | −53.598 | 11.286 | 1.00 | 29.46 | C |
| ATOM | 2013 | CD1 | LEU | A | 133 | 60.264 | −53.365 | 10.920 | 1.00 | 27.57 | C |
| ATOM | 2017 | CD2 | LEU | A | 133 | 62.596 | −53.578 | 10.052 | 1.00 | 24.77 | C |
| ATOM | 2021 | C | LEU | A | 133 | 63.964 | −51.543 | 13.730 | 1.00 | 32.07 | C |
| ATOM | 2022 | O | LEU | A | 133 | 64.597 | −50.719 | 13.068 | 1.00 | 32.07 | O |
| ATOM | 2024 | N | LYS | A | 134 | 63.665 | −51.373 | 15.020 | 1.00 | 32.16 | N |
| ATOM | 2025 | CA | LYS | A | 134 | 64.062 | −50.178 | 15.767 | 1.00 | 32.51 | C |
| ATOM | 2027 | CB | LYS | A | 134 | 63.478 | −50.215 | 17.186 | 1.00 | 32.54 | C |
| ATOM | 2030 | CG | LYS | A | 134 | 64.226 | −51.130 | 18.165 | 1.00 | 36.12 | C |
| ATOM | 2033 | CD | LYS | A | 134 | 63.521 | −51.195 | 19.521 | 1.00 | 36.37 | C |
| ATOM | 2036 | CE | LYS | A | 134 | 64.442 | −51.707 | 20.620 | 1.00 | 36.60 | C |
| ATOM | 2039 | NZ | LYS | A | 134 | 63.891 | −51.408 | 21.978 | 1.00 | 37.35 | N |
| ATOM | 2043 | C | LYS | A | 134 | 65.582 | −49.978 | 15.831 | 1.00 | 32.46 | C |
| ATOM | 2044 | O | LYS | A | 134 | 66.048 | −48.862 | 16.058 | 1.00 | 32.20 | O |
| ATOM | 2046 | N | GLU | A | 135 | 66.347 | −51.055 | 15.642 | 1.00 | 32.82 | N |
| ATOM | 2047 | CA | GLU | A | 135 | 67.815 | −50.977 | 15.655 | 1.00 | 33.11 | C |
| ATOM | 2049 | CB | GLU | A | 135 | 68.438 | −52.380 | 15.759 | 1.00 | 33.80 | C |
| ATOM | 2052 | CG | GLU | A | 135 | 68.051 | −53.174 | 17.014 | 1.00 | 37.61 | C |
| ATOM | 2055 | CD | GLU | A | 135 | 68.414 | −52.472 | 18.322 | 1.00 | 43.02 | C |
| ATOM | 2056 | OE1 | GLU | A | 135 | 69.243 | −51.536 | 18.301 | 1.00 | 43.54 | O |
| ATOM | 2057 | OE2 | GLU | A | 135 | 67.872 | −52.864 | 19.381 | 1.00 | 46.53 | O |
| ATOM | 2058 | C | GLU | A | 135 | 68.406 | −50.243 | 14.443 | 1.00 | 31.83 | C |
| ATOM | 2059 | O | GLU | A | 135 | 69.534 | −49.752 | 14.512 | 1.00 | 31.59 | O |
| ATOM | 2061 | N | ASP | A | 136 | 67.650 | −50.179 | 13.345 | 1.00 | 30.44 | N |
| ATOM | 2062 | CA | ASP | A | 136 | 68.060 | −49.453 | 12.138 | 1.00 | 28.91 | C |
| ATOM | 2064 | CB | ASP | A | 136 | 67.644 | −50.243 | 10.891 | 1.00 | 29.19 | C |
| ATOM | 2067 | CG | ASP | A | 136 | 68.128 | −49.609 | 9.594 | 1.00 | 31.06 | C |
| ATOM | 2068 | OD1 | ASP | A | 136 | 68.564 | −48.439 | 9.606 | 1.00 | 35.55 | O |
| ATOM | 2069 | OD2 | ASP | A | 136 | 68.064 | −50.286 | 8.549 | 1.00 | 34.56 | O |
| ATOM | 2070 | C | ASP | A | 136 | 67.430 | −48.058 | 12.141 | 1.00 | 27.38 | C |
| ATOM | 2071 | O | ASP | A | 136 | 66.292 | −47.884 | 11.722 | 1.00 | 26.60 | O |
| ATOM | 2073 | N | ILE | A | 137 | 68.187 | −47.064 | 12.598 | 1.00 | 26.48 | N |
| ATOM | 2074 | CA | ILE | A | 137 | 67.656 | −45.713 | 12.803 | 1.00 | 26.13 | C |
| ATOM | 2076 | CB | ILE | A | 137 | 68.610 | −44.865 | 13.661 | 1.00 | 25.62 | C |
| ATOM | 2078 | CG1 | ILE | A | 137 | 68.839 | −45.537 | 15.020 | 1.00 | 28.03 | C |
| ATOM | 2081 | CD1 | ILE | A | 137 | 67.571 | −46.035 | 15.700 | 1.00 | 28.59 | C |
| ATOM | 2085 | CG2 | ILE | A | 137 | 68.064 | −43.461 | 13.854 | 1.00 | 22.91 | C |
| ATOM | 2089 | C | ILE | A | 137 | 67.358 | −44.977 | 11.496 | 1.00 | 27.13 | C |
| ATOM | 2090 | O | ILE | A | 137 | 66.354 | −44.265 | 11.399 | 1.00 | 28.15 | O |
| ATOM | 2092 | N | LYS | A | 138 | 68.230 | −45.136 | 10.502 | 1.00 | 27.01 | N |
| ATOM | 2093 | CA | LYS | A | 138 | 67.969 | −44.623 | 9.156 | 1.00 | 26.64 | C |
| ATOM | 2095 | CB | LYS | A | 138 | 68.993 | −45.178 | 8.157 | 1.00 | 28.39 | C |
| ATOM | 2098 | CG | LYS | A | 138 | 70.151 | −44.245 | 7.807 | 1.00 | 32.14 | C |
| ATOM | 2101 | CD | LYS | A | 138 | 71.022 | −44.874 | 6.709 | 1.00 | 38.28 | C |
| ATOM | 2104 | CE | LYS | A | 138 | 71.858 | −43.837 | 5.972 | 1.00 | 41.36 | C |
| ATOM | 2107 | NZ | LYS | A | 138 | 72.680 | −44.443 | 4.885 | 1.00 | 40.92 | N |
| ATOM | 2111 | C | LYS | A | 138 | 66.567 | −45.009 | 8.681 | 1.00 | 25.05 | C |
| ATOM | 2112 | O | LYS | A | 138 | 65.827 | −44.170 | 8.150 | 1.00 | 24.81 | O |
| ATOM | 2114 | N | ALA | A | 139 | 66.221 | −46.282 | 8.876 | 1.00 | 22.85 | N |
| ATOM | 2115 | CA | ALA | A | 139 | 64.957 | −46.835 | 8.405 | 1.00 | 21.98 | C |
| ATOM | 2117 | CB | ALA | A | 139 | 64.986 | −48.349 | 8.474 | 1.00 | 22.02 | C |
| ATOM | 2121 | C | ALA | A | 139 | 63.777 | −46.294 | 9.202 | 1.00 | 21.49 | C |
| ATOM | 2122 | O | ALA | A | 139 | 62.753 | −45.917 | 8.633 | 1.00 | 21.39 | O |
| ATOM | 2124 | N | ILE | A | 140 | 63.922 | −46.252 | 10.518 | 1.00 | 20.92 | N |
| ATOM | 2125 | CA | ILE | A | 140 | 62.882 | −45.694 | 11.366 | 1.00 | 20.56 | C |
| ATOM | 2127 | CB | ILE | A | 140 | 63.245 | −45.810 | 12.859 | 1.00 | 20.40 | C |

APPENDIX 1-continued

| ATOM | 2129 | CG1 | ILE | A | 140 | 63.319 | −47.281 | 13.278 | 1.00 | 21.59 | C |
|---|---|---|---|---|---|---|---|---|---|---|---|
| ATOM | 2132 | CD1 | ILE | A | 140 | 62.031 | −48.075 | 13.047 | 1.00 | 18.82 | C |
| ATOM | 2136 | CG2 | ILE | A | 140 | 62.223 | −45.099 | 13.720 | 1.00 | 20.44 | C |
| ATOM | 2140 | C | ILE | A | 140 | 62.640 | −44.234 | 10.981 | 1.00 | 20.43 | C |
| ATOM | 2141 | O | ILE | A | 140 | 61.495 | −43.788 | 10.915 | 1.00 | 21.00 | O |
| ATOM | 2143 | N | LEU | A | 141 | 63.716 | −43.500 | 10.707 | 1.00 | 19.96 | N |
| ATOM | 2144 | CA | LEU | A | 141 | 63.598 | −42.114 | 10.239 | 1.00 | 19.90 | C |
| ATOM | 2146 | CB | LEU | A | 141 | 64.968 | −41.432 | 10.124 | 1.00 | 20.05 | C |
| ATOM | 2149 | CG | LEU | A | 141 | 65.429 | −40.669 | 11.359 | 1.00 | 21.37 | C |
| ATOM | 2151 | CD1 | LEU | A | 141 | 66.855 | −40.215 | 11.165 | 1.00 | 19.36 | C |
| ATOM | 2155 | CD2 | LEU | A | 141 | 64.495 | −39.480 | 11.627 | 1.00 | 20.19 | C |
| ATOM | 2159 | C | LEU | A | 141 | 62.894 | −42.035 | 8.901 | 1.00 | 18.88 | C |
| ATOM | 2160 | O | LEU | A | 141 | 62.067 | −41.161 | 8.706 | 1.00 | 18.87 | O |
| ATOM | 2162 | N | SER | A | 142 | 63.233 | −42.938 | 7.982 | 1.00 | 18.38 | N |
| ATOM | 2163 | CA | SER | A | 142 | 62.579 | −42.963 | 6.677 | 1.00 | 18.87 | C |
| ATOM | 2165 | CB | SER | A | 142 | 63.227 | −43.992 | 5.755 | 1.00 | 18.85 | C |
| ATOM | 2168 | OG | SER | A | 142 | 64.441 | −43.499 | 5.224 | 1.00 | 24.59 | O |
| ATOM | 2170 | C | SER | A | 142 | 61.093 | −43.262 | 6.819 | 1.00 | 18.39 | C |
| ATOM | 2171 | O | SER | A | 142 | 60.257 | −42.650 | 6.152 | 1.00 | 18.06 | O |
| ATOM | 2173 | N | LEU | A | 143 | 60.772 | −44.206 | 7.696 | 1.00 | 17.92 | N |
| ATOM | 2174 | CA | LEU | A | 143 | 59.392 | −44.581 | 7.928 | 1.00 | 17.92 | C |
| ATOM | 2176 | CB | LEU | A | 143 | 59.312 | −45.750 | 8.905 | 1.00 | 17.59 | C |
| ATOM | 2179 | CG | LEU | A | 143 | 57.928 | −46.353 | 9.099 | 1.00 | 18.56 | C |
| ATOM | 2181 | CD1 | LEU | A | 143 | 57.368 | −46.849 | 7.762 | 1.00 | 16.28 | C |
| ATOM | 2185 | CD2 | LEU | A | 143 | 57.994 | −47.480 | 10.140 | 1.00 | 12.92 | C |
| ATOM | 2189 | C | LEU | A | 143 | 58.625 | −43.379 | 8.464 | 1.00 | 17.94 | C |
| ATOM | 2190 | O | LEU | A | 143 | 57.545 | −43.056 | 7.958 | 1.00 | 19.38 | O |
| ATOM | 2192 | N | TYR | A | 144 | 59.196 | −42.710 | 9.464 | 1.00 | 16.49 | N |
| ATOM | 2193 | CA | TYR | A | 144 | 58.591 | −41.509 | 10.038 | 1.00 | 16.63 | C |
| ATOM | 2195 | CB | TYR | A | 144 | 59.527 | −40.881 | 11.091 | 1.00 | 16.88 | C |
| ATOM | 2198 | CG | TYR | A | 144 | 59.109 | −39.513 | 11.614 | 1.00 | 16.47 | C |
| ATOM | 2199 | CD1 | TYR | A | 144 | 58.142 | −39.376 | 12.617 | 1.00 | 17.87 | C |
| ATOM | 2201 | CE1 | TYR | A | 144 | 57.773 | −38.107 | 13.102 | 1.00 | 17.50 | C |
| ATOM | 2203 | CZ | TYR | A | 144 | 58.380 | −36.971 | 12.569 | 1.00 | 20.12 | C |
| ATOM | 2204 | OH | TYR | A | 144 | 58.040 | −35.708 | 13.007 | 1.00 | 23.04 | O |
| ATOM | 2206 | CE2 | TYR | A | 144 | 59.335 | −37.092 | 11.575 | 1.00 | 17.73 | C |
| ATOM | 2208 | CD2 | TYR | A | 144 | 59.694 | −38.354 | 11.108 | 1.00 | 20.73 | C |
| ATOM | 2210 | C | TYR | A | 144 | 58.249 | −40.500 | 8.949 | 1.00 | 16.24 | C |
| ATOM | 2211 | O | TYR | A | 144 | 57.127 | −39.998 | 8.904 | 1.00 | 16.38 | O |
| ATOM | 2213 | N | GLU | A | 145 | 59.206 | −40.240 | 8.057 | 1.00 | 16.21 | N |
| ATOM | 2214 | CA | GLU | A | 145 | 59.044 | −39.217 | 7.023 | 1.00 | 16.50 | C |
| ATOM | 2216 | CB | GLU | A | 145 | 60.362 | −38.931 | 6.309 | 1.00 | 16.55 | C |
| ATOM | 2219 | CG | GLU | A | 145 | 61.487 | −38.436 | 7.214 | 1.00 | 19.48 | C |
| ATOM | 2222 | CD | GLU | A | 145 | 61.341 | −36.995 | 7.676 | 1.00 | 24.18 | C |
| ATOM | 2223 | OE1 | GLU | A | 145 | 60.328 | −36.326 | 7.360 | 1.00 | 25.12 | O |
| ATOM | 2224 | OE2 | GLU | A | 145 | 62.272 | −36.534 | 8.374 | 1.00 | 30.41 | O |
| ATOM | 2225 | C | GLU | A | 145 | 57.995 | −39.615 | 6.002 | 1.00 | 16.20 | C |
| ATOM | 2226 | O | GLU | A | 145 | 57.247 | −38.768 | 5.523 | 1.00 | 17.56 | O |
| ATOM | 2228 | N | ALA | A | 146 | 57.928 | −40.902 | 5.683 | 1.00 | 15.45 | N |
| ATOM | 2229 | CA | ALA | A | 146 | 56.947 | −41.396 | 4.725 | 1.00 | 14.88 | C |
| ATOM | 2231 | CB | ALA | A | 146 | 57.236 | −42.843 | 4.359 | 1.00 | 14.69 | C |
| ATOM | 2235 | C | ALA | A | 146 | 55.540 | −41.266 | 5.277 | 1.00 | 14.01 | C |
| ATOM | 2236 | O | ALA | A | 146 | 54.617 | −40.964 | 4.540 | 1.00 | 13.57 | O |
| ATOM | 2238 | N | SER | A | 147 | 55.385 | −41.474 | 6.579 | 1.00 | 14.63 | N |
| ATOM | 2239 | CA | SER | A | 147 | 54.061 | −41.533 | 7.197 | 1.00 | 15.33 | C |
| ATOM | 2241 | CB | SER | A | 147 | 54.185 | −41.828 | 8.695 | 1.00 | 14.91 | C |
| ATOM | 2244 | OG | SER | A | 147 | 54.504 | −40.663 | 9.423 | 1.00 | 16.45 | O |
| ATOM | 2246 | C | SER | A | 147 | 53.212 | −40.269 | 6.988 | 1.00 | 16.17 | C |
| ATOM | 2247 | O | SER | A | 147 | 51.985 | −40.346 | 6.986 | 1.00 | 16.00 | O |
| ATOM | 2249 | N | PHE | A | 148 | 53.864 | −39.118 | 6.820 | 1.00 | 16.36 | N |
| ATOM | 2250 | CA | PHE | A | 148 | 53.157 | −37.850 | 6.658 | 1.00 | 15.19 | C |
| ATOM | 2252 | CB | PHE | A | 148 | 54.055 | −36.678 | 7.067 | 1.00 | 15.31 | C |
| ATOM | 2255 | CG | PHE | A | 148 | 54.380 | −36.649 | 8.531 | 1.00 | 12.93 | C |
| ATOM | 2256 | CD1 | PHE | A | 148 | 55.501 | −37.310 | 9.016 | 1.00 | 15.72 | C |
| ATOM | 2258 | CE1 | PHE | A | 148 | 55.817 | −37.301 | 10.371 | 1.00 | 11.87 | C |
| ATOM | 2260 | CZ | PHE | A | 148 | 55.001 | −36.628 | 11.261 | 1.00 | 12.42 | C |
| ATOM | 2262 | CE2 | PHE | A | 148 | 53.871 | −35.957 | 10.787 | 1.00 | 15.49 | C |
| ATOM | 2264 | CD2 | PHE | A | 148 | 53.572 | −35.970 | 9.424 | 1.00 | 10.40 | C |
| ATOM | 2266 | C | PHE | A | 148 | 52.621 | −37.627 | 5.242 | 1.00 | 16.28 | C |
| ATOM | 2267 | O | PHE | A | 148 | 51.908 | −36.653 | 4.998 | 1.00 | 17.46 | O |
| ATOM | 2269 | N | LEU | A | 149 | 52.952 | −38.516 | 4.308 | 1.00 | 16.51 | N |
| ATOM | 2270 | CA | LEU | A | 149 | 52.374 | −38.463 | 2.963 | 1.00 | 16.07 | C |
| ATOM | 2272 | CB | LEU | A | 149 | 53.410 | −38.866 | 1.911 | 1.00 | 15.09 | C |
| ATOM | 2275 | CG | LEU | A | 149 | 54.466 | −37.796 | 1.583 | 1.00 | 17.25 | C |
| ATOM | 2277 | CD1 | LEU | A | 149 | 55.499 | −37.629 | 2.714 | 1.00 | 8.39 | C |
| ATOM | 2281 | CD2 | LEU | A | 149 | 55.169 | −38.124 | 0.265 | 1.00 | 15.29 | C |
| ATOM | 2285 | C | LEU | A | 149 | 51.123 | −39.343 | 2.865 | 1.00 | 17.09 | C |
| ATOM | 2286 | O | LEU | A | 149 | 50.629 | −39.619 | 1.769 | 1.00 | 18.27 | O |
| ATOM | 2288 | N | ALA | A | 150 | 50.600 | −39.758 | 4.015 | 1.00 | 16.86 | N |
| ATOM | 2289 | CA | ALA | A | 150 | 49.436 | −40.618 | 4.070 | 1.00 | 17.38 | C |

APPENDIX 1-continued

| ATOM | 2291 | CB | ALA | A | 150 | 49.184 | −41.071 | 5.499 | 1.00 | 16.69 | C |
|---|---|---|---|---|---|---|---|---|---|---|---|
| ATOM | 2295 | C | ALA | A | 150 | 48.191 | −39.934 | 3.523 | 1.00 | 18.43 | C |
| ATOM | 2296 | O | ALA | A | 150 | 48.045 | −38.715 | 3.610 | 1.00 | 17.31 | O |
| ATOM | 2298 | N | LEU | A | 151 | 47.302 | −40.748 | 2.958 | 1.00 | 19.16 | N |
| ATOM | 2299 | CA | LEU | A | 151 | 45.975 | −40.315 | 2.560 | 1.00 | 18.86 | C |
| ATOM | 2301 | CB | LEU | A | 151 | 45.615 | −40.901 | 1.194 | 1.00 | 19.43 | C |
| ATOM | 2304 | CG | LEU | A | 151 | 46.562 | −40.592 | 0.027 | 1.00 | 20.03 | C |
| ATOM | 2306 | CD1 | LEU | A | 151 | 45.910 | −41.014 | −1.287 | 1.00 | 17.51 | C |
| ATOM | 2310 | CD2 | LEU | A | 151 | 46.938 | −39.122 | −0.020 | 1.00 | 12.04 | C |
| ATOM | 2314 | C | LEU | A | 151 | 44.996 | −40.820 | 3.604 | 1.00 | 18.10 | C |
| ATOM | 2315 | O | LEU | A | 151 | 45.347 | −41.693 | 4.399 | 1.00 | 18.33 | O |
| ATOM | 2317 | N | GLU | A | 152 | 43.776 | −40.277 | 3.601 | 1.00 | 16.98 | N |
| ATOM | 2318 | CA | GLU | A | 152 | 42.715 | −40.777 | 4.468 | 1.00 | 16.71 | C |
| ATOM | 2320 | CB | GLU | A | 152 | 41.402 | −40.056 | 4.215 | 1.00 | 16.62 | C |
| ATOM | 2323 | CG | GLU | A | 152 | 41.343 | −38.679 | 4.839 | 1.00 | 20.72 | C |
| ATOM | 2326 | CD | GLU | A | 152 | 39.957 | −38.085 | 4.813 | 1.00 | 21.47 | C |
| ATOM | 2327 | OE1 | GLU | A | 152 | 39.588 | −37.500 | 3.770 | 1.00 | 21.16 | O |
| ATOM | 2328 | OE2 | GLU | A | 152 | 39.255 | −38.197 | 5.842 | 1.00 | 20.77 | O |
| ATOM | 2329 | C | GLU | A | 152 | 42.513 | −42.264 | 4.256 | 1.00 | 16.79 | C |
| ATOM | 2330 | O | GLU | A | 152 | 42.488 | −42.743 | 3.120 | 1.00 | 17.14 | O |
| ATOM | 2332 | N | GLY | A | 153 | 42.398 | −42.992 | 5.361 | 1.00 | 17.10 | N |
| ATOM | 2333 | CA | GLY | A | 153 | 42.193 | −44.434 | 5.321 | 1.00 | 16.68 | C |
| ATOM | 2336 | C | GLY | A | 153 | 43.449 | −45.280 | 5.205 | 1.00 | 15.90 | C |
| ATOM | 2337 | O | GLY | A | 153 | 43.356 | −46.508 | 5.215 | 1.00 | 15.88 | O |
| ATOM | 2339 | N | GLU | A | 154 | 44.620 | −44.653 | 5.089 | 1.00 | 14.94 | N |
| ATOM | 2340 | CA | GLU | A | 154 | 45.869 | −45.414 | 5.090 | 1.00 | 15.59 | C |
| ATOM | 2342 | CB | GLU | A | 154 | 46.934 | −44.738 | 4.228 | 1.00 | 15.38 | C |
| ATOM | 2345 | CG | GLU | A | 154 | 46.607 | −44.803 | 2.747 | 1.00 | 15.65 | C |
| ATOM | 2348 | CD | GLU | A | 154 | 47.740 | −44.311 | 1.864 | 1.00 | 18.08 | C |
| ATOM | 2349 | OE1 | GLU | A | 154 | 48.355 | −43.266 | 2.194 | 1.00 | 13.19 | O |
| ATOM | 2350 | OE2 | GLU | A | 154 | 48.005 | −44.966 | 0.825 | 1.00 | 13.56 | O |
| ATOM | 2351 | C | GLU | A | 154 | 46.352 | −45.637 | 6.529 | 1.00 | 15.87 | C |
| ATOM | 2352 | O | GLU | A | 154 | 47.347 | −45.070 | 6.969 | 1.00 | 16.19 | O |
| ATOM | 2354 | N | ASN | A | 155 | 45.628 | −46.493 | 7.240 | 1.00 | 15.55 | N |
| ATOM | 2355 | CA | ASN | A | 155 | 45.861 | −46.753 | 8.653 | 1.00 | 15.76 | C |
| ATOM | 2357 | CB | ASN | A | 155 | 44.825 | −47.762 | 9.180 | 1.00 | 16.25 | C |
| ATOM | 2360 | CG | ASN | A | 155 | 44.853 | −49.080 | 8.423 | 1.00 | 14.85 | C |
| ATOM | 2361 | OD1 | ASN | A | 155 | 44.665 | −49.116 | 7.212 | 1.00 | 13.33 | O |
| ATOM | 2362 | ND2 | ASN | A | 155 | 45.097 | −50.160 | 9.134 | 1.00 | 12.78 | N |
| ATOM | 2365 | C | ASN | A | 155 | 47.263 | −47.260 | 8.984 | 1.00 | 15.84 | C |
| ATOM | 2366 | O | ASN | A | 155 | 47.732 | −47.076 | 10.108 | 1.00 | 14.90 | O |
| ATOM | 2368 | N | ILE | A | 156 | 47.923 | −47.907 | 8.021 | 1.00 | 15.44 | N |
| ATOM | 2369 | CA | ILE | A | 156 | 49.255 | −48.446 | 8.254 | 1.00 | 15.42 | C |
| ATOM | 2371 | CB | ILE | A | 156 | 49.616 | −49.526 | 7.220 | 1.00 | 15.75 | C |
| ATOM | 2373 | CG1 | ILE | A | 156 | 48.749 | −50.766 | 7.457 | 1.00 | 17.79 | C |
| ATOM | 2376 | CD1 | ILE | A | 156 | 49.062 | −51.899 | 6.535 | 1.00 | 23.00 | C |
| ATOM | 2380 | CG2 | ILE | A | 156 | 51.078 | −49.917 | 7.326 | 1.00 | 14.73 | C |
| ATOM | 2384 | C | ILE | A | 156 | 50.304 | −47.337 | 8.318 | 1.00 | 16.34 | C |
| ATOM | 2385 | O | ILE | A | 156 | 51.244 | −47.419 | 9.103 | 1.00 | 17.37 | O |
| ATOM | 2387 | N | LEU | A | 157 | 50.140 | −46.292 | 7.517 | 1.00 | 16.79 | N |
| ATOM | 2388 | CA | LEU | A | 157 | 51.022 | −45.137 | 7.616 | 1.00 | 17.34 | C |
| ATOM | 2390 | CB | LEU | A | 157 | 50.823 | −44.186 | 6.437 | 1.00 | 17.21 | C |
| ATOM | 2393 | CG | LEU | A | 157 | 51.173 | −44.788 | 5.072 | 1.00 | 15.12 | C |
| ATOM | 2395 | CD1 | LEU | A | 157 | 50.923 | −43.812 | 3.947 | 1.00 | 12.69 | C |
| ATOM | 2399 | CD2 | LEU | A | 157 | 52.594 | −45.249 | 5.047 | 1.00 | 15.60 | C |
| ATOM | 2403 | C | LEU | A | 157 | 50.800 | −44.428 | 8.952 | 1.00 | 18.32 | C |
| ATOM | 2404 | O | LEU | A | 157 | 51.751 | −43.997 | 9.588 | 1.00 | 18.18 | O |
| ATOM | 2406 | N | ASP | A | 158 | 49.551 | −44.345 | 9.400 | 1.00 | 19.27 | N |
| ATOM | 2407 | CA | ASP | A | 158 | 49.258 | −43.784 | 10.721 | 1.00 | 19.57 | C |
| ATOM | 2409 | CB | ASP | A | 158 | 47.747 | −43.677 | 10.960 | 1.00 | 18.96 | C |
| ATOM | 2412 | CG | ASP | A | 158 | 47.112 | −42.492 | 10.224 | 1.00 | 22.24 | C |
| ATOM | 2413 | OD1 | ASP | A | 158 | 47.680 | −42.013 | 9.216 | 1.00 | 23.78 | O |
| ATOM | 2414 | OD2 | ASP | A | 158 | 46.025 | −42.048 | 10.651 | 1.00 | 22.36 | O |
| ATOM | 2415 | C | ASP | A | 158 | 49.915 | −44.602 | 11.830 | 1.00 | 19.81 | C |
| ATOM | 2416 | O | ASP | A | 158 | 50.439 | −44.038 | 12.788 | 1.00 | 19.90 | O |
| ATOM | 2418 | N | GLU | A | 159 | 49.887 | −45.926 | 11.688 | 1.00 | 20.82 | N |
| ATOM | 2419 | CA | GLU | A | 159 | 50.496 | −46.838 | 12.660 | 1.00 | 20.62 | C |
| ATOM | 2421 | CB | GLU | A | 159 | 50.021 | −48.274 | 12.415 | 1.00 | 21.05 | C |
| ATOM | 2424 | CG | GLU | A | 159 | 48.552 | −48.504 | 12.764 | 1.00 | 26.10 | C |
| ATOM | 2427 | CD | GLU | A | 159 | 48.001 | −49.837 | 12.250 | 1.00 | 31.55 | C |
| ATOM | 2428 | OE1 | GLU | A | 159 | 48.803 | −50.695 | 11.814 | 1.00 | 33.98 | O |
| ATOM | 2429 | OE2 | GLU | A | 159 | 46.762 | −50.025 | 12.298 | 1.00 | 30.97 | O |
| ATOM | 2430 | C | GLU | A | 159 | 52.019 | −46.767 | 12.585 | 1.00 | 19.71 | C |
| ATOM | 2431 | O | GLU | A | 159 | 52.703 | −46.879 | 13.596 | 1.00 | 19.92 | O |
| ATOM | 2433 | N | ALA | A | 160 | 52.540 | −46.593 | 11.376 | 1.00 | 19.00 | N |
| ATOM | 2434 | CA | ALA | A | 160 | 53.970 | −46.408 | 11.169 | 1.00 | 18.47 | C |
| ATOM | 2436 | CB | ALA | A | 160 | 54.285 | −46.338 | 9.675 | 1.00 | 16.51 | C |
| ATOM | 2440 | C | ALA | A | 160 | 54.465 | −45.149 | 11.889 | 1.00 | 18.12 | C |
| ATOM | 2441 | O | ALA | A | 160 | 55.519 | −45.161 | 12.512 | 1.00 | 17.45 | O |
| ATOM | 2443 | N | LYS | A | 161 | 53.695 | −44.070 | 11.807 | 1.00 | 18.62 | N |

APPENDIX 1-continued

| | | | | | | | | | | |
|---|---|---|---|---|---|---|---|---|---|---|
| ATOM | 2444 | CA | LYS | A | 161 | 54.059 | −42.836 | 12.474 | 1.00 | 20.31 | C |
| ATOM | 2446 | CB | LYS | A | 161 | 53.020 | −41.741 | 12.229 | 1.00 | 20.68 | C |
| ATOM | 2449 | CG | LYS | A | 161 | 53.518 | −40.345 | 12.595 | 1.00 | 23.13 | C |
| ATOM | 2452 | CD | LYS | A | 161 | 52.384 | −39.357 | 12.792 | 1.00 | 25.25 | C |
| ATOM | 2455 | CE | LYS | A | 161 | 51.729 | −38.985 | 11.488 | 1.00 | 25.89 | C |
| ATOM | 2458 | NZ | LYS | A | 161 | 50.523 | −38.158 | 11.743 | 1.00 | 29.77 | N |
| ATOM | 2462 | C | LYS | A | 161 | 54.215 | −43.076 | 13.972 | 1.00 | 21.54 | C |
| ATOM | 2463 | O | LYS | A | 161 | 55.273 | −42.812 | 14.533 | 1.00 | 23.15 | O |
| ATOM | 2465 | N | VAL | A | 162 | 53.171 | −43.600 | 14.608 | 1.00 | 21.22 | N |
| ATOM | 2466 | CA | VAL | A | 162 | 53.181 | −43.828 | 16.051 | 1.00 | 20.51 | C |
| ATOM | 2468 | CB | VAL | A | 162 | 51.830 | −44.437 | 16.533 | 1.00 | 20.85 | C |
| ATOM | 2470 | CG1 | VAL | A | 162 | 51.887 | −44.807 | 18.010 | 1.00 | 20.30 | C |
| ATOM | 2474 | CG2 | VAL | A | 162 | 50.680 | −43.468 | 16.279 | 1.00 | 16.19 | C |
| ATOM | 2478 | C | VAL | A | 162 | 54.360 | −44.719 | 16.473 | 1.00 | 20.71 | C |
| ATOM | 2479 | O | VAL | A | 162 | 54.976 | −44.491 | 17.514 | 1.00 | 21.67 | O |
| ATOM | 2481 | N | PHE | A | 163 | 54.669 | −45.717 | 15.651 | 1.00 | 20.50 | N |
| ATOM | 2482 | CA | PHE | A | 163 | 55.743 | −46.678 | 15.924 | 1.00 | 20.68 | C |
| ATOM | 2484 | CB | PHE | A | 163 | 55.613 | −47.861 | 14.949 | 1.00 | 20.40 | C |
| ATOM | 2487 | CG | PHE | A | 163 | 56.771 | −48.828 | 14.960 | 1.00 | 18.51 | C |
| ATOM | 2488 | CD1 | PHE | A | 163 | 56.819 | −49.868 | 15.876 | 1.00 | 17.62 | C |
| ATOM | 2490 | CE1 | PHE | A | 163 | 57.870 | −50.785 | 15.866 | 1.00 | 16.93 | C |
| ATOM | 2492 | CZ | PHE | A | 163 | 58.884 | −50.675 | 14.920 | 1.00 | 15.97 | C |
| ATOM | 2494 | CE2 | PHE | A | 163 | 58.837 | −49.648 | 13.985 | 1.00 | 18.38 | C |
| ATOM | 2496 | CD2 | PHE | A | 163 | 57.779 | −48.737 | 14.005 | 1.00 | 18.12 | C |
| ATOM | 2498 | C | PHE | A | 163 | 57.106 | −45.998 | 15.803 | 1.00 | 21.49 | C |
| ATOM | 2499 | O | PHE | A | 163 | 57.936 | −46.086 | 16.705 | 1.00 | 21.23 | O |
| ATOM | 2501 | N | ALA | A | 164 | 57.323 | −45.311 | 14.688 | 1.00 | 22.41 | N |
| ATOM | 2502 | CA | ALA | A | 164 | 58.558 | −44.564 | 14.473 | 1.00 | 23.01 | C |
| ATOM | 2504 | CB | ALA | A | 164 | 58.499 | −43.802 | 13.149 | 1.00 | 22.58 | C |
| ATOM | 2508 | C | ALA | A | 164 | 58.819 | −43.595 | 15.625 | 1.00 | 23.79 | C |
| ATOM | 2509 | O | ALA | A | 164 | 59.877 | −43.646 | 16.237 | 1.00 | 24.21 | O |
| ATOM | 2511 | N | ILE | A | 165 | 57.848 | −42.732 | 15.917 | 1.00 | 24.41 | N |
| ATOM | 2512 | CA | ILE | A | 165 | 57.994 | −41.703 | 16.943 | 1.00 | 25.72 | C |
| ATOM | 2514 | CB | ILE | A | 165 | 56.692 | −40.881 | 17.129 | 1.00 | 25.90 | C |
| ATOM | 2516 | CG1 | ILE | A | 165 | 56.446 | −39.976 | 15.921 | 1.00 | 27.50 | C |
| ATOM | 2519 | CD1 | ILE | A | 165 | 55.312 | −38.984 | 16.110 | 1.00 | 29.50 | C |
| ATOM | 2523 | CG2 | ILE | A | 165 | 56.776 | −40.020 | 18.377 | 1.00 | 26.20 | C |
| ATOM | 2527 | C | ILE | A | 165 | 58.396 | −42.307 | 18.288 | 1.00 | 27.31 | C |
| ATOM | 2528 | O | ILE | A | 165 | 59.373 | −41.880 | 18.900 | 1.00 | 27.00 | O |
| ATOM | 2530 | N | SER | A | 166 | 57.653 | −43.315 | 18.734 | 1.00 | 28.52 | N |
| ATOM | 2531 | CA | SER | A | 166 | 57.888 | −43.906 | 20.043 | 1.00 | 28.85 | C |
| ATOM | 2533 | CB | SER | A | 166 | 56.927 | −45.074 | 20.306 | 1.00 | 28.71 | C |
| ATOM | 2536 | OG | SER | A | 166 | 57.305 | −46.238 | 19.588 | 1.00 | 29.11 | O |
| ATOM | 2538 | C | SER | A | 166 | 59.343 | −44.355 | 20.185 | 1.00 | 29.63 | C |
| ATOM | 2539 | O | SER | A | 166 | 59.927 | −44.231 | 21.259 | 1.00 | 30.04 | O |
| ATOM | 2541 | N | HIS | A | 167 | 59.925 | −44.855 | 19.098 | 1.00 | 30.55 | N |
| ATOM | 2542 | CA | HIS | A | 167 | 61.303 | −45.346 | 19.119 | 1.00 | 32.12 | C |
| ATOM | 2544 | CB | HIS | A | 167 | 61.479 | −46.544 | 18.178 | 1.00 | 32.45 | C |
| ATOM | 2547 | CG | HIS | A | 167 | 60.919 | −47.827 | 18.725 | 1.00 | 39.05 | C |
| ATOM | 2548 | ND1 | HIS | A | 167 | 60.459 | −48.846 | 17.917 | 1.00 | 42.96 | N |
| ATOM | 2550 | CE1 | HIS | A | 167 | 60.029 | −49.844 | 18.671 | 1.00 | 43.16 | C |
| ATOM | 2552 | NE2 | HIS | A | 167 | 60.184 | −49.507 | 19.939 | 1.00 | 42.42 | N |
| ATOM | 2554 | CD2 | HIS | A | 167 | 60.739 | −48.250 | 20.001 | 1.00 | 42.90 | C |
| ATOM | 2556 | C | HIS | A | 167 | 62.344 | −44.269 | 18.826 | 1.00 | 32.14 | C |
| ATOM | 2557 | O | HIS | A | 167 | 63.475 | −44.383 | 19.285 | 1.00 | 33.11 | O |
| ATOM | 2559 | N | LEU | A | 168 | 61.971 | −43.230 | 18.084 | 1.00 | 32.08 | N |
| ATOM | 2560 | CA | LEU | A | 168 | 62.864 | −42.087 | 17.862 | 1.00 | 32.28 | C |
| ATOM | 2562 | CB | LEU | A | 168 | 62.381 | −41.237 | 16.678 | 1.00 | 31.81 | C |
| ATOM | 2565 | CG | LEU | A | 168 | 62.424 | −41.885 | 15.288 | 1.00 | 29.10 | C |
| ATOM | 2567 | CD1 | LEU | A | 168 | 61.731 | −40.998 | 14.274 | 1.00 | 21.41 | C |
| ATOM | 2571 | CD2 | LEU | A | 168 | 63.849 | −42.204 | 14.849 | 1.00 | 23.48 | C |
| ATOM | 2575 | C | LEU | A | 168 | 62.981 | −41.206 | 19.111 | 1.00 | 33.66 | C |
| ATOM | 2576 | O | LEU | A | 168 | 64.044 | −40.658 | 19.397 | 1.00 | 33.20 | O |
| ATOM | 2578 | N | LYS | A | 169 | 61.881 | −41.086 | 19.848 | 1.00 | 36.11 | N |
| ATOM | 2579 | CA | LYS | A | 169 | 61.786 | −40.181 | 20.998 | 1.00 | 37.70 | C |
| ATOM | 2581 | CB | LYS | A | 169 | 60.315 | −40.050 | 21.421 | 1.00 | 37.80 | C |
| ATOM | 2584 | CG | LYS | A | 169 | 59.992 | −38.859 | 22.309 | 1.00 | 41.71 | C |
| ATOM | 2587 | CD | LYS | A | 169 | 58.478 | −38.569 | 22.345 | 1.00 | 44.58 | C |
| ATOM | 2590 | CE | LYS | A | 169 | 58.036 | −37.704 | 21.160 | 1.00 | 45.75 | C |
| ATOM | 2593 | NZ | LYS | A | 169 | 56.591 | −37.345 | 21.192 | 1.00 | 43.84 | N |
| ATOM | 2597 | C | LYS | A | 169 | 62.659 | −40.642 | 22.176 | 1.00 | 38.59 | C |
| ATOM | 2598 | O | LYS | A | 169 | 63.166 | −39.817 | 22.939 | 1.00 | 37.70 | O |
| ATOM | 2600 | N | GLU | A | 170 | 62.849 | −41.954 | 22.304 | 1.00 | 40.22 | N |
| ATOM | 2601 | CA | GLU | A | 170 | 63.670 | −42.523 | 23.380 | 1.00 | 41.64 | C |
| ATOM | 2603 | CB | GLU | A | 170 | 62.947 | −43.714 | 24.032 | 1.00 | 41.66 | C |
| ATOM | 2606 | CG | GLU | A | 170 | 61.570 | −43.379 | 24.620 | 1.00 | 43.09 | C |
| ATOM | 2609 | CD | GLU | A | 170 | 61.615 | −42.245 | 25.636 | 1.00 | 46.14 | C |
| ATOM | 2610 | OE1 | GLU | A | 170 | 62.239 | −42.418 | 26.707 | 1.00 | 48.22 | O |
| ATOM | 2611 | OE2 | GLU | A | 170 | 61.023 | −41.178 | 25.363 | 1.00 | 47.78 | O |
| ATOM | 2612 | C | GLU | A | 170 | 65.063 | −42.941 | 22.882 | 1.00 | 42.52 | C |

APPENDIX 1-continued

| ATOM | 2613 | O   | GLU | A | 170 | 65.528 | −44.050 | 23.159 | 1.00 | 41.63 | O |
|------|------|-----|-----|---|-----|--------|---------|--------|------|-------|---|
| ATOM | 2615 | N   | LEU | A | 171 | 65.719 | −42.038 | 22.152 | 1.00 | 43.75 | N |
| ATOM | 2616 | CA  | LEU | A | 171 | 67.086 | −42.247 | 21.675 | 1.00 | 44.67 | C |
| ATOM | 2618 | CB  | LEU | A | 171 | 67.165 | −42.090 | 20.152 | 1.00 | 44.05 | C |
| ATOM | 2621 | CG  | LEU | A | 171 | 66.660 | −43.241 | 19.282 | 1.00 | 43.10 | C |
| ATOM | 2623 | CD1 | LEU | A | 171 | 66.666 | −42.836 | 17.816 | 1.00 | 42.94 | C |
| ATOM | 2627 | CD2 | LEU | A | 171 | 67.487 | −44.495 | 19.481 | 1.00 | 41.69 | C |
| ATOM | 2631 | C   | LEU | A | 171 | 68.026 | −41.239 | 22.323 | 1.00 | 45.97 | C |
| ATOM | 2632 | O   | LEU | A | 171 | 67.711 | −40.048 | 22.400 | 1.00 | 45.99 | O |
| ATOM | 2634 | N   | SER | A | 172 | 69.183 | −41.722 | 22.776 | 1.00 | 47.57 | N |
| ATOM | 2635 | CA  | SER | A | 172 | 70.232 | −40.854 | 23.314 | 1.00 | 48.79 | C |
| ATOM | 2637 | CB  | SER | A | 172 | 70.887 | −41.476 | 24.554 | 1.00 | 49.01 | C |
| ATOM | 2640 | OG  | SER | A | 172 | 70.147 | −41.178 | 25.726 | 1.00 | 50.28 | O |
| ATOM | 2642 | C   | SER | A | 172 | 71.296 | −40.564 | 22.256 | 1.00 | 49.34 | C |
| ATOM | 2643 | O   | SER | A | 172 | 71.616 | −41.417 | 21.416 | 1.00 | 49.13 | O |
| ATOM | 2645 | N   | GLU | A | 173 | 71.838 | −39.350 | 22.320 | 1.00 | 49.90 | N |
| ATOM | 2646 | CA  | GLU | A | 173 | 72.919 | −38.900 | 21.441 | 1.00 | 50.29 | C |
| ATOM | 2648 | CB  | GLU | A | 173 | 73.304 | −37.459 | 21.819 | 1.00 | 50.50 | C |
| ATOM | 2651 | CG  | GLU | A | 173 | 74.414 | −36.821 | 20.988 | 1.00 | 51.47 | C |
| ATOM | 2654 | CD  | GLU | A | 173 | 74.555 | −35.329 | 21.257 | 1.00 | 53.10 | C |
| ATOM | 2655 | OE1 | GLU | A | 173 | 73.522 | −34.662 | 21.480 | 1.00 | 53.40 | O |
| ATOM | 2656 | OE2 | GLU | A | 173 | 75.695 | −34.818 | 21.241 | 1.00 | 55.08 | O |
| ATOM | 2657 | C   | GLU | A | 173 | 74.139 | −39.826 | 21.519 | 1.00 | 49.97 | C |
| ATOM | 2658 | O   | GLU | A | 173 | 74.787 | −40.100 | 20.504 | 1.00 | 49.13 | O |
| ATOM | 2660 | N   | GLU | A | 174 | 74.419 | −40.323 | 22.724 | 1.00 | 50.10 | N |
| ATOM | 2661 | CA  | GLU | A | 174 | 75.610 | −41.127 | 22.990 | 1.00 | 50.67 | C |
| ATOM | 2663 | CB  | GLU | A | 174 | 75.826 | −41.290 | 24.502 | 1.00 | 51.28 | C |
| ATOM | 2666 | CG  | GLU | A | 174 | 76.235 | −39.999 | 25.224 | 1.00 | 53.48 | C |
| ATOM | 2669 | CD  | GLU | A | 174 | 75.055 | −39.119 | 25.632 | 1.00 | 57.27 | C |
| ATOM | 2670 | OE1 | GLU | A | 174 | 73.975 | −39.212 | 25.001 | 1.00 | 57.63 | O |
| ATOM | 2671 | OE2 | GLU | A | 174 | 75.214 | −38.324 | 26.587 | 1.00 | 57.70 | O |
| ATOM | 2672 | C   | GLU | A | 174 | 75.566 | −42.500 | 22.321 | 1.00 | 50.40 | C |
| ATOM | 2673 | O   | GLU | A | 174 | 76.612 | −43.076 | 22.017 | 1.00 | 50.44 | O |
| ATOM | 2675 | N   | LYS | A | 175 | 74.363 | −43.015 | 22.082 | 1.00 | 50.05 | N |
| ATOM | 2676 | CA  | LYS | A | 175 | 74.192 | −44.347 | 21.492 | 1.00 | 49.51 | C |
| ATOM | 2678 | CB  | LYS | A | 175 | 72.820 | −44.928 | 21.859 | 1.00 | 50.11 | C |
| ATOM | 2681 | CG  | LYS | A | 175 | 72.507 | −44.943 | 23.356 | 1.00 | 52.68 | C |
| ATOM | 2684 | CD  | LYS | A | 175 | 71.119 | −45.522 | 23.632 | 1.00 | 54.40 | C |
| ATOM | 2687 | CE  | LYS | A | 175 | 70.933 | −45.874 | 25.106 | 1.00 | 54.94 | C |
| ATOM | 2690 | NZ  | LYS | A | 175 | 71.780 | −47.027 | 25.528 | 1.00 | 54.51 | N |
| ATOM | 2694 | C   | LYS | A | 175 | 74.333 | −44.335 | 19.970 | 1.00 | 48.28 | C |
| ATOM | 2695 | O   | LYS | A | 175 | 74.935 | −45.242 | 19.399 | 1.00 | 47.51 | O |
| ATOM | 2697 | N   | ILE | A | 176 | 73.775 | −43.311 | 19.322 | 1.00 | 47.24 | N |
| ATOM | 2698 | CA  | ILE | A | 176 | 73.623 | −43.301 | 17.856 | 1.00 | 46.13 | C |
| ATOM | 2700 | CB  | ILE | A | 176 | 72.214 | −42.811 | 17.439 | 1.00 | 45.78 | C |
| ATOM | 2702 | CG1 | ILE | A | 176 | 72.000 | −41.327 | 17.788 | 1.00 | 44.12 | C |
| ATOM | 2705 | CD1 | ILE | A | 176 | 70.595 | −40.830 | 17.518 | 1.00 | 39.62 | C |
| ATOM | 2709 | CG2 | ILE | A | 176 | 71.154 | −43.685 | 18.086 | 1.00 | 45.67 | C |
| ATOM | 2713 | C   | ILE | A | 176 | 74.669 | −42.486 | 17.097 | 1.00 | 45.92 | C |
| ATOM | 2714 | O   | ILE | A | 176 | 74.983 | −42.799 | 15.945 | 1.00 | 45.28 | O |
| ATOM | 2716 | N   | GLY | A | 177 | 75.186 | −41.440 | 17.739 | 1.00 | 45.76 | N |
| ATOM | 2717 | CA  | GLY | A | 177 | 76.150 | −40.531 | 17.122 | 1.00 | 45.48 | C |
| ATOM | 2720 | C   | GLY | A | 177 | 75.651 | −39.107 | 17.209 | 1.00 | 45.05 | C |
| ATOM | 2721 | O   | GLY | A | 177 | 74.472 | −38.879 | 17.464 | 1.00 | 45.46 | O |
| ATOM | 2723 | N   | LYS | A | 178 | 76.548 | −38.149 | 17.001 | 1.00 | 44.56 | N |
| ATOM | 2724 | CA  | LYS | A | 178 | 76.185 | −36.731 | 17.034 | 1.00 | 44.02 | C |
| ATOM | 2726 | CB  | LYS | A | 178 | 77.446 | −35.850 | 17.054 | 1.00 | 44.19 | C |
| ATOM | 2729 | CG  | LYS | A | 178 | 77.210 | −34.339 | 16.906 | 1.00 | 46.02 | C |
| ATOM | 2732 | CD  | LYS | A | 178 | 76.446 | −33.747 | 18.081 | 1.00 | 48.86 | C |
| ATOM | 2735 | CE  | LYS | A | 178 | 76.178 | −32.256 | 17.883 | 1.00 | 49.84 | C |
| ATOM | 2738 | NZ  | LYS | A | 178 | 77.393 | −31.420 | 18.104 | 1.00 | 49.97 | N |
| ATOM | 2742 | C   | LYS | A | 178 | 75.290 | −36.365 | 15.846 | 1.00 | 43.03 | C |
| ATOM | 2743 | O   | LYS | A | 178 | 74.349 | −35.583 | 15.997 | 1.00 | 42.69 | O |
| ATOM | 2745 | N   | GLU | A | 179 | 75.572 | −36.937 | 14.677 | 1.00 | 41.61 | N |
| ATOM | 2746 | CA  | GLU | A | 179 | 74.888 | −36.524 | 13.452 | 1.00 | 40.74 | C |
| ATOM | 2748 | CB  | GLU | A | 179 | 75.817 | −36.640 | 12.234 | 1.00 | 40.84 | C |
| ATOM | 2751 | CG  | GLU | A | 179 | 75.804 | −37.963 | 11.488 | 1.00 | 42.17 | C |
| ATOM | 2754 | CD  | GLU | A | 179 | 76.684 | −37.916 | 10.252 | 1.00 | 44.54 | C |
| ATOM | 2755 | OE1 | GLU | A | 179 | 76.170 | −38.174 |  9.143 | 1.00 | 45.44 | O |
| ATOM | 2756 | OE2 | GLU | A | 179 | 77.886 | −37.597 | 10.388 | 1.00 | 43.08 | O |
| ATOM | 2757 | C   | GLU | A | 179 | 73.543 | −37.226 | 13.217 | 1.00 | 39.29 | C |
| ATOM | 2758 | O   | GLU | A | 179 | 72.686 | −36.686 | 12.517 | 1.00 | 39.47 | O |
| ATOM | 2760 | N   | LEU | A | 180 | 73.353 | −38.414 | 13.782 | 1.00 | 37.43 | N |
| ATOM | 2761 | CA  | LEU | A | 180 | 72.022 | −39.025 | 13.799 | 1.00 | 36.29 | C |
| ATOM | 2763 | CB  | LEU | A | 180 | 72.070 | −40.507 | 14.191 | 1.00 | 36.48 | C |
| ATOM | 2766 | CG  | LEU | A | 180 | 72.206 | −41.541 | 13.068 | 1.00 | 37.27 | C |
| ATOM | 2768 | CD1 | LEU | A | 180 | 72.037 | −42.929 | 13.639 | 1.00 | 38.80 | C |
| ATOM | 2772 | CD2 | LEU | A | 180 | 71.195 | −41.318 | 11.949 | 1.00 | 37.95 | C |
| ATOM | 2776 | C   | LEU | A | 180 | 71.119 | −38.264 | 14.765 | 1.00 | 35.24 | C |
| ATOM | 2777 | O   | LEU | A | 180 | 69.948 | −38.028 | 14.473 | 1.00 | 35.11 | O |

APPENDIX 1-continued

| ATOM | 2779 | N | ALA | A | 181 | 71.667 | −37.879 | 15.912 | 1.00 | 33.91 | N |
|------|------|-----|-----|---|-----|--------|---------|--------|------|-------|---|
| ATOM | 2780 | CA | ALA | A | 181 | 70.915 | −37.104 | 16.892 | 1.00 | 33.10 | C |
| ATOM | 2782 | CB | ALA | A | 181 | 71.797 | −36.741 | 18.078 | 1.00 | 32.58 | C |
| ATOM | 2786 | C | ALA | A | 181 | 70.348 | −35.848 | 16.246 | 1.00 | 32.64 | C |
| ATOM | 2787 | O | ALA | A | 181 | 69.168 | −35.539 | 16.403 | 1.00 | 32.91 | O |
| ATOM | 2789 | N | GLU | A | 182 | 71.195 | −35.134 | 15.513 | 1.00 | 32.24 | N |
| ATOM | 2790 | CA | GLU | A | 182 | 70.777 | −33.927 | 14.814 | 1.00 | 32.25 | C |
| ATOM | 2792 | CB | GLU | A | 182 | 71.965 | −33.257 | 14.116 | 1.00 | 33.87 | C |
| ATOM | 2795 | CG | GLU | A | 182 | 72.871 | −32.443 | 15.053 | 1.00 | 38.91 | C |
| ATOM | 2798 | CD | GLU | A | 182 | 74.082 | −31.827 | 14.340 | 1.00 | 46.46 | C |
| ATOM | 2799 | OE1 | GLU | A | 182 | 74.328 | −32.150 | 13.152 | 1.00 | 52.06 | O |
| ATOM | 2800 | OE2 | GLU | A | 182 | 74.792 | −31.016 | 14.976 | 1.00 | 50.12 | O |
| ATOM | 2801 | C | GLU | A | 182 | 69.684 | −34.241 | 13.805 | 1.00 | 30.14 | C |
| ATOM | 2802 | O | GLU | A | 182 | 68.708 | −33.506 | 13.714 | 1.00 | 30.62 | O |
| ATOM | 2804 | N | GLN | A | 183 | 69.846 | −35.333 | 13.059 | 1.00 | 27.72 | N |
| ATOM | 2805 | CA | GLN | A | 183 | 68.834 | −35.765 | 12.091 | 1.00 | 25.84 | C |
| ATOM | 2807 | CB | GLN | A | 183 | 69.326 | −36.967 | 11.274 | 1.00 | 26.42 | C |
| ATOM | 2810 | CG | GLN | A | 183 | 70.351 | −36.638 | 10.186 | 1.00 | 28.35 | C |
| ATOM | 2813 | CD | GLN | A | 183 | 69.758 | −35.878 | 9.006 | 1.00 | 32.28 | C |
| ATOM | 2814 | OE1 | GLN | A | 183 | 68.614 | −36.106 | 8.604 | 1.00 | 36.40 | O |
| ATOM | 2815 | NE2 | GLN | A | 183 | 70.542 | −34.971 | 8.444 | 1.00 | 33.91 | N |
| ATOM | 2818 | C | GLN | A | 183 | 67.513 | −36.117 | 12.774 | 1.00 | 23.95 | C |
| ATOM | 2819 | O | GLN | A | 183 | 66.438 | −35.767 | 12.277 | 1.00 | 23.10 | O |
| ATOM | 2821 | N | VAL | A | 184 | 67.606 | −36.805 | 13.912 | 1.00 | 22.75 | N |
| ATOM | 2822 | CA | VAL | A | 184 | 66.428 | −37.238 | 14.665 | 1.00 | 21.10 | C |
| ATOM | 2824 | CB | VAL | A | 184 | 66.802 | −38.184 | 15.824 | 1.00 | 21.25 | C |
| ATOM | 2826 | CG1 | VAL | A | 184 | 65.639 | −38.336 | 16.796 | 1.00 | 20.05 | C |
| ATOM | 2830 | CG2 | VAL | A | 184 | 67.229 | −39.539 | 15.286 | 1.00 | 19.78 | C |
| ATOM | 2834 | C | VAL | A | 184 | 65.671 | −36.051 | 15.230 | 1.00 | 20.63 | C |
| ATOM | 2835 | O | VAL | A | 184 | 64.448 | −35.967 | 15.086 | 1.00 | 21.39 | O |
| ATOM | 2837 | N | ASN | A | 185 | 66.397 | −35.136 | 15.862 | 1.00 | 19.15 | N |
| ATOM | 2838 | CA | ASN | A | 185 | 65.781 | −33.958 | 16.450 | 1.00 | 19.06 | C |
| ATOM | 2840 | CB | ASN | A | 185 | 66.798 | −33.155 | 17.265 | 1.00 | 19.99 | C |
| ATOM | 2843 | CG | ASN | A | 185 | 67.350 | −33.937 | 18.462 | 1.00 | 21.37 | C |
| ATOM | 2844 | OD1 | ASN | A | 185 | 66.692 | −34.825 | 19.017 | 1.00 | 22.33 | O |
| ATOM | 2845 | ND2 | ASN | A | 185 | 68.570 | −33.608 | 18.854 | 1.00 | 20.88 | N |
| ATOM | 2848 | C | ASN | A | 185 | 65.151 | −33.082 | 15.383 | 1.00 | 18.27 | C |
| ATOM | 2849 | O | ASN | A | 185 | 64.051 | −32.570 | 15.567 | 1.00 | 18.55 | O |
| ATOM | 2851 | N | HIS | A | 186 | 65.853 | −32.922 | 14.267 | 1.00 | 18.12 | N |
| ATOM | 2852 | CA | HIS | A | 186 | 65.325 | −32.200 | 13.103 | 1.00 | 17.96 | C |
| ATOM | 2854 | CB | HIS | A | 186 | 66.357 | −32.213 | 11.969 | 1.00 | 18.19 | C |
| ATOM | 2857 | CG | HIS | A | 186 | 66.006 | −31.338 | 10.806 | 1.00 | 19.45 | C |
| ATOM | 2858 | ND1 | HIS | A | 186 | 66.056 | −29.963 | 10.866 | 1.00 | 22.50 | N |
| ATOM | 2860 | CE1 | HIS | A | 186 | 65.718 | −29.461 | 9.692 | 1.00 | 22.65 | C |
| ATOM | 2862 | NE2 | HIS | A | 186 | 65.461 | −30.461 | 8.868 | 1.00 | 21.22 | N |
| ATOM | 2864 | CD2 | HIS | A | 186 | 65.642 | −31.646 | 9.538 | 1.00 | 21.25 | C |
| ATOM | 2866 | C | HIS | A | 186 | 64.002 | −32.814 | 12.620 | 1.00 | 16.71 | C |
| ATOM | 2867 | O | HIS | A | 186 | 63.042 | −32.089 | 12.370 | 1.00 | 15.76 | O |
| ATOM | 2869 | N | ALA | A | 187 | 63.956 | −34.142 | 12.509 | 1.00 | 15.66 | N |
| ATOM | 2870 | CA | ALA | A | 187 | 62.749 | −34.844 | 12.052 | 1.00 | 15.45 | C |
| ATOM | 2872 | CB | ALA | A | 187 | 63.045 | −36.323 | 11.783 | 1.00 | 13.51 | C |
| ATOM | 2876 | C | ALA | A | 187 | 61.606 | −34.705 | 13.056 | 1.00 | 16.57 | C |
| ATOM | 2877 | O | ALA | A | 187 | 60.455 | −34.462 | 12.666 | 1.00 | 17.16 | O |
| ATOM | 2879 | N | LEU | A | 188 | 61.923 | −34.846 | 14.344 | 1.00 | 17.33 | N |
| ATOM | 2880 | CA | LEU | A | 188 | 60.916 | −34.712 | 15.402 | 1.00 | 18.39 | C |
| ATOM | 2882 | CB | LEU | A | 188 | 61.440 | −35.277 | 16.725 | 1.00 | 18.54 | C |
| ATOM | 2885 | CG | LEU | A | 188 | 61.685 | −36.799 | 16.774 | 1.00 | 20.88 | C |
| ATOM | 2887 | CD1 | LEU | A | 188 | 62.370 | −37.204 | 18.079 | 1.00 | 14.03 | C |
| ATOM | 2891 | CD2 | LEU | A | 188 | 60.389 | −37.601 | 16.583 | 1.00 | 18.90 | C |
| ATOM | 2895 | C | LEU | A | 188 | 60.425 | −33.270 | 15.586 | 1.00 | 19.27 | C |
| ATOM | 2896 | O | LEU | A | 188 | 59.314 | −33.059 | 16.053 | 1.00 | 19.68 | O |
| ATOM | 2898 | N | GLU | A | 189 | 61.243 | −32.287 | 15.214 | 1.00 | 20.30 | N |
| ATOM | 2899 | CA | GLU | A | 189 | 60.827 | −30.881 | 15.238 | 1.00 | 21.36 | C |
| ATOM | 2901 | CB | GLU | A | 189 | 62.026 | −29.962 | 14.957 | 1.00 | 21.99 | C |
| ATOM | 2904 | CG | GLU | A | 189 | 61.699 | −28.470 | 14.954 | 1.00 | 26.04 | C |
| ATOM | 2907 | CD | GLU | A | 189 | 62.841 | −27.608 | 14.433 | 1.00 | 32.64 | C |
| ATOM | 2908 | OE1 | GLU | A | 189 | 63.272 | −27.809 | 13.276 | 1.00 | 35.76 | O |
| ATOM | 2909 | OE2 | GLU | A | 189 | 63.297 | −26.713 | 15.181 | 1.00 | 37.28 | O |
| ATOM | 2910 | C | GLU | A | 189 | 59.731 | −30.618 | 14.206 | 1.00 | 21.74 | C |
| ATOM | 2911 | O | GLU | A | 189 | 58.759 | −29.913 | 14.484 | 1.00 | 22.33 | O |
| ATOM | 2913 | N | LEU | A | 190 | 59.916 | −31.172 | 13.013 | 1.00 | 21.35 | N |
| ATOM | 2914 | CA | LEU | A | 190 | 58.983 | −31.008 | 11.911 | 1.00 | 21.78 | C |
| ATOM | 2916 | CB | LEU | A | 190 | 58.922 | −29.537 | 11.472 | 1.00 | 22.20 | C |
| ATOM | 2919 | CG | LEU | A | 190 | 57.780 | −29.113 | 10.548 | 1.00 | 24.65 | C |
| ATOM | 2921 | CD1 | LEU | A | 190 | 56.457 | −29.141 | 11.279 | 1.00 | 20.76 | C |
| ATOM | 2925 | CD2 | LEU | A | 190 | 58.036 | −27.722 | 9.966 | 1.00 | 24.14 | C |
| ATOM | 2929 | C | LEU | A | 190 | 59.466 | −31.894 | 10.756 | 1.00 | 21.36 | C |
| ATOM | 2930 | O | LEU | A | 190 | 60.628 | −31.830 | 10.375 | 1.00 | 21.03 | O |
| ATOM | 2932 | N | PRO | A | 191 | 58.584 | −32.745 | 10.213 | 1.00 | 21.29 | N |
| ATOM | 2933 | CA | PRO | A | 191 | 59.000 | −33.644 | 9.145 | 1.00 | 20.66 | C |

APPENDIX 1-continued

| | | | | | | | | | | |
|---|---|---|---|---|---|---|---|---|---|---|
| ATOM | 2935 | CB | PRO | A | 191 | 57.850 | −34.642 | 9.072 | 1.00 | 20.81 | C |
| ATOM | 2938 | CG | PRO | A | 191 | 56.679 | −33.890 | 9.530 | 1.00 | 20.77 | C |
| ATOM | 2941 | CD | PRO | A | 191 | 57.159 | −32.911 | 10.542 | 1.00 | 20.89 | C |
| ATOM | 2944 | C | PRO | A | 191 | 59.175 | −32.932 | 7.804 | 1.00 | 21.01 | C |
| ATOM | 2945 | O | PRO | A | 191 | 58.554 | −31.892 | 7.561 | 1.00 | 20.86 | O |
| ATOM | 2946 | N | LEU | A | 192 | 60.004 | −33.515 | 6.942 | 1.00 | 20.69 | N |
| ATOM | 2947 | CA | LEU | A | 192 | 60.315 | −32.939 | 5.638 | 1.00 | 20.28 | C |
| ATOM | 2949 | CB | LEU | A | 192 | 61.095 | −33.940 | 4.789 | 1.00 | 20.87 | C |
| ATOM | 2952 | CG | LEU | A | 192 | 62.521 | −34.245 | 5.250 | 1.00 | 24.52 | C |
| ATOM | 2954 | CD1 | LEU | A | 192 | 63.020 | −35.527 | 4.593 | 1.00 | 24.37 | C |
| ATOM | 2958 | CD2 | LEU | A | 192 | 63.449 | −33.072 | 4.958 | 1.00 | 23.68 | C |
| ATOM | 2962 | C | LEU | A | 192 | 59.070 | −32.523 | 4.878 | 1.00 | 19.68 | C |
| ATOM | 2963 | O | LEU | A | 192 | 59.019 | −31.429 | 4.329 | 1.00 | 20.16 | O |
| ATOM | 2965 | N | HIS | A | 193 | 58.060 | −33.388 | 4.853 | 1.00 | 19.46 | N |
| ATOM | 2966 | CA | HIS | A | 193 | 56.841 | −33.102 | 4.087 | 1.00 | 19.61 | C |
| ATOM | 2968 | CB | HIS | A | 193 | 55.856 | −34.273 | 4.164 | 1.00 | 18.91 | C |
| ATOM | 2971 | CG | HIS | A | 193 | 54.730 | −34.176 | 3.183 | 1.00 | 18.53 | C |
| ATOM | 2972 | ND1 | HIS | A | 193 | 54.934 | −34.015 | 1.829 | 1.00 | 16.78 | N |
| ATOM | 2974 | CE1 | HIS | A | 193 | 53.767 | −33.955 | 1.216 | 1.00 | 16.41 | C |
| ATOM | 2976 | NE2 | HIS | A | 193 | 52.814 | −34.076 | 2.121 | 1.00 | 17.58 | N |
| ATOM | 2978 | CD2 | HIS | A | 193 | 53.390 | −34.217 | 3.359 | 1.00 | 21.13 | C |
| ATOM | 2980 | C | HIS | A | 193 | 56.136 | −31.799 | 4.503 | 1.00 | 20.58 | C |
| ATOM | 2981 | O | HIS | A | 193 | 55.449 | −31.194 | 3.690 | 1.00 | 20.81 | O |
| ATOM | 2983 | N | ARG | A | 194 | 56.310 | −31.378 | 5.756 | 1.00 | 21.61 | N |
| ATOM | 2984 | CA | ARG | A | 194 | 55.652 | −30.177 | 6.275 | 1.00 | 22.78 | C |
| ATOM | 2986 | CB | ARG | A | 194 | 55.055 | −30.463 | 7.645 | 1.00 | 22.74 | C |
| ATOM | 2989 | CG | ARG | A | 194 | 53.936 | −31.466 | 7.599 | 1.00 | 24.13 | C |
| ATOM | 2992 | CD | ARG | A | 194 | 53.244 | −31.577 | 8.937 | 1.00 | 25.19 | C |
| ATOM | 2995 | NE | ARG | A | 194 | 52.115 | −32.498 | 8.878 | 1.00 | 26.72 | N |
| ATOM | 2997 | CZ | ARG | A | 194 | 51.461 | −32.967 | 9.939 | 1.00 | 24.95 | C |
| ATOM | 2998 | NH1 | ARG | A | 194 | 51.811 | −32.609 | 11.169 | 1.00 | 25.40 | N |
| ATOM | 3001 | NH2 | ARG | A | 194 | 50.447 | −33.799 | 9.763 | 1.00 | 23.76 | N |
| ATOM | 3004 | C | ARG | A | 194 | 56.579 | −28.971 | 6.387 | 1.00 | 23.86 | C |
| ATOM | 3005 | O | ARG | A | 194 | 56.105 | −27.853 | 6.626 | 1.00 | 24.87 | O |
| ATOM | 3007 | N | ARG | A | 195 | 57.884 | −29.195 | 6.209 | 1.00 | 22.92 | N |
| ATOM | 3008 | CA | ARG | A | 195 | 58.872 | −28.121 | 6.258 | 1.00 | 21.47 | C |
| ATOM | 3010 | CB | ARG | A | 195 | 60.222 | −28.670 | 6.706 | 1.00 | 21.67 | C |
| ATOM | 3013 | CG | ARG | A | 195 | 61.179 | −27.620 | 7.232 | 1.00 | 21.84 | C |
| ATOM | 3016 | CD | ARG | A | 195 | 62.519 | −28.226 | 7.535 | 1.00 | 20.35 | C |
| ATOM | 3019 | NE | ARG | A | 195 | 62.447 | −29.168 | 8.648 | 1.00 | 19.52 | N |
| ATOM | 3021 | CZ | ARG | A | 195 | 62.561 | −28.842 | 9.934 | 1.00 | 21.51 | C |
| ATOM | 3022 | NH1 | ARG | A | 195 | 62.762 | −27.580 | 10.310 | 1.00 | 20.60 | N |
| ATOM | 3025 | NH2 | ARG | A | 195 | 62.476 | −29.793 | 10.860 | 1.00 | 23.45 | N |
| ATOM | 3028 | C | ARG | A | 195 | 59.018 | −27.465 | 4.895 | 1.00 | 20.90 | C |
| ATOM | 3029 | O | ARG | A | 195 | 58.986 | −28.146 | 3.862 | 1.00 | 21.00 | O |
| ATOM | 3031 | N | THR | A | 196 | 59.187 | −26.141 | 4.897 | 1.00 | 20.22 | N |
| ATOM | 3032 | CA | THR | A | 196 | 59.382 | −25.379 | 3.661 | 1.00 | 18.71 | C |
| ATOM | 3034 | CB | THR | A | 196 | 59.332 | −23.880 | 3.913 | 1.00 | 18.34 | C |
| ATOM | 3036 | OG1 | THR | A | 196 | 60.229 | −23.559 | 4.977 | 1.00 | 18.15 | O |
| ATOM | 3038 | CG2 | THR | A | 196 | 57.922 | −23.435 | 4.282 | 1.00 | 16.30 | C |
| ATOM | 3042 | C | THR | A | 196 | 60.731 | −25.696 | 3.020 | 1.00 | 19.40 | C |
| ATOM | 3043 | O | THR | A | 196 | 61.688 | −26.131 | 3.696 | 1.00 | 19.33 | O |
| ATOM | 3045 | N | GLN | A | 197 | 60.809 | −25.448 | 1.716 | 1.00 | 18.56 | N |
| ATOM | 3046 | CA | GLN | A | 197 | 61.934 | −25.917 | 0.920 | 1.00 | 18.45 | C |
| ATOM | 3048 | CB | GLN | A | 197 | 61.623 | −25.783 | −0.576 | 1.00 | 19.04 | C |
| ATOM | 3051 | CG | GLN | A | 197 | 62.363 | −26.781 | −1.484 | 1.00 | 20.45 | C |
| ATOM | 3054 | CD | GLN | A | 197 | 63.690 | −26.254 | −2.029 | 1.00 | 23.06 | C |
| ATOM | 3055 | OE1 | GLN | A | 197 | 64.326 | −25.377 | −1.435 | 1.00 | 22.28 | O |
| ATOM | 3056 | NE2 | GLN | A | 197 | 64.113 | −26.798 | −3.168 | 1.00 | 23.25 | N |
| ATOM | 3059 | C | GLN | A | 197 | 63.250 | −25.217 | 1.292 | 1.00 | 18.75 | C |
| ATOM | 3060 | O | GLN | A | 197 | 64.264 | −25.899 | 1.487 | 1.00 | 20.24 | O |
| ATOM | 3062 | N | ARG | A | 198 | 63.238 | −23.885 | 1.415 | 1.00 | 16.75 | N |
| ATOM | 3063 | CA | ARG | A | 198 | 64.460 | −23.132 | 1.751 | 1.00 | 16.08 | C |
| ATOM | 3065 | CB | ARG | A | 198 | 64.243 | −21.626 | 1.617 | 1.00 | 14.41 | C |
| ATOM | 3068 | CG | ARG | A | 198 | 64.010 | −21.157 | 0.186 | 1.00 | 16.34 | C |
| ATOM | 3071 | CD | ARG | A | 198 | 65.263 | −21.285 | −0.701 | 1.00 | 18.13 | C |
| ATOM | 3074 | NE | ARG | A | 198 | 65.406 | −22.597 | −1.339 | 1.00 | 18.36 | N |
| ATOM | 3076 | CZ | ARG | A | 198 | 66.411 | −22.933 | −2.149 | 1.00 | 17.71 | C |
| ATOM | 3077 | NH1 | ARG | A | 198 | 67.374 | −22.061 | −2.424 | 1.00 | 19.46 | N |
| ATOM | 3080 | NH2 | ARG | A | 198 | 66.465 | −24.148 | −2.689 | 1.00 | 17.52 | N |
| ATOM | 3083 | C | ARG | A | 198 | 65.010 | −23.439 | 3.142 | 1.00 | 17.39 | C |
| ATOM | 3084 | O | ARG | A | 198 | 66.231 | −23.523 | 3.319 | 1.00 | 18.40 | O |
| ATOM | 3086 | N | LEU | A | 199 | 64.126 | −23.602 | 4.125 | 1.00 | 18.03 | N |
| ATOM | 3087 | CA | LEU | A | 199 | 64.551 | −23.907 | 5.491 | 1.00 | 18.94 | C |
| ATOM | 3089 | CB | LEU | A | 199 | 63.361 | −23.914 | 6.440 | 1.00 | 20.48 | C |
| ATOM | 3092 | CG | LEU | A | 199 | 62.877 | −22.553 | 6.916 | 1.00 | 23.96 | C |
| ATOM | 3094 | CD1 | LEU | A | 199 | 61.583 | −22.719 | 7.705 | 1.00 | 24.08 | C |
| ATOM | 3098 | CD2 | LEU | A | 199 | 63.961 | −21.896 | 7.753 | 1.00 | 22.94 | C |
| ATOM | 3102 | C | LEU | A | 199 | 65.252 | −25.253 | 5.568 | 1.00 | 18.95 | C |
| ATOM | 3103 | O | LEU | A | 199 | 66.288 | −25.384 | 6.207 | 1.00 | 19.37 | O |

APPENDIX 1-continued

| ATOM | 3105 | N | GLU | A | 200 | 64.678 | −26.257 | 4.918 | 1.00 | 19.33 | N |
|---|---|---|---|---|---|---|---|---|---|---|---|
| ATOM | 3106 | CA | GLU | A | 200 | 65.324 | −27.562 | 4.822 | 1.00 | 19.05 | C |
| ATOM | 3108 | CB | GLU | A | 200 | 64.409 | −28.552 | 4.102 | 1.00 | 18.90 | C |
| ATOM | 3111 | CG | GLU | A | 200 | 64.942 | −29.958 | 3.983 | 1.00 | 18.52 | C |
| ATOM | 3114 | CD | GLU | A | 200 | 65.404 | −30.546 | 5.299 | 1.00 | 24.43 | C |
| ATOM | 3115 | OE1 | GLU | A | 200 | 64.818 | −30.236 | 6.361 | 1.00 | 24.97 | O |
| ATOM | 3116 | OE2 | GLU | A | 200 | 66.360 | −31.343 | 5.264 | 1.00 | 29.77 | O |
| ATOM | 3117 | C | GLU | A | 200 | 66.669 | −27.471 | 4.103 | 1.00 | 19.17 | C |
| ATOM | 3118 | O | GLU | A | 200 | 67.625 | −28.151 | 4.489 | 1.00 | 19.91 | O |
| ATOM | 3120 | N | ALA | A | 201 | 66.748 | −26.631 | 3.071 | 1.00 | 18.52 | N |
| ATOM | 3121 | CA | ALA | A | 201 | 67.988 | −26.490 | 2.306 | 1.00 | 18.74 | C |
| ATOM | 3123 | CB | ALA | A | 201 | 67.765 | −25.669 | 1.041 | 1.00 | 17.65 | C |
| ATOM | 3127 | C | ALA | A | 201 | 69.100 | −25.874 | 3.151 | 1.00 | 19.12 | C |
| ATOM | 3128 | O | ALA | A | 201 | 70.237 | −26.357 | 3.136 | 1.00 | 19.39 | O |
| ATOM | 3130 | N | VAL | A | 202 | 68.781 | −24.812 | 3.886 | 1.00 | 18.58 | N |
| ATOM | 3131 | CA | VAL | A | 202 | 69.795 | −24.140 | 4.686 | 1.00 | 18.09 | C |
| ATOM | 3133 | CB | VAL | A | 202 | 69.290 | −22.805 | 5.297 | 1.00 | 18.62 | C |
| ATOM | 3135 | CG1 | VAL | A | 202 | 68.341 | −23.045 | 6.453 | 1.00 | 17.88 | C |
| ATOM | 3139 | CG2 | VAL | A | 202 | 70.468 | −21.968 | 5.752 | 1.00 | 17.48 | C |
| ATOM | 3143 | C | VAL | A | 202 | 70.297 | −25.076 | 5.776 | 1.00 | 17.71 | C |
| ATOM | 3144 | O | VAL | A | 202 | 71.491 | −25.105 | 6.074 | 1.00 | 19.28 | O |
| ATOM | 3146 | N | TRP | A | 203 | 69.387 | −25.864 | 6.340 | 1.00 | 16.99 | N |
| ATOM | 3147 | CA | TRP | A | 203 | 69.738 | −26.815 | 7.378 | 1.00 | 16.69 | C |
| ATOM | 3149 | CB | TRP | A | 203 | 68.482 | −27.357 | 8.073 | 1.00 | 17.28 | C |
| ATOM | 3152 | CG | TRP | A | 203 | 68.807 | −28.148 | 9.286 | 1.00 | 17.11 | C |
| ATOM | 3153 | CD1 | TRP | A | 203 | 68.935 | −27.678 | 10.554 | 1.00 | 17.84 | C |
| ATOM | 3155 | NE1 | TRP | A | 203 | 69.271 | −28.704 | 11.406 | 1.00 | 17.21 | N |
| ATOM | 3157 | CE2 | TRP | A | 203 | 69.373 | −29.861 | 10.685 | 1.00 | 16.55 | C |
| ATOM | 3158 | CD2 | TRP | A | 203 | 69.086 | −29.547 | 9.344 | 1.00 | 17.54 | C |
| ATOM | 3159 | CE3 | TRP | A | 203 | 69.126 | −30.565 | 8.393 | 1.00 | 19.66 | C |
| ATOM | 3161 | CZ3 | TRP | A | 203 | 69.436 | −31.854 | 8.807 | 1.00 | 21.37 | C |
| ATOM | 3163 | CH2 | TRP | A | 203 | 69.712 | −32.133 | 10.143 | 1.00 | 21.02 | C |
| ATOM | 3165 | CZ2 | TRP | A | 203 | 69.686 | −31.150 | 11.097 | 1.00 | 20.22 | C |
| ATOM | 3167 | C | TRP | A | 203 | 70.564 | −27.959 | 6.799 | 1.00 | 16.20 | C |
| ATOM | 3168 | O | TRP | A | 203 | 71.653 | −28.235 | 7.288 | 1.00 | 16.09 | O |
| ATOM | 3170 | N | SER | A | 204 | 70.053 | −28.610 | 5.756 | 1.00 | 16.35 | N |
| ATOM | 3171 | CA | SER | A | 204 | 70.722 | −29.792 | 5.179 | 1.00 | 16.36 | C |
| ATOM | 3173 | CB | SER | A | 204 | 69.856 | −30.454 | 4.102 | 1.00 | 16.65 | C |
| ATOM | 3176 | OG | SER | A | 204 | 68.755 | −31.118 | 4.693 | 1.00 | 17.66 | O |
| ATOM | 3178 | C | SER | A | 204 | 72.098 | −29.489 | 4.604 | 1.00 | 14.94 | C |
| ATOM | 3179 | O | SER | A | 204 | 72.999 | −30.329 | 4.678 | 1.00 | 14.23 | O |
| ATOM | 3181 | N | ILE | A | 205 | 72.268 | −28.304 | 4.028 | 1.00 | 14.13 | N |
| ATOM | 3182 | CA | ILE | A | 205 | 73.580 | −27.919 | 3.506 | 1.00 | 14.35 | C |
| ATOM | 3184 | CB | ILE | A | 205 | 73.544 | −26.563 | 2.778 | 1.00 | 14.82 | C |
| ATOM | 3186 | CG1 | ILE | A | 205 | 72.869 | −26.729 | 1.412 | 1.00 | 14.39 | C |
| ATOM | 3189 | CD1 | ILE | A | 205 | 72.455 | −25.425 | 0.755 | 1.00 | 11.85 | C |
| ATOM | 3193 | CG2 | ILE | A | 205 | 74.954 | −26.011 | 2.614 | 1.00 | 12.68 | C |
| ATOM | 3197 | C | ILE | A | 205 | 74.619 | −27.914 | 4.633 | 1.00 | 13.92 | C |
| ATOM | 3198 | O | ILE | A | 205 | 75.690 | −28.484 | 4.489 | 1.00 | 11.72 | O |
| ATOM | 3200 | N | GLU | A | 206 | 74.273 | −27.307 | 5.765 | 1.00 | 15.11 | N |
| ATOM | 3201 | CA | GLU | A | 206 | 75.152 | −27.312 | 6.938 | 1.00 | 15.74 | C |
| ATOM | 3203 | CB | GLU | A | 206 | 74.561 | −26.447 | 8.059 | 1.00 | 16.58 | C |
| ATOM | 3206 | CG | GLU | A | 206 | 75.451 | −26.307 | 9.311 | 1.00 | 20.35 | C |
| ATOM | 3209 | CD | GLU | A | 206 | 76.720 | −25.486 | 9.089 | 1.00 | 23.18 | C |
| ATOM | 3210 | OE1 | GLU | A | 206 | 76.929 | −24.975 | 7.966 | 1.00 | 26.36 | O |
| ATOM | 3211 | OE2 | GLU | A | 206 | 77.507 | −25.351 | 10.057 | 1.00 | 20.56 | O |
| ATOM | 3212 | C | GLU | A | 206 | 75.433 | −28.726 | 7.450 | 1.00 | 14.77 | C |
| ATOM | 3213 | O | GLU | A | 206 | 76.559 | −29.028 | 7.848 | 1.00 | 14.90 | O |
| ATOM | 3215 | N | ALA | A | 207 | 74.419 | −29.587 | 7.440 | 1.00 | 13.71 | N |
| ATOM | 3216 | CA | ALA | A | 207 | 74.599 | −30.980 | 7.844 | 1.00 | 13.82 | C |
| ATOM | 3218 | CB | ALA | A | 207 | 73.270 | −31.683 | 7.919 | 1.00 | 12.84 | C |
| ATOM | 3222 | C | ALA | A | 207 | 75.526 | −31.721 | 6.881 | 1.00 | 15.05 | C |
| ATOM | 3223 | O | ALA | A | 207 | 76.524 | −32.325 | 7.294 | 1.00 | 13.97 | O |
| ATOM | 3225 | N | TYR | A | 208 | 75.189 | −31.665 | 5.595 | 1.00 | 16.57 | N |
| ATOM | 3226 | CA | TYR | A | 208 | 75.949 | −32.371 | 4.564 | 1.00 | 17.16 | C |
| ATOM | 3228 | CB | TYR | A | 208 | 75.304 | −32.148 | 3.188 | 1.00 | 16.84 | C |
| ATOM | 3231 | CG | TYR | A | 208 | 75.655 | −33.205 | 2.166 | 1.00 | 18.47 | C |
| ATOM | 3232 | CD1 | TYR | A | 208 | 75.244 | −34.519 | 2.332 | 1.00 | 20.52 | C |
| ATOM | 3234 | CE1 | TYR | A | 208 | 75.564 | −35.493 | 1.406 | 1.00 | 22.10 | C |
| ATOM | 3236 | CZ | TYR | A | 208 | 76.295 | −35.158 | 0.292 | 1.00 | 20.93 | C |
| ATOM | 3237 | OH | TYR | A | 208 | 76.614 | −36.127 | −0.625 | 1.00 | 26.11 | O |
| ATOM | 3239 | CE2 | TYR | A | 208 | 76.715 | −33.863 | 0.099 | 1.00 | 21.06 | C |
| ATOM | 3241 | CD2 | TYR | A | 208 | 76.392 | −32.892 | 1.032 | 1.00 | 20.04 | C |
| ATOM | 3243 | C | TYR | A | 208 | 77.408 | −31.911 | 4.564 | 1.00 | 17.97 | C |
| ATOM | 3244 | O | TYR | A | 208 | 78.330 | −32.723 | 4.516 | 1.00 | 17.30 | O |
| ATOM | 3246 | N | ARG | A | 209 | 77.598 | −30.598 | 4.637 | 1.00 | 19.31 | N |
| ATOM | 3247 | CA | ARG | A | 209 | 78.924 | −29.981 | 4.664 | 1.00 | 20.26 | C |
| ATOM | 3249 | CB | ARG | A | 209 | 78.772 | −28.486 | 4.944 | 1.00 | 20.16 | C |
| ATOM | 3252 | CG | ARG | A | 209 | 80.011 | −27.681 | 4.695 | 1.00 | 23.03 | C |
| ATOM | 3255 | CD | ARG | A | 209 | 79.957 | −26.376 | 5.426 | 1.00 | 24.02 | C |

APPENDIX 1-continued

| ATOM | 3258 | NE | ARG | A | 209 | 79.057 | −25.427 | 4.788 | 1.00 | 22.04 | N |
|---|---|---|---|---|---|---|---|---|---|---|---|
| ATOM | 3260 | CZ | ARG | A | 209 | 79.416 | −24.509 | 3.887 | 1.00 | 21.79 | C |
| ATOM | 3261 | NH1 | ARG | A | 209 | 80.671 | −24.395 | 3.461 | 1.00 | 15.73 | N |
| ATOM | 3264 | NH2 | ARG | A | 209 | 78.493 | −23.692 | 3.401 | 1.00 | 27.01 | N |
| ATOM | 3267 | C | ARG | A | 209 | 79.873 | −30.606 | 5.701 | 1.00 | 21.41 | C |
| ATOM | 3268 | O | ARG | A | 209 | 81.064 | −30.753 | 5.437 | 1.00 | 22.06 | O |
| ATOM | 3270 | N | LYS | A | 210 | 79.340 | −30.960 | 6.871 | 1.00 | 22.53 | N |
| ATOM | 3271 | CA | LYS | A | 210 | 80.119 | −31.572 | 7.952 | 1.00 | 23.50 | C |
| ATOM | 3273 | CB | LYS | A | 210 | 79.377 | −31.439 | 9.286 | 1.00 | 23.64 | C |
| ATOM | 3276 | CG | LYS | A | 210 | 79.234 | −30.016 | 9.809 | 1.00 | 24.69 | C |
| ATOM | 3279 | CD | LYS | A | 210 | 78.235 | −29.961 | 10.975 | 1.00 | 27.65 | C |
| ATOM | 3282 | CE | LYS | A | 210 | 77.837 | −28.528 | 11.324 | 1.00 | 29.43 | C |
| ATOM | 3285 | NZ | LYS | A | 210 | 76.521 | −28.453 | 12.020 | 1.00 | 27.05 | N |
| ATOM | 3289 | C | LYS | A | 210 | 80.449 | −33.056 | 7.731 | 1.00 | 25.07 | C |
| ATOM | 3290 | O | LYS | A | 210 | 81.412 | −33.558 | 8.310 | 1.00 | 24.91 | O |
| ATOM | 3292 | N | LYS | A | 211 | 79.646 | −33.761 | 6.932 | 1.00 | 26.97 | N |
| ATOM | 3293 | CA | LYS | A | 211 | 79.879 | −35.187 | 6.671 | 1.00 | 28.62 | C |
| ATOM | 3295 | CB | LYS | A | 211 | 78.755 | −35.804 | 5.829 | 1.00 | 29.48 | C |
| ATOM | 3298 | CG | LYS | A | 211 | 77.364 | −35.837 | 6.474 | 1.00 | 32.60 | C |
| ATOM | 3301 | CD | LYS | A | 211 | 76.459 | −36.843 | 5.737 | 1.00 | 37.94 | C |
| ATOM | 3304 | CE | LYS | A | 211 | 74.963 | −36.588 | 5.964 | 1.00 | 42.00 | C |
| ATOM | 3307 | NZ | LYS | A | 211 | 74.515 | −36.865 | 7.362 | 1.00 | 43.99 | N |
| ATOM | 3311 | C | LYS | A | 211 | 81.198 | −35.368 | 5.934 | 1.00 | 29.70 | C |
| ATOM | 3312 | O | LYS | A | 211 | 81.512 | −34.609 | 5.015 | 1.00 | 30.26 | O |
| ATOM | 3314 | N | GLU | A | 212 | 81.962 | −36.380 | 6.335 | 1.00 | 30.49 | N |
| ATOM | 3315 | CA | GLU | A | 212 | 83.295 | −36.608 | 5.785 | 1.00 | 30.93 | C |
| ATOM | 3317 | CB | GLU | A | 212 | 84.095 | −37.536 | 6.702 | 1.00 | 31.80 | C |
| ATOM | 3320 | CG | GLU | A | 212 | 85.518 | −37.811 | 6.217 | 1.00 | 35.83 | C |
| ATOM | 3323 | CD | GLU | A | 212 | 86.410 | −38.439 | 7.279 | 1.00 | 40.51 | C |
| ATOM | 3324 | OE1 | GLU | A | 212 | 86.043 | −38.408 | 8.476 | 1.00 | 42.71 | O |
| ATOM | 3325 | OE2 | GLU | A | 212 | 87.486 | −38.960 | 6.907 | 1.00 | 40.43 | O |
| ATOM | 3326 | C | GLU | A | 212 | 83.246 | −37.184 | 4.372 | 1.00 | 30.27 | C |
| ATOM | 3327 | O | GLU | A | 212 | 84.097 | −36.868 | 3.540 | 1.00 | 31.06 | O |
| ATOM | 3329 | N | ASP | A | 213 | 82.252 | −38.023 | 4.103 | 1.00 | 28.55 | N |
| ATOM | 3330 | CA | ASP | A | 213 | 82.118 | −38.656 | 2.796 | 1.00 | 27.73 | C |
| ATOM | 3332 | CB | ASP | A | 213 | 81.807 | −40.150 | 2.971 | 1.00 | 28.70 | C |
| ATOM | 3335 | CG | ASP | A | 213 | 80.425 | −40.408 | 3.558 | 1.00 | 31.61 | C |
| ATOM | 3336 | OD1 | ASP | A | 213 | 79.835 | −39.498 | 4.185 | 1.00 | 34.37 | O |
| ATOM | 3337 | OD2 | ASP | A | 213 | 79.933 | −41.542 | 3.389 | 1.00 | 37.46 | O |
| ATOM | 3338 | C | ASP | A | 213 | 81.057 | −37.969 | 1.918 | 1.00 | 25.89 | C |
| ATOM | 3339 | O | ASP | A | 213 | 80.453 | −38.602 | 1.045 | 1.00 | 25.29 | O |
| ATOM | 3341 | N | ALA | A | 214 | 80.840 | −36.675 | 2.151 | 1.00 | 23.65 | N |
| ATOM | 3342 | CA | ALA | A | 214 | 79.869 | −35.899 | 1.381 | 1.00 | 21.07 | C |
| ATOM | 3344 | CB | ALA | A | 214 | 79.659 | −34.538 | 2.015 | 1.00 | 20.78 | C |
| ATOM | 3348 | C | ALA | A | 214 | 80.341 | −35.735 | −0.055 | 1.00 | 18.82 | C |
| ATOM | 3349 | O | ALA | A | 214 | 81.521 | −35.517 | −0.298 | 1.00 | 18.38 | O |
| ATOM | 3351 | N | ASN | A | 215 | 79.422 | −35.848 | −1.007 | 1.00 | 17.54 | N |
| ATOM | 3352 | CA | ASN | A | 215 | 79.768 | −35.635 | −2.408 | 1.00 | 16.55 | C |
| ATOM | 3354 | CB | ASN | A | 215 | 78.649 | −36.133 | −3.326 | 1.00 | 15.72 | C |
| ATOM | 3357 | CG | ASN | A | 215 | 79.015 | −36.034 | −4.790 | 1.00 | 15.82 | C |
| ATOM | 3358 | OD1 | ASN | A | 215 | 79.297 | −34.946 | −5.306 | 1.00 | 12.43 | O |
| ATOM | 3359 | ND2 | ASN | A | 215 | 79.023 | −37.168 | −5.468 | 1.00 | 16.94 | N |
| ATOM | 3362 | C | ASN | A | 215 | 80.080 | −34.150 | −2.639 | 1.00 | 15.79 | C |
| ATOM | 3363 | O | ASN | A | 215 | 79.210 | −33.292 | −2.499 | 1.00 | 14.49 | O |
| ATOM | 3365 | N | GLN | A | 216 | 81.332 | −33.857 | −2.978 | 1.00 | 16.27 | N |
| ATOM | 3366 | CA | GLN | A | 216 | 81.806 | −32.468 | −3.054 | 1.00 | 16.53 | C |
| ATOM | 3368 | CB | GLN | A | 216 | 83.336 | −32.423 | −3.113 | 1.00 | 16.76 | C |
| ATOM | 3371 | CG | GLN | A | 216 | 84.028 | −33.071 | −1.905 | 1.00 | 20.08 | C |
| ATOM | 3374 | CD | GLN | A | 216 | 83.592 | −32.471 | −0.569 | 1.00 | 23.47 | C |
| ATOM | 3375 | OE1 | GLN | A | 216 | 84.024 | −31.378 | −0.189 | 1.00 | 24.87 | O |
| ATOM | 3376 | NE2 | GLN | A | 216 | 82.739 | −33.194 | 0.153 | 1.00 | 23.11 | N |
| ATOM | 3379 | C | GLN | A | 216 | 81.205 | −31.695 | −4.227 | 1.00 | 15.89 | C |
| ATOM | 3380 | O | GLN | A | 216 | 81.028 | −30.478 | −4.140 | 1.00 | 16.63 | O |
| ATOM | 3382 | N | VAL | A | 217 | 80.881 | −32.401 | −5.309 | 1.00 | 15.02 | N |
| ATOM | 3383 | CA | VAL | A | 217 | 80.212 | −31.790 | −6.454 | 1.00 | 13.80 | C |
| ATOM | 3385 | CB | VAL | A | 217 | 80.154 | −32.742 | −7.662 | 1.00 | 14.59 | C |
| ATOM | 3387 | CG1 | VAL | A | 217 | 79.177 | −32.209 | −8.726 | 1.00 | 13.00 | C |
| ATOM | 3391 | CG2 | VAL | A | 217 | 81.555 | −32.954 | −8.240 | 1.00 | 9.07 | C |
| ATOM | 3395 | C | VAL | A | 217 | 78.799 | −31.397 | −6.084 | 1.00 | 13.21 | C |
| ATOM | 3396 | O | VAL | A | 217 | 78.361 | −30.287 | −6.364 | 1.00 | 13.41 | O |
| ATOM | 3398 | N | LEU | A | 218 | 78.089 | −32.323 | −5.453 | 1.00 | 13.47 | N |
| ATOM | 3399 | CA | LEU | A | 218 | 76.721 | −32.080 | −5.008 | 1.00 | 13.08 | C |
| ATOM | 3401 | CB | LEU | A | 218 | 76.120 | −33.368 | −4.434 | 1.00 | 12.26 | C |
| ATOM | 3404 | CG | LEU | A | 218 | 74.640 | −33.367 | −4.039 | 1.00 | 12.25 | C |
| ATOM | 3406 | CD1 | LEU | A | 218 | 73.762 | −32.784 | −5.134 | 1.00 | 6.53 | C |
| ATOM | 3410 | CD2 | LEU | A | 218 | 74.203 | −34.781 | −3.689 | 1.00 | 5.69 | C |
| ATOM | 3414 | C | LEU | A | 218 | 76.682 | −30.946 | −3.972 | 1.00 | 13.78 | C |
| ATOM | 3415 | O | LEU | A | 218 | 75.867 | −30.021 | −4.076 | 1.00 | 12.92 | O |
| ATOM | 3417 | N | LEU | A | 219 | 77.583 | −31.014 | −2.991 | 1.00 | 13.86 | N |
| ATOM | 3418 | CA | LEU | A | 219 | 77.710 | −29.965 | −1.981 | 1.00 | 13.37 | C |

APPENDIX 1-continued

| | | | | | | | | | | |
|---|---|---|---|---|---|---|---|---|---|---|
| ATOM | 3420 | CB | LEU | A | 219 | 78.860 | −30.279 | −1.015 | 1.00 | 13.97 | C |
| ATOM | 3423 | CG | LEU | A | 219 | 79.174 | −29.259 | 0.094 | 1.00 | 13.38 | C |
| ATOM | 3425 | CD1 | LEU | A | 219 | 77.910 | −28.906 | 0.910 | 1.00 | 7.90 | C |
| ATOM | 3429 | CD2 | LEU | A | 219 | 80.281 | −29.796 | 0.996 | 1.00 | 8.87 | C |
| ATOM | 3433 | C | LEU | A | 219 | 77.946 | −28.610 | −2.629 | 1.00 | 13.03 | C |
| ATOM | 3434 | O | LEU | A | 219 | 77.262 | −27.640 | −2.307 | 1.00 | 12.64 | O |
| ATOM | 3436 | N | GLU | A | 220 | 78.905 | −28.548 | −3.549 | 1.00 | 13.28 | N |
| ATOM | 3437 | CA | GLU | A | 220 | 79.276 | −27.269 | −4.171 | 1.00 | 14.02 | C |
| ATOM | 3439 | CB | GLU | A | 220 | 80.548 | −27.408 | −5.022 | 1.00 | 13.85 | C |
| ATOM | 3442 | CG | GLU | A | 220 | 81.027 | −26.078 | −5.618 | 1.00 | 14.99 | C |
| ATOM | 3445 | CD | GLU | A | 220 | 82.386 | −26.155 | −6.305 | 1.00 | 13.51 | C |
| ATOM | 3446 | OE1 | GLU | A | 220 | 82.967 | −27.262 | −6.413 | 1.00 | 10.78 | O |
| ATOM | 3447 | OE2 | GLU | A | 220 | 82.875 | −25.084 | −6.731 | 1.00 | 15.71 | O |
| ATOM | 3448 | C | GLU | A | 220 | 78.130 | −26.668 | −4.995 | 1.00 | 14.29 | C |
| ATOM | 3449 | O | GLU | A | 220 | 77.928 | −25.455 | −4.982 | 1.00 | 15.62 | O |
| ATOM | 3451 | N | LEU | A | 221 | 77.380 | −27.513 | −5.696 | 1.00 | 14.42 | N |
| ATOM | 3452 | CA | LEU | A | 221 | 76.221 | −27.059 | −6.471 | 1.00 | 14.42 | C |
| ATOM | 3454 | CB | LEU | A | 221 | 75.672 | −28.214 | −7.315 | 1.00 | 14.48 | C |
| ATOM | 3457 | CG | LEU | A | 221 | 74.489 | −27.918 | −8.241 | 1.00 | 13.15 | C |
| ATOM | 3459 | CD1 | LEU | A | 221 | 74.895 | −27.012 | −9.386 | 1.00 | 3.14 | C |
| ATOM | 3463 | CD2 | LEU | A | 221 | 73.919 | −29.218 | −8.761 | 1.00 | 11.66 | C |
| ATOM | 3467 | C | LEU | A | 221 | 75.122 | −26.503 | −5.557 | 1.00 | 14.55 | C |
| ATOM | 3468 | O | LEU | A | 221 | 74.581 | −25.419 | −5.804 | 1.00 | 14.29 | O |
| ATOM | 3470 | N | ALA | A | 222 | 74.805 | −27.246 | −4.499 | 1.00 | 14.74 | N |
| ATOM | 3471 | CA | ALA | A | 222 | 73.802 | −26.816 | −3.520 | 1.00 | 14.77 | C |
| ATOM | 3473 | CB | ALA | A | 222 | 73.661 | −27.845 | −2.404 | 1.00 | 13.62 | C |
| ATOM | 3477 | C | ALA | A | 222 | 74.122 | −25.439 | −2.937 | 1.00 | 15.47 | C |
| ATOM | 3478 | O | ALA | A | 222 | 73.217 | −24.628 | −2.736 | 1.00 | 17.17 | O |
| ATOM | 3480 | N | ILE | A | 223 | 75.401 | −25.171 | −2.680 | 1.00 | 15.03 | N |
| ATOM | 3481 | CA | ILE | A | 223 | 75.816 | −23.883 | −2.131 | 1.00 | 14.70 | C |
| ATOM | 3483 | CB | ILE | A | 223 | 77.262 | −23.931 | −1.578 | 1.00 | 14.73 | C |
| ATOM | 3485 | CG1 | ILE | A | 223 | 77.343 | −24.885 | −0.377 | 1.00 | 14.63 | C |
| ATOM | 3488 | CD1 | ILE | A | 223 | 78.751 | −25.300 | 0.007 | 1.00 | 9.76 | C |
| ATOM | 3492 | CG2 | ILE | A | 223 | 77.720 | −22.548 | −1.150 | 1.00 | 12.34 | C |
| ATOM | 3496 | C | ILE | A | 223 | 75.677 | −22.787 | −3.191 | 1.00 | 15.33 | C |
| ATOM | 3497 | O | ILE | A | 223 | 75.057 | −21.743 | −2.936 | 1.00 | 15.78 | O |
| ATOM | 3499 | N | LEU | A | 224 | 76.249 | −23.026 | −4.372 | 1.00 | 15.28 | N |
| ATOM | 3500 | CA | LEU | A | 224 | 76.109 | −22.101 | −5.506 | 1.00 | 15.28 | C |
| ATOM | 3502 | CB | LEU | A | 224 | 76.693 | −22.695 | −6.792 | 1.00 | 15.38 | C |
| ATOM | 3505 | CG | LEU | A | 224 | 78.067 | −22.187 | −7.225 | 1.00 | 18.98 | C |
| ATOM | 3507 | CD1 | LEU | A | 224 | 79.101 | −22.377 | −6.128 | 1.00 | 20.71 | C |
| ATOM | 3511 | CD2 | LEU | A | 224 | 78.509 | −22.885 | −8.509 | 1.00 | 20.84 | C |
| ATOM | 3515 | C | LEU | A | 224 | 74.650 | −21.748 | −5.747 | 1.00 | 15.02 | C |
| ATOM | 3516 | O | LEU | A | 224 | 74.298 | −20.569 | −5.825 | 1.00 | 15.33 | O |
| ATOM | 3518 | N | ASP | A | 225 | 73.807 | −22.776 | −5.838 | 1.00 | 14.27 | N |
| ATOM | 3519 | CA | ASP | A | 225 | 72.402 | −22.593 | −6.200 | 1.00 | 13.87 | C |
| ATOM | 3521 | CB | ASP | A | 225 | 71.752 | −23.931 | −6.558 | 1.00 | 13.21 | C |
| ATOM | 3524 | CG | ASP | A | 225 | 70.416 | −23.759 | −7.228 | 1.00 | 11.77 | C |
| ATOM | 3525 | OD1 | ASP | A | 225 | 70.381 | −23.575 | −8.460 | 1.00 | 15.81 | O |
| ATOM | 3526 | OD2 | ASP | A | 225 | 69.386 | −23.818 | −6.529 | 1.00 | 14.91 | O |
| ATOM | 3527 | C | ASP | A | 225 | 71.591 | −21.893 | −5.111 | 1.00 | 13.91 | C |
| ATOM | 3528 | O | ASP | A | 225 | 70.694 | −21.119 | −5.422 | 1.00 | 14.90 | O |
| ATOM | 3530 | N | TYR | A | 226 | 71.905 | −22.155 | −3.845 | 1.00 | 13.95 | N |
| ATOM | 3531 | CA | TYR | A | 226 | 71.197 | −21.510 | −2.742 | 1.00 | 15.40 | C |
| ATOM | 3533 | CB | TYR | A | 226 | 71.577 | −22.130 | −1.392 | 1.00 | 16.25 | C |
| ATOM | 3536 | CG | TYR | A | 226 | 70.802 | −21.542 | −0.228 | 1.00 | 16.29 | C |
| ATOM | 3537 | CD1 | TYR | A | 226 | 71.203 | −20.353 | 0.379 | 1.00 | 17.70 | C |
| ATOM | 3539 | CE1 | TYR | A | 226 | 70.487 | −19.803 | 1.439 | 1.00 | 16.58 | C |
| ATOM | 3541 | CZ | TYR | A | 226 | 69.361 | −20.447 | 1.901 | 1.00 | 18.63 | C |
| ATOM | 3542 | OH | TYR | A | 226 | 68.638 | −19.921 | 2.942 | 1.00 | 16.92 | O |
| ATOM | 3544 | CE2 | TYR | A | 226 | 68.946 | −21.628 | 1.316 | 1.00 | 19.18 | C |
| ATOM | 3546 | CD2 | TYR | A | 226 | 69.665 | −22.165 | 0.255 | 1.00 | 18.06 | C |
| ATOM | 3548 | C | TYR | A | 226 | 71.482 | −20.014 | −2.712 | 1.00 | 16.97 | C |
| ATOM | 3549 | O | TYR | A | 226 | 70.561 | −19.205 | −2.557 | 1.00 | 17.79 | O |
| ATOM | 3551 | N | ASN | A | 227 | 72.758 | −19.655 | −2.851 | 1.00 | 17.52 | N |
| ATOM | 3552 | CA | ASN | A | 227 | 73.159 | −18.252 | −2.845 | 1.00 | 17.45 | C |
| ATOM | 3554 | CB | ASN | A | 227 | 74.679 | −18.125 | −2.710 | 1.00 | 17.25 | C |
| ATOM | 3557 | CG | ASN | A | 227 | 75.161 | −18.463 | −1.318 | 1.00 | 14.98 | C |
| ATOM | 3558 | OD1 | ASN | A | 227 | 74.378 | −18.487 | −0.366 | 1.00 | 16.17 | O |
| ATOM | 3559 | ND2 | ASN | A | 227 | 76.446 | −18.733 | −1.188 | 1.00 | 11.54 | N |
| ATOM | 3562 | C | ASN | A | 227 | 72.674 | −17.492 | −4.064 | 1.00 | 17.98 | C |
| ATOM | 3563 | O | ASN | A | 227 | 72.431 | −16.289 | −3.985 | 1.00 | 18.37 | O |
| ATOM | 3565 | N | MET | A | 228 | 72.528 | −18.190 | −5.186 | 1.00 | 19.19 | N |
| ATOM | 3566 | CA | MET | A | 228 | 72.028 | −17.568 | −6.405 | 1.00 | 20.00 | C |
| ATOM | 3568 | CB | MET | A | 228 | 72.115 | −18.531 | −7.583 | 1.00 | 20.90 | C |
| ATOM | 3571 | CG | MET | A | 228 | 71.478 | −17.996 | −8.861 | 1.00 | 24.50 | C |
| ATOM | 3574 | SD | MET | A | 228 | 71.047 | −19.298 | −10.019 | 1.00 | 32.87 | S |
| ATOM | 3575 | CE | MET | A | 228 | 69.767 | −20.178 | −9.117 | 1.00 | 20.31 | C |
| ATOM | 3579 | C | MET | A | 228 | 70.588 | −17.149 | −6.196 | 1.00 | 19.82 | C |
| ATOM | 3580 | O | MET | A | 228 | 70.220 | −16.005 | −6.464 | 1.00 | 20.14 | O |

APPENDIX 1-continued

| ATOM | 3582 | N | ILE | A | 229 | 69.781 | −18.089 | −5.718 | 1.00 | 19.86 | N |
|---|---|---|---|---|---|---|---|---|---|---|---|
| ATOM | 3583 | CA | ILE | A | 229 | 68.369 | −17.837 | −5.445 | 1.00 | 19.70 | C |
| ATOM | 3585 | CB | ILE | A | 229 | 67.642 | −19.129 | −4.991 | 1.00 | 19.09 | C |
| ATOM | 3587 | CG1 | ILE | A | 229 | 67.547 | −20.114 | −6.149 | 1.00 | 17.67 | C |
| ATOM | 3590 | CD1 | ILE | A | 229 | 67.026 | −21.465 | −5.740 | 1.00 | 18.73 | C |
| ATOM | 3594 | CG2 | ILE | A | 229 | 66.247 | −18.822 | −4.481 | 1.00 | 15.65 | C |
| ATOM | 3598 | C | ILE | A | 229 | 68.218 | −16.745 | −4.380 | 1.00 | 21.11 | C |
| ATOM | 3599 | O | ILE | A | 229 | 67.354 | −15.872 | −4.493 | 1.00 | 22.14 | O |
| ATOM | 3601 | N | GLN | A | 230 | 69.066 | −16.788 | −3.357 | 1.00 | 21.50 | N |
| ATOM | 3602 | CA | GLN | A | 230 | 69.041 | −15.768 | −2.321 | 1.00 | 22.18 | C |
| ATOM | 3604 | CB | GLN | A | 230 | 70.138 | −16.003 | −1.288 | 1.00 | 22.21 | C |
| ATOM | 3607 | CG | GLN | A | 230 | 69.965 | −15.131 | −0.066 | 1.00 | 24.09 | C |
| ATOM | 3610 | CD | GLN | A | 230 | 70.892 | −15.507 | 1.053 | 1.00 | 25.30 | C |
| ATOM | 3611 | OE1 | GLN | A | 230 | 72.040 | −15.077 | 1.081 | 1.00 | 26.06 | O |
| ATOM | 3612 | NE2 | GLN | A | 230 | 70.393 | −16.298 | 1.999 | 1.00 | 23.59 | N |
| ATOM | 3615 | C | GLN | A | 230 | 69.208 | −14.369 | −2.900 | 1.00 | 22.26 | C |
| ATOM | 3616 | O | GLN | A | 230 | 68.591 | −13.421 | −2.422 | 1.00 | 23.58 | O |
| ATOM | 3618 | N | SER | A | 231 | 70.052 | −14.232 | −3.915 | 1.00 | 21.90 | N |
| ATOM | 3619 | CA | SER | A | 231 | 70.283 | −12.918 | −4.514 | 1.00 | 21.86 | C |
| ATOM | 3621 | CB | SER | A | 231 | 71.611 | −12.883 | −5.287 | 1.00 | 21.12 | C |
| ATOM | 3624 | OG | SER | A | 231 | 71.491 | −13.518 | −6.537 | 1.00 | 24.84 | O |
| ATOM | 3626 | C | SER | A | 231 | 69.097 | −12.496 | −5.392 | 1.00 | 20.18 | C |
| ATOM | 3627 | O | SER | A | 231 | 68.885 | −11.306 | −5.629 | 1.00 | 20.45 | O |
| ATOM | 3629 | N | VAL | A | 232 | 68.326 | −13.470 | −5.869 | 1.00 | 19.16 | N |
| ATOM | 3630 | CA | VAL | A | 232 | 67.046 | −13.171 | −6.516 | 1.00 | 18.13 | C |
| ATOM | 3632 | CB | VAL | A | 232 | 66.445 | −14.397 | −7.236 | 1.00 | 18.01 | C |
| ATOM | 3634 | CG1 | VAL | A | 232 | 65.037 | −14.087 | −7.753 | 1.00 | 15.57 | C |
| ATOM | 3638 | CG2 | VAL | A | 232 | 67.360 | −14.834 | −8.373 | 1.00 | 11.93 | C |
| ATOM | 3642 | C | VAL | A | 232 | 66.061 | −12.632 | −5.479 | 1.00 | 18.11 | C |
| ATOM | 3643 | O | VAL | A | 232 | 65.354 | −11.665 | −5.747 | 1.00 | 17.35 | O |
| ATOM | 3645 | N | TYR | A | 233 | 66.032 | −13.244 | −4.294 | 1.00 | 18.30 | N |
| ATOM | 3646 | CA | TYR | A | 233 | 65.204 | −12.730 | −3.202 | 1.00 | 18.66 | C |
| ATOM | 3648 | CB | TYR | A | 233 | 65.255 | −13.628 | −1.965 | 1.00 | 18.13 | C |
| ATOM | 3651 | CG | TYR | A | 233 | 64.779 | −15.052 | −2.158 | 1.00 | 16.87 | C |
| ATOM | 3652 | CD1 | TYR | A | 233 | 63.932 | −15.407 | −3.210 | 1.00 | 18.84 | C |
| ATOM | 3654 | CE1 | TYR | A | 233 | 63.505 | −16.722 | −3.377 | 1.00 | 18.16 | C |
| ATOM | 3656 | CZ | TYR | A | 233 | 63.909 | −17.679 | −2.475 | 1.00 | 16.04 | C |
| ATOM | 3657 | OH | TYR | A | 233 | 63.491 | −18.971 | −2.632 | 1.00 | 17.36 | O |
| ATOM | 3659 | CE2 | TYR | A | 233 | 64.742 | −17.349 | −1.419 | 1.00 | 15.74 | C |
| ATOM | 3661 | CD2 | TYR | A | 233 | 65.162 | −16.048 | −1.262 | 1.00 | 14.72 | C |
| ATOM | 3663 | C | TYR | A | 233 | 65.642 | −11.326 | −2.811 | 1.00 | 19.90 | C |
| ATOM | 3664 | O | TYR | A | 233 | 64.812 | −10.444 | −2.593 | 1.00 | 20.31 | O |
| ATOM | 3666 | N | GLN | A | 234 | 66.948 | −11.117 | −2.724 | 1.00 | 21.64 | N |
| ATOM | 3667 | CA | GLN | A | 234 | 67.465 | −9.798 | −2.405 | 1.00 | 22.71 | C |
| ATOM | 3669 | CB | GLN | A | 234 | 68.988 | −9.832 | −2.254 | 1.00 | 22.62 | C |
| ATOM | 3672 | CG | GLN | A | 234 | 69.412 | −10.450 | −0.925 | 1.00 | 25.66 | C |
| ATOM | 3675 | CD | GLN | A | 234 | 70.886 | −10.829 | −0.847 | 1.00 | 29.48 | C |
| ATOM | 3676 | OE1 | GLN | A | 234 | 71.711 | −10.388 | −1.654 | 1.00 | 31.88 | O |
| ATOM | 3677 | NE2 | GLN | A | 234 | 71.222 | −11.653 | 0.144 | 1.00 | 26.29 | N |
| ATOM | 3680 | C | GLN | A | 234 | 67.003 | −8.764 | −3.434 | 1.00 | 23.28 | C |
| ATOM | 3681 | O | GLN | A | 234 | 66.599 | −7.669 | −3.054 | 1.00 | 23.39 | O |
| ATOM | 3683 | N | ARG | A | 235 | 67.017 | −9.116 | −4.720 | 1.00 | 24.29 | N |
| ATOM | 3684 | CA | ARG | A | 235 | 66.543 | −8.188 | −5.757 | 1.00 | 25.70 | C |
| ATOM | 3686 | CB | ARG | A | 235 | 66.903 | −8.673 | −7.172 | 1.00 | 26.02 | C |
| ATOM | 3689 | CG | ARG | A | 235 | 66.453 | −7.706 | −8.277 | 1.00 | 31.24 | C |
| ATOM | 3692 | CD | ARG | A | 235 | 67.168 | −7.912 | −9.620 | 1.00 | 37.34 | C |
| ATOM | 3695 | NE | ARG | A | 235 | 67.158 | −9.314 | −10.049 | 1.00 | 43.96 | N |
| ATOM | 3697 | CZ | ARG | A | 235 | 68.235 | −10.097 | −10.187 | 1.00 | 48.83 | C |
| ATOM | 3698 | NH1 | ARG | A | 235 | 69.468 | −9.644 | −9.955 | 1.00 | 49.02 | N |
| ATOM | 3701 | NH2 | ARG | A | 235 | 68.076 | −11.361 | −10.575 | 1.00 | 49.59 | N |
| ATOM | 3704 | C | ARG | A | 235 | 65.035 | −7.948 | −5.628 | 1.00 | 25.62 | C |
| ATOM | 3705 | O | ARG | A | 235 | 64.566 | −6.817 | −5.728 | 1.00 | 26.36 | O |
| ATOM | 3707 | N | ASP | A | 236 | 64.283 | −9.013 | −5.387 | 1.00 | 25.71 | N |
| ATOM | 3708 | CA | ASP | A | 236 | 62.840 | −8.906 | −5.197 | 1.00 | 26.23 | C |
| ATOM | 3710 | CB | ASP | A | 236 | 62.229 | −10.291 | −4.939 | 1.00 | 25.67 | C |
| ATOM | 3713 | CG | ASP | A | 236 | 62.331 | −11.222 | −6.141 | 1.00 | 26.60 | C |
| ATOM | 3714 | OD1 | ASP | A | 236 | 62.449 | −10.736 | −7.293 | 1.00 | 24.55 | O |
| ATOM | 3715 | OD2 | ASP | A | 236 | 62.289 | −12.451 | −5.925 | 1.00 | 24.17 | O |
| ATOM | 3716 | C | ASP | A | 236 | 62.510 | −7.982 | −4.023 | 1.00 | 26.70 | C |
| ATOM | 3717 | O | ASP | A | 236 | 61.727 | −7.045 | −4.159 | 1.00 | 26.54 | O |
| ATOM | 3719 | N | LEU | A | 237 | 63.120 | −8.259 | −2.875 | 1.00 | 27.19 | N |
| ATOM | 3720 | CA | LEU | A | 237 | 62.841 | −7.526 | −1.649 | 1.00 | 27.53 | C |
| ATOM | 3722 | CB | LEU | A | 237 | 63.583 | −8.172 | −0.475 | 1.00 | 26.81 | C |
| ATOM | 3725 | CG | LEU | A | 237 | 63.382 | −7.580 | 0.922 | 1.00 | 25.84 | C |
| ATOM | 3727 | CD1 | LEU | A | 237 | 61.918 | −7.449 | 1.268 | 1.00 | 23.19 | C |
| ATOM | 3731 | CD2 | LEU | A | 237 | 64.103 | −8.424 | 1.960 | 1.00 | 24.06 | C |
| ATOM | 3735 | C | LEU | A | 237 | 63.207 | −6.048 | −1.781 | 1.00 | 29.70 | C |
| ATOM | 3736 | O | LEU | A | 237 | 62.472 | −5.188 | −1.291 | 1.00 | 29.95 | O |
| ATOM | 3738 | N | ARG | A | 238 | 64.328 | −5.754 | −2.445 | 1.00 | 31.65 | N |
| ATOM | 3739 | CA | ARG | A | 238 | 64.733 | −4.363 | −2.704 | 1.00 | 33.35 | C |

APPENDIX 1-continued

| ATOM | 3741 | CB | ARG | A | 238 | 66.086 | −4.276 | −3.436 | 1.00 | 33.92 | C |
|---|---|---|---|---|---|---|---|---|---|---|---|
| ATOM | 3744 | CG | ARG | A | 238 | 67.321 | −4.340 | −2.522 | 1.00 | 37.39 | C |
| ATOM | 3747 | CD | ARG | A | 238 | 68.577 | −3.791 | −3.213 | 1.00 | 40.93 | C |
| ATOM | 3750 | NE | ARG | A | 238 | 68.871 | −4.468 | −4.484 | 1.00 | 44.17 | N |
| ATOM | 3752 | CZ | ARG | A | 238 | 69.576 | −5.596 | −4.624 | 1.00 | 42.76 | C |
| ATOM | 3753 | NH1 | ARG | A | 238 | 70.095 | −6.229 | −3.572 | 1.00 | 40.79 | N |
| ATOM | 3756 | NH2 | ARG | A | 238 | 69.764 | −6.100 | −5.841 | 1.00 | 40.46 | N |
| ATOM | 3759 | C | ARG | A | 238 | 63.676 | −3.613 | −3.509 | 1.00 | 33.94 | C |
| ATOM | 3760 | O | ARG | A | 238 | 63.364 | −2.463 | −3.197 | 1.00 | 35.96 | O |
| ATOM | 3762 | N | GLU | A | 239 | 63.139 | −4.260 | −4.539 | 1.00 | 33.49 | N |
| ATOM | 3763 | CA | GLU | A | 239 | 62.105 | −3.661 | −5.381 | 1.00 | 34.02 | C |
| ATOM | 3765 | CB | GLU | A | 239 | 61.872 | −4.534 | −6.617 | 1.00 | 35.73 | C |
| ATOM | 3768 | CG | GLU | A | 239 | 60.916 | −3.949 | −7.657 | 1.00 | 43.69 | C |
| ATOM | 3771 | CD | GLU | A | 239 | 60.865 | −4.780 | −8.944 | 1.00 | 53.52 | C |
| ATOM | 3772 | OE1 | GLU | A | 239 | 61.938 | −5.028 | −9.542 | 1.00 | 56.61 | O |
| ATOM | 3773 | OE2 | GLU | A | 239 | 59.750 | −5.176 | −9.358 | 1.00 | 57.59 | O |
| ATOM | 3774 | C | GLU | A | 239 | 60.802 | −3.494 | −4.601 | 1.00 | 32.16 | C |
| ATOM | 3775 | O | GLU | A | 239 | 60.096 | −2.499 | −4.754 | 1.00 | 32.78 | O |
| ATOM | 3777 | N | THR | A | 240 | 60.495 | −4.475 | −3.764 | 1.00 | 29.87 | N |
| ATOM | 3778 | CA | THR | A | 240 | 59.300 | −4.445 | −2.935 | 1.00 | 28.58 | C |
| ATOM | 3780 | CB | THR | A | 240 | 59.005 | −5.846 | −2.359 | 1.00 | 27.73 | C |
| ATOM | 3782 | OG1 | THR | A | 240 | 58.792 | −6.757 | −3.443 | 1.00 | 27.30 | O |
| ATOM | 3784 | CG2 | THR | A | 240 | 57.781 | −5.834 | −1.476 | 1.00 | 24.26 | C |
| ATOM | 3788 | C | THR | A | 240 | 59.448 | −3.414 | −1.816 | 1.00 | 28.92 | C |
| ATOM | 3789 | O | THR | A | 240 | 58.492 | −2.712 | −1.484 | 1.00 | 28.92 | O |
| ATOM | 3791 | N | SER | A | 241 | 60.645 | −3.312 | −1.246 | 1.00 | 29.02 | N |
| ATOM | 3792 | CA | SER | A | 241 | 60.936 | −2.251 | −0.280 | 1.00 | 29.30 | C |
| ATOM | 3794 | CB | SER | A | 241 | 62.387 | −2.313 | 0.195 | 1.00 | 29.37 | C |
| ATOM | 3797 | OG | SER | A | 241 | 62.560 | −3.360 | 1.130 | 1.00 | 31.18 | O |
| ATOM | 3799 | C | SER | A | 241 | 60.642 | −0.878 | −0.865 | 1.00 | 29.06 | C |
| ATOM | 3800 | O | SER | A | 241 | 59.961 | −0.083 | −0.231 | 1.00 | 28.96 | O |
| ATOM | 3802 | N | ARG | A | 242 | 61.139 | −0.611 | −2.071 | 1.00 | 30.15 | N |
| ATOM | 3803 | CA | ARG | A | 242 | 60.921 | 0.690 | −2.729 | 1.00 | 31.62 | C |
| ATOM | 3805 | CB | ARG | A | 242 | 61.502 | 0.721 | −4.153 | 1.00 | 32.75 | C |
| ATOM | 3808 | CG | ARG | A | 242 | 62.980 | 1.119 | −4.241 | 1.00 | 38.72 | C |
| ATOM | 3811 | CD | ARG | A | 242 | 63.328 | 1.686 | −5.627 | 1.00 | 46.19 | C |
| ATOM | 3814 | NE | ARG | A | 242 | 62.847 | 0.824 | −6.716 | 1.00 | 52.17 | N |
| ATOM | 3816 | CZ | ARG | A | 242 | 63.543 | −0.155 | −7.301 | 1.00 | 55.43 | C |
| ATOM | 3817 | NH1 | ARG | A | 242 | 62.984 | −0.869 | −8.276 | 1.00 | 55.55 | N |
| ATOM | 3820 | NH2 | ARG | A | 242 | 64.790 | −0.435 | −6.927 | 1.00 | 57.13 | N |
| ATOM | 3823 | C | ARG | A | 242 | 59.442 | 1.038 | −2.786 | 1.00 | 30.15 | C |
| ATOM | 3824 | O | ARG | A | 242 | 59.043 | 2.150 | −2.434 | 1.00 | 30.56 | O |
| ATOM | 3826 | N | TRP | A | 243 | 58.634 | 0.084 | −3.231 | 1.00 | 28.89 | N |
| ATOM | 3827 | CA | TRP | A | 243 | 57.188 | 0.267 | −3.271 | 1.00 | 28.06 | C |
| ATOM | 3829 | CB | TRP | A | 243 | 56.506 | −0.978 | −3.861 | 1.00 | 27.63 | C |
| ATOM | 3832 | CG | TRP | A | 243 | 55.039 | −1.063 | −3.572 | 1.00 | 26.01 | C |
| ATOM | 3833 | CD1 | TRP | A | 243 | 54.030 | −0.482 | −4.281 | 1.00 | 28.68 | C |
| ATOM | 3835 | NE1 | TRP | A | 243 | 52.816 | −0.782 | −3.703 | 1.00 | 28.99 | N |
| ATOM | 3837 | CE2 | TRP | A | 243 | 53.030 | −1.564 | −2.600 | 1.00 | 20.27 | C |
| ATOM | 3838 | CD2 | TRP | A | 243 | 54.418 | −1.764 | −2.485 | 1.00 | 19.64 | C |
| ATOM | 3839 | CE3 | TRP | A | 243 | 54.906 | −2.529 | −1.418 | 1.00 | 21.12 | C |
| ATOM | 3841 | CZ3 | TRP | A | 243 | 54.005 | −3.069 | −0.521 | 1.00 | 19.24 | C |
| ATOM | 3843 | CH2 | TRP | A | 243 | 52.626 | −2.851 | −0.663 | 1.00 | 23.00 | C |
| ATOM | 3845 | CZ2 | TRP | A | 243 | 52.123 | −2.103 | −1.698 | 1.00 | 21.52 | C |
| ATOM | 3847 | C | TRP | A | 243 | 56.660 | 0.579 | −1.865 | 1.00 | 27.62 | C |
| ATOM | 3848 | O | TRP | A | 243 | 55.895 | 1.520 | −1.676 | 1.00 | 27.74 | O |
| ATOM | 3850 | N | TRP | A | 244 | 57.100 | −0.204 | −0.887 | 1.00 | 26.79 | N |
| ATOM | 3851 | CA | TRP | A | 244 | 56.627 | −0.082 | 0.490 | 1.00 | 26.29 | C |
| ATOM | 3853 | CB | TRP | A | 244 | 57.172 | −1.243 | 1.321 | 1.00 | 25.46 | C |
| ATOM | 3856 | CG | TRP | A | 244 | 56.644 | −1.319 | 2.705 | 1.00 | 23.15 | C |
| ATOM | 3857 | CD1 | TRP | A | 244 | 57.369 | −1.283 | 3.861 | 1.00 | 23.24 | C |
| ATOM | 3859 | NE1 | TRP | A | 244 | 56.535 | −1.384 | 4.946 | 1.00 | 23.78 | N |
| ATOM | 3861 | CE2 | TRP | A | 244 | 55.243 | −1.490 | 4.503 | 1.00 | 23.38 | C |
| ATOM | 3862 | CD2 | TRP | A | 244 | 55.272 | −1.448 | 3.096 | 1.00 | 24.53 | C |
| ATOM | 3863 | CE3 | TRP | A | 244 | 54.063 | −1.529 | 2.392 | 1.00 | 24.59 | C |
| ATOM | 3865 | CZ3 | TRP | A | 244 | 52.887 | −1.651 | 3.101 | 1.00 | 20.46 | C |
| ATOM | 3867 | CH2 | TRP | A | 244 | 52.890 | −1.697 | 4.500 | 1.00 | 22.43 | C |
| ATOM | 3869 | CZ2 | TRP | A | 244 | 54.053 | −1.616 | 5.219 | 1.00 | 24.18 | C |
| ATOM | 3871 | C | TRP | A | 244 | 57.002 | 1.249 | 1.143 | 1.00 | 26.77 | C |
| ATOM | 3872 | O | TRP | A | 244 | 56.183 | 1.852 | 1.837 | 1.00 | 25.73 | O |
| ATOM | 3874 | N | ARG | A | 245 | 58.231 | 1.703 | 0.933 | 1.00 | 28.23 | N |
| ATOM | 3875 | CA | ARG | A | 245 | 58.668 | 2.972 | 1.519 | 1.00 | 30.83 | C |
| ATOM | 3877 | CB | ARG | A | 245 | 60.194 | 3.145 | 1.433 | 1.00 | 31.39 | C |
| ATOM | 3880 | CG | ARG | A | 245 | 60.911 | 2.560 | 2.660 | 1.00 | 37.50 | C |
| ATOM | 3883 | CD | ARG | A | 245 | 62.411 | 2.813 | 2.666 | 1.00 | 44.44 | C |
| ATOM | 3886 | NE | ARG | A | 245 | 63.130 | 1.800 | 1.893 | 1.00 | 49.18 | N |
| ATOM | 3888 | CZ | ARG | A | 245 | 63.510 | 1.926 | 0.621 | 1.00 | 53.23 | C |
| ATOM | 3889 | NH1 | ARG | A | 245 | 64.149 | 0.922 | 0.032 | 1.00 | 54.44 | N |
| ATOM | 3892 | NH2 | ARG | A | 245 | 63.260 | 3.036 | −0.074 | 1.00 | 54.41 | N |
| ATOM | 3895 | C | ARG | A | 245 | 57.927 | 4.155 | 0.902 | 1.00 | 31.00 | C |

APPENDIX 1-continued

| | | | | | | | | | | | |
|---|---|---|---|---|---|---|---|---|---|---|---|
| ATOM | 3896 | O | ARG | A | 245 | 57.562 | 5.096 | 1.603 | 1.00 | 30.87 | O |
| ATOM | 3898 | N | ARG | A | 246 | 57.672 | 4.084 | −0.399 | 1.00 | 31.87 | N |
| ATOM | 3899 | CA | ARG | A | 246 | 56.943 | 5.140 | −1.091 | 1.00 | 32.47 | C |
| ATOM | 3901 | CB | ARG | A | 246 | 57.126 | 5.026 | −2.608 | 1.00 | 34.15 | C |
| ATOM | 3904 | CG | ARG | A | 246 | 58.396 | 5.733 | −3.103 | 1.00 | 42.54 | C |
| ATOM | 3907 | CD | ARG | A | 246 | 58.820 | 5.323 | −4.516 | 1.00 | 52.53 | C |
| ATOM | 3910 | NE | ARG | A | 246 | 57.752 | 5.471 | −5.508 | 1.00 | 61.41 | N |
| ATOM | 3912 | CZ | ARG | A | 246 | 57.911 | 5.319 | −6.824 | 1.00 | 68.27 | C |
| ATOM | 3913 | NH1 | ARG | A | 246 | 59.105 | 5.028 | −7.339 | 1.00 | 71.09 | N |
| ATOM | 3916 | NH2 | ARG | A | 246 | 56.868 | 5.472 | −7.638 | 1.00 | 69.80 | N |
| ATOM | 3919 | C | ARG | A | 246 | 55.465 | 5.190 | −0.710 | 1.00 | 30.26 | C |
| ATOM | 3920 | O | ARG | A | 246 | 54.894 | 6.275 | −0.598 | 1.00 | 32.45 | O |
| ATOM | 3922 | N | VAL | A | 247 | 54.847 | 4.037 | −0.494 | 1.00 | 27.09 | N |
| ATOM | 3923 | CA | VAL | A | 247 | 53.481 | 4.013 | 0.040 | 1.00 | 25.76 | C |
| ATOM | 3925 | CB | VAL | A | 247 | 52.904 | 2.581 | 0.070 | 1.00 | 25.78 | C |
| ATOM | 3927 | CG1 | VAL | A | 247 | 51.497 | 2.566 | 0.660 | 1.00 | 23.89 | C |
| ATOM | 3931 | CG2 | VAL | A | 247 | 52.892 | 1.988 | −1.330 | 1.00 | 24.93 | C |
| ATOM | 3935 | C | VAL | A | 247 | 53.456 | 4.640 | 1.446 | 1.00 | 25.37 | C |
| ATOM | 3936 | O | VAL | A | 247 | 52.497 | 5.309 | 1.809 | 1.00 | 25.32 | O |
| ATOM | 3938 | N | GLY | A | 248 | 54.520 | 4.414 | 2.219 | 1.00 | 24.97 | N |
| ATOM | 3939 | CA | GLY | A | 248 | 54.779 | 5.135 | 3.468 | 1.00 | 23.78 | C |
| ATOM | 3942 | C | GLY | A | 248 | 53.741 | 4.971 | 4.559 | 1.00 | 23.10 | C |
| ATOM | 3943 | O | GLY | A | 248 | 53.625 | 5.806 | 5.447 | 1.00 | 22.20 | O |
| ATOM | 3945 | N | LEU | A | 249 | 53.004 | 3.877 | 4.516 | 1.00 | 24.18 | N |
| ATOM | 3946 | CA | LEU | A | 249 | 51.839 | 3.723 | 5.377 | 1.00 | 25.74 | C |
| ATOM | 3948 | CB | LEU | A | 249 | 50.958 | 2.584 | 4.857 | 1.00 | 25.16 | C |
| ATOM | 3951 | CG | LEU | A | 249 | 49.458 | 2.750 | 5.072 | 1.00 | 25.16 | C |
| ATOM | 3953 | CD1 | LEU | A | 249 | 48.930 | 4.030 | 4.424 | 1.00 | 23.83 | C |
| ATOM | 3957 | CD2 | LEU | A | 249 | 48.746 | 1.521 | 4.519 | 1.00 | 23.25 | C |
| ATOM | 3961 | C | LEU | A | 249 | 52.219 | 3.493 | 6.845 | 1.00 | 27.35 | C |
| ATOM | 3962 | O | LEU | A | 249 | 51.562 | 4.024 | 7.747 | 1.00 | 27.47 | O |
| ATOM | 3964 | N | ALA | A | 250 | 53.277 | 2.714 | 7.079 | 1.00 | 28.70 | N |
| ATOM | 3965 | CA | ALA | A | 250 | 53.732 | 2.415 | 8.442 | 1.00 | 29.93 | C |
| ATOM | 3967 | CB | ALA | A | 250 | 54.728 | 1.273 | 8.437 | 1.00 | 30.24 | C |
| ATOM | 3971 | C | ALA | A | 250 | 54.340 | 3.645 | 9.101 | 1.00 | 30.67 | C |
| ATOM | 3972 | O | ALA | A | 250 | 54.256 | 3.814 | 10.320 | 1.00 | 31.97 | O |
| ATOM | 3974 | N | THR | A | 251 | 54.949 | 4.500 | 8.286 | 1.00 | 30.88 | N |
| ATOM | 3975 | CA | THR | A | 251 | 55.484 | 5.773 | 8.754 | 1.00 | 30.79 | C |
| ATOM | 3977 | CB | THR | A | 251 | 56.355 | 6.437 | 7.674 | 1.00 | 30.36 | C |
| ATOM | 3979 | OG1 | THR | A | 251 | 57.329 | 5.498 | 7.205 | 1.00 | 26.92 | O |
| ATOM | 3981 | CG2 | THR | A | 251 | 57.057 | 7.667 | 8.235 | 1.00 | 29.77 | C |
| ATOM | 3985 | C | THR | A | 251 | 54.391 | 6.766 | 9.161 | 1.00 | 31.81 | C |
| ATOM | 3986 | O | THR | A | 251 | 54.578 | 7.524 | 10.111 | 1.00 | 34.30 | O |
| ATOM | 3988 | N | LYS | A | 252 | 53.263 | 6.770 | 8.452 | 1.00 | 31.78 | N |
| ATOM | 3989 | CA | LYS | A | 252 | 52.210 | 7.770 | 8.686 | 1.00 | 32.29 | C |
| ATOM | 3991 | CB | LYS | A | 252 | 51.529 | 8.170 | 7.369 | 1.00 | 32.78 | C |
| ATOM | 3994 | CG | LYS | A | 252 | 52.459 | 8.823 | 6.338 | 1.00 | 35.10 | C |
| ATOM | 3997 | CD | LYS | A | 252 | 52.882 | 10.238 | 6.730 | 1.00 | 39.23 | C |
| ATOM | 4000 | CE | LYS | A | 252 | 53.945 | 10.775 | 5.776 | 1.00 | 41.74 | C |
| ATOM | 4003 | NZ | LYS | A | 252 | 54.463 | 12.107 | 6.183 | 1.00 | 42.94 | N |
| ATOM | 4007 | C | LYS | A | 252 | 51.165 | 7.309 | 9.703 | 1.00 | 31.68 | C |
| ATOM | 4008 | O | LYS | A | 252 | 50.545 | 8.134 | 10.367 | 1.00 | 31.90 | O |
| ATOM | 4010 | N | LEU | A | 253 | 50.962 | 6.001 | 9.814 | 1.00 | 31.58 | N |
| ATOM | 4011 | CA | LEU | A | 253 | 50.116 | 5.449 | 10.866 | 1.00 | 31.41 | C |
| ATOM | 4013 | CB | LEU | A | 253 | 49.391 | 4.201 | 10.370 | 1.00 | 30.57 | C |
| ATOM | 4016 | CG | LEU | A | 253 | 48.566 | 4.376 | 9.096 | 1.00 | 31.21 | C |
| ATOM | 4018 | CD1 | LEU | A | 253 | 47.842 | 3.089 | 8.773 | 1.00 | 31.56 | C |
| ATOM | 4022 | CD2 | LEU | A | 253 | 47.580 | 5.521 | 9.212 | 1.00 | 32.60 | C |
| ATOM | 4026 | C | LEU | A | 253 | 50.981 | 5.118 | 12.080 | 1.00 | 31.78 | C |
| ATOM | 4027 | O | LEU | A | 253 | 51.865 | 4.260 | 12.006 | 1.00 | 32.06 | O |
| ATOM | 4029 | N | HIS | A | 254 | 50.732 | 5.806 | 13.192 | 1.00 | 32.11 | N |
| ATOM | 4030 | CA | HIS | A | 254 | 51.542 | 5.629 | 14.405 | 1.00 | 33.05 | C |
| ATOM | 4032 | CB | HIS | A | 254 | 51.271 | 6.750 | 15.430 | 1.00 | 34.30 | C |
| ATOM | 4035 | CG | HIS | A | 254 | 49.898 | 6.713 | 16.042 | 1.00 | 41.82 | C |
| ATOM | 4036 | ND1 | HIS | A | 254 | 48.794 | 7.278 | 15.437 | 1.00 | 46.79 | N |
| ATOM | 4038 | CE1 | HIS | A | 254 | 47.733 | 7.104 | 16.206 | 1.00 | 48.23 | C |
| ATOM | 4040 | NE2 | HIS | A | 254 | 48.108 | 6.452 | 17.293 | 1.00 | 46.70 | N |
| ATOM | 4042 | CD2 | HIS | A | 254 | 49.457 | 6.196 | 17.216 | 1.00 | 46.49 | C |
| ATOM | 4044 | C | HIS | A | 254 | 51.350 | 4.254 | 15.044 | 1.00 | 31.06 | C |
| ATOM | 4045 | O | HIS | A | 254 | 52.284 | 3.703 | 15.610 | 1.00 | 30.95 | O |
| ATOM | 4047 | N | PHE | A | 255 | 50.145 | 3.707 | 14.932 | 1.00 | 30.16 | N |
| ATOM | 4048 | CA | PHE | A | 255 | 49.803 | 2.405 | 15.520 | 1.00 | 29.65 | C |
| ATOM | 4050 | CB | PHE | A | 255 | 48.288 | 2.308 | 15.738 | 1.00 | 29.40 | C |
| ATOM | 4053 | CG | PHE | A | 255 | 47.501 | 2.234 | 14.462 | 1.00 | 28.96 | C |
| ATOM | 4054 | CD1 | PHE | A | 255 | 47.088 | 3.390 | 13.816 | 1.00 | 29.52 | C |
| ATOM | 4056 | CE1 | PHE | A | 255 | 46.380 | 3.325 | 12.631 | 1.00 | 27.79 | C |
| ATOM | 4058 | CZ | PHE | A | 255 | 46.074 | 2.099 | 12.079 | 1.00 | 27.35 | C |
| ATOM | 4060 | CE2 | PHE | A | 255 | 46.478 | 0.943 | 12.710 | 1.00 | 28.82 | C |
| ATOM | 4062 | CD2 | PHE | A | 255 | 47.189 | 1.011 | 13.896 | 1.00 | 27.34 | C |
| ATOM | 4064 | C | PHE | A | 255 | 50.244 | 1.220 | 14.661 | 1.00 | 29.59 | C |

APPENDIX 1-continued

| | | | | | | | | | | |
|---|---|---|---|---|---|---|---|---|---|---|
| ATOM | 4065 | O | PHE | A | 255 | 50.298 | 0.088 | 15.139 | 1.00 | 29.60 | O |
| ATOM | 4067 | N | ALA | A | 256 | 50.543 | 1.479 | 13.390 | 1.00 | 29.88 | N |
| ATOM | 4068 | CA | ALA | A | 256 | 50.767 | 0.410 | 12.418 | 1.00 | 29.61 | C |
| ATOM | 4070 | CB | ALA | A | 256 | 50.745 | 0.980 | 11.015 | 1.00 | 29.60 | C |
| ATOM | 4074 | C | ALA | A | 256 | 52.068 | −0.344 | 12.647 | 1.00 | 29.65 | C |
| ATOM | 4075 | O | ALA | A | 256 | 53.076 | 0.243 | 13.039 | 1.00 | 29.60 | O |
| ATOM | 4077 | N | ARG | A | 257 | 52.035 | −1.649 | 12.387 | 1.00 | 30.36 | N |
| ATOM | 4078 | CA | ARG | A | 257 | 53.240 | −2.478 | 12.385 | 1.00 | 30.24 | C |
| ATOM | 4080 | CB | ARG | A | 257 | 52.924 | −3.904 | 12.839 | 1.00 | 29.56 | C |
| ATOM | 4083 | CG | ARG | A | 257 | 52.496 | −4.014 | 14.286 | 1.00 | 31.34 | C |
| ATOM | 4086 | CD | ARG | A | 257 | 52.158 | −5.450 | 14.640 | 1.00 | 33.32 | C |
| ATOM | 4089 | NE | ARG | A | 257 | 50.984 | −5.926 | 13.912 | 1.00 | 34.21 | N |
| ATOM | 4091 | CZ | ARG | A | 257 | 50.711 | −7.204 | 13.657 | 1.00 | 40.51 | C |
| ATOM | 4092 | NH1 | ARG | A | 257 | 51.533 | −8.168 | 14.063 | 1.00 | 44.76 | N |
| ATOM | 4095 | NH2 | ARG | A | 257 | 49.611 | −7.525 | 12.977 | 1.00 | 42.49 | N |
| ATOM | 4098 | C | ARG | A | 257 | 53.845 | −2.526 | 10.982 | 1.00 | 30.05 | C |
| ATOM | 4099 | O | ARG | A | 257 | 53.130 | −2.759 | 10.004 | 1.00 | 28.85 | O |
| ATOM | 4101 | N | ASP | A | 258 | 55.158 | −2.290 | 10.903 | 1.00 | 30.41 | N |
| ATOM | 4102 | CA | ASP | A | 258 | 55.934 | −2.486 | 9.679 | 1.00 | 30.29 | C |
| ATOM | 4104 | CB | ASP | A | 258 | 57.100 | −1.486 | 9.616 | 1.00 | 30.46 | C |
| ATOM | 4107 | CG | ASP | A | 258 | 57.892 | −1.558 | 8.301 | 1.00 | 30.96 | C |
| ATOM | 4108 | OD1 | ASP | A | 258 | 57.613 | −2.420 | 7.447 | 1.00 | 29.66 | O |
| ATOM | 4109 | OD2 | ASP | A | 258 | 58.811 | −0.737 | 8.119 | 1.00 | 34.44 | O |
| ATOM | 4110 | C | ASP | A | 258 | 56.453 | −3.929 | 9.670 | 1.00 | 30.30 | C |
| ATOM | 4111 | O | ASP | A | 258 | 57.355 | −4.284 | 10.441 | 1.00 | 29.85 | O |
| ATOM | 4113 | N | ARG | A | 259 | 55.874 | −4.756 | 8.803 | 1.00 | 29.36 | N |
| ATOM | 4114 | CA | ARG | A | 259 | 56.272 | −6.147 | 8.706 | 1.00 | 30.06 | C |
| ATOM | 4116 | CB | ARG | A | 259 | 55.242 | −7.029 | 9.423 | 1.00 | 31.33 | C |
| ATOM | 4119 | CG | ARG | A | 259 | 55.229 | −6.847 | 10.938 | 1.00 | 35.62 | C |
| ATOM | 4122 | CD | ARG | A | 259 | 54.305 | −7.840 | 11.634 | 1.00 | 43.50 | C |
| ATOM | 4125 | NE | ARG | A | 259 | 54.908 | −9.166 | 11.805 | 1.00 | 49.86 | N |
| ATOM | 4127 | CZ | ARG | A | 259 | 55.756 | −9.506 | 12.779 | 1.00 | 53.74 | C |
| ATOM | 4128 | NH1 | ARG | A | 259 | 56.142 | −8.623 | 13.702 | 1.00 | 55.51 | N |
| ATOM | 4131 | NH2 | ARG | A | 259 | 56.229 | −10.746 | 12.827 | 1.00 | 54.56 | N |
| ATOM | 4134 | C | ARG | A | 259 | 56.463 | −6.567 | 7.244 | 1.00 | 29.15 | C |
| ATOM | 4135 | O | ARG | A | 259 | 55.895 | −7.565 | 6.793 | 1.00 | 29.19 | O |
| ATOM | 4137 | N | LEU | A | 260 | 57.272 | −5.804 | 6.511 | 1.00 | 27.50 | N |
| ATOM | 4138 | CA | LEU | A | 260 | 57.531 | −6.109 | 5.109 | 1.00 | 26.23 | C |
| ATOM | 4140 | CB | LEU | A | 260 | 58.064 | −4.889 | 4.346 | 1.00 | 25.40 | C |
| ATOM | 4143 | CG | LEU | A | 260 | 58.363 | −5.176 | 2.865 | 1.00 | 24.10 | C |
| ATOM | 4145 | CD1 | LEU | A | 260 | 57.111 | −5.665 | 2.120 | 1.00 | 17.33 | C |
| ATOM | 4149 | CD2 | LEU | A | 260 | 58.937 | −3.969 | 2.188 | 1.00 | 24.52 | C |
| ATOM | 4153 | C | LEU | A | 260 | 58.521 | −7.257 | 4.979 | 1.00 | 25.74 | C |
| ATOM | 4154 | O | LEU | A | 260 | 58.303 | −8.181 | 4.193 | 1.00 | 26.84 | O |
| ATOM | 4156 | N | ILE | A | 261 | 59.611 | −7.187 | 5.733 | 1.00 | 23.99 | N |
| ATOM | 4157 | CA | ILE | A | 261 | 60.636 | −8.219 | 5.673 | 1.00 | 23.51 | C |
| ATOM | 4159 | CB | ILE | A | 261 | 61.860 | −7.867 | 6.561 | 1.00 | 23.42 | C |
| ATOM | 4161 | CG1 | ILE | A | 261 | 62.589 | −6.629 | 6.001 | 1.00 | 26.27 | C |
| ATOM | 4164 | CD1 | ILE | A | 261 | 63.300 | −5.770 | 7.055 | 1.00 | 22.43 | C |
| ATOM | 4168 | CG2 | ILE | A | 261 | 62.811 | −9.043 | 6.643 | 1.00 | 18.52 | C |
| ATOM | 4172 | C | ILE | A | 261 | 60.047 | −9.577 | 6.077 | 1.00 | 22.92 | C |
| ATOM | 4173 | O | ILE | A | 261 | 60.236 | −10.577 | 5.380 | 1.00 | 21.46 | O |
| ATOM | 4175 | N | GLU | A | 262 | 59.321 | −9.599 | 7.189 | 1.00 | 22.77 | N |
| ATOM | 4176 | CA | GLU | A | 262 | 58.728 | −10.834 | 7.680 | 1.00 | 23.47 | C |
| ATOM | 4178 | CB | GLU | A | 262 | 58.051 | −10.637 | 9.038 | 1.00 | 24.41 | C |
| ATOM | 4181 | CG | GLU | A | 262 | 59.003 | −10.303 | 10.182 | 1.00 | 28.29 | C |
| ATOM | 4184 | CD | GLU | A | 262 | 59.126 | −8.804 | 10.450 | 1.00 | 35.49 | C |
| ATOM | 4185 | OE1 | GLU | A | 262 | 59.085 | −7.998 | 9.487 | 1.00 | 34.06 | O |
| ATOM | 4186 | OE2 | GLU | A | 262 | 59.272 | −8.439 | 11.639 | 1.00 | 41.58 | O |
| ATOM | 4187 | C | GLU | A | 262 | 57.711 | −11.356 | 6.677 | 1.00 | 23.14 | C |
| ATOM | 4188 | O | GLU | A | 262 | 57.590 | −12.568 | 6.486 | 1.00 | 22.49 | O |
| ATOM | 4190 | N | SER | A | 263 | 56.991 | −10.439 | 6.034 | 1.00 | 22.16 | N |
| ATOM | 4191 | CA | SER | A | 263 | 56.000 | −10.819 | 5.035 | 1.00 | 21.96 | C |
| ATOM | 4193 | CB | SER | A | 263 | 55.117 | −9.631 | 4.634 | 1.00 | 22.71 | C |
| ATOM | 4196 | OG | SER | A | 263 | 54.192 | −9.324 | 5.672 | 1.00 | 24.34 | O |
| ATOM | 4198 | C | SER | A | 263 | 56.678 | −11.415 | 3.817 | 1.00 | 20.76 | C |
| ATOM | 4199 | O | SER | A | 263 | 56.148 | −12.332 | 3.199 | 1.00 | 18.64 | O |
| ATOM | 4201 | N | PHE | A | 264 | 57.855 | −10.904 | 3.475 | 1.00 | 20.69 | N |
| ATOM | 4202 | CA | PHE | A | 264 | 58.581 | −11.438 | 2.332 | 1.00 | 20.32 | C |
| ATOM | 4204 | CB | PHE | A | 264 | 59.670 | −10.485 | 1.862 | 1.00 | 19.12 | C |
| ATOM | 4207 | CG | PHE | A | 264 | 60.233 | −10.873 | 0.547 | 1.00 | 17.93 | C |
| ATOM | 4208 | CD1 | PHE | A | 264 | 59.613 | −10.479 | −0.618 | 1.00 | 16.80 | C |
| ATOM | 4210 | CE1 | PHE | A | 264 | 60.101 | −10.876 | −1.837 | 1.00 | 16.86 | C |
| ATOM | 4212 | CZ | PHE | A | 264 | 61.226 | −11.681 | −1.900 | 1.00 | 20.16 | C |
| ATOM | 4214 | CE2 | PHE | A | 264 | 61.849 | −12.089 | −0.744 | 1.00 | 17.10 | C |
| ATOM | 4216 | CD2 | PHE | A | 264 | 61.343 | −11.699 | 0.472 | 1.00 | 19.87 | C |
| ATOM | 4218 | C | PHE | A | 264 | 59.177 | −12.816 | 2.636 | 1.00 | 21.04 | C |
| ATOM | 4219 | O | PHE | A | 264 | 59.137 | −13.714 | 1.793 | 1.00 | 20.17 | O |
| ATOM | 4221 | N | TYR | A | 265 | 59.736 | −12.962 | 3.836 | 1.00 | 21.97 | N |
| ATOM | 4222 | CA | TYR | A | 265 | 60.197 | −14.256 | 4.341 | 1.00 | 22.83 | C |

APPENDIX 1-continued

| | | | | | | | | | | |
|---|---|---|---|---|---|---|---|---|---|---|
| ATOM | 4224 | CB | TYR | A | 265 | 60.674 | −14.108 | 5.790 | 1.00 | 23.02 | C |
| ATOM | 4227 | CG | TYR | A | 265 | 60.829 | −15.397 | 6.566 | 1.00 | 29.40 | C |
| ATOM | 4228 | CD1 | TYR | A | 265 | 61.998 | −16.148 | 6.484 | 1.00 | 34.40 | C |
| ATOM | 4230 | CE1 | TYR | A | 265 | 62.146 | −17.326 | 7.214 | 1.00 | 37.24 | C |
| ATOM | 4232 | CZ | TYR | A | 265 | 61.120 | −17.759 | 8.042 | 1.00 | 37.62 | C |
| ATOM | 4233 | OH | TYR | A | 265 | 61.266 | −18.924 | 8.761 | 1.00 | 42.46 | O |
| ATOM | 4235 | CE2 | TYR | A | 265 | 59.953 | −17.024 | 8.150 | 1.00 | 35.20 | C |
| ATOM | 4237 | CD2 | TYR | A | 265 | 59.815 | −15.849 | 7.419 | 1.00 | 34.49 | C |
| ATOM | 4239 | C | TYR | A | 265 | 59.078 | −15.285 | 4.247 | 1.00 | 22.14 | C |
| ATOM | 4240 | O | TYR | A | 265 | 59.304 | −16.413 | 3.828 | 1.00 | 23.08 | O |
| ATOM | 4242 | N | TRP | A | 266 | 57.876 | −14.881 | 4.642 | 1.00 | 21.35 | N |
| ATOM | 4243 | CA | TRP | A | 266 | 56.679 | −15.712 | 4.511 | 1.00 | 20.58 | C |
| ATOM | 4245 | CB | TRP | A | 266 | 55.456 | −14.941 | 5.028 | 1.00 | 20.00 | C |
| ATOM | 4248 | CG | TRP | A | 266 | 54.150 | −15.640 | 4.901 | 1.00 | 20.69 | C |
| ATOM | 4249 | CD1 | TRP | A | 266 | 53.306 | −15.618 | 3.826 | 1.00 | 21.65 | C |
| ATOM | 4251 | NE1 | TRP | A | 266 | 52.183 | −16.371 | 4.087 | 1.00 | 20.12 | N |
| ATOM | 4253 | CE2 | TRP | A | 266 | 52.284 | −16.885 | 5.352 | 1.00 | 22.19 | C |
| ATOM | 4254 | CD2 | TRP | A | 266 | 53.507 | −16.440 | 5.896 | 1.00 | 21.10 | C |
| ATOM | 4255 | CE3 | TRP | A | 266 | 53.844 | −16.820 | 7.195 | 1.00 | 21.72 | C |
| ATOM | 4257 | CZ3 | TRP | A | 266 | 52.973 | −17.635 | 7.895 | 1.00 | 25.91 | C |
| ATOM | 4259 | CH2 | TRP | A | 266 | 51.768 | −18.067 | 7.327 | 1.00 | 24.55 | C |
| ATOM | 4261 | CZ2 | TRP | A | 266 | 51.406 | −17.701 | 6.061 | 1.00 | 25.05 | C |
| ATOM | 4263 | C | TRP | A | 266 | 56.486 | −16.145 | 3.054 | 1.00 | 20.13 | C |
| ATOM | 4264 | O | TRP | A | 266 | 56.375 | −17.336 | 2.768 | 1.00 | 21.08 | O |
| ATOM | 4266 | N | ALA | A | 267 | 56.480 | −15.182 | 2.137 | 1.00 | 18.67 | N |
| ATOM | 4267 | CA | ALA | A | 267 | 56.264 | −15.472 | 0.719 | 1.00 | 18.28 | C |
| ATOM | 4269 | CB | ALA | A | 267 | 56.228 | −14.187 | −0.091 | 1.00 | 17.55 | C |
| ATOM | 4273 | C | ALA | A | 267 | 57.304 | −16.437 | 0.139 | 1.00 | 17.99 | C |
| ATOM | 4274 | O | ALA | A | 267 | 56.968 | −17.253 | −0.711 | 1.00 | 19.18 | O |
| ATOM | 4276 | N | VAL | A | 268 | 58.549 | −16.354 | 0.605 | 1.00 | 17.57 | N |
| ATOM | 4277 | CA | VAL | A | 268 | 59.601 | −17.300 | 0.192 | 1.00 | 16.55 | C |
| ATOM | 4279 | CB | VAL | A | 268 | 60.972 | −16.948 | 0.824 | 1.00 | 15.16 | C |
| ATOM | 4281 | CG1 | VAL | A | 268 | 61.953 | −18.080 | 0.659 | 1.00 | 14.00 | C |
| ATOM | 4285 | CG2 | VAL | A | 268 | 61.532 | −15.696 | 0.190 | 1.00 | 12.76 | C |
| ATOM | 4289 | C | VAL | A | 268 | 59.208 | −18.745 | 0.517 | 1.00 | 16.99 | C |
| ATOM | 4290 | O | VAL | A | 268 | 59.478 | −19.663 | −0.257 | 1.00 | 17.36 | O |
| ATOM | 4292 | N | GLY | A | 269 | 58.551 | −18.934 | 1.654 | 1.00 | 17.99 | N |
| ATOM | 4293 | CA | GLY | A | 269 | 57.964 | −20.225 | 1.993 | 1.00 | 18.12 | C |
| ATOM | 4296 | C | GLY | A | 269 | 56.865 | −20.692 | 1.051 | 1.00 | 17.71 | C |
| ATOM | 4297 | O | GLY | A | 269 | 56.739 | −21.893 | 0.810 | 1.00 | 20.02 | O |
| ATOM | 4299 | N | VAL | A | 270 | 56.068 | −19.757 | 0.532 | 1.00 | 15.99 | N |
| ATOM | 4300 | CA | VAL | A | 270 | 54.952 | −20.092 | −0.358 | 1.00 | 16.46 | C |
| ATOM | 4302 | CB | VAL | A | 270 | 53.895 | −18.959 | −0.401 | 1.00 | 16.76 | C |
| ATOM | 4304 | CG1 | VAL | A | 270 | 52.904 | −19.176 | −1.540 | 1.00 | 14.34 | C |
| ATOM | 4308 | CG2 | VAL | A | 270 | 53.168 | −18.863 | 0.931 | 1.00 | 15.01 | C |
| ATOM | 4312 | C | VAL | A | 270 | 55.403 | −20.409 | −1.790 | 1.00 | 17.14 | C |
| ATOM | 4313 | O | VAL | A | 270 | 54.893 | −21.350 | −2.403 | 1.00 | 17.58 | O |
| ATOM | 4315 | N | ALA | A | 271 | 56.344 | −19.622 | −2.318 | 1.00 | 16.61 | N |
| ATOM | 4316 | CA | ALA | A | 271 | 56.869 | −19.828 | −3.672 | 1.00 | 16.49 | C |
| ATOM | 4318 | CB | ALA | A | 271 | 56.105 | −18.989 | −4.669 | 1.00 | 15.65 | C |
| ATOM | 4322 | C | ALA | A | 271 | 58.362 | −19.495 | −3.729 | 1.00 | 18.32 | C |
| ATOM | 4323 | O | ALA | A | 271 | 58.753 | −18.336 | −3.920 | 1.00 | 18.32 | O |
| ATOM | 4325 | N | PHE | A | 272 | 59.196 | −20.521 | −3.580 | 1.00 | 18.87 | N |
| ATOM | 4326 | CA | PHE | A | 272 | 60.628 | −20.318 | −3.446 | 1.00 | 18.58 | C |
| ATOM | 4328 | CB | PHE | A | 272 | 61.246 | −21.406 | −2.581 | 1.00 | 18.99 | C |
| ATOM | 4331 | CG | PHE | A | 272 | 61.436 | −22.698 | −3.291 | 1.00 | 21.53 | C |
| ATOM | 4332 | CD1 | PHE | A | 272 | 62.586 | −22.942 | −4.013 | 1.00 | 24.73 | C |
| ATOM | 4334 | CE1 | PHE | A | 272 | 62.753 | −24.140 | −4.677 | 1.00 | 25.53 | C |
| ATOM | 4336 | CZ | PHE | A | 272 | 61.768 | −25.098 | −4.626 | 1.00 | 23.65 | C |
| ATOM | 4338 | CE2 | PHE | A | 272 | 60.625 | −24.867 | −3.916 | 1.00 | 22.26 | C |
| ATOM | 4340 | CD2 | PHE | A | 272 | 60.459 | −23.675 | −3.247 | 1.00 | 24.18 | C |
| ATOM | 4342 | C | PHE | A | 272 | 61.353 | −20.257 | −4.774 | 1.00 | 19.15 | C |
| ATOM | 4343 | O | PHE | A | 272 | 62.367 | −19.580 | −4.873 | 1.00 | 19.58 | O |
| ATOM | 4345 | N | GLU | A | 273 | 60.849 | −20.951 | −5.793 | 1.00 | 19.97 | N |
| ATOM | 4346 | CA | GLU | A | 273 | 61.595 | −21.081 | −7.048 | 1.00 | 20.05 | C |
| ATOM | 4348 | CB | GLU | A | 273 | 60.874 | −21.975 | −8.063 | 1.00 | 20.71 | C |
| ATOM | 4351 | CG | GLU | A | 273 | 60.715 | −23.430 | −7.648 | 1.00 | 23.15 | C |
| ATOM | 4354 | CD | GLU | A | 273 | 59.417 | −23.709 | −6.916 | 1.00 | 28.01 | C |
| ATOM | 4355 | OE1 | GLU | A | 273 | 58.852 | −22.767 | −6.327 | 1.00 | 32.28 | O |
| ATOM | 4356 | OE2 | GLU | A | 273 | 58.958 | −24.875 | −6.933 | 1.00 | 34.22 | O |
| ATOM | 4357 | C | GLU | A | 273 | 61.858 | −19.709 | −7.665 | 1.00 | 19.88 | C |
| ATOM | 4358 | O | GLU | A | 273 | 60.973 | −18.852 | −7.665 | 1.00 | 20.82 | O |
| ATOM | 4360 | N | PRO | A | 274 | 63.069 | −19.503 | −8.213 | 1.00 | 19.39 | N |
| ATOM | 4361 | CA | PRO | A | 274 | 63.489 | −18.180 | −8.653 | 1.00 | 19.28 | C |
| ATOM | 4363 | CB | PRO | A | 274 | 64.836 | −18.445 | −9.336 | 1.00 | 19.79 | C |
| ATOM | 4366 | CG | PRO | A | 274 | 64.845 | −19.885 | −9.629 | 1.00 | 19.06 | C |
| ATOM | 4369 | CD | PRO | A | 274 | 64.069 | −20.527 | −8.555 | 1.00 | 19.21 | C |
| ATOM | 4372 | C | PRO | A | 274 | 62.512 | −17.504 | −9.609 | 1.00 | 19.22 | C |
| ATOM | 4373 | O | PRO | A | 274 | 62.280 | −16.305 | −9.489 | 1.00 | 20.35 | O |
| ATOM | 4374 | N | GLN | A | 275 | 61.928 | −18.262 | −10.532 | 1.00 | 19.49 | N |

APPENDIX 1-continued

| ATOM | 4375 | CA | GLN | A | 275 | 60.957 | −17.691 | −11.475 | 1.00 | 19.56 | C |
|---|---|---|---|---|---|---|---|---|---|---|---|
| ATOM | 4377 | CB | GLN | A | 275 | 60.544 | −18.713 | −12.539 | 1.00 | 20.27 | C |
| ATOM | 4380 | CG | GLN | A | 275 | 59.793 | −19.952 | −12.035 | 1.00 | 21.82 | C |
| ATOM | 4383 | CD | GLN | A | 275 | 60.719 | −21.085 | −11.619 | 1.00 | 27.78 | C |
| ATOM | 4384 | OE1 | GLN | A | 275 | 61.861 | −20.854 | −11.201 | 1.00 | 26.35 | O |
| ATOM | 4385 | NE2 | GLN | A | 275 | 60.224 | −22.324 | −11.723 | 1.00 | 30.59 | N |
| ATOM | 4388 | C | GLN | A | 275 | 59.700 | −17.083 | −10.837 | 1.00 | 19.47 | C |
| ATOM | 4389 | O | GLN | A | 275 | 59.027 | −16.293 | −11.481 | 1.00 | 18.56 | O |
| ATOM | 4391 | N | TYR | A | 276 | 59.379 | −17.433 | −9.588 | 1.00 | 20.01 | N |
| ATOM | 4392 | CA | TYR | A | 276 | 58.154 | −16.910 | −8.954 | 1.00 | 20.87 | C |
| ATOM | 4394 | CB | TYR | A | 276 | 57.511 | −17.974 | −8.045 | 1.00 | 21.44 | C |
| ATOM | 4397 | CG | TYR | A | 276 | 57.110 | −19.235 | −8.779 | 1.00 | 22.50 | C |
| ATOM | 4398 | CD1 | TYR | A | 276 | 56.284 | −19.182 | −9.898 | 1.00 | 19.93 | C |
| ATOM | 4400 | CE1 | TYR | A | 276 | 55.919 | −20.335 | −10.572 | 1.00 | 21.58 | C |
| ATOM | 4402 | CZ | TYR | A | 276 | 56.380 | −21.562 | −10.130 | 1.00 | 25.30 | C |
| ATOM | 4403 | OH | TYR | A | 276 | 56.017 | −22.708 | −10.794 | 1.00 | 30.57 | O |
| ATOM | 4405 | CE2 | TYR | A | 276 | 57.200 | −21.645 | −9.022 | 1.00 | 23.76 | C |
| ATOM | 4407 | CD2 | TYR | A | 276 | 57.555 | −20.482 | −8.350 | 1.00 | 24.50 | C |
| ATOM | 4409 | C | TYR | A | 276 | 58.344 | −15.583 | −8.193 | 1.00 | 20.15 | C |
| ATOM | 4410 | O | TYR | A | 276 | 57.736 | −15.371 | −7.149 | 1.00 | 20.74 | O |
| ATOM | 4412 | N | SER | A | 277 | 59.156 | −14.681 | −8.731 | 1.00 | 19.69 | N |
| ATOM | 4413 | CA | SER | A | 277 | 59.308 | −13.353 | −8.141 | 1.00 | 19.79 | C |
| ATOM | 4415 | CB | SER | A | 277 | 60.273 | −12.494 | −8.961 | 1.00 | 19.15 | C |
| ATOM | 4418 | OG | SER | A | 277 | 61.606 | −12.879 | −8.708 | 1.00 | 18.79 | O |
| ATOM | 4420 | C | SER | A | 277 | 57.970 | −12.629 | −7.992 | 1.00 | 19.59 | C |
| ATOM | 4421 | O | SER | A | 277 | 57.685 | −12.061 | −6.939 | 1.00 | 20.41 | O |
| ATOM | 4423 | N | ASP | A | 278 | 57.152 | −12.648 | −9.038 | 1.00 | 19.45 | N |
| ATOM | 4424 | CA | ASP | A | 278 | 55.851 | −11.990 | −8.980 | 1.00 | 20.09 | C |
| ATOM | 4426 | CB | ASP | A | 278 | 55.105 | −12.115 | −10.311 | 1.00 | 20.84 | C |
| ATOM | 4429 | CG | ASP | A | 278 | 55.628 | −11.168 | −11.368 | 1.00 | 22.85 | C |
| ATOM | 4430 | OD1 | ASP | A | 278 | 56.248 | −10.146 | −11.014 | 1.00 | 33.08 | O |
| ATOM | 4431 | OD2 | ASP | A | 278 | 55.407 | −11.439 | −12.561 | 1.00 | 28.05 | O |
| ATOM | 4432 | C | ASP | A | 278 | 54.984 | −12.538 | −7.850 | 1.00 | 19.48 | C |
| ATOM | 4433 | O | ASP | A | 278 | 54.317 | −11.777 | −7.166 | 1.00 | 19.06 | O |
| ATOM | 4435 | N | CYS | A | 279 | 54.997 | −13.851 | −7.652 | 1.00 | 18.86 | N |
| ATOM | 4436 | CA | CYS | A | 279 | 54.188 | −14.455 | −6.608 | 1.00 | 19.06 | C |
| ATOM | 4438 | CB | CYS | A | 279 | 54.171 | −15.977 | −6.746 | 1.00 | 20.08 | C |
| ATOM | 4441 | SG | CYS | A | 279 | 53.085 | −16.784 | −5.541 | 1.00 | 19.71 | S |
| ATOM | 4443 | C | CYS | A | 279 | 54.692 | −14.071 | −5.224 | 1.00 | 19.24 | C |
| ATOM | 4444 | O | CYS | A | 279 | 53.901 | −13.766 | −4.323 | 1.00 | 19.67 | O |
| ATOM | 4446 | N | ARG | A | 280 | 56.008 | −14.096 | −5.048 | 1.00 | 18.79 | N |
| ATOM | 4447 | CA | ARG | A | 280 | 56.593 | −13.653 | −3.793 | 1.00 | 18.97 | C |
| ATOM | 4449 | CB | ARG | A | 280 | 58.112 | −13.786 | −3.829 | 1.00 | 19.49 | C |
| ATOM | 4452 | CG | ARG | A | 280 | 58.617 | −15.207 | −3.693 | 1.00 | 18.21 | C |
| ATOM | 4455 | CD | ARG | A | 280 | 60.143 | −15.230 | −3.494 | 1.00 | 17.68 | C |
| ATOM | 4458 | NE | ARG | A | 280 | 60.868 | −14.866 | −4.710 | 1.00 | 14.15 | N |
| ATOM | 4460 | CZ | ARG | A | 280 | 61.018 | −15.657 | −5.769 | 1.00 | 15.41 | C |
| ATOM | 4461 | NH1 | ARG | A | 280 | 60.495 | −16.878 | −5.786 | 1.00 | 19.91 | N |
| ATOM | 4464 | NH2 | ARG | A | 280 | 61.684 | −15.221 | −6.827 | 1.00 | 18.53 | N |
| ATOM | 4467 | C | ARG | A | 280 | 56.205 | −12.206 | −3.510 | 1.00 | 19.13 | C |
| ATOM | 4468 | O | ARG | A | 280 | 55.772 | −11.869 | −2.417 | 1.00 | 19.04 | O |
| ATOM | 4470 | N | ASN | A | 281 | 56.348 | −11.354 | −4.514 | 1.00 | 20.54 | N |
| ATOM | 4471 | CA | ASN | A | 281 | 56.056 | −9.939 | −4.349 | 1.00 | 21.33 | C |
| ATOM | 4473 | CB | ASN | A | 281 | 56.518 | −9.167 | −5.580 | 1.00 | 21.84 | C |
| ATOM | 4476 | CG | ASN | A | 281 | 58.031 | −9.117 | −5.694 | 1.00 | 24.61 | C |
| ATOM | 4477 | OD1 | ASN | A | 281 | 58.742 | −9.247 | −4.697 | 1.00 | 27.33 | O |
| ATOM | 4478 | ND2 | ASN | A | 281 | 58.530 | −8.933 | −6.909 | 1.00 | 24.11 | N |
| ATOM | 4481 | C | ASN | A | 281 | 54.587 | −9.657 | −4.056 | 1.00 | 21.18 | C |
| ATOM | 4482 | O | ASN | A | 281 | 54.265 | −8.831 | −3.204 | 1.00 | 21.72 | O |
| ATOM | 4484 | N | SER | A | 282 | 53.689 | −10.363 | −4.724 | 1.00 | 20.74 | N |
| ATOM | 4485 | CA | SER | A | 282 | 52.282 | −10.050 | −4.563 | 1.00 | 21.09 | C |
| ATOM | 4487 | CB | SER | A | 282 | 51.469 | −10.450 | −5.808 | 1.00 | 20.40 | C |
| ATOM | 4490 | OG | SER | A | 282 | 50.469 | −11.383 | −5.509 | 1.00 | 26.21 | O |
| ATOM | 4492 | C | SER | A | 282 | 51.743 | −10.620 | −3.233 | 1.00 | 20.92 | C |
| ATOM | 4493 | O | SER | A | 282 | 50.850 | −10.026 | −2.626 | 1.00 | 21.89 | O |
| ATOM | 4495 | N | VAL | A | 283 | 52.318 | −11.726 | −2.755 | 1.00 | 19.67 | N |
| ATOM | 4496 | CA | VAL | A | 283 | 51.992 | −12.254 | −1.420 | 1.00 | 17.46 | C |
| ATOM | 4498 | CB | VAL | A | 283 | 52.470 | −13.725 | −1.265 | 1.00 | 17.08 | C |
| ATOM | 4500 | CG1 | VAL | A | 283 | 52.247 | −14.238 | 0.158 | 1.00 | 15.97 | C |
| ATOM | 4504 | CG2 | VAL | A | 283 | 51.753 | −14.616 | −2.241 | 1.00 | 12.54 | C |
| ATOM | 4508 | C | VAL | A | 283 | 52.585 | −11.372 | −0.302 | 1.00 | 17.57 | C |
| ATOM | 4509 | O | VAL | A | 283 | 51.959 | −11.168 | 0.741 | 1.00 | 17.42 | O |
| ATOM | 4511 | N | ALA | A | 284 | 53.787 | −10.846 | −0.528 | 1.00 | 18.06 | N |
| ATOM | 4512 | CA | ALA | A | 284 | 54.451 | −9.967 | 0.450 | 1.00 | 18.13 | C |
| ATOM | 4514 | CB | ALA | A | 284 | 55.874 | −9.678 | 0.025 | 1.00 | 16.24 | C |
| ATOM | 4518 | C | ALA | A | 284 | 53.681 | −8.660 | 0.642 | 1.00 | 18.68 | C |
| ATOM | 4519 | O | ALA | A | 284 | 53.438 | −8.241 | 1.766 | 1.00 | 20.09 | O |
| ATOM | 4521 | N | LYS | A | 285 | 53.288 | −8.029 | −0.459 | 1.00 | 19.10 | N |
| ATOM | 4522 | CA | LYS | A | 285 | 52.470 | −6.823 | −0.397 | 1.00 | 19.09 | C |
| ATOM | 4524 | CB | LYS | A | 285 | 52.195 | −6.274 | −1.803 | 1.00 | 19.20 | C |

APPENDIX 1-continued

| | | | | | | | | | | |
|---|---|---|---|---|---|---|---|---|---|---|
| ATOM | 4527 | CG | LYS | A | 285 | 53.430 | −5.805 | −2.569 | 1.00 | 21.42 | C |
| ATOM | 4530 | CD | LYS | A | 285 | 53.113 | −5.515 | −4.041 | 1.00 | 25.96 | C |
| ATOM | 4533 | CE | LYS | A | 285 | 54.358 | −5.051 | −4.793 | 1.00 | 30.90 | C |
| ATOM | 4536 | NZ | LYS | A | 285 | 54.070 | −4.041 | −5.866 | 1.00 | 34.43 | N |
| ATOM | 4540 | C | LYS | A | 285 | 51.142 | −7.110 | 0.316 | 1.00 | 18.92 | C |
| ATOM | 4541 | O | LYS | A | 285 | 50.758 | −6.379 | 1.227 | 1.00 | 19.78 | O |
| ATOM | 4543 | N | MET | A | 286 | 50.446 | −8.171 | −0.085 | 1.00 | 17.63 | N |
| ATOM | 4544 | CA | MET | A | 286 | 49.159 | −8.478 | 0.519 | 1.00 | 17.41 | C |
| ATOM | 4546 | CB | MET | A | 286 | 48.492 | −9.700 | −0.132 | 1.00 | 17.52 | C |
| ATOM | 4549 | CG | MET | A | 286 | 47.910 | −9.484 | −1.539 | 1.00 | 16.52 | C |
| ATOM | 4552 | SD | MET | A | 286 | 47.112 | −7.888 | −1.833 | 1.00 | 19.64 | S |
| ATOM | 4553 | CE | MET | A | 286 | 48.523 | −6.929 | −2.405 | 1.00 | 14.62 | C |
| ATOM | 4557 | C | MET | A | 286 | 49.318 | −8.717 | 2.011 | 1.00 | 18.00 | C |
| ATOM | 4558 | O | MET | A | 286 | 48.550 | −8.186 | 2.819 | 1.00 | 19.27 | O |
| ATOM | 4560 | N | PHE | A | 287 | 50.317 | −9.499 | 2.397 | 1.00 | 18.02 | N |
| ATOM | 4561 | CA | PHE | A | 287 | 50.474 | −9.812 | 3.818 | 1.00 | 18.38 | C |
| ATOM | 4563 | CB | PHE | A | 287 | 51.476 | −10.960 | 4.032 | 1.00 | 19.21 | C |
| ATOM | 4566 | CG | PHE | A | 287 | 51.220 | −11.788 | 5.275 | 1.00 | 24.14 | C |
| ATOM | 4567 | CD1 | PHE | A | 287 | 52.181 | −12.681 | 5.721 | 1.00 | 30.66 | C |
| ATOM | 4569 | CE1 | PHE | A | 287 | 51.965 | −13.454 | 6.861 | 1.00 | 33.02 | C |
| ATOM | 4571 | CZ | PHE | A | 287 | 50.777 | −13.330 | 7.577 | 1.00 | 31.77 | C |
| ATOM | 4573 | CE2 | PHE | A | 287 | 49.817 | −12.444 | 7.151 | 1.00 | 29.66 | C |
| ATOM | 4575 | CD2 | PHE | A | 287 | 50.035 | −11.677 | 6.006 | 1.00 | 28.16 | C |
| ATOM | 4577 | C | PHE | A | 287 | 50.865 | −8.569 | 4.611 | 1.00 | 16.94 | C |
| ATOM | 4578 | O | PHE | A | 287 | 50.506 | −8.440 | 5.774 | 1.00 | 14.32 | O |
| ATOM | 4580 | N | SER | A | 288 | 51.578 | −7.646 | 3.964 | 1.00 | 17.30 | N |
| ATOM | 4581 | CA | SER | A | 288 | 51.918 | −6.364 | 4.576 | 1.00 | 17.86 | C |
| ATOM | 4583 | CB | SER | A | 288 | 52.901 | −5.598 | 3.705 | 1.00 | 18.10 | C |
| ATOM | 4586 | OG | SER | A | 288 | 54.074 | −6.356 | 3.501 | 1.00 | 22.26 | O |
| ATOM | 4588 | C | SER | A | 288 | 50.683 | −5.509 | 4.836 | 1.00 | 17.60 | C |
| ATOM | 4589 | O | SER | A | 288 | 50.596 | −4.866 | 5.883 | 1.00 | 17.11 | O |
| ATOM | 4591 | N | PHE | A | 289 | 49.734 | −5.510 | 3.896 | 1.00 | 17.48 | N |
| ATOM | 4592 | CA | PHE | A | 289 | 48.457 | −4.796 | 4.083 | 1.00 | 17.47 | C |
| ATOM | 4594 | CB | PHE | A | 289 | 47.658 | −4.677 | 2.777 | 1.00 | 17.93 | C |
| ATOM | 4597 | CG | PHE | A | 289 | 48.041 | −3.490 | 1.955 | 1.00 | 19.51 | C |
| ATOM | 4598 | CD1 | PHE | A | 289 | 47.715 | −2.208 | 2.379 | 1.00 | 19.83 | C |
| ATOM | 4600 | CE1 | PHE | A | 289 | 48.092 | −1.093 | 1.635 | 1.00 | 21.90 | C |
| ATOM | 4602 | CZ | PHE | A | 289 | 48.800 | −1.258 | 0.452 | 1.00 | 22.70 | C |
| ATOM | 4604 | CE2 | PHE | A | 289 | 49.137 | −2.536 | 0.023 | 1.00 | 23.24 | C |
| ATOM | 4606 | CD2 | PHE | A | 289 | 48.758 | −3.644 | 0.776 | 1.00 | 23.63 | C |
| ATOM | 4608 | C | PHE | A | 289 | 47.600 | −5.460 | 5.135 | 1.00 | 17.18 | C |
| ATOM | 4609 | O | PHE | A | 289 | 47.081 | −4.782 | 6.018 | 1.00 | 16.93 | O |
| ATOM | 4611 | N | VAL | A | 290 | 47.461 | −6.783 | 5.033 | 1.00 | 17.53 | N |
| ATOM | 4612 | CA | VAL | A | 290 | 46.686 | −7.573 | 5.994 | 1.00 | 16.67 | C |
| ATOM | 4614 | CB | VAL | A | 290 | 46.829 | −9.092 | 5.727 | 1.00 | 17.16 | C |
| ATOM | 4616 | CG1 | VAL | A | 290 | 46.181 | −9.910 | 6.839 | 1.00 | 16.81 | C |
| ATOM | 4620 | CG2 | VAL | A | 290 | 46.222 | −9.460 | 4.381 | 1.00 | 14.02 | C |
| ATOM | 4624 | C | VAL | A | 290 | 47.115 | −7.262 | 7.427 | 1.00 | 17.08 | C |
| ATOM | 4625 | O | VAL | A | 290 | 46.271 | −7.143 | 8.308 | 1.00 | 17.75 | O |
| ATOM | 4627 | N | THR | A | 291 | 48.424 | −7.126 | 7.645 | 1.00 | 17.15 | N |
| ATOM | 4628 | CA | THR | A | 291 | 48.985 | −6.752 | 8.951 | 1.00 | 17.58 | C |
| ATOM | 4630 | CB | THR | A | 291 | 50.526 | −6.575 | 8.879 | 1.00 | 17.62 | C |
| ATOM | 4632 | OG1 | THR | A | 291 | 51.127 | −7.762 | 8.364 | 1.00 | 20.13 | O |
| ATOM | 4634 | CG2 | THR | A | 291 | 51.111 | −6.283 | 10.245 | 1.00 | 16.15 | C |
| ATOM | 4638 | C | THR | A | 291 | 48.424 | −5.434 | 9.474 | 1.00 | 16.88 | C |
| ATOM | 4639 | O | THR | A | 291 | 48.019 | −5.333 | 10.628 | 1.00 | 17.71 | O |
| ATOM | 4641 | N | ILE | A | 292 | 48.439 | −4.416 | 8.627 | 1.00 | 16.65 | N |
| ATOM | 4642 | CA | ILE | A | 292 | 47.965 | −3.097 | 9.014 | 1.00 | 16.25 | C |
| ATOM | 4644 | CB | ILE | A | 292 | 48.375 | −2.018 | 7.991 | 1.00 | 16.11 | C |
| ATOM | 4646 | CG1 | ILE | A | 292 | 49.900 | −1.892 | 7.956 | 1.00 | 16.85 | C |
| ATOM | 4649 | CD1 | ILE | A | 292 | 50.435 | −0.771 | 7.054 | 1.00 | 16.26 | C |
| ATOM | 4653 | CG2 | ILE | A | 292 | 47.752 | −0.671 | 8.344 | 1.00 | 15.32 | C |
| ATOM | 4657 | C | ILE | A | 292 | 46.455 | −3.112 | 9.176 | 1.00 | 16.13 | C |
| ATOM | 4658 | O | ILE | A | 292 | 45.943 | −2.597 | 10.161 | 1.00 | 16.23 | O |
| ATOM | 4660 | N | ILE | A | 293 | 45.744 | −3.710 | 8.222 | 1.00 | 16.03 | N |
| ATOM | 4661 | CA | ILE | A | 293 | 44.288 | −3.725 | 8.268 | 1.00 | 16.25 | C |
| ATOM | 4663 | CB | ILE | A | 293 | 43.656 | −4.367 | 7.010 | 1.00 | 16.69 | C |
| ATOM | 4665 | CG1 | ILE | A | 293 | 44.080 | −3.637 | 5.725 | 1.00 | 15.82 | C |
| ATOM | 4668 | CD1 | ILE | A | 293 | 43.514 | −2.279 | 5.579 | 1.00 | 19.58 | C |
| ATOM | 4672 | CG2 | ILE | A | 293 | 42.128 | −4.372 | 7.109 | 1.00 | 13.37 | C |
| ATOM | 4676 | C | ILE | A | 293 | 43.835 | −4.478 | 9.512 | 1.00 | 17.75 | C |
| ATOM | 4677 | O | ILE | A | 293 | 42.946 | −4.026 | 10.226 | 1.00 | 17.47 | O |
| ATOM | 4679 | N | ASP | A | 294 | 44.470 | −5.618 | 9.778 | 1.00 | 20.03 | N |
| ATOM | 4680 | CA | ASP | A | 294 | 44.151 | −6.440 | 10.943 | 1.00 | 20.51 | C |
| ATOM | 4682 | CB | ASP | A | 294 | 45.027 | −7.699 | 10.954 | 1.00 | 22.36 | C |
| ATOM | 4685 | CG | ASP | A | 294 | 44.728 | −8.636 | 12.119 | 1.00 | 25.69 | C |
| ATOM | 4686 | OD1 | ASP | A | 294 | 43.622 | −8.590 | 12.702 | 1.00 | 37.35 | O |
| ATOM | 4687 | OD2 | ASP | A | 294 | 45.621 | −9.442 | 12.441 | 1.00 | 32.79 | O |
| ATOM | 4688 | C | ASP | A | 294 | 44.336 | −5.627 | 12.213 | 1.00 | 19.61 | C |
| ATOM | 4689 | O | ASP | A | 294 | 43.463 | −5.617 | 13.068 | 1.00 | 20.88 | O |

APPENDIX 1-continued

| | | | | | | | | | | |
|---|---|---|---|---|---|---|---|---|---|---|
| ATOM | 4691 | N | ASP | A | 295 | 45.457 | −4.926 | 12.324 | 1.00 | 18.57 | N |
| ATOM | 4692 | CA | ASP | A | 295 | 45.650 | −3.975 | 13.417 | 1.00 | 18.59 | C |
| ATOM | 4694 | CB | ASP | A | 295 | 46.898 | −3.111 | 13.183 | 1.00 | 19.56 | C |
| ATOM | 4697 | CG | ASP | A | 295 | 48.204 | −3.851 | 13.473 | 1.00 | 24.22 | C |
| ATOM | 4698 | OD1 | ASP | A | 295 | 48.174 | −4.916 | 14.131 | 1.00 | 25.29 | O |
| ATOM | 4699 | OD2 | ASP | A | 295 | 49.272 | −3.347 | 13.048 | 1.00 | 28.75 | O |
| ATOM | 4700 | C | ASP | A | 295 | 44.433 | −3.062 | 13.585 | 1.00 | 17.26 | C |
| ATOM | 4701 | O | ASP | A | 295 | 43.967 | −2.842 | 14.700 | 1.00 | 17.26 | O |
| ATOM | 4703 | N | ILE | A | 296 | 43.921 | −2.542 | 12.473 | 1.00 | 16.54 | N |
| ATOM | 4704 | CA | ILE | A | 296 | 42.797 | −1.600 | 12.495 | 1.00 | 15.83 | C |
| ATOM | 4706 | CB | ILE | A | 296 | 42.503 | −1.033 | 11.086 | 1.00 | 15.84 | C |
| ATOM | 4708 | CG1 | ILE | A | 296 | 43.626 | −0.086 | 10.655 | 1.00 | 16.73 | C |
| ATOM | 4711 | CD1 | ILE | A | 296 | 43.682 | 0.168 | 9.163 | 1.00 | 14.31 | C |
| ATOM | 4715 | CG2 | ILE | A | 296 | 41.162 | −0.310 | 11.060 | 1.00 | 15.97 | C |
| ATOM | 4719 | C | ILE | A | 296 | 41.531 | −2.234 | 13.065 | 1.00 | 15.34 | C |
| ATOM | 4720 | O | ILE | A | 296 | 40.844 | −1.621 | 13.878 | 1.00 | 14.22 | O |
| ATOM | 4722 | N | TYR | A | 297 | 41.234 | −3.462 | 12.647 | 1.00 | 15.33 | N |
| ATOM | 4723 | CA | TYR | A | 297 | 40.043 | −4.171 | 13.132 | 1.00 | 15.57 | C |
| ATOM | 4725 | CB | TYR | A | 297 | 39.638 | −5.273 | 12.155 | 1.00 | 15.40 | C |
| ATOM | 4728 | CG | TYR | A | 297 | 38.925 | −4.807 | 10.902 | 1.00 | 15.08 | C |
| ATOM | 4729 | CD1 | TYR | A | 297 | 39.630 | −4.258 | 9.840 | 1.00 | 15.91 | C |
| ATOM | 4731 | CE1 | TYR | A | 297 | 38.982 | −3.851 | 8.676 | 1.00 | 18.67 | C |
| ATOM | 4733 | CZ | TYR | A | 297 | 37.614 | −4.010 | 8.561 | 1.00 | 19.58 | C |
| ATOM | 4734 | OH | TYR | A | 297 | 36.969 | −3.612 | 7.408 | 1.00 | 19.14 | O |
| ATOM | 4736 | CE2 | TYR | A | 297 | 36.894 | −4.564 | 9.605 | 1.00 | 19.40 | C |
| ATOM | 4738 | CD2 | TYR | A | 297 | 37.549 | −4.963 | 10.761 | 1.00 | 16.57 | C |
| ATOM | 4740 | C | TYR | A | 297 | 40.234 | −4.777 | 14.529 | 1.00 | 15.89 | C |
| ATOM | 4741 | O | TYR | A | 297 | 39.266 | −4.939 | 15.282 | 1.00 | 16.95 | O |
| ATOM | 4743 | N | ASP | A | 298 | 41.474 | −5.111 | 14.877 | 1.00 | 16.19 | N |
| ATOM | 4744 | CA | ASP | A | 298 | 41.753 | −5.797 | 16.133 | 1.00 | 16.54 | C |
| ATOM | 4746 | CB | ASP | A | 298 | 43.083 | −6.545 | 16.049 | 1.00 | 17.40 | C |
| ATOM | 4749 | CG | ASP | A | 298 | 43.280 | −7.525 | 17.190 | 1.00 | 18.90 | C |
| ATOM | 4750 | OD1 | ASP | A | 298 | 42.282 | −8.124 | 17.655 | 1.00 | 24.58 | O |
| ATOM | 4751 | OD2 | ASP | A | 298 | 44.444 | −7.711 | 17.605 | 1.00 | 23.92 | O |
| ATOM | 4752 | C | ASP | A | 298 | 41.775 | −4.851 | 17.323 | 1.00 | 15.49 | C |
| ATOM | 4753 | O | ASP | A | 298 | 41.167 | −5.135 | 18.338 | 1.00 | 14.90 | O |
| ATOM | 4755 | N | VAL | A | 299 | 42.472 | −3.728 | 17.197 | 1.00 | 15.94 | N |
| ATOM | 4756 | CA | VAL | A | 299 | 42.685 | −2.835 | 18.346 | 1.00 | 15.93 | C |
| ATOM | 4758 | CB | VAL | A | 299 | 44.133 | −2.950 | 18.885 | 1.00 | 16.02 | C |
| ATOM | 4760 | CG1 | VAL | A | 299 | 44.322 | −4.270 | 19.588 | 1.00 | 19.85 | C |
| ATOM | 4764 | CG2 | VAL | A | 299 | 45.150 | −2.779 | 17.768 | 1.00 | 15.17 | C |
| ATOM | 4768 | C | VAL | A | 299 | 42.381 | −1.352 | 18.141 | 1.00 | 14.96 | C |
| ATOM | 4769 | O | VAL | A | 299 | 41.961 | −0.695 | 19.085 | 1.00 | 16.18 | O |
| ATOM | 4771 | N | TYR | A | 300 | 42.589 | −0.812 | 16.944 | 1.00 | 14.23 | N |
| ATOM | 4772 | CA | TYR | A | 300 | 42.570 | 0.645 | 16.776 | 1.00 | 14.38 | C |
| ATOM | 4774 | CB | TYR | A | 300 | 43.553 | 1.094 | 15.685 | 1.00 | 14.27 | C |
| ATOM | 4777 | CG | TYR | A | 300 | 43.766 | 2.600 | 15.656 | 1.00 | 15.93 | C |
| ATOM | 4778 | CD1 | TYR | A | 300 | 44.629 | 3.215 | 16.550 | 1.00 | 16.44 | C |
| ATOM | 4780 | CE1 | TYR | A | 300 | 44.825 | 4.589 | 16.532 | 1.00 | 17.44 | C |
| ATOM | 4782 | CZ | TYR | A | 300 | 44.148 | 5.372 | 15.616 | 1.00 | 16.16 | C |
| ATOM | 4783 | OH | TYR | A | 300 | 44.347 | 6.732 | 15.607 | 1.00 | 16.93 | O |
| ATOM | 4785 | CE2 | TYR | A | 300 | 43.283 | 4.793 | 14.719 | 1.00 | 15.86 | C |
| ATOM | 4787 | CD2 | TYR | A | 300 | 43.090 | 3.410 | 14.742 | 1.00 | 17.88 | C |
| ATOM | 4789 | C | TYR | A | 300 | 41.182 | 1.219 | 16.488 | 1.00 | 13.74 | C |
| ATOM | 4790 | O | TYR | A | 300 | 40.763 | 2.178 | 17.130 | 1.00 | 13.75 | O |
| ATOM | 4792 | N | GLY | A | 301 | 40.482 | 0.641 | 15.521 | 1.00 | 13.36 | N |
| ATOM | 4793 | CA | GLY | A | 301 | 39.238 | 1.213 | 15.030 | 1.00 | 13.35 | C |
| ATOM | 4796 | C | GLY | A | 301 | 38.017 | 0.879 | 15.856 | 1.00 | 13.38 | C |
| ATOM | 4797 | O | GLY | A | 301 | 37.901 | −0.228 | 16.373 | 1.00 | 15.55 | O |
| ATOM | 4799 | N | THR | A | 302 | 37.101 | 1.838 | 15.975 | 1.00 | 13.15 | N |
| ATOM | 4800 | CA | THR | A | 302 | 35.788 | 1.584 | 16.567 | 1.00 | 12.98 | C |
| ATOM | 4802 | CB | THR | A | 302 | 35.041 | 2.883 | 16.861 | 1.00 | 12.52 | C |
| ATOM | 4804 | OG1 | THR | A | 302 | 34.895 | 3.621 | 15.646 | 1.00 | 11.42 | O |
| ATOM | 4806 | CG2 | THR | A | 302 | 35.796 | 3.726 | 17.877 | 1.00 | 9.39 | C |
| ATOM | 4810 | C | THR | A | 302 | 34.928 | 0.787 | 15.597 | 1.00 | 13.88 | C |
| ATOM | 4811 | O | THR | A | 302 | 35.199 | 0.761 | 14.392 | 1.00 | 13.49 | O |
| ATOM | 4813 | N | LEU | A | 303 | 33.872 | 0.166 | 16.116 | 1.00 | 14.79 | N |
| ATOM | 4814 | CA | LEU | A | 303 | 32.992 | −0.669 | 15.289 | 1.00 | 14.49 | C |
| ATOM | 4816 | CB | LEU | A | 303 | 31.948 | −1.382 | 16.152 | 1.00 | 14.62 | C |
| ATOM | 4819 | CG | LEU | A | 303 | 31.078 | −2.460 | 15.498 | 1.00 | 16.79 | C |
| ATOM | 4821 | CD1 | LEU | A | 303 | 31.932 | −3.624 | 14.973 | 1.00 | 12.94 | C |
| ATOM | 4825 | CD2 | LEU | A | 303 | 30.026 | −2.948 | 16.493 | 1.00 | 11.28 | C |
| ATOM | 4829 | C | LEU | A | 303 | 32.323 | 0.157 | 14.185 | 1.00 | 14.27 | C |
| ATOM | 4830 | O | LEU | A | 303 | 32.179 | −0.326 | 13.069 | 1.00 | 12.64 | O |
| ATOM | 4832 | N | ASP | A | 304 | 31.943 | 1.400 | 14.500 | 1.00 | 15.41 | N |
| ATOM | 4833 | CA | ASP | A | 304 | 31.381 | 2.329 | 13.510 | 1.00 | 15.64 | C |
| ATOM | 4835 | CB | ASP | A | 304 | 31.055 | 3.686 | 14.142 | 1.00 | 16.20 | C |
| ATOM | 4838 | CG | ASP | A | 304 | 29.726 | 3.698 | 14.876 | 1.00 | 17.84 | C |
| ATOM | 4839 | OD1 | ASP | A | 304 | 29.071 | 2.641 | 14.957 | 1.00 | 19.62 | O |
| ATOM | 4840 | OD2 | ASP | A | 304 | 29.334 | 4.782 | 15.370 | 1.00 | 18.67 | O |

APPENDIX 1-continued

| ATOM | 4841 | C | ASP | A | 304 | 32.332 | 2.554 | 12.344 | 1.00 | 16.15 | C |
|---|---|---|---|---|---|---|---|---|---|---|---|
| ATOM | 4842 | O | ASP | A | 304 | 31.928 | 2.457 | 11.183 | 1.00 | 16.74 | O |
| ATOM | 4844 | N | GLU | A | 305 | 33.588 | 2.864 | 12.657 | 1.00 | 16.40 | N |
| ATOM | 4845 | CA | GLU | A | 305 | 34.629 | 3.042 | 11.635 | 1.00 | 16.14 | C |
| ATOM | 4847 | CB | GLU | A | 305 | 35.956 | 3.430 | 12.284 | 1.00 | 16.55 | C |
| ATOM | 4850 | CG | GLU | A | 305 | 35.982 | 4.814 | 12.910 | 1.00 | 16.50 | C |
| ATOM | 4853 | CD | GLU | A | 305 | 37.280 | 5.090 | 13.653 | 1.00 | 15.99 | C |
| ATOM | 4854 | OE1 | GLU | A | 305 | 37.950 | 4.125 | 14.080 | 1.00 | 11.26 | O |
| ATOM | 4855 | OE2 | GLU | A | 305 | 37.630 | 6.273 | 13.813 | 1.00 | 14.81 | O |
| ATOM | 4856 | C | GLU | A | 305 | 34.850 | 1.773 | 10.818 | 1.00 | 15.75 | C |
| ATOM | 4857 | O | GLU | A | 305 | 35.061 | 1.831 | 9.611 | 1.00 | 14.67 | O |
| ATOM | 4859 | N | LEU | A | 306 | 34.812 | 0.628 | 11.488 | 1.00 | 16.45 | N |
| ATOM | 4860 | CA | LEU | A | 306 | 35.040 | −0.647 | 10.819 | 1.00 | 17.34 | C |
| ATOM | 4862 | CB | LEU | A | 306 | 35.154 | −1.783 | 11.840 | 1.00 | 16.81 | C |
| ATOM | 4865 | CG | LEU | A | 306 | 36.360 | −1.714 | 12.780 | 1.00 | 14.74 | C |
| ATOM | 4867 | CD1 | LEU | A | 306 | 36.460 | −2.987 | 13.597 | 1.00 | 11.90 | C |
| ATOM | 4871 | CD2 | LEU | A | 306 | 37.648 | −1.477 | 12.008 | 1.00 | 13.18 | C |
| ATOM | 4875 | C | LEU | A | 306 | 33.952 | −0.951 | 9.792 | 1.00 | 18.32 | C |
| ATOM | 4876 | O | LEU | A | 306 | 34.236 | −1.539 | 8.748 | 1.00 | 18.25 | O |
| ATOM | 4878 | N | GLU | A | 307 | 32.716 | −0.552 | 10.089 | 1.00 | 20.11 | N |
| ATOM | 4879 | CA | GLU | A | 307 | 31.614 | −0.687 | 9.133 | 1.00 | 21.12 | C |
| ATOM | 4881 | CB | GLU | A | 307 | 30.274 | −0.262 | 9.751 | 1.00 | 22.22 | C |
| ATOM | 4884 | CG | GLU | A | 307 | 29.616 | −1.301 | 10.662 | 1.00 | 27.31 | C |
| ATOM | 4887 | CD | GLU | A | 307 | 28.797 | −2.351 | 9.912 | 1.00 | 35.75 | C |
| ATOM | 4888 | OE1 | GLU | A | 307 | 28.483 | −2.149 | 8.717 | 1.00 | 40.29 | O |
| ATOM | 4889 | OE2 | GLU | A | 307 | 28.456 | −3.385 | 10.529 | 1.00 | 42.00 | O |
| ATOM | 4890 | C | GLU | A | 307 | 31.901 | 0.161 | 7.901 | 1.00 | 19.87 | C |
| ATOM | 4891 | O | GLU | A | 307 | 31.781 | −0.319 | 6.777 | 1.00 | 20.57 | O |
| ATOM | 4893 | N | LEU | A | 308 | 32.291 | 1.414 | 8.123 | 1.00 | 18.78 | N |
| ATOM | 4894 | CA | LEU | A | 308 | 32.592 | 2.336 | 7.027 | 1.00 | 18.39 | C |
| ATOM | 4896 | CB | LEU | A | 308 | 32.999 | 3.715 | 7.559 | 1.00 | 17.90 | C |
| ATOM | 4899 | CG | LEU | A | 308 | 31.906 | 4.545 | 8.235 | 1.00 | 18.12 | C |
| ATOM | 4901 | CD1 | LEU | A | 308 | 32.457 | 5.894 | 8.670 | 1.00 | 18.52 | C |
| ATOM | 4905 | CD2 | LEU | A | 308 | 30.716 | 4.733 | 7.310 | 1.00 | 17.00 | C |
| ATOM | 4909 | C | LEU | A | 308 | 33.685 | 1.789 | 6.118 | 1.00 | 17.92 | C |
| ATOM | 4910 | O | LEU | A | 308 | 33.565 | 1.843 | 4.889 | 1.00 | 17.37 | O |
| ATOM | 4912 | N | PHE | A | 309 | 34.739 | 1.251 | 6.726 | 1.00 | 17.16 | N |
| ATOM | 4913 | CA | PHE | A | 309 | 35.852 | 0.703 | 5.964 | 1.00 | 16.57 | C |
| ATOM | 4915 | CB | PHE | A | 309 | 37.037 | 0.399 | 6.876 | 1.00 | 16.76 | C |
| ATOM | 4918 | CG | PHE | A | 309 | 38.317 | 0.143 | 6.135 | 1.00 | 14.62 | C |
| ATOM | 4919 | CD1 | PHE | A | 309 | 38.645 | −1.132 | 5.705 | 1.00 | 13.65 | C |
| ATOM | 4921 | CE1 | PHE | A | 309 | 39.819 | −1.368 | 5.014 | 1.00 | 12.54 | C |
| ATOM | 4923 | CZ | PHE | A | 309 | 40.672 | −0.343 | 4.756 | 1.00 | 10.64 | C |
| ATOM | 4925 | CE2 | PHE | A | 309 | 40.361 | 0.935 | 5.178 | 1.00 | 12.58 | C |
| ATOM | 4927 | CD2 | PHE | A | 309 | 39.187 | 1.173 | 5.863 | 1.00 | 11.35 | C |
| ATOM | 4929 | C | PHE | A | 309 | 35.444 | −0.552 | 5.203 | 1.00 | 16.22 | C |
| ATOM | 4930 | O | PHE | A | 309 | 35.823 | −0.721 | 4.053 | 1.00 | 15.99 | O |
| ATOM | 4932 | N | THR | A | 310 | 34.682 | −1.433 | 5.844 | 1.00 | 16.65 | N |
| ATOM | 4933 | CA | THR | A | 310 | 34.201 | −2.641 | 5.180 | 1.00 | 16.88 | C |
| ATOM | 4935 | CB | THR | A | 310 | 33.377 | −3.533 | 6.130 | 1.00 | 17.36 | C |
| ATOM | 4937 | OG1 | THR | A | 310 | 34.142 | −3.829 | 7.307 | 1.00 | 15.20 | O |
| ATOM | 4939 | CG2 | THR | A | 310 | 32.970 | −4.836 | 5.437 | 1.00 | 16.45 | C |
| ATOM | 4943 | C | THR | A | 310 | 33.343 | −2.256 | 3.978 | 1.00 | 17.73 | C |
| ATOM | 4944 | O | THR | A | 310 | 33.484 | −2.821 | 2.891 | 1.00 | 18.32 | O |
| ATOM | 4946 | N | ASP | A | 311 | 32.468 | −1.275 | 4.186 | 1.00 | 18.11 | N |
| ATOM | 4947 | CA | ASP | A | 311 | 31.586 | −0.781 | 3.135 | 1.00 | 17.62 | C |
| ATOM | 4949 | CB | ASP | A | 311 | 30.621 | 0.257 | 3.705 | 1.00 | 18.07 | C |
| ATOM | 4952 | CG | ASP | A | 311 | 29.672 | 0.799 | 2.661 | 1.00 | 19.82 | C |
| ATOM | 4953 | OD1 | ASP | A | 311 | 28.815 | 0.024 | 2.192 | 1.00 | 28.04 | O |
| ATOM | 4954 | OD2 | ASP | A | 311 | 29.783 | 1.994 | 2.311 | 1.00 | 25.85 | O |
| ATOM | 4955 | C | ASP | A | 311 | 32.391 | −0.157 | 1.996 | 1.00 | 17.13 | C |
| ATOM | 4956 | O | ASP | A | 311 | 32.088 | −0.381 | 0.818 | 1.00 | 16.48 | O |
| ATOM | 4958 | N | ALA | A | 312 | 33.403 | 0.634 | 2.360 | 1.00 | 15.61 | N |
| ATOM | 4959 | CA | ALA | A | 312 | 34.294 | 1.235 | 1.389 | 1.00 | 14.20 | C |
| ATOM | 4961 | CB | ALA | A | 312 | 35.403 | 1.959 | 2.076 | 1.00 | 14.10 | C |
| ATOM | 4965 | C | ALA | A | 312 | 34.861 | 0.167 | 0.470 | 1.00 | 14.98 | C |
| ATOM | 4966 | O | ALA | A | 312 | 34.812 | 0.324 | −0.756 | 1.00 | 16.36 | O |
| ATOM | 4968 | N | VAL | A | 313 | 35.365 | −0.922 | 1.058 | 1.00 | 14.33 | N |
| ATOM | 4969 | CA | VAL | A | 313 | 36.002 | −1.996 | 0.290 | 1.00 | 14.21 | C |
| ATOM | 4971 | CB | VAL | A | 313 | 36.804 | −2.977 | 1.189 | 1.00 | 14.76 | C |
| ATOM | 4973 | CG1 | VAL | A | 313 | 37.369 | −4.145 | 0.361 | 1.00 | 11.15 | C |
| ATOM | 4977 | CG2 | VAL | A | 313 | 37.932 | −2.246 | 1.892 | 1.00 | 11.08 | C |
| ATOM | 4981 | C | VAL | A | 313 | 34.993 | −2.769 | −0.554 | 1.00 | 14.54 | C |
| ATOM | 4982 | O | VAL | A | 313 | 35.301 | −3.130 | −1.683 | 1.00 | 14.88 | O |
| ATOM | 4984 | N | GLU | A | 314 | 33.801 | −3.018 | −0.015 | 1.00 | 15.40 | N |
| ATOM | 4985 | CA | GLU | A | 314 | 32.730 | −3.683 | −0.771 | 1.00 | 16.05 | C |
| ATOM | 4987 | CB | GLU | A | 314 | 31.485 | −3.897 | 0.101 | 1.00 | 16.15 | C |
| ATOM | 4990 | CG | GLU | A | 314 | 31.607 | −5.034 | 1.117 | 1.00 | 17.87 | C |
| ATOM | 4993 | CD | GLU | A | 314 | 30.407 | −5.144 | 2.062 | 1.00 | 21.90 | C |
| ATOM | 4994 | OE1 | GLU | A | 314 | 29.539 | −4.244 | 2.069 | 1.00 | 28.09 | O |

APPENDIX 1-continued

| ATOM | 4995 | OE2 | GLU | A | 314 | 30.331 | −6.140 | 2.810 | 1.00 | 23.32 | O |
|---|---|---|---|---|---|---|---|---|---|---|---|
| ATOM | 4996 | C | GLU | A | 314 | 32.338 | −2.896 | −2.022 | 1.00 | 16.52 | C |
| ATOM | 4997 | O | GLU | A | 314 | 32.116 | −3.473 | −3.081 | 1.00 | 16.88 | O |
| ATOM | 4999 | N | ARG | A | 315 | 32.255 | −1.579 | −1.899 | 1.00 | 17.15 | N |
| ATOM | 5000 | CA | ARG | A | 315 | 31.809 | −0.742 | −3.008 | 1.00 | 18.03 | C |
| ATOM | 5002 | CB | ARG | A | 315 | 31.191 | 0.551 | −2.474 | 1.00 | 18.37 | C |
| ATOM | 5005 | CG | ARG | A | 315 | 29.910 | 0.296 | −1.684 | 1.00 | 24.14 | C |
| ATOM | 5008 | CD | ARG | A | 315 | 29.125 | 1.561 | −1.389 | 1.00 | 30.56 | C |
| ATOM | 5011 | NE | ARG | A | 315 | 29.929 | 2.511 | −0.629 | 1.00 | 38.03 | N |
| ATOM | 5013 | CZ | ARG | A | 315 | 30.499 | 3.614 | −1.117 | 1.00 | 43.73 | C |
| ATOM | 5014 | NH1 | ARG | A | 315 | 30.359 | 3.966 | −2.399 | 1.00 | 44.78 | N |
| ATOM | 5017 | NH2 | ARG | A | 315 | 31.213 | 4.381 | −0.300 | 1.00 | 44.82 | N |
| ATOM | 5020 | C | ARG | A | 315 | 32.923 | −0.454 | −4.016 | 1.00 | 17.73 | C |
| ATOM | 5021 | O | ARG | A | 315 | 32.650 | −0.212 | −5.188 | 1.00 | 18.37 | O |
| ATOM | 5023 | N | TRP | A | 316 | 34.171 | −0.481 | −3.556 | 1.00 | 17.47 | N |
| ATOM | 5024 | CA | TRP | A | 316 | 35.338 | −0.281 | −4.419 | 1.00 | 16.53 | C |
| ATOM | 5026 | CB | TRP | A | 316 | 35.608 | −1.537 | −5.249 | 1.00 | 15.40 | C |
| ATOM | 5029 | CG | TRP | A | 316 | 37.036 | −1.614 | −5.669 | 1.00 | 14.64 | C |
| ATOM | 5030 | CD1 | TRP | A | 316 | 37.544 | −1.323 | −6.896 | 1.00 | 14.50 | C |
| ATOM | 5032 | NE1 | TRP | A | 316 | 38.906 | −1.487 | −6.892 | 1.00 | 16.54 | N |
| ATOM | 5034 | CE2 | TRP | A | 316 | 39.302 | −1.869 | −5.640 | 1.00 | 14.11 | C |
| ATOM | 5035 | CD2 | TRP | A | 316 | 38.151 | −1.956 | −4.843 | 1.00 | 11.90 | C |
| ATOM | 5036 | CE3 | TRP | A | 316 | 38.283 | −2.338 | −3.506 | 1.00 | 13.84 | C |
| ATOM | 5038 | CZ3 | TRP | A | 316 | 39.537 | −2.612 | −3.017 | 1.00 | 13.63 | C |
| ATOM | 5040 | CH2 | TRP | A | 316 | 40.665 | −2.520 | −3.836 | 1.00 | 17.90 | C |
| ATOM | 5042 | CZ2 | TRP | A | 316 | 40.568 | −2.154 | −5.151 | 1.00 | 17.45 | C |
| ATOM | 5044 | C | TRP | A | 316 | 35.215 | 0.967 | −5.308 | 1.00 | 17.27 | C |
| ATOM | 5045 | O | TRP | A | 316 | 35.450 | 0.935 | −6.513 | 1.00 | 17.36 | O |
| ATOM | 5047 | N | ASP | A | 317 | 34.845 | 2.067 | −4.671 | 1.00 | 19.42 | N |
| ATOM | 5048 | CA | ASP | A | 317 | 34.645 | 3.346 | −5.320 | 1.00 | 20.29 | C |
| ATOM | 5050 | CB | ASP | A | 317 | 33.186 | 3.782 | −5.133 | 1.00 | 20.62 | C |
| ATOM | 5053 | CG | ASP | A | 317 | 32.924 | 5.220 | −5.560 | 1.00 | 21.12 | C |
| ATOM | 5054 | OD1 | ASP | A | 317 | 33.659 | 5.761 | −6.415 | 1.00 | 19.88 | O |
| ATOM | 5055 | OD2 | ASP | A | 317 | 31.952 | 5.805 | −5.039 | 1.00 | 27.88 | O |
| ATOM | 5056 | C | ASP | A | 317 | 35.600 | 4.326 | −4.651 | 1.00 | 21.82 | C |
| ATOM | 5057 | O | ASP | A | 317 | 35.543 | 4.523 | −3.442 | 1.00 | 21.54 | O |
| ATOM | 5059 | N | VAL | A | 318 | 36.497 | 4.908 | −5.440 | 1.00 | 24.54 | N |
| ATOM | 5060 | CA | VAL | A | 318 | 37.442 | 5.892 | −4.936 | 1.00 | 25.84 | C |
| ATOM | 5062 | CB | VAL | A | 318 | 38.522 | 6.234 | −5.985 | 1.00 | 25.61 | C |
| ATOM | 5064 | CG1 | VAL | A | 318 | 37.930 | 7.053 | −7.128 | 1.00 | 22.86 | C |
| ATOM | 5068 | CG2 | VAL | A | 318 | 39.671 | 6.978 | −5.331 | 1.00 | 23.84 | C |
| ATOM | 5072 | C | VAL | A | 318 | 36.719 | 7.168 | −4.534 | 1.00 | 28.43 | C |
| ATOM | 5073 | O | VAL | A | 318 | 37.088 | 7.792 | −3.544 | 1.00 | 27.88 | O |
| ATOM | 5075 | N | ASN | A | 319 | 35.674 | 7.530 | −5.284 | 1.00 | 32.04 | N |
| ATOM | 5076 | CA | ASN | A | 319 | 34.969 | 8.816 | −5.101 | 1.00 | 35.31 | C |
| ATOM | 5078 | CB | ASN | A | 319 | 34.119 | 9.178 | −6.336 | 1.00 | 35.75 | C |
| ATOM | 5081 | CG | ASN | A | 319 | 34.915 | 9.136 | −7.653 | 1.00 | 40.12 | C |
| ATOM | 5082 | OD1 | ASN | A | 319 | 35.868 | 9.902 | −7.848 | 1.00 | 43.06 | O |
| ATOM | 5083 | ND2 | ASN | A | 319 | 34.508 | 8.246 | −8.567 | 1.00 | 34.41 | N |
| ATOM | 5086 | C | ASN | A | 319 | 34.073 | 8.811 | −3.868 | 1.00 | 37.28 | C |
| ATOM | 5087 | O | ASN | A | 319 | 33.141 | 9.607 | −3.776 | 1.00 | 38.17 | O |
| ATOM | 5089 | N | ALA | A | 320 | 34.336 | 7.885 | −2.947 | 1.00 | 39.03 | N |
| ATOM | 5090 | CA | ALA | A | 320 | 33.756 | 7.899 | −1.615 | 1.00 | 40.48 | C |
| ATOM | 5092 | CB | ALA | A | 320 | 32.559 | 6.975 | −1.550 | 1.00 | 40.67 | C |
| ATOM | 5096 | C | ALA | A | 320 | 34.837 | 7.489 | −0.608 | 1.00 | 41.93 | C |
| ATOM | 5097 | O | ALA | A | 320 | 34.636 | 6.636 | 0.254 | 1.00 | 42.74 | O |
| ATOM | 5099 | N | ILE | A | 321 | 36.006 | 8.095 | −0.771 | 1.00 | 42.86 | N |
| ATOM | 5100 | CA | ILE | A | 321 | 37.055 | 8.073 | 0.232 | 1.00 | 42.96 | C |
| ATOM | 5102 | CB | ILE | A | 321 | 38.414 | 8.457 | −0.407 | 1.00 | 42.98 | C |
| ATOM | 5104 | CG1 | ILE | A | 321 | 39.575 | 8.031 | 0.478 | 1.00 | 44.97 | C |
| ATOM | 5107 | CD1 | ILE | A | 321 | 40.896 | 8.642 | 0.060 | 1.00 | 46.59 | C |
| ATOM | 5111 | CG2 | ILE | A | 321 | 38.496 | 9.958 | −0.702 | 1.00 | 43.87 | C |
| ATOM | 5115 | C | ILE | A | 321 | 36.678 | 9.089 | 1.314 | 1.00 | 43.79 | C |
| ATOM | 5116 | O | ILE | A | 321 | 36.938 | 8.870 | 2.498 | 1.00 | 45.72 | O |
| ATOM | 5118 | N | ASN | A | 322 | 36.024 | 10.177 | 0.887 | 1.00 | 42.17 | N |
| ATOM | 5119 | CA | ASN | A | 322 | 35.695 | 11.340 | 1.729 | 1.00 | 40.19 | C |
| ATOM | 5121 | CB | ASN | A | 322 | 34.859 | 12.346 | 0.922 | 1.00 | 40.65 | C |
| ATOM | 5124 | CG | ASN | A | 322 | 35.585 | 12.869 | −0.313 | 1.00 | 42.39 | C |
| ATOM | 5125 | OD1 | ASN | A | 322 | 36.640 | 13.497 | −0.208 | 1.00 | 44.33 | O |
| ATOM | 5126 | ND2 | ASN | A | 322 | 35.013 | 12.619 | −1.490 | 1.00 | 41.11 | N |
| ATOM | 5129 | C | ASN | A | 322 | 34.945 | 11.044 | 3.028 | 1.00 | 37.45 | C |
| ATOM | 5130 | O | ASN | A | 322 | 35.014 | 11.824 | 3.969 | 1.00 | 37.12 | O |
| ATOM | 5132 | N | ASP | A | 323 | 34.229 | 9.927 | 3.069 | 1.00 | 35.06 | N |
| ATOM | 5133 | CA | ASP | A | 323 | 33.381 | 9.576 | 4.210 | 1.00 | 33.48 | C |
| ATOM | 5135 | CB | ASP | A | 323 | 32.206 | 8.694 | 3.745 | 1.00 | 35.16 | C |
| ATOM | 5138 | CG | ASP | A | 323 | 31.671 | 9.088 | 2.358 | 1.00 | 39.08 | C |
| ATOM | 5139 | OD1 | ASP | A | 323 | 31.625 | 10.303 | 2.052 | 1.00 | 44.10 | O |
| ATOM | 5140 | OD2 | ASP | A | 323 | 31.310 | 8.177 | 1.575 | 1.00 | 38.71 | O |
| ATOM | 5141 | C | ASP | A | 323 | 34.170 | 8.852 | 5.313 | 1.00 | 30.30 | C |
| ATOM | 5142 | O | ASP | A | 323 | 33.743 | 8.825 | 6.466 | 1.00 | 30.13 | O |

APPENDIX 1-continued

| | | | | | | | | | | |
|---|---|---|---|---|---|---|---|---|---|---|
| ATOM | 5144 | N | LEU | A | 324 | 35.309 | 8.258 | 4.953 | 1.00 | 27.17 | N |
| ATOM | 5145 | CA | LEU | A | 324 | 36.182 | 7.573 | 5.915 | 1.00 | 23.84 | C |
| ATOM | 5147 | CB | LEU | A | 324 | 37.198 | 6.696 | 5.181 | 1.00 | 22.54 | C |
| ATOM | 5150 | CG | LEU | A | 324 | 36.673 | 5.538 | 4.328 | 1.00 | 20.51 | C |
| ATOM | 5152 | CD1 | LEU | A | 324 | 37.803 | 4.942 | 3.516 | 1.00 | 17.04 | C |
| ATOM | 5156 | CD2 | LEU | A | 324 | 36.012 | 4.456 | 5.176 | 1.00 | 17.06 | C |
| ATOM | 5160 | C | LEU | A | 324 | 36.953 | 8.560 | 6.802 | 1.00 | 22.30 | C |
| ATOM | 5161 | O | LEU | A | 324 | 37.312 | 9.648 | 6.353 | 1.00 | 22.20 | O |
| ATOM | 5163 | N | PRO | A | 325 | 37.232 | 8.180 | 8.063 | 1.00 | 20.38 | N |
| ATOM | 5164 | CA | PRO | A | 325 | 38.151 | 8.993 | 8.858 | 1.00 | 19.43 | C |
| ATOM | 5166 | CB | PRO | A | 325 | 38.181 | 8.280 | 10.218 | 1.00 | 19.10 | C |
| ATOM | 5169 | CG | PRO | A | 325 | 37.658 | 6.937 | 9.974 | 1.00 | 20.10 | C |
| ATOM | 5172 | CD | PRO | A | 325 | 36.704 | 7.045 | 8.834 | 1.00 | 20.49 | C |
| ATOM | 5175 | C | PRO | A | 325 | 39.548 | 9.050 | 8.232 | 1.00 | 18.15 | C |
| ATOM | 5176 | O | PRO | A | 325 | 39.892 | 8.201 | 7.421 | 1.00 | 17.37 | O |
| ATOM | 5177 | N | ASP | A | 326 | 40.336 | 10.047 | 8.620 | 1.00 | 17.88 | N |
| ATOM | 5178 | CA | ASP | A | 326 | 41.611 | 10.331 | 7.958 | 1.00 | 17.65 | C |
| ATOM | 5180 | CB | ASP | A | 326 | 42.367 | 11.460 | 8.673 | 1.00 | 18.15 | C |
| ATOM | 5183 | CG | ASP | A | 326 | 41.739 | 12.825 | 8.440 | 1.00 | 17.32 | C |
| ATOM | 5184 | OD1 | ASP | A | 326 | 40.763 | 12.890 | 7.662 | 1.00 | 20.36 | O |
| ATOM | 5185 | OD2 | ASP | A | 326 | 42.215 | 13.826 | 9.030 | 1.00 | 12.44 | O |
| ATOM | 5186 | C | ASP | A | 326 | 42.513 | 9.115 | 7.794 | 1.00 | 17.23 | C |
| ATOM | 5187 | O | ASP | A | 326 | 42.926 | 8.805 | 6.673 | 1.00 | 17.06 | O |
| ATOM | 5189 | N | TYR | A | 327 | 42.816 | 8.418 | 8.886 | 1.00 | 15.83 | N |
| ATOM | 5190 | CA | TYR | A | 327 | 43.757 | 7.302 | 8.791 | 1.00 | 14.44 | C |
| ATOM | 5192 | CB | TYR | A | 327 | 44.073 | 6.702 | 10.166 | 1.00 | 14.37 | C |
| ATOM | 5195 | CG | TYR | A | 327 | 42.996 | 5.836 | 10.774 | 1.00 | 12.94 | C |
| ATOM | 5196 | CD1 | TYR | A | 327 | 41.914 | 6.400 | 11.437 | 1.00 | 10.39 | C |
| ATOM | 5198 | CE1 | TYR | A | 327 | 40.931 | 5.611 | 12.006 | 1.00 | 13.24 | C |
| ATOM | 5200 | CZ | TYR | A | 327 | 41.028 | 4.239 | 11.927 | 1.00 | 11.47 | C |
| ATOM | 5201 | OH | TYR | A | 327 | 40.056 | 3.451 | 12.496 | 1.00 | 9.36 | O |
| ATOM | 5203 | CE2 | TYR | A | 327 | 42.101 | 3.654 | 11.284 | 1.00 | 11.89 | C |
| ATOM | 5205 | CD2 | TYR | A | 327 | 43.081 | 4.452 | 10.719 | 1.00 | 7.67 | C |
| ATOM | 5207 | C | TYR | A | 327 | 43.270 | 6.242 | 7.805 | 1.00 | 13.74 | C |
| ATOM | 5208 | O | TYR | A | 327 | 44.073 | 5.644 | 7.088 | 1.00 | 13.73 | O |
| ATOM | 5210 | N | MET | A | 328 | 41.959 | 6.038 | 7.742 | 1.00 | 13.03 | N |
| ATOM | 5211 | CA | MET | A | 328 | 41.387 | 5.066 | 6.815 | 1.00 | 13.75 | C |
| ATOM | 5213 | CB | MET | A | 328 | 39.964 | 4.686 | 7.241 | 1.00 | 13.89 | C |
| ATOM | 5216 | CG | MET | A | 328 | 39.903 | 3.782 | 8.475 | 1.00 | 14.06 | C |
| ATOM | 5219 | SD | MET | A | 328 | 38.205 | 3.354 | 8.967 | 1.00 | 13.00 | S |
| ATOM | 5220 | CE | MET | A | 328 | 38.465 | 1.789 | 9.798 | 1.00 | 11.82 | C |
| ATOM | 5224 | C | MET | A | 328 | 41.412 | 5.544 | 5.349 | 1.00 | 14.27 | C |
| ATOM | 5225 | O | MET | A | 328 | 41.503 | 4.720 | 4.431 | 1.00 | 14.37 | O |
| ATOM | 5227 | N | LYS | A | 329 | 41.326 | 6.858 | 5.126 | 1.00 | 15.46 | N |
| ATOM | 5228 | CA | LYS | A | 329 | 41.433 | 7.424 | 3.768 | 1.00 | 16.19 | C |
| ATOM | 5230 | CB | LYS | A | 329 | 41.362 | 8.948 | 3.781 | 1.00 | 16.83 | C |
| ATOM | 5233 | CG | LYS | A | 329 | 39.973 | 9.537 | 3.873 | 1.00 | 20.82 | C |
| ATOM | 5236 | CD | LYS | A | 329 | 40.039 | 10.924 | 4.485 | 1.00 | 25.45 | C |
| ATOM | 5239 | CE | LYS | A | 329 | 38.742 | 11.676 | 4.337 | 1.00 | 27.53 | C |
| ATOM | 5242 | NZ | LYS | A | 329 | 38.554 | 12.532 | 5.521 | 1.00 | 27.07 | N |
| ATOM | 5246 | C | LYS | A | 329 | 42.754 | 7.035 | 3.151 | 1.00 | 15.90 | C |
| ATOM | 5247 | O | LYS | A | 329 | 42.813 | 6.598 | 2.000 | 1.00 | 16.89 | O |
| ATOM | 5249 | N | LEU | A | 330 | 43.813 | 7.205 | 3.933 | 1.00 | 14.92 | N |
| ATOM | 5250 | CA | LEU | A | 330 | 45.153 | 6.854 | 3.509 | 1.00 | 14.91 | C |
| ATOM | 5252 | CB | LEU | A | 330 | 46.166 | 7.329 | 4.554 | 1.00 | 15.21 | C |
| ATOM | 5255 | CG | LEU | A | 330 | 47.605 | 7.498 | 4.083 | 1.00 | 16.18 | C |
| ATOM | 5257 | CD1 | LEU | A | 330 | 47.673 | 8.516 | 2.958 | 1.00 | 16.06 | C |
| ATOM | 5261 | CD2 | LEU | A | 330 | 48.471 | 7.935 | 5.243 | 1.00 | 17.93 | C |
| ATOM | 5265 | C | LEU | A | 330 | 45.301 | 5.350 | 3.278 | 1.00 | 15.28 | C |
| ATOM | 5266 | O | LEU | A | 330 | 45.853 | 4.929 | 2.263 | 1.00 | 17.00 | O |
| ATOM | 5268 | N | ACYS | A | 331 | 44.798 | 4.546 | 4.209 | 0.50 | 14.63 | N |
| ATOM | 5269 | N | BCYS | A | 331 | 44.808 | 4.552 | 4.224 | 0.50 | 15.33 | N |
| ATOM | 5270 | CA | ACYS | A | 331 | 44.931 | 3.097 | 4.121 | 0.50 | 13.93 | C |
| ATOM | 5271 | CA | BCYS | A | 331 | 44.892 | 3.095 | 4.144 | 0.50 | 15.34 | C |
| ATOM | 5274 | CB | ACYS | A | 331 | 44.513 | 2.447 | 5.439 | 0.50 | 14.00 | C |
| ATOM | 5275 | CB | BCYS | A | 331 | 44.331 | 2.466 | 5.420 | 0.50 | 15.61 | C |
| ATOM | 5280 | SG | ACYS | A | 331 | 44.757 | 0.659 | 5.474 | 0.50 | 9.77 | S |
| ATOM | 5281 | SG | BCYS | A | 331 | 45.460 | 2.456 | 6.817 | 0.50 | 17.77 | S |
| ATOM | 5284 | C | ACYS | A | 331 | 44.114 | 2.506 | 2.970 | 0.50 | 14.47 | C |
| ATOM | 5285 | C | BCYS | A | 331 | 44.125 | 2.537 | 2.954 | 0.50 | 15.16 | C |
| ATOM | 5286 | O | ACYS | A | 331 | 44.589 | 1.619 | 2.257 | 0.50 | 14.22 | O |
| ATOM | 5287 | O | BCYS | A | 331 | 44.640 | 1.706 | 2.202 | 0.50 | 14.99 | O |
| ATOM | 5290 | N | PHE | A | 332 | 42.886 | 2.990 | 2.801 | 1.00 | 15.02 | N |
| ATOM | 5291 | CA | PHE | A | 332 | 42.007 | 2.504 | 1.739 | 1.00 | 15.70 | C |
| ATOM | 5293 | CB | PHE | A | 332 | 40.591 | 3.086 | 1.883 | 1.00 | 16.91 | C |
| ATOM | 5296 | CG | PHE | A | 332 | 39.696 | 2.782 | 0.715 | 1.00 | 18.22 | C |
| ATOM | 5297 | CD1 | PHE | A | 332 | 39.111 | 1.537 | 0.583 | 1.00 | 20.06 | C |
| ATOM | 5299 | CE1 | PHE | A | 332 | 38.291 | 1.242 | −0.508 | 1.00 | 18.34 | C |
| ATOM | 5301 | CZ | PHE | A | 332 | 38.060 | 2.197 | −1.474 | 1.00 | 16.81 | C |
| ATOM | 5303 | CE2 | PHE | A | 332 | 38.648 | 3.449 | −1.356 | 1.00 | 19.38 | C |

APPENDIX 1-continued

| ATOM | 5305 | CD2 | PHE | A | 332 | 39.459 | 3.737 | −0.266 | 1.00 | 20.23 | C |
|---|---|---|---|---|---|---|---|---|---|---|---|
| ATOM | 5307 | C | PHE | A | 332 | 42.566 | 2.835 | 0.365 | 1.00 | 14.28 | C |
| ATOM | 5308 | O | PHE | A | 332 | 42.642 | 1.972 | −0.490 | 1.00 | 15.28 | O |
| ATOM | 5310 | N | LEU | A | 333 | 42.976 | 4.080 | 0.170 | 1.00 | 14.04 | N |
| ATOM | 5311 | CA | LEU | A | 333 | 43.539 | 4.513 | −1.110 | 1.00 | 14.40 | C |
| ATOM | 5313 | CB | LEU | A | 333 | 43.795 | 6.026 | −1.109 | 1.00 | 13.69 | C |
| ATOM | 5316 | CG | LEU | A | 333 | 44.175 | 6.650 | −2.458 | 1.00 | 12.53 | C |
| ATOM | 5318 | CD1 | LEU | A | 333 | 43.315 | 6.103 | −3.568 | 1.00 | 9.21 | C |
| ATOM | 5322 | CD2 | LEU | A | 333 | 44.074 | 8.182 | −2.403 | 1.00 | 5.83 | C |
| ATOM | 5326 | C | LEU | A | 333 | 44.827 | 3.761 | −1.472 | 1.00 | 14.58 | C |
| ATOM | 5327 | O | LEU | A | 333 | 45.021 | 3.408 | −2.634 | 1.00 | 15.12 | O |
| ATOM | 5329 | N | ALA | A | 334 | 45.694 | 3.517 | −0.486 | 1.00 | 13.94 | N |
| ATOM | 5330 | CA | ALA | A | 334 | 46.893 | 2.693 | −0.699 | 1.00 | 14.13 | C |
| ATOM | 5332 | CB | ALA | A | 334 | 47.703 | 2.584 | 0.585 | 1.00 | 12.74 | C |
| ATOM | 5336 | C | ALA | A | 334 | 46.500 | 1.298 | −1.204 | 1.00 | 14.10 | C |
| ATOM | 5337 | O | ALA | A | 334 | 47.035 | 0.795 | −2.196 | 1.00 | 13.54 | O |
| ATOM | 5339 | N | LEU | A | 335 | 45.540 | 0.699 | −0.515 | 1.00 | 14.19 | N |
| ATOM | 5340 | CA | LEU | A | 335 | 45.011 | −0.604 | −0.878 | 1.00 | 15.38 | C |
| ATOM | 5342 | CB | LEU | A | 335 | 43.981 | −1.032 | 0.166 | 1.00 | 15.83 | C |
| ATOM | 5345 | CG | LEU | A | 335 | 43.336 | −2.395 | 0.008 | 1.00 | 16.89 | C |
| ATOM | 5347 | CD1 | LEU | A | 335 | 44.377 | −3.505 | 0.133 | 1.00 | 16.87 | C |
| ATOM | 5351 | CD2 | LEU | A | 335 | 42.260 | −2.525 | 1.063 | 1.00 | 15.39 | C |
| ATOM | 5355 | C | LEU | A | 335 | 44.355 | −0.582 | −2.260 | 1.00 | 15.12 | C |
| ATOM | 5356 | O | LEU | A | 335 | 44.571 | −1.477 | −3.084 | 1.00 | 14.74 | O |
| ATOM | 5358 | N | TYR | A | 336 | 43.555 | 0.450 | −2.499 | 1.00 | 13.32 | N |
| ATOM | 5359 | CA | TYR | A | 336 | 42.829 | 0.594 | −3.758 | 1.00 | 12.46 | C |
| ATOM | 5361 | CB | TYR | A | 336 | 42.017 | 1.881 | −3.697 | 1.00 | 12.29 | C |
| ATOM | 5364 | CG | TYR | A | 336 | 41.034 | 2.111 | −4.810 | 1.00 | 13.39 | C |
| ATOM | 5365 | CD1 | TYR | A | 336 | 39.785 | 1.499 | −4.795 | 1.00 | 15.98 | C |
| ATOM | 5367 | CE1 | TYR | A | 336 | 38.864 | 1.728 | −5.798 | 1.00 | 14.25 | C |
| ATOM | 5369 | CZ | TYR | A | 336 | 39.177 | 2.594 | −6.827 | 1.00 | 16.95 | C |
| ATOM | 5370 | OH | TYR | A | 336 | 38.262 | 2.826 | −7.830 | 1.00 | 17.48 | O |
| ATOM | 5372 | CE2 | TYR | A | 336 | 40.408 | 3.222 | −6.855 | 1.00 | 17.10 | C |
| ATOM | 5374 | CD2 | TYR | A | 336 | 41.324 | 2.983 | −5.845 | 1.00 | 12.44 | C |
| ATOM | 5376 | C | TYR | A | 336 | 43.801 | 0.636 | −4.936 | 1.00 | 11.66 | C |
| ATOM | 5377 | O | TYR | A | 336 | 43.667 | −0.121 | −5.895 | 1.00 | 10.26 | O |
| ATOM | 5379 | N | ASN | A | 337 | 44.789 | 1.521 | −4.836 | 1.00 | 10.76 | N |
| ATOM | 5380 | CA | ASN | A | 337 | 45.795 | 1.674 | −5.865 | 1.00 | 9.77 | C |
| ATOM | 5382 | CB | ASN | A | 337 | 46.737 | 2.822 | −5.516 | 1.00 | 9.39 | C |
| ATOM | 5385 | CG | ASN | A | 337 | 46.102 | 4.182 | −5.716 | 1.00 | 9.44 | C |
| ATOM | 5386 | OD1 | ASN | A | 337 | 45.004 | 4.288 | −6.251 | 1.00 | 15.48 | O |
| ATOM | 5387 | ND2 | ASN | A | 337 | 46.794 | 5.231 | −5.290 | 1.00 | 5.51 | N |
| ATOM | 5390 | C | ASN | A | 337 | 46.593 | 0.399 | −6.062 | 1.00 | 10.42 | C |
| ATOM | 5391 | O | ASN | A | 337 | 46.827 | −0.021 | −7.189 | 1.00 | 12.27 | O |
| ATOM | 5393 | N | THR | A | 338 | 46.999 | −0.228 | −4.966 | 1.00 | 10.42 | N |
| ATOM | 5394 | CA | THR | A | 338 | 47.808 | −1.437 | −5.047 | 1.00 | 9.59 | C |
| ATOM | 5396 | CB | THR | A | 338 | 48.206 | −1.935 | −3.644 | 1.00 | 9.20 | C |
| ATOM | 5398 | OG1 | THR | A | 338 | 49.030 | −0.951 | −3.013 | 1.00 | 10.32 | O |
| ATOM | 5400 | CG2 | THR | A | 338 | 48.971 | −3.239 | −3.730 | 1.00 | 6.16 | C |
| ATOM | 5404 | C | THR | A | 338 | 47.080 | −2.544 | −5.810 | 1.00 | 9.77 | C |
| ATOM | 5405 | O | THR | A | 338 | 47.643 | −3.123 | −6.736 | 1.00 | 9.33 | O |
| ATOM | 5407 | N | ILE | A | 339 | 45.835 | −2.822 | −5.424 | 1.00 | 10.69 | N |
| ATOM | 5408 | CA | ILE | A | 339 | 45.037 | −3.873 | −6.066 | 1.00 | 11.11 | C |
| ATOM | 5410 | CB | ILE | A | 339 | 43.731 | −4.183 | −5.299 | 1.00 | 10.99 | C |
| ATOM | 5412 | CG1 | ILE | A | 339 | 44.009 | −4.543 | −3.832 | 1.00 | 11.57 | C |
| ATOM | 5415 | CD1 | ILE | A | 339 | 45.176 | −5.465 | −3.611 | 1.00 | 11.93 | C |
| ATOM | 5419 | CG2 | ILE | A | 339 | 42.969 | −5.318 | −5.968 | 1.00 | 10.25 | C |
| ATOM | 5423 | C | ILE | A | 339 | 44.702 | −3.500 | −7.516 | 1.00 | 11.94 | C |
| ATOM | 5424 | O | ILE | A | 339 | 44.814 | −4.330 | −8.411 | 1.00 | 13.78 | O |
| ATOM | 5426 | N | ASN | A | 340 | 44.321 | −2.257 | −7.767 | 1.00 | 11.14 | N |
| ATOM | 5427 | CA | ASN | A | 340 | 44.093 | −1.845 | −9.146 | 1.00 | 12.07 | C |
| ATOM | 5429 | CB | ASN | A | 340 | 43.630 | −0.380 | −9.236 | 1.00 | 11.61 | C |
| ATOM | 5432 | CG | ASN | A | 340 | 42.224 | −0.167 | −8.686 | 1.00 | 12.18 | C |
| ATOM | 5433 | OD1 | ASN | A | 340 | 41.467 | −1.118 | −8.486 | 1.00 | 12.96 | O |
| ATOM | 5434 | ND2 | ASN | A | 340 | 41.869 | 1.092 | −8.445 | 1.00 | 13.65 | N |
| ATOM | 5437 | C | ASN | A | 340 | 45.347 | −2.049 | −9.996 | 1.00 | 12.28 | C |
| ATOM | 5438 | O | ASN | A | 340 | 45.253 | −2.444 | −11.149 | 1.00 | 13.92 | O |
| ATOM | 5440 | N | GLU | A | 341 | 46.518 | −1.788 | −9.426 | 1.00 | 12.30 | N |
| ATOM | 5441 | CA | AGLU | A | 341 | 47.749 | −1.939 | −10.195 | 0.50 | 12.50 | C |
| ATOM | 5442 | CA | BGLU | A | 341 | 47.800 | −1.937 | −10.125 | 0.50 | 12.27 | C |
| ATOM | 5445 | CB | AGLU | A | 341 | 48.922 | −1.199 | −9.548 | 0.50 | 12.74 | C |
| ATOM | 5446 | CB | BGLU | A | 341 | 48.923 | −1.381 | −9.235 | 0.50 | 12.30 | C |
| ATOM | 5451 | CG | AGLU | A | 341 | 49.242 | 0.087 | −10.291 | 0.50 | 15.08 | C |
| ATOM | 5452 | CG | BGLU | A | 341 | 50.323 | −1.358 | −9.837 | 0.50 | 13.55 | C |
| ATOM | 5457 | CD | AGLU | A | 341 | 49.793 | 1.171 | −9.405 | 0.50 | 17.89 | C |
| ATOM | 5458 | CD | BGLU | A | 341 | 51.343 | −0.733 | −8.887 | 0.50 | 14.23 | C |
| ATOM | 5459 | OE1 | AGLU | A | 341 | 49.712 | 1.030 | −8.165 | 0.50 | 20.72 | O |
| ATOM | 5460 | OE1 | BGLU | A | 341 | 51.062 | −0.650 | −7.667 | 0.50 | 15.78 | O |
| ATOM | 5461 | OE2 | AGLU | A | 341 | 50.298 | 2.170 | −9.958 | 0.50 | 17.56 | O |
| ATOM | 5462 | OE2 | BGLU | A | 341 | 52.421 | −0.319 | −9.358 | 0.50 | 11.79 | O |

APPENDIX 1-continued

| ATOM | 5463 | C | GLU | A | 341 | 48.068 | −3.404 | −10.477 | 1.00 | 12.01 | C |
|---|---|---|---|---|---|---|---|---|---|---|---|
| ATOM | 5464 | O | GLU | A | 341 | 48.536 | −3.729 | −11.560 | 1.00 | 11.80 | O |
| ATOM | 5466 | N | ILE | A | 342 | 47.776 | −4.295 | −9.538 | 1.00 | 12.43 | N |
| ATOM | 5467 | CA | ILE | A | 342 | 47.925 | −5.726 | −9.800 | 1.00 | 12.18 | C |
| ATOM | 5469 | CB | ILE | A | 342 | 47.743 | −6.566 | −8.528 | 1.00 | 11.60 | C |
| ATOM | 5471 | CG1 | ILE | A | 342 | 48.871 | −6.291 | −7.527 | 1.00 | 12.00 | C |
| ATOM | 5474 | CD1 | ILE | A | 342 | 48.615 | −6.861 | −6.144 | 1.00 | 10.85 | C |
| ATOM | 5478 | CG2 | ILE | A | 342 | 47.726 | −8.034 | −8.863 | 1.00 | 8.35 | C |
| ATOM | 5482 | C | ILE | A | 342 | 46.919 | −6.152 | −10.887 | 1.00 | 13.54 | C |
| ATOM | 5483 | O | ILE | A | 342 | 47.251 | −6.943 | −11.777 | 1.00 | 15.29 | O |
| ATOM | 5485 | N | ALA | A | 343 | 45.702 | −5.611 | −10.829 | 1.00 | 13.12 | N |
| ATOM | 5486 | CA | ALA | A | 343 | 44.718 | −5.832 | −11.890 | 1.00 | 12.52 | C |
| ATOM | 5488 | CB | ALA | A | 343 | 43.398 | −5.134 | −11.569 | 1.00 | 11.07 | C |
| ATOM | 5492 | C | ALA | A | 343 | 45.249 | −5.362 | −13.246 | 1.00 | 12.15 | C |
| ATOM | 5493 | O | ALA | A | 343 | 45.048 | −6.035 | −14.258 | 1.00 | 13.04 | O |
| ATOM | 5495 | N | TYR | A | 344 | 45.924 | −4.217 | −13.265 | 1.00 | 11.46 | N |
| ATOM | 5496 | CA | TYR | A | 344 | 46.483 | −3.695 | −14.509 | 1.00 | 11.43 | C |
| ATOM | 5498 | CB | TYR | A | 344 | 47.136 | −2.333 | −14.301 | 1.00 | 10.28 | C |
| ATOM | 5501 | CG | TYR | A | 344 | 47.745 | −1.804 | −15.563 | 1.00 | 6.11 | C |
| ATOM | 5502 | CD1 | TYR | A | 344 | 46.979 | −1.106 | −16.488 | 1.00 | 5.19 | C |
| ATOM | 5504 | CE1 | TYR | A | 344 | 47.540 | −0.630 | −17.671 | 1.00 | 5.77 | C |
| ATOM | 5506 | CZ | TYR | A | 344 | 48.874 | −0.861 | −17.933 | 1.00 | 3.91 | C |
| ATOM | 5507 | OH | TYR | A | 344 | 49.432 | −0.399 | −19.099 | 1.00 | 8.41 | O |
| ATOM | 5509 | CE2 | TYR | A | 344 | 49.652 | −1.549 | −17.027 | 1.00 | 3.93 | C |
| ATOM | 5511 | CD2 | TYR | A | 344 | 49.084 | −2.022 | −15.852 | 1.00 | 5.43 | C |
| ATOM | 5513 | C | TYR | A | 344 | 47.514 | −4.656 | −15.080 | 1.00 | 13.12 | C |
| ATOM | 5514 | O | TYR | A | 344 | 47.511 | −4.944 | −16.271 | 1.00 | 12.48 | O |
| ATOM | 5516 | N | ASP | A | 345 | 48.400 | −5.148 | −14.215 | 1.00 | 14.96 | N |
| ATOM | 5517 | CA | ASP | A | 345 | 49.454 | −6.073 | −14.632 | 1.00 | 14.86 | C |
| ATOM | 5519 | CB | ASP | A | 345 | 50.278 | −6.552 | −13.428 | 1.00 | 14.44 | C |
| ATOM | 5522 | CG | ASP | A | 345 | 51.136 | −5.446 | −12.817 | 1.00 | 16.57 | C |
| ATOM | 5523 | OD1 | ASP | A | 345 | 51.487 | −4.467 | −13.513 | 1.00 | 18.74 | O |
| ATOM | 5524 | OD2 | ASP | A | 345 | 51.466 | −5.561 | −11.625 | 1.00 | 23.50 | O |
| ATOM | 5525 | C | ASP | A | 345 | 48.855 | −7.258 | −15.365 | 1.00 | 14.39 | C |
| ATOM | 5526 | O | ASP | A | 345 | 49.292 | −7.592 | −16.458 | 1.00 | 14.24 | O |
| ATOM | 5528 | N | ASN | A | 346 | 47.841 | −7.874 | −14.763 | 1.00 | 15.32 | N |
| ATOM | 5529 | CA | ASN | A | 346 | 47.186 | −9.042 | −15.347 | 1.00 | 14.92 | C |
| ATOM | 5531 | CB | ASN | A | 346 | 46.266 | −9.713 | −14.339 | 1.00 | 14.83 | C |
| ATOM | 5534 | CG | ASN | A | 346 | 47.026 | −10.475 | −13.303 | 1.00 | 15.26 | C |
| ATOM | 5535 | OD1 | ASN | A | 346 | 47.258 | −11.672 | −13.453 | 1.00 | 19.10 | O |
| ATOM | 5536 | ND2 | ASN | A | 346 | 47.469 | −9.782 | −12.260 | 1.00 | 16.18 | N |
| ATOM | 5539 | C | ASN | A | 346 | 46.409 | −8.719 | −16.609 | 1.00 | 15.60 | C |
| ATOM | 5540 | O | ASN | A | 346 | 46.378 | −9.527 | −17.544 | 1.00 | 16.80 | O |
| ATOM | 5542 | N | LEU | A | 347 | 45.787 | −7.546 | −16.648 | 1.00 | 14.76 | N |
| ATOM | 5543 | CA | LEU | A | 347 | 45.130 | −7.112 | −17.868 | 1.00 | 14.61 | C |
| ATOM | 5545 | CB | LEU | A | 347 | 44.352 | −5.809 | −17.651 | 1.00 | 14.92 | C |
| ATOM | 5548 | CG | LEU | A | 347 | 43.721 | −5.218 | −18.914 | 1.00 | 14.84 | C |
| ATOM | 5550 | CD1 | LEU | A | 347 | 42.715 | −6.190 | −19.497 | 1.00 | 11.67 | C |
| ATOM | 5554 | CD2 | LEU | A | 347 | 43.088 | −3.876 | −18.614 | 1.00 | 11.92 | C |
| ATOM | 5558 | C | LEU | A | 347 | 46.178 | −6.947 | −18.965 | 1.00 | 14.97 | C |
| ATOM | 5559 | O | LEU | A | 347 | 45.967 | −7.398 | −20.081 | 1.00 | 15.96 | O |
| ATOM | 5561 | N | LYS | A | 348 | 47.307 | −6.318 | −18.640 | 1.00 | 15.37 | N |
| ATOM | 5562 | CA | LYS | A | 348 | 48.382 | −6.112 | −19.613 | 1.00 | 16.52 | C |
| ATOM | 5564 | CB | LYS | A | 348 | 49.518 | −5.265 | −19.022 | 1.00 | 16.29 | C |
| ATOM | 5567 | CG | LYS | A | 348 | 50.569 | −4.841 | −20.050 | 1.00 | 17.74 | C |
| ATOM | 5570 | CD | LYS | A | 348 | 51.624 | −3.879 | −19.481 | 1.00 | 21.53 | C |
| ATOM | 5573 | CE | LYS | A | 348 | 52.924 | −4.574 | −19.086 | 1.00 | 23.19 | C |
| ATOM | 5576 | NZ | LYS | A | 348 | 52.791 | −5.374 | −17.844 | 1.00 | 26.07 | N |
| ATOM | 5580 | C | LYS | A | 348 | 48.953 | −7.440 | −20.109 | 1.00 | 17.40 | C |
| ATOM | 5581 | O | LYS | A | 348 | 49.088 | −7.645 | −21.311 | 1.00 | 16.65 | O |
| ATOM | 5583 | N | ASP | A | 349 | 49.280 | −8.336 | −19.185 | 1.00 | 18.21 | N |
| ATOM | 5584 | CA | ASP | A | 349 | 50.060 | −9.521 | −19.535 | 1.00 | 20.43 | C |
| ATOM | 5586 | CB | ASP | A | 349 | 51.031 | −9.873 | −18.400 | 1.00 | 20.31 | C |
| ATOM | 5589 | CG | ASP | A | 349 | 52.074 | −8.793 | −18.172 | 1.00 | 21.16 | C |
| ATOM | 5590 | OD1 | ASP | A | 349 | 52.285 | −7.949 | −19.075 | 1.00 | 24.16 | O |
| ATOM | 5591 | OD2 | ASP | A | 349 | 52.681 | −8.780 | −17.085 | 1.00 | 25.79 | O |
| ATOM | 5592 | C | ASP | A | 349 | 49.221 | −10.740 | −19.927 | 1.00 | 21.21 | C |
| ATOM | 5593 | O | ASP | A | 349 | 49.687 | −11.572 | −20.707 | 1.00 | 21.34 | O |
| ATOM | 5595 | N | LYS | A | 350 | 47.997 | −10.841 | −19.403 | 1.00 | 21.88 | N |
| ATOM | 5596 | CA | LYS | A | 350 | 47.118 | −11.991 | −19.694 | 1.00 | 21.16 | C |
| ATOM | 5598 | CB | LYS | A | 350 | 46.741 | −12.705 | −18.403 | 1.00 | 20.09 | C |
| ATOM | 5601 | CG | LYS | A | 350 | 47.926 | −13.179 | −17.600 | 1.00 | 24.60 | C |
| ATOM | 5604 | CD | LYS | A | 350 | 47.459 | −13.855 | −16.313 | 1.00 | 31.14 | C |
| ATOM | 5607 | CE | LYS | A | 350 | 48.615 | −14.176 | −15.384 | 1.00 | 32.30 | C |
| ATOM | 5610 | NZ | LYS | A | 350 | 48.163 | −14.116 | −13.979 | 1.00 | 29.99 | N |
| ATOM | 5614 | C | LYS | A | 350 | 45.836 | −11.644 | −20.454 | 1.00 | 20.16 | C |
| ATOM | 5615 | O | LYS | A | 350 | 45.106 | −12.539 | −20.854 | 1.00 | 20.90 | O |
| ATOM | 5617 | N | GLY | A | 351 | 45.549 | −10.363 | −20.639 | 1.00 | 19.21 | N |
| ATOM | 5618 | CA | GLY | A | 351 | 44.363 | −9.955 | −21.388 | 1.00 | 18.87 | C |
| ATOM | 5621 | C | GLY | A | 351 | 43.044 | −10.298 | −20.716 | 1.00 | 18.23 | C |

APPENDIX 1-continued

| ATOM | 5622 | O | GLY | A | 351 | 42.040 | −10.496 | −21.391 | 1.00 | 17.31 | O |
|---|---|---|---|---|---|---|---|---|---|---|---|
| ATOM | 5624 | N | GLU | A | 352 | 43.044 | −10.371 | −19.388 | 1.00 | 18.71 | N |
| ATOM | 5625 | CA | GLU | A | 352 | 41.823 | −10.635 | −18.628 | 1.00 | 19.80 | C |
| ATOM | 5627 | CB | GLU | A | 352 | 41.901 | −11.988 | −17.912 | 1.00 | 20.50 | C |
| ATOM | 5630 | CG | GLU | A | 352 | 42.232 | −13.192 | −18.813 | 1.00 | 23.98 | C |
| ATOM | 5633 | CD | GLU | A | 352 | 41.035 | −13.738 | −19.579 | 1.00 | 29.52 | C |
| ATOM | 5634 | OE1 | GLU | A | 352 | 40.005 | −13.031 | −19.692 | 1.00 | 32.18 | O |
| ATOM | 5635 | OE2 | GLU | A | 352 | 41.134 | −14.881 | −20.080 | 1.00 | 35.96 | O |
| ATOM | 5636 | C | GLU | A | 352 | 41.603 | −9.547 | −17.592 | 1.00 | 19.63 | C |
| ATOM | 5637 | O | GLU | A | 352 | 42.551 | −8.960 | −17.082 | 1.00 | 20.46 | O |
| ATOM | 5639 | N | ASN | A | 353 | 40.341 | −9.278 | −17.290 | 1.00 | 19.72 | N |
| ATOM | 5640 | CA | ASN | A | 353 | 39.981 | −8.404 | −16.187 | 1.00 | 18.98 | C |
| ATOM | 5642 | CB | ASN | A | 353 | 38.768 | −7.557 | −16.551 | 1.00 | 18.32 | C |
| ATOM | 5645 | CG | ASN | A | 353 | 38.301 | −6.702 | −15.406 | 1.00 | 20.99 | C |
| ATOM | 5646 | OD1 | ASN | A | 353 | 38.931 | −6.667 | −14.337 | 1.00 | 20.74 | O |
| ATOM | 5647 | ND2 | ASN | A | 353 | 37.184 | −6.006 | −15.609 | 1.00 | 22.54 | N |
| ATOM | 5650 | C | ASN | A | 353 | 39.686 | −9.246 | −14.953 | 1.00 | 17.99 | C |
| ATOM | 5651 | O | ASN | A | 353 | 38.593 | −9.773 | −14.805 | 1.00 | 18.92 | O |
| ATOM | 5653 | N | ILE | A | 354 | 40.668 | −9.357 | −14.067 | 1.00 | 16.81 | N |
| ATOM | 5654 | CA | ILE | A | 354 | 40.537 | −10.173 | −12.864 | 1.00 | 15.17 | C |
| ATOM | 5656 | CB | ILE | A | 354 | 41.836 | −10.976 | −12.586 | 1.00 | 15.39 | C |
| ATOM | 5658 | CG1 | ILE | A | 354 | 43.010 | −10.051 | −12.225 | 1.00 | 17.00 | C |
| ATOM | 5661 | CD1 | ILE | A | 354 | 44.125 | −10.749 | −11.461 | 1.00 | 20.37 | C |
| ATOM | 5665 | CG2 | ILE | A | 354 | 42.196 | −11.815 | −13.782 | 1.00 | 12.65 | C |
| ATOM | 5669 | C | ILE | A | 354 | 40.180 | −9.331 | −11.629 | 1.00 | 14.45 | C |
| ATOM | 5670 | O | ILE | A | 354 | 40.099 | −9.847 | −10.511 | 1.00 | 12.79 | O |
| ATOM | 5672 | N | LEU | A | 355 | 39.950 | −8.039 | −11.835 | 1.00 | 14.19 | N |
| ATOM | 5673 | CA | LEU | A | 355 | 39.719 | −7.129 | −10.718 | 1.00 | 14.17 | C |
| ATOM | 5675 | CB | LEU | A | 355 | 39.480 | −5.705 | −11.231 | 1.00 | 12.42 | C |
| ATOM | 5678 | CG | LEU | A | 355 | 39.391 | −4.650 | −10.137 | 1.00 | 11.47 | C |
| ATOM | 5680 | CD1 | LEU | A | 355 | 40.646 | −4.678 | −9.292 | 1.00 | 6.95 | C |
| ATOM | 5684 | CD2 | LEU | A | 355 | 39.148 | −3.272 | −10.730 | 1.00 | 9.67 | C |
| ATOM | 5688 | C | LEU | A | 355 | 38.587 | −7.565 | −9.758 | 1.00 | 14.65 | C |
| ATOM | 5689 | O | LEU | A | 355 | 38.759 | −7.508 | −8.543 | 1.00 | 14.60 | O |
| ATOM | 5691 | N | PRO | A | 356 | 37.434 | −8.006 | −10.293 | 1.00 | 15.55 | N |
| ATOM | 5692 | CA | PRO | A | 356 | 36.341 | −8.425 | −9.401 | 1.00 | 15.63 | C |
| ATOM | 5694 | CB | PRO | A | 356 | 35.284 | −8.968 | −10.370 | 1.00 | 15.81 | C |
| ATOM | 5697 | CG | PRO | A | 356 | 35.536 | −8.248 | −11.636 | 1.00 | 15.52 | C |
| ATOM | 5700 | CD | PRO | A | 356 | 37.035 | −8.089 | −11.710 | 1.00 | 15.21 | C |
| ATOM | 5703 | C | PRO | A | 356 | 36.731 | −9.505 | −8.411 | 1.00 | 15.51 | C |
| ATOM | 5704 | O | PRO | A | 356 | 36.235 | −9.512 | −7.295 | 1.00 | 16.14 | O |
| ATOM | 5705 | N | TYR | A | 357 | 37.617 | −10.404 | −8.825 | 1.00 | 16.37 | N |
| ATOM | 5706 | CA | TYR | A | 357 | 38.049 | −11.519 | −7.982 | 1.00 | 16.67 | C |
| ATOM | 5708 | CB | TYR | A | 357 | 38.720 | −12.603 | −8.830 | 1.00 | 17.29 | C |
| ATOM | 5711 | CG | TYR | A | 357 | 37.909 | −13.005 | −10.052 | 1.00 | 21.26 | C |
| ATOM | 5712 | CD1 | TYR | A | 357 | 36.674 | −13.619 | −9.917 | 1.00 | 25.64 | C |
| ATOM | 5714 | CE1 | TYR | A | 357 | 35.927 | −13.982 | −11.025 | 1.00 | 25.97 | C |
| ATOM | 5716 | CZ | TYR | A | 357 | 36.409 | −13.730 | −12.287 | 1.00 | 27.46 | C |
| ATOM | 5717 | OH | TYR | A | 357 | 35.657 | −14.100 | −13.376 | 1.00 | 34.19 | O |
| ATOM | 5719 | CE2 | TYR | A | 357 | 37.632 | −13.118 | −12.455 | 1.00 | 25.17 | C |
| ATOM | 5721 | CD2 | TYR | A | 357 | 38.376 | −12.761 | −11.339 | 1.00 | 25.11 | C |
| ATOM | 5723 | C | TYR | A | 357 | 38.984 | −11.063 | −6.861 | 1.00 | 16.92 | C |
| ATOM | 5724 | O | TYR | A | 357 | 38.933 | −11.603 | −5.754 | 1.00 | 18.10 | O |
| ATOM | 5726 | N | LEU | A | 358 | 39.823 | −10.066 | −7.148 | 1.00 | 17.16 | N |
| ATOM | 5727 | CA | LEU | A | 358 | 40.752 | −9.498 | −6.158 | 1.00 | 16.20 | C |
| ATOM | 5729 | CB | LEU | A | 358 | 41.808 | −8.629 | −6.844 | 1.00 | 16.00 | C |
| ATOM | 5732 | CG | LEU | A | 358 | 42.646 | −9.282 | −7.950 | 1.00 | 14.84 | C |
| ATOM | 5734 | CD1 | LEU | A | 358 | 43.805 | −8.382 | −8.330 | 1.00 | 10.56 | C |
| ATOM | 5738 | CD2 | LEU | A | 358 | 43.170 | −10.648 | −7.512 | 1.00 | 12.82 | C |
| ATOM | 5742 | C | LEU | A | 358 | 40.010 | −8.664 | −5.124 | 1.00 | 16.18 | C |
| ATOM | 5743 | O | LEU | A | 358 | 40.300 | −8.731 | −3.928 | 1.00 | 15.89 | O |
| ATOM | 5745 | N | THR | A | 359 | 39.043 | −7.885 | −5.592 | 1.00 | 16.77 | N |
| ATOM | 5746 | CA | THR | A | 359 | 38.249 | −7.034 | −4.720 | 1.00 | 17.41 | C |
| ATOM | 5748 | CB | THR | A | 359 | 37.443 | −6.006 | −5.536 | 1.00 | 16.65 | C |
| ATOM | 5750 | OG1 | THR | A | 359 | 36.632 | −6.687 | −6.489 | 1.00 | 18.62 | O |
| ATOM | 5752 | CG2 | THR | A | 359 | 38.374 | −5.068 | −6.291 | 1.00 | 17.08 | C |
| ATOM | 5756 | C | THR | A | 359 | 37.325 | −7.889 | −3.845 | 1.00 | 18.90 | C |
| ATOM | 5757 | O | THR | A | 359 | 37.211 | −7.661 | −2.642 | 1.00 | 19.65 | O |
| ATOM | 5759 | N | LYS | A | 360 | 36.685 | −8.889 | −4.441 | 1.00 | 19.60 | N |
| ATOM | 5760 | CA | LYS | A | 360 | 35.891 | −9.848 | −3.668 | 1.00 | 20.45 | C |
| ATOM | 5762 | CB | LYS | A | 360 | 35.377 | −10.962 | −4.580 | 1.00 | 20.46 | C |
| ATOM | 5765 | CG | LYS | A | 360 | 34.546 | −12.035 | −3.897 | 1.00 | 24.40 | C |
| ATOM | 5768 | CD | LYS | A | 360 | 33.185 | −11.503 | −3.435 | 1.00 | 30.15 | C |
| ATOM | 5771 | CE | LYS | A | 360 | 32.364 | −12.598 | −2.738 | 1.00 | 31.64 | C |
| ATOM | 5774 | NZ | LYS | A | 360 | 31.450 | −12.051 | −1.693 | 1.00 | 28.80 | N |
| ATOM | 5778 | C | LYS | A | 360 | 36.713 | −10.438 | −2.511 | 1.00 | 20.23 | C |
| ATOM | 5779 | O | LYS | A | 360 | 36.252 | −10.486 | −1.367 | 1.00 | 20.87 | O |
| ATOM | 5781 | N | ALA | A | 361 | 37.933 | −10.876 | −2.817 | 1.00 | 19.45 | N |
| ATOM | 5782 | CA | ALA | A | 361 | 38.849 | −11.396 | −1.801 | 1.00 | 18.14 | C |
| ATOM | 5784 | CB | ALA | A | 361 | 40.219 | −11.632 | −2.401 | 1.00 | 17.05 | C |

APPENDIX 1-continued

| ATOM | 5788 | C | ALA | A | 361 | 38.959 | −10.452 | −0.597 | 1.00 | 18.20 | C |
|---|---|---|---|---|---|---|---|---|---|---|---|
| ATOM | 5789 | O | ALA | A | 361 | 38.850 | −10.889 | 0.554 | 1.00 | 18.81 | O |
| ATOM | 5791 | N | TRP | A | 362 | 39.168 | −9.164 | −0.869 | 1.00 | 16.65 | N |
| ATOM | 5792 | CA | TRP | A | 362 | 39.345 | −8.168 | 0.194 | 1.00 | 15.23 | C |
| ATOM | 5794 | CB | TRP | A | 362 | 39.963 | −6.887 | −0.363 | 1.00 | 14.11 | C |
| ATOM | 5797 | CG | TRP | A | 362 | 41.421 | −6.998 | −0.437 | 1.00 | 12.95 | C |
| ATOM | 5798 | CD1 | TRP | A | 362 | 42.179 | −7.247 | −1.540 | 1.00 | 9.85 | C |
| ATOM | 5800 | NE1 | TRP | A | 362 | 43.499 | −7.320 | −1.196 | 1.00 | 12.46 | N |
| ATOM | 5802 | CE2 | TRP | A | 362 | 43.612 | −7.121 | 0.156 | 1.00 | 14.43 | C |
| ATOM | 5803 | CD2 | TRP | A | 362 | 42.320 | −6.914 | 0.660 | 1.00 | 14.03 | C |
| ATOM | 5804 | CE3 | TRP | A | 362 | 42.155 | −6.685 | 2.029 | 1.00 | 14.93 | C |
| ATOM | 5806 | CZ3 | TRP | A | 362 | 43.267 | −6.663 | 2.830 | 1.00 | 14.69 | C |
| ATOM | 5808 | CH2 | TRP | A | 362 | 44.542 | −6.866 | 2.299 | 1.00 | 14.56 | C |
| ATOM | 5810 | CZ2 | TRP | A | 362 | 44.735 | −7.094 | 0.968 | 1.00 | 15.89 | C |
| ATOM | 5812 | C | TRP | A | 362 | 38.054 | −7.854 | 0.949 | 1.00 | 15.33 | C |
| ATOM | 5813 | O | TRP | A | 362 | 38.079 | −7.629 | 2.160 | 1.00 | 14.82 | O |
| ATOM | 5815 | N | ALA | A | 363 | 36.936 | −7.830 | 0.231 | 1.00 | 15.17 | N |
| ATOM | 5816 | CA | ALA | A | 363 | 35.630 | −7.651 | 0.849 | 1.00 | 14.51 | C |
| ATOM | 5818 | CB | ALA | A | 363 | 34.540 | −7.591 | −0.216 | 1.00 | 12.83 | C |
| ATOM | 5822 | C | ALA | A | 363 | 35.372 | −8.798 | 1.831 | 1.00 | 14.93 | C |
| ATOM | 5823 | O | ALA | A | 363 | 34.947 | −8.562 | 2.966 | 1.00 | 14.26 | O |
| ATOM | 5825 | N | ASP | A | 364 | 35.657 | −10.029 | 1.394 | 1.00 | 15.09 | N |
| ATOM | 5826 | CA | ASP | A | 364 | 35.445 | −11.221 | 2.219 | 1.00 | 14.96 | C |
| ATOM | 5828 | CB | ASP | A | 364 | 35.697 | −12.506 | 1.420 | 1.00 | 14.65 | C |
| ATOM | 5831 | CG | ASP | A | 364 | 34.607 | −12.792 | 0.386 | 1.00 | 15.43 | C |
| ATOM | 5832 | OD1 | ASP | A | 364 | 33.604 | −12.050 | 0.292 | 1.00 | 18.73 | O |
| ATOM | 5833 | OD2 | ASP | A | 364 | 34.761 | −13.775 | −0.356 | 1.00 | 22.17 | O |
| ATOM | 5834 | C | ASP | A | 364 | 36.323 | −11.204 | 3.460 | 1.00 | 15.67 | C |
| ATOM | 5835 | O | ASP | A | 364 | 35.844 | −11.466 | 4.565 | 1.00 | 17.80 | O |
| ATOM | 5837 | N | LEU | A | 365 | 37.598 | −10.873 | 3.289 | 1.00 | 15.88 | N |
| ATOM | 5838 | CA | LEU | A | 365 | 38.510 | −10.769 | 4.423 | 1.00 | 16.76 | C |
| ATOM | 5840 | CB | LEU | A | 365 | 39.925 | −10.452 | 3.949 | 1.00 | 17.27 | C |
| ATOM | 5843 | CG | LEU | A | 365 | 40.998 | −10.353 | 5.036 | 1.00 | 17.42 | C |
| ATOM | 5845 | CD1 | LEU | A | 365 | 40.987 | −11.590 | 5.902 | 1.00 | 12.95 | C |
| ATOM | 5849 | CD2 | LEU | A | 365 | 42.368 | −10.142 | 4.411 | 1.00 | 17.41 | C |
| ATOM | 5853 | C | LEU | A | 365 | 38.064 | −9.687 | 5.391 | 1.00 | 18.04 | C |
| ATOM | 5854 | O | LEU | A | 365 | 38.058 | −9.887 | 6.613 | 1.00 | 19.09 | O |
| ATOM | 5856 | N | CYS | A | 366 | 37.692 | −8.537 | 4.841 | 1.00 | 18.42 | N |
| ATOM | 5857 | CA | CYS | A | 366 | 37.265 | −7.417 | 5.664 | 1.00 | 18.05 | C |
| ATOM | 5859 | CB | CYS | A | 366 | 37.106 | −6.141 | 4.829 | 1.00 | 18.27 | C |
| ATOM | 5862 | SG | CYS | A | 366 | 38.695 | −5.330 | 4.422 | 1.00 | 17.97 | S |
| ATOM | 5864 | C | CYS | A | 366 | 35.987 | −7.755 | 6.414 | 1.00 | 17.44 | C |
| ATOM | 5865 | O | CYS | A | 366 | 35.820 | −7.355 | 7.559 | 1.00 | 18.14 | O |
| ATOM | 5867 | N | ASN | A | 367 | 35.092 | −8.508 | 5.790 | 1.00 | 17.59 | N |
| ATOM | 5868 | CA | ASN | A | 367 | 33.872 | −8.920 | 6.486 | 1.00 | 17.07 | C |
| ATOM | 5870 | CB | ASN | A | 367 | 32.826 | −9.441 | 5.510 | 1.00 | 15.44 | C |
| ATOM | 5873 | CG | ASN | A | 367 | 31.893 | −8.359 | 5.058 | 1.00 | 16.48 | C |
| ATOM | 5874 | OD1 | ASN | A | 367 | 31.084 | −7.857 | 5.844 | 1.00 | 21.26 | O |
| ATOM | 5875 | ND2 | ASN | A | 367 | 32.004 | −7.972 | 3.798 | 1.00 | 14.60 | N |
| ATOM | 5878 | C | ASN | A | 367 | 34.149 | −9.942 | 7.579 | 1.00 | 17.69 | C |
| ATOM | 5879 | O | ASN | A | 367 | 33.453 | −9.961 | 8.596 | 1.00 | 18.52 | O |
| ATOM | 5881 | N | ALA | A | 368 | 35.162 | −10.781 | 7.370 | 1.00 | 17.11 | N |
| ATOM | 5882 | CA | ALA | A | 368 | 35.560 | −11.751 | 8.381 | 1.00 | 16.83 | C |
| ATOM | 5884 | CB | ALA | A | 368 | 36.539 | −12.765 | 7.802 | 1.00 | 16.79 | C |
| ATOM | 5888 | C | ALA | A | 368 | 36.172 | −11.040 | 9.584 | 1.00 | 16.35 | C |
| ATOM | 5889 | O | ALA | A | 368 | 35.901 | −11.406 | 10.725 | 1.00 | 15.97 | O |
| ATOM | 5891 | N | PHE | A | 369 | 37.002 | −10.030 | 9.333 | 1.00 | 16.26 | N |
| ATOM | 5892 | CA | PHE | A | 369 | 37.503 | −9.200 | 10.427 | 1.00 | 16.89 | C |
| ATOM | 5894 | CB | PHE | A | 369 | 38.446 | −8.088 | 9.943 | 1.00 | 16.81 | C |
| ATOM | 5897 | CG | PHE | A | 369 | 39.788 | −8.565 | 9.461 | 1.00 | 19.32 | C |
| ATOM | 5898 | CD1 | PHE | A | 369 | 40.414 | −9.671 | 10.022 | 1.00 | 21.86 | C |
| ATOM | 5900 | CE1 | PHE | A | 369 | 41.655 | −10.081 | 9.572 | 1.00 | 21.61 | C |
| ATOM | 5902 | CZ | PHE | A | 369 | 42.292 | −9.380 | 8.577 | 1.00 | 23.30 | C |
| ATOM | 5904 | CE2 | PHE | A | 369 | 41.694 | −8.260 | 8.031 | 1.00 | 21.86 | C |
| ATOM | 5906 | CD2 | PHE | A | 369 | 40.456 | −7.858 | 8.474 | 1.00 | 20.80 | C |
| ATOM | 5908 | C | PHE | A | 369 | 36.339 | −8.543 | 11.152 | 1.00 | 15.84 | C |
| ATOM | 5909 | O | PHE | A | 369 | 36.302 | −8.514 | 12.375 | 1.00 | 16.60 | O |
| ATOM | 5911 | N | LEU | A | 370 | 35.400 | −8.004 | 10.386 | 1.00 | 15.25 | N |
| ATOM | 5912 | CA | LEU | A | 370 | 34.288 | −7.259 | 10.954 | 1.00 | 15.74 | C |
| ATOM | 5914 | CB | LEU | A | 370 | 33.418 | −6.679 | 9.842 | 1.00 | 15.97 | C |
| ATOM | 5917 | CG | LEU | A | 370 | 32.208 | −5.850 | 10.264 | 1.00 | 16.08 | C |
| ATOM | 5919 | CD1 | LEU | A | 370 | 32.618 | −4.682 | 11.162 | 1.00 | 13.02 | C |
| ATOM | 5923 | CD2 | LEU | A | 370 | 31.495 | −5.358 | 9.018 | 1.00 | 15.46 | C |
| ATOM | 5927 | C | LEU | A | 370 | 33.456 | −8.151 | 11.857 | 1.00 | 14.86 | C |
| ATOM | 5928 | O | LEU | A | 370 | 33.019 | −7.724 | 12.922 | 1.00 | 13.61 | O |
| ATOM | 5930 | N | GLN | A | 371 | 33.248 | −9.388 | 11.415 | 1.00 | 14.96 | N |
| ATOM | 5931 | CA | GLN | A | 371 | 32.540 | −10.379 | 12.204 | 1.00 | 15.51 | C |
| ATOM | 5933 | CB | GLN | A | 371 | 32.484 | −11.722 | 11.464 | 1.00 | 15.87 | C |
| ATOM | 5936 | CG | GLN | A | 371 | 31.720 | −12.828 | 12.202 | 1.00 | 16.69 | C |
| ATOM | 5939 | CD | GLN | A | 371 | 30.310 | −12.407 | 12.564 | 1.00 | 16.34 | C |

APPENDIX 1-continued

| | | | | | | | | | | |
|---|---|---|---|---|---|---|---|---|---|---|
| ATOM | 5940 | OE1 | GLN | A | 371 | 30.058 | −11.910 | 13.665 | 1.00 | 18.89 | O |
| ATOM | 5941 | NE2 | GLN | A | 371 | 29.388 | −12.570 | 11.626 | 1.00 | 18.01 | N |
| ATOM | 5944 | C | GLN | A | 371 | 33.219 | −10.558 | 13.555 | 1.00 | 15.77 | C |
| ATOM | 5945 | O | GLN | A | 371 | 32.542 | −10.625 | 14.586 | 1.00 | 16.34 | O |
| ATOM | 5947 | N | GLU | A | 372 | 34.550 | −10.634 | 13.543 | 1.00 | 15.39 | N |
| ATOM | 5948 | CA | GLU | A | 372 | 35.314 | −10.832 | 14.772 | 1.00 | 15.88 | C |
| ATOM | 5950 | CB | GLU | A | 372 | 36.797 | −11.110 | 14.478 | 1.00 | 16.07 | C |
| ATOM | 5953 | CG | GLU | A | 372 | 37.080 | −12.546 | 14.058 | 1.00 | 19.38 | C |
| ATOM | 5956 | CD | GLU | A | 372 | 38.513 | −12.769 | 13.600 | 1.00 | 24.01 | C |
| ATOM | 5957 | OE1 | GLU | A | 372 | 39.316 | −11.816 | 13.649 | 1.00 | 32.49 | O |
| ATOM | 5958 | OE2 | GLU | A | 372 | 38.841 | −13.905 | 13.193 | 1.00 | 29.37 | O |
| ATOM | 5959 | C | GLU | A | 372 | 35.154 | −9.641 | 15.711 | 1.00 | 15.23 | C |
| ATOM | 5960 | O | GLU | A | 372 | 34.964 | −9.820 | 16.909 | 1.00 | 15.07 | O |
| ATOM | 5962 | N | ALA | A | 373 | 35.216 | −8.435 | 15.157 | 1.00 | 15.04 | N |
| ATOM | 5963 | CA | ALA | A | 373 | 34.969 | −7.225 | 15.927 | 1.00 | 15.94 | C |
| ATOM | 5965 | CB | ALA | A | 373 | 35.169 | −5.989 | 15.066 | 1.00 | 14.89 | C |
| ATOM | 5969 | C | ALA | A | 373 | 33.558 | −7.251 | 16.495 | 1.00 | 16.92 | C |
| ATOM | 5970 | O | ALA | A | 373 | 33.355 | −6.992 | 17.681 | 1.00 | 17.49 | O |
| ATOM | 5972 | N | LYS | A | 374 | 32.586 | −7.584 | 15.652 | 1.00 | 17.90 | N |
| ATOM | 5973 | CA | LYS | A | 374 | 31.191 | −7.622 | 16.083 | 1.00 | 19.15 | C |
| ATOM | 5975 | CB | LYS | A | 374 | 30.255 | −7.953 | 14.920 | 1.00 | 20.40 | C |
| ATOM | 5978 | CG | LYS | A | 374 | 29.877 | −6.757 | 14.066 | 1.00 | 23.48 | C |
| ATOM | 5981 | CD | LYS | A | 374 | 28.920 | −7.172 | 12.962 | 1.00 | 28.64 | C |
| ATOM | 5984 | CE | LYS | A | 374 | 28.478 | −5.991 | 12.113 | 1.00 | 29.85 | C |
| ATOM | 5987 | NZ | LYS | A | 374 | 27.970 | −6.432 | 10.777 | 1.00 | 29.46 | N |
| ATOM | 5991 | C | LYS | A | 374 | 30.971 | −8.612 | 17.216 | 1.00 | 18.39 | C |
| ATOM | 5992 | O | LYS | A | 374 | 30.240 | −8.312 | 18.148 | 1.00 | 18.53 | O |
| ATOM | 5994 | N | TRP | A | 375 | 31.602 | −9.782 | 17.138 | 1.00 | 17.94 | N |
| ATOM | 5995 | CA | TRP | A | 375 | 31.497 | −10.780 | 18.208 | 1.00 | 17.60 | C |
| ATOM | 5997 | CB | TRP | A | 375 | 32.153 | −12.107 | 17.803 | 1.00 | 17.34 | C |
| ATOM | 6000 | CG | TRP | A | 375 | 31.346 | −12.981 | 16.887 | 1.00 | 14.45 | C |
| ATOM | 6001 | CD1 | TRP | A | 375 | 29.982 | −13.070 | 16.812 | 1.00 | 16.34 | C |
| ATOM | 6003 | NE1 | TRP | A | 375 | 29.617 | −14.007 | 15.875 | 1.00 | 13.18 | N |
| ATOM | 6005 | CE2 | TRP | A | 375 | 30.749 | −14.557 | 15.337 | 1.00 | 12.63 | C |
| ATOM | 6006 | CD2 | TRP | A | 375 | 31.859 | −13.938 | 15.958 | 1.00 | 12.50 | C |
| ATOM | 6007 | CE3 | TRP | A | 375 | 33.147 | −14.329 | 15.582 | 1.00 | 11.36 | C |
| ATOM | 6009 | CZ3 | TRP | A | 375 | 33.289 | −15.304 | 14.610 | 1.00 | 13.99 | C |
| ATOM | 6011 | CH2 | TRP | A | 375 | 32.166 | −15.898 | 14.005 | 1.00 | 15.83 | C |
| ATOM | 6013 | CZ2 | TRP | A | 375 | 30.891 | −15.540 | 14.355 | 1.00 | 13.88 | C |
| ATOM | 6015 | C | TRP | A | 375 | 32.137 | −10.279 | 19.502 | 1.00 | 18.44 | C |
| ATOM | 6016 | O | TRP | A | 375 | 31.573 | −10.448 | 20.583 | 1.00 | 18.39 | O |
| ATOM | 6018 | N | LEU | A | 376 | 33.314 | −9.669 | 19.381 | 1.00 | 19.75 | N |
| ATOM | 6019 | CA | LEU | A | 376 | 34.029 | −9.118 | 20.532 | 1.00 | 21.68 | C |
| ATOM | 6021 | CB | LEU | A | 376 | 35.381 | −8.530 | 20.107 | 1.00 | 23.12 | C |
| ATOM | 6024 | CG | LEU | A | 376 | 36.368 | −8.303 | 21.266 | 1.00 | 30.40 | C |
| ATOM | 6026 | CD1 | LEU | A | 376 | 37.399 | −9.451 | 21.302 | 1.00 | 34.97 | C |
| ATOM | 6030 | CD2 | LEU | A | 376 | 37.071 | −6.929 | 21.198 | 1.00 | 31.18 | C |
| ATOM | 6034 | C | LEU | A | 376 | 33.196 | −8.035 | 21.219 | 1.00 | 20.89 | C |
| ATOM | 6035 | O | LEU | A | 376 | 33.004 | −8.069 | 22.430 | 1.00 | 21.07 | O |
| ATOM | 6037 | N | TYR | A | 377 | 32.698 | −7.092 | 20.428 | 1.00 | 20.33 | N |
| ATOM | 6038 | CA | TYR | A | 377 | 31.883 | −5.993 | 20.927 | 1.00 | 20.67 | C |
| ATOM | 6040 | CB | TYR | A | 377 | 31.477 | −5.076 | 19.772 | 1.00 | 20.85 | C |
| ATOM | 6043 | CG | TYR | A | 377 | 30.673 | −3.867 | 20.205 | 1.00 | 22.25 | C |
| ATOM | 6044 | CD1 | TYR | A | 377 | 31.306 | −2.683 | 20.572 | 1.00 | 23.31 | C |
| ATOM | 6046 | CE1 | TYR | A | 377 | 30.579 | −1.575 | 20.969 | 1.00 | 23.53 | C |
| ATOM | 6048 | CZ | TYR | A | 377 | 29.198 | −1.638 | 21.000 | 1.00 | 24.30 | C |
| ATOM | 6049 | OH | TYR | A | 377 | 28.474 | −0.538 | 21.402 | 1.00 | 26.73 | O |
| ATOM | 6051 | CE2 | TYR | A | 377 | 28.543 | −2.801 | 20.639 | 1.00 | 22.45 | C |
| ATOM | 6053 | CD2 | TYR | A | 377 | 29.280 | −3.908 | 20.249 | 1.00 | 22.07 | C |
| ATOM | 6055 | C | TYR | A | 377 | 30.620 | −6.464 | 21.644 | 1.00 | 21.34 | C |
| ATOM | 6056 | O | TYR | A | 377 | 30.291 | −5.967 | 22.726 | 1.00 | 21.24 | O |
| ATOM | 6058 | N | ASN | A | 378 | 29.907 | −7.407 | 21.029 | 1.00 | 21.84 | N |
| ATOM | 6059 | CA | ASN | A | 378 | 28.639 | −7.905 | 21.575 | 1.00 | 22.09 | C |
| ATOM | 6061 | CB | ASN | A | 378 | 27.737 | −8.422 | 20.445 | 1.00 | 21.73 | C |
| ATOM | 6064 | CG | ASN | A | 378 | 27.166 | −7.300 | 19.594 | 1.00 | 20.87 | C |
| ATOM | 6065 | OD1 | ASN | A | 378 | 26.647 | −6.315 | 20.116 | 1.00 | 27.66 | O |
| ATOM | 6066 | ND2 | ASN | A | 378 | 27.252 | −7.445 | 18.286 | 1.00 | 17.61 | N |
| ATOM | 6069 | C | ASN | A | 378 | 28.827 | −8.985 | 22.642 | 1.00 | 22.65 | C |
| ATOM | 6070 | O | ASN | A | 378 | 27.853 | −9.461 | 23.215 | 1.00 | 21.54 | O |
| ATOM | 6072 | N | LYS | A | 379 | 30.084 | −9.350 | 22.904 | 1.00 | 24.61 | N |
| ATOM | 6073 | CA | LYS | A | 379 | 30.444 | −10.414 | 23.850 | 1.00 | 25.49 | C |
| ATOM | 6075 | CB | LYS | A | 379 | 30.133 | −9.997 | 25.295 | 1.00 | 26.24 | C |
| ATOM | 6078 | CG | LYS | A | 379 | 30.943 | −8.799 | 25.790 | 1.00 | 30.21 | C |
| ATOM | 6081 | CD | LYS | A | 379 | 30.509 | −8.384 | 27.194 | 1.00 | 37.13 | C |
| ATOM | 6084 | CE | LYS | A | 379 | 31.545 | −7.490 | 27.876 | 1.00 | 41.56 | C |
| ATOM | 6087 | NZ | LYS | A | 379 | 31.669 | −6.147 | 27.238 | 1.00 | 42.65 | N |
| ATOM | 6091 | C | LYS | A | 379 | 29.768 | −11.739 | 23.493 | 1.00 | 24.88 | C |
| ATOM | 6092 | O | LYS | A | 379 | 29.346 | −12.490 | 24.374 | 1.00 | 25.87 | O |
| ATOM | 6094 | N | SER | A | 380 | 29.684 | −12.021 | 22.193 | 1.00 | 23.82 | N |
| ATOM | 6095 | CA | SER | A | 380 | 29.046 | −13.241 | 21.702 | 1.00 | 22.71 | C |

APPENDIX 1-continued

| ATOM | 6097 | CB | SER | A | 380 | 28.757 | −13.146 | 20.201 | 1.00 | 22.21 | C |
|---|---|---|---|---|---|---|---|---|---|---|---|
| ATOM | 6100 | OG | SER | A | 380 | 27.753 | −12.185 | 19.935 | 1.00 | 23.40 | O |
| ATOM | 6102 | C | SER | A | 380 | 29.920 | −14.455 | 21.981 | 1.00 | 21.70 | C |
| ATOM | 6103 | O | SER | A | 380 | 31.138 | −14.347 | 22.113 | 1.00 | 20.41 | O |
| ATOM | 6105 | N | THR | A | 381 | 29.276 | −15.612 | 22.069 | 1.00 | 21.44 | N |
| ATOM | 6106 | CA | THR | A | 381 | 29.965 | −16.868 | 22.339 | 1.00 | 21.90 | C |
| ATOM | 6108 | CB | THR | A | 381 | 29.603 | −17.402 | 23.738 | 1.00 | 21.79 | C |
| ATOM | 6110 | OG1 | THR | A | 381 | 28.181 | −17.514 | 23.852 | 1.00 | 21.72 | O |
| ATOM | 6112 | CG2 | THR | A | 381 | 30.126 | −16.456 | 24.822 | 1.00 | 21.88 | C |
| ATOM | 6116 | C | THR | A | 381 | 29.588 | −17.892 | 21.258 | 1.00 | 21.57 | C |
| ATOM | 6117 | O | THR | A | 381 | 28.876 | −18.860 | 21.539 | 1.00 | 21.91 | O |
| ATOM | 6119 | N | PRO | A | 382 | 30.074 | −17.677 | 20.017 | 1.00 | 20.04 | N |
| ATOM | 6120 | CA | PRO | A | 382 | 29.695 | −18.521 | 18.892 | 1.00 | 19.83 | C |
| ATOM | 6122 | CB | PRO | A | 382 | 30.328 | −17.809 | 17.696 | 1.00 | 20.07 | C |
| ATOM | 6125 | CG | PRO | A | 382 | 31.515 | −17.127 | 18.263 | 1.00 | 20.37 | C |
| ATOM | 6128 | CD | PRO | A | 382 | 31.105 | −16.692 | 19.637 | 1.00 | 19.89 | C |
| ATOM | 6131 | C | PRO | A | 382 | 30.242 | −19.938 | 19.006 | 1.00 | 19.76 | C |
| ATOM | 6132 | O | PRO | A | 382 | 31.224 | −20.177 | 19.719 | 1.00 | 20.31 | O |
| ATOM | 6133 | N | THR | A | 383 | 29.601 | −20.864 | 18.299 | 1.00 | 18.95 | N |
| ATOM | 6134 | CA | THR | A | 383 | 30.034 | −22.258 | 18.273 | 1.00 | 18.77 | C |
| ATOM | 6136 | CB | THR | A | 383 | 28.981 | −23.149 | 17.588 | 1.00 | 19.63 | C |
| ATOM | 6138 | OG1 | THR | A | 383 | 28.694 | −22.634 | 16.277 | 1.00 | 20.80 | O |
| ATOM | 6140 | CG2 | THR | A | 383 | 27.701 | −23.183 | 18.414 | 1.00 | 16.56 | C |
| ATOM | 6144 | C | THR | A | 383 | 31.351 | −22.375 | 17.520 | 1.00 | 18.13 | C |
| ATOM | 6145 | O | THR | A | 383 | 31.705 | −21.475 | 16.752 | 1.00 | 18.02 | O |
| ATOM | 6147 | N | PHE | A | 384 | 32.075 | −23.473 | 17.745 | 1.00 | 17.33 | N |
| ATOM | 6148 | CA | PHE | A | 384 | 33.358 | −23.680 | 17.077 | 1.00 | 16.74 | C |
| ATOM | 6150 | CB | PHE | A | 384 | 34.002 | −25.016 | 17.462 | 1.00 | 16.69 | C |
| ATOM | 6153 | CG | PHE | A | 384 | 35.303 | −25.284 | 16.727 | 1.00 | 18.57 | C |
| ATOM | 6154 | CD1 | PHE | A | 384 | 36.487 | −24.662 | 17.125 | 1.00 | 15.55 | C |
| ATOM | 6156 | CE1 | PHE | A | 384 | 37.680 | −24.891 | 16.451 | 1.00 | 14.53 | C |
| ATOM | 6158 | CZ | PHE | A | 384 | 37.700 | −25.732 | 15.364 | 1.00 | 14.74 | C |
| ATOM | 6160 | CE2 | PHE | A | 384 | 36.524 | −26.347 | 14.939 | 1.00 | 15.29 | C |
| ATOM | 6162 | CD2 | PHE | A | 384 | 35.335 | −26.120 | 15.616 | 1.00 | 18.30 | C |
| ATOM | 6164 | C | PHE | A | 384 | 33.214 | −23.615 | 15.557 | 1.00 | 16.96 | C |
| ATOM | 6165 | O | PHE | A | 384 | 34.044 | −23.015 | 14.872 | 1.00 | 16.67 | O |
| ATOM | 6167 | N | ASP | A | 385 | 32.161 | −24.235 | 15.034 | 1.00 | 18.03 | N |
| ATOM | 6168 | CA | ASP | A | 385 | 31.939 | −24.264 | 13.587 | 1.00 | 18.66 | C |
| ATOM | 6170 | CB | ASP | A | 385 | 30.774 | −25.201 | 13.220 | 1.00 | 18.48 | C |
| ATOM | 6173 | CG | ASP | A | 385 | 31.118 | −26.674 | 13.425 | 1.00 | 17.10 | C |
| ATOM | 6174 | OD1 | ASP | A | 385 | 32.317 | −27.005 | 13.495 | 1.00 | 20.97 | O |
| ATOM | 6175 | OD2 | ASP | A | 385 | 30.196 | −27.509 | 13.514 | 1.00 | 22.63 | O |
| ATOM | 6176 | C | ASP | A | 385 | 31.727 | −22.865 | 13.006 | 1.00 | 19.02 | C |
| ATOM | 6177 | O | ASP | A | 385 | 32.262 | −22.558 | 11.940 | 1.00 | 20.10 | O |
| ATOM | 6179 | N | ASP | A | 386 | 30.983 | −22.013 | 13.707 | 1.00 | 19.37 | N |
| ATOM | 6180 | CA | ASP | A | 386 | 30.793 | −20.627 | 13.248 | 1.00 | 19.83 | C |
| ATOM | 6182 | CB | ASP | A | 386 | 29.613 | −19.953 | 13.960 | 1.00 | 20.91 | C |
| ATOM | 6185 | CG | ASP | A | 386 | 28.257 | −20.503 | 13.517 | 1.00 | 25.38 | C |
| ATOM | 6186 | OD1 | ASP | A | 386 | 28.188 | −21.255 | 12.514 | 1.00 | 30.04 | O |
| ATOM | 6187 | OD2 | ASP | A | 386 | 27.252 | −20.178 | 14.182 | 1.00 | 34.85 | O |
| ATOM | 6188 | C | ASP | A | 386 | 32.050 | −19.776 | 13.409 | 1.00 | 18.64 | C |
| ATOM | 6189 | O | ASP | A | 386 | 32.391 | −19.021 | 12.505 | 1.00 | 18.66 | O |
| ATOM | 6191 | N | TYR | A | 387 | 32.738 | −19.894 | 14.544 | 1.00 | 18.41 | N |
| ATOM | 6192 | CA | TYR | A | 387 | 33.961 | −19.107 | 14.777 | 1.00 | 18.58 | C |
| ATOM | 6194 | CB | TYR | A | 387 | 34.470 | −19.237 | 16.214 | 1.00 | 18.41 | C |
| ATOM | 6197 | CG | TYR | A | 387 | 35.731 | −18.444 | 16.486 | 1.00 | 20.51 | C |
| ATOM | 6198 | CD1 | TYR | A | 387 | 36.987 | −18.991 | 16.260 | 1.00 | 25.70 | C |
| ATOM | 6200 | CE1 | TYR | A | 387 | 38.149 | −18.259 | 16.500 | 1.00 | 26.65 | C |
| ATOM | 6202 | CZ | TYR | A | 387 | 38.057 | −16.968 | 16.986 | 1.00 | 29.48 | C |
| ATOM | 6203 | OH | TYR | A | 387 | 39.197 | −16.236 | 17.235 | 1.00 | 32.42 | O |
| ATOM | 6205 | CE2 | TYR | A | 387 | 36.822 | −16.405 | 17.221 | 1.00 | 27.61 | C |
| ATOM | 6207 | CD2 | TYR | A | 387 | 35.668 | −17.143 | 16.971 | 1.00 | 25.22 | C |
| ATOM | 6209 | C | TYR | A | 387 | 35.049 | −19.558 | 13.835 | 1.00 | 18.22 | C |
| ATOM | 6210 | O | TYR | A | 387 | 35.601 | −18.757 | 13.087 | 1.00 | 17.74 | O |
| ATOM | 6212 | N | PHE | A | 388 | 35.354 | −20.852 | 13.879 | 1.00 | 18.67 | N |
| ATOM | 6213 | CA | PHE | A | 388 | 36.435 | −21.396 | 13.071 | 1.00 | 18.28 | C |
| ATOM | 6215 | CB | PHE | A | 388 | 36.648 | −22.893 | 13.299 | 1.00 | 18.71 | C |
| ATOM | 6218 | CG | PHE | A | 388 | 37.776 | −23.442 | 12.491 | 1.00 | 20.24 | C |
| ATOM | 6219 | CD1 | PHE | A | 388 | 39.088 | −23.130 | 12.821 | 1.00 | 16.48 | C |
| ATOM | 6221 | CE1 | PHE | A | 388 | 40.142 | −23.605 | 12.059 | 1.00 | 19.99 | C |
| ATOM | 6223 | CZ | PHE | A | 388 | 39.892 | −24.392 | 10.943 | 1.00 | 21.72 | C |
| ATOM | 6225 | CE2 | PHE | A | 388 | 38.583 | −24.688 | 10.590 | 1.00 | 24.82 | C |
| ATOM | 6227 | CD2 | PHE | A | 388 | 37.531 | −24.210 | 11.362 | 1.00 | 21.91 | C |
| ATOM | 6229 | C | PHE | A | 388 | 36.189 | −21.150 | 11.604 | 1.00 | 16.97 | C |
| ATOM | 6230 | O | PHE | A | 388 | 37.110 | −20.777 | 10.885 | 1.00 | 18.29 | O |
| ATOM | 6232 | N | GLY | A | 389 | 34.951 | −21.356 | 11.170 | 1.00 | 15.96 | N |
| ATOM | 6233 | CA | GLY | A | 389 | 34.555 | −21.080 | 9.790 | 1.00 | 16.08 | C |
| ATOM | 6236 | C | GLY | A | 389 | 34.930 | −19.679 | 9.338 | 1.00 | 15.85 | C |
| ATOM | 6237 | O | GLY | A | 389 | 35.394 | −19.485 | 8.225 | 1.00 | 17.12 | O |
| ATOM | 6239 | N | ASN | A | 390 | 34.730 | −18.702 | 10.212 | 1.00 | 15.50 | N |

APPENDIX 1-continued

| ATOM | 6240 | CA | ASN | A | 390 | 35.160 | −17.337 | 9.953 | 1.00 | 15.29 | C |
|---|---|---|---|---|---|---|---|---|---|---|---|
| ATOM | 6242 | CB | ASN | A | 390 | 34.453 | −16.386 | 10.917 | 1.00 | 14.58 | C |
| ATOM | 6245 | CG | ASN | A | 390 | 34.578 | −14.942 | 10.500 | 1.00 | 16.26 | C |
| ATOM | 6246 | OD1 | ASN | A | 390 | 33.953 | −14.516 | 9.528 | 1.00 | 19.33 | O |
| ATOM | 6247 | ND2 | ASN | A | 390 | 35.388 | −14.172 | 11.234 | 1.00 | 11.57 | N |
| ATOM | 6250 | C | ASN | A | 390 | 36.680 | −17.191 | 10.111 | 1.00 | 16.42 | C |
| ATOM | 6251 | O | ASN | A | 390 | 37.333 | −16.463 | 9.357 | 1.00 | 17.12 | O |
| ATOM | 6253 | N | ALA | A | 391 | 37.231 | −17.890 | 11.102 | 1.00 | 16.29 | N |
| ATOM | 6254 | CA | ALA | A | 391 | 38.632 | −17.768 | 11.460 | 1.00 | 16.32 | C |
| ATOM | 6256 | CB | ALA | A | 391 | 38.935 | −18.610 | 12.685 | 1.00 | 16.29 | C |
| ATOM | 6260 | C | ALA | A | 391 | 39.587 | −18.128 | 10.328 | 1.00 | 17.19 | C |
| ATOM | 6261 | O | ALA | A | 391 | 40.603 | −17.460 | 10.150 | 1.00 | 18.59 | O |
| ATOM | 6263 | N | TRP | A | 392 | 39.296 | −19.176 | 9.564 | 1.00 | 17.74 | N |
| ATOM | 6264 | CA | TRP | A | 392 | 40.227 | −19.552 | 8.498 | 1.00 | 17.73 | C |
| ATOM | 6266 | CB | TRP | A | 392 | 40.053 | −21.005 | 8.024 | 1.00 | 18.15 | C |
| ATOM | 6269 | CG | TRP | A | 392 | 38.758 | −21.397 | 7.371 | 1.00 | 18.01 | C |
| ATOM | 6270 | CD1 | TRP | A | 392 | 37.728 | −22.100 | 7.945 | 1.00 | 22.06 | C |
| ATOM | 6272 | NE1 | TRP | A | 392 | 36.730 | −22.319 | 7.025 | 1.00 | 19.55 | N |
| ATOM | 6274 | CE2 | TRP | A | 392 | 37.110 | −21.775 | 5.827 | 1.00 | 15.70 | C |
| ATOM | 6275 | CD2 | TRP | A | 392 | 38.388 | −21.197 | 6.006 | 1.00 | 16.64 | C |
| ATOM | 6276 | CE3 | TRP | A | 392 | 39.006 | −20.578 | 4.916 | 1.00 | 16.17 | C |
| ATOM | 6278 | CZ3 | TRP | A | 392 | 38.337 | −20.554 | 3.696 | 1.00 | 17.82 | C |
| ATOM | 6280 | CH2 | TRP | A | 392 | 37.072 | −21.125 | 3.555 | 1.00 | 16.95 | C |
| ATOM | 6282 | CZ2 | TRP | A | 392 | 36.439 | −21.736 | 4.611 | 1.00 | 17.70 | C |
| ATOM | 6284 | C | TRP | A | 392 | 40.175 | −18.546 | 7.358 | 1.00 | 17.93 | C |
| ATOM | 6285 | O | TRP | A | 392 | 41.138 | −18.393 | 6.613 | 1.00 | 18.60 | O |
| ATOM | 6287 | N | LYS | A | 393 | 39.056 | −17.842 | 7.243 | 1.00 | 18.79 | N |
| ATOM | 6288 | CA | LYS | A | 393 | 38.957 | −16.741 | 6.303 | 1.00 | 19.11 | C |
| ATOM | 6290 | CB | LYS | A | 393 | 37.489 | −16.404 | 6.019 | 1.00 | 19.71 | C |
| ATOM | 6293 | CG | LYS | A | 393 | 36.692 | −17.548 | 5.361 | 1.00 | 23.76 | C |
| ATOM | 6296 | CD | LYS | A | 393 | 35.243 | −17.111 | 5.105 | 1.00 | 32.08 | C |
| ATOM | 6299 | CE | LYS | A | 393 | 34.489 | −18.013 | 4.132 | 1.00 | 35.08 | C |
| ATOM | 6302 | NZ | LYS | A | 393 | 33.860 | −19.184 | 4.819 | 1.00 | 41.63 | N |
| ATOM | 6306 | C | LYS | A | 393 | 39.740 | −15.526 | 6.837 | 1.00 | 17.96 | C |
| ATOM | 6307 | O | LYS | A | 393 | 40.536 | −14.934 | 6.105 | 1.00 | 17.30 | O |
| ATOM | 6309 | N | SER | A | 394 | 39.549 | −15.191 | 8.114 | 1.00 | 17.21 | N |
| ATOM | 6310 | CA | SER | A | 394 | 40.243 | −14.056 | 8.727 | 1.00 | 17.57 | C |
| ATOM | 6312 | CB | SER | A | 394 | 39.678 | −13.741 | 10.117 | 1.00 | 18.73 | C |
| ATOM | 6315 | OG | SER | A | 394 | 40.097 | −14.679 | 11.092 | 1.00 | 19.38 | O |
| ATOM | 6317 | C | SER | A | 394 | 41.753 | −14.255 | 8.828 | 1.00 | 17.97 | C |
| ATOM | 6318 | O | SER | A | 394 | 42.482 | −13.304 | 9.097 | 1.00 | 18.69 | O |
| ATOM | 6320 | N | SER | A | 395 | 42.224 | −15.483 | 8.611 | 1.00 | 18.04 | N |
| ATOM | 6321 | CA | SER | A | 395 | 43.663 | −15.753 | 8.549 | 1.00 | 17.80 | C |
| ATOM | 6323 | CB | SER | A | 395 | 43.931 | −17.248 | 8.341 | 1.00 | 17.23 | C |
| ATOM | 6326 | OG | SER | A | 395 | 43.621 | −17.657 | 7.022 | 1.00 | 17.01 | O |
| ATOM | 6328 | C | SER | A | 395 | 44.361 | −14.960 | 7.443 | 1.00 | 17.85 | C |
| ATOM | 6329 | O | SER | A | 395 | 45.549 | −14.651 | 7.568 | 1.00 | 17.80 | O |
| ATOM | 6331 | N | SER | A | 396 | 43.605 | −14.637 | 6.386 | 1.00 | 16.98 | N |
| ATOM | 6332 | CA | SER | A | 396 | 44.119 | −14.054 | 5.137 | 1.00 | 17.11 | C |
| ATOM | 6334 | CB | SER | A | 396 | 45.134 | −12.927 | 5.377 | 1.00 | 16.44 | C |
| ATOM | 6337 | OG | SER | A | 396 | 46.445 | −13.431 | 5.553 | 1.00 | 15.62 | O |
| ATOM | 6339 | C | SER | A | 396 | 44.704 | −15.114 | 4.193 | 1.00 | 17.03 | C |
| ATOM | 6340 | O | SER | A | 396 | 45.119 | −14.788 | 3.080 | 1.00 | 16.74 | O |
| ATOM | 6342 | N | GLY | A | 397 | 44.722 | −16.375 | 4.629 | 1.00 | 16.65 | N |
| ATOM | 6343 | CA | GLY | A | 397 | 45.150 | −17.487 | 3.773 | 1.00 | 16.98 | C |
| ATOM | 6346 | C | GLY | A | 397 | 44.462 | −17.567 | 2.415 | 1.00 | 15.97 | C |
| ATOM | 6347 | O | GLY | A | 397 | 45.121 | −17.563 | 1.381 | 1.00 | 16.15 | O |
| ATOM | 6349 | N | PRO | A | 398 | 43.128 | −17.653 | 2.405 | 1.00 | 15.97 | N |
| ATOM | 6350 | CA | PRO | A | 398 | 42.423 | −17.639 | 1.128 | 1.00 | 16.89 | C |
| ATOM | 6352 | CB | PRO | A | 398 | 40.954 | −17.514 | 1.541 | 1.00 | 16.76 | C |
| ATOM | 6355 | CG | PRO | A | 398 | 40.898 | −18.068 | 2.905 | 1.00 | 17.51 | C |
| ATOM | 6358 | CD | PRO | A | 398 | 42.199 | −17.720 | 3.545 | 1.00 | 15.87 | C |
| ATOM | 6361 | C | PRO | A | 398 | 42.823 | −16.455 | 0.245 | 1.00 | 16.96 | C |
| ATOM | 6362 | O | PRO | A | 398 | 43.060 | −16.630 | −0.953 | 1.00 | 15.67 | O |
| ATOM | 6363 | N | LEU | A | 399 | 42.907 | −15.267 | 0.845 | 1.00 | 17.42 | N |
| ATOM | 6364 | CA | LEU | A | 399 | 43.167 | −14.057 | 0.081 | 1.00 | 18.17 | C |
| ATOM | 6366 | CB | LEU | A | 399 | 43.085 | −12.805 | 0.956 | 1.00 | 18.47 | C |
| ATOM | 6369 | CG | LEU | A | 399 | 43.337 | −11.493 | 0.198 | 1.00 | 18.57 | C |
| ATOM | 6371 | CD1 | LEU | A | 399 | 42.370 | −10.407 | 0.635 | 1.00 | 19.49 | C |
| ATOM | 6375 | CD2 | LEU | A | 399 | 44.784 | −11.051 | 0.359 | 1.00 | 17.72 | C |
| ATOM | 6379 | C | LEU | A | 399 | 44.529 | −14.156 | −0.564 | 1.00 | 18.47 | C |
| ATOM | 6380 | O | LEU | A | 399 | 44.656 | −13.968 | −1.777 | 1.00 | 18.45 | O |
| ATOM | 6382 | N | GLN | A | 400 | 45.534 | −14.468 | 0.250 | 1.00 | 17.29 | N |
| ATOM | 6383 | CA | GLN | A | 400 | 46.889 | −14.653 | −0.246 | 1.00 | 17.28 | C |
| ATOM | 6385 | CB | GLN | A | 400 | 47.806 | −15.178 | 0.855 | 1.00 | 17.64 | C |
| ATOM | 6388 | CG | GLN | A | 400 | 48.103 | −14.172 | 1.957 | 1.00 | 20.06 | C |
| ATOM | 6391 | CD | GLN | A | 400 | 49.064 | −14.712 | 2.998 | 1.00 | 22.79 | C |
| ATOM | 6392 | OE1 | GLN | A | 400 | 50.063 | −15.357 | 2.662 | 1.00 | 26.66 | O |
| ATOM | 6393 | NE2 | GLN | A | 400 | 48.779 | −14.440 | 4.270 | 1.00 | 23.20 | N |
| ATOM | 6396 | C | GLN | A | 400 | 46.911 | −15.615 | −1.421 | 1.00 | 17.50 | C |

APPENDIX 1-continued

| | | | | | | | | | | |
|---|---|---|---|---|---|---|---|---|---|---|
| ATOM | 6397 | O | GLN | A | 400 | 47.584 | −15.360 | −2.421 | 1.00 | 18.78 | O |
| ATOM | 6399 | N | LEU | A | 401 | 46.164 | −16.711 | −1.315 | 1.00 | 17.11 | N |
| ATOM | 6400 | CA | LEU | A | 401 | 46.221 | −17.751 | −2.344 | 1.00 | 17.07 | C |
| ATOM | 6402 | CB | LEU | A | 401 | 45.699 | −19.086 | −1.815 | 1.00 | 16.18 | C |
| ATOM | 6405 | CG | LEU | A | 401 | 46.625 | −19.745 | −0.788 | 1.00 | 15.41 | C |
| ATOM | 6407 | CD1 | LEU | A | 401 | 46.020 | −21.034 | −0.275 | 1.00 | 15.00 | C |
| ATOM | 6411 | CD2 | LEU | A | 401 | 47.992 | −20.002 | −1.382 | 1.00 | 11.49 | C |
| ATOM | 6415 | C | LEU | A | 401 | 45.507 | −17.337 | −3.624 | 1.00 | 17.35 | C |
| ATOM | 6416 | O | LEU | A | 401 | 45.909 | −17.744 | −4.712 | 1.00 | 18.56 | O |
| ATOM | 6418 | N | VAL | A | 402 | 44.475 | −16.510 | −3.507 | 1.00 | 17.20 | N |
| ATOM | 6419 | CA | VAL | A | 402 | 43.854 | −15.929 | −4.694 | 1.00 | 17.04 | C |
| ATOM | 6421 | CB | VAL | A | 402 | 42.638 | −15.060 | −4.330 | 1.00 | 16.83 | C |
| ATOM | 6423 | CG1 | VAL | A | 402 | 42.189 | −14.242 | −5.526 | 1.00 | 16.23 | C |
| ATOM | 6427 | CG2 | VAL | A | 402 | 41.495 | −15.938 | −3.807 | 1.00 | 14.08 | C |
| ATOM | 6431 | C | VAL | A | 402 | 44.906 | −15.107 | −5.456 | 1.00 | 17.06 | C |
| ATOM | 6432 | O | VAL | A | 402 | 45.104 | −15.282 | −6.654 | 1.00 | 16.97 | O |
| ATOM | 6434 | N | PHE | A | 403 | 45.612 | −14.246 | −4.742 | 1.00 | 17.15 | N |
| ATOM | 6435 | CA | PHE | A | 403 | 46.661 | −13.449 | −5.352 | 1.00 | 18.02 | C |
| ATOM | 6437 | CB | PHE | A | 403 | 47.166 | −12.380 | −4.381 | 1.00 | 18.40 | C |
| ATOM | 6440 | CG | PHE | A | 403 | 46.228 | −11.211 | −4.253 | 1.00 | 16.89 | C |
| ATOM | 6441 | CD1 | PHE | A | 403 | 45.130 | −11.270 | −3.401 | 1.00 | 18.92 | C |
| ATOM | 6443 | CE1 | PHE | A | 403 | 44.253 | −10.204 | −3.292 | 1.00 | 18.88 | C |
| ATOM | 6445 | CZ | PHE | A | 403 | 44.465 | −9.067 | −4.052 | 1.00 | 21.23 | C |
| ATOM | 6447 | CE2 | PHE | A | 403 | 45.556 | −9.002 | −4.908 | 1.00 | 18.67 | C |
| ATOM | 6449 | CD2 | PHE | A | 403 | 46.424 | −10.071 | −5.004 | 1.00 | 15.42 | C |
| ATOM | 6451 | C | PHE | A | 403 | 47.790 | −14.329 | −5.868 | 1.00 | 18.82 | C |
| ATOM | 6452 | O | PHE | A | 403 | 48.321 | −14.081 | −6.954 | 1.00 | 19.35 | O |
| ATOM | 6454 | N | ALA | A | 404 | 48.128 | −15.373 | −5.114 | 1.00 | 18.63 | N |
| ATOM | 6455 | CA | ALA | A | 404 | 49.131 | −16.339 | −5.556 | 1.00 | 17.59 | C |
| ATOM | 6457 | CB | ALA | A | 404 | 49.348 | −17.400 | −4.502 | 1.00 | 16.79 | C |
| ATOM | 6461 | C | ALA | A | 404 | 48.724 | −16.984 | −6.883 | 1.00 | 17.58 | C |
| ATOM | 6462 | O | ALA | A | 404 | 49.557 | −17.128 | −7.783 | 1.00 | 16.70 | O |
| ATOM | 6464 | N | TYR | A | 405 | 47.451 | −17.373 | −6.995 | 1.00 | 17.29 | N |
| ATOM | 6465 | CA | TYR | A | 405 | 46.942 | −18.006 | −8.218 | 1.00 | 17.42 | C |
| ATOM | 6467 | CB | TYR | A | 405 | 45.422 | −18.176 | −8.183 | 1.00 | 16.99 | C |
| ATOM | 6470 | CG | TYR | A | 405 | 44.846 | −18.697 | −9.479 | 1.00 | 17.27 | C |
| ATOM | 6471 | CD1 | TYR | A | 405 | 44.809 | −20.058 | −9.743 | 1.00 | 20.07 | C |
| ATOM | 6473 | CE1 | TYR | A | 405 | 44.276 | −20.550 | −10.932 | 1.00 | 22.26 | C |
| ATOM | 6475 | CZ | TYR | A | 405 | 43.786 | −19.668 | −11.879 | 1.00 | 26.25 | C |
| ATOM | 6476 | OH | TYR | A | 405 | 43.268 | −20.156 | −13.067 | 1.00 | 25.57 | O |
| ATOM | 6478 | CE2 | TYR | A | 405 | 43.823 | −18.301 | −11.637 | 1.00 | 20.59 | C |
| ATOM | 6480 | CD2 | TYR | A | 405 | 44.353 | −17.829 | −10.445 | 1.00 | 18.93 | C |
| ATOM | 6482 | C | TYR | A | 405 | 47.298 | −17.204 | −9.452 | 1.00 | 17.58 | C |
| ATOM | 6483 | O | TYR | A | 405 | 47.773 | −17.760 | −10.434 | 1.00 | 18.44 | O |
| ATOM | 6485 | N | PHE | A | 406 | 47.068 | −15.898 | −9.401 | 1.00 | 18.39 | N |
| ATOM | 6486 | CA | PHE | A | 406 | 47.265 | −15.059 | −10.577 | 1.00 | 18.51 | C |
| ATOM | 6488 | CB | PHE | A | 406 | 46.485 | −13.752 | −10.446 | 1.00 | 18.24 | C |
| ATOM | 6491 | CG | PHE | A | 406 | 45.002 | −13.943 | −10.486 | 1.00 | 17.37 | C |
| ATOM | 6492 | CD1 | PHE | A | 406 | 44.367 | −14.241 | −11.681 | 1.00 | 17.72 | C |
| ATOM | 6494 | CE1 | PHE | A | 406 | 43.006 | −14.428 | −11.722 | 1.00 | 16.27 | C |
| ATOM | 6496 | CZ | PHE | A | 406 | 42.257 | −14.318 | −10.563 | 1.00 | 16.45 | C |
| ATOM | 6498 | CE2 | PHE | A | 406 | 42.874 | −14.023 | −9.371 | 1.00 | 13.88 | C |
| ATOM | 6500 | CD2 | PHE | A | 406 | 44.241 | −13.840 | −9.335 | 1.00 | 16.63 | C |
| ATOM | 6502 | C | PHE | A | 406 | 48.732 | −14.795 | −10.858 | 1.00 | 18.16 | C |
| ATOM | 6503 | O | PHE | A | 406 | 49.090 | −14.506 | −11.985 | 1.00 | 19.24 | O |
| ATOM | 6505 | N | ALA | A | 407 | 49.582 | −14.896 | −9.848 | 1.00 | 18.51 | N |
| ATOM | 6506 | CA | ALA | A | 407 | 51.014 | −14.685 | −10.050 | 1.00 | 20.28 | C |
| ATOM | 6508 | CB | ALA | A | 407 | 51.653 | −14.150 | −8.781 | 1.00 | 19.88 | C |
| ATOM | 6512 | C | ALA | A | 407 | 51.730 | −15.956 | −10.501 | 1.00 | 21.89 | C |
| ATOM | 6513 | O | ALA | A | 407 | 52.816 | −15.882 | −11.057 | 1.00 | 21.80 | O |
| ATOM | 6515 | N | VAL | A | 408 | 51.121 | −17.112 | −10.249 | 1.00 | 24.28 | N |
| ATOM | 6516 | CA | VAL | A | 408 | 51.728 | −18.414 | −10.543 | 1.00 | 25.70 | C |
| ATOM | 6518 | CB | VAL | A | 408 | 51.447 | −19.400 | −9.410 | 1.00 | 25.52 | C |
| ATOM | 6520 | CG1 | VAL | A | 408 | 51.696 | −20.832 | −9.863 | 1.00 | 25.95 | C |
| ATOM | 6524 | CG2 | VAL | A | 408 | 52.290 | −19.057 | −8.202 | 1.00 | 26.22 | C |
| ATOM | 6528 | C | VAL | A | 408 | 51.198 | −19.018 | −11.842 | 1.00 | 28.31 | C |
| ATOM | 6529 | O | VAL | A | 408 | 51.957 | −19.568 | −12.631 | 1.00 | 27.49 | O |
| ATOM | 6531 | N | VAL | A | 409 | 49.892 | −18.924 | −12.057 | 1.00 | 31.68 | N |
| ATOM | 6532 | CA | VAL | A | 409 | 49.278 | −19.504 | −13.244 | 1.00 | 34.10 | C |
| ATOM | 6534 | CB | VAL | A | 409 | 47.745 | −19.504 | −13.133 | 1.00 | 33.82 | C |
| ATOM | 6536 | CG1 | VAL | A | 409 | 47.106 | −19.782 | −14.466 | 1.00 | 34.76 | C |
| ATOM | 6540 | CG2 | VAL | A | 409 | 47.311 | −20.543 | −12.121 | 1.00 | 35.18 | C |
| ATOM | 6544 | C | VAL | A | 409 | 49.706 | −18.767 | −14.508 | 1.00 | 36.79 | C |
| ATOM | 6545 | O | VAL | A | 409 | 49.712 | −17.538 | −14.549 | 1.00 | 37.53 | O |
| ATOM | 6547 | N | GLN | A | 410 | 50.071 | −19.534 | −15.532 | 1.00 | 39.83 | N |
| ATOM | 6548 | CA | GLN | A | 410 | 50.398 | −18.979 | −16.837 | 1.00 | 41.91 | C |
| ATOM | 6550 | CB | GLN | A | 410 | 51.194 | −19.996 | −17.665 | 1.00 | 43.77 | C |
| ATOM | 6553 | CG | GLN | A | 410 | 51.931 | −19.387 | −18.876 | 1.00 | 49.79 | C |
| ATOM | 6556 | CD | GLN | A | 410 | 52.277 | −20.418 | −19.963 | 1.00 | 56.08 | C |
| ATOM | 6557 | OE1 | GLN | A | 410 | 52.241 | −21.633 | −19.735 | 1.00 | 58.83 | O |

APPENDIX 1-continued

| ATOM | 6558 | NE2 | GLN | A | 410 | 52.611 | −19.926 | −21.153 | 1.00 | 55.44 | N |
|---|---|---|---|---|---|---|---|---|---|---|---|
| ATOM | 6561 | C | GLN | A | 410 | 49.104 | −18.585 | −17.558 | 1.00 | 40.93 | C |
| ATOM | 6562 | O | GLN | A | 410 | 48.940 | −17.425 | −17.951 | 1.00 | 41.41 | O |
| ATOM | 6564 | N | ASN | A | 411 | 48.187 | −19.547 | −17.706 | 1.00 | 39.04 | N |
| ATOM | 6565 | CA | ASN | A | 411 | 46.905 | −19.324 | −18.387 | 1.00 | 37.73 | C |
| ATOM | 6567 | CB | ASN | A | 411 | 46.731 | −20.320 | −19.532 | 1.00 | 37.58 | C |
| ATOM | 6570 | CG | ASN | A | 411 | 47.746 | −20.125 | −20.630 | 1.00 | 37.46 | C |
| ATOM | 6571 | OD1 | ASN | A | 411 | 47.896 | −19.025 | −21.164 | 1.00 | 36.26 | O |
| ATOM | 6572 | ND2 | ASN | A | 411 | 48.449 | −21.194 | −20.982 | 1.00 | 38.10 | N |
| ATOM | 6575 | C | ASN | A | 411 | 45.718 | −19.455 | −17.448 | 1.00 | 36.52 | C |
| ATOM | 6576 | O | ASN | A | 411 | 45.467 | −20.528 | −16.909 | 1.00 | 36.35 | O |
| ATOM | 6578 | N | ILE | A | 412 | 44.971 | −18.369 | −17.285 | 1.00 | 36.03 | N |
| ATOM | 6579 | CA | ILE | A | 412 | 43.825 | −18.346 | −16.380 | 1.00 | 36.69 | C |
| ATOM | 6581 | CB | ILE | A | 412 | 43.282 | −16.918 | −16.200 | 1.00 | 37.17 | C |
| ATOM | 6583 | CG1 | ILE | A | 412 | 44.380 | −15.961 | −15.723 | 1.00 | 39.66 | C |
| ATOM | 6586 | CD1 | ILE | A | 412 | 43.975 | −14.491 | −15.792 | 1.00 | 39.53 | C |
| ATOM | 6590 | CG2 | ILE | A | 412 | 42.139 | −16.905 | −15.201 | 1.00 | 40.15 | C |
| ATOM | 6594 | C | ILE | A | 412 | 42.697 | −19.226 | −16.925 | 1.00 | 36.46 | C |
| ATOM | 6595 | O | ILE | A | 412 | 42.558 | −19.374 | −18.134 | 1.00 | 36.73 | O |
| ATOM | 6597 | N | LYS | A | 413 | 41.897 | −19.805 | −16.032 | 1.00 | 36.40 | N |
| ATOM | 6598 | CA | LYS | A | 413 | 40.749 | −20.622 | −16.434 | 1.00 | 36.79 | C |
| ATOM | 6600 | CB | LYS | A | 413 | 41.087 | −22.102 | −16.292 | 1.00 | 37.04 | C |
| ATOM | 6603 | CG | LYS | A | 413 | 42.257 | −22.533 | −17.149 | 1.00 | 41.24 | C |
| ATOM | 6606 | CD | LYS | A | 413 | 42.495 | −24.027 | −17.053 | 1.00 | 46.37 | C |
| ATOM | 6609 | CE | LYS | A | 413 | 43.488 | −24.497 | −18.102 | 1.00 | 47.62 | C |
| ATOM | 6612 | NZ | LYS | A | 413 | 43.623 | −25.980 | −18.089 | 1.00 | 49.22 | N |
| ATOM | 6616 | C | LYS | A | 413 | 39.488 | −20.289 | −15.628 | 1.00 | 36.33 | C |
| ATOM | 6617 | O | LYS | A | 413 | 39.522 | −20.241 | −14.394 | 1.00 | 35.00 | O |
| ATOM | 6619 | N | LYS | A | 414 | 38.381 | −20.071 | −16.343 | 1.00 | 36.30 | N |
| ATOM | 6620 | CA | LYS | A | 414 | 37.108 | −19.665 | −15.735 | 1.00 | 36.02 | C |
| ATOM | 6622 | CB | LYS | A | 414 | 35.979 | −19.665 | −16.779 | 1.00 | 36.18 | C |
| ATOM | 6625 | CG | LYS | A | 414 | 34.622 | −19.190 | −16.222 | 1.00 | 41.37 | C |
| ATOM | 6628 | CD | LYS | A | 414 | 33.688 | −18.591 | −17.298 | 1.00 | 45.90 | C |
| ATOM | 6631 | CE | LYS | A | 414 | 33.104 | −19.652 | −18.237 | 1.00 | 47.59 | C |
| ATOM | 6634 | NZ | LYS | A | 414 | 32.125 | −20.563 | −17.572 | 1.00 | 47.85 | N |
| ATOM | 6638 | C | LYS | A | 414 | 36.723 | −20.559 | −14.557 | 1.00 | 35.11 | C |
| ATOM | 6639 | O | LYS | A | 414 | 36.341 | −20.066 | −13.493 | 1.00 | 35.15 | O |
| ATOM | 6641 | N | GLU | A | 415 | 36.834 | −21.871 | −14.749 | 1.00 | 33.73 | N |
| ATOM | 6642 | CA | GLU | A | 415 | 36.429 | −22.835 | −13.724 | 1.00 | 32.94 | C |
| ATOM | 6644 | CB | GLU | A | 415 | 36.382 | −24.253 | −14.310 | 1.00 | 33.28 | C |
| ATOM | 6647 | CG | GLU | A | 415 | 36.060 | −25.340 | −13.285 | 1.00 | 38.04 | C |
| ATOM | 6650 | CD | GLU | A | 415 | 35.859 | −26.706 | −13.906 | 1.00 | 43.41 | C |
| ATOM | 6651 | OE1 | GLU | A | 415 | 36.344 | −26.923 | −15.037 | 1.00 | 47.72 | O |
| ATOM | 6652 | OE2 | GLU | A | 415 | 35.220 | −27.564 | −13.257 | 1.00 | 45.87 | O |
| ATOM | 6653 | C | GLU | A | 415 | 37.340 | −22.785 | −12.486 | 1.00 | 30.55 | C |
| ATOM | 6654 | O | GLU | A | 415 | 36.875 | −22.938 | −11.357 | 1.00 | 29.03 | O |
| ATOM | 6656 | N | GLU | A | 416 | 38.633 | −22.575 | −12.699 | 1.00 | 29.00 | N |
| ATOM | 6657 | CA | GLU | A | 416 | 39.565 | −22.459 | −11.585 | 1.00 | 28.18 | C |
| ATOM | 6659 | CB | GLU | A | 416 | 41.005 | −22.381 | −12.093 | 1.00 | 28.41 | C |
| ATOM | 6662 | CG | GLU | A | 416 | 41.504 | −23.662 | −12.739 | 1.00 | 29.21 | C |
| ATOM | 6665 | CD | GLU | A | 416 | 42.948 | −23.576 | −13.186 | 1.00 | 31.23 | C |
| ATOM | 6666 | OE1 | GLU | A | 416 | 43.381 | −22.515 | −13.681 | 1.00 | 37.41 | O |
| ATOM | 6667 | OE2 | GLU | A | 416 | 43.658 | −24.583 | −13.049 | 1.00 | 39.19 | O |
| ATOM | 6668 | C | GLU | A | 416 | 39.229 | −21.232 | −10.736 | 1.00 | 27.53 | C |
| ATOM | 6669 | O | GLU | A | 416 | 39.164 | −21.326 | −9.515 | 1.00 | 25.71 | O |
| ATOM | 6671 | N | ILE | A | 417 | 39.000 | −20.090 | −11.383 | 1.00 | 28.17 | N |
| ATOM | 6672 | CA | ILE | A | 417 | 38.673 | −18.869 | −10.644 | 1.00 | 29.32 | C |
| ATOM | 6674 | CB | ILE | A | 417 | 38.889 | −17.556 | −11.477 | 1.00 | 29.41 | C |
| ATOM | 6676 | CG1 | ILE | A | 417 | 37.945 | −17.448 | −12.661 | 1.00 | 33.17 | C |
| ATOM | 6679 | CD1 | ILE | A | 417 | 38.232 | −16.225 | −13.522 | 1.00 | 37.63 | C |
| ATOM | 6683 | CG2 | ILE | A | 417 | 40.313 | −17.469 | −11.992 | 1.00 | 30.67 | C |
| ATOM | 6687 | C | ILE | A | 417 | 37.270 | −18.938 | −10.019 | 1.00 | 28.55 | C |
| ATOM | 6688 | O | ILE | A | 417 | 37.065 | −18.456 | −8.908 | 1.00 | 28.52 | O |
| ATOM | 6690 | N | GLU | A | 418 | 36.320 | −19.558 | −10.710 | 1.00 | 28.77 | N |
| ATOM | 6691 | CA | GLU | A | 418 | 35.000 | −19.811 | −10.118 | 1.00 | 29.37 | C |
| ATOM | 6693 | CB | GLU | A | 418 | 34.084 | −20.562 | −11.091 | 1.00 | 29.70 | C |
| ATOM | 6696 | CG | GLU | A | 418 | 33.386 | −19.642 | −12.103 | 1.00 | 34.62 | C |
| ATOM | 6699 | CD | GLU | A | 418 | 32.662 | −20.391 | −13.231 | 1.00 | 39.25 | C |
| ATOM | 6700 | OE1 | GLU | A | 418 | 32.662 | −21.644 | −13.247 | 1.00 | 37.70 | O |
| ATOM | 6701 | OE2 | GLU | A | 418 | 32.092 | −19.711 | −14.110 | 1.00 | 40.61 | O |
| ATOM | 6702 | C | GLU | A | 418 | 35.146 | −20.589 | −8.816 | 1.00 | 28.68 | C |
| ATOM | 6703 | O | GLU | A | 418 | 34.510 | −20.265 | −7.816 | 1.00 | 29.24 | O |
| ATOM | 6705 | N | ASN | A | 419 | 36.011 | −21.595 | −8.823 | 1.00 | 28.36 | N |
| ATOM | 6706 | CA | ASN | A | 419 | 36.233 | −22.414 | −7.635 | 1.00 | 27.94 | C |
| ATOM | 6708 | CB | ASN | A | 419 | 36.925 | −23.729 | −8.008 | 1.00 | 27.24 | C |
| ATOM | 6711 | CG | ASN | A | 419 | 35.945 | −24.773 | −8.496 | 1.00 | 28.86 | C |
| ATOM | 6712 | OD1 | ASN | A | 419 | 35.470 | −25.609 | −7.725 | 1.00 | 33.67 | O |
| ATOM | 6713 | ND2 | ASN | A | 419 | 35.611 | −24.712 | −9.771 | 1.00 | 30.80 | N |
| ATOM | 6716 | C | ASN | A | 419 | 36.987 | −21.680 | −6.529 | 1.00 | 28.15 | C |
| ATOM | 6717 | O | ASN | A | 419 | 36.761 | −21.941 | −5.344 | 1.00 | 27.94 | O |

APPENDIX 1-continued

| ATOM | 6719 | N | LEU | A | 420 | 37.868 | −20.756 | −6.913 | 1.00 | 28.22 | N |
|---|---|---|---|---|---|---|---|---|---|---|---|
| ATOM | 6720 | CA | LEU | A | 420 | 38.505 | −19.866 | −5.945 | 1.00 | 28.08 | C |
| ATOM | 6722 | CB | LEU | A | 420 | 39.486 | −18.906 | −6.632 | 1.00 | 27.57 | C |
| ATOM | 6725 | CG | LEU | A | 420 | 40.804 | −19.498 | −7.142 | 1.00 | 26.93 | C |
| ATOM | 6727 | CD1 | LEU | A | 420 | 41.615 | −18.442 | −7.883 | 1.00 | 21.67 | C |
| ATOM | 6731 | CD2 | LEU | A | 420 | 41.609 | −20.119 | −6.004 | 1.00 | 22.68 | C |
| ATOM | 6735 | C | LEU | A | 420 | 37.454 | −19.068 | −5.162 | 1.00 | 29.46 | C |
| ATOM | 6736 | O | LEU | A | 420 | 37.514 | −18.996 | −3.936 | 1.00 | 29.59 | O |
| ATOM | 6738 | N | GLN | A | 421 | 36.489 | −18.485 | −5.871 | 1.00 | 31.06 | N |
| ATOM | 6739 | CA | GLN | A | 421 | 35.430 | −17.688 | −5.233 | 1.00 | 32.60 | C |
| ATOM | 6741 | CB | GLN | A | 421 | 34.538 | −17.030 | −6.286 | 1.00 | 33.15 | C |
| ATOM | 6744 | CG | GLN | A | 421 | 35.190 | −15.880 | −6.998 | 1.00 | 36.48 | C |
| ATOM | 6747 | CD | GLN | A | 421 | 34.181 | −14.962 | −7.639 | 1.00 | 41.39 | C |
| ATOM | 6748 | OE1 | GLN | A | 421 | 34.099 | −13.778 | −7.300 | 1.00 | 46.29 | O |
| ATOM | 6749 | NE2 | GLN | A | 421 | 33.395 | −15.502 | −8.569 | 1.00 | 43.36 | N |
| ATOM | 6752 | C | GLN | A | 421 | 34.543 | −18.486 | −4.276 | 1.00 | 32.84 | C |
| ATOM | 6753 | O | GLN | A | 421 | 34.009 | −17.923 | −3.320 | 1.00 | 32.60 | O |
| ATOM | 6755 | N | LYS | A | 422 | 34.380 | −19.783 | −4.552 | 1.00 | 33.10 | N |
| ATOM | 6756 | CA | LYS | A | 422 | 33.589 | −20.684 | −3.704 | 1.00 | 33.01 | C |
| ATOM | 6758 | CB | LYS | A | 422 | 33.026 | −21.847 | −4.533 | 1.00 | 33.85 | C |
| ATOM | 6761 | CG | LYS | A | 422 | 32.067 | −21.450 | −5.650 | 1.00 | 37.74 | C |
| ATOM | 6764 | CD | LYS | A | 422 | 31.792 | −22.637 | −6.576 | 1.00 | 42.89 | C |
| ATOM | 6767 | CE | LYS | A | 422 | 30.949 | −22.241 | −7.791 | 1.00 | 46.16 | C |
| ATOM | 6770 | NZ | LYS | A | 422 | 30.975 | −23.307 | −8.845 | 1.00 | 44.93 | N |
| ATOM | 6774 | C | LYS | A | 422 | 34.418 | −21.263 | −2.559 | 1.00 | 31.85 | C |
| ATOM | 6775 | O | LYS | A | 422 | 33.918 | −22.077 | −1.792 | 1.00 | 31.74 | O |
| ATOM | 6777 | N | TYR | A | 423 | 35.679 | −20.850 | −2.457 | 1.00 | 31.54 | N |
| ATOM | 6778 | CA | TYR | A | 423 | 36.625 | −21.387 | −1.473 | 1.00 | 31.88 | C |
| ATOM | 6780 | CB | TYR | A | 423 | 36.243 | −20.978 | −0.049 | 1.00 | 32.14 | C |
| ATOM | 6783 | CG | TYR | A | 423 | 36.306 | −19.488 | 0.108 | 1.00 | 34.99 | C |
| ATOM | 6784 | CD1 | TYR | A | 423 | 37.532 | −18.844 | 0.243 | 1.00 | 38.45 | C |
| ATOM | 6786 | CE1 | TYR | A | 423 | 37.610 | −17.463 | 0.359 | 1.00 | 39.93 | C |
| ATOM | 6788 | CZ | TYR | A | 423 | 36.459 | −16.711 | 0.333 | 1.00 | 41.43 | C |
| ATOM | 6789 | OH | TYR | A | 423 | 36.566 | −15.347 | 0.450 | 1.00 | 46.46 | O |
| ATOM | 6791 | CE2 | TYR | A | 423 | 35.222 | −17.320 | 0.183 | 1.00 | 40.38 | C |
| ATOM | 6793 | CD2 | TYR | A | 423 | 35.154 | −18.709 | 0.064 | 1.00 | 39.66 | C |
| ATOM | 6795 | C | TYR | A | 423 | 36.804 | −22.888 | −1.619 | 1.00 | 30.75 | C |
| ATOM | 6796 | O | TYR | A | 423 | 36.601 | −23.664 | −0.683 | 1.00 | 31.19 | O |
| ATOM | 6798 | N | HIS | A | 424 | 37.202 | −23.280 | −2.820 | 1.00 | 29.71 | N |
| ATOM | 6799 | CA | HIS | A | 424 | 37.529 | −24.659 | −3.095 | 1.00 | 29.55 | C |
| ATOM | 6801 | CB | HIS | A | 424 | 38.046 | −24.811 | −4.528 | 1.00 | 29.55 | C |
| ATOM | 6804 | CG | HIS | A | 424 | 38.156 | −26.232 | −4.983 | 1.00 | 33.09 | C |
| ATOM | 6805 | ND1 | HIS | A | 424 | 39.369 | −26.863 | −5.169 | 1.00 | 33.16 | N |
| ATOM | 6807 | CE1 | HIS | A | 424 | 39.157 | −28.105 | −5.570 | 1.00 | 35.89 | C |
| ATOM | 6809 | NE2 | HIS | A | 424 | 37.851 | −28.303 | −5.642 | 1.00 | 36.09 | N |
| ATOM | 6811 | CD2 | HIS | A | 424 | 37.202 | −27.148 | −5.278 | 1.00 | 33.63 | C |
| ATOM | 6813 | C | HIS | A | 424 | 38.575 | −25.129 | −2.093 | 1.00 | 28.60 | C |
| ATOM | 6814 | O | HIS | A | 424 | 39.387 | −24.339 | −1.611 | 1.00 | 28.26 | O |
| ATOM | 6816 | N | ASP | A | 425 | 38.543 | −26.423 | −1.793 | 1.00 | 28.17 | N |
| ATOM | 6817 | CA | ASP | A | 425 | 39.435 | −27.031 | −0.802 | 1.00 | 27.44 | C |
| ATOM | 6819 | CB | ASP | A | 425 | 39.238 | −28.546 | −0.794 | 1.00 | 27.96 | C |
| ATOM | 6822 | CG | ASP | A | 425 | 37.854 | −28.954 | −0.302 | 1.00 | 30.64 | C |
| ATOM | 6823 | OD1 | ASP | A | 425 | 37.346 | −28.327 | 0.658 | 1.00 | 34.80 | O |
| ATOM | 6824 | OD2 | ASP | A | 425 | 37.283 | −29.909 | −0.874 | 1.00 | 34.42 | O |
| ATOM | 6825 | C | ASP | A | 425 | 40.920 | −26.710 | −0.994 | 1.00 | 25.25 | C |
| ATOM | 6826 | O | ASP | A | 425 | 41.666 | −26.613 | −0.022 | 1.00 | 25.57 | O |
| ATOM | 6828 | N | THR | A | 426 | 41.339 | −26.549 | −2.243 | 1.00 | 23.30 | N |
| ATOM | 6829 | CA | THR | A | 426 | 42.724 | −26.225 | −2.564 | 1.00 | 22.46 | C |
| ATOM | 6831 | CB | THR | A | 426 | 42.870 | −25.912 | −4.049 | 1.00 | 22.03 | C |
| ATOM | 6833 | OG1 | THR | A | 426 | 42.320 | −26.994 | −4.802 | 1.00 | 28.59 | O |
| ATOM | 6835 | CG2 | THR | A | 426 | 44.310 | −25.747 | −4.418 | 1.00 | 20.27 | C |
| ATOM | 6839 | C | THR | A | 426 | 43.250 | −25.044 | −1.762 | 1.00 | 21.80 | C |
| ATOM | 6840 | O | THR | A | 426 | 44.406 | −25.052 | −1.343 | 1.00 | 21.28 | O |
| ATOM | 6842 | N | ILE | A | 427 | 42.407 | −24.037 | −1.548 | 1.00 | 21.03 | N |
| ATOM | 6843 | CA | ILE | A | 427 | 42.804 | −22.885 | −0.753 | 1.00 | 21.51 | C |
| ATOM | 6845 | CB | ILE | A | 427 | 42.540 | −21.548 | −1.487 | 1.00 | 20.95 | C |
| ATOM | 6847 | CG1 | ILE | A | 427 | 41.059 | −21.215 | −1.544 | 1.00 | 20.68 | C |
| ATOM | 6850 | CD1 | ILE | A | 427 | 40.795 | −19.868 | −2.154 | 1.00 | 20.51 | C |
| ATOM | 6854 | CG2 | ILE | A | 427 | 43.114 | −21.592 | −2.883 | 1.00 | 20.86 | C |
| ATOM | 6858 | C | ILE | A | 427 | 42.186 | −22.849 | 0.652 | 1.00 | 22.31 | C |
| ATOM | 6859 | O | ILE | A | 427 | 42.747 | −22.224 | 1.551 | 1.00 | 23.88 | O |
| ATOM | 6861 | N | SER | A | 428 | 41.054 | −23.511 | 0.866 | 1.00 | 21.82 | N |
| ATOM | 6862 | CA | SER | A | 428 | 40.474 | −23.516 | 2.206 | 1.00 | 22.33 | C |
| ATOM | 6864 | CB | SER | A | 428 | 39.028 | −24.017 | 2.198 | 1.00 | 21.31 | C |
| ATOM | 6867 | OG | SER | A | 428 | 38.972 | −25.370 | 1.821 | 1.00 | 24.55 | O |
| ATOM | 6869 | C | SER | A | 428 | 41.343 | −24.344 | 3.157 | 1.00 | 22.40 | C |
| ATOM | 6870 | O | SER | A | 428 | 41.712 | −23.879 | 4.229 | 1.00 | 22.34 | O |
| ATOM | 6872 | N | ARG | A | 429 | 41.707 | −25.550 | 2.742 | 1.00 | 22.23 | N |
| ATOM | 6873 | CA | ARG | A | 429 | 42.416 | −26.464 | 3.628 | 1.00 | 22.93 | C |
| ATOM | 6875 | CB | ARG | A | 429 | 42.585 | −27.832 | 2.964 | 1.00 | 23.58 | C |

APPENDIX 1-continued

| | | | | | | | | | | |
|---|---|---|---|---|---|---|---|---|---|---|
| ATOM | 6878 | CG | ARG | A | 429 | 41.284 | −28.562 | 2.862 | 1.00 | 27.96 | C |
| ATOM | 6881 | CD | ARG | A | 429 | 41.461 | −29.989 | 2.472 | 1.00 | 36.79 | C |
| ATOM | 6884 | NE | ARG | A | 429 | 40.155 | −30.586 | 2.201 | 1.00 | 43.35 | N |
| ATOM | 6886 | CZ | ARG | A | 429 | 39.813 | −31.223 | 1.082 | 1.00 | 44.66 | C |
| ATOM | 6887 | NH1 | ARG | A | 429 | 40.679 | −31.385 | 0.080 | 1.00 | 43.44 | N |
| ATOM | 6890 | NH2 | ARG | A | 429 | 38.584 | −31.708 | 0.970 | 1.00 | 46.29 | N |
| ATOM | 6893 | C | ARG | A | 429 | 43.752 | −25.950 | 4.180 | 1.00 | 22.07 | C |
| ATOM | 6894 | O | ARG | A | 429 | 43.982 | −26.054 | 5.370 | 1.00 | 22.38 | O |
| ATOM | 6896 | N | PRO | A | 430 | 44.633 | −25.399 | 3.329 | 1.00 | 21.78 | N |
| ATOM | 6897 | CA | PRO | A | 430 | 45.868 | −24.818 | 3.863 | 1.00 | 21.02 | C |
| ATOM | 6899 | CB | PRO | A | 430 | 46.559 | −24.243 | 2.626 | 1.00 | 20.87 | C |
| ATOM | 6902 | CG | PRO | A | 430 | 46.004 | −24.985 | 1.491 | 1.00 | 23.01 | C |
| ATOM | 6905 | CD | PRO | A | 430 | 44.593 | −25.339 | 1.860 | 1.00 | 22.62 | C |
| ATOM | 6908 | C | PRO | A | 430 | 45.599 | −23.695 | 4.840 | 1.00 | 20.48 | C |
| ATOM | 6909 | O | PRO | A | 430 | 46.359 | −23.497 | 5.788 | 1.00 | 20.34 | O |
| ATOM | 6910 | N | SER | A | 431 | 44.518 | −22.963 | 4.603 | 1.00 | 19.97 | N |
| ATOM | 6911 | CA | SER | A | 431 | 44.127 | −21.885 | 5.490 | 1.00 | 19.52 | C |
| ATOM | 6913 | CB | SER | A | 431 | 43.082 | −21.004 | 4.815 | 1.00 | 20.32 | C |
| ATOM | 6916 | OG | SER | A | 431 | 43.532 | −20.607 | 3.532 | 1.00 | 19.38 | O |
| ATOM | 6918 | C | SER | A | 431 | 43.605 | −22.428 | 6.817 | 1.00 | 18.44 | C |
| ATOM | 6919 | O | SER | A | 431 | 43.778 | −21.793 | 7.845 | 1.00 | 18.95 | O |
| ATOM | 6921 | N | HIS | A | 432 | 42.972 | −23.596 | 6.799 | 1.00 | 17.54 | N |
| ATOM | 6922 | CA | HIS | A | 432 | 42.640 | −24.289 | 8.041 | 1.00 | 18.72 | C |
| ATOM | 6924 | CB | HIS | A | 432 | 42.035 | −25.679 | 7.782 | 1.00 | 19.51 | C |
| ATOM | 6927 | CG | HIS | A | 432 | 40.631 | −25.662 | 7.268 | 1.00 | 21.68 | C |
| ATOM | 6928 | ND1 | HIS | A | 432 | 40.151 | −24.683 | 6.425 | 1.00 | 30.18 | N |
| ATOM | 6930 | CE1 | HIS | A | 432 | 38.889 | −24.938 | 6.129 | 1.00 | 29.72 | C |
| ATOM | 6932 | NE2 | HIS | A | 432 | 38.538 | −26.058 | 6.733 | 1.00 | 27.31 | N |
| ATOM | 6934 | CD2 | HIS | A | 432 | 39.612 | −26.535 | 7.445 | 1.00 | 26.70 | C |
| ATOM | 6936 | C | HIS | A | 432 | 43.920 | −24.471 | 8.864 | 1.00 | 18.63 | C |
| ATOM | 6937 | O | HIS | A | 432 | 43.962 | −24.117 | 10.043 | 1.00 | 17.64 | O |
| ATOM | 6939 | N | ILE | A | 433 | 44.957 | −25.029 | 8.235 | 1.00 | 18.12 | N |
| ATOM | 6940 | CA | ILE | A | 433 | 46.215 | −25.307 | 8.929 | 1.00 | 18.72 | C |
| ATOM | 6942 | CB | ILE | A | 433 | 47.280 | −25.963 | 8.016 | 1.00 | 18.77 | C |
| ATOM | 6944 | CG1 | ILE | A | 433 | 46.783 | −27.280 | 7.409 | 1.00 | 21.09 | C |
| ATOM | 6947 | CD1 | ILE | A | 433 | 46.524 | −28.349 | 8.411 | 1.00 | 23.35 | C |
| ATOM | 6951 | CG2 | ILE | A | 433 | 48.565 | −26.224 | 8.796 | 1.00 | 16.10 | C |
| ATOM | 6955 | C | ILE | A | 433 | 46.793 | −24.004 | 9.473 | 1.00 | 18.88 | C |
| ATOM | 6956 | O | ILE | A | 433 | 47.226 | −23.941 | 10.617 | 1.00 | 18.88 | O |
| ATOM | 6958 | N | PHE | A | 434 | 46.780 | −22.975 | 8.635 | 1.00 | 18.66 | N |
| ATOM | 6959 | CA | PHE | A | 434 | 47.313 | −21.666 | 8.968 | 1.00 | 18.88 | C |
| ATOM | 6961 | CB | PHE | A | 434 | 47.073 | −20.731 | 7.769 | 1.00 | 19.86 | C |
| ATOM | 6964 | CG | PHE | A | 434 | 47.579 | −19.312 | 7.934 | 1.00 | 22.12 | C |
| ATOM | 6965 | CD1 | PHE | A | 434 | 48.493 | −18.947 | 8.924 | 1.00 | 23.34 | C |
| ATOM | 6967 | CE1 | PHE | A | 434 | 48.940 | −17.627 | 9.027 | 1.00 | 23.55 | C |
| ATOM | 6969 | CZ | PHE | A | 434 | 48.494 | −16.667 | 8.126 | 1.00 | 21.56 | C |
| ATOM | 6971 | CE2 | PHE | A | 434 | 47.601 | −17.025 | 7.127 | 1.00 | 25.55 | C |
| ATOM | 6973 | CD2 | PHE | A | 434 | 47.153 | −18.337 | 7.034 | 1.00 | 24.16 | C |
| ATOM | 6975 | C | PHE | A | 434 | 46.677 | −21.149 | 10.253 | 1.00 | 18.81 | C |
| ATOM | 6976 | O | PHE | A | 434 | 47.370 | −20.896 | 11.240 | 1.00 | 19.27 | O |
| ATOM | 6978 | N | ARG | A | 435 | 45.357 | −21.023 | 10.257 | 1.00 | 18.71 | N |
| ATOM | 6979 | CA | ARG | A | 435 | 44.650 | −20.554 | 11.450 | 1.00 | 18.49 | C |
| ATOM | 6981 | CB | ARG | A | 435 | 43.149 | −20.424 | 11.169 | 1.00 | 18.78 | C |
| ATOM | 6984 | CG | ARG | A | 435 | 42.265 | −20.203 | 12.401 | 1.00 | 20.05 | C |
| ATOM | 6987 | CD | ARG | A | 435 | 42.636 | −18.948 | 13.173 | 1.00 | 20.50 | C |
| ATOM | 6990 | NE | ARG | A | 435 | 42.392 | −17.736 | 12.398 | 1.00 | 20.69 | N |
| ATOM | 6992 | CZ | ARG | A | 435 | 42.866 | −16.531 | 12.710 | 1.00 | 18.20 | C |
| ATOM | 6993 | NH1 | ARG | A | 435 | 43.628 | −16.354 | 13.783 | 1.00 | 16.34 | N |
| ATOM | 6996 | NH2 | ARG | A | 435 | 42.590 | −15.499 | 11.930 | 1.00 | 18.57 | N |
| ATOM | 6999 | C | ARG | A | 435 | 44.897 | −21.441 | 12.679 | 1.00 | 18.35 | C |
| ATOM | 7000 | O | ARG | A | 435 | 45.029 | −20.930 | 13.783 | 1.00 | 19.10 | O |
| ATOM | 7002 | N | LEU | A | 436 | 44.965 | −22.757 | 12.497 | 1.00 | 18.51 | N |
| ATOM | 7003 | CA | LEU | A | 436 | 45.078 | −23.670 | 13.638 | 1.00 | 18.31 | C |
| ATOM | 7005 | CB | LEU | A | 436 | 44.722 | −25.106 | 13.244 | 1.00 | 18.73 | C |
| ATOM | 7008 | CG | LEU | A | 436 | 43.249 | −25.412 | 12.891 | 1.00 | 18.89 | C |
| ATOM | 7010 | CD1 | LEU | A | 436 | 43.103 | −26.835 | 12.324 | 1.00 | 13.86 | C |
| ATOM | 7014 | CD2 | LEU | A | 436 | 42.326 | −25.223 | 14.081 | 1.00 | 11.25 | C |
| ATOM | 7018 | C | LEU | A | 436 | 46.473 | −23.610 | 14.244 | 1.00 | 18.76 | C |
| ATOM | 7019 | O | LEU | A | 436 | 46.618 | −23.631 | 15.461 | 1.00 | 19.39 | O |
| ATOM | 7021 | N | CYS | A | 437 | 47.493 | −23.527 | 13.395 | 1.00 | 19.06 | N |
| ATOM | 7022 | CA | CYS | A | 437 | 48.869 | −23.352 | 13.846 | 1.00 | 19.36 | C |
| ATOM | 7024 | CB | CYS | A | 437 | 49.831 | −23.321 | 12.655 | 1.00 | 19.50 | C |
| ATOM | 7027 | SG | CYS | A | 437 | 50.151 | −24.940 | 11.899 | 1.00 | 22.20 | S |
| ATOM | 7029 | C | CYS | A | 437 | 49.005 | −22.063 | 14.651 | 1.00 | 20.85 | C |
| ATOM | 7030 | O | CYS | A | 437 | 49.531 | −22.070 | 15.767 | 1.00 | 20.54 | O |
| ATOM | 7032 | N | ASN | A | 438 | 48.526 | −20.959 | 14.080 | 1.00 | 22.04 | N |
| ATOM | 7033 | CA | ASN | A | 438 | 48.545 | −19.675 | 14.761 | 1.00 | 22.16 | C |
| ATOM | 7035 | CB | ASN | A | 438 | 47.798 | −18.620 | 13.940 | 1.00 | 23.23 | C |
| ATOM | 7038 | CG | ASN | A | 438 | 47.863 | −17.218 | 14.556 | 1.00 | 23.29 | C |
| ATOM | 7039 | OD1 | ASN | A | 438 | 47.842 | −17.043 | 15.776 | 1.00 | 29.89 | O |

APPENDIX 1-continued

| ATOM | 7040 | ND2 | ASN | A | 438 | 47.920 | −16.215 | 13.700 | 1.00 | 23.81 | N |
|---|---|---|---|---|---|---|---|---|---|---|---|
| ATOM | 7043 | C | ASN | A | 438 | 47.922 | −19.803 | 16.134 | 1.00 | 22.70 | C |
| ATOM | 7044 | O | ASN | A | 438 | 48.567 | −19.522 | 17.145 | 1.00 | 24.60 | O |
| ATOM | 7046 | N | ASP | A | 439 | 46.670 | −20.238 | 16.170 | 1.00 | 22.82 | N |
| ATOM | 7047 | CA | ASP | A | 439 | 45.913 | −20.274 | 17.422 | 1.00 | 22.80 | C |
| ATOM | 7049 | CB | ASP | A | 439 | 44.447 | −20.613 | 17.151 | 1.00 | 22.49 | C |
| ATOM | 7052 | CG | ASP | A | 439 | 43.692 | −19.457 | 16.523 | 1.00 | 22.19 | C |
| ATOM | 7053 | OD1 | ASP | A | 439 | 44.344 | −18.481 | 16.083 | 1.00 | 21.84 | O |
| ATOM | 7054 | OD2 | ASP | A | 439 | 42.445 | −19.526 | 16.474 | 1.00 | 23.84 | O |
| ATOM | 7055 | C | ASP | A | 439 | 46.518 | −21.231 | 18.445 | 1.00 | 22.94 | C |
| ATOM | 7056 | O | ASP | A | 439 | 46.460 | −20.977 | 19.652 | 1.00 | 22.06 | O |
| ATOM | 7058 | N | LEU | A | 440 | 47.107 | −22.320 | 17.960 | 1.00 | 23.94 | N |
| ATOM | 7059 | CA | LEU | A | 440 | 47.855 | −23.236 | 18.828 | 1.00 | 25.10 | C |
| ATOM | 7061 | CB | LEU | A | 440 | 48.435 | −24.403 | 18.026 | 1.00 | 24.61 | C |
| ATOM | 7064 | CG | LEU | A | 440 | 47.518 | −25.600 | 17.819 | 1.00 | 24.36 | C |
| ATOM | 7066 | CD1 | LEU | A | 440 | 48.216 | −26.596 | 16.916 | 1.00 | 25.39 | C |
| ATOM | 7070 | CD2 | LEU | A | 440 | 47.145 | −26.231 | 19.152 | 1.00 | 21.29 | C |
| ATOM | 7074 | C | LEU | A | 440 | 48.994 | −22.531 | 19.556 | 1.00 | 25.35 | C |
| ATOM | 7075 | O | LEU | A | 440 | 49.214 | −22.764 | 20.741 | 1.00 | 26.43 | O |
| ATOM | 7077 | N | ALA | A | 441 | 49.712 | −21.681 | 18.831 | 1.00 | 25.10 | N |
| ATOM | 7078 | CA | ALA | A | 441 | 50.892 | −21.009 | 19.355 | 1.00 | 24.74 | C |
| ATOM | 7080 | CB | ALA | A | 441 | 51.572 | −20.207 | 18.249 | 1.00 | 24.15 | C |
| ATOM | 7084 | C | ALA | A | 441 | 50.548 | −20.106 | 20.535 | 1.00 | 25.07 | C |
| ATOM | 7085 | O | ALA | A | 441 | 51.312 | −20.034 | 21.495 | 1.00 | 24.89 | O |
| ATOM | 7087 | N | SER | A | 442 | 49.393 | −19.443 | 20.469 | 1.00 | 25.14 | N |
| ATOM | 7088 | CA | SER | A | 442 | 48.966 | −18.510 | 21.516 | 1.00 | 25.55 | C |
| ATOM | 7090 | CB | SER | A | 442 | 48.481 | −17.209 | 20.882 | 1.00 | 25.07 | C |
| ATOM | 7093 | OG | SER | A | 442 | 47.508 | −17.474 | 19.897 | 1.00 | 27.87 | O |
| ATOM | 7095 | C | SER | A | 442 | 47.879 | −19.066 | 22.448 | 1.00 | 26.22 | C |
| ATOM | 7096 | O | SER | A | 442 | 47.468 | −18.392 | 23.398 | 1.00 | 25.43 | O |
| ATOM | 7098 | N | ALA | A | 443 | 47.436 | −20.296 | 22.194 | 1.00 | 26.79 | N |
| ATOM | 7099 | CA | ALA | A | 443 | 46.314 | −20.873 | 22.929 | 1.00 | 27.22 | C |
| ATOM | 7101 | CB | ALA | A | 443 | 46.131 | −22.334 | 22.556 | 1.00 | 27.55 | C |
| ATOM | 7105 | C | ALA | A | 443 | 46.474 | −20.740 | 24.435 | 1.00 | 28.37 | C |
| ATOM | 7106 | O | ALA | A | 443 | 45.653 | −20.104 | 25.092 | 1.00 | 28.82 | O |
| ATOM | 7108 | N | SER | A | 444 | 47.537 | −21.325 | 24.979 | 1.00 | 29.79 | N |
| ATOM | 7109 | CA | SER | A | 444 | 47.677 | −21.439 | 26.437 | 1.00 | 30.42 | C |
| ATOM | 7111 | CB | SER | A | 444 | 48.835 | −22.377 | 26.819 | 1.00 | 30.42 | C |
| ATOM | 7114 | OG | SER | A | 444 | 50.079 | −21.704 | 26.838 | 1.00 | 35.09 | O |
| ATOM | 7116 | C | SER | A | 444 | 47.825 | −20.082 | 27.120 | 1.00 | 30.19 | C |
| ATOM | 7117 | O | SER | A | 444 | 47.308 | −19.884 | 28.215 | 1.00 | 30.28 | O |
| ATOM | 7119 | N | ALA | A | 445 | 48.520 | −19.153 | 26.468 | 1.00 | 31.06 | N |
| ATOM | 7120 | CA | ALA | A | 445 | 48.665 | −17.792 | 26.984 | 1.00 | 31.76 | C |
| ATOM | 7122 | CB | ALA | A | 445 | 49.669 | −17.000 | 26.149 | 1.00 | 31.08 | C |
| ATOM | 7126 | C | ALA | A | 445 | 47.316 | −17.078 | 27.011 | 1.00 | 32.95 | C |
| ATOM | 7127 | O | ALA | A | 445 | 46.928 | −16.517 | 28.039 | 1.00 | 34.62 | O |
| ATOM | 7129 | N | GLU | A | 446 | 46.602 | −17.107 | 25.887 | 1.00 | 33.61 | N |
| ATOM | 7130 | CA | GLU | A | 446 | 45.315 | −16.414 | 25.766 | 1.00 | 34.10 | C |
| ATOM | 7132 | CB | GLU | A | 446 | 44.805 | −16.438 | 24.314 | 1.00 | 34.56 | C |
| ATOM | 7135 | CG | GLU | A | 446 | 45.647 | −15.607 | 23.327 | 1.00 | 37.05 | C |
| ATOM | 7138 | CD | GLU | A | 446 | 45.093 | −15.604 | 21.898 | 1.00 | 39.71 | C |
| ATOM | 7139 | OE1 | GLU | A | 446 | 43.878 | −15.817 | 21.707 | 1.00 | 44.12 | O |
| ATOM | 7140 | OE2 | GLU | A | 446 | 45.875 | −15.376 | 20.956 | 1.00 | 42.43 | O |
| ATOM | 7141 | C | GLU | A | 446 | 44.269 | −17.003 | 26.713 | 1.00 | 33.79 | C |
| ATOM | 7142 | O | GLU | A | 446 | 43.495 | −16.263 | 27.316 | 1.00 | 33.16 | O |
| ATOM | 7144 | N | ILE | A | 447 | 44.263 | −18.330 | 26.844 | 1.00 | 34.58 | N |
| ATOM | 7145 | CA | ILE | A | 447 | 43.341 | −19.029 | 27.749 | 1.00 | 35.30 | C |
| ATOM | 7147 | CB | ILE | A | 447 | 43.423 | −20.565 | 27.570 | 1.00 | 35.29 | C |
| ATOM | 7149 | CG1 | ILE | A | 447 | 42.832 | −20.984 | 26.221 | 1.00 | 36.11 | C |
| ATOM | 7152 | CD1 | ILE | A | 447 | 43.148 | −22.424 | 25.839 | 1.00 | 34.34 | C |
| ATOM | 7156 | CG2 | ILE | A | 447 | 42.672 | −21.285 | 28.682 | 1.00 | 33.95 | C |
| ATOM | 7160 | C | ILE | A | 447 | 43.618 | −18.678 | 29.211 | 1.00 | 36.55 | C |
| ATOM | 7161 | O | ILE | A | 447 | 42.689 | −18.587 | 30.017 | 1.00 | 36.36 | O |
| ATOM | 7163 | N | ALA | A | 448 | 44.895 | −18.485 | 29.541 | 1.00 | 38.20 | N |
| ATOM | 7164 | CA | ALA | A | 448 | 45.306 | −18.044 | 30.877 | 1.00 | 39.13 | C |
| ATOM | 7166 | CB | ALA | A | 448 | 46.829 | −18.057 | 30.997 | 1.00 | 38.88 | C |
| ATOM | 7170 | C | ALA | A | 448 | 44.753 | −16.651 | 31.198 | 1.00 | 40.09 | C |
| ATOM | 7171 | O | ALA | A | 448 | 44.246 | −16.431 | 32.299 | 1.00 | 40.94 | O |
| ATOM | 7173 | N | ARG | A | 449 | 44.837 | −15.727 | 30.235 | 1.00 | 40.74 | N |
| ATOM | 7174 | CA | ARG | A | 449 | 44.231 | −14.389 | 30.370 | 1.00 | 41.49 | C |
| ATOM | 7176 | CB | ARG | A | 449 | 44.747 | −13.427 | 29.287 | 1.00 | 42.44 | C |
| ATOM | 7179 | CG | ARG | A | 449 | 46.261 | −13.208 | 29.228 | 1.00 | 45.54 | C |
| ATOM | 7182 | CD | ARG | A | 449 | 46.598 | −12.016 | 28.311 | 1.00 | 48.80 | C |
| ATOM | 7185 | NE | ARG | A | 449 | 47.788 | −12.251 | 27.482 | 1.00 | 53.07 | N |
| ATOM | 7187 | CZ | ARG | A | 449 | 47.798 | −12.442 | 26.157 | 1.00 | 54.07 | C |
| ATOM | 7188 | NH1 | ARG | A | 449 | 46.678 | −12.426 | 25.433 | 1.00 | 53.70 | N |
| ATOM | 7191 | NH2 | ARG | A | 449 | 48.958 | −12.648 | 25.539 | 1.00 | 55.16 | N |
| ATOM | 7194 | C | ARG | A | 449 | 42.695 | −14.412 | 30.287 | 1.00 | 41.08 | C |
| ATOM | 7195 | O | ARG | A | 449 | 42.051 | −13.372 | 30.425 | 1.00 | 40.93 | O |
| ATOM | 7197 | N | GLY | A | 450 | 42.114 | −15.581 | 30.027 | 1.00 | 41.08 | N |

APPENDIX 1-continued

| | | | | | | | | | | |
|---|---|---|---|---|---|---|---|---|---|---|
| ATOM | 7198 | CA | GLY | A | 450 | 40.664 | −15.737 | 29.988 | 1.00 | 41.35 | C |
| ATOM | 7201 | C | GLY | A | 450 | 40.008 | −15.231 | 28.714 | 1.00 | 41.81 | C |
| ATOM | 7202 | O | GLY | A | 450 | 38.809 | −14.957 | 28.703 | 1.00 | 42.43 | O |
| ATOM | 7204 | N | GLU | A | 451 | 40.783 | −15.106 | 27.639 | 1.00 | 42.01 | N |
| ATOM | 7205 | CA | GLU | A | 451 | 40.243 | −14.698 | 26.341 | 1.00 | 42.21 | C |
| ATOM | 7207 | CB | GLU | A | 451 | 41.323 | −14.027 | 25.485 | 1.00 | 42.94 | C |
| ATOM | 7210 | CG | GLU | A | 451 | 41.686 | −12.618 | 25.944 | 1.00 | 46.13 | C |
| ATOM | 7213 | CD | GLU | A | 451 | 42.918 | −12.064 | 25.247 | 1.00 | 51.32 | C |
| ATOM | 7214 | OE1 | GLU | A | 451 | 43.014 | −12.174 | 24.003 | 1.00 | 55.77 | O |
| ATOM | 7215 | OE2 | GLU | A | 451 | 43.793 | −11.512 | 25.946 | 1.00 | 54.02 | O |
| ATOM | 7216 | C | GLU | A | 451 | 39.671 | −15.914 | 25.616 | 1.00 | 41.36 | C |
| ATOM | 7217 | O | GLU | A | 451 | 40.216 | −17.018 | 25.721 | 1.00 | 41.67 | O |
| ATOM | 7219 | N | THR | A | 452 | 38.578 | −15.704 | 24.883 | 1.00 | 39.62 | N |
| ATOM | 7220 | CA | THR | A | 452 | 37.870 | −16.789 | 24.199 | 1.00 | 38.05 | C |
| ATOM | 7222 | CB | THR | A | 452 | 36.359 | −16.744 | 24.516 | 1.00 | 38.38 | C |
| ATOM | 7224 | OG1 | THR | A | 452 | 35.815 | −15.487 | 24.099 | 1.00 | 39.80 | O |
| ATOM | 7226 | CG2 | THR | A | 452 | 36.112 | −16.922 | 26.014 | 1.00 | 38.40 | C |
| ATOM | 7230 | C | THR | A | 452 | 38.050 | −16.790 | 22.672 | 1.00 | 36.23 | C |
| ATOM | 7231 | O | THR | A | 452 | 37.741 | −17.790 | 22.019 | 1.00 | 36.26 | O |
| ATOM | 7233 | N | ALA | A | 453 | 38.550 | −15.689 | 22.108 | 1.00 | 33.88 | N |
| ATOM | 7234 | CA | ALA | A | 453 | 38.696 | −15.557 | 20.651 | 1.00 | 32.34 | C |
| ATOM | 7236 | CB | ALA | A | 453 | 38.826 | −14.081 | 20.260 | 1.00 | 32.25 | C |
| ATOM | 7240 | C | ALA | A | 453 | 39.893 | −16.364 | 20.137 | 1.00 | 30.59 | C |
| ATOM | 7241 | O | ALA | A | 453 | 40.921 | −15.803 | 19.742 | 1.00 | 29.94 | O |
| ATOM | 7243 | N | ASN | A | 454 | 39.734 | −17.685 | 20.143 | 1.00 | 28.78 | N |
| ATOM | 7244 | CA | ASN | A | 454 | 40.806 | −18.619 | 19.808 | 1.00 | 28.21 | C |
| ATOM | 7246 | CB | ASN | A | 454 | 41.827 | −18.703 | 20.961 | 1.00 | 28.44 | C |
| ATOM | 7249 | CG | ASN | A | 454 | 43.004 | −19.643 | 20.656 | 1.00 | 30.86 | C |
| ATOM | 7250 | OD1 | ASN | A | 454 | 42.859 | −20.870 | 20.679 | 1.00 | 31.68 | O |
| ATOM | 7251 | ND2 | ASN | A | 454 | 44.178 | −19.064 | 20.394 | 1.00 | 26.67 | N |
| ATOM | 7254 | C | ASN | A | 454 | 40.205 | −19.994 | 19.508 | 1.00 | 27.11 | C |
| ATOM | 7255 | O | ASN | A | 454 | 39.375 | −20.496 | 20.272 | 1.00 | 26.51 | O |
| ATOM | 7257 | N | SER | A | 455 | 40.629 | −20.595 | 18.397 | 1.00 | 25.67 | N |
| ATOM | 7258 | CA | SER | A | 455 | 40.076 | −21.868 | 17.934 | 1.00 | 24.70 | C |
| ATOM | 7260 | CB | SER | A | 455 | 40.839 | −22.350 | 16.701 | 1.00 | 24.98 | C |
| ATOM | 7263 | OG | SER | A | 455 | 40.737 | −21.396 | 15.657 | 1.00 | 26.20 | O |
| ATOM | 7265 | C | SER | A | 455 | 40.091 | −22.952 | 19.008 | 1.00 | 23.69 | C |
| ATOM | 7266 | O | SER | A | 455 | 39.084 | −23.631 | 19.220 | 1.00 | 22.56 | O |
| ATOM | 7268 | N | VAL | A | 456 | 41.233 | −23.105 | 19.682 | 1.00 | 23.36 | N |
| ATOM | 7269 | CA | VAL | A | 456 | 41.387 | −24.106 | 20.747 | 1.00 | 22.71 | C |
| ATOM | 7271 | CB | VAL | A | 456 | 42.810 | −24.100 | 21.347 | 1.00 | 22.74 | C |
| ATOM | 7273 | CG1 | VAL | A | 456 | 42.946 | −25.179 | 22.420 | 1.00 | 17.64 | C |
| ATOM | 7277 | CG2 | VAL | A | 456 | 43.852 | −24.291 | 20.254 | 1.00 | 22.47 | C |
| ATOM | 7281 | C | VAL | A | 456 | 40.397 | −23.849 | 21.873 | 1.00 | 22.79 | C |
| ATOM | 7282 | O | VAL | A | 456 | 39.705 | −24.759 | 22.329 | 1.00 | 22.39 | O |
| ATOM | 7284 | N | SER | A | 457 | 40.336 | −22.597 | 22.311 | 1.00 | 24.04 | N |
| ATOM | 7285 | CA | SER | A | 457 | 39.400 | −22.183 | 23.358 | 1.00 | 25.06 | C |
| ATOM | 7287 | CB | SER | A | 457 | 39.544 | −20.684 | 23.633 | 1.00 | 24.32 | C |
| ATOM | 7290 | OG | SER | A | 457 | 38.420 | −20.192 | 24.330 | 1.00 | 27.39 | O |
| ATOM | 7292 | C | SER | A | 457 | 37.943 | −22.531 | 23.006 | 1.00 | 25.81 | C |
| ATOM | 7293 | O | SER | A | 457 | 37.251 | −23.168 | 23.802 | 1.00 | 25.51 | O |
| ATOM | 7295 | N | CYS | A | 458 | 37.491 | −22.126 | 21.817 | 1.00 | 26.61 | N |
| ATOM | 7296 | CA | CYS | A | 458 | 36.118 | −22.425 | 21.365 | 1.00 | 27.38 | C |
| ATOM | 7298 | CB | CYS | A | 458 | 35.836 | −21.830 | 19.986 | 1.00 | 27.10 | C |
| ATOM | 7301 | SG | CYS | A | 458 | 35.524 | −20.076 | 20.036 | 1.00 | 33.51 | S |
| ATOM | 7303 | C | CYS | A | 458 | 35.837 | −23.917 | 21.330 | 1.00 | 26.81 | C |
| ATOM | 7304 | O | CYS | A | 458 | 34.720 | −24.351 | 21.627 | 1.00 | 26.86 | O |
| ATOM | 7306 | N | TYR | A | 459 | 36.848 | −24.695 | 20.963 | 1.00 | 26.30 | N |
| ATOM | 7307 | CA | TYR | A | 459 | 36.714 | −26.140 | 20.968 | 1.00 | 26.58 | C |
| ATOM | 7309 | CB | TYR | A | 459 | 37.974 | −26.811 | 20.430 | 1.00 | 27.07 | C |
| ATOM | 7312 | CG | TYR | A | 459 | 37.703 | −28.140 | 19.772 | 1.00 | 28.23 | C |
| ATOM | 7313 | CD1 | TYR | A | 459 | 37.722 | −29.317 | 20.509 | 1.00 | 29.39 | C |
| ATOM | 7315 | CE1 | TYR | A | 459 | 37.473 | −30.543 | 19.907 | 1.00 | 33.43 | C |
| ATOM | 7317 | CZ | TYR | A | 459 | 37.201 | −30.598 | 18.552 | 1.00 | 34.05 | C |
| ATOM | 7318 | OH | TYR | A | 459 | 36.956 | −31.810 | 17.961 | 1.00 | 37.25 | O |
| ATOM | 7320 | CE2 | TYR | A | 459 | 37.177 | −29.438 | 17.796 | 1.00 | 33.32 | C |
| ATOM | 7322 | CD2 | TYR | A | 459 | 37.424 | −28.217 | 18.410 | 1.00 | 30.09 | C |
| ATOM | 7324 | C | TYR | A | 459 | 36.415 | −26.608 | 22.386 | 1.00 | 26.59 | C |
| ATOM | 7325 | O | TYR | A | 459 | 35.420 | −27.299 | 22.611 | 1.00 | 26.74 | O |
| ATOM | 7327 | N | MET | A | 460 | 37.254 | −26.202 | 23.340 | 1.00 | 26.73 | N |
| ATOM | 7328 | CA | MET | A | 460 | 37.032 | −26.537 | 24.754 | 1.00 | 27.29 | C |
| ATOM | 7330 | CB | MET | A | 460 | 37.959 | −25.746 | 25.678 | 1.00 | 27.58 | C |
| ATOM | 7333 | CG | MET | A | 460 | 39.424 | −26.091 | 25.575 | 1.00 | 28.59 | C |
| ATOM | 7336 | SD | MET | A | 460 | 40.422 | −24.891 | 26.471 | 1.00 | 33.42 | S |
| ATOM | 7337 | CE | MET | A | 460 | 39.811 | −25.085 | 28.148 | 1.00 | 22.63 | C |
| ATOM | 7341 | C | MET | A | 460 | 35.602 | −26.249 | 25.174 | 1.00 | 26.99 | C |
| ATOM | 7342 | O | MET | A | 460 | 34.963 | −27.088 | 25.797 | 1.00 | 27.19 | O |
| ATOM | 7344 | N | ARG | A | 461 | 35.107 | −25.063 | 24.831 | 1.00 | 27.64 | N |
| ATOM | 7345 | CA | ARG | A | 461 | 33.786 | −24.622 | 25.283 | 1.00 | 28.90 | C |
| ATOM | 7347 | CB | ARG | A | 461 | 33.582 | −23.138 | 25.001 | 1.00 | 29.19 | C |

APPENDIX 1-continued

| ATOM | 7350 | CG | ARG | A | 461 | 34.423 | −22.213 | 25.876 | 1.00 | 34.67 | C |
|---|---|---|---|---|---|---|---|---|---|---|---|
| ATOM | 7353 | CD | ARG | A | 461 | 34.017 | −20.760 | 25.653 | 1.00 | 40.90 | C |
| ATOM | 7356 | NE | ARG | A | 461 | 34.080 | −20.420 | 24.232 | 1.00 | 47.05 | N |
| ATOM | 7358 | CZ | ARG | A | 461 | 33.450 | −19.398 | 23.650 | 1.00 | 51.83 | C |
| ATOM | 7359 | NH1 | ARG | A | 461 | 32.691 | −18.560 | 24.353 | 1.00 | 52.55 | N |
| ATOM | 7362 | NH2 | ARG | A | 461 | 33.590 | −19.209 | 22.341 | 1.00 | 53.43 | N |
| ATOM | 7365 | C | ARG | A | 461 | 32.648 | −25.433 | 24.658 | 1.00 | 28.92 | C |
| ATOM | 7366 | O | ARG | A | 461 | 31.759 | −25.915 | 25.374 | 1.00 | 28.78 | O |
| ATOM | 7368 | N | THR | A | 462 | 32.684 | −25.591 | 23.335 | 1.00 | 28.97 | N |
| ATOM | 7369 | CA | THR | A | 462 | 31.671 | −26.376 | 22.619 | 1.00 | 28.80 | C |
| ATOM | 7371 | CB | THR | A | 462 | 31.962 | −26.447 | 21.101 | 1.00 | 28.77 | C |
| ATOM | 7373 | OG1 | THR | A | 462 | 32.215 | −25.132 | 20.588 | 1.00 | 30.56 | O |
| ATOM | 7375 | CG2 | THR | A | 462 | 30.784 | −27.059 | 20.354 | 1.00 | 28.56 | C |
| ATOM | 7379 | C | THR | A | 462 | 31.597 | −27.802 | 23.170 | 1.00 | 28.81 | C |
| ATOM | 7380 | O | THR | A | 462 | 30.523 | −28.272 | 23.552 | 1.00 | 28.93 | O |
| ATOM | 7382 | N | LYS | A | 463 | 32.750 | −28.468 | 23.237 | 1.00 | 28.48 | N |
| ATOM | 7383 | CA | LYS | A | 463 | 32.826 | −29.871 | 23.666 | 1.00 | 28.46 | C |
| ATOM | 7385 | CB | LYS | A | 463 | 33.985 | −30.576 | 22.947 | 1.00 | 28.99 | C |
| ATOM | 7388 | CG | LYS | A | 463 | 33.895 | −30.559 | 21.423 | 1.00 | 31.83 | C |
| ATOM | 7391 | CD | LYS | A | 463 | 32.798 | −31.484 | 20.899 | 1.00 | 34.23 | C |
| ATOM | 7394 | CE | LYS | A | 463 | 32.884 | −31.655 | 19.378 | 1.00 | 36.55 | C |
| ATOM | 7397 | NZ | LYS | A | 463 | 32.245 | −32.930 | 18.922 | 1.00 | 36.99 | N |
| ATOM | 7401 | C | LYS | A | 463 | 32.985 | −30.077 | 25.183 | 1.00 | 27.40 | C |
| ATOM | 7402 | O | LYS | A | 463 | 33.100 | −31.214 | 25.630 | 1.00 | 28.09 | O |
| ATOM | 7404 | N | GLY | A | 464 | 32.999 | −28.999 | 25.966 | 1.00 | 25.81 | N |
| ATOM | 7405 | CA | GLY | A | 464 | 33.180 | −29.101 | 27.417 | 1.00 | 24.54 | C |
| ATOM | 7408 | C | GLY | A | 464 | 34.334 | −30.003 | 27.828 | 1.00 | 24.07 | C |
| ATOM | 7409 | O | GLY | A | 464 | 34.141 | −30.962 | 28.579 | 1.00 | 24.88 | O |
| ATOM | 7411 | N | ILE | A | 465 | 35.532 | −29.694 | 27.333 | 1.00 | 23.11 | N |
| ATOM | 7412 | CA | ILE | A | 465 | 36.733 | −30.501 | 27.582 | 1.00 | 22.58 | C |
| ATOM | 7414 | CB | ILE | A | 465 | 37.069 | −31.390 | 26.359 | 1.00 | 22.56 | C |
| ATOM | 7416 | CG1 | ILE | A | 465 | 37.399 | −30.522 | 25.129 | 1.00 | 23.34 | C |
| ATOM | 7419 | CD1 | ILE | A | 465 | 37.588 | −31.291 | 23.838 | 1.00 | 23.22 | C |
| ATOM | 7423 | CG2 | ILE | A | 465 | 35.912 | −32.343 | 26.065 | 1.00 | 19.03 | C |
| ATOM | 7427 | C | ILE | A | 465 | 37.937 | −29.612 | 27.914 | 1.00 | 23.14 | C |
| ATOM | 7428 | O | ILE | A | 465 | 37.919 | −28.402 | 27.645 | 1.00 | 23.01 | O |
| ATOM | 7430 | N | SER | A | 466 | 38.985 | −30.219 | 28.475 | 1.00 | 23.46 | N |
| ATOM | 7431 | CA | SER | A | 466 | 40.175 | −29.478 | 28.912 | 1.00 | 24.13 | C |
| ATOM | 7433 | CB | SER | A | 466 | 41.078 | −30.368 | 29.767 | 1.00 | 23.99 | C |
| ATOM | 7436 | OG | SER | A | 466 | 41.779 | −31.300 | 28.962 | 1.00 | 24.12 | O |
| ATOM | 7438 | C | SER | A | 466 | 40.991 | −28.944 | 27.737 | 1.00 | 25.51 | C |
| ATOM | 7439 | O | SER | A | 466 | 40.756 | −29.323 | 26.586 | 1.00 | 25.67 | O |
| ATOM | 7441 | N | GLU | A | 467 | 41.954 | −28.072 | 28.040 | 1.00 | 26.32 | N |
| ATOM | 7442 | CA | GLU | A | 467 | 42.893 | −27.579 | 27.038 | 1.00 | 26.67 | C |
| ATOM | 7444 | CB | GLU | A | 467 | 43.846 | −26.522 | 27.615 | 1.00 | 26.94 | C |
| ATOM | 7447 | CG | GLU | A | 467 | 44.869 | −26.009 | 26.580 | 1.00 | 28.82 | C |
| ATOM | 7450 | CD | GLU | A | 467 | 45.890 | −25.028 | 27.134 | 1.00 | 31.99 | C |
| ATOM | 7451 | OE1 | GLU | A | 467 | 45.949 | −24.820 | 28.365 | 1.00 | 33.18 | O |
| ATOM | 7452 | OE2 | GLU | A | 467 | 46.651 | −24.467 | 26.315 | 1.00 | 36.65 | O |
| ATOM | 7453 | C | GLU | A | 467 | 43.712 | −28.722 | 26.448 | 1.00 | 27.51 | C |
| ATOM | 7454 | O | GLU | A | 467 | 43.909 | −28.778 | 25.228 | 1.00 | 27.65 | O |
| ATOM | 7456 | N | GLU | A | 468 | 44.198 | −29.619 | 27.307 | 1.00 | 28.14 | N |
| ATOM | 7457 | CA | GLU | A | 468 | 45.045 | −30.726 | 26.852 | 1.00 | 28.74 | C |
| ATOM | 7459 | CB | GLU | A | 468 | 45.509 | −31.604 | 28.027 | 1.00 | 29.23 | C |
| ATOM | 7462 | CG | GLU | A | 468 | 46.695 | −32.521 | 27.680 | 1.00 | 33.07 | C |
| ATOM | 7465 | CD | GLU | A | 468 | 47.081 | −33.490 | 28.806 | 1.00 | 39.73 | C |
| ATOM | 7466 | OE1 | GLU | A | 468 | 46.600 | −33.326 | 29.953 | 1.00 | 41.82 | O |
| ATOM | 7467 | OE2 | GLU | A | 468 | 47.876 | −34.422 | 28.536 | 1.00 | 41.60 | O |
| ATOM | 7468 | C | GLU | A | 468 | 44.320 | −31.568 | 25.794 | 1.00 | 28.05 | C |
| ATOM | 7469 | O | GLU | A | 468 | 44.910 | −31.907 | 24.762 | 1.00 | 27.12 | O |
| ATOM | 7471 | N | LEU | A | 469 | 43.046 | −31.883 | 26.045 | 1.00 | 27.29 | N |
| ATOM | 7472 | CA | LEU | A | 469 | 42.235 | −32.635 | 25.079 | 1.00 | 26.86 | C |
| ATOM | 7474 | CB | LEU | A | 469 | 40.931 | −33.153 | 25.697 | 1.00 | 27.30 | C |
| ATOM | 7477 | CG | LEU | A | 469 | 40.978 | −34.562 | 26.307 | 1.00 | 30.60 | C |
| ATOM | 7479 | CD1 | LEU | A | 469 | 40.877 | −34.523 | 27.846 | 1.00 | 32.31 | C |
| ATOM | 7483 | CD2 | LEU | A | 469 | 39.867 | −35.431 | 25.716 | 1.00 | 32.48 | C |
| ATOM | 7487 | C | LEU | A | 469 | 41.918 | −31.804 | 23.840 | 1.00 | 26.10 | C |
| ATOM | 7488 | O | LEU | A | 469 | 42.103 | −32.273 | 22.715 | 1.00 | 27.20 | O |
| ATOM | 7490 | N | ALA | A | 470 | 41.445 | −30.577 | 24.038 | 1.00 | 23.96 | N |
| ATOM | 7491 | CA | ALA | A | 470 | 41.167 | −29.683 | 22.908 | 1.00 | 22.98 | C |
| ATOM | 7493 | CB | ALA | A | 470 | 40.690 | −28.335 | 23.404 | 1.00 | 22.29 | C |
| ATOM | 7497 | C | ALA | A | 470 | 42.392 | −29.513 | 21.992 | 1.00 | 22.39 | C |
| ATOM | 7498 | O | ALA | A | 470 | 42.265 | −29.503 | 20.768 | 1.00 | 22.37 | O |
| ATOM | 7500 | N | THR | A | 471 | 43.572 | −29.394 | 22.595 | 1.00 | 21.56 | N |
| ATOM | 7501 | CA | THR | A | 471 | 44.822 | −29.205 | 21.861 | 1.00 | 20.64 | C |
| ATOM | 7503 | CB | THR | A | 471 | 45.979 | −28.953 | 22.846 | 1.00 | 20.31 | C |
| ATOM | 7505 | OG1 | THR | A | 471 | 45.692 | −27.771 | 23.607 | 1.00 | 22.15 | O |
| ATOM | 7507 | CG2 | THR | A | 471 | 47.312 | −28.793 | 22.128 | 1.00 | 15.59 | C |
| ATOM | 7511 | C | THR | A | 471 | 45.129 | −30.417 | 20.987 | 1.00 | 21.70 | C |
| ATOM | 7512 | O | THR | A | 471 | 45.395 | −30.283 | 19.791 | 1.00 | 21.36 | O |

APPENDIX 1-continued

| ATOM | 7514 | N | GLU | A | 472 | 45.078 | −31.597 | 21.596 | 1.00 | 22.71 | N |
|---|---|---|---|---|---|---|---|---|---|---|---|
| ATOM | 7515 | CA | GLU | A | 472 | 45.234 | −32.868 | 20.884 | 1.00 | 23.00 | C |
| ATOM | 7517 | CB | GLU | A | 472 | 45.001 | −34.021 | 21.868 | 1.00 | 24.07 | C |
| ATOM | 7520 | CG | GLU | A | 472 | 45.424 | −35.402 | 21.377 | 1.00 | 30.42 | C |
| ATOM | 7523 | CD | GLU | A | 472 | 45.044 | −36.498 | 22.363 | 1.00 | 36.53 | C |
| ATOM | 7524 | OE1 | GLU | A | 472 | 45.271 | −36.319 | 23.584 | 1.00 | 38.66 | O |
| ATOM | 7525 | OE2 | GLU | A | 472 | 44.511 | −37.534 | 21.913 | 1.00 | 41.79 | O |
| ATOM | 7526 | C | GLU | A | 472 | 44.246 | −32.964 | 19.710 | 1.00 | 21.89 | C |
| ATOM | 7527 | O | GLU | A | 472 | 44.637 | −33.288 | 18.587 | 1.00 | 20.82 | O |
| ATOM | 7529 | N | SER | A | 473 | 42.974 | −32.663 | 19.986 | 1.00 | 20.61 | N |
| ATOM | 7530 | CA | SER | A | 473 | 41.916 | −32.661 | 18.973 | 1.00 | 19.87 | C |
| ATOM | 7532 | CB | SER | A | 473 | 40.581 | −32.227 | 19.582 | 1.00 | 19.51 | C |
| ATOM | 7535 | OG | SER | A | 473 | 40.062 | −33.213 | 20.454 | 1.00 | 22.15 | O |
| ATOM | 7537 | C | SER | A | 473 | 42.235 | −31.749 | 17.797 | 1.00 | 19.71 | C |
| ATOM | 7538 | O | SER | A | 473 | 41.918 | −32.071 | 16.653 | 1.00 | 19.59 | O |
| ATOM | 7540 | N | VAL | A | 474 | 42.847 | −30.605 | 18.080 | 1.00 | 19.65 | N |
| ATOM | 7541 | CA | VAL | A | 474 | 43.264 | −29.695 | 17.021 | 1.00 | 19.59 | C |
| ATOM | 7543 | CB | VAL | A | 474 | 43.553 | −28.291 | 17.559 | 1.00 | 19.88 | C |
| ATOM | 7545 | CG1 | VAL | A | 474 | 44.178 | −27.432 | 16.480 | 1.00 | 18.67 | C |
| ATOM | 7549 | CG2 | VAL | A | 474 | 42.264 | −27.658 | 18.070 | 1.00 | 16.28 | C |
| ATOM | 7553 | C | VAL | A | 474 | 44.475 | −30.237 | 16.260 | 1.00 | 20.08 | C |
| ATOM | 7554 | O | VAL | A | 474 | 44.597 | −30.002 | 15.061 | 1.00 | 20.61 | O |
| ATOM | 7556 | N | MET | A | 475 | 45.351 | −30.977 | 16.938 | 1.00 | 21.01 | N |
| ATOM | 7557 | CA | MET | A | 475 | 46.462 | −31.651 | 16.252 | 1.00 | 21.55 | C |
| ATOM | 7559 | CB | MET | A | 475 | 47.414 | −32.341 | 17.234 | 1.00 | 22.63 | C |
| ATOM | 7562 | CG | MET | A | 475 | 47.997 | −31.482 | 18.367 | 1.00 | 30.07 | C |
| ATOM | 7565 | SD | MET | A | 475 | 49.500 | −30.595 | 17.922 | 1.00 | 47.99 | S |
| ATOM | 7566 | CE | MET | A | 475 | 50.479 | −30.884 | 19.398 | 1.00 | 40.84 | C |
| ATOM | 7570 | C | MET | A | 475 | 45.906 | −32.700 | 15.277 | 1.00 | 21.02 | C |
| ATOM | 7571 | O | MET | A | 475 | 46.397 | −32.843 | 14.161 | 1.00 | 21.64 | O |
| ATOM | 7573 | N | ASN | A | 476 | 44.881 | −33.434 | 15.697 | 1.00 | 20.62 | N |
| ATOM | 7574 | CA | ASN | A | 476 | 44.282 | −34.457 | 14.839 | 1.00 | 20.93 | C |
| ATOM | 7576 | CB | ASN | A | 476 | 43.254 | −35.285 | 15.610 | 1.00 | 20.98 | C |
| ATOM | 7579 | CG | ASN | A | 476 | 43.895 | −36.197 | 16.630 | 1.00 | 22.89 | C |
| ATOM | 7580 | OD1 | ASN | A | 476 | 45.036 | −36.633 | 16.450 | 1.00 | 26.51 | O |
| ATOM | 7581 | ND2 | ASN | A | 476 | 43.169 | −36.493 | 17.713 | 1.00 | 17.27 | N |
| ATOM | 7584 | C | ASN | A | 476 | 43.632 | −33.844 | 13.618 | 1.00 | 20.64 | C |
| ATOM | 7585 | O | ASN | A | 476 | 43.672 | −34.402 | 12.526 | 1.00 | 18.83 | O |
| ATOM | 7587 | N | LEU | A | 477 | 43.040 | −32.678 | 13.818 | 1.00 | 21.79 | N |
| ATOM | 7588 | CA | LEU | A | 477 | 42.367 | −31.972 | 12.751 | 1.00 | 22.89 | C |
| ATOM | 7590 | CB | LEU | A | 477 | 41.603 | −30.790 | 13.346 | 1.00 | 23.74 | C |
| ATOM | 7593 | CG | LEU | A | 477 | 40.622 | −29.999 | 12.477 | 1.00 | 29.60 | C |
| ATOM | 7595 | CD1 | LEU | A | 477 | 40.042 | −30.830 | 11.317 | 1.00 | 34.90 | C |
| ATOM | 7599 | CD2 | LEU | A | 477 | 39.511 | −29.441 | 13.373 | 1.00 | 29.89 | C |
| ATOM | 7603 | C | LEU | A | 477 | 43.382 | −31.522 | 11.703 | 1.00 | 22.43 | C |
| ATOM | 7604 | O | LEU | A | 477 | 43.102 | −31.516 | 10.499 | 1.00 | 22.51 | O |
| ATOM | 7606 | N | ILE | A | 478 | 44.573 | −31.164 | 12.171 | 1.00 | 21.44 | N |
| ATOM | 7607 | CA | ILE | A | 478 | 45.642 | −30.754 | 11.286 | 1.00 | 20.64 | C |
| ATOM | 7609 | CB | ILE | A | 478 | 46.809 | −30.120 | 12.072 | 1.00 | 20.87 | C |
| ATOM | 7611 | CG1 | ILE | A | 478 | 46.393 | −28.737 | 12.583 | 1.00 | 21.03 | C |
| ATOM | 7614 | CD1 | ILE | A | 478 | 47.353 | −28.116 | 13.594 | 1.00 | 19.55 | C |
| ATOM | 7618 | CG2 | ILE | A | 478 | 48.048 | −30.001 | 11.194 | 1.00 | 18.72 | C |
| ATOM | 7622 | C | ILE | A | 478 | 46.130 | −31.951 | 10.483 | 1.00 | 20.33 | C |
| ATOM | 7623 | O | ILE | A | 478 | 46.282 | −31.855 | 9.267 | 1.00 | 19.87 | O |
| ATOM | 7625 | N | ASP | A | 479 | 46.370 | −33.074 | 11.160 | 1.00 | 19.79 | N |
| ATOM | 7626 | CA | ASP | A | 479 | 46.816 | −34.291 | 10.473 | 1.00 | 20.12 | C |
| ATOM | 7628 | CB | ASP | A | 479 | 47.015 | −35.459 | 11.449 | 1.00 | 20.05 | C |
| ATOM | 7631 | CG | ASP | A | 479 | 48.220 | −35.277 | 12.376 | 1.00 | 23.05 | C |
| ATOM | 7632 | OD1 | ASP | A | 479 | 49.212 | −34.626 | 11.987 | 1.00 | 25.33 | O |
| ATOM | 7633 | OD2 | ASP | A | 479 | 48.181 | −35.812 | 13.511 | 1.00 | 30.92 | O |
| ATOM | 7634 | C | ASP | A | 479 | 45.803 | −34.683 | 9.393 | 1.00 | 19.28 | C |
| ATOM | 7635 | O | ASP | A | 479 | 46.178 | −34.989 | 8.258 | 1.00 | 18.51 | O |
| ATOM | 7637 | N | GLU | A | 480 | 44.524 | −34.647 | 9.759 | 1.00 | 19.19 | N |
| ATOM | 7638 | CA | GLU | A | 480 | 43.424 | −34.983 | 8.861 | 1.00 | 19.72 | C |
| ATOM | 7640 | CB | GLU | A | 480 | 42.106 | −34.917 | 9.632 | 1.00 | 21.23 | C |
| ATOM | 7643 | CG | GLU | A | 480 | 40.879 | −35.315 | 8.839 | 1.00 | 29.29 | C |
| ATOM | 7646 | CD | GLU | A | 480 | 39.640 | −35.419 | 9.711 | 1.00 | 37.36 | C |
| ATOM | 7647 | OE1 | GLU | A | 480 | 39.567 | −36.368 | 10.528 | 1.00 | 41.70 | O |
| ATOM | 7648 | OE2 | GLU | A | 480 | 38.743 | −34.555 | 9.573 | 1.00 | 39.55 | O |
| ATOM | 7649 | C | GLU | A | 480 | 43.395 | −34.059 | 7.642 | 1.00 | 17.87 | C |
| ATOM | 7650 | O | GLU | A | 480 | 43.318 | −34.522 | 6.502 | 1.00 | 16.40 | O |
| ATOM | 7652 | N | THR | A | 481 | 43.485 | −32.758 | 7.887 | 1.00 | 16.85 | N |
| ATOM | 7653 | CA | THR | A | 481 | 43.599 | −31.774 | 6.806 | 1.00 | 16.53 | C |
| ATOM | 7655 | CB | THR | A | 481 | 43.710 | −30.341 | 7.371 | 1.00 | 16.09 | C |
| ATOM | 7657 | OG1 | THR | A | 481 | 42.582 | −30.075 | 8.213 | 1.00 | 16.37 | O |
| ATOM | 7659 | CG2 | THR | A | 481 | 43.738 | −29.323 | 6.258 | 1.00 | 11.58 | C |
| ATOM | 7663 | C | THR | A | 481 | 44.779 | −32.066 | 5.855 | 1.00 | 16.79 | C |
| ATOM | 7664 | O | THR | A | 481 | 44.632 | −31.976 | 4.628 | 1.00 | 17.41 | O |
| ATOM | 7666 | N | TRP | A | 482 | 45.936 | −32.432 | 6.404 | 1.00 | 15.60 | N |
| ATOM | 7667 | CA | TRP | A | 482 | 47.075 | −32.809 | 5.560 | 1.00 | 15.80 | C |

APPENDIX 1-continued

| | | | | | | | | | | |
|---|---|---|---|---|---|---|---|---|---|---|
| ATOM | 7669 | CB | TRP | A | 482 | 48.326 | −33.108 | 6.397 | 1.00 | 16.21 | C |
| ATOM | 7672 | CG | TRP | A | 482 | 49.175 | −31.904 | 6.612 | 1.00 | 15.02 | C |
| ATOM | 7673 | CD1 | TRP | A | 482 | 49.213 | −31.115 | 7.721 | 1.00 | 16.82 | C |
| ATOM | 7675 | NE1 | TRP | A | 482 | 50.103 | −30.091 | 7.544 | 1.00 | 17.08 | N |
| ATOM | 7677 | CE2 | TRP | A | 482 | 50.659 | −30.200 | 6.301 | 1.00 | 17.12 | C |
| ATOM | 7678 | CD2 | TRP | A | 482 | 50.095 | −31.337 | 5.685 | 1.00 | 14.82 | C |
| ATOM | 7679 | CE3 | TRP | A | 482 | 50.500 | −31.678 | 4.395 | 1.00 | 20.11 | C |
| ATOM | 7681 | CZ3 | TRP | A | 482 | 51.445 | −30.889 | 3.771 | 1.00 | 19.38 | C |
| ATOM | 7683 | CH2 | TRP | A | 482 | 51.990 | −29.762 | 4.412 | 1.00 | 19.29 | C |
| ATOM | 7685 | CZ2 | TRP | A | 482 | 51.607 | −29.403 | 5.673 | 1.00 | 16.00 | C |
| ATOM | 7687 | C | TRP | A | 482 | 46.754 | −33.998 | 4.647 | 1.00 | 16.39 | C |
| ATOM | 7688 | O | TRP | A | 482 | 47.137 | −33.994 | 3.471 | 1.00 | 15.85 | O |
| ATOM | 7690 | N | LYS | A | 483 | 46.055 | −35.003 | 5.182 | 1.00 | 15.77 | N |
| ATOM | 7691 | CA | LYS | A | 483 | 45.663 | −36.171 | 4.386 | 1.00 | 16.30 | C |
| ATOM | 7693 | CB | LYS | A | 483 | 44.863 | −37.180 | 5.224 | 1.00 | 16.44 | C |
| ATOM | 7696 | CG | LYS | A | 483 | 45.672 | −37.910 | 6.285 | 1.00 | 16.04 | C |
| ATOM | 7699 | CD | LYS | A | 483 | 44.763 | −38.613 | 7.264 | 1.00 | 17.03 | C |
| ATOM | 7702 | CE | LYS | A | 483 | 45.543 | −39.387 | 8.318 | 1.00 | 18.84 | C |
| ATOM | 7705 | NZ | LYS | A | 483 | 44.649 | −40.266 | 9.136 | 1.00 | 16.98 | N |
| ATOM | 7709 | C | LYS | A | 483 | 44.847 | −35.743 | 3.168 | 1.00 | 16.93 | C |
| ATOM | 7710 | O | LYS | A | 483 | 45.089 | −36.214 | 2.062 | 1.00 | 16.54 | O |
| ATOM | 7712 | N | LYS | A | 484 | 43.893 | −34.839 | 3.384 | 1.00 | 18.05 | N |
| ATOM | 7713 | CA | LYS | A | 484 | 43.064 | −34.301 | 2.303 | 1.00 | 18.18 | C |
| ATOM | 7715 | CB | LYS | A | 484 | 41.936 | −33.442 | 2.867 | 1.00 | 18.45 | C |
| ATOM | 7718 | CG | LYS | A | 484 | 40.857 | −34.248 | 3.547 | 1.00 | 18.57 | C |
| ATOM | 7721 | CD | LYS | A | 484 | 39.842 | −33.382 | 4.264 | 1.00 | 19.33 | C |
| ATOM | 7724 | CE | LYS | A | 484 | 38.807 | −34.231 | 4.976 | 1.00 | 21.41 | C |
| ATOM | 7727 | NZ | LYS | A | 484 | 38.185 | −33.491 | 6.094 | 1.00 | 26.22 | N |
| ATOM | 7731 | C | LYS | A | 484 | 43.860 | −33.494 | 1.275 | 1.00 | 18.62 | C |
| ATOM | 7732 | O | LYS | A | 484 | 43.608 | −33.606 | 0.075 | 1.00 | 19.13 | O |
| ATOM | 7734 | N | MET | A | 485 | 44.811 | −32.681 | 1.731 | 1.00 | 18.03 | N |
| ATOM | 7735 | CA | MET | A | 485 | 45.677 | −31.950 | 0.796 | 1.00 | 17.61 | C |
| ATOM | 7737 | CB | MET | A | 485 | 46.591 | −30.959 | 1.517 | 1.00 | 16.44 | C |
| ATOM | 7740 | CG | MET | A | 485 | 45.877 | −29.817 | 2.185 | 1.00 | 17.69 | C |
| ATOM | 7743 | SD | MET | A | 485 | 47.004 | −28.497 | 2.661 | 1.00 | 17.20 | S |
| ATOM | 7744 | CE | MET | A | 485 | 48.111 | −29.345 | 3.795 | 1.00 | 13.42 | C |
| ATOM | 7748 | C | MET | A | 485 | 46.550 | −32.913 | 0.006 | 1.00 | 18.05 | C |
| ATOM | 7749 | O | MET | A | 485 | 46.803 | −32.689 | −1.170 | 1.00 | 19.86 | O |
| ATOM | 7751 | N | ASN | A | 486 | 47.022 | −33.971 | 0.660 | 1.00 | 17.77 | N |
| ATOM | 7752 | CA | ASN | A | 486 | 47.872 | −34.946 | 0.003 | 1.00 | 17.80 | C |
| ATOM | 7754 | CB | ASN | A | 486 | 48.325 | −36.031 | 0.982 | 1.00 | 17.37 | C |
| ATOM | 7757 | CG | ASN | A | 486 | 49.317 | −35.522 | 2.001 | 1.00 | 16.94 | C |
| ATOM | 7758 | OD1 | ASN | A | 486 | 49.989 | −34.502 | 1.789 | 1.00 | 15.02 | O |
| ATOM | 7759 | ND2 | ASN | A | 486 | 49.418 | −36.230 | 3.123 | 1.00 | 7.80 | N |
| ATOM | 7762 | C | ASN | A | 486 | 47.150 | −35.594 | −1.162 | 1.00 | 18.79 | C |
| ATOM | 7763 | O | ASN | A | 486 | 47.756 | −35.846 | −2.207 | 1.00 | 18.53 | O |
| ATOM | 7765 | N | LYS | A | 487 | 45.859 | −35.867 | −0.970 | 1.00 | 19.13 | N |
| ATOM | 7766 | CA | LYS | A | 487 | 45.028 | −36.466 | −2.009 | 1.00 | 19.86 | C |
| ATOM | 7768 | CB | LYS | A | 487 | 43.661 | −36.864 | −1.442 | 1.00 | 20.17 | C |
| ATOM | 7771 | CG | LYS | A | 487 | 42.715 | −37.453 | −2.480 | 1.00 | 21.08 | C |
| ATOM | 7774 | CD | LYS | A | 487 | 41.541 | −38.168 | −1.858 | 1.00 | 22.67 | C |
| ATOM | 7777 | CE | LYS | A | 487 | 40.606 | −38.668 | −2.937 | 1.00 | 25.20 | C |
| ATOM | 7780 | NZ | LYS | A | 487 | 39.380 | −39.301 | −2.397 | 1.00 | 27.35 | N |
| ATOM | 7784 | C | LYS | A | 487 | 44.853 | −35.508 | −3.184 | 1.00 | 20.99 | C |
| ATOM | 7785 | O | LYS | A | 487 | 44.919 | −35.917 | −4.342 | 1.00 | 20.73 | O |
| ATOM | 7787 | N | GLU | A | 488 | 44.632 | −34.231 | −2.879 | 1.00 | 22.48 | N |
| ATOM | 7788 | CA | GLU | A | 488 | 44.454 | −33.211 | −3.906 | 1.00 | 23.99 | C |
| ATOM | 7790 | CB | GLU | A | 488 | 44.145 | −31.851 | −3.271 | 1.00 | 26.10 | C |
| ATOM | 7793 | CG | GLU | A | 488 | 43.663 | −30.775 | −4.249 | 1.00 | 32.01 | C |
| ATOM | 7796 | CD | GLU | A | 488 | 42.360 | −31.138 | −4.954 | 1.00 | 37.30 | C |
| ATOM | 7797 | OE1 | GLU | A | 488 | 41.597 | −31.989 | −4.438 | 1.00 | 42.21 | O |
| ATOM | 7798 | OE2 | GLU | A | 488 | 42.104 | −30.565 | −6.032 | 1.00 | 41.25 | O |
| ATOM | 7799 | C | GLU | A | 488 | 45.699 | −33.096 | −4.772 | 1.00 | 23.29 | C |
| ATOM | 7800 | O | GLU | A | 488 | 45.603 | −33.021 | −5.992 | 1.00 | 24.93 | O |
| ATOM | 7802 | N | LYS | A | 489 | 46.868 | −33.096 | −4.148 | 1.00 | 21.28 | N |
| ATOM | 7803 | CA | LYS | A | 489 | 48.110 | −33.036 | −4.905 | 1.00 | 21.84 | C |
| ATOM | 7805 | CB | LYS | A | 489 | 49.296 | −32.802 | −3.956 | 1.00 | 21.21 | C |
| ATOM | 7808 | CG | LYS | A | 489 | 50.660 | −32.658 | −4.633 | 1.00 | 22.30 | C |
| ATOM | 7811 | CD | LYS | A | 489 | 50.726 | −31.466 | −5.582 | 1.00 | 23.69 | C |
| ATOM | 7814 | CE | LYS | A | 489 | 51.964 | −31.513 | −6.476 | 1.00 | 26.17 | C |
| ATOM | 7817 | NZ | LYS | A | 489 | 53.233 | −31.562 | −5.701 | 1.00 | 26.97 | N |
| ATOM | 7821 | C | LYS | A | 489 | 48.334 | −34.295 | −5.769 | 1.00 | 22.22 | C |
| ATOM | 7822 | O | LYS | A | 489 | 48.826 | −34.199 | −6.885 | 1.00 | 22.17 | O |
| ATOM | 7824 | N | LEU | A | 490 | 47.955 | −35.461 | −5.251 | 1.00 | 23.59 | N |
| ATOM | 7825 | CA | LEU | A | 490 | 48.236 | −36.739 | −5.903 | 1.00 | 25.11 | C |
| ATOM | 7827 | CB | LEU | A | 490 | 48.206 | −37.869 | −4.868 | 1.00 | 24.75 | C |
| ATOM | 7830 | CG | LEU | A | 490 | 48.588 | −39.255 | −5.381 | 1.00 | 24.96 | C |
| ATOM | 7832 | CD1 | LEU | A | 490 | 50.037 | −39.251 | −5.794 | 1.00 | 28.66 | C |
| ATOM | 7836 | CD2 | LEU | A | 490 | 48.334 | −40.326 | −4.334 | 1.00 | 26.08 | C |
| ATOM | 7840 | C | LEU | A | 490 | 47.254 | −37.025 | −7.049 | 1.00 | 27.22 | C |

APPENDIX 1-continued

| | | | | | | | | | | | |
|---|---|---|---|---|---|---|---|---|---|---|---|
| ATOM | 7841 | O | LEU | A | 490 | 47.668 | −37.174 | −8.199 | 1.00 | 26.80 | O |
| ATOM | 7843 | N | SER | A | 491 | 45.967 | −37.117 | −6.711 | 1.00 | 30.11 | N |
| ATOM | 7844 | CA | SER | A | 491 | 44.871 | −37.239 | −7.677 | 1.00 | 32.75 | C |
| ATOM | 7846 | CB | SER | A | 491 | 43.696 | −38.004 | −7.058 | 1.00 | 32.45 | C |
| ATOM | 7849 | OG | SER | A | 491 | 44.153 | −39.120 | −6.314 | 1.00 | 33.27 | O |
| ATOM | 7851 | C | SER | A | 491 | 44.482 | −35.807 | −7.993 | 1.00 | 35.81 | C |
| ATOM | 7852 | O | SER | A | 491 | 45.366 | −34.976 | −8.190 | 1.00 | 39.71 | O |
| ATOM | 7854 | N | GLY | A | 492 | 43.194 | −35.488 | −8.031 | 1.00 | 36.89 | N |
| ATOM | 7855 | CA | GLY | A | 492 | 42.782 | −34.083 | −7.975 | 1.00 | 38.51 | C |
| ATOM | 7858 | C | GLY | A | 492 | 42.948 | −33.426 | −9.324 | 1.00 | 39.51 | C |
| ATOM | 7859 | O | GLY | A | 492 | 44.023 | −33.483 | −9.926 | 1.00 | 39.21 | O |
| ATOM | 7861 | N | SER | A | 493 | 41.885 | −32.785 | −9.793 | 1.00 | 40.76 | N |
| ATOM | 7862 | CA | SER | A | 493 | 41.744 | −32.527 | −11.221 | 1.00 | 42.11 | C |
| ATOM | 7864 | CB | SER | A | 493 | 40.536 | −33.308 | −11.779 | 1.00 | 42.40 | C |
| ATOM | 7867 | OG | SER | A | 493 | 39.367 | −33.119 | −10.991 | 1.00 | 42.24 | O |
| ATOM | 7869 | C | SER | A | 493 | 41.661 | −31.055 | −11.620 | 1.00 | 42.90 | C |
| ATOM | 7870 | O | SER | A | 493 | 42.195 | −30.688 | −12.667 | 1.00 | 45.63 | O |
| ATOM | 7872 | N | LEU | A | 494 | 41.019 | −30.214 | −10.812 | 1.00 | 41.80 | N |
| ATOM | 7873 | CA | LEU | A | 494 | 40.745 | −28.833 | −11.234 | 1.00 | 41.69 | C |
| ATOM | 7875 | CB | LEU | A | 494 | 39.819 | −28.134 | −10.234 | 1.00 | 42.85 | C |
| ATOM | 7878 | CG | LEU | A | 494 | 38.410 | −28.738 | −10.171 | 1.00 | 48.25 | C |
| ATOM | 7880 | CD1 | LEU | A | 494 | 37.681 | −28.348 | −8.874 | 1.00 | 51.97 | C |
| ATOM | 7884 | CD2 | LEU | A | 494 | 37.591 | −28.341 | −11.407 | 1.00 | 50.78 | C |
| ATOM | 7888 | C | LEU | A | 494 | 42.019 | −28.002 | −11.465 | 1.00 | 39.71 | C |
| ATOM | 7889 | O | LEU | A | 494 | 42.341 | −27.665 | −12.613 | 1.00 | 39.89 | O |
| ATOM | 7891 | N | PHE | A | 495 | 42.741 | −27.697 | −10.385 | 1.00 | 36.46 | N |
| ATOM | 7892 | CA | PHE | A | 495 | 43.918 | −26.830 | −10.449 | 1.00 | 33.36 | C |
| ATOM | 7894 | CB | PHE | A | 495 | 44.174 | −26.182 | −9.091 | 1.00 | 33.16 | C |
| ATOM | 7897 | CG | PHE | A | 495 | 43.100 | −25.232 | −8.675 | 1.00 | 30.77 | C |
| ATOM | 7898 | CD1 | PHE | A | 495 | 43.098 | −23.929 | −9.139 | 1.00 | 27.11 | C |
| ATOM | 7900 | CE1 | PHE | A | 495 | 42.110 | −23.050 | −8.762 | 1.00 | 29.33 | C |
| ATOM | 7902 | CZ | PHE | A | 495 | 41.101 | −23.470 | −7.922 | 1.00 | 30.73 | C |
| ATOM | 7904 | CE2 | PHE | A | 495 | 41.091 | −24.769 | −7.460 | 1.00 | 32.49 | C |
| ATOM | 7906 | CD2 | PHE | A | 495 | 42.085 | −25.643 | −7.839 | 1.00 | 30.06 | C |
| ATOM | 7908 | C | PHE | A | 495 | 45.173 | −27.557 | −10.895 | 1.00 | 31.67 | C |
| ATOM | 7909 | O | PHE | A | 495 | 45.347 | −28.740 | −10.630 | 1.00 | 31.25 | O |
| ATOM | 7911 | N | ALA | A | 496 | 46.057 | −26.831 | −11.565 | 1.00 | 30.99 | N |
| ATOM | 7912 | CA | ALA | A | 496 | 47.342 | −27.383 | −11.959 | 1.00 | 30.97 | C |
| ATOM | 7914 | CB | ALA | A | 496 | 48.020 | −26.492 | −13.009 | 1.00 | 30.95 | C |
| ATOM | 7918 | C | ALA | A | 496 | 48.240 | −27.566 | −10.733 | 1.00 | 30.01 | C |
| ATOM | 7919 | O | ALA | A | 496 | 48.142 | −26.828 | −9.750 | 1.00 | 28.13 | O |
| ATOM | 7921 | N | LYS | A | 497 | 49.124 | −28.556 | −10.823 | 1.00 | 29.98 | N |
| ATOM | 7922 | CA | LYS | A | 497 | 49.983 | −28.956 | −9.722 | 1.00 | 29.48 | C |
| ATOM | 7924 | CB | LYS | A | 497 | 50.875 | −30.129 | −10.153 | 1.00 | 29.84 | C |
| ATOM | 7927 | CG | LYS | A | 497 | 50.112 | −31.456 | −10.266 | 1.00 | 36.81 | C |
| ATOM | 7930 | CD | LYS | A | 497 | 51.052 | −32.675 | −10.271 | 1.00 | 43.99 | C |
| ATOM | 7933 | CE | LYS | A | 497 | 50.275 | −33.997 | −10.386 | 1.00 | 48.85 | C |
| ATOM | 7936 | NZ | LYS | A | 497 | 50.937 | −35.142 | −9.664 | 1.00 | 52.33 | N |
| ATOM | 7940 | C | LYS | A | 497 | 50.817 | −27.817 | −9.125 | 1.00 | 27.48 | C |
| ATOM | 7941 | O | LYS | A | 497 | 50.933 | −27.723 | −7.909 | 1.00 | 26.08 | O |
| ATOM | 7943 | N | PRO | A | 498 | 51.397 | −26.947 | −9.973 | 1.00 | 26.23 | N |
| ATOM | 7944 | CA | PRO | A | 498 | 52.157 | −25.819 | −9.443 | 1.00 | 24.44 | C |
| ATOM | 7946 | CB | PRO | A | 498 | 52.439 | −24.980 | −10.689 | 1.00 | 24.60 | C |
| ATOM | 7949 | CG | PRO | A | 498 | 52.485 | −25.960 | −11.776 | 1.00 | 23.99 | C |
| ATOM | 7952 | CD | PRO | A | 498 | 51.438 | −26.970 | −11.446 | 1.00 | 25.63 | C |
| ATOM | 7955 | C | PRO | A | 498 | 51.369 | −25.004 | −8.442 | 1.00 | 23.21 | C |
| ATOM | 7956 | O | PRO | A | 498 | 51.925 | −24.597 | −7.427 | 1.00 | 23.94 | O |
| ATOM | 7957 | N | PHE | A | 499 | 50.087 | −24.771 | −8.722 | 1.00 | 21.85 | N |
| ATOM | 7958 | CA | PHE | A | 499 | 49.257 | −23.989 | −7.818 | 1.00 | 21.24 | C |
| ATOM | 7960 | CB | PHE | A | 499 | 48.010 | −23.418 | −8.497 | 1.00 | 20.57 | C |
| ATOM | 7963 | CG | PHE | A | 499 | 47.144 | −22.647 | −7.551 | 1.00 | 19.75 | C |
| ATOM | 7964 | CD1 | PHE | A | 499 | 47.593 | −21.452 | −7.008 | 1.00 | 18.26 | C |
| ATOM | 7966 | CE1 | PHE | A | 499 | 46.814 | −20.743 | −6.090 | 1.00 | 18.02 | C |
| ATOM | 7968 | CZ | PHE | A | 499 | 45.575 | −21.237 | −5.705 | 1.00 | 15.99 | C |
| ATOM | 7970 | CE2 | PHE | A | 499 | 45.131 | −22.442 | −6.225 | 1.00 | 18.43 | C |
| ATOM | 7972 | CD2 | PHE | A | 499 | 45.921 | −23.148 | −7.134 | 1.00 | 19.13 | C |
| ATOM | 7974 | C | PHE | A | 499 | 48.848 | −24.777 | −6.576 | 1.00 | 21.26 | C |
| ATOM | 7975 | O | PHE | A | 499 | 48.859 | −24.240 | −5.479 | 1.00 | 21.95 | O |
| ATOM | 7977 | N | VAL | A | 500 | 48.481 | −26.042 | −6.739 | 1.00 | 20.90 | N |
| ATOM | 7978 | CA | VAL | A | 500 | 48.164 | −26.870 | −5.581 | 1.00 | 20.48 | C |
| ATOM | 7980 | CB | VAL | A | 500 | 47.767 | −28.309 | −5.986 | 1.00 | 21.13 | C |
| ATOM | 7982 | CG1 | VAL | A | 500 | 47.639 | −29.211 | −4.754 | 1.00 | 15.52 | C |
| ATOM | 7986 | CG2 | VAL | A | 500 | 46.460 | −28.287 | −6.774 | 1.00 | 21.57 | C |
| ATOM | 7990 | C | VAL | A | 500 | 49.351 | −26.899 | −4.624 | 1.00 | 19.82 | C |
| ATOM | 7991 | O | VAL | A | 500 | 49.191 | −26.760 | −3.414 | 1.00 | 19.55 | O |
| ATOM | 7993 | N | GLU | A | 501 | 50.541 | −27.057 | −5.183 | 1.00 | 19.75 | N |
| ATOM | 7994 | CA | GLU | A | 501 | 51.755 | −27.114 | −4.390 | 1.00 | 20.23 | C |
| ATOM | 7996 | CB | GLU | A | 501 | 52.941 | −27.494 | −5.275 | 1.00 | 20.80 | C |
| ATOM | 7999 | CG | GLU | A | 501 | 54.264 | −27.676 | −4.545 | 1.00 | 23.16 | C |
| ATOM | 8002 | CD | GLU | A | 501 | 54.295 | −28.896 | −3.648 | 1.00 | 27.14 | C |

APPENDIX 1-continued

| ATOM | 8003 | OE1 | GLU | A | 501 | 53.352 | −29.734 | −3.686 | 1.00 | 27.24 | O |
|------|------|-----|-----|---|-----|--------|---------|--------|------|-------|---|
| ATOM | 8004 | OE2 | GLU | A | 501 | 55.282 | −29.003 | −2.896 | 1.00 | 28.49 | O |
| ATOM | 8005 | C | GLU | A | 501 | 52.016 | −25.781 | −3.698 | 1.00 | 19.44 | C |
| ATOM | 8006 | O | GLU | A | 501 | 52.481 | −25.756 | −2.562 | 1.00 | 19.54 | O |
| ATOM | 8008 | N | THR | A | 502 | 51.725 | −24.680 | −4.382 | 1.00 | 18.86 | N |
| ATOM | 8009 | CA | THR | A | 502 | 51.856 | −23.362 | −3.772 | 1.00 | 18.38 | C |
| ATOM | 8011 | CB | THR | A | 502 | 51.539 | −22.251 | −4.763 | 1.00 | 18.24 | C |
| ATOM | 8013 | OG1 | THR | A | 502 | 52.503 | −22.282 | −5.823 | 1.00 | 20.38 | O |
| ATOM | 8015 | CG2 | THR | A | 502 | 51.588 | −20.902 | −4.081 | 1.00 | 19.60 | C |
| ATOM | 8019 | C | THR | A | 502 | 50.920 | −23.259 | −2.579 | 1.00 | 18.14 | C |
| ATOM | 8020 | O | THR | A | 502 | 51.323 | −22.821 | −1.501 | 1.00 | 18.35 | O |
| ATOM | 8022 | N | ALA | A | 503 | 49.683 | −23.704 | −2.772 | 1.00 | 17.11 | N |
| ATOM | 8023 | CA | ALA | A | 503 | 48.687 | −23.684 | −1.711 | 1.00 | 17.25 | C |
| ATOM | 8025 | CB | ALA | A | 503 | 47.343 | −24.182 | −2.228 | 1.00 | 16.45 | C |
| ATOM | 8029 | C | ALA | A | 503 | 49.165 | −24.508 | −0.511 | 1.00 | 17.44 | C |
| ATOM | 8030 | O | ALA | A | 503 | 49.188 | −24.011 | 0.607 | 1.00 | 18.65 | O |
| ATOM | 8032 | N | ILE | A | 504 | 49.585 | −25.747 | −0.749 | 1.00 | 17.37 | N |
| ATOM | 8033 | CA | ILE | A | 504 | 50.147 | −26.579 | 0.320 | 1.00 | 17.19 | C |
| ATOM | 8035 | CB | ILE | A | 504 | 50.598 | −27.970 | −0.205 | 1.00 | 17.91 | C |
| ATOM | 8037 | CG1 | ILE | A | 504 | 49.376 | −28.836 | −0.562 | 1.00 | 20.02 | C |
| ATOM | 8040 | CD1 | ILE | A | 504 | 49.670 | −30.002 | −1.524 | 1.00 | 13.50 | C |
| ATOM | 8044 | CG2 | ILE | A | 504 | 51.448 | −28.702 | 0.838 | 1.00 | 17.57 | C |
| ATOM | 8048 | C | ILE | A | 504 | 51.309 | −25.872 | 1.044 | 1.00 | 16.63 | C |
| ATOM | 8049 | O | ILE | A | 504 | 51.448 | −25.996 | 2.275 | 1.00 | 13.35 | O |
| ATOM | 8051 | N | ASN | A | 505 | 52.115 | −25.111 | 0.294 | 1.00 | 16.69 | N |
| ATOM | 8052 | CA | ASN | A | 505 | 53.260 | −24.405 | 0.885 | 1.00 | 17.13 | C |
| ATOM | 8054 | CB | ASN | A | 505 | 54.120 | −23.736 | −0.182 | 1.00 | 17.81 | C |
| ATOM | 8057 | CG | ASN | A | 505 | 54.947 | −24.727 | −0.980 | 1.00 | 18.31 | C |
| ATOM | 8058 | OD1 | ASN | A | 505 | 55.281 | −25.811 | −0.501 | 1.00 | 22.01 | O |
| ATOM | 8059 | ND2 | ASN | A | 505 | 55.280 | −24.357 | −2.205 | 1.00 | 15.11 | N |
| ATOM | 8062 | C | ASN | A | 505 | 52.873 | −23.378 | 1.941 | 1.00 | 17.83 | C |
| ATOM | 8063 | O | ASN | A | 505 | 53.645 | −23.122 | 2.859 | 1.00 | 18.43 | O |
| ATOM | 8065 | N | LEU | A | 506 | 51.684 | −22.796 | 1.834 | 1.00 | 18.40 | N |
| ATOM | 8066 | CA | LEU | A | 506 | 51.235 | −21.861 | 2.858 | 1.00 | 18.74 | C |
| ATOM | 8068 | CB | LEU | A | 506 | 49.973 | −21.106 | 2.416 | 1.00 | 20.63 | C |
| ATOM | 8071 | CG | LEU | A | 506 | 49.365 | −20.100 | 3.419 | 1.00 | 20.63 | C |
| ATOM | 8073 | CD1 | LEU | A | 506 | 49.177 | −18.729 | 2.800 | 1.00 | 17.23 | C |
| ATOM | 8077 | CD2 | LEU | A | 506 | 48.044 | −20.623 | 3.945 | 1.00 | 17.29 | C |
| ATOM | 8081 | C | LEU | A | 506 | 51.022 | −22.598 | 4.178 | 1.00 | 17.22 | C |
| ATOM | 8082 | O | LEU | A | 506 | 51.364 | −22.083 | 5.235 | 1.00 | 16.26 | O |
| ATOM | 8084 | N | ALA | A | 507 | 50.492 | −23.815 | 4.111 | 1.00 | 16.66 | N |
| ATOM | 8085 | CA | ALA | A | 507 | 50.397 | −24.666 | 5.300 | 1.00 | 15.83 | C |
| ATOM | 8087 | CB | ALA | A | 507 | 49.675 | −25.972 | 4.984 | 1.00 | 14.75 | C |
| ATOM | 8091 | C | ALA | A | 507 | 51.780 | −24.946 | 5.862 | 1.00 | 16.10 | C |
| ATOM | 8092 | O | ALA | A | 507 | 51.986 | −24.878 | 7.071 | 1.00 | 16.30 | O |
| ATOM | 8094 | N | ARG | A | 508 | 52.731 | −25.251 | 4.979 | 1.00 | 17.61 | N |
| ATOM | 8095 | CA | ARG | A | 508 | 54.116 | −25.504 | 5.392 | 1.00 | 17.53 | C |
| ATOM | 8097 | CB | ARG | A | 508 | 54.987 | −25.888 | 4.205 | 1.00 | 17.44 | C |
| ATOM | 8100 | CG | ARG | A | 508 | 54.619 | −27.205 | 3.595 | 1.00 | 21.11 | C |
| ATOM | 8103 | CD | ARG | A | 508 | 55.602 | −27.634 | 2.531 | 1.00 | 19.20 | C |
| ATOM | 8106 | NE | ARG | A | 508 | 55.335 | −29.024 | 2.160 | 1.00 | 21.78 | N |
| ATOM | 8108 | CZ | ARG | A | 508 | 54.926 | −29.456 | 0.968 | 1.00 | 19.87 | C |
| ATOM | 8109 | NH1 | ARG | A | 508 | 54.742 | −28.624 | −0.051 | 1.00 | 17.50 | N |
| ATOM | 8112 | NH2 | ARG | A | 508 | 54.718 | −30.755 | 0.792 | 1.00 | 21.11 | N |
| ATOM | 8115 | C | ARG | A | 508 | 54.700 | −24.280 | 6.054 | 1.00 | 18.16 | C |
| ATOM | 8116 | O | ARG | A | 508 | 55.252 | −24.367 | 7.148 | 1.00 | 18.30 | O |
| ATOM | 8118 | N | GLN | A | 509 | 54.565 | −23.134 | 5.396 | 1.00 | 18.99 | N |
| ATOM | 8119 | CA | GLN | A | 509 | 55.054 | −21.879 | 5.960 | 1.00 | 20.33 | C |
| ATOM | 8121 | CB | GLN | A | 509 | 54.765 | −20.717 | 5.011 | 1.00 | 20.49 | C |
| ATOM | 8124 | CG | GLN | A | 509 | 55.204 | −19.360 | 5.523 | 1.00 | 22.03 | C |
| ATOM | 8127 | CD | GLN | A | 509 | 56.678 | −19.288 | 5.821 | 1.00 | 21.97 | C |
| ATOM | 8128 | OE1 | GLN | A | 509 | 57.506 | −19.664 | 4.999 | 1.00 | 27.73 | O |
| ATOM | 8129 | NE2 | GLN | A | 509 | 57.019 | −18.789 | 6.998 | 1.00 | 29.26 | N |
| ATOM | 8132 | C | GLN | A | 509 | 54.450 | −21.604 | 7.345 | 1.00 | 21.32 | C |
| ATOM | 8133 | O | GLN | A | 509 | 55.134 | −21.067 | 8.219 | 1.00 | 22.25 | O |
| ATOM | 8135 | N | SER | A | 510 | 53.184 | −21.980 | 7.541 | 1.00 | 20.79 | N |
| ATOM | 8136 | CA | SER | A | 510 | 52.524 | −21.826 | 8.832 | 1.00 | 20.10 | C |
| ATOM | 8138 | CB | SER | A | 510 | 51.047 | −22.189 | 8.720 | 1.00 | 19.90 | C |
| ATOM | 8141 | OG | SER | A | 510 | 50.416 | −21.459 | 7.692 | 1.00 | 18.71 | O |
| ATOM | 8143 | C | SER | A | 510 | 53.183 | −22.696 | 9.904 | 1.00 | 20.38 | C |
| ATOM | 8144 | O | SER | A | 510 | 53.431 | −22.243 | 11.020 | 1.00 | 19.76 | O |
| ATOM | 8146 | N | HIS | A | 511 | 53.471 | −23.945 | 9.561 | 1.00 | 20.90 | N |
| ATOM | 8147 | CA | HIS | A | 511 | 54.139 | −24.851 | 10.499 | 1.00 | 22.22 | C |
| ATOM | 8149 | CB | HIS | A | 511 | 54.324 | −26.250 | 9.894 | 1.00 | 22.59 | C |
| ATOM | 8152 | CG | HIS | A | 511 | 53.096 | −27.095 | 9.951 | 1.00 | 21.60 | C |
| ATOM | 8153 | ND1 | HIS | A | 511 | 52.612 | −27.618 | 11.131 | 1.00 | 21.90 | N |
| ATOM | 8155 | CE1 | HIS | A | 511 | 51.521 | −28.319 | 10.883 | 1.00 | 22.43 | C |
| ATOM | 8157 | NE2 | HIS | A | 511 | 51.278 | −28.266 | 9.586 | 1.00 | 24.05 | N |
| ATOM | 8159 | CD2 | HIS | A | 511 | 52.248 | −27.504 | 8.979 | 1.00 | 22.11 | C |
| ATOM | 8161 | C | HIS | A | 511 | 55.497 | −24.328 | 10.939 | 1.00 | 22.27 | C |

APPENDIX 1-continued

| | | | | | | | | | |
|---|---|---|---|---|---|---|---|---|---|
| ATOM | 8162 | O | HIS | A | 511 | 55.908 | −24.552 | 12.068 | 1.00 | 22.96 | O |
| ATOM | 8164 | N | CYS | A | 512 | 56.191 | −23.645 | 10.038 | 1.00 | 23.22 | N |
| ATOM | 8165 | CA | CYS | A | 512 | 57.523 | −23.129 | 10.321 | 1.00 | 24.23 | C |
| ATOM | 8167 | CB | CYS | A | 512 | 58.329 | −23.010 | 9.031 | 1.00 | 24.32 | C |
| ATOM | 8170 | SG | CYS | A | 512 | 58.656 | −24.595 | 8.249 | 1.00 | 22.30 | S |
| ATOM | 8172 | C | CYS | A | 512 | 57.479 | −21.782 | 11.024 | 1.00 | 25.86 | C |
| ATOM | 8173 | O | CYS | A | 512 | 58.350 | −21.495 | 11.837 | 1.00 | 26.42 | O |
| ATOM | 8175 | N | THR | A | 513 | 56.482 | −20.957 | 10.705 | 1.00 | 27.61 | N |
| ATOM | 8176 | CA | THR | A | 513 | 56.318 | −19.654 | 11.361 | 1.00 | 29.15 | C |
| ATOM | 8178 | CB | THR | A | 513 | 55.331 | −18.741 | 10.593 | 1.00 | 29.25 | C |
| ATOM | 8180 | OG1 | THR | A | 513 | 55.971 | −18.221 | 9.422 | 1.00 | 28.09 | O |
| ATOM | 8182 | CG2 | THR | A | 513 | 54.873 | −17.577 | 11.464 | 1.00 | 26.32 | C |
| ATOM | 8186 | C | THR | A | 513 | 55.870 | −19.769 | 12.830 | 1.00 | 31.47 | C |
| ATOM | 8187 | O | THR | A | 513 | 56.363 | −19.028 | 13.683 | 1.00 | 30.56 | O |
| ATOM | 8189 | N | TYR | A | 514 | 54.955 | −20.694 | 13.126 | 1.00 | 34.30 | N |
| ATOM | 8190 | CA | TYR | A | 514 | 54.379 | −20.792 | 14.479 | 1.00 | 35.87 | C |
| ATOM | 8192 | CB | TYR | A | 514 | 52.847 | −20.940 | 14.416 | 1.00 | 34.25 | C |
| ATOM | 8195 | CG | TYR | A | 514 | 52.221 | −19.733 | 13.751 | 1.00 | 30.20 | C |
| ATOM | 8196 | CD1 | TYR | A | 514 | 52.264 | −18.478 | 14.363 | 1.00 | 31.58 | C |
| ATOM | 8198 | CE1 | TYR | A | 514 | 51.724 | −17.349 | 13.747 | 1.00 | 29.95 | C |
| ATOM | 8200 | CZ | TYR | A | 514 | 51.142 | −17.468 | 12.506 | 1.00 | 32.59 | C |
| ATOM | 8201 | OH | TYR | A | 514 | 50.615 | −16.358 | 11.893 | 1.00 | 34.88 | O |
| ATOM | 8203 | CE2 | TYR | A | 514 | 51.094 | −18.703 | 11.872 | 1.00 | 32.82 | C |
| ATOM | 8205 | CD2 | TYR | A | 514 | 51.641 | −19.822 | 12.494 | 1.00 | 30.70 | C |
| ATOM | 8207 | C | TYR | A | 514 | 55.075 | −21.864 | 15.318 | 1.00 | 39.29 | C |
| ATOM | 8208 | O | TYR | A | 514 | 54.486 | −22.865 | 15.728 | 1.00 | 39.16 | O |
| ATOM | 8210 | N | HIS | A | 515 | 56.349 | −21.596 | 15.587 | 1.00 | 43.59 | N |
| ATOM | 8211 | CA | HIS | A | 515 | 57.228 | −22.479 | 16.359 | 1.00 | 46.79 | C |
| ATOM | 8213 | CB | HIS | A | 515 | 58.604 | −22.525 | 15.688 | 1.00 | 46.96 | C |
| ATOM | 8216 | CG | HIS | A | 515 | 59.284 | −21.188 | 15.629 | 1.00 | 50.00 | C |
| ATOM | 8217 | ND1 | HIS | A | 515 | 59.273 | −20.400 | 14.498 | 1.00 | 50.33 | N |
| ATOM | 8219 | CE1 | HIS | A | 515 | 59.930 | −19.279 | 14.738 | 1.00 | 52.29 | C |
| ATOM | 8221 | NE2 | HIS | A | 515 | 60.357 | −19.306 | 15.989 | 1.00 | 52.99 | N |
| ATOM | 8223 | CD2 | HIS | A | 515 | 59.961 | −20.486 | 16.570 | 1.00 | 52.28 | C |
| ATOM | 8225 | C | HIS | A | 515 | 57.408 | −21.967 | 17.791 | 1.00 | 48.92 | C |
| ATOM | 8226 | O | HIS | A | 515 | 56.807 | −20.962 | 18.187 | 1.00 | 48.55 | O |
| ATOM | 8228 | N | ASN | A | 516 | 58.242 | −22.680 | 18.551 | 1.00 | 51.56 | N |
| ATOM | 8229 | CA | ASN | A | 516 | 58.764 | −22.219 | 19.842 | 1.00 | 53.22 | C |
| ATOM | 8231 | CB | ASN | A | 516 | 57.896 | −22.727 | 21.001 | 1.00 | 53.73 | C |
| ATOM | 8234 | CG | ASN | A | 516 | 56.965 | −21.661 | 21.543 | 1.00 | 55.64 | C |
| ATOM | 8235 | OD1 | ASN | A | 516 | 57.063 | −21.274 | 22.708 | 1.00 | 57.77 | O |
| ATOM | 8236 | ND2 | ASN | A | 516 | 56.064 | −21.173 | 20.698 | 1.00 | 56.49 | N |
| ATOM | 8239 | C | ASN | A | 516 | 60.214 | −22.679 | 20.035 | 1.00 | 54.14 | C |
| ATOM | 8240 | O | ASN | A | 516 | 61.060 | −21.929 | 20.529 | 1.00 | 54.93 | O |
| ATOM | 8242 | N | THR | A | 521 | 67.064 | −21.371 | 22.423 | 1.00 | 68.24 | N |
| ATOM | 8243 | CA | THR | A | 521 | 66.660 | −20.234 | 21.600 | 1.00 | 68.31 | C |
| ATOM | 8245 | CB | THR | A | 521 | 66.789 | −20.549 | 20.083 | 1.00 | 68.39 | C |
| ATOM | 8247 | OG1 | THR | A | 521 | 67.897 | −21.429 | 19.852 | 1.00 | 68.01 | O |
| ATOM | 8249 | CG2 | THR | A | 521 | 66.985 | −19.266 | 19.278 | 1.00 | 68.04 | C |
| ATOM | 8253 | C | THR | A | 521 | 65.209 | −19.850 | 21.908 | 1.00 | 68.29 | C |
| ATOM | 8254 | O | THR | A | 521 | 64.321 | −20.708 | 21.905 | 1.00 | 68.26 | O |
| ATOM | 8256 | N | SER | A | 522 | 64.976 | −18.563 | 22.166 | 1.00 | 68.25 | N |
| ATOM | 8257 | CA | SER | A | 522 | 63.631 | −18.058 | 22.473 | 1.00 | 68.36 | C |
| ATOM | 8259 | CB | SER | A | 522 | 63.714 | −16.694 | 23.171 | 1.00 | 68.48 | C |
| ATOM | 8262 | OG | SER | A | 522 | 63.836 | −15.635 | 22.234 | 1.00 | 67.70 | O |
| ATOM | 8264 | C | SER | A | 522 | 62.809 | −17.947 | 21.186 | 1.00 | 68.90 | C |
| ATOM | 8265 | O | SER | A | 522 | 63.381 | −17.966 | 20.091 | 1.00 | 68.97 | O |
| ATOM | 8267 | N | PRO | A | 523 | 61.468 | −17.822 | 21.308 | 1.00 | 69.43 | N |
| ATOM | 8268 | CA | PRO | A | 523 | 60.602 | −17.766 | 20.117 | 1.00 | 69.50 | C |
| ATOM | 8270 | CB | PRO | A | 523 | 59.226 | −17.386 | 20.690 | 1.00 | 69.57 | C |
| ATOM | 8273 | CG | PRO | A | 523 | 59.253 | −17.849 | 22.099 | 1.00 | 69.97 | C |
| ATOM | 8276 | CD | PRO | A | 523 | 60.687 | −17.777 | 22.561 | 1.00 | 69.52 | C |
| ATOM | 8279 | C | PRO | A | 523 | 61.065 | −16.739 | 19.075 | 1.00 | 69.50 | C |
| ATOM | 8280 | O | PRO | A | 523 | 61.295 | −17.101 | 17.915 | 1.00 | 69.97 | O |
| ATOM | 8281 | N | ASP | A | 524 | 61.211 | −15.482 | 19.496 | 1.00 | 68.93 | N |
| ATOM | 8282 | CA | ASP | A | 524 | 61.683 | −14.408 | 18.618 | 1.00 | 68.26 | C |
| ATOM | 8284 | CB | ASP | A | 524 | 60.918 | −13.105 | 18.886 | 1.00 | 68.53 | C |
| ATOM | 8287 | CG | ASP | A | 524 | 59.544 | −13.090 | 18.232 | 1.00 | 69.51 | C |
| ATOM | 8288 | OD1 | ASP | A | 524 | 59.451 | −13.409 | 17.022 | 1.00 | 68.29 | O |
| ATOM | 8289 | OD2 | ASP | A | 524 | 58.560 | −12.753 | 18.927 | 1.00 | 69.69 | O |
| ATOM | 8290 | C | ASP | A | 524 | 63.185 | −14.211 | 18.809 | 1.00 | 67.06 | C |
| ATOM | 8291 | O | ASP | A | 524 | 63.625 | −13.672 | 19.824 | 1.00 | 67.48 | O |
| ATOM | 8293 | N | GLU | A | 525 | 63.938 | −14.637 | 17.796 | 1.00 | 65.37 | N |
| ATOM | 8294 | CA | GLU | A | 525 | 65.403 | −14.833 | 17.815 | 1.00 | 64.34 | C |
| ATOM | 8296 | CB | GLU | A | 525 | 65.996 | −15.095 | 19.216 | 1.00 | 64.46 | C |
| ATOM | 8299 | CG | GLU | A | 525 | 66.657 | −13.867 | 19.874 | 1.00 | 65.56 | C |
| ATOM | 8302 | CD | GLU | A | 525 | 67.334 | −14.182 | 21.215 | 1.00 | 68.38 | C |
| ATOM | 8303 | OE1 | GLU | A | 525 | 67.271 | −15.343 | 21.679 | 1.00 | 69.09 | O |
| ATOM | 8304 | OE2 | GLU | A | 525 | 67.934 | −13.261 | 21.812 | 1.00 | 69.29 | O |
| ATOM | 8305 | C | GLU | A | 525 | 65.684 | −16.023 | 16.893 | 1.00 | 62.76 | C |

APPENDIX 1-continued

| ATOM | 8306 | O   | GLU | A | 525 | 66.605 | −15.985 | 16.075 | 1.00 | 62.36 | O |
| ---- | ---- | --- | --- | - | --- | ------ | ------- | ------ | ---- | ----- | - |
| ATOM | 8308 | N   | LEU | A | 526 | 64.879 | −17.076 | 17.041 | 1.00 | 60.82 | N |
| ATOM | 8309 | CA  | LEU | A | 526 | 64.851 | −18.175 | 16.079 | 1.00 | 59.35 | C |
| ATOM | 8311 | CB  | LEU | A | 526 | 64.027 | −19.355 | 16.621 | 1.00 | 59.35 | C |
| ATOM | 8314 | CG  | LEU | A | 526 | 63.869 | −20.605 | 15.735 | 1.00 | 59.00 | C |
| ATOM | 8316 | CD1 | LEU | A | 526 | 65.212 | −21.129 | 15.233 | 1.00 | 58.18 | C |
| ATOM | 8320 | CD2 | LEU | A | 526 | 63.114 | −21.708 | 16.479 | 1.00 | 57.29 | C |
| ATOM | 8324 | C   | LEU | A | 526 | 64.279 | −17.675 | 14.746 | 1.00 | 58.24 | C |
| ATOM | 8325 | O   | LEU | A | 526 | 64.798 | −18.018 | 13.680 | 1.00 | 58.01 | O |
| ATOM | 8327 | N   | THR | A | 527 | 63.219 | −16.864 | 14.814 | 1.00 | 56.56 | N |
| ATOM | 8328 | CA  | THR | A | 527 | 62.641 | −16.227 | 13.626 | 1.00 | 55.44 | C |
| ATOM | 8330 | CB  | THR | A | 527 | 61.398 | −15.364 | 13.982 | 1.00 | 55.35 | C |
| ATOM | 8332 | OG1 | THR | A | 527 | 60.408 | −16.178 | 14.625 | 1.00 | 55.68 | O |
| ATOM | 8334 | CG2 | THR | A | 527 | 60.788 | −14.728 | 12.733 | 1.00 | 51.94 | C |
| ATOM | 8338 | C   | THR | A | 527 | 63.679 | −15.339 | 12.941 | 1.00 | 55.46 | C |
| ATOM | 8339 | O   | THR | A | 527 | 63.885 | −15.431 | 11.730 | 1.00 | 55.61 | O |
| ATOM | 8341 | N   | ARG | A | 528 | 64.337 | −14.494 | 13.731 | 1.00 | 55.44 | N |
| ATOM | 8342 | CA  | ARG | A | 528 | 65.379 | −13.591 | 13.232 | 1.00 | 55.76 | C |
| ATOM | 8344 | CB  | ARG | A | 528 | 65.896 | −12.707 | 14.379 | 1.00 | 56.27 | C |
| ATOM | 8347 | CG  | ARG | A | 528 | 66.933 | −11.656 | 13.983 | 1.00 | 59.93 | C |
| ATOM | 8350 | CD  | ARG | A | 528 | 67.442 | −10.872 | 15.201 | 1.00 | 65.08 | C |
| ATOM | 8353 | NE  | ARG | A | 528 | 68.019 | −11.741 | 16.236 | 1.00 | 69.64 | N |
| ATOM | 8355 | CZ  | ARG | A | 528 | 69.252 | −12.259 | 16.216 | 1.00 | 72.42 | C |
| ATOM | 8356 | NH1 | ARG | A | 528 | 70.092 | −12.017 | 15.209 | 1.00 | 72.24 | N |
| ATOM | 8359 | NH2 | ARG | A | 528 | 69.653 | −13.037 | 17.219 | 1.00 | 72.90 | N |
| ATOM | 8362 | C   | ARG | A | 528 | 66.541 | −14.353 | 12.571 | 1.00 | 54.88 | C |
| ATOM | 8363 | O   | ARG | A | 528 | 67.081 | −13.896 | 11.563 | 1.00 | 55.27 | O |
| ATOM | 8365 | N   | LYS | A | 529 | 66.918 | −15.501 | 13.139 | 1.00 | 53.44 | N |
| ATOM | 8366 | CA  | LYS | A | 529 | 67.976 | −16.348 | 12.565 | 1.00 | 52.75 | C |
| ATOM | 8368 | CB  | LYS | A | 529 | 68.468 | −17.393 | 13.580 | 1.00 | 52.56 | C |
| ATOM | 8371 | CG  | LYS | A | 529 | 69.462 | −16.838 | 14.594 | 1.00 | 54.23 | C |
| ATOM | 8374 | CD  | LYS | A | 529 | 69.995 | −17.901 | 15.556 | 1.00 | 54.76 | C |
| ATOM | 8377 | CE  | LYS | A | 529 | 70.895 | −17.263 | 16.621 | 1.00 | 55.90 | C |
| ATOM | 8380 | NZ  | LYS | A | 529 | 71.540 | −18.258 | 17.524 | 1.00 | 55.71 | N |
| ATOM | 8384 | C   | LYS | A | 529 | 67.528 | −17.041 | 11.274 | 1.00 | 52.02 | C |
| ATOM | 8385 | O   | LYS | A | 529 | 68.297 | −17.134 | 10.314 | 1.00 | 51.94 | O |
| ATOM | 8387 | N   | ARG | A | 530 | 66.292 | −17.535 | 11.261 | 1.00 | 51.11 | N |
| ATOM | 8388 | CA  | ARG | A | 530 | 65.730 | −18.162 | 10.068 | 1.00 | 50.43 | C |
| ATOM | 8390 | CB  | ARG | A | 530 | 64.382 | −18.827 | 10.384 | 1.00 | 50.26 | C |
| ATOM | 8393 | CG  | ARG | A | 530 | 64.511 | −20.115 | 11.201 | 1.00 | 49.87 | C |
| ATOM | 8396 | CD  | ARG | A | 530 | 63.156 | −20.742 | 11.540 | 1.00 | 49.26 | C |
| ATOM | 8399 | NE  | ARG | A | 530 | 63.299 | −22.047 | 12.196 | 1.00 | 47.40 | N |
| ATOM | 8401 | CZ  | ARG | A | 530 | 62.288 | −22.856 | 12.520 | 1.00 | 49.75 | C |
| ATOM | 8402 | NH1 | ARG | A | 530 | 61.028 | −22.519 | 12.251 | 1.00 | 50.99 | N |
| ATOM | 8405 | NH2 | ARG | A | 530 | 62.533 | −24.020 | 13.113 | 1.00 | 51.56 | N |
| ATOM | 8408 | C   | ARG | A | 530 | 65.591 | −17.135 | 8.937  | 1.00 | 50.22 | C |
| ATOM | 8409 | O   | ARG | A | 530 | 65.951 | −17.414 | 7.789  | 1.00 | 50.45 | O |
| ATOM | 8411 | N   | VAL | A | 531 | 65.095 | −15.944 | 9.271  | 1.00 | 49.41 | N |
| ATOM | 8412 | CA  | VAL | A | 531 | 64.958 | −14.857 | 8.291  | 1.00 | 48.42 | C |
| ATOM | 8414 | CB  | VAL | A | 531 | 64.188 | −13.636 | 8.891  | 1.00 | 48.66 | C |
| ATOM | 8416 | CG1 | VAL | A | 531 | 64.109 | −12.479 | 7.890  | 1.00 | 47.11 | C |
| ATOM | 8420 | CG2 | VAL | A | 531 | 62.788 | −14.051 | 9.329  | 1.00 | 47.42 | C |
| ATOM | 8424 | C   | VAL | A | 531 | 66.333 | −14.423 | 7.751  | 1.00 | 47.05 | C |
| ATOM | 8425 | O   | VAL | A | 531 | 66.501 | −14.245 | 6.546  | 1.00 | 47.38 | O |
| ATOM | 8427 | N   | LEU | A | 532 | 67.309 | −14.265 | 8.641  | 1.00 | 45.54 | N |
| ATOM | 8428 | CA  | LEU | A | 532 | 68.670 | −13.905 | 8.232  | 1.00 | 44.51 | C |
| ATOM | 8430 | CB  | LEU | A | 532 | 69.604 | −13.792 | 9.447  | 1.00 | 44.81 | C |
| ATOM | 8433 | CG  | LEU | A | 532 | 69.906 | −12.382 | 9.972  | 1.00 | 46.31 | C |
| ATOM | 8435 | CD1 | LEU | A | 532 | 68.632 | −11.547 | 10.163 | 1.00 | 45.86 | C |
| ATOM | 8439 | CD2 | LEU | A | 532 | 70.715 | −12.472 | 11.269 | 1.00 | 45.01 | C |
| ATOM | 8443 | C   | LEU | A | 532 | 69.251 | −14.909 | 7.239  | 1.00 | 43.07 | C |
| ATOM | 8444 | O   | LEU | A | 532 | 69.769 | −14.526 | 6.189  | 1.00 | 42.09 | O |
| ATOM | 8446 | N   | SER | A | 533 | 69.149 | −16.193 | 7.581  | 1.00 | 41.93 | N |
| ATOM | 8447 | CA  | SER | A | 533 | 69.714 | −17.273 | 6.765  | 1.00 | 40.78 | C |
| ATOM | 8449 | CB  | SER | A | 533 | 69.710 | −18.585 | 7.552  | 1.00 | 40.65 | C |
| ATOM | 8452 | OG  | SER | A | 533 | 68.403 | −19.135 | 7.595  | 1.00 | 41.90 | O |
| ATOM | 8454 | C   | SER | A | 533 | 68.970 | −17.484 | 5.439  | 1.00 | 38.88 | C |
| ATOM | 8455 | O   | SER | A | 533 | 69.523 | −18.069 | 4.508  | 1.00 | 38.00 | O |
| ATOM | 8457 | N   | VAL | A | 534 | 67.725 | −17.017 | 5.370  | 1.00 | 37.22 | N |
| ATOM | 8458 | CA  | VAL | A | 534 | 66.895 | −17.169 | 4.180  | 1.00 | 36.56 | C |
| ATOM | 8460 | CB  | VAL | A | 534 | 65.414 | −17.407 | 4.560  | 1.00 | 35.93 | C |
| ATOM | 8462 | CG1 | VAL | A | 534 | 64.484 | −17.102 | 3.392  | 1.00 | 32.65 | C |
| ATOM | 8466 | CG2 | VAL | A | 534 | 65.228 | −18.829 | 5.019  | 1.00 | 32.66 | C |
| ATOM | 8470 | C   | VAL | A | 534 | 67.013 | −15.976 | 3.231  | 1.00 | 37.95 | C |
| ATOM | 8471 | O   | VAL | A | 534 | 67.189 | −16.163 | 2.022  | 1.00 | 38.77 | O |
| ATOM | 8473 | N   | ILE | A | 535 | 66.929 | −14.761 | 3.770  | 1.00 | 38.59 | N |
| ATOM | 8474 | CA  | ILE | A | 535 | 66.937 | −13.554 | 2.940  | 1.00 | 39.64 | C |
| ATOM | 8476 | CB  | ILE | A | 535 | 65.989 | −12.474 | 3.493  | 1.00 | 39.52 | C |
| ATOM | 8478 | CG1 | ILE | A | 535 | 64.563 | −12.999 | 3.629  | 1.00 | 38.45 | C |
| ATOM | 8481 | CD1 | ILE | A | 535 | 63.899 | −13.290 | 2.315  | 1.00 | 41.93 | C |

APPENDIX 1-continued

| ATOM | 8485 | CG2 | ILE | A | 535 | 66.018 | −11.239 | 2.591 | 1.00 | 41.43 | C |
|---|---|---|---|---|---|---|---|---|---|---|---|
| ATOM | 8489 | C | ILE | A | 535 | 68.318 | −12.905 | 2.814 | 1.00 | 40.82 | C |
| ATOM | 8490 | O | ILE | A | 535 | 68.828 | −12.726 | 1.706 | 1.00 | 41.22 | O |
| ATOM | 8492 | N | THR | A | 536 | 68.912 | −12.556 | 3.953 | 1.00 | 41.78 | N |
| ATOM | 8493 | CA | THR | A | 536 | 69.995 | −11.568 | 3.989 | 1.00 | 42.39 | C |
| ATOM | 8495 | CB | THR | A | 536 | 69.833 | −10.632 | 5.217 | 1.00 | 42.80 | C |
| ATOM | 8497 | OG1 | THR | A | 536 | 69.789 | −11.410 | 6.418 | 1.00 | 46.53 | O |
| ATOM | 8499 | CG2 | THR | A | 536 | 68.540 | −9.814 | 5.110 | 1.00 | 41.77 | C |
| ATOM | 8503 | C | THR | A | 536 | 71.413 | −12.162 | 3.955 | 1.00 | 41.92 | C |
| ATOM | 8504 | O | THR | A | 536 | 72.239 | −11.739 | 3.143 | 1.00 | 42.54 | O |
| ATOM | 8506 | N | GLU | A | 537 | 71.693 | −13.128 | 4.826 | 1.00 | 40.62 | N |
| ATOM | 8507 | CA | GLU | A | 537 | 73.035 | −13.709 | 4.933 | 1.00 | 39.78 | C |
| ATOM | 8509 | CB | GLU | A | 537 | 73.319 | −14.147 | 6.376 | 1.00 | 40.55 | C |
| ATOM | 8512 | CG | GLU | A | 537 | 73.642 | −13.013 | 7.338 | 1.00 | 41.76 | C |
| ATOM | 8515 | CD | GLU | A | 537 | 73.948 | −13.519 | 8.742 | 1.00 | 45.87 | C |
| ATOM | 8516 | OE1 | GLU | A | 537 | 75.134 | −13.513 | 9.139 | 1.00 | 48.56 | O |
| ATOM | 8517 | OE2 | GLU | A | 537 | 73.005 | −13.939 | 9.446 | 1.00 | 46.99 | O |
| ATOM | 8518 | C | GLU | A | 537 | 73.209 | −14.911 | 3.992 | 1.00 | 38.20 | C |
| ATOM | 8519 | O | GLU | A | 537 | 72.405 | −15.847 | 4.040 | 1.00 | 37.11 | O |
| ATOM | 8521 | N | PRO | A | 538 | 74.252 | −14.889 | 3.133 | 1.00 | 36.56 | N |
| ATOM | 8522 | CA | PRO | A | 538 | 74.595 | −16.059 | 2.320 | 1.00 | 35.27 | C |
| ATOM | 8524 | CB | PRO | A | 538 | 75.641 | −15.518 | 1.337 | 1.00 | 34.98 | C |
| ATOM | 8527 | CG | PRO | A | 538 | 75.435 | −14.073 | 1.313 | 1.00 | 36.61 | C |
| ATOM | 8530 | CD | PRO | A | 538 | 75.002 | −13.703 | 2.690 | 1.00 | 37.15 | C |
| ATOM | 8533 | C | PRO | A | 538 | 75.199 | −17.199 | 3.117 | 1.00 | 33.85 | C |
| ATOM | 8534 | O | PRO | A | 538 | 75.684 | −16.999 | 4.226 | 1.00 | 34.31 | O |
| ATOM | 8535 | N | ILE | A | 539 | 75.162 | −18.386 | 2.529 | 1.00 | 32.85 | N |
| ATOM | 8536 | CA | ILE | A | 539 | 75.828 | −19.562 | 3.077 | 1.00 | 32.36 | C |
| ATOM | 8538 | CB | ILE | A | 539 | 75.251 | −20.854 | 2.449 | 1.00 | 31.82 | C |
| ATOM | 8540 | CG1 | ILE | A | 539 | 73.789 | −21.032 | 2.854 | 1.00 | 30.21 | C |
| ATOM | 8543 | CD1 | ILE | A | 539 | 73.150 | −22.267 | 2.262 | 1.00 | 32.80 | C |
| ATOM | 8547 | CG2 | ILE | A | 539 | 76.042 | −22.065 | 2.859 | 1.00 | 29.71 | C |
| ATOM | 8551 | C | ILE | A | 539 | 77.329 | −19.452 | 2.794 | 1.00 | 32.68 | C |
| ATOM | 8552 | O | ILE | A | 539 | 77.729 | −18.941 | 1.745 | 1.00 | 31.56 | O |
| ATOM | 8554 | N | LEU | A | 540 | 78.154 | −19.914 | 3.734 | 1.00 | 34.01 | N |
| ATOM | 8555 | CA | LEU | A | 540 | 79.608 | −19.813 | 3.586 | 1.00 | 35.36 | C |
| ATOM | 8557 | CB | LEU | A | 540 | 80.357 | −20.383 | 4.806 | 1.00 | 35.94 | C |
| ATOM | 8560 | CG | LEU | A | 540 | 80.523 | −19.526 | 6.069 | 1.00 | 38.17 | C |
| ATOM | 8562 | CD1 | LEU | A | 540 | 81.512 | −20.197 | 7.028 | 1.00 | 39.26 | C |
| ATOM | 8566 | CD2 | LEU | A | 540 | 80.990 | −18.113 | 5.742 | 1.00 | 39.10 | C |
| ATOM | 8570 | C | LEU | A | 540 | 80.044 | −20.561 | 2.332 | 1.00 | 35.45 | C |
| ATOM | 8571 | O | LEU | A | 540 | 79.758 | −21.748 | 2.206 | 1.00 | 34.76 | O |
| ATOM | 8573 | N | PRO | A | 541 | 80.745 | −19.874 | 1.408 | 1.00 | 36.29 | N |
| ATOM | 8574 | CA | PRO | A | 541 | 81.115 | −20.499 | 0.137 | 1.00 | 36.75 | C |
| ATOM | 8576 | CB | PRO | A | 541 | 82.013 | −19.447 | −0.532 | 1.00 | 36.53 | C |
| ATOM | 8579 | CG | PRO | A | 541 | 82.422 | −18.532 | 0.551 | 1.00 | 36.20 | C |
| ATOM | 8582 | CD | PRO | A | 541 | 81.285 | −18.507 | 1.508 | 1.00 | 36.11 | C |
| ATOM | 8585 | C | PRO | A | 541 | 81.861 | −21.822 | 0.297 | 1.00 | 37.40 | C |
| ATOM | 8586 | O | PRO | A | 541 | 82.580 | −22.018 | 1.275 | 1.00 | 37.11 | O |
| ATOM | 8587 | N | PHE | A | 542 | 81.669 | −22.717 | −0.667 | 1.00 | 38.70 | N |
| ATOM | 8588 | CA | PHE | A | 542 | 82.309 | −24.028 | −0.669 | 1.00 | 39.81 | C |
| ATOM | 8590 | CB | PHE | A | 542 | 81.910 | −24.784 | −1.944 | 1.00 | 38.81 | C |
| ATOM | 8593 | CG | PHE | A | 542 | 82.618 | −26.094 | −2.131 | 1.00 | 35.15 | C |
| ATOM | 8594 | CD1 | PHE | A | 542 | 82.312 | −27.184 | −1.330 | 1.00 | 33.52 | C |
| ATOM | 8596 | CE1 | PHE | A | 542 | 82.960 | −28.403 | −1.504 | 1.00 | 32.93 | C |
| ATOM | 8598 | CZ | PHE | A | 542 | 83.921 | −28.540 | −2.490 | 1.00 | 32.40 | C |
| ATOM | 8600 | CE2 | PHE | A | 542 | 84.234 | −27.457 | −3.301 | 1.00 | 32.40 | C |
| ATOM | 8602 | CD2 | PHE | A | 542 | 83.582 | −26.243 | −3.119 | 1.00 | 33.20 | C |
| ATOM | 8604 | C | PHE | A | 542 | 83.830 | −23.894 | −0.575 | 1.00 | 42.56 | C |
| ATOM | 8605 | O | PHE | A | 542 | 84.423 | −23.060 | −1.260 | 1.00 | 42.24 | O |
| ATOM | 8607 | N | GLU | A | 543 | 84.445 | −24.699 | 0.291 | 1.00 | 46.36 | N |
| ATOM | 8608 | CA | GLU | A | 543 | 85.910 | −24.774 | 0.414 | 1.00 | 49.96 | C |
| ATOM | 8610 | CB | GLU | A | 543 | 86.360 | −24.329 | 1.815 | 1.00 | 50.34 | C |
| ATOM | 8613 | CG | GLU | A | 543 | 86.299 | −22.818 | 2.046 | 1.00 | 52.01 | C |
| ATOM | 8616 | CD | GLU | A | 543 | 86.218 | −22.443 | 3.521 | 1.00 | 54.80 | C |
| ATOM | 8617 | OE1 | GLU | A | 543 | 85.219 | −22.811 | 4.179 | 1.00 | 54.78 | O |
| ATOM | 8618 | OE2 | GLU | A | 543 | 87.148 | −21.771 | 4.018 | 1.00 | 54.99 | O |
| ATOM | 8619 | C | GLU | A | 543 | 86.392 | −26.205 | 0.134 | 1.00 | 52.48 | C |
| ATOM | 8620 | O | GLU | A | 543 | 85.596 | −27.147 | 0.148 | 1.00 | 53.17 | O |
| ATOM | 8622 | N | ARG | A | 544 | 87.691 | −26.358 | −0.126 | 1.00 | 55.15 | N |
| ATOM | 8623 | CA | ARG | A | 544 | 88.300 | −27.677 | −0.349 | 1.00 | 56.80 | C |
| ATOM | 8625 | CB | ARG | A | 544 | 88.913 | −27.762 | −1.755 | 1.00 | 57.52 | C |
| ATOM | 8628 | CG | ARG | A | 544 | 87.890 | −27.687 | −2.886 | 1.00 | 61.04 | C |
| ATOM | 8631 | CD | ARG | A | 544 | 88.551 | −27.708 | −4.270 | 1.00 | 66.09 | C |
| ATOM | 8634 | NE | ARG | A | 544 | 87.581 | −27.496 | −5.355 | 1.00 | 70.23 | N |
| ATOM | 8636 | CZ | ARG | A | 544 | 87.150 | −26.307 | −5.794 | 1.00 | 71.81 | C |
| ATOM | 8637 | NH1 | ARG | A | 544 | 87.587 | −25.170 | −5.253 | 1.00 | 72.03 | N |
| ATOM | 8640 | NH2 | ARG | A | 544 | 86.263 | −26.251 | −6.786 | 1.00 | 70.51 | N |
| ATOM | 8643 | C | ARG | A | 544 | 89.357 | −27.961 | 0.723 | 1.00 | 57.03 | C |
| ATOM | 8644 | O | ARG | A | 544 | 89.018 | −28.161 | 1.891 | 1.00 | 57.24 | O |

APPENDIX 1-continued

| ATOM | 8646 | OXT | ARG | A | 544 | 90.565 | −27.989 | 0.467 | 1.00 | 57.03 | O |
|---|---|---|---|---|---|---|---|---|---|---|---|
| ATOM | 8647 | N | SER | B | 6 | 64.883 | 38.854 | 11.944 | 1.00 | 48.47 | N |
| ATOM | 8648 | CA | SER | B | 6 | 64.548 | 37.415 | 11.723 | 1.00 | 48.78 | C |
| ATOM | 8650 | CB | SER | B | 6 | 63.144 | 37.289 | 11.108 | 1.00 | 49.12 | C |
| ATOM | 8653 | OG | SER | B | 6 | 62.743 | 35.935 | 10.961 | 1.00 | 48.81 | O |
| ATOM | 8655 | C | SER | B | 6 | 65.606 | 36.778 | 10.815 | 1.00 | 48.64 | C |
| ATOM | 8656 | O | SER | B | 6 | 65.544 | 36.920 | 9.589 | 1.00 | 49.03 | O |
| ATOM | 8660 | N | ALA | B | 7 | 66.577 | 36.090 | 11.423 | 1.00 | 47.61 | N |
| ATOM | 8661 | CA | ALA | B | 7 | 67.705 | 35.498 | 10.687 | 1.00 | 47.15 | C |
| ATOM | 8663 | CB | ALA | B | 7 | 68.947 | 35.450 | 11.572 | 1.00 | 46.50 | C |
| ATOM | 8667 | C | ALA | B | 7 | 67.379 | 34.097 | 10.157 | 1.00 | 46.96 | C |
| ATOM | 8668 | O | ALA | B | 7 | 66.659 | 33.336 | 10.801 | 1.00 | 46.12 | O |
| ATOM | 8670 | N | ASN | B | 8 | 67.924 | 33.764 | 8.986 | 1.00 | 47.48 | N |
| ATOM | 8671 | CA | ASN | B | 8 | 67.707 | 32.453 | 8.365 | 1.00 | 48.21 | C |
| ATOM | 8673 | CB | ASN | B | 8 | 67.071 | 32.612 | 6.979 | 1.00 | 48.47 | C |
| ATOM | 8676 | CG | ASN | B | 8 | 66.763 | 31.273 | 6.314 | 1.00 | 50.21 | C |
| ATOM | 8677 | OD1 | ASN | B | 8 | 66.453 | 30.285 | 6.985 | 1.00 | 49.98 | O |
| ATOM | 8678 | ND2 | ASN | B | 8 | 66.844 | 31.240 | 4.987 | 1.00 | 50.79 | N |
| ATOM | 8681 | C | ASN | B | 8 | 68.997 | 31.639 | 8.242 | 1.00 | 48.33 | C |
| ATOM | 8682 | O | ASN | B | 8 | 69.946 | 32.061 | 7.576 | 1.00 | 48.66 | O |
| ATOM | 8684 | N | TYR | B | 9 | 69.017 | 30.475 | 8.891 | 1.00 | 48.45 | N |
| ATOM | 8685 | CA | TYR | B | 9 | 70.125 | 29.523 | 8.780 | 1.00 | 48.48 | C |
| ATOM | 8687 | CB | TYR | B | 9 | 70.836 | 29.375 | 10.128 | 1.00 | 47.96 | C |
| ATOM | 8690 | CG | TYR | B | 9 | 71.296 | 30.682 | 10.733 | 1.00 | 44.69 | C |
| ATOM | 8691 | CD1 | TYR | B | 9 | 72.053 | 31.592 | 9.991 | 1.00 | 41.23 | C |
| ATOM | 8693 | CE1 | TYR | B | 9 | 72.476 | 32.789 | 10.549 | 1.00 | 40.89 | C |
| ATOM | 8695 | CZ | TYR | B | 9 | 72.148 | 33.084 | 11.865 | 1.00 | 38.45 | C |
| ATOM | 8696 | OH | TYR | B | 9 | 72.562 | 34.261 | 12.441 | 1.00 | 36.53 | O |
| ATOM | 8698 | CE2 | TYR | B | 9 | 71.406 | 32.199 | 12.616 | 1.00 | 37.50 | C |
| ATOM | 8700 | CD2 | TYR | B | 9 | 70.988 | 31.005 | 12.053 | 1.00 | 40.50 | C |
| ATOM | 8702 | C | TYR | B | 9 | 69.653 | 28.148 | 8.297 | 1.00 | 49.85 | C |
| ATOM | 8703 | O | TYR | B | 9 | 70.414 | 27.177 | 8.344 | 1.00 | 49.70 | O |
| ATOM | 8705 | N | GLU | B | 10 | 68.404 | 28.068 | 7.830 | 1.00 | 51.51 | N |
| ATOM | 8706 | CA | GLU | B | 10 | 67.851 | 26.818 | 7.302 | 1.00 | 52.34 | C |
| ATOM | 8708 | CB | GLU | B | 10 | 66.328 | 26.919 | 7.127 | 1.00 | 52.98 | C |
| ATOM | 8711 | CG | GLU | B | 10 | 65.517 | 26.763 | 8.428 | 1.00 | 54.93 | C |
| ATOM | 8714 | CD | GLU | B | 10 | 64.829 | 25.401 | 8.555 | 1.00 | 59.05 | C |
| ATOM | 8715 | OE1 | GLU | B | 10 | 64.239 | 24.928 | 7.554 | 1.00 | 58.28 | O |
| ATOM | 8716 | OE2 | GLU | B | 10 | 64.863 | 24.812 | 9.661 | 1.00 | 59.68 | O |
| ATOM | 8717 | C | GLU | B | 10 | 68.520 | 26.506 | 5.964 | 1.00 | 52.09 | C |
| ATOM | 8718 | O | GLU | B | 10 | 68.645 | 27.398 | 5.119 | 1.00 | 51.52 | O |
| ATOM | 8720 | N | PRO | B | 11 | 68.955 | 25.243 | 5.766 | 1.00 | 52.25 | N |
| ATOM | 8721 | CA | PRO | B | 11 | 69.667 | 24.890 | 4.539 | 1.00 | 51.99 | C |
| ATOM | 8723 | CB | PRO | B | 11 | 70.325 | 23.556 | 4.897 | 1.00 | 51.92 | C |
| ATOM | 8726 | CG | PRO | B | 11 | 69.359 | 22.916 | 5.845 | 1.00 | 52.20 | C |
| ATOM | 8729 | CD | PRO | B | 11 | 68.682 | 24.050 | 6.596 | 1.00 | 52.52 | C |
| ATOM | 8732 | C | PRO | B | 11 | 68.706 | 24.708 | 3.366 | 1.00 | 51.28 | C |
| ATOM | 8733 | O | PRO | B | 11 | 67.663 | 24.071 | 3.521 | 1.00 | 51.73 | O |
| ATOM | 8734 | N | ASN | B | 12 | 69.053 | 25.272 | 2.212 | 1.00 | 50.08 | N |
| ATOM | 8735 | CA | ASN | B | 12 | 68.276 | 25.058 | 0.995 | 1.00 | 49.62 | C |
| ATOM | 8737 | CB | ASN | B | 12 | 68.717 | 26.028 | −0.107 | 1.00 | 50.33 | C |
| ATOM | 8740 | CG | ASN | B | 12 | 68.497 | 27.485 | 0.264 | 1.00 | 51.11 | C |
| ATOM | 8741 | OD1 | ASN | B | 12 | 67.361 | 27.942 | 0.396 | 1.00 | 52.95 | O |
| ATOM | 8742 | ND2 | ASN | B | 12 | 69.588 | 28.226 | 0.415 | 1.00 | 52.33 | N |
| ATOM | 8745 | C | ASN | B | 12 | 68.417 | 23.619 | 0.490 | 1.00 | 48.51 | C |
| ATOM | 8746 | O | ASN | B | 12 | 69.419 | 22.952 | 0.749 | 1.00 | 47.86 | O |
| ATOM | 8748 | N | SER | B | 13 | 67.404 | 23.148 | −0.231 | 1.00 | 48.33 | N |
| ATOM | 8749 | CA | SER | B | 13 | 67.445 | 21.828 | −0.870 | 1.00 | 48.08 | C |
| ATOM | 8751 | CB | SER | B | 13 | 66.064 | 21.460 | −1.436 | 1.00 | 47.79 | C |
| ATOM | 8754 | OG | SER | B | 13 | 65.432 | 22.584 | −2.032 | 1.00 | 46.89 | O |
| ATOM | 8756 | C | SER | B | 13 | 68.513 | 21.756 | −1.973 | 1.00 | 48.18 | C |
| ATOM | 8757 | O | SER | B | 13 | 69.066 | 20.686 | −2.238 | 1.00 | 49.34 | O |
| ATOM | 8759 | N | TRP | B | 14 | 68.806 | 22.896 | −2.599 | 1.00 | 47.36 | N |
| ATOM | 8760 | CA | TRP | B | 14 | 69.817 | 22.967 | −3.662 | 1.00 | 46.99 | C |
| ATOM | 8762 | CB | TRP | B | 14 | 69.450 | 24.044 | −4.700 | 1.00 | 47.52 | C |
| ATOM | 8765 | CG | TRP | B | 14 | 69.013 | 25.376 | −4.144 | 1.00 | 49.89 | C |
| ATOM | 8766 | CD1 | TRP | B | 14 | 67.729 | 25.824 | −4.011 | 1.00 | 53.42 | C |
| ATOM | 8768 | NE1 | TRP | B | 14 | 67.719 | 27.089 | −3.472 | 1.00 | 55.27 | N |
| ATOM | 8770 | CE2 | TRP | B | 14 | 69.012 | 27.487 | −3.254 | 1.00 | 55.66 | C |
| ATOM | 8771 | CD2 | TRP | B | 14 | 69.856 | 26.431 | −3.667 | 1.00 | 51.66 | C |
| ATOM | 8772 | CE3 | TRP | B | 14 | 71.241 | 26.587 | −3.546 | 1.00 | 54.94 | C |
| ATOM | 8774 | CZ3 | TRP | B | 14 | 71.739 | 27.781 | −3.017 | 1.00 | 58.44 | C |
| ATOM | 8776 | CH2 | TRP | B | 14 | 70.872 | 28.814 | −2.616 | 1.00 | 60.63 | C |
| ATOM | 8778 | CZ2 | TRP | B | 14 | 69.509 | 28.687 | −2.729 | 1.00 | 59.38 | C |
| ATOM | 8780 | C | TRP | B | 14 | 71.258 | 23.173 | −3.153 | 1.00 | 46.41 | C |
| ATOM | 8781 | O | TRP | B | 14 | 72.206 | 23.074 | −3.934 | 1.00 | 46.06 | O |
| ATOM | 8783 | N | ASP | B | 15 | 71.428 | 23.445 | −1.858 | 1.00 | 45.51 | N |
| ATOM | 8784 | CA | ASP | B | 15 | 72.766 | 23.592 | −1.266 | 1.00 | 44.70 | C |
| ATOM | 8786 | CB | ASP | B | 15 | 72.678 | 23.776 | 0.262 | 1.00 | 45.12 | C |
| ATOM | 8789 | CG | ASP | B | 15 | 72.262 | 25.190 | 0.679 | 1.00 | 46.08 | C |

APPENDIX 1-continued

| | | | | | | | | | | |
|---|---|---|---|---|---|---|---|---|---|---|
| ATOM | 8790 | OD1 | ASP | B | 15 | 72.430 | 26.145 | −0.115 | 1.00 | 48.86 | O |
| ATOM | 8791 | OD2 | ASP | B | 15 | 71.783 | 25.344 | 1.825 | 1.00 | 46.92 | O |
| ATOM | 8792 | C | ASP | B | 15 | 73.660 | 22.384 | −1.575 | 1.00 | 43.48 | C |
| ATOM | 8793 | O | ASP | B | 15 | 73.185 | 21.249 | −1.618 | 1.00 | 43.00 | O |
| ATOM | 8795 | N | TYR | B | 16 | 74.954 | 22.640 | −1.775 | 1.00 | 42.61 | N |
| ATOM | 8796 | CA | TYR | B | 16 | 75.926 | 21.588 | −2.104 | 1.00 | 41.65 | C |
| ATOM | 8798 | CB | TYR | B | 16 | 77.252 | 22.201 | −2.568 | 1.00 | 40.79 | C |
| ATOM | 8801 | CG | TYR | B | 16 | 77.187 | 22.928 | −3.895 | 1.00 | 35.80 | C |
| ATOM | 8802 | CD1 | TYR | B | 16 | 76.745 | 22.279 | −5.047 | 1.00 | 30.88 | C |
| ATOM | 8804 | CE1 | TYR | B | 16 | 76.695 | 22.940 | −6.269 | 1.00 | 27.07 | C |
| ATOM | 8806 | CZ | TYR | B | 16 | 77.103 | 24.258 | −6.355 | 1.00 | 27.18 | C |
| ATOM | 8807 | OH | TYR | B | 16 | 77.054 | 24.904 | −7.574 | 1.00 | 22.85 | O |
| ATOM | 8809 | CE2 | TYR | B | 16 | 77.561 | 24.921 | −5.226 | 1.00 | 25.86 | C |
| ATOM | 8811 | CD2 | TYR | B | 16 | 77.602 | 24.255 | −4.007 | 1.00 | 28.91 | C |
| ATOM | 8813 | C | TYR | B | 16 | 76.206 | 20.623 | −0.945 | 1.00 | 43.36 | C |
| ATOM | 8814 | O | TYR | B | 16 | 76.778 | 19.554 | −1.161 | 1.00 | 42.69 | O |
| ATOM | 8816 | N | ASP | B | 17 | 75.842 | 21.016 | 0.277 | 1.00 | 45.64 | N |
| ATOM | 8817 | CA | ASP | B | 17 | 75.901 | 20.115 | 1.434 | 1.00 | 47.24 | C |
| ATOM | 8819 | CB | ASP | B | 17 | 75.721 | 20.892 | 2.754 | 1.00 | 47.11 | C |
| ATOM | 8822 | CG | ASP | B | 17 | 77.032 | 21.465 | 3.302 | 1.00 | 48.46 | C |
| ATOM | 8823 | OD1 | ASP | B | 17 | 78.108 | 21.257 | 2.697 | 1.00 | 48.72 | O |
| ATOM | 8824 | OD2 | ASP | B | 17 | 76.985 | 22.122 | 4.367 | 1.00 | 49.78 | O |
| ATOM | 8825 | C | ASP | B | 17 | 74.829 | 19.022 | 1.316 | 1.00 | 49.37 | C |
| ATOM | 8826 | O | ASP | B | 17 | 75.110 | 17.842 | 1.559 | 1.00 | 49.22 | O |
| ATOM | 8828 | N | TYR | B | 18 | 73.613 | 19.424 | 0.934 | 1.00 | 51.34 | N |
| ATOM | 8829 | CA | TYR | B | 18 | 72.478 | 18.502 | 0.789 | 1.00 | 53.17 | C |
| ATOM | 8831 | CB | TYR | B | 18 | 71.158 | 19.285 | 0.752 | 1.00 | 54.17 | C |
| ATOM | 8834 | CG | TYR | B | 18 | 69.908 | 18.425 | 0.805 | 1.00 | 60.93 | C |
| ATOM | 8835 | CD1 | TYR | B | 18 | 69.363 | 18.023 | 2.029 | 1.00 | 66.26 | C |
| ATOM | 8837 | CE1 | TYR | B | 18 | 68.206 | 17.235 | 2.084 | 1.00 | 68.59 | C |
| ATOM | 8839 | CZ | TYR | B | 18 | 67.583 | 16.848 | 0.905 | 1.00 | 70.46 | C |
| ATOM | 8840 | OH | TYR | B | 18 | 66.443 | 16.077 | 0.953 | 1.00 | 72.07 | O |
| ATOM | 8842 | CE2 | TYR | B | 18 | 68.103 | 17.239 | −0.325 | 1.00 | 68.49 | C |
| ATOM | 8844 | CD2 | TYR | B | 18 | 69.257 | 18.027 | −0.369 | 1.00 | 65.55 | C |
| ATOM | 8846 | C | TYR | B | 18 | 72.628 | 17.633 | −0.463 | 1.00 | 53.15 | C |
| ATOM | 8847 | O | TYR | B | 18 | 72.673 | 16.406 | −0.371 | 1.00 | 52.95 | O |
| ATOM | 8849 | N | LEU | B | 19 | 72.700 | 18.272 | −1.631 | 1.00 | 54.03 | N |
| ATOM | 8850 | CA | LEU | B | 19 | 73.021 | 17.570 | −2.879 | 1.00 | 54.66 | C |
| ATOM | 8852 | CB | LEU | B | 19 | 72.740 | 18.453 | −4.101 | 1.00 | 54.30 | C |
| ATOM | 8855 | CG | LEU | B | 19 | 71.271 | 18.702 | −4.471 | 1.00 | 53.94 | C |
| ATOM | 8857 | CD1 | LEU | B | 19 | 71.146 | 19.852 | −5.467 | 1.00 | 51.72 | C |
| ATOM | 8861 | CD2 | LEU | B | 19 | 70.628 | 17.434 | −5.028 | 1.00 | 53.44 | C |
| ATOM | 8865 | C | LEU | B | 19 | 74.497 | 17.224 | −2.832 | 1.00 | 55.92 | C |
| ATOM | 8866 | O | LEU | B | 19 | 75.211 | 17.701 | −1.953 | 1.00 | 57.53 | O |
| ATOM | 8868 | N | LEU | B | 20 | 74.962 | 16.388 | −3.756 | 1.00 | 56.38 | N |
| ATOM | 8869 | CA | LEU | B | 20 | 76.402 | 16.155 | −3.906 | 1.00 | 57.08 | C |
| ATOM | 8871 | CB | LEU | B | 20 | 77.081 | 17.498 | −4.246 | 1.00 | 56.62 | C |
| ATOM | 8874 | CG | LEU | B | 20 | 78.138 | 17.576 | −5.347 | 1.00 | 56.12 | C |
| ATOM | 8876 | CD1 | LEU | B | 20 | 77.603 | 17.034 | −6.666 | 1.00 | 54.24 | C |
| ATOM | 8880 | CD2 | LEU | B | 20 | 78.606 | 19.019 | −5.517 | 1.00 | 53.19 | C |
| ATOM | 8884 | C | LEU | B | 20 | 77.043 | 15.522 | −2.643 | 1.00 | 58.82 | C |
| ATOM | 8885 | O | LEU | B | 20 | 78.253 | 15.659 | −2.414 | 1.00 | 59.10 | O |
| ATOM | 8887 | N | SER | B | 21 | 76.234 | 14.821 | −1.841 | 1.00 | 60.11 | N |
| ATOM | 8888 | CA | SER | B | 21 | 76.674 | 14.298 | −0.538 | 1.00 | 60.95 | C |
| ATOM | 8890 | CB | SER | B | 21 | 75.613 | 14.577 | 0.530 | 1.00 | 61.07 | C |
| ATOM | 8893 | OG | SER | B | 21 | 76.125 | 14.354 | 1.834 | 1.00 | 59.55 | O |
| ATOM | 8895 | C | SER | B | 21 | 76.967 | 12.798 | −0.596 | 1.00 | 61.73 | C |
| ATOM | 8896 | O | SER | B | 21 | 76.246 | 12.037 | −1.241 | 1.00 | 62.23 | O |
| ATOM | 8898 | N | ILE | B | 28 | 82.844 | 12.022 | −4.394 | 1.00 | 61.01 | N |
| ATOM | 8899 | CA | ILE | B | 28 | 81.876 | 13.095 | −4.606 | 1.00 | 60.50 | C |
| ATOM | 8901 | CB | ILE | B | 28 | 80.417 | 12.542 | −4.583 | 1.00 | 60.55 | C |
| ATOM | 8903 | CG1 | ILE | B | 28 | 80.255 | 11.402 | −5.599 | 1.00 | 61.10 | C |
| ATOM | 8906 | CD1 | ILE | B | 28 | 78.832 | 10.870 | −5.726 | 1.00 | 60.87 | C |
| ATOM | 8910 | CG2 | ILE | B | 28 | 79.407 | 13.642 | −4.884 | 1.00 | 59.57 | C |
| ATOM | 8914 | C | ILE | B | 28 | 82.033 | 14.219 | −3.567 | 1.00 | 59.90 | C |
| ATOM | 8915 | O | ILE | B | 28 | 81.181 | 15.103 | −3.479 | 1.00 | 60.41 | O |
| ATOM | 8917 | N | GLU | B | 29 | 83.127 | 14.200 | −2.803 | 1.00 | 58.90 | N |
| ATOM | 8918 | CA | GLU | B | 29 | 83.319 | 15.151 | −1.698 | 1.00 | 58.52 | C |
| ATOM | 8920 | CB | GLU | B | 29 | 83.679 | 14.411 | −0.406 | 1.00 | 58.96 | C |
| ATOM | 8923 | CG | GLU | B | 29 | 82.494 | 13.674 | 0.216 | 1.00 | 61.50 | C |
| ATOM | 8926 | CD | GLU | B | 29 | 82.712 | 13.325 | 1.675 | 1.00 | 65.34 | C |
| ATOM | 8927 | OE1 | GLU | B | 29 | 82.996 | 14.249 | 2.469 | 1.00 | 67.85 | O |
| ATOM | 8928 | OE2 | GLU | B | 29 | 82.586 | 12.131 | 2.032 | 1.00 | 67.47 | O |
| ATOM | 8929 | C | GLU | B | 29 | 84.351 | 16.244 | −1.996 | 1.00 | 57.31 | C |
| ATOM | 8930 | O | GLU | B | 29 | 84.126 | 17.408 | −1.655 | 1.00 | 57.65 | O |
| ATOM | 8932 | N | VAL | B | 30 | 85.474 | 15.881 | −2.616 | 1.00 | 55.38 | N |
| ATOM | 8933 | CA | VAL | B | 30 | 86.434 | 16.881 | −3.117 | 1.00 | 53.51 | C |
| ATOM | 8935 | CB | VAL | B | 30 | 87.709 | 16.218 | −3.704 | 1.00 | 53.54 | C |
| ATOM | 8937 | CG1 | VAL | B | 30 | 88.466 | 17.184 | −4.622 | 1.00 | 52.01 | C |
| ATOM | 8941 | CG2 | VAL | B | 30 | 88.611 | 15.719 | −2.576 | 1.00 | 53.28 | C |

APPENDIX 1-continued

| ATOM | 8945 | C | VAL | B | 30 | 85.756 | 17.752 | −4.181 | 1.00 | 51.69 | C |
|---|---|---|---|---|---|---|---|---|---|---|---|
| ATOM | 8946 | O | VAL | B | 30 | 86.089 | 18.926 | −4.354 | 1.00 | 51.90 | O |
| ATOM | 8948 | N | TYR | B | 31 | 84.808 | 17.145 | −4.888 | 1.00 | 49.16 | N |
| ATOM | 8949 | CA | TYR | B | 31 | 83.926 | 17.825 | −5.827 | 1.00 | 47.48 | C |
| ATOM | 8951 | CB | TYR | B | 31 | 83.041 | 16.759 | −6.481 | 1.00 | 48.12 | C |
| ATOM | 8954 | CG | TYR | B | 31 | 82.324 | 17.145 | −7.749 | 1.00 | 51.51 | C |
| ATOM | 8955 | CD1 | TYR | B | 31 | 82.972 | 17.108 | −8.985 | 1.00 | 55.27 | C |
| ATOM | 8957 | CE1 | TYR | B | 31 | 82.297 | 17.439 | −10.162 | 1.00 | 58.69 | C |
| ATOM | 8959 | CZ | TYR | B | 31 | 80.948 | 17.792 | −10.106 | 1.00 | 61.93 | C |
| ATOM | 8960 | OH | TYR | B | 31 | 80.249 | 18.124 | −11.251 | 1.00 | 60.06 | O |
| ATOM | 8962 | CE2 | TYR | B | 31 | 80.285 | 17.814 | −8.888 | 1.00 | 61.49 | C |
| ATOM | 8964 | CD2 | TYR | B | 31 | 80.975 | 17.484 | −7.721 | 1.00 | 57.69 | C |
| ATOM | 8966 | C | TYR | B | 31 | 83.074 | 18.867 | −5.088 | 1.00 | 44.90 | C |
| ATOM | 8967 | O | TYR | B | 31 | 82.977 | 20.018 | −5.512 | 1.00 | 43.94 | O |
| ATOM | 8969 | N | LYS | B | 32 | 82.486 | 18.445 | −3.970 | 1.00 | 42.56 | N |
| ATOM | 8970 | CA | LYS | B | 32 | 81.599 | 19.278 | −3.141 | 1.00 | 40.47 | C |
| ATOM | 8972 | CB | LYS | B | 32 | 80.934 | 18.409 | −2.054 | 1.00 | 40.96 | C |
| ATOM | 8975 | CG | LYS | B | 32 | 80.533 | 19.121 | −0.751 | 1.00 | 41.25 | C |
| ATOM | 8978 | CD | LYS | B | 32 | 80.081 | 18.110 | 0.311 | 1.00 | 42.15 | C |
| ATOM | 8981 | CE | LYS | B | 32 | 80.368 | 18.587 | 1.733 | 1.00 | 43.11 | C |
| ATOM | 8984 | NZ | LYS | B | 32 | 80.378 | 17.457 | 2.713 | 1.00 | 41.98 | N |
| ATOM | 8988 | C | LYS | B | 32 | 82.301 | 20.475 | −2.500 | 1.00 | 38.14 | C |
| ATOM | 8989 | O | LYS | B | 32 | 81.766 | 21.581 | −2.506 | 1.00 | 37.75 | O |
| ATOM | 8991 | N | ASP | B | 33 | 83.481 | 20.248 | −1.930 | 1.00 | 35.83 | N |
| ATOM | 8992 | CA | ASP | B | 33 | 84.219 | 21.316 | −1.239 | 1.00 | 34.43 | C |
| ATOM | 8994 | CB | ASP | B | 33 | 85.416 | 20.748 | −0.464 | 1.00 | 35.02 | C |
| ATOM | 8997 | CG | ASP | B | 33 | 84.997 | 20.030 | 0.810 | 1.00 | 37.63 | C |
| ATOM | 8998 | OD1 | ASP | B | 33 | 84.337 | 20.672 | 1.661 | 1.00 | 41.48 | O |
| ATOM | 8999 | OD2 | ASP | B | 33 | 85.328 | 18.831 | 0.960 | 1.00 | 38.68 | O |
| ATOM | 9000 | C | ASP | B | 33 | 84.684 | 22.409 | −2.194 | 1.00 | 31.96 | C |
| ATOM | 9001 | O | ASP | B | 33 | 84.751 | 23.578 | −1.814 | 1.00 | 31.22 | O |
| ATOM | 9003 | N | LYS | B | 34 | 84.997 | 22.018 | −3.427 | 1.00 | 29.68 | N |
| ATOM | 9004 | CA | LYS | B | 34 | 85.373 | 22.959 | −4.474 | 1.00 | 28.34 | C |
| ATOM | 9006 | CB | LYS | B | 34 | 85.877 | 22.211 | −5.702 | 1.00 | 28.95 | C |
| ATOM | 9009 | CG | LYS | B | 34 | 86.675 | 23.073 | −6.661 | 1.00 | 32.79 | C |
| ATOM | 9012 | CD | LYS | B | 34 | 87.396 | 22.216 | −7.690 | 1.00 | 37.60 | C |
| ATOM | 9015 | CE | LYS | B | 34 | 88.828 | 22.670 | −7.896 | 1.00 | 38.74 | C |
| ATOM | 9018 | NZ | LYS | B | 34 | 89.579 | 21.684 | −8.723 | 1.00 | 40.14 | N |
| ATOM | 9022 | C | LYS | B | 34 | 84.193 | 23.833 | −4.872 | 1.00 | 25.98 | C |
| ATOM | 9023 | O | LYS | B | 34 | 84.334 | 25.044 | −5.011 | 1.00 | 26.13 | O |
| ATOM | 9025 | N | ALA | B | 35 | 83.036 | 23.207 | −5.056 | 1.00 | 23.61 | N |
| ATOM | 9026 | CA | ALA | B | 35 | 81.813 | 23.912 | −5.423 | 1.00 | 21.89 | C |
| ATOM | 9028 | CB | ALA | B | 35 | 80.662 | 22.923 | −5.583 | 1.00 | 21.48 | C |
| ATOM | 9032 | C | ALA | B | 35 | 81.467 | 24.962 | −4.374 | 1.00 | 20.57 | C |
| ATOM | 9033 | O | ALA | B | 35 | 81.184 | 26.113 | −4.705 | 1.00 | 20.10 | O |
| ATOM | 9035 | N | LYS | B | 36 | 81.493 | 24.551 | −3.111 | 1.00 | 19.17 | N |
| ATOM | 9036 | CA | LYS | B | 36 | 81.265 | 25.457 | −1.992 | 1.00 | 18.70 | C |
| ATOM | 9038 | CB | LYS | B | 36 | 81.391 | 24.705 | −0.655 | 1.00 | 18.72 | C |
| ATOM | 9041 | CG | LYS | B | 36 | 80.136 | 23.913 | −0.283 | 1.00 | 20.73 | C |
| ATOM | 9044 | CD | LYS | B | 36 | 80.423 | 22.712 | 0.623 | 1.00 | 22.10 | C |
| ATOM | 9047 | CE | LYS | B | 36 | 80.652 | 23.097 | 2.077 | 1.00 | 21.54 | C |
| ATOM | 9050 | NZ | LYS | B | 36 | 81.251 | 21.958 | 2.849 | 1.00 | 20.74 | N |
| ATOM | 9054 | C | LYS | B | 36 | 82.232 | 26.641 | −2.025 | 1.00 | 18.21 | C |
| ATOM | 9055 | O | LYS | B | 36 | 81.818 | 27.794 | −1.835 | 1.00 | 18.06 | O |
| ATOM | 9057 | N | LYS | B | 37 | 83.510 | 26.348 | −2.269 | 1.00 | 17.44 | N |
| ATOM | 9058 | CA | LYS | B | 37 | 84.559 | 27.368 | −2.321 | 1.00 | 17.41 | C |
| ATOM | 9060 | CB | LYS | B | 37 | 85.935 | 26.698 | −2.442 | 1.00 | 18.08 | C |
| ATOM | 9063 | CG | LYS | B | 37 | 87.138 | 27.639 | −2.366 | 1.00 | 22.32 | C |
| ATOM | 9066 | CD | LYS | B | 37 | 88.429 | 26.837 | −2.154 | 1.00 | 29.04 | C |
| ATOM | 9069 | CE | LYS | B | 37 | 89.661 | 27.721 | −1.954 | 1.00 | 30.38 | C |
| ATOM | 9072 | NZ | LYS | B | 37 | 90.117 | 28.346 | −3.226 | 1.00 | 32.86 | N |
| ATOM | 9076 | C | LYS | B | 37 | 84.328 | 28.338 | −3.481 | 1.00 | 15.98 | C |
| ATOM | 9077 | O | LYS | B | 37 | 84.416 | 29.543 | −3.305 | 1.00 | 16.55 | O |
| ATOM | 9079 | N | LEU | B | 38 | 84.014 | 27.808 | −4.659 | 1.00 | 14.47 | N |
| ATOM | 9080 | CA | LEU | B | 38 | 83.742 | 28.643 | −5.831 | 1.00 | 13.74 | C |
| ATOM | 9082 | CB | LEU | B | 38 | 83.618 | 27.780 | −7.093 | 1.00 | 13.39 | C |
| ATOM | 9085 | CG | LEU | B | 38 | 84.842 | 26.938 | −7.477 | 1.00 | 12.68 | C |
| ATOM | 9087 | CD1 | LEU | B | 38 | 84.482 | 25.960 | −8.593 | 1.00 | 8.31 | C |
| ATOM | 9091 | CD2 | LEU | B | 38 | 86.024 | 27.823 | −7.864 | 1.00 | 8.06 | C |
| ATOM | 9095 | C | LEU | B | 38 | 82.472 | 29.480 | −5.641 | 1.00 | 13.46 | C |
| ATOM | 9096 | O | LEU | B | 38 | 82.472 | 30.685 | −5.901 | 1.00 | 12.46 | O |
| ATOM | 9098 | N | GLU | B | 39 | 81.396 | 28.826 | −5.200 | 1.00 | 13.50 | N |
| ATOM | 9099 | CA | GLU | B | 39 | 80.141 | 29.497 | −4.875 | 1.00 | 13.46 | C |
| ATOM | 9101 | CB | GLU | B | 39 | 79.177 | 28.519 | −4.211 | 1.00 | 13.91 | C |
| ATOM | 9104 | CG | GLU | B | 39 | 77.793 | 29.091 | −3.923 | 1.00 | 17.09 | C |
| ATOM | 9107 | CD | GLU | B | 39 | 76.833 | 28.076 | −3.300 | 1.00 | 18.78 | C |
| ATOM | 9108 | OE1 | GLU | B | 39 | 77.304 | 27.126 | −2.631 | 1.00 | 16.35 | O |
| ATOM | 9109 | OE2 | GLU | B | 39 | 75.600 | 28.248 | −3.467 | 1.00 | 18.53 | O |
| ATOM | 9110 | C | GLU | B | 39 | 80.382 | 30.684 | −3.948 | 1.00 | 13.70 | C |
| ATOM | 9111 | O | GLU | B | 39 | 79.900 | 31.789 | −4.208 | 1.00 | 14.66 | O |

APPENDIX 1-continued

| | | | | | | | | | | |
|---|---|---|---|---|---|---|---|---|---|---|
| ATOM | 9113 | N | ALA | B | 40 | 81.138 | 30.453 | −2.878 | 1.00 | 13.12 N |
| ATOM | 9114 | CA | ALA | B | 40 | 81.488 | 31.509 | −1.927 | 1.00 | 12.47 C |
| ATOM | 9116 | CB | ALA | B | 40 | 82.497 | 30.986 | −0.895 | 1.00 | 11.95 C |
| ATOM | 9120 | C | ALA | B | 40 | 82.044 | 32.746 | −2.623 | 1.00 | 11.90 C |
| ATOM | 9121 | O | ALA | B | 40 | 81.578 | 33.862 | −2.389 | 1.00 | 12.67 O |
| ATOM | 9123 | N | GLU | B | 41 | 83.034 | 32.543 | −3.484 | 1.00 | 11.40 N |
| ATOM | 9124 | CA | GLU | B | 41 | 83.698 | 33.650 | −4.167 | 1.00 | 11.33 C |
| ATOM | 9126 | CB | GLU | B | 41 | 84.852 | 33.127 | −5.022 | 1.00 | 12.06 C |
| ATOM | 9129 | CG | GLU | B | 41 | 85.802 | 34.207 | −5.532 | 1.00 | 15.88 C |
| ATOM | 9132 | CD | GLU | B | 41 | 87.145 | 33.650 | −6.011 | 1.00 | 20.21 C |
| ATOM | 9133 | OE1 | GLU | B | 41 | 87.643 | 32.661 | −5.423 | 1.00 | 21.00 O |
| ATOM | 9134 | OE2 | GLU | B | 41 | 87.709 | 34.217 | −6.972 | 1.00 | 22.71 O |
| ATOM | 9135 | C | GLU | B | 41 | 82.720 | 34.460 | −5.018 | 1.00 | 10.64 C |
| ATOM | 9136 | O | GLU | B | 41 | 82.741 | 35.679 | −4.983 | 1.00 | 11.27 O |
| ATOM | 9138 | N | VAL | B | 42 | 81.848 | 33.789 | −5.762 | 1.00 | 10.57 N |
| ATOM | 9139 | CA | VAL | B | 42 | 80.860 | 34.486 | −6.586 | 1.00 | 10.29 C |
| ATOM | 9141 | CB | VAL | B | 42 | 80.024 | 33.519 | −7.442 | 1.00 | 9.81 C |
| ATOM | 9143 | CG1 | VAL | B | 42 | 78.897 | 34.270 | −8.119 | 1.00 | 8.26 C |
| ATOM | 9147 | CG2 | VAL | B | 42 | 80.893 | 32.815 | −8.480 | 1.00 | 6.04 C |
| ATOM | 9151 | C | VAL | B | 42 | 79.921 | 35.320 | −5.718 | 1.00 | 12.18 C |
| ATOM | 9152 | O | VAL | B | 42 | 79.659 | 36.479 | −6.025 | 1.00 | 13.93 O |
| ATOM | 9154 | N | ARG | B | 43 | 79.424 | 34.732 | −4.631 | 1.00 | 13.43 N |
| ATOM | 9155 | CA | ARG | B | 43 | 78.572 | 35.450 | −3.678 | 1.00 | 13.22 C |
| ATOM | 9157 | CB | ARG | B | 43 | 78.221 | 34.555 | −2.485 | 1.00 | 13.74 C |
| ATOM | 9160 | CG | ARG | B | 43 | 77.471 | 35.270 | −1.337 | 1.00 | 16.34 C |
| ATOM | 9163 | CD | ARG | B | 43 | 78.427 | 35.901 | −0.294 | 1.00 | 17.10 C |
| ATOM | 9166 | NE | ARG | B | 43 | 77.708 | 36.654 | 0.734 | 1.00 | 15.55 N |
| ATOM | 9168 | CZ | ARG | B | 43 | 78.258 | 37.538 | 1.566 | 1.00 | 12.32 C |
| ATOM | 9169 | NH1 | ARG | B | 43 | 77.496 | 38.164 | 2.452 | 1.00 | 12.93 N |
| ATOM | 9172 | NH2 | ARG | B | 43 | 79.557 | 37.813 | 1.521 | 1.00 | 15.37 N |
| ATOM | 9175 | C | ARG | B | 43 | 79.252 | 36.723 | −3.188 | 1.00 | 13.14 C |
| ATOM | 9176 | O | ARG | B | 43 | 78.620 | 37.780 | −3.106 | 1.00 | 12.59 O |
| ATOM | 9178 | N | ARG | B | 44 | 80.535 | 36.612 | −2.849 | 1.00 | 13.11 N |
| ATOM | 9179 | CA | ARG | B | 44 | 81.314 | 37.770 | −2.422 | 1.00 | 12.87 C |
| ATOM | 9181 | CB | ARG | B | 44 | 82.766 | 37.385 | −2.142 | 1.00 | 12.31 C |
| ATOM | 9184 | CG | ARG | B | 44 | 83.574 | 38.495 | −1.490 | 1.00 | 12.75 C |
| ATOM | 9187 | CD | ARG | B | 44 | 85.021 | 38.097 | −1.274 | 1.00 | 11.37 C |
| ATOM | 9190 | NE | ARG | B | 44 | 85.677 | 37.787 | −2.537 | 1.00 | 11.31 N |
| ATOM | 9192 | CZ | ARG | B | 44 | 86.840 | 37.155 | −2.662 | 1.00 | 12.26 C |
| ATOM | 9193 | NH1 | ARG | B | 44 | 87.519 | 36.743 | −1.596 | 1.00 | 13.75 N |
| ATOM | 9196 | NH2 | ARG | B | 44 | 87.324 | 36.929 | −3.875 | 1.00 | 12.62 N |
| ATOM | 9199 | C | ARG | B | 44 | 81.282 | 38.861 | −3.484 | 1.00 | 13.22 C |
| ATOM | 9200 | O | ARG | B | 44 | 81.045 | 40.029 | −3.175 | 1.00 | 13.74 O |
| ATOM | 9202 | N | GLU | B | 45 | 81.515 | 38.477 | −4.735 | 1.00 | 13.28 N |
| ATOM | 9203 | CA | GLU | B | 45 | 81.644 | 39.452 | −5.811 | 1.00 | 12.72 C |
| ATOM | 9205 | CB | GLU | B | 45 | 82.265 | 38.817 | −7.055 | 1.00 | 13.40 C |
| ATOM | 9208 | CG | GLU | B | 45 | 83.717 | 38.364 | −6.861 | 1.00 | 14.06 C |
| ATOM | 9211 | CD | GLU | B | 45 | 84.634 | 39.491 | −6.420 | 1.00 | 16.74 C |
| ATOM | 9212 | OE1 | GLU | B | 45 | 84.613 | 40.557 | −7.075 | 1.00 | 21.90 O |
| ATOM | 9213 | OE2 | GLU | B | 45 | 85.370 | 39.314 | −5.420 | 1.00 | 13.76 O |
| ATOM | 9214 | C | GLU | B | 45 | 80.306 | 40.093 | −6.125 | 1.00 | 12.58 C |
| ATOM | 9215 | O | GLU | B | 45 | 80.244 | 41.283 | −6.397 | 1.00 | 12.39 O |
| ATOM | 9217 | N | ILE | B | 46 | 79.229 | 39.319 | −6.052 | 1.00 | 13.42 N |
| ATOM | 9218 | CA | ILE | B | 46 | 77.893 | 39.878 | −6.242 | 1.00 | 13.38 C |
| ATOM | 9220 | CB | ILE | B | 46 | 76.803 | 38.779 | −6.316 | 1.00 | 14.14 C |
| ATOM | 9222 | CG1 | ILE | B | 46 | 77.038 | 37.858 | −7.521 | 1.00 | 13.45 C |
| ATOM | 9225 | CD1 | ILE | B | 46 | 76.166 | 36.623 | −7.527 | 1.00 | 9.11 C |
| ATOM | 9229 | CG2 | ILE | B | 46 | 75.408 | 39.405 | −6.412 | 1.00 | 10.01 C |
| ATOM | 9233 | C | ILE | B | 46 | 77.571 | 40.879 | −5.124 | 1.00 | 13.50 C |
| ATOM | 9234 | O | ILE | B | 46 | 76.929 | 41.896 | −5.374 | 1.00 | 15.08 O |
| ATOM | 9236 | N | ASN | B | 47 | 78.041 | 40.602 | −3.905 | 1.00 | 12.99 N |
| ATOM | 9237 | CA | ASN | B | 47 | 77.787 | 41.477 | −2.750 | 1.00 | 12.52 C |
| ATOM | 9239 | CB | ASN | B | 47 | 77.773 | 40.663 | −1.454 | 1.00 | 12.54 C |
| ATOM | 9242 | CG | ASN | B | 47 | 76.471 | 39.917 | −1.249 | 1.00 | 12.61 C |
| ATOM | 9243 | OD1 | ASN | B | 47 | 75.498 | 40.478 | −0.755 | 1.00 | 15.74 O |
| ATOM | 9244 | ND2 | ASN | B | 47 | 76.452 | 38.645 | −1.620 | 1.00 | 7.01 N |
| ATOM | 9247 | C | ASN | B | 47 | 78.763 | 42.647 | −2.612 | 1.00 | 12.79 C |
| ATOM | 9248 | O | ASN | B | 47 | 78.590 | 43.503 | −1.745 | 1.00 | 13.08 O |
| ATOM | 9250 | N | ASN | B | 48 | 79.776 | 42.692 | −3.471 | 1.00 | 13.46 N |
| ATOM | 9251 | CA | ASN | B | 48 | 80.757 | 43.776 | −3.465 | 1.00 | 13.69 C |
| ATOM | 9253 | CB | ASN | B | 48 | 81.633 | 43.689 | −4.724 | 1.00 | 13.85 C |
| ATOM | 9256 | CG | ASN | B | 48 | 82.776 | 44.691 | −4.724 | 1.00 | 12.53 C |
| ATOM | 9257 | OD1 | ASN | B | 48 | 83.054 | 45.347 | −3.723 | 1.00 | 10.59 O |
| ATOM | 9258 | ND2 | ASN | B | 48 | 83.439 | 44.814 | −5.861 | 1.00 | 8.19 N |
| ATOM | 9261 | C | ASN | B | 48 | 80.087 | 45.143 | −3.386 | 1.00 | 13.86 C |
| ATOM | 9262 | O | ASN | B | 48 | 79.442 | 45.573 | −4.326 | 1.00 | 14.56 O |
| ATOM | 9264 | N | GLU | B | 49 | 80.256 | 45.822 | −2.261 | 1.00 | 15.14 N |
| ATOM | 9265 | CA | GLU | B | 49 | 79.594 | 47.101 | −2.025 | 1.00 | 16.03 C |
| ATOM | 9267 | CB | GLU | B | 49 | 79.592 | 47.438 | −0.529 | 1.00 | 16.78 C |
| ATOM | 9270 | CG | GLU | B | 49 | 78.891 | 46.411 | 0.361 | 1.00 | 16.28 C |

APPENDIX 1-continued

| | | | | | | | | | | |
|---|---|---|---|---|---|---|---|---|---|---|
| ATOM | 9273 | CD | GLU | B | 49 | 79.834 | 45.362 | 0.949 | 1.00 | 20.23 | C |
| ATOM | 9274 | OE1 | GLU | B | 49 | 80.995 | 45.249 | 0.486 | 1.00 | 17.56 | O |
| ATOM | 9275 | OE2 | GLU | B | 49 | 79.403 | 44.645 | 1.883 | 1.00 | 19.62 | O |
| ATOM | 9276 | C | GLU | B | 49 | 80.211 | 48.271 | −2.800 | 1.00 | 16.41 | C |
| ATOM | 9277 | O | GLU | B | 49 | 79.580 | 49.312 | −2.921 | 1.00 | 16.61 | O |
| ATOM | 9279 | N | LYS | B | 50 | 81.439 | 48.109 | −3.294 | 1.00 | 16.71 | N |
| ATOM | 9280 | CA | LYS | B | 50 | 82.107 | 49.140 | −4.097 | 1.00 | 17.09 | C |
| ATOM | 9282 | CB | LYS | B | 50 | 83.452 | 49.554 | −3.466 | 1.00 | 17.11 | C |
| ATOM | 9285 | CG | LYS | B | 50 | 83.335 | 50.329 | −2.157 | 1.00 | 19.17 | C |
| ATOM | 9288 | CD | LYS | B | 50 | 84.590 | 51.151 | −1.875 | 1.00 | 21.81 | C |
| ATOM | 9291 | CE | LYS | B | 50 | 84.498 | 51.902 | −0.555 | 1.00 | 23.59 | C |
| ATOM | 9294 | NZ | LYS | B | 50 | 84.350 | 50.998 | 0.615 | 1.00 | 21.79 | N |
| ATOM | 9298 | C | LYS | B | 50 | 82.338 | 48.649 | −5.523 | 1.00 | 16.99 | C |
| ATOM | 9299 | O | LYS | B | 50 | 83.294 | 49.060 | −6.185 | 1.00 | 17.71 | O |
| ATOM | 9301 | N | ALA | B | 51 | 81.461 | 47.776 | −5.998 | 1.00 | 17.34 | N |
| ATOM | 9302 | CA | ALA | B | 51 | 81.572 | 47.244 | −7.353 | 1.00 | 18.17 | C |
| ATOM | 9304 | CB | ALA | B | 51 | 80.598 | 46.077 | −7.558 | 1.00 | 16.96 | C |
| ATOM | 9308 | C | ALA | B | 51 | 81.297 | 48.341 | −8.372 | 1.00 | 18.69 | C |
| ATOM | 9309 | O | ALA | B | 51 | 80.430 | 49.191 | −8.162 | 1.00 | 17.88 | O |
| ATOM | 9311 | N | GLU | B | 52 | 82.041 | 48.317 | −9.472 | 1.00 | 20.08 | N |
| ATOM | 9312 | CA | GLU | B | 52 | 81.792 | 49.231 | −10.581 | 1.00 | 21.52 | C |
| ATOM | 9314 | CB | GLU | B | 52 | 82.901 | 49.118 | −11.635 | 1.00 | 22.96 | C |
| ATOM | 9317 | CG | GLU | B | 52 | 83.356 | 50.463 | −12.221 | 1.00 | 30.88 | C |
| ATOM | 9320 | CD | GLU | B | 52 | 84.392 | 51.200 | −11.358 | 1.00 | 38.65 | C |
| ATOM | 9321 | OE1 | GLU | B | 52 | 84.620 | 50.803 | −10.192 | 1.00 | 40.61 | O |
| ATOM | 9322 | OE2 | GLU | B | 52 | 84.979 | 52.190 | −11.854 | 1.00 | 43.64 | O |
| ATOM | 9323 | C | GLU | B | 52 | 80.425 | 48.879 | −11.175 | 1.00 | 20.30 | C |
| ATOM | 9324 | O | GLU | B | 52 | 80.070 | 47.708 | −11.258 | 1.00 | 19.47 | O |
| ATOM | 9326 | N | PHE | B | 53 | 79.658 | 49.887 | −11.578 | 1.00 | 20.29 | N |
| ATOM | 9327 | CA | PHE | B | 53 | 78.264 | 49.668 | −11.986 | 1.00 | 20.32 | C |
| ATOM | 9329 | CB | PHE | B | 53 | 77.560 | 50.990 | −12.310 | 1.00 | 20.20 | C |
| ATOM | 9332 | CG | PHE | B | 53 | 77.380 | 51.903 | −11.124 | 1.00 | 21.60 | C |
| ATOM | 9333 | CD1 | PHE | B | 53 | 77.052 | 51.401 | −9.868 | 1.00 | 20.90 | C |
| ATOM | 9335 | CE1 | PHE | B | 53 | 76.885 | 52.254 | −8.782 | 1.00 | 21.56 | C |
| ATOM | 9337 | CZ | PHE | B | 53 | 77.024 | 53.617 | −8.948 | 1.00 | 22.59 | C |
| ATOM | 9339 | CE2 | PHE | B | 53 | 77.342 | 54.131 | −10.197 | 1.00 | 21.70 | C |
| ATOM | 9341 | CD2 | PHE | B | 53 | 77.513 | 53.278 | −11.276 | 1.00 | 21.01 | C |
| ATOM | 9343 | C | PHE | B | 53 | 78.117 | 48.723 | −13.174 | 1.00 | 20.26 | C |
| ATOM | 9344 | O | PHE | B | 53 | 77.372 | 47.749 | −13.103 | 1.00 | 21.14 | O |
| ATOM | 9346 | N | LEU | B | 54 | 78.820 | 49.011 | −14.260 | 1.00 | 20.40 | N |
| ATOM | 9347 | CA | LEU | B | 54 | 78.700 | 48.208 | −15.472 | 1.00 | 20.90 | C |
| ATOM | 9349 | CB | LEU | B | 54 | 79.411 | 48.894 | −16.647 | 1.00 | 21.53 | C |
| ATOM | 9352 | CG | LEU | B | 54 | 78.824 | 50.246 | −17.072 | 1.00 | 24.00 | C |
| ATOM | 9354 | CD1 | LEU | B | 54 | 79.749 | 50.975 | −18.050 | 1.00 | 26.24 | C |
| ATOM | 9358 | CD2 | LEU | B | 54 | 77.438 | 50.069 | −17.673 | 1.00 | 21.58 | C |
| ATOM | 9362 | C | LEU | B | 54 | 79.243 | 46.793 | −15.251 | 1.00 | 20.35 | C |
| ATOM | 9363 | O | LEU | B | 54 | 78.685 | 45.818 | −15.763 | 1.00 | 21.81 | O |
| ATOM | 9365 | N | THR | B | 55 | 80.313 | 46.682 | −14.472 | 1.00 | 18.78 | N |
| ATOM | 9366 | CA | THR | B | 55 | 80.917 | 45.383 | −14.179 | 1.00 | 18.03 | C |
| ATOM | 9368 | CB | THR | B | 55 | 82.299 | 45.559 | −13.520 | 1.00 | 17.23 | C |
| ATOM | 9370 | OG1 | THR | B | 55 | 83.121 | 46.326 | −14.399 | 1.00 | 18.09 | O |
| ATOM | 9372 | CG2 | THR | B | 55 | 82.963 | 44.218 | −13.259 | 1.00 | 15.26 | C |
| ATOM | 9376 | C | THR | B | 55 | 80.013 | 44.502 | −13.308 | 1.00 | 16.91 | C |
| ATOM | 9377 | O | THR | B | 55 | 79.960 | 43.291 | −13.505 | 1.00 | 16.12 | O |
| ATOM | 9379 | N | LEU | B | 56 | 79.308 | 45.113 | −12.361 | 1.00 | 15.75 | N |
| ATOM | 9380 | CA | LEU | B | 56 | 78.365 | 44.388 | −11.515 | 1.00 | 15.83 | C |
| ATOM | 9382 | CB | LEU | B | 56 | 77.834 | 45.299 | −10.403 | 1.00 | 16.00 | C |
| ATOM | 9385 | CG | LEU | B | 56 | 76.761 | 44.754 | −9.451 | 1.00 | 16.57 | C |
| ATOM | 9387 | CD1 | LEU | B | 56 | 77.269 | 43.576 | −8.630 | 1.00 | 11.81 | C |
| ATOM | 9391 | CD2 | LEU | B | 56 | 76.265 | 45.875 | −8.546 | 1.00 | 16.49 | C |
| ATOM | 9395 | C | LEU | B | 56 | 77.206 | 43.838 | −12.348 | 1.00 | 16.22 | C |
| ATOM | 9396 | O | LEU | B | 56 | 76.833 | 42.674 | −12.206 | 1.00 | 15.75 | O |
| ATOM | 9398 | N | LEU | B | 57 | 76.640 | 44.679 | −13.214 | 1.00 | 16.11 | N |
| ATOM | 9399 | CA | LEU | B | 57 | 75.524 | 44.263 | −14.060 | 1.00 | 15.93 | C |
| ATOM | 9401 | CB | LEU | B | 57 | 74.981 | 45.429 | −14.892 | 1.00 | 15.36 | C |
| ATOM | 9404 | CG | LEU | B | 57 | 74.372 | 46.615 | −14.132 | 1.00 | 14.37 | C |
| ATOM | 9406 | CD1 | LEU | B | 57 | 74.113 | 47.771 | −15.081 | 1.00 | 11.63 | C |
| ATOM | 9410 | CD2 | LEU | B | 57 | 73.100 | 46.241 | −13.394 | 1.00 | 6.32 | C |
| ATOM | 9414 | C | LEU | B | 57 | 75.960 | 43.132 | −14.981 | 1.00 | 17.19 | C |
| ATOM | 9415 | O | LEU | B | 57 | 75.233 | 42.155 | −15.154 | 1.00 | 17.60 | O |
| ATOM | 9417 | N | GLU | B | 58 | 77.150 | 43.257 | −15.566 | 1.00 | 18.01 | N |
| ATOM | 9418 | CA | GLU | B | 58 | 77.672 | 42.200 | −16.440 | 1.00 | 18.65 | C |
| ATOM | 9420 | CB | GLU | B | 58 | 78.968 | 42.632 | −17.135 | 1.00 | 18.84 | C |
| ATOM | 9423 | CG | GLU | B | 58 | 78.753 | 43.535 | −18.344 | 1.00 | 24.47 | C |
| ATOM | 9426 | CD | GLU | B | 58 | 80.058 | 44.038 | −18.945 | 1.00 | 30.72 | C |
| ATOM | 9427 | OE1 | GLU | B | 58 | 81.133 | 43.532 | −18.554 | 1.00 | 36.44 | O |
| ATOM | 9428 | OE2 | GLU | B | 58 | 80.007 | 44.940 | −19.811 | 1.00 | 35.35 | O |
| ATOM | 9429 | C | GLU | B | 58 | 77.899 | 40.911 | −15.656 | 1.00 | 17.82 | C |
| ATOM | 9430 | O | GLU | B | 58 | 77.599 | 39.818 | −16.146 | 1.00 | 18.63 | O |
| ATOM | 9432 | N | LEU | B | 59 | 78.429 | 41.043 | −14.443 | 1.00 | 16.80 | N |

APPENDIX 1-continued

| | | | | | | | | | | |
|---|---|---|---|---|---|---|---|---|---|---|
| ATOM | 9433 | CA | LEU | B | 59 | 78.659 | 39.888 | −13.589 | 1.00 | 16.40 | C |
| ATOM | 9435 | CB | LEU | B | 59 | 79.329 | 40.290 | −12.264 | 1.00 | 16.00 | C |
| ATOM | 9438 | CG | LEU | B | 59 | 79.346 | 39.240 | −11.145 | 1.00 | 15.18 | C |
| ATOM | 9440 | CD1 | LEU | B | 59 | 79.890 | 37.921 | −11.659 | 1.00 | 10.29 | C |
| ATOM | 9444 | CD2 | LEU | B | 59 | 80.146 | 39.728 | −9.950 | 1.00 | 10.60 | C |
| ATOM | 9448 | C | LEU | B | 59 | 77.327 | 39.189 | −13.341 | 1.00 | 15.64 | C |
| ATOM | 9449 | O | LEU | B | 59 | 77.215 | 37.975 | −13.532 | 1.00 | 16.67 | O |
| ATOM | 9451 | N | ILE | B | 60 | 76.318 | 39.962 | −12.954 | 1.00 | 13.99 | N |
| ATOM | 9452 | CA | ILE | B | 60 | 75.012 | 39.403 | −12.666 | 1.00 | 13.53 | C |
| ATOM | 9454 | CB | ILE | B | 60 | 74.025 | 40.468 | −12.146 | 1.00 | 13.60 | C |
| ATOM | 9456 | CG1 | ILE | B | 60 | 74.458 | 40.979 | −10.765 | 1.00 | 12.49 | C |
| ATOM | 9459 | CD1 | ILE | B | 60 | 73.702 | 42.213 | −10.308 | 1.00 | 12.82 | C |
| ATOM | 9463 | CG2 | ILE | B | 60 | 72.632 | 39.889 | −12.024 | 1.00 | 10.70 | C |
| ATOM | 9467 | C | ILE | B | 60 | 74.450 | 38.712 | −13.903 | 1.00 | 13.93 | C |
| ATOM | 9468 | O | ILE | B | 60 | 73.940 | 37.595 | −13.816 | 1.00 | 14.15 | O |
| ATOM | 9470 | N | ASP | B | 61 | 74.569 | 39.363 | −15.055 | 1.00 | 14.81 | N |
| ATOM | 9471 | CA | ASP | B | 61 | 74.071 | 38.801 | −16.315 | 1.00 | 14.75 | C |
| ATOM | 9473 | CB | ASP | B | 61 | 74.324 | 39.772 | −17.482 | 1.00 | 14.89 | C |
| ATOM | 9476 | CG | ASP | B | 61 | 73.563 | 39.394 | −18.753 | 1.00 | 15.23 | C |
| ATOM | 9477 | OD1 | ASP | B | 61 | 72.482 | 38.777 | −18.663 | 1.00 | 18.70 | O |
| ATOM | 9478 | OD2 | ASP | B | 61 | 74.040 | 39.734 | −19.852 | 1.00 | 18.00 | O |
| ATOM | 9479 | C | ASP | B | 61 | 74.736 | 37.457 | −16.602 | 1.00 | 14.52 | C |
| ATOM | 9480 | O | ASP | B | 61 | 74.064 | 36.490 | −16.959 | 1.00 | 13.91 | O |
| ATOM | 9482 | N | ASN | B | 62 | 76.054 | 37.401 | −16.437 | 1.00 | 14.06 | N |
| ATOM | 9483 | CA | ASN | B | 62 | 76.791 | 36.178 | −16.711 | 1.00 | 14.95 | C |
| ATOM | 9485 | CB | ASN | B | 62 | 78.295 | 36.429 | −16.626 | 1.00 | 15.37 | C |
| ATOM | 9488 | CG | ASN | B | 62 | 78.816 | 37.190 | −17.821 | 1.00 | 16.57 | C |
| ATOM | 9489 | OD1 | ASN | B | 62 | 78.345 | 36.994 | −18.949 | 1.00 | 14.84 | O |
| ATOM | 9490 | ND2 | ASN | B | 62 | 79.791 | 38.068 | −17.587 | 1.00 | 15.38 | N |
| ATOM | 9493 | C | ASN | B | 62 | 76.389 | 35.053 | −15.771 | 1.00 | 15.15 | C |
| ATOM | 9494 | O | ASN | B | 62 | 76.118 | 33.932 | −16.214 | 1.00 | 15.85 | O |
| ATOM | 9496 | N | VAL | B | 63 | 76.336 | 35.360 | −14.477 | 1.00 | 14.69 | N |
| ATOM | 9497 | CA | VAL | B | 63 | 75.876 | 34.394 | −13.487 | 1.00 | 13.71 | C |
| ATOM | 9499 | CB | VAL | B | 63 | 75.739 | 35.019 | −12.077 | 1.00 | 14.21 | C |
| ATOM | 9501 | CG1 | VAL | B | 63 | 74.972 | 34.071 | −11.116 | 1.00 | 11.92 | C |
| ATOM | 9505 | CG2 | VAL | B | 63 | 77.099 | 35.365 | −11.525 | 1.00 | 9.30 | C |
| ATOM | 9509 | C | VAL | B | 63 | 74.552 | 33.794 | −13.920 | 1.00 | 12.66 | C |
| ATOM | 9510 | O | VAL | B | 63 | 74.412 | 32.582 | −13.930 | 1.00 | 12.79 | O |
| ATOM | 9512 | N | GLN | B | 64 | 73.600 | 34.641 | −14.305 | 1.00 | 13.68 | N |
| ATOM | 9513 | CA | GLN | B | 64 | 72.258 | 34.177 | −14.709 | 1.00 | 14.66 | C |
| ATOM | 9515 | CB | GLN | B | 64 | 71.266 | 35.352 | −14.830 | 1.00 | 13.97 | C |
| ATOM | 9518 | CG | GLN | B | 64 | 70.994 | 36.047 | −13.495 | 1.00 | 13.24 | C |
| ATOM | 9521 | CD | GLN | B | 64 | 69.708 | 36.856 | −13.454 | 1.00 | 13.96 | C |
| ATOM | 9522 | OE1 | GLN | B | 64 | 69.040 | 36.911 | −12.421 | 1.00 | 18.65 | O |
| ATOM | 9523 | NE2 | GLN | B | 64 | 69.362 | 37.493 | −14.562 | 1.00 | 11.65 | N |
| ATOM | 9526 | C | GLN | B | 64 | 72.292 | 33.361 | −16.003 | 1.00 | 15.39 | C |
| ATOM | 9527 | O | GLN | B | 64 | 71.722 | 32.266 | −16.067 | 1.00 | 14.79 | O |
| ATOM | 9529 | N | ARG | B | 65 | 72.974 | 33.881 | −17.020 | 1.00 | 16.01 | N |
| ATOM | 9530 | CA | ARG | B | 65 | 73.067 | 33.186 | −18.302 | 1.00 | 16.84 | C |
| ATOM | 9532 | CB | ARG | B | 65 | 73.740 | 34.059 | −19.360 | 1.00 | 17.41 | C |
| ATOM | 9535 | CG | ARG | B | 65 | 72.895 | 35.256 | −19.778 | 1.00 | 18.72 | C |
| ATOM | 9538 | CD | ARG | B | 65 | 73.497 | 35.987 | −20.947 | 1.00 | 19.71 | C |
| ATOM | 9541 | NE | ARG | B | 65 | 73.369 | 35.221 | −22.182 | 1.00 | 26.28 | N |
| ATOM | 9543 | CZ | ARG | B | 65 | 73.811 | 35.622 | −23.374 | 1.00 | 30.59 | C |
| ATOM | 9544 | NH1 | ARG | B | 65 | 74.421 | 36.799 | −23.511 | 1.00 | 27.82 | N |
| ATOM | 9547 | NH2 | ARG | B | 65 | 73.642 | 34.838 | −24.436 | 1.00 | 32.71 | N |
| ATOM | 9550 | C | ARG | B | 65 | 73.782 | 31.842 | −18.191 | 1.00 | 17.09 | C |
| ATOM | 9551 | O | ARG | B | 65 | 73.387 | 30.874 | −18.855 | 1.00 | 17.32 | O |
| ATOM | 9553 | N | LEU | B | 66 | 74.809 | 31.770 | −17.341 | 1.00 | 15.97 | N |
| ATOM | 9554 | CA | LEU | B | 66 | 75.549 | 30.517 | −17.153 | 1.00 | 15.00 | C |
| ATOM | 9556 | CB | LEU | B | 66 | 76.893 | 30.772 | −16.453 | 1.00 | 14.70 | C |
| ATOM | 9559 | CG | LEU | B | 66 | 77.952 | 31.521 | −17.283 | 1.00 | 12.62 | C |
| ATOM | 9561 | CD1 | LEU | B | 66 | 79.057 | 32.081 | −16.391 | 1.00 | 8.94 | C |
| ATOM | 9565 | CD2 | LEU | B | 66 | 78.533 | 30.634 | −18.366 | 1.00 | 7.32 | C |
| ATOM | 9569 | C | LEU | B | 66 | 74.731 | 29.449 | −16.406 | 1.00 | 14.71 | C |
| ATOM | 9570 | O | LEU | B | 66 | 75.162 | 28.306 | −16.288 | 1.00 | 14.62 | O |
| ATOM | 9572 | N | GLY | B | 67 | 73.557 | 29.820 | −15.903 | 1.00 | 14.95 | N |
| ATOM | 9573 | CA | GLY | B | 67 | 72.635 | 28.853 | −15.300 | 1.00 | 15.26 | C |
| ATOM | 9576 | C | GLY | B | 67 | 72.611 | 28.867 | −13.785 | 1.00 | 15.44 | C |
| ATOM | 9577 | O | GLY | B | 67 | 71.950 | 28.028 | −13.176 | 1.00 | 16.14 | O |
| ATOM | 9579 | N | LEU | B | 68 | 73.304 | 29.831 | −13.178 | 1.00 | 14.71 | N |
| ATOM | 9580 | CA | LEU | B | 68 | 73.492 | 29.869 | −11.725 | 1.00 | 14.50 | C |
| ATOM | 9582 | CB | LEU | B | 68 | 74.936 | 30.262 | −11.394 | 1.00 | 14.16 | C |
| ATOM | 9585 | CG | LEU | B | 68 | 76.016 | 29.288 | −11.860 | 1.00 | 13.08 | C |
| ATOM | 9587 | CD1 | LEU | B | 68 | 77.371 | 29.948 | −11.787 | 1.00 | 8.19 | C |
| ATOM | 9591 | CD2 | LEU | B | 68 | 75.976 | 28.020 | −11.013 | 1.00 | 11.07 | C |
| ATOM | 9595 | C | LEU | B | 68 | 72.552 | 30.838 | −11.016 | 1.00 | 14.81 | C |
| ATOM | 9596 | O | LEU | B | 68 | 72.589 | 30.943 | −9.797 | 1.00 | 15.06 | O |
| ATOM | 9598 | N | GLY | B | 69 | 71.715 | 31.544 | −11.768 | 1.00 | 15.08 | N |
| ATOM | 9599 | CA | GLY | B | 69 | 70.816 | 32.539 | −11.191 | 1.00 | 14.97 | C |

APPENDIX 1-continued

| ATOM | 9602 | C | GLY | B | 69 | 70.007 | 32.042 | −10.006 | 1.00 | 14.72 | C |
|---|---|---|---|---|---|---|---|---|---|---|---|
| ATOM | 9603 | O | GLY | B | 69 | 69.908 | 32.729 | −8.998 | 1.00 | 15.67 | O |
| ATOM | 9605 | N | TYR | B | 70 | 69.437 | 30.847 | −10.122 | 1.00 | 15.09 | N |
| ATOM | 9606 | CA | TYR | B | 70 | 68.586 | 30.273 | −9.065 | 1.00 | 15.84 | C |
| ATOM | 9608 | CB | TYR | B | 70 | 68.073 | 28.886 | −9.481 | 1.00 | 15.07 | C |
| ATOM | 9611 | CG | TYR | B | 70 | 69.095 | 27.776 | −9.344 | 1.00 | 13.28 | C |
| ATOM | 9612 | CD1 | TYR | B | 70 | 70.078 | 27.583 | −10.309 | 1.00 | 10.92 | C |
| ATOM | 9614 | CE1 | TYR | B | 70 | 71.020 | 26.571 | −10.183 | 1.00 | 12.66 | C |
| ATOM | 9616 | CZ | TYR | B | 70 | 70.982 | 25.740 | −9.077 | 1.00 | 15.33 | C |
| ATOM | 9617 | OH | TYR | B | 70 | 71.909 | 24.740 | −8.929 | 1.00 | 13.26 | O |
| ATOM | 9619 | CE2 | TYR | B | 70 | 70.014 | 25.916 | −8.106 | 1.00 | 12.99 | C |
| ATOM | 9621 | CD2 | TYR | B | 70 | 69.084 | 26.928 | −8.241 | 1.00 | 11.29 | C |
| ATOM | 9623 | C | TYR | B | 70 | 69.302 | 30.154 | −7.723 | 1.00 | 17.70 | C |
| ATOM | 9624 | O | TYR | B | 70 | 68.670 | 30.085 | −6.678 | 1.00 | 21.15 | O |
| ATOM | 9626 | N | ARG | B | 71 | 70.624 | 30.126 | −7.768 | 1.00 | 17.91 | N |
| ATOM | 9627 | CA | ARG | B | 71 | 71.448 | 29.851 | −6.609 | 1.00 | 18.30 | C |
| ATOM | 9629 | CB | ARG | B | 71 | 72.646 | 29.024 | −7.083 | 1.00 | 18.32 | C |
| ATOM | 9632 | CG | ARG | B | 71 | 73.780 | 28.859 | −6.108 | 1.00 | 20.58 | C |
| ATOM | 9635 | CD | ARG | B | 71 | 74.748 | 27.803 | −6.612 | 1.00 | 20.77 | C |
| ATOM | 9638 | NE | ARG | B | 71 | 74.081 | 26.514 | −6.729 | 1.00 | 22.51 | N |
| ATOM | 9640 | CZ | ARG | B | 71 | 73.903 | 25.655 | −5.731 | 1.00 | 23.11 | C |
| ATOM | 9641 | NH1 | ARG | B | 71 | 74.350 | 25.911 | −4.514 | 1.00 | 25.15 | N |
| ATOM | 9644 | NH2 | ARG | B | 71 | 73.264 | 24.521 | −5.956 | 1.00 | 26.65 | N |
| ATOM | 9647 | C | ARG | B | 71 | 71.898 | 31.131 | −5.891 | 1.00 | 18.75 | C |
| ATOM | 9648 | O | ARG | B | 71 | 72.317 | 31.075 | −4.730 | 1.00 | 18.06 | O |
| ATOM | 9650 | N | PHE | B | 72 | 71.805 | 32.273 | −6.578 | 1.00 | 19.13 | N |
| ATOM | 9651 | CA | PHE | B | 72 | 72.245 | 33.561 | −6.035 | 1.00 | 18.99 | C |
| ATOM | 9653 | CB | PHE | B | 72 | 73.466 | 34.067 | −6.802 | 1.00 | 19.20 | C |
| ATOM | 9656 | CG | PHE | B | 72 | 74.665 | 33.186 | −6.678 | 1.00 | 17.20 | C |
| ATOM | 9657 | CD1 | PHE | B | 72 | 75.477 | 33.264 | −5.567 | 1.00 | 13.20 | C |
| ATOM | 9659 | CE1 | PHE | B | 72 | 76.592 | 32.453 | −5.452 | 1.00 | 17.06 | C |
| ATOM | 9661 | CZ | PHE | B | 72 | 76.903 | 31.559 | −6.461 | 1.00 | 16.63 | C |
| ATOM | 9663 | CE2 | PHE | B | 72 | 76.103 | 31.483 | −7.575 | 1.00 | 16.38 | C |
| ATOM | 9665 | CD2 | PHE | B | 72 | 74.991 | 32.293 | −7.682 | 1.00 | 16.36 | C |
| ATOM | 9667 | C | PHE | B | 72 | 71.156 | 34.618 | −6.123 | 1.00 | 19.06 | C |
| ATOM | 9668 | O | PHE | B | 72 | 71.445 | 35.800 | −6.280 | 1.00 | 17.60 | O |
| ATOM | 9670 | N | GLU | B | 73 | 69.904 | 34.204 | −5.995 | 1.00 | 20.54 | N |
| ATOM | 9671 | CA | GLU | B | 73 | 68.804 | 35.097 | −6.302 | 1.00 | 22.01 | C |
| ATOM | 9673 | CB | GLU | B | 73 | 67.486 | 34.340 | −6.386 | 1.00 | 22.80 | C |
| ATOM | 9676 | CG | GLU | B | 73 | 66.339 | 35.221 | −6.820 | 1.00 | 28.79 | C |
| ATOM | 9679 | CD | GLU | B | 73 | 65.066 | 34.454 | −7.040 | 1.00 | 35.71 | C |
| ATOM | 9680 | OE1 | GLU | B | 73 | 65.099 | 33.444 | −7.775 | 1.00 | 41.78 | O |
| ATOM | 9681 | OE2 | GLU | B | 73 | 64.029 | 34.877 | −6.491 | 1.00 | 40.65 | O |
| ATOM | 9682 | C | GLU | B | 73 | 68.688 | 36.247 | −5.314 | 1.00 | 22.08 | C |
| ATOM | 9683 | O | GLU | B | 73 | 68.551 | 37.400 | −5.730 | 1.00 | 22.85 | O |
| ATOM | 9685 | N | SER | B | 74 | 68.731 | 35.953 | −4.017 | 1.00 | 21.68 | N |
| ATOM | 9686 | CA | SER | B | 74 | 68.605 | 37.021 | −3.013 | 1.00 | 21.91 | C |
| ATOM | 9688 | CB | SER | B | 74 | 68.324 | 36.455 | −1.623 | 1.00 | 21.64 | C |
| ATOM | 9691 | OG | SER | B | 74 | 69.005 | 35.236 | −1.449 | 1.00 | 28.40 | O |
| ATOM | 9693 | C | SER | B | 74 | 69.839 | 37.924 | −3.003 | 1.00 | 20.34 | C |
| ATOM | 9694 | O | SER | B | 74 | 69.740 | 39.116 | −2.725 | 1.00 | 20.35 | O |
| ATOM | 9696 | N | ASP | B | 75 | 70.995 | 37.353 | −3.317 | 1.00 | 19.90 | N |
| ATOM | 9697 | CA | ASP | B | 75 | 72.215 | 38.134 | −3.510 | 1.00 | 18.61 | C |
| ATOM | 9699 | CB | ASP | B | 75 | 73.408 | 37.202 | −3.761 | 1.00 | 18.73 | C |
| ATOM | 9702 | CG | ASP | B | 75 | 73.823 | 36.415 | −2.516 | 1.00 | 20.70 | C |
| ATOM | 9703 | OD1 | ASP | B | 75 | 73.848 | 37.000 | −1.410 | 1.00 | 20.76 | O |
| ATOM | 9704 | OD2 | ASP | B | 75 | 74.141 | 35.210 | −2.647 | 1.00 | 25.11 | O |
| ATOM | 9705 | C | ASP | B | 75 | 72.050 | 39.108 | −4.679 | 1.00 | 17.25 | C |
| ATOM | 9706 | O | ASP | B | 75 | 72.412 | 40.278 | −4.586 | 1.00 | 15.83 | O |
| ATOM | 9708 | N | ILE | B | 76 | 71.483 | 38.621 | −5.777 | 1.00 | 17.11 | N |
| ATOM | 9709 | CA | ILE | B | 76 | 71.293 | 39.443 | −6.966 | 1.00 | 16.05 | C |
| ATOM | 9711 | CB | ILE | B | 76 | 70.902 | 38.583 | −8.195 | 1.00 | 16.10 | C |
| ATOM | 9713 | CG1 | ILE | B | 76 | 72.111 | 37.768 | −8.665 | 1.00 | 15.10 | C |
| ATOM | 9716 | CD1 | ILE | B | 76 | 71.744 | 36.506 | −9.406 | 1.00 | 11.65 | C |
| ATOM | 9720 | CG2 | ILE | B | 76 | 70.375 | 39.455 | −9.344 | 1.00 | 12.09 | C |
| ATOM | 9724 | C | ILE | B | 76 | 70.265 | 40.543 | −6.710 | 1.00 | 16.87 | C |
| ATOM | 9725 | O | ILE | B | 76 | 70.449 | 41.672 | −7.163 | 1.00 | 18.28 | O |
| ATOM | 9727 | N | ARG | B | 77 | 69.198 | 40.231 | −5.980 | 1.00 | 16.96 | N |
| ATOM | 9728 | CA | ARG | B | 77 | 68.194 | 41.248 | −5.651 | 1.00 | 18.72 | C |
| ATOM | 9730 | CB | ARG | B | 77 | 67.021 | 40.645 | −4.874 | 1.00 | 20.75 | C |
| ATOM | 9733 | CG | ARG | B | 77 | 66.166 | 39.656 | −5.661 | 1.00 | 29.90 | C |
| ATOM | 9736 | CD | ARG | B | 77 | 65.265 | 38.856 | −4.720 | 1.00 | 40.32 | C |
| ATOM | 9739 | NE | ARG | B | 77 | 64.403 | 39.739 | −3.935 | 1.00 | 48.74 | N |
| ATOM | 9741 | CZ | ARG | B | 77 | 63.323 | 40.363 | −4.409 | 1.00 | 58.45 | C |
| ATOM | 9742 | NH1 | ARG | B | 77 | 62.941 | 40.209 | −5.677 | 1.00 | 61.84 | N |
| ATOM | 9745 | NH2 | ARG | B | 77 | 62.612 | 41.149 | −3.608 | 1.00 | 61.27 | N |
| ATOM | 9748 | C | ARG | B | 77 | 68.824 | 42.359 | −4.820 | 1.00 | 17.11 | C |
| ATOM | 9749 | O | ARG | B | 77 | 68.705 | 43.539 | −5.144 | 1.00 | 16.80 | O |
| ATOM | 9751 | N | GLY | B | 78 | 69.507 | 41.962 | −3.752 | 1.00 | 15.79 | N |
| ATOM | 9752 | CA | GLY | B | 78 | 70.179 | 42.899 | −2.865 | 1.00 | 15.46 | C |

APPENDIX 1-continued

| ATOM | 9755 | C | GLY | B | 78 | 71.246 | 43.712 | −3.564 | 1.00 | 15.64 | C |
|---|---|---|---|---|---|---|---|---|---|---|---|
| ATOM | 9756 | O | GLY | B | 78 | 71.489 | 44.862 | −3.199 | 1.00 | 17.03 | O |
| ATOM | 9758 | N | ALA | B | 79 | 71.885 | 43.119 | −4.569 | 1.00 | 15.27 | N |
| ATOM | 9759 | CA | ALA | B | 79 | 72.904 | 43.817 | −5.344 | 1.00 | 15.39 | C |
| ATOM | 9761 | CB | ALA | B | 79 | 73.746 | 42.825 | −6.147 | 1.00 | 14.40 | C |
| ATOM | 9765 | C | ALA | B | 79 | 72.242 | 44.845 | −6.261 | 1.00 | 15.93 | C |
| ATOM | 9766 | O | ALA | B | 79 | 72.778 | 45.936 | −6.470 | 1.00 | 15.93 | O |
| ATOM | 9768 | N | LEU | B | 80 | 71.074 | 44.492 | −6.790 | 1.00 | 16.63 | N |
| ATOM | 9769 | CA | LEU | B | 80 | 70.282 | 45.416 | −7.599 | 1.00 | 18.25 | C |
| ATOM | 9771 | CB | LEU | B | 80 | 69.142 | 44.682 | −8.318 | 1.00 | 18.14 | C |
| ATOM | 9774 | CG | LEU | B | 80 | 69.583 | 43.825 | −9.500 | 1.00 | 17.03 | C |
| ATOM | 9776 | CD1 | LEU | B | 80 | 68.451 | 42.934 | −9.958 | 1.00 | 16.74 | C |
| ATOM | 9780 | CD2 | LEU | B | 80 | 70.083 | 44.711 | −10.629 | 1.00 | 12.66 | C |
| ATOM | 9784 | C | LEU | B | 80 | 69.716 | 46.539 | −6.746 | 1.00 | 19.03 | C |
| ATOM | 9785 | O | LEU | B | 80 | 69.682 | 47.693 | −7.175 | 1.00 | 18.91 | O |
| ATOM | 9787 | N | ASP | B | 81 | 69.276 | 46.203 | −5.537 | 1.00 | 20.51 | N |
| ATOM | 9788 | CA | ASP | B | 81 | 68.782 | 47.216 | −4.617 | 1.00 | 21.82 | C |
| ATOM | 9790 | CB | ASP | B | 81 | 68.362 | 46.599 | −3.283 | 1.00 | 22.67 | C |
| ATOM | 9793 | CG | ASP | B | 81 | 67.442 | 47.512 | −2.487 | 1.00 | 28.11 | C |
| ATOM | 9794 | OD1 | ASP | B | 81 | 66.340 | 47.835 | −2.986 | 1.00 | 34.60 | O |
| ATOM | 9795 | OD2 | ASP | B | 81 | 67.814 | 47.902 | −1.360 | 1.00 | 34.51 | O |
| ATOM | 9796 | C | ASP | B | 81 | 69.855 | 48.271 | −4.398 | 1.00 | 21.60 | C |
| ATOM | 9797 | O | ASP | B | 81 | 69.604 | 49.460 | −4.567 | 1.00 | 22.28 | O |
| ATOM | 9799 | N | AARG | B | 82 | 71.048 | 47.810 | −4.034 | 0.50 | 21.77 | N |
| ATOM | 9800 | N | BARG | B | 82 | 71.060 | 47.835 | −4.037 | 0.50 | 21.42 | N |
| ATOM | 9801 | CA | AARG | B | 82 | 72.210 | 48.668 | −3.815 | 0.50 | 21.62 | C |
| ATOM | 9802 | CA | BARG | B | 82 | 72.170 | 48.761 | −3.802 | 0.50 | 20.97 | C |
| ATOM | 9805 | CB | AARG | B | 82 | 73.395 | 47.796 | −3.398 | 0.50 | 21.78 | C |
| ATOM | 9806 | CB | BARG | B | 82 | 73.377 | 48.032 | −3.207 | 0.50 | 20.77 | C |
| ATOM | 9811 | CG | AARG | B | 82 | 74.632 | 48.551 | −2.977 | 0.50 | 21.50 | C |
| ATOM | 9812 | CG | BARG | B | 82 | 74.483 | 48.970 | −2.749 | 0.50 | 19.14 | C |
| ATOM | 9817 | CD | AARG | B | 82 | 75.727 | 47.582 | −2.543 | 0.50 | 22.44 | C |
| ATOM | 9818 | CD | BARG | B | 82 | 75.729 | 48.220 | −2.295 | 0.50 | 17.73 | C |
| ATOM | 9823 | NE | AARG | B | 82 | 75.222 | 46.533 | −1.655 | 0.50 | 22.33 | N |
| ATOM | 9824 | NE | BARG | B | 82 | 75.472 | 47.340 | −1.155 | 0.50 | 15.30 | N |
| ATOM | 9827 | CZ | AARG | B | 82 | 75.137 | 45.245 | −1.979 | 0.50 | 18.58 | C |
| ATOM | 9828 | CZ | BARG | B | 82 | 75.716 | 47.658 | 0.112 | 0.50 | 9.61 | C |
| ATOM | 9829 | NH1 | AARG | B | 82 | 74.666 | 44.374 | −1.100 | 0.50 | 19.31 | N |
| ATOM | 9830 | NH1 | BARG | B | 82 | 75.453 | 46.790 | 1.074 | 0.50 | 10.27 | N |
| ATOM | 9835 | NH2 | AARG | B | 82 | 75.532 | 44.826 | −3.173 | 0.50 | 16.77 | N |
| ATOM | 9836 | NH2 | BARG | B | 82 | 76.225 | 48.838 | 0.419 | 0.50 | 10.60 | N |
| ATOM | 9841 | C | AARG | B | 82 | 72.572 | 49.461 | −5.069 | 0.50 | 21.39 | C |
| ATOM | 9842 | C | BARG | B | 82 | 72.583 | 49.484 | −5.082 | 0.50 | 21.04 | C |
| ATOM | 9843 | O | AARG | B | 82 | 72.945 | 50.628 | −4.987 | 0.50 | 21.43 | O |
| ATOM | 9844 | O | BARG | B | 82 | 73.011 | 50.634 | −5.030 | 0.50 | 21.11 | O |
| ATOM | 9847 | N | PHE | B | 83 | 72.461 | 48.810 | −6.225 | 1.00 | 21.32 | N |
| ATOM | 9848 | CA | PHE | B | 83 | 72.709 | 49.442 | −7.524 | 1.00 | 20.89 | C |
| ATOM | 9850 | CB | PHE | B | 83 | 72.515 | 48.422 | −8.655 | 1.00 | 20.59 | C |
| ATOM | 9853 | CG | PHE | B | 83 | 72.552 | 49.020 | −10.035 | 1.00 | 20.93 | C |
| ATOM | 9854 | CD1 | PHE | B | 83 | 73.763 | 49.277 | −10.664 | 1.00 | 20.95 | C |
| ATOM | 9856 | CE1 | PHE | B | 83 | 73.800 | 49.831 | −11.936 | 1.00 | 20.41 | C |
| ATOM | 9858 | CZ | PHE | B | 83 | 72.621 | 50.133 | −12.595 | 1.00 | 21.33 | C |
| ATOM | 9860 | CE2 | PHE | B | 83 | 71.407 | 49.879 | −11.982 | 1.00 | 22.56 | C |
| ATOM | 9862 | CD2 | PHE | B | 83 | 71.375 | 49.324 | −10.709 | 1.00 | 22.55 | C |
| ATOM | 9864 | C | PHE | B | 83 | 71.797 | 50.654 | −7.741 | 1.00 | 21.23 | C |
| ATOM | 9865 | O | PHE | B | 83 | 72.244 | 51.683 | −8.243 | 1.00 | 21.52 | O |
| ATOM | 9867 | N | VAL | B | 84 | 70.531 | 50.532 | −7.346 | 1.00 | 21.76 | N |
| ATOM | 9868 | CA | VAL | B | 84 | 69.567 | 51.624 | −7.497 | 1.00 | 22.25 | C |
| ATOM | 9870 | CB | VAL | B | 84 | 68.105 | 51.130 | −7.366 | 1.00 | 22.54 | C |
| ATOM | 9872 | CG1 | VAL | B | 84 | 67.127 | 52.289 | −7.571 | 1.00 | 19.41 | C |
| ATOM | 9876 | CG2 | VAL | B | 84 | 67.823 | 50.009 | −8.361 | 1.00 | 19.62 | C |
| ATOM | 9880 | C | VAL | B | 84 | 69.804 | 52.726 | −6.464 | 1.00 | 23.27 | C |
| ATOM | 9881 | O | VAL | B | 84 | 69.968 | 53.891 | −6.826 | 1.00 | 23.34 | O |
| ATOM | 9883 | N | SER | B | 85 | 69.837 | 52.347 | −5.187 | 1.00 | 24.43 | N |
| ATOM | 9884 | CA | SER | B | 85 | 69.931 | 53.311 | −4.079 | 1.00 | 25.59 | C |
| ATOM | 9886 | CB | SER | B | 85 | 69.773 | 52.598 | −2.730 | 1.00 | 25.76 | C |
| ATOM | 9889 | OG | SER | B | 85 | 70.966 | 51.936 | −2.345 | 1.00 | 28.79 | O |
| ATOM | 9891 | C | SER | B | 85 | 71.222 | 54.147 | −4.070 | 1.00 | 25.80 | C |
| ATOM | 9892 | O | SER | B | 85 | 71.237 | 55.262 | −3.539 | 1.00 | 25.61 | O |
| ATOM | 9894 | N | SER | B | 86 | 72.294 | 53.608 | −4.647 | 1.00 | 25.84 | N |
| ATOM | 9895 | CA | SER | B | 86 | 73.557 | 54.329 | −4.745 | 1.00 | 26.12 | C |
| ATOM | 9897 | CB | SER | B | 86 | 74.736 | 53.354 | −4.674 | 1.00 | 26.10 | C |
| ATOM | 9900 | OG | SER | B | 86 | 74.773 | 52.496 | −5.799 | 1.00 | 25.33 | O |
| ATOM | 9902 | C | SER | B | 86 | 73.630 | 55.169 | −6.026 | 1.00 | 27.01 | C |
| ATOM | 9903 | O | SER | B | 86 | 74.671 | 55.754 | −6.332 | 1.00 | 26.74 | O |
| ATOM | 9905 | N | GLY | B | 87 | 72.526 | 55.223 | −6.771 | 1.00 | 27.80 | N |
| ATOM | 9906 | CA | GLY | B | 87 | 72.423 | 56.076 | −7.955 | 1.00 | 27.61 | C |
| ATOM | 9909 | C | GLY | B | 87 | 72.990 | 55.452 | −9.220 | 1.00 | 27.86 | C |
| ATOM | 9910 | O | GLY | B | 87 | 73.196 | 56.144 | −10.221 | 1.00 | 28.30 | O |
| ATOM | 9912 | N | GLY | B | 88 | 73.243 | 54.147 | −9.190 | 1.00 | 27.52 | N |

APPENDIX 1-continued

| | | | | | | | | | | |
|---|---|---|---|---|---|---|---|---|---|---|
| ATOM | 9913 | CA | GLY | B | 88 | 73.755 | 53.453 | −10.367 | 1.00 | 27.36 | C |
| ATOM | 9916 | C | GLY | B | 88 | 72.811 | 53.557 | −11.554 | 1.00 | 27.07 | C |
| ATOM | 9917 | O | GLY | B | 88 | 73.249 | 53.733 | −12.694 | 1.00 | 27.18 | O |
| ATOM | 9919 | N | PHE | B | 89 | 71.512 | 53.463 | −11.289 | 1.00 | 26.60 | N |
| ATOM | 9920 | CA | PHE | B | 89 | 70.525 | 53.475 | −12.362 | 1.00 | 26.75 | C |
| ATOM | 9922 | CB | PHE | B | 89 | 69.150 | 53.030 | −11.846 | 1.00 | 26.20 | C |
| ATOM | 9925 | CG | PHE | B | 89 | 68.167 | 52.700 | −12.935 | 1.00 | 24.08 | C |
| ATOM | 9926 | CD1 | PHE | B | 89 | 68.462 | 51.735 | −13.891 | 1.00 | 24.55 | C |
| ATOM | 9928 | CE1 | PHE | B | 89 | 67.552 | 51.427 | −14.907 | 1.00 | 22.92 | C |
| ATOM | 9930 | CZ | PHE | B | 89 | 66.336 | 52.082 | −14.965 | 1.00 | 23.72 | C |
| ATOM | 9932 | CE2 | PHE | B | 89 | 66.026 | 53.044 | −14.010 | 1.00 | 25.36 | C |
| ATOM | 9934 | CD2 | PHE | B | 89 | 66.939 | 53.344 | −13.000 | 1.00 | 24.97 | C |
| ATOM | 9936 | C | PHE | B | 89 | 70.464 | 54.862 | −12.992 | 1.00 | 28.10 | C |
| ATOM | 9937 | O | PHE | B | 89 | 70.479 | 54.990 | −14.219 | 1.00 | 28.61 | O |
| ATOM | 9939 | N | ASP | B | 90 | 70.428 | 55.895 | −12.150 | 1.00 | 28.87 | N |
| ATOM | 9940 | CA | ASP | B | 90 | 70.424 | 57.283 | −12.619 | 1.00 | 29.31 | C |
| ATOM | 9942 | CB | ASP | B | 90 | 70.369 | 58.267 | −11.435 | 1.00 | 30.20 | C |
| ATOM | 9945 | CG | ASP | B | 90 | 69.689 | 59.592 | −11.796 | 1.00 | 35.08 | C |
| ATOM | 9946 | OD1 | ASP | B | 90 | 68.489 | 59.562 | −12.148 | 1.00 | 41.57 | O |
| ATOM | 9947 | OD2 | ASP | B | 90 | 70.343 | 60.661 | −11.713 | 1.00 | 36.53 | O |
| ATOM | 9948 | C | ASP | B | 90 | 71.666 | 57.558 | −13.467 | 1.00 | 28.83 | C |
| ATOM | 9949 | O | ASP | B | 90 | 71.590 | 58.238 | −14.492 | 1.00 | 28.69 | O |
| ATOM | 9951 | N | ALA | B | 91 | 72.804 | 57.013 | −13.040 | 1.00 | 28.69 | N |
| ATOM | 9952 | CA | ALA | B | 91 | 74.079 | 57.231 | −13.729 | 1.00 | 28.58 | C |
| ATOM | 9954 | CB | ALA | B | 91 | 75.238 | 56.654 | −12.906 | 1.00 | 28.14 | C |
| ATOM | 9958 | C | ALA | B | 91 | 74.084 | 56.636 | −15.137 | 1.00 | 28.25 | C |
| ATOM | 9959 | O | ALA | B | 91 | 74.486 | 57.300 | −16.092 | 1.00 | 28.14 | O |
| ATOM | 9961 | N | VAL | B | 92 | 73.637 | 55.388 | −15.261 | 1.00 | 27.93 | N |
| ATOM | 9962 | CA | VAL | B | 92 | 73.674 | 54.696 | −16.550 | 1.00 | 27.65 | C |
| ATOM | 9964 | CB | VAL | B | 92 | 73.433 | 53.164 | −16.416 | 1.00 | 27.48 | C |
| ATOM | 9966 | CG1 | VAL | B | 92 | 74.505 | 52.532 | −15.551 | 1.00 | 23.58 | C |
| ATOM | 9970 | CG2 | VAL | B | 92 | 72.053 | 52.869 | −15.861 | 1.00 | 28.01 | C |
| ATOM | 9974 | C | VAL | B | 92 | 72.685 | 55.313 | −17.536 | 1.00 | 28.14 | C |
| ATOM | 9975 | O | VAL | B | 92 | 72.979 | 55.407 | −18.728 | 1.00 | 28.47 | O |
| ATOM | 9977 | N | THR | B | 93 | 71.529 | 55.753 | −17.039 | 1.00 | 28.50 | N |
| ATOM | 9978 | CA | THR | B | 93 | 70.538 | 56.414 | −17.892 | 1.00 | 28.67 | C |
| ATOM | 9980 | CB | THR | B | 93 | 69.208 | 56.708 | −17.154 | 1.00 | 28.40 | C |
| ATOM | 9982 | OG1 | THR | B | 93 | 69.425 | 57.657 | −16.104 | 1.00 | 29.60 | O |
| ATOM | 9984 | CG2 | THR | B | 93 | 68.612 | 55.436 | −16.579 | 1.00 | 28.96 | C |
| ATOM | 9988 | C | THR | B | 93 | 71.079 | 57.715 | −18.481 | 1.00 | 28.92 | C |
| ATOM | 9989 | O | THR | B | 93 | 70.649 | 58.128 | −19.553 | 1.00 | 29.54 | O |
| ATOM | 9991 | N | LYS | B | 94 | 72.019 | 58.355 | −17.789 | 1.00 | 29.23 | N |
| ATOM | 9992 | CA | LYS | B | 94 | 72.629 | 59.587 | −18.297 | 1.00 | 30.17 | C |
| ATOM | 9994 | CB | LYS | B | 94 | 72.918 | 60.566 | −17.141 | 1.00 | 30.56 | C |
| ATOM | 9997 | CG | LYS | B | 94 | 71.692 | 61.007 | −16.331 | 1.00 | 34.56 | C |
| ATOM | 10000 | CD | LYS | B | 94 | 70.653 | 61.747 | −17.185 | 1.00 | 41.93 | C |
| ATOM | 10003 | CE | LYS | B | 94 | 69.275 | 61.775 | −16.518 | 1.00 | 46.78 | C |
| ATOM | 10006 | NZ | LYS | B | 94 | 68.163 | 61.856 | −17.518 | 1.00 | 45.92 | N |
| ATOM | 10010 | C | LYS | B | 94 | 73.908 | 59.367 | −19.125 | 1.00 | 29.35 | C |
| ATOM | 10011 | O | LYS | B | 94 | 74.482 | 60.339 | −19.615 | 1.00 | 30.59 | O |
| ATOM | 10013 | N | THR | B | 95 | 74.345 | 58.119 | −19.305 | 1.00 | 28.07 | N |
| ATOM | 10014 | CA | THR | B | 95 | 75.658 | 57.854 | −19.922 | 1.00 | 26.85 | C |
| ATOM | 10016 | CB | THR | B | 95 | 76.745 | 57.665 | −18.839 | 1.00 | 26.84 | C |
| ATOM | 10018 | OG1 | THR | B | 95 | 76.483 | 56.470 | −18.092 | 1.00 | 26.04 | O |
| ATOM | 10020 | CG2 | THR | B | 95 | 76.788 | 58.861 | −17.888 | 1.00 | 26.33 | C |
| ATOM | 10024 | C | THR | B | 95 | 75.765 | 56.645 | −20.861 | 1.00 | 26.37 | C |
| ATOM | 10025 | O | THR | B | 95 | 76.606 | 56.656 | −21.760 | 1.00 | 26.38 | O |
| ATOM | 10027 | N | SER | B | 96 | 74.948 | 55.610 | −20.655 | 1.00 | 25.35 | N |
| ATOM | 10028 | CA | SER | B | 96 | 75.172 | 54.314 | −21.308 | 1.00 | 24.42 | C |
| ATOM | 10030 | CB | SER | B | 96 | 76.055 | 53.449 | −20.409 | 1.00 | 24.35 | C |
| ATOM | 10033 | OG | SER | B | 96 | 76.202 | 52.142 | −20.932 | 1.00 | 24.77 | O |
| ATOM | 10035 | C | SER | B | 96 | 73.892 | 53.540 | −21.631 | 1.00 | 24.01 | C |
| ATOM | 10036 | O | SER | B | 96 | 73.109 | 53.211 | −20.740 | 1.00 | 23.55 | O |
| ATOM | 10038 | N | LEU | B | 97 | 73.702 | 53.229 | −22.910 | 1.00 | 23.48 | N |
| ATOM | 10039 | CA | LEU | B | 97 | 72.568 | 52.423 | −23.351 | 1.00 | 22.24 | C |
| ATOM | 10041 | CB | LEU | B | 97 | 72.443 | 52.453 | −24.877 | 1.00 | 22.40 | C |
| ATOM | 10044 | CG | LEU | B | 97 | 71.212 | 51.750 | −25.464 | 1.00 | 22.64 | C |
| ATOM | 10046 | CD1 | LEU | B | 97 | 69.935 | 52.503 | −25.117 | 1.00 | 19.62 | C |
| ATOM | 10050 | CD2 | LEU | B | 97 | 71.346 | 51.603 | −26.969 | 1.00 | 23.82 | C |
| ATOM | 10054 | C | LEU | B | 97 | 72.727 | 50.988 | −22.883 | 1.00 | 20.77 | C |
| ATOM | 10055 | O | LEU | B | 97 | 71.755 | 50.352 | −22.492 | 1.00 | 20.47 | O |
| ATOM | 10057 | N | HIS | B | 98 | 73.955 | 50.480 | −22.943 | 1.00 | 20.09 | N |
| ATOM | 10058 | CA | HIS | B | 98 | 74.252 | 49.112 | −22.517 | 1.00 | 19.77 | C |
| ATOM | 10060 | CB | HIS | B | 98 | 75.736 | 48.786 | −22.738 | 1.00 | 19.72 | C |
| ATOM | 10063 | CG | HIS | B | 98 | 76.151 | 47.444 | −22.215 | 1.00 | 22.81 | C |
| ATOM | 10064 | ND1 | HIS | B | 98 | 75.554 | 46.269 | −22.619 | 1.00 | 23.34 | N |
| ATOM | 10066 | CE1 | HIS | B | 98 | 76.118 | 45.251 | −21.993 | 1.00 | 22.61 | C |
| ATOM | 10068 | NE2 | HIS | B | 98 | 77.064 | 45.722 | −21.201 | 1.00 | 27.27 | N |
| ATOM | 10070 | CD2 | HIS | B | 98 | 77.108 | 47.092 | −21.322 | 1.00 | 25.81 | C |
| ATOM | 10072 | C | HIS | B | 98 | 73.862 | 48.928 | −21.052 | 1.00 | 18.84 | C |

APPENDIX 1-continued

| | | | | | | | | | | |
|---|---|---|---|---|---|---|---|---|---|---|
| ATOM | 10073 | O | HIS | B | 98 | 73.128 | 47.998 | −20.709 | 1.00 | 17.29 | O |
| ATOM | 10075 | N | GLY | B | 99 | 74.340 | 49.833 | −20.202 | 1.00 | 18.20 | N |
| ATOM | 10076 | CA | GLY | B | 99 | 74.023 | 49.803 | −18.779 | 1.00 | 17.26 | C |
| ATOM | 10079 | C | GLY | B | 99 | 72.536 | 49.941 | −18.538 | 1.00 | 16.93 | C |
| ATOM | 10080 | O | GLY | B | 99 | 71.958 | 49.206 | −17.741 | 1.00 | 17.18 | O |
| ATOM | 10082 | N | THR | B | 100 | 71.914 | 50.875 | −19.246 | 1.00 | 16.49 | N |
| ATOM | 10083 | CA | THR | B | 100 | 70.496 | 51.144 | −19.079 | 1.00 | 16.09 | C |
| ATOM | 10085 | CB | THR | B | 100 | 70.067 | 52.381 | −19.885 | 1.00 | 16.31 | C |
| ATOM | 10087 | OG1 | THR | B | 100 | 70.820 | 53.517 | −19.442 | 1.00 | 15.45 | O |
| ATOM | 10089 | CG2 | THR | B | 100 | 68.579 | 52.662 | −19.706 | 1.00 | 13.65 | C |
| ATOM | 10093 | C | THR | B | 100 | 69.663 | 49.944 | −19.502 | 1.00 | 16.21 | C |
| ATOM | 10094 | O | THR | B | 100 | 68.809 | 49.484 | −18.749 | 1.00 | 16.53 | O |
| ATOM | 10096 | N | ALA | B | 101 | 69.925 | 49.432 | −20.699 | 1.00 | 16.10 | N |
| ATOM | 10097 | CA | ALA | B | 101 | 69.173 | 48.295 | −21.228 | 1.00 | 15.62 | C |
| ATOM | 10099 | CB | ALA | B | 101 | 69.590 | 48.005 | −22.656 | 1.00 | 14.94 | C |
| ATOM | 10103 | C | ALA | B | 101 | 69.344 | 47.050 | −20.355 | 1.00 | 15.19 | C |
| ATOM | 10104 | O | ALA | B | 101 | 68.377 | 46.331 | −20.088 | 1.00 | 15.37 | O |
| ATOM | 10106 | N | LEU | B | 102 | 70.570 | 46.808 | −19.906 | 1.00 | 14.63 | N |
| ATOM | 10107 | CA | LEU | B | 102 | 70.870 | 45.637 | −19.087 | 1.00 | 14.71 | C |
| ATOM | 10109 | CB | LEU | B | 102 | 72.386 | 45.406 | −18.992 | 1.00 | 13.92 | C |
| ATOM | 10112 | CG | LEU | B | 102 | 72.865 | 44.181 | −18.209 | 1.00 | 13.02 | C |
| ATOM | 10114 | CD1 | LEU | B | 102 | 72.131 | 42.914 | −18.635 | 1.00 | 10.45 | C |
| ATOM | 10118 | CD2 | LEU | B | 102 | 74.360 | 43.996 | −18.367 | 1.00 | 7.35 | C |
| ATOM | 10122 | C | LEU | B | 102 | 70.268 | 45.775 | −17.697 | 1.00 | 15.21 | C |
| ATOM | 10123 | O | LEU | B | 102 | 69.675 | 44.826 | −17.185 | 1.00 | 15.85 | O |
| ATOM | 10125 | N | SER | B | 103 | 70.412 | 46.950 | −17.087 | 1.00 | 15.38 | N |
| ATOM | 10126 | CA | SER | B | 103 | 69.852 | 47.177 | −15.756 | 1.00 | 15.40 | C |
| ATOM | 10128 | CB | SER | B | 103 | 70.368 | 48.483 | −15.141 | 1.00 | 16.04 | C |
| ATOM | 10131 | OG | SER | B | 103 | 70.205 | 49.589 | −16.011 | 1.00 | 17.82 | O |
| ATOM | 10133 | C | SER | B | 103 | 68.329 | 47.171 | −15.816 | 1.00 | 15.54 | C |
| ATOM | 10134 | O | SER | B | 103 | 67.670 | 46.623 | −14.928 | 1.00 | 15.63 | O |
| ATOM | 10136 | N | PHE | B | 104 | 67.771 | 47.759 | −16.871 | 1.00 | 15.00 | N |
| ATOM | 10137 | CA | PHE | B | 104 | 66.331 | 47.747 | −17.056 | 1.00 | 15.05 | C |
| ATOM | 10139 | CB | PHE | B | 104 | 65.933 | 48.364 | −18.399 | 1.00 | 15.62 | C |
| ATOM | 10142 | CG | PHE | B | 104 | 64.445 | 48.436 | −18.610 | 1.00 | 15.05 | C |
| ATOM | 10143 | CD1 | PHE | B | 104 | 63.751 | 47.357 | −19.128 | 1.00 | 16.50 | C |
| ATOM | 10145 | CE1 | PHE | B | 104 | 62.376 | 47.425 | −19.324 | 1.00 | 19.68 | C |
| ATOM | 10147 | CZ | PHE | B | 104 | 61.686 | 48.577 | −18.995 | 1.00 | 16.19 | C |
| ATOM | 10149 | CE2 | PHE | B | 104 | 62.368 | 49.657 | −18.473 | 1.00 | 13.76 | C |
| ATOM | 10151 | CD2 | PHE | B | 104 | 63.738 | 49.584 | −18.283 | 1.00 | 15.00 | C |
| ATOM | 10153 | C | PHE | B | 104 | 65.834 | 46.319 | −16.983 | 1.00 | 15.00 | C |
| ATOM | 10154 | O | PHE | B | 104 | 64.974 | 45.998 | −16.158 | 1.00 | 16.23 | O |
| ATOM | 10156 | N | ARG | B | 105 | 66.395 | 45.463 | −17.831 | 1.00 | 14.08 | N |
| ATOM | 10157 | CA | ARG | B | 105 | 65.986 | 44.063 | −17.889 | 1.00 | 14.06 | C |
| ATOM | 10159 | CB | ARG | B | 105 | 66.743 | 43.309 | −18.988 | 1.00 | 14.27 | C |
| ATOM | 10162 | CG | ARG | B | 105 | 66.461 | 41.808 | −19.011 | 1.00 | 13.50 | C |
| ATOM | 10165 | CD | ARG | B | 105 | 66.936 | 41.164 | −20.294 | 1.00 | 12.74 | C |
| ATOM | 10168 | NE | ARG | B | 105 | 68.391 | 41.180 | −20.429 | 1.00 | 14.09 | N |
| ATOM | 10170 | CZ | ARG | B | 105 | 69.232 | 40.315 | −19.865 | 1.00 | 11.59 | C |
| ATOM | 10171 | NH1 | ARG | B | 105 | 68.796 | 39.340 | −19.083 | 1.00 | 16.77 | N |
| ATOM | 10174 | NH2 | ARG | B | 105 | 70.532 | 40.436 | −20.078 | 1.00 | 15.03 | N |
| ATOM | 10177 | C | ARG | B | 105 | 66.162 | 43.345 | −16.551 | 1.00 | 13.99 | C |
| ATOM | 10178 | O | ARG | B | 105 | 65.239 | 42.682 | −16.089 | 1.00 | 14.90 | O |
| ATOM | 10180 | N | LEU | B | 106 | 67.332 | 43.468 | −15.929 | 1.00 | 13.46 | N |
| ATOM | 10181 | CA | LEU | B | 106 | 67.584 | 42.741 | −14.680 | 1.00 | 13.96 | C |
| ATOM | 10183 | CB | LEU | B | 106 | 69.051 | 42.839 | −14.254 | 1.00 | 13.53 | C |
| ATOM | 10186 | CG | LEU | B | 106 | 70.091 | 42.293 | −15.239 | 1.00 | 12.65 | C |
| ATOM | 10188 | CD1 | LEU | B | 106 | 71.503 | 42.626 | −14.741 | 1.00 | 9.23 | C |
| ATOM | 10192 | CD2 | LEU | B | 106 | 69.921 | 40.809 | −15.472 | 1.00 | 6.67 | C |
| ATOM | 10196 | C | LEU | B | 106 | 66.677 | 43.241 | −13.552 | 1.00 | 14.63 | C |
| ATOM | 10197 | O | LEU | B | 106 | 66.173 | 42.448 | −12.762 | 1.00 | 15.27 | O |
| ATOM | 10199 | N | LEU | B | 107 | 66.458 | 44.551 | −13.491 | 1.00 | 14.67 | N |
| ATOM | 10200 | CA | LEU | B | 107 | 65.586 | 45.137 | −12.477 | 1.00 | 14.25 | C |
| ATOM | 10202 | CB | LEU | B | 107 | 65.628 | 46.660 | −12.564 | 1.00 | 14.40 | C |
| ATOM | 10205 | CG | LEU | B | 107 | 66.887 | 47.308 | −11.999 | 1.00 | 12.30 | C |
| ATOM | 10207 | CD1 | LEU | B | 107 | 67.049 | 48.692 | −12.571 | 1.00 | 7.43 | C |
| ATOM | 10211 | CD2 | LEU | B | 107 | 66.824 | 47.340 | −10.475 | 1.00 | 7.16 | C |
| ATOM | 10215 | C | LEU | B | 107 | 64.142 | 44.652 | −12.612 | 1.00 | 14.77 | C |
| ATOM | 10216 | O | LEU | B | 107 | 63.538 | 44.206 | −11.630 | 1.00 | 14.29 | O |
| ATOM | 10218 | N | ARG | B | 108 | 63.592 | 44.737 | −13.821 | 1.00 | 15.25 | N |
| ATOM | 10219 | CA | ARG | B | 108 | 62.222 | 44.261 | −14.060 | 1.00 | 15.49 | C |
| ATOM | 10221 | CB | ARG | B | 108 | 61.740 | 44.576 | −15.482 | 1.00 | 14.33 | C |
| ATOM | 10224 | CG | ARG | B | 108 | 60.359 | 44.011 | −15.784 | 1.00 | 13.69 | C |
| ATOM | 10227 | CD | ARG | B | 108 | 59.670 | 44.725 | −16.944 | 1.00 | 14.55 | C |
| ATOM | 10230 | NE | ARG | B | 108 | 59.210 | 46.070 | −16.585 | 1.00 | 14.46 | N |
| ATOM | 10232 | CZ | ARG | B | 108 | 58.646 | 46.926 | −17.437 | 1.00 | 11.54 | C |
| ATOM | 10233 | NH1 | ARG | B | 108 | 58.454 | 46.593 | −18.704 | 1.00 | 14.47 | N |
| ATOM | 10236 | NH2 | ARG | B | 108 | 58.273 | 48.125 | −17.022 | 1.00 | 12.97 | N |
| ATOM | 10239 | C | ARG | B | 108 | 62.116 | 42.765 | −13.796 | 1.00 | 15.68 | C |
| ATOM | 10240 | O | ARG | B | 108 | 61.127 | 42.298 | −13.208 | 1.00 | 15.93 | O |

APPENDIX 1-continued

| ATOM | 10242 | N | GLN | B | 109 | 63.134 | 42.023 | −14.228 | 1.00 | 15.71 | N |
|---|---|---|---|---|---|---|---|---|---|---|---|
| ATOM | 10243 | CA | GLN | B | 109 | 63.177 | 40.579 | −14.012 | 1.00 | 16.54 | C |
| ATOM | 10245 | CB | GLN | B | 109 | 64.498 | 39.986 | −14.522 | 1.00 | 16.76 | C |
| ATOM | 10248 | CG | GLN | B | 109 | 64.609 | 38.459 | −14.387 | 1.00 | 17.37 | C |
| ATOM | 10251 | CD | GLN | B | 109 | 66.016 | 37.939 | −14.642 | 1.00 | 17.59 | C |
| ATOM | 10252 | OE1 | GLN | B | 109 | 66.864 | 38.634 | −15.208 | 1.00 | 18.95 | O |
| ATOM | 10253 | NE2 | GLN | B | 109 | 66.268 | 36.709 | −14.221 | 1.00 | 15.92 | N |
| ATOM | 10256 | C | GLN | B | 109 | 63.008 | 40.254 | −12.536 | 1.00 | 17.26 | C |
| ATOM | 10257 | O | GLN | B | 109 | 62.312 | 39.311 | −12.184 | 1.00 | 19.23 | O |
| ATOM | 10259 | N | HIS | B | 110 | 63.639 | 41.040 | −11.674 | 1.00 | 17.44 | N |
| ATOM | 10260 | CA | HIS | B | 110 | 63.621 | 40.755 | −10.241 | 1.00 | 18.03 | C |
| ATOM | 10262 | CB | HIS | B | 110 | 65.033 | 40.933 | −9.667 | 1.00 | 18.14 | C |
| ATOM | 10265 | CG | HIS | B | 110 | 65.980 | 39.860 | −10.110 | 1.00 | 18.35 | C |
| ATOM | 10266 | ND1 | HIS | B | 110 | 66.176 | 38.701 | −9.390 | 1.00 | 19.17 | N |
| ATOM | 10268 | CE1 | HIS | B | 110 | 67.037 | 37.930 | −10.028 | 1.00 | 19.08 | C |
| ATOM | 10270 | NE2 | HIS | B | 110 | 67.396 | 38.540 | −11.144 | 1.00 | 15.83 | N |
| ATOM | 10272 | CD2 | HIS | B | 110 | 66.744 | 39.746 | −11.222 | 1.00 | 15.87 | C |
| ATOM | 10274 | C | HIS | B | 110 | 62.561 | 41.554 | −9.473 | 1.00 | 18.48 | C |
| ATOM | 10275 | O | HIS | B | 110 | 62.619 | 41.669 | −8.246 | 1.00 | 18.21 | O |
| ATOM | 10277 | N | GLY | B | 111 | 61.588 | 42.093 | −10.207 | 1.00 | 18.75 | N |
| ATOM | 10278 | CA | GLY | B | 111 | 60.413 | 42.721 | −9.613 | 1.00 | 18.98 | C |
| ATOM | 10281 | C | GLY | B | 111 | 60.509 | 44.196 | −9.265 | 1.00 | 19.81 | C |
| ATOM | 10282 | O | GLY | B | 111 | 59.596 | 44.726 | −8.635 | 1.00 | 20.39 | O |
| ATOM | 10284 | N | PHE | B | 112 | 61.597 | 44.864 | −9.655 | 1.00 | 20.29 | N |
| ATOM | 10285 | CA | PHE | B | 112 | 61.740 | 46.301 | −9.398 | 1.00 | 20.92 | C |
| ATOM | 10287 | CB | PHE | B | 112 | 63.200 | 46.746 | −9.510 | 1.00 | 20.72 | C |
| ATOM | 10290 | CG | PHE | B | 112 | 64.079 | 46.239 | −8.400 | 1.00 | 23.40 | C |
| ATOM | 10291 | CD1 | PHE | B | 112 | 64.259 | 46.986 | −7.241 | 1.00 | 24.03 | C |
| ATOM | 10293 | CE1 | PHE | B | 112 | 65.071 | 46.521 | −6.217 | 1.00 | 25.01 | C |
| ATOM | 10295 | CZ | PHE | B | 112 | 65.718 | 45.299 | −6.348 | 1.00 | 24.81 | C |
| ATOM | 10297 | CE2 | PHE | B | 112 | 65.551 | 44.550 | −7.499 | 1.00 | 22.54 | C |
| ATOM | 10299 | CD2 | PHE | B | 112 | 64.737 | 45.018 | −8.516 | 1.00 | 25.22 | C |
| ATOM | 10301 | C | PHE | B | 112 | 60.892 | 47.101 | −10.376 | 1.00 | 21.54 | C |
| ATOM | 10302 | O | PHE | B | 112 | 60.670 | 46.671 | −11.505 | 1.00 | 22.97 | O |
| ATOM | 10304 | N | GLU | B | 113 | 60.417 | 48.261 | −9.937 | 1.00 | 21.84 | N |
| ATOM | 10305 | CA | GLU | B | 113 | 59.687 | 49.176 | −10.811 | 1.00 | 22.54 | C |
| ATOM | 10307 | CB | GLU | B | 113 | 58.781 | 50.129 | −10.015 | 1.00 | 23.84 | C |
| ATOM | 10310 | CG | GLU | B | 113 | 57.290 | 49.807 | −10.092 | 1.00 | 31.72 | C |
| ATOM | 10313 | CD | GLU | B | 113 | 56.401 | 51.051 | −9.956 | 1.00 | 38.67 | C |
| ATOM | 10314 | OE1 | GLU | B | 113 | 56.886 | 52.091 | −9.453 | 1.00 | 35.63 | O |
| ATOM | 10315 | OE2 | GLU | B | 113 | 55.213 | 50.983 | −10.355 | 1.00 | 43.29 | O |
| ATOM | 10316 | C | GLU | B | 113 | 60.655 | 50.009 | −11.651 | 1.00 | 20.65 | C |
| ATOM | 10317 | O | GLU | B | 113 | 61.524 | 50.701 | −11.117 | 1.00 | 18.56 | O |
| ATOM | 10319 | N | VAL | B | 114 | 60.480 | 49.938 | −12.965 | 1.00 | 19.18 | N |
| ATOM | 10320 | CA | VAL | B | 114 | 61.234 | 50.749 | −13.903 | 1.00 | 17.42 | C |
| ATOM | 10322 | CB | VAL | B | 114 | 62.468 | 50.005 | −14.455 | 1.00 | 17.60 | C |
| ATOM | 10324 | CG1 | VAL | B | 114 | 63.606 | 50.049 | −13.453 | 1.00 | 17.18 | C |
| ATOM | 10328 | CG2 | VAL | B | 114 | 62.119 | 48.567 | −14.827 | 1.00 | 14.25 | C |
| ATOM | 10332 | C | VAL | B | 114 | 60.326 | 51.133 | −15.056 | 1.00 | 17.15 | C |
| ATOM | 10333 | O | VAL | B | 114 | 59.516 | 50.329 | −15.519 | 1.00 | 16.77 | O |
| ATOM | 10335 | N | SER | B | 115 | 60.476 | 52.370 | −15.509 | 1.00 | 17.50 | N |
| ATOM | 10336 | CA | SER | B | 115 | 59.654 | 52.937 | −16.560 | 1.00 | 17.82 | C |
| ATOM | 10338 | CB | SER | B | 115 | 59.297 | 54.381 | −16.201 | 1.00 | 18.13 | C |
| ATOM | 10341 | OG | SER | B | 115 | 58.501 | 54.983 | −17.208 | 1.00 | 21.17 | O |
| ATOM | 10343 | C | SER | B | 115 | 60.410 | 52.919 | −17.878 | 1.00 | 17.73 | C |
| ATOM | 10344 | O | SER | B | 115 | 61.635 | 52.960 | −17.899 | 1.00 | 17.41 | O |
| ATOM | 10346 | N | GLN | B | 116 | 59.674 | 52.876 | −18.984 | 1.00 | 18.27 | N |
| ATOM | 10347 | CA | GLN | B | 116 | 60.288 | 52.972 | −20.304 | 1.00 | 17.86 | C |
| ATOM | 10349 | CB | GLN | B | 116 | 59.264 | 52.661 | −21.388 | 1.00 | 17.57 | C |
| ATOM | 10352 | CG | GLN | B | 116 | 58.150 | 53.677 | −21.508 | 1.00 | 17.76 | C |
| ATOM | 10355 | CD | GLN | B | 116 | 57.264 | 53.437 | −22.707 | 1.00 | 17.92 | C |
| ATOM | 10356 | OE1 | GLN | B | 116 | 57.410 | 52.443 | −23.423 | 1.00 | 16.41 | O |
| ATOM | 10357 | NE2 | GLN | B | 116 | 56.334 | 54.354 | −22.937 | 1.00 | 17.49 | N |
| ATOM | 10360 | C | GLN | B | 116 | 60.917 | 54.345 | −20.564 | 1.00 | 18.48 | C |
| ATOM | 10361 | O | GLN | B | 116 | 61.710 | 54.496 | −21.490 | 1.00 | 18.49 | O |
| ATOM | 10363 | N | GLU | B | 117 | 60.561 | 55.340 | −19.751 | 1.00 | 19.64 | N |
| ATOM | 10364 | CA | GLU | B | 117 | 61.135 | 56.688 | −19.869 | 1.00 | 20.82 | C |
| ATOM | 10366 | CB | GLU | B | 117 | 60.381 | 57.694 | −18.986 | 1.00 | 21.40 | C |
| ATOM | 10369 | CG | GLU | B | 117 | 58.875 | 57.811 | −19.258 | 1.00 | 26.23 | C |
| ATOM | 10372 | CD | GLU | B | 117 | 58.536 | 58.649 | −20.486 | 1.00 | 33.68 | C |
| ATOM | 10373 | OE1 | GLU | B | 117 | 59.219 | 58.514 | −21.526 | 1.00 | 37.95 | O |
| ATOM | 10374 | OE2 | GLU | B | 117 | 57.568 | 59.441 | −20.414 | 1.00 | 38.43 | O |
| ATOM | 10375 | C | GLU | B | 117 | 62.617 | 56.692 | −19.500 | 1.00 | 20.57 | C |
| ATOM | 10376 | O | GLU | B | 117 | 63.321 | 57.674 | −19.746 | 1.00 | 21.48 | O |
| ATOM | 10378 | N | ALA | B | 118 | 63.080 | 55.597 | −18.903 | 1.00 | 20.14 | N |
| ATOM | 10379 | CA | ALA | B | 118 | 64.498 | 55.381 | −18.653 | 1.00 | 20.12 | C |
| ATOM | 10381 | CB | ALA | B | 118 | 64.703 | 54.037 | −17.973 | 1.00 | 19.71 | C |
| ATOM | 10385 | C | ALA | B | 118 | 65.356 | 55.463 | −19.921 | 1.00 | 20.46 | C |
| ATOM | 10386 | O | ALA | B | 118 | 66.550 | 55.721 | −19.829 | 1.00 | 21.08 | O |
| ATOM | 10388 | N | PHE | B | 119 | 64.757 | 55.235 | −21.092 | 1.00 | 20.70 | N |

APPENDIX 1-continued

| ATOM | 10389 | CA  | PHE | B | 119 | 65.491 | 55.273 | −22.367 | 1.00 | 21.14 | C |
| ATOM | 10391 | CB  | PHE | B | 119 | 64.970 | 54.171 | −23.298 | 1.00 | 20.40 | C |
| ATOM | 10394 | CG  | PHE | B | 119 | 65.206 | 52.777 | −22.788 | 1.00 | 19.10 | C |
| ATOM | 10395 | CD1 | PHE | B | 119 | 66.462 | 52.198 | −22.868 | 1.00 | 17.86 | C |
| ATOM | 10397 | CE1 | PHE | B | 119 | 66.679 | 50.899 | −22.401 | 1.00 | 17.10 | C |
| ATOM | 10399 | CZ  | PHE | B | 119 | 65.630 | 50.170 | −21.862 | 1.00 | 17.94 | C |
| ATOM | 10401 | CE2 | PHE | B | 119 | 64.374 | 50.733 | −21.782 | 1.00 | 17.83 | C |
| ATOM | 10403 | CD2 | PHE | B | 119 | 64.163 | 52.031 | −22.244 | 1.00 | 20.16 | C |
| ATOM | 10405 | C   | PHE | B | 119 | 65.411 | 56.626 | −23.095 | 1.00 | 22.24 | C |
| ATOM | 10406 | O   | PHE | B | 119 | 65.893 | 56.758 | −24.223 | 1.00 | 22.20 | O |
| ATOM | 10408 | N   | SER | B | 120 | 64.812 | 57.625 | −22.451 | 1.00 | 24.13 | N |
| ATOM | 10409 | CA  | SER | B | 120 | 64.542 | 58.925 | −23.087 | 1.00 | 25.19 | C |
| ATOM | 10411 | CB  | SER | B | 120 | 63.829 | 59.853 | −22.105 | 1.00 | 25.36 | C |
| ATOM | 10414 | OG  | SER | B | 120 | 64.675 | 60.154 | −21.007 | 1.00 | 25.48 | O |
| ATOM | 10416 | C   | SER | B | 120 | 65.800 | 59.632 | −23.581 | 1.00 | 25.73 | C |
| ATOM | 10417 | O   | SER | B | 120 | 65.824 | 60.162 | −24.688 | 1.00 | 26.49 | O |
| ATOM | 10419 | N   | GLY | B | 121 | 66.839 | 59.636 | −22.753 | 1.00 | 26.46 | N |
| ATOM | 10420 | CA  | GLY | B | 121 | 68.092 | 60.312 | −23.081 | 1.00 | 27.28 | C |
| ATOM | 10423 | C   | GLY | B | 121 | 68.813 | 59.815 | −24.327 | 1.00 | 28.31 | C |
| ATOM | 10424 | O   | GLY | B | 121 | 69.723 | 60.485 | −24.819 | 1.00 | 28.79 | O |
| ATOM | 10426 | N   | PHE | B | 122 | 68.421 | 58.645 | −24.834 | 1.00 | 29.36 | N |
| ATOM | 10427 | CA  | PHE | B | 122 | 69.051 | 58.052 | −26.022 | 1.00 | 30.12 | C |
| ATOM | 10429 | CB  | PHE | B | 122 | 69.321 | 56.565 | −25.779 | 1.00 | 29.81 | C |
| ATOM | 10432 | CG  | PHE | B | 122 | 70.054 | 56.285 | −24.499 | 1.00 | 27.48 | C |
| ATOM | 10433 | CD1 | PHE | B | 122 | 71.432 | 56.437 | −24.427 | 1.00 | 26.82 | C |
| ATOM | 10435 | CE1 | PHE | B | 122 | 72.118 | 56.179 | −23.247 | 1.00 | 27.23 | C |
| ATOM | 10437 | CZ  | PHE | B | 122 | 71.424 | 55.765 | −22.119 | 1.00 | 27.22 | C |
| ATOM | 10439 | CE2 | PHE | B | 122 | 70.045 | 55.609 | −22.177 | 1.00 | 28.12 | C |
| ATOM | 10441 | CD2 | PHE | B | 122 | 69.368 | 55.870 | −23.366 | 1.00 | 28.41 | C |
| ATOM | 10443 | C   | PHE | B | 122 | 68.221 | 58.225 | −27.301 | 1.00 | 31.15 | C |
| ATOM | 10444 | O   | PHE | B | 122 | 68.514 | 57.596 | −28.320 | 1.00 | 30.71 | O |
| ATOM | 10446 | N   | LYS | B | 123 | 67.194 | 59.073 | −27.242 | 1.00 | 32.65 | N |
| ATOM | 10447 | CA  | LYS | B | 123 | 66.355 | 59.370 | −28.401 | 1.00 | 33.99 | C |
| ATOM | 10449 | CB  | LYS | B | 123 | 64.872 | 59.295 | −28.023 | 1.00 | 34.60 | C |
| ATOM | 10452 | CG  | LYS | B | 123 | 64.341 | 57.859 | −27.935 | 1.00 | 37.48 | C |
| ATOM | 10455 | CD  | LYS | B | 123 | 63.127 | 57.727 | −27.014 | 1.00 | 42.03 | C |
| ATOM | 10458 | CE  | LYS | B | 123 | 61.829 | 58.160 | −27.676 | 1.00 | 42.87 | C |
| ATOM | 10461 | NZ  | LYS | B | 123 | 61.236 | 57.080 | −28.516 | 1.00 | 44.11 | N |
| ATOM | 10465 | C   | LYS | B | 123 | 66.710 | 60.743 | −28.972 | 1.00 | 34.42 | C |
| ATOM | 10466 | O   | LYS | B | 123 | 67.167 | 61.628 | −28.245 | 1.00 | 34.43 | O |
| ATOM | 10468 | N   | ASP | B | 124 | 66.500 | 60.906 | −30.277 | 1.00 | 35.22 | N |
| ATOM | 10469 | CA  | ASP | B | 124 | 66.917 | 62.118 | −30.999 | 1.00 | 36.02 | C |
| ATOM | 10471 | CB  | ASP | B | 124 | 67.408 | 61.758 | −32.424 | 1.00 | 35.79 | C |
| ATOM | 10474 | CG  | ASP | B | 124 | 66.304 | 61.198 | −33.327 | 1.00 | 35.25 | C |
| ATOM | 10475 | OD1 | ASP | B | 124 | 65.102 | 61.351 | −33.015 | 1.00 | 34.10 | O |
| ATOM | 10476 | OD2 | ASP | B | 124 | 66.652 | 60.592 | −34.363 | 1.00 | 34.85 | O |
| ATOM | 10477 | C   | ASP | B | 124 | 65.823 | 63.201 | −31.027 | 1.00 | 36.71 | C |
| ATOM | 10478 | O   | ASP | B | 124 | 64.827 | 63.111 | −30.305 | 1.00 | 36.49 | O |
| ATOM | 10480 | N   | GLN | B | 125 | 66.033 | 64.223 | −31.857 | 1.00 | 37.90 | N |
| ATOM | 10481 | CA  | GLN | B | 125 | 65.081 | 65.331 | −32.048 | 1.00 | 38.69 | C |
| ATOM | 10483 | CB  | GLN | B | 125 | 65.479 | 66.158 | −33.284 | 1.00 | 38.91 | C |
| ATOM | 10486 | CG  | GLN | B | 125 | 66.900 | 66.755 | −33.251 | 1.00 | 40.89 | C |
| ATOM | 10489 | CD  | GLN | B | 125 | 66.940 | 68.279 | −33.183 | 1.00 | 43.09 | C |
| ATOM | 10490 | OE1 | GLN | B | 125 | 65.978 | 68.965 | −33.531 | 1.00 | 44.49 | O |
| ATOM | 10491 | NE2 | GLN | B | 125 | 68.074 | 68.814 | −32.746 | 1.00 | 43.53 | N |
| ATOM | 10494 | C   | GLN | B | 125 | 63.626 | 64.865 | −32.222 | 1.00 | 38.47 | C |
| ATOM | 10495 | O   | GLN | B | 125 | 62.710 | 65.437 | −31.625 | 1.00 | 38.32 | O |
| ATOM | 10497 | N   | ASN | B | 126 | 63.433 | 63.821 | −33.029 | 1.00 | 38.16 | N |
| ATOM | 10498 | CA  | ASN | B | 126 | 62.099 | 63.376 | −33.454 | 1.00 | 37.55 | C |
| ATOM | 10500 | CB  | ASN | B | 126 | 62.119 | 63.054 | −34.953 | 1.00 | 37.83 | C |
| ATOM | 10503 | CG  | ASN | B | 126 | 62.911 | 64.069 | −35.759 | 1.00 | 38.62 | C |
| ATOM | 10504 | OD1 | ASN | B | 126 | 62.735 | 65.278 | −35.606 | 1.00 | 39.51 | O |
| ATOM | 10505 | ND2 | ASN | B | 126 | 63.794 | 63.577 | −36.620 | 1.00 | 37.66 | N |
| ATOM | 10508 | C   | ASN | B | 126 | 61.569 | 62.158 | −32.688 | 1.00 | 36.58 | C |
| ATOM | 10509 | O   | ASN | B | 126 | 60.651 | 61.481 | −33.154 | 1.00 | 35.56 | O |
| ATOM | 10511 | N   | GLY | B | 127 | 62.147 | 61.881 | −31.520 | 1.00 | 36.10 | N |
| ATOM | 10512 | CA  | GLY | B | 127 | 61.726 | 60.748 | −30.692 | 1.00 | 35.68 | C |
| ATOM | 10515 | C   | GLY | B | 127 | 62.149 | 59.386 | −31.224 | 1.00 | 35.16 | C |
| ATOM | 10516 | O   | GLY | B | 127 | 61.557 | 58.363 | −30.863 | 1.00 | 34.95 | O |
| ATOM | 10518 | N   | ASN | B | 128 | 63.168 | 59.373 | −32.082 | 1.00 | 34.38 | N |
| ATOM | 10519 | CA  | ASN | B | 128 | 63.747 | 58.133 | −32.594 | 1.00 | 33.52 | C |
| ATOM | 10521 | CB  | ASN | B | 128 | 63.949 | 58.223 | −34.108 | 1.00 | 33.53 | C |
| ATOM | 10524 | CG  | ASN | B | 128 | 62.639 | 58.247 | −34.872 | 1.00 | 33.33 | C |
| ATOM | 10525 | OD1 | ASN | B | 128 | 61.733 | 57.456 | −34.602 | 1.00 | 33.76 | O |
| ATOM | 10526 | ND2 | ASN | B | 128 | 62.535 | 59.152 | −35.837 | 1.00 | 32.74 | N |
| ATOM | 10529 | C   | ASN | B | 128 | 65.078 | 57.845 | −31.907 | 1.00 | 32.50 | C |
| ATOM | 10530 | O   | ASN | B | 128 | 65.786 | 58.766 | −31.502 | 1.00 | 32.13 | O |
| ATOM | 10532 | N   | PHE | B | 129 | 65.413 | 56.566 | −31.770 | 1.00 | 31.65 | N |
| ATOM | 10533 | CA  | PHE | B | 129 | 66.679 | 56.173 | −31.154 | 1.00 | 30.65 | C |
| ATOM | 10535 | CB  | PHE | B | 129 | 66.744 | 54.650 | −30.954 | 1.00 | 30.52 | C |

APPENDIX 1-continued

| ATOM | 10538 | CG | PHE | B | 129 | 65.924 | 54.155 | −29.791 | 1.00 | 27.36 | C |
| ATOM | 10539 | CD1 | PHE | B | 129 | 66.433 | 54.196 | −28.502 | 1.00 | 26.85 | C |
| ATOM | 10541 | CE1 | PHE | B | 129 | 65.683 | 53.750 | −27.422 | 1.00 | 25.98 | C |
| ATOM | 10543 | CZ | PHE | B | 129 | 64.405 | 53.255 | −27.622 | 1.00 | 26.31 | C |
| ATOM | 10545 | CE2 | PHE | B | 129 | 63.882 | 53.207 | −28.899 | 1.00 | 26.76 | C |
| ATOM | 10547 | CD2 | PHE | B | 129 | 64.645 | 53.661 | −29.981 | 1.00 | 27.19 | C |
| ATOM | 10549 | C | PHE | B | 129 | 67.845 | 56.664 | −32.012 | 1.00 | 30.53 | C |
| ATOM | 10550 | O | PHE | B | 129 | 67.877 | 56.421 | −33.218 | 1.00 | 30.46 | O |
| ATOM | 10552 | N | LEU | B | 130 | 68.782 | 57.372 | −31.379 | 1.00 | 30.69 | N |
| ATOM | 10553 | CA | LEU | B | 130 | 69.953 | 57.939 | −32.058 | 1.00 | 30.52 | C |
| ATOM | 10555 | CB | LEU | B | 130 | 70.924 | 58.543 | −31.034 | 1.00 | 30.31 | C |
| ATOM | 10558 | CG | LEU | B | 130 | 70.550 | 59.935 | −30.506 | 1.00 | 31.18 | C |
| ATOM | 10560 | CD1 | LEU | B | 130 | 71.216 | 60.226 | −29.164 | 1.00 | 30.08 | C |
| ATOM | 10564 | CD2 | LEU | B | 130 | 70.905 | 61.026 | −31.528 | 1.00 | 30.64 | C |
| ATOM | 10568 | C | LEU | B | 130 | 70.674 | 56.903 | −32.922 | 1.00 | 30.82 | C |
| ATOM | 10569 | O | LEU | B | 130 | 70.952 | 55.796 | −32.473 | 1.00 | 30.38 | O |
| ATOM | 10571 | N | GLU | B | 131 | 70.977 | 57.286 | −34.159 | 1.00 | 32.16 | N |
| ATOM | 10572 | CA | GLU | B | 131 | 71.503 | 56.365 | −35.168 | 1.00 | 33.12 | C |
| ATOM | 10574 | CB | GLU | B | 131 | 71.568 | 57.065 | −36.538 | 1.00 | 33.71 | C |
| ATOM | 10577 | CG | GLU | B | 131 | 71.897 | 56.151 | −37.733 | 1.00 | 36.43 | C |
| ATOM | 10580 | CD | GLU | B | 131 | 70.710 | 55.319 | −38.223 | 1.00 | 40.75 | C |
| ATOM | 10581 | OE1 | GLU | B | 131 | 69.735 | 55.119 | −37.462 | 1.00 | 41.45 | O |
| ATOM | 10582 | OE2 | GLU | B | 131 | 70.761 | 54.855 | −39.383 | 1.00 | 43.48 | O |
| ATOM | 10583 | C | GLU | B | 131 | 72.879 | 55.799 | −34.811 | 1.00 | 33.09 | C |
| ATOM | 10584 | O | GLU | B | 131 | 73.115 | 54.606 | −34.992 | 1.00 | 33.35 | O |
| ATOM | 10586 | N | ASN | B | 132 | 73.779 | 56.641 | −34.304 | 1.00 | 32.84 | N |
| ATOM | 10587 | CA | ASN | B | 132 | 75.158 | 56.209 | −34.023 | 1.00 | 33.04 | C |
| ATOM | 10589 | CB | ASN | B | 132 | 76.092 | 57.424 | −33.821 | 1.00 | 33.50 | C |
| ATOM | 10592 | CG | ASN | B | 132 | 75.826 | 58.187 | −32.522 | 1.00 | 35.16 | C |
| ATOM | 10593 | OD1 | ASN | B | 132 | 75.156 | 57.695 | −31.610 | 1.00 | 39.01 | O |
| ATOM | 10594 | ND2 | ASN | B | 132 | 76.369 | 59.396 | −32.437 | 1.00 | 36.19 | N |
| ATOM | 10597 | C | ASN | B | 132 | 75.312 | 55.196 | −32.869 | 1.00 | 32.26 | C |
| ATOM | 10598 | O | ASN | B | 132 | 76.409 | 54.699 | −32.623 | 1.00 | 31.64 | O |
| ATOM | 10600 | N | LEU | B | 133 | 74.217 | 54.900 | −32.170 | 1.00 | 32.21 | N |
| ATOM | 10601 | CA | LEU | B | 133 | 74.195 | 53.828 | −31.166 | 1.00 | 32.15 | C |
| ATOM | 10603 | CB | LEU | B | 133 | 72.879 | 53.847 | −30.373 | 1.00 | 31.75 | C |
| ATOM | 10606 | CG | LEU | B | 133 | 72.699 | 54.968 | −29.346 | 1.00 | 30.29 | C |
| ATOM | 10608 | CD1 | LEU | B | 133 | 71.251 | 55.031 | −28.881 | 1.00 | 28.69 | C |
| ATOM | 10612 | CD2 | LEU | B | 133 | 73.638 | 54.778 | −28.164 | 1.00 | 25.64 | C |
| ATOM | 10616 | C | LEU | B | 133 | 74.397 | 52.434 | −31.774 | 1.00 | 32.15 | C |
| ATOM | 10617 | O | LEU | B | 133 | 74.749 | 51.494 | −31.061 | 1.00 | 32.64 | O |
| ATOM | 10619 | N | LYS | B | 134 | 74.174 | 52.301 | −33.079 | 1.00 | 31.79 | N |
| ATOM | 10620 | CA | LYS | B | 134 | 74.377 | 51.030 | −33.773 | 1.00 | 32.43 | C |
| ATOM | 10622 | CB | LYS | B | 134 | 73.833 | 51.106 | −35.206 | 1.00 | 32.65 | C |
| ATOM | 10625 | CG | LYS | B | 134 | 74.690 | 51.920 | −36.177 | 1.00 | 36.00 | C |
| ATOM | 10628 | CD | LYS | B | 134 | 73.923 | 52.234 | −37.451 | 1.00 | 36.62 | C |
| ATOM | 10631 | CE | LYS | B | 134 | 74.789 | 52.877 | −38.511 | 1.00 | 36.99 | C |
| ATOM | 10634 | NZ | LYS | B | 134 | 73.959 | 53.264 | −39.689 | 1.00 | 37.62 | N |
| ATOM | 10638 | C | LYS | B | 134 | 75.842 | 50.585 | −33.793 | 1.00 | 32.51 | C |
| ATOM | 10639 | O | LYS | B | 134 | 76.126 | 49.406 | −33.988 | 1.00 | 32.95 | O |
| ATOM | 10641 | N | GLU | B | 135 | 76.765 | 51.524 | −33.592 | 1.00 | 32.81 | N |
| ATOM | 10642 | CA | GLU | B | 135 | 78.191 | 51.200 | −33.495 | 1.00 | 33.04 | C |
| ATOM | 10644 | CB | GLU | B | 135 | 79.042 | 52.470 | −33.565 | 1.00 | 33.88 | C |
| ATOM | 10647 | CG | GLU | B | 135 | 78.901 | 53.249 | −34.873 | 1.00 | 37.74 | C |
| ATOM | 10650 | CD | GLU | B | 135 | 79.689 | 54.550 | −34.872 | 1.00 | 43.53 | C |
| ATOM | 10651 | OE1 | GLU | B | 135 | 80.633 | 54.690 | −34.057 | 1.00 | 43.50 | O |
| ATOM | 10652 | OE2 | GLU | B | 135 | 79.365 | 55.435 | −35.698 | 1.00 | 47.71 | O |
| ATOM | 10653 | C | GLU | B | 135 | 78.534 | 50.442 | −32.215 | 1.00 | 32.14 | C |
| ATOM | 10654 | O | GLU | B | 135 | 79.621 | 49.875 | −32.113 | 1.00 | 32.81 | O |
| ATOM | 10656 | N | ASP | B | 136 | 77.621 | 50.453 | −31.239 | 1.00 | 30.60 | N |
| ATOM | 10657 | CA | ASP | B | 136 | 77.782 | 49.695 | −30.000 | 1.00 | 29.16 | C |
| ATOM | 10659 | CB | ASP | B | 136 | 77.489 | 50.593 | −28.794 | 1.00 | 29.30 | C |
| ATOM | 10662 | CG | ASP | B | 136 | 77.839 | 49.938 | −27.468 | 1.00 | 31.46 | C |
| ATOM | 10663 | OD1 | ASP | B | 136 | 78.540 | 48.901 | −27.456 | 1.00 | 35.77 | O |
| ATOM | 10664 | OD2 | ASP | B | 136 | 77.406 | 50.466 | −26.425 | 1.00 | 35.43 | O |
| ATOM | 10665 | C | ASP | B | 136 | 76.859 | 48.471 | −30.010 | 1.00 | 27.89 | C |
| ATOM | 10666 | O | ASP | B | 136 | 75.735 | 48.513 | −29.506 | 1.00 | 27.26 | O |
| ATOM | 10668 | N | ILE | B | 137 | 77.356 | 47.379 | −30.583 | 1.00 | 26.87 | N |
| ATOM | 10669 | CA | ILE | B | 137 | 76.580 | 46.148 | −30.737 | 1.00 | 26.04 | C |
| ATOM | 10671 | CB | ILE | B | 137 | 77.390 | 45.066 | −31.487 | 1.00 | 25.62 | C |
| ATOM | 10673 | CG1 | ILE | B | 137 | 77.815 | 45.559 | −32.877 | 1.00 | 27.86 | C |
| ATOM | 10676 | CD1 | ILE | B | 137 | 76.657 | 45.925 | −33.792 | 1.00 | 29.16 | C |
| ATOM | 10680 | CG2 | ILE | B | 137 | 76.584 | 43.792 | −31.633 | 1.00 | 24.19 | C |
| ATOM | 10684 | C | ILE | B | 137 | 76.146 | 45.591 | −29.382 | 1.00 | 26.70 | C |
| ATOM | 10685 | O | ILE | B | 137 | 75.042 | 45.071 | −29.242 | 1.00 | 27.81 | O |
| ATOM | 10687 | N | LYS | B | 138 | 77.026 | 45.706 | −28.392 | 1.00 | 27.23 | N |
| ATOM | 10688 | CA | LYS | B | 138 | 76.743 | 45.284 | −27.020 | 1.00 | 26.65 | C |
| ATOM | 10690 | CB | LYS | B | 138 | 77.948 | 45.605 | −26.123 | 1.00 | 27.89 | C |
| ATOM | 10693 | CG | LYS | B | 138 | 78.281 | 44.564 | −25.065 | 1.00 | 31.52 | C |
| ATOM | 10696 | CD | LYS | B | 138 | 79.355 | 45.109 | −24.115 | 1.00 | 38.18 | C |

APPENDIX 1-continued

| | | | | | | | | | | |
|---|---|---|---|---|---|---|---|---|---|---|
| ATOM | 10699 | CE | LYS | B | 138 | 79.767 | 44.111 | −23.024 | 1.00 | 40.71 | C |
| ATOM | 10702 | NZ | LYS | B | 138 | 81.165 | 43.608 | −23.172 | 1.00 | 39.68 | N |
| ATOM | 10706 | C | LYS | B | 138 | 75.487 | 45.990 | −26.491 | 1.00 | 25.04 | C |
| ATOM | 10707 | O | LYS | B | 138 | 74.595 | 45.347 | −25.921 | 1.00 | 24.33 | O |
| ATOM | 10709 | N | ALA | B | 139 | 75.425 | 47.310 | −26.685 | 1.00 | 23.67 | N |
| ATOM | 10710 | CA | ALA | B | 139 | 74.258 | 48.110 | −26.280 | 1.00 | 23.10 | C |
| ATOM | 10712 | CB | ALA | B | 139 | 74.537 | 49.605 | −26.450 | 1.00 | 22.12 | C |
| ATOM | 10716 | C | ALA | B | 139 | 72.996 | 47.715 | −27.059 | 1.00 | 22.42 | C |
| ATOM | 10717 | O | ALA | B | 139 | 71.910 | 47.588 | −26.486 | 1.00 | 22.30 | O |
| ATOM | 10719 | N | ILE | B | 140 | 73.150 | 47.523 | −28.364 | 1.00 | 21.67 | N |
| ATOM | 10720 | CA | ILE | B | 140 | 72.043 | 47.111 | −29.216 | 1.00 | 20.72 | C |
| ATOM | 10722 | CB | ILE | B | 140 | 72.481 | 47.013 | −30.693 | 1.00 | 20.38 | C |
| ATOM | 10724 | CG1 | ILE | B | 140 | 72.768 | 48.406 | −31.249 | 1.00 | 20.37 | C |
| ATOM | 10727 | CD1 | ILE | B | 140 | 71.550 | 49.299 | −31.327 | 1.00 | 17.94 | C |
| ATOM | 10731 | CG2 | ILE | B | 140 | 71.410 | 46.343 | −31.535 | 1.00 | 20.43 | C |
| ATOM | 10735 | C | ILE | B | 140 | 71.465 | 45.781 | −28.740 | 1.00 | 20.20 | C |
| ATOM | 10736 | O | ILE | B | 140 | 70.243 | 45.630 | −28.647 | 1.00 | 20.13 | O |
| ATOM | 10738 | N | LEU | B | 141 | 72.341 | 44.832 | −28.419 | 1.00 | 19.56 | N |
| ATOM | 10739 | CA | LEU | B | 141 | 71.900 | 43.532 | −27.903 | 1.00 | 19.42 | C |
| ATOM | 10741 | CB | LEU | B | 141 | 73.076 | 42.564 | −27.736 | 1.00 | 18.92 | C |
| ATOM | 10744 | CG | LEU | B | 141 | 73.594 | 41.924 | −29.025 | 1.00 | 20.88 | C |
| ATOM | 10746 | CD1 | LEU | B | 141 | 74.872 | 41.159 | −28.749 | 1.00 | 18.48 | C |
| ATOM | 10750 | CD2 | LEU | B | 141 | 72.543 | 41.010 | −29.649 | 1.00 | 19.79 | C |
| ATOM | 10754 | C | LEU | B | 141 | 71.141 | 43.649 | −26.583 | 1.00 | 18.99 | C |
| ATOM | 10755 | O | LEU | B | 141 | 70.174 | 42.928 | −26.372 | 1.00 | 18.79 | O |
| ATOM | 10757 | N | SER | B | 142 | 71.576 | 44.549 | −25.701 | 1.00 | 18.99 | N |
| ATOM | 10758 | CA | SER | B | 142 | 70.907 | 44.738 | −24.409 | 1.00 | 18.94 | C |
| ATOM | 10760 | CB | SER | B | 142 | 71.745 | 45.601 | −23.468 | 1.00 | 18.67 | C |
| ATOM | 10763 | OG | SER | B | 142 | 72.985 | 44.989 | −23.197 | 1.00 | 23.20 | O |
| ATOM | 10765 | C | SER | B | 142 | 69.542 | 45.377 | −24.598 | 1.00 | 18.42 | C |
| ATOM | 10766 | O | SER | B | 142 | 68.583 | 45.031 | −23.903 | 1.00 | 18.43 | O |
| ATOM | 10768 | N | LEU | B | 143 | 69.460 | 46.314 | −25.537 | 1.00 | 17.73 | N |
| ATOM | 10769 | CA | LEU | B | 143 | 68.187 | 46.919 | −25.887 | 1.00 | 17.79 | C |
| ATOM | 10771 | CB | LEU | B | 143 | 68.397 | 48.034 | −26.912 | 1.00 | 17.79 | C |
| ATOM | 10774 | CG | LEU | B | 143 | 67.188 | 48.927 | −27.208 | 1.00 | 18.37 | C |
| ATOM | 10776 | CD1 | LEU | B | 143 | 66.690 | 49.626 | −25.948 | 1.00 | 15.94 | C |
| ATOM | 10780 | CD2 | LEU | B | 143 | 67.541 | 49.937 | −28.294 | 1.00 | 13.43 | C |
| ATOM | 10784 | C | LEU | B | 143 | 67.240 | 45.840 | −26.426 | 1.00 | 17.63 | C |
| ATOM | 10785 | O | LEU | B | 143 | 66.132 | 45.662 | −25.909 | 1.00 | 17.09 | O |
| ATOM | 10787 | N | TYR | B | 144 | 67.697 | 45.105 | −27.441 | 1.00 | 16.96 | N |
| ATOM | 10788 | CA | TYR | B | 144 | 66.934 | 43.989 | −27.999 | 1.00 | 16.71 | C |
| ATOM | 10790 | CB | TYR | B | 144 | 67.793 | 43.179 | −28.979 | 1.00 | 16.77 | C |
| ATOM | 10793 | CG | TYR | B | 144 | 67.160 | 41.896 | −29.497 | 1.00 | 16.66 | C |
| ATOM | 10794 | CD1 | TYR | B | 144 | 66.195 | 41.920 | −30.500 | 1.00 | 18.99 | C |
| ATOM | 10796 | CE1 | TYR | B | 144 | 65.617 | 40.733 | −30.981 | 1.00 | 18.24 | C |
| ATOM | 10798 | CZ | TYR | B | 144 | 66.018 | 39.515 | −30.457 | 1.00 | 20.28 | C |
| ATOM | 10799 | OH | TYR | B | 144 | 65.455 | 38.344 | −30.921 | 1.00 | 22.86 | O |
| ATOM | 10801 | CE2 | TYR | B | 144 | 66.982 | 39.470 | −29.461 | 1.00 | 18.13 | C |
| ATOM | 10803 | CD2 | TYR | B | 144 | 67.544 | 40.654 | −28.990 | 1.00 | 20.74 | C |
| ATOM | 10805 | C | TYR | B | 144 | 66.412 | 43.093 | −26.887 | 1.00 | 16.99 | C |
| ATOM | 10806 | O | TYR | B | 144 | 65.208 | 42.845 | −26.799 | 1.00 | 18.37 | O |
| ATOM | 10808 | N | GLU | B | 145 | 67.309 | 42.636 | −26.019 | 1.00 | 16.70 | N |
| ATOM | 10809 | CA | GLU | B | 145 | 66.928 | 41.699 | −24.956 | 1.00 | 17.05 | C |
| ATOM | 10811 | CB | GLU | B | 145 | 68.162 | 41.137 | −24.248 | 1.00 | 17.15 | C |
| ATOM | 10814 | CG | GLU | B | 145 | 69.093 | 40.339 | −25.162 | 1.00 | 18.79 | C |
| ATOM | 10817 | CD | GLU | B | 145 | 68.601 | 38.946 | −25.483 | 1.00 | 23.46 | C |
| ATOM | 10818 | OE1 | GLU | B | 145 | 67.435 | 38.606 | −25.169 | 1.00 | 26.98 | O |
| ATOM | 10819 | OE2 | GLU | B | 145 | 69.400 | 38.176 | −26.054 | 1.00 | 29.40 | O |
| ATOM | 10820 | C | GLU | B | 145 | 65.964 | 42.304 | −23.934 | 1.00 | 16.69 | C |
| ATOM | 10821 | O | GLU | B | 145 | 65.086 | 41.602 | −23.434 | 1.00 | 17.65 | O |
| ATOM | 10823 | N | ALA | B | 146 | 66.115 | 43.594 | −23.635 | 1.00 | 16.19 | N |
| ATOM | 10824 | CA | ALA | B | 146 | 65.214 | 44.278 | −22.696 | 1.00 | 15.30 | C |
| ATOM | 10826 | CB | ALA | B | 146 | 65.763 | 45.640 | −22.314 | 1.00 | 14.49 | C |
| ATOM | 10830 | C | ALA | B | 146 | 63.802 | 44.425 | −23.266 | 1.00 | 15.06 | C |
| ATOM | 10831 | O | ALA | B | 146 | 62.816 | 44.303 | −22.531 | 1.00 | 14.47 | O |
| ATOM | 10833 | N | SER | B | 147 | 63.707 | 44.667 | −24.570 | 1.00 | 14.70 | N |
| ATOM | 10834 | CA | SER | B | 147 | 62.422 | 44.946 | −25.205 | 1.00 | 15.84 | C |
| ATOM | 10836 | CB | SER | B | 147 | 62.589 | 45.147 | −26.718 | 1.00 | 15.84 | C |
| ATOM | 10839 | OG | SER | B | 147 | 62.818 | 43.920 | −27.383 | 1.00 | 17.77 | O |
| ATOM | 10841 | C | SER | B | 147 | 61.386 | 43.851 | −24.931 | 1.00 | 17.09 | C |
| ATOM | 10842 | O | SER | B | 147 | 60.203 | 44.138 | −24.734 | 1.00 | 18.31 | O |
| ATOM | 10844 | N | PHE | B | 148 | 61.833 | 42.600 | −24.878 | 1.00 | 17.25 | N |
| ATOM | 10845 | CA | PHE | B | 148 | 60.922 | 41.484 | −24.649 | 1.00 | 16.14 | C |
| ATOM | 10847 | CB | PHE | B | 148 | 61.609 | 40.154 | −24.964 | 1.00 | 15.49 | C |
| ATOM | 10850 | CG | PHE | B | 148 | 61.971 | 40.012 | −26.407 | 1.00 | 14.49 | C |
| ATOM | 10851 | CD1 | PHE | B | 148 | 61.050 | 39.541 | −27.324 | 1.00 | 14.20 | C |
| ATOM | 10853 | CE1 | PHE | B | 148 | 61.381 | 39.431 | −28.672 | 1.00 | 14.58 | C |
| ATOM | 10855 | CZ | PHE | B | 148 | 62.629 | 39.814 | −29.115 | 1.00 | 11.47 | C |
| ATOM | 10857 | CE2 | PHE | B | 148 | 63.553 | 40.296 | −28.208 | 1.00 | 15.42 | C |
| ATOM | 10859 | CD2 | PHE | B | 148 | 63.220 | 40.398 | −26.861 | 1.00 | 13.40 | C |

APPENDIX 1-continued

| ATOM | 10861 | C | PHE | B | 148 | 60.314 | 41.456 | −23.255 | 1.00 | 16.76 | C |
| --- | --- | --- | --- | --- | --- | --- | --- | --- | --- | --- | --- |
| ATOM | 10862 | O | PHE | B | 148 | 59.461 | 40.612 | −22.988 | 1.00 | 18.26 | O |
| ATOM | 10864 | N | LEU | B | 149 | 60.725 | 42.365 | −22.369 | 1.00 | 17.06 | N |
| ATOM | 10865 | CA | LEU | B | 149 | 60.083 | 42.475 | −21.045 | 1.00 | 17.69 | C |
| ATOM | 10867 | CB | LEU | B | 149 | 61.120 | 42.731 | −19.937 | 1.00 | 16.45 | C |
| ATOM | 10870 | CG | LEU | B | 149 | 61.863 | 41.475 | −19.453 | 1.00 | 16.92 | C |
| ATOM | 10872 | CD1 | LEU | B | 149 | 62.801 | 40.939 | −20.521 | 1.00 | 9.82 | C |
| ATOM | 10876 | CD2 | LEU | B | 149 | 62.634 | 41.738 | −18.158 | 1.00 | 14.46 | C |
| ATOM | 10880 | C | LEU | B | 149 | 58.978 | 43.545 | −21.042 | 1.00 | 18.44 | C |
| ATOM | 10881 | O | LEU | B | 149 | 58.475 | 43.927 | −19.983 | 1.00 | 19.20 | O |
| ATOM | 10883 | N | ALA | B | 150 | 58.585 | 43.998 | −22.232 | 1.00 | 18.19 | N |
| ATOM | 10884 | CA | ALA | B | 150 | 57.581 | 45.050 | −22.368 | 1.00 | 17.96 | C |
| ATOM | 10886 | CB | ALA | B | 150 | 57.379 | 45.412 | −23.832 | 1.00 | 16.76 | C |
| ATOM | 10890 | C | ALA | B | 150 | 56.251 | 44.653 | −21.755 | 1.00 | 18.74 | C |
| ATOM | 10891 | O | ALA | B | 150 | 55.888 | 43.474 | −21.734 | 1.00 | 19.06 | O |
| ATOM | 10893 | N | LEU | B | 151 | 55.541 | 45.655 | −21.248 | 1.00 | 18.68 | N |
| ATOM | 10894 | CA | LEU | B | 151 | 54.165 | 45.496 | −20.819 | 1.00 | 19.10 | C |
| ATOM | 10896 | CB | LEU | B | 151 | 53.954 | 46.127 | −19.442 | 1.00 | 19.19 | C |
| ATOM | 10899 | CG | LEU | B | 151 | 54.793 | 45.595 | −18.277 | 1.00 | 19.03 | C |
| ATOM | 10901 | CD1 | LEU | B | 151 | 54.565 | 46.447 | −17.023 | 1.00 | 15.48 | C |
| ATOM | 10905 | CD2 | LEU | B | 151 | 54.485 | 44.130 | −18.008 | 1.00 | 11.45 | C |
| ATOM | 10909 | C | LEU | B | 151 | 53.285 | 46.189 | −21.849 | 1.00 | 19.15 | C |
| ATOM | 10910 | O | LEU | B | 151 | 53.782 | 46.932 | −22.702 | 1.00 | 19.79 | O |
| ATOM | 10912 | N | GLU | B | 152 | 51.979 | 45.952 | −21.783 | 1.00 | 18.56 | N |
| ATOM | 10913 | CA | GLU | B | 152 | 51.060 | 46.650 | −22.672 | 1.00 | 17.83 | C |
| ATOM | 10915 | CB | GLU | B | 152 | 49.606 | 46.302 | −22.369 | 1.00 | 17.60 | C |
| ATOM | 10918 | CG | GLU | B | 152 | 49.134 | 45.017 | −23.013 | 1.00 | 21.05 | C |
| ATOM | 10921 | CD | GLU | B | 152 | 47.628 | 44.969 | −23.136 | 1.00 | 23.21 | C |
| ATOM | 10922 | OE1 | GLU | B | 152 | 46.987 | 44.275 | −22.317 | 1.00 | 24.13 | O |
| ATOM | 10923 | OE2 | GLU | B | 152 | 47.091 | 45.649 | −24.037 | 1.00 | 22.06 | O |
| ATOM | 10924 | C | GLU | B | 152 | 51.253 | 48.148 | −22.540 | 1.00 | 17.26 | C |
| ATOM | 10925 | O | GLU | B | 152 | 51.424 | 48.665 | −21.435 | 1.00 | 17.17 | O |
| ATOM | 10927 | N | GLY | B | 153 | 51.236 | 48.833 | −23.678 | 1.00 | 17.21 | N |
| ATOM | 10928 | CA | GLY | B | 153 | 51.340 | 50.284 | −23.708 | 1.00 | 16.98 | C |
| ATOM | 10931 | C | GLY | B | 153 | 52.751 | 50.832 | −23.609 | 1.00 | 17.22 | C |
| ATOM | 10932 | O | GLY | B | 153 | 52.931 | 52.043 | −23.609 | 1.00 | 18.36 | O |
| ATOM | 10934 | N | GLU | B | 154 | 53.758 | 49.965 | −23.520 | 1.00 | 17.26 | N |
| ATOM | 10935 | CA | GLU | B | 154 | 55.147 | 50.426 | −23.521 | 1.00 | 16.95 | C |
| ATOM | 10937 | CB | GLU | B | 154 | 56.031 | 49.548 | −22.625 | 1.00 | 16.80 | C |
| ATOM | 10940 | CG | GLU | B | 154 | 55.745 | 49.761 | −21.141 | 1.00 | 16.73 | C |
| ATOM | 10943 | CD | GLU | B | 154 | 56.617 | 48.921 | −20.222 | 1.00 | 18.67 | C |
| ATOM | 10944 | OE1 | GLU | B | 154 | 56.961 | 47.776 | −20.586 | 1.00 | 15.50 | O |
| ATOM | 10945 | OE2 | GLU | B | 154 | 56.946 | 49.401 | −19.116 | 1.00 | 16.67 | O |
| ATOM | 10946 | C | GLU | B | 154 | 55.652 | 50.482 | −24.959 | 1.00 | 16.64 | C |
| ATOM | 10947 | O | GLU | B | 154 | 56.440 | 49.646 | −25.403 | 1.00 | 17.07 | O |
| ATOM | 10949 | N | ASN | B | 155 | 55.168 | 51.490 | −25.673 | 1.00 | 16.57 | N |
| ATOM | 10950 | CA | ASN | B | 155 | 55.489 | 51.705 | −27.087 | 1.00 | 17.00 | C |
| ATOM | 10952 | CB | ASN | B | 155 | 54.658 | 52.874 | −27.647 | 1.00 | 16.55 | C |
| ATOM | 10955 | CG | ASN | B | 155 | 54.862 | 54.169 | −26.862 | 1.00 | 17.46 | C |
| ATOM | 10956 | OD1 | ASN | B | 155 | 54.556 | 54.244 | −25.665 | 1.00 | 16.21 | O |
| ATOM | 10957 | ND2 | ASN | B | 155 | 55.379 | 55.195 | −27.534 | 1.00 | 15.36 | N |
| ATOM | 10960 | C | ASN | B | 155 | 56.978 | 51.947 | −27.374 | 1.00 | 17.12 | C |
| ATOM | 10961 | O | ASN | B | 155 | 57.455 | 51.623 | −28.464 | 1.00 | 17.70 | O |
| ATOM | 10963 | N | ILE | B | 156 | 57.705 | 52.514 | −26.410 | 1.00 | 16.75 | N |
| ATOM | 10964 | CA | ILE | B | 156 | 59.142 | 52.751 | −26.579 | 1.00 | 17.02 | C |
| ATOM | 10966 | CB | ILE | B | 156 | 59.747 | 53.516 | −25.394 | 1.00 | 16.98 | C |
| ATOM | 10968 | CG1 | ILE | B | 156 | 59.209 | 54.944 | −25.344 | 1.00 | 18.01 | C |
| ATOM | 10971 | CD1 | ILE | B | 156 | 59.759 | 55.743 | −24.174 | 1.00 | 22.11 | C |
| ATOM | 10975 | CG2 | ILE | B | 156 | 61.263 | 53.528 | −25.489 | 1.00 | 15.85 | C |
| ATOM | 10979 | C | ILE | B | 156 | 59.890 | 51.431 | −26.701 | 1.00 | 17.81 | C |
| ATOM | 10980 | O | ILE | B | 156 | 60.736 | 51.265 | −27.584 | 1.00 | 18.73 | O |
| ATOM | 10982 | N | LEU | B | 157 | 59.588 | 50.502 | −25.800 | 1.00 | 17.50 | N |
| ATOM | 10983 | CA | LEU | B | 157 | 60.209 | 49.189 | −25.841 | 1.00 | 17.85 | C |
| ATOM | 10985 | CB | LEU | B | 157 | 59.764 | 48.326 | −24.649 | 1.00 | 18.12 | C |
| ATOM | 10988 | CG | LEU | B | 157 | 60.213 | 48.793 | −23.257 | 1.00 | 16.86 | C |
| ATOM | 10990 | CD1 | LEU | B | 157 | 59.785 | 47.793 | −22.187 | 1.00 | 15.12 | C |
| ATOM | 10994 | CD2 | LEU | B | 157 | 61.715 | 49.001 | −23.211 | 1.00 | 14.35 | C |
| ATOM | 10998 | C | LEU | B | 157 | 59.886 | 48.494 | −27.159 | 1.00 | 18.64 | C |
| ATOM | 10999 | O | LEU | B | 157 | 60.739 | 47.810 | −27.718 | 1.00 | 18.33 | O |
| ATOM | 11001 | N | ASP | B | 158 | 58.660 | 48.677 | −27.656 | 1.00 | 19.51 | N |
| ATOM | 11002 | CA | ASP | B | 158 | 58.270 | 48.138 | −28.965 | 1.00 | 19.82 | C |
| ATOM | 11004 | CB | ASP | B | 158 | 56.789 | 48.399 | −29.255 | 1.00 | 19.82 | C |
| ATOM | 11007 | CG | ASP | B | 158 | 55.874 | 47.369 | −28.617 | 1.00 | 22.44 | C |
| ATOM | 11008 | OD1 | ASP | B | 158 | 56.302 | 46.678 | −27.666 | 1.00 | 25.77 | O |
| ATOM | 11009 | OD2 | ASP | B | 158 | 54.713 | 47.259 | −29.068 | 1.00 | 24.60 | O |
| ATOM | 11010 | C | ASP | B | 158 | 59.124 | 48.732 | −30.078 | 1.00 | 19.74 | C |
| ATOM | 11011 | O | ASP | B | 158 | 59.614 | 48.012 | −30.943 | 1.00 | 19.23 | O |
| ATOM | 11013 | N | GLU | B | 159 | 59.300 | 50.049 | −30.044 | 1.00 | 20.53 | N |
| ATOM | 11014 | CA | GLU | B | 159 | 60.181 | 50.735 | −30.989 | 1.00 | 21.17 | C |
| ATOM | 11016 | CB | GLU | B | 159 | 60.149 | 52.248 | −30.754 | 1.00 | 22.23 | C |

APPENDIX 1-continued

| | | | | | | | | | | |
|---|---|---|---|---|---|---|---|---|---|---|
| ATOM | 11019 | CG | GLU | B | 159 | 58.810 | 52.912 | −31.059 | 1.00 | 25.93 | C |
| ATOM | 11022 | CD | GLU | B | 159 | 58.660 | 54.274 | −30.385 | 1.00 | 32.63 | C |
| ATOM | 11023 | OE1 | GLU | B | 159 | 59.692 | 54.914 | −30.047 | 1.00 | 33.46 | O |
| ATOM | 11024 | OE2 | GLU | B | 159 | 57.496 | 54.703 | −30.199 | 1.00 | 34.47 | O |
| ATOM | 11025 | C | GLU | B | 159 | 61.619 | 50.239 | −30.850 | 1.00 | 20.42 | C |
| ATOM | 11026 | O | GLU | B | 159 | 62.309 | 50.018 | −31.846 | 1.00 | 20.71 | O |
| ATOM | 11028 | N | ALA | B | 160 | 62.058 | 50.070 | −29.605 | 1.00 | 19.27 | N |
| ATOM | 11029 | CA | ALA | B | 160 | 63.400 | 49.585 | −29.318 | 1.00 | 18.91 | C |
| ATOM | 11031 | CB | ALA | B | 160 | 63.607 | 49.463 | −27.821 | 1.00 | 18.45 | C |
| ATOM | 11035 | C | ALA | B | 160 | 63.647 | 48.245 | −29.996 | 1.00 | 18.88 | C |
| ATOM | 11036 | O | ALA | B | 160 | 64.690 | 48.037 | −30.600 | 1.00 | 19.92 | O |
| ATOM | 11038 | N | LYS | B | 161 | 62.681 | 47.342 | −29.907 | 1.00 | 19.49 | N |
| ATOM | 11039 | CA | LYS | B | 161 | 62.806 | 46.044 | −30.549 | 1.00 | 20.61 | C |
| ATOM | 11041 | CB | LYS | B | 161 | 61.551 | 45.185 | −30.337 | 1.00 | 20.62 | C |
| ATOM | 11044 | CG | LYS | B | 161 | 61.745 | 43.722 | −30.728 | 1.00 | 23.49 | C |
| ATOM | 11047 | CD | LYS | B | 161 | 60.437 | 42.937 | −30.813 | 1.00 | 26.14 | C |
| ATOM | 11050 | CE | LYS | B | 161 | 59.926 | 42.500 | −29.450 | 1.00 | 27.36 | C |
| ATOM | 11053 | NZ | LYS | B | 161 | 58.817 | 41.518 | −29.583 | 1.00 | 28.82 | N |
| ATOM | 11057 | C | LYS | B | 161 | 63.067 | 46.246 | −32.033 | 1.00 | 21.10 | C |
| ATOM | 11058 | O | LYS | B | 161 | 64.101 | 45.824 | −32.542 | 1.00 | 22.42 | O |
| ATOM | 11060 | N | VAL | B | 162 | 62.142 | 46.922 | −32.711 | 1.00 | 21.17 | N |
| ATOM | 11061 | CA | VAL | B | 162 | 62.239 | 47.144 | −34.156 | 1.00 | 20.73 | C |
| ATOM | 11063 | CB | VAL | B | 162 | 61.091 | 48.044 | −34.675 | 1.00 | 21.27 | C |
| ATOM | 11065 | CG1 | VAL | B | 162 | 61.278 | 48.367 | −36.156 | 1.00 | 19.53 | C |
| ATOM | 11069 | CG2 | VAL | B | 162 | 59.746 | 47.371 | −34.439 | 1.00 | 18.18 | C |
| ATOM | 11073 | C | VAL | B | 162 | 63.582 | 47.767 | −34.524 | 1.00 | 20.33 | C |
| ATOM | 11074 | O | VAL | B | 162 | 64.262 | 47.293 | −35.431 | 1.00 | 20.38 | O |
| ATOM | 11076 | N | PHE | B | 163 | 63.952 | 48.819 | −33.800 | 1.00 | 20.40 | N |
| ATOM | 11077 | CA | PHE | B | 163 | 65.227 | 49.517 | −34.000 | 1.00 | 20.69 | C |
| ATOM | 11079 | CB | PHE | B | 163 | 65.350 | 50.654 | −32.982 | 1.00 | 20.35 | C |
| ATOM | 11082 | CG | PHE | B | 163 | 66.678 | 51.367 | −33.003 | 1.00 | 19.94 | C |
| ATOM | 11083 | CD1 | PHE | B | 163 | 66.935 | 52.361 | −33.938 | 1.00 | 18.75 | C |
| ATOM | 11085 | CE1 | PHE | B | 163 | 68.153 | 53.031 | −33.949 | 1.00 | 16.42 | C |
| ATOM | 11087 | CZ | PHE | B | 163 | 69.125 | 52.716 | −33.013 | 1.00 | 16.18 | C |
| ATOM | 11089 | CE2 | PHE | B | 163 | 68.879 | 51.737 | −32.068 | 1.00 | 17.55 | C |
| ATOM | 11091 | CD2 | PHE | B | 163 | 67.658 | 51.072 | −32.060 | 1.00 | 18.96 | C |
| ATOM | 11093 | C | PHE | B | 163 | 66.400 | 48.559 | −33.861 | 1.00 | 21.43 | C |
| ATOM | 11094 | O | PHE | B | 163 | 67.276 | 48.495 | −34.724 | 1.00 | 21.26 | O |
| ATOM | 11096 | N | ALA | B | 164 | 66.402 | 47.809 | −32.767 | 1.00 | 22.69 | N |
| ATOM | 11097 | CA | ALA | B | 164 | 67.482 | 46.877 | −32.481 | 1.00 | 23.59 | C |
| ATOM | 11099 | CB | ALA | B | 164 | 67.299 | 46.253 | −31.094 | 1.00 | 22.57 | C |
| ATOM | 11103 | C | ALA | B | 164 | 67.571 | 45.795 | −33.558 | 1.00 | 24.62 | C |
| ATOM | 11104 | O | ALA | B | 164 | 68.654 | 45.541 | −34.094 | 1.00 | 24.65 | O |
| ATOM | 11106 | N | ILE | B | 165 | 66.436 | 45.177 | −33.888 | 1.00 | 25.49 | N |
| ATOM | 11107 | CA | ILE | B | 165 | 66.429 | 44.065 | −34.847 | 1.00 | 26.70 | C |
| ATOM | 11109 | CB | ILE | B | 165 | 65.033 | 43.417 | −35.013 | 1.00 | 26.48 | C |
| ATOM | 11111 | CG1 | ILE | B | 165 | 64.549 | 42.810 | −33.701 | 1.00 | 27.74 | C |
| ATOM | 11114 | CD1 | ILE | B | 165 | 63.187 | 42.148 | −33.801 | 1.00 | 29.76 | C |
| ATOM | 11118 | CG2 | ILE | B | 165 | 65.082 | 42.297 | −36.042 | 1.00 | 26.39 | C |
| ATOM | 11122 | C | ILE | B | 165 | 66.931 | 44.513 | −36.222 | 1.00 | 28.02 | C |
| ATOM | 11123 | O | ILE | B | 165 | 67.757 | 43.833 | −36.832 | 1.00 | 28.59 | O |
| ATOM | 11125 | N | SER | B | 166 | 66.451 | 45.661 | −36.698 | 1.00 | 28.72 | N |
| ATOM | 11126 | CA | SER | B | 166 | 66.789 | 46.123 | −38.044 | 1.00 | 29.28 | C |
| ATOM | 11128 | CB | SER | B | 166 | 66.049 | 47.429 | −38.387 | 1.00 | 29.30 | C |
| ATOM | 11131 | OG | SER | B | 166 | 66.376 | 48.478 | −37.493 | 1.00 | 28.32 | O |
| ATOM | 11133 | C | SER | B | 166 | 68.300 | 46.284 | −38.226 | 1.00 | 30.17 | C |
| ATOM | 11134 | O | SER | B | 166 | 68.831 | 46.042 | −39.312 | 1.00 | 30.00 | O |
| ATOM | 11136 | N | HIS | B | 167 | 68.991 | 46.670 | −37.158 | 1.00 | 31.31 | N |
| ATOM | 11137 | CA | HIS | B | 167 | 70.438 | 46.875 | −37.223 | 1.00 | 32.64 | C |
| ATOM | 11139 | CB | HIS | B | 167 | 70.862 | 48.000 | −36.270 | 1.00 | 32.70 | C |
| ATOM | 11142 | CG | HIS | B | 167 | 70.457 | 49.361 | −36.756 | 1.00 | 39.52 | C |
| ATOM | 11143 | ND1 | HIS | B | 167 | 71.350 | 50.400 | −36.916 | 1.00 | 42.89 | N |
| ATOM | 11145 | CE1 | HIS | B | 167 | 70.711 | 51.460 | −37.381 | 1.00 | 42.59 | C |
| ATOM | 11147 | NE2 | HIS | B | 167 | 69.441 | 51.142 | −37.549 | 1.00 | 41.80 | N |
| ATOM | 11149 | CD2 | HIS | B | 167 | 69.258 | 49.833 | −37.175 | 1.00 | 43.19 | C |
| ATOM | 11151 | C | HIS | B | 167 | 71.218 | 45.577 | −36.997 | 1.00 | 32.89 | C |
| ATOM | 11152 | O | HIS | B | 167 | 72.192 | 45.321 | −37.702 | 1.00 | 33.78 | O |
| ATOM | 11154 | N | LEU | B | 168 | 70.773 | 44.754 | −36.047 | 1.00 | 32.82 | N |
| ATOM | 11155 | CA | LEU | B | 168 | 71.368 | 43.432 | −35.810 | 1.00 | 32.63 | C |
| ATOM | 11157 | CB | LEU | B | 168 | 70.706 | 42.752 | −34.602 | 1.00 | 32.18 | C |
| ATOM | 11160 | CG | LEU | B | 168 | 70.985 | 43.375 | −33.232 | 1.00 | 29.18 | C |
| ATOM | 11162 | CD1 | LEU | B | 168 | 69.986 | 42.892 | −32.195 | 1.00 | 22.43 | C |
| ATOM | 11166 | CD2 | LEU | B | 168 | 72.398 | 43.070 | −32.789 | 1.00 | 24.79 | C |
| ATOM | 11170 | C | LEU | B | 168 | 71.251 | 42.502 | −37.020 | 1.00 | 33.86 | C |
| ATOM | 11171 | O | LEU | B | 168 | 72.181 | 41.759 | −37.328 | 1.00 | 33.62 | O |
| ATOM | 11173 | N | LYS | B | 169 | 70.106 | 42.544 | −37.696 | 1.00 | 36.00 | N |
| ATOM | 11174 | CA | LYS | B | 169 | 69.822 | 41.627 | −38.805 | 1.00 | 37.86 | C |
| ATOM | 11176 | CB | LYS | B | 169 | 68.366 | 41.781 | −39.264 | 1.00 | 37.94 | C |
| ATOM | 11179 | CG | LYS | B | 169 | 67.911 | 40.724 | −40.261 | 1.00 | 41.68 | C |
| ATOM | 11182 | CD | LYS | B | 169 | 66.387 | 40.736 | −40.488 | 1.00 | 44.82 | C |

APPENDIX 1-continued

| ATOM | 11185 | CE  | LYS | B | 169 | 65.644 | 39.757 | −39.569 | 1.00 | 46.91 | C |
|------|-------|-----|-----|---|-----|--------|--------|---------|------|-------|---|
| ATOM | 11188 | NZ  | LYS | B | 169 | 64.290 | 39.386 | −40.107 | 1.00 | 45.39 | N |
| ATOM | 11192 | C   | LYS | B | 169 | 70.786 | 41.811 | −39.989 | 1.00 | 38.99 | C |
| ATOM | 11193 | O   | LYS | B | 169 | 71.134 | 40.840 | −40.665 | 1.00 | 38.82 | O |
| ATOM | 11195 | N   | GLU | B | 170 | 71.222 | 43.047 | −40.224 | 1.00 | 40.23 | N |
| ATOM | 11196 | CA  | GLU | B | 170 | 72.152 | 43.340 | −41.311 | 1.00 | 41.60 | C |
| ATOM | 11198 | CB  | GLU | B | 170 | 71.698 | 44.582 | −42.094 | 1.00 | 41.71 | C |
| ATOM | 11201 | CG  | GLU | B | 170 | 70.342 | 44.437 | −42.789 | 1.00 | 43.65 | C |
| ATOM | 11204 | CD  | GLU | B | 170 | 70.341 | 43.390 | −43.900 | 1.00 | 46.26 | C |
| ATOM | 11205 | OE1 | GLU | B | 170 | 71.147 | 43.519 | −44.846 | 1.00 | 48.74 | O |
| ATOM | 11206 | OE2 | GLU | B | 170 | 69.524 | 42.444 | −43.833 | 1.00 | 47.40 | O |
| ATOM | 11207 | C   | GLU | B | 170 | 73.565 | 43.533 | −40.766 | 1.00 | 42.62 | C |
| ATOM | 11208 | O   | GLU | B | 170 | 74.179 | 44.584 | −40.964 | 1.00 | 42.44 | O |
| ATOM | 11210 | N   | LEU | B | 171 | 74.070 | 42.513 | −40.072 | 1.00 | 43.83 | N |
| ATOM | 11211 | CA  | LEU | B | 171 | 75.457 | 42.505 | −39.597 | 1.00 | 44.73 | C |
| ATOM | 11213 | CB  | LEU | B | 171 | 75.528 | 42.421 | −38.068 | 1.00 | 44.06 | C |
| ATOM | 11216 | CG  | LEU | B | 171 | 75.188 | 43.682 | −37.266 | 1.00 | 43.28 | C |
| ATOM | 11218 | CD1 | LEU | B | 171 | 75.547 | 43.471 | −35.806 | 1.00 | 43.25 | C |
| ATOM | 11222 | CD2 | LEU | B | 171 | 75.885 | 44.923 | −37.801 | 1.00 | 40.54 | C |
| ATOM | 11226 | C   | LEU | B | 171 | 76.232 | 41.345 | −40.212 | 1.00 | 46.20 | C |
| ATOM | 11227 | O   | LEU | B | 171 | 75.673 | 40.271 | −40.464 | 1.00 | 46.15 | O |
| ATOM | 11229 | N   | SER | B | 172 | 77.523 | 41.585 | −40.449 | 1.00 | 47.65 | N |
| ATOM | 11230 | CA  | SER | B | 172 | 78.430 | 40.597 | −41.025 | 1.00 | 48.88 | C |
| ATOM | 11232 | CB  | SER | B | 172 | 79.135 | 41.175 | −42.256 | 1.00 | 49.37 | C |
| ATOM | 11235 | OG  | SER | B | 172 | 78.205 | 41.711 | −43.186 | 1.00 | 51.22 | O |
| ATOM | 11237 | C   | SER | B | 172 | 79.477 | 40.189 | −39.996 | 1.00 | 49.65 | C |
| ATOM | 11238 | O   | SER | B | 172 | 80.018 | 41.039 | −39.277 | 1.00 | 49.85 | O |
| ATOM | 11240 | N   | GLU | B | 173 | 79.780 | 38.892 | −39.950 | 1.00 | 50.22 | N |
| ATOM | 11241 | CA  | GLU | B | 173 | 80.777 | 38.343 | −39.023 | 1.00 | 50.43 | C |
| ATOM | 11243 | CB  | GLU | B | 173 | 80.913 | 36.823 | −39.238 | 1.00 | 50.69 | C |
| ATOM | 11246 | CG  | GLU | B | 173 | 82.007 | 36.138 | −38.405 | 1.00 | 51.84 | C |
| ATOM | 11249 | CD  | GLU | B | 173 | 81.921 | 34.615 | −38.424 | 1.00 | 53.22 | C |
| ATOM | 11250 | OE1 | GLU | B | 173 | 81.216 | 34.051 | −39.291 | 1.00 | 52.39 | O |
| ATOM | 11251 | OE2 | GLU | B | 173 | 82.573 | 33.982 | −37.566 | 1.00 | 54.62 | O |
| ATOM | 11252 | C   | GLU | B | 173 | 82.148 | 39.019 | −39.149 | 1.00 | 50.15 | C |
| ATOM | 11253 | O   | GLU | B | 173 | 82.967 | 38.919 | −38.241 | 1.00 | 49.68 | O |
| ATOM | 11255 | N   | GLU | B | 174 | 82.383 | 39.707 | −40.266 | 1.00 | 50.44 | N |
| ATOM | 11256 | CA  | GLU | B | 174 | 83.688 | 40.301 | −40.567 | 1.00 | 51.06 | C |
| ATOM | 11258 | CB  | GLU | B | 174 | 83.883 | 40.405 | −42.089 | 1.00 | 51.51 | C |
| ATOM | 11261 | CG  | GLU | B | 174 | 83.578 | 39.113 | −42.868 | 1.00 | 53.45 | C |
| ATOM | 11264 | CD  | GLU | B | 174 | 84.277 | 37.887 | −42.296 | 1.00 | 56.91 | C |
| ATOM | 11265 | OE1 | GLU | B | 174 | 85.513 | 37.935 | −42.112 | 1.00 | 57.85 | O |
| ATOM | 11266 | OE2 | GLU | B | 174 | 83.592 | 36.873 | −42.033 | 1.00 | 57.98 | O |
| ATOM | 11267 | C   | GLU | B | 174 | 83.886 | 41.675 | −39.918 | 1.00 | 50.70 | C |
| ATOM | 11268 | O   | GLU | B | 174 | 84.989 | 41.999 | −39.470 | 1.00 | 50.69 | O |
| ATOM | 11270 | N   | LYS | B | 175 | 82.821 | 42.475 | −39.872 | 1.00 | 50.21 | N |
| ATOM | 11271 | CA  | LYS | B | 175 | 82.875 | 43.811 | −39.264 | 1.00 | 49.68 | C |
| ATOM | 11273 | CB  | LYS | B | 175 | 81.605 | 44.611 | −39.581 | 1.00 | 50.24 | C |
| ATOM | 11276 | CG  | LYS | B | 175 | 81.254 | 44.700 | −41.066 | 1.00 | 52.51 | C |
| ATOM | 11279 | CD  | LYS | B | 175 | 80.061 | 45.624 | −41.313 | 1.00 | 54.12 | C |
| ATOM | 11282 | CE  | LYS | B | 175 | 79.682 | 45.672 | −42.790 | 1.00 | 54.57 | C |
| ATOM | 11285 | NZ  | LYS | B | 175 | 80.815 | 46.127 | −43.648 | 1.00 | 54.21 | N |
| ATOM | 11289 | C   | LYS | B | 175 | 83.040 | 43.700 | −37.749 | 1.00 | 48.49 | C |
| ATOM | 11290 | O   | LYS | B | 175 | 83.704 | 44.525 | −37.125 | 1.00 | 48.25 | O |
| ATOM | 11292 | N   | ILE | B | 176 | 82.418 | 42.673 | −37.175 | 1.00 | 47.54 | N |
| ATOM | 11293 | CA  | ILE | B | 176 | 82.507 | 42.375 | −35.744 | 1.00 | 46.56 | C |
| ATOM | 11295 | CB  | ILE | B | 176 | 81.098 | 42.319 | −35.091 | 1.00 | 46.07 | C |
| ATOM | 11297 | CG1 | ILE | B | 176 | 80.266 | 41.150 | −35.642 | 1.00 | 44.01 | C |
| ATOM | 11300 | CD1 | ILE | B | 176 | 78.794 | 41.235 | −35.303 | 1.00 | 40.86 | C |
| ATOM | 11304 | CG2 | ILE | B | 176 | 80.368 | 43.638 | −35.306 | 1.00 | 45.78 | C |
| ATOM | 11308 | C   | ILE | B | 176 | 83.244 | 41.045 | −35.563 | 1.00 | 46.35 | C |
| ATOM | 11309 | O   | ILE | B | 176 | 83.653 | 40.427 | −36.541 | 1.00 | 46.03 | O |
| ATOM | 11311 | N   | GLY | B | 177 | 83.424 | 40.610 | −34.319 | 1.00 | 46.30 | N |
| ATOM | 11312 | CA  | GLY | B | 177 | 84.106 | 39.341 | −34.046 | 1.00 | 46.19 | C |
| ATOM | 11315 | C   | GLY | B | 177 | 83.267 | 38.118 | −34.393 | 1.00 | 45.84 | C |
| ATOM | 11316 | O   | GLY | B | 177 | 82.070 | 38.229 | −34.664 | 1.00 | 46.23 | O |
| ATOM | 11318 | N   | LYS | B | 178 | 83.900 | 36.948 | −34.393 | 1.00 | 45.15 | N |
| ATOM | 11319 | CA  | LYS | B | 178 | 83.173 | 35.686 | −34.536 | 1.00 | 44.35 | C |
| ATOM | 11321 | CB  | LYS | B | 178 | 84.135 | 34.510 | −34.753 | 1.00 | 44.51 | C |
| ATOM | 11324 | CG  | LYS | B | 178 | 83.465 | 33.144 | −34.622 | 1.00 | 46.27 | C |
| ATOM | 11327 | CD  | LYS | B | 178 | 84.165 | 32.063 | −35.419 | 1.00 | 48.89 | C |
| ATOM | 11330 | CE  | LYS | B | 178 | 83.334 | 30.785 | −35.434 | 1.00 | 49.86 | C |
| ATOM | 11333 | NZ  | LYS | B | 178 | 83.989 | 29.702 | −36.218 | 1.00 | 50.30 | N |
| ATOM | 11337 | C   | LYS | B | 178 | 82.293 | 35.427 | −33.307 | 1.00 | 43.25 | C |
| ATOM | 11338 | O   | LYS | B | 178 | 81.140 | 35.006 | −33.440 | 1.00 | 42.98 | O |
| ATOM | 11340 | N   | GLU | B | 179 | 82.836 | 35.675 | −32.117 | 1.00 | 42.01 | N |
| ATOM | 11341 | CA  | GLU | B | 179 | 82.088 | 35.437 | −30.880 | 1.00 | 41.17 | C |
| ATOM | 11343 | CB  | GLU | B | 179 | 83.010 | 35.467 | −29.647 | 1.00 | 41.20 | C |
| ATOM | 11346 | CG  | GLU | B | 179 | 83.403 | 36.847 | −29.138 | 1.00 | 42.43 | C |
| ATOM | 11349 | CD  | GLU | B | 179 | 84.257 | 36.773 | −27.883 | 1.00 | 44.81 | C |

APPENDIX 1-continued

| | | | | | | | | | | |
|---|---|---|---|---|---|---|---|---|---|---|
| ATOM | 11350 | OE1 | GLU | B | 179 | 83.740 | 37.107 | −26.794 | 1.00 | 45.22 | O |
| ATOM | 11351 | OE2 | GLU | B | 179 | 85.438 | 36.367 | −27.985 | 1.00 | 42.41 | O |
| ATOM | 11352 | C | GLU | B | 179 | 80.923 | 36.419 | −30.733 | 1.00 | 39.82 | C |
| ATOM | 11353 | O | GLU | B | 179 | 79.893 | 36.082 | −30.151 | 1.00 | 40.22 | O |
| ATOM | 11355 | N | LEU | B | 180 | 81.087 | 37.627 | −31.265 | 1.00 | 38.19 | N |
| ATOM | 11356 | CA | LEU | B | 180 | 80.001 | 38.601 | −31.301 | 1.00 | 36.94 | C |
| ATOM | 11358 | CB | LEU | B | 180 | 80.557 | 40.005 | −31.562 | 1.00 | 36.89 | C |
| ATOM | 11361 | CG | LEU | B | 180 | 79.649 | 41.226 | −31.340 | 1.00 | 37.50 | C |
| ATOM | 11363 | CD1 | LEU | B | 180 | 78.489 | 40.940 | −30.393 | 1.00 | 39.28 | C |
| ATOM | 11367 | CD2 | LEU | B | 180 | 80.466 | 42.409 | −30.827 | 1.00 | 37.31 | C |
| ATOM | 11371 | C | LEU | B | 180 | 78.961 | 38.205 | −32.359 | 1.00 | 35.94 | C |
| ATOM | 11372 | O | LEU | B | 180 | 77.763 | 38.429 | −32.172 | 1.00 | 35.92 | O |
| ATOM | 11374 | N | ALA | B | 181 | 79.421 | 37.605 | −33.458 | 1.00 | 34.89 | N |
| ATOM | 11375 | CA | ALA | B | 181 | 78.521 | 37.071 | −34.489 | 1.00 | 33.89 | C |
| ATOM | 11377 | CB | ALA | B | 181 | 79.319 | 36.544 | −35.681 | 1.00 | 33.20 | C |
| ATOM | 11381 | C | ALA | B | 181 | 77.616 | 35.972 | −33.932 | 1.00 | 33.29 | C |
| ATOM | 11382 | O | ALA | B | 181 | 76.416 | 35.970 | −34.192 | 1.00 | 33.41 | O |
| ATOM | 11384 | N | GLU | B | 182 | 78.193 | 35.044 | −33.168 | 1.00 | 32.95 | N |
| ATOM | 11385 | CA | GLU | B | 182 | 77.415 | 33.959 | −32.554 | 1.00 | 32.47 | C |
| ATOM | 11387 | CB | GLU | B | 182 | 78.330 | 32.913 | −31.903 | 1.00 | 33.23 | C |
| ATOM | 11390 | CG | GLU | B | 182 | 78.903 | 31.901 | −32.900 | 1.00 | 38.76 | C |
| ATOM | 11393 | CD | GLU | B | 182 | 80.089 | 31.104 | −32.358 | 1.00 | 46.12 | C |
| ATOM | 11394 | OE1 | GLU | B | 182 | 80.432 | 31.251 | −31.161 | 1.00 | 53.48 | O |
| ATOM | 11395 | OE2 | GLU | B | 182 | 80.683 | 30.326 | −33.140 | 1.00 | 48.05 | O |
| ATOM | 11396 | C | GLU | B | 182 | 76.411 | 34.497 | −31.539 | 1.00 | 30.26 | C |
| ATOM | 11397 | O | GLU | B | 182 | 75.285 | 34.011 | −31.474 | 1.00 | 30.91 | O |
| ATOM | 11399 | N | GLN | B | 183 | 76.820 | 35.504 | −30.766 | 1.00 | 27.88 | N |
| ATOM | 11400 | CA | GLN | B | 183 | 75.934 | 36.159 | −29.797 | 1.00 | 26.22 | C |
| ATOM | 11402 | CB | GLN | B | 183 | 76.662 | 37.284 | −29.042 | 1.00 | 26.65 | C |
| ATOM | 11405 | CG | GLN | B | 183 | 77.538 | 36.829 | −27.875 | 1.00 | 28.31 | C |
| ATOM | 11408 | CD | GLN | B | 183 | 76.759 | 36.141 | −26.769 | 1.00 | 30.87 | C |
| ATOM | 11409 | OE1 | GLN | B | 183 | 75.557 | 36.349 | −26.610 | 1.00 | 34.80 | O |
| ATOM | 11410 | NE2 | GLN | B | 183 | 77.445 | 35.311 | −25.999 | 1.00 | 33.35 | N |
| ATOM | 11413 | C | GLN | B | 183 | 74.694 | 36.739 | −30.467 | 1.00 | 24.60 | C |
| ATOM | 11414 | O | GLN | B | 183 | 73.576 | 36.553 | −29.972 | 1.00 | 23.70 | O |
| ATOM | 11416 | N | VAL | B | 184 | 74.905 | 37.443 | −31.582 | 1.00 | 23.09 | N |
| ATOM | 11417 | CA | VAL | B | 184 | 73.813 | 38.062 | −32.349 | 1.00 | 21.38 | C |
| ATOM | 11419 | CB | VAL | B | 184 | 74.345 | 38.953 | −33.508 | 1.00 | 21.70 | C |
| ATOM | 11421 | CG1 | VAL | B | 184 | 73.195 | 39.445 | −34.392 | 1.00 | 19.46 | C |
| ATOM | 11425 | CG2 | VAL | B | 184 | 75.147 | 40.132 | −32.962 | 1.00 | 20.43 | C |
| ATOM | 11429 | C | VAL | B | 184 | 72.877 | 37.002 | −32.924 | 1.00 | 20.07 | C |
| ATOM | 11430 | O | VAL | B | 184 | 71.661 | 37.092 | −32.765 | 1.00 | 19.93 | O |
| ATOM | 11432 | N | ASN | B | 185 | 73.446 | 36.000 | −33.585 | 1.00 | 19.38 | N |
| ATOM | 11433 | CA | ASN | B | 185 | 72.656 | 34.900 | −34.139 | 1.00 | 19.54 | C |
| ATOM | 11435 | CB | ASN | B | 185 | 73.556 | 33.865 | −34.824 | 1.00 | 19.91 | C |
| ATOM | 11438 | CG | ASN | B | 185 | 74.126 | 34.365 | −36.148 | 1.00 | 21.54 | C |
| ATOM | 11439 | OD1 | ASN | B | 185 | 73.403 | 34.916 | −36.980 | 1.00 | 22.70 | O |
| ATOM | 11440 | ND2 | ASN | B | 185 | 75.429 | 34.163 | −36.349 | 1.00 | 21.22 | N |
| ATOM | 11443 | C | ASN | B | 185 | 71.822 | 34.226 | −33.064 | 1.00 | 18.96 | C |
| ATOM | 11444 | O | ASN | B | 185 | 70.635 | 33.962 | −33.261 | 1.00 | 19.39 | O |
| ATOM | 11446 | N | HIS | B | 186 | 72.453 | 33.970 | −31.922 | 1.00 | 18.64 | N |
| ATOM | 11447 | CA | HIS | B | 186 | 71.778 | 33.393 | −30.761 | 1.00 | 18.00 | C |
| ATOM | 11449 | CB | HIS | B | 186 | 72.771 | 33.265 | −29.606 | 1.00 | 18.39 | C |
| ATOM | 11452 | CG | HIS | B | 186 | 72.250 | 32.500 | −28.428 | 1.00 | 20.53 | C |
| ATOM | 11453 | ND1 | HIS | B | 186 | 72.158 | 31.124 | −28.414 | 1.00 | 23.41 | N |
| ATOM | 11455 | CE1 | HIS | B | 186 | 71.689 | 30.728 | −27.244 | 1.00 | 23.43 | C |
| ATOM | 11457 | NE2 | HIS | B | 186 | 71.481 | 31.796 | −26.496 | 1.00 | 22.88 | N |
| ATOM | 11459 | CD2 | HIS | B | 186 | 71.829 | 32.917 | −27.211 | 1.00 | 21.33 | C |
| ATOM | 11461 | C | HIS | B | 186 | 70.581 | 34.244 | −30.340 | 1.00 | 16.85 | C |
| ATOM | 11462 | O | HIS | B | 186 | 69.492 | 33.718 | −30.094 | 1.00 | 16.23 | O |
| ATOM | 11464 | N | ALA | B | 187 | 70.788 | 35.559 | −30.274 | 1.00 | 16.03 | N |
| ATOM | 11465 | CA | ALA | B | 187 | 69.738 | 36.496 | −29.870 | 1.00 | 15.40 | C |
| ATOM | 11467 | CB | ALA | B | 187 | 70.308 | 37.884 | −29.674 | 1.00 | 13.81 | C |
| ATOM | 11471 | C | ALA | B | 187 | 68.583 | 36.534 | −30.866 | 1.00 | 16.36 | C |
| ATOM | 11472 | O | ALA | B | 187 | 67.422 | 36.515 | −30.459 | 1.00 | 16.33 | O |
| ATOM | 11474 | N | LEU | B | 188 | 68.898 | 36.579 | −32.162 | 1.00 | 17.87 | N |
| ATOM | 11475 | CA | LEU | B | 188 | 67.862 | 36.576 | −33.209 | 1.00 | 18.60 | C |
| ATOM | 11477 | CB | LEU | B | 188 | 68.448 | 36.922 | −34.579 | 1.00 | 18.53 | C |
| ATOM | 11480 | CG | LEU | B | 188 | 69.069 | 38.309 | −34.731 | 1.00 | 20.29 | C |
| ATOM | 11482 | CD1 | LEU | B | 188 | 69.627 | 38.474 | −36.145 | 1.00 | 15.82 | C |
| ATOM | 11486 | CD2 | LEU | B | 188 | 68.066 | 39.408 | −34.401 | 1.00 | 18.27 | C |
| ATOM | 11490 | C | LEU | B | 188 | 67.123 | 35.242 | −33.302 | 1.00 | 19.33 | C |
| ATOM | 11491 | O | LEU | B | 188 | 65.937 | 35.222 | −33.619 | 1.00 | 19.98 | O |
| ATOM | 11493 | N | GLU | B | 189 | 67.817 | 34.133 | −33.041 | 1.00 | 19.94 | N |
| ATOM | 11494 | CA | GLU | B | 189 | 67.163 | 32.820 | −32.974 | 1.00 | 21.03 | C |
| ATOM | 11496 | CB | GLU | B | 189 | 68.180 | 31.732 | −32.612 | 1.00 | 21.46 | C |
| ATOM | 11499 | CG | GLU | B | 189 | 67.636 | 30.301 | −32.648 | 1.00 | 26.25 | C |
| ATOM | 11502 | CD | GLU | B | 189 | 68.581 | 29.294 | −32.010 | 1.00 | 31.11 | C |
| ATOM | 11503 | OE1 | GLU | B | 189 | 68.956 | 29.496 | −30.840 | 1.00 | 36.55 | O |
| ATOM | 11504 | OE2 | GLU | B | 189 | 68.938 | 28.294 | −32.666 | 1.00 | 34.01 | O |

APPENDIX 1-continued

| | | | | | | | | | | |
|---|---|---|---|---|---|---|---|---|---|---|
| ATOM | 11505 | C | GLU | B | 189 | 66.022 | 32.844 | −31.945 | 1.00 | 21.47 | C |
| ATOM | 11506 | O | GLU | B | 189 | 64.921 | 32.369 | −32.210 | 1.00 | 21.87 | O |
| ATOM | 11508 | N | LEU | B | 190 | 66.307 | 33.408 | −30.777 | 1.00 | 21.59 | N |
| ATOM | 11509 | CA | LEU | B | 190 | 65.357 | 33.505 | −29.679 | 1.00 | 21.97 | C |
| ATOM | 11511 | CB | LEU | B | 190 | 65.006 | 32.114 | −29.131 | 1.00 | 22.14 | C |
| ATOM | 11514 | CG | LEU | B | 190 | 63.792 | 32.034 | −28.196 | 1.00 | 25.30 | C |
| ATOM | 11516 | CD1 | LEU | B | 190 | 62.506 | 32.358 | −28.950 | 1.00 | 19.09 | C |
| ATOM | 11520 | CD2 | LEU | B | 190 | 63.693 | 30.662 | −27.517 | 1.00 | 22.75 | C |
| ATOM | 11524 | C | LEU | B | 190 | 66.034 | 34.341 | −28.590 | 1.00 | 22.26 | C |
| ATOM | 11525 | O | LEU | B | 190 | 67.231 | 34.160 | −28.336 | 1.00 | 22.65 | O |
| ATOM | 11527 | N | PRO | B | 191 | 65.295 | 35.269 | −27.958 | 1.00 | 21.56 | N |
| ATOM | 11528 | CA | PRO | B | 191 | 65.899 | 36.089 | −26.917 | 1.00 | 20.80 | C |
| ATOM | 11530 | CB | PRO | B | 191 | 65.000 | 37.316 | −26.890 | 1.00 | 21.08 | C |
| ATOM | 11533 | CG | PRO | B | 191 | 63.662 | 36.791 | −27.242 | 1.00 | 21.92 | C |
| ATOM | 11536 | CD | PRO | B | 191 | 63.896 | 35.657 | −28.212 | 1.00 | 22.13 | C |
| ATOM | 11539 | C | PRO | B | 191 | 65.885 | 35.390 | −25.562 | 1.00 | 21.09 | C |
| ATOM | 11540 | O | PRO | B | 191 | 65.105 | 34.455 | −25.361 | 1.00 | 21.24 | O |
| ATOM | 11541 | N | LEU | B | 192 | 66.731 | 35.866 | −24.647 | 1.00 | 20.11 | N |
| ATOM | 11542 | CA | LEU | B | 192 | 66.899 | 35.267 | −23.323 | 1.00 | 19.67 | C |
| ATOM | 11544 | CB | LEU | B | 192 | 67.835 | 36.128 | −22.472 | 1.00 | 20.37 | C |
| ATOM | 11547 | CG | LEU | B | 192 | 69.299 | 36.212 | −22.923 | 1.00 | 23.99 | C |
| ATOM | 11549 | CD1 | LEU | B | 192 | 70.032 | 37.371 | −22.243 | 1.00 | 24.02 | C |
| ATOM | 11553 | CD2 | LEU | B | 192 | 70.011 | 34.894 | −22.663 | 1.00 | 23.49 | C |
| ATOM | 11557 | C | LEU | B | 192 | 65.583 | 35.085 | −22.576 | 1.00 | 19.31 | C |
| ATOM | 11558 | O | LEU | B | 192 | 65.322 | 34.011 | −22.019 | 1.00 | 20.25 | O |
| ATOM | 11560 | N | HIS | B | 193 | 64.755 | 36.127 | −22.577 | 1.00 | 18.28 | N |
| ATOM | 11561 | CA | HIS | B | 193 | 63.482 | 36.110 | −21.858 | 1.00 | 18.62 | C |
| ATOM | 11563 | CB | HIS | B | 193 | 62.751 | 37.450 | −21.992 | 1.00 | 18.42 | C |
| ATOM | 11566 | CG | HIS | B | 193 | 61.609 | 37.616 | −21.038 | 1.00 | 18.33 | C |
| ATOM | 11567 | ND1 | HIS | B | 193 | 61.765 | 37.534 | −19.671 | 1.00 | 18.12 | N |
| ATOM | 11569 | CE1 | HIS | B | 193 | 60.596 | 37.734 | −19.083 | 1.00 | 17.54 | C |
| ATOM | 11571 | NE2 | HIS | B | 193 | 59.688 | 37.944 | −20.018 | 1.00 | 17.57 | N |
| ATOM | 11573 | CD2 | HIS | B | 193 | 60.296 | 37.878 | −21.251 | 1.00 | 22.36 | C |
| ATOM | 11575 | C | HIS | B | 193 | 62.554 | 34.988 | −22.302 | 1.00 | 19.69 | C |
| ATOM | 11576 | O | HIS | B | 193 | 61.725 | 34.536 | −21.515 | 1.00 | 20.11 | O |
| ATOM | 11578 | N | ARG | B | 194 | 62.685 | 34.537 | −23.548 | 1.00 | 20.56 | N |
| ATOM | 11579 | CA | ARG | B | 194 | 61.864 | 33.437 | −24.046 | 1.00 | 22.15 | C |
| ATOM | 11581 | CB | ARG | B | 194 | 61.352 | 33.753 | −25.445 | 1.00 | 22.16 | C |
| ATOM | 11584 | CG | ARG | B | 194 | 60.462 | 34.975 | −25.484 | 1.00 | 23.96 | C |
| ATOM | 11587 | CD | ARG | B | 194 | 59.755 | 35.109 | −26.811 | 1.00 | 25.22 | C |
| ATOM | 11590 | NE | ARG | B | 194 | 58.896 | 36.290 | −26.833 | 1.00 | 26.33 | N |
| ATOM | 11592 | CZ | ARG | B | 194 | 58.332 | 36.806 | −27.925 | 1.00 | 24.20 | C |
| ATOM | 11593 | NH1 | ARG | B | 194 | 58.518 | 36.256 | −29.121 | 1.00 | 25.70 | N |
| ATOM | 11596 | NH2 | ARG | B | 194 | 57.576 | 37.888 | −27.816 | 1.00 | 23.60 | N |
| ATOM | 11599 | C | ARG | B | 194 | 62.570 | 32.075 | −24.053 | 1.00 | 23.48 | C |
| ATOM | 11600 | O | ARG | B | 194 | 61.904 | 31.053 | −24.189 | 1.00 | 25.36 | O |
| ATOM | 11602 | N | ARG | B | 195 | 63.897 | 32.050 | −23.902 | 1.00 | 22.67 | N |
| ATOM | 11603 | CA | ARG | B | 195 | 64.654 | 30.794 | −23.936 | 1.00 | 21.30 | C |
| ATOM | 11605 | CB | ARG | B | 195 | 66.105 | 31.079 | −24.302 | 1.00 | 21.39 | C |
| ATOM | 11608 | CG | ARG | B | 195 | 66.886 | 29.867 | −24.742 | 1.00 | 21.47 | C |
| ATOM | 11611 | CD | ARG | B | 195 | 68.323 | 30.241 | −25.060 | 1.00 | 21.44 | C |
| ATOM | 11614 | NE | ARG | B | 195 | 68.432 | 31.224 | −26.141 | 1.00 | 20.11 | N |
| ATOM | 11616 | CZ | ARG | B | 195 | 68.427 | 30.936 | −27.446 | 1.00 | 22.99 | C |
| ATOM | 11617 | NH1 | ARG | B | 195 | 68.311 | 29.679 | −27.883 | 1.00 | 21.23 | N |
| ATOM | 11620 | NH2 | ARG | B | 195 | 68.540 | 31.920 | −28.332 | 1.00 | 26.18 | N |
| ATOM | 11623 | C | ARG | B | 195 | 64.602 | 30.095 | −22.590 | 1.00 | 20.50 | C |
| ATOM | 11624 | O | ARG | B | 195 | 64.617 | 30.752 | −21.554 | 1.00 | 21.55 | O |
| ATOM | 11626 | N | THR | B | 196 | 64.552 | 28.767 | −22.593 | 1.00 | 20.35 | N |
| ATOM | 11627 | CA | THR | B | 196 | 64.555 | 28.011 | −21.328 | 1.00 | 19.52 | C |
| ATOM | 11629 | CB | THR | B | 196 | 64.182 | 26.502 | −21.498 | 1.00 | 19.58 | C |
| ATOM | 11631 | OG1 | THR | B | 196 | 65.060 | 25.872 | −22.438 | 1.00 | 17.84 | O |
| ATOM | 11633 | CG2 | THR | B | 196 | 62.736 | 26.346 | −21.953 | 1.00 | 15.41 | C |
| ATOM | 11637 | C | THR | B | 196 | 65.916 | 28.128 | −20.645 | 1.00 | 18.43 | C |
| ATOM | 11638 | O | THR | B | 196 | 66.919 | 28.415 | −21.293 | 1.00 | 18.12 | O |
| ATOM | 11640 | N | GLN | B | 197 | 65.926 | 27.899 | −19.335 | 1.00 | 17.17 | N |
| ATOM | 11641 | CA | GLN | B | 197 | 67.087 | 28.172 | −18.501 | 1.00 | 17.20 | C |
| ATOM | 11643 | CB | GLN | B | 197 | 66.690 | 28.085 | −17.018 | 1.00 | 17.39 | C |
| ATOM | 11646 | CG | GLN | B | 197 | 67.515 | 28.969 | −16.072 | 1.00 | 19.60 | C |
| ATOM | 11649 | CD | GLN | B | 197 | 68.758 | 28.289 | −15.508 | 1.00 | 22.54 | C |
| ATOM | 11650 | OE1 | GLN | B | 197 | 69.183 | 27.229 | −15.978 | 1.00 | 22.58 | O |
| ATOM | 11651 | NE2 | GLN | B | 197 | 69.346 | 28.906 | −14.487 | 1.00 | 22.18 | N |
| ATOM | 11654 | C | GLN | B | 197 | 68.285 | 27.248 | −18.803 | 1.00 | 17.52 | C |
| ATOM | 11655 | O | GLN | B | 197 | 69.419 | 27.727 | −18.906 | 1.00 | 18.43 | O |
| ATOM | 11657 | N | ARG | B | 198 | 68.041 | 25.943 | −18.940 | 1.00 | 16.18 | N |
| ATOM | 11658 | CA | ARG | B | 198 | 69.120 | 24.981 | −19.194 | 1.00 | 16.69 | C |
| ATOM | 11660 | CB | ARG | B | 198 | 68.641 | 23.538 | −19.005 | 1.00 | 15.67 | C |
| ATOM | 11663 | CG | ARG | B | 198 | 68.201 | 23.183 | −17.597 | 1.00 | 15.18 | C |
| ATOM | 11666 | CD | ARG | B | 198 | 69.376 | 23.008 | −16.639 | 1.00 | 16.81 | C |
| ATOM | 11669 | NE | ARG | B | 198 | 69.913 | 24.279 | −16.153 | 1.00 | 18.44 | N |
| ATOM | 11671 | CZ | ARG | B | 198 | 70.934 | 24.393 | −15.302 | 1.00 | 17.91 | C |

APPENDIX 1-continued

| | | | | | | | | | | |
|---|---|---|---|---|---|---|---|---|---|---|
| ATOM | 11672 | NH1 | ARG | B | 198 | 71.546 | 23.312 | −14.820 | 1.00 | 17.59 N |
| ATOM | 11675 | NH2 | ARG | B | 198 | 71.339 | 25.597 | −14.920 | 1.00 | 17.06 N |
| ATOM | 11678 | C | ARG | B | 198 | 69.710 | 25.141 | −20.595 | 1.00 | 18.02 C |
| ATOM | 11679 | O | ARG | B | 198 | 70.927 | 25.033 | −20.780 | 1.00 | 18.32 O |
| ATOM | 11681 | N | LEU | B | 199 | 68.856 | 25.391 | −21.584 | 1.00 | 18.62 N |
| ATOM | 11682 | CA | LEU | B | 199 | 69.338 | 25.599 | −22.942 | 1.00 | 19.22 C |
| ATOM | 11684 | CB | LEU | B | 199 | 68.191 | 25.787 | −23.928 | 1.00 | 20.05 C |
| ATOM | 11687 | CG | LEU | B | 199 | 67.554 | 24.491 | −24.421 | 1.00 | 23.38 C |
| ATOM | 11689 | CD1 | LEU | B | 199 | 66.370 | 24.822 | −25.325 | 1.00 | 24.54 C |
| ATOM | 11693 | CD2 | LEU | B | 199 | 68.588 | 23.616 | −25.139 | 1.00 | 22.02 C |
| ATOM | 11697 | C | LEU | B | 199 | 70.250 | 26.802 | −23.005 | 1.00 | 19.41 C |
| ATOM | 11698 | O | LEU | B | 199 | 71.288 | 26.751 | −23.658 | 1.00 | 20.28 O |
| ATOM | 11700 | N | GLU | B | 200 | 69.868 | 27.885 | −22.333 | 1.00 | 19.03 N |
| ATOM | 11701 | CA | GLU | B | 200 | 70.716 | 29.068 | −22.296 | 1.00 | 19.14 C |
| ATOM | 11703 | CB | GLU | B | 200 | 70.025 | 30.235 | −21.592 | 1.00 | 18.98 C |
| ATOM | 11706 | CG | GLU | B | 200 | 70.877 | 31.492 | −21.484 | 1.00 | 17.68 C |
| ATOM | 11709 | CD | GLU | B | 200 | 71.430 | 31.959 | −22.816 | 1.00 | 23.55 C |
| ATOM | 11710 | OE1 | GLU | B | 200 | 70.754 | 31.793 | −23.847 | 1.00 | 25.99 O |
| ATOM | 11711 | OE2 | GLU | B | 200 | 72.543 | 32.516 | −22.837 | 1.00 | 29.25 O |
| ATOM | 11712 | C | GLU | B | 200 | 72.029 | 28.753 | −21.603 | 1.00 | 19.49 C |
| ATOM | 11713 | O | GLU | B | 200 | 73.086 | 29.187 | −22.060 | 1.00 | 20.17 O |
| ATOM | 11715 | N | ALA | B | 201 | 71.958 | 27.998 | −20.509 | 1.00 | 18.86 N |
| ATOM | 11716 | CA | ALA | B | 201 | 73.153 | 27.617 | −19.766 | 1.00 | 19.01 C |
| ATOM | 11718 | CB | ALA | B | 201 | 72.782 | 26.801 | −18.536 | 1.00 | 18.47 C |
| ATOM | 11722 | C | ALA | B | 201 | 74.109 | 26.835 | −20.656 | 1.00 | 19.34 C |
| ATOM | 11723 | O | ALA | B | 201 | 75.266 | 27.234 | −20.838 | 1.00 | 20.50 O |
| ATOM | 11725 | N | VAL | B | 202 | 73.614 | 25.742 | −21.237 | 1.00 | 18.86 N |
| ATOM | 11726 | CA | VAL | B | 202 | 74.455 | 24.855 | −22.044 | 1.00 | 18.25 C |
| ATOM | 11728 | CB | VAL | B | 202 | 73.665 | 23.622 | −22.586 | 1.00 | 18.35 C |
| ATOM | 11730 | CG1 | VAL | B | 202 | 72.750 | 24.015 | −23.711 | 1.00 | 16.77 C |
| ATOM | 11734 | CG2 | VAL | B | 202 | 74.622 | 22.531 | −23.048 | 1.00 | 16.57 C |
| ATOM | 11738 | C | VAL | B | 202 | 75.121 | 25.618 | −23.185 | 1.00 | 17.55 C |
| ATOM | 11739 | O | VAL | B | 202 | 76.262 | 25.334 | −23.543 | 1.00 | 18.86 O |
| ATOM | 11741 | N | TRP | B | 203 | 74.417 | 26.598 | −23.740 | 1.00 | 16.56 N |
| ATOM | 11742 | CA | TRP | B | 203 | 74.976 | 27.421 | −24.799 | 1.00 | 16.59 C |
| ATOM | 11744 | CB | TRP | B | 203 | 73.873 | 28.155 | −25.558 | 1.00 | 16.92 C |
| ATOM | 11747 | CG | TRP | B | 203 | 74.399 | 28.864 | −26.754 | 1.00 | 18.88 C |
| ATOM | 11748 | CD1 | TRP | B | 203 | 74.532 | 28.364 | −28.019 | 1.00 | 17.65 C |
| ATOM | 11750 | NE1 | TRP | B | 203 | 75.090 | 29.309 | −28.842 | 1.00 | 15.37 N |
| ATOM | 11752 | CE2 | TRP | B | 203 | 75.328 | 30.445 | −28.114 | 1.00 | 16.30 C |
| ATOM | 11753 | CD2 | TRP | B | 203 | 74.907 | 30.197 | −26.792 | 1.00 | 18.21 C |
| ATOM | 11754 | CE3 | TRP | B | 203 | 75.048 | 31.205 | −25.837 | 1.00 | 17.36 C |
| ATOM | 11756 | CZ3 | TRP | B | 203 | 75.591 | 32.410 | −26.224 | 1.00 | 20.82 C |
| ATOM | 11758 | CH2 | TRP | B | 203 | 75.997 | 32.632 | −27.549 | 1.00 | 20.62 C |
| ATOM | 11760 | CZ2 | TRP | B | 203 | 75.872 | 31.662 | −28.506 | 1.00 | 19.32 C |
| ATOM | 11762 | C | TRP | B | 203 | 75.994 | 28.424 | −24.250 | 1.00 | 16.78 C |
| ATOM | 11763 | O | TRP | B | 203 | 77.085 | 28.565 | −24.808 | 1.00 | 16.80 O |
| ATOM | 11765 | N | SER | B | 204 | 75.643 | 29.115 | −23.165 | 1.00 | 16.20 N |
| ATOM | 11766 | CA | SER | B | 204 | 76.510 | 30.159 | −22.615 | 1.00 | 15.80 C |
| ATOM | 11768 | CB | SER | B | 204 | 75.758 | 31.040 | −21.623 | 1.00 | 15.90 C |
| ATOM | 11771 | OG | SER | B | 204 | 75.049 | 32.049 | −22.314 | 1.00 | 18.88 O |
| ATOM | 11773 | C | SER | B | 204 | 77.782 | 29.613 | −21.973 | 1.00 | 15.47 C |
| ATOM | 11774 | O | SER | B | 204 | 78.836 | 30.239 | −22.075 | 1.00 | 15.64 O |
| ATOM | 11776 | N | ILE | B | 205 | 77.700 | 28.457 | −21.320 | 1.00 | 14.25 N |
| ATOM | 11777 | CA | ILE | B | 205 | 78.903 | 27.830 | −20.785 | 1.00 | 13.83 C |
| ATOM | 11779 | CB | ILE | B | 205 | 78.599 | 26.525 | −20.013 | 1.00 | 14.16 C |
| ATOM | 11781 | CG1 | ILE | B | 205 | 77.851 | 26.854 | −18.711 | 1.00 | 13.77 C |
| ATOM | 11784 | CD1 | ILE | B | 205 | 77.428 | 25.655 | −17.887 | 1.00 | 9.36 C |
| ATOM | 11788 | CG2 | ILE | B | 205 | 79.893 | 25.778 | −19.710 | 1.00 | 11.61 C |
| ATOM | 11792 | C | ILE | B | 205 | 79.915 | 27.576 | −21.907 | 1.00 | 14.14 C |
| ATOM | 11793 | O | ILE | B | 205 | 81.103 | 27.832 | −21.739 | 1.00 | 13.11 O |
| ATOM | 11795 | N | GLU | B | 206 | 79.438 | 27.110 | −23.060 | 1.00 | 15.22 N |
| ATOM | 11796 | CA | GLU | B | 206 | 80.317 | 26.851 | −24.209 | 1.00 | 15.60 C |
| ATOM | 11798 | CB | GLU | B | 206 | 79.560 | 26.067 | −25.289 | 1.00 | 16.51 C |
| ATOM | 11801 | CG | GLU | B | 206 | 80.357 | 25.729 | −26.563 | 1.00 | 19.18 C |
| ATOM | 11804 | CD | GLU | B | 206 | 81.507 | 24.764 | −26.334 | 1.00 | 22.94 C |
| ATOM | 11805 | OE1 | GLU | B | 206 | 81.580 | 24.144 | −25.248 | 1.00 | 27.63 O |
| ATOM | 11806 | OE2 | GLU | B | 206 | 82.345 | 24.627 | −27.254 | 1.00 | 22.01 O |
| ATOM | 11807 | C | GLU | B | 206 | 80.921 | 28.138 | −24.794 | 1.00 | 14.48 C |
| ATOM | 11808 | O | GLU | B | 206 | 82.082 | 28.147 | −25.194 | 1.00 | 14.32 O |
| ATOM | 11810 | N | ALA | B | 207 | 80.135 | 29.212 | −24.837 | 1.00 | 14.37 N |
| ATOM | 11811 | CA | ALA | B | 207 | 80.599 | 30.505 | −25.365 | 1.00 | 14.47 C |
| ATOM | 11813 | CB | ALA | B | 207 | 79.417 | 31.407 | −25.656 | 1.00 | 13.19 C |
| ATOM | 11817 | C | ALA | B | 207 | 81.570 | 31.205 | −24.407 | 1.00 | 15.42 C |
| ATOM | 11818 | O | ALA | B | 207 | 82.619 | 31.719 | −24.823 | 1.00 | 14.00 O |
| ATOM | 11820 | N | TYR | B | 208 | 81.208 | 31.217 | −23.126 | 1.00 | 16.83 N |
| ATOM | 11821 | CA | TYR | B | 208 | 82.036 | 31.822 | −22.085 | 1.00 | 17.39 C |
| ATOM | 11823 | CB | TYR | B | 208 | 81.295 | 31.775 | −20.748 | 1.00 | 16.80 C |
| ATOM | 11826 | CG | TYR | B | 208 | 81.878 | 32.675 | −19.681 | 1.00 | 19.11 C |
| ATOM | 11827 | CD1 | TYR | B | 208 | 81.906 | 34.059 | −19.849 | 1.00 | 20.27 C |

APPENDIX 1-continued

| | | | | | | | | | | |
|---|---|---|---|---|---|---|---|---|---|---|
| ATOM | 11829 | CE1 | TYR | B | 208 | 82.435 | 34.893 | −18.870 | 1.00 | 21.22 | C |
| ATOM | 11831 | CZ | TYR | B | 208 | 82.939 | 34.342 | −17.708 | 1.00 | 21.24 | C |
| ATOM | 11832 | OH | TYR | B | 208 | 83.460 | 35.154 | −16.739 | 1.00 | 25.72 | O |
| ATOM | 11834 | CE2 | TYR | B | 208 | 82.925 | 32.974 | −17.514 | 1.00 | 21.97 | C |
| ATOM | 11836 | CD2 | TYR | B | 208 | 82.393 | 32.146 | −18.496 | 1.00 | 20.32 | C |
| ATOM | 11838 | C | TYR | B | 208 | 83.387 | 31.109 | −21.970 | 1.00 | 18.26 | C |
| ATOM | 11839 | O | TYR | B | 208 | 84.420 | 31.740 | −21.752 | 1.00 | 17.72 | O |
| ATOM | 11841 | N | ARG | B | 209 | 83.361 | 29.788 | −22.123 | 1.00 | 19.60 | N |
| ATOM | 11842 | CA | ARG | B | 209 | 84.554 | 28.948 | −22.032 | 1.00 | 20.63 | C |
| ATOM | 11844 | CB | ARG | B | 209 | 84.149 | 27.488 | −22.263 | 1.00 | 20.66 | C |
| ATOM | 11847 | CG | ARG | B | 209 | 85.258 | 26.471 | −22.151 | 1.00 | 23.66 | C |
| ATOM | 11850 | CD | ARG | B | 209 | 84.896 | 25.207 | −22.904 | 1.00 | 24.35 | C |
| ATOM | 11853 | NE | ARG | B | 209 | 83.848 | 24.450 | −22.231 | 1.00 | 21.90 | N |
| ATOM | 11855 | CZ | ARG | B | 209 | 84.045 | 23.557 | −21.259 | 1.00 | 21.36 | C |
| ATOM | 11856 | NH1 | ARG | B | 209 | 85.265 | 23.282 | −20.795 | 1.00 | 16.58 | N |
| ATOM | 11859 | NH2 | ARG | B | 209 | 82.998 | 22.929 | −20.743 | 1.00 | 26.47 | N |
| ATOM | 11862 | C | ARG | B | 209 | 85.631 | 29.362 | −23.038 | 1.00 | 21.82 | C |
| ATOM | 11863 | O | ARG | B | 209 | 86.825 | 29.247 | −22.756 | 1.00 | 22.67 | O |
| ATOM | 11865 | N | LYS | B | 210 | 85.208 | 29.845 | −24.204 | 1.00 | 22.93 | N |
| ATOM | 11866 | CA | LYS | B | 210 | 86.138 | 30.254 | −25.263 | 1.00 | 23.88 | C |
| ATOM | 11868 | CB | LYS | B | 210 | 85.450 | 30.192 | −26.631 | 1.00 | 23.97 | C |
| ATOM | 11871 | CG | LYS | B | 210 | 84.944 | 28.810 | −27.024 | 1.00 | 24.44 | C |
| ATOM | 11874 | CD | LYS | B | 210 | 83.911 | 28.911 | −28.133 | 1.00 | 27.36 | C |
| ATOM | 11877 | CE | LYS | B | 210 | 83.281 | 27.570 | −28.444 | 1.00 | 28.72 | C |
| ATOM | 11880 | NZ | LYS | B | 210 | 82.157 | 27.723 | −29.405 | 1.00 | 27.56 | N |
| ATOM | 11884 | C | LYS | B | 210 | 86.732 | 31.652 | −25.060 | 1.00 | 25.02 | C |
| ATOM | 11885 | O | LYS | B | 210 | 87.806 | 31.935 | −25.585 | 1.00 | 25.55 | O |
| ATOM | 11887 | N | LYS | B | 211 | 86.042 | 32.523 | −24.320 | 1.00 | 26.93 | N |
| ATOM | 11888 | CA | LYS | B | 211 | 86.548 | 33.875 | −24.042 | 1.00 | 28.85 | C |
| ATOM | 11890 | CB | LYS | B | 211 | 85.579 | 34.667 | −23.155 | 1.00 | 29.58 | C |
| ATOM | 11893 | CG | LYS | B | 211 | 84.262 | 35.079 | −23.817 | 1.00 | 32.78 | C |
| ATOM | 11896 | CD | LYS | B | 211 | 83.566 | 36.177 | −23.005 | 1.00 | 37.23 | C |
| ATOM | 11899 | CE | LYS | B | 211 | 82.125 | 36.395 | −23.454 | 1.00 | 40.81 | C |
| ATOM | 11902 | NZ | LYS | B | 211 | 82.027 | 36.756 | −24.893 | 1.00 | 43.15 | N |
| ATOM | 11906 | C | LYS | B | 211 | 87.918 | 33.816 | −23.356 | 1.00 | 30.15 | C |
| ATOM | 11907 | O | LYS | B | 211 | 88.113 | 33.043 | −22.411 | 1.00 | 30.30 | O |
| ATOM | 11909 | N | GLU | B | 212 | 88.859 | 34.628 | −23.838 | 1.00 | 30.90 | N |
| ATOM | 11910 | CA | GLU | B | 212 | 90.217 | 34.637 | −23.292 | 1.00 | 31.34 | C |
| ATOM | 11912 | CB | GLU | B | 212 | 91.193 | 35.334 | −24.250 | 1.00 | 32.12 | C |
| ATOM | 11915 | CG | GLU | B | 212 | 92.669 | 35.267 | −23.794 | 1.00 | 35.82 | C |
| ATOM | 11918 | CD | GLU | B | 212 | 93.661 | 35.001 | −24.929 | 1.00 | 39.82 | C |
| ATOM | 11919 | OE1 | GLU | B | 212 | 93.233 | 34.620 | −26.041 | 1.00 | 42.39 | O |
| ATOM | 11920 | OE2 | GLU | B | 212 | 94.881 | 35.156 | −24.699 | 1.00 | 39.88 | O |
| ATOM | 11921 | C | GLU | B | 212 | 90.267 | 35.286 | −21.909 | 1.00 | 30.16 | C |
| ATOM | 11922 | O | GLU | B | 212 | 91.099 | 34.917 | −21.085 | 1.00 | 30.48 | O |
| ATOM | 11924 | N | ASP | B | 213 | 89.374 | 36.238 | −21.655 | 1.00 | 28.63 | N |
| ATOM | 11925 | CA | ASP | B | 213 | 89.293 | 36.890 | −20.344 | 1.00 | 27.81 | C |
| ATOM | 11927 | CB | ASP | B | 213 | 89.228 | 38.419 | −20.504 | 1.00 | 28.13 | C |
| ATOM | 11930 | CG | ASP | B | 213 | 88.096 | 38.880 | −21.418 | 1.00 | 31.91 | C |
| ATOM | 11931 | OD1 | ASP | B | 213 | 87.454 | 38.028 | −22.078 | 1.00 | 35.70 | O |
| ATOM | 11932 | OD2 | ASP | B | 213 | 87.853 | 40.105 | −21.479 | 1.00 | 36.60 | O |
| ATOM | 11933 | C | ASP | B | 213 | 88.111 | 36.363 | −19.512 | 1.00 | 26.08 | C |
| ATOM | 11934 | O | ASP | B | 213 | 87.454 | 37.120 | −18.797 | 1.00 | 26.21 | O |
| ATOM | 11936 | N | ALA | B | 214 | 87.854 | 35.059 | −19.598 | 1.00 | 23.51 | N |
| ATOM | 11937 | CA | ALA | B | 214 | 86.750 | 34.442 | −18.866 | 1.00 | 21.13 | C |
| ATOM | 11939 | CB | ALA | B | 214 | 86.362 | 33.133 | −19.511 | 1.00 | 21.07 | C |
| ATOM | 11943 | C | ALA | B | 214 | 87.158 | 34.208 | −17.419 | 1.00 | 19.11 | C |
| ATOM | 11944 | O | ALA | B | 214 | 88.244 | 33.692 | −17.166 | 1.00 | 18.32 | O |
| ATOM | 11946 | N | ASN | B | 215 | 86.293 | 34.595 | −16.479 | 1.00 | 17.00 | N |
| ATOM | 11947 | CA | ASN | B | 215 | 86.528 | 34.338 | −15.060 | 1.00 | 15.97 | C |
| ATOM | 11949 | CB | ASN | B | 215 | 85.507 | 35.084 | −14.189 | 1.00 | 15.62 | C |
| ATOM | 11952 | CG | ASN | B | 215 | 85.790 | 34.945 | −12.690 | 1.00 | 16.18 | C |
| ATOM | 11953 | OD1 | ASN | B | 215 | 85.766 | 33.841 | −12.134 | 1.00 | 12.71 | O |
| ATOM | 11954 | ND2 | ASN | B | 215 | 86.049 | 36.071 | −12.031 | 1.00 | 17.08 | N |
| ATOM | 11957 | C | ASN | B | 215 | 86.480 | 32.830 | −14.791 | 1.00 | 15.80 | C |
| ATOM | 11958 | O | ASN | B | 215 | 85.444 | 32.187 | −14.964 | 1.00 | 15.66 | O |
| ATOM | 11960 | N | GLN | B | 216 | 87.609 | 32.275 | −14.368 | 1.00 | 15.71 | N |
| ATOM | 11961 | CA | GLN | B | 216 | 87.751 | 30.832 | −14.231 | 1.00 | 16.29 | C |
| ATOM | 11963 | CB | GLN | B | 216 | 89.220 | 30.461 | −14.040 | 1.00 | 16.24 | C |
| ATOM | 11966 | CG | GLN | B | 216 | 90.104 | 30.863 | −15.220 | 1.00 | 19.78 | C |
| ATOM | 11969 | CD | GLN | B | 216 | 89.645 | 30.249 | −16.534 | 1.00 | 23.16 | C |
| ATOM | 11970 | OE1 | GLN | B | 216 | 90.015 | 29.123 | −16.871 | 1.00 | 25.74 | O |
| ATOM | 11971 | NE2 | GLN | B | 216 | 88.837 | 30.993 | −17.286 | 1.00 | 23.59 | N |
| ATOM | 11974 | C | GLN | B | 216 | 86.902 | 30.273 | −13.090 | 1.00 | 16.43 | C |
| ATOM | 11975 | O | GLN | B | 216 | 86.283 | 29.211 | −13.238 | 1.00 | 16.99 | O |
| ATOM | 11977 | N | VAL | B | 217 | 86.857 | 30.991 | −11.971 | 1.00 | 15.28 | N |
| ATOM | 11978 | CA | VAL | B | 217 | 86.033 | 30.579 | −10.838 | 1.00 | 14.30 | C |
| ATOM | 11980 | CB | VAL | B | 217 | 86.155 | 31.559 | −9.654 | 1.00 | 14.53 | C |
| ATOM | 11982 | CG1 | VAL | B | 217 | 85.180 | 31.169 | −8.536 | 1.00 | 13.56 | C |
| ATOM | 11986 | CG2 | VAL | B | 217 | 87.591 | 31.607 | −9.144 | 1.00 | 9.92 | C |

APPENDIX 1-continued

| | | | | | | | | | | |
|---|---|---|---|---|---|---|---|---|---|---|
| ATOM | 11990 | C | VAL | B | 217 | 84.563 | 30.473 | −11.256 | 1.00 | 13.94 | C |
| ATOM | 11991 | O | VAL | B | 217 | 83.919 | 29.447 | −11.051 | 1.00 | 14.19 | O |
| ATOM | 11993 | N | LEU | B | 218 | 84.049 | 31.539 | −11.857 | 1.00 | 13.24 | N |
| ATOM | 11994 | CA | LEU | B | 218 | 82.668 | 31.573 | −12.303 | 1.00 | 12.51 | C |
| ATOM | 11996 | CB | LEU | B | 218 | 82.345 | 32.938 | −12.904 | 1.00 | 11.55 | C |
| ATOM | 11999 | CG | LEU | B | 218 | 80.940 | 33.178 | −13.471 | 1.00 | 12.38 | C |
| ATOM | 12001 | CD1 | LEU | B | 218 | 79.829 | 32.666 | −12.538 | 1.00 | 6.13 | C |
| ATOM | 12005 | CD2 | LEU | B | 218 | 80.771 | 34.672 | −13.777 | 1.00 | 5.08 | C |
| ATOM | 12009 | C | LEU | B | 218 | 82.398 | 30.464 | −13.316 | 1.00 | 13.27 | C |
| ATOM | 12010 | O | LEU | B | 218 | 81.343 | 29.819 | −13.262 | 1.00 | 13.54 | O |
| ATOM | 12012 | N | LEU | B | 219 | 83.357 | 30.245 | −14.221 | 1.00 | 13.34 | N |
| ATOM | 12013 | CA | LEU | B | 219 | 83.257 | 29.209 | −15.254 | 1.00 | 12.59 | C |
| ATOM | 12015 | CB | LEU | B | 219 | 84.433 | 29.301 | −16.223 | 1.00 | 12.96 | C |
| ATOM | 12018 | CG | LEU | B | 219 | 84.587 | 28.183 | −17.265 | 1.00 | 12.77 | C |
| ATOM | 12020 | CD1 | LEU | B | 219 | 83.293 | 27.926 | −18.024 | 1.00 | 5.60 | C |
| ATOM | 12024 | CD2 | LEU | B | 219 | 85.725 | 28.533 | −18.224 | 1.00 | 10.15 | C |
| ATOM | 12028 | C | LEU | B | 219 | 83.225 | 27.818 | −14.659 | 1.00 | 12.92 | C |
| ATOM | 12029 | O | LEU | B | 219 | 82.365 | 27.005 | −15.008 | 1.00 | 13.24 | O |
| ATOM | 12031 | N | GLU | B | 220 | 84.174 | 27.531 | −13.775 | 1.00 | 12.89 | N |
| ATOM | 12032 | CA | GLU | B | 220 | 84.237 | 26.211 | −13.172 | 1.00 | 13.07 | C |
| ATOM | 12034 | CB | GLU | B | 220 | 85.442 | 26.074 | −12.258 | 1.00 | 13.54 | C |
| ATOM | 12037 | CG | GLU | B | 220 | 85.602 | 24.663 | −11.719 | 1.00 | 14.51 | C |
| ATOM | 12040 | CD | GLU | B | 220 | 86.971 | 24.382 | −11.155 | 1.00 | 13.18 | C |
| ATOM | 12041 | OE1 | GLU | B | 220 | 87.748 | 25.338 | −10.917 | 1.00 | 11.03 | O |
| ATOM | 12042 | OE2 | GLU | B | 220 | 87.258 | 23.184 | −10.952 | 1.00 | 15.01 | O |
| ATOM | 12043 | C | GLU | B | 220 | 82.973 | 25.884 | −12.394 | 1.00 | 13.97 | C |
| ATOM | 12044 | O | GLU | B | 220 | 82.505 | 24.754 | −12.438 | 1.00 | 15.47 | O |
| ATOM | 12046 | N | LEU | B | 221 | 82.423 | 26.865 | −11.682 | 1.00 | 13.71 | N |
| ATOM | 12047 | CA | LEU | B | 221 | 81.206 | 26.645 | −10.911 | 1.00 | 13.62 | C |
| ATOM | 12049 | CB | LEU | B | 221 | 80.883 | 27.874 | −10.056 | 1.00 | 13.55 | C |
| ATOM | 12052 | CG | LEU | B | 221 | 79.673 | 27.780 | −9.112 | 1.00 | 13.36 | C |
| ATOM | 12054 | CD1 | LEU | B | 221 | 79.907 | 26.790 | −7.974 | 1.00 | 5.36 | C |
| ATOM | 12058 | CD2 | LEU | B | 221 | 79.341 | 29.163 | −8.561 | 1.00 | 11.48 | C |
| ATOM | 12062 | C | LEU | B | 221 | 80.046 | 26.313 | −11.850 | 1.00 | 14.45 | C |
| ATOM | 12063 | O | LEU | B | 221 | 79.260 | 25.407 | −11.576 | 1.00 | 15.34 | O |
| ATOM | 12065 | N | ALA | B | 222 | 79.963 | 27.038 | −12.964 | 1.00 | 14.56 | N |
| ATOM | 12066 | CA | ALA | B | 222 | 78.929 | 26.822 | −13.979 | 1.00 | 14.23 | C |
| ATOM | 12068 | CB | ALA | B | 222 | 79.114 | 27.809 | −15.126 | 1.00 | 13.99 | C |
| ATOM | 12072 | C | ALA | B | 222 | 78.919 | 25.391 | −14.513 | 1.00 | 14.13 | C |
| ATOM | 12073 | O | ALA | B | 222 | 77.869 | 24.770 | −14.605 | 1.00 | 13.50 | O |
| ATOM | 12075 | N | ILE | B | 223 | 80.093 | 24.871 | −14.856 | 1.00 | 15.00 | N |
| ATOM | 12076 | CA | ILE | B | 223 | 80.209 | 23.498 | −15.356 | 1.00 | 15.35 | C |
| ATOM | 12078 | CB | ILE | B | 223 | 81.631 | 23.181 | −15.854 | 1.00 | 15.31 | C |
| ATOM | 12080 | CG1 | ILE | B | 223 | 82.022 | 24.094 | −17.018 | 1.00 | 15.24 | C |
| ATOM | 12083 | CD1 | ILE | B | 223 | 83.500 | 24.052 | −17.330 | 1.00 | 11.25 | C |
| ATOM | 12087 | CG2 | ILE | B | 223 | 81.730 | 21.720 | −16.296 | 1.00 | 13.41 | C |
| ATOM | 12091 | C | ILE | B | 223 | 79.881 | 22.498 | −14.252 | 1.00 | 15.97 | C |
| ATOM | 12092 | O | ILE | B | 223 | 79.180 | 21.498 | −14.477 | 1.00 | 16.87 | O |
| ATOM | 12094 | N | LEU | B | 224 | 80.393 | 22.781 | −13.061 | 1.00 | 15.24 | N |
| ATOM | 12095 | CA | LEU | B | 224 | 80.202 | 21.914 | −11.905 | 1.00 | 16.03 | C |
| ATOM | 12097 | CB | LEU | B | 224 | 81.012 | 22.450 | −10.720 | 1.00 | 16.87 | C |
| ATOM | 12100 | CG | LEU | B | 224 | 81.398 | 21.486 | −9.604 | 1.00 | 19.31 | C |
| ATOM | 12102 | CD1 | LEU | B | 224 | 82.677 | 21.947 | −8.915 | 1.00 | 18.36 | C |
| ATOM | 12106 | CD2 | LEU | B | 224 | 80.252 | 21.354 | −8.602 | 1.00 | 22.58 | C |
| ATOM | 12110 | C | LEU | B | 224 | 78.718 | 21.810 | −11.558 | 1.00 | 16.27 | C |
| ATOM | 12111 | O | LEU | B | 224 | 78.178 | 20.709 | −11.448 | 1.00 | 17.89 | O |
| ATOM | 12113 | N | ASP | B | 225 | 78.053 | 22.957 | −11.432 | 1.00 | 15.39 | N |
| ATOM | 12114 | CA | ASP | B | 225 | 76.632 | 22.994 | −11.082 | 1.00 | 14.07 | C |
| ATOM | 12116 | CB | ASP | B | 225 | 76.175 | 24.445 | −10.849 | 1.00 | 13.66 | C |
| ATOM | 12119 | CG | ASP | B | 225 | 74.860 | 24.540 | −10.078 | 1.00 | 11.65 | C |
| ATOM | 12120 | OD1 | ASP | B | 225 | 74.844 | 24.220 | −8.879 | 1.00 | 13.94 | O |
| ATOM | 12121 | OD2 | ASP | B | 225 | 73.841 | 24.951 | −10.664 | 1.00 | 12.79 | O |
| ATOM | 12122 | C | ASP | B | 225 | 75.771 | 22.327 | −12.159 | 1.00 | 14.25 | C |
| ATOM | 12123 | O | ASP | B | 225 | 74.913 | 21.513 | −11.846 | 1.00 | 15.30 | O |
| ATOM | 12125 | N | TYR | B | 226 | 76.003 | 22.667 | −13.424 | 1.00 | 14.55 | N |
| ATOM | 12126 | CA | TYR | B | 226 | 75.221 | 22.100 | −14.528 | 1.00 | 15.33 | C |
| ATOM | 12128 | CB | TYR | B | 226 | 75.718 | 22.615 | −15.880 | 1.00 | 15.41 | C |
| ATOM | 12131 | CG | TYR | B | 226 | 74.866 | 22.201 | −17.064 | 1.00 | 16.23 | C |
| ATOM | 12132 | CD1 | TYR | B | 226 | 75.035 | 20.957 | −17.678 | 1.00 | 17.02 | C |
| ATOM | 12134 | CE1 | TYR | B | 226 | 74.255 | 20.580 | −18.768 | 1.00 | 15.10 | C |
| ATOM | 12136 | CZ | TYR | B | 226 | 73.294 | 21.452 | −19.250 | 1.00 | 17.43 | C |
| ATOM | 12137 | OH | TYR | B | 226 | 72.511 | 21.096 | −20.319 | 1.00 | 15.92 | O |
| ATOM | 12139 | CE2 | TYR | B | 226 | 73.110 | 22.686 | −18.661 | 1.00 | 16.10 | C |
| ATOM | 12141 | CD2 | TYR | B | 226 | 73.892 | 23.055 | −17.577 | 1.00 | 16.82 | C |
| ATOM | 12143 | C | TYR | B | 226 | 75.268 | 20.577 | −14.510 | 1.00 | 16.96 | C |
| ATOM | 12144 | O | TYR | B | 226 | 74.231 | 19.921 | −14.593 | 1.00 | 19.18 | O |
| ATOM | 12146 | N | ASN | B | 227 | 76.467 | 20.014 | −14.395 | 1.00 | 17.75 | N |
| ATOM | 12147 | CA | ASN | B | 227 | 76.614 | 18.561 | −14.371 | 1.00 | 17.68 | C |
| ATOM | 12149 | CB | ASN | B | 227 | 78.086 | 18.139 | −14.488 | 1.00 | 16.82 | C |
| ATOM | 12152 | CG | ASN | B | 227 | 78.632 | 18.303 | −15.900 | 1.00 | 14.72 | C |

APPENDIX 1-continued

| ATOM | 12153 | OD1 | ASN | B | 227 | 77.883 | 18.512 | −16.855 | 1.00 | 16.14 | O |
|---|---|---|---|---|---|---|---|---|---|---|---|
| ATOM | 12154 | ND2 | ASN | B | 227 | 79.942 | 18.209 | −16.037 | 1.00 | 11.36 | N |
| ATOM | 12157 | C | ASN | B | 227 | 75.970 | 17.948 | −13.138 | 1.00 | 18.57 | C |
| ATOM | 12158 | O | ASN | B | 227 | 75.389 | 16.864 | −13.220 | 1.00 | 19.90 | O |
| ATOM | 12160 | N | MET | B | 228 | 76.055 | 18.638 | −12.003 | 1.00 | 18.84 | N |
| ATOM | 12161 | CA | MET | B | 228 | 75.392 | 18.173 | −10.793 | 1.00 | 19.65 | C |
| ATOM | 12163 | CB | MET | B | 228 | 75.653 | 19.126 | −9.639 | 1.00 | 20.86 | C |
| ATOM | 12166 | CG | MET | B | 228 | 74.939 | 18.739 | −8.352 | 1.00 | 24.77 | C |
| ATOM | 12169 | SD | MET | B | 228 | 74.627 | 20.171 | −7.322 | 1.00 | 34.08 | S |
| ATOM | 12170 | CE | MET | B | 228 | 73.252 | 20.947 | −8.177 | 1.00 | 21.79 | C |
| ATOM | 12174 | C | MET | B | 228 | 73.886 | 18.057 | −11.029 | 1.00 | 20.36 | C |
| ATOM | 12175 | O | MET | B | 228 | 73.289 | 17.011 | −10.747 | 1.00 | 19.80 | O |
| ATOM | 12177 | N | ILE | B | 229 | 73.283 | 19.131 | −11.549 | 1.00 | 19.71 | N |
| ATOM | 12178 | CA | ILE | B | 229 | 71.856 | 19.139 | −11.852 | 1.00 | 19.13 | C |
| ATOM | 12180 | CB | ILE | B | 229 | 71.360 | 20.532 | −12.330 | 1.00 | 19.77 | C |
| ATOM | 12182 | CG1 | ILE | B | 229 | 71.412 | 21.544 | −11.176 | 1.00 | 18.86 | C |
| ATOM | 12185 | CD1 | ILE | B | 229 | 71.104 | 22.968 | −11.591 | 1.00 | 18.21 | C |
| ATOM | 12189 | CG2 | ILE | B | 229 | 69.936 | 20.448 | −12.883 | 1.00 | 14.42 | C |
| ATOM | 12193 | C | ILE | B | 229 | 71.537 | 18.080 | −12.901 | 1.00 | 20.72 | C |
| ATOM | 12194 | O | ILE | B | 229 | 70.537 | 17.368 | −12.778 | 1.00 | 21.03 | O |
| ATOM | 12196 | N | GLN | B | 230 | 72.389 | 17.951 | −13.918 | 1.00 | 21.54 | N |
| ATOM | 12197 | CA | GLN | B | 230 | 72.172 | 16.916 | −14.928 | 1.00 | 21.86 | C |
| ATOM | 12199 | CB | GLN | B | 230 | 73.239 | 16.936 | −16.026 | 1.00 | 21.39 | C |
| ATOM | 12202 | CG | GLN | B | 230 | 72.760 | 16.232 | −17.284 | 1.00 | 22.27 | C |
| ATOM | 12205 | CD | GLN | B | 230 | 73.845 | 16.005 | −18.316 | 1.00 | 26.28 | C |
| ATOM | 12206 | OE1 | GLN | B | 230 | 74.848 | 15.325 | −18.054 | 1.00 | 27.63 | O |
| ATOM | 12207 | NE2 | GLN | B | 230 | 73.633 | 16.540 | −19.517 | 1.00 | 23.18 | N |
| ATOM | 12210 | C | GLN | B | 230 | 72.103 | 15.526 | −14.285 | 1.00 | 22.16 | C |
| ATOM | 12211 | O | GLN | B | 230 | 71.338 | 14.678 | −14.725 | 1.00 | 23.81 | O |
| ATOM | 12213 | N | SER | B | 231 | 72.883 | 15.300 | −13.234 | 1.00 | 21.57 | N |
| ATOM | 12214 | CA | SER | B | 231 | 72.842 | 14.023 | −12.537 | 1.00 | 21.30 | C |
| ATOM | 12216 | CB | SER | B | 231 | 73.993 | 13.908 | −11.543 | 1.00 | 21.05 | C |
| ATOM | 12219 | OG | SER | B | 231 | 73.694 | 14.627 | −10.360 | 1.00 | 28.21 | O |
| ATOM | 12221 | C | SER | B | 231 | 71.509 | 13.810 | −11.818 | 1.00 | 19.77 | C |
| ATOM | 12222 | O | SER | B | 231 | 71.044 | 12.677 | −11.707 | 1.00 | 20.50 | O |
| ATOM | 12224 | N | VAL | B | 232 | 70.909 | 14.888 | −11.320 | 1.00 | 18.70 | N |
| ATOM | 12225 | CA | VAL | B | 232 | 69.572 | 14.818 | −10.712 | 1.00 | 17.74 | C |
| ATOM | 12227 | CB | VAL | B | 232 | 69.177 | 16.144 | −10.008 | 1.00 | 17.54 | C |
| ATOM | 12229 | CG1 | VAL | B | 232 | 67.734 | 16.092 | −9.533 | 1.00 | 16.93 | C |
| ATOM | 12233 | CG2 | VAL | B | 232 | 70.106 | 16.434 | −8.837 | 1.00 | 12.46 | C |
| ATOM | 12237 | C | VAL | B | 232 | 68.507 | 14.454 | −11.756 | 1.00 | 17.57 | C |
| ATOM | 12238 | O | VAL | B | 232 | 67.603 | 13.671 | −11.476 | 1.00 | 16.98 | O |
| ATOM | 12240 | N | TYR | B | 233 | 68.627 | 15.010 | −12.957 | 1.00 | 17.65 | N |
| ATOM | 12241 | CA | TYR | B | 233 | 67.708 | 14.676 | −14.038 | 1.00 | 18.54 | C |
| ATOM | 12243 | CB | TYR | B | 233 | 67.971 | 15.536 | −15.281 | 1.00 | 18.25 | C |
| ATOM | 12246 | CG | TYR | B | 233 | 67.759 | 17.024 | −15.109 | 1.00 | 16.48 | C |
| ATOM | 12247 | CD1 | TYR | B | 233 | 66.982 | 17.532 | −14.076 | 1.00 | 16.87 | C |
| ATOM | 12249 | CE1 | TYR | B | 233 | 66.791 | 18.898 | −13.927 | 1.00 | 19.52 | C |
| ATOM | 12251 | CZ | TYR | B | 233 | 67.362 | 19.774 | −14.823 | 1.00 | 16.87 | C |
| ATOM | 12252 | OH | TYR | B | 233 | 67.151 | 21.126 | −14.664 | 1.00 | 16.45 | O |
| ATOM | 12254 | CE2 | TYR | B | 233 | 68.128 | 19.295 | −15.869 | 1.00 | 16.67 | C |
| ATOM | 12256 | CD2 | TYR | B | 233 | 68.320 | 17.927 | −16.008 | 1.00 | 16.37 | C |
| ATOM | 12258 | C | TYR | B | 233 | 67.837 | 13.203 | −14.409 | 1.00 | 20.38 | C |
| ATOM | 12259 | O | TYR | B | 233 | 66.841 | 12.512 | −14.627 | 1.00 | 19.61 | O |
| ATOM | 12261 | N | GLN | B | 234 | 69.077 | 12.732 | −14.484 | 1.00 | 22.17 | N |
| ATOM | 12262 | CA | GLN | B | 234 | 69.344 | 11.335 | −14.790 | 1.00 | 23.14 | C |
| ATOM | 12264 | CB | GLN | B | 234 | 70.850 | 11.104 | −14.985 | 1.00 | 22.82 | C |
| ATOM | 12267 | CG | GLN | B | 234 | 71.334 | 11.599 | −16.355 | 1.00 | 25.57 | C |
| ATOM | 12270 | CD | GLN | B | 234 | 72.841 | 11.795 | −16.451 | 1.00 | 29.72 | C |
| ATOM | 12271 | OE1 | GLN | B | 234 | 73.605 | 11.309 | −15.611 | 1.00 | 33.47 | O |
| ATOM | 12272 | NE2 | GLN | B | 234 | 73.275 | 12.512 | −17.489 | 1.00 | 26.11 | N |
| ATOM | 12275 | C | GLN | B | 234 | 68.738 | 10.410 | −13.728 | 1.00 | 23.92 | C |
| ATOM | 12276 | O | GLN | B | 234 | 68.224 | 9.343 | −14.063 | 1.00 | 24.41 | O |
| ATOM | 12278 | N | ARG | B | 235 | 68.761 | 10.825 | −12.464 | 1.00 | 24.63 | N |
| ATOM | 12279 | CA | ARG | B | 235 | 68.102 | 10.053 | −11.415 | 1.00 | 25.50 | C |
| ATOM | 12281 | CB | ARG | B | 235 | 68.514 | 10.523 | −10.017 | 1.00 | 26.04 | C |
| ATOM | 12284 | CG | ARG | B | 235 | 67.894 | 9.695 | −8.893 | 1.00 | 31.26 | C |
| ATOM | 12287 | CD | ARG | B | 235 | 68.614 | 9.854 | −7.551 | 1.00 | 37.28 | C |
| ATOM | 12290 | NE | ARG | B | 235 | 68.672 | 11.251 | −7.115 | 1.00 | 43.87 | N |
| ATOM | 12292 | CZ | ARG | B | 235 | 69.755 | 12.034 | −7.154 | 1.00 | 48.76 | C |
| ATOM | 12293 | NH1 | ARG | B | 235 | 70.929 | 11.582 | −7.603 | 1.00 | 49.24 | N |
| ATOM | 12296 | NH2 | ARG | B | 235 | 69.664 | 13.291 | −6.729 | 1.00 | 49.39 | N |
| ATOM | 12299 | C | ARG | B | 235 | 66.590 | 10.134 | −11.592 | 1.00 | 25.89 | C |
| ATOM | 12300 | O | ARG | B | 235 | 65.905 | 9.114 | −11.507 | 1.00 | 26.65 | O |
| ATOM | 12302 | N | ASP | B | 236 | 66.076 | 11.335 | −11.857 | 1.00 | 25.46 | N |
| ATOM | 12303 | CA | ASP | B | 236 | 64.645 | 11.517 | −12.108 | 1.00 | 25.83 | C |
| ATOM | 12305 | CB | ASP | B | 236 | 64.321 | 12.983 | −12.439 | 1.00 | 25.43 | C |
| ATOM | 12308 | CG | ASP | B | 236 | 64.495 | 13.925 | −11.258 | 1.00 | 26.34 | C |
| ATOM | 12309 | OD1 | ASP | B | 236 | 64.577 | 13.468 | −10.094 | 1.00 | 25.45 | O |
| ATOM | 12310 | OD2 | ASP | B | 236 | 64.552 | 15.147 | −11.508 | 1.00 | 24.68 | O |

APPENDIX 1-continued

| | | | | | | | | | | |
|---|---|---|---|---|---|---|---|---|---|---|
| ATOM | 12311 | C | ASP | B | 236 | 64.160 | 10.642 | −13.270 | 1.00 | 26.07 | C |
| ATOM | 12312 | O | ASP | B | 236 | 63.139 | 9.964 | −13.165 | 1.00 | 25.47 | O |
| ATOM | 12314 | N | LEU | B | 237 | 64.896 | 10.676 | −14.376 | 1.00 | 26.92 | N |
| ATOM | 12315 | CA | LEU | B | 237 | 64.510 | 9.968 | −15.594 | 1.00 | 27.78 | C |
| ATOM | 12317 | CB | LEU | B | 237 | 65.410 | 10.383 | −16.767 | 1.00 | 27.40 | C |
| ATOM | 12320 | CG | LEU | B | 237 | 65.195 | 9.726 | −18.137 | 1.00 | 25.46 | C |
| ATOM | 12322 | CD1 | LEU | B | 237 | 63.730 | 9.638 | −18.503 | 1.00 | 24.69 | C |
| ATOM | 12326 | CD2 | LEU | B | 237 | 65.949 | 10.486 | −19.212 | 1.00 | 23.42 | C |
| ATOM | 12330 | C | LEU | B | 237 | 64.545 | 8.453 | −15.421 | 1.00 | 30.07 | C |
| ATOM | 12331 | O | LEU | B | 237 | 63.699 | 7.753 | −15.985 | 1.00 | 30.83 | O |
| ATOM | 12333 | N | ARG | B | 238 | 65.516 | 7.945 | −14.660 | 1.00 | 31.75 | N |
| ATOM | 12334 | CA | ARG | B | 238 | 65.608 | 6.500 | −14.406 | 1.00 | 32.98 | C |
| ATOM | 12336 | CB | ARG | B | 238 | 66.862 | 6.137 | −13.592 | 1.00 | 33.58 | C |
| ATOM | 12339 | CG | ARG | B | 238 | 68.159 | 6.099 | −14.397 | 1.00 | 36.70 | C |
| ATOM | 12342 | CD | ARG | B | 238 | 69.265 | 5.306 | −13.681 | 1.00 | 40.82 | C |
| ATOM | 12345 | NE | ARG | B | 238 | 69.652 | 5.857 | −12.371 | 1.00 | 44.46 | N |
| ATOM | 12347 | CZ | ARG | B | 238 | 70.579 | 6.802 | −12.158 | 1.00 | 43.76 | C |
| ATOM | 12348 | NH1 | ARG | B | 238 | 71.248 | 7.367 | −13.166 | 1.00 | 42.21 | N |
| ATOM | 12351 | NH2 | ARG | B | 238 | 70.835 | 7.198 | −10.912 | 1.00 | 41.18 | N |
| ATOM | 12354 | C | ARG | B | 238 | 64.363 | 6.005 | −13.678 | 1.00 | 33.04 | C |
| ATOM | 12355 | O | ARG | B | 238 | 63.812 | 4.963 | −14.025 | 1.00 | 34.30 | O |
| ATOM | 12357 | N | GLU | B | 239 | 63.928 | 6.765 | −12.678 | 1.00 | 33.01 | N |
| ATOM | 12358 | CA | GLU | B | 239 | 62.771 | 6.412 | −11.861 | 1.00 | 33.59 | C |
| ATOM | 12360 | CB | GLU | B | 239 | 62.672 | 7.355 | −10.657 | 1.00 | 35.06 | C |
| ATOM | 12363 | CG | GLU | B | 239 | 61.711 | 6.896 | −9.561 | 1.00 | 42.92 | C |
| ATOM | 12366 | CD | GLU | B | 239 | 61.683 | 7.843 | −8.362 | 1.00 | 53.62 | C |
| ATOM | 12367 | OE1 | GLU | B | 239 | 62.683 | 8.567 | −8.141 | 1.00 | 57.64 | O |
| ATOM | 12368 | OE2 | GLU | B | 239 | 60.660 | 7.861 | −7.637 | 1.00 | 57.88 | O |
| ATOM | 12369 | C | GLU | B | 239 | 61.486 | 6.464 | −12.679 | 1.00 | 31.91 | C |
| ATOM | 12370 | O | GLU | B | 239 | 60.657 | 5.553 | −12.614 | 1.00 | 32.53 | O |
| ATOM | 12372 | N | THR | B | 240 | 61.326 | 7.526 | −13.459 | 1.00 | 29.79 | N |
| ATOM | 12373 | CA | THR | B | 240 | 60.177 | 7.652 | −14.342 | 1.00 | 28.34 | C |
| ATOM | 12375 | CB | THR | B | 240 | 60.079 | 9.077 | −14.916 | 1.00 | 27.73 | C |
| ATOM | 12377 | OG1 | THR | B | 240 | 59.964 | 10.005 | −13.833 | 1.00 | 27.37 | O |
| ATOM | 12379 | CG2 | THR | B | 240 | 58.864 | 9.224 | −15.820 | 1.00 | 25.05 | C |
| ATOM | 12383 | C | THR | B | 240 | 60.208 | 6.598 | −15.463 | 1.00 | 28.19 | C |
| ATOM | 12384 | O | THR | B | 240 | 59.155 | 6.136 | −15.905 | 1.00 | 28.32 | O |
| ATOM | 12386 | N | SER | B | 241 | 61.402 | 6.213 | −15.911 | 1.00 | 28.18 | N |
| ATOM | 12387 | CA | SER | B | 241 | 61.535 | 5.111 | −16.873 | 1.00 | 28.98 | C |
| ATOM | 12389 | CB | SER | B | 241 | 62.983 | 4.919 | −17.322 | 1.00 | 29.08 | C |
| ATOM | 12392 | OG | SER | B | 241 | 63.289 | 5.768 | −18.407 | 1.00 | 31.47 | O |
| ATOM | 12394 | C | SER | B | 241 | 61.005 | 3.797 | −16.311 | 1.00 | 29.33 | C |
| ATOM | 12395 | O | SER | B | 241 | 60.295 | 3.078 | −17.010 | 1.00 | 29.19 | O |
| ATOM | 12397 | N | ARG | B | 242 | 61.348 | 3.484 | −15.061 | 1.00 | 30.11 | N |
| ATOM | 12398 | CA | ARG | B | 242 | 60.841 | 2.269 | −14.409 | 1.00 | 31.50 | C |
| ATOM | 12400 | CB | ARG | B | 242 | 61.344 | 2.149 | −12.966 | 1.00 | 32.60 | C |
| ATOM | 12403 | CG | ARG | B | 242 | 62.679 | 1.395 | −12.830 | 1.00 | 39.21 | C |
| ATOM | 12406 | CD | ARG | B | 242 | 62.898 | 0.897 | −11.394 | 1.00 | 46.39 | C |
| ATOM | 12409 | NE | ARG | B | 242 | 62.812 | 1.988 | −10.415 | 1.00 | 52.27 | N |
| ATOM | 12411 | CZ | ARG | B | 242 | 63.847 | 2.686 | −9.938 | 1.00 | 55.67 | C |
| ATOM | 12412 | NH1 | ARG | B | 242 | 63.632 | 3.660 | −9.055 | 1.00 | 55.49 | N |
| ATOM | 12415 | NH2 | ARG | B | 242 | 65.095 | 2.424 | −10.327 | 1.00 | 57.25 | N |
| ATOM | 12418 | C | ARG | B | 242 | 59.315 | 2.228 | −14.433 | 1.00 | 30.76 | C |
| ATOM | 12419 | O | ARG | B | 242 | 58.713 | 1.273 | −14.928 | 1.00 | 32.00 | O |
| ATOM | 12421 | N | TRP | B | 243 | 58.696 | 3.274 | −13.904 | 1.00 | 29.80 | N |
| ATOM | 12422 | CA | TRP | B | 243 | 57.248 | 3.428 | −13.980 | 1.00 | 28.69 | C |
| ATOM | 12424 | CB | TRP | B | 243 | 56.852 | 4.819 | −13.486 | 1.00 | 28.10 | C |
| ATOM | 12427 | CG | TRP | B | 243 | 55.458 | 5.196 | −13.808 | 1.00 | 24.46 | C |
| ATOM | 12428 | CD1 | TRP | B | 243 | 54.346 | 4.874 | −13.101 | 1.00 | 28.58 | C |
| ATOM | 12430 | NE1 | TRP | B | 243 | 53.231 | 5.411 | −13.702 | 1.00 | 29.43 | N |
| ATOM | 12432 | CE2 | TRP | B | 243 | 53.619 | 6.092 | −14.823 | 1.00 | 19.73 | C |
| ATOM | 12433 | CD2 | TRP | B | 243 | 55.017 | 5.978 | −14.921 | 1.00 | 19.48 | C |
| ATOM | 12434 | CE3 | TRP | B | 243 | 55.668 | 6.587 | −15.995 | 1.00 | 21.43 | C |
| ATOM | 12436 | CZ3 | TRP | B | 243 | 54.913 | 7.286 | −16.923 | 1.00 | 18.77 | C |
| ATOM | 12438 | CH2 | TRP | B | 243 | 53.522 | 7.377 | −16.799 | 1.00 | 22.46 | C |
| ATOM | 12440 | CZ2 | TRP | B | 243 | 52.859 | 6.785 | −15.755 | 1.00 | 21.65 | C |
| ATOM | 12442 | C | TRP | B | 243 | 56.734 | 3.213 | −15.409 | 1.00 | 28.58 | C |
| ATOM | 12443 | O | TRP | B | 243 | 55.820 | 2.422 | −15.632 | 1.00 | 29.05 | O |
| ATOM | 12445 | N | TRP | B | 244 | 57.338 | 3.917 | −16.365 | 1.00 | 27.34 | N |
| ATOM | 12446 | CA | TRP | B | 244 | 56.883 | 3.900 | −17.755 | 1.00 | 26.52 | C |
| ATOM | 12448 | CB | TRP | B | 244 | 57.659 | 4.940 | −18.557 | 1.00 | 26.19 | C |
| ATOM | 12451 | CG | TRP | B | 244 | 57.218 | 5.115 | −19.975 | 1.00 | 23.64 | C |
| ATOM | 12452 | CD1 | TRP | B | 244 | 57.972 | 4.925 | −21.083 | 1.00 | 24.42 | C |
| ATOM | 12454 | NE1 | TRP | B | 244 | 57.238 | 5.200 | −22.211 | 1.00 | 24.86 | N |
| ATOM | 12456 | CE2 | TRP | B | 244 | 55.978 | 5.578 | −21.840 | 1.00 | 22.00 | C |
| ATOM | 12457 | CD2 | TRP | B | 244 | 55.925 | 5.532 | −20.436 | 1.00 | 24.65 | C |
| ATOM | 12458 | CE3 | TRP | B | 244 | 54.728 | 5.871 | −19.795 | 1.00 | 24.31 | C |
| ATOM | 12460 | CZ3 | TRP | B | 244 | 53.648 | 6.241 | −20.565 | 1.00 | 21.89 | C |
| ATOM | 12462 | CH2 | TRP | B | 244 | 53.733 | 6.273 | −21.964 | 1.00 | 22.49 | C |
| ATOM | 12464 | CZ2 | TRP | B | 244 | 54.889 | 5.950 | −22.617 | 1.00 | 22.73 | C |

APPENDIX 1-continued

| | | | | | | | | | | |
|---|---|---|---|---|---|---|---|---|---|---|
| ATOM | 12466 | C | TRP | B | 244 | 57.027 | 2.532 | −18.415 | 1.00 | 26.35 | C |
| ATOM | 12467 | O | TRP | B | 244 | 56.131 | 2.086 | −19.119 | 1.00 | 24.28 | O |
| ATOM | 12469 | N | ARG | B | 245 | 58.154 | 1.871 | −18.187 | 1.00 | 28.23 | N |
| ATOM | 12470 | CA | ARG | B | 245 | 58.378 | 0.549 | −18.771 | 1.00 | 30.73 | C |
| ATOM | 12472 | CB | ARG | B | 245 | 59.841 | 0.106 | −18.608 | 1.00 | 31.78 | C |
| ATOM | 12475 | CG | ARG | B | 245 | 60.727 | 0.494 | −19.799 | 1.00 | 37.60 | C |
| ATOM | 12478 | CD | ARG | B | 245 | 62.147 | −0.077 | −19.693 | 1.00 | 44.15 | C |
| ATOM | 12481 | NE | ARG | B | 245 | 63.034 | 0.795 | −18.915 | 1.00 | 49.07 | N |
| ATOM | 12483 | CZ | ARG | B | 245 | 63.314 | 0.666 | −17.613 | 1.00 | 53.61 | C |
| ATOM | 12484 | NH1 | ARG | B | 245 | 64.140 | 1.534 | −17.033 | 1.00 | 53.90 | N |
| ATOM | 12487 | NH2 | ARG | B | 245 | 62.788 | −0.314 | −16.878 | 1.00 | 55.27 | N |
| ATOM | 12490 | C | ARG | B | 245 | 57.412 | −0.504 | −18.219 | 1.00 | 30.43 | C |
| ATOM | 12491 | O | ARG | B | 245 | 56.966 | −1.371 | −18.963 | 1.00 | 30.12 | O |
| ATOM | 12493 | N | ARG | B | 246 | 57.079 | −0.413 | −16.934 | 1.00 | 30.99 | N |
| ATOM | 12494 | CA | ARG | B | 246 | 56.122 | −1.343 | −16.312 | 1.00 | 31.60 | C |
| ATOM | 12496 | CB | ARG | B | 246 | 56.188 | −1.288 | −14.774 | 1.00 | 33.70 | C |
| ATOM | 12499 | CG | ARG | B | 246 | 57.010 | −2.434 | −14.159 | 1.00 | 42.26 | C |
| ATOM | 12502 | CD | ARG | B | 246 | 57.582 | −2.098 | −12.776 | 1.00 | 53.96 | C |
| ATOM | 12505 | NE | ARG | B | 246 | 56.564 | −1.651 | −11.817 | 1.00 | 63.57 | N |
| ATOM | 12507 | CZ | ARG | B | 246 | 56.753 | −1.544 | −10.498 | 1.00 | 69.41 | C |
| ATOM | 12508 | NH1 | ARG | B | 246 | 57.921 | −1.866 | −9.941 | 1.00 | 70.68 | N |
| ATOM | 12511 | NH2 | ARG | B | 246 | 55.757 | −1.123 | −9.722 | 1.00 | 71.34 | N |
| ATOM | 12514 | C | ARG | B | 246 | 54.698 | −1.109 | −16.791 | 1.00 | 28.27 | C |
| ATOM | 12515 | O | ARG | B | 246 | 53.949 | −2.061 | −16.987 | 1.00 | 28.49 | O |
| ATOM | 12517 | N | VAL | B | 247 | 54.325 | 0.148 | −16.987 | 1.00 | 25.55 | N |
| ATOM | 12518 | CA | VAL | B | 247 | 53.032 | 0.460 | −17.595 | 1.00 | 24.33 | C |
| ATOM | 12520 | CB | VAL | B | 247 | 52.780 | 1.978 | −17.638 | 1.00 | 23.92 | C |
| ATOM | 12522 | CG1 | VAL | B | 247 | 51.526 | 2.303 | −18.429 | 1.00 | 22.50 | C |
| ATOM | 12526 | CG2 | VAL | B | 247 | 52.675 | 2.526 | −16.226 | 1.00 | 23.13 | C |
| ATOM | 12530 | C | VAL | B | 247 | 52.964 | −0.153 | −19.004 | 1.00 | 24.00 | C |
| ATOM | 12531 | O | VAL | B | 247 | 51.929 | −0.693 | −19.406 | 1.00 | 23.41 | O |
| ATOM | 12533 | N | GLY | B | 248 | 54.080 | −0.071 | −19.729 | 1.00 | 23.31 | N |
| ATOM | 12534 | CA | GLY | B | 248 | 54.277 | −0.778 | −20.994 | 1.00 | 23.13 | C |
| ATOM | 12537 | C | GLY | B | 248 | 53.256 | −0.487 | −22.074 | 1.00 | 23.62 | C |
| ATOM | 12538 | O | GLY | B | 248 | 52.871 | −1.379 | −22.826 | 1.00 | 23.94 | O |
| ATOM | 12540 | N | LEU | B | 249 | 52.840 | 0.767 | −22.176 | 1.00 | 25.00 | N |
| ATOM | 12541 | CA | LEU | B | 249 | 51.691 | 1.123 | −23.013 | 1.00 | 26.64 | C |
| ATOM | 12543 | CB | LEU | B | 249 | 51.045 | 2.413 | −22.495 | 1.00 | 26.22 | C |
| ATOM | 12546 | CG | LEU | B | 249 | 49.518 | 2.511 | −22.519 | 1.00 | 25.67 | C |
| ATOM | 12548 | CD1 | LEU | B | 249 | 48.839 | 1.210 | −22.074 | 1.00 | 22.73 | C |
| ATOM | 12552 | CD2 | LEU | B | 249 | 49.081 | 3.691 | −21.646 | 1.00 | 20.40 | C |
| ATOM | 12556 | C | LEU | B | 249 | 52.059 | 1.250 | −24.495 | 1.00 | 28.64 | C |
| ATOM | 12557 | O | LEU | B | 249 | 51.299 | 0.815 | −25.360 | 1.00 | 28.54 | O |
| ATOM | 12559 | N | ALA | B | 250 | 53.224 | 1.830 | −24.785 | 1.00 | 30.89 | N |
| ATOM | 12560 | CA | ALA | B | 250 | 53.702 | 1.970 | −26.170 | 1.00 | 31.80 | C |
| ATOM | 12562 | CB | ALA | B | 250 | 54.894 | 2.900 | −26.222 | 1.00 | 32.53 | C |
| ATOM | 12566 | C | ALA | B | 250 | 54.071 | 0.625 | −26.790 | 1.00 | 32.71 | C |
| ATOM | 12567 | O | ALA | B | 250 | 53.944 | 0.437 | −28.007 | 1.00 | 34.22 | O |
| ATOM | 12569 | N | THR | B | 251 | 54.543 | −0.295 | −25.949 | 1.00 | 32.25 | N |
| ATOM | 12570 | CA | THR | B | 251 | 54.864 | −1.651 | −26.373 | 1.00 | 31.90 | C |
| ATOM | 12572 | CB | THR | B | 251 | 55.533 | −2.449 | −25.241 | 1.00 | 31.39 | C |
| ATOM | 12574 | OG1 | THR | B | 251 | 56.767 | −1.825 | −24.883 | 1.00 | 32.89 | O |
| ATOM | 12576 | CG2 | THR | B | 251 | 55.808 | −3.873 | −25.674 | 1.00 | 31.67 | C |
| ATOM | 12580 | C | THR | B | 251 | 53.616 | −2.405 | −26.784 | 1.00 | 32.40 | C |
| ATOM | 12581 | O | THR | B | 251 | 53.611 | −3.087 | −27.811 | 1.00 | 34.18 | O |
| ATOM | 12583 | N | LYS | B | 252 | 52.562 | −2.281 | −25.981 | 1.00 | 32.28 | N |
| ATOM | 12584 | CA | LYS | B | 252 | 51.356 | −3.090 | −26.164 | 1.00 | 32.62 | C |
| ATOM | 12586 | CB | LYS | B | 252 | 50.634 | −3.289 | −24.827 | 1.00 | 32.87 | C |
| ATOM | 12589 | CG | LYS | B | 252 | 51.444 | −4.094 | −23.797 | 1.00 | 35.03 | C |
| ATOM | 12592 | CD | LYS | B | 252 | 51.356 | −5.599 | −24.043 | 1.00 | 37.32 | C |
| ATOM | 12595 | CE | LYS | B | 252 | 52.373 | −6.367 | −23.209 | 1.00 | 39.70 | C |
| ATOM | 12598 | NZ | LYS | B | 252 | 52.202 | −7.840 | −23.336 | 1.00 | 40.83 | N |
| ATOM | 12602 | C | LYS | B | 252 | 50.409 | −2.494 | −27.197 | 1.00 | 32.21 | C |
| ATOM | 12603 | O | LYS | B | 252 | 49.682 | −3.225 | −27.859 | 1.00 | 33.55 | O |
| ATOM | 12605 | N | LEU | B | 253 | 50.420 | −1.172 | −27.330 | 1.00 | 31.92 | N |
| ATOM | 12606 | CA | LEU | B | 253 | 49.608 | −0.484 | −28.327 | 1.00 | 32.16 | C |
| ATOM | 12608 | CB | LEU | B | 253 | 48.999 | 0.785 | −27.730 | 1.00 | 32.43 | C |
| ATOM | 12611 | CG | LEU | B | 253 | 48.096 | 0.552 | −26.509 | 1.00 | 32.13 | C |
| ATOM | 12613 | CD1 | LEU | B | 253 | 47.870 | 1.842 | −25.735 | 1.00 | 29.32 | C |
| ATOM | 12617 | CD2 | LEU | B | 253 | 46.773 | −0.064 | −26.920 | 1.00 | 31.21 | C |
| ATOM | 12621 | C | LEU | B | 253 | 50.462 | −0.155 | −29.553 | 1.00 | 32.55 | C |
| ATOM | 12622 | O | LEU | B | 253 | 51.409 | 0.639 | −29.475 | 1.00 | 32.24 | O |
| ATOM | 12624 | N | HIS | B | 254 | 50.123 | −0.783 | −30.678 | 1.00 | 32.82 | N |
| ATOM | 12625 | CA | HIS | B | 254 | 50.958 | −0.743 | −31.882 | 1.00 | 34.02 | C |
| ATOM | 12627 | CB | HIS | B | 254 | 50.508 | −1.819 | −32.885 | 1.00 | 34.99 | C |
| ATOM | 12630 | CG | HIS | B | 254 | 49.203 | −1.517 | −33.562 | 1.00 | 40.81 | C |
| ATOM | 12631 | ND1 | HIS | B | 254 | 48.003 | −1.473 | −32.884 | 1.00 | 46.40 | N |
| ATOM | 12633 | CE1 | HIS | B | 254 | 47.030 | −1.188 | −33.733 | 1.00 | 47.23 | C |
| ATOM | 12635 | NE2 | HIS | B | 254 | 47.554 | −1.046 | −34.937 | 1.00 | 45.87 | N |
| ATOM | 12637 | CD2 | HIS | B | 254 | 48.911 | −1.249 | −34.858 | 1.00 | 45.87 | C |

APPENDIX 1-continued

| ATOM | 12639 | C | HIS | B | 254 | 50.988 | 0.638 | −32.546 | 1.00 | 33.59 | C |
|---|---|---|---|---|---|---|---|---|---|---|---|
| ATOM | 12640 | O | HIS | B | 254 | 51.977 | 1.004 | −33.175 | 1.00 | 33.49 | O |
| ATOM | 12642 | N | PHE | B | 255 | 49.906 | 1.397 | −32.399 | 1.00 | 33.23 | N |
| ATOM | 12643 | CA | PHE | B | 255 | 49.822 | 2.750 | −32.954 | 1.00 | 32.76 | C |
| ATOM | 12645 | CB | PHE | B | 255 | 48.352 | 3.162 | −33.115 | 1.00 | 32.23 | C |
| ATOM | 12648 | CG | PHE | B | 255 | 47.639 | 3.375 | −31.806 | 1.00 | 34.07 | C |
| ATOM | 12649 | CD1 | PHE | B | 255 | 47.714 | 4.598 | −31.149 | 1.00 | 35.73 | C |
| ATOM | 12651 | CE1 | PHE | B | 255 | 47.078 | 4.793 | −29.932 | 1.00 | 36.53 | C |
| ATOM | 12653 | CZ | PHE | B | 255 | 46.358 | 3.758 | −29.356 | 1.00 | 35.90 | C |
| ATOM | 12655 | CE2 | PHE | B | 255 | 46.281 | 2.531 | −30.000 | 1.00 | 34.97 | C |
| ATOM | 12657 | CD2 | PHE | B | 255 | 46.919 | 2.346 | −31.216 | 1.00 | 35.32 | C |
| ATOM | 12659 | C | PHE | B | 255 | 50.569 | 3.795 | −32.100 | 1.00 | 32.70 | C |
| ATOM | 12660 | O | PHE | B | 255 | 50.889 | 4.879 | −32.587 | 1.00 | 33.05 | O |
| ATOM | 12662 | N | ALA | B | 256 | 50.846 | 3.466 | −30.837 | 1.00 | 32.71 | N |
| ATOM | 12663 | CA | ALA | B | 256 | 51.324 | 4.451 | −29.855 | 1.00 | 32.49 | C |
| ATOM | 12665 | CB | ALA | B | 256 | 51.100 | 3.931 | −28.435 | 1.00 | 31.46 | C |
| ATOM | 12669 | C | ALA | B | 256 | 52.791 | 4.857 | −30.031 | 1.00 | 32.88 | C |
| ATOM | 12670 | O | ALA | B | 256 | 53.655 | 4.023 | −30.300 | 1.00 | 31.57 | O |
| ATOM | 12672 | N | ARG | B | 257 | 53.047 | 6.155 | −29.863 | 1.00 | 34.38 | N |
| ATOM | 12673 | CA | ARG | B | 257 | 54.405 | 6.705 | −29.842 | 1.00 | 34.26 | C |
| ATOM | 12675 | CB | ARG | B | 257 | 54.406 | 8.155 | −30.345 | 1.00 | 34.10 | C |
| ATOM | 12678 | CG | ARG | B | 257 | 53.944 | 8.342 | −31.792 | 1.00 | 36.63 | C |
| ATOM | 12681 | CD | ARG | B | 257 | 53.800 | 9.830 | −32.132 | 1.00 | 38.52 | C |
| ATOM | 12684 | NE | ARG | B | 257 | 52.619 | 10.425 | −31.501 | 1.00 | 41.28 | N |
| ATOM | 12686 | CZ | ARG | B | 257 | 52.429 | 11.732 | −31.304 | 1.00 | 46.94 | C |
| ATOM | 12687 | NH1 | ARG | B | 257 | 53.344 | 12.624 | −31.678 | 1.00 | 49.83 | N |
| ATOM | 12690 | NH2 | ARG | B | 257 | 51.311 | 12.154 | −30.714 | 1.00 | 47.41 | N |
| ATOM | 12693 | C | ARG | B | 257 | 54.952 | 6.678 | −28.416 | 1.00 | 33.80 | C |
| ATOM | 12694 | O | ARG | B | 257 | 54.274 | 7.127 | −27.484 | 1.00 | 33.65 | O |
| ATOM | 12696 | N | ASP | B | 258 | 56.166 | 6.147 | −28.253 | 1.00 | 33.38 | N |
| ATOM | 12697 | CA | ASP | B | 258 | 56.916 | 6.253 | −26.992 | 1.00 | 32.84 | C |
| ATOM | 12699 | CB | ASP | B | 258 | 57.869 | 5.060 | −26.821 | 1.00 | 32.27 | C |
| ATOM | 12702 | CG | ASP | B | 258 | 58.615 | 5.079 | −25.484 | 1.00 | 33.79 | C |
| ATOM | 12703 | OD1 | ASP | B | 258 | 58.403 | 6.016 | −24.682 | 1.00 | 27.94 | O |
| ATOM | 12704 | OD2 | ASP | B | 258 | 59.416 | 4.151 | −25.230 | 1.00 | 34.26 | O |
| ATOM | 12705 | C | ASP | B | 258 | 57.701 | 7.580 | −26.970 | 1.00 | 32.65 | C |
| ATOM | 12706 | O | ASP | B | 258 | 58.719 | 7.723 | −27.655 | 1.00 | 32.02 | O |
| ATOM | 12708 | N | ARG | B | 259 | 57.226 | 8.532 | −26.169 | 1.00 | 32.74 | N |
| ATOM | 12709 | CA | ARG | B | 259 | 57.801 | 9.880 | −26.112 | 1.00 | 33.33 | C |
| ATOM | 12711 | CB | ARG | B | 259 | 56.780 | 10.881 | −26.663 | 1.00 | 34.08 | C |
| ATOM | 12714 | CG | ARG | B | 259 | 56.680 | 10.902 | −28.179 | 1.00 | 39.83 | C |
| ATOM | 12717 | CD | ARG | B | 259 | 57.587 | 11.969 | −28.800 | 1.00 | 47.10 | C |
| ATOM | 12720 | NE | ARG | B | 259 | 57.378 | 12.074 | −30.243 | 1.00 | 52.94 | N |
| ATOM | 12722 | CZ | ARG | B | 259 | 57.833 | 11.203 | −31.149 | 1.00 | 57.88 | C |
| ATOM | 12723 | NH1 | ARG | B | 259 | 58.545 | 10.137 | −30.782 | 1.00 | 58.91 | N |
| ATOM | 12726 | NH2 | ARG | B | 259 | 57.573 | 11.396 | −32.439 | 1.00 | 58.39 | N |
| ATOM | 12729 | C | ARG | B | 259 | 58.219 | 10.286 | −24.688 | 1.00 | 31.97 | C |
| ATOM | 12730 | O | ARG | B | 259 | 58.035 | 11.444 | −24.289 | 1.00 | 31.74 | O |
| ATOM | 12732 | N | LEU | B | 260 | 58.787 | 9.345 | −23.930 | 1.00 | 29.99 | N |
| ATOM | 12733 | CA | LEU | B | 260 | 59.111 | 9.599 | −22.523 | 1.00 | 28.89 | C |
| ATOM | 12735 | CB | LEU | B | 260 | 59.407 | 8.294 | −21.760 | 1.00 | 28.53 | C |
| ATOM | 12738 | CG | LEU | B | 260 | 59.795 | 8.420 | −20.273 | 1.00 | 27.86 | C |
| ATOM | 12740 | CD1 | LEU | B | 260 | 58.752 | 9.159 | −19.462 | 1.00 | 23.05 | C |
| ATOM | 12744 | CD2 | LEU | B | 260 | 60.025 | 7.057 | −19.673 | 1.00 | 31.60 | C |
| ATOM | 12748 | C | LEU | B | 260 | 60.292 | 10.552 | −22.408 | 1.00 | 27.72 | C |
| ATOM | 12749 | O | LEU | B | 260 | 60.210 | 11.582 | −21.729 | 1.00 | 28.38 | O |
| ATOM | 12751 | N | ILE | B | 261 | 61.382 | 10.216 | −23.085 | 1.00 | 25.46 | N |
| ATOM | 12752 | CA | ILE | B | 261 | 62.592 | 11.029 | −23.012 | 1.00 | 24.56 | C |
| ATOM | 12754 | CB | ILE | B | 261 | 63.741 | 10.422 | −23.854 | 1.00 | 24.32 | C |
| ATOM | 12756 | CG1 | ILE | B | 261 | 64.113 | 9.023 | −23.328 | 1.00 | 26.66 | C |
| ATOM | 12759 | CD1 | ILE | B | 261 | 64.701 | 8.083 | −24.377 | 1.00 | 24.42 | C |
| ATOM | 12763 | CG2 | ILE | B | 261 | 64.954 | 11.334 | −23.817 | 1.00 | 20.66 | C |
| ATOM | 12767 | C | ILE | B | 261 | 62.277 | 12.467 | −23.460 | 1.00 | 23.83 | C |
| ATOM | 12768 | O | ILE | B | 261 | 62.652 | 13.432 | −22.788 | 1.00 | 21.34 | O |
| ATOM | 12770 | N | GLU | B | 262 | 61.562 | 12.595 | −24.578 | 1.00 | 23.36 | N |
| ATOM | 12771 | CA | GLU | B | 262 | 61.151 | 13.902 | −25.087 | 1.00 | 23.51 | C |
| ATOM | 12773 | CB | GLU | B | 262 | 60.390 | 13.764 | −26.413 | 1.00 | 24.09 | C |
| ATOM | 12776 | CG | GLU | B | 262 | 61.253 | 13.340 | −27.603 | 1.00 | 28.89 | C |
| ATOM | 12779 | CD | GLU | B | 262 | 61.363 | 11.821 | −27.788 | 1.00 | 36.03 | C |
| ATOM | 12780 | OE1 | GLU | B | 262 | 61.521 | 11.079 | −26.784 | 1.00 | 35.08 | O |
| ATOM | 12781 | OE2 | GLU | B | 262 | 61.309 | 11.372 | −28.958 | 1.00 | 41.14 | O |
| ATOM | 12782 | C | GLU | B | 262 | 60.283 | 14.628 | −24.053 | 1.00 | 22.99 | C |
| ATOM | 12783 | O | GLU | B | 262 | 60.440 | 15.832 | −23.827 | 1.00 | 21.89 | O |
| ATOM | 12785 | N | SER | B | 263 | 59.374 | 13.888 | −23.421 | 1.00 | 22.63 | N |
| ATOM | 12786 | CA | SER | B | 263 | 58.494 | 14.468 | −22.409 | 1.00 | 22.10 | C |
| ATOM | 12788 | CB | SER | B | 263 | 57.418 | 13.472 | −21.970 | 1.00 | 22.50 | C |
| ATOM | 12791 | OG | SER | B | 263 | 56.408 | 13.370 | −22.961 | 1.00 | 24.94 | O |
| ATOM | 12793 | C | SER | B | 263 | 59.286 | 14.958 | −21.209 | 1.00 | 20.61 | C |
| ATOM | 12794 | O | SER | B | 263 | 58.994 | 16.009 | −20.658 | 1.00 | 18.48 | O |
| ATOM | 12796 | N | PHE | B | 264 | 60.302 | 14.205 | −20.810 | 1.00 | 21.00 | N |

APPENDIX 1-continued

| ATOM | 12797 | CA | PHE | B | 264 | 61.139 | 14.645 | −19.703 | 1.00 | 20.52 | C |
|---|---|---|---|---|---|---|---|---|---|---|---|
| ATOM | 12799 | CB | PHE | B | 264 | 62.095 | 13.548 | −19.246 | 1.00 | 19.25 | C |
| ATOM | 12802 | CG | PHE | B | 264 | 62.627 | 13.797 | −17.888 | 1.00 | 18.67 | C |
| ATOM | 12803 | CD1 | PHE | B | 264 | 61.911 | 13.396 | −16.771 | 1.00 | 17.30 | C |
| ATOM | 12805 | CE1 | PHE | B | 264 | 62.373 | 13.658 | −15.513 | 1.00 | 15.98 | C |
| ATOM | 12807 | CZ | PHE | B | 264 | 63.557 | 14.354 | −15.356 | 1.00 | 20.53 | C |
| ATOM | 12809 | CE2 | PHE | B | 264 | 64.266 | 14.781 | −16.461 | 1.00 | 18.60 | C |
| ATOM | 12811 | CD2 | PHE | B | 264 | 63.793 | 14.513 | −17.717 | 1.00 | 19.97 | C |
| ATOM | 12813 | C | PHE | B | 264 | 61.934 | 15.906 | −20.055 | 1.00 | 21.18 | C |
| ATOM | 12814 | O | PHE | B | 264 | 62.070 | 16.811 | −19.235 | 1.00 | 21.13 | O |
| ATOM | 12816 | N | TYR | B | 265 | 62.464 | 15.946 | −21.273 | 1.00 | 22.16 | N |
| ATOM | 12817 | CA | TYR | B | 265 | 63.206 | 17.098 | −21.773 | 1.00 | 23.19 | C |
| ATOM | 12819 | CB | TYR | B | 265 | 63.668 | 16.832 | −23.210 | 1.00 | 23.48 | C |
| ATOM | 12822 | CG | TYR | B | 265 | 64.017 | 18.064 | −24.015 | 1.00 | 29.92 | C |
| ATOM | 12823 | CD1 | TYR | B | 265 | 65.240 | 18.714 | −23.835 | 1.00 | 35.18 | C |
| ATOM | 12825 | CE1 | TYR | B | 265 | 65.574 | 19.839 | −24.583 | 1.00 | 37.23 | C |
| ATOM | 12827 | CZ | TYR | B | 265 | 64.684 | 20.320 | −25.530 | 1.00 | 38.30 | C |
| ATOM | 12828 | OH | TYR | B | 265 | 65.016 | 21.436 | −26.269 | 1.00 | 42.78 | O |
| ATOM | 12830 | CE2 | TYR | B | 265 | 63.462 | 19.687 | −25.729 | 1.00 | 35.17 | C |
| ATOM | 12832 | CD2 | TYR | B | 265 | 63.139 | 18.565 | −24.977 | 1.00 | 32.59 | C |
| ATOM | 12834 | C | TYR | B | 265 | 62.326 | 18.337 | −21.701 | 1.00 | 22.75 | C |
| ATOM | 12835 | O | TYR | B | 265 | 62.764 | 19.406 | −21.267 | 1.00 | 23.58 | O |
| ATOM | 12837 | N | TRP | B | 266 | 61.078 | 18.166 | −22.119 | 1.00 | 21.59 | N |
| ATOM | 12838 | CA | TRP | B | 266 | 60.050 | 19.190 | −21.990 | 1.00 | 20.37 | C |
| ATOM | 12840 | CB | TRP | B | 266 | 58.734 | 18.643 | −22.526 | 1.00 | 20.30 | C |
| ATOM | 12843 | CG | TRP | B | 266 | 57.601 | 19.570 | −22.424 | 1.00 | 20.24 | C |
| ATOM | 12844 | CD1 | TRP | B | 266 | 56.763 | 19.729 | −21.363 | 1.00 | 20.28 | C |
| ATOM | 12846 | NE1 | TRP | B | 266 | 55.814 | 20.679 | −21.651 | 1.00 | 20.11 | N |
| ATOM | 12848 | CE2 | TRP | B | 266 | 56.028 | 21.145 | −22.922 | 1.00 | 22.59 | C |
| ATOM | 12849 | CD2 | TRP | B | 266 | 57.145 | 20.464 | −23.438 | 1.00 | 21.18 | C |
| ATOM | 12850 | CE3 | TRP | B | 266 | 57.573 | 20.754 | −24.736 | 1.00 | 22.79 | C |
| ATOM | 12852 | CZ3 | TRP | B | 266 | 56.885 | 21.706 | −25.464 | 1.00 | 25.95 | C |
| ATOM | 12854 | CH2 | TRP | B | 266 | 55.776 | 22.368 | −24.925 | 1.00 | 24.56 | C |
| ATOM | 12856 | CZ2 | TRP | B | 266 | 55.332 | 22.104 | −23.659 | 1.00 | 25.55 | C |
| ATOM | 12858 | C | TRP | B | 266 | 59.854 | 19.605 | −20.547 | 1.00 | 19.47 | C |
| ATOM | 12859 | O | TRP | B | 266 | 59.797 | 20.787 | −20.244 | 1.00 | 20.67 | O |
| ATOM | 12861 | N | ALA | B | 267 | 59.736 | 18.623 | −19.660 | 1.00 | 18.53 | N |
| ATOM | 12862 | CA | ALA | B | 267 | 59.499 | 18.882 | −18.240 | 1.00 | 17.60 | C |
| ATOM | 12864 | CB | ALA | B | 267 | 59.270 | 17.585 | −17.505 | 1.00 | 17.46 | C |
| ATOM | 12868 | C | ALA | B | 267 | 60.631 | 19.664 | −17.585 | 1.00 | 17.74 | C |
| ATOM | 12869 | O | ALA | B | 267 | 60.398 | 20.395 | −16.633 | 1.00 | 18.27 | O |
| ATOM | 12871 | N | VAL | B | 268 | 61.850 | 19.505 | −18.096 | 1.00 | 18.33 | N |
| ATOM | 12872 | CA | VAL | B | 268 | 63.018 | 20.236 | −17.592 | 1.00 | 17.43 | C |
| ATOM | 12874 | CB | VAL | B | 268 | 64.332 | 19.613 | −18.123 | 1.00 | 17.15 | C |
| ATOM | 12876 | CG1 | VAL | B | 268 | 65.522 | 20.542 | −17.903 | 1.00 | 13.64 | C |
| ATOM | 12880 | CG2 | VAL | B | 268 | 64.566 | 18.259 | −17.464 | 1.00 | 15.60 | C |
| ATOM | 12884 | C | VAL | B | 268 | 62.943 | 21.717 | −17.968 | 1.00 | 17.91 | C |
| ATOM | 12885 | O | VAL | B | 268 | 63.488 | 22.575 | −17.265 | 1.00 | 18.01 | O |
| ATOM | 12887 | N | GLY | B | 269 | 62.282 | 22.006 | −19.087 | 1.00 | 18.16 | N |
| ATOM | 12888 | CA | GLY | B | 269 | 62.007 | 23.381 | −19.496 | 1.00 | 17.58 | C |
| ATOM | 12891 | C | GLY | B | 269 | 61.069 | 24.062 | −18.523 | 1.00 | 17.55 | C |
| ATOM | 12892 | O | GLY | B | 269 | 61.250 | 25.239 | −18.206 | 1.00 | 19.16 | O |
| ATOM | 12894 | N | VAL | B | 270 | 60.090 | 23.310 | −18.022 | 1.00 | 16.05 | N |
| ATOM | 12895 | CA | VAL | B | 270 | 59.058 | 23.870 | −17.169 | 1.00 | 15.65 | C |
| ATOM | 12897 | CB | VAL | B | 270 | 57.799 | 22.998 | −17.154 | 1.00 | 15.67 | C |
| ATOM | 12899 | CG1 | VAL | B | 270 | 56.784 | 23.542 | −16.158 | 1.00 | 12.64 | C |
| ATOM | 12903 | CG2 | VAL | B | 270 | 57.194 | 22.939 | −18.546 | 1.00 | 14.23 | C |
| ATOM | 12907 | C | VAL | B | 270 | 59.532 | 24.105 | −15.741 | 1.00 | 16.19 | C |
| ATOM | 12908 | O | VAL | B | 270 | 59.205 | 25.133 | −15.142 | 1.00 | 17.24 | O |
| ATOM | 12910 | N | ALA | B | 271 | 60.282 | 23.156 | −15.192 | 1.00 | 16.15 | N |
| ATOM | 12911 | CA | ALA | B | 271 | 60.764 | 23.247 | −13.806 | 1.00 | 16.22 | C |
| ATOM | 12913 | CB | ALA | B | 271 | 59.785 | 22.566 | −12.858 | 1.00 | 14.70 | C |
| ATOM | 12917 | C | ALA | B | 271 | 62.161 | 22.621 | −13.702 | 1.00 | 16.92 | C |
| ATOM | 12918 | O | ALA | B | 271 | 62.299 | 21.406 | −13.577 | 1.00 | 16.47 | O |
| ATOM | 12920 | N | PHE | B | 272 | 63.188 | 23.464 | −13.756 | 1.00 | 17.73 | N |
| ATOM | 12921 | CA | PHE | B | 272 | 64.564 | 22.998 | −13.927 | 1.00 | 19.08 | C |
| ATOM | 12923 | CB | PHE | B | 272 | 65.321 | 23.942 | −14.861 | 1.00 | 19.69 | C |
| ATOM | 12926 | CG | PHE | B | 272 | 65.744 | 25.224 | −14.213 | 1.00 | 20.99 | C |
| ATOM | 12927 | CD1 | PHE | B | 272 | 66.957 | 25.309 | −13.544 | 1.00 | 24.32 | C |
| ATOM | 12929 | CE1 | PHE | B | 272 | 67.353 | 26.488 | −12.947 | 1.00 | 24.57 | C |
| ATOM | 12931 | CZ | PHE | B | 272 | 66.535 | 27.599 | −13.014 | 1.00 | 25.03 | C |
| ATOM | 12933 | CE2 | PHE | B | 272 | 65.324 | 27.530 | −13.679 | 1.00 | 22.70 | C |
| ATOM | 12935 | CD2 | PHE | B | 272 | 64.934 | 26.343 | −14.272 | 1.00 | 22.88 | C |
| ATOM | 12937 | C | PHE | B | 272 | 65.344 | 22.850 | −12.625 | 1.00 | 19.52 | C |
| ATOM | 12938 | O | PHE | B | 272 | 66.277 | 22.051 | −12.553 | 1.00 | 19.57 | O |
| ATOM | 12940 | N | GLU | B | 273 | 64.971 | 23.624 | −11.608 | 1.00 | 20.16 | N |
| ATOM | 12941 | CA | GLU | B | 273 | 65.741 | 23.675 | −10.371 | 1.00 | 20.65 | C |
| ATOM | 12943 | CB | GLU | B | 273 | 65.181 | 24.727 | −9.405 | 1.00 | 20.99 | C |
| ATOM | 12946 | CG | GLU | B | 273 | 65.316 | 26.176 | −9.883 | 1.00 | 22.85 | C |
| ATOM | 12949 | CD | GLU | B | 273 | 64.088 | 26.682 | −10.628 | 1.00 | 27.28 | C |

APPENDIX 1-continued

| | | | | | | | | | | |
|---|---|---|---|---|---|---|---|---|---|---|
| ATOM | 12950 | OE1 | GLU | B | 273 | 63.673 | 27.837 | −10.391 | 1.00 | 31.35 | O |
| ATOM | 12951 | OE2 | GLU | B | 273 | 63.530 | 25.929 | −11.450 | 1.00 | 31.83 | O |
| ATOM | 12952 | C | GLU | B | 273 | 65.750 | 22.299 | −9.711 | 1.00 | 20.45 | C |
| ATOM | 12953 | O | GLU | B | 273 | 64.729 | 21.625 | −9.670 | 1.00 | 21.36 | O |
| ATOM | 12955 | N | PRO | B | 274 | 66.904 | 21.873 | −9.188 | 1.00 | 20.01 | N |
| ATOM | 12956 | CA | PRO | B | 274 | 67.015 | 20.492 | −8.703 | 1.00 | 19.83 | C |
| ATOM | 12958 | CB | PRO | B | 274 | 68.357 | 20.478 | −7.951 | 1.00 | 19.83 | C |
| ATOM | 12961 | CG | PRO | B | 274 | 68.845 | 21.897 | −7.936 | 1.00 | 19.28 | C |
| ATOM | 12964 | CD | PRO | B | 274 | 68.165 | 22.615 | −9.037 | 1.00 | 19.35 | C |
| ATOM | 12967 | C | PRO | B | 274 | 65.872 | 20.024 | −7.799 | 1.00 | 19.29 | C |
| ATOM | 12968 | O | PRO | B | 274 | 65.471 | 18.867 | −7.878 | 1.00 | 21.29 | O |
| ATOM | 12969 | N | GLN | B | 275 | 65.340 | 20.908 | −6.967 | 1.00 | 19.08 | N |
| ATOM | 12970 | CA | GLN | B | 275 | 64.287 | 20.532 | −6.007 | 1.00 | 19.66 | C |
| ATOM | 12972 | CB | GLN | B | 275 | 64.018 | 21.677 | −5.021 | 1.00 | 19.32 | C |
| ATOM | 12975 | CG | GLN | B | 275 | 63.679 | 23.030 | −5.650 | 1.00 | 21.51 | C |
| ATOM | 12978 | CD | GLN | B | 275 | 64.905 | 23.899 | −5.919 | 1.00 | 26.18 | C |
| ATOM | 12979 | OE1 | GLN | B | 275 | 65.947 | 23.405 | −6.351 | 1.00 | 25.97 | O |
| ATOM | 12980 | NE2 | GLN | B | 275 | 64.777 | 25.204 | −5.677 | 1.00 | 27.95 | N |
| ATOM | 12983 | C | GLN | B | 275 | 62.959 | 20.077 | −6.641 | 1.00 | 20.56 | C |
| ATOM | 12984 | O | GLN | B | 275 | 62.171 | 19.376 | −5.992 | 1.00 | 20.08 | O |
| ATOM | 12986 | N | TYR | B | 276 | 62.723 | 20.444 | −7.903 | 1.00 | 20.07 | N |
| ATOM | 12987 | CA | TYR | B | 276 | 61.442 | 20.181 | −8.554 | 1.00 | 20.27 | C |
| ATOM | 12989 | CB | TYR | B | 276 | 61.105 | 21.332 | −9.508 | 1.00 | 20.86 | C |
| ATOM | 12992 | CG | TYR | B | 276 | 60.869 | 22.660 | −8.810 | 1.00 | 22.46 | C |
| ATOM | 12993 | CD1 | TYR | B | 276 | 59.986 | 22.761 | −7.738 | 1.00 | 21.03 | C |
| ATOM | 12995 | CE1 | TYR | B | 276 | 59.762 | 23.969 | −7.108 | 1.00 | 21.89 | C |
| ATOM | 12997 | CZ | TYR | B | 276 | 60.410 | 25.098 | −7.550 | 1.00 | 25.18 | C |
| ATOM | 12998 | OH | TYR | B | 276 | 60.176 | 26.299 | −6.921 | 1.00 | 31.83 | O |
| ATOM | 13000 | CE2 | TYR | B | 276 | 61.284 | 25.032 | −8.611 | 1.00 | 23.66 | C |
| ATOM | 13002 | CD2 | TYR | B | 276 | 61.507 | 23.819 | −9.238 | 1.00 | 24.15 | C |
| ATOM | 13004 | C | TYR | B | 276 | 61.360 | 18.821 | −9.278 | 1.00 | 20.12 | C |
| ATOM | 13005 | O | TYR | B | 276 | 60.750 | 18.697 | −10.344 | 1.00 | 19.49 | O |
| ATOM | 13007 | N | SER | B | 277 | 61.948 | 17.791 | −8.682 | 1.00 | 19.98 | N |
| ATOM | 13008 | CA | SER | B | 277 | 61.841 | 16.447 | −9.234 | 1.00 | 19.57 | C |
| ATOM | 13010 | CB | SER | B | 277 | 62.556 | 15.437 | −8.338 | 1.00 | 18.90 | C |
| ATOM | 13013 | OG | SER | B | 277 | 63.950 | 15.509 | −8.547 | 1.00 | 19.52 | O |
| ATOM | 13015 | C | SER | B | 277 | 60.382 | 16.041 | −9.424 | 1.00 | 20.31 | C |
| ATOM | 13016 | O | SER | B | 277 | 60.011 | 15.551 | −10.495 | 1.00 | 21.30 | O |
| ATOM | 13018 | N | ASP | B | 278 | 59.559 | 16.251 | −8.394 | 1.00 | 20.02 | N |
| ATOM | 13019 | CA | ASP | B | 278 | 58.149 | 15.879 | −8.460 | 1.00 | 20.05 | C |
| ATOM | 13021 | CB | ASP | B | 278 | 57.404 | 16.258 | −7.178 | 1.00 | 21.33 | C |
| ATOM | 13024 | CG | ASP | B | 278 | 57.767 | 15.380 | −6.002 | 1.00 | 24.28 | C |
| ATOM | 13025 | OD1 | ASP | B | 278 | 58.485 | 14.374 | −6.188 | 1.00 | 32.22 | O |
| ATOM | 13026 | OD2 | ASP | B | 278 | 57.330 | 15.707 | −4.876 | 1.00 | 30.56 | O |
| ATOM | 13027 | C | ASP | B | 278 | 57.479 | 16.551 | −9.642 | 1.00 | 19.68 | C |
| ATOM | 13028 | O | ASP | B | 278 | 56.819 | 15.893 | −10.447 | 1.00 | 19.85 | O |
| ATOM | 13030 | N | CYS | B | 279 | 57.652 | 17.863 | −9.754 | 1.00 | 19.27 | N |
| ATOM | 13031 | CA | CYS | B | 279 | 57.076 | 18.586 | −10.871 | 1.00 | 19.01 | C |
| ATOM | 13033 | CB | CYS | B | 279 | 57.382 | 20.076 | −10.783 | 1.00 | 19.07 | C |
| ATOM | 13036 | SG | CYS | B | 279 | 56.476 | 21.038 | −11.994 | 1.00 | 21.99 | S |
| ATOM | 13038 | C | CYS | B | 279 | 57.562 | 18.010 | −12.203 | 1.00 | 18.56 | C |
| ATOM | 13039 | O | CYS | B | 279 | 56.762 | 17.799 | −13.108 | 1.00 | 18.25 | O |
| ATOM | 13041 | N | ARG | B | 280 | 58.859 | 17.730 | −12.310 | 1.00 | 18.41 | N |
| ATOM | 13042 | CA | ARG | B | 280 | 59.416 | 17.197 | −13.561 | 1.00 | 18.94 | C |
| ATOM | 13044 | CB | ARG | B | 280 | 60.945 | 17.080 | −13.505 | 1.00 | 18.75 | C |
| ATOM | 13047 | CG | ARG | B | 280 | 61.656 | 18.382 | −13.810 | 1.00 | 18.50 | C |
| ATOM | 13050 | CD | ARG | B | 280 | 63.150 | 18.188 | −13.957 | 1.00 | 17.74 | C |
| ATOM | 13053 | NE | ARG | B | 280 | 63.753 | 17.708 | −12.721 | 1.00 | 13.97 | N |
| ATOM | 13055 | CZ | ARG | B | 280 | 64.014 | 18.462 | −11.661 | 1.00 | 15.77 | C |
| ATOM | 13056 | NH1 | ARG | B | 280 | 63.726 | 19.756 | −11.660 | 1.00 | 18.71 | N |
| ATOM | 13059 | NH2 | ARG | B | 280 | 64.562 | 17.909 | −10.582 | 1.00 | 20.38 | N |
| ATOM | 13062 | C | ARG | B | 280 | 58.821 | 15.851 | −13.902 | 1.00 | 19.15 | C |
| ATOM | 13063 | O | ARG | B | 280 | 58.471 | 15.601 | −15.052 | 1.00 | 18.90 | O |
| ATOM | 13065 | N | ASN | B | 281 | 58.708 | 14.991 | −12.895 | 1.00 | 20.06 | N |
| ATOM | 13066 | CA | ASN | B | 281 | 58.178 | 13.648 | −13.090 | 1.00 | 20.75 | C |
| ATOM | 13068 | CB | ASN | B | 281 | 58.464 | 12.784 | −11.860 | 1.00 | 20.99 | C |
| ATOM | 13071 | CG | ASN | B | 281 | 59.972 | 12.554 | −11.641 | 1.00 | 25.66 | C |
| ATOM | 13072 | OD1 | ASN | B | 281 | 60.746 | 12.419 | −12.596 | 1.00 | 28.16 | O |
| ATOM | 13073 | ND2 | ASN | B | 281 | 60.385 | 12.520 | −10.381 | 1.00 | 25.36 | N |
| ATOM | 13076 | C | ASN | B | 281 | 56.689 | 13.693 | −13.408 | 1.00 | 20.49 | C |
| ATOM | 13077 | O | ASN | B | 281 | 56.209 | 12.991 | −14.296 | 1.00 | 19.74 | O |
| ATOM | 13079 | N | SER | B | 282 | 55.970 | 14.555 | −12.702 | 1.00 | 20.45 | N |
| ATOM | 13080 | CA | SER | B | 282 | 54.537 | 14.701 | −12.901 | 1.00 | 20.12 | C |
| ATOM | 13082 | CB | SER | B | 282 | 53.956 | 15.651 | −11.854 | 1.00 | 20.65 | C |
| ATOM | 13085 | OG | SER | B | 282 | 52.595 | 15.359 | −11.618 | 1.00 | 22.82 | O |
| ATOM | 13087 | C | SER | B | 282 | 54.215 | 15.190 | −14.312 | 1.00 | 19.43 | C |
| ATOM | 13088 | O | SER | B | 282 | 53.323 | 14.652 | −14.974 | 1.00 | 19.76 | O |
| ATOM | 13090 | N | VAL | B | 283 | 54.953 | 16.195 | −14.775 | 1.00 | 18.29 | N |
| ATOM | 13091 | CA | VAL | B | 283 | 54.768 | 16.726 | −16.127 | 1.00 | 16.97 | C |
| ATOM | 13093 | CB | VAL | B | 283 | 55.511 | 18.073 | −16.319 | 1.00 | 16.72 | C |

APPENDIX 1-continued

| ATOM | 13095 | CG1 | VAL | B | 283 | 55.569 | 18.478 | −17.788 | 1.00 | 16.10 | C |
|---|---|---|---|---|---|---|---|---|---|---|---|
| ATOM | 13099 | CG2 | VAL | B | 283 | 54.837 | 19.148 | −15.509 | 1.00 | 11.99 | C |
| ATOM | 13103 | C | VAL | B | 283 | 55.190 | 15.716 | −17.196 | 1.00 | 17.36 | C |
| ATOM | 13104 | O | VAL | B | 283 | 54.528 | 15.593 | −18.229 | 1.00 | 17.90 | O |
| ATOM | 13106 | N | ALA | B | 284 | 56.275 | 14.988 | −16.947 | 1.00 | 17.45 | N |
| ATOM | 13107 | CA | ALA | B | 284 | 56.758 | 13.992 | −17.906 | 1.00 | 17.41 | C |
| ATOM | 13109 | CB | ALA | B | 284 | 58.094 | 13.417 | −17.466 | 1.00 | 15.89 | C |
| ATOM | 13113 | C | ALA | B | 284 | 55.732 | 12.878 | −18.107 | 1.00 | 18.47 | C |
| ATOM | 13114 | O | ALA | B | 284 | 55.487 | 12.456 | −19.237 | 1.00 | 19.32 | O |
| ATOM | 13116 | N | LYS | B | 285 | 55.128 | 12.422 | −17.009 | 1.00 | 19.17 | N |
| ATOM | 13117 | CA | LYS | B | 285 | 54.095 | 11.380 | −17.050 | 1.00 | 19.22 | C |
| ATOM | 13119 | CB | LYS | B | 285 | 53.741 | 10.919 | −15.630 | 1.00 | 19.40 | C |
| ATOM | 13122 | CG | LYS | B | 285 | 54.872 | 10.185 | −14.896 | 1.00 | 21.47 | C |
| ATOM | 13125 | CD | LYS | B | 285 | 54.543 | 10.003 | −13.422 | 1.00 | 26.37 | C |
| ATOM | 13128 | CE | LYS | B | 285 | 55.594 | 9.183 | −12.694 | 1.00 | 30.54 | C |
| ATOM | 13131 | NZ | LYS | B | 285 | 55.085 | 8.669 | −11.388 | 1.00 | 33.42 | N |
| ATOM | 13135 | C | LYS | B | 285 | 52.829 | 11.855 | −17.767 | 1.00 | 18.79 | C |
| ATOM | 13136 | O | LYS | B | 285 | 52.285 | 11.159 | −18.627 | 1.00 | 17.49 | O |
| ATOM | 13138 | N | MET | B | 286 | 52.364 | 13.046 | −17.416 | 1.00 | 18.67 | N |
| ATOM | 13139 | CA | MET | B | 286 | 51.183 | 13.603 | −18.066 | 1.00 | 17.87 | C |
| ATOM | 13141 | CB | MET | B | 286 | 50.803 | 14.943 | −17.441 | 1.00 | 17.79 | C |
| ATOM | 13144 | CG | MET | B | 286 | 50.283 | 14.840 | −16.008 | 1.00 | 15.56 | C |
| ATOM | 13147 | SD | MET | B | 286 | 49.110 | 13.495 | −15.755 | 1.00 | 17.16 | S |
| ATOM | 13148 | CE | MET | B | 286 | 50.186 | 12.126 | −15.346 | 1.00 | 13.71 | C |
| ATOM | 13152 | C | MET | B | 286 | 51.409 | 13.752 | −19.558 | 1.00 | 18.49 | C |
| ATOM | 13153 | O | MET | B | 286 | 50.586 | 13.306 | −20.354 | 1.00 | 20.49 | O |
| ATOM | 13155 | N | PHE | B | 287 | 52.537 | 14.336 | −19.946 | 1.00 | 18.40 | N |
| ATOM | 13156 | CA | PHE | B | 287 | 52.808 | 14.567 | −21.362 | 1.00 | 18.66 | C |
| ATOM | 13158 | CB | PHE | B | 287 | 54.040 | 15.469 | −21.547 | 1.00 | 20.00 | C |
| ATOM | 13161 | CG | PHE | B | 287 | 54.026 | 16.310 | −22.817 | 1.00 | 24.97 | C |
| ATOM | 13162 | CD1 | PHE | B | 287 | 52.947 | 16.300 | −23.705 | 1.00 | 30.68 | C |
| ATOM | 13164 | CE1 | PHE | B | 287 | 52.954 | 17.078 | −24.852 | 1.00 | 30.97 | C |
| ATOM | 13166 | CZ | PHE | B | 287 | 54.019 | 17.892 | −25.119 | 1.00 | 32.06 | C |
| ATOM | 13168 | CE2 | PHE | B | 287 | 55.089 | 17.933 | −24.243 | 1.00 | 31.07 | C |
| ATOM | 13170 | CD2 | PHE | B | 287 | 55.087 | 17.151 | −23.097 | 1.00 | 28.48 | C |
| ATOM | 13172 | C | PHE | B | 287 | 52.978 | 13.252 | −22.116 | 1.00 | 17.87 | C |
| ATOM | 13173 | O | PHE | B | 287 | 52.718 | 13.175 | −23.315 | 1.00 | 16.55 | O |
| ATOM | 13175 | N | SER | B | 288 | 53.403 | 12.206 | −21.413 | 1.00 | 18.39 | N |
| ATOM | 13176 | CA | SER | B | 288 | 53.520 | 10.894 | −22.037 | 1.00 | 18.35 | C |
| ATOM | 13178 | CB | SER | B | 288 | 54.306 | 9.946 | −21.154 | 1.00 | 17.99 | C |
| ATOM | 13181 | OG | SER | B | 288 | 55.617 | 10.437 | −20.969 | 1.00 | 22.94 | O |
| ATOM | 13183 | C | SER | B | 288 | 52.136 | 10.333 | −22.343 | 1.00 | 18.48 | C |
| ATOM | 13184 | O | SER | B | 288 | 51.889 | 9.873 | −23.451 | 1.00 | 19.11 | O |
| ATOM | 13186 | N | PHE | B | 289 | 51.232 | 10.396 | −21.372 | 1.00 | 18.18 | N |
| ATOM | 13187 | CA | PHE | B | 289 | 49.855 | 9.965 | −21.594 | 1.00 | 18.11 | C |
| ATOM | 13189 | CB | PHE | B | 289 | 49.042 | 9.977 | −20.295 | 1.00 | 18.57 | C |
| ATOM | 13192 | CG | PHE | B | 289 | 49.139 | 8.711 | −19.504 | 1.00 | 18.20 | C |
| ATOM | 13193 | CD1 | PHE | B | 289 | 48.556 | 7.545 | −19.968 | 1.00 | 18.92 | C |
| ATOM | 13195 | CE1 | PHE | B | 289 | 48.646 | 6.365 | −19.241 | 1.00 | 21.23 | C |
| ATOM | 13197 | CZ | PHE | B | 289 | 49.309 | 6.347 | −18.025 | 1.00 | 22.20 | C |
| ATOM | 13199 | CE2 | PHE | B | 289 | 49.890 | 7.506 | −17.546 | 1.00 | 23.50 | C |
| ATOM | 13201 | CD2 | PHE | B | 289 | 49.800 | 8.684 | −18.286 | 1.00 | 24.62 | C |
| ATOM | 13203 | C | PHE | B | 289 | 49.168 | 10.844 | −22.630 | 1.00 | 18.51 | C |
| ATOM | 13204 | O | PHE | B | 289 | 48.442 | 10.339 | −23.484 | 1.00 | 19.51 | O |
| ATOM | 13206 | N | VAL | B | 290 | 49.387 | 12.153 | −22.559 | 1.00 | 18.16 | N |
| ATOM | 13207 | CA | VAL | B | 290 | 48.790 | 13.074 | −23.534 | 1.00 | 17.57 | C |
| ATOM | 13209 | CB | VAL | B | 290 | 49.261 | 14.532 | −23.312 | 1.00 | 17.57 | C |
| ATOM | 13211 | CG1 | VAL | B | 290 | 48.855 | 15.404 | −24.498 | 1.00 | 17.88 | C |
| ATOM | 13215 | CG2 | VAL | B | 290 | 48.700 | 15.097 | −22.002 | 1.00 | 13.02 | C |
| ATOM | 13219 | C | VAL | B | 290 | 49.134 | 12.653 | −24.970 | 1.00 | 17.90 | C |
| ATOM | 13220 | O | VAL | B | 290 | 48.286 | 12.683 | −25.866 | 1.00 | 18.78 | O |
| ATOM | 13222 | N | THR | B | 291 | 50.384 | 12.259 | −25.176 | 1.00 | 17.74 | N |
| ATOM | 13223 | CA | THR | B | 291 | 50.855 | 11.837 | −26.483 | 1.00 | 17.95 | C |
| ATOM | 13225 | CB | THR | B | 291 | 52.333 | 11.447 | −26.420 | 1.00 | 18.41 | C |
| ATOM | 13227 | OG1 | THR | B | 291 | 53.124 | 12.629 | −26.260 | 1.00 | 21.17 | O |
| ATOM | 13229 | CG2 | THR | B | 291 | 52.762 | 10.727 | −27.680 | 1.00 | 17.99 | C |
| ATOM | 13233 | C | THR | B | 291 | 50.055 | 10.651 | −26.998 | 1.00 | 18.29 | C |
| ATOM | 13234 | O | THR | B | 291 | 49.633 | 10.632 | −28.159 | 1.00 | 19.30 | O |
| ATOM | 13236 | N | ILE | B | 292 | 49.840 | 9.661 | −26.138 | 1.00 | 17.08 | N |
| ATOM | 13237 | CA | ILE | B | 292 | 49.097 | 8.480 | −26.549 | 1.00 | 16.79 | C |
| ATOM | 13239 | CB | ILE | B | 292 | 49.217 | 7.343 | −25.528 | 1.00 | 17.07 | C |
| ATOM | 13241 | CG1 | ILE | B | 292 | 50.680 | 6.927 | −25.377 | 1.00 | 15.64 | C |
| ATOM | 13244 | CD1 | ILE | B | 292 | 50.876 | 5.738 | −24.488 | 1.00 | 16.03 | C |
| ATOM | 13248 | CG2 | ILE | B | 292 | 48.374 | 6.138 | −25.976 | 1.00 | 15.60 | C |
| ATOM | 13252 | C | ILE | B | 292 | 47.619 | 8.794 | −26.788 | 1.00 | 16.39 | C |
| ATOM | 13253 | O | ILE | B | 292 | 47.049 | 8.387 | −27.801 | 1.00 | 15.98 | O |
| ATOM | 13255 | N | ILE | B | 293 | 47.007 | 9.516 | −25.856 | 1.00 | 16.87 | N |
| ATOM | 13256 | CA | ILE | B | 293 | 45.576 | 9.813 | −25.931 | 1.00 | 16.97 | C |
| ATOM | 13258 | CB | ILE | B | 293 | 45.038 | 10.467 | −24.635 | 1.00 | 17.10 | C |
| ATOM | 13260 | CG1 | ILE | B | 293 | 45.298 | 9.575 | −23.415 | 1.00 | 15.92 | C |

APPENDIX 1-continued

| | | | | | | | | | | |
|---|---|---|---|---|---|---|---|---|---|---|
| ATOM | 13263 | CD1 | ILE | B | 293 | 44.447 | 8.382 | −23.354 | 1.00 | 19.33 | C |
| ATOM | 13267 | CG2 | ILE | B | 293 | 43.545 | 10.770 | −24.769 | 1.00 | 12.01 | C |
| ATOM | 13271 | C | ILE | B | 293 | 45.272 | 10.737 | −27.109 | 1.00 | 18.45 | C |
| ATOM | 13272 | O | ILE | B | 293 | 44.232 | 10.608 | −27.746 | 1.00 | 19.12 | O |
| ATOM | 13274 | N | ASP | B | 294 | 46.176 | 11.666 | −27.402 | 1.00 | 20.04 | N |
| ATOM | 13275 | CA | ASP | B | 294 | 46.022 | 12.503 | −28.589 | 1.00 | 20.87 | C |
| ATOM | 13277 | CB | ASP | B | 294 | 47.143 | 13.550 | −28.676 | 1.00 | 21.91 | C |
| ATOM | 13280 | CG | ASP | B | 294 | 46.999 | 14.474 | −29.880 | 1.00 | 25.51 | C |
| ATOM | 13281 | OD1 | ASP | B | 294 | 45.859 | 14.741 | −30.330 | 1.00 | 37.55 | O |
| ATOM | 13282 | OD2 | ASP | B | 294 | 48.037 | 14.933 | −30.384 | 1.00 | 32.86 | O |
| ATOM | 13283 | C | ASP | B | 294 | 45.990 | 11.621 | −29.842 | 1.00 | 20.09 | C |
| ATOM | 13284 | O | ASP | B | 294 | 45.084 | 11.748 | −30.655 | 1.00 | 20.67 | O |
| ATOM | 13286 | N | ASP | B | 295 | 46.967 | 10.725 | −29.985 | 1.00 | 18.78 | N |
| ATOM | 13287 | CA | ASP | B | 295 | 46.981 | 9.780 | −31.096 | 1.00 | 18.93 | C |
| ATOM | 13289 | CB | ASP | B | 295 | 48.031 | 8.683 | −30.888 | 1.00 | 20.45 | C |
| ATOM | 13292 | CG | ASP | B | 295 | 49.444 | 9.154 | −31.119 | 1.00 | 24.00 | C |
| ATOM | 13293 | OD1 | ASP | B | 295 | 49.649 | 10.115 | −31.892 | 1.00 | 25.19 | O |
| ATOM | 13294 | OD2 | ASP | B | 295 | 50.357 | 8.531 | −30.525 | 1.00 | 30.29 | O |
| ATOM | 13295 | C | ASP | B | 295 | 45.636 | 9.087 | −31.235 | 1.00 | 18.09 | C |
| ATOM | 13296 | O | ASP | B | 295 | 45.128 | 8.928 | −32.340 | 1.00 | 19.33 | O |
| ATOM | 13298 | N | ILE | B | 296 | 45.079 | 8.649 | −30.112 | 1.00 | 16.55 | N |
| ATOM | 13299 | CA | ILE | B | 296 | 43.816 | 7.925 | −30.125 | 1.00 | 15.98 | C |
| ATOM | 13301 | CB | ILE | B | 296 | 43.411 | 7.463 | −28.706 | 1.00 | 15.69 | C |
| ATOM | 13303 | CG1 | ILE | B | 296 | 44.357 | 6.359 | −28.231 | 1.00 | 16.99 | C |
| ATOM | 13306 | CD1 | ILE | B | 296 | 44.121 | 5.906 | −26.801 | 1.00 | 13.46 | C |
| ATOM | 13310 | CG2 | ILE | B | 296 | 41.995 | 6.922 | −28.701 | 1.00 | 14.84 | C |
| ATOM | 13314 | C | ILE | B | 296 | 42.700 | 8.764 | −30.756 | 1.00 | 15.21 | C |
| ATOM | 13315 | O | ILE | B | 296 | 42.007 | 8.290 | −31.653 | 1.00 | 14.11 | O |
| ATOM | 13317 | N | TYR | B | 297 | 42.546 | 9.999 | −30.279 | 1.00 | 15.44 | N |
| ATOM | 13318 | CA | TYR | B | 297 | 41.499 | 10.921 | −30.755 | 1.00 | 15.69 | C |
| ATOM | 13320 | CB | TYR | B | 297 | 41.322 | 12.098 | −29.788 | 1.00 | 15.76 | C |
| ATOM | 13323 | CG | TYR | B | 297 | 40.545 | 11.798 | −28.524 | 1.00 | 14.67 | C |
| ATOM | 13324 | CD1 | TYR | B | 297 | 41.143 | 11.154 | −27.454 | 1.00 | 16.18 | C |
| ATOM | 13326 | CE1 | TYR | B | 297 | 40.443 | 10.898 | −26.286 | 1.00 | 18.37 | C |
| ATOM | 13328 | CZ | TYR | B | 297 | 39.128 | 11.294 | −26.178 | 1.00 | 19.71 | C |
| ATOM | 13329 | OH | TYR | B | 297 | 38.430 | 11.036 | −25.022 | 1.00 | 20.24 | O |
| ATOM | 13331 | CE2 | TYR | B | 297 | 38.512 | 11.943 | −27.227 | 1.00 | 19.56 | C |
| ATOM | 13333 | CD2 | TYR | B | 297 | 39.221 | 12.190 | −28.391 | 1.00 | 15.92 | C |
| ATOM | 13335 | C | TYR | B | 297 | 41.807 | 11.484 | −32.132 | 1.00 | 15.56 | C |
| ATOM | 13336 | O | TYR | B | 297 | 40.906 | 11.663 | −32.943 | 1.00 | 17.25 | O |
| ATOM | 13338 | N | ASP | B | 298 | 43.080 | 11.761 | −32.384 | 1.00 | 15.97 | N |
| ATOM | 13339 | CA | ASP | B | 298 | 43.518 | 12.312 | −33.660 | 1.00 | 17.44 | C |
| ATOM | 13341 | CB | ASP | B | 298 | 44.999 | 12.733 | −33.596 | 1.00 | 18.62 | C |
| ATOM | 13344 | CG | ASP | B | 298 | 45.455 | 13.513 | −34.832 | 1.00 | 19.01 | C |
| ATOM | 13345 | OD1 | ASP | B | 298 | 44.685 | 14.343 | −35.345 | 1.00 | 25.00 | O |
| ATOM | 13346 | OD2 | ASP | B | 298 | 46.599 | 13.311 | −35.279 | 1.00 | 23.84 | O |
| ATOM | 13347 | C | ASP | B | 298 | 43.321 | 11.326 | −34.804 | 1.00 | 16.87 | C |
| ATOM | 13348 | O | ASP | B | 298 | 42.796 | 11.709 | −35.846 | 1.00 | 18.14 | O |
| ATOM | 13350 | N | VAL | B | 299 | 43.727 | 10.070 | −34.609 | 1.00 | 15.93 | N |
| ATOM | 13351 | CA | VAL | B | 299 | 43.800 | 9.115 | −35.721 | 1.00 | 16.58 | C |
| ATOM | 13353 | CB | VAL | B | 299 | 45.257 | 8.977 | −36.235 | 1.00 | 17.12 | C |
| ATOM | 13355 | CG1 | VAL | B | 299 | 45.771 | 10.325 | −36.708 | 1.00 | 21.04 | C |
| ATOM | 13359 | CG2 | VAL | B | 299 | 46.159 | 8.404 | −35.161 | 1.00 | 15.17 | C |
| ATOM | 13363 | C | VAL | B | 299 | 43.254 | 7.699 | −35.496 | 1.00 | 16.10 | C |
| ATOM | 13364 | O | VAL | B | 299 | 42.716 | 7.098 | −36.436 | 1.00 | 15.92 | O |
| ATOM | 13366 | N | TYR | B | 300 | 43.394 | 7.138 | −34.297 | 1.00 | 15.08 | N |
| ATOM | 13367 | CA | TYR | B | 300 | 43.108 | 5.712 | −34.147 | 1.00 | 14.75 | C |
| ATOM | 13369 | CB | TYR | B | 300 | 43.954 | 5.070 | −33.046 | 1.00 | 15.03 | C |
| ATOM | 13372 | CG | TYR | B | 300 | 43.879 | 3.561 | −33.089 | 1.00 | 16.13 | C |
| ATOM | 13373 | CD1 | TYR | B | 300 | 44.717 | 2.830 | −33.921 | 1.00 | 17.83 | C |
| ATOM | 13375 | CE1 | TYR | B | 300 | 44.642 | 1.440 | −33.985 | 1.00 | 17.70 | C |
| ATOM | 13377 | CZ | TYR | B | 300 | 43.713 | 0.765 | −33.216 | 1.00 | 17.51 | C |
| ATOM | 13378 | OH | TYR | B | 300 | 43.640 | −0.613 | −33.285 | 1.00 | 19.11 | O |
| ATOM | 13380 | CE2 | TYR | B | 300 | 42.854 | 1.471 | −32.391 | 1.00 | 18.38 | C |
| ATOM | 13382 | CD2 | TYR | B | 300 | 42.940 | 2.867 | −32.333 | 1.00 | 17.63 | C |
| ATOM | 13384 | C | TYR | B | 300 | 41.630 | 5.410 | −33.915 | 1.00 | 13.88 | C |
| ATOM | 13385 | O | TYR | B | 300 | 41.070 | 4.529 | −34.559 | 1.00 | 12.62 | O |
| ATOM | 13387 | N | GLY | B | 301 | 41.005 | 6.140 | −33.000 | 1.00 | 14.29 | N |
| ATOM | 13388 | CA | GLY | B | 301 | 39.658 | 5.798 | −32.539 | 1.00 | 14.39 | C |
| ATOM | 13391 | C | GLY | B | 301 | 38.506 | 6.381 | −33.347 | 1.00 | 13.86 | C |
| ATOM | 13392 | O | GLY | B | 301 | 38.567 | 7.520 | −33.803 | 1.00 | 13.36 | O |
| ATOM | 13394 | N | THR | B | 302 | 37.447 | 5.590 | −33.495 | 1.00 | 13.78 | N |
| ATOM | 13395 | CA | THR | B | 302 | 36.217 | 6.035 | −34.142 | 1.00 | 13.66 | C |
| ATOM | 13397 | CB | THR | B | 302 | 35.290 | 4.857 | −34.477 | 1.00 | 13.51 | C |
| ATOM | 13399 | OG1 | THR | B | 302 | 34.843 | 4.251 | −33.254 | 1.00 | 16.25 | O |
| ATOM | 13401 | CG2 | THR | B | 302 | 35.999 | 3.809 | −35.355 | 1.00 | 7.50 | C |
| ATOM | 13405 | C | THR | B | 302 | 35.473 | 6.940 | −33.180 | 1.00 | 14.64 | C |
| ATOM | 13406 | O | THR | B | 302 | 35.662 | 6.844 | −31.966 | 1.00 | 15.85 | O |
| ATOM | 13408 | N | LEU | B | 303 | 34.608 | 7.798 | −33.713 | 1.00 | 15.25 | N |
| ATOM | 13409 | CA | LEU | B | 303 | 33.882 | 8.773 | −32.883 | 1.00 | 15.04 | C |

APPENDIX 1-continued

| | | | | | | | | | | |
|---|---|---|---|---|---|---|---|---|---|---|
| ATOM | 13411 | CB  | LEU | B | 303 | 32.968 | 9.647  | −33.739 | 1.00 | 14.21 C |
| ATOM | 13414 | CG  | LEU | B | 303 | 32.494 | 10.948 | −33.092 | 1.00 | 17.04 C |
| ATOM | 13416 | CD1 | LEU | B | 303 | 33.670 | 11.897 | −32.842 | 1.00 | 12.42 C |
| ATOM | 13420 | CD2 | LEU | B | 303 | 31.429 | 11.617 | −33.984 | 1.00 | 15.09 C |
| ATOM | 13424 | C   | LEU | B | 303 | 33.070 | 8.117  | −31.766 | 1.00 | 15.41 C |
| ATOM | 13425 | O   | LEU | B | 303 | 32.981 | 8.669  | −30.675 | 1.00 | 16.38 O |
| ATOM | 13427 | N   | ASP | B | 304 | 32.482 | 6.951  | −32.036 | 1.00 | 16.29 N |
| ATOM | 13428 | CA  | ASP | B | 304 | 31.761 | 6.196  | −31.003 | 1.00 | 17.01 C |
| ATOM | 13430 | CB  | ASP | B | 304 | 31.129 | 4.923  | −31.574 | 1.00 | 17.38 C |
| ATOM | 13433 | CG  | ASP | B | 304 | 29.925 | 5.198  | −32.452 | 1.00 | 19.47 C |
| ATOM | 13434 | OD1 | ASP | B | 304 | 29.499 | 6.370  | −32.577 | 1.00 | 20.88 O |
| ATOM | 13435 | OD2 | ASP | B | 304 | 29.401 | 4.216  | −33.023 | 1.00 | 20.92 O |
| ATOM | 13436 | C   | ASP | B | 304 | 32.706 | 5.800  | −29.878 | 1.00 | 17.83 C |
| ATOM | 13437 | O   | ASP | B | 304 | 32.355 | 5.892  | −28.694 | 1.00 | 18.36 O |
| ATOM | 13439 | N   | GLU | B | 305 | 33.898 | 5.341  | −30.257 | 1.00 | 18.03 N |
| ATOM | 13440 | CA  | GLU | B | 305 | 34.901 | 4.905  | −29.285 | 1.00 | 17.38 C |
| ATOM | 13442 | CB  | GLU | B | 305 | 36.086 | 4.230  | −29.983 | 1.00 | 17.32 C |
| ATOM | 13445 | CG  | GLU | B | 305 | 35.729 | 2.871  | −30.592 | 1.00 | 17.07 C |
| ATOM | 13448 | CD  | GLU | B | 305 | 36.903 | 2.187  | −31.281 | 1.00 | 16.86 C |
| ATOM | 13449 | OE1 | GLU | B | 305 | 37.901 | 2.867  | −31.610 | 1.00 | 11.15 O |
| ATOM | 13450 | OE2 | GLU | B | 305 | 36.815 | 0.956  | −31.499 | 1.00 | 15.96 O |
| ATOM | 13451 | C   | GLU | B | 305 | 35.375 | 6.071  | −28.437 | 1.00 | 17.24 C |
| ATOM | 13452 | O   | GLU | B | 305 | 35.583 | 5.917  | −27.228 | 1.00 | 16.52 O |
| ATOM | 13454 | N   | LEU | B | 306 | 35.517 | 7.237  | −29.069 | 1.00 | 17.03 N |
| ATOM | 13455 | CA  | LEU | B | 306 | 36.012 | 8.421  | −28.374 | 1.00 | 17.64 C |
| ATOM | 13457 | CB  | LEU | B | 306 | 36.419 | 9.515  | −29.374 | 1.00 | 17.28 C |
| ATOM | 13460 | CG  | LEU | B | 306 | 37.545 | 9.153  | −30.359 | 1.00 | 16.34 C |
| ATOM | 13462 | CD1 | LEU | B | 306 | 37.842 | 10.288 | −31.342 | 1.00 | 10.85 C |
| ATOM | 13466 | CD2 | LEU | B | 306 | 38.817 | 8.737  | −29.624 | 1.00 | 14.09 C |
| ATOM | 13470 | C   | LEU | B | 306 | 34.987 | 8.941  | −27.359 | 1.00 | 19.06 C |
| ATOM | 13471 | O   | LEU | B | 306 | 35.369 | 9.435  | −26.296 | 1.00 | 19.45 O |
| ATOM | 13473 | N   | GLU | B | 307 | 33.697 | 8.818  | −27.682 | 1.00 | 20.45 N |
| ATOM | 13474 | CA  | GLU | B | 307 | 32.620 | 9.204  | −26.757 | 1.00 | 21.22 C |
| ATOM | 13476 | CB  | GLU | B | 307 | 31.245 | 9.134  | −27.438 | 1.00 | 22.86 C |
| ATOM | 13479 | CG  | GLU | B | 307 | 30.811 | 10.407 | −28.204 | 1.00 | 27.10 C |
| ATOM | 13482 | CD  | GLU | B | 307 | 30.340 | 11.554 | −27.293 | 1.00 | 34.91 C |
| ATOM | 13483 | OE1 | GLU | B | 307 | 30.292 | 11.394 | −26.049 | 1.00 | 38.72 O |
| ATOM | 13484 | OE2 | GLU | B | 307 | 30.021 | 12.638 | −27.830 | 1.00 | 42.10 O |
| ATOM | 13485 | C   | GLU | B | 307 | 32.622 | 8.313  | −25.519 | 1.00 | 20.59 C |
| ATOM | 13486 | O   | GLU | B | 307 | 32.476 | 8.796  | −24.396 | 1.00 | 21.69 O |
| ATOM | 13488 | N   | LEU | B | 308 | 32.790 | 7.011  | −25.719 | 1.00 | 19.50 N |
| ATOM | 13489 | CA  | LEU | B | 308 | 32.883 | 6.086  | −24.594 | 1.00 | 19.04 C |
| ATOM | 13491 | CB  | LEU | B | 308 | 33.016 | 4.635  | −25.079 | 1.00 | 19.13 C |
| ATOM | 13494 | CG  | LEU | B | 308 | 31.740 | 3.918  | −25.533 | 1.00 | 18.67 C |
| ATOM | 13496 | CD1 | LEU | B | 308 | 32.073 | 2.546  | −26.139 | 1.00 | 19.50 C |
| ATOM | 13500 | CD2 | LEU | B | 308 | 30.769 | 3.768  | −24.374 | 1.00 | 17.20 C |
| ATOM | 13504 | C   | LEU | B | 308 | 34.059 | 6.430  | −23.684 | 1.00 | 18.68 C |
| ATOM | 13505 | O   | LEU | B | 308 | 33.962 | 6.302  | −22.469 | 1.00 | 19.37 O |
| ATOM | 13507 | N   | PHE | B | 309 | 35.172 | 6.859  | −24.272 | 1.00 | 18.05 N |
| ATOM | 13508 | CA  | PHE | B | 309 | 36.386 | 7.110  | −23.504 | 1.00 | 17.15 C |
| ATOM | 13510 | CB  | PHE | B | 309 | 37.605 | 7.172  | −24.432 | 1.00 | 17.28 C |
| ATOM | 13513 | CG  | PHE | B | 309 | 38.920 | 7.113  | −23.708 | 1.00 | 14.61 C |
| ATOM | 13514 | CD1 | PHE | B | 309 | 39.495 | 5.901  | −23.396 | 1.00 | 12.78 C |
| ATOM | 13516 | CE1 | PHE | B | 309 | 40.698 | 5.844  | −22.724 | 1.00 | 15.12 C |
| ATOM | 13518 | CZ  | PHE | B | 309 | 41.340 | 7.013  | −22.355 | 1.00 | 12.95 C |
| ATOM | 13520 | CE2 | PHE | B | 309 | 40.772 | 8.222  | −22.654 | 1.00 | 11.41 C |
| ATOM | 13522 | CD2 | PHE | B | 309 | 39.569 | 8.270  | −23.328 | 1.00 | 12.83 C |
| ATOM | 13524 | C   | PHE | B | 309 | 36.245 | 8.404  | −22.716 | 1.00 | 16.87 C |
| ATOM | 13525 | O   | PHE | B | 309 | 36.602 | 8.475  | −21.549 | 1.00 | 16.52 O |
| ATOM | 13527 | N   | THR | B | 310 | 35.714 | 9.429  | −23.368 | 1.00 | 17.61 N |
| ATOM | 13528 | CA  | THR | B | 310 | 35.441 | 10.686 | −22.695 | 1.00 | 17.56 C |
| ATOM | 13530 | CB  | THR | B | 310 | 34.800 | 11.696 | −23.631 | 1.00 | 16.99 C |
| ATOM | 13532 | OG1 | THR | B | 310 | 35.560 | 11.767 | −24.843 | 1.00 | 15.50 O |
| ATOM | 13534 | CG2 | THR | B | 310 | 34.749 | 13.051 | −22.964 | 1.00 | 15.81 C |
| ATOM | 13538 | C   | THR | B | 310 | 34.500 | 10.455 | −21.526 | 1.00 | 18.58 C |
| ATOM | 13539 | O   | THR | B | 310 | 34.669 | 11.052 | −20.462 | 1.00 | 20.74 O |
| ATOM | 13541 | N   | ASP | B | 311 | 33.518 | 9.580  | −21.726 | 1.00 | 18.13 N |
| ATOM | 13542 | CA  | ASP | B | 311 | 32.553 | 9.275  | −20.684 | 1.00 | 17.51 C |
| ATOM | 13544 | CB  | ASP | B | 311 | 31.429 | 8.389  | −21.219 | 1.00 | 17.83 C |
| ATOM | 13547 | CG  | ASP | B | 311 | 30.258 | 8.314  | −20.275 | 1.00 | 18.25 C |
| ATOM | 13548 | OD1 | ASP | B | 311 | 29.480 | 9.277  | −20.208 | 1.00 | 26.72 O |
| ATOM | 13549 | OD2 | ASP | B | 311 | 30.105 | 7.288  | −19.597 | 1.00 | 29.05 O |
| ATOM | 13550 | C   | ASP | B | 311 | 33.257 | 8.580  | −19.540 | 1.00 | 16.69 C |
| ATOM | 13551 | O   | ASP | B | 311 | 33.103 | 8.976  | −18.389 | 1.00 | 17.50 O |
| ATOM | 13553 | N   | ALA | B | 312 | 34.039 | 7.555  | −19.867 | 1.00 | 15.64 N |
| ATOM | 13554 | CA  | ALA | B | 312 | 34.816 | 6.819  | −18.871 | 1.00 | 15.21 C |
| ATOM | 13556 | CB  | ALA | B | 312 | 35.721 | 5.812  | −19.540 | 1.00 | 14.61 C |
| ATOM | 13560 | C   | ALA | B | 312 | 35.645 | 7.756  | −18.007 | 1.00 | 15.22 C |
| ATOM | 13561 | O   | ALA | B | 312 | 35.733 | 7.563  | −16.798 | 1.00 | 16.10 O |
| ATOM | 13563 | N   | VAL | B | 313 | 36.246 | 8.770  | −18.624 | 1.00 | 14.13 N |

APPENDIX 1-continued

| | | | | | | | | | | |
|---|---|---|---|---|---|---|---|---|---|---|
| ATOM | 13564 | CA | VAL | B | 313 | 37.075 | 9.700 | −17.881 | 1.00 | 14.22 | C |
| ATOM | 13566 | CB | VAL | B | 313 | 37.978 | 10.538 | −18.804 | 1.00 | 15.19 | C |
| ATOM | 13568 | CG1 | VAL | B | 313 | 38.749 | 11.572 | −17.997 | 1.00 | 11.03 | C |
| ATOM | 13572 | CG2 | VAL | B | 313 | 38.945 | 9.627 | −19.568 | 1.00 | 10.79 | C |
| ATOM | 13576 | C | VAL | B | 313 | 36.211 | 10.593 | −16.998 | 1.00 | 15.13 | C |
| ATOM | 13577 | O | VAL | B | 313 | 36.531 | 10.796 | −15.830 | 1.00 | 14.94 | O |
| ATOM | 13579 | N | GLU | B | 314 | 35.108 | 11.101 | −17.547 | 1.00 | 16.20 | N |
| ATOM | 13580 | CA | GLU | B | 314 | 34.193 | 11.950 | −16.781 | 1.00 | 16.05 | C |
| ATOM | 13582 | CB | GLU | B | 314 | 33.036 | 12.419 | −17.653 | 1.00 | 16.20 | C |
| ATOM | 13585 | CG | GLU | B | 314 | 33.422 | 13.497 | −18.652 | 1.00 | 18.20 | C |
| ATOM | 13588 | CD | GLU | B | 314 | 32.325 | 13.808 | −19.654 | 1.00 | 21.40 | C |
| ATOM | 13589 | OE1 | GLU | B | 314 | 31.197 | 13.296 | −19.491 | 1.00 | 27.84 | O |
| ATOM | 13590 | OE2 | GLU | B | 314 | 32.598 | 14.567 | −20.610 | 1.00 | 23.02 | O |
| ATOM | 13591 | C | GLU | B | 314 | 33.652 | 11.243 | −15.540 | 1.00 | 17.02 | C |
| ATOM | 13592 | O | GLU | B | 314 | 33.656 | 11.806 | −14.444 | 1.00 | 17.47 | O |
| ATOM | 13594 | N | ARG | B | 315 | 33.198 | 10.008 | −15.709 | 1.00 | 17.74 | N |
| ATOM | 13595 | CA | ARG | B | 315 | 32.628 | 9.249 | −14.598 | 1.00 | 18.10 | C |
| ATOM | 13597 | CB | ARG | B | 315 | 31.817 | 8.066 | −15.121 | 1.00 | 18.91 | C |
| ATOM | 13600 | CG | ARG | B | 315 | 30.589 | 8.473 | −15.915 | 1.00 | 24.08 | C |
| ATOM | 13603 | CD | ARG | B | 315 | 29.633 | 7.310 | −16.138 | 1.00 | 30.60 | C |
| ATOM | 13606 | NE | ARG | B | 315 | 30.214 | 6.283 | −17.002 | 1.00 | 37.06 | N |
| ATOM | 13608 | CZ | ARG | B | 315 | 30.788 | 5.147 | −16.593 | 1.00 | 43.47 | C |
| ATOM | 13609 | NH1 | ARG | B | 315 | 30.881 | 4.833 | −15.298 | 1.00 | 44.16 | N |
| ATOM | 13612 | NH2 | ARG | B | 315 | 31.269 | 4.303 | −17.505 | 1.00 | 45.37 | N |
| ATOM | 13615 | C | ARG | B | 315 | 33.685 | 8.755 | −13.617 | 1.00 | 17.47 | C |
| ATOM | 13616 | O | ARG | B | 315 | 33.374 | 8.508 | −12.457 | 1.00 | 18.44 | O |
| ATOM | 13618 | N | TRP | B | 316 | 34.923 | 8.609 | −14.092 | 1.00 | 17.26 | N |
| ATOM | 13619 | CA | TRP | B | 316 | 36.069 | 8.177 | −13.272 | 1.00 | 16.33 | C |
| ATOM | 13621 | CB | TRP | B | 316 | 36.580 | 9.323 | −12.393 | 1.00 | 15.45 | C |
| ATOM | 13624 | CG | TRP | B | 316 | 38.014 | 9.122 | −11.965 | 1.00 | 14.66 | C |
| ATOM | 13625 | CD1 | TRP | B | 316 | 38.454 | 8.750 | −10.734 | 1.00 | 14.27 | C |
| ATOM | 13627 | NE1 | TRP | B | 316 | 39.818 | 8.647 | −10.724 | 1.00 | 13.62 | N |
| ATOM | 13629 | CE2 | TRP | B | 316 | 40.293 | 8.949 | −11.970 | 1.00 | 14.25 | C |
| ATOM | 13630 | CD2 | TRP | B | 316 | 39.182 | 9.247 | −12.783 | 1.00 | 13.26 | C |
| ATOM | 13631 | CE3 | TRP | B | 316 | 39.396 | 9.587 | −14.123 | 1.00 | 15.54 | C |
| ATOM | 13633 | CZ3 | TRP | B | 316 | 40.702 | 9.625 | −14.598 | 1.00 | 16.04 | C |
| ATOM | 13635 | CH2 | TRP | B | 316 | 41.788 | 9.321 | −13.757 | 1.00 | 16.70 | C |
| ATOM | 13637 | CZ2 | TRP | B | 316 | 41.603 | 8.980 | −12.447 | 1.00 | 16.20 | C |
| ATOM | 13639 | C | TRP | B | 316 | 35.762 | 6.947 | −12.423 | 1.00 | 16.99 | C |
| ATOM | 13640 | O | TRP | B | 316 | 36.080 | 6.881 | −11.236 | 1.00 | 17.00 | O |
| ATOM | 13642 | N | ASP | B | 317 | 35.150 | 5.964 | −13.058 | 1.00 | 18.49 | N |
| ATOM | 13643 | CA | ASP | B | 317 | 34.668 | 4.786 | −12.365 | 1.00 | 19.92 | C |
| ATOM | 13645 | CB | ASP | B | 317 | 33.141 | 4.721 | −12.514 | 1.00 | 19.90 | C |
| ATOM | 13648 | CG | ASP | B | 317 | 32.564 | 3.356 | −12.237 | 1.00 | 18.95 | C |
| ATOM | 13649 | OD1 | ASP | B | 317 | 32.961 | 2.692 | −11.264 | 1.00 | 16.57 | O |
| ATOM | 13650 | OD2 | ASP | B | 317 | 31.667 | 2.957 | −13.002 | 1.00 | 28.92 | O |
| ATOM | 13651 | C | ASP | B | 317 | 35.381 | 3.591 | −12.974 | 1.00 | 21.12 | C |
| ATOM | 13652 | O | ASP | B | 317 | 35.173 | 3.274 | −14.137 | 1.00 | 21.51 | O |
| ATOM | 13654 | N | VAL | B | 318 | 36.256 | 2.960 | −12.195 | 1.00 | 23.35 | N |
| ATOM | 13655 | CA | VAL | B | 318 | 36.988 | 1.787 | −12.666 | 1.00 | 25.52 | C |
| ATOM | 13657 | CB | VAL | B | 318 | 38.007 | 1.290 | −11.630 | 1.00 | 25.08 | C |
| ATOM | 13659 | CG1 | VAL | B | 318 | 37.305 | 0.608 | −10.476 | 1.00 | 23.89 | C |
| ATOM | 13663 | CG2 | VAL | B | 318 | 39.001 | 0.351 | −12.280 | 1.00 | 22.25 | C |
| ATOM | 13667 | C | VAL | B | 318 | 36.053 | 0.628 | −13.015 | 1.00 | 28.28 | C |
| ATOM | 13668 | O | VAL | B | 318 | 36.313 | −0.098 | −13.967 | 1.00 | 26.89 | O |
| ATOM | 13670 | N | ASN | B | 319 | 34.958 | 0.487 | −12.261 | 1.00 | 32.28 | N |
| ATOM | 13671 | CA | ASN | B | 319 | 34.049 | −0.668 | −12.379 | 1.00 | 35.37 | C |
| ATOM | 13673 | CB | ASN | B | 319 | 33.052 | −0.731 | −11.196 | 1.00 | 35.86 | C |
| ATOM | 13676 | CG | ASN | B | 319 | 33.746 | −0.763 | −9.810 | 1.00 | 40.22 | C |
| ATOM | 13677 | OD1 | ASN | B | 319 | 34.413 | −1.742 | −9.450 | 1.00 | 42.18 | O |
| ATOM | 13678 | ND2 | ASN | B | 319 | 33.557 | 0.304 | −9.025 | 1.00 | 34.94 | N |
| ATOM | 13681 | C | ASN | B | 319 | 33.272 | −0.690 | −13.694 | 1.00 | 37.16 | C |
| ATOM | 13682 | O | ASN | B | 319 | 32.409 | −1.539 | −13.874 | 1.00 | 38.69 | O |
| ATOM | 13684 | N | ALA | B | 320 | 33.559 | 0.251 | −14.594 | 1.00 | 38.94 | N |
| ATOM | 13685 | CA | ALA | B | 320 | 33.027 | 0.223 | −15.957 | 1.00 | 40.53 | C |
| ATOM | 13687 | CB | ALA | B | 320 | 31.974 | 1.304 | −16.140 | 1.00 | 41.10 | C |
| ATOM | 13691 | C | ALA | B | 320 | 34.164 | 0.383 | −16.972 | 1.00 | 41.77 | C |
| ATOM | 13692 | O | ALA | B | 320 | 34.085 | 1.157 | −17.926 | 1.00 | 42.42 | O |
| ATOM | 13694 | N | ILE | B | 321 | 35.236 | −0.358 | −16.729 | 1.00 | 42.81 | N |
| ATOM | 13695 | CA | ILE | B | 321 | 36.306 | −0.547 | −17.695 | 1.00 | 42.93 | C |
| ATOM | 13697 | CB | ILE | B | 321 | 37.560 | −1.128 | −16.988 | 1.00 | 43.23 | C |
| ATOM | 13699 | CG1 | ILE | B | 321 | 38.804 | −0.999 | −17.852 | 1.00 | 44.69 | C |
| ATOM | 13702 | CD1 | ILE | B | 321 | 40.018 | −1.619 | −17.201 | 1.00 | 45.95 | C |
| ATOM | 13706 | CG2 | ILE | B | 321 | 37.354 | −2.597 | −16.591 | 1.00 | 44.13 | C |
| ATOM | 13710 | C | ILE | B | 321 | 35.798 | −1.512 | −18.773 | 1.00 | 43.65 | C |
| ATOM | 13711 | O | ILE | B | 321 | 36.136 | −1.377 | −19.949 | 1.00 | 45.47 | O |
| ATOM | 13713 | N | ASN | B | 322 | 34.946 | −2.454 | −18.355 | 1.00 | 42.07 | N |
| ATOM | 13714 | CA | ASN | B | 322 | 34.412 | −3.510 | −19.215 | 1.00 | 40.07 | C |
| ATOM | 13716 | CB | ASN | B | 322 | 33.561 | −4.472 | −18.377 | 1.00 | 41.01 | C |
| ATOM | 13719 | CG | ASN | B | 322 | 34.387 | −5.295 | −17.398 | 1.00 | 43.10 | C |

APPENDIX 1-continued

| | | | | | | | | | | |
|---|---|---|---|---|---|---|---|---|---|---|
| ATOM | 13720 | OD1 | ASN | B | 322 | 35.468 | −5.800 | −17.731 | 1.00 | 44.97 | O |
| ATOM | 13721 | ND2 | ASN | B | 322 | 33.868 | −5.451 | −16.187 | 1.00 | 42.25 | N |
| ATOM | 13724 | C | ASN | B | 322 | 33.578 | −3.069 | −20.423 | 1.00 | 37.76 | C |
| ATOM | 13725 | O | ASN | B | 322 | 33.256 | −3.897 | −21.273 | 1.00 | 38.08 | O |
| ATOM | 13727 | N | ASP | B | 323 | 33.212 | −1.794 | −20.498 | 1.00 | 35.07 | N |
| ATOM | 13728 | CA | ASP | B | 323 | 32.456 | −1.280 | −21.642 | 1.00 | 33.38 | C |
| ATOM | 13730 | CB | ASP | B | 323 | 31.575 | −0.091 | −21.228 | 1.00 | 34.99 | C |
| ATOM | 13733 | CG | ASP | B | 323 | 30.816 | −0.333 | −19.927 | 1.00 | 38.70 | C |
| ATOM | 13734 | OD1 | ASP | B | 323 | 30.318 | −1.463 | −19.723 | 1.00 | 44.24 | O |
| ATOM | 13735 | OD2 | ASP | B | 323 | 30.715 | 0.616 | −19.113 | 1.00 | 39.65 | O |
| ATOM | 13736 | C | ASP | B | 323 | 33.392 | −0.832 | −22.766 | 1.00 | 30.44 | C |
| ATOM | 13737 | O | ASP | B | 323 | 33.028 | −0.877 | −23.935 | 1.00 | 31.42 | O |
| ATOM | 13739 | N | LEU | B | 324 | 34.589 | −0.383 | −22.402 | 1.00 | 27.27 | N |
| ATOM | 13740 | CA | LEU | B | 324 | 35.561 | 0.136 | −23.363 | 1.00 | 23.75 | C |
| ATOM | 13742 | CB | LEU | B | 324 | 36.727 | 0.808 | −22.620 | 1.00 | 23.04 | C |
| ATOM | 13745 | CG | LEU | B | 324 | 36.451 | 2.117 | −21.869 | 1.00 | 20.44 | C |
| ATOM | 13747 | CD1 | LEU | B | 324 | 37.676 | 2.588 | −21.089 | 1.00 | 16.65 | C |
| ATOM | 13751 | CD2 | LEU | B | 324 | 36.016 | 3.192 | −22.837 | 1.00 | 17.76 | C |
| ATOM | 13755 | C | LEU | B | 324 | 36.129 | −0.956 | −24.275 | 1.00 | 22.15 | C |
| ATOM | 13756 | O | LEU | B | 324 | 36.216 | −2.123 | −23.876 | 1.00 | 21.79 | O |
| ATOM | 13758 | N | PRO | B | 325 | 36.522 | −0.581 | −25.506 | 1.00 | 20.45 | N |
| ATOM | 13759 | CA | PRO | B | 325 | 37.323 | −1.486 | −26.334 | 1.00 | 19.14 | C |
| ATOM | 13761 | CB | PRO | B | 325 | 37.505 | −0.725 | −27.651 | 1.00 | 18.46 | C |
| ATOM | 13764 | CG | PRO | B | 325 | 36.926 | 0.614 | −27.466 | 1.00 | 19.98 | C |
| ATOM | 13767 | CD | PRO | B | 325 | 36.088 | 0.621 | −26.241 | 1.00 | 20.76 | C |
| ATOM | 13770 | C | PRO | B | 325 | 38.684 | −1.791 | −25.704 | 1.00 | 18.87 | C |
| ATOM | 13771 | O | PRO | B | 325 | 39.215 | −0.973 | −24.943 | 1.00 | 17.70 | O |
| ATOM | 13772 | N | ASP | B | 326 | 39.237 | −2.958 | −26.037 | 1.00 | 18.03 | N |
| ATOM | 13773 | CA | ASP | B | 326 | 40.427 | −3.486 | −25.368 | 1.00 | 17.58 | C |
| ATOM | 13775 | CB | ASP | B | 326 | 40.916 | −4.767 | −26.054 | 1.00 | 18.21 | C |
| ATOM | 13778 | CG | ASP | B | 326 | 39.932 | −5.924 | −25.922 | 1.00 | 17.05 | C |
| ATOM | 13779 | OD1 | ASP | B | 326 | 38.906 | −5.773 | −25.224 | 1.00 | 18.68 | O |
| ATOM | 13780 | OD2 | ASP | B | 326 | 40.188 | −6.987 | −26.520 | 1.00 | 14.18 | O |
| ATOM | 13781 | C | ASP | B | 326 | 41.570 | −2.482 | −25.293 | 1.00 | 17.83 | C |
| ATOM | 13782 | O | ASP | B | 326 | 42.147 | −2.277 | −24.219 | 1.00 | 18.93 | O |
| ATOM | 13784 | N | TYR | B | 327 | 41.899 | −1.843 | −26.413 | 1.00 | 16.28 | N |
| ATOM | 13785 | CA | TYR | B | 327 | 43.030 | −0.919 | −26.418 | 1.00 | 14.41 | C |
| ATOM | 13787 | CB | TYR | B | 327 | 43.369 | −0.440 | −27.839 | 1.00 | 14.21 | C |
| ATOM | 13790 | CG | TYR | B | 327 | 42.441 | 0.598 | −28.434 | 1.00 | 12.82 | C |
| ATOM | 13791 | CD1 | TYR | B | 327 | 41.266 | 0.232 | −29.083 | 1.00 | 11.59 | C |
| ATOM | 13793 | CE1 | TYR | B | 327 | 40.428 | 1.194 | −29.629 | 1.00 | 14.08 | C |
| ATOM | 13795 | CZ | TYR | B | 327 | 40.773 | 2.536 | −29.532 | 1.00 | 12.34 | C |
| ATOM | 13796 | OH | TYR | B | 327 | 39.965 | 3.529 | −30.060 | 1.00 | 10.34 | O |
| ATOM | 13798 | CE2 | TYR | B | 327 | 41.933 | 2.902 | −28.894 | 1.00 | 10.85 | C |
| ATOM | 13800 | CD2 | TYR | B | 327 | 42.755 | 1.946 | −28.362 | 1.00 | 8.17 | C |
| ATOM | 13802 | C | TYR | B | 327 | 42.757 | 0.234 | −25.460 | 1.00 | 14.32 | C |
| ATOM | 13803 | O | TYR | B | 327 | 43.667 | 0.699 | −24.760 | 1.00 | 14.81 | O |
| ATOM | 13805 | N | MET | B | 328 | 41.495 | 0.661 | −25.403 | 1.00 | 13.55 | N |
| ATOM | 13806 | CA | MET | B | 328 | 41.074 | 1.712 | −24.481 | 1.00 | 14.08 | C |
| ATOM | 13808 | CB | MET | B | 328 | 39.728 | 2.298 | −24.905 | 1.00 | 13.92 | C |
| ATOM | 13811 | CG | MET | B | 328 | 39.828 | 3.143 | −26.140 | 1.00 | 14.37 | C |
| ATOM | 13814 | SD | MET | B | 328 | 38.290 | 3.955 | −26.573 | 1.00 | 12.26 | S |
| ATOM | 13815 | CE | MET | B | 328 | 38.909 | 5.421 | −27.417 | 1.00 | 13.00 | C |
| ATOM | 13819 | C | MET | B | 328 | 40.998 | 1.238 | −23.030 | 1.00 | 14.20 | C |
| ATOM | 13820 | O | MET | B | 328 | 41.250 | 2.021 | −22.115 | 1.00 | 14.05 | O |
| ATOM | 13822 | N | LYS | B | 329 | 40.643 | −0.028 | −22.821 | 1.00 | 15.10 | N |
| ATOM | 13823 | CA | LYS | B | 329 | 40.630 | −0.606 | −21.478 | 1.00 | 15.89 | C |
| ATOM | 13825 | CB | LYS | B | 329 | 40.363 | −2.116 | −21.532 | 1.00 | 17.28 | C |
| ATOM | 13828 | CG | LYS | B | 329 | 38.896 | −2.473 | −21.634 | 1.00 | 20.84 | C |
| ATOM | 13831 | CD | LYS | B | 329 | 38.664 | −3.931 | −21.969 | 1.00 | 24.16 | C |
| ATOM | 13834 | CE | LYS | B | 329 | 37.232 | −4.336 | −21.638 | 1.00 | 27.79 | C |
| ATOM | 13837 | NZ | LYS | B | 329 | 36.674 | −5.298 | −22.613 | 1.00 | 26.15 | N |
| ATOM | 13841 | C | LYS | B | 329 | 41.963 | −0.348 | −20.806 | 1.00 | 15.46 | C |
| ATOM | 13842 | O | LYS | B | 329 | 42.024 | 0.235 | −19.729 | 1.00 | 15.21 | O |
| ATOM | 13844 | N | LEU | B | 330 | 43.027 | −0.762 | −21.484 | 1.00 | 15.37 | N |
| ATOM | 13845 | CA | LEU | B | 330 | 44.385 | −0.697 | −20.954 | 1.00 | 15.24 | C |
| ATOM | 13847 | CB | LEU | B | 330 | 45.323 | −1.404 | −21.933 | 1.00 | 15.47 | C |
| ATOM | 13850 | CG | LEU | B | 330 | 46.642 | −1.982 | −21.444 | 1.00 | 16.80 | C |
| ATOM | 13852 | CD1 | LEU | B | 330 | 46.427 | −3.085 | −20.410 | 1.00 | 16.57 | C |
| ATOM | 13856 | CD2 | LEU | B | 330 | 47.406 | −2.511 | −22.654 | 1.00 | 18.67 | C |
| ATOM | 13860 | C | LEU | B | 330 | 44.818 | 0.758 | −20.733 | 1.00 | 15.71 | C |
| ATOM | 13861 | O | LEU | B | 330 | 45.311 | 1.124 | −19.657 | 1.00 | 16.15 | O |
| ATOM | 13863 | N | ACYS | B | 331 | 44.615 | 1.583 | −21.754 | 0.50 | 15.25 | N |
| ATOM | 13864 | N | BCYS | B | 331 | 44.628 | 1.583 | −21.760 | 0.50 | 15.88 | N |
| ATOM | 13865 | CA | ACYS | B | 331 | 44.936 | 3.001 | −21.681 | 0.50 | 14.26 | C |
| ATOM | 13866 | CA | BCYS | B | 331 | 44.911 | 3.012 | −21.675 | 0.50 | 15.48 | C |
| ATOM | 13869 | CB | ACYS | B | 331 | 44.556 | 3.683 | −22.995 | 0.50 | 14.04 | C |
| ATOM | 13870 | CB | BCYS | B | 331 | 44.424 | 3.717 | −22.936 | 0.50 | 15.49 | C |
| ATOM | 13875 | SG | ACYS | B | 331 | 45.108 | 5.391 | −23.131 | 0.50 | 11.76 | S |
| ATOM | 13876 | SG | BCYS | B | 331 | 45.579 | 3.645 | −24.291 | 0.50 | 17.45 | S |

APPENDIX 1-continued

| ATOM | 13879 | C | ACYS | B | 331 | 44.225 | 3.684 | −20.510 | 0.50 | 14.40 | C |
|---|---|---|---|---|---|---|---|---|---|---|---|
| ATOM | 13880 | C | BCYS | B | 331 | 44.232 | 3.650 | −20.476 | 0.50 | 15.03 | C |
| ATOM | 13881 | O | ACYS | B | 331 | 44.838 | 4.461 | −19.774 | 0.50 | 14.06 | O |
| ATOM | 13882 | O | BCYS | B | 331 | 44.867 | 4.363 | −19.697 | 0.50 | 14.71 | O |
| ATOM | 13885 | N | PHE | B | 332 | 42.936 | 3.393 | −20.338 | 1.00 | 14.55 | N |
| ATOM | 13886 | CA | PHE | B | 332 | 42.161 | 3.984 | −19.255 | 1.00 | 15.52 | C |
| ATOM | 13888 | CB | PHE | B | 332 | 40.673 | 3.660 | −19.386 | 1.00 | 16.28 | C |
| ATOM | 13891 | CG | PHE | B | 332 | 39.845 | 4.208 | −18.256 | 1.00 | 19.29 | C |
| ATOM | 13892 | CD1 | PHE | B | 332 | 39.407 | 5.523 | −18.274 | 1.00 | 19.62 | C |
| ATOM | 13894 | CE1 | PHE | B | 332 | 38.655 | 6.031 | −17.227 | 1.00 | 18.67 | C |
| ATOM | 13896 | CZ | PHE | B | 332 | 38.353 | 5.231 | −16.142 | 1.00 | 16.97 | C |
| ATOM | 13898 | CE2 | PHE | B | 332 | 38.790 | 3.931 | −16.108 | 1.00 | 18.43 | C |
| ATOM | 13900 | CD2 | PHE | B | 332 | 39.536 | 3.421 | −17.156 | 1.00 | 20.41 | C |
| ATOM | 13902 | C | PHE | B | 332 | 42.675 | 3.538 | −17.885 | 1.00 | 14.48 | C |
| ATOM | 13903 | O | PHE | B | 332 | 42.924 | 4.357 | −17.013 | 1.00 | 14.07 | O |
| ATOM | 13905 | N | LEU | B | 333 | 42.860 | 2.239 | −17.711 | 1.00 | 14.61 | N |
| ATOM | 13906 | CA | LEU | B | 333 | 43.276 | 1.720 | −16.418 | 1.00 | 14.22 | C |
| ATOM | 13908 | CB | LEU | B | 333 | 43.239 | 0.185 | −16.400 | 1.00 | 13.21 | C |
| ATOM | 13911 | CG | LEU | B | 333 | 43.521 | −0.459 | −15.040 | 1.00 | 13.37 | C |
| ATOM | 13913 | CD1 | LEU | B | 333 | 42.680 | 0.164 | −13.930 | 1.00 | 10.22 | C |
| ATOM | 13917 | CD2 | LEU | B | 333 | 43.293 | −1.955 | −15.103 | 1.00 | 8.11 | C |
| ATOM | 13921 | C | LEU | B | 333 | 44.656 | 2.240 | −16.036 | 1.00 | 14.28 | C |
| ATOM | 13922 | O | LEU | B | 333 | 44.897 | 2.528 | −14.871 | 1.00 | 15.54 | O |
| ATOM | 13924 | N | ALA | B | 334 | 45.550 | 2.371 | −17.014 | 1.00 | 13.82 | N |
| ATOM | 13925 | CA | ALA | B | 334 | 46.874 | 2.952 | −16.769 | 1.00 | 13.62 | C |
| ATOM | 13927 | CB | ALA | B | 334 | 47.718 | 2.889 | −18.025 | 1.00 | 13.34 | C |
| ATOM | 13931 | C | ALA | B | 334 | 46.777 | 4.393 | −16.288 | 1.00 | 14.17 | C |
| ATOM | 13932 | O | ALA | B | 334 | 47.452 | 4.779 | −15.338 | 1.00 | 15.62 | O |
| ATOM | 13934 | N | LEU | B | 335 | 45.947 | 5.184 | −16.963 | 1.00 | 14.35 | N |
| ATOM | 13935 | CA | LEU | B | 335 | 45.723 | 6.580 | −16.607 | 1.00 | 14.33 | C |
| ATOM | 13937 | CB | LEU | B | 335 | 44.861 | 7.256 | −17.682 | 1.00 | 15.56 | C |
| ATOM | 13940 | CG | LEU | B | 335 | 44.541 | 8.748 | −17.512 | 1.00 | 17.65 | C |
| ATOM | 13942 | CD1 | LEU | B | 335 | 45.787 | 9.613 | −17.669 | 1.00 | 14.16 | C |
| ATOM | 13946 | CD2 | LEU | B | 335 | 43.447 | 9.172 | −18.495 | 1.00 | 14.60 | C |
| ATOM | 13950 | C | LEU | B | 335 | 45.037 | 6.665 | −15.248 | 1.00 | 13.80 | C |
| ATOM | 13951 | O | LEU | B | 335 | 45.472 | 7.396 | −14.372 | 1.00 | 13.76 | O |
| ATOM | 13953 | N | TYR | B | 336 | 43.973 | 5.886 | −15.082 | 1.00 | 13.24 | N |
| ATOM | 13954 | CA | TYR | B | 336 | 43.235 | 5.812 | −13.826 | 1.00 | 12.46 | C |
| ATOM | 13956 | CB | TYR | B | 336 | 42.188 | 4.706 | −13.911 | 1.00 | 12.60 | C |
| ATOM | 13959 | CG | TYR | B | 336 | 41.174 | 4.701 | −12.790 | 1.00 | 14.72 | C |
| ATOM | 13960 | CD1 | TYR | B | 336 | 40.079 | 5.566 | −12.810 | 1.00 | 16.98 | C |
| ATOM | 13962 | CE1 | TYR | B | 336 | 39.133 | 5.553 | −11.793 | 1.00 | 13.34 | C |
| ATOM | 13964 | CZ | TYR | B | 336 | 39.274 | 4.670 | −10.743 | 1.00 | 16.89 | C |
| ATOM | 13965 | OH | TYR | B | 336 | 38.348 | 4.649 | −9.729 | 1.00 | 18.69 | O |
| ATOM | 13967 | CE2 | TYR | B | 336 | 40.345 | 3.798 | −10.704 | 1.00 | 17.64 | C |
| ATOM | 13969 | CD2 | TYR | B | 336 | 41.286 | 3.814 | −11.730 | 1.00 | 13.75 | C |
| ATOM | 13971 | C | TYR | B | 336 | 44.158 | 5.562 | −12.636 | 1.00 | 12.04 | C |
| ATOM | 13972 | O | TYR | B | 336 | 44.120 | 6.296 | −11.652 | 1.00 | 12.01 | O |
| ATOM | 13974 | N | ASN | B | 337 | 44.995 | 4.534 | −12.730 | 1.00 | 11.13 | N |
| ATOM | 13975 | CA | ASN | B | 337 | 45.918 | 4.212 | −11.646 | 1.00 | 10.21 | C |
| ATOM | 13977 | CB | ASN | B | 337 | 46.635 | 2.889 | −11.913 | 1.00 | 9.74 | C |
| ATOM | 13980 | CG | ASN | B | 337 | 45.706 | 1.693 | −11.840 | 1.00 | 10.79 | C |
| ATOM | 13981 | OD1 | ASN | B | 337 | 44.601 | 1.791 | −11.311 | 1.00 | 16.13 | O |
| ATOM | 13982 | ND2 | ASN | B | 337 | 46.153 | 0.550 | −12.369 | 1.00 | 8.28 | N |
| ATOM | 13985 | C | ASN | B | 337 | 46.937 | 5.319 | −11.415 | 1.00 | 10.08 | C |
| ATOM | 13986 | O | ASN | B | 337 | 47.159 | 5.728 | −10.282 | 1.00 | 11.29 | O |
| ATOM | 13988 | N | THR | B | 338 | 47.547 | 5.803 | −12.491 | 1.00 | 10.00 | N |
| ATOM | 13989 | CA | THR | B | 338 | 48.571 | 6.848 | −12.403 | 1.00 | 10.09 | C |
| ATOM | 13991 | CB | THR | B | 338 | 49.077 | 7.253 | −13.809 | 1.00 | 10.88 | C |
| ATOM | 13993 | OG1 | THR | B | 338 | 49.627 | 6.102 | −14.465 | 1.00 | 10.50 | O |
| ATOM | 13995 | CG2 | THR | B | 338 | 50.137 | 8.365 | −13.727 | 1.00 | 5.80 | C |
| ATOM | 13999 | C | THR | B | 338 | 48.041 | 8.089 | −11.694 | 1.00 | 10.55 | C |
| ATOM | 14000 | O | THR | B | 338 | 48.674 | 8.592 | −10.757 | 1.00 | 10.03 | O |
| ATOM | 14002 | N | ILE | B | 339 | 46.881 | 8.574 | −12.140 | 1.00 | 10.19 | N |
| ATOM | 14003 | CA | ILE | B | 339 | 46.253 | 9.735 | −11.514 | 1.00 | 10.96 | C |
| ATOM | 14005 | CB | ILE | B | 339 | 45.007 | 10.233 | −12.286 | 1.00 | 10.74 | C |
| ATOM | 14007 | CG1 | ILE | B | 339 | 45.343 | 10.556 | −13.754 | 1.00 | 10.45 | C |
| ATOM | 14010 | CD1 | ILE | B | 339 | 46.679 | 11.224 | −13.953 | 1.00 | 10.85 | C |
| ATOM | 14014 | CG2 | ILE | B | 339 | 44.436 | 11.465 | −11.613 | 1.00 | 9.41 | C |
| ATOM | 14018 | C | ILE | B | 339 | 45.893 | 9.478 | −10.035 | 1.00 | 11.92 | C |
| ATOM | 14019 | O | ILE | B | 339 | 46.194 | 10.313 | −9.173 | 1.00 | 13.70 | O |
| ATOM | 14021 | N | ASN | B | 340 | 45.286 | 8.335 | −9.725 | 1.00 | 10.85 | N |
| ATOM | 14022 | CA | ASN | B | 340 | 44.963 | 8.024 | −8.330 | 1.00 | 10.25 | C |
| ATOM | 14024 | CB | ASN | B | 340 | 44.146 | 6.739 | −8.203 | 1.00 | 9.53 | C |
| ATOM | 14027 | CG | ASN | B | 340 | 42.775 | 6.845 | −8.830 | 1.00 | 12.20 | C |
| ATOM | 14028 | OD1 | ASN | B | 340 | 42.251 | 7.943 | −9.039 | 1.00 | 13.10 | O |
| ATOM | 14029 | ND2 | ASN | B | 340 | 42.186 | 5.694 | −9.153 | 1.00 | 13.08 | N |
| ATOM | 14032 | C | ASN | B | 340 | 46.222 | 7.902 | −7.485 | 1.00 | 11.03 | C |
| ATOM | 14033 | O | ASN | B | 340 | 46.181 | 8.110 | −6.269 | 1.00 | 11.05 | O |
| ATOM | 14035 | N | GLU | B | 341 | 47.335 | 7.543 | −8.124 | 1.00 | 11.88 | N |

APPENDIX 1-continued

| | | | | | | | | | | |
|---|---|---|---|---|---|---|---|---|---|---|
| ATOM | 14036 | CA | GLU | B | 341 | 48.619 | 7.433 | −7.434 | 1.00 | 12.69 | C |
| ATOM | 14038 | CB | GLU | B | 341 | 49.650 | 6.745 | −8.329 | 1.00 | 14.26 | C |
| ATOM | 14041 | CG | GLU | B | 341 | 50.972 | 6.373 | −7.653 | 1.00 | 24.71 | C |
| ATOM | 14044 | CD | GLU | B | 341 | 51.950 | 5.703 | −8.617 | 1.00 | 38.29 | C |
| ATOM | 14045 | OE1 | GLU | B | 341 | 53.119 | 6.149 | −8.686 | 1.00 | 46.78 | O |
| ATOM | 14046 | OE2 | GLU | B | 341 | 51.546 | 4.743 | −9.320 | 1.00 | 46.75 | O |
| ATOM | 14047 | C | GLU | B | 341 | 49.117 | 8.809 | −7.020 | 1.00 | 11.22 | C |
| ATOM | 14048 | O | GLU | B | 341 | 49.564 | 8.989 | −5.898 | 1.00 | 10.21 | O |
| ATOM | 14050 | N | ILE | B | 342 | 49.031 | 9.773 | −7.934 | 1.00 | 11.58 | N |
| ATOM | 14051 | CA | ILE | B | 342 | 49.442 | 11.145 | −7.658 | 1.00 | 11.56 | C |
| ATOM | 14053 | CB | ILE | B | 342 | 49.443 | 12.001 | −8.949 | 1.00 | 12.11 | C |
| ATOM | 14055 | CG1 | ILE | B | 342 | 50.595 | 11.582 | −9.860 | 1.00 | 13.42 | C |
| ATOM | 14058 | CD1 | ILE | B | 342 | 50.452 | 12.080 | −11.287 | 1.00 | 12.74 | C |
| ATOM | 14062 | CG2 | ILE | B | 342 | 49.575 | 13.481 | −8.646 | 1.00 | 7.54 | C |
| ATOM | 14066 | C | ILE | B | 342 | 48.532 | 11.760 | −6.591 | 1.00 | 12.57 | C |
| ATOM | 14067 | O | ILE | B | 342 | 48.996 | 12.505 | −5.734 | 1.00 | 14.17 | O |
| ATOM | 14069 | N | ALA | B | 343 | 47.243 | 11.437 | −6.635 | 1.00 | 12.30 | N |
| ATOM | 14070 | CA | ALA | B | 343 | 46.301 | 11.910 | −5.623 | 1.00 | 12.11 | C |
| ATOM | 14072 | CB | ALA | B | 343 | 44.881 | 11.496 | −5.981 | 1.00 | 11.62 | C |
| ATOM | 14076 | C | ALA | B | 343 | 46.688 | 11.380 | −4.243 | 1.00 | 12.90 | C |
| ATOM | 14077 | O | ALA | B | 343 | 46.656 | 12.119 | −3.248 | 1.00 | 14.47 | O |
| ATOM | 14079 | N | TYR | B | 344 | 47.073 | 10.104 | −4.196 | 1.00 | 12.86 | N |
| ATOM | 14080 | CA | TYR | B | 344 | 47.562 | 9.480 | −2.964 | 1.00 | 11.90 | C |
| ATOM | 14082 | CB | TYR | B | 344 | 47.878 | 7.989 | −3.165 | 1.00 | 11.32 | C |
| ATOM | 14085 | CG | TYR | B | 344 | 48.448 | 7.352 | −1.923 | 1.00 | 5.70 | C |
| ATOM | 14086 | CD1 | TYR | B | 344 | 47.614 | 6.860 | −0.928 | 1.00 | 4.60 | C |
| ATOM | 14088 | CE1 | TYR | B | 344 | 48.138 | 6.301 | 0.228 | 1.00 | 4.71 | C |
| ATOM | 14090 | CZ | TYR | B | 344 | 49.504 | 6.244 | 0.395 | 1.00 | 2.00 | C |
| ATOM | 14091 | OH | TYR | B | 344 | 50.028 | 5.692 | 1.532 | 1.00 | 6.52 | O |
| ATOM | 14093 | CE2 | TYR | B | 344 | 50.345 | 6.732 | −0.572 | 1.00 | 2.00 | C |
| ATOM | 14095 | CD2 | TYR | B | 344 | 49.819 | 7.287 | −1.719 | 1.00 | 2.87 | C |
| ATOM | 14097 | C | TYR | B | 344 | 48.798 | 10.184 | −2.422 | 1.00 | 12.46 | C |
| ATOM | 14098 | O | TYR | B | 344 | 48.893 | 10.413 | −1.224 | 1.00 | 12.96 | O |
| ATOM | 14100 | N | ASP | B | 345 | 49.747 | 10.509 | −3.296 | 1.00 | 13.52 | N |
| ATOM | 14101 | CA | ASP | B | 345 | 50.954 | 11.230 | −2.878 | 1.00 | 14.39 | C |
| ATOM | 14103 | CB | ASP | B | 345 | 51.839 | 11.583 | −4.082 | 1.00 | 14.28 | C |
| ATOM | 14106 | CG | ASP | B | 345 | 52.569 | 10.380 | −4.659 | 1.00 | 17.59 | C |
| ATOM | 14107 | OD1 | ASP | B | 345 | 52.720 | 9.361 | −3.951 | 1.00 | 21.20 | O |
| ATOM | 14108 | OD2 | ASP | B | 345 | 53.009 | 10.466 | −5.830 | 1.00 | 24.42 | O |
| ATOM | 14109 | C | ASP | B | 345 | 50.592 | 12.511 | −2.138 | 1.00 | 14.27 | C |
| ATOM | 14110 | O | ASP | B | 345 | 51.136 | 12.784 | −1.079 | 1.00 | 13.47 | O |
| ATOM | 14112 | N | ASN | B | 346 | 49.672 | 13.292 | −2.705 | 1.00 | 15.07 | N |
| ATOM | 14113 | CA | ASN | B | 346 | 49.266 | 14.562 | −2.099 | 1.00 | 15.37 | C |
| ATOM | 14115 | CB | ASN | B | 346 | 48.500 | 15.430 | −3.100 | 1.00 | 15.43 | C |
| ATOM | 14118 | CG | ASN | B | 346 | 49.413 | 16.064 | −4.114 | 1.00 | 16.36 | C |
| ATOM | 14119 | OD1 | ASN | B | 346 | 49.869 | 17.194 | −3.929 | 1.00 | 19.33 | O |
| ATOM | 14120 | ND2 | ASN | B | 346 | 49.721 | 15.330 | −5.174 | 1.00 | 15.63 | N |
| ATOM | 14123 | C | ASN | B | 346 | 48.453 | 14.376 | −0.826 | 1.00 | 15.35 | C |
| ATOM | 14124 | O | ASN | B | 346 | 48.601 | 15.141 | 0.128 | 1.00 | 14.31 | O |
| ATOM | 14126 | N | LEU | B | 347 | 47.601 | 13.355 | −0.801 | 1.00 | 15.31 | N |
| ATOM | 14127 | CA | LEU | B | 347 | 46.898 | 13.026 | 0.428 | 1.00 | 14.92 | C |
| ATOM | 14129 | CB | LEU | B | 347 | 45.934 | 11.868 | 0.205 | 1.00 | 14.76 | C |
| ATOM | 14132 | CG | LEU | B | 347 | 45.049 | 11.490 | 1.398 | 1.00 | 16.42 | C |
| ATOM | 14134 | CD1 | LEU | B | 347 | 44.343 | 12.715 | 1.979 | 1.00 | 14.04 | C |
| ATOM | 14138 | CD2 | LEU | B | 347 | 44.045 | 10.416 | 0.999 | 1.00 | 10.08 | C |
| ATOM | 14142 | C | LEU | B | 347 | 47.926 | 12.708 | 1.519 | 1.00 | 15.54 | C |
| ATOM | 14143 | O | LEU | B | 347 | 47.884 | 13.278 | 2.601 | 1.00 | 17.24 | O |
| ATOM | 14145 | N | LYS | B | 348 | 48.881 | 11.840 | 1.211 | 1.00 | 15.74 | N |
| ATOM | 14146 | CA | LYS | B | 348 | 49.935 | 11.467 | 2.158 | 1.00 | 16.65 | C |
| ATOM | 14148 | CB | LYS | B | 348 | 50.886 | 10.468 | 1.490 | 1.00 | 16.49 | C |
| ATOM | 14151 | CG | LYS | B | 348 | 51.943 | 9.856 | 2.391 | 1.00 | 17.97 | C |
| ATOM | 14154 | CD | LYS | B | 348 | 52.819 | 8.851 | 1.621 | 1.00 | 21.19 | C |
| ATOM | 14157 | CE | LYS | B | 348 | 54.204 | 9.399 | 1.256 | 1.00 | 22.84 | C |
| ATOM | 14160 | NZ | LYS | B | 348 | 54.260 | 10.176 | −0.004 | 1.00 | 24.37 | N |
| ATOM | 14164 | C | LYS | B | 348 | 50.734 | 12.673 | 2.657 | 1.00 | 17.77 | C |
| ATOM | 14165 | O | LYS | B | 348 | 50.910 | 12.866 | 3.862 | 1.00 | 18.58 | O |
| ATOM | 14167 | N | ASP | B | 349 | 51.221 | 13.479 | 1.724 | 1.00 | 18.87 | N |
| ATOM | 14168 | CA | ASP | B | 349 | 52.179 | 14.534 | 2.044 | 1.00 | 19.87 | C |
| ATOM | 14170 | CB | ASP | B | 349 | 53.155 | 14.718 | 0.879 | 1.00 | 20.01 | C |
| ATOM | 14173 | CG | ASP | B | 349 | 54.010 | 13.479 | 0.633 | 1.00 | 21.35 | C |
| ATOM | 14174 | OD1 | ASP | B | 349 | 54.069 | 12.608 | 1.523 | 1.00 | 23.56 | O |
| ATOM | 14175 | OD2 | ASP | B | 349 | 54.626 | 13.377 | −0.447 | 1.00 | 25.12 | O |
| ATOM | 14176 | C | ASP | B | 349 | 51.544 | 15.871 | 2.420 | 1.00 | 19.82 | C |
| ATOM | 14177 | O | ASP | B | 349 | 52.149 | 16.645 | 3.139 | 1.00 | 21.01 | O |
| ATOM | 14179 | N | LYS | B | 350 | 50.336 | 16.143 | 1.950 | 1.00 | 20.14 | N |
| ATOM | 14180 | CA | LYS | B | 350 | 49.688 | 17.424 | 2.227 | 1.00 | 20.29 | C |
| ATOM | 14182 | CB | LYS | B | 350 | 49.479 | 18.190 | 0.923 | 1.00 | 20.04 | C |
| ATOM | 14185 | CG | LYS | B | 350 | 50.760 | 18.489 | 0.170 | 1.00 | 23.22 | C |
| ATOM | 14188 | CD | LYS | B | 350 | 50.433 | 19.125 | −1.168 | 1.00 | 31.38 | C |
| ATOM | 14191 | CE | LYS | B | 350 | 51.681 | 19.508 | −1.954 | 1.00 | 32.47 | C |

APPENDIX 1-continued

| | | | | | | | | | | |
|---|---|---|---|---|---|---|---|---|---|---|
| ATOM | 14194 | NZ   | LYS | B | 350 | 51.313 | 19.744 | −3.370  | 1.00 | 29.78 N |
| ATOM | 14198 | C    | LYS | B | 350 | 48.356 | 17.310 | 2.972   | 1.00 | 20.08 C |
| ATOM | 14199 | O    | LYS | B | 350 | 47.831 | 18.315 | 3.441   | 1.00 | 21.09 O |
| ATOM | 14201 | N    | GLY | B | 351 | 47.806 | 16.104 | 3.081   | 1.00 | 19.11 N |
| ATOM | 14202 | CA   | GLY | B | 351 | 46.551 | 15.899 | 3.797   | 1.00 | 18.35 C |
| ATOM | 14205 | C    | GLY | B | 351 | 45.336 | 16.452 | 3.080   | 1.00 | 18.36 C |
| ATOM | 14206 | O    | GLY | B | 351 | 44.336 | 16.763 | 3.714   | 1.00 | 18.14 O |
| ATOM | 14208 | N    | GLU | B | 352 | 45.423 | 16.566 | 1.757   | 1.00 | 19.29 N |
| ATOM | 14209 | CA   | GLU | B | 352 | 44.339 | 17.104 | 0.939   | 1.00 | 20.17 C |
| ATOM | 14211 | CB   | GLU | B | 352 | 44.776 | 18.404 | 0.251   | 1.00 | 20.76 C |
| ATOM | 14214 | CG   | GLU | B | 352 | 45.102 | 19.567 | 1.196   | 1.00 | 23.95 C |
| ATOM | 14217 | CD   | GLU | B | 352 | 43.875 | 20.161 | 1.878   | 1.00 | 28.83 C |
| ATOM | 14218 | OE1  | GLU | B | 352 | 42.754 | 20.032 | 1.333   | 1.00 | 28.49 O |
| ATOM | 14219 | OE2  | GLU | B | 352 | 44.040 | 20.762 | 2.966   | 1.00 | 35.13 O |
| ATOM | 14220 | C    | GLU | B | 352 | 43.943 | 16.097 | −0.130  | 1.00 | 20.14 C |
| ATOM | 14221 | O    | GLU | B | 352 | 44.802 | 15.409 | −0.685  | 1.00 | 20.62 O |
| ATOM | 14223 | N    | ASN | B | 353 | 42.641 | 16.012 | −0.404  | 1.00 | 19.53 N |
| ATOM | 14224 | CA   | ASN | B | 353 | 42.140 | 15.254 | −1.532  | 1.00 | 18.31 C |
| ATOM | 14226 | CB   | ASN | B | 353 | 40.779 | 14.641 | −1.236  | 1.00 | 18.23 C |
| ATOM | 14229 | CG   | ASN | B | 353 | 40.241 | 13.851 | −2.414  | 1.00 | 19.94 C |
| ATOM | 14230 | OD1  | ASN | B | 353 | 40.927 | 13.679 | −3.422  | 1.00 | 18.91 O |
| ATOM | 14231 | ND2  | ASN | B | 353 | 39.017 | 13.364 | −2.293  | 1.00 | 23.60 N |
| ATOM | 14234 | C    | ASN | B | 353 | 42.023 | 16.150 | −2.751  | 1.00 | 17.97 C |
| ATOM | 14235 | O    | ASN | B | 353 | 41.043 | 16.877 | −2.896  | 1.00 | 19.13 O |
| ATOM | 14237 | N    | ILE | B | 354 | 43.012 | 16.072 | −3.634  | 1.00 | 16.21 N |
| ATOM | 14238 | CA   | ILE | B | 354 | 43.015 | 16.859 | −4.852  | 1.00 | 14.55 C |
| ATOM | 14240 | CB   | ILE | B | 354 | 44.415 | 17.426 | −5.129  | 1.00 | 15.27 C |
| ATOM | 14242 | CG1  | ILE | B | 354 | 45.388 | 16.315 | −5.545  | 1.00 | 15.94 C |
| ATOM | 14245 | CD1  | ILE | B | 354 | 46.671 | 16.828 | −6.126  | 1.00 | 19.64 C |
| ATOM | 14249 | CG2  | ILE | B | 354 | 44.930 | 18.140 | −3.902  | 1.00 | 12.01 C |
| ATOM | 14253 | C    | ILE | B | 354 | 42.554 | 16.066 | −6.072  | 1.00 | 14.06 C |
| ATOM | 14254 | O    | ILE | B | 354 | 42.687 | 16.536 | −7.208  | 1.00 | 12.64 O |
| ATOM | 14256 | N    | LEU | B | 355 | 42.007 | 14.871 | −5.846  | 1.00 | 13.89 N |
| ATOM | 14257 | CA   | LEU | B | 355 | 41.636 | 13.996 | −6.955  | 1.00 | 14.02 C |
| ATOM | 14259 | CB   | LEU | B | 355 | 41.099 | 12.641 | −6.464  | 1.00 | 13.01 C |
| ATOM | 14262 | CG   | LEU | B | 355 | 40.891 | 11.570 | −7.552  | 1.00 | 12.70 C |
| ATOM | 14264 | CD1  | LEU | B | 355 | 42.184 | 11.255 | −8.292  | 1.00 | 8.91 C  |
| ATOM | 14268 | CD2  | LEU | B | 355 | 40.328 | 10.293 | −6.959  | 1.00 | 11.46 C |
| ATOM | 14272 | C    | LEU | B | 355 | 40.629 | 14.677 | −7.881  | 1.00 | 15.15 C |
| ATOM | 14273 | O    | LEU | B | 355 | 40.824 | 14.687 | −9.103  | 1.00 | 15.76 O |
| ATOM | 14275 | N    | PRO | B | 356 | 39.567 | 15.277 | −7.310  | 1.00 | 15.69 N |
| ATOM | 14276 | CA   | PRO | B | 356 | 38.588 | 15.911 | −8.193  | 1.00 | 15.84 C |
| ATOM | 14278 | CB   | PRO | B | 356 | 37.643 | 16.626 | −7.216  | 1.00 | 15.92 C |
| ATOM | 14281 | CG   | PRO | B | 356 | 37.785 | 15.879 | −5.934  | 1.00 | 14.63 C |
| ATOM | 14284 | CD   | PRO | B | 356 | 39.215 | 15.450 | −5.885  | 1.00 | 14.65 C |
| ATOM | 14287 | C    | PRO | B | 356 | 39.213 | 16.906 | −9.175  | 1.00 | 15.91 C |
| ATOM | 14288 | O    | PRO | B | 356 | 38.775 | 16.986 | −10.320 | 1.00 | 17.51 O |
| ATOM | 14289 | N    | TYR | B | 357 | 40.236 | 17.636 | −8.743  | 1.00 | 15.73 N |
| ATOM | 14290 | CA   | TYR | B | 357 | 40.881 | 18.631 | −9.610  | 1.00 | 16.23 C |
| ATOM | 14292 | CB   | TYR | B | 357 | 41.723 | 19.615 | −8.784  | 1.00 | 15.93 C |
| ATOM | 14295 | CG   | TYR | B | 357 | 40.999 | 20.092 | −7.540  | 1.00 | 20.66 C |
| ATOM | 14296 | CD1  | TYR | B | 357 | 39.804 | 20.803 | −7.633  | 1.00 | 26.03 C |
| ATOM | 14298 | CE1  | TYR | B | 357 | 39.118 | 21.225 | −6.495  | 1.00 | 23.97 C |
| ATOM | 14300 | CZ   | TYR | B | 357 | 39.627 | 20.933 | −5.252  | 1.00 | 27.38 C |
| ATOM | 14301 | OH   | TYR | B | 357 | 38.962 | 21.350 | −4.118  | 1.00 | 32.89 O |
| ATOM | 14303 | CE2  | TYR | B | 357 | 40.808 | 20.220 | −5.134  | 1.00 | 26.43 C |
| ATOM | 14305 | CD2  | TYR | B | 357 | 41.482 | 19.801 | −6.276  | 1.00 | 24.51 C |
| ATOM | 14307 | C    | TYR | B | 357 | 41.711 | 17.973 | −10.721 | 1.00 | 16.38 C |
| ATOM | 14308 | O    | TYR | B | 357 | 41.704 | 18.441 | −11.867 | 1.00 | 17.20 O |
| ATOM | 14310 | N    | LEU | B | 358 | 42.396 | 16.877 | −10.398 | 1.00 | 16.21 N |
| ATOM | 14311 | CA   | LEU | B | 358 | 43.185 | 16.150 | −11.395 | 1.00 | 15.98 C |
| ATOM | 14313 | CB   | LEU | B | 358 | 44.086 | 15.105 | −10.725 | 1.00 | 16.16 C |
| ATOM | 14316 | CG   | LEU | B | 358 | 45.086 | 15.561 | −9.655  | 1.00 | 15.44 C |
| ATOM | 14318 | CD1  | LEU | B | 358 | 45.836 | 14.356 | −9.073  | 1.00 | 9.30 C  |
| ATOM | 14322 | CD2  | LEU | B | 358 | 46.066 | 16.601 | −10.202 | 1.00 | 12.13 C |
| ATOM | 14326 | C    | LEU | B | 358 | 42.278 | 15.480 | −12.440 | 1.00 | 15.92 C |
| ATOM | 14327 | O    | LEU | B | 358 | 42.495 | 15.614 | −13.639 | 1.00 | 14.71 O |
| ATOM | 14329 | N    | THR | B | 359 | 41.252 | 14.777 | −11.974 | 1.00 | 16.60 N |
| ATOM | 14330 | CA   | THR | B | 359 | 40.301 | 14.127 | −12.862 | 1.00 | 17.22 C |
| ATOM | 14332 | CB   | THR | B | 359 | 39.284 | 13.291 | −12.084 | 1.00 | 16.72 C |
| ATOM | 14334 | OG1  | THR | B | 359 | 38.617 | 14.125 | −11.138 | 1.00 | 17.96 O |
| ATOM | 14336 | CG2  | THR | B | 359 | 39.972 | 12.154 | −11.355 | 1.00 | 17.03 C |
| ATOM | 14340 | C    | THR | B | 359 | 39.525 | 15.119 | −13.722 | 1.00 | 19.12 C |
| ATOM | 14341 | O    | THR | B | 359 | 39.177 | 14.806 | −14.863 | 1.00 | 20.95 O |
| ATOM | 14343 | N    | LYS | B | 360 | 39.233 | 16.301 | −13.183 | 1.00 | 20.20 N |
| ATOM | 14344 | CA   | LYS | B | 360 | 38.542 | 17.340 | −13.958 | 1.00 | 20.41 C |
| ATOM | 14346 | CB   | LYS | B | 360 | 38.157 | 18.526 | −13.080 | 1.00 | 20.61 C |
| ATOM | 14349 | CG   | LYS | B | 360 | 37.581 | 19.736 | −13.839 | 1.00 | 24.40 C |
| ATOM | 14352 | CD   | LYS | B | 360 | 36.233 | 19.445 | −14.489 | 1.00 | 28.55 C |
| ATOM | 14355 | CE   | LYS | B | 360 | 35.611 | 20.716 | −15.054 | 1.00 | 30.13 C |

APPENDIX 1-continued

| ATOM | 14358 | NZ | LYS | B | 360 | 34.583 | 20.436 | −16.094 | 1.00 | 29.00 | N |
|---|---|---|---|---|---|---|---|---|---|---|---|
| ATOM | 14362 | C | LYS | B | 360 | 39.410 | 17.819 | −15.108 | 1.00 | 20.46 | C |
| ATOM | 14363 | O | LYS | B | 360 | 38.913 | 18.001 | −16.215 | 1.00 | 22.09 | O |
| ATOM | 14365 | N | ALA | B | 361 | 40.701 | 18.025 | −14.845 | 1.00 | 19.21 | N |
| ATOM | 14366 | CA | ALA | B | 361 | 41.618 | 18.479 | −15.885 | 1.00 | 18.03 | C |
| ATOM | 14368 | CB | ALA | B | 361 | 43.014 | 18.667 | −15.333 | 1.00 | 17.16 | C |
| ATOM | 14372 | C | ALA | B | 361 | 41.633 | 17.499 | −17.048 | 1.00 | 17.75 | C |
| ATOM | 14373 | O | ALA | B | 361 | 41.536 | 17.907 | −18.206 | 1.00 | 19.49 | O |
| ATOM | 14375 | N | TRP | B | 362 | 41.739 | 16.210 | −16.735 | 1.00 | 16.54 | N |
| ATOM | 14376 | CA | TRP | B | 362 | 41.714 | 15.161 | −17.760 | 1.00 | 16.29 | C |
| ATOM | 14378 | CB | TRP | B | 362 | 42.037 | 13.796 | −17.153 | 1.00 | 15.85 | C |
| ATOM | 14381 | CG | TRP | B | 362 | 43.484 | 13.580 | −17.128 | 1.00 | 14.86 | C |
| ATOM | 14382 | CD1 | TRP | B | 362 | 44.306 | 13.657 | −16.053 | 1.00 | 11.87 | C |
| ATOM | 14384 | NE1 | TRP | B | 362 | 45.605 | 13.435 | −16.440 | 1.00 | 15.32 | N |
| ATOM | 14386 | CE2 | TRP | B | 362 | 45.630 | 13.213 | −17.792 | 1.00 | 15.07 | C |
| ATOM | 14387 | CD2 | TRP | B | 362 | 44.312 | 13.306 | −18.257 | 1.00 | 12.81 | C |
| ATOM | 14388 | CE3 | TRP | B | 362 | 44.060 | 13.119 | −19.614 | 1.00 | 13.50 | C |
| ATOM | 14390 | CZ3 | TRP | B | 362 | 45.118 | 12.849 | −20.453 | 1.00 | 13.63 | C |
| ATOM | 14392 | CH2 | TRP | B | 362 | 46.421 | 12.761 | −19.967 | 1.00 | 14.21 | C |
| ATOM | 14394 | CZ2 | TRP | B | 362 | 46.700 | 12.938 | −18.640 | 1.00 | 16.67 | C |
| ATOM | 14396 | C | TRP | B | 362 | 40.406 | 15.085 | −18.541 | 1.00 | 16.06 | C |
| ATOM | 14397 | O | TRP | B | 362 | 40.426 | 14.901 | −19.760 | 1.00 | 16.19 | O |
| ATOM | 14399 | N | ALA | B | 363 | 39.283 | 15.224 | −17.840 | 1.00 | 15.51 | N |
| ATOM | 14400 | CA | ALA | B | 363 | 37.974 | 15.244 | −18.485 | 1.00 | 15.12 | C |
| ATOM | 14402 | CB | ALA | B | 363 | 36.854 | 15.331 | −17.452 | 1.00 | 13.50 | C |
| ATOM | 14406 | C | ALA | B | 363 | 37.895 | 16.413 | −19.465 | 1.00 | 15.66 | C |
| ATOM | 14407 | O | ALA | B | 363 | 37.372 | 16.255 | −20.575 | 1.00 | 15.88 | O |
| ATOM | 14409 | N | ASP | B | 364 | 38.427 | 17.568 | −19.063 | 1.00 | 14.27 | N |
| ATOM | 14410 | CA | ASP | B | 364 | 38.424 | 18.748 | −19.923 | 1.00 | 15.12 | C |
| ATOM | 14412 | CB | ASP | B | 364 | 38.874 | 20.003 | −19.162 | 1.00 | 15.25 | C |
| ATOM | 14415 | CG | ASP | B | 364 | 37.838 | 20.497 | −18.168 | 1.00 | 15.91 | C |
| ATOM | 14416 | OD1 | ASP | B | 364 | 36.677 | 20.034 | −18.198 | 1.00 | 20.98 | O |
| ATOM | 14417 | OD2 | ASP | B | 364 | 38.197 | 21.346 | −17.336 | 1.00 | 22.28 | O |
| ATOM | 14418 | C | ASP | B | 364 | 39.311 | 18.564 | −21.143 | 1.00 | 15.25 | C |
| ATOM | 14419 | O | ASP | B | 364 | 38.992 | 19.056 | −22.220 | 1.00 | 16.41 | O |
| ATOM | 14421 | N | LEU | B | 365 | 40.428 | 17.868 | −20.977 | 1.00 | 16.10 | N |
| ATOM | 14422 | CA | LEU | B | 365 | 41.332 | 17.656 | −22.086 | 1.00 | 16.42 | C |
| ATOM | 14424 | CB | LEU | B | 365 | 42.672 | 17.104 | −21.607 | 1.00 | 15.96 | C |
| ATOM | 14427 | CG | LEU | B | 365 | 43.677 | 16.852 | −22.738 | 1.00 | 15.86 | C |
| ATOM | 14429 | CD1 | LEU | B | 365 | 43.892 | 18.104 | −23.536 | 1.00 | 11.79 | C |
| ATOM | 14433 | CD2 | LEU | B | 365 | 44.997 | 16.314 | −22.210 | 1.00 | 16.31 | C |
| ATOM | 14437 | C | LEU | B | 365 | 40.673 | 16.705 | −23.077 | 1.00 | 17.01 | C |
| ATOM | 14438 | O | LEU | B | 365 | 40.628 | 16.969 | −24.282 | 1.00 | 17.06 | O |
| ATOM | 14440 | N | CYS | B | 366 | 40.143 | 15.607 | −22.559 | 1.00 | 17.19 | N |
| ATOM | 14441 | CA | CYS | B | 366 | 39.452 | 14.646 | −23.400 | 1.00 | 17.88 | C |
| ATOM | 14443 | CB | CYS | B | 366 | 39.016 | 13.438 | −22.574 | 1.00 | 18.28 | C |
| ATOM | 14446 | SG | CYS | B | 366 | 40.448 | 12.465 | −22.017 | 1.00 | 19.51 | S |
| ATOM | 14448 | C | CYS | B | 366 | 38.278 | 15.288 | −24.131 | 1.00 | 16.95 | C |
| ATOM | 14449 | O | CYS | B | 366 | 38.055 | 15.001 | −25.300 | 1.00 | 17.64 | O |
| ATOM | 14451 | N | ASN | B | 367 | 37.559 | 16.186 | −23.463 | 1.00 | 17.32 | N |
| ATOM | 14452 | CA | ASN | B | 367 | 36.461 | 16.913 | −24.115 | 1.00 | 16.82 | C |
| ATOM | 14454 | CB | ASN | B | 367 | 35.572 | 17.626 | −23.099 | 1.00 | 14.42 | C |
| ATOM | 14457 | CG | ASN | B | 367 | 34.459 | 16.719 | −22.571 | 1.00 | 16.19 | C |
| ATOM | 14458 | OD1 | ASN | B | 367 | 33.560 | 16.329 | −23.313 | 1.00 | 19.75 | O |
| ATOM | 14459 | ND2 | ASN | B | 367 | 34.529 | 16.366 | −21.294 | 1.00 | 16.43 | N |
| ATOM | 14462 | C | ASN | B | 367 | 36.930 | 17.866 | −25.208 | 1.00 | 17.41 | C |
| ATOM | 14463 | O | ASN | B | 367 | 36.222 | 18.077 | −26.185 | 1.00 | 19.06 | O |
| ATOM | 14465 | N | ALA | B | 368 | 38.124 | 18.428 | −25.058 | 1.00 | 17.51 | N |
| ATOM | 14466 | CA | ALA | B | 368 | 38.687 | 19.283 | −26.095 | 1.00 | 16.21 | C |
| ATOM | 14468 | CB | ALA | B | 368 | 39.837 | 20.091 | −25.542 | 1.00 | 15.07 | C |
| ATOM | 14472 | C | ALA | B | 368 | 39.140 | 18.424 | −27.276 | 1.00 | 16.54 | C |
| ATOM | 14473 | O | ALA | B | 368 | 38.943 | 18.787 | −28.433 | 1.00 | 16.90 | O |
| ATOM | 14475 | N | PHE | B | 369 | 39.750 | 17.280 | −26.983 | 1.00 | 16.71 | N |
| ATOM | 14476 | CA | PHE | B | 369 | 40.063 | 16.318 | −28.025 | 1.00 | 16.46 | C |
| ATOM | 14478 | CB | PHE | B | 369 | 40.770 | 15.083 | −27.458 | 1.00 | 17.02 | C |
| ATOM | 14481 | CG | PHE | B | 369 | 42.182 | 15.320 | −26.992 | 1.00 | 19.76 | C |
| ATOM | 14482 | CD1 | PHE | B | 369 | 42.980 | 16.313 | −27.547 | 1.00 | 22.26 | C |
| ATOM | 14484 | CE1 | PHE | B | 369 | 44.279 | 16.496 | −27.114 | 1.00 | 21.94 | C |
| ATOM | 14486 | CZ | PHE | B | 369 | 44.807 | 15.679 | −26.145 | 1.00 | 22.55 | C |
| ATOM | 14488 | CE2 | PHE | B | 369 | 44.039 | 14.675 | −25.601 | 1.00 | 21.91 | C |
| ATOM | 14490 | CD2 | PHE | B | 369 | 42.735 | 14.496 | −26.026 | 1.00 | 21.14 | C |
| ATOM | 14492 | C | PHE | B | 369 | 38.799 | 15.864 | −28.740 | 1.00 | 15.48 | C |
| ATOM | 14493 | O | PHE | B | 369 | 38.787 | 15.763 | −29.953 | 1.00 | 15.19 | O |
| ATOM | 14495 | N | LEU | B | 370 | 37.739 | 15.582 | −27.986 | 1.00 | 15.87 | N |
| ATOM | 14496 | CA | LEU | B | 370 | 36.506 | 15.070 | −28.577 | 1.00 | 15.80 | C |
| ATOM | 14498 | CB | LEU | B | 370 | 35.478 | 14.717 | −27.500 | 1.00 | 16.05 | C |
| ATOM | 14501 | CG | LEU | B | 370 | 34.194 | 14.042 | −28.015 | 1.00 | 15.11 | C |
| ATOM | 14503 | CD1 | LEU | B | 370 | 34.509 | 12.770 | −28.799 | 1.00 | 11.25 | C |
| ATOM | 14507 | CD2 | LEU | B | 370 | 33.272 | 13.740 | −26.857 | 1.00 | 13.79 | C |
| ATOM | 14511 | C | LEU | B | 370 | 35.906 | 16.086 | −29.524 | 1.00 | 16.00 | C |

APPENDIX 1-continued

| ATOM | 14512 | O | LEU | B | 370 | 35.404 | 15.729 | −30.598 | 1.00 | 17.16 | O |
|---|---|---|---|---|---|---|---|---|---|---|---|
| ATOM | 14514 | N | GLN | B | 371 | 35.958 | 17.349 | −29.113 | 1.00 | 15.48 | N |
| ATOM | 14515 | CA | GLN | B | 371 | 35.486 | 18.454 | −29.932 | 1.00 | 15.64 | C |
| ATOM | 14517 | CB | GLN | B | 371 | 35.634 | 19.777 | −29.179 | 1.00 | 15.46 | C |
| ATOM | 14520 | CG | GLN | B | 371 | 35.206 | 21.006 | −29.971 | 1.00 | 16.71 | C |
| ATOM | 14523 | CD | GLN | B | 371 | 33.746 | 20.985 | −30.320 | 1.00 | 13.91 | C |
| ATOM | 14524 | OE1 | GLN | B | 371 | 33.375 | 20.698 | −31.450 | 1.00 | 15.41 | O |
| ATOM | 14525 | NE2 | GLN | B | 371 | 32.904 | 21.275 | −29.343 | 1.00 | 17.06 | N |
| ATOM | 14528 | C | GLN | B | 371 | 36.244 | 18.505 | −31.259 | 1.00 | 15.65 | C |
| ATOM | 14529 | O | GLN | B | 371 | 35.633 | 18.714 | −32.305 | 1.00 | 16.37 | O |
| ATOM | 14531 | N | GLU | B | 372 | 37.561 | 18.305 | −31.215 | 1.00 | 15.73 | N |
| ATOM | 14532 | CA | GLU | B | 372 | 38.372 | 18.260 | −32.435 | 1.00 | 16.08 | C |
| ATOM | 14534 | CB | GLU | B | 372 | 39.860 | 18.167 | −32.110 | 1.00 | 16.01 | C |
| ATOM | 14537 | CG | GLU | B | 372 | 40.462 | 19.474 | −31.687 | 1.00 | 19.10 | C |
| ATOM | 14540 | CD | GLU | B | 372 | 41.909 | 19.363 | −31.252 | 1.00 | 23.05 | C |
| ATOM | 14541 | OE1 | GLU | B | 372 | 42.475 | 18.251 | −31.273 | 1.00 | 32.06 | O |
| ATOM | 14542 | OE2 | GLU | B | 372 | 42.485 | 20.401 | −30.881 | 1.00 | 27.32 | O |
| ATOM | 14543 | C | GLU | B | 372 | 37.970 | 17.103 | −33.343 | 1.00 | 16.13 | C |
| ATOM | 14544 | O | GLU | B | 372 | 37.835 | 17.281 | −34.550 | 1.00 | 17.33 | O |
| ATOM | 14546 | N | ALA | B | 373 | 37.760 | 15.928 | −32.761 | 1.00 | 15.96 | N |
| ATOM | 14547 | CA | ALA | B | 373 | 37.333 | 14.772 | −33.535 | 1.00 | 16.64 | C |
| ATOM | 14549 | CB | ALA | B | 373 | 37.282 | 13.518 | −32.659 | 1.00 | 15.39 | C |
| ATOM | 14553 | C | ALA | B | 373 | 35.979 | 15.025 | −34.198 | 1.00 | 17.35 | C |
| ATOM | 14554 | O | ALA | B | 373 | 35.781 | 14.658 | −35.358 | 1.00 | 17.83 | O |
| ATOM | 14556 | N | LYS | B | 374 | 35.052 | 15.649 | −33.471 | 1.00 | 18.32 | N |
| ATOM | 14557 | CA | LYS | B | 374 | 33.701 | 15.903 | −34.010 | 1.00 | 19.70 | C |
| ATOM | 14559 | CB | LYS | B | 374 | 32.754 | 16.428 | −32.929 | 1.00 | 20.53 | C |
| ATOM | 14562 | CG | LYS | B | 374 | 32.259 | 15.355 | −31.976 | 1.00 | 25.09 | C |
| ATOM | 14565 | CD | LYS | B | 374 | 31.376 | 15.934 | −30.869 | 1.00 | 28.97 | C |
| ATOM | 14568 | CE | LYS | B | 374 | 30.781 | 14.829 | −30.006 | 1.00 | 29.47 | C |
| ATOM | 14571 | NZ | LYS | B | 374 | 30.201 | 15.348 | −28.737 | 1.00 | 30.82 | N |
| ATOM | 14575 | C | LYS | B | 374 | 33.734 | 16.884 | −35.176 | 1.00 | 18.71 | C |
| ATOM | 14576 | O | LYS | B | 374 | 33.002 | 16.723 | −36.148 | 1.00 | 17.84 | O |
| ATOM | 14578 | N | TRP | B | 375 | 34.581 | 17.901 | −35.065 | 1.00 | 18.32 | N |
| ATOM | 14579 | CA | TRP | B | 375 | 34.749 | 18.864 | −36.139 | 1.00 | 17.88 | C |
| ATOM | 14581 | CB | TRP | B | 375 | 35.672 | 20.019 | −35.724 | 1.00 | 16.84 | C |
| ATOM | 14584 | CG | TRP | B | 375 | 35.029 | 21.093 | −34.901 | 1.00 | 15.31 | C |
| ATOM | 14585 | CD1 | TRP | B | 375 | 33.709 | 21.445 | −34.887 | 1.00 | 17.15 | C |
| ATOM | 14587 | NE1 | TRP | B | 375 | 33.509 | 22.496 | −34.031 | 1.00 | 13.26 | N |
| ATOM | 14589 | CE2 | TRP | B | 375 | 34.707 | 22.857 | −33.480 | 1.00 | 10.19 | C |
| ATOM | 14590 | CD2 | TRP | B | 375 | 35.690 | 21.997 | −34.007 | 1.00 | 13.16 | C |
| ATOM | 14591 | CE3 | TRP | B | 375 | 37.020 | 22.161 | −33.600 | 1.00 | 12.02 | C |
| ATOM | 14593 | CZ3 | TRP | B | 375 | 37.319 | 23.167 | −32.681 | 1.00 | 14.69 | C |
| ATOM | 14595 | CH2 | TRP | B | 375 | 36.315 | 23.997 | −32.170 | 1.00 | 16.14 | C |
| ATOM | 14597 | CZ2 | TRP | B | 375 | 35.003 | 23.857 | −32.558 | 1.00 | 13.73 | C |
| ATOM | 14599 | C | TRP | B | 375 | 35.314 | 18.177 | −37.373 | 1.00 | 18.55 | C |
| ATOM | 14600 | O | TRP | B | 375 | 34.883 | 18.469 | −38.487 | 1.00 | 19.56 | O |
| ATOM | 14602 | N | LEU | B | 376 | 36.284 | 17.285 | −37.179 | 1.00 | 19.65 | N |
| ATOM | 14603 | CA | LEU | B | 376 | 36.853 | 16.530 | −38.292 | 1.00 | 21.62 | C |
| ATOM | 14605 | CB | LEU | B | 376 | 38.060 | 15.700 | −37.857 | 1.00 | 23.00 | C |
| ATOM | 14608 | CG | LEU | B | 376 | 38.856 | 15.074 | −39.015 | 1.00 | 29.39 | C |
| ATOM | 14610 | CD1 | LEU | B | 376 | 39.681 | 16.142 | −39.751 | 1.00 | 34.17 | C |
| ATOM | 14614 | CD2 | LEU | B | 376 | 39.758 | 13.934 | −38.529 | 1.00 | 30.95 | C |
| ATOM | 14618 | C | LEU | B | 376 | 35.791 | 15.629 | −38.920 | 1.00 | 20.99 | C |
| ATOM | 14619 | O | LEU | B | 376 | 35.558 | 15.694 | −40.126 | 1.00 | 21.94 | O |
| ATOM | 14621 | N | TYR | B | 377 | 35.132 | 14.817 | −38.103 | 1.00 | 19.88 | N |
| ATOM | 14622 | CA | TYR | B | 377 | 34.070 | 13.935 | −38.594 | 1.00 | 20.68 | C |
| ATOM | 14624 | CB | TYR | B | 377 | 33.384 | 13.228 | −37.430 | 1.00 | 21.02 | C |
| ATOM | 14627 | CG | TYR | B | 377 | 32.350 | 12.194 | −37.827 | 1.00 | 22.29 | C |
| ATOM | 14628 | CD1 | TYR | B | 377 | 32.714 | 10.866 | −38.056 | 1.00 | 25.15 | C |
| ATOM | 14630 | CE1 | TYR | B | 377 | 31.759 | 9.908 | −38.407 | 1.00 | 24.92 | C |
| ATOM | 14632 | CZ | TYR | B | 377 | 30.428 | 10.278 | −38.521 | 1.00 | 24.98 | C |
| ATOM | 14633 | OH | TYR | B | 377 | 29.489 | 9.340 | −38.866 | 1.00 | 28.20 | O |
| ATOM | 14635 | CE2 | TYR | B | 377 | 30.042 | 11.585 | −38.295 | 1.00 | 22.14 | C |
| ATOM | 14637 | CD2 | TYR | B | 377 | 31.005 | 12.534 | −37.945 | 1.00 | 23.27 | C |
| ATOM | 14639 | C | TYR | B | 377 | 33.020 | 14.689 | −39.389 | 1.00 | 21.44 | C |
| ATOM | 14640 | O | TYR | B | 377 | 32.677 | 14.290 | −40.496 | 1.00 | 22.45 | O |
| ATOM | 14642 | N | ASN | B | 378 | 32.508 | 15.774 | −38.814 | 1.00 | 22.31 | N |
| ATOM | 14643 | CA | ASN | B | 378 | 31.422 | 16.545 | −39.427 | 1.00 | 22.28 | C |
| ATOM | 14645 | CB | ASN | B | 378 | 30.632 | 17.294 | −38.349 | 1.00 | 22.49 | C |
| ATOM | 14648 | CG | ASN | B | 378 | 29.792 | 16.369 | −37.490 | 1.00 | 22.55 | C |
| ATOM | 14649 | OD1 | ASN | B | 378 | 29.269 | 15.360 | −37.962 | 1.00 | 27.91 | O |
| ATOM | 14650 | ND2 | ASN | B | 378 | 29.634 | 16.728 | −36.227 | 1.00 | 21.74 | N |
| ATOM | 14653 | C | ASN | B | 378 | 31.892 | 17.543 | −40.483 | 1.00 | 22.22 | C |
| ATOM | 14654 | O | ASN | B | 378 | 31.081 | 18.265 | −41.054 | 1.00 | 20.28 | O |
| ATOM | 14656 | N | LYS | B | 379 | 33.199 | 17.585 | −40.730 | 1.00 | 23.59 | N |
| ATOM | 14657 | CA | LYS | B | 379 | 33.783 | 18.496 | −41.711 | 1.00 | 25.11 | C |
| ATOM | 14659 | CB | LYS | B | 379 | 33.382 | 18.077 | −43.135 | 1.00 | 25.86 | C |
| ATOM | 14662 | CG | LYS | B | 379 | 33.990 | 16.735 | −43.560 | 1.00 | 29.75 | C |
| ATOM | 14665 | CD | LYS | B | 379 | 33.339 | 16.169 | −44.820 | 1.00 | 37.47 | C |

APPENDIX 1-continued

| | | | | | | | | | | |
|---|---|---|---|---|---|---|---|---|---|---|
| ATOM | 14668 | CE | LYS | B | 379 | 34.249 | 15.148 | −45.512 | 1.00 | 41.99 | C |
| ATOM | 14671 | NZ | LYS | B | 379 | 34.924 | 14.228 | −44.545 | 1.00 | 43.15 | N |
| ATOM | 14675 | C | LYS | B | 379 | 33.416 | 19.954 | −41.409 | 1.00 | 24.70 | C |
| ATOM | 14676 | O | LYS | B | 379 | 33.180 | 20.749 | −42.316 | 1.00 | 24.74 | O |
| ATOM | 14678 | N | SER | B | 380 | 33.391 | 20.291 | −40.117 | 1.00 | 23.98 | N |
| ATOM | 14679 | CA | SER | B | 380 | 33.058 | 21.637 | −39.666 | 1.00 | 22.30 | C |
| ATOM | 14681 | CB | SER | B | 380 | 32.828 | 21.671 | −38.154 | 1.00 | 22.07 | C |
| ATOM | 14684 | OG | SER | B | 380 | 31.557 | 21.141 | −37.813 | 1.00 | 24.80 | O |
| ATOM | 14686 | C | SER | B | 380 | 34.160 | 22.615 | −40.035 | 1.00 | 21.05 | C |
| ATOM | 14687 | O | SER | B | 380 | 35.304 | 22.230 | −40.254 | 1.00 | 18.77 | O |
| ATOM | 14689 | N | THR | B | 381 | 33.797 | 23.890 | −40.096 | 1.00 | 20.77 | N |
| ATOM | 14690 | CA | THR | B | 381 | 34.729 | 24.940 | −40.480 | 1.00 | 20.78 | C |
| ATOM | 14692 | CB | THR | B | 381 | 34.436 | 25.427 | −41.921 | 1.00 | 21.72 | C |
| ATOM | 14694 | OG1 | THR | B | 381 | 33.019 | 25.577 | −42.102 | 1.00 | 22.85 | O |
| ATOM | 14696 | CG2 | THR | B | 381 | 34.954 | 24.420 | −42.932 | 1.00 | 20.93 | C |
| ATOM | 14700 | C | THR | B | 381 | 34.639 | 26.079 | −39.470 | 1.00 | 19.47 | C |
| ATOM | 14701 | O | THR | B | 381 | 34.331 | 27.215 | −39.828 | 1.00 | 19.25 | O |
| ATOM | 14703 | N | PRO | B | 382 | 34.930 | 25.778 | −38.192 | 1.00 | 18.98 | N |
| ATOM | 14704 | CA | PRO | B | 382 | 34.801 | 26.794 | −37.149 | 1.00 | 18.70 | C |
| ATOM | 14706 | CB | PRO | B | 382 | 35.165 | 26.033 | −35.875 | 1.00 | 19.04 | C |
| ATOM | 14709 | CG | PRO | B | 382 | 36.047 | 24.915 | −36.338 | 1.00 | 18.25 | C |
| ATOM | 14712 | CD | PRO | B | 382 | 35.543 | 24.534 | −37.679 | 1.00 | 18.70 | C |
| ATOM | 14715 | C | PRO | B | 382 | 35.739 | 27.987 | −37.348 | 1.00 | 18.01 | C |
| ATOM | 14716 | O | PRO | B | 382 | 36.781 | 27.865 | −37.989 | 1.00 | 18.37 | O |
| ATOM | 14717 | N | THR | B | 383 | 35.357 | 29.131 | −36.797 | 1.00 | 17.46 | N |
| ATOM | 14718 | CA | THR | B | 383 | 36.167 | 30.338 | −36.876 | 1.00 | 17.12 | C |
| ATOM | 14720 | CB | THR | B | 383 | 35.445 | 31.535 | −36.243 | 1.00 | 18.32 | C |
| ATOM | 14722 | OG1 | THR | B | 383 | 35.274 | 31.293 | −34.839 | 1.00 | 17.62 | O |
| ATOM | 14724 | CG2 | THR | B | 383 | 34.075 | 31.785 | −36.908 | 1.00 | 14.15 | C |
| ATOM | 14728 | C | THR | B | 383 | 37.460 | 30.139 | −36.104 | 1.00 | 17.10 | C |
| ATOM | 14729 | O | THR | B | 383 | 37.595 | 29.183 | −35.335 | 1.00 | 18.78 | O |
| ATOM | 14731 | N | PHE | B | 384 | 38.404 | 31.051 | −36.277 | 1.00 | 15.89 | N |
| ATOM | 14732 | CA | PHE | B | 384 | 39.644 | 30.986 | −35.520 | 1.00 | 15.57 | C |
| ATOM | 14734 | CB | PHE | B | 384 | 40.625 | 32.062 | −35.984 | 1.00 | 15.29 | C |
| ATOM | 14737 | CG | PHE | B | 384 | 41.838 | 32.174 | −35.120 | 1.00 | 15.96 | C |
| ATOM | 14738 | CD1 | PHE | B | 384 | 42.932 | 31.347 | −35.334 | 1.00 | 13.73 | C |
| ATOM | 14740 | CE1 | PHE | B | 384 | 44.054 | 31.442 | −34.527 | 1.00 | 14.08 | C |
| ATOM | 14742 | CZ | PHE | B | 384 | 44.088 | 32.370 | −33.480 | 1.00 | 14.22 | C |
| ATOM | 14744 | CE2 | PHE | B | 384 | 42.997 | 33.194 | −33.250 | 1.00 | 13.73 | C |
| ATOM | 14746 | CD2 | PHE | B | 384 | 41.878 | 33.093 | −34.070 | 1.00 | 17.46 | C |
| ATOM | 14748 | C | PHE | B | 384 | 39.406 | 31.090 | −34.007 | 1.00 | 15.87 | C |
| ATOM | 14749 | O | PHE | B | 384 | 40.029 | 30.369 | −33.238 | 1.00 | 16.32 | O |
| ATOM | 14751 | N | ASP | B | 385 | 38.503 | 31.969 | −33.577 | 1.00 | 17.06 | N |
| ATOM | 14752 | CA | ASP | B | 385 | 38.250 | 32.138 | −32.141 | 1.00 | 17.47 | C |
| ATOM | 14754 | CB | ASP | B | 385 | 37.252 | 33.267 | −31.860 | 1.00 | 16.73 | C |
| ATOM | 14757 | CG | ASP | B | 385 | 37.820 | 34.650 | −32.148 | 1.00 | 13.98 | C |
| ATOM | 14758 | OD1 | ASP | B | 385 | 39.040 | 34.807 | −32.288 | 1.00 | 13.45 | O |
| ATOM | 14759 | OD2 | ASP | B | 385 | 37.025 | 35.597 | −32.240 | 1.00 | 20.82 | O |
| ATOM | 14760 | C | ASP | B | 385 | 37.761 | 30.847 | −31.494 | 1.00 | 18.08 | C |
| ATOM | 14761 | O | ASP | B | 385 | 38.224 | 30.494 | −30.416 | 1.00 | 18.18 | O |
| ATOM | 14763 | N | ASP | B | 386 | 36.839 | 30.149 | −32.158 | 1.00 | 18.96 | N |
| ATOM | 14764 | CA | ASP | B | 386 | 36.289 | 28.894 | −31.641 | 1.00 | 19.56 | C |
| ATOM | 14766 | CB | ASP | B | 386 | 35.018 | 28.487 | −32.386 | 1.00 | 19.25 | C |
| ATOM | 14769 | CG | ASP | B | 386 | 33.848 | 29.394 | −32.086 | 1.00 | 25.69 | C |
| ATOM | 14770 | OD1 | ASP | B | 386 | 33.968 | 30.349 | −31.275 | 1.00 | 29.37 | O |
| ATOM | 14771 | OD2 | ASP | B | 386 | 32.782 | 29.142 | −32.680 | 1.00 | 37.04 | O |
| ATOM | 14772 | C | ASP | B | 386 | 37.289 | 27.759 | −31.726 | 1.00 | 18.80 | C |
| ATOM | 14773 | O | ASP | B | 386 | 37.462 | 27.016 | −30.762 | 1.00 | 18.56 | O |
| ATOM | 14775 | N | TYR | B | 387 | 37.939 | 27.617 | −32.875 | 1.00 | 18.41 | N |
| ATOM | 14776 | CA | TYR | B | 387 | 38.939 | 26.563 | −33.035 | 1.00 | 18.76 | C |
| ATOM | 14778 | CB | TYR | B | 387 | 39.518 | 26.546 | −34.449 | 1.00 | 19.09 | C |
| ATOM | 14781 | CG | TYR | B | 387 | 40.560 | 25.476 | −34.630 | 1.00 | 21.22 | C |
| ATOM | 14782 | CD1 | TYR | B | 387 | 40.191 | 24.152 | −34.861 | 1.00 | 25.12 | C |
| ATOM | 14784 | CE1 | TYR | B | 387 | 41.139 | 23.157 | −35.012 | 1.00 | 24.90 | C |
| ATOM | 14786 | CZ | TYR | B | 387 | 42.476 | 23.478 | −34.932 | 1.00 | 29.40 | C |
| ATOM | 14787 | OH | TYR | B | 387 | 43.432 | 22.495 | −35.087 | 1.00 | 32.17 | O |
| ATOM | 14789 | CE2 | TYR | B | 387 | 42.865 | 24.789 | −34.698 | 1.00 | 28.78 | C |
| ATOM | 14791 | CD2 | TYR | B | 387 | 41.907 | 25.776 | −34.547 | 1.00 | 23.54 | C |
| ATOM | 14793 | C | TYR | B | 387 | 40.063 | 26.752 | −32.030 | 1.00 | 18.02 | C |
| ATOM | 14794 | O | TYR | B | 387 | 40.387 | 25.852 | −31.267 | 1.00 | 17.96 | O |
| ATOM | 14796 | N | PHE | B | 388 | 40.658 | 27.933 | −32.033 | 1.00 | 18.09 | N |
| ATOM | 14797 | CA | PHE | B | 388 | 41.744 | 28.224 | −31.109 | 1.00 | 17.94 | C |
| ATOM | 14799 | CB | PHE | B | 388 | 42.326 | 29.600 | −31.405 | 1.00 | 18.49 | C |
| ATOM | 14802 | CG | PHE | B | 388 | 43.524 | 29.923 | −30.582 | 1.00 | 20.80 | C |
| ATOM | 14803 | CD1 | PHE | B | 388 | 44.731 | 29.301 | −30.834 | 1.00 | 15.90 | C |
| ATOM | 14805 | CE1 | PHE | B | 388 | 45.838 | 29.587 | −30.068 | 1.00 | 18.77 | C |
| ATOM | 14807 | CZ | PHE | B | 388 | 45.752 | 30.499 | −29.037 | 1.00 | 21.03 | C |
| ATOM | 14809 | CE2 | PHE | B | 388 | 44.556 | 31.122 | −28.770 | 1.00 | 23.90 | C |
| ATOM | 14811 | CD2 | PHE | B | 388 | 43.443 | 30.831 | −29.538 | 1.00 | 22.37 | C |
| ATOM | 14813 | C | PHE | B | 388 | 41.312 | 28.153 | −29.642 | 1.00 | 16.94 | C |

APPENDIX 1-continued

| | | | | | | | | | | |
|---|---|---|---|---|---|---|---|---|---|---|
| ATOM | 14814 | O | PHE | B | 388 | 42.097 | 27.758 | −28.790 | 1.00 | 17.81 | O |
| ATOM | 14816 | N | GLY | B | 389 | 40.068 | 28.534 | −29.353 | 1.00 | 16.08 | N |
| ATOM | 14817 | CA | GLY | B | 389 | 39.525 | 28.474 | −28.000 | 1.00 | 14.92 | C |
| ATOM | 14820 | C | GLY | B | 389 | 39.608 | 27.070 | −27.447 | 1.00 | 15.74 | C |
| ATOM | 14821 | O | GLY | B | 389 | 39.961 | 26.868 | −26.287 | 1.00 | 17.64 | O |
| ATOM | 14823 | N | ASN | B | 390 | 39.282 | 26.101 | −28.297 | 1.00 | 15.28 | N |
| ATOM | 14824 | CA | ASN | B | 390 | 39.427 | 24.699 | −27.978 | 1.00 | 14.62 | C |
| ATOM | 14826 | CB | ASN | B | 390 | 38.534 | 23.872 | −28.897 | 1.00 | 14.84 | C |
| ATOM | 14829 | CG | ASN | B | 390 | 38.448 | 22.421 | −28.472 | 1.00 | 14.88 | C |
| ATOM | 14830 | OD1 | ASN | B | 390 | 37.918 | 22.112 | −27.413 | 1.00 | 19.79 | O |
| ATOM | 14831 | ND2 | ASN | B | 390 | 38.967 | 21.526 | −29.296 | 1.00 | 8.97 | N |
| ATOM | 14834 | C | ASN | B | 390 | 40.877 | 24.224 | −28.105 | 1.00 | 15.00 | C |
| ATOM | 14835 | O | ASN | B | 390 | 41.323 | 23.397 | −27.322 | 1.00 | 16.30 | O |
| ATOM | 14837 | N | ALA | B | 391 | 41.603 | 24.741 | −29.092 | 1.00 | 15.37 | N |
| ATOM | 14838 | CA | ALA | B | 391 | 42.967 | 24.287 | −29.385 | 1.00 | 14.99 | C |
| ATOM | 14840 | CB | ALA | B | 391 | 43.468 | 24.877 | −30.690 | 1.00 | 14.64 | C |
| ATOM | 14844 | C | ALA | B | 391 | 43.953 | 24.580 | −28.278 | 1.00 | 15.29 | C |
| ATOM | 14845 | O | ALA | B | 391 | 44.803 | 23.758 | −27.996 | 1.00 | 17.57 | O |
| ATOM | 14847 | N | TRP | B | 392 | 43.871 | 25.732 | −27.634 | 1.00 | 16.03 | N |
| ATOM | 14848 | CA | TRP | B | 392 | 44.813 | 25.982 | −26.546 | 1.00 | 17.23 | C |
| ATOM | 14850 | CB | TRP | B | 392 | 44.912 | 27.476 | −26.167 | 1.00 | 18.07 | C |
| ATOM | 14853 | CG | TRP | B | 392 | 43.728 | 28.128 | −25.525 | 1.00 | 17.09 | C |
| ATOM | 14854 | CD1 | TRP | B | 392 | 42.868 | 29.015 | −26.111 | 1.00 | 20.34 | C |
| ATOM | 14856 | NE1 | TRP | B | 392 | 41.923 | 29.427 | −25.208 | 1.00 | 18.34 | N |
| ATOM | 14858 | CE2 | TRP | B | 392 | 42.171 | 28.826 | −24.003 | 1.00 | 14.64 | C |
| ATOM | 14859 | CD2 | TRP | B | 392 | 43.311 | 28.006 | −24.163 | 1.00 | 15.29 | C |
| ATOM | 14860 | CE3 | TRP | B | 392 | 43.778 | 27.270 | −23.063 | 1.00 | 16.69 | C |
| ATOM | 14862 | CZ3 | TRP | B | 392 | 43.107 | 27.385 | −21.857 | 1.00 | 19.38 | C |
| ATOM | 14864 | CH2 | TRP | B | 392 | 41.972 | 28.220 | −21.732 | 1.00 | 18.81 | C |
| ATOM | 14866 | CZ2 | TRP | B | 392 | 41.494 | 28.939 | −22.792 | 1.00 | 15.59 | C |
| ATOM | 14868 | C | TRP | B | 392 | 44.603 | 25.073 | −25.330 | 1.00 | 17.36 | C |
| ATOM | 14869 | O | TRP | B | 392 | 45.524 | 24.889 | −24.545 | 1.00 | 19.29 | O |
| ATOM | 14871 | N | LYS | B | 393 | 43.421 | 24.480 | −25.195 | 1.00 | 17.67 | N |
| ATOM | 14872 | CA | LYS | B | 393 | 43.154 | 23.466 | −24.162 | 1.00 | 18.16 | C |
| ATOM | 14874 | CB | LYS | B | 393 | 41.652 | 23.391 | −23.843 | 1.00 | 19.24 | C |
| ATOM | 14877 | CG | LYS | B | 393 | 41.018 | 24.718 | −23.352 | 1.00 | 24.75 | C |
| ATOM | 14880 | CD | LYS | B | 393 | 39.556 | 24.527 | −22.950 | 1.00 | 31.62 | C |
| ATOM | 14883 | CE | LYS | B | 393 | 38.894 | 25.820 | −22.454 | 1.00 | 35.24 | C |
| ATOM | 14886 | NZ | LYS | B | 393 | 38.513 | 26.723 | −23.584 | 1.00 | 41.45 | N |
| ATOM | 14890 | C | LYS | B | 393 | 43.642 | 22.081 | −24.598 | 1.00 | 17.55 | C |
| ATOM | 14891 | O | LYS | B | 393 | 44.168 | 21.318 | −23.796 | 1.00 | 16.86 | O |
| ATOM | 14893 | N | SER | B | 394 | 43.460 | 21.754 | −25.872 | 1.00 | 18.02 | N |
| ATOM | 14894 | CA | SER | B | 394 | 43.863 | 20.444 | −26.389 | 1.00 | 18.30 | C |
| ATOM | 14896 | CB | SER | B | 394 | 43.247 | 20.183 | −27.759 | 1.00 | 18.56 | C |
| ATOM | 14899 | OG | SER | B | 394 | 43.723 | 21.113 | −28.708 | 1.00 | 19.78 | O |
| ATOM | 14901 | C | SER | B | 394 | 45.369 | 20.307 | −26.485 | 1.00 | 18.26 | C |
| ATOM | 14902 | O | SER | B | 394 | 45.872 | 19.196 | −26.626 | 1.00 | 18.34 | O |
| ATOM | 14904 | N | SER | B | 395 | 46.085 | 21.432 | −26.420 | 1.00 | 18.15 | N |
| ATOM | 14905 | CA | SER | B | 395 | 47.545 | 21.415 | −26.340 | 1.00 | 17.82 | C |
| ATOM | 14907 | CB | SER | B | 395 | 48.105 | 22.841 | −26.221 | 1.00 | 18.00 | C |
| ATOM | 14910 | OG | SER | B | 395 | 47.883 | 23.400 | −24.931 | 1.00 | 15.24 | O |
| ATOM | 14912 | C | SER | B | 395 | 47.996 | 20.594 | −25.132 | 1.00 | 18.16 | C |
| ATOM | 14913 | O | SER | B | 395 | 49.087 | 20.028 | −25.142 | 1.00 | 18.62 | O |
| ATOM | 14915 | N | SER | B | 396 | 47.135 | 20.548 | −24.110 | 1.00 | 17.42 | N |
| ATOM | 14916 | CA | SER | B | 396 | 47.403 | 19.930 | −22.808 | 1.00 | 17.40 | C |
| ATOM | 14918 | CB | SER | B | 396 | 48.154 | 18.588 | −22.919 | 1.00 | 17.74 | C |
| ATOM | 14921 | OG | SER | B | 396 | 49.556 | 18.761 | −23.041 | 1.00 | 16.91 | O |
| ATOM | 14923 | C | SER | B | 396 | 48.138 | 20.885 | −21.878 | 1.00 | 16.63 | C |
| ATOM | 14924 | O | SER | B | 396 | 48.479 | 20.515 | −20.765 | 1.00 | 16.92 | O |
| ATOM | 14926 | N | GLY | B | 397 | 48.356 | 22.120 | −22.320 | 1.00 | 16.76 | N |
| ATOM | 14927 | CA | GLY | B | 397 | 49.013 | 23.133 | −21.487 | 1.00 | 16.96 | C |
| ATOM | 14930 | C | GLY | B | 397 | 48.332 | 23.369 | −20.146 | 1.00 | 16.88 | C |
| ATOM | 14931 | O | GLY | B | 397 | 48.968 | 23.309 | −19.100 | 1.00 | 17.22 | O |
| ATOM | 14933 | N | PRO | B | 398 | 47.027 | 23.662 | −20.162 | 1.00 | 16.83 | N |
| ATOM | 14934 | CA | PRO | B | 398 | 46.339 | 23.817 | −18.884 | 1.00 | 16.78 | C |
| ATOM | 14936 | CB | PRO | B | 398 | 44.885 | 24.081 | −19.294 | 1.00 | 16.50 | C |
| ATOM | 14939 | CG | PRO | B | 398 | 44.985 | 24.636 | −20.671 | 1.00 | 17.53 | C |
| ATOM | 14942 | CD | PRO | B | 398 | 46.141 | 23.943 | −21.304 | 1.00 | 16.58 | C |
| ATOM | 14945 | C | PRO | B | 398 | 46.447 | 22.590 | −17.972 | 1.00 | 16.11 | C |
| ATOM | 14946 | O | PRO | B | 398 | 46.615 | 22.746 | −16.774 | 1.00 | 16.39 | O |
| ATOM | 14947 | N | LEU | B | 399 | 46.360 | 21.387 | −18.529 | 1.00 | 17.24 | N |
| ATOM | 14948 | CA | LEU | B | 399 | 46.457 | 20.162 | −17.722 | 1.00 | 17.58 | C |
| ATOM | 14950 | CB | LEU | B | 399 | 46.142 | 18.910 | −18.550 | 1.00 | 17.05 | C |
| ATOM | 14953 | CG | LEU | B | 399 | 46.180 | 17.581 | −17.784 | 1.00 | 20.38 | C |
| ATOM | 14955 | CD1 | LEU | B | 399 | 45.007 | 16.668 | −18.156 | 1.00 | 21.31 | C |
| ATOM | 14959 | CD2 | LEU | B | 399 | 47.525 | 16.843 | −17.966 | 1.00 | 19.29 | C |
| ATOM | 14963 | C | LEU | B | 399 | 47.841 | 20.035 | −17.090 | 1.00 | 18.34 | C |
| ATOM | 14964 | O | LEU | B | 399 | 47.950 | 19.741 | −15.897 | 1.00 | 18.31 | O |
| ATOM | 14966 | N | GLN | B | 400 | 48.888 | 20.255 | −17.886 | 1.00 | 17.51 | N |
| ATOM | 14967 | CA | GLN | B | 400 | 50.257 | 20.166 | −17.387 | 1.00 | 17.30 | C |

APPENDIX 1-continued

| ATOM | 14969 | CB | GLN | B | 400 | 51.264 | 20.494 | −18.485 | 1.00 | 17.79 | C |
|---|---|---|---|---|---|---|---|---|---|---|---|
| ATOM | 14972 | CG | GLN | B | 400 | 51.391 | 19.417 | −19.548 | 1.00 | 20.06 | C |
| ATOM | 14975 | CD | GLN | B | 400 | 52.402 | 19.758 | −20.624 | 1.00 | 21.76 | C |
| ATOM | 14976 | OE1 | GLN | B | 400 | 53.447 | 20.341 | −20.348 | 1.00 | 25.47 | O |
| ATOM | 14977 | NE2 | GLN | B | 400 | 52.106 | 19.373 | −21.858 | 1.00 | 25.16 | N |
| ATOM | 14980 | C | GLN | B | 400 | 50.464 | 21.104 | −16.212 | 1.00 | 17.25 | C |
| ATOM | 14981 | O | GLN | B | 400 | 51.066 | 20.731 | −15.205 | 1.00 | 18.72 | O |
| ATOM | 14983 | N | LEU | B | 401 | 49.939 | 22.311 | −16.325 | 1.00 | 16.70 | N |
| ATOM | 14984 | CA | LEU | B | 401 | 50.162 | 23.318 | −15.300 | 1.00 | 17.29 | C |
| ATOM | 14986 | CB | LEU | B | 401 | 49.900 | 24.714 | −15.861 | 1.00 | 16.74 | C |
| ATOM | 14989 | CG | LEU | B | 401 | 50.960 | 25.122 | −16.894 | 1.00 | 17.79 | C |
| ATOM | 14991 | CD1 | LEU | B | 401 | 50.728 | 26.535 | −17.421 | 1.00 | 16.38 | C |
| ATOM | 14995 | CD2 | LEU | B | 401 | 52.378 | 24.984 | −16.308 | 1.00 | 12.70 | C |
| ATOM | 14999 | C | LEU | B | 401 | 49.350 | 23.069 | −14.034 | 1.00 | 18.12 | C |
| ATOM | 15000 | O | LEU | B | 401 | 49.826 | 23.339 | −12.926 | 1.00 | 18.82 | O |
| ATOM | 15002 | N | VAL | B | 402 | 48.135 | 22.545 | −14.187 | 1.00 | 17.92 | N |
| ATOM | 15003 | CA | VAL | B | 402 | 47.360 | 22.108 | −13.031 | 1.00 | 17.06 | C |
| ATOM | 15005 | CB | VAL | B | 402 | 46.025 | 21.493 | −13.444 | 1.00 | 16.81 | C |
| ATOM | 15007 | CG1 | VAL | B | 402 | 45.356 | 20.820 | −12.249 | 1.00 | 16.61 | C |
| ATOM | 15011 | CG2 | VAL | B | 402 | 45.128 | 22.560 | −14.039 | 1.00 | 13.84 | C |
| ATOM | 15015 | C | VAL | B | 402 | 48.169 | 21.077 | −12.246 | 1.00 | 17.74 | C |
| ATOM | 15016 | O | VAL | B | 402 | 48.323 | 21.194 | −11.040 | 1.00 | 18.28 | O |
| ATOM | 15018 | N | PHE | B | 403 | 48.707 | 20.082 | −12.946 | 1.00 | 17.77 | N |
| ATOM | 15019 | CA | PHE | B | 403 | 49.545 | 19.079 | −12.316 | 1.00 | 17.93 | C |
| ATOM | 15021 | CB | PHE | B | 403 | 49.859 | 17.941 | −13.287 | 1.00 | 18.14 | C |
| ATOM | 15024 | CG | PHE | B | 403 | 48.789 | 16.884 | −13.344 | 1.00 | 17.67 | C |
| ATOM | 15025 | CD1 | PHE | B | 403 | 47.728 | 16.995 | −14.229 | 1.00 | 18.37 | C |
| ATOM | 15027 | CE1 | PHE | B | 403 | 46.745 | 16.023 | −14.279 | 1.00 | 19.30 | C |
| ATOM | 15029 | CZ | PHE | B | 403 | 46.817 | 14.920 | −13.436 | 1.00 | 20.55 | C |
| ATOM | 15031 | CE2 | PHE | B | 403 | 47.878 | 14.795 | −12.556 | 1.00 | 19.05 | C |
| ATOM | 15033 | CD2 | PHE | B | 403 | 48.851 | 15.772 | −12.511 | 1.00 | 17.45 | C |
| ATOM | 15035 | C | PHE | B | 403 | 50.828 | 19.680 | −11.755 | 1.00 | 18.51 | C |
| ATOM | 15036 | O | PHE | B | 403 | 51.283 | 19.268 | −10.684 | 1.00 | 18.72 | O |
| ATOM | 15038 | N | ALA | B | 404 | 51.405 | 20.649 | −12.465 | 1.00 | 18.05 | N |
| ATOM | 15039 | CA | ALA | B | 404 | 52.610 | 21.328 | −11.975 | 1.00 | 17.65 | C |
| ATOM | 15041 | CB | ALA | B | 404 | 53.228 | 22.195 | −13.060 | 1.00 | 16.65 | C |
| ATOM | 15045 | C | ALA | B | 404 | 52.313 | 22.159 | −10.723 | 1.00 | 17.63 | C |
| ATOM | 15046 | O | ALA | B | 404 | 53.128 | 22.211 | −9.804 | 1.00 | 17.86 | O |
| ATOM | 15048 | N | TYR | B | 405 | 51.146 | 22.797 | −10.676 | 1.00 | 17.74 | N |
| ATOM | 15049 | CA | TYR | B | 405 | 50.737 | 23.536 | −9.478 | 1.00 | 17.66 | C |
| ATOM | 15051 | CB | TYR | B | 405 | 49.301 | 24.061 | −9.606 | 1.00 | 16.56 | C |
| ATOM | 15054 | CG | TYR | B | 405 | 48.763 | 24.664 | −8.334 | 1.00 | 18.44 | C |
| ATOM | 15055 | CD1 | TYR | B | 405 | 49.020 | 25.994 | −8.005 | 1.00 | 21.48 | C |
| ATOM | 15057 | CE1 | TYR | B | 405 | 48.528 | 26.552 | −6.829 | 1.00 | 22.32 | C |
| ATOM | 15059 | CZ | TYR | B | 405 | 47.777 | 25.776 | −5.966 | 1.00 | 24.60 | C |
| ATOM | 15060 | OH | TYR | B | 405 | 47.293 | 26.318 | −4.794 | 1.00 | 24.67 | O |
| ATOM | 15062 | CE2 | TYR | B | 405 | 47.505 | 24.454 | −6.277 | 1.00 | 20.72 | C |
| ATOM | 15064 | CD2 | TYR | B | 405 | 47.997 | 23.906 | −7.450 | 1.00 | 19.91 | C |
| ATOM | 15066 | C | TYR | B | 405 | 50.870 | 22.651 | −8.234 | 1.00 | 17.91 | C |
| ATOM | 15067 | O | TYR | B | 405 | 51.516 | 23.035 | −7.265 | 1.00 | 18.91 | O |
| ATOM | 15069 | N | PHE | B | 406 | 50.285 | 21.459 | −8.271 | 1.00 | 17.90 | N |
| ATOM | 15070 | CA | PHE | B | 406 | 50.287 | 20.585 | −7.092 | 1.00 | 18.27 | C |
| ATOM | 15072 | CB | PHE | B | 406 | 49.269 | 19.452 | −7.250 | 1.00 | 17.96 | C |
| ATOM | 15075 | CG | PHE | B | 406 | 47.847 | 19.930 | −7.236 | 1.00 | 17.04 | C |
| ATOM | 15076 | CD1 | PHE | B | 406 | 47.254 | 20.334 | −6.050 | 1.00 | 18.42 | C |
| ATOM | 15078 | CE1 | PHE | B | 406 | 45.944 | 20.789 | −6.029 | 1.00 | 17.34 | C |
| ATOM | 15080 | CZ | PHE | B | 406 | 45.207 | 20.846 | −7.210 | 1.00 | 16.34 | C |
| ATOM | 15082 | CE2 | PHE | B | 406 | 45.787 | 20.457 | −8.394 | 1.00 | 14.13 | C |
| ATOM | 15084 | CD2 | PHE | B | 406 | 47.110 | 20.009 | −8.406 | 1.00 | 17.40 | C |
| ATOM | 15086 | C | PHE | B | 406 | 51.673 | 20.045 | −6.735 | 1.00 | 18.49 | C |
| ATOM | 15087 | O | PHE | B | 406 | 51.958 | 19.827 | −5.568 | 1.00 | 19.16 | O |
| ATOM | 15089 | N | ALA | B | 407 | 52.537 | 19.868 | −7.729 | 1.00 | 19.29 | N |
| ATOM | 15090 | CA | ALA | B | 407 | 53.919 | 19.457 | −7.488 | 1.00 | 20.20 | C |
| ATOM | 15092 | CB | ALA | B | 407 | 54.481 | 18.799 | −8.728 | 1.00 | 20.07 | C |
| ATOM | 15096 | C | ALA | B | 407 | 54.844 | 20.601 | −7.042 | 1.00 | 22.13 | C |
| ATOM | 15097 | O | ALA | B | 407 | 55.879 | 20.348 | −6.435 | 1.00 | 22.29 | O |
| ATOM | 15099 | N | VAL | B | 408 | 54.487 | 21.847 | −7.353 | 1.00 | 24.41 | N |
| ATOM | 15100 | CA | VAL | B | 408 | 55.353 | 22.999 | −7.072 | 1.00 | 25.78 | C |
| ATOM | 15102 | CB | VAL | B | 408 | 55.368 | 23.991 | −8.254 | 1.00 | 25.81 | C |
| ATOM | 15104 | CG1 | VAL | B | 408 | 56.010 | 25.309 | −7.853 | 1.00 | 25.93 | C |
| ATOM | 15108 | CG2 | VAL | B | 408 | 56.095 | 23.385 | −9.447 | 1.00 | 25.72 | C |
| ATOM | 15112 | C | VAL | B | 408 | 54.933 | 23.748 | −5.809 | 1.00 | 28.22 | C |
| ATOM | 15113 | O | VAL | B | 408 | 55.776 | 24.151 | −5.017 | 1.00 | 28.39 | O |
| ATOM | 15115 | N | VAL | B | 409 | 53.632 | 23.936 | −5.626 | 1.00 | 31.39 | N |
| ATOM | 15116 | CA | VAL | B | 409 | 53.120 | 24.679 | −4.484 | 1.00 | 33.83 | C |
| ATOM | 15118 | CB | VAL | B | 409 | 51.655 | 25.106 | −4.702 | 1.00 | 33.75 | C |
| ATOM | 15120 | CG1 | VAL | B | 409 | 51.042 | 25.639 | −3.421 | 1.00 | 35.27 | C |
| ATOM | 15124 | CG2 | VAL | B | 409 | 51.582 | 26.156 | −5.785 | 1.00 | 34.78 | C |
| ATOM | 15128 | C | VAL | B | 409 | 53.239 | 23.851 | −3.210 | 1.00 | 36.82 | C |
| ATOM | 15129 | O | VAL | B | 409 | 52.872 | 22.680 | −3.182 | 1.00 | 37.37 | O |

APPENDIX 1-continued

| | | | | | | | | | | | |
|---|---|---|---|---|---|---|---|---|---|---|---|
| ATOM | 15131 | N | GLN | B | 410 | 53.762 | 24.481 | −2.161 | 1.00 | 39.92 | N |
| ATOM | 15132 | CA | GLN | B | 410 | 53.922 | 23.848 | −0.857 | 1.00 | 41.63 | C |
| ATOM | 15134 | CB | GLN | B | 410 | 54.907 | 24.669 | −0.016 | 1.00 | 43.82 | C |
| ATOM | 15137 | CG | GLN | B | 410 | 55.557 | 23.922 | 1.151 | 1.00 | 49.70 | C |
| ATOM | 15140 | CD | GLN | B | 410 | 56.469 | 24.829 | 1.971 | 1.00 | 56.21 | C |
| ATOM | 15141 | OE1 | GLN | B | 410 | 57.165 | 25.686 | 1.417 | 1.00 | 60.99 | O |
| ATOM | 15142 | NE2 | GLN | B | 410 | 56.465 | 24.651 | 3.293 | 1.00 | 55.19 | N |
| ATOM | 15145 | C | GLN | B | 410 | 52.559 | 23.749 | −0.168 | 1.00 | 40.91 | C |
| ATOM | 15146 | O | GLN | B | 410 | 52.087 | 22.648 | 0.131 | 1.00 | 41.39 | O |
| ATOM | 15148 | N | ASN | B | 411 | 51.919 | 24.898 | 0.055 | 1.00 | 39.55 | N |
| ATOM | 15149 | CA | ASN | B | 411 | 50.586 | 24.941 | 0.671 | 1.00 | 38.41 | C |
| ATOM | 15151 | CB | ASN | B | 411 | 50.572 | 25.915 | 1.847 | 1.00 | 38.05 | C |
| ATOM | 15154 | CG | ASN | B | 411 | 51.384 | 25.412 | 3.018 | 1.00 | 37.70 | C |
| ATOM | 15155 | OD1 | ASN | B | 411 | 51.090 | 24.359 | 3.583 | 1.00 | 34.08 | O |
| ATOM | 15156 | ND2 | ASN | B | 411 | 52.421 | 26.160 | 3.384 | 1.00 | 38.90 | N |
| ATOM | 15159 | C | ASN | B | 411 | 49.486 | 25.315 | −0.317 | 1.00 | 37.54 | C |
| ATOM | 15160 | O | ASN | B | 411 | 49.443 | 26.437 | −0.824 | 1.00 | 37.31 | O |
| ATOM | 15162 | N | ILE | B | 412 | 48.587 | 24.369 | −0.561 | 1.00 | 37.00 | N |
| ATOM | 15163 | CA | ILE | B | 412 | 47.490 | 24.550 | −1.501 | 1.00 | 37.00 | C |
| ATOM | 15165 | CB | ILE | B | 412 | 46.743 | 23.229 | −1.708 | 1.00 | 37.15 | C |
| ATOM | 15167 | CG1 | ILE | B | 412 | 47.648 | 22.208 | −2.390 | 1.00 | 39.56 | C |
| ATOM | 15170 | CD1 | ILE | B | 412 | 47.120 | 20.791 | −2.291 | 1.00 | 40.67 | C |
| ATOM | 15174 | CG2 | ILE | B | 412 | 45.496 | 23.439 | −2.539 | 1.00 | 41.23 | C |
| ATOM | 15178 | C | ILE | B | 412 | 46.506 | 25.588 | −0.971 | 1.00 | 36.72 | C |
| ATOM | 15179 | O | ILE | B | 412 | 46.360 | 25.743 | 0.242 | 1.00 | 36.62 | O |
| ATOM | 15181 | N | LYS | B | 413 | 45.844 | 26.299 | −1.883 | 1.00 | 36.30 | N |
| ATOM | 15182 | CA | LYS | B | 413 | 44.857 | 27.309 | −1.519 | 1.00 | 36.38 | C |
| ATOM | 15184 | CB | LYS | B | 413 | 45.453 | 28.708 | −1.700 | 1.00 | 36.79 | C |
| ATOM | 15187 | CG | LYS | B | 413 | 46.673 | 28.932 | −0.818 | 1.00 | 40.58 | C |
| ATOM | 15190 | CD | LYS | B | 413 | 47.210 | 30.339 | −0.877 | 1.00 | 46.29 | C |
| ATOM | 15193 | CE | LYS | B | 413 | 48.338 | 30.512 | 0.139 | 1.00 | 47.89 | C |
| ATOM | 15196 | NZ | LYS | B | 413 | 48.983 | 31.846 | 0.044 | 1.00 | 49.06 | N |
| ATOM | 15200 | C | LYS | B | 413 | 43.622 | 27.134 | −2.375 | 1.00 | 36.15 | C |
| ATOM | 15201 | O | LYS | B | 413 | 43.727 | 27.011 | −3.591 | 1.00 | 37.20 | O |
| ATOM | 15203 | N | LYS | B | 414 | 42.451 | 27.117 | −1.748 | 1.00 | 35.96 | N |
| ATOM | 15204 | CA | LYS | B | 414 | 41.207 | 26.837 | −2.467 | 1.00 | 35.71 | C |
| ATOM | 15206 | CB | LYS | B | 414 | 40.017 | 26.794 | −1.503 | 1.00 | 36.25 | C |
| ATOM | 15209 | CG | LYS | B | 414 | 38.715 | 26.292 | −2.139 | 1.00 | 40.45 | C |
| ATOM | 15212 | CD | LYS | B | 414 | 37.639 | 25.973 | −1.090 | 1.00 | 45.77 | C |
| ATOM | 15215 | CE | LYS | B | 414 | 37.054 | 27.234 | −0.451 | 1.00 | 46.82 | C |
| ATOM | 15218 | NZ | LYS | B | 414 | 36.316 | 28.078 | −1.437 | 1.00 | 47.29 | N |
| ATOM | 15222 | C | LYS | B | 414 | 40.940 | 27.854 | −3.576 | 1.00 | 34.67 | C |
| ATOM | 15223 | O | LYS | B | 414 | 40.404 | 27.506 | −4.627 | 1.00 | 34.64 | O |
| ATOM | 15225 | N | GLU | B | 415 | 41.304 | 29.110 | −3.344 | 1.00 | 33.56 | N |
| ATOM | 15226 | CA | GLU | B | 415 | 41.075 | 30.142 | −4.346 | 1.00 | 33.01 | C |
| ATOM | 15228 | CB | GLU | B | 415 | 41.354 | 31.536 | −3.776 | 1.00 | 33.31 | C |
| ATOM | 15231 | CG | GLU | B | 415 | 40.982 | 32.664 | −4.740 | 1.00 | 38.15 | C |
| ATOM | 15234 | CD | GLU | B | 415 | 41.040 | 34.045 | −4.102 | 1.00 | 44.38 | C |
| ATOM | 15235 | OE1 | GLU | B | 415 | 42.046 | 34.354 | −3.421 | 1.00 | 48.38 | O |
| ATOM | 15236 | OE2 | GLU | B | 415 | 40.082 | 34.826 | −4.297 | 1.00 | 46.55 | O |
| ATOM | 15237 | C | GLU | B | 415 | 41.939 | 29.883 | −5.581 | 1.00 | 30.64 | C |
| ATOM | 15238 | O | GLU | B | 415 | 41.467 | 29.987 | −6.715 | 1.00 | 29.03 | O |
| ATOM | 15240 | N | GLU | B | 416 | 43.198 | 29.533 | −5.347 | 1.00 | 28.88 | N |
| ATOM | 15241 | CA | GLU | B | 416 | 44.134 | 29.287 | −6.433 | 1.00 | 28.18 | C |
| ATOM | 15243 | CB | GLU | B | 416 | 45.512 | 28.927 | −5.879 | 1.00 | 27.80 | C |
| ATOM | 15246 | CG | GLU | B | 416 | 46.251 | 30.110 | −5.281 | 1.00 | 28.18 | C |
| ATOM | 15249 | CD | GLU | B | 416 | 47.632 | 29.748 | −4.785 | 1.00 | 30.77 | C |
| ATOM | 15250 | OE1 | GLU | B | 416 | 47.831 | 28.618 | −4.304 | 1.00 | 38.12 | O |
| ATOM | 15251 | OE2 | GLU | B | 416 | 48.532 | 30.597 | −4.867 | 1.00 | 39.33 | O |
| ATOM | 15252 | C | GLU | B | 416 | 43.635 | 28.194 | −7.372 | 1.00 | 28.47 | C |
| ATOM | 15253 | O | GLU | B | 416 | 43.665 | 28.366 | −8.590 | 1.00 | 27.41 | O |
| ATOM | 15255 | N | ILE | B | 417 | 43.169 | 27.081 | −6.803 | 1.00 | 28.87 | N |
| ATOM | 15256 | CA | ILE | B | 417 | 42.705 | 25.946 | −7.609 | 1.00 | 29.70 | C |
| ATOM | 15258 | CB | ILE | B | 417 | 42.712 | 24.589 | −6.825 | 1.00 | 30.57 | C |
| ATOM | 15260 | CG1 | ILE | B | 417 | 41.792 | 24.611 | −5.612 | 1.00 | 34.16 | C |
| ATOM | 15263 | CD1 | ILE | B | 417 | 42.218 | 23.603 | −4.535 | 1.00 | 37.78 | C |
| ATOM | 15267 | CG2 | ILE | B | 417 | 44.122 | 24.239 | −6.351 | 1.00 | 30.55 | C |
| ATOM | 15271 | C | ILE | B | 417 | 41.349 | 26.216 | −8.258 | 1.00 | 28.90 | C |
| ATOM | 15272 | O | ILE | B | 417 | 41.078 | 25.728 | −9.350 | 1.00 | 29.33 | O |
| ATOM | 15274 | N | GLU | B | 418 | 40.506 | 27.008 | −7.609 | 1.00 | 29.32 | N |
| ATOM | 15275 | CA | GLU | B | 418 | 39.269 | 27.470 | −8.244 | 1.00 | 29.58 | C |
| ATOM | 15277 | CB | GLU | B | 418 | 38.429 | 28.291 | −7.270 | 1.00 | 29.92 | C |
| ATOM | 15280 | CG | GLU | B | 418 | 37.592 | 27.423 | −6.339 | 1.00 | 35.12 | C |
| ATOM | 15283 | CD | GLU | B | 418 | 36.912 | 28.207 | −5.228 | 1.00 | 40.09 | C |
| ATOM | 15284 | OE1 | GLU | B | 418 | 37.154 | 29.433 | −5.101 | 1.00 | 39.64 | O |
| ATOM | 15285 | OE2 | GLU | B | 418 | 36.134 | 27.581 | −4.474 | 1.00 | 42.62 | O |
| ATOM | 15286 | C | GLU | B | 418 | 39.570 | 28.281 | −9.506 | 1.00 | 29.38 | C |
| ATOM | 15287 | O | GLU | B | 418 | 38.905 | 28.118 | −10.532 | 1.00 | 29.16 | O |
| ATOM | 15289 | N | ASN | B | 419 | 40.584 | 29.139 | −9.430 | 1.00 | 28.62 | N |
| ATOM | 15290 | CA | ASN | B | 419 | 40.996 | 29.925 | −10.578 | 1.00 | 27.70 | C |

APPENDIX 1-continued

| ATOM | 15292 | CB  | ASN | B | 419 | 41.862 | 31.103 | −10.139 | 1.00 | 27.76 | C |
| ---- | ----- | --- | --- | - | --- | ------ | ------ | ------- | ---- | ----- | - |
| ATOM | 15295 | CG  | ASN | B | 419 | 41.027 | 32.329 | −9.789  | 1.00 | 30.05 | C |
| ATOM | 15296 | OD1 | ASN | B | 419 | 40.426 | 32.946 | −10.670 | 1.00 | 33.99 | O |
| ATOM | 15297 | ND2 | ASN | B | 419 | 40.974 | 32.678 | −8.505  | 1.00 | 28.62 | N |
| ATOM | 15300 | C   | ASN | B | 419 | 41.692 | 29.085 | −11.638 | 1.00 | 28.30 | C |
| ATOM | 15301 | O   | ASN | B | 419 | 41.631 | 29.414 | −12.826 | 1.00 | 28.75 | O |
| ATOM | 15303 | N   | LEU | B | 420 | 42.343 | 28.000 | −11.221 | 1.00 | 28.29 | N |
| ATOM | 15304 | CA  | LEU | B | 420 | 42.918 | 27.050 | −12.173 | 1.00 | 27.94 | C |
| ATOM | 15306 | CB  | LEU | B | 420 | 43.743 | 25.964 | −11.468 | 1.00 | 28.03 | C |
| ATOM | 15309 | CG  | LEU | B | 420 | 45.145 | 26.316 | −10.953 | 1.00 | 27.38 | C |
| ATOM | 15311 | CD1 | LEU | B | 420 | 45.698 | 25.181 | −10.100 | 1.00 | 23.69 | C |
| ATOM | 15315 | CD2 | LEU | B | 420 | 46.089 | 26.618 | −12.097 | 1.00 | 23.35 | C |
| ATOM | 15319 | C   | LEU | B | 420 | 41.800 | 26.406 | −12.987 | 1.00 | 29.01 | C |
| ATOM | 15320 | O   | LEU | B | 420 | 41.906 | 26.290 | −14.202 | 1.00 | 28.72 | O |
| ATOM | 15322 | N   | GLN | B | 421 | 40.724 | 26.006 | −12.314 | 1.00 | 30.82 | N |
| ATOM | 15323 | CA  | GLN | B | 421 | 39.575 | 25.395 | −12.990 | 1.00 | 32.50 | C |
| ATOM | 15325 | CB  | GLN | B | 421 | 38.576 | 24.834 | −11.970 | 1.00 | 32.85 | C |
| ATOM | 15328 | CG  | GLN | B | 421 | 39.116 | 23.657 | −11.189 | 1.00 | 36.59 | C |
| ATOM | 15331 | CD  | GLN | B | 421 | 38.050 | 22.914 | −10.420 | 1.00 | 40.68 | C |
| ATOM | 15332 | OE1 | GLN | B | 421 | 37.934 | 21.689 | −10.524 | 1.00 | 44.45 | O |
| ATOM | 15333 | NE2 | GLN | B | 421 | 37.265 | 23.646 | −9.636  | 1.00 | 42.01 | N |
| ATOM | 15336 | C   | GLN | B | 421 | 38.865 | 26.354 | −13.955 | 1.00 | 32.96 | C |
| ATOM | 15337 | O   | GLN | B | 421 | 38.269 | 25.910 | −14.937 | 1.00 | 33.31 | O |
| ATOM | 15339 | N   | LYS | B | 422 | 38.935 | 27.658 | −13.686 | 1.00 | 32.66 | N |
| ATOM | 15340 | CA  | LYS | B | 422 | 38.340 | 28.655 | −14.573 | 1.00 | 32.68 | C |
| ATOM | 15342 | CB  | LYS | B | 422 | 37.799 | 29.841 | −13.768 | 1.00 | 33.55 | C |
| ATOM | 15345 | CG  | LYS | B | 422 | 36.676 | 29.502 | −12.786 | 1.00 | 36.94 | C |
| ATOM | 15348 | CD  | LYS | B | 422 | 36.399 | 30.688 | −11.850 | 1.00 | 42.73 | C |
| ATOM | 15351 | CE  | LYS | B | 422 | 35.518 | 30.302 | −10.653 | 1.00 | 46.86 | C |
| ATOM | 15354 | NZ  | LYS | B | 422 | 35.616 | 31.295 | −9.523  | 1.00 | 46.07 | N |
| ATOM | 15358 | C   | LYS | B | 422 | 39.350 | 29.151 | −15.606 | 1.00 | 32.09 | C |
| ATOM | 15359 | O   | LYS | B | 422 | 39.128 | 30.168 | −16.254 | 1.00 | 31.90 | O |
| ATOM | 15361 | N   | TYR | B | 423 | 40.461 | 28.435 | −15.758 | 1.00 | 32.07 | N |
| ATOM | 15362 | CA  | TYR | B | 423 | 41.509 | 28.796 | −16.719 | 1.00 | 32.08 | C |
| ATOM | 15364 | CB  | TYR | B | 423 | 41.056 | 28.540 | −18.159 | 1.00 | 32.37 | C |
| ATOM | 15367 | CG  | TYR | B | 423 | 40.711 | 27.106 | −18.444 | 1.00 | 34.30 | C |
| ATOM | 15368 | CD1 | TYR | B | 423 | 41.698 | 26.182 | −18.739 | 1.00 | 35.24 | C |
| ATOM | 15370 | CE1 | TYR | B | 423 | 41.383 | 24.866 | −19.005 | 1.00 | 38.80 | C |
| ATOM | 15372 | CZ  | TYR | B | 423 | 40.059 | 24.460 | −18.982 | 1.00 | 39.78 | C |
| ATOM | 15373 | OH  | TYR | B | 423 | 39.732 | 23.153 | −19.244 | 1.00 | 43.38 | O |
| ATOM | 15375 | CE2 | TYR | B | 423 | 39.061 | 25.361 | −18.697 | 1.00 | 39.46 | C |
| ATOM | 15377 | CD2 | TYR | B | 423 | 39.389 | 26.677 | −18.430 | 1.00 | 39.47 | C |
| ATOM | 15379 | C   | TYR | B | 423 | 41.963 | 30.242 | −16.576 | 1.00 | 30.88 | C |
| ATOM | 15380 | O   | TYR | B | 423 | 41.962 | 31.003 | −17.542 | 1.00 | 31.01 | O |
| ATOM | 15382 | N   | HIS | B | 424 | 42.365 | 30.610 | −15.366 | 1.00 | 30.24 | N |
| ATOM | 15383 | CA  | HIS | B | 424 | 42.907 | 31.939 | −15.112 | 1.00 | 29.00 | C |
| ATOM | 15385 | CB  | HIS | B | 424 | 43.327 | 32.066 | −13.646 | 1.00 | 28.70 | C |
| ATOM | 15388 | CG  | HIS | B | 424 | 43.837 | 33.423 | −13.284 | 1.00 | 32.16 | C |
| ATOM | 15389 | ND1 | HIS | B | 424 | 45.181 | 33.717 | −13.210 | 1.00 | 31.41 | N |
| ATOM | 15391 | CE1 | HIS | B | 424 | 45.333 | 34.988 | −12.888 | 1.00 | 33.21 | C |
| ATOM | 15393 | NE2 | HIS | B | 424 | 44.137 | 35.530 | −12.752 | 1.00 | 33.13 | N |
| ATOM | 15395 | CD2 | HIS | B | 424 | 43.183 | 34.575 | −13.003 | 1.00 | 33.86 | C |
| ATOM | 15397 | C   | HIS | B | 424 | 44.091 | 32.221 | −16.035 | 1.00 | 27.68 | C |
| ATOM | 15398 | O   | HIS | B | 424 | 44.805 | 31.315 | −16.439 | 1.00 | 27.22 | O |
| ATOM | 15400 | N   | ASP | B | 425 | 44.288 | 33.493 | −16.358 | 1.00 | 27.93 | N |
| ATOM | 15401 | CA  | ASP | B | 425 | 45.369 | 33.932 | −17.250 | 1.00 | 27.06 | C |
| ATOM | 15403 | CB  | ASP | B | 425 | 45.588 | 35.441 | −17.108 | 1.00 | 27.55 | C |
| ATOM | 15406 | CG  | ASP | B | 425 | 44.468 | 36.259 | −17.703 | 1.00 | 29.33 | C |
| ATOM | 15407 | OD1 | ASP | B | 425 | 43.702 | 35.740 | −18.547 | 1.00 | 34.93 | O |
| ATOM | 15408 | OD2 | ASP | B | 425 | 44.362 | 37.440 | −17.324 | 1.00 | 35.04 | O |
| ATOM | 15409 | C   | ASP | B | 425 | 46.700 | 33.243 | −17.017 | 1.00 | 24.99 | C |
| ATOM | 15410 | O   | ASP | B | 425 | 47.443 | 32.998 | −17.954 | 1.00 | 26.19 | O |
| ATOM | 15412 | N   | THR | B | 426 | 47.005 | 32.956 | −15.761 | 1.00 | 24.27 | N |
| ATOM | 15413 | CA  | THR | B | 426 | 48.288 | 32.380 | −15.379 | 1.00 | 23.04 | C |
| ATOM | 15415 | CB  | THR | B | 426 | 48.342 | 32.107 | −13.861 | 1.00 | 22.71 | C |
| ATOM | 15417 | OG1 | THR | B | 426 | 48.157 | 33.339 | −13.150 | 1.00 | 26.44 | O |
| ATOM | 15419 | CG2 | THR | B | 426 | 49.665 | 31.504 | −13.468 | 1.00 | 20.26 | C |
| ATOM | 15423 | C   | THR | B | 426 | 48.588 | 31.107 | −16.154 | 1.00 | 21.99 | C |
| ATOM | 15424 | O   | THR | B | 426 | 49.718 | 30.910 | −16.583 | 1.00 | 22.57 | O |
| ATOM | 15426 | N   | ILE | B | 427 | 47.585 | 30.253 | −16.343 | 1.00 | 21.32 | N |
| ATOM | 15427 | CA  | ILE | B | 427 | 47.768 | 29.044 | −17.147 | 1.00 | 21.60 | C |
| ATOM | 15429 | CB  | ILE | B | 427 | 47.187 | 27.788 | −16.449 | 1.00 | 21.56 | C |
| ATOM | 15431 | CG1 | ILE | B | 427 | 45.659 | 27.799 | −16.420 | 1.00 | 21.85 | C |
| ATOM | 15434 | CD1 | ILE | B | 427 | 45.077 | 26.512 | −15.877 | 1.00 | 18.12 | C |
| ATOM | 15438 | CG2 | ILE | B | 427 | 47.720 | 27.677 | −15.021 | 1.00 | 20.49 | C |
| ATOM | 15442 | C   | ILE | B | 427 | 47.244 | 29.185 | −18.596 | 1.00 | 22.63 | C |
| ATOM | 15443 | O   | ILE | B | 427 | 47.764 | 28.523 | −19.511 | 1.00 | 23.44 | O |
| ATOM | 15445 | N   | SER | B | 428 | 46.257 | 30.055 | −18.828 | 1.00 | 21.73 | N |
| ATOM | 15446 | CA  | SER | B | 428 | 45.691 | 30.185 | −20.178 | 1.00 | 21.85 | C |
| ATOM | 15448 | CB  | SER | B | 428 | 44.376 | 30.959 | −20.174 | 1.00 | 21.48 | C |

APPENDIX 1-continued

| ATOM | 15451 | OG | SER | B | 428 | 44.582 | 32.335 | −19.958 | 1.00 | 22.89 | O |
|---|---|---|---|---|---|---|---|---|---|---|---|
| ATOM | 15453 | C | SER | B | 428 | 46.667 | 30.818 | −21.158 | 1.00 | 21.72 | C |
| ATOM | 15454 | O | SER | B | 428 | 46.800 | 30.360 | −22.285 | 1.00 | 21.98 | O |
| ATOM | 15456 | N | ARG | B | 429 | 47.359 | 31.865 | −20.731 | 1.00 | 21.99 | N |
| ATOM | 15457 | CA | ARG | B | 429 | 48.264 | 32.576 | −21.634 | 1.00 | 22.80 | C |
| ATOM | 15459 | CB | ARG | B | 429 | 48.783 | 33.875 | −21.005 | 1.00 | 23.65 | C |
| ATOM | 15462 | CG | ARG | B | 429 | 48.145 | 35.141 | −21.575 | 1.00 | 29.02 | C |
| ATOM | 15465 | CD | ARG | B | 429 | 47.172 | 35.807 | −20.639 | 1.00 | 38.00 | C |
| ATOM | 15468 | NE | ARG | B | 429 | 45.769 | 35.651 | −21.032 | 1.00 | 44.68 | N |
| ATOM | 15470 | CZ | ARG | B | 429 | 45.137 | 36.391 | −21.947 | 1.00 | 45.10 | C |
| ATOM | 15471 | NH1 | ARG | B | 429 | 45.778 | 37.332 | −22.623 | 1.00 | 43.52 | N |
| ATOM | 15474 | NH2 | ARG | B | 429 | 43.853 | 36.169 | −22.204 | 1.00 | 46.57 | N |
| ATOM | 15477 | C | ARG | B | 429 | 49.426 | 31.725 | −22.145 | 1.00 | 21.92 | C |
| ATOM | 15478 | O | ARG | B | 429 | 49.659 | 31.680 | −23.348 | 1.00 | 21.67 | O |
| ATOM | 15480 | N | PRO | B | 430 | 50.159 | 31.049 | −21.240 | 1.00 | 21.35 | N |
| ATOM | 15481 | CA | PRO | B | 430 | 51.228 | 30.146 | −21.692 | 1.00 | 20.56 | C |
| ATOM | 15483 | CB | PRO | B | 430 | 51.730 | 29.495 | −20.405 | 1.00 | 20.61 | C |
| ATOM | 15486 | CG | PRO | B | 430 | 51.221 | 30.310 | −19.299 | 1.00 | 22.82 | C |
| ATOM | 15489 | CD | PRO | B | 430 | 50.072 | 31.130 | −19.775 | 1.00 | 21.56 | C |
| ATOM | 15492 | C | PRO | B | 430 | 50.715 | 29.064 | −22.627 | 1.00 | 19.69 | C |
| ATOM | 15493 | O | PRO | B | 430 | 51.420 | 28.630 | −23.543 | 1.00 | 17.76 | O |
| ATOM | 15494 | N | SER | B | 431 | 49.486 | 28.630 | −22.367 | 1.00 | 20.10 | N |
| ATOM | 15495 | CA | SER | B | 431 | 48.818 | 27.637 | −23.190 | 1.00 | 19.87 | C |
| ATOM | 15497 | CB | SER | B | 431 | 47.523 | 27.185 | −22.508 | 1.00 | 20.63 | C |
| ATOM | 15500 | OG | SER | B | 431 | 47.810 | 26.550 | −21.265 | 1.00 | 20.83 | O |
| ATOM | 15502 | C | SER | B | 431 | 48.552 | 28.166 | −24.601 | 1.00 | 19.02 | C |
| ATOM | 15503 | O | SER | B | 431 | 48.728 | 27.425 | −25.574 | 1.00 | 18.43 | O |
| ATOM | 15505 | N | HIS | B | 432 | 48.157 | 29.441 | −24.705 | 1.00 | 17.73 | N |
| ATOM | 15506 | CA | HIS | B | 432 | 48.016 | 30.115 | −25.999 | 1.00 | 17.66 | C |
| ATOM | 15508 | CB | HIS | B | 432 | 47.720 | 31.612 | −25.842 | 1.00 | 18.48 | C |
| ATOM | 15511 | CG | HIS | B | 432 | 46.387 | 31.922 | −25.242 | 1.00 | 21.18 | C |
| ATOM | 15512 | ND1 | HIS | B | 432 | 45.569 | 30.959 | −24.693 | 1.00 | 29.61 | N |
| ATOM | 15514 | CE1 | HIS | B | 432 | 44.471 | 31.529 | −24.230 | 1.00 | 28.07 | C |
| ATOM | 15516 | NE2 | HIS | B | 432 | 44.558 | 32.827 | −24.442 | 1.00 | 24.46 | N |
| ATOM | 15518 | CD2 | HIS | B | 432 | 45.747 | 33.100 | −25.071 | 1.00 | 23.89 | C |
| ATOM | 15520 | C | HIS | B | 432 | 49.297 | 30.003 | −26.801 | 1.00 | 17.43 | C |
| ATOM | 15521 | O | HIS | B | 432 | 49.256 | 29.672 | −27.973 | 1.00 | 16.84 | O |
| ATOM | 15523 | N | ILE | B | 433 | 50.427 | 30.303 | −26.158 | 1.00 | 18.30 | N |
| ATOM | 15524 | CA | ILE | B | 433 | 51.743 | 30.309 | −26.817 | 1.00 | 19.13 | C |
| ATOM | 15526 | CB | ILE | B | 433 | 52.859 | 30.822 | −25.874 | 1.00 | 19.72 | C |
| ATOM | 15528 | CG1 | ILE | B | 433 | 52.601 | 32.263 | −25.414 | 1.00 | 22.36 | C |
| ATOM | 15531 | CD1 | ILE | B | 433 | 52.455 | 33.237 | −26.513 | 1.00 | 24.58 | C |
| ATOM | 15535 | CG2 | ILE | B | 433 | 54.225 | 30.718 | −26.536 | 1.00 | 17.43 | C |
| ATOM | 15539 | C | ILE | B | 433 | 52.139 | 28.898 | −27.252 | 1.00 | 20.08 | C |
| ATOM | 15540 | O | ILE | B | 433 | 52.630 | 28.686 | −28.366 | 1.00 | 20.63 | O |
| ATOM | 15542 | N | PHE | B | 434 | 51.942 | 27.945 | −26.347 | 1.00 | 19.69 | N |
| ATOM | 15543 | CA | PHE | B | 434 | 52.188 | 26.534 | −26.617 | 1.00 | 19.00 | C |
| ATOM | 15545 | CB | PHE | B | 434 | 51.711 | 25.736 | −25.398 | 1.00 | 19.70 | C |
| ATOM | 15548 | CG | PHE | B | 434 | 51.864 | 24.238 | −25.500 | 1.00 | 22.29 | C |
| ATOM | 15549 | CD1 | PHE | B | 434 | 52.639 | 23.624 | −26.477 | 1.00 | 21.87 | C |
| ATOM | 15551 | CE1 | PHE | B | 434 | 52.756 | 22.239 | −26.519 | 1.00 | 22.23 | C |
| ATOM | 15553 | CZ | PHE | B | 434 | 52.116 | 21.456 | −25.569 | 1.00 | 20.94 | C |
| ATOM | 15555 | CE2 | PHE | B | 434 | 51.357 | 22.054 | −24.582 | 1.00 | 24.34 | C |
| ATOM | 15557 | CD2 | PHE | B | 434 | 51.233 | 23.432 | −24.549 | 1.00 | 24.47 | C |
| ATOM | 15559 | C | PHE | B | 434 | 51.474 | 26.130 | −27.899 | 1.00 | 18.88 | C |
| ATOM | 15560 | O | PHE | B | 434 | 52.104 | 25.644 | −28.840 | 1.00 | 19.79 | O |
| ATOM | 15562 | N | ARG | B | 435 | 50.171 | 26.377 | −27.962 | 1.00 | 18.36 | N |
| ATOM | 15563 | CA | ARG | B | 435 | 49.401 | 25.989 | −29.133 | 1.00 | 18.31 | C |
| ATOM | 15565 | CB | ARG | B | 435 | 47.905 | 26.221 | −28.907 | 1.00 | 18.44 | C |
| ATOM | 15568 | CG | ARG | B | 435 | 47.030 | 26.060 | −30.162 | 1.00 | 18.66 | C |
| ATOM | 15571 | CD | ARG | B | 435 | 47.243 | 24.735 | −30.870 | 1.00 | 20.84 | C |
| ATOM | 15574 | NE | ARG | B | 435 | 46.750 | 23.601 | −30.095 | 1.00 | 20.54 | N |
| ATOM | 15576 | CZ | ARG | B | 435 | 46.962 | 22.327 | −30.410 | 1.00 | 18.63 | C |
| ATOM | 15577 | NH1 | ARG | B | 435 | 47.681 | 22.001 | −31.481 | 1.00 | 15.31 | N |
| ATOM | 15580 | NH2 | ARG | B | 435 | 46.464 | 21.370 | −29.634 | 1.00 | 19.18 | N |
| ATOM | 15583 | C | ARG | B | 435 | 49.870 | 26.693 | −30.409 | 1.00 | 18.19 | C |
| ATOM | 15584 | O | ARG | B | 435 | 49.975 | 26.058 | −31.456 | 1.00 | 18.26 | O |
| ATOM | 15586 | N | LEU | B | 436 | 50.149 | 27.991 | −30.319 | 1.00 | 18.18 | N |
| ATOM | 15587 | CA | LEU | B | 436 | 50.529 | 28.778 | −31.498 | 1.00 | 18.60 | C |
| ATOM | 15589 | CB | LEU | B | 436 | 50.426 | 30.279 | −31.194 | 1.00 | 18.65 | C |
| ATOM | 15592 | CG | LEU | B | 436 | 49.013 | 30.828 | −30.933 | 1.00 | 18.58 | C |
| ATOM | 15594 | CD1 | LEU | B | 436 | 49.070 | 32.272 | −30.443 | 1.00 | 14.53 | C |
| ATOM | 15598 | CD2 | LEU | B | 436 | 48.128 | 30.715 | −32.167 | 1.00 | 12.32 | C |
| ATOM | 15602 | C | LEU | B | 436 | 51.932 | 28.431 | −32.028 | 1.00 | 19.03 | C |
| ATOM | 15603 | O | LEU | B | 436 | 52.153 | 28.400 | −33.232 | 1.00 | 19.41 | O |
| ATOM | 15605 | N | CYS | B | 437 | 52.875 | 28.171 | −31.131 | 1.00 | 20.14 | N |
| ATOM | 15606 | CA | CYS | B | 437 | 54.214 | 27.732 | −31.532 | 1.00 | 20.76 | C |
| ATOM | 15608 | CB | CYS | B | 437 | 55.127 | 27.622 | −30.318 | 1.00 | 20.35 | C |
| ATOM | 15611 | SG | CYS | B | 437 | 55.604 | 29.223 | −29.661 | 1.00 | 22.24 | S |
| ATOM | 15613 | C | CYS | B | 437 | 54.174 | 26.395 | −32.258 | 1.00 | 21.65 | C |

APPENDIX 1-continued

| | | | | | | | | | | |
|---|---|---|---|---|---|---|---|---|---|---|
| ATOM | 15614 | O | CYS | B | 437 | 54.779 | 26.239 | −33.323 | 1.00 | 21.72 | O |
| ATOM | 15616 | N | ASN | B | 438 | 53.457 | 25.440 | −31.671 | 1.00 | 22.25 | N |
| ATOM | 15617 | CA | ASN | B | 438 | 53.293 | 24.116 | −32.255 | 1.00 | 22.51 | C |
| ATOM | 15619 | CB | ASN | B | 438 | 52.428 | 23.246 | −31.332 | 1.00 | 23.13 | C |
| ATOM | 15622 | CG | ASN | B | 438 | 52.157 | 21.859 | −31.895 | 1.00 | 22.55 | C |
| ATOM | 15623 | OD1 | ASN | B | 438 | 52.742 | 21.440 | −32.885 | 1.00 | 31.37 | O |
| ATOM | 15624 | ND2 | ASN | B | 438 | 51.270 | 21.139 | −31.248 | 1.00 | 23.98 | N |
| ATOM | 15627 | C | ASN | B | 438 | 52.672 | 24.212 | −33.640 | 1.00 | 23.19 | C |
| ATOM | 15628 | O | ASN | B | 438 | 53.166 | 23.597 | −34.597 | 1.00 | 24.74 | O |
| ATOM | 15630 | N | ASP | B | 439 | 51.600 | 24.991 | −33.753 | 1.00 | 22.68 | N |
| ATOM | 15631 | CA | ASP | B | 439 | 50.900 | 25.125 | −35.030 | 1.00 | 22.77 | C |
| ATOM | 15633 | CB | ASP | B | 439 | 49.510 | 25.726 | −34.836 | 1.00 | 22.55 | C |
| ATOM | 15636 | CG | ASP | B | 439 | 48.531 | 24.723 | −34.262 | 1.00 | 21.72 | C |
| ATOM | 15637 | OD1 | ASP | B | 439 | 48.964 | 23.857 | −33.476 | 1.00 | 22.53 | O |
| ATOM | 15638 | OD2 | ASP | B | 439 | 47.336 | 24.791 | −34.603 | 1.00 | 23.74 | O |
| ATOM | 15639 | C | ASP | B | 439 | 51.710 | 25.903 | −36.053 | 1.00 | 22.77 | C |
| ATOM | 15640 | O | ASP | B | 439 | 51.631 | 25.613 | −37.244 | 1.00 | 22.42 | O |
| ATOM | 15642 | N | LEU | B | 440 | 52.498 | 26.871 | −35.589 | 1.00 | 23.21 | N |
| ATOM | 15643 | CA | LEU | B | 440 | 53.408 | 27.605 | −36.471 | 1.00 | 23.98 | C |
| ATOM | 15645 | CB | LEU | B | 440 | 54.140 | 28.709 | −35.705 | 1.00 | 23.92 | C |
| ATOM | 15648 | CG | LEU | B | 440 | 53.480 | 30.084 | −35.649 | 1.00 | 23.77 | C |
| ATOM | 15650 | CD1 | LEU | B | 440 | 54.222 | 30.982 | −34.676 | 1.00 | 27.08 | C |
| ATOM | 15654 | CD2 | LEU | B | 440 | 53.471 | 30.712 | −37.016 | 1.00 | 22.99 | C |
| ATOM | 15658 | C | LEU | B | 440 | 54.436 | 26.679 | −37.140 | 1.00 | 24.88 | C |
| ATOM | 15659 | O | LEU | B | 440 | 54.763 | 26.853 | −38.316 | 1.00 | 25.63 | O |
| ATOM | 15661 | N | ALA | B | 441 | 54.932 | 25.698 | −36.387 | 1.00 | 24.62 | N |
| ATOM | 15662 | CA | ALA | B | 441 | 55.981 | 24.793 | −36.862 | 1.00 | 24.00 | C |
| ATOM | 15664 | CB | ALA | B | 441 | 56.486 | 23.931 | −35.709 | 1.00 | 23.61 | C |
| ATOM | 15668 | C | ALA | B | 441 | 55.515 | 23.907 | −38.011 | 1.00 | 23.92 | C |
| ATOM | 15669 | O | ALA | B | 441 | 56.243 | 23.696 | −38.974 | 1.00 | 24.43 | O |
| ATOM | 15671 | N | SER | B | 442 | 54.295 | 23.398 | −37.904 | 1.00 | 24.56 | N |
| ATOM | 15672 | CA | SER | B | 442 | 53.730 | 22.507 | −38.915 | 1.00 | 24.82 | C |
| ATOM | 15674 | CB | SER | B | 442 | 52.907 | 21.418 | −38.218 | 1.00 | 25.09 | C |
| ATOM | 15677 | OG | SER | B | 442 | 51.899 | 21.997 | −37.398 | 1.00 | 29.33 | O |
| ATOM | 15679 | C | SER | B | 442 | 52.850 | 23.239 | −39.944 | 1.00 | 24.46 | C |
| ATOM | 15680 | O | SER | B | 442 | 52.336 | 22.613 | −40.882 | 1.00 | 24.20 | O |
| ATOM | 15682 | N | ALA | B | 443 | 52.692 | 24.555 | −39.773 | 1.00 | 23.79 | N |
| ATOM | 15683 | CA | ALA | B | 443 | 51.751 | 25.352 | −40.561 | 1.00 | 22.33 | C |
| ATOM | 15685 | CB | ALA | B | 443 | 51.939 | 26.827 | −40.264 | 1.00 | 21.29 | C |
| ATOM | 15689 | C | ALA | B | 443 | 51.876 | 25.112 | −42.054 | 1.00 | 22.54 | C |
| ATOM | 15690 | O | ALA | B | 443 | 50.948 | 24.616 | −42.689 | 1.00 | 22.37 | O |
| ATOM | 15692 | N | SER | B | 444 | 53.034 | 25.449 | −42.607 | 1.00 | 23.67 | N |
| ATOM | 15693 | CA | SER | B | 444 | 53.186 | 25.505 | −44.053 | 1.00 | 24.77 | C |
| ATOM | 15695 | CB | SER | B | 444 | 54.483 | 26.227 | −44.438 | 1.00 | 24.33 | C |
| ATOM | 15698 | OG | SER | B | 444 | 55.600 | 25.382 | −44.310 | 1.00 | 29.42 | O |
| ATOM | 15700 | C | SER | B | 444 | 53.091 | 24.122 | −44.704 | 1.00 | 25.09 | C |
| ATOM | 15701 | O | SER | B | 444 | 52.620 | 24.001 | −45.843 | 1.00 | 25.49 | O |
| ATOM | 15703 | N | ALA | B | 445 | 53.510 | 23.086 | −43.980 | 1.00 | 25.41 | N |
| ATOM | 15704 | CA | ALA | B | 445 | 53.411 | 21.717 | −44.482 | 1.00 | 26.23 | C |
| ATOM | 15706 | CB | ALA | B | 445 | 54.244 | 20.774 | −43.640 | 1.00 | 25.83 | C |
| ATOM | 15710 | C | ALA | B | 445 | 51.952 | 21.253 | −44.535 | 1.00 | 27.75 | C |
| ATOM | 15711 | O | ALA | B | 445 | 51.514 | 20.694 | −45.547 | 1.00 | 28.82 | O |
| ATOM | 15713 | N | GLU | B | 446 | 51.200 | 21.496 | −43.461 | 1.00 | 28.44 | N |
| ATOM | 15714 | CA | GLU | B | 446 | 49.766 | 21.168 | −43.435 | 1.00 | 29.32 | C |
| ATOM | 15716 | CB | GLU | B | 446 | 49.205 | 21.244 | −42.007 | 1.00 | 29.63 | C |
| ATOM | 15719 | CG | GLU | B | 446 | 49.636 | 20.080 | −41.125 | 1.00 | 32.37 | C |
| ATOM | 15722 | CD | GLU | B | 446 | 49.175 | 20.209 | −39.680 | 1.00 | 39.10 | C |
| ATOM | 15723 | OE1 | GLU | B | 446 | 48.071 | 20.744 | −39.438 | 1.00 | 45.26 | O |
| ATOM | 15724 | OE2 | GLU | B | 446 | 49.913 | 19.758 | −38.777 | 1.00 | 40.42 | O |
| ATOM | 15725 | C | GLU | B | 446 | 48.932 | 22.043 | −44.389 | 1.00 | 29.18 | C |
| ATOM | 15726 | O | GLU | B | 446 | 47.978 | 21.560 | −44.997 | 1.00 | 28.80 | O |
| ATOM | 15728 | N | ILE | B | 447 | 49.290 | 23.317 | −44.524 | 1.00 | 29.38 | N |
| ATOM | 15729 | CA | ILE | B | 447 | 48.598 | 24.208 | −45.462 | 1.00 | 29.77 | C |
| ATOM | 15731 | CB | ILE | B | 447 | 49.071 | 25.676 | −45.312 | 1.00 | 29.91 | C |
| ATOM | 15733 | CG1 | ILE | B | 447 | 48.562 | 26.259 | −43.990 | 1.00 | 30.26 | C |
| ATOM | 15736 | CD1 | ILE | B | 447 | 49.269 | 27.519 | −43.566 | 1.00 | 29.22 | C |
| ATOM | 15740 | CG2 | ILE | B | 447 | 48.583 | 26.534 | −46.475 | 1.00 | 25.60 | C |
| ATOM | 15744 | C | ILE | B | 447 | 48.784 | 23.747 | −46.907 | 1.00 | 31.06 | C |
| ATOM | 15745 | O | ILE | B | 447 | 47.897 | 23.927 | −47.734 | 1.00 | 31.19 | O |
| ATOM | 15747 | N | ALA | B | 448 | 49.937 | 23.152 | −47.200 | 1.00 | 32.75 | N |
| ATOM | 15748 | CA | ALA | B | 448 | 50.216 | 22.607 | −48.526 | 1.00 | 33.94 | C |
| ATOM | 15750 | CB | ALA | B | 448 | 51.694 | 22.279 | −48.654 | 1.00 | 34.47 | C |
| ATOM | 15754 | C | ALA | B | 448 | 49.367 | 21.366 | −48.825 | 1.00 | 35.48 | C |
| ATOM | 15755 | O | ALA | B | 448 | 48.876 | 21.217 | −49.939 | 1.00 | 36.06 | O |
| ATOM | 15757 | N | ARG | B | 449 | 49.197 | 20.486 | −47.835 | 1.00 | 37.10 | N |
| ATOM | 15758 | CA | ARG | B | 449 | 48.324 | 19.305 | −47.969 | 1.00 | 38.26 | C |
| ATOM | 15760 | CB | ARG | B | 449 | 48.489 | 18.339 | −46.787 | 1.00 | 39.28 | C |
| ATOM | 15763 | CG | ARG | B | 449 | 49.867 | 17.725 | −46.625 | 1.00 | 44.41 | C |
| ATOM | 15766 | CD | ARG | B | 449 | 49.858 | 16.573 | −45.603 | 1.00 | 48.39 | C |
| ATOM | 15769 | NE | ARG | B | 449 | 50.939 | 16.714 | −44.620 | 1.00 | 50.95 | N |

APPENDIX 1-continued

| ATOM | 15771 | CZ | ARG | B | 449 | 50.781 | 16.813 | −43.297 | 1.00 | 50.45 | C |
|---|---|---|---|---|---|---|---|---|---|---|---|
| ATOM | 15772 | NH1 | ARG | B | 449 | 49.579 | 16.749 | −42.733 | 1.00 | 48.57 | N |
| ATOM | 15775 | NH2 | ARG | B | 449 | 51.851 | 16.956 | −42.520 | 1.00 | 50.04 | N |
| ATOM | 15778 | C | ARG | B | 449 | 46.848 | 19.668 | −48.040 | 1.00 | 37.74 | C |
| ATOM | 15779 | O | ARG | B | 449 | 46.030 | 18.837 | −48.418 | 1.00 | 38.10 | O |
| ATOM | 15781 | N | GLY | B | 450 | 46.506 | 20.887 | −47.635 | 1.00 | 37.69 | N |
| ATOM | 15782 | CA | GLY | B | 450 | 45.124 | 21.352 | −47.653 | 1.00 | 37.69 | C |
| ATOM | 15785 | C | GLY | B | 450 | 44.357 | 20.983 | −46.396 | 1.00 | 37.78 | C |
| ATOM | 15786 | O | GLY | B | 450 | 43.141 | 20.809 | −46.446 | 1.00 | 38.32 | O |
| ATOM | 15788 | N | GLU | B | 451 | 45.060 | 20.866 | −45.267 | 1.00 | 37.11 | N |
| ATOM | 15789 | CA | GLU | B | 451 | 44.413 | 20.592 | −43.983 | 1.00 | 36.64 | C |
| ATOM | 15791 | CB | GLU | B | 451 | 45.261 | 19.660 | −43.111 | 1.00 | 37.70 | C |
| ATOM | 15794 | CG | GLU | B | 451 | 45.064 | 18.181 | −43.442 | 1.00 | 41.62 | C |
| ATOM | 15797 | CD | GLU | B | 451 | 46.092 | 17.283 | −42.775 | 1.00 | 46.25 | C |
| ATOM | 15798 | OE1 | GLU | B | 451 | 46.040 | 17.121 | −41.532 | 1.00 | 47.91 | O |
| ATOM | 15799 | OE2 | GLU | B | 451 | 46.948 | 16.732 | −43.501 | 1.00 | 49.29 | O |
| ATOM | 15800 | C | GLU | B | 451 | 44.115 | 21.891 | −43.248 | 1.00 | 34.73 | C |
| ATOM | 15801 | O | GLU | B | 451 | 44.908 | 22.834 | −43.274 | 1.00 | 34.16 | O |
| ATOM | 15803 | N | THR | B | 452 | 42.964 | 21.909 | −42.583 | 1.00 | 32.80 | N |
| ATOM | 15804 | CA | THR | B | 452 | 42.411 | 23.115 | −41.989 | 1.00 | 31.18 | C |
| ATOM | 15806 | CB | THR | B | 452 | 40.911 | 23.255 | −42.355 | 1.00 | 31.64 | C |
| ATOM | 15808 | OG1 | THR | B | 452 | 40.165 | 22.173 | −41.791 | 1.00 | 32.65 | O |
| ATOM | 15810 | CG2 | THR | B | 452 | 40.730 | 23.277 | −43.878 | 1.00 | 29.23 | C |
| ATOM | 15814 | C | THR | B | 452 | 42.573 | 23.174 | −40.469 | 1.00 | 29.72 | C |
| ATOM | 15815 | O | THR | B | 452 | 42.567 | 24.259 | −39.893 | 1.00 | 29.47 | O |
| ATOM | 15817 | N | ALA | B | 453 | 42.718 | 22.020 | −39.819 | 1.00 | 28.62 | N |
| ATOM | 15818 | CA | ALA | B | 453 | 42.876 | 21.971 | −38.364 | 1.00 | 27.16 | C |
| ATOM | 15820 | CB | ALA | B | 453 | 42.593 | 20.573 | −37.853 | 1.00 | 26.02 | C |
| ATOM | 15824 | C | ALA | B | 453 | 44.275 | 22.443 | −37.929 | 1.00 | 26.32 | C |
| ATOM | 15825 | O | ALA | B | 453 | 45.119 | 21.646 | −37.530 | 1.00 | 26.61 | O |
| ATOM | 15827 | N | ASN | B | 454 | 44.497 | 23.751 | −38.000 | 1.00 | 24.18 | N |
| ATOM | 15828 | CA | ASN | B | 454 | 45.764 | 24.357 | −37.606 | 1.00 | 23.29 | C |
| ATOM | 15830 | CB | ASN | B | 454 | 46.843 | 24.077 | −38.665 | 1.00 | 22.87 | C |
| ATOM | 15833 | CG | ASN | B | 454 | 48.181 | 24.741 | −38.349 | 1.00 | 22.94 | C |
| ATOM | 15834 | OD1 | ASN | B | 454 | 48.369 | 25.930 | −38.602 | 1.00 | 24.63 | O |
| ATOM | 15835 | ND2 | ASN | B | 454 | 49.127 | 23.962 | −37.827 | 1.00 | 21.89 | N |
| ATOM | 15838 | C | ASN | B | 454 | 45.542 | 25.859 | −37.404 | 1.00 | 21.96 | C |
| ATOM | 15839 | O | ASN | B | 454 | 45.028 | 26.541 | −38.287 | 1.00 | 22.37 | O |
| ATOM | 15841 | N | SER | B | 455 | 45.922 | 26.369 | −36.242 | 1.00 | 20.32 | N |
| ATOM | 15842 | CA | SER | B | 455 | 45.627 | 27.753 | −35.870 | 1.00 | 19.88 | C |
| ATOM | 15844 | CB | SER | B | 455 | 46.399 | 28.121 | −34.609 | 1.00 | 19.55 | C |
| ATOM | 15847 | OG | SER | B | 455 | 45.987 | 27.295 | −33.539 | 1.00 | 19.87 | O |
| ATOM | 15849 | C | SER | B | 455 | 45.937 | 28.762 | −36.975 | 1.00 | 19.31 | C |
| ATOM | 15850 | O | SER | B | 455 | 45.166 | 29.696 | −37.210 | 1.00 | 18.96 | O |
| ATOM | 15852 | N | VAL | B | 456 | 47.059 | 28.563 | −37.657 | 1.00 | 18.38 | N |
| ATOM | 15853 | CA | VAL | B | 456 | 47.493 | 29.488 | −38.689 | 1.00 | 17.04 | C |
| ATOM | 15855 | CB | VAL | B | 456 | 48.949 | 29.247 | −39.087 | 1.00 | 17.08 | C |
| ATOM | 15857 | CG1 | VAL | B | 456 | 49.373 | 30.233 | −40.169 | 1.00 | 13.96 | C |
| ATOM | 15861 | CG2 | VAL | B | 456 | 49.839 | 29.366 | −37.870 | 1.00 | 13.64 | C |
| ATOM | 15865 | C | VAL | B | 456 | 46.624 | 29.343 | −39.905 | 1.00 | 17.23 | C |
| ATOM | 15866 | O | VAL | B | 456 | 46.222 | 30.331 | −40.501 | 1.00 | 18.52 | O |
| ATOM | 15868 | N | SER | B | 457 | 46.338 | 28.101 | −40.271 | 1.00 | 17.87 | N |
| ATOM | 15869 | CA | SER | B | 457 | 45.474 | 27.813 | −41.410 | 1.00 | 17.55 | C |
| ATOM | 15871 | CB | SER | B | 457 | 45.343 | 26.303 | −41.598 | 1.00 | 17.69 | C |
| ATOM | 15874 | OG | SER | B | 457 | 44.401 | 26.015 | −42.611 | 1.00 | 17.14 | O |
| ATOM | 15876 | C | SER | B | 457 | 44.095 | 28.399 | −41.196 | 1.00 | 17.12 | C |
| ATOM | 15877 | O | SER | B | 457 | 43.455 | 28.863 | −42.120 | 1.00 | 16.99 | O |
| ATOM | 15879 | N | CYS | B | 458 | 43.652 | 28.358 | −39.951 | 1.00 | 18.30 | N |
| ATOM | 15880 | CA | CYS | B | 458 | 42.337 | 28.823 | −39.568 | 1.00 | 18.96 | C |
| ATOM | 15882 | CB | CYS | B | 458 | 42.030 | 28.310 | −38.159 | 1.00 | 19.74 | C |
| ATOM | 15885 | SG | CYS | B | 458 | 40.316 | 28.094 | −37.856 | 1.00 | 21.97 | S |
| ATOM | 15887 | C | CYS | B | 458 | 42.280 | 30.345 | −39.602 | 1.00 | 17.64 | C |
| ATOM | 15888 | O | CYS | B | 458 | 41.287 | 30.930 | −40.011 | 1.00 | 17.38 | O |
| ATOM | 15890 | N | TYR | B | 459 | 43.356 | 30.978 | −39.157 | 1.00 | 17.81 | N |
| ATOM | 15891 | CA | TYR | B | 459 | 43.463 | 32.427 | −39.203 | 1.00 | 18.66 | C |
| ATOM | 15893 | CB | TYR | B | 459 | 44.752 | 32.888 | −38.512 | 1.00 | 18.82 | C |
| ATOM | 15896 | CG | TYR | B | 459 | 44.745 | 34.329 | −38.046 | 1.00 | 19.88 | C |
| ATOM | 15897 | CD1 | TYR | B | 459 | 45.002 | 35.367 | −38.936 | 1.00 | 21.14 | C |
| ATOM | 15899 | CE1 | TYR | B | 459 | 45.008 | 36.692 | −38.516 | 1.00 | 22.60 | C |
| ATOM | 15901 | CZ | TYR | B | 459 | 44.764 | 36.990 | −37.190 | 1.00 | 22.72 | C |
| ATOM | 15902 | OH | TYR | B | 459 | 44.771 | 38.304 | −36.790 | 1.00 | 30.20 | O |
| ATOM | 15904 | CE2 | TYR | B | 459 | 44.510 | 35.979 | −36.279 | 1.00 | 20.11 | C |
| ATOM | 15906 | CD2 | TYR | B | 459 | 44.506 | 34.653 | −36.708 | 1.00 | 20.19 | C |
| ATOM | 15908 | C | TYR | B | 459 | 43.410 | 32.903 | −40.658 | 1.00 | 18.23 | C |
| ATOM | 15909 | O | TYR | B | 459 | 42.671 | 33.825 | −40.969 | 1.00 | 17.86 | O |
| ATOM | 15911 | N | MET | B | 460 | 44.171 | 32.257 | −41.542 | 1.00 | 18.77 | N |
| ATOM | 15912 | CA | MET | B | 460 | 44.127 | 32.549 | −42.983 | 1.00 | 19.43 | C |
| ATOM | 15914 | CB | MET | B | 460 | 44.895 | 31.502 | −43.787 | 1.00 | 20.18 | C |
| ATOM | 15917 | CG | MET | B | 460 | 46.397 | 31.555 | −43.697 | 1.00 | 22.86 | C |
| ATOM | 15920 | SD | MET | B | 460 | 47.095 | 30.222 | −44.688 | 1.00 | 27.17 | S |

APPENDIX 1-continued

| ATOM | 15921 | CE | MET | B | 460 | 46.492 | 30.645 | −46.323 | 1.00 | 13.86 | C |
|---|---|---|---|---|---|---|---|---|---|---|---|
| ATOM | 15925 | C | MET | B | 460 | 42.720 | 32.516 | −43.522 | 1.00 | 19.28 | C |
| ATOM | 15926 | O | MET | B | 460 | 42.278 | 33.450 | −44.185 | 1.00 | 19.45 | O |
| ATOM | 15928 | N | ARG | B | 461 | 42.032 | 31.410 | −43.259 | 1.00 | 19.47 | N |
| ATOM | 15929 | CA | ARG | B | 461 | 40.690 | 31.192 | −43.784 | 1.00 | 20.04 | C |
| ATOM | 15931 | CB | ARG | B | 461 | 40.285 | 29.733 | −43.598 | 1.00 | 20.96 | C |
| ATOM | 15934 | CG | ARG | B | 461 | 38.857 | 29.383 | −44.071 | 1.00 | 30.90 | C |
| ATOM | 15937 | CD | ARG | B | 461 | 38.546 | 27.881 | −43.927 | 1.00 | 38.84 | C |
| ATOM | 15940 | NE | ARG | B | 461 | 39.169 | 27.321 | −42.724 | 1.00 | 45.44 | N |
| ATOM | 15942 | CZ | ARG | B | 461 | 40.371 | 26.735 | −42.677 | 1.00 | 49.44 | C |
| ATOM | 15943 | NH1 | ARG | B | 461 | 40.841 | 26.292 | −41.509 | 1.00 | 45.70 | N |
| ATOM | 15946 | NH2 | ARG | B | 461 | 41.110 | 26.591 | −43.782 | 1.00 | 49.92 | N |
| ATOM | 15949 | C | ARG | B | 461 | 39.666 | 32.116 | −43.135 | 1.00 | 17.59 | C |
| ATOM | 15950 | O | ARG | B | 461 | 38.758 | 32.586 | −43.805 | 1.00 | 17.29 | O |
| ATOM | 15952 | N | THR | B | 462 | 39.813 | 32.370 | −41.837 | 1.00 | 16.54 | N |
| ATOM | 15953 | CA | THR | B | 462 | 38.921 | 33.284 | −41.126 | 1.00 | 15.49 | C |
| ATOM | 15955 | CB | THR | B | 462 | 39.222 | 33.309 | −39.609 | 1.00 | 15.13 | C |
| ATOM | 15957 | OG1 | THR | B | 462 | 38.948 | 32.021 | −39.058 | 1.00 | 15.06 | O |
| ATOM | 15959 | CG2 | THR | B | 462 | 38.371 | 34.337 | −38.879 | 1.00 | 9.62 | C |
| ATOM | 15963 | C | THR | B | 462 | 39.024 | 34.687 | −41.711 | 1.00 | 15.44 | C |
| ATOM | 15964 | O | THR | B | 462 | 38.003 | 35.316 | −41.987 | 1.00 | 16.12 | O |
| ATOM | 15966 | N | LYS | B | 463 | 40.256 | 35.146 | −41.929 | 1.00 | 14.96 | N |
| ATOM | 15967 | CA | LYS | B | 463 | 40.526 | 36.494 | −42.431 | 1.00 | 15.15 | C |
| ATOM | 15969 | CB | LYS | B | 463 | 41.889 | 36.976 | −41.930 | 1.00 | 15.42 | C |
| ATOM | 15972 | CG | LYS | B | 463 | 42.000 | 37.194 | −40.417 | 1.00 | 19.93 | C |
| ATOM | 15975 | CD | LYS | B | 463 | 40.751 | 37.850 | −39.816 | 1.00 | 24.60 | C |
| ATOM | 15978 | CE | LYS | B | 463 | 41.060 | 38.829 | −38.699 | 1.00 | 26.69 | C |
| ATOM | 15981 | NZ | LYS | B | 463 | 40.981 | 40.225 | −39.225 | 1.00 | 24.76 | N |
| ATOM | 15985 | C | LYS | B | 463 | 40.502 | 36.639 | −43.951 | 1.00 | 14.57 | C |
| ATOM | 15986 | O | LYS | B | 463 | 40.312 | 37.743 | −44.462 | 1.00 | 14.03 | O |
| ATOM | 15988 | N | GLY | B | 464 | 40.712 | 35.539 | −44.667 | 1.00 | 13.99 | N |
| ATOM | 15989 | CA | GLY | B | 464 | 40.841 | 35.580 | −46.120 | 1.00 | 13.37 | C |
| ATOM | 15992 | C | GLY | B | 464 | 42.142 | 36.231 | −46.542 | 1.00 | 13.27 | C |
| ATOM | 15993 | O | GLY | B | 464 | 42.172 | 37.025 | −47.471 | 1.00 | 13.56 | O |
| ATOM | 15995 | N | ILE | B | 465 | 43.221 | 35.898 | −45.847 | 1.00 | 13.64 | N |
| ATOM | 15996 | CA | ILE | B | 465 | 44.529 | 36.476 | −46.127 | 1.00 | 15.05 | C |
| ATOM | 15998 | CB | ILE | B | 465 | 45.049 | 37.332 | −44.935 | 1.00 | 15.19 | C |
| ATOM | 16000 | CG1 | ILE | B | 465 | 45.365 | 36.451 | −43.710 | 1.00 | 16.18 | C |
| ATOM | 16003 | CD1 | ILE | B | 465 | 45.741 | 37.224 | −42.451 | 1.00 | 13.60 | C |
| ATOM | 16007 | CG2 | ILE | B | 465 | 44.042 | 38.419 | −44.592 | 1.00 | 11.63 | C |
| ATOM | 16011 | C | ILE | B | 465 | 45.531 | 35.375 | −46.451 | 1.00 | 16.34 | C |
| ATOM | 16012 | O | ILE | B | 465 | 45.257 | 34.188 | −46.258 | 1.00 | 16.93 | O |
| ATOM | 16014 | N | SER | B | 466 | 46.700 | 35.779 | −46.934 | 1.00 | 17.84 | N |
| ATOM | 16015 | CA | SER | B | 466 | 47.764 | 34.835 | −47.268 | 1.00 | 18.68 | C |
| ATOM | 16017 | CB | SER | B | 466 | 48.867 | 35.535 | −48.057 | 1.00 | 18.26 | C |
| ATOM | 16020 | OG | SER | B | 466 | 49.572 | 36.448 | −47.233 | 1.00 | 18.06 | O |
| ATOM | 16022 | C | SER | B | 466 | 48.376 | 34.202 | −46.022 | 1.00 | 20.07 | C |
| ATOM | 16023 | O | SER | B | 466 | 48.154 | 34.652 | −44.894 | 1.00 | 20.37 | O |
| ATOM | 16025 | N | GLU | B | 467 | 49.169 | 33.161 | −46.246 | 1.00 | 21.18 | N |
| ATOM | 16026 | CA | GLU | B | 467 | 49.906 | 32.507 | −45.176 | 1.00 | 21.39 | C |
| ATOM | 16028 | CB | GLU | B | 467 | 50.611 | 31.260 | −45.707 | 1.00 | 21.20 | C |
| ATOM | 16031 | CG | GLU | B | 467 | 51.204 | 30.391 | −44.621 | 1.00 | 23.32 | C |
| ATOM | 16034 | CD | GLU | B | 467 | 52.011 | 29.225 | −45.150 | 1.00 | 27.21 | C |
| ATOM | 16035 | OE1 | GLU | B | 467 | 51.874 | 28.868 | −46.343 | 1.00 | 30.36 | O |
| ATOM | 16036 | OE2 | GLU | B | 467 | 52.790 | 28.663 | −44.352 | 1.00 | 30.37 | O |
| ATOM | 16037 | C | GLU | B | 467 | 50.925 | 33.444 | −44.527 | 1.00 | 22.15 | C |
| ATOM | 16038 | O | GLU | B | 467 | 51.182 | 33.347 | −43.330 | 1.00 | 23.83 | O |
| ATOM | 16040 | N | GLU | B | 468 | 51.506 | 34.346 | −45.310 | 1.00 | 22.98 | N |
| ATOM | 16041 | CA | GLU | B | 468 | 52.544 | 35.236 | −44.799 | 1.00 | 23.24 | C |
| ATOM | 16043 | CB | GLU | B | 468 | 53.245 | 35.981 | −45.938 | 1.00 | 24.25 | C |
| ATOM | 16046 | CG | GLU | B | 468 | 54.555 | 36.643 | −45.502 | 1.00 | 29.56 | C |
| ATOM | 16049 | CD | GLU | B | 468 | 55.013 | 37.781 | −46.413 | 1.00 | 35.60 | C |
| ATOM | 16050 | OE1 | GLU | B | 468 | 54.396 | 38.020 | −47.479 | 1.00 | 36.06 | O |
| ATOM | 16051 | OE2 | GLU | B | 468 | 56.009 | 38.442 | −46.046 | 1.00 | 37.98 | O |
| ATOM | 16052 | C | GLU | B | 468 | 51.966 | 36.234 | −43.801 | 1.00 | 22.22 | C |
| ATOM | 16053 | O | GLU | B | 468 | 52.568 | 36.486 | −42.758 | 1.00 | 22.43 | O |
| ATOM | 16055 | N | LEU | B | 469 | 50.806 | 36.806 | −44.118 | 1.00 | 21.75 | N |
| ATOM | 16056 | CA | LEU | B | 469 | 50.136 | 37.719 | −43.184 | 1.00 | 21.45 | C |
| ATOM | 16058 | CB | LEU | B | 469 | 49.000 | 38.494 | −43.858 | 1.00 | 22.36 | C |
| ATOM | 16061 | CG | LEU | B | 469 | 49.365 | 39.834 | −44.496 | 1.00 | 27.45 | C |
| ATOM | 16063 | CD1 | LEU | B | 469 | 49.466 | 39.726 | −46.033 | 1.00 | 30.95 | C |
| ATOM | 16067 | CD2 | LEU | B | 469 | 48.322 | 40.873 | −44.095 | 1.00 | 31.35 | C |
| ATOM | 16071 | C | LEU | B | 469 | 49.596 | 36.969 | −41.967 | 1.00 | 18.63 | C |
| ATOM | 16072 | O | LEU | B | 469 | 49.701 | 37.453 | −40.846 | 1.00 | 18.64 | O |
| ATOM | 16074 | N | ALA | B | 470 | 49.023 | 35.792 | −42.194 | 1.00 | 15.97 | N |
| ATOM | 16075 | CA | ALA | B | 470 | 48.534 | 34.959 | −41.101 | 1.00 | 15.14 | C |
| ATOM | 16077 | CB | ALA | B | 470 | 47.952 | 33.667 | −41.637 | 1.00 | 15.02 | C |
| ATOM | 16081 | C | ALA | B | 470 | 49.653 | 34.658 | −40.118 | 1.00 | 14.59 | C |
| ATOM | 16082 | O | ALA | B | 470 | 49.449 | 34.702 | −38.900 | 1.00 | 12.83 | O |
| ATOM | 16084 | N | THR | B | 471 | 50.835 | 34.364 | −40.657 | 1.00 | 14.22 | N |

APPENDIX 1-continued

| | | | | | | | | | | |
|---|---|---|---|---|---|---|---|---|---|---|
| ATOM | 16085 | CA | THR | B | 471 | 51.995 | 34.038 | −39.836 | 1.00 | 14.86 | C |
| ATOM | 16087 | CB | THR | B | 471 | 53.167 | 33.512 | −40.706 | 1.00 | 14.55 | C |
| ATOM | 16089 | OG1 | THR | B | 471 | 52.731 | 32.360 | −41.437 | 1.00 | 13.22 | O |
| ATOM | 16091 | CG2 | THR | B | 471 | 54.361 | 33.127 | −39.846 | 1.00 | 8.88 | C |
| ATOM | 16095 | C | THR | B | 471 | 52.416 | 35.255 | −39.004 | 1.00 | 15.80 | C |
| ATOM | 16096 | O | THR | B | 471 | 52.566 | 35.172 | −37.781 | 1.00 | 15.84 | O |
| ATOM | 16098 | N | GLU | B | 472 | 52.566 | 36.386 | −39.677 | 1.00 | 16.48 | N |
| ATOM | 16099 | CA | GLU | B | 472 | 52.859 | 37.656 | −39.019 | 1.00 | 17.64 | C |
| ATOM | 16101 | CB | GLU | B | 472 | 52.844 | 38.782 | −40.061 | 1.00 | 18.33 | C |
| ATOM | 16104 | CG | GLU | B | 472 | 53.379 | 40.109 | −39.564 | 1.00 | 25.22 | C |
| ATOM | 16107 | CD | GLU | B | 472 | 53.249 | 41.204 | −40.605 | 1.00 | 33.82 | C |
| ATOM | 16108 | OE1 | GLU | B | 472 | 53.894 | 41.092 | −41.674 | 1.00 | 37.62 | O |
| ATOM | 16109 | OE2 | GLU | B | 472 | 52.496 | 42.172 | −40.352 | 1.00 | 36.62 | O |
| ATOM | 16110 | C | GLU | B | 472 | 51.861 | 37.955 | −37.888 | 1.00 | 16.57 | C |
| ATOM | 16111 | O | GLU | B | 472 | 52.259 | 38.242 | −36.762 | 1.00 | 16.22 | O |
| ATOM | 16113 | N | SER | B | 473 | 50.569 | 37.880 | −38.201 | 1.00 | 16.11 | N |
| ATOM | 16114 | CA | SER | B | 473 | 49.511 | 38.127 | −37.222 | 1.00 | 15.94 | C |
| ATOM | 16116 | CB | SER | B | 473 | 48.135 | 37.974 | −37.872 | 1.00 | 16.19 | C |
| ATOM | 16119 | OG | SER | B | 473 | 47.989 | 38.830 | −38.993 | 1.00 | 18.75 | O |
| ATOM | 16121 | C | SER | B | 473 | 49.599 | 37.193 | −36.014 | 1.00 | 15.73 | C |
| ATOM | 16122 | O | SER | B | 473 | 49.345 | 37.611 | −34.887 | 1.00 | 14.53 | O |
| ATOM | 16124 | N | VAL | B | 474 | 49.951 | 35.931 | −36.253 | 1.00 | 16.02 | N |
| ATOM | 16125 | CA | VAL | B | 474 | 50.108 | 34.963 | −35.165 | 1.00 | 16.14 | C |
| ATOM | 16127 | CB | VAL | B | 474 | 50.140 | 33.502 | −35.684 | 1.00 | 15.37 | C |
| ATOM | 16129 | CG1 | VAL | B | 474 | 50.594 | 32.561 | −34.601 | 1.00 | 13.08 | C |
| ATOM | 16133 | CG2 | VAL | B | 474 | 48.767 | 33.087 | −36.191 | 1.00 | 11.54 | C |
| ATOM | 16137 | C | VAL | B | 474 | 51.358 | 35.278 | −34.335 | 1.00 | 17.47 | C |
| ATOM | 16138 | O | VAL | B | 474 | 51.377 | 35.038 | −33.130 | 1.00 | 17.05 | O |
| ATOM | 16140 | N | MET | B | 475 | 52.386 | 35.842 | −34.962 | 1.00 | 18.50 | N |
| ATOM | 16141 | CA | MET | B | 475 | 53.573 | 36.251 | −34.217 | 1.00 | 20.29 | C |
| ATOM | 16143 | CB | MET | B | 475 | 54.699 | 36.692 | −35.143 | 1.00 | 22.08 | C |
| ATOM | 16146 | CG | MET | B | 475 | 55.071 | 35.707 | −36.231 | 1.00 | 28.44 | C |
| ATOM | 16149 | SD | MET | B | 475 | 56.648 | 34.919 | −35.969 | 1.00 | 42.67 | S |
| ATOM | 16150 | CE | MET | B | 475 | 57.367 | 35.163 | −37.600 | 1.00 | 30.81 | C |
| ATOM | 16154 | C | MET | B | 475 | 53.218 | 37.417 | −33.316 | 1.00 | 19.92 | C |
| ATOM | 16155 | O | MET | B | 475 | 53.605 | 37.442 | −32.152 | 1.00 | 19.67 | O |
| ATOM | 16157 | N | ASN | B | 476 | 52.494 | 38.390 | −33.865 | 1.00 | 20.28 | N |
| ATOM | 16158 | CA | ASN | B | 476 | 52.129 | 39.587 | −33.107 | 1.00 | 21.78 | C |
| ATOM | 16160 | CB | ASN | B | 476 | 51.343 | 40.578 | −33.972 | 1.00 | 22.56 | C |
| ATOM | 16163 | CG | ASN | B | 476 | 52.223 | 41.316 | −34.981 | 1.00 | 27.45 | C |
| ATOM | 16164 | OD1 | ASN | B | 476 | 53.423 | 41.517 | −34.765 | 1.00 | 34.13 | O |
| ATOM | 16165 | ND2 | ASN | B | 476 | 51.617 | 41.737 | −36.086 | 1.00 | 32.95 | N |
| ATOM | 16168 | C | ASN | B | 476 | 51.308 | 39.202 | −31.895 | 1.00 | 21.47 | C |
| ATOM | 16169 | O | ASN | B | 476 | 51.488 | 39.739 | −30.802 | 1.00 | 21.39 | O |
| ATOM | 16171 | N | LEU | B | 477 | 50.426 | 38.236 | −32.107 | 1.00 | 21.52 | N |
| ATOM | 16172 | CA | LEU | B | 477 | 49.550 | 37.741 | −31.072 | 1.00 | 21.65 | C |
| ATOM | 16174 | CB | LEU | B | 477 | 48.575 | 36.737 | −31.688 | 1.00 | 21.80 | C |
| ATOM | 16177 | CG | LEU | B | 477 | 47.298 | 36.403 | −30.921 | 1.00 | 29.34 | C |
| ATOM | 16179 | CD1 | LEU | B | 477 | 46.655 | 37.641 | −30.283 | 1.00 | 31.33 | C |
| ATOM | 16183 | CD2 | LEU | B | 477 | 46.323 | 35.697 | −31.869 | 1.00 | 33.64 | C |
| ATOM | 16187 | C | LEU | B | 477 | 50.364 | 37.123 | −29.934 | 1.00 | 21.00 | C |
| ATOM | 16188 | O | LEU | B | 477 | 50.038 | 37.292 | −28.758 | 1.00 | 21.26 | O |
| ATOM | 16190 | N | ILE | B | 478 | 51.437 | 36.425 | −30.285 | 1.00 | 20.88 | N |
| ATOM | 16191 | CA | ILE | B | 478 | 52.343 | 35.874 | −29.286 | 1.00 | 20.29 | C |
| ATOM | 16193 | CB | ILE | B | 478 | 53.399 | 34.962 | −29.912 | 1.00 | 20.06 | C |
| ATOM | 16195 | CG1 | ILE | B | 478 | 52.766 | 33.659 | −30.399 | 1.00 | 19.03 | C |
| ATOM | 16198 | CD1 | ILE | B | 478 | 53.701 | 32.844 | −31.280 | 1.00 | 18.48 | C |
| ATOM | 16202 | CG2 | ILE | B | 478 | 54.495 | 34.670 | −28.906 | 1.00 | 19.59 | C |
| ATOM | 16206 | C | ILE | B | 478 | 53.066 | 36.986 | −28.538 | 1.00 | 20.55 | C |
| ATOM | 16207 | O | ILE | B | 478 | 53.236 | 36.890 | −27.322 | 1.00 | 20.34 | O |
| ATOM | 16209 | N | ASP | B | 479 | 53.501 | 38.027 | −29.256 | 1.00 | 19.49 | N |
| ATOM | 16210 | CA | ASP | B | 479 | 54.169 | 39.154 | −28.607 | 1.00 | 20.02 | C |
| ATOM | 16212 | CB | ASP | B | 479 | 54.598 | 40.246 | −29.606 | 1.00 | 20.61 | C |
| ATOM | 16215 | CG | ASP | B | 479 | 55.757 | 39.820 | −30.510 | 1.00 | 21.25 | C |
| ATOM | 16216 | OD1 | ASP | B | 479 | 56.768 | 39.298 | −30.012 | 1.00 | 22.48 | O |
| ATOM | 16217 | OD2 | ASP | B | 479 | 55.664 | 40.030 | −31.737 | 1.00 | 29.16 | O |
| ATOM | 16218 | C | ASP | B | 479 | 53.227 | 39.755 | −27.573 | 1.00 | 19.47 | C |
| ATOM | 16219 | O | ASP | B | 479 | 53.639 | 40.102 | −26.469 | 1.00 | 18.58 | O |
| ATOM | 16221 | N | GLU | B | 480 | 51.954 | 39.850 | −27.938 | 1.00 | 19.80 | N |
| ATOM | 16222 | CA | GLU | B | 480 | 50.950 | 40.490 | −27.091 | 1.00 | 20.52 | C |
| ATOM | 16224 | CB | GLU | B | 480 | 49.684 | 40.776 | −27.913 | 1.00 | 21.52 | C |
| ATOM | 16227 | CG | GLU | B | 480 | 49.022 | 42.120 | −27.642 | 1.00 | 28.59 | C |
| ATOM | 16230 | CD | GLU | B | 480 | 49.917 | 43.311 | −27.957 | 1.00 | 36.32 | C |
| ATOM | 16231 | OE1 | GLU | B | 480 | 50.734 | 43.236 | −28.904 | 1.00 | 39.57 | O |
| ATOM | 16232 | OE2 | GLU | B | 480 | 49.802 | 44.330 | −27.242 | 1.00 | 40.57 | O |
| ATOM | 16233 | C | GLU | B | 480 | 50.635 | 39.609 | −25.877 | 1.00 | 19.60 | C |
| ATOM | 16234 | O | GLU | B | 480 | 50.439 | 40.111 | −24.762 | 1.00 | 19.00 | O |
| ATOM | 16236 | N | THR | B | 481 | 50.602 | 38.296 | −26.093 | 1.00 | 18.24 | N |
| ATOM | 16237 | CA | THR | B | 481 | 50.408 | 37.352 | −25.001 | 1.00 | 17.14 | C |
| ATOM | 16239 | CB | THR | B | 481 | 50.282 | 35.920 | −25.517 | 1.00 | 17.51 | C |

APPENDIX 1-continued

| | | | | | | | | | | |
|---|---|---|---|---|---|---|---|---|---|---|
| ATOM | 16241 | OG1 | THR | B | 481 | 49.198 | 35.852 | −26.454 | 1.00 | 17.24 | O |
| ATOM | 16243 | CG2 | THR | B | 481 | 50.038 | 34.943 | −24.357 | 1.00 | 12.60 | C |
| ATOM | 16247 | C | THR | B | 481 | 51.560 | 37.436 | −24.000 | 1.00 | 17.65 | C |
| ATOM | 16248 | O | THR | B | 481 | 51.330 | 37.380 | −22.790 | 1.00 | 18.63 | O |
| ATOM | 16250 | N | TRP | B | 482 | 52.788 | 37.592 | −24.500 | 1.00 | 16.03 | N |
| ATOM | 16251 | CA | TRP | B | 482 | 53.949 | 37.758 | −23.623 | 1.00 | 15.61 | C |
| ATOM | 16253 | CB | TRP | B | 482 | 55.267 | 37.743 | −24.412 | 1.00 | 16.18 | C |
| ATOM | 16256 | CG | TRP | B | 482 | 55.862 | 36.380 | −24.503 | 1.00 | 12.24 | C |
| ATOM | 16257 | CD1 | TRP | B | 482 | 55.688 | 35.486 | −25.505 | 1.00 | 17.04 | C |
| ATOM | 16259 | NE1 | TRP | B | 482 | 56.373 | 34.329 | −25.237 | 1.00 | 18.27 | N |
| ATOM | 16261 | CE2 | TRP | B | 482 | 57.006 | 34.460 | −24.033 | 1.00 | 16.69 | C |
| ATOM | 16262 | CD2 | TRP | B | 482 | 56.706 | 35.748 | −23.542 | 1.00 | 13.90 | C |
| ATOM | 16263 | CE3 | TRP | B | 482 | 57.239 | 36.141 | −22.309 | 1.00 | 19.79 | C |
| ATOM | 16265 | CZ3 | TRP | B | 482 | 58.048 | 35.239 | −21.609 | 1.00 | 19.61 | C |
| ATOM | 16267 | CH2 | TRP | B | 482 | 58.335 | 33.963 | −22.134 | 1.00 | 19.45 | C |
| ATOM | 16269 | CZ2 | TRP | B | 482 | 57.820 | 33.557 | −23.339 | 1.00 | 16.58 | C |
| ATOM | 16271 | C | TRP | B | 482 | 53.844 | 39.020 | −22.775 | 1.00 | 15.85 | C |
| ATOM | 16272 | O | TRP | B | 482 | 54.053 | 38.972 | −21.566 | 1.00 | 16.02 | O |
| ATOM | 16274 | N | LYS | B | 483 | 53.508 | 40.143 | −23.403 | 1.00 | 16.63 | N |
| ATOM | 16275 | CA | LYS | B | 483 | 53.289 | 41.382 | −22.666 | 1.00 | 16.51 | C |
| ATOM | 16277 | CB | LYS | B | 483 | 52.685 | 42.459 | −23.555 | 1.00 | 16.85 | C |
| ATOM | 16280 | CG | LYS | B | 483 | 53.622 | 43.028 | −24.597 | 1.00 | 17.06 | C |
| ATOM | 16283 | CD | LYS | B | 483 | 53.017 | 44.249 | −25.266 | 1.00 | 17.24 | C |
| ATOM | 16286 | CE | LYS | B | 483 | 53.793 | 44.650 | −26.519 | 1.00 | 19.91 | C |
| ATOM | 16289 | NZ | LYS | B | 483 | 53.361 | 45.964 | −27.077 | 1.00 | 17.47 | N |
| ATOM | 16293 | C | LYS | B | 483 | 52.371 | 41.135 | −21.479 | 1.00 | 18.03 | C |
| ATOM | 16294 | O | LYS | B | 483 | 52.665 | 41.569 | −20.367 | 1.00 | 20.06 | O |
| ATOM | 16296 | N | LYS | B | 484 | 51.275 | 40.415 | −21.703 | 1.00 | 18.71 | N |
| ATOM | 16297 | CA | LYS | B | 484 | 50.311 | 40.144 | −20.624 | 1.00 | 18.89 | C |
| ATOM | 16299 | CB | LYS | B | 484 | 48.990 | 39.626 | −21.201 | 1.00 | 19.16 | C |
| ATOM | 16302 | CG | LYS | B | 484 | 48.181 | 40.722 | −21.895 | 1.00 | 18.50 | C |
| ATOM | 16305 | CD | LYS | B | 484 | 46.984 | 40.151 | −22.621 | 1.00 | 20.68 | C |
| ATOM | 16308 | CE | LYS | B | 484 | 46.186 | 41.211 | −23.370 | 1.00 | 23.96 | C |
| ATOM | 16311 | NZ | LYS | B | 484 | 45.464 | 40.617 | −24.542 | 1.00 | 28.47 | N |
| ATOM | 16315 | C | LYS | B | 484 | 50.854 | 39.205 | −19.533 | 1.00 | 18.92 | C |
| ATOM | 16316 | O | LYS | B | 484 | 50.587 | 39.417 | −18.352 | 1.00 | 19.71 | O |
| ATOM | 16318 | N | MET | B | 485 | 51.618 | 38.185 | −19.926 | 1.00 | 18.18 | N |
| ATOM | 16319 | CA | MET | B | 485 | 52.302 | 37.315 | −18.965 | 1.00 | 17.49 | C |
| ATOM | 16321 | CB | MET | B | 485 | 53.084 | 36.211 | −19.673 | 1.00 | 17.28 | C |
| ATOM | 16324 | CG | MET | B | 485 | 52.227 | 35.249 | −20.462 | 1.00 | 19.16 | C |
| ATOM | 16327 | SD | MET | B | 485 | 53.072 | 33.713 | −20.826 | 1.00 | 16.74 | S |
| ATOM | 16328 | CE | MET | B | 485 | 54.442 | 34.310 | −21.800 | 1.00 | 16.94 | C |
| ATOM | 16332 | C | MET | B | 485 | 53.280 | 38.111 | −18.123 | 1.00 | 18.05 | C |
| ATOM | 16333 | O | MET | B | 485 | 53.380 | 37.899 | −16.917 | 1.00 | 19.44 | O |
| ATOM | 16335 | N | ASN | B | 486 | 54.012 | 39.013 | −18.768 | 1.00 | 17.71 | N |
| ATOM | 16336 | CA | ASN | B | 486 | 54.960 | 39.865 | −18.071 | 1.00 | 17.79 | C |
| ATOM | 16338 | CB | ASN | B | 486 | 55.627 | 40.842 | −19.045 | 1.00 | 18.13 | C |
| ATOM | 16341 | CG | ASN | B | 486 | 56.576 | 40.153 | −20.024 | 1.00 | 18.10 | C |
| ATOM | 16342 | OD1 | ASN | B | 486 | 57.168 | 39.115 | −19.717 | 1.00 | 16.50 | O |
| ATOM | 16343 | ND2 | ASN | B | 486 | 56.742 | 40.751 | −21.203 | 1.00 | 9.57 | N |
| ATOM | 16346 | C | ASN | B | 486 | 54.294 | 40.635 | −16.935 | 1.00 | 18.50 | C |
| ATOM | 16347 | O | ASN | B | 486 | 54.877 | 40.774 | −15.859 | 1.00 | 17.83 | O |
| ATOM | 16349 | N | LYS | B | 487 | 53.072 | 41.117 | −17.173 | 1.00 | 19.57 | N |
| ATOM | 16350 | CA | LYS | B | 487 | 52.323 | 41.883 | −16.164 | 1.00 | 20.63 | C |
| ATOM | 16352 | CB | LYS | B | 487 | 51.088 | 42.531 | −16.791 | 1.00 | 20.49 | C |
| ATOM | 16355 | CG | LYS | B | 487 | 50.358 | 43.492 | −15.862 | 1.00 | 21.89 | C |
| ATOM | 16358 | CD | LYS | B | 487 | 49.409 | 44.401 | −16.629 | 1.00 | 24.87 | C |
| ATOM | 16361 | CE | LYS | B | 487 | 48.680 | 45.379 | −15.704 | 1.00 | 29.00 | C |
| ATOM | 16364 | NZ | LYS | B | 487 | 47.418 | 45.917 | −16.325 | 1.00 | 28.97 | N |
| ATOM | 16368 | C | LYS | B | 487 | 51.893 | 41.014 | −14.981 | 1.00 | 21.34 | C |
| ATOM | 16369 | O | LYS | B | 487 | 52.018 | 41.416 | −13.822 | 1.00 | 20.66 | O |
| ATOM | 16371 | N | GLU | B | 488 | 51.384 | 39.827 | −15.287 | 1.00 | 22.31 | N |
| ATOM | 16372 | CA | GLU | B | 488 | 50.997 | 38.858 | −14.268 | 1.00 | 23.77 | C |
| ATOM | 16374 | CB | GLU | B | 488 | 50.461 | 37.592 | −14.940 | 1.00 | 24.98 | C |
| ATOM | 16377 | CG | GLU | B | 488 | 49.890 | 36.543 | −13.991 | 1.00 | 31.46 | C |
| ATOM | 16380 | CD | GLU | B | 488 | 48.678 | 37.032 | −13.224 | 1.00 | 37.56 | C |
| ATOM | 16381 | OE1 | GLU | B | 488 | 47.955 | 37.915 | −13.739 | 1.00 | 41.02 | O |
| ATOM | 16382 | OE2 | GLU | B | 488 | 48.449 | 36.518 | −12.105 | 1.00 | 41.97 | O |
| ATOM | 16383 | C | GLU | B | 488 | 52.171 | 38.508 | −13.345 | 1.00 | 22.92 | C |
| ATOM | 16384 | O | GLU | B | 488 | 52.000 | 38.420 | −12.133 | 1.00 | 24.11 | O |
| ATOM | 16386 | N | LYS | B | 489 | 53.354 | 38.308 | −13.919 | 1.00 | 21.63 | N |
| ATOM | 16387 | CA | LYS | B | 489 | 54.539 | 37.972 | −13.133 | 1.00 | 22.22 | C |
| ATOM | 16389 | CB | LYS | B | 489 | 55.699 | 37.552 | −14.051 | 1.00 | 21.37 | C |
| ATOM | 16392 | CG | LYS | B | 489 | 57.023 | 37.253 | −13.338 | 1.00 | 21.61 | C |
| ATOM | 16395 | CD | LYS | B | 489 | 56.891 | 36.139 | −12.298 | 1.00 | 23.04 | C |
| ATOM | 16398 | CE | LYS | B | 489 | 58.166 | 35.927 | −11.489 | 1.00 | 23.96 | C |
| ATOM | 16401 | NZ | LYS | B | 489 | 59.345 | 35.655 | −12.343 | 1.00 | 26.89 | N |
| ATOM | 16405 | C | LYS | B | 489 | 54.975 | 39.145 | −12.257 | 1.00 | 22.89 | C |
| ATOM | 16406 | O | LYS | B | 489 | 55.447 | 38.951 | −11.138 | 1.00 | 22.65 | O |
| ATOM | 16408 | N | LEU | B | 490 | 54.797 | 40.354 | −12.780 | 1.00 | 24.17 | N |

APPENDIX 1-continued

| | | | | | | | | | | |
|---|---|---|---|---|---|---|---|---|---|---|
| ATOM | 16409 | CA | LEU | B | 490 | 55.322 | 41.566 | −12.174 | 1.00 | 25.54 | C |
| ATOM | 16411 | CB | LEU | B | 490 | 55.631 | 42.565 | −13.287 | 1.00 | 25.27 | C |
| ATOM | 16414 | CG | LEU | B | 490 | 56.331 | 43.868 | −12.950 | 1.00 | 25.47 | C |
| ATOM | 16416 | CD1 | LEU | B | 490 | 57.620 | 43.616 | −12.200 | 1.00 | 29.26 | C |
| ATOM | 16420 | CD2 | LEU | B | 490 | 56.605 | 44.607 | −14.243 | 1.00 | 27.84 | C |
| ATOM | 16424 | C | LEU | B | 490 | 54.342 | 42.143 | −11.143 | 1.00 | 27.20 | C |
| ATOM | 16425 | O | LEU | B | 490 | 54.669 | 42.254 | −9.970 | 1.00 | 26.26 | O |
| ATOM | 16427 | N | SER | B | 491 | 53.142 | 42.497 | −11.592 | 1.00 | 30.29 | N |
| ATOM | 16428 | CA | SER | B | 491 | 52.039 | 42.867 | −10.706 | 1.00 | 32.69 | C |
| ATOM | 16430 | CB | SER | B | 491 | 51.104 | 43.840 | −11.416 | 1.00 | 32.26 | C |
| ATOM | 16433 | OG | SER | B | 491 | 51.842 | 44.739 | −12.226 | 1.00 | 34.32 | O |
| ATOM | 16435 | C | SER | B | 491 | 51.325 | 41.560 | −10.390 | 1.00 | 35.71 | C |
| ATOM | 16436 | O | SER | B | 491 | 51.961 | 40.513 | −10.370 | 1.00 | 38.56 | O |
| ATOM | 16438 | N | GLY | B | 492 | 50.016 | 41.586 | −10.163 | 1.00 | 37.35 | N |
| ATOM | 16439 | CA | GLY | B | 492 | 49.259 | 40.328 | −10.115 | 1.00 | 38.82 | C |
| ATOM | 16442 | C | GLY | B | 492 | 49.400 | 39.660 | −8.765 | 1.00 | 39.55 | C |
| ATOM | 16443 | O | GLY | B | 492 | 50.502 | 39.521 | −8.243 | 1.00 | 39.41 | O |
| ATOM | 16445 | N | SER | B | 493 | 48.274 | 39.227 | −8.211 | 1.00 | 41.09 | N |
| ATOM | 16446 | CA | SER | B | 493 | 48.170 | 38.994 | −6.772 | 1.00 | 41.98 | C |
| ATOM | 16448 | CB | SER | B | 493 | 47.344 | 40.129 | −6.155 | 1.00 | 41.97 | C |
| ATOM | 16451 | OG | SER | B | 493 | 46.005 | 40.082 | −6.622 | 1.00 | 41.03 | O |
| ATOM | 16453 | C | SER | B | 493 | 47.532 | 37.669 | −6.365 | 1.00 | 42.25 | C |
| ATOM | 16454 | O | SER | B | 493 | 47.214 | 37.486 | −5.187 | 1.00 | 43.88 | O |
| ATOM | 16456 | N | LEU | B | 494 | 47.336 | 36.748 | −7.302 | 1.00 | 41.48 | N |
| ATOM | 16457 | CA | LEU | B | 494 | 46.654 | 35.509 | −6.960 | 1.00 | 41.11 | C |
| ATOM | 16459 | CB | LEU | B | 494 | 45.665 | 35.113 | −8.052 | 1.00 | 42.32 | C |
| ATOM | 16462 | CG | LEU | B | 494 | 44.604 | 34.100 | −7.610 | 1.00 | 46.31 | C |
| ATOM | 16464 | CD1 | LEU | B | 494 | 43.966 | 34.473 | −6.272 | 1.00 | 50.47 | C |
| ATOM | 16468 | CD2 | LEU | B | 494 | 43.549 | 33.969 | −8.685 | 1.00 | 49.74 | C |
| ATOM | 16472 | C | LEU | B | 494 | 47.635 | 34.381 | −6.653 | 1.00 | 38.89 | C |
| ATOM | 16473 | O | LEU | B | 494 | 47.708 | 33.920 | −5.513 | 1.00 | 39.50 | O |
| ATOM | 16475 | N | PHE | B | 495 | 48.399 | 33.951 | −7.653 | 1.00 | 36.02 | N |
| ATOM | 16476 | CA | PHE | B | 495 | 49.338 | 32.845 | −7.472 | 1.00 | 33.50 | C |
| ATOM | 16478 | CB | PHE | B | 495 | 49.496 | 32.044 | −8.765 | 1.00 | 33.01 | C |
| ATOM | 16481 | CG | PHE | B | 495 | 48.244 | 31.366 | −9.213 | 1.00 | 30.25 | C |
| ATOM | 16482 | CD1 | PHE | B | 495 | 47.968 | 30.070 | −8.824 | 1.00 | 26.23 | C |
| ATOM | 16484 | CE1 | PHE | B | 495 | 46.812 | 29.435 | −9.244 | 1.00 | 29.38 | C |
| ATOM | 16486 | CZ | PHE | B | 495 | 45.911 | 30.099 | −10.063 | 1.00 | 30.71 | C |
| ATOM | 16488 | CE2 | PHE | B | 495 | 46.174 | 31.397 | −10.458 | 1.00 | 31.82 | C |
| ATOM | 16490 | CD2 | PHE | B | 495 | 47.339 | 32.025 | −10.033 | 1.00 | 30.88 | C |
| ATOM | 16492 | C | PHE | B | 495 | 50.701 | 33.340 | −7.020 | 1.00 | 31.74 | C |
| ATOM | 16493 | O | PHE | B | 495 | 51.091 | 34.465 | −7.308 | 1.00 | 29.96 | O |
| ATOM | 16495 | N | ALA | B | 496 | 51.426 | 32.474 | −6.319 | 1.00 | 31.59 | N |
| ATOM | 16496 | CA | ALA | B | 496 | 52.781 | 32.785 | −5.884 | 1.00 | 31.49 | C |
| ATOM | 16498 | CB | ALA | B | 496 | 53.264 | 31.747 | −4.882 | 1.00 | 31.51 | C |
| ATOM | 16502 | C | ALA | B | 496 | 53.719 | 32.855 | −7.092 | 1.00 | 30.52 | C |
| ATOM | 16503 | O | ALA | B | 496 | 53.483 | 32.208 | −8.115 | 1.00 | 29.70 | O |
| ATOM | 16505 | N | LYS | B | 497 | 54.779 | 33.649 | −6.967 | 1.00 | 29.89 | N |
| ATOM | 16506 | CA | LYS | B | 497 | 55.707 | 33.861 | −8.075 | 1.00 | 30.53 | C |
| ATOM | 16508 | CB | LYS | B | 497 | 56.777 | 34.902 | −7.707 | 1.00 | 31.65 | C |
| ATOM | 16511 | CG | LYS | B | 497 | 56.223 | 36.336 | −7.603 | 1.00 | 37.13 | C |
| ATOM | 16514 | CD | LYS | B | 497 | 57.329 | 37.397 | −7.715 | 1.00 | 43.09 | C |
| ATOM | 16517 | CE | LYS | B | 497 | 56.742 | 38.806 | −7.904 | 1.00 | 48.67 | C |
| ATOM | 16520 | NZ | LYS | B | 497 | 57.647 | 39.736 | −8.665 | 1.00 | 50.69 | N |
| ATOM | 16524 | C | LYS | B | 497 | 56.348 | 32.566 | −8.613 | 1.00 | 28.82 | C |
| ATOM | 16525 | O | LYS | B | 497 | 56.487 | 32.417 | −9.834 | 1.00 | 28.95 | O |
| ATOM | 16527 | N | PRO | B | 498 | 56.713 | 31.619 | −7.724 | 1.00 | 26.35 | N |
| ATOM | 16528 | CA | PRO | B | 498 | 57.282 | 30.362 | −8.229 | 1.00 | 25.10 | C |
| ATOM | 16530 | CB | PRO | B | 498 | 57.481 | 29.525 | −6.957 | 1.00 | 24.98 | C |
| ATOM | 16533 | CG | PRO | B | 498 | 57.611 | 30.517 | −5.873 | 1.00 | 24.86 | C |
| ATOM | 16536 | CD | PRO | B | 498 | 56.685 | 31.641 | −6.252 | 1.00 | 25.79 | C |
| ATOM | 16539 | C | PRO | B | 498 | 56.383 | 29.619 | −9.219 | 1.00 | 23.70 | C |
| ATOM | 16540 | O | PRO | B | 498 | 56.887 | 29.017 | −10.162 | 1.00 | 23.87 | O |
| ATOM | 16541 | N | PHE | B | 499 | 55.069 | 29.659 | −9.006 | 1.00 | 22.74 | N |
| ATOM | 16542 | CA | PHE | B | 499 | 54.141 | 29.015 | −9.928 | 1.00 | 21.67 | C |
| ATOM | 16544 | CB | PHE | B | 499 | 52.787 | 28.746 | −9.271 | 1.00 | 21.16 | C |
| ATOM | 16547 | CG | PHE | B | 499 | 51.789 | 28.128 | −10.209 | 1.00 | 20.10 | C |
| ATOM | 16548 | CD1 | PHE | B | 499 | 51.976 | 26.845 | −10.681 | 1.00 | 17.88 | C |
| ATOM | 16550 | CE1 | PHE | B | 499 | 51.084 | 26.281 | −11.570 | 1.00 | 18.25 | C |
| ATOM | 16552 | CZ | PHE | B | 499 | 49.992 | 27.002 | −11.997 | 1.00 | 16.84 | C |
| ATOM | 16554 | CE2 | PHE | B | 499 | 49.798 | 28.282 | −11.536 | 1.00 | 18.24 | C |
| ATOM | 16556 | CD2 | PHE | B | 499 | 50.698 | 28.844 | −10.655 | 1.00 | 19.01 | C |
| ATOM | 16558 | C | PHE | B | 499 | 53.955 | 29.831 | −11.215 | 1.00 | 21.85 | C |
| ATOM | 16559 | O | PHE | B | 499 | 53.889 | 29.266 | −12.311 | 1.00 | 20.84 | O |
| ATOM | 16561 | N | VAL | B | 500 | 53.875 | 31.154 | −11.080 | 1.00 | 22.14 | N |
| ATOM | 16562 | CA | VAL | B | 500 | 53.711 | 32.033 | −12.244 | 1.00 | 20.94 | C |
| ATOM | 16564 | CB | VAL | B | 500 | 53.614 | 33.507 | −11.833 | 1.00 | 21.12 | C |
| ATOM | 16566 | CG1 | VAL | B | 500 | 53.488 | 34.401 | −13.066 | 1.00 | 17.61 | C |
| ATOM | 16570 | CG2 | VAL | B | 500 | 52.425 | 33.717 | −10.887 | 1.00 | 21.31 | C |
| ATOM | 16574 | C | VAL | B | 500 | 54.869 | 31.843 | −13.217 | 1.00 | 21.15 | C |

APPENDIX 1-continued

| ATOM | 16575 | O | VAL | B | 500 | 54.672 | 31.808 | −14.429 | 1.00 | 22.48 | O |
|---|---|---|---|---|---|---|---|---|---|---|---|
| ATOM | 16577 | N | GLU | B | 501 | 56.074 | 31.689 | −12.683 | 1.00 | 21.08 | N |
| ATOM | 16578 | CA | GLU | B | 501 | 57.246 | 31.446 | −13.510 | 1.00 | 20.88 | C |
| ATOM | 16580 | CB | GLU | B | 501 | 58.513 | 31.652 | −12.677 | 1.00 | 22.06 | C |
| ATOM | 16583 | CG | GLU | B | 501 | 59.818 | 31.655 | −13.477 | 1.00 | 23.77 | C |
| ATOM | 16586 | CD | GLU | B | 501 | 60.053 | 32.939 | −14.246 | 1.00 | 25.66 | C |
| ATOM | 16587 | OE1 | GLU | B | 501 | 59.226 | 33.870 | −14.167 | 1.00 | 25.29 | O |
| ATOM | 16588 | OE2 | GLU | B | 501 | 61.089 | 33.019 | −14.934 | 1.00 | 29.65 | O |
| ATOM | 16589 | C | GLU | B | 501 | 57.213 | 30.037 | −14.118 | 1.00 | 19.93 | C |
| ATOM | 16590 | O | GLU | B | 501 | 57.621 | 29.832 | −15.256 | 1.00 | 20.86 | O |
| ATOM | 16592 | N | THR | B | 502 | 56.725 | 29.063 | −13.364 | 1.00 | 19.13 | N |
| ATOM | 16593 | CA | THR | B | 502 | 56.559 | 27.720 | −13.904 | 1.00 | 18.29 | C |
| ATOM | 16595 | CB | THR | B | 502 | 55.943 | 26.768 | −12.870 | 1.00 | 17.85 | C |
| ATOM | 16597 | OG1 | THR | B | 502 | 56.822 | 26.654 | −11.745 | 1.00 | 18.95 | O |
| ATOM | 16599 | CG2 | THR | B | 502 | 55.708 | 25.395 | −13.475 | 1.00 | 18.10 | C |
| ATOM | 16603 | C | THR | B | 502 | 55.657 | 27.788 | −15.130 | 1.00 | 18.19 | C |
| ATOM | 16604 | O | THR | B | 502 | 56.004 | 27.285 | −16.200 | 1.00 | 18.59 | O |
| ATOM | 16606 | N | ALA | B | 503 | 54.507 | 28.435 | −14.961 | 1.00 | 17.01 | N |
| ATOM | 16607 | CA | ALA | B | 503 | 53.574 | 28.662 | −16.051 | 1.00 | 16.79 | C |
| ATOM | 16609 | CB | ALA | B | 503 | 52.397 | 29.513 | −15.572 | 1.00 | 16.20 | C |
| ATOM | 16613 | C | ALA | B | 503 | 54.269 | 29.315 | −17.254 | 1.00 | 16.84 | C |
| ATOM | 16614 | O | ALA | B | 503 | 54.203 | 28.794 | −18.362 | 1.00 | 17.02 | O |
| ATOM | 16616 | N | ILE | B | 504 | 54.955 | 30.434 | −17.035 | 1.00 | 15.79 | N |
| ATOM | 16617 | CA | ILE | B | 504 | 55.655 | 31.104 | −18.129 | 1.00 | 16.42 | C |
| ATOM | 16619 | CB | ILE | B | 504 | 56.375 | 32.388 | −17.663 | 1.00 | 16.84 | C |
| ATOM | 16621 | CG1 | ILE | B | 504 | 55.353 | 33.465 | −17.279 | 1.00 | 20.25 | C |
| ATOM | 16624 | CD1 | ILE | B | 504 | 55.903 | 34.533 | −16.379 | 1.00 | 15.32 | C |
| ATOM | 16628 | CG2 | ILE | B | 504 | 57.283 | 32.920 | −18.757 | 1.00 | 15.95 | C |
| ATOM | 16632 | C | ILE | B | 504 | 56.669 | 30.172 | −18.797 | 1.00 | 16.44 | C |
| ATOM | 16633 | O | ILE | B | 504 | 56.842 | 30.214 | −20.019 | 1.00 | 15.28 | O |
| ATOM | 16635 | N | ASN | B | 505 | 57.324 | 29.319 | −18.010 | 1.00 | 16.41 | N |
| ATOM | 16636 | CA | ASN | B | 505 | 58.317 | 28.396 | −18.574 | 1.00 | 17.85 | C |
| ATOM | 16638 | CB | ASN | B | 505 | 59.014 | 27.562 | −17.486 | 1.00 | 18.33 | C |
| ATOM | 16641 | CG | ASN | B | 505 | 60.048 | 28.353 | −16.700 | 1.00 | 16.57 | C |
| ATOM | 16642 | OD1 | ASN | B | 505 | 60.589 | 29.350 | −17.171 | 1.00 | 18.65 | O |
| ATOM | 16643 | ND2 | ASN | B | 505 | 60.333 | 27.898 | −15.500 | 1.00 | 16.08 | N |
| ATOM | 16646 | C | ASN | B | 505 | 57.736 | 27.470 | −19.638 | 1.00 | 17.74 | C |
| ATOM | 16647 | O | ASN | B | 505 | 58.438 | 27.104 | −20.579 | 1.00 | 18.71 | O |
| ATOM | 16649 | N | LEU | B | 506 | 56.463 | 27.102 | −19.496 | 1.00 | 17.83 | N |
| ATOM | 16650 | CA | LEU | B | 506 | 55.774 | 26.300 | −20.517 | 1.00 | 18.37 | C |
| ATOM | 16652 | CB | LEU | B | 506 | 54.326 | 26.030 | −20.125 | 1.00 | 19.29 | C |
| ATOM | 16655 | CG | LEU | B | 506 | 53.554 | 25.067 | −21.033 | 1.00 | 20.58 | C |
| ATOM | 16657 | CD1 | LEU | B | 506 | 53.607 | 23.668 | −20.465 | 1.00 | 18.95 | C |
| ATOM | 16661 | CD2 | LEU | B | 506 | 52.110 | 25.515 | −21.179 | 1.00 | 17.98 | C |
| ATOM | 16665 | C | LEU | B | 506 | 55.796 | 26.998 | −21.871 | 1.00 | 17.25 | C |
| ATOM | 16666 | O | LEU | B | 506 | 56.022 | 26.363 | −22.884 | 1.00 | 17.95 | O |
| ATOM | 16668 | N | ALA | B | 507 | 55.565 | 28.304 | −21.876 | 1.00 | 16.97 | N |
| ATOM | 16669 | CA | ALA | B | 507 | 55.693 | 29.099 | −23.089 | 1.00 | 16.34 | C |
| ATOM | 16671 | CB | ALA | B | 507 | 55.272 | 30.538 | −22.831 | 1.00 | 14.72 | C |
| ATOM | 16675 | C | ALA | B | 507 | 57.130 | 29.048 | −23.595 | 1.00 | 17.17 | C |
| ATOM | 16676 | O | ALA | B | 507 | 57.373 | 28.848 | −24.784 | 1.00 | 17.32 | O |
| ATOM | 16678 | N | ARG | B | 508 | 58.089 | 29.212 | −22.692 | 1.00 | 17.41 | N |
| ATOM | 16679 | CA | ARG | B | 508 | 59.487 | 29.194 | −23.091 | 1.00 | 17.12 | C |
| ATOM | 16681 | CB | ARG | B | 508 | 60.397 | 29.443 | −21.902 | 1.00 | 17.38 | C |
| ATOM | 16684 | CG | ARG | B | 508 | 60.275 | 30.838 | −21.354 | 1.00 | 21.02 | C |
| ATOM | 16687 | CD | ARG | B | 508 | 61.325 | 31.143 | −20.323 | 1.00 | 18.85 | C |
| ATOM | 16690 | NE | ARG | B | 508 | 61.271 | 32.565 | −19.993 | 1.00 | 21.55 | N |
| ATOM | 16692 | CZ | ARG | B | 508 | 60.993 | 33.082 | −18.797 | 1.00 | 20.04 | C |
| ATOM | 16693 | NH1 | ARG | B | 508 | 60.760 | 32.313 | −17.734 | 1.00 | 16.21 | N |
| ATOM | 16696 | NH2 | ARG | B | 508 | 60.967 | 34.401 | −18.665 | 1.00 | 21.31 | N |
| ATOM | 16699 | C | ARG | B | 508 | 59.836 | 27.874 | −23.740 | 1.00 | 17.83 | C |
| ATOM | 16700 | O | ARG | B | 508 | 60.387 | 27.850 | −24.841 | 1.00 | 17.31 | O |
| ATOM | 16702 | N | GLN | B | 509 | 59.501 | 26.779 | −23.062 | 1.00 | 19.12 | N |
| ATOM | 16703 | CA | GLN | B | 509 | 59.777 | 25.440 | −23.578 | 1.00 | 20.34 | C |
| ATOM | 16705 | CB | GLN | B | 509 | 59.297 | 24.377 | −22.590 | 1.00 | 21.03 | C |
| ATOM | 16708 | CG | GLN | B | 509 | 59.548 | 22.947 | −23.033 | 1.00 | 21.80 | C |
| ATOM | 16711 | CD | GLN | B | 509 | 60.998 | 22.676 | −23.344 | 1.00 | 23.32 | C |
| ATOM | 16712 | OE1 | GLN | B | 509 | 61.875 | 22.927 | −22.528 | 1.00 | 27.09 | O |
| ATOM | 16713 | NE2 | GLN | B | 509 | 61.261 | 22.158 | −24.534 | 1.00 | 31.09 | N |
| ATOM | 16716 | C | GLN | B | 509 | 59.109 | 25.235 | −24.941 | 1.00 | 22.09 | C |
| ATOM | 16717 | O | GLN | B | 509 | 59.669 | 24.563 | −25.819 | 1.00 | 22.75 | O |
| ATOM | 16719 | N | SER | B | 510 | 57.922 | 25.824 | −25.114 | 1.00 | 21.19 | N |
| ATOM | 16720 | CA | SER | B | 510 | 57.225 | 25.782 | −26.392 | 1.00 | 20.82 | C |
| ATOM | 16722 | CB | SER | B | 510 | 55.862 | 26.469 | −26.289 | 1.00 | 21.05 | C |
| ATOM | 16725 | OG | SER | B | 510 | 55.029 | 25.799 | −25.358 | 1.00 | 19.96 | O |
| ATOM | 16727 | C | SER | B | 510 | 58.056 | 26.428 | −27.501 | 1.00 | 20.73 | C |
| ATOM | 16728 | O | SER | B | 510 | 58.278 | 25.816 | −28.550 | 1.00 | 20.43 | O |
| ATOM | 16730 | N | HIS | B | 511 | 58.528 | 27.649 | −27.265 | 1.00 | 20.87 | N |
| ATOM | 16731 | CA | HIS | B | 511 | 59.375 | 28.343 | −28.243 | 1.00 | 21.91 | C |
| ATOM | 16733 | CB | HIS | B | 511 | 59.892 | 29.675 | −27.704 | 1.00 | 21.61 | C |

APPENDIX 1-continued

| | | | | | | | | | | |
|---|---|---|---|---|---|---|---|---|---|---|
| ATOM | 16736 | CG | HIS | B | 511 | 58.862 | 30.754 | −27.673 | 1.00 | 22.41 | C |
| ATOM | 16737 | ND1 | HIS | B | 511 | 58.474 | 31.439 | −28.803 | 1.00 | 22.39 | N |
| ATOM | 16739 | CE1 | HIS | B | 511 | 57.558 | 32.333 | −28.479 | 1.00 | 22.43 | C |
| ATOM | 16741 | NE2 | HIS | B | 511 | 57.343 | 32.255 | −27.178 | 1.00 | 25.82 | N |
| ATOM | 16743 | CD2 | HIS | B | 511 | 58.147 | 31.275 | −26.649 | 1.00 | 23.81 | C |
| ATOM | 16745 | C | HIS | B | 511 | 60.566 | 27.488 | −28.630 | 1.00 | 22.41 | C |
| ATOM | 16746 | O | HIS | B | 511 | 60.896 | 27.380 | −29.802 | 1.00 | 22.66 | O |
| ATOM | 16748 | N | CYS | B | 512 | 61.198 | 26.880 | −27.632 | 1.00 | 23.19 | N |
| ATOM | 16749 | CA | CYS | B | 512 | 62.396 | 26.079 | −27.850 | 1.00 | 24.69 | C |
| ATOM | 16751 | CB | CYS | B | 512 | 63.135 | 25.891 | −26.530 | 1.00 | 24.68 | C |
| ATOM | 16754 | SG | CYS | B | 512 | 63.677 | 27.455 | −25.811 | 1.00 | 27.11 | S |
| ATOM | 16756 | C | CYS | B | 512 | 62.121 | 24.715 | −28.490 | 1.00 | 25.89 | C |
| ATOM | 16757 | O | CYS | B | 512 | 62.927 | 24.241 | −29.280 | 1.00 | 25.89 | O |
| ATOM | 16759 | N | THR | B | 513 | 61.000 | 24.087 | −28.140 | 1.00 | 27.54 | N |
| ATOM | 16760 | CA | THR | B | 513 | 60.627 | 22.795 | −28.718 | 1.00 | 28.97 | C |
| ATOM | 16762 | CB | THR | B | 513 | 59.455 | 22.148 | −27.962 | 1.00 | 28.82 | C |
| ATOM | 16764 | OG1 | THR | B | 513 | 59.949 | 21.546 | −26.763 | 1.00 | 29.92 | O |
| ATOM | 16766 | CG2 | THR | B | 513 | 58.780 | 21.074 | −28.805 | 1.00 | 26.03 | C |
| ATOM | 16770 | C | THR | B | 513 | 60.255 | 22.903 | −30.193 | 1.00 | 31.24 | C |
| ATOM | 16771 | O | THR | B | 513 | 60.662 | 22.065 | −30.996 | 1.00 | 30.43 | O |
| ATOM | 16773 | N | TYR | B | 514 | 59.496 | 23.939 | −30.544 | 1.00 | 34.06 | N |
| ATOM | 16774 | CA | TYR | B | 514 | 58.957 | 24.083 | −31.900 | 1.00 | 35.61 | C |
| ATOM | 16776 | CB | TYR | B | 514 | 57.484 | 24.473 | −31.825 | 1.00 | 34.62 | C |
| ATOM | 16779 | CG | TYR | B | 514 | 56.666 | 23.420 | −31.122 | 1.00 | 30.11 | C |
| ATOM | 16780 | CD1 | TYR | B | 514 | 56.364 | 22.220 | −31.750 | 1.00 | 30.04 | C |
| ATOM | 16782 | CE1 | TYR | B | 514 | 55.617 | 21.237 | −31.110 | 1.00 | 29.71 | C |
| ATOM | 16784 | CZ | TYR | B | 514 | 55.170 | 21.447 | −29.824 | 1.00 | 31.94 | C |
| ATOM | 16785 | OH | TYR | B | 514 | 54.433 | 20.472 | −29.193 | 1.00 | 34.49 | O |
| ATOM | 16787 | CE2 | TYR | B | 514 | 55.461 | 22.634 | −29.169 | 1.00 | 32.21 | C |
| ATOM | 16789 | CD2 | TYR | B | 514 | 56.211 | 23.610 | −29.821 | 1.00 | 30.80 | C |
| ATOM | 16791 | C | TYR | B | 514 | 59.770 | 25.053 | −32.763 | 1.00 | 38.62 | C |
| ATOM | 16792 | O | TYR | B | 514 | 59.471 | 26.241 | −32.859 | 1.00 | 38.41 | O |
| ATOM | 16794 | N | HIS | B | 515 | 60.796 | 24.502 | −33.400 | 1.00 | 43.15 | N |
| ATOM | 16795 | CA | HIS | B | 515 | 61.773 | 25.263 | −34.181 | 1.00 | 46.70 | C |
| ATOM | 16797 | CB | HIS | B | 515 | 63.159 | 25.123 | −33.535 | 1.00 | 46.77 | C |
| ATOM | 16800 | CG | HIS | B | 515 | 63.598 | 23.700 | −33.358 | 1.00 | 49.82 | C |
| ATOM | 16801 | ND1 | HIS | B | 515 | 63.411 | 23.005 | −32.181 | 1.00 | 50.36 | N |
| ATOM | 16803 | CE1 | HIS | B | 515 | 63.884 | 21.779 | −32.316 | 1.00 | 52.07 | C |
| ATOM | 16805 | NE2 | HIS | B | 515 | 64.366 | 21.650 | −33.539 | 1.00 | 52.64 | N |
| ATOM | 16807 | CD2 | HIS | B | 515 | 64.196 | 22.835 | −34.213 | 1.00 | 52.54 | C |
| ATOM | 16809 | C | HIS | B | 515 | 61.802 | 24.734 | −35.622 | 1.00 | 48.71 | C |
| ATOM | 16810 | O | HIS | B | 515 | 60.968 | 23.898 | −35.998 | 1.00 | 48.30 | O |
| ATOM | 16812 | N | ASN | B | 516 | 62.751 | 25.236 | −36.417 | 1.00 | 51.12 | N |
| ATOM | 16813 | CA | ASN | B | 516 | 63.000 | 24.745 | −37.779 | 1.00 | 53.12 | C |
| ATOM | 16815 | CB | ASN | B | 516 | 62.211 | 25.576 | −38.807 | 1.00 | 53.90 | C |
| ATOM | 16818 | CG | ASN | B | 516 | 60.700 | 25.320 | −38.754 | 1.00 | 56.25 | C |
| ATOM | 16819 | OD1 | ASN | B | 516 | 60.234 | 24.209 | −39.024 | 1.00 | 58.97 | O |
| ATOM | 16820 | ND2 | ASN | B | 516 | 59.932 | 26.356 | −38.417 | 1.00 | 56.55 | N |
| ATOM | 16823 | C | ASN | B | 516 | 64.494 | 24.791 | −38.125 | 1.00 | 53.78 | C |
| ATOM | 16824 | O | ASN | B | 516 | 65.343 | 24.290 | −37.379 | 1.00 | 54.33 | O |
| ATOM | 16826 | N | HIS | B | 520 | 74.438 | 24.782 | −40.199 | 1.00 | 69.52 | N |
| ATOM | 16827 | CA | HIS | B | 520 | 73.028 | 24.665 | −39.835 | 1.00 | 69.72 | C |
| ATOM | 16829 | CB | HIS | B | 520 | 72.146 | 25.329 | −40.904 | 1.00 | 70.13 | C |
| ATOM | 16832 | CG | HIS | B | 520 | 71.042 | 26.175 | −40.343 | 1.00 | 72.46 | C |
| ATOM | 16833 | ND1 | HIS | B | 520 | 70.208 | 25.744 | −39.332 | 1.00 | 75.25 | N |
| ATOM | 16835 | CE1 | HIS | B | 520 | 69.335 | 26.694 | −39.046 | 1.00 | 74.23 | C |
| ATOM | 16837 | NE2 | HIS | B | 520 | 69.569 | 27.724 | −39.839 | 1.00 | 74.51 | N |
| ATOM | 16839 | CD2 | HIS | B | 520 | 70.629 | 27.425 | −40.661 | 1.00 | 72.94 | C |
| ATOM | 16841 | C | HIS | B | 520 | 72.646 | 23.188 | −39.656 | 1.00 | 69.01 | C |
| ATOM | 16842 | O | HIS | B | 520 | 73.382 | 22.295 | −40.084 | 1.00 | 68.65 | O |
| ATOM | 16844 | N | THR | B | 521 | 71.502 | 22.942 | −39.018 | 1.00 | 68.37 | N |
| ATOM | 16845 | CA | THR | B | 521 | 71.023 | 21.583 | −38.746 | 1.00 | 68.19 | C |
| ATOM | 16847 | CB | THR | B | 521 | 71.182 | 21.227 | −37.248 | 1.00 | 68.16 | C |
| ATOM | 16849 | OG1 | THR | B | 521 | 72.440 | 21.714 | −36.763 | 1.00 | 68.25 | O |
| ATOM | 16851 | CG2 | THR | B | 521 | 71.108 | 19.719 | −37.034 | 1.00 | 67.64 | C |
| ATOM | 16855 | C | THR | B | 521 | 69.550 | 21.433 | −39.131 | 1.00 | 68.06 | C |
| ATOM | 16856 | O | THR | B | 521 | 68.817 | 22.422 | −39.202 | 1.00 | 67.99 | O |
| ATOM | 16858 | N | SER | B | 522 | 69.128 | 20.194 | −39.380 | 1.00 | 68.09 | N |
| ATOM | 16859 | CA | SER | B | 522 | 67.731 | 19.886 | −39.699 | 1.00 | 68.28 | C |
| ATOM | 16861 | CB | SER | B | 522 | 67.643 | 18.538 | −40.420 | 1.00 | 68.20 | C |
| ATOM | 16864 | OG | SER | B | 522 | 68.133 | 17.489 | −39.602 | 1.00 | 67.15 | O |
| ATOM | 16866 | C | SER | B | 522 | 66.870 | 19.857 | −38.424 | 1.00 | 68.80 | C |
| ATOM | 16867 | O | SER | B | 522 | 67.408 | 19.708 | −37.325 | 1.00 | 68.89 | O |
| ATOM | 16869 | N | PRO | B | 523 | 65.532 | 19.999 | −38.567 | 1.00 | 69.27 | N |
| ATOM | 16870 | CA | PRO | B | 523 | 64.611 | 19.985 | −37.410 | 1.00 | 69.42 | C |
| ATOM | 16872 | CB | PRO | B | 523 | 63.221 | 20.001 | −38.067 | 1.00 | 69.45 | C |
| ATOM | 16875 | CG | PRO | B | 523 | 63.430 | 20.682 | −39.371 | 1.00 | 69.63 | C |
| ATOM | 16878 | CD | PRO | B | 523 | 64.820 | 20.313 | −39.824 | 1.00 | 69.25 | C |
| ATOM | 16881 | C | PRO | B | 523 | 64.752 | 18.776 | −36.458 | 1.00 | 69.17 | C |
| ATOM | 16882 | O | PRO | B | 523 | 64.897 | 18.969 | −35.245 | 1.00 | 68.88 | O |

APPENDIX 1-continued

| | | | | | | | | | | |
|---|---|---|---|---|---|---|---|---|---|---|
| ATOM | 16883 | N | ASP | B | 524 | 64.698 | 17.556 | −37.002 | 1.00 | 68.83 | N |
| ATOM | 16884 | CA | ASP | B | 524 | 64.872 | 16.324 | −36.208 | 1.00 | 68.18 | C |
| ATOM | 16886 | CB | ASP | B | 524 | 63.995 | 15.184 | −36.749 | 1.00 | 68.01 | C |
| ATOM | 16889 | CG | ASP | B | 524 | 62.530 | 15.349 | −36.388 | 1.00 | 69.08 | C |
| ATOM | 16890 | OD1 | ASP | B | 524 | 62.227 | 15.878 | −35.293 | 1.00 | 68.36 | O |
| ATOM | 16891 | OD2 | ASP | B | 524 | 61.680 | 14.934 | −37.202 | 1.00 | 69.43 | O |
| ATOM | 16892 | C | ASP | B | 524 | 66.341 | 15.896 | −36.175 | 1.00 | 66.99 | C |
| ATOM | 16893 | O | ASP | B | 524 | 66.754 | 14.981 | −36.891 | 1.00 | 67.26 | O |
| ATOM | 16895 | N | GLU | B | 525 | 67.097 | 16.568 | −35.309 | 1.00 | 65.16 | N |
| ATOM | 16896 | CA | GLU | B | 525 | 68.556 | 16.430 | −35.155 | 1.00 | 64.15 | C |
| ATOM | 16898 | CB | GLU | B | 525 | 69.310 | 16.361 | −36.495 | 1.00 | 64.53 | C |
| ATOM | 16901 | CG | GLU | B | 525 | 69.815 | 14.955 | −36.862 | 1.00 | 65.79 | C |
| ATOM | 16904 | CD | GLU | B | 525 | 70.828 | 14.966 | −37.994 | 1.00 | 68.11 | C |
| ATOM | 16905 | OE1 | GLU | B | 525 | 71.916 | 15.553 | −37.813 | 1.00 | 68.91 | O |
| ATOM | 16906 | OE2 | GLU | B | 525 | 70.540 | 14.377 | −39.060 | 1.00 | 68.89 | O |
| ATOM | 16907 | C | GLU | B | 525 | 69.086 | 17.596 | −34.313 | 1.00 | 62.63 | C |
| ATOM | 16908 | O | GLU | B | 525 | 70.042 | 17.434 | −33.553 | 1.00 | 62.41 | O |
| ATOM | 16910 | N | LEU | B | 526 | 68.476 | 18.772 | −34.474 | 1.00 | 60.84 | N |
| ATOM | 16911 | CA | LEU | B | 526 | 68.624 | 19.861 | −33.503 | 1.00 | 59.29 | C |
| ATOM | 16913 | CB | LEU | B | 526 | 68.054 | 21.175 | −34.051 | 1.00 | 59.08 | C |
| ATOM | 16916 | CG | LEU | B | 526 | 68.377 | 22.446 | −33.255 | 1.00 | 58.48 | C |
| ATOM | 16918 | CD1 | LEU | B | 526 | 69.872 | 22.756 | −33.298 | 1.00 | 57.97 | C |
| ATOM | 16922 | CD2 | LEU | B | 526 | 67.567 | 23.628 | −33.773 | 1.00 | 56.17 | C |
| ATOM | 16926 | C | LEU | B | 526 | 67.921 | 19.479 | −32.194 | 1.00 | 57.75 | C |
| ATOM | 16927 | O | LEU | B | 526 | 68.363 | 19.864 | −31.111 | 1.00 | 57.36 | O |
| ATOM | 16929 | N | THR | B | 527 | 66.826 | 18.727 | −32.307 | 1.00 | 56.15 | N |
| ATOM | 16930 | CA | THR | B | 527 | 66.132 | 18.165 | −31.148 | 1.00 | 55.07 | C |
| ATOM | 16932 | CB | THR | B | 527 | 64.801 | 17.495 | −31.562 | 1.00 | 54.60 | C |
| ATOM | 16934 | OG1 | THR | B | 527 | 63.918 | 18.487 | −32.102 | 1.00 | 54.27 | O |
| ATOM | 16936 | CG2 | THR | B | 527 | 64.128 | 16.810 | −30.373 | 1.00 | 51.53 | C |
| ATOM | 16940 | C | THR | B | 527 | 67.012 | 17.148 | −30.420 | 1.00 | 55.32 | C |
| ATOM | 16941 | O | THR | B | 527 | 67.201 | 17.246 | −29.205 | 1.00 | 55.42 | O |
| ATOM | 16943 | N | ARG | B | 528 | 67.551 | 16.183 | −31.164 | 1.00 | 55.16 | N |
| ATOM | 16944 | CA | ARG | B | 528 | 68.395 | 15.140 | −30.574 | 1.00 | 55.45 | C |
| ATOM | 16946 | CB | ARG | B | 528 | 68.781 | 14.084 | −31.622 | 1.00 | 56.04 | C |
| ATOM | 16949 | CG | ARG | B | 528 | 69.600 | 12.906 | −31.070 | 1.00 | 59.35 | C |
| ATOM | 16952 | CD | ARG | B | 528 | 69.957 | 11.888 | −32.155 | 1.00 | 64.75 | C |
| ATOM | 16955 | NE | ARG | B | 528 | 70.689 | 12.485 | −33.278 | 1.00 | 69.31 | N |
| ATOM | 16957 | CZ | ARG | B | 528 | 71.986 | 12.804 | −33.273 | 1.00 | 72.03 | C |
| ATOM | 16958 | NH1 | ARG | B | 528 | 72.741 | 12.600 | −32.195 | 1.00 | 71.44 | N |
| ATOM | 16961 | NH2 | ARG | B | 528 | 72.536 | 13.342 | −34.361 | 1.00 | 72.52 | N |
| ATOM | 16964 | C | ARG | B | 528 | 69.649 | 15.726 | −29.911 | 1.00 | 54.78 | C |
| ATOM | 16965 | O | ARG | B | 528 | 70.075 | 15.238 | −28.863 | 1.00 | 55.19 | O |
| ATOM | 16967 | N | LYS | B | 529 | 70.230 | 16.765 | −30.513 | 1.00 | 53.55 | N |
| ATOM | 16968 | CA | LYS | B | 529 | 71.410 | 17.426 | −29.936 | 1.00 | 52.74 | C |
| ATOM | 16970 | CB | LYS | B | 529 | 72.099 | 18.339 | −30.961 | 1.00 | 52.37 | C |
| ATOM | 16973 | CG | LYS | B | 529 | 72.943 | 17.560 | −31.967 | 1.00 | 54.13 | C |
| ATOM | 16976 | CD | LYS | B | 529 | 73.914 | 18.429 | −32.750 | 1.00 | 54.48 | C |
| ATOM | 16979 | CE | LYS | B | 529 | 74.734 | 17.567 | −33.708 | 1.00 | 55.21 | C |
| ATOM | 16982 | NZ | LYS | B | 529 | 75.867 | 18.301 | −34.338 | 1.00 | 55.62 | N |
| ATOM | 16986 | C | LYS | B | 529 | 71.061 | 18.201 | −28.664 | 1.00 | 51.97 | C |
| ATOM | 16987 | O | LYS | B | 529 | 71.798 | 18.142 | −27.679 | 1.00 | 51.98 | O |
| ATOM | 16989 | N | ARG | B | 530 | 69.934 | 18.911 | −28.687 | 1.00 | 51.17 | N |
| ATOM | 16990 | CA | ARG | B | 530 | 69.453 | 19.645 | −27.513 | 1.00 | 50.47 | C |
| ATOM | 16992 | CB | ARG | B | 530 | 68.253 | 20.534 | −27.874 | 1.00 | 50.29 | C |
| ATOM | 16995 | CG | ARG | B | 530 | 68.628 | 21.833 | −28.587 | 1.00 | 49.82 | C |
| ATOM | 16998 | CD | ARG | B | 530 | 67.393 | 22.633 | −29.003 | 1.00 | 48.99 | C |
| ATOM | 17001 | NE | ARG | B | 530 | 67.732 | 23.924 | −29.607 | 1.00 | 47.15 | N |
| ATOM | 17003 | CZ | ARG | B | 530 | 66.839 | 24.803 | −30.067 | 1.00 | 49.12 | C |
| ATOM | 17004 | NH1 | ARG | B | 530 | 65.537 | 24.547 | −30.002 | 1.00 | 50.15 | N |
| ATOM | 17007 | NH2 | ARG | B | 530 | 67.247 | 25.950 | −30.595 | 1.00 | 50.51 | N |
| ATOM | 17010 | C | ARG | B | 530 | 69.088 | 18.694 | −26.366 | 1.00 | 50.04 | C |
| ATOM | 17011 | O | ARG | B | 530 | 69.489 | 18.921 | −25.217 | 1.00 | 49.90 | O |
| ATOM | 17013 | N | VAL | B | 531 | 68.342 | 17.633 | −26.684 | 1.00 | 49.06 | N |
| ATOM | 17014 | CA | VAL | B | 531 | 67.954 | 16.627 | −25.687 | 1.00 | 48.01 | C |
| ATOM | 17016 | CB | VAL | B | 531 | 67.043 | 15.520 | −26.288 | 1.00 | 48.13 | C |
| ATOM | 17018 | CG1 | VAL | B | 531 | 66.850 | 14.371 | −25.295 | 1.00 | 46.58 | C |
| ATOM | 17022 | CG2 | VAL | B | 531 | 65.695 | 16.096 | −26.698 | 1.00 | 47.13 | C |
| ATOM | 17026 | C | VAL | B | 531 | 69.193 | 15.985 | −25.066 | 1.00 | 46.96 | C |
| ATOM | 17027 | O | VAL | B | 531 | 69.256 | 15.795 | −23.850 | 1.00 | 46.96 | O |
| ATOM | 17029 | N | LEU | B | 532 | 70.176 | 15.666 | −25.906 | 1.00 | 45.51 | N |
| ATOM | 17030 | CA | LEU | B | 532 | 71.425 | 15.063 | −25.439 | 1.00 | 44.29 | C |
| ATOM | 17032 | CB | LEU | B | 532 | 72.322 | 14.660 | −26.624 | 1.00 | 44.69 | C |
| ATOM | 17035 | CG | LEU | B | 532 | 72.216 | 13.227 | −27.179 | 1.00 | 45.27 | C |
| ATOM | 17037 | CD1 | LEU | B | 532 | 70.780 | 12.702 | −27.262 | 1.00 | 45.14 | C |
| ATOM | 17041 | CD2 | LEU | B | 532 | 72.889 | 13.161 | −28.540 | 1.00 | 44.64 | C |
| ATOM | 17045 | C | LEU | B | 532 | 72.185 | 15.994 | −24.488 | 1.00 | 42.95 | C |
| ATOM | 17046 | O | LEU | B | 532 | 72.652 | 15.562 | −23.432 | 1.00 | 42.21 | O |
| ATOM | 17048 | N | SER | B | 533 | 72.288 | 17.270 | −24.860 | 1.00 | 41.47 | N |
| ATOM | 17049 | CA | SER | B | 533 | 73.056 | 18.252 | −24.087 | 1.00 | 40.59 | C |

APPENDIX 1-continued

| ATOM | 17051 | CB  | SER | B | 533 | 73.207 | 19.550 | −24.884 | 1.00 | 40.46 | C |
| ATOM | 17054 | OG  | SER | B | 533 | 71.951 | 20.188 | −25.072 | 1.00 | 42.07 | O |
| ATOM | 17056 | C   | SER | B | 533 | 72.425 | 18.559 | −22.725 | 1.00 | 39.43 | C |
| ATOM | 17057 | O   | SER | B | 533 | 73.117 | 18.985 | −21.792 | 1.00 | 38.30 | O |
| ATOM | 17059 | N   | VAL | B | 534 | 71.114 | 18.341 | −22.628 | 1.00 | 38.04 | N |
| ATOM | 17060 | CA  | VAL | B | 534 | 70.351 | 18.636 | −21.420 | 1.00 | 37.19 | C |
| ATOM | 17062 | CB  | VAL | B | 534 | 68.938 | 19.181 | −21.773 | 1.00 | 36.30 | C |
| ATOM | 17064 | CG1 | VAL | B | 534 | 67.966 | 18.984 | −20.620 | 1.00 | 31.83 | C |
| ATOM | 17068 | CG2 | VAL | B | 534 | 69.022 | 20.648 | −22.172 | 1.00 | 32.17 | C |
| ATOM | 17072 | C   | VAL | B | 534 | 70.226 | 17.429 | −20.488 | 1.00 | 38.15 | C |
| ATOM | 17073 | O   | VAL | B | 534 | 70.283 | 17.589 | −19.269 | 1.00 | 38.33 | O |
| ATOM | 17075 | N   | ILE | B | 535 | 70.059 | 16.233 | −21.053 | 1.00 | 39.60 | N |
| ATOM | 17076 | CA  | ILE | B | 535 | 69.784 | 15.035 | −20.249 | 1.00 | 40.91 | C |
| ATOM | 17078 | CB  | ILE | B | 535 | 68.569 | 14.222 | −20.787 | 1.00 | 41.23 | C |
| ATOM | 17080 | CG1 | ILE | B | 535 | 67.311 | 15.090 | −20.903 | 1.00 | 40.90 | C |
| ATOM | 17083 | CD1 | ILE | B | 535 | 66.884 | 15.730 | −19.603 | 1.00 | 41.66 | C |
| ATOM | 17087 | CG2 | ILE | B | 535 | 68.288 | 13.030 | −19.874 | 1.00 | 41.53 | C |
| ATOM | 17091 | C   | ILE | B | 535 | 70.969 | 14.084 | −20.179 | 1.00 | 41.86 | C |
| ATOM | 17092 | O   | ILE | B | 535 | 71.482 | 13.800 | −19.094 | 1.00 | 42.32 | O |
| ATOM | 17094 | N   | THR | B | 536 | 71.397 | 13.585 | −21.334 | 1.00 | 42.66 | N |
| ATOM | 17095 | CA  | THR | B | 536 | 72.316 | 12.446 | −21.373 | 1.00 | 43.85 | C |
| ATOM | 17097 | CB  | THR | B | 536 | 72.004 | 11.531 | −22.584 | 1.00 | 44.49 | C |
| ATOM | 17099 | OG1 | THR | B | 536 | 71.755 | 12.333 | −23.745 | 1.00 | 47.98 | O |
| ATOM | 17101 | CG2 | THR | B | 536 | 70.764 | 10.671 | −22.301 | 1.00 | 44.85 | C |
| ATOM | 17105 | C   | THR | B | 536 | 73.810 | 12.821 | −21.340 | 1.00 | 43.27 | C |
| ATOM | 17106 | O   | THR | B | 536 | 74.572 | 12.217 | −20.588 | 1.00 | 43.08 | O |
| ATOM | 17108 | N   | GLU | B | 537 | 74.220 | 13.811 | −22.134 | 1.00 | 42.95 | N |
| ATOM | 17109 | CA  | GLU | B | 537 | 75.645 | 14.184 | −22.253 | 1.00 | 42.39 | C |
| ATOM | 17111 | CB  | GLU | B | 537 | 75.965 | 14.643 | −23.678 | 1.00 | 42.99 | C |
| ATOM | 17114 | CG  | GLU | B | 537 | 76.089 | 13.519 | −24.691 | 1.00 | 46.08 | C |
| ATOM | 17117 | CD  | GLU | B | 537 | 76.491 | 14.026 | −26.068 | 1.00 | 51.01 | C |
| ATOM | 17118 | OE1 | GLU | B | 537 | 75.987 | 15.098 | −26.479 | 1.00 | 52.31 | O |
| ATOM | 17119 | OE2 | GLU | B | 537 | 77.309 | 13.354 | −26.738 | 1.00 | 51.28 | O |
| ATOM | 17120 | C   | GLU | B | 537 | 76.064 | 15.297 | −21.281 | 1.00 | 40.65 | C |
| ATOM | 17121 | O   | GLU | B | 537 | 75.546 | 16.414 | −21.364 | 1.00 | 40.26 | O |
| ATOM | 17123 | N   | PRO | B | 538 | 77.019 | 15.007 | −20.377 | 1.00 | 38.40 | N |
| ATOM | 17124 | CA  | PRO | B | 538 | 77.535 | 16.062 | −19.502 | 1.00 | 36.97 | C |
| ATOM | 17126 | CB  | PRO | B | 538 | 78.424 | 15.311 | −18.493 | 1.00 | 36.84 | C |
| ATOM | 17129 | CG  | PRO | B | 538 | 78.198 | 13.862 | −18.723 | 1.00 | 38.72 | C |
| ATOM | 17132 | CD  | PRO | B | 538 | 77.652 | 13.705 | −20.107 | 1.00 | 39.09 | C |
| ATOM | 17135 | C   | PRO | B | 538 | 78.370 | 17.087 | −20.251 | 1.00 | 35.22 | C |
| ATOM | 17136 | O   | PRO | B | 538 | 78.875 | 16.802 | −21.334 | 1.00 | 34.58 | O |
| ATOM | 17137 | N   | ILE | B | 539 | 78.505 | 18.268 | −19.656 | 1.00 | 34.24 | N |
| ATOM | 17138 | CA  | ILE | B | 539 | 79.364 | 19.312 | −20.186 | 1.00 | 33.91 | C |
| ATOM | 17140 | CB  | ILE | B | 539 | 79.039 | 20.688 | −19.559 | 1.00 | 33.35 | C |
| ATOM | 17142 | CG1 | ILE | B | 539 | 77.627 | 21.119 | −19.946 | 1.00 | 33.50 | C |
| ATOM | 17145 | CD1 | ILE | B | 539 | 77.251 | 22.499 | −19.461 | 1.00 | 33.21 | C |
| ATOM | 17149 | CG2 | ILE | B | 539 | 80.022 | 21.745 | −20.023 | 1.00 | 31.40 | C |
| ATOM | 17153 | C   | ILE | B | 539 | 80.808 | 18.925 | −19.895 | 1.00 | 35.11 | C |
| ATOM | 17154 | O   | ILE | B | 539 | 81.137 | 18.532 | −18.772 | 1.00 | 34.38 | O |
| ATOM | 17156 | N   | LEU | B | 540 | 81.654 | 19.016 | −20.920 | 1.00 | 36.65 | N |
| ATOM | 17157 | CA  | LEU | B | 540 | 83.070 | 18.673 | −20.803 | 1.00 | 38.13 | C |
| ATOM | 17159 | CB  | LEU | B | 540 | 83.811 | 19.047 | −22.093 | 1.00 | 38.67 | C |
| ATOM | 17162 | CG  | LEU | B | 540 | 83.700 | 18.017 | −23.225 | 1.00 | 42.34 | C |
| ATOM | 17164 | CD1 | LEU | B | 540 | 83.619 | 18.686 | −24.610 | 1.00 | 45.32 | C |
| ATOM | 17168 | CD2 | LEU | B | 540 | 84.862 | 17.015 | −23.154 | 1.00 | 40.46 | C |
| ATOM | 17172 | C   | LEU | B | 540 | 83.703 | 19.383 | −19.603 | 1.00 | 38.81 | C |
| ATOM | 17173 | O   | LEU | B | 540 | 83.588 | 20.603 | −19.482 | 1.00 | 38.96 | O |
| ATOM | 17175 | N   | PRO | B | 541 | 84.378 | 18.626 | −18.717 | 1.00 | 39.33 | N |
| ATOM | 17176 | CA  | PRO | B | 541 | 84.871 | 19.216 | −17.476 | 1.00 | 40.17 | C |
| ATOM | 17178 | CB  | PRO | B | 541 | 85.641 | 18.066 | −16.813 | 1.00 | 39.97 | C |
| ATOM | 17181 | CG  | PRO | B | 541 | 85.952 | 17.130 | −17.903 | 1.00 | 39.37 | C |
| ATOM | 17184 | CD  | PRO | B | 541 | 84.811 | 17.226 | −18.857 | 1.00 | 39.33 | C |
| ATOM | 17187 | C   | PRO | B | 541 | 85.785 | 20.412 | −17.694 | 1.00 | 41.36 | C |
| ATOM | 17188 | O   | PRO | B | 541 | 86.351 | 20.586 | −18.777 | 1.00 | 41.39 | O |
| ATOM | 17189 | N   | PHE | B | 542 | 85.902 | 21.228 | −16.654 | 1.00 | 42.74 | N |
| ATOM | 17190 | CA  | PHE | B | 542 | 86.712 | 22.434 | −16.686 | 1.00 | 43.92 | C |
| ATOM | 17192 | CB  | PHE | B | 542 | 86.505 | 23.217 | −15.388 | 1.00 | 43.15 | C |
| ATOM | 17195 | CG  | PHE | B | 542 | 87.402 | 24.405 | −15.246 | 1.00 | 40.84 | C |
| ATOM | 17196 | CD1 | PHE | B | 542 | 87.347 | 25.444 | −16.163 | 1.00 | 39.06 | C |
| ATOM | 17198 | CE1 | PHE | B | 542 | 88.182 | 26.548 | −16.034 | 1.00 | 39.49 | C |
| ATOM | 17200 | CZ  | PHE | B | 542 | 89.076 | 26.619 | −14.974 | 1.00 | 37.53 | C |
| ATOM | 17202 | CE2 | PHE | B | 542 | 89.132 | 25.591 | −14.052 | 1.00 | 36.94 | C |
| ATOM | 17204 | CD2 | PHE | B | 542 | 88.301 | 24.491 | −14.192 | 1.00 | 38.64 | C |
| ATOM | 17206 | C   | PHE | B | 542 | 88.196 | 22.106 | −16.885 | 1.00 | 46.63 | C |
| ATOM | 17207 | O   | PHE | B | 542 | 88.735 | 21.202 | −16.244 | 1.00 | 46.58 | O |
| ATOM | 17209 | N   | GLU | B | 543 | 88.838 | 22.841 | −17.790 | 1.00 | 49.74 | N |
| ATOM | 17210 | CA  | GLU | B | 543 | 90.273 | 22.697 | −18.056 | 1.00 | 52.67 | C |
| ATOM | 17212 | CB  | GLU | B | 543 | 90.500 | 22.140 | −19.467 | 1.00 | 53.00 | C |
| ATOM | 17215 | CG  | GLU | B | 543 | 89.851 | 20.773 | −19.716 | 1.00 | 54.45 | C |

APPENDIX 1-continued

| | | | | | | | | | | |
|---|---|---|---|---|---|---|---|---|---|---|
| ATOM | 17218 | CD | GLU | B | 543 | 89.450 | 20.557 | −21.170 | 1.00 | 56.08 | C |
| ATOM | 17219 | OE1 | GLU | B | 543 | 88.675 | 21.377 | −21.711 | 1.00 | 55.47 | O |
| ATOM | 17220 | OE2 | GLU | B | 543 | 89.904 | 19.557 | −21.767 | 1.00 | 56.19 | O |
| ATOM | 17221 | C | GLU | B | 543 | 90.958 | 24.062 | −17.902 | 1.00 | 54.66 | C |
| ATOM | 17222 | O | GLU | B | 543 | 90.371 | 25.100 | −18.228 | 1.00 | 55.40 | O |
| ATOM | 17224 | N | ARG | B | 544 | 92.196 | 24.052 | −17.411 | 1.00 | 56.34 | N |
| ATOM | 17225 | CA | ARG | B | 544 | 92.930 | 25.282 | −17.094 | 1.00 | 57.83 | C |
| ATOM | 17227 | CB | ARG | B | 544 | 93.526 | 25.175 | −15.685 | 1.00 | 58.69 | C |
| ATOM | 17230 | CG | ARG | B | 544 | 92.489 | 24.914 | −14.599 | 1.00 | 61.11 | C |
| ATOM | 17233 | CD | ARG | B | 544 | 93.098 | 24.984 | −13.205 | 1.00 | 65.32 | C |
| ATOM | 17236 | NE | ARG | B | 544 | 92.069 | 25.106 | −12.167 | 1.00 | 68.58 | N |
| ATOM | 17238 | CZ | ARG | B | 544 | 91.674 | 24.138 | −11.337 | 1.00 | 70.53 | C |
| ATOM | 17239 | NH1 | ARG | B | 544 | 92.219 | 22.922 | −11.371 | 1.00 | 71.79 | N |
| ATOM | 17242 | NH2 | ARG | B | 544 | 90.720 | 24.395 | −10.447 | 1.00 | 70.07 | N |
| ATOM | 17245 | C | ARG | B | 544 | 94.033 | 25.586 | −18.119 | 1.00 | 58.07 | C |
| ATOM | 17246 | O | ARG | B | 544 | 93.768 | 25.795 | −19.305 | 1.00 | 58.07 | O |
| ATOM | 17248 | OXT | ARG | B | 544 | 95.223 | 25.640 | −17.797 | 1.00 | 58.05 | O |
| ATOM | 17249 | O2 | EDO | C | 1 | 77.661 | −43.007 | −16.443 | 1.00 | 43.00 | O |
| ATOM | 17251 | C2 | EDO | C | 1 | 76.783 | −42.969 | −15.309 | 1.00 | 44.22 | C |
| ATOM | 17254 | C1 | EDO | C | 1 | 77.576 | −42.916 | −14.007 | 1.00 | 41.25 | C |
| ATOM | 17257 | O1 | EDO | C | 1 | 78.695 | −42.041 | −14.162 | 1.00 | 43.89 | O |
| ATOM | 17259 | O2 | EDO | D | 1 | 50.330 | −35.935 | 6.828 | 1.00 | 44.73 | O |
| ATOM | 17261 | C2 | EDO | D | 1 | 49.060 | −36.295 | 7.378 | 1.00 | 45.21 | C |
| ATOM | 17264 | C1 | EDO | D | 1 | 49.137 | −37.691 | 7.987 | 1.00 | 45.66 | C |
| ATOM | 17267 | O1 | EDO | D | 1 | 50.152 | −37.735 | 8.995 | 1.00 | 39.86 | O |
| ATOM | 17269 | O2 | EDO | E | 1 | 56.102 | −25.006 | −6.675 | 1.00 | 35.20 | O |
| ATOM | 17271 | C2 | EDO | E | 1 | 55.115 | −24.022 | −6.312 | 1.00 | 39.87 | C |
| ATOM | 17274 | C1 | EDO | E | 1 | 55.627 | −22.972 | −5.321 | 1.00 | 36.36 | C |
| ATOM | 17277 | O1 | EDO | E | 1 | 56.896 | −23.345 | −4.763 | 1.00 | 38.87 | O |
| ATOM | 17279 | O2 | EDO | F | 1 | 61.382 | 26.747 | −13.014 | 1.00 | 37.16 | O |
| ATOM | 17281 | C2 | EDO | F | 1 | 60.319 | 26.976 | −12.075 | 1.00 | 39.91 | C |
| ATOM | 17284 | C1 | EDO | F | 1 | 60.295 | 28.440 | −11.630 | 1.00 | 42.58 | C |
| ATOM | 17287 | O1 | EDO | F | 1 | 60.843 | 28.589 | −10.311 | 1.00 | 42.11 | O |
| ATOM | 17289 | O2 | EDO | G | 1 | 36.330 | 8.565 | −39.005 | 1.00 | 47.10 | O |
| ATOM | 17291 | C2 | EDO | G | 1 | 35.245 | 7.630 | −39.096 | 1.00 | 49.42 | C |
| ATOM | 17294 | C1 | EDO | G | 1 | 34.960 | 6.978 | −37.743 | 1.00 | 48.88 | C |
| ATOM | 17297 | O1 | EDO | G | 1 | 34.932 | 7.961 | −36.704 | 1.00 | 45.94 | O |
| ATOM | 17299 | O2 | EDO | H | 1 | 41.479 | 22.293 | −17.292 | 1.00 | 35.35 | O |
| ATOM | 17301 | C2 | EDO | H | 1 | 42.167 | 22.883 | −16.188 | 1.00 | 36.60 | C |
| ATOM | 17304 | C1 | EDO | H | 1 | 41.528 | 22.474 | −14.866 | 1.00 | 36.89 | C |
| ATOM | 17307 | O1 | EDO | H | 1 | 40.146 | 22.180 | −15.068 | 1.00 | 40.64 | O |
| ATOM | 17309 | O2 | EDO | I | 1 | 63.131 | 34.770 | −14.264 | 1.00 | 54.30 | O |
| ATOM | 17311 | C2 | EDO | I | 1 | 62.720 | 34.806 | −12.892 | 1.00 | 53.62 | C |
| ATOM | 17314 | C1 | EDO | I | 1 | 63.896 | 35.136 | −11.984 | 1.00 | 51.08 | C |
| ATOM | 17317 | O1 | EDO | I | 1 | 63.368 | 35.673 | −10.768 | 1.00 | 48.31 | O |
| ATOM | 17319 | O2 | EDO | J | 1 | 59.151 | −30.232 | 2.286 | 1.00 | 44.49 | O |
| ATOM | 17321 | C2 | EDO | J | 1 | 58.706 | −30.950 | 1.125 | 1.00 | 42.28 | C |
| ATOM | 17324 | C1 | EDO | J | 1 | 58.774 | −30.052 | −0.105 | 1.00 | 40.11 | C |
| ATOM | 17327 | O1 | EDO | J | 1 | 59.229 | −28.751 | 0.291 | 1.00 | 36.58 | O |
| ATOM | 17329 | O2 | EDO | K | 1 | 57.235 | −48.102 | −15.555 | 1.00 | 69.20 | O |
| ATOM | 17331 | C2 | EDO | K | 1 | 56.504 | −48.728 | −14.489 | 1.00 | 68.39 | C |
| ATOM | 17334 | C1 | EDO | K | 1 | 55.610 | −47.707 | −13.786 | 1.00 | 67.00 | C |
| ATOM | 17337 | O1 | EDO | K | 1 | 56.359 | −46.520 | −13.502 | 1.00 | 63.83 | O |
| ATOM | 17339 | O2 | EDO | L | 1 | 62.259 | −27.697 | −29.101 | 1.00 | 41.14 | O |
| ATOM | 17341 | C2 | EDO | L | 1 | 61.689 | −26.383 | −29.134 | 1.00 | 47.27 | C |
| ATOM | 17344 | C1 | EDO | L | 1 | 60.177 | −26.441 | −28.906 | 1.00 | 47.64 | C |
| ATOM | 17347 | O1 | EDO | L | 1 | 59.752 | −27.796 | −28.701 | 1.00 | 50.95 | O |
| ATOM | 17349 | O2 | EDO | M | 1 | 81.050 | −42.461 | −15.315 | 1.00 | 47.87 | O |
| ATOM | 17351 | C2 | EDO | M | 1 | 81.860 | −42.153 | −16.466 | 1.00 | 48.16 | C |
| ATOM | 17354 | C1 | EDO | M | 1 | 81.056 | −41.499 | −17.586 | 1.00 | 47.34 | C |
| ATOM | 17357 | O1 | EDO | M | 1 | 79.693 | −41.937 | −17.575 | 1.00 | 48.08 | O |
| ATOM | 17359 | O2 | EDO | N | 1 | 28.354 | −3.375 | 4.402 | 1.00 | 51.07 | O |
| ATOM | 17361 | C2 | EDO | N | 1 | 29.104 | −3.578 | 5.608 | 1.00 | 54.76 | C |
| ATOM | 17364 | C1 | EDO | N | 1 | 28.967 | −5.027 | 6.081 | 1.00 | 56.35 | C |
| ATOM | 17367 | O1 | EDO | N | 1 | 29.372 | −5.939 | 5.050 | 1.00 | 53.02 | O |
| ATOM | 17369 | O2 | EDO | O | 1 | 48.766 | 0.661 | −13.390 | 1.00 | 45.65 | O |
| ATOM | 17371 | C2 | EDO | O | 1 | 50.117 | 1.103 | −13.583 | 1.00 | 52.86 | C |
| ATOM | 17374 | C1 | EDO | O | 1 | 50.184 | 2.630 | −13.577 | 1.00 | 54.50 | C |
| ATOM | 17377 | O1 | EDO | O | 1 | 50.984 | 3.091 | −12.475 | 1.00 | 57.04 | O |
| ATOM | 17379 | O | HOH | W | 1 | 60.687 | −41.700 | 3.860 | 1.00 | 11.23 | O |
| ATOM | 17382 | O | HOH | W | 2 | 57.035 | −34.744 | −10.325 | 1.00 | 19.60 | O |
| ATOM | 17385 | O | HOH | W | 3 | 57.953 | −36.264 | 5.870 | 1.00 | 10.26 | O |
| ATOM | 17388 | O | HOH | W | 4 | 70.638 | 29.975 | −18.112 | 1.00 | 18.09 | O |
| ATOM | 17391 | O | HOH | W | 5 | 84.932 | 24.597 | −26.740 | 1.00 | 11.78 | O |
| ATOM | 17394 | O | HOH | W | 6 | 68.858 | −38.920 | 7.795 | 1.00 | 19.90 | O |
| ATOM | 17397 | O | HOH | W | 7 | 39.088 | 11.823 | 10.564 | 1.00 | 10.95 | O |
| ATOM | 17400 | O | HOH | W | 8 | 48.412 | −9.808 | 11.114 | 1.00 | 24.66 | O |
| ATOM | 17403 | O | HOH | W | 9 | 61.169 | 7.818 | −25.284 | 1.00 | 31.12 | O |
| ATOM | 17406 | O | HOH | W | 10 | 47.599 | 7.531 | 13.059 | 1.00 | 18.61 | O |
| ATOM | 17409 | O | HOH | W | 11 | 64.039 | −29.833 | −3.258 | 1.00 | 16.41 | O |

APPENDIX 1-continued

| ATOM | 17412 | O | HOH | W | 12 | 42.935 | −38.107 | 10.309 | 1.00 | 22.38 | O |
|---|---|---|---|---|---|---|---|---|---|---|---|
| ATOM | 17415 | O | HOH | W | 13 | 32.087 | 6.522 | −8.854 | 1.00 | 18.71 | O |
| ATOM | 17418 | O | HOH | W | 14 | 31.936 | −16.886 | −1.578 | 1.00 | 27.02 | O |
| ATOM | 17421 | O | HOH | W | 15 | 37.784 | 29.459 | −21.498 | 1.00 | 33.19 | O |
| ATOM | 17424 | O | HOH | W | 16 | 53.861 | −30.927 | 12.149 | 1.00 | 27.93 | O |
| ATOM | 17427 | O | HOH | W | 17 | 70.063 | 31.639 | −14.308 | 1.00 | 12.62 | O |
| ATOM | 17430 | O | HOH | W | 18 | 84.074 | 36.299 | −9.580 | 1.00 | 12.24 | O |
| ATOM | 17433 | O | HOH | W | 19 | 39.692 | 35.076 | −6.963 | 1.00 | 22.90 | O |
| ATOM | 17436 | O | HOH | W | 20 | 41.191 | −34.300 | −1.248 | 1.00 | 22.27 | O |
| ATOM | 17439 | O | HOH | W | 21 | 43.143 | 32.516 | −47.841 | 1.00 | 10.32 | O |
| ATOM | 17442 | O | HOH | W | 22 | 30.933 | −18.194 | 10.415 | 1.00 | 23.53 | O |
| ATOM | 17445 | O | HOH | W | 23 | 51.413 | 16.562 | −9.613 | 1.00 | 17.16 | O |
| ATOM | 17448 | O | HOH | W | 24 | 53.453 | −31.542 | −1.575 | 1.00 | 27.60 | O |
| ATOM | 17451 | O | HOH | W | 25 | 34.185 | 9.497 | 9.218 | 1.00 | 20.29 | O |
| ATOM | 17454 | O | HOH | W | 26 | 70.482 | −44.878 | −22.511 | 1.00 | 19.16 | O |
| ATOM | 17457 | O | HOH | W | 27 | 61.126 | −25.351 | −11.285 | 1.00 | 30.79 | O |
| ATOM | 17460 | O | HOH | W | 28 | 82.202 | 46.630 | −18.365 | 1.00 | 19.68 | O |
| ATOM | 17463 | O | HOH | W | 29 | 42.016 | 9.773 | 11.682 | 1.00 | 5.49 | O |
| ATOM | 17466 | O | HOH | W | 30 | 52.552 | 9.222 | 12.917 | 1.00 | 20.96 | O |
| ATOM | 17469 | O | HOH | W | 31 | 53.315 | −4.004 | 7.707 | 1.00 | 22.13 | O |
| ATOM | 17472 | O | HOH | W | 32 | 64.807 | −47.148 | 18.948 | 1.00 | 28.71 | O |
| ATOM | 17475 | O | HOH | W | 33 | 87.987 | 23.967 | −22.136 | 1.00 | 15.14 | O |
| ATOM | 17478 | O | HOH | W | 34 | 61.924 | 43.652 | −5.371 | 1.00 | 24.37 | O |
| ATOM | 17481 | O | HOH | W | 35 | 49.569 | −32.537 | 13.686 | 1.00 | 27.90 | O |
| ATOM | 17484 | O | HOH | W | 36 | 77.969 | 23.424 | −22.801 | 1.00 | 17.03 | O |
| ATOM | 17487 | O | HOH | W | 37 | 80.807 | 47.407 | −31.377 | 1.00 | 8.36 | O |
| ATOM | 17490 | O | HOH | W | 38 | 46.696 | −14.204 | 10.301 | 1.00 | 20.38 | O |
| ATOM | 17493 | O | HOH | W | 39 | 32.536 | −20.230 | 2.767 | 1.00 | 30.33 | O |
| ATOM | 17496 | O | HOH | W | 40 | 67.794 | −37.856 | 19.719 | 1.00 | 25.28 | O |
| ATOM | 17499 | O | HOH | W | 41 | 47.941 | 20.855 | −36.616 | 1.00 | 23.14 | O |
| ATOM | 17502 | O | HOH | W | 42 | 62.977 | 54.761 | −32.676 | 1.00 | 18.97 | O |
| ATOM | 17505 | O | HOH | W | 43 | 52.751 | −50.583 | −4.033 | 1.00 | 22.75 | O |
| ATOM | 17508 | O | HOH | W | 44 | 31.039 | 32.019 | −32.115 | 1.00 | 31.94 | O |
| ATOM | 17511 | O | HOH | W | 45 | 42.029 | 26.557 | 1.145 | 1.00 | 29.11 | O |
| ATOM | 17514 | O | HOH | W | 46 | 31.869 | 4.285 | −20.561 | 1.00 | 28.89 | O |
| ATOM | 17517 | O | HOH | W | 47 | 74.093 | −42.929 | −1.070 | 1.00 | 16.27 | O |
| ATOM | 17520 | O | HOH | W | 48 | 40.858 | −34.802 | −4.714 | 1.00 | 15.94 | O |
| ATOM | 17523 | O | HOH | W | 49 | 37.278 | −5.018 | −27.726 | 1.00 | 12.76 | O |
| ATOM | 17526 | O | HOH | W | 50 | 83.275 | −36.108 | −3.577 | 1.00 | 8.23 | O |
| ATOM | 17529 | O | HOH | W | 51 | 80.764 | 20.265 | −23.409 | 1.00 | 16.65 | O |
| ATOM | 17532 | O | HOH | W | 52 | 31.595 | 3.922 | 2.971 | 1.00 | 23.66 | O |
| ATOM | 17535 | O | HOH | W | 53 | 57.415 | −26.762 | −3.471 | 1.00 | 28.77 | O |
| ATOM | 17538 | O | HOH | W | 54 | 72.526 | 10.018 | −12.123 | 1.00 | 27.04 | O |
| ATOM | 17541 | O | HOH | W | 55 | 87.476 | 49.890 | 0.772 | 1.00 | 2.00 | O |
| ATOM | 17544 | O | HOH | W | 56 | 33.973 | −23.668 | 7.434 | 1.00 | 24.56 | O |
| ATOM | 17547 | O | HOH | W | 57 | 52.409 | −44.924 | −11.036 | 1.00 | 25.63 | O |
| ATOM | 17550 | O | HOH | W | 58 | 51.617 | −24.152 | 16.093 | 1.00 | 29.65 | O |
| ATOM | 17553 | O | HOH | W | 59 | 60.767 | −28.228 | −12.288 | 1.00 | 29.39 | O |
| ATOM | 17556 | O | HOH | W | 60 | 53.918 | −56.125 | 0.008 | 1.00 | 28.78 | O |
| ATOM | 17559 | O | HOH | W | 61 | 33.210 | −6.327 | −3.576 | 1.00 | 34.39 | O |
| ATOM | 17562 | O | HOH | W | 62 | 41.640 | 14.903 | 3.307 | 1.00 | 15.68 | O |
| ATOM | 17565 | O | HOH | W | 63 | 58.660 | −57.902 | 16.689 | 1.00 | 12.91 | O |
| ATOM | 17568 | O | HOH | W | 64 | 51.057 | −36.200 | −2.118 | 1.00 | 26.86 | O |
| ATOM | 17571 | O | HOH | W | 65 | 66.814 | −24.153 | 22.063 | 1.00 | 35.44 | O |
| ATOM | 17574 | O | HOH | W | 66 | 29.022 | −28.733 | 26.291 | 1.00 | 17.80 | O |
| ATOM | 17577 | O | HOH | W | 67 | 90.189 | −22.222 | 4.963 | 1.00 | 19.58 | O |
| ATOM | 17580 | O | HOH | W | 68 | 78.682 | −42.748 | 19.875 | 1.00 | 28.90 | O |
| ATOM | 17583 | O | HOH | W | 69 | 56.469 | −31.804 | −2.878 | 1.00 | 31.63 | O |
| ATOM | 17586 | O | HOH | W | 70 | 41.401 | 20.399 | −1.163 | 1.00 | 29.63 | O |
| ATOM | 17589 | O | HOH | W | 71 | 53.598 | −11.238 | 8.837 | 1.00 | 28.06 | O |
| ATOM | 17592 | O | HOH | W | 72 | 75.612 | −15.475 | −6.124 | 1.00 | 23.91 | O |
| ATOM | 17595 | O | HOH | W | 73 | 68.376 | −34.458 | −18.543 | 1.00 | 16.52 | O |
| ATOM | 17598 | O | HOH | W | 74 | 69.339 | −31.552 | −15.520 | 1.00 | 17.52 | O |
| ATOM | 17601 | O | HOH | W | 75 | 69.286 | −41.965 | −19.351 | 1.00 | 24.29 | O |
| ATOM | 17604 | O | HOH | W | 76 | 75.463 | −46.593 | −7.759 | 1.00 | 19.91 | O |
| ATOM | 17607 | O | HOH | W | 77 | 63.711 | −35.486 | −0.007 | 1.00 | 5.12 | O |
| ATOM | 17610 | O | HOH | W | 78 | 62.685 | −33.036 | 0.733 | 1.00 | 15.71 | O |
| ATOM | 17613 | O | HOH | W | 79 | 65.190 | −28.298 | 0.653 | 1.00 | 17.26 | O |
| ATOM | 17616 | O | HOH | W | 80 | 74.263 | −38.930 | −2.404 | 1.00 | 12.17 | O |
| ATOM | 17619 | O | HOH | W | 81 | 76.242 | −38.951 | −0.599 | 1.00 | 14.40 | O |
| ATOM | 17622 | O | HOH | W | 82 | 65.958 | −51.251 | 6.374 | 1.00 | 21.04 | O |
| ATOM | 17625 | O | HOH | W | 83 | 64.794 | −53.762 | 7.147 | 1.00 | 16.67 | O |
| ATOM | 17628 | O | HOH | W | 84 | 69.920 | −48.364 | 6.636 | 1.00 | 23.24 | O |
| ATOM | 17631 | O | HOH | W | 85 | 59.007 | −35.681 | 0.128 | 1.00 | 21.30 | O |
| ATOM | 17634 | O | HOH | W | 86 | 47.141 | −47.469 | 0.295 | 1.00 | 8.84 | O |
| ATOM | 17637 | O | HOH | W | 87 | 32.623 | 28.895 | −35.533 | 1.00 | 4.99 | O |
| ATOM | 17640 | O | HOH | W | 88 | 49.914 | −40.645 | 8.973 | 1.00 | 22.44 | O |
| ATOM | 17643 | O | HOH | W | 89 | 43.107 | −38.127 | 1.800 | 1.00 | 14.68 | O |
| ATOM | 17646 | O | HOH | W | 90 | 42.398 | −41.782 | 7.963 | 1.00 | 17.43 | O |
| ATOM | 17649 | O | HOH | W | 91 | 41.442 | −48.239 | 5.460 | 1.00 | 2.00 | O |

APPENDIX 1-continued

| | | | | | | | | | | | |
|---|---|---|---|---|---|---|---|---|---|---|---|
| ATOM | 17652 | O | HOH | W | 92 | 62.411 | −31.955 | 8.352 | 1.00 | 20.44 | O |
| ATOM | 17655 | O | HOH | W | 93 | 60.871 | −20.177 | 4.347 | 1.00 | 20.57 | O |
| ATOM | 17658 | O | HOH | W | 94 | 58.610 | −23.989 | 0.527 | 1.00 | 15.61 | O |
| ATOM | 17661 | O | HOH | W | 95 | 77.170 | −36.427 | −8.109 | 1.00 | 17.54 | O |
| ATOM | 17664 | O | HOH | W | 96 | 69.010 | −23.558 | −4.094 | 1.00 | 5.17 | O |
| ATOM | 17667 | O | HOH | W | 97 | 67.976 | −19.417 | −1.601 | 1.00 | 27.30 | O |
| ATOM | 17670 | O | HOH | W | 98 | 55.120 | −15.695 | −9.971 | 1.00 | 15.80 | O |
| ATOM | 17673 | O | HOH | W | 99 | 40.221 | −8.919 | 14.184 | 1.00 | 24.31 | O |
| ATOM | 17676 | O | HOH | W | 100 | 75.311 | −46.315 | −17.890 | 1.00 | 12.75 | O |
| ATOM | 17679 | O | HOH | W | 101 | 36.689 | 12.147 | −8.452 | 1.00 | 13.56 | O |
| ATOM | 17682 | O | HOH | W | 102 | 49.409 | 4.411 | −3.957 | 1.00 | 20.53 | O |
| ATOM | 17685 | O | HOH | W | 103 | 51.208 | −3.216 | −6.796 | 1.00 | 27.29 | O |
| ATOM | 17688 | O | HOH | W | 104 | 50.423 | −11.431 | −14.044 | 1.00 | 25.17 | O |
| ATOM | 17691 | O | HOH | W | 105 | 35.050 | −4.248 | −9.227 | 1.00 | 15.36 | O |
| ATOM | 17694 | O | HOH | W | 106 | 40.522 | −39.592 | 8.121 | 1.00 | 13.31 | O |
| ATOM | 17697 | O | HOH | W | 107 | 44.392 | −41.412 | −4.710 | 1.00 | 25.85 | O |
| ATOM | 17700 | O | HOH | W | 108 | 90.651 | −25.293 | 0.822 | 1.00 | 20.51 | O |
| ATOM | 17703 | O | HOH | W | 109 | 75.686 | 25.603 | −1.188 | 1.00 | 19.35 | O |
| ATOM | 17706 | O | HOH | W | 110 | 79.161 | 27.994 | −0.849 | 1.00 | 24.23 | O |
| ATOM | 17709 | O | HOH | W | 111 | 30.975 | 6.748 | −35.336 | 1.00 | 22.85 | O |
| ATOM | 17712 | O | HOH | W | 112 | 81.633 | 50.321 | 0.940 | 1.00 | 16.36 | O |
| ATOM | 17715 | O | HOH | W | 113 | 81.501 | 41.972 | −14.894 | 1.00 | 5.20 | O |
| ATOM | 17718 | O | HOH | W | 114 | 77.799 | 33.970 | −22.161 | 1.00 | 19.08 | O |
| ATOM | 17721 | O | HOH | W | 115 | 69.029 | 32.450 | −3.346 | 1.00 | 27.97 | O |
| ATOM | 17724 | O | HOH | W | 116 | 67.333 | 54.975 | −36.644 | 1.00 | 5.32 | O |
| ATOM | 17727 | O | HOH | W | 117 | 71.581 | 36.620 | −26.421 | 1.00 | 26.94 | O |
| ATOM | 17730 | O | HOH | W | 118 | 68.657 | 33.764 | −26.041 | 1.00 | 20.83 | O |
| ATOM | 17733 | O | HOH | W | 119 | 57.118 | 40.798 | −25.352 | 1.00 | 22.78 | O |
| ATOM | 17736 | O | HOH | W | 120 | 57.109 | 43.195 | −30.729 | 1.00 | 20.51 | O |
| ATOM | 17739 | O | HOH | W | 121 | 64.944 | 22.448 | −22.022 | 1.00 | 23.64 | O |
| ATOM | 17742 | O | HOH | W | 122 | 65.055 | 24.670 | −18.404 | 1.00 | 17.02 | O |
| ATOM | 17745 | O | HOH | W | 123 | 73.576 | 24.897 | −13.394 | 1.00 | 9.07 | O |
| ATOM | 17748 | O | HOH | W | 124 | 50.432 | 18.994 | −27.696 | 1.00 | 23.95 | O |
| ATOM | 17751 | O | HOH | W | 125 | 42.778 | 15.381 | −31.371 | 1.00 | 23.30 | O |
| ATOM | 17754 | O | HOH | W | 126 | 43.937 | 16.439 | −33.443 | 1.00 | 40.87 | O |
| ATOM | 17757 | O | HOH | W | 127 | 30.460 | 12.584 | −23.332 | 1.00 | 27.55 | O |
| ATOM | 17760 | O | HOH | W | 128 | 31.399 | 25.056 | −38.256 | 1.00 | 17.13 | O |
| ATOM | 17763 | O | HOH | W | 129 | 45.704 | 22.675 | −34.062 | 1.00 | 34.00 | O |
| ATOM | 17766 | O | HOH | W | 130 | 35.949 | 19.963 | −9.142 | 1.00 | 30.59 | O |
| ATOM | 17769 | O | HOH | W | 131 | 40.354 | 36.564 | −35.731 | 1.00 | 19.72 | O |
| ATOM | 17772 | O | HOH | W | 132 | 38.318 | 34.494 | −35.413 | 1.00 | 7.26 | O |
| ATOM | 17775 | O | HOH | W | 133 | 57.188 | 36.811 | −31.845 | 1.00 | 24.17 | O |
| ATOM | 17778 | O | HOH | W | 134 | 58.146 | 38.433 | −16.715 | 1.00 | 27.12 | O |
| ATOM | 17781 | O | HOH | W | 135 | 92.188 | 21.084 | −22.452 | 1.00 | 21.22 | O |
| ATOM | 17784 | O | HOH | W | 136 | 50.818 | −42.619 | −4.261 | 1.00 | 23.46 | O |
| ATOM | 17787 | O | HOH | W | 137 | 41.418 | −14.439 | 3.492 | 1.00 | 24.49 | O |
| ATOM | 17790 | O | HOH | W | 138 | 60.691 | −22.131 | 0.873 | 1.00 | 26.59 | O |
| ATOM | 17793 | O | HOH | W | 139 | 63.812 | −50.432 | −16.555 | 1.00 | 18.97 | O |
| ATOM | 17796 | O | HOH | W | 140 | 66.799 | −43.436 | −15.556 | 1.00 | 26.39 | O |
| ATOM | 17799 | O | HOH | W | 141 | 36.831 | 23.369 | −20.144 | 1.00 | 24.83 | O |
| ATOM | 17802 | O | HOH | W | 142 | 69.526 | −39.429 | 2.654 | 1.00 | 17.65 | O |
| ATOM | 17805 | O | HOH | W | 143 | 76.413 | 42.942 | 0.826 | 1.00 | 32.70 | O |
| ATOM | 17808 | O | HOH | W | 144 | 43.360 | −29.899 | −8.145 | 1.00 | 33.98 | O |
| ATOM | 17811 | O | HOH | W | 145 | 49.576 | 35.961 | −9.667 | 1.00 | 26.92 | O |
| ATOM | 17814 | O | HOH | W | 146 | 47.057 | −32.984 | −9.280 | 1.00 | 33.16 | O |
| ATOM | 17817 | O | HOH | W | 147 | 54.276 | −39.999 | −12.465 | 1.00 | 31.06 | O |
| ATOM | 17820 | O | HOH | W | 148 | 49.138 | −11.535 | −7.738 | 1.00 | 21.23 | O |
| ATOM | 17823 | O | HOH | W | 149 | 51.464 | 33.092 | −16.231 | 1.00 | 39.45 | O |
| ATOM | 17826 | O | HOH | W | 150 | 37.234 | 23.654 | −4.671 | 1.00 | 29.14 | O |
| ATOM | 17829 | O | HOH | W | 151 | 54.632 | −49.110 | −8.260 | 1.00 | 27.54 | O |
| ATOM | 17832 | O | HOH | W | 152 | 32.712 | −14.896 | 2.375 | 1.00 | 24.37 | O |
| ATOM | 17835 | O | HOH | W | 153 | 40.313 | 31.980 | −26.077 | 1.00 | 18.77 | O |
| ATOM | 17838 | O | HOH | W | 154 | 63.860 | −40.924 | 4.353 | 1.00 | 27.96 | O |
| ATOM | 17841 | O | HOH | W | 155 | 47.606 | −39.199 | 11.721 | 1.00 | 31.76 | O |
| ATOM | 17844 | O | HOH | W | 156 | 46.777 | −7.365 | 16.313 | 1.00 | 32.28 | O |
| ATOM | 17847 | O | HOH | W | 157 | 39.606 | −17.036 | −19.091 | 1.00 | 24.83 | O |
| ATOM | 17850 | O | HOH | W | 158 | 45.372 | −31.614 | −12.501 | 1.00 | 30.91 | O |
| ATOM | 17853 | O | HOH | W | 159 | 59.419 | −24.763 | 13.202 | 1.00 | 40.00 | O |
| ATOM | 17856 | O | HOH | W | 160 | 86.758 | −24.726 | 6.593 | 1.00 | 15.69 | O |
| ATOM | 17859 | O | HOH | W | 161 | 78.705 | 45.595 | 5.075 | 1.00 | 26.92 | O |
| ATOM | 17862 | O | HOH | W | 162 | 75.448 | 26.421 | −14.430 | 1.00 | 18.50 | O |
| ATOM | 17865 | O | HOH | W | 163 | 59.126 | 47.335 | −13.817 | 1.00 | 25.69 | O |
| ATOM | 17868 | O | HOH | W | 164 | 57.117 | 51.918 | −18.780 | 1.00 | 21.01 | O |
| ATOM | 17871 | O | HOH | W | 165 | 68.807 | 35.000 | −18.130 | 1.00 | 18.00 | O |
| ATOM | 17874 | O | HOH | W | 166 | 65.330 | 37.902 | −18.096 | 1.00 | 30.56 | O |
| ATOM | 17877 | O | HOH | W | 167 | 53.156 | 15.720 | −3.604 | 1.00 | 22.56 | O |
| ATOM | 17880 | O | HOH | W | 168 | 58.196 | 19.642 | −7.395 | 1.00 | 22.98 | O |
| ATOM | 17883 | O | HOH | W | 169 | 55.559 | 23.000 | −41.753 | 1.00 | 16.76 | O |
| ATOM | 17886 | O | HOH | W | 170 | 64.909 | 32.691 | −17.810 | 1.00 | 40.95 | O |

We claim:

1. A recombinant microbial host cell comprising a nucleic acid encoding a polypeptide having isoprene synthase activity and providing improved growth activity when the polypeptide is expressed in a host cell, wherein the polypeptide has at least 90% sequence identity to SEQ ID NO:1 and comprises a substitution at a residue corresponding to K134, K138, L143, I156, E159, F163, S166, H167, E170, K414, or Q421 of SEQ ID NO:1, wherein the substitution is selected from the group consisting of K134P, K138C, L143F, L143V, I156G, E159G, E159Q, F163C, F163E, F163Q, F163V, F163Y, S166C, S166D, S166G, S166P, S166V, H167M, E170G, E170H, E170K, E170N, E170R, E170S, E170W, K414F, K414G, K414N, K414P, and Q421R, and wherein a host cell expressing the polypeptide has at least 50% more growth compared to the growth of a host cell expressing a parent polypeptide which does not comprise said substitution at a residue corresponding to SEQ ID NO:1 under similar growth conditions.

2. A recombinant microbial host cell comprising a nucleic acid encoding a polypeptide having isoprene synthase activity and providing improved growth activity when the polypeptide is expressed in a host cell, wherein the polypeptide has at least 90% sequence identity to SEQ ID NO:1 and comprises a substitution at a residue corresponding to E29, N47, S86, K94, E131, K134, I156, V162, K169, K178, E179, S231, R242, F369, K414, or Q421 of SEQ ID NO:1, wherein the substitution is selected from the group consisting of E29N, N47V, S86C, K94A, E131F, K134E, K134P, I156G, V162P, K169C, K178E, E179T, S231D, S231K, S231R, S231T, S231V, R242N, R242I, F369C, K414C, K414F, K414G, K414N, and Q421D, and wherein a host cell expressing the polypeptide has at least 50% more growth compared to the growth of a host cell expressing a parent polypeptide which does not comprise said substitution at a residue corresponding to SEQ ID NO:1 under similar growth conditions.

3. A recombinant microbial host cell comprising a nucleic acid encoding a polypeptide having isoprene synthase activity and providing improved growth activity when the polypeptide is expressed in a host cell, wherein the polypeptide has at least 90% sequence identity to SEQ ID NO:1 and comprises a substitution at a residue corresponding to K50, D81, K134, I137, L143, I156, E159, S166, H167, K169, E170, or K414 of SEQ ID NO:1, wherein the substitution is selected from the group consisting of K50S, D81F, K134E, K134P, I137N, L143V, I156G, E159D, E159G, E159Q, S166C, S166W, H167M, H167N, K169C, E170H, E170K, E170W, K414C, K414F, K414G, K414N, and K414P, and wherein a host cell expressing the polypeptide has at least 30% more growth compared to the growth of a host cell expressing a parent polypeptide which does not comprise said substitution at a residue corresponding to SEQ ID NO:1 under similar growth conditions.

4. A recombinant microbial host cell comprising a nucleic acid encoding a polypeptide having isoprene synthase activity and providing improved growth activity when the polypeptide is expressed in a host cell, wherein the polypeptide has at least 90% sequence identity to SEQ ID NO:1 and comprises a substitution at a residue corresponding to V30, V84, K134, I140, L143, F163, S166, K169, E170 or S172 of SEQ ID NO:1, wherein the substitution is selected from the group consisting of V30K, V84T, K134C, K134D, K134E, I140S, I140T, L143F, L143I, L143M, L143V, F163I, F163M, S166P, S166V, K169Q, E170H, E170K, and S172V, and wherein the polypeptide has at least 20% increase in specific activity of isoprene synthase compared to a parent polypeptide which does not comprise said substitution at a residue corresponding to SEQ ID NO: 1 and at least 20% more growth in a host cell expressing the polypeptide compared to the growth of a host cell expressing a parent polypeptide which does not comprise said substitution at a residue corresponding to SEQ ID NO: 1 under similar growth conditions.

5. A recombinant microbial host cell comprising a nucleic acid encoding a polypeptide with isoprene synthase properties wherein the polypeptide has at least 90% sequence identity to SEQ ID NO:1 and comprises a substitution at a residue corresponding to N47, G87, I156, V162, E170, S231, R242, V409, or K414 of SEQ ID NO:1, wherein the substitution is selected from the group consisting of N47V, G87R, I156G, V162P, E170H, S231T, R242N, V409T, and K414F, and wherein the polypeptide has at least 30% increase in specific activity of isoprene synthase as compared to a parent polypeptide which does not comprise said substitution at a residue corresponding to SEQ ID NO:1 and at least 30% more growth when the polypeptide is expressed in a host cell, as compared to a parent polypeptide which does not comprise said substitution at a residue corresponding to SEQ ID NO:1 under similar growth conditions.

6. A recombinant microbial host cell comprising a nucleic acid encoding a polypeptide with isoprene synthase properties wherein the polypeptide has at least 90% sequence identity to SEQ ID NO:1 and comprises a substitution at a residue corresponding to E2, Y18, L19, S21, T24, E26, S27, E29, K37, V42, N47, N48, E49, L56, D81, R82, V84, T93, K94, T95, S120, K123, N126, E131, N132, K134, I137, A139, L143, L151, N155, S166, H167, K169, E170, L171, K175, E179, L180, Q197, I229, S231, T240, R242, R245, R246, V247, T251, A271, S282, L306, D317, N319, F369, Q371, L376, K379, S380, G389, W392, K393, V408, V409, Q421, K422, Y423, R429, C437, S444, I447, S455, C458, R461, G464, S466, A470, S473, V500, T502, L506, T513, E525 or V531 of SEQ ID NO:1, wherein the substitution is selected from the group consisting of E2A or K or P, Y18D or E or K or S, L19Y, S21W, T24L or V, E26C, S27D or N, E29N, K37C or D or P or Q or S, V42M, N47D or S, N48D or G or T, E49L or V, L56E or F or G or I or K or T or V or Y, D81Q, R82N or T or V or Y, V84M, T93C or F or R or S, K94G or P, T95D or F or G or I or N or W, S120C or G or M or Q, K123V, N126E, E131H or K or L or M or T or W or Y, N132I or P, K134A, I137T, A139C or Q, L143C or D or E or H or K or M or Q or T or V or Y, L151A or F, N155A or C or G or H or Q or R or S or W, S166N, H167F or I or N or Q or V, K169A or C or H or N or Q or V, E170L or S or W or Y, L171A or N or Q or T or V or Y, K175C or F or I or Q or R, E179D, L180A or I, Q197C or D or N, I229C, S231A, T240C, R242G, R245C or K or M or Q or T or V, R246N, V247L or M, T251D or E or N or P or Q or S, A271T, S282Y, L306C, D317N, N319M, F369C or D or E or G or S, Q371F, L376I or M, K379G or Q, S380E, G389A or D or E or K or N or Q or S or V, W392Y, K393C or I or T or V, V408T, V409T, Q421H, K422D, Y423N or S, R429E or F or Q, C437M, S444D or E, I447T, S455A, C458T, R461A, G464C or M or N or Q or S, S466D, A470I or L, S473I, V500A or C, T502M, L506M, T513C or G or K or N, E525F or R, and V531E or H or K or Q or R or S, and wherein the polypeptide has (i) minimum performance indices (PI) relative to a parent polypeptide which does not comprise said substitution at a residue corresponding to SEQ ID NO: 1 for specific activity and expression are greater than or equal to a PI of 0.9 and where at least one PI relative to a parent polypeptide which does not comprise said substitution at a residue corresponding to SEQ ID NO:1 for specific activity or growth is greater than or equal to a PI of 1.0; or (ii) minimum performance indices (PI) relative to a parent polypeptide which does not comprise said substitution at a residue corresponding to SEQ ID NO:1 for specific activity and expression are greater than or equal to a PI of 0.8 and where at least one PI relative to a parent polypeptide which does not comprise said substitution at a residue corresponding to SEQ ID NO:1 for specific activity or growth is greater than or equal to a PI of 1.2; or (iii) minimum performance indices (PI) relative to a parent polypeptide which does not comprise said substitution at a residue corresponding to SEQ ID NO:1 for specific activity and expression are greater than or equal to a PI of 0.5 and where at least one PI relative to a parent polypeptide which does not comprise said substitution at a residue corresponding to SEQ ID NO:1 for specific activity or growth is greater than or equal to a PI of 1.5.

7. A recombinant microbial host cell comprising a nucleic acid encoding a polypeptide with improved isoprene synthase properties wherein the polypeptide has at least 90% sequence identity to SEQ ID NO:1 and comprises a substitution at a residue corresponding to E2, S6, Y18, L20, S22, D23, T24, D25, E26, S27, I28, E29, V30, Y31, K32, K36, K37, V42, R44, N47, N48, E49, K50, F53, L54, T55, L56, E58, L59, L68, R71, S74, R77, G78, A79, D81, R82, F83, V84, S86, G87, A91, T93, K94, T95, L97, H98, G99, Q109, S115, Q116, E117, A118, S120, K123, Q125, N126, G127, N128, L130, E131, N132, L133, K134, D136, I137, K138, A139, I140, L143, L151, G153, N155, I156, E159, A160, K161, V162, F163, A164, S166, H167, K169, E170, L171, S172, K175, I176, G177, K178, E179, L180, A181, E182, L190, R194, Q197, S204, K211, N215, V217, L219, L221, M228, I229, S231, V232, R235, S241, R242, R245, R246, V247, T251, H254, A271, F272, D278, C279, S282, I296, T302, D317, N319, A320, Y327, C331, K348, G351, Y357, A361, D364, L365, A368, F369, L370, Q371, A373, Y377, S380, T383, D386, G389, W392, K393, A407, V408, V409, Q410, N411, K414, K422, Y423, H424, S428, R429, H432, L436, C437, L440, S444, I447, A448, S457, M460, R461, T462, K463, G464, I465, S466, E468, A470, T471, E472, S473, M475, E480, L490, G492, L494, A496, V500, E501, T502, A503, S510, T513, H515, A519, E525, V531, T536, E537, L540, P541, F542, or R544 of SEQ ID NO:1, wherein the substitution is selected from the group consisting of E2C or D or N or T or V, S6N or T, Y18A or Q or R, L20T, S22Q, D23N, T24C, D25T, E26D or H or K or M or R or S or V, S27A or C or G or H or I or L or M or P or Q, 128D or N, E29Q, V30A or D or E or M or R or T, Y31N, K32E, K36A or C or D or E or M or N or P or Q, K37A or E or G or H or M or N or R or T, V42F or I, R44N or Q, N47A or G or H or M or Q or T or W, N48H or I or K, E49A or C, K50A or D or E or F or H or S or Y, F53E or H or N or P or Q or V, L54M, T55C or D or E, L56C or N, E58N, L59H or T, L68I, R71K or M, S74D or E or N or Y, R77L, G78A or D or F or L or M, A79Q or T, D81A or F or G or M or R or S or T or V, R82A or E or H or I or K or M or N or Q or S, F83W, V84A, S86A or D or M, G87D or P, A91K or W, T93A or D or E or G or L or N or P or Y, K94A or D or E or H or I or L or M or N or R or S or T, T95A or E or P or Q or S or V or Y, L97F, H98A or D or F or G or I or L or M or N or Q, G99E or F or M, Q109E, S115A, Q116A or C or D or E or I or P, E117C or F or L or M or V, A118M, S120H or T or V, K123L or T, Q125E or I or Y, N126A or C or D or M or T or V, G127C, N128C or D or P or Q, L130E, E131A or C or P or Q or S or V, N132C or D or F or H or L or R or W or Y, L133D, K134E or M or Q or S or T or V, D136E, I137E or H or N, K138I or N, A139N, I140M or W, L143S, L151C or H or I, G153C, N155I or T or V or Y, I156D or N or T, E159M, A160I, K161A or C or N or Q, V162S, F163E or Q, A164T, S166A or D or G, H167A or E or G or K or M or R or S or T or W, K169D or I or M or S or T, E170H or K or M or Q or T or V, L171H or K or R or S, S172A or C, K175S, I176M, G177A or C, K178A or F or R or S or T, E179A or C or L or M or N, L180C or Q or T, A181H or Q or S or V, E182S, L190I or M, R194L, Q197S, S204C, K211A or N or Q, N215C or H, V217I, L219C, L221M, M228F or Y, I229V, S231K or Q or T, V232I, R235K, S241A or M or T, R242A or D or E or F or I or M or N or Q or S or T, R245I or L, R246D or K, V247T, T251A or G or K or R, H254D, A271C or V, F272D or G or P or W, D278A or E or N or Q or S or T or V or W, C279A, S282A or Q, I296V, T302H, D317E or Q, N319F, A320C, Y327M, C331P, K348R or Y, G351D or N, Y357M, A361T, D364E or V, L365C or M, A368N, F369M or N or R or T or V, L370G or Q, Q371C or S, A373G, Y377W, S380A or C or D or Q or T or V, T383S, D386E or N, G389H or I, W392I or S or T or V, K393Q, A407G, V408I, V409H or I, Q410C or D or K or L or M or T, N411G, K414E or G or L or N or P, K422A or N or T, Y423Q, H424E or P or Q or V, S428E or Q, R429I or L or T or W or Y, H432E, L436M or Y, C437K or T, L440I, S444P, I447A or E or M or Q or S, A448E or M or N or P or Q or V, S457N or T, M460Q or R or S, R461D or E or G or Q or S or T, T462Q, K463A or D or E, G464L or R, I465A or C or G or S or T, S466P, E468D, A470M, T471E or H or Q, E472D or S, S473L or V, M475T, E480N, L490A or D or E or F or H or M, G492C, L494D, A496P or T, V500L or M, E501D, T502A or C or R or V, A503I, S510C or V, T513V, H515N, A519S or T, E525A or C or P or Q or S, V531A or M or T, T536A or F or G, E537K or T, L540A or P, P541M, F542P, and R544C, and wherein the polypeptide has (i) minimum performance indices (PI) relative to a parent polypeptide which does not comprise said substitution at a residue corresponding to SEQ ID NO:1 for specific activity and expression are greater than or equal to a PI of 0.9 and where at least one PI relative to a parent polypeptide which does not comprise said substitution at a residue corresponding to SEQ ID NO:1 for specific activity or growth is greater than or equal to a PI of 1.0; or (ii) minimum performance indices (P1) relative to a parent polypeptide which does not comprise said substitution at a residue corresponding to SEQ ID NO:1 for specific activity and expression are greater than or equal to a PI of 0.8 and where at least one PI relative to a parent polypeptide which does not comprise said substitution at a residue corresponding to SEQ ID NO:1 for specific activity or growth is greater than or equal to a PI of 1.2.

8. A recombinant microbial host cell comprising a nucleic acid encoding a polypeptide having isoprene synthase activity, wherein the polypeptide has at least 90% sequence identity to SEQ ID NO:1 and comprises a substitution at a residue corresponding to S22, K36, R43, E58, G87, F89, A118, L151, G153, Q234, V247, H254, S282, A391, W392, C437, I447, T481, E488, T502 or F542 of SEQ ID NO:1, wherein the substitution is selected from the group consisting of S22K or R, K36H or W, R43E, E58F, G87S or R, F89D, A118E, L151Y, G153P, Q234R, V247I, H254C, S282H or W, or T or Y, A391G, W392C, C437L, I447V, T481Y, E488L, T502F and F542N, and wherein the polypeptide has at least 30% increase in specific activity of isoprene synthase compared to a parent polypeptide which does not comprise said substitution at a residue corresponding to SEQ ID NO:1.

9. A recombinant microbial host cell comprising a nucleic acid encoding a polypeptide having isoprene synthase activity and providing improved growth activity when the polypeptide is expressed in a host cell, wherein the polypeptide has at least 90% sequence identity to SEQ ID NO:1 and comprises a substitution at a residue corresponding to V30, K134, L143, I156, E159, S172, K414, or Q421 of SEQ ID NO:1, wherein the substitution is selected from the group consisting of V30K, K134C or P, L143I, I156G, E159D, S172V, K414F, and Q421R or D, and wherein a host cell expressing the polypeptide has at least 20% more growth compared to the growth of a host cell expressing a parent polypeptide which does not comprise said substitution at a residue corresponding to SEQ ID NO:1 under similar growth conditions.

10. The host cell of any one of claims 1-9 wherein the host cell is selected from the group consisting of a bacterial, algal, fungal, yeast, cyanobacterial, and Clostridial cell.

11. The host cell of claim 10 wherein the host cell is a bacterial cell.

12. The host cell of claim 11 wherein the bacterial cell is a gram-positive bacterial cell or gram-negative bacterial cell.

13. The host cell of claim 12 wherein the bacterial cell is selected from the group consisting of a *E. coli, L. acidophilus, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes, Clostridium* sp., *Corynebacterium* sp., and *C. glutamicum* cell.

14. The host cell of claim 10 wherein the host cell is an algal cell.

15. The host cell of claim 14 wherein the algal cell is selected from the group consisting of green alga, red alga, glaucophyte, chlorarachniophyte, euglenid, chromista, and dinoflagellate cell.

16. The host cell of claim 15 wherein the host cell is a fungal cell.

17. The host cell of claim 16 wherein the fungal cell is a filamentous fungi.

18. The host cell of claim 10 wherein the host cell is a yeast cell.

19. The host cell of claim 18 wherein the yeast cell is selected from the group consisting of a *Saccharomyces* sp., *Schizosaccharomyces* sp., *Pichia* sp., and *Candida* sp. cell.

20. The host cell of claim 19 wherein the yeast cell is a *Saccharomyces cerevisiae* cell.

* * * * *

SEQUENCE LISTING

<160> NUMBER OF SEQ ID NOS: 41

<210> SEQ ID NO 1
<211> LENGTH: 544
<212> TYPE: PRT
<213> ORGANISM: Populus alba

<400> SEQUENCE: 1

```
Met Glu Ala Arg Arg Ser Ala Asn Tyr Glu Pro Asn Ser Trp Asp Tyr
 1               5                  10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365
```

```
Phe Leu Gln Glu Ala Lys Trp Leu Tyr Asn Lys Ser Thr Pro Thr Phe
370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
            405                 410                 415

Ile Glu Asn Leu Gln Lys Tyr His Asp Thr Ile Ser Arg Pro Ser His
                420                 425                 430

Ile Phe Arg Leu Cys Asn Asp Leu Ala Ser Ala Ser Glu Ile Ala
            435                 440                 445

Arg Gly Glu Thr Ala Asn Ser Val Ser Cys Tyr Met Arg Thr Lys Gly
450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
                515                 520                 525

Lys Arg Val Leu Ser Val Ile Thr Glu Pro Ile Leu Pro Phe Glu Arg
530                 535                 540
```

<210> SEQ ID NO 2
<211> LENGTH: 47
<212> TYPE: DNA
<213> ORGANISM: Artificial Sequence
<220> FEATURE:
<223> OTHER INFORMATION: Synthetic Construct

<400> SEQUENCE: 2
ggagatatac atatggaagc acgtcgctct gcgaactacg aacctaa        47

<210> SEQ ID NO 3
<211> LENGTH: 47
<212> TYPE: DNA
<213> ORGANISM: Artificial Sequence
<220> FEATURE:
<223> OTHER INFORMATION: Synthetic Construct

<400> SEQUENCE: 3
ttaggttcgt agttcgcaga gcgacgtgct tccatatgta tatctcc        47

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
taatacgact cactataggg        20

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct

<400> SEQUENCE: 5

```
gctagttatt gctcagcgg                                                   19

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
gcactgtctt tccgtctgct gc                                               22

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
cttcggcaac gcatggaaat                                                  20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ctcgtacagg ctcaggatag                                                  20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ttacgtccca acgctcaact                                                  20

<210> SEQ ID NO 10
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 10
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggatttt gccgatttcg gcctattggt taaaaaatg agctgattta     420 acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
```

-continued

```
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg caacgctac    1200 ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500 gatcctttt ttctgcgcgt aatctgctgc ttgcaaacaa aaaaaccacc gctaccagcg   1560
gtggtttgtt tgccggatca agagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt cctgcgtta   2160 tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac accgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
```

```
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag gtggtttttc ttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg cgcgcattg    3840 cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa agacaccgg    4560 catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgaagca gtcgctctg cgaactacga    5100 acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
```

```
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt tttctttcgt    5940
aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgctaaggat ccgaattcga    6720
gctccgtcga caagcttgcg gccgcactcg agcaccacca ccaccaccac tgagatccgg    6780
ctgctaacaa agcccgaaag gaagctgagt tggctgctgc caccgctgag caataactag    6840
cataacccct tggggcctct aaacgggtct tgaggggttt tttgctgaaa ggaggaacta    6900
tatccggat                                                             6909
```

<210> SEQ ID NO 11
<211> LENGTH: 81
<212> TYPE: DNA
<213> ORGANISM: Artificial Sequence
<220> FEATURE:
<223> OTHER INFORMATION: Synthetic Construct

<400> SEQUENCE: 11

```
aaagtagccg aagatgacgg tttgtcacat ggagttggca ggatgtttga ttaaaagcaa      60
ttaaccctca ctaaagggcg g                                                81
```

<210> SEQ ID NO 12
<211> LENGTH: 199
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 112

<223> OTHER INFORMATION: n = any nucleotide

<400> SEQUENCE: 12

```
taaatcttac ccggcgcaga acaggatacc atgttttttt acctcctttg caccttcatg    60
gtggtcagtg cgtcctgctg atgtgctcag tatcaccgcc agtggtattt angtcaacac   120
cgccagagat aatttatcac cgcagatggt tatctgtatg ttttttatat gaatttaata   180
cgactcacta tagggctcg                                                199
```

<210> SEQ ID NO 13
<211> LENGTH: 24
<212> TYPE: DNA
<213> ORGANISM: Artificial Sequence
<220> FEATURE:
<223> OTHER INFORMATION: Synthetic Construct

<400> SEQUENCE: 13

```
aaagaccgac caagcgacgt ctga                                           24
```

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14

```
gctctgaata gtgatagagt ca                                             22
```

<210> SEQ ID NO 15
<211> LENGTH: 445
<212> TYPE: DNA
<213> ORGANISM: Artificial Sequence
<220> FEATURE:
<223> OTHER INFORMATION: Synthetic Construct

<400> SEQUENCE: 15

```
aaagaccgac caagcgacgt ctgagagctc cctggcgaat tcggtaccaa taaaagagct    60
ttattttcat gatctgtgtg ttggttttttg tgtgcggcgc ggaagttcct attctctaga   120
aagtatagga acttcctcga gccctatagt gagtcgtatt aaattcatat aaaaaacata   180
cagataacca tctgcggtga taaattatct ctggcggtgt tgacataaat accactggcg   240
gtgatactga gcacatcagc aggacgcact gaccaccatg aaggtgcaaa ggaggtaaaa   300
aaacatggta tcctgttctg cgccgggtaa gatttacctg ttcggtgaac acgccgtagt   360
ttatggcgaa actgcaattg cgtgtgcggt ggaactgcgt acccgtgttc gcgcggaact   420
caatgactct atcactattc agagc                                         445
```

<210> SEQ ID NO 16
<211> LENGTH: 445
<212> TYPE: DNA
<213> ORGANISM: Artificial Sequence
<220> FEATURE:
<223> OTHER INFORMATION: Synthetic Construct

<400> SEQUENCE: 16

```
aaagaccgac caagcgacgt ctgagagctc cctggcgaat tcggtaccaa taaaagagct    60
ttattttcat gatctgtgtg ttggttttttg tgtgcggcgc ggaagttcct attctctaga   120
aagtatagga acttcctcga gccctatagt gagtcgtatt aaattcatat aaaaaacata   180
cagataacca tctgcggtga taaattatct ctggcggtgt tgacctaaat accactggcg   240
```

```
gtgatactga gcacatcagc aggacgcact gaccaccatg aaggtgcaaa ggaggtaaaa    300
aaacatggta tcctgttctg cgccgggtaa gatttacctg ttcggtgaac acgccgtagt    360
ttatggcgaa actgcaattg cgtgtgcggt ggaactgcgt acccgtgttc gcgcggaact    420
caatgactct atcactattc agagc                                         445
```

<210> SEQ ID NO 17
<211> LENGTH: 442
<212> TYPE: DNA
<213> ORGANISM: Artificial Sequence
<220> FEATURE:
<223> OTHER INFORMATION: Synthetic Construct

<400> SEQUENCE: 17

```
aaagaccgac caagcgacgt ctgagagctc cctggcgaat tcggtaccaa taaaagagct     60
ttattttcat gatctgtgtg ttggttttg tgtgcggcgc ggaagttcct attctctaga    120
aagtatagga acttcctcga gccctatagt gagtcgtatt aaattcatat aaaaaacata    180
cagataacca tctgcggtga taaattatct ctggcggtgt tgacctaaat accactggcg    240
gtgatactga gcacatcagc aggacgcact gaccaccatg aaggtgcaaa ggtaaaaaaa    300
catggtatcc tgttctgcgc cgggtaagat ttacctgttc ggtgaacacg ccgtagttta    360
tggcgaaact gcaattgcgt gtgcggtgga actgcgtacc cgtgttcgcg cggaactcaa    420
tgactctatc actattcaga gc                                            442
```

<210> SEQ ID NO 18
<211> LENGTH: 445
<212> TYPE: DNA
<213> ORGANISM: Artificial Sequence
<220> FEATURE:
<223> OTHER INFORMATION: Synthetic Construct

<400> SEQUENCE: 18

```
aaagaccgac caagcgacgt ctgagagctc cctggcgaat tcggtaccaa taaaagagct     60
ttattttcat gatctgtgtg ttggttttg tgtgcggcgc ggaagttcct attctctaga    120
aagtatagga acttcctcga gccctatagt gagtcgtatt aaattcatat aaaaaacata    180
cagataacca tctgcggtga taaattatct ctggcggtgt tgacgtaaat accactggcg    240
gtgatactga gcacatcagc aggacgcact gaccaccatg aaggtgcaaa ggaggtaaaa    300
aaacatggta tcctgttctg cgccgggtaa gatttacctg ttcggtgaac acgccgtagt    360
ttatggcgaa actgcaattg cgtgtgcggt ggaactgcgt acccgtgttc gcgcggaact    420
caatgactct atcactattc agagc                                         445
```

<210> SEQ ID NO 19
<211> LENGTH: 73
<212> TYPE: DNA
<213> ORGANISM: Artificial Sequence
<220> FEATURE:
<223> OTHER INFORMATION: Synthetic Construct

<400> SEQUENCE: 19

```
tatttaattt ttaatcatct aatttgacaa tcattcaaca aagttgttac aattaaccct     60
cactaagggg cgg                                                       73
```

<210> SEQ ID NO 20
<211> LENGTH: 147
<212> TYPE: DNA

```
<213> ORGANISM: Artificial Sequence
<220> FEATURE:
<223> OTHER INFORMATION: Synthetic Construct

<400> SEQUENCE: 20
tcaacagctg tatccccgtt gagggtgagt tttgcttttg tatcagccat atattccacc    60
agctatttgt tagtgaataa aagtggttga attatttgct caggatgtgg cathgtcaag   120
ggctaatacg actcactata gggctcg                                        147

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct

<400> SEQUENCE: 21
ggcagtatag gctgttcaca aaatc                                          25

<210> SEQ ID NO 22
<211> LENGTH: 23
<212> TYPE: DNA
<213> ORGANISM: Artificial Sequence
<220> FEATURE:
<223> OTHER INFORMATION: Synthetic Construct

<400> SEQUENCE: 22
cttgacccag cgtgcctttc agc                                            23

<210> SEQ ID NO 23
<211> LENGTH: 31
<212> TYPE: DNA
<213> ORGANISM: Artificial Sequence
<220> FEATURE:
<223> OTHER INFORMATION: Synthetic Construct

<400> SEQUENCE: 23
gaaaaactga gtggtagcct gttcgcgaaa c                                   31

<210> SEQ ID NO 24
<211> LENGTH: 31
<212> TYPE: DNA
<213> ORGANISM: Artificial Sequence
<220> FEATURE:
<223> OTHER INFORMATION: Synthetic Construct

<400> SEQUENCE: 24
aggctaccac tcagtttttc cttgttcatc t                                   31

<210> SEQ ID NO 25
<211> LENGTH: 6858
<212> TYPE: DNA
<213> ORGANISM: Artificial Sequence
<220> FEATURE:
<223> OTHER INFORMATION: Synthetic Construct

<400> SEQUENCE: 25
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
```

-continued

```
caatttatca gacaatctgt gtgggcactc gaccggaatt atcgattaac tttattatta    360
aaaattaaag aggtatatat taatgtatcg attaaataag gaggaataaa ccatggaagc    420
tcgtcgttct gcgaactacg aacctaacag ctgggactat gattacctgc tgtcctccga    480
cacggacgag tccatcgaag tatacaaaga caaagcgaaa aagctggaag ccgaagttcg    540
tcgcgagatt aataacgaaa aagcagaatt tctgaccctg ctggaactga ttgacaacgt    600
ccagcgcctg ggcctgggtt accgtttcga gtctgatatc cgtggtgcgc tggatcgctt    660
cgtttcctcc ggcggcttcg atgcggtaac caagacttcc ctgcacggta cggcactgtc    720
tttccgtctg ctgcgtcaac acggttttga ggtttctcag gaagcgttca gcggcttcaa    780
agaccaaaac ggcaacttcc tggagaacct gaaggaagat atcaaagcta tcctgagcct    840
gtacgaggcc agcttcctgg ctctggaagg cgaaaacatc ctggacgagg cgaaggtttt    900
cgcaatctct catctgaaag aactgtctga agaaagatc ggtaaagagc tggcagaaca    960
ggtgaaccat gcactggaac tgccactgca tcgccgtact cagcgtctgg aagcagtatg    1020
gtctatcgag gcctaccgta aaaggagga cgcgaatcag gttctgctgg agctggcaat    1080
tctggattac aacatgatcc agtctgtata ccagcgtgat ctgcgtgaaa cgtcccgttg    1140
gtggcgtcgt gtgggtctgg cgaccaaact gcactttgct cgtgaccgcc tgattgagag    1200
cttctactgg gccgtgggtg tagcattcga accgcaatac tccgactgcc gtaactccgt    1260
cgcaaaaatg ttttctttcg taaccattat cgacgatatc tacgatgtat acggcaccct    1320
ggacgaactg gagctgtttta ctgatgcagt tgagcgttgg gacgtaaacg ccatcaacga    1380
cctgccggat tacatgaaac tgtgctttct ggctctgtat aacactatta acgaaatcgc    1440
ctacgacaac ctgaaagata aggtgagaa catcctgccg tatctgacca agcctgggc    1500
tgacctgtgc aacgctttcc tgcaagaagc caagtggctg tacaacaaat ctactccgac    1560
ctttgacgac tacttcggca acgcatggaa atcctcttct ggcccgctgc aactggtgtt    1620
cgcttacttc gctgtcgtgc agaacattaa aaaggaagag atcgaaaacc tgcaaaaata    1680
ccatgacacc atctctcgtc cttcccatat cttccgtctg tgcaatgacc tggctagcgc    1740
gtctgcggaa attgcgcgtg gtgaaaccgc aaatagcgtt tcttgttaca tgcgcactaa    1800
aggtatctcc gaagaactgg ctaccgaaag cgtgatgaat ctgatcgatg aaacctggaa    1860
aaagatgaac aaggaaaaac tgagtggtag cctgttcgcg aaaccgttcg tggaaaccgc    1920
gatcaacctg gcacgtcaat ctcactgcac ttatcataac ggcgacgcgc atacctctcc    1980
ggatgagctg acccgcaaac gcgttctgtc tgtaatcact gaaccgattc tgccgtttga    2040
acgctaactg cataaaggag gtaaaaaaac atggtatcct gttctgcgcc gggtaagatt    2100
tacctgttcg gtgaacacgc cgtagtttat ggcgaaactg caattgcgtg tgcggtggaa    2160
ctgcgtaccc gtgttcgcgc ggaactcaat gactctatca ctattcagag ccagatcggc    2220
cgcaccggtc tggatttcga aaagcaccct tatgtgtctg cggtaattga aaaatgcgc    2280
aaatctattc ctattaacgg tgttttcttg accgtcgatt ccgacatccc ggtgggctcc    2340
ggtctgggta gcagcgcagc cgttactatc gcgtctattg gtgcgctgaa cgagctgttc    2400
ggctttggcc tcagcctgca agaaatcgct aaactgggcc acgaaatcga aattaaagta    2460
cagggtgccg cgtccccaac cgatacgtat gttttctacct tcggcggcgt ggttaccatc    2520
ccggaacgtc gcaaactgaa aactccggac tgcggcattg tgattggcga taccggcgtt    2580
ttctcctcca ccaaagagtt agtagctaac gtacgtcagc tgcgcgaaag ctacccggat    2640
```

```
ttgatcgaac cgctgatgac ctctattggc aaaatctctc gtatcggcga caactggtt    2700 ctgtctggcg actacgcatc catcggccgc ctgatgaacg tcaaccaggg tctcctggac   2760
gccctgggcg ttaacatctt agaactgagc cagctgatct attccgctcg tgcggcaggt   2820
gcgtttggcg ctaaaatcac gggcgctggc ggcggtggct gtatggttgc gctgaccgct   2880
ccggaaaaat gcaaccaagt ggcagaagcg gtagcaggcg ctggcggtaa agtgactatc   2940
actaaaccga ccgagcaagg tctgaaagta gattaaagtc tagttaaagt ttaaacggtc   3000
tccagcttgg ctgttttggc ggatgagaga agattttcag cctgatacag attaaatcag   3060
aacgcagaag cggtctgata aaacagaatt tgcctggcgg cagtagcgcg gtggtcccac   3120
ctgaccccat gccgaactca gaagtgaaac gccgtagcgc cgatggtagt gtggggtctc   3180
cccatgcgag agtagggaac tgccaggcat caaataaaac gaaaggctca gtcgaaagac   3240
tgggcctttc gttttatctg ttgtttgtcg gtgaacgctc tcctgagtag acaaatccg   3300 ccgggagcgg atttgaacgt tgcgaagcaa cggcccggag ggtggcgggc aggacgcccg   3360
ccataaactg ccaggcatca aattaagcag aaggccatcc tgacggatgg cctttttgcg   3420
tttctacaaa ctcttttttgt ttatttttct aaatacattc aaatatgtat ccgctcatga   3480
gacaataacc ctgataaatg cttcaataat attgaaaaag gaagagtatg agtattcaac   3540
atttccgtgt cgcccttatt cccttttttg cggcattttg ccttcctgtt tttgctcacc   3600
cagaaacgct ggtgaaagta aaagatgctg aagatcagtt gggtgcacga gtgggttaca   3660
tcgaactgga tctcaacagc ggtaagatcc ttgagagttt tcgccccgaa gaacgttttc   3720
caatgatgag cacttttaaa gttctgctat gtggcgcggt attatcccgt gttgacgccg   3780
ggcaagagca actcggtcgc cgcatacact attctcagaa tgacttggtt gagtactcac   3840
cagtcacaga aaagcatctt acggatggca tgacagtaag agaattatgc agtgctgcca   3900
taaccatgag tgataacact gcggccaact tacttctgac aacgatcgga ggaccgaagg   3960
agctaaccgc ttttttgcac aacatggggg atcatgtaac tcgccttgat cgttgggaac   4020
cggagctgaa tgaagccata ccaaacgacg agcgtgacac cacgatgcct gtagcaatgg   4080
caacaacgtt gcgcaaacta ttaactggcg aactacttac tctagcttcc cggcaacaat   4140
taatagactg gatggaggcg gataaagttg caggaccact tctgcgctcg gcccttccgg   4200
ctggctggtt tattgctgat aaatctggag ccggtgagcg tgggtctcgc ggtatcattg   4260
cagcactggg gccagatggt aagccctccc gtatcgtagt tatctacacg acggggagtc   4320
aggcaactat ggatgaacga aatagacaga tcgctgagat aggtgcctca ctgattaagc   4380
attggtaact gtcagaccaa gtttactcat atatacttta gattgattta aaacttcatt   4440
tttaatttaa aaggatctag gtgaagatcc ttttttgataa tctcatgacc aaaatccctt   4500
aacgtgagtt ttcgttccac tgagcgtcag accccgtaga aagatcaaa ggatcttctt    4560 gagatccttt ttttctgcgc gtaatctgct gcttgcaaac aaaaaaacca ccgctaccag   4620
cggtggtttg tttgccggat caagagctac caactctttt tccgaaggta actggcttca   4680
gcagagcgca gataccaaat actgtccttc tagtgtagcc gtagttaggc caccacttca   4740
agaactctgt agcaccgcct acatacctcg ctctgctaat cctgttacca gtggctgctg   4800
ccagtggcga taagtcgtgt cttaccgggt tggactcaag acgatagtta ccggataagg   4860
cgcagcggtc gggctgaacg gggggttcgt gcacacagcc cagcttggag cgaacgacct   4920
acaccgaact gagataccta cagcgtgagc tatgagaaag cgccacgctt cccgaaggga   4980
gaaaggcgga caggtatccg gtaagcggca gggtcggaac aggagagcgc acgagggagc   5040
```

```
ttccaggggg aaacgcctgg tatctttata gtcctgtcgg gtttcgccac ctctgacttg    5100
agcgtcgatt tttgtgatgc tcgtcagggg ggcggagcct atggaaaaac gccagcaacg    5160
cggccttttt acggttcctg gccttttgct ggccttttgc tcacatgttc tttcctgcgt    5220
tatcccctga ttctgtggat aaccgtatta ccgcctttga gtgagctgat accgctcgcc    5280
gcagccgaac gaccgagcgc agcgagtcag tgagcgagga agcggaagag cgcctgatgc    5340
ggtattttct ccttacgcat ctgtgcggta tttcacaccg catatggtgc actctcagta    5400
caatctgctc tgatgccgca tagttaagcc agtatacact ccgctatcgc tacgtgactg    5460
ggtcatggct gcgccccgac acccgccaac cccgctgac gcgccctgac gggcttgtct    5520
gctcccggca tccgcttaca gacaagctgt gaccgtctcc gggagctgca tgtgtcagag    5580
gttttcaccg tcatcaccga aacgcgcgag gcagcagatc aattcgcgcg cgaaggcgaa    5640
gcggcatgca tttacgttga caccatcgaa tggtgcaaaa cctttcgcgg tatggcatga    5700
tagcgcccgg aagagagtca attcaggggt gtgaatgtga aaccagtaac gttatacgat    5760
gtcgcagagt atgccggtgt ctcttatcag accgtttccc gcgtggtgaa ccaggccagc    5820
cacgtttctg cgaaaacgcg ggaaaaagtg gaagcggcga tggcggagct gaattacatt    5880
cccaaccgcg tggcacaaca actggcgggc aaacagtcgt tgctgattgg cgttgccacc    5940
tccagtctgg ccctgcacgc gccgtcgcaa attgtcgcgg cgattaaatc tcgcgccgat    6000
caactgggtg ccagcgtggt ggtgtcgatg gtagaacgaa gcggcgtcga agcctgtaaa    6060
gcggcggtgc acaatcttct cgcgcaacgc gtcagtgggc tgatcattaa ctatccgctg    6120
gatgaccagg atgccattgc tgtggaagct gcctgcacta atgttccggc gttatttctt    6180
gatgtctctg accagacacc catcaacagt attatttct cccatgaaga cggtacgcga    6240
ctgggcgtgg agcatctggt cgcattgggt caccagcaaa tcgcgctgtt agcgggccca    6300
ttaagttctg tctcggcgcg tctgcgtctg gctggctggc ataaatatct cactcgcaat    6360
caaattcagc cgatagcgga acgggaaggc gactggagtg ccatgtccgg ttttcaacaa    6420
accatgcaaa tgctgaatga gggcatcgtt cccactgcga tgctggttgc caacgatcag    6480
atggcgctgg gcgcaatgcg cgccattacc gagtccgggc tgcgcgttgg tgcggatatc    6540
tcggtagtgg gatacgacga taccgaagac agctcatgtt atatcccgcc gtcaaccacc    6600
atcaaacagg attttcgcct gctggggcaa ccagcgtgg accgcttgct gcaactctct    6660
cagggccagg cggtgaaggg caatcagctg ttgcccgtct cactggtgaa agaaaaacc    6720 accctggcgc ccaatacgca aaccgcctct ccccgcgcgt tggccgattc attaatgcag    6780
ctggcacgac aggtttcccg actggaaagc gggcagtgag cgcaacgcaa ttaatgtgag    6840
ttagcgcgaa ttgatctg                                                  6858
```

<210> SEQ ID NO 26
<211> LENGTH: 559
<212> TYPE: PRT
<213> ORGANISM: Artificial Sequence
<220> FEATURE:
<223> OTHER INFORMATION: Synthetic Construct

<400> SEQUENCE: 26

```
Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30
```

```
Asp Lys Ala Lys Lys Leu Glu Ala Glu Val Arg Arg Glu Ile Asn Asn
             35                  40                  45

Glu Lys Ala Glu Phe Leu Thr Leu Leu Glu Leu Ile Asp Asn Val Gln
 50                  55                  60

Arg Leu Gly Leu Gly Tyr Arg Phe Glu Ser Asp Ile Arg Gly Ala Leu
 65                      70                  75                  80

Asp Arg Phe Val Ser Ser Gly Phe Asp Ala Val Thr Lys Thr Ser
                 85                  90                  95

Leu His Gly Thr Ala Leu Ser Phe Arg Leu Leu Arg Gln His Gly Phe
                100                 105                 110

Glu Val Ser Gln Glu Ala Phe Ser Gly Phe Lys Asp Gln Asn Gly Asn
            115                 120                 125

Phe Leu Glu Asn Leu Lys Glu Asp Ile Lys Ala Ile Leu Ser Leu Tyr
        130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
```

```
                450             455              460
Ile Ser Glu Glu Leu Ala Thr Glu Ser Val Met Asn Leu Ile Asp Glu
465                 470                  475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
530                 535                 540

Glu Asn Leu Tyr Phe Gln Gly Leu Glu His His His His His His
545                 550                 555

<210> SEQ ID NO 27
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 27
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg     180
gttccgattt agtgctttac ggcacctcga ccccaaaaaa cttgattagg gtgatggttc     240
acgtagtggg ccatcgccct gatagacggt ttttcgccct tgacgttgg agtccacgtt     300
ctttaatagt ggactcttgt tccaaactgg aacaacactc aaccctatct cggtctattc     360
ttttgattta agggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa agtttatgc atttcttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgtttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440
cgtgagtttt cgttccactg agcgtcagac cccgtagaaa agatcaaagg atcttcttga    1500
```

```
gatcctttt  ttctgcgcgt  aatctgctgc  ttgcaaacaa  aaaaaccacc  gctaccagcg   1560
gtggtttgtt  tgccggatca  agagctacca  actcttttc  cgaaggtaac  tggcttcagc   1620
agagcgcaga  taccaaatac  tgtccttcta  gtgtagccgt  agttaggcca  ccacttcaag   1680
aactctgtag  caccgcctac  atacctcgct  ctgctaatcc  tgttaccagt  ggctgctgcc   1740
agtggcgata  agtcgtgtct  taccgggttg  gactcaagac  gatagttacc  ggataaggcg   1800
cagcggtcgg  gctgaacggg  gggttcgtgc  acacagccca  gcttggagcg  aacgacctac   1860
accgaactga  gatacctaca  gcgtgagcta  tgagaaagcg  ccacgcttcc  cgaagggaga   1920
aaggcggaca  ggtatccggt  aagcggcagg  gtcggaacag  gagagcgcac  gagggagctt   1980
ccagggggaa  acgcctggta  tctttatagt  cctgtcgggt  ttcgccacct  ctgacttgag   2040
cgtcgatttt  tgtgatgctc  gtcagggggg  cggagcctat  ggaaaaacgc  cagcaacgcg   2100 gccttttac   ggttcctggc  cttttgctgg  ccttttgctc  acatgttctt  tcctgcgtta   2160
tcccctgatt  ctgtggataa  ccgtattacc  gcctttgagt  gagctgatac  cgctcgccgc   2220
agccgaacga  ccgagcgcag  cgagtcagtg  agcgaggaag  cggaagagcg  cctgatgcgg   2280
tattttctcc  ttacgcatct  gtgcggtatt  tcacaccgca  tatatggtgc  actctcagta   2340
caatctgctc  tgatgccgca  tagttaagcc  agtatacact  ccgctatcgc  tacgtgactg   2400
ggtcatggct  gcgccccgac  acccgccaac  acccgctgac  gcgccctgac  gggcttgtct   2460
gctcccggca  tccgcttaca  gacaagctgt  gaccgtctcc  gggagctgca  tgtgtcagag   2520
gttttcaccg  tcatcaccga  aacgcgcgag  gcagctgcgg  taaagctcat  cagcgtggtc   2580
gtgaagcgat  tcacagatgt  ctgcctgttc  atccgcgtcc  agctcgttga  gtttctccag   2640
aagcgttaat  gtctggcttc  tgataaagcg  ggccatgtta  agggcggttt  ttcctgtttt   2700
ggtcactgat  gcctccgtgt  aagggggatt  tctgttcatg  ggggtaatga  taccgatgaa   2760
acgagagagg  atgctcacga  tacgggttac  tgatgatgaa  catgcccggt  tactggaacg   2820
ttgtgagggt  aaacaactgg  cggtatggat  gcggcgggac  cagagaaaaa  tcactcaggg   2880
tcaatgccag  cgcttcgtta  atacagatgt  aggtgttcca  cagggtagcc  agcagcatcc   2940
tgcgatgcag  atccggaaca  taatggtgca  gggcgctgac  ttccgcgttt  ccagactta   3000 cgaaacacgg  aaaccgaaga  ccattcatgt  tgttgctcag  gtcgcagacg  ttttgcagca   3060
gcagtcgctt  cacgttcgct  cgcgtatcgg  tgattcattc  tgctaaccag  taaggcaacc   3120
ccgccagcct  agccgggtcc  tcaacgacag  gagcacgatc  atgcgcaccc  gtggggccgc   3180
catgccggcg  ataatggcct  gcttctcgcc  gaaacgtttg  gtggcgggac  cagtgacgaa   3240
ggcttgagcg  agggcgtgca  agattccgaa  taccgcaagc  gacaggccga  tcatcgtcgc   3300
gctccagcga  aagcggtcct  cgccgaaaat  gacccagagc  gctgccggca  cctgtcctac   3360
gagttgcatg  ataaagaaga  cagtcataag  tgcggcgacg  atagtcatgc  cccgcgccca   3420
ccggaaggag  ctgactgggt  tgaaggctct  caagggcatc  ggtcgagatc  ccggtgccta   3480
atgagtgagc  taacttacat  taattgcgtt  gcgctcactg  cccgctttcc  agtcgggaaa   3540
cctgtcgtgc  cagctgcatt  aatgaatcgg  ccaacgcgcg  gggagaggcg  gtttgcgtat   3600
tgggcgccag  ggtggtttt   cttttcacca  gtgagacggg  caacagctga  ttgcccttca   3660
ccgcctggcc  ctgagagagt  tgcagcaagc  ggtccacgct  ggtttgcccc  agcaggcgaa   3720
aatcctgttt  gatggtggtt  aacgcggga   tataacatga  gctgtcttcg  gtatcgtcgt   3780
atcccactac  cgagatatcc  gcaccaacgc  gcagcccgga  ctcggtaatg  gcgcgcattg   3840
```

-continued

```
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatggaagct cgtcgttctg cgaactacga   5100
acctaacagc tgggactatg attacctgct gtcctccgac acggacgagt ccatcgaagt   5160
atacaaagac aaagcgaaaa agctggaagc cgaagttcgt cgcgagatta ataacgaaaa   5220
agcagaattt ctgaccctgc tggaactgat tgacaacgtc cagcgcctgg gcctgggtta   5280
ccgtttcgag tctgatatcc gtggtgcgct ggatcgcttc gtttcctccg gcggcttcga   5340
tgcggtaacc aagacttccc tgcacggtac ggcactgtct ttccgtctgc tgcgtcaaca   5400
cggttttgag gttctcagg aagcgttcag cggcttcaaa gaccaaaacg gcaacttcct   5460
ggagaacctg aaggaagata tcaaagctat cctgagcctg tacgaggcca gcttcctggc   5520
tctggaaggc gaaaacatcc tggacgaggc gaaggttttc gcaatctctc atctgaaaga   5580
actgtctgaa gaaaagatcg gtaaagagct ggcagaacag gtgaaccatg cactggaact   5640
gccactgcat cgccgtactc agcgtctgga agcagtatgg tctatcgagg cctaccgtaa   5700
aaaggaggac gcgaatcagg ttctgctgga gctggcaatt ctggattaca acatgatcca   5760
gtctgtatac cagcgtgatc tgcgtgaaac gtcccgttgg tggcgtcgtg tgggtctggc   5820
gaccaaactg cactttgctc gtgaccgcct gattgagagc ttctactggg ccgtgggtgt   5880
agcattcgaa ccgcaatact ccgactgccg taactccgtc gcaaaaatgt ttctttcgt    5940
aaccattatc gacgatatct acgatgtata cggcaccctg gacgaactgg agctgtttac   6000
tgatgcagtt gagcgttggg acgtaaacgc catcaacgac ctgccggatt acatgaaact   6060
gtgcttcctg gctctgtata acactattaa cgaaatcgcc tacgacaacc tgaaagataa   6120
aggtgagaac atcctgccgt atctgaccaa agcctgggct gacctgtgca acgctttcct   6180
gcaagaagcc aagtggctgt acaacaaatc tactccgacc tttgacgact acttcggcaa   6240
```

-continued

```
cgcatggaaa tcctcttctg gcccgctgca actggtgttc gcttacttcg ctgtcgtgca    6300
gaacattaaa aaggaagaga tcgaaaacct gcaaaaatac catgcacca tctctcgtcc     6360 ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgcgaaaacc tgtattttca    6720
gggcctcgag caccaccacc accaccactg agatccggct gctaacaaag cccgaaagga    6780
agctgagttg gctgctgcca ccgctgagca ataactagca taaccccttg gggcctctaa    6840
acgggtcttg aggggttttt tgctgaaagg aggaactata tccggat                  6887
```

<210> SEQ ID NO 28
<211> LENGTH: 559
<212> TYPE: PRT
<213> ORGANISM: Artificial Sequence
<220> FEATURE:
<223> OTHER INFORMATION: Synthetic Construct

<400> SEQUENCE: 28

```
Met Glu Ala Arg Arg Ser Ala Asn Tyr Glu Pro Asn Ser Trp Asp Tyr
  1               5                  10                  15

Asp Tyr Leu Leu Ser Ser Asp Thr Asp Glu Ser Ile Glu Val Tyr Lys
             20                  25                  30

Asp Lys Ala Lys Lys Leu Glu Ala Glu Val Arg Arg Glu Ile Asn Asn
         35                  40                  45

Glu Lys Ala Glu Phe Leu Thr Leu Leu Glu Leu Ile Asp Asn Val Gln
     50                  55                  60

Arg Leu Gly Leu Gly Tyr Arg Phe Glu Ser Asp Ile Arg Gly Ala Leu
 65                  70                  75                  80

Asp Arg Phe Val Ser Ser Gly Gly Phe Asp Ala Val Thr Lys Thr Ser
                 85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
```

```
                 245                 250                 255
Arg Asp Arg Leu Ile Glu Ser Phe Tyr Trp Ala Val Gly Val Ala Phe
            260                 265                 270
Glu Pro Gln Tyr Ser Asp Cys Arg Asn Ser Val Ala Lys Met Phe Ser
        275                 280                 285
Phe Val Thr Ile Ile Asp Asp Ile Tyr Asp Val Tyr Gly Thr Leu Asp
    290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
            340                 345                 350
Asn Ile Leu Pro Tyr Leu Thr Lys Ala Trp Ala Asp Leu Cys Asn Ala
        355                 360                 365
Phe Leu Gln Glu Ala Lys Trp Leu Tyr Asn Lys Ser Thr Pro Thr Phe
    370                 375                 380
Asp Asp Tyr Phe Gly Asn Ala Trp Lys Ser Ser Gly Pro Leu Gln
385                 390                 395                 400
Leu Val Phe Ala Tyr Phe Ala Val Val Gln Asn Ile Lys Lys Glu Glu
                405                 410                 415
Ile Glu Asn Leu Gln Lys Tyr His Asp Thr Ile Ser Arg Pro Ser His
            420                 425                 430
Ile Phe Arg Leu Cys Asn Asp Leu Ala Ser Ala Ser Ala Glu Ile Ala
        435                 440                 445
Arg Gly Glu Thr Ala Asn Ser Val Ser Cys Tyr Met Arg Thr Lys Gly
    450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Ser Gly Ser Leu Phe Ala
                485                 490                 495
Lys Pro Phe Val Glu Thr Ala Ile Asn Leu Ala Arg Gln Ser His Cys
            500                 505                 510
Thr Tyr His Asn Gly Asp Ala His Thr Ser Pro Asp Glu Leu Thr Arg
        515                 520                 525
Lys Arg Val Leu Ser Val Ile Thr Glu Pro Ile Leu Pro Phe Glu Arg
    530                 535                 540
Glu Asn Leu Tyr Phe Gln Gly Leu Glu His His His His His His
545                 550                 555

<210> SEQ ID NO 29
<211> LENGTH: 6887
<212> TYPE: DNA
<213> ORGANISM: Artificial Sequence
<220> FEATURE:
<223> OTHER INFORMATION: Synthetic Construct

<400> SEQUENCE: 29
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccttagg      180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
```

```
ctttaatagt ggactcttgt tccaaactgg aacaacactc aaccctatct cggtctattc    360
ttttgattta taagggatttt tgccgatttc ggcctattgg ttaaaaaatg agctgattta   420
acaaaaattt aacgcgaatt ttaacaaaat attaacgttt acaatttcag gtggcacttt   480
tcggggaaat gtgcgcggaa cccctatttg tttattttc taaatacatt caaatatgta    540
tccgctcatg aattaattct tagaaaaact catcgagcat caaatgaaac tgcaatttat   600
tcatatcagg attatcaata ccatattttt gaaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga gacgaaatac gcgatcgctg ttaaaaggac   960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gttttattgt tcatgaccaa aatcccttaa  1440
cgtgagtttt cgttccactg agcgtcagac cccgtagaaa agatcaaagg atcttcttga  1500
gatccttttt tctgcgcgt aatctgctgc ttgcaaacaa aaaaaccacc gctaccagcg   1560
gtggtttgtt tgccggatca agagctacca actctttttc cgaaggtaac tggcttcagc  1620
agagcgcaga taccaaatac tgtccttcta gtgtagccgt agttaggcca ccacttcaag  1680
aactctgtag caccgcctac atacctcgct ctgctaatcc tgttaccagt ggctgctgcc  1740
agtggcgata agtcgtgtct taccgggttg gactcaagac gatagttacc ggataaggcg  1800
cagcggtcgg gctgaacggg gggttcgtgc acacagccca gcttggagcg aacgacctac  1860
accgaactga gatacctaca gcgtgagcta tgagaaagcg ccacgcttcc cgaagggaga  1920
aaggcggaca ggtatccggt aagcggcagg gtcggaacag gagagcgcac gagggagctt  1980 ccaggggga acgcctggta tctttatagt cctgtcgggt ttcgccacct ctgacttgag   2040
cgtcgatttt tgtgatgctc gtcagggggg cggagcctat ggaaaaacgc cagcaacgcg  2100 gccttttttac ggttcctggc cttttgctgg ccttttgctc acatgttctt tcctgcgtta  2160
tcccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac acccgctgac gcgccctgac gggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt ttcctgtttt  2700
```

-continued

```
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag gtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacgcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccacttt tcccgcgttt    4500 tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
```

```
ttttgtttaa ctttaagaag gagatataca tatggaagct cgtcgttctg cgaactacga    5100
acctaacagc tgggactatg attacctgct gtcctccgac acggacgagt ccatcgaagt    5160
atacaaagac aaagcgaaaa agctggaagc cgaagttcgt cgcgagatta ataacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaaagatcg gtaaagagct ggcagaacag gtgaaccatg cactggaact    5640
gccactgcat cgccgtactc agcgtctgga agcagtatgg tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940 aaccattatc gacgatatct acgatgtata cggcaccctg gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gagtggtagc ctgttcgcga aaccgttcgt ggaaaccgcg atcaacctgg cacgtcaatc    6600
tcactgcact tatcataacg gcgacgcgca tacctctccg gatgagctga cccgcaaacg    6660
cgttctgtct gtaatcactg aaccgattct gccgtttgaa cgcgaaaacc tgtatttca    6720 gggcctcgag caccaccacc accaccactg agatccggct gctaacaaag cccgaaagga    6780
agctgagttg gctgctgcca ccgctgagca ataactagca taaccccttg ggcctctaa    6840 acgggtcttg agggggtttt tgctgaaagg aggaactata tccggat             6887
```

<210> SEQ ID NO 30
<211> LENGTH: 30
<212> TYPE: DNA
<213> ORGANISM: Artificial Sequence
<220> FEATURE:
<223> OTHER INFORMATION: Synthetic Construct

<400> SEQUENCE: 30
tatacatatg cgtcgctctg cgaactacga                              30

<210> SEQ ID NO 31
<211> LENGTH: 30
<212> TYPE: DNA
<213> ORGANISM: Artificial Sequence -continued

```
<220> FEATURE:
<223> OTHER INFORMATION: Synthetic Construct

<400> SEQUENCE: 31
cagagcgacg catatgtata tctccttctt                                              30

<210> SEQ ID NO 32
<211> LENGTH: 30
<212> TYPE: DNA
<213> ORGANISM: Artificial Sequence
<220> FEATURE:
<223> OTHER INFORMATION: Synthetic Construct

<400> SEQUENCE: 32
tatacatatg gcacgtcgct ctgcgaacta                                              30

<210> SEQ ID NO 33
<211> LENGTH: 30
<212> TYPE: DNA
<213> ORGANISM: Artificial Sequence
<220> FEATURE:
<223> OTHER INFORMATION: Synthetic Construct

<400> SEQUENCE: 33
agcgacgtgc catatgtata tctccttctt                                              30

<210> SEQ ID NO 34
<211> LENGTH: 543
<212> TYPE: PRT
<213> ORGANISM: Populus alba

<400> SEQUENCE: 34
```

Met Ala Arg Arg Ser Ala Asn Tyr Glu Pro Asn Ser Trp Asp Tyr Asp
 1               5                  10                  15

Tyr Leu Leu Ser Ser Asp Thr Asp Glu Ser Ile Glu Val Tyr Lys Asp
            20                  25                  30

Lys Ala Lys Lys Leu Glu Ala Glu Val Arg Arg Glu Ile Asn Asn Glu
        35                  40                  45

Lys Ala Glu Phe Leu Thr Leu Leu Glu Leu Ile Asp Asn Val Gln Arg
    50                  55                  60

Leu Gly Leu Gly Tyr Arg Phe Glu Ser Asp Ile Arg Gly Ala Leu Asp
65                  70                  75                  80

Arg Phe Val Ser Ser Gly Gly Phe Asp Ala Val Thr Lys Thr Ser Leu
                85                  90                  95

His Gly Thr Ala Leu Ser Phe Arg Leu Leu Arg Gln His Gly Phe Glu
            100                 105                 110

Val Ser Gln Glu Ala Phe Ser Gly Phe Lys Asp Gln Asn Gly Asn Phe
        115                 120                 125

Leu Glu Asn Leu Lys Glu Asp Ile Lys Ala Ile Leu Ser Leu Tyr Glu
    130                 135                 140

Ala Ser Phe Leu Ala Leu Glu Gly Glu Asn Ile Leu Asp Glu Ala Lys
145                 150                 155                 160

Val Phe Ala Ile Ser His Leu Lys Glu Leu Ser Glu Glu Lys Ile Gly
                165                 170                 175

Lys Glu Leu Ala Glu Gln Val Asn His Ala Leu Glu Leu Pro Leu His
            180                 185                 190

Arg Arg Thr Gln Arg Leu Glu Ala Val Trp Ser Ile Glu Ala Tyr Arg
        195                 200                 205

Lys Lys Glu Asp Ala Asn Gln Val Leu Leu Glu Leu Ala Ile Leu Asp

```
Tyr Asn Met Ile Gln Ser Val Tyr Gln Arg Asp Leu Arg Glu Thr Ser
225                 230                 235                 240

Arg Trp Trp Arg Arg Val Gly Leu Ala Thr Lys Leu His Phe Ala Arg
            245                 250                 255

Asp Arg Leu Ile Glu Ser Phe Tyr Trp Ala Val Gly Val Ala Phe Glu
        260                 265                 270

Pro Gln Tyr Ser Asp Cys Arg Asn Ser Val Ala Lys Met Phe Ser Phe
    275                 280                 285

Val Thr Ile Ile Asp Asp Ile Tyr Asp Val Tyr Gly Thr Leu Asp Glu
290                 295                 300

Leu Glu Leu Phe Thr Asp Ala Val Glu Arg Trp Asp Val Asn Ala Ile
305                 310                 315                 320

Asn Asp Leu Pro Asp Tyr Met Lys Leu Cys Phe Leu Ala Leu Tyr Asn
            325                 330                 335

Thr Ile Asn Glu Ile Ala Tyr Asp Asn Leu Lys Asp Lys Gly Glu Asn
        340                 345                 350

Ile Leu Pro Tyr Leu Thr Lys Ala Trp Ala Asp Leu Cys Asn Ala Phe
    355                 360                 365

Leu Gln Glu Ala Lys Trp Leu Tyr Asn Lys Ser Thr Pro Thr Phe Asp
370                 375                 380

Asp Tyr Phe Gly Asn Ala Trp Lys Ser Ser Gly Pro Leu Gln Leu
385                 390                 395                 400

Val Phe Ala Tyr Phe Ala Val Val Gln Asn Ile Lys Lys Glu Ile
            405                 410                 415

Glu Asn Leu Gln Lys Tyr His Asp Thr Ile Ser Arg Pro Ser His Ile
        420                 425                 430

Phe Arg Leu Cys Asn Asp Leu Ala Ser Ala Ser Ala Glu Ile Ala Arg
    435                 440                 445

Gly Glu Thr Ala Asn Ser Val Ser Cys Tyr Met Arg Thr Lys Gly Ile
450                 455                 460

Ser Glu Glu Leu Ala Thr Glu Ser Val Met Asn Leu Ile Asp Glu Thr
465                 470                 475                 480

Trp Lys Lys Met Asn Lys Glu Lys Leu Gly Gly Ser Leu Phe Ala Lys
            485                 490                 495

Pro Phe Val Glu Thr Ala Ile Asn Leu Ala Arg Gln Ser His Cys Thr
        500                 505                 510

Tyr His Asn Gly Asp Ala His Thr Ser Pro Asp Glu Leu Thr Arg Lys
    515                 520                 525

Arg Val Leu Ser Val Ile Thr Glu Pro Ile Leu Pro Phe Glu Arg
530                 535                 540
```

<210> SEQ ID NO 35
<211> LENGTH: 6906
<212> TYPE: DNA
<213> ORGANISM: Artificial Sequence
<220> FEATURE:
<223> OTHER INFORMATION: Synthetic Construct

<400> SEQUENCE: 35

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg       180 gttccgattt agtgctttac ggcacctcga ccccaaaaaa cttgattagg gtgatggttc     240
```

```
acgtagtggg ccatcgccct gatagacggt ttttcgccct ttgacgttgg agtccacgtt      300
ctttaatagt ggactcttgt tccaaactgg aacaacactc aaccctatct cggtctattc      360
ttttgattta taagggatttt tgccgatttc ggcctattgg ttaaaaaatg agctgattta     420
acaaaaattt aacgcgaatt ttaacaaaat attaacgttt acaatttcag gtggcacttt      480
tcggggaaat gtgcgcggaa cccctatttg tttatttttc taaatacatt caaatatgta      540
tccgctcatg aattaattct tagaaaaact catcgagcat caaatgaaac tgcaatttat      600
tcatatcagg attatcaata ccatattttt gaaaaagccg tttctgtaat aaggagaaa      660 actcaccgag gcagttccat aggatggcaa gatcctggta tcggtctgcg attccgactc      720
gtccaacatc aatacaacct attaatttcc cctcgtcaaa aataaggtta tcaagtgaga      780
aatcaccatg agtgacgact gaatccggtg agaatggcaa aagtttatgc atttctttcc     840
agacttgttc aacaggccag ccattacgct cgtcatcaaa atcactcgca tcaaccaaac      900
cgttattcat tcgtgattgc gcctgagcga gacgaaatac gcgatcgctg ttaaaaggac      960
aattacaaac aggaatcgaa tgcaaccggc gcaggaacac tgccagcgca tcaacaatat      1020 ttcacctga atcaggatat tcttctaata cctggaatgc tgttttcccg gggatcgcag       1080
tggtgagtaa ccatgcatca tcaggagtac ggataaaatg cttgatggtc ggaagaggca     1140
taaattccgt cagccagttt agtctgacca tctcatctgt aacatcattg gcaacgctac      1200
ctttgccatg tttcagaaac aactctggcg catcgggctt cccatacaat cgatagattg      1260
tcgcacctga ttgcccgaca ttatcgcgag cccatttata cccatataaa tcagcatcca      1320
tgttggaatt taatcgcggc ctagagcaag acgtttcccg ttgaatatgg ctcataacac     1380
cccttgtatt actgtttatg taagcagaca gttttattgt tcatgaccaa aatcccttaa     1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg     1560
gtggtttgtt tgccggatca agagctacca actctttttc cgaaggtaac tggcttcagc     1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg     1800
cagcggtcgg gctgaacggg gggttcgtgc acacagccca gcttggagcg aacgacctac     1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag     2040
cgtcgatttt tgtgatgctc gtcagggggg cggagcctat ggaaaaacgc cagcaacgcg     2100 gccttttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg   2280 tatttttctcc ttacgcatct gtgcggtatt tcacaccgca tatatggtgc actctcagta   2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
```

```
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccctc ggtgatgtcg gcgatatagg cgccagcaac cgcacctgtg    4920
gcgccggtga tgccggccac gatgcgtccg gcgtagagga tcgagatctc gatcccgcga    4980
```

-continued

```
aattaatacg actcactata ggggaattgt gagcggataa caattcccct ctagaaataa       5040
ttttgtttaa ctttaagaag gagatataca tatggcacgt cgctctgcga actacgaacc       5100
taacagctgg gactatgatt acctgctgtc ctccgacacg gacgagtcca tcgaagtata       5160
caaagacaaa gcgaaaaagc tggaagccga agttcgtcgc gagattaata cgaaaaagc       5220 agaatttctg accctgctgg aactgattga caacgtccag cgcctgggcc tgggttaccg       5280
tttcgagtct gatatccgtg gtgcgctgga tcgcttcgtt cctccggcg gcttcgatgc        5340 ggtaaccaag acttccctgc acggtacggc actgtctttc cgtctgctgc gtcaacacgg       5400
ttttgaggtt tctcaggaag cgttcagcgg cttcaaagac caaaacggca acttcctgga       5460
gaacctgaag gaagatatca agctatcct gagcctgtac gaggccagct tcctggctct        5520
ggaaggcgaa acatcctgg acgaggcgaa ggttttcgca atctctcatc tgaaagaact        5580
gtctgaagaa aagatcggta aagagctggc agaacaggtg aaccatgcac tggaactgcc       5640
actgcatcgc cgtactcagc gtctggaagc agtatggtct atcgaggcct accgtaaaaa       5700
ggaggacgcg aatcaggttc tgctggagct ggcaattctg gattacaaca tgatccagtc       5760
tgtataccag cgtgatctgc gtgaaacgtc ccgttggtgg cgtcgtgtgg gtctggcgac       5820
caaactgcac tttgctcgtg accgcctgat tgagagcttc tactgggccg tgggtgtagc       5880
attcgaaccg caatactccg actgccgtaa ctccgtcgca aaaatgtttt ctttcgtaac       5940
cattatcgac gatatctacg atgtatacgg caccctggac gaactggagc tgtttactga       6000
tgcagttgag cgttgggacg taaacgccat caacgacctg ccggattaca tgaaactgtg       6060
ctttctggct ctgtataaca ctattaacga aatcgcctac gacaacctga agataaagg       6120 tgagaacatc ctgccgtatc tgaccaaagc ctgggctgac ctgtgcaacg ctttcctgca       6180
agaagccaag tggctgtaca acaaatctac tccgaccttt gacgactact tcggcaacgc       6240
atggaaatcc tcttctggcc cgctgcaact ggtgttcgct tacttcgctg tcgtgcagaa       6300
cattaaaaag gaagagatcg aaaacctgca aaaataccat gacaccatct ctcgtccttc       6360
ccatatcttc cgtctgtgca atgacctggc tagcgcgtct gcggaaattg cgcgtggtga       6420
aaccgcaaat agcgtttctt gttacatgcg cactaaaggt atctccgaag aactggctac       6480
cgaaagcgtg atgaatctga tcgatgaaac ctggaaaaag atgaacaagg aaaaactggg       6540
tggtagcctg ttcgcgaaac cgttcgtgga accgcgatc aacctggcac gtcaatctca       6600
ctgcacttat cataacggcg acgcgcatac ctctccggat gagctgaccc gcaaacgcgt       6660
tctgtctgta atcactgaac cgattctgcc gtttgaacgc taaggatccg aattcgagct       6720
ccgtcgacaa gcttgcggcc gcactcgagc accaccacca ccaccactga gatccggctg       6780
ctaacaaagc ccgaaggaa gctgagttgg ctgctgccac cgctgagcaa taactagcat        6840
aaccccttgg ggcctctaaa cgggtcttga ggggttttt gctgaaagga ggaactatat        6900
ccggat                                                                  6906
```

<210> SEQ ID NO 36
<211> LENGTH: 542
<212> TYPE: PRT
<213> ORGANISM: Populus alba

<400> SEQUENCE: 36

```
Met Arg Arg Ser Ala Asn Tyr Glu Pro Asn Ser Trp Asp Tyr Asp Tyr
  1               5                  10                  15

Leu Leu Ser Ser Asp Thr Asp Glu Ser Ile Glu Val Tyr Lys Asp Lys
```

```
              20                  25                  30
Ala Lys Lys Leu Glu Ala Glu Val Arg Arg Glu Ile Asn Asn Glu Lys
            35                  40                  45
Ala Glu Phe Leu Thr Leu Leu Glu Leu Ile Asp Asn Val Gln Arg Leu
        50                  55                  60
Gly Leu Gly Tyr Arg Phe Glu Ser Asp Ile Arg Gly Ala Leu Asp Arg
65                  70                  75                  80
Phe Val Ser Ser Gly Gly Phe Asp Ala Val Thr Lys Thr Ser Leu His
                85                  90                  95
Gly Thr Ala Leu Ser Phe Arg Leu Leu Arg Gln His Gly Phe Glu Val
            100                 105                 110
Ser Gln Glu Ala Phe Ser Gly Phe Lys Asp Gln Asn Gly Asn Phe Leu
        115                 120                 125
Glu Asn Leu Lys Glu Asp Ile Lys Ala Ile Leu Ser Leu Tyr Glu Ala
    130                 135                 140
Ser Phe Leu Ala Leu Glu Gly Glu Asn Ile Leu Asp Glu Ala Lys Val
145                 150                 155                 160
Phe Ala Ile Ser His Leu Lys Glu Leu Ser Glu Glu Lys Ile Gly Lys
                165                 170                 175
Glu Leu Ala Glu Gln Val Asn His Ala Leu Glu Leu Pro Leu His Arg
            180                 185                 190
Arg Thr Gln Arg Leu Glu Ala Val Trp Ser Ile Glu Ala Tyr Arg Lys
        195                 200                 205
Lys Glu Asp Ala Asn Gln Val Leu Leu Glu Leu Ala Ile Leu Asp Tyr
    210                 215                 220
Asn Met Ile Gln Ser Val Tyr Gln Arg Asp Leu Arg Glu Thr Ser Arg
225                 230                 235                 240
Trp Trp Arg Arg Val Gly Leu Ala Thr Lys Leu His Phe Ala Arg Asp
                245                 250                 255
Arg Leu Ile Glu Ser Phe Tyr Trp Ala Val Gly Val Ala Phe Glu Pro
            260                 265                 270
Gln Tyr Ser Asp Cys Arg Asn Ser Val Ala Lys Met Phe Ser Phe Val
        275                 280                 285
Thr Ile Ile Asp Asp Ile Tyr Asp Val Tyr Gly Thr Leu Asp Glu Leu
    290                 295                 300
Glu Leu Phe Thr Asp Ala Val Glu Arg Trp Asp Val Asn Ala Ile Asn
305                 310                 315                 320
Asp Leu Pro Asp Tyr Met Lys Leu Cys Phe Leu Ala Leu Tyr Asn Thr
                325                 330                 335
Ile Asn Glu Ile Ala Tyr Asp Asn Leu Lys Asp Lys Gly Glu Asn Ile
            340                 345                 350
Leu Pro Tyr Leu Thr Lys Ala Trp Ala Asp Leu Cys Asn Ala Phe Leu
        355                 360                 365
Gln Glu Ala Lys Trp Leu Tyr Asn Lys Ser Thr Pro Thr Phe Asp Asp
    370                 375                 380
Tyr Phe Gly Asn Ala Trp Lys Ser Ser Gly Pro Leu Gln Leu Val
385                 390                 395                 400
Phe Ala Tyr Phe Ala Val Val Gln Asn Ile Lys Lys Glu Glu Ile Glu
                405                 410                 415
Asn Leu Gln Lys Tyr His Asp Thr Ile Ser Arg Pro Ser His Ile Phe
            420                 425                 430
Arg Leu Cys Asn Asp Leu Ala Ser Ala Ser Ala Glu Ile Ala Arg Gly
        435                 440                 445
```

Glu Thr Ala Asn Ser Val Ser Cys Tyr Met Arg Thr Lys Gly Ile Ser
            450                 455                 460

Glu Glu Leu Ala Thr Glu Ser Val Met Asn Leu Ile Asp Glu Thr Trp
465                 470                 475                 480

Lys Lys Met Asn Lys Glu Lys Leu Gly Gly Ser Leu Phe Ala Lys Pro
                485                 490                 495

Phe Val Glu Thr Ala Ile Asn Leu Ala Arg Gln Ser His Cys Thr Tyr
            500                 505                 510

His Asn Gly Asp Ala His Thr Ser Pro Asp Glu Leu Thr Arg Lys Arg
        515                 520                 525

Val Leu Ser Val Ile Thr Glu Pro Ile Leu Pro Phe Glu Arg
    530                 535                 540

<210> SEQ ID NO 37
<211> LENGTH: 6903
<212> TYPE: DNA
<213> ORGANISM: Artificial Sequence
<220> FEATURE:
<223> OTHER INFORMATION: Synthetic Construct

<400> SEQUENCE: 37
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggct ccctttaggg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttg tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa agtttatgc atttctttcc     840 agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440 cgtgagtttt cgttccactg agcgtcagac cccgtagaaa agatcaaagg atcttcttga    1500

```
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcaggggg cggagcctat ggaaaaacgc cagcaacgcg    2100
gcctttttac ggttcctggc cttttgctgg ccttttgctc acatgttctt cctgcgtta    2160 tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt ttcctgtttt    2700
ggtcactgat gcctccgtgt aagggggatt tctgttcatg gggtaatga taccgatgaa    2760 acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
```

```
gcatttgcat ggtttgttga aaaccggaca tggcactcca gtcgccttcc cgttccgcta   3960
tcggctgaat ttgattgcga gtgagatatt tatgccagcc agccgacgc agacgcgccg    4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcgtcgc tctgcgaact acgaacctaa   5100
cagctgggac tatgattacc tgctgtcctc cgacacggac gagtccatcg aagtatacaa   5160
agacaaagcg aaaagctgg aagccgaagt tcgtcgcgag attaataacg aaaaagcaga   5220
atttctgacc ctgctggaac tgattgacaa cgtccagcgc ctgggcctgg gttaccgttt   5280
cgagtctgat atccgtggtg cgctggatcg cttcgtttcc tccggcggct tcgatgcggt   5340
aaccaagact tccctgcacg gtacggcact gtctttccgt ctgctgcgtc aacacggttt   5400
tgaggtttct caggaagcgt tcagcggctt caaagaccaa aacggcaact tcctggagaa   5460
cctgaaggaa gatatcaaag ctatcctgag cctgtacgag gccagcttcc tggctctgga   5520
aggcgaaaac atcctggacg aggcgaaggt tttcgcaatc tctcatctga agaactgtc   5580
tgaagaaaag atcggtaaag agctggcaga acaggtgaac catgcactgg aactgccact   5640
gcatcgccgt actcagcgtc tggaagcagt atggtctatc gaggcctacc gtaaaaagga   5700
ggacgcgaat caggttctgc tggagctggc aattctggat tacaacatga tccagtctgt   5760
ataccagcgt gatctgcgtg aaacgtcccg ttggtggcgt cgtgtgggtc tggcgaccaa   5820
actgcacttt gctcgtgacc gcctgattga gagcttctac tgggcgtgg gtgtagcatt   5880
cgaaccgcaa tactccgact gccgtaactc cgtcgcaaaa atgttttctt tcgtaaccat   5940
tatcgacgat atctacgatg tatacggcac cctggacgaa ctggagctgt ttactgatgc   6000
agttgagcgt gggacgtaa acgccatcaa cgacctgccg gattacatga aactgtgctt   6060
tctggctctg tataacacta ttaacgaaat cgcctacgac aacctgaaag ataaaggtga   6120
gaacatcctg ccgtatctga ccaaagcctg gctgacctg tgcaacgctt tcctgcaaga   6180
agccaagtgg ctgtacaaca aatctactcc gaccttgac gactacttcg gcaacgcatg   6240
```

-continued

```
gaaatcctct tctggcccgc tgcaactggt gttcgcttac ttcgctgtcg tgcagaacat    6300
taaaaaggaa gagatcgaaa acctgcaaaa ataccatgac accatctctc gtccttccca    6360
tatcttccgt ctgtgcaatg acctggctag cgcgtctgcg gaaattgcgc gtggtgaaac    6420
cgcaaatagc gtttcttgtt acatgcgcac taaaggtatc tccgaagaac tggctaccga    6480
aagcgtgatg aatctgatcg atgaaacctg gaaaagatg aacaaggaaa actgggtgg     6540 tagcctgttc gcgaaaccgt tcgtggaaac cgcgatcaac ctggcacgtc aatctcactg    6600
cacttatcat aacggcgacg cgcataccte tccggatgag ctgacccgca aacgcgttct    6660
gtctgtaatc actgaaccga ttctgccgtt tgaacgctaa ggatccgaat tcgagctccg    6720
tcgacaagct tgcggccgca ctcgagcacc accaccacca ccactgagat ccggctgcta    6780
acaaagcccg aaaggaagct gagttggctg ctgccaccgc tgagcaataa ctagcataac    6840
cccttggggc ctctaaacgg gtcttgaggg gttttttgct gaaaggagga actatatccg    6900
gat                                                                 6903
```

<210> SEQ ID NO 38
<211> LENGTH: 595
<212> TYPE: PRT
<213> ORGANISM: Populus alba

<400> SEQUENCE: 38

```
Met Ala Thr Glu Leu Leu Cys Leu His Arg Pro Ile Ser Leu Thr His
  1               5                  10                  15

Lys Leu Phe Arg Asn Pro Leu Pro Lys Val Ile Gln Ala Thr Pro Leu
             20                  25                  30

Thr Leu Lys Leu Arg Cys Ser Val Ser Thr Glu Asn Val Ser Phe Thr
         35                  40                  45

Glu Thr Glu Thr Glu Ala Arg Arg Ser Ala Asn Tyr Glu Pro Asn Ser
     50                  55                  60

Trp Asp Tyr Asp Tyr Leu Leu Ser Ser Asp Thr Asp Glu Ser Ile Glu
 65                  70                  75                  80

Val Tyr Lys Asp Lys Ala Lys Lys Leu Glu Ala Glu Val Arg Arg Glu
                 85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Gly Ala Leu Asp Arg Phe Val Ser Ser Gly Gly Phe Asp Ala Val Thr
    130                 135                 140

Lys Thr Ser Leu His Gly Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255
```

Glu Ala Tyr Arg Lys Lys Glu Asp Ala Asn Gln Val Leu Leu Glu Leu
                260                 265                 270

Ala Ile Leu Asp Tyr Asn Met Ile Gln Ser Val Tyr Gln Arg Asp Leu
            275                 280                 285

Arg Glu Thr Ser Arg Trp Trp Arg Arg Val Gly Leu Ala Thr Lys Leu
        290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Asp Tyr Phe Gly Asn Ala Trp Lys Ser Ser Ser Gly
        435                 440                 445

Pro Leu Gln Leu Val Phe Ala Tyr Phe Ala Val Val Gln Asn Ile Lys
    450                 455                 460

Lys Glu Glu Ile Glu Asn Leu Gln Lys Tyr His Asp Thr Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
        515                 520                 525

Ile Asp Glu Thr Trp Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595

<210> SEQ ID NO 39
<211> LENGTH: 560
<212> TYPE: PRT
<213> ORGANISM: Populus alba

<400> SEQUENCE: 39

Met Arg Cys Ser Val Ser Thr Glu Asn Val Ser Phe Thr Glu Thr Glu
1               5                   10                  15

Thr Glu Ala Arg Arg Ser Ala Asn Tyr Glu Pro Asn Ser Trp Asp Tyr

-continued

```
                20                  25                  30
Asp Tyr Leu Leu Ser Ser Asp Thr Asp Glu Ser Ile Glu Val Tyr Lys
            35                  40                  45

Asp Lys Ala Lys Lys Leu Glu Ala Glu Val Arg Arg Glu Ile Asn Asn
 50                  55                  60

Glu Lys Ala Glu Phe Leu Thr Leu Leu Glu Leu Ile Asp Asn Val Gln
 65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
            115                 120                 125

Glu Val Ser Gln Glu Ala Phe Ser Gly Phe Lys Asp Gln Asn Gly Asn
            130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
            195                 200                 205

His Arg Arg Thr Gln Arg Leu Glu Ala Val Trp Ser Ile Glu Ala Tyr
            210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
            275                 280                 285

Glu Pro Gln Tyr Ser Asp Cys Arg Asn Ser Val Ala Lys Met Phe Ser
            290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Asp Lys Gly Glu
            355                 360                 365

Asn Ile Leu Pro Tyr Leu Thr Lys Ala Trp Ala Asp Leu Cys Asn Ala
            370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Thr Ile Ser Arg Pro Ser His
            435                 440                 445
```

```
Ile Phe Arg Leu Cys Asn Asp Leu Ala Ser Ala Ser Ala Glu Ile Ala
    450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
                500                 505                 510

Lys Pro Phe Val Glu Thr Ala Ile Asn Leu Ala Arg Gln Ser His Cys
            515                 520                 525

Thr Tyr His Asn Gly Asp Ala His Thr Ser Pro Asp Glu Leu Thr Arg
        530                 535                 540

Lys Arg Val Leu Ser Val Ile Thr Glu Pro Ile Leu Pro Phe Glu Arg
545                 550                 555                 560

<210> SEQ ID NO 40
<211> LENGTH: 560
<212> TYPE: PRT
<213> ORGANISM: Populus alba

<400> SEQUENCE: 40

Leu Arg Cys Ser Val Ser Thr Glu Asn Val Ser Phe Thr Glu Thr Glu
 1               5                  10                  15

Thr Glu Ala Arg Arg Ser Ala Asn Tyr Glu Pro Asn Ser Trp Asp Tyr
                20                  25                  30

Asp Tyr Leu Leu Ser Ser Asp Thr Asp Glu Ser Ile Glu Val Tyr Lys
            35                  40                  45

Asp Lys Ala Lys Lys Leu Glu Ala Glu Val Arg Arg Glu Ile Asn Asn
50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
        195                 200                 205

His Arg Arg Thr Gln Arg Leu Glu Ala Val Trp Ser Ile Glu Ala Tyr
    210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
```

```
            260                 265                 270
Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
    290                 295                 300

Phe Val Thr Ile Ile Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Asp Lys Gly Glu
        355                 360                 365

Asn Ile Leu Pro Tyr Leu Thr Lys Ala Trp Ala Asp Leu Cys Asn Ala
    370                 375                 380

Phe Leu Gln Glu Ala Lys Trp Leu Tyr Asn Lys Ser Thr Pro Thr Phe
385                 390                 395                 400

Asp Asp Tyr Phe Gly Asn Ala Trp Lys Ser Ser Gly Pro Leu Gln
                405                 410                 415

Leu Val Phe Ala Tyr Phe Ala Val Val Gln Asn Ile Lys Lys Glu Glu
            420                 425                 430

Ile Glu Asn Leu Gln Lys Tyr His Asp Thr Ile Ser Arg Pro Ser His
        435                 440                 445

Ile Phe Arg Leu Cys Asn Asp Leu Ala Ser Ala Ser Ala Glu Ile Ala
    450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
                485                 490                 495

Thr Trp Lys Lys Met Asn Lys Glu Lys Leu Gly Gly Ser Leu Phe Ala
            500                 505                 510

Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
    530                 535                 540

Lys Arg Val Leu Ser Val Ile Thr Glu Pro Ile Leu Pro Phe Glu Arg
545                 550                 555                 560

<210> SEQ ID NO 41
<211> LENGTH: 593
<212> TYPE: PRT
<213> ORGANISM: Populus alba

<400> SEQUENCE: 41

Met Ala Thr Glu Leu Leu Cys Leu His Arg Pro Ile Ser Leu Thr His
1               5                  10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Ala Arg Arg Ser Ala Asn Tyr Glu Pro Asn Ser Trp Asp
    50                  55                  60

Tyr Asp Tyr Leu Leu Ser Ser Asp Thr Asp Glu Ser Ile Glu Val Tyr
65                  70                  75                  80
```

```
Lys Asp Lys Ala Lys Lys Leu Glu Ala Glu Val Arg Arg Glu Ile Asn
                85                  90                  95

Asn Glu Lys Ala Glu Phe Leu Thr Leu Leu Glu Leu Ile Asp Asn Val
            100                 105                 110

Gln Arg Leu Gly Leu Gly Tyr Arg Phe Glu Ser Asp Ile Arg Gly Ala
            115                 120                 125

Leu Asp Arg Phe Val Ser Ser Gly Phe Asp Ala Val Thr Lys Thr
            130                 135                 140

Ser Leu His Gly Thr Ala Leu Ser Phe Arg Leu Leu Arg Gln His Gly
145                 150                 155                 160

Phe Glu Val Ser Gln Glu Ala Phe Ser Gly Phe Lys Asp Gln Asn Gly
                165                 170                 175

Asn Phe Leu Glu Asn Leu Lys Glu Asp Ile Lys Ala Ile Leu Ser Leu
            180                 185                 190

Tyr Glu Ala Ser Phe Leu Ala Leu Glu Gly Glu Asn Ile Leu Asp Glu
            195                 200                 205

Ala Lys Val Phe Ala Ile Ser His Leu Lys Glu Leu Ser Glu Glu Lys
            210                 215                 220

Ile Gly Lys Glu Leu Ala Glu Gln Val Asn His Ala Leu Glu Leu Pro
225                 230                 235                 240

Leu His Arg Arg Thr Gln Arg Leu Glu Ala Val Trp Ser Ile Glu Ala
                245                 250                 255

Tyr Arg Lys Lys Glu Asp Ala Asn Gln Val Leu Leu Glu Leu Ala Ile
            260                 265                 270

Leu Asp Tyr Asn Met Ile Gln Ser Val Tyr Gln Arg Asp Leu Arg Glu
            275                 280                 285

Thr Ser Arg Trp Trp Arg Arg Val Gly Leu Ala Thr Lys Leu His Phe
290                 295                 300

Ala Arg Asp Arg Leu Ile Glu Ser Phe Tyr Trp Ala Val Gly Val Ala
305                 310                 315                 320

Phe Glu Pro Gln Tyr Ser Asp Cys Arg Asn Ser Val Ala Lys Met Phe
                325                 330                 335

Ser Phe Val Thr Ile Ile Asp Asp Ile Tyr Asp Val Tyr Gly Thr Leu
            340                 345                 350

Asp Glu Leu Glu Leu Phe Thr Asp Ala Val Glu Arg Trp Asp Val Asn
            355                 360                 365

Ala Ile Asn Asp Leu Pro Asp Tyr Met Lys Leu Cys Phe Leu Ala Leu
370                 375                 380

Tyr Asn Thr Ile Asn Glu Ile Ala Tyr Asp Asn Leu Lys Asp Lys Gly
385                 390                 395                 400

Glu Asn Ile Leu Pro Tyr Leu Thr Lys Ala Trp Ala Asp Leu Cys Asn
                405                 410                 415

Ala Phe Leu Gln Glu Ala Lys Trp Leu Tyr Asn Lys Ser Thr Pro Thr
            420                 425                 430

Phe Asp Asp Tyr Phe Gly Asn Ala Trp Lys Ser Ser Ser Gly Pro Leu
            435                 440                 445

Gln Leu Val Phe Ala Tyr Phe Ala Val Val Gln Asn Ile Lys Lys Glu
            450                 455                 460

Glu Ile Glu Asn Leu Gln Lys Tyr His Asp Thr Ile Ser Arg Pro Ser
465                 470                 475                 480

His Ile Phe Arg Leu Cys Asn Asp Leu Ala Ser Ala Ser Ala Glu Ile
                485                 490                 495

Ala Arg Gly Glu Thr Ala Asn Ser Val Ser Cys Tyr Met Arg Thr Lys
```

-continued

```
                500                     505                     510
Gly Ile Ser Glu Glu Leu Ala Thr Glu Ser Val Met Asn Leu Ile Asp
            515                     520                     525

Glu Thr Trp Lys Lys Met Asn Lys Glu Lys Leu Gly Gly Ser Leu Phe
        530                     535                     540

Ala Lys Pro Phe Val Glu Thr Ala Ile Asn Leu Ala Arg Gln Ser His
545                     550                     555                     560

Cys Thr Tyr His Asn Gly Asp Ala His Thr Ser Pro Asp Glu Leu Thr
                565                     570                     575

Arg Lys Arg Val Leu Ser Val Ile Thr Glu Pro Ile Leu Pro Phe Glu
            580                     585                     590

Arg
```